US007119091B2

(12) United States Patent
Habashita et al.

(10) Patent No.: US 7,119,091 B2
(45) Date of Patent: Oct. 10, 2006

(54) TRIAZASPIRO[5.5]UNDECANE DERIVATIVES AND PHARMACEUTICAL COMPOSITIONS COMPRISING THEREOF, AS AN ACTIVE INGREDIENT

(75) Inventors: Hiromu Habashita, Mishima-gun (JP); Shin-ichi Hamano, Mishima-gun (JP); Shiro Shibayama, Mishima-gun (JP); Yoshikazu Takaoka, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 306 days.

(21) Appl. No.: 10/148,382

(22) PCT Filed: Dec. 1, 2000

(86) PCT No.: PCT/JP00/08517

§ 371 (c)(1),
(2), (4) Date: May 8, 2003

(87) PCT Pub. No.: WO01/40227

PCT Pub. Date: Jun. 7, 2001

(65) Prior Publication Data

US 2004/0097511 A1 May 20, 2004

(30) Foreign Application Priority Data

Dec. 3, 1999 (JP) ................................ 11-344967
Jan. 27, 2000 (JP) ............................ 2000-018673
Feb. 4, 2000 (JP) ............................ 2000-027968
May 19, 2000 (JP) ............................ 2000-147882

(51) Int. Cl.
*A61K 31/497* (2006.01)
*C07D 237/00* (2006.01)
*C07D 239/00* (2006.01)
*C07D 241/00* (2006.01)

(52) U.S. Cl. ................................. 514/253.01; 549/231
(58) Field of Classification Search ........... 514/253.01; 544/231
See application file for complete search history.

(56) References Cited

U.S. PATENT DOCUMENTS 6,288,083 B1 * 9/2001 Luly et al. .................. 514/318
6,288,084 B1 * 9/2001 Luly et al. .................. 514/318

FOREIGN PATENT DOCUMENTS

EP 268868 A2 6/1988
GB 2127807 A1 4/1984
WO WO 93/13101 A1 7/1993
WO WO 97/11940 A1 4/1997
WO WO 98/25605 A1 6/1998

OTHER PUBLICATIONS

Maeda et al, "Novel Low Molecular Weight Spirodiketopiperazine Derivatives Potently Inhibit R5 HIV-1 Infection through Antagonistic Effects on CCR5" Journal of Biological Chemistry, vol. 276(37), pp. 35194-35200 (2001).*
Cascieri and Springer, "The chemokine/chemokine-receptor family: potential and progress for therapeutic intervention" Current Opinion in Chemical Biology, vol. 4(4), pp. 420-427 (2000).*
Horuk and Ng, "Chemokine Receptor Antagonists" Medicinal Research Reviews, vol. 20(2), pp. 155-168 (2000).*
S. Blazickova, et al. "Immunomodulatory characteristics of synthetic cyclic dipeptides". International Journal of Immunotherapy. vol. 10, No. 3, pp. 89-93, 1994.

* cited by examiner

*Primary Examiner*—James O. Wilson
*Assistant Examiner*—Zachary C. Tucker
(74) *Attorney, Agent, or Firm*—Sughrue Mion, PLLC

(57) ABSTRACT

Triazaspiro[5.5]undecane derivatives, quaternary ammonium salts thereof, N-oxides thereof, non-toxic salts thereof, or pharmaceutical compositions comprising them, as an active ingredient.

(I)

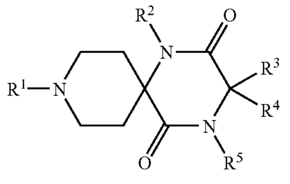

So the compounds of the formula (I) regulate the effect of chemokine/chemokine receptor, they are used for prevention and treatment of various inflammatory diseases, asthma, atopic dermatitis, urticaria, allergic diseases, nephritis, nephropathy, hepatitis, arthritis or rheumatoid arthritis etc.

7 Claims, No Drawings

TRIAZASPIRO[5.5]UNDECANE DERIVATIVES AND PHARMACEUTICAL COMPOSITIONS COMPRISING THEREOF, AS AN ACTIVE INGREDIENT

This application was filed under 35 U.S.C. 371, and is the U.S. National Stage of PCT/JP00/08517, filed Dec. 1, 2000.

TECHNICAL FIELD

The present invention relates to triazaspiro[5.5]undecane derivatives and pharmaceutical compositions comprising thereof, as an active ingredient.

More particularly, it relates to triazaspiro[5.5]undecane derivatives of the formula (I)

(I)

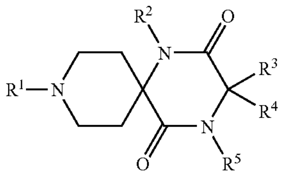

(wherein all the symbols have the same meaning as defined hereinafter), quaternary ammonium salts thereof, N-oxides thereof, non-toxic salts thereof, the methods for preparation thereof and pharmaceutical compositions comprising thereof, as an active ingredient.

BACKGROUND OF THE INVENTION

Chemokine is known as a basic protein having endogeneous leukocyte chemotactic and activating abilities and strong heparin-binding ability. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the AGM region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naïve T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokine is deeply related to the migration of these various cells. For example, MIP3β, SLC and its receptor CCR7 play an important role in the migration and homing of naïve T cell, memory T cell and the mature dendritic cell which captured an antigen into a topical lymphoid tissue for the dendritic cells to encounter efficiently with the T cells. The T cell and dendritic cell necessary for controlling antigen-specific immune responses are hardly observed in the secondary lymph node of a PLT mouse having deficiency in the expression of SLC (*J. Exp. Med.,* 189(3), 451 (1999)).

MDC, TARC and its receptor CCR4 play an important role in the migration of Th2 cell into topical sites in immune and inflammatory responses in which the Th2 cell is related. In a rat fluminant hepatitis model (P. acnes+LPS), an anti-TARC antibody suppressed increase of the amount of ALT in blood and increase of the expressing amounts of TNFα and FasL in the liver and also improved lethality of the rats (*J. Clin. Invest.,* 102, 1933 (1998)). Also, an anti-MDC antibody decreased the number of eosinophils accumulated in the lung interstitium and suppressed airway hypersensitivity in a mouse OVA-induced airway hypersensitivity model (*J. Immunology,* 163, 403 (1999)).

MCP-1 and its receptor CCR2 are related to the infiltration of macrophage into inflammation sites. An anti-MCP-1 antibody showed an effect to suppress infiltration of monocyte and macrophage into glomerulus in a rat anti-Thy1.1 antibody glomerular nephritis model (*Kidney Int.,* 51, 770 (1997)).

Thus, chemokine receptors are greatly related to the control of inflammation and immune responses through a mechanism in which they are expressed at certain specified periods in variously specific cells and the effector cells are accumulated in a region where chemokine is produced.

Acquired immunodeficiency syndrome (called AIDS) which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with pneumocystis carinii pneumonia and the like various opportunistic infections. Such conditions are the onset of AIDS, and it is well known that they induce and worsen Kaposi sarcoma and the like malignant tumors.

As the recent preventive and therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell,* 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

In 1996, a cell membrane protein called Fusin was identified as a factor other than the CD4 molecule, which is related to the HIV infection (*Science,* 272, 872 (1996)). It was confirmed that this Fusin molecule is a receptor (namely, CXCR4) of stromal derived factor-1 (hereinafter referred to as "SDF-1"). In addition, it was confirmed also in vitro that the SDF-1 specifically inhibits infection of T cell tropic (X4) HIV (*Nature,* 382, 829 (1996), *Nature,* 32, 833 (1996)). That is, it is considered that the HIV infection was inhibited by the binding of SDF-1 to CXCR4 preceding HIV, thereby depriving HIV of a foothold for infecting cells.

Also at that time, it was discovered that another chemokine receptor CCR5, which is a receptor of RANTES, MIP-1α and MIP-1β, is also used at the time of the infection with a macrophage tropic (R5) HIV (*Science,* 212, 1955 (1996)).

Accordingly, substances which can compete with CXCR4 and CCR5 for HIV, or which can bind to HIV virus thus causing the virus unable to bind to CXCR4 and CCR5, could become HIV infection inhibitors. Also, there is a case in which a low molecular compound initially discovered as an HIV infection inhibitor was actually a CXCR4 antagonist (*Nature Medicine,* 4, 72 (1998)).

Based on the above, it is considered that the chemokine/chemokine receptors are deeply related to the inflammation, immune disease or HIV infection. For example, it is considered that they are related to the inhibition of various inflammatory diseases, asthma, atopic dermatitis, nettle rash, allergic diseases (allergic bronchopulmonary aspergillosis, allergic eosinophilic gastroenteritis and the like), glomerular nephritis, nephropathy, hepatitis, arthritis, chronic rheumatoid arthritis, psoriasis, rhinitis, conjunctivitis and ischemia-reperfusion injury, in the treatment of multiple sclerosis, ulcerative colitis, acute respiratory distress syndrome, shock accompanied by bacterial infection, diabetes mellitus and autoimmune diseases, and in transplanted organ rejection reactions, immunosuppression, metastasis prevention and acquired immunodeficiency syndrome.

On the other hand, in specification of WO97/11940, it is described that compounds of the formula (Z)

(Z)

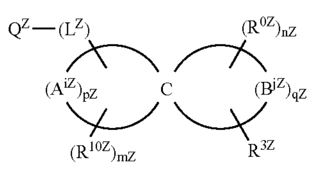

(wherein the atoms $A^{iZ}$ and $B^{iZ}$ are independently selected from carbon, nitrogen, oxygen or sulfur, provided that at least one atom of $A^{iZ}$ is carbon, and at least one atom $B^{iZ}$ is carbon;

the rings of the spirobicycle formed by $A^{iZ}$ and $B^{iZ}$, respectively, may optionally be partly unsaturated, pZ and qZ are independently numbers from 2 to 6, mZ is a number from 0 to pZ, $R^{10Z}$ is the same or different and is a non-interfering substituent independently selected from hydrogen, alkyl, halosubstituted alkyl, alkenyl, alkynyl, cycloalkyl, =O, =S etc., nZ is a number from 0 to qZ, $R^{0Z}$ is the same or different and is a non-interfering substituent independently selected from hydrogen, alkyl, halosubstituted alkyl, alkenyl, alkynyl, cycloalkyl, =O, =S etc., the linking group $-(L^Z)-$ is a bond or a divalent substituted or unsubstituted chain of from 1 to 10 atoms selected from the group consisting of carbon, nitrogen, sulfur, and oxygen, $Q^Z$ is a basic group containing one or more basic radicals, and $R^{3Z}$ is an acidic group containing one or more acid radicals) are useful in inhibition platelet aggregation.

In specification of WO98/25605, it is described that compounds of the formula (Y)

(Y)

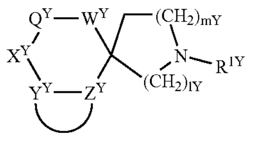

(wherein mY or lY are each independently 0, 1, 2, 3, 4 or 5, $R^{1Y}$ is hydrogen, C1–8 alkyl, C2–8 alkenyl, C2–8 alkynyl etc., $W^Y$ is a bond, C1–3 alkyl or C1–3 alkyl substituted with oxo etc., $Q^Y$ is —$NR^2$—, —O—, —S—, —S(O)— or —$SO_2$—, $X^Y$ is a bond, C1–3 alkyl or C1–3 alkyl substituted with oxo etc., $Y^Y$-$Z^Y$ ring is phenyl, naphthyl or hetero aryl.

With the proviso that the definition of each symbol is a excerpt partially.) are useful as modulators of the chemokine receptors.

DISCLOSURE OF THE INVENTION

The present inventors have investigated to find compounds regulating chemokine/chemokine receptors, so that the present inventors have found that the purpose has been achieved by triazaspiro[5.5]undecane derivatives of the formula (I).

The present invention relates to i) triazaspiro[5.5]undecane derivatives of the formula (I)

(I)

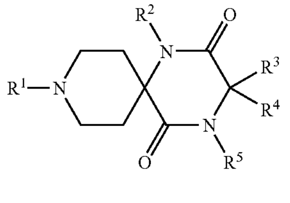

[wherein $R^1$ is (1) hydrogen, (2) C1–18 alkyl, (3) C2–18 alkenyl, (4) C2–18 alkynyl,
(5) —$COR^6$,
(6) —$CONR^7R^8$,
(7) —$COOR^9$,
(8) —$SO_2R^{10}$,
(9) —$COCOOR^{11}$,
(10) —$CONR^{12}COR^{13}$,
(11) Cyc 1, or
(12) C1–18 alkyl, C2–18 alkenyl or C2–18 alkynyl substituted by 1–5 of optionally selected from (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc 1, (n) keto or (o) —$N(SO_2R^{24})_2$,
(wherein $R^6$–$R^9$, $R^{11}$–$R^{21}$, $R^{23}$, $R^{25}$ and $R^{27}$–$R^{29}$ are each independently,
(1) hydrogen,
(2) C1–8alkyl,
(3) C2–8 alkenyl,
(4) C2–8 alkynyl,
(5) Cyc 1, or
(6) C1–8 alkyl, C2–8 alkenyl or C2–8 alkynyl substituted by 1–5 of optionally selected from (a) Cyc 1, (b) halogen, (c) —$OR^{30}$, (d) —$SR^{31}$, (e) —$NR^{32}R^{33}$, (f) —$COOR^{34}$, (g) —$CONR^{35}R^{36}$, (h) —$NR^{37}COR^{38}$, (i) —$NR^{39}SO_2R^{40}$ or (j) —$N(SO_2R^{40})_2$, or
$R^7$ and $R^8$, $R^{20}$ and $R^{21}$, $R^{23}$ and $R^{29}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{195}$—(C2–6 alkylene)-, (wherein $R^{195}$ is hydrogen, C1–8 alkyl, phenyl or C1–8alkyl substituted by phenyl.),
$R^{10}$, $R^{22}$, $R^{24}$ and $R^{26}$ are each independently,
(1) C1–8alkyl,
(2) C2–8 alkenyl,
(3) C2–8 alkynyl,
(4) Cyc 1, or
(5) C1–8 alkyl, C2–8 alkenyl or C2–8 alkynyl substituted by 1–5 of optionally selected from (a) Cyc 1, (b) halogen, (c) —$OR^{30}$, (d) —$SR^{31}$, (e) —$NR^{32}R^{33}$, (f) —$COOR^{34}$, (g) —$CONR^{35}R^{36}$, (h) —$NR^{37}COR^{38}$, (i) —$NR^{39}SO_2R^{40}$ or (j) —$N(SO_2R^{40})_2$,
(wherein $R^{30}$–$R^{37}$ and $R^{39}$ are each independently, hydrogen, C1–8 alkyl, Cyc 1 or C1–8 alkyl substituted by Cyc 1, or
$R^{35}$ and $R^{36}$, taken together, are 1) C2–6 alkylene, 2) —(C2–6 alkylene)-O—(C2–6 alkylene)-, 3) —(C2–6 alkylene)-S—(C2–6 alkylene)- or 4) –(C2–6 alkylene)-$NR^{196}$—(C2–6 alkylene)-, (wherein $R^{196}$ is hydrogen, C1–8 alkyl, phenyl or C1–8 alkyl substituted by phenyl.),
$R^{38}$ and $R^{40}$ are each independently C1–8 alkyl, Cyc 1 or C1–8 alkyl substituted by Cyc 1.)
Cyc 1 is C3–15 mono-, bi- or tri-(fused or spiro) carbocyclic ring or 3–15 membered mono-, bi- or tri-(fused or spiro) cyclic hetero ring containing 1–4 nitrogen atom(s), 1–3 oxygen atom(s) and/or 1–3 sulfur atom(s).

With the proviso that, Cyc 1 may be optionally substituted by 1–5 of $R^{51}$,
$R^5$ is
(1) C1–8 alkyl,
(2) C2–8 alkenyl,
(3) C2–8 alkynyl,
(4) halogen,
(5) nitro,
(6) trifluoromethyl,
(7) trifluoromethoxy,
(8) nitrile,
(9) keto,
(10) Cyc 2
(11) —$OR^{52}$,
(12) —$SR^{53}$,
(13) —$NR^{54}R^{55}$,
(14) —$COOR^{56}$,
(15) —$CONR^{57}R^{56}$,
(16) —$NR^{59}COR^{60}$,
(17) —$SO_2NR^{61}R^{62}$,
(18) —$OCOR^{63}$,
(19) —$NR^{64}SO_2R^{65}$,
(20) —$NR^{66}COOR^{67}$,
(21) —$NR^{68}CONR^{69}R^{70}$,
(22) —$B(OR^{71})_2$,
(23) —$SO_2R^{72}$,
(24) —$N(SO_2R^{72})_2$, or
(25) C1–8 alkyl, C2–8 alkenyl or C2–8 alkynyl substituted by 1–5 of optionally selected from (a) halogen, (b) Cyc 2, (c) —$OR^{52}$, (d) —$SR^{53}$, (e) —$NR^{54}R^{55}$, (f) —$COOR^{56}$, (g) —$CONR^{57}R^{58}$, (h) —$NR^{59}COR^{60}$, (i) —$SO_2NR^{61}R^{62}$, (j) —$OCOR^{63}$, (k) —$NR^{64}SO_2R^{65}$, (l) —$NR^{66}COOR^{67}$, (m) —$NR^{68}CON$ $R^{69}R^{70}$, (n) —$B(OR^{71})_2$, (o) —$SO_2R^{72}$ or (p) —$N(SO_2R^{72})_2$.)
(wherein $R^{52}$–$R^{62}$, $R^{64}$, $R^{66}$ and $R^{68}$–$R^{71}$ are each independently 1) hydrogen, 2) C1–8 alkyl, 3) C2–8 alkenyl, 4) C2–8 alkynyl, 5) Cyc 2 or 6) C1–8 alkyl, C2-8 alkenyl or C2–8 alkynyl substituted by Cyc 2, —$OR^{73}$, —$COOR^{74}$ or —$NR^{75}R^{76}$, or $R^{57}$ and $R^{58}$, $R^{61}$ and $R^{67}$, $R^{69}$ and $R^{70}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{197}$—(C2–6 alkylene)-, (wherein $R^{197}$ is hydrogen, C1–8 alkyl, phenyl or C1–8alkyl substituted by phenyl.),
$R^{63}$, $R^{65}$, $R^{67}$ and $R^{72}$ are each independently 1) C1–8 alkyl, 2) C2–8 alkenyl, 3) C2–8 alkynyl, 4) Cyc 2 or 5) C1–8 alkyl, C2–8 alkenyl or C2–8 alkynyl substituted by Cyc 2, —$OR^{73}$, —$COOR^{74}$ or —$NR^{75}R^{76}$,
(wherein $R^{73}$–$R^{76}$ are independently hydrogen, C1–8 alkyl, Cyc 2 or C1–8 alkyl substituted by Cyc 2.)
Cyc 2 is the same meaning as Cyc 1.

With the proviso that, Cyc 2 may be optionally substituted by 1–5 of $R^{77}$,
$R^{77}$ is
1) C1–8alkyl,
2) halogen,
3) nitro,
4) trifluoromethyl,
5) trifluoromethoxy,
6) nitrile,
7) —$OR^{78}$,
8) —$NR^{79}R^{80}$,
9) —$COOR^{81}$,
10) —$SR^{82}$,
11) —$CONR^{83}R^{84}$,
12) C2–8 alkenyl,
13) C2–8 alkynyl,
14) keto,
15) Cyc 6,
16) —$NR^{161}COR^{162}$,
17) —$SO_2NR^{163}R^{164}$,
18) —$OCOR^{165}$,
19) —$NR^{166}SO_2R^{167}$,
20) —$NR^{168}COOR^{169}$,
21) —$NR^{170}CONR^{171}R^{172}$,

22) —$SO_2R^{173}$,

23) —$N(SO_2R^{167})_2$, or

24) C1–8 alkyl, C2–8 alkenyl or C2–8 alkynyl substituted by 1–5 of optionally selected from (a) halogen, (b) —$OR^{78}$, (c) —$NR^{79}R^{80}$, (d) —$COOR^{81}$, (e) —$SR^{82}$, (f) —$CONR^{83}R^{84}$, (g) keto, (h) Cyc 6, (i) —$NR^{161}COR^{162}$, (j) —$SO_2NR^{163}R^{164}$ (k) —$OCOR^{165}$, (l) —$NR^{166}SO_2R^{167}$, (m) —$NR^{168}COOR^{169}$, (n) —$NR^{170}CONR^{171}R^{172}$, (o) —$SO_2R^{173}$ or (p) —$N(SO_2R^{167})_2$.)

(wherein $R^{78}$–$R^{84}$, $R^{161}$–$R^{164}$, $R^{166}$, $R^{168}$ and $R^{170}$–$R^{172}$ are each independently (a) hydrogen, (b) C1–8 alkyl, (c) C2–8 alkenyl, (d) C2–8 alkynyl, (e) Cyc 6 or (f) C1–8 alkyl, C2–8 alkenyl or C2–8 alkynyl substituted by Cyc 6, —$OR^{174}$, —$COOR^{175}$, —$NR^{176}R^{177}$ or —$CONR^{178}R^{179}$, or $R^{83}$ and $R^{84}$, $R^{163}$ and $R^{164}$, $R^{171}$ and $R^{172}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{198}$—(C2–6 alkylene)-, (wherein $R^{198}$ is hydrogen, C1–8 alkyl, phenyl or C1–8 alkyl substituted by phenyl.), $R^{165}$, $R^{167}$, $R^{169}$ and $R^{173}$ are each independently (a) C1–8 alkyl, (b) C2–8 alkenyl, (c) C2–8 alkynyl, (d) Cyc 6 or (e) C1–8 alkyl, C2–8 alkenyl, C2–8 alkynyl substituted by Cyc 6, —$OR^{174}$, —$COOR^{175}$, —$NR^{176}R^{177}$ or —$CONR^{178}R^{179}$.)

(wherein $R^{174}$–$R^{177}$ are each independently 1) hydrogen, 2) C1–8 alkyl, 3) Cyc 6 or 4) C1–8 alkyl substituted by Cyc 6, or $R^{178}$ and $R^{179}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{199}$—(C2–6 alkylene)-(wherein $R^{199}$ is hydrogen, C1–8 alkyl, phenyl or C1–8 alkyl substituted by phenyl.), Cyc 6 is C3–8 mono-carbocyclic ring or 3–8 membered mono-cyclic hetero ring containing 1–4 nitrogen atom(s), 1–2 oxygen atom(s) and/or 1–2 sulfur atom(s).

With the proviso that, Cyc 6 may be optionally substituted by 1–5 of $R^{180}$, $R^{180}$ is, (1) C1–8 alkyl, (2) halogen, (3) nitro, (4) trifluoromethyl, (5) trifluoromethoxy, (6) nitrile, (7) —$OR^{181}$, (8) —$NR^{182}R^{183}$, (9) —$COOR^{184}$,

(10) —$SR^{185}$, or

(11) —$CONR^{186}R^{187}$, (wherein $R^{181}$–$R^{187}$ are each independently 1) hydrogen, 2) C1–8 alkyl, 3) phenyl or 4) C1–8 alkyl substituted by phenyl, $R^{182}$ and $R^{183}$, $R^{186}$ and $R^{187}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{200}$—(C2–6 alkylene)-, (wherein $R^{200}$ is hydrogen, C1–8 alkyl, phenyl or C1–8 alkyl substituted by phenyl.).), $R^2$ is (1) hydrogen, (2) C1–8 alkyl, (3) C2–8 alkenyl, (4) C2–8 alkynyl, (5) —$OR^{90}$, (6) Cyc 3, or (7) C1–8 alkyl, C2–8 alkenyl or C2–8 alkynyl substituted by 1–5 of optionally selected from (a) halogen, (b) —$OR^{90}$, (c) —$SR^{91}$, (d) —$NR^{92}R^{93}$, (e) —$COOR^{94}$, (f) —$CONR^{95}R^{96}$, (g) —$NR^{97}COR^{98}$, (h) —$SO_2NR^{99}R^{100}$, (i) —$OCOR^{101}$, (j) —$NR^{102}SO_2R^{103}$, (k) —$NR^{104}COOR^{105}$, (l) —$NR^{106}CONR^{107}R^{108}$, (m) Cyc3, (n) keto or (o) —$N(SO_2R^{103})_2$, (wherein $R^{90}$–$R^{100}$, $R^{102}$, $R^{104}$ and $R^{106}$–$R^{108}$ are each independently 1) hydrogen, 2) C1–8 alkyl, 3) C2–8 alkenyl, 4) C2–8 alkynyl, 5) Cyc 3 or 6) C1–8 alkyl, C2–8 alkenyl or C2–8 alkynyl substituted by Cyc 3, or $R^{95}$ and $R^{96}$, $R^{99}$ and $R^{100}$, $R^{107}$ and $R^{108}$, taken together, are 1) C2–6 alkylene 2) —(C2–6 alkylene)-O—(C2–6 alkylene)-, 3) —(C2–6 alkylene)-S—(C2–6 alkylene)- or 4) —(C2–6 alkylene)-$NR^{201}$—(C2–6 alkylene)-, (wherein $R^{201}$ is hydrogen, C1–8 alkyl, phenyl or C1–8 alkyl substituted by phenyl.), $R^{101}$, $R^{103}$ and $R^{105}$ are each independently 1) C1–8 alkyl, 2) C2–8 alkenyl, 3) C2–8 alkynyl or 4) Cyc 3, or C1–8 alkyl, C2–8alkenyl or C2–8alkynyl substituted by Cyc 3, Cyc 3 is the same meaning as Cyc 1.

With the proviso that, Cyc 3 may be optionally substituted by 1–5 of $R^{109}$, $R^{109}$ is the same meaning as $R^{51}$)

$R^3$ and $R^4$ are each independently (1) hydrogen, (2) C1–8 alkyl, (3) C2–8 alkenyl, (4) C2–8 alkynyl, (5) —$COOR^{120}$, (6) —$CONR^{121}R^{122}$, (7) Cyc 4, or (8) C1–8 alkyl, C2–8 alkenyl or C2–8 alkynyl substituted by 1–5 of optionally selected from (a) halogen, (b) nitrile, (c) Cyc 4, (d) —$COOR^{120}$, (e) —$CONR^{121}R^{122}$, (f) —$OR^{123}$, (g) —$SR^{124}$, (h) —$NR^{125}R^{126}$, (i) —$NR^{127}COR^{128}$, (j) —$SO_2NR^{129}R^{130}$, (k) —$OCOR^{131}$, (l) —$NR^{132}SO_2R^{133}$, (m) —$NR^{134}COOR^{135}$, (n) —$NR^{136}CONR^{137}R^{138}$, (o) —S—$SR^{139}$, (p) —NHC(=NH)$NHR^{140}$, (q) keto, (r) —$NR^{145}CONR^{146}COR^{147}$ or (s) —$N(SO_2R^{133})_2$, (wherein $R^{120}$–$R^{130}$ $R^{132}$ $R^{134}$ $R^{136}$–$R^{138}$, $R^{145}$ and $R^{146}$ are each independently 1) hydrogen, 2) C1–8 alkyl, 3) C2–8 alkenyl, 4) C2–8 alkynyl, 5) Cyc 4 or 6) C1–8 alkyl, C2–8 alkenyl or C2–8 alkynyl substituted by Cyc 4, halogen, —$OR^{148}$, —$SR^{149}$, —$COOR^{150}$ or —$NHCOR^{141}$, or $R^{121}$ and $R^{122}$ $R^{129}$ and $R^{130}$, $R^{137}$ and $R^{138}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{201}$—(C2–6 alkylene)-, (wherein $R^{202}$ is hydrogen, C1–8 alkyl, phenyl or C1–8 alkyl substituted by phenyl.), $R^{131}$, $R^{133}$, $R^{135}$, $R^{139}$ and $R^{147}$ are each independently 1) C1–8 alkyl, 2) C2–8 alkenyl, 3) C2–8 alkynyl, 4) Cyc 4 or 5) C1–8 alkyl, C2–8 alkenyl or C2–8 alkynyl substituted by Cyc 4, halogen, —$OR^{148}$, —$SR^{149}$, —$COOR^{150}$ or —$NHCOR^{141}$, $R^{140}$ is hydrogen, —$COOR^{142}$ or —$SO_2R^{143}$, (wherein $R^{141}$–$R^{143}$ are each independently 1) C1–8 alkyl, 2) C2–8 alkenyl, 3) C2–8 alkynyl, 4) Cyc 4 or 5) C1–8 alkyl, C2–8 alkenyl or C2–8 alkynyl substituted by Cyc 4, $R^{148}$–$R^{150}$ are each independently 1) hydrogen, 2) C1–8 alkyl, 3) C2–8 alkenyl, 4) C2–8 alkynyl, 5) Cyc 4 or 6) C1–8 alkyl, C2–8 alkenyl or C2–8 alkynyl substituted by Cyc 4, Cyc 4 is the same meaning as Cyc 1.

With the proviso that, Cyc 4 may be optionally substituted by 1–5 of $R^{144}$, $R^{144}$ is the same meaning as $R^{51}$.) or $R^3$ and $R^4$, taken together, are

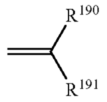

(wherein $R^{190}$ and $R^{191}$ are each independently the same meaning as $R^3$ or $R^4$.), $R^5$ is (1) hydrogen, (2) C1–8 alkyl, (3) Cyc 5, or (4) C1–8alkyl substituted by Cyc 5.

(wherein Cyc 5 is the same meaning as Cyc 1.

With the proviso that, Cyc 5 may be optionally substituted by 1–5 of $R^{160}$, $R^{160}$ is the same meaning as $R^{51}$.)], quaternary ammonium salts thereof, N-oxides thereof or non-toxic salts thereof, ii) the methods for preparation of compounds of the formula (I), quaternary ammonium salts thereof, N-oxides thereof or non-toxic salts thereof, and iii) pharmaceutical compositions comprising compounds of the formula (I), quaternary ammonium salts thereof, N-oxides thereof or non-toxic salts thereof, as an active ingredient.

In the present invention, C1–18 alkyl means methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl or isomeric groups thereof.

C2–18 alkenyl means C2–18 alkylene optionally having 1–9 double bond(s) (preferably 1–4 double bond(s)), concretely, vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl or isomeric groups thereof.

C2–18 alkynyl means C2–18 alkylene optionally having 1–9 triple bond(s) (preferably 1–4 triple bond(s)), concretely, ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, butadiynyl, pentadiynyl, hexadiynyl, heptadiynyl, octadiynyl, nonadiynyl, decadiynyl, undecadiynyl, dodecadiynyl, tridecadiynyl, tetradecadiynyl, pentadecadiynyl, hexadecadiynyl, heptadecadiynyl, octadecadiynyl, hexatriynyl, heptatriynyl, octatriynyl, nonatriynyl, decatriynyl, undecatriynyl, dodecatriynyl, tridecatriynyl, tetradecatriynyl, pentadecatriynyl, hexadecatriynyl, heptadecatriynyl, octadecatriynyl or isomeric groups thereof.

Halogen is chlorine, bromine, fluorine or iodine.

C1–8 alkyl means methyl, ethyl, propyl, butyl, pentyl, hexyl, heptyl, octyl or isomeric groups thereof.

C2–8 alkenyl means C2–8 alkylene optionally having 1–4 double bond(s), concretely, vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl or isomeric groups thereof.

C2–8 alkynyl means C2–8 alkylene optionally having 1–4 triple bond(s), concretely, ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl or isomeric groups thereof.

C2–6 alkylene means methylene, ethylene, trimethylene, tetramethylene, pentamethylene, hexamethylene or isomeric groups thereof.

C3–15 mono-, bi- or tri-(fused or spiro)carbocyclic ring means concretely, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, indene, naphthalene, indan, tetrahydronaphthalene, bicyclo[3.3.0]octane, bicyclo[4.3.0]nonane, bicyclo[4.4.0]decane, spiro[4.4]nonane, spiro[4.5]decane, spiro[5.5]undecane, bicyclo[3.1.1]heptane, bicyclo[3.3.1]hept-2-ene, fluorene or anthracene etc.

3–15 membered mono-, bi- or tri-(fused or spiro)cyclic hetero ring containing 1–4 nitrogen atom(s), 1–3 oxygen atom(s) and/or 1–3 sulfur atom(s) means 3–15 membered mono-, bi- or tri-(fused or spiro)cyclic hetero aryl containing 1–4 nitrogen atom(s), 1–3 oxygen atom(s) and/or 1–3 sulfur atom(s), and partially or fully saturated one.

3–15 membered mono-, bi- or tri-(fused or spiro)cyclic hetero aryl containing 1–4 nitrogen atom(s), 1–3 oxygen atom(s) and/or 1–3 sulfur atom(s) is pyrrole, imidazole, triazole, tetrazole, pyrazole, pyridine, pyrazine, pyrimidine, pyridazine, azepine, diazepine, furan, pyran, oxepine, thiophene, thiain (thiopyran), thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, acridine, dibenzofuran or dibenzothiophene etc.

In above 3–15 membered mono-, bi- or tri-(fused or spiro)cyclic hetero ring containing 1–4 nitrogen atom(s), 1–3 oxygen atom(s) and/or 1–3 sulfur atom(s), partially or fully saturated one is pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, benzodioxalane, benzodioxane, benzodithiolane, benzodithiane, 2,4,6-trioxaspiro[bicyclo[3.3.0]octane-3,1'-cyclohexane], 1,3-dioxolano[4,5-g]chromene or 2-oxabicyclo[2.2.1]heptane etc.

C3–8 mono-carbocyclic ring is concretely, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene or benzene etc.

3–8 membered mono-cyclic hetero ring containing 1–4 nitrogen atom(s), 1–2 oxygen atom(s) and/or 1–2 sulfur atom(s) means 3–8 membered mono-cyclic hetero aryl containing 1–4 nitrogen atom(s), 1–2 oxygen atom and/or 1–2 sulfur atom(s) and partially or fully saturated one.

3–8 membered mono-cyclic hetero aryl containing 1–4 nitrogen atom(s), 1–2 oxygen atom(s) and/or 1–2 sulfur atom(s) is pyrrole, imidazole, triazole, tetrazole, pyrazole, pyridine, pyrazine, pyrimidine, pyridazine, azepine, diazepine, furan, pyran, oxepine, thiophene, thiain (thiopyran), thiepine, oxazole, isoxazole, thiazole, isothiazole, furazan, oxadiazole, oxazine, oxadiazine, oxazepine, oxadiazepine, thiadiazole, thiazine, thiadiazine, thiazepine or thiadiazepine etc.

In above 3–8 membered mono-cyclic hetero ring containing 1–4 nitrogen atom(s), 1–2 oxygen atom(s) and/or 1–2 sulfur atom(s), partially or fully saturated one is pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine, thiomorpholine, dioxolane, dioxane, dithiolane or dithiane etc.

In the present invention, each group represented by $R^1$, $R^2$, $R^3$, $R^4$ or $R^5$ is all preferable.

Preferred $R^1$ is C1–18 alkyl substituted by Cyc 1, C2–18 alkenyl substituted by Cyc 1 or C2–18 alkynyl substituted by Cyc 1, and more preferred $R^1$ is C1–6 alkyl substituted by Cyc 1.

Preferred Cyc 1 is C3–10 mono- or bi-(fused or spiro) carbocyclic ring or 3–10 membered mono- or bi-(fused or spiro) cyclic hetero ring containing 1–4 nitrogen atom(s), 1–2 oxygen atom(s) and/or 1–2 sulfur atom(s), and more preferred Cyc 1 is C5–7 mono-carbocyclic aryl or 5–10 membered mono-cyclic hetero ring containing 1–4 nitrogen atom(s), 2 oxygen atoms and/or 1 sulfur atom.

Preferred Cyc 1 concretely is benzene, pyrazole, imidazole, furan, thiophene, benzodioxane, thiazole or quinoline.

Preferred $R^{51}$ which is a substituent of Cyc 1, is Cyc 2, —$OR^{52}$, —$SR^{53}$ or —$NR^{54}R^{55}$. Preferred $R^{52}$, $R^{53}$, $R^{54}$ and $R^{55}$ are C1–8 alkyl or Cyc 2, and more preferred $R^{52}$, $R^{53}$, $R^{54}$ and $R^{55}$ are methyl, ethyl, propyl or phenyl.

Preferred Cyc 2 is C5–7 mono-carbocyclic aryl or 5–7 membered mono-cyclic hetero aryl containing 1–4 nitrogen atom(s), 1 oxygen atom and/or 1 sulfur atom, and more preferred Cyc 2 is benzene.

Preferred $R^{77}$ which is a substituent of Cyc 2 is —$CONR^{83}R^{84}$, —$NR^{161}COR^{162}$, —$SO_2NR^{163}R^{164}$, —$NR^{166}SO_2R^{167}$, C1–8 alkyl substituted by —$CONR^{83}R^{84}$, C1–8 alkyl substituted by —$NR^{161}COR^{162}$, C1–8 alkyl substituted by —$SO_2NR^{163}R^{164}$ or C1–8 alkyl substituted by —$NR^{166}SO_2R^{167}$. Preferred $R^{83}$, $R^{84}$, $R^{161}$, $R^{162}$, $R^{163}$, $R^{164}$, $R^{166}$ and $R^{167}$ are C1–8 alkyl, Cyc 6, C1–8 alkyl substituted by —$NR^{176}R^{177}$, and more preferred $R^{83}$, $R^{84}$, $R^{161}$, $R^{162}$, $R^{163}$, $R^{164}$, $R^{166}$ and $R^{167}$ are methyl, ethyl, propyl, phenyl or dimethylaminoethyl etc.

Most preferred $R^1$ is phenylethyl, phenylpropyl, phenylbutyl, phenylpentyl, phenylhexyl, 4-methoxyphenylmethyl, 4-propyloxyphenylmethyl, 4-phenyloxyphenylmethyl, 3,5-dimethyl-1-phenylpyrazol-4-ylmethyl, 2-phenylimidazol-4-ylmethyl, 5-ethylfuran-2-ylmethyl, 5-ethylthiophen-2-ylmethyl, 3-chloro-5-methyl-1-phenylpyrazol-4-ylmethyl, 1,4-benzodioxan-6-ylmethyl, 4-(4-methylsulfonylaminophenyloxy)phenylmethyl, 4-(4-(2-dimethylaminoethylsulfonylamino)phenyloxy) phenylmethyl, 4-(4-dimethylaminosulfonylphenyloxy) phenylmethyl, 4-(4-methylcarbonylaminophenyloxy) phenylmethyl, 4-(4-(2-dimethylaminoethylcarbonylamino) phenyloxy)phenylmethyl or 4-(4-dimethylaminocarbonylphenyloxy)phenylmethyl etc.

Preferred $R^2$ is C1–8 alkyl, C2–8 alkenyl, C2–8 alkynyl, C1–8 alkyl substituted by Cyc 3. Most preferred $R^2$ is C1–4 alkyl, C2–4 alkenyl or C2–4 alkynyl.

Most preferred $R^2$ is ethyl, propyl, butyl, 2-propenyl, 2-butenyl, 2-propynyl, phenylmethyl, thiophen-2-ylmethyl or 2-butynyl etc.

Preferred $R^3$ or $R^4$ is hydrogen, C1–8 alkyl, C1–8 alkyl substituted by Cyc4, C1–8alkyl substituted by —$OR^{123}$, C1–8 alkyl substituted by Cyc4 and —$OR^{123}$, C1–8 alkyl substituted by —$NR^{127}COR^{128}$, C1–8 alkyl substituted by —$NR^{132}SO_2R^{133}$, C1–8 alkyl substituted by —$NR^{134}COOR^{135}$ or C1–8 alkyl substituted by —$NR^{136}CONR^{137}R^{138}$. More preferred $R^3$ or $R^4$ is C1–4 alkyl, C1–4 alkyl substituted by Cyc4, C1–4 alkyl substituted by —$OR^{123}$, C1–4 alkyl substituted by Cyc4 and —$OR^{123}$, C1–4 alkyl substituted by —$NR^{127}COR^{128}$, C1–4 alkyl substituted by —$NR^{132}SO_2R^{133}$, C1–4 alkyl substituted by —$NR^{134}COOR^{135}$ or C1–4 alkyl substituted by —$NR^{136}CONR^{137}R^{138}$.

Preferred Cyc 4 is benzene or cyclohexane.

Preferred $R^{123}$ is hydrogen, C1–4 alkyl, Cyc 4 or C1–4 alkyl substituted by Cyc 4, and more preferred $R^{123}$ is hydrogen, methyl, ethyl, phenyl or phenylmethyl.

Preferred $R^{127}$, $R^{132}$, $R^{134}$, $R^{136}$ and $R^{138}$ are hydrogen or methyl.

Preferred $R^{128}$, $R^{133}$, $R^{135}$ and $R^{137}$ are Cyc 4 or C1–4 alkyl substituted by Cyc 4, and more preferred $R^{128}$, $R^{133}$, $R^{135}$ and $R^{137}$ are phenyl, phenylmethyl or phenylethyl.

Preferred $R^{144}$ which is a substitute of Cyc 4, is C1–4 alkyl, halogen, phenyl or phenyloxy, and more preferred $R^{144}$ is methyl, fluorine, chlorine, phenyl or phenyloxy.

Most preferred $R^3$ or $R^4$ is propyl, 1-methylpropyl, 2-methylpropyl, cyclohexylmethyl, 1-hydroxy-2-methylpropyl, 1-hydroxy-1-cyclohexylmethyl, 3-(cyclopentylethylcarbonyl)aminobutyl, 3-(benzyloxycarbonyl) aminopropyl, 3-(phenylcarbonyl)aminobutyl, 3-(phenylmethylcarbonyl) aminobutyl, 3-(phenylethylcarbonyl)aminobutyl, 3-(phenylethenylcarbonyl)aminobutyl, 3-(4-phenylphenylcarbonyl)aminobutyl, 3-(4-phenyloxyphenylaminocarbonyl) aminobutyl, 3-(4-chlorophenylaminocarbonyl)aminobutyl, 3-(4-fluorophenylaminocarbonyl)aminobutyl, 3-(phenylmethylaminocarbonyl)aminobutyl, 3-(4-trifluoromethylsulfonyl)aminobutyl, 4-(cyclopentylethylcarbonyl)aminobutyl, 4-(benzyloxycarbonyl)aminobutyl, 4-(phenylcarbonyl)aminobutyl, 4-(phenylmethylcarbonyl)aminobutyl, 4-(phenylethylcarbonyl)aminobutyl, 4-(phenylethenylcarbonyl)aminobutyl, 4-(4-phenylphenylcarbonyl)aminobutyl, 4-(4-phenyloxyphenylaminocarbonyl)aminobutyl, 4-(4-chlorophenylaminocarbonyl)aminobutyl, 4-(4-fluorophenylaminocarbonyl)aminobutyl, 4-(phenylmethylaminocarbonyl)aminobutyl or 4-(4-trifluoromethylsulfonyl) aminobutyl.

Preferred $R^5$ is hydrogen or methyl.

In the compounds of the present invention of the formula (I), the compound of the formula (Ia)

(Ia)

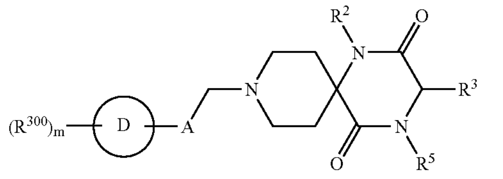

(wherein $R^2$ is C1–8 alkyl, $R^3$ is C1–8 alkyl or C3–7 cycloalkyl(C1–4)alkyl, $R^5$ is hydrogen or C1–8alkyl, A is a bond or C1–10 alkylene, D ring is C3–10 mono- or bi-(fused or spiro) carbocyclic ring or 3–10 membered mono- or bi-(fused or spiro)cyclic hetero ring, m is 0 or an integer of 1–4, $R^{300}$ is C1–4 alkyl, C1–4 alkoxy, phenyl, phenoxy or benzyloxy.)

is preferable.

Preferred C3–10 carbocyclic ring represented by D ring is C3–10 mono- or bi-carbocyclic ring, and more preferred C3–10 carbocyclic ring is C3–7 mono-carbocyclic ring or C8–10 bi-carbocyclic ring.

Preferred 3–10 membered cyclic hetero ring represented by D ring is 3–10 membered mono- or bi-cyclic hetero aryl containing 1–4 nitrogen atom(s), 1–2 oxygen atom(s) and/or 1 sulfur atom or partially or fully saturated one. More preferred 3–10 membered cyclic hetero ring is 5–7 membered mono- or 8–10 membered bi-cyclic hetero aryl containing 1–4 nitrogen atom(s), 1–2 oxygen atom(s) and/or 1 sulfur atom or partially or fully saturated one.

Unless otherwise specified, all isomers are included in the present invention. For example, alkyl, alkoxy and alkylene groups include straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomer (D-, L-, d-, l-isomer), polar compounds generated by chromatographic separation (more polar compound, less polar compound), equilibrium compounds, mixtures thereof at voluntary ratios and racemic mixtures are also included in the present invention.

[Salts]

Non-toxic salts of the present invention include all pharmaceutically acceptable salts, for example, general salts, acid addition salts, hydrate salts.

The compounds of the present invention represented by the formula (I) may be converted into the corresponding salts by conventional means. Water-soluble salts are preferred. Suitable salts, for example, include: salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine).

The compounds of the present invention represented by the formula (I) may be converted into the corresponding acid addition salts by conventional means. Water-soluble salts are preferred. Suitable salts, for example, include: salts of inorganic acids e.g. hydrochloride, hydrobromide, sulfate, phosphate, nitrate; salts of organic acids e.g. acetate, trifluoroacetate, lactate, tartrate, oxalate, fumarate, maleate, citrate, benzoate, methanesulfonate, ethanesulfonate, benzenesulfonate, toluenesulfonate, isethionate, glucuronate, gluconate.

The compounds of the present invention of the formula (I) and salts thereof may be converted into the corresponding hydrates by conventional means.

All of the compounds of the formula (I) or non-toxic salts thereof are preferable, concretely, the compounds described in the example or non-toxic salts thereof.

Quaternary ammonium salts of the compounds of the formula (I) are the compounds where nitrogen of the compounds represented by the formula (I) is quaternalized by $R^0$.

$R^0$ is C1–8 alkyl or C1–8 alkyl substituted by phenyl.

N-oxides of the compounds represented by the formula (I) are the compounds where nitrogen of the compounds represented by the formula (I) is oxidized.

[Methods for Preparation of the Compounds of the Present Invention]

The compounds of the present invention of the formula (I) may be prepared by the following methods or the methods described in examples.

Among the compounds of the present invention of the formula (I), the compounds where nitrogens are not quaternary ammonium salts or N-oxides, i.e., the compounds of the formula (I-1)

(I-1)

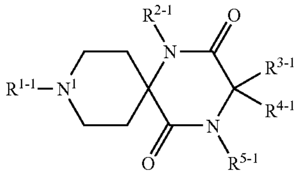

(wherein $R^{1-1}$, $R^{2-1}$ $R^{3-1}$, $R^{4-1}$ and $R^{5-1}$ have the same meaning as $R^1$, $R^2$, $R^3$, $R^4$ and $R^5$ respectively, and $N^1$ is nitrogen. With the proviso that, any nitrogen are not quaternary ammonium salts or N-oxides.)

may be prepared by the following methods.

Among the compounds of the present invention represented by the formula (I-1), the compounds in which any $R^{1-1}$, $R^{2-1}$, $R^{3-1}$, $R^{4-1}$ and $R^{5-1}$ are not a group containing carboxyl, hydroxy, amino or thiol, i.e., the compounds of the formula (I-1A)

(I-1A)

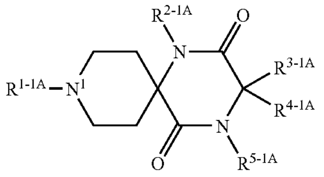

(wherein $R^{1-1A}$, $R^{2-1A}$, $R^{3-1A}$, $R^{4-1A}$ and $R^{5-1A}$ have the same meaning as $R^{1-1}$, $R^{2-1}$, $R^{3-1}$, $R^{4-1}$ and $R^{5-1}$ respectively. With the proviso that, all of them are not a group containing carboxyl, hydroxy, amino or thiol, and the other symbol have the same meanings as defined hereinbefore.)

may be prepared by the following methods.

Among the compounds of the formula (I-1 A), the compounds in which $R^1$ does not represent hydrogen, i.e., the compounds of the formula (I-1A-1)

(I-1A-1)

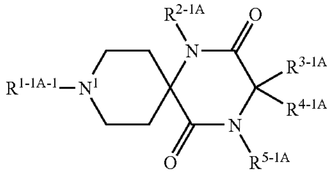

(wherein $R^{1-1A-1}$ have the same meaning as $R^{1-1A}$. With the proviso that, $R^{1-1A-1}$ is not hydrogen and the other symbols have the same meanings as defined hereinbefore.)

may be prepared by cyclization of the compounds of the formula (II-1)

(II-1)

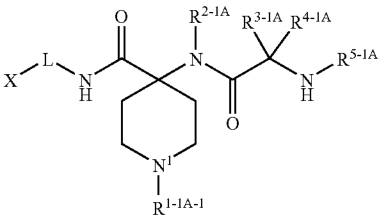

(wherein X-L-NH— is an amino terminus of aminated polystyrene resin, and the other symbols have the same meaning as defined hereinbefore.), or the compounds of the formula (II-2)

(II-2)

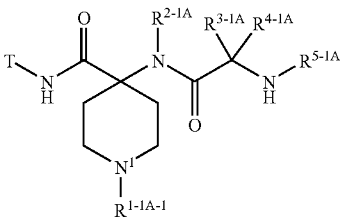

(wherein T is C1–8 alkyl, C3–8 mono-carbocyclic ring or C1–8 alkyl substituted by C3–8 mono-carbocyclic ring.).

The cyclization of compounds of the formula (II-1) is well known. For example, it may be carried out by heating in an organic solvent (toluene etc.) in the presence of acid (acetic acid, trifluoroacetic acid or hydrochloric acid etc.) at 60–120° C. This cyclization reaction is carried out with the cleavage from polystyrene resin.

If necessary, the conversion to desired non-toxic salts may be carried out by the conventional method in succession to this reaction.

The cyclization of compounds of the formula (II-2) is well known. For example, it may be carried out by heating in an organic solvent (dichloroethane or toluene etc.), with tertiary amine (triethylamine or diisopropylethylamine etc.) at 60–120° C. This cyclization reaction is carried out with the cleavage of T group.

Among the compounds of the formula (I-1A), the compounds in which $R^1$ is hydrogen, i.e., the compounds of the formula (I-1A)

(I-1A-2)

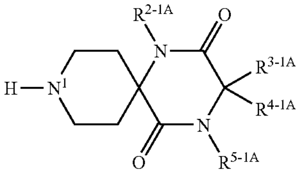

(wherein all of the symbols have the same meanings as defined hereinbefore.)

may be prepared by the removal of an amino-protecting group of the compounds in which $R^{1A-1}$ is an amino-protecting group, i.e., the compounds of the formula (I-1A-1-1)

(I-1A-1-1)

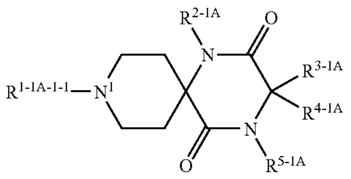

(wherein $R^{1-1A-1-1}$ is an amino-protecting group, and the other symbols have the same meaning as defined hereinbefore.)

A protecting group of amino includes, for example, benzyl, benzyloxycarbonyl, allyloxycarbonyl, t-butoxycarbonyl or trifluoroacetyl etc.

The protecting group of amino includes the above one, in addition, the other protecting group which is removable selectively and easily, for example, one described in T. W. Greene et. al., Protective Groups in Organic Synthesis, Third Edition, Wiley-Interscience, New York, 1999.

The removal of a protecting group of amino is well known. For example, it is (1) the alkaline hydrolysis,
(2) the removal of a protecting group in an acidic condition,
(3) the removal of a protecting group by hydrogenolysis, or
(4) the removal of a protecting group using metal complex etc.

Concrete descriptions of these methods are as follows:

(1) The removal of protecting group by alkaline hydrolysis condition (e.g. trifluoroacetyl group) may be carried out, for example, in an organic solvent (methanol, tetrahydrofuran or dioxane etc.) with hydroxide of alkaline metal (sodium hydroxide, potassium hydroxide or lithium hydroxide etc.), hydroxide of alkaline earth metal (barium hydroxide or calcium hydroxide etc.), carbonate (sodium carbonate or potassium carbonate etc.), or an aqueous solution thereof or a mixture thereof at 0–40° C.

(2) The removal of protecting group in an acidic condition (e.g. t-butoxycarbonyl group) may be carried out, for example, in an organic solvent (dichloromethane, chloroform, dioxane, ethyl acetate or anisole etc.), organic acid (acetic acid, trifluoroacetic acid or methanesulfonic acid etc.) or inorganic acid (hydrochloric acid or sulfuric acid etc.), or a mixture thereof (hydrogen bromide/acetic acid etc.) at 0–100° C.

(3) The removal of a protecting group by hydrogenolysis (e.g. benzyl, benzyloxycarbonyl or allyloxycarbonyl) may be carried out, for example, in a solvent (ether (tetrahydrofuran, dioxane, dimethoxyethane or diethylether etc.), alcohol(methanol or ethanol etc.), benzene(benzene or toluene etc.), ketone (acetone or methylethylketone etc.), nitrile (acetonitrile etc.), amide (dimethylformamide etc.), water, ethyl acetate, acetic acid or a mixture thereof etc.) in the presence of a catalyst (palladium on carbon, palladium black, palladium hydroxide, platinum oxide, Raney nickel etc.), at atmospheric or positive pressure under an atmosphere of hydrogen or in the presence of ammonium formate at 0–200° C.

(4) The removal of a protecting group using metal complex may be carried out, for example, in an organic solvent (dichloromethane, dimethylformamide or tetrahydrofuran etc.) in the presence of a trap reagent (tributyltin hydride or dimedone etc.) and/or an organic acid (acetic acid etc.) with metal complex (tetrakis(triphenylphosphine)palladium(O) complex etc.) at 0–40° C.

Moreover, the compounds of the formula (I-1A-1) may be prepared with the compounds of the formula (I-1A-2) by the following methods of (a)–(g).

(a) Among the compounds of the formula (I-1A-1), the compounds, in which $R^{1A-1}$ is C1–18 alkyl, C2–18 alkenyl, C2–18 alkynyl, or C1–18 alkyl, C2–18 alkenyl or C2–18 alkynyl substituted by various substituents, and in which $R^{1A-1}$ bonds with $N^1$ through —$CH_2$—, i.e., the compounds of the formula (I-1A-1a)

(I-1A-1a)

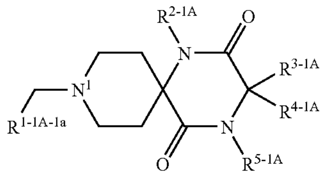

(wherein $R^{1-1A-1a}$ is C1–17 alkyl, C2–17 alkenyl, C2–17 alkynyl, or C1–17 alkyl, C2–17 alkenyl or C2–17 alkynyl substituted by 1–5 of optionally selected from (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc 1, (n) keto, (o) —$N(SO_2R^{24})_2$. With the proviso that, $R^{1-1A-1a}$ is not a group containing carboxyl, hydroxy, amino or thiol, and the other symbols have the same meaning as defined hereinbefore.)

may be prepared by the reductive amination of the compounds of the formula (I-1A-2) with the compounds the formula (III)

$R^{1-1A-1a}$—CHO (III)

(wherein all of the symbols have the same meanings as defined hereinbefore.)

The reductive amination is well known. For example, it may be carried out in an organic solvent (dichloroethane, dichloromethane, dimethylformamide, acetic acid or a mixture thereof etc.) in the presence of a reducing agent (sodium triacetoxyborohydride or sodium cyanoborohydride etc.) at 0–40° C.

Moreover, the reductive amination may be carried out with the compounds in which nitrogen of $R^1$ is oxidized to N-oxide.

(b) Among the compounds of the formula (I-1A-1), the compounds, in which $R^{1A-1}$ is C1–18 alkyl, C2–18 alkenyl, C2–18 alkynyl, or C1–18 alkyl, C2–18 alkenyl or C2–18 alkynyl substituted by various substituents, and in which $R^{1A-1}$ bonds with $N^1$ through —$CHR^{A-1b}$— (wherein $R^{A-1b}$ is C1–17 alkyl, C2–17 alkenyl or C2–17 alkynyl.), i.e., the compounds of the formula (I-1A-1b)

(I-1A-1b)

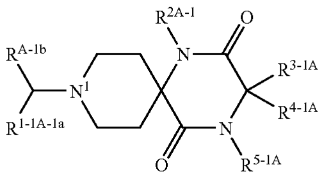

(wherein $R^{A-1b}$ is C1–17 alkyl, C2–17 alkenyl or C2–17 alkynyl, and the other symbols have the same meanings as defined hereinbefore.)

may be prepared by reductive amination of the compounds of the formula (1-1A-2) with the compounds the formula (IV)

(IV)

(wherein all of the symbols have the same meanings as defined hereinbefore.)

The reductive amination is well known. For example, it may be carried out in an organic solvent (dichloroethane or dichloromethane etc.) in the presence of tertiary amine (triethylamine or diisopropylethylamine etc.) with Lewis acid (titanium tetrachloride etc.), at 0–40° C., and subsequently by the addition of a reducing agent (sodium triacetoxyborohydride or sodium cyanoborohydride etc.) at 0–40° C.

(c) Among the compounds of the formula (I-1A-1), the compounds in which $R^{1A-1}$ is $COR^6$, i.e., the compounds of the formula (I-1A-1c)

(I-1A-1c)

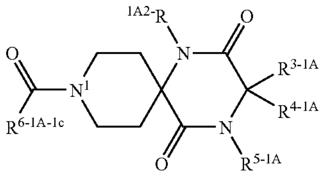

(wherein $R^{6-1A-1c}$ has the same meaning as $R^6$. With the proviso that, $R^{6A-1A-1c}$ is not a group containing carboxyl, hydroxy, amino or thiol, and any nitrogen atoms are not quaternary ammonium salt nor N-oxide, and the other symbols have the same meaning as defined hereinbefore.)

may be prepared by the amidation of the compounds of the formula (I-1A-2) with the compounds of the formula (V)

(V)

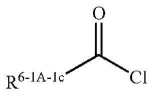

(wherein all of the symbols have the same meanings as defined hereinbefore.).

The amidation is well known. For example, it may be carried out in an organic solvent (chloroform, dichloromethane, diethylether, tetrahydrofuran, dioxane or dimethylformamide etc.) in the presence of tertiary amine (isopropylethylamine, pyridine, triethylamine, dimethylaniline or dimethylaminopyridine etc.) or an aqueous alkali solution (solution of bicarbonate or solution of sodium hydroxide etc.) at 0–40° C.

(d) Among the compounds of the formula (I-1A-1), the compounds in which $R^{1-1A-1}$ is $SO_2R^{10}$, i.e., the compounds of the formula (I-1A-1d)

(I-1A-1d)

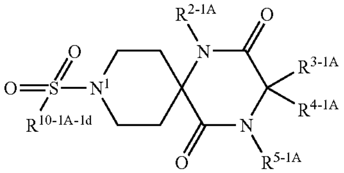

(wherein $R^{10-1A-1d}$ has the same meaning as $R^{10}$, With the proviso that, $R^{10-1A-1d}$ is not a group containing carboxyl, hydroxy, amino or thiol, and any nitrogen atoms are not quaternary ammonium salt nor N-oxide, and the other symbols have the same meaning as defined hereinbefore.)

may be prepared by the sulfonamidation of the compounds of the formula (I-1A-2) with the compounds of the formula (VI)

(VI)

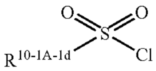

(wherein all of the symbols have the same meanings as defined hereinbefore.).

The sulfonamidation is well known. For example, it may be carried out in an inert organic solvent (chloroform, dichloromethane, dichloroethane, diethylether or tetrahydrofuran etc.) in the presence of tertiary amine (diisopropylethylamine, pyridine, triethylamine, dimethylaniline or dimethylaminopyridine etc.) at 0–40° C.

(e) Among the compounds of the formula (I-1A-1), the compounds in which $R^{I-1A-1}$ is $CONR^7R^8$, i.e., the compounds of the formula (I-1A-1e)

(I-1A-1e)

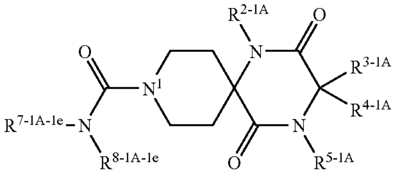

(wherein $R^{7-1A-1e}$ and $R^{8-1A-1e}$ have the same meaning as $R^7$ and $R^8$, With the proviso that, $R^{10-1A-1d}$ is not a group containing carboxyl, hydroxy, amino or thiol, and any nitrogen atoms are not quaternary ammonium salt nor N-oxide, and the other symbols have the same meaning as defined hereinbefore.)

may be prepared by the reaction of the compounds of the formula (I-1A-2) with the compounds of the formula (VII-1)

(VII-1)

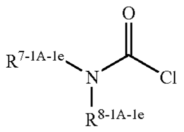

(wherein all of the symbols have the same meanings as defined hereinbefore.)

or with the compounds of the formula (VII-2)

(VII-2)

$R^{7-1A-1e}$—N═C═O (wherein all of the symbols have the same meanings as defined hereinbefore.)

The reaction with the compounds of the formula (VII-1) is well known. For example, it may be carried out in an organic solvent (chloroform, dichloromethane, diethylether or tetrahydrofuran etc.), in the presence of a tertiary amine (isopropylethylamine, pyridine, triethylamine, dimethylaniline or dimethylaminopyridine etc.) at 0–40° C.

The reaction with the compounds of the formula (VII-2) is well known. For example, it may be carried out in an inert organic solvent (chloroform, dichloromethane, dichloroethane, dimethylformamide, diethylether or tetrahydrofuran etc.) at 0–40° C.

(f) Among the compounds of the formula (I-1A-1), the compounds in which $R^{1-1A-1}$ is —$CH^2$—CH(OH)—$R^{A-1f}$ ($R^{A-1f}$ is C1–16 alkyl, C2–16 alkenyl, C2–16 alkynyl, or C1–16 alkyl, C2–16 alkenyl or C2–16 alkynyl substituted by various substituents.), i.e., the compounds of the formula (I-1A-1f)

(I-1A-1f)

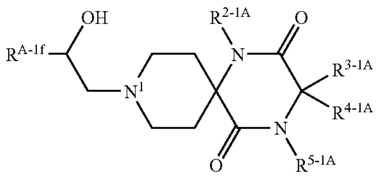

(wherein $R^{A-1f}$ is C1–16alkyl, C2–16 alkenyl, C2–16 alkynyl, or C1–16 alkyl, C2–16 alkenyl or C2–16 alkynyl substituted by 1–4 of optionally selected from (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc 1, (n) keto, (o) —$(SO_2R^{24})_2$, and any nitrogen atoms are not quaternary ammonium salt nor N-oxide and the other symbols have the same meaning as defined hereinbefore.)

may be prepared by the reaction of the compounds of the formula (1–1A-2) with the compounds the formula (VIII)

(VIII)

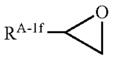

(wherein all of the symbols have the same meanings as defined hereinbefore.).

The reaction is well known, and it may be carried out in an organic solvent (methanol, ethanol, 2-propanol, tetrahydrofuran or acetonitrile etc.), in the presence or absence of a tertiary amine (triethylamine or N-methylmorpholine etc.) at 40–100° C.

(g) Among the compounds of the formula (I-1A-1), the compounds in which $R^{1-1A-1}$ is —$CH_2$—C(═O)—$R^{A-1g}$ ($R^{A-1g}$ has the same meaning as $R^{A-1f}$), i.e., the compounds of the formula (I-1A-1g)

(I-1A-1g)

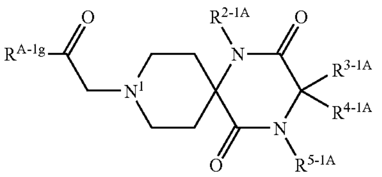

(wherein $R^{A-1g}$ has the same meaning as $R^{A-1f}$, and the other symbols have the same meanings as defined hereinbefore.)

may be prepared by the reaction of the compounds of the formula (I-1A-2) with the compounds of the formula (IX-1)

(IX-1)

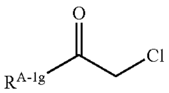

(wherein all of the symbols have the same meanings as defined hereinbefore.)

or with the compounds of the formula (IX-2)

(IX-2)

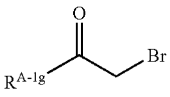

(wherein all of the symbols have the same meanings as defined hereinbefore.).

The reaction is well known, and it may be carried out in an organic solvent (chloroform, dichloromethane, diethylether, tetrahydrofuran, dioxane or dimethylformamide etc.) in the presence of a tertiary amine (isopropylethylamine, pyridine, triethylamine, dimethylaniline or dimethylaminopyridine etc.) at 0–40° C.

Moreover, the compounds of the formula (I-1A-1) may be prepared by the methods described in (h).

(h) Among the compounds of the formula (I-1A-1), the compounds in which $R^{1-1A-1}$ is 2-propenyl ($—CH_2CH=CH_2$), i.e., the compounds of the formula (I-1A-1h)

(I-1A-1h)

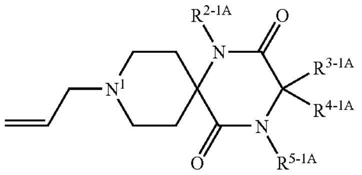

(wherein all of the symbols have the same meanings as defined hereinbefore.)

may be prepared by the reaction of the compounds in which $R^{1-1A-1}$ is 2-propenyloxycarbonyl ($—COO—CH_2CH=CH_2$) among the compounds of the formula (I-1A-1) prepared by the above method, i.e., the compounds of the formula (I-1A-1–2)

(I-1A-1-2)

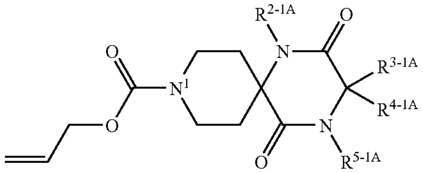

(wherein all of the symbols have the same meanings as defined hereinbefore.) with a metal complex.

The reaction with a metal complex is well known, and it may be carried out, for example, in an organic solvent (tetrahydrofuran or acetic acid etc.), with a metal complex (tetrakis(triphenylphosphine)palladium(0) complex etc.), at 0–40° C.

Among the compounds of the (I-1), the compounds in which at least one group of $R^1$, $R^2$, $R^3$, $R^4$ and $R^5$ represents a group containing carboxyl, hydroxy, amino or thiol, i.e., the compounds of the formula (I-1B)

(I-1B)

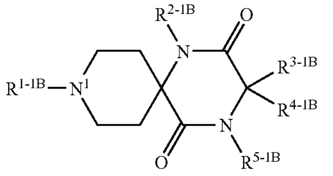

(wherein $R^{1-1B}$, $R^{2-1B}$, $R^{3-1B}$, $R^{4-1B}$ and $R^{5-1B}$ have the same meanings as $R^{1-1}$, $R^{2-1}$, $R^{3-1}$, $R^{4-1}$ and $R^{5-1}$, respectively. With the proviso that, at least one group represents a group containing carboxyl, hydroxy, amino or thiol, and the other symbols have the same meanings as defined hereinbefore.)

may be prepared by the removal of a protecting group of the compounds in which at least one group of $R^{1-1}$, $R^{2-1}$, $R^{3-1}$, $R^{4-1}$ or $R^{5-1}$ represents a group containing carboxyl, hydroxy, amino and thiol protected by a protecting group, i.e., the compounds of the formula (I-1A-3)

(I-1A-3)

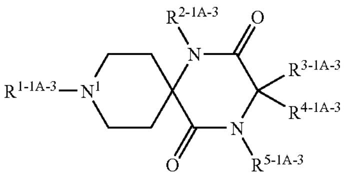

(wherein $R^{1-1A-3}$ $R^{2-1A-3}$, $R^{3-1A-3}$, $R^{4-1A-3}$ and $R^{5-1A-3}$ have the same meanings of $R^{1-1}$, $R^{2-1}$, $R^{3-1}$, $R^{4-1}$ and $R^{5-1}$, respectively. With the proviso that, at least one group represents a group containing carboxyl, hydroxy, amino or thiol protected by a protecting group and the other symbols have the same meanings as defined hereinbefore.)

A protecting group of carboxyl includes, for example, methyl, ethyl, t-butyl, benzyl or allyl.

A protecting group of hydroxy includes, for example, methoxymethyl, 2-tetrahydropyranyl, t-butyldimethylsilyl, t-butyldiphenylsilyl, acetyl or benzyl.

A protecting group of amino includes, for example, benzyloxycarbonyl, allyloxycarbonyl, t-butoxycarbonyl, trifluoroacetyl or 9-fluorenylmethoxycarbonyl.

A protecting group of thiol includes, for example, benzyl, methoxybenzyl, acetoamidomethyl, triphenylmethyl or acetyl.

The protecting group of carboxyl, hydroxy, amino or thiol includes the above one, and in addition the other protecting group which is removable selectively and easily, for example, one described in T. W. Greene et. al., Protective Groups in Organic Synthesis, Third Edition, Wiley-Interscience, New York, 1999.

The removal of a protecting group of amino may be carried out by the method described hereinbefore.

The removal of a protecting group of carboxyl, hydroxy or thiol is well known. For example, it is (1) the alkaline hydrolysis, (2) the removal of a protecting group in an acidic condition, (3) the removal of a protecting group by hydrogenolysis, or (4) the removal of a protecting group containing silyl or (5) the removal of a protecting group using metal complex etc.

Among these methods, (1), (2), (3) and (5) may be carried out by the same methods of the removal of a protecting group of amino.

Concretely describing (4), the removal of a protecting group containing silyl may be carried out, for example, in an organic solvent (tetrahydrofuran or acetonitrile etc.), with tetrabutylammoniumfluoride at 0–40° C.

As well known to the person in the art, the aimed compounds of the present invention may be prepared easily by choice of these removal of a protecting group.

Moreover, the compounds of the formula (I-1A-1) may be prepared by the methods described in (j)-(m) with the compounds of the formula (I-1B-1)

(I-1B-1)

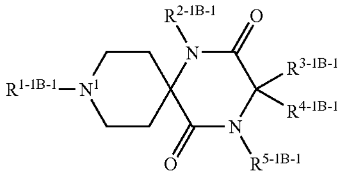

(wherein $R^{1-1B-1}$, $R^{2-1B-1}$, $R^{3-1B-1}$, $R^{4-1B-1}$ and $R^{5-1B-1}$ have the same meanings of $R^{1-1}$, $R^{2-1}$, $R^{3-1}$, $R^{4-1}$ and $R^{5-1}$, respectively. With the proviso that, at least one group represents a group containing amino, and the other symbols have the same meanings as defined hereinbefore.)

(j) Among the compounds of the formula (I-1A-1), the compounds in which at least one group of $R^{1-1A-1}$, $R^{2-1A}$, $R^{3-1A}$, $R^{4-1A}$ and $R^{5-1A}$ represent a group containing amide, i.e., the compounds of the formula (I-1A-1j)

(I-1A-1j)

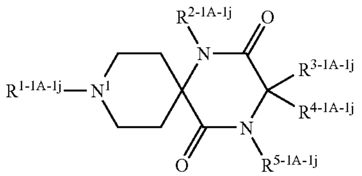

(wherein $R^{1-1A-1j}$, $R^{2-1A-1j}$, $R^{3-1A-1j}$; $R^{4-1A-1j}$ and $R^{5-1A-1j}$ have the same meanings as $R^{1-1}$, $R^{2-1}$, $R^{3-1}$, $R^{4-1}$ and $R^{5-1}$, respectively. With the proviso that, at least one group represents a group containing amide and the other symbols have the same meanings as defined hereinbefore.)

may be prepared by the amidation of the compounds of the formula (I-1B-1).

The amidation may be carried out by the method described herein before.

(k) Among the compounds of the formula (I-1A-1), the compounds in which at least one group of $R^{1-1A-1}$, $R^{2-1A}$, $R^{3-1A}$, $R^{4-1A}$ and $R^{5-1A}$ represents a group containing sulfonamide, i.e., the compounds of the formula (I-1A-1k)

(I-1A-1k)

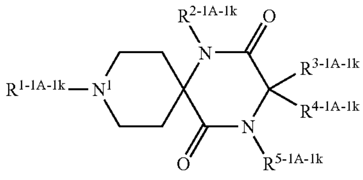

(wherein $R^{1-1A-1k}$, $R^{2-1A-1k}$, $R^{3-1A-1k}$, $R^{4-1A-1k}$ and $R^{5-1A-1k}$ have the same meanings as $R^{1-1}$, $R^{2-1}$, $R^{3-1}$, $R^{4-1}$ and $R^{5-1}$, respectively. With the proviso that, at least one group represents a group containing sulfon amide and the other symbols have the same meanings as defined hereinbefore.)

may be prepared by the sulfonamidation of the compounds of the formula (I-1B-1).

The sulfonamidation may be carried out the method described hereinbefore.

(m) Among the compounds of the formula (I-1A-1), the compounds in which at least one group of $R^{1-1A-1}$, $R^{2-1A}$, $R^{3-1A}$, $R^{4-1A}$ and $R^{5-1A}$ represents a group containing urea, i.e., the compounds of the formula (I-1A-1m)

(I-1A-1m)

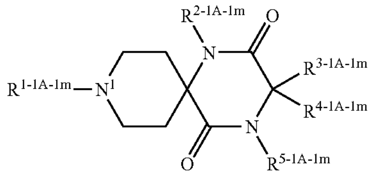

(wherein $R^{1-1A-1m}$, $R^{2-1A-1m}$, $R^{3-1A-1m}$, $R^{4-1A-1m}$ and $R^{5-1A-1m}$ have the same meanings as $R^{1-1}$, $R^{2-1}$, $R^{3-1}$ $R^{4-1}$ and $R^{5-1}$, respectively. With the proviso that, at least one group represents a group containing urea and the other symbols have the same meanings as defined hereinbefore.)

may be prepared by the urea formation of the compounds of the formula (I-1B-1).

The urea formation may be carried out the method described hereinbefore.

Among the compounds of the formula (I-1), the compounds in which at least one group of $R^{1-1}$, $R^{2-1}$, $R^{3-1}$, $R^{4-1}$ and $R^{5-1}$ represents a group containing hydroxy, and/or $R^1$ represents a group containing carboxyl, i.e., the compounds of the formula (I-1B-2)

(I-1B-2)

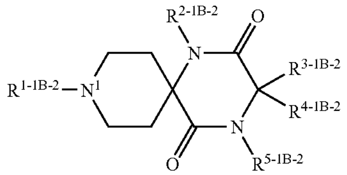

(wherein $R^{1-1B-2}$, $R^{2-1B-2}$, $R^{3-1B-2}$, $R^{4-1B-2}$ and $R^{5-1B-2}$ have the same meanings as $R^{1-1}$, $R^{2-1}$, $R^{3-1}$, $R^{4-1}$ and $R^{5-1}$, respectively. With the proviso that, at least one group of $R^{1-1B-2}$, $R^{2-1B-2}$, $R^{3-1B-2}$, $R^{4-1B-2}$ and $R^{5-1B-2}$ represents a group containing hydroxy and/or $R^{1B-2}$ includes carboxyl and the other symbols have the same meanings as defined hereinbefore.) may be prepared by the method described in (n).

(n) Among the compounds of the formula (I-1B-2), the compounds in which $R^{1-1B-2}$ is C1–18 alkyl, C2–18 alkenyl, C2–18 alkynyl or C1–18 alkyl, C2–18 alkenyl or C2–18 alkynyl substituted by various substituent, and in which that $R^{1-1B-2}$ bonds to $N^1$ atom through —$CH_2$—, i.e., the compounds of the formula (I-1B-1n)

(I-1B-1n)

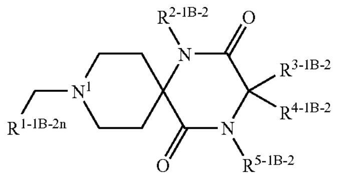

(wherein $R^{1-1B-2n}$ is C1–17alkyl, C2–17 alkenyl, C2–17 alkynyl, or C1–17 alkyl, C2–17 alkenyl or C2–17 alkynyl substituted by 1–5 of optionally selected from (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc 1, (n) keto, (o) —$N(SO_2R^{24})_2$. With the proviso that, at least one group of $R^{1-1B-2n}$, $R^{2-1B-2}$, $R^{3-1B-2}$, $R^{4-1B-2}$ and $R^{5-1B-2}$ represents a group containing hydroxy, and/or $R^{1B-2n}$ represents a group containing carboxyl, and any nitrogen atoms are not quaternary ammonium salt nor N-oxide and the other symbols have the same meaning as defined hereinbefore.)

may be prepared by the reductive amination of the compounds in which $R^1$ is hydrogen, and at least one group of $R^{2-1}$, $R^{3-1}$, $R^{4-1}$ and $R^{5-1}$ represents a group containing hydroxy among the compounds of the formula (I-1B) prepared by the above method, i.e., the compounds of the formula (I-1B-3)

(I-1B-3)

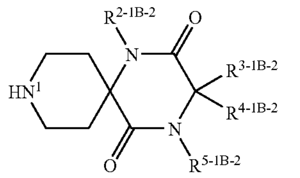

(wherein all of the symbols have the same meanings as defined hereinbefore.)

with the compounds of the formula (X)

$R^{1-1B-2n}$—CHO (X)

(wherein all of the symbols have the same meanings as defined hereinbefore.)

The reductive amination may be carried out by the method described hereinbefore.

Moreover, the reductive amination may be carried out in the compounds in which nitrogen in $R^1$ represents N-oxide.

Among the compounds of the present invention of the formula (I), the compounds in which at least one nitrogen is quaternary ammonium salt, i.e., the compounds of the formula (I-2)

(I-2)

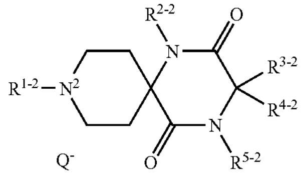

(wherein $R^{1-2}$, $R^{2-2}$, $R^{3-2}$, $R^{4-2}$ and $R^{5-2}$ have the same meanings as $R^1$, $R^2$, $R^3$, $R^4$ and $R^5$, respectively, and $N^2$ is nitrogen. With the proviso that, at least one nitrogen is quaternary ammonium salt and Q is halogen.)

may be prepared by the reaction of the compounds of the formula (I-1) with the compounds of the formula (XI)

$R^0$-Q (XI)

(wherein $R^0$ is C1–8 alkyl or C1–8 alkyl substituted by phenyl and Q is halogen.)

The reaction is well known and it may be carried out, for example, in an organic solvent (acetone, dimethylformamide or methyl ethyl ketone etc.) at 0–40° C.

Among the compounds of the formula (I), the compounds in which at least one nitrogen represents N-oxide, i.e. the compounds of the formula (I-3)

(I-3)

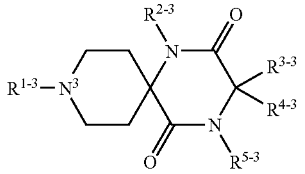

(wherein $R^{1-3}$, $R^{2-3}$, $R^{3-3}$, $R^{4-3}$ and $R^{5-3}$ have the same meanings of $R^1$, $R^2$, $R^3$, $R^4$ and $R^5$, respectively, and $N^3$ is nitrogen. With the proviso that, at least one nitrogen represents N-oxide.)

may be prepared by the oxidation of the compounds of the formula (I-1).

The oxidation is well known and it may be carried out, for example, in a suitable organic solvent (dichloromethane, chloroform, benzene, hexane or t-butyl alcohol etc.) in the presence of a excessive oxidizing reagent (hydrogen peroxide, sodium periodate, acyl nitrite, sodium perborate, peroxidized acid (for example, 3-chloroperbenzoic acid, peracetic acid etc.), OXONE (brand name, Potassium peroxymonosulfate is abbreviated as. OXONE.), potassium permanganate or chromic acid etc.) at 20–60° C.

The compounds of the (II-1) may be prepared according to the following Schemes 1–3.

Scheme (1)

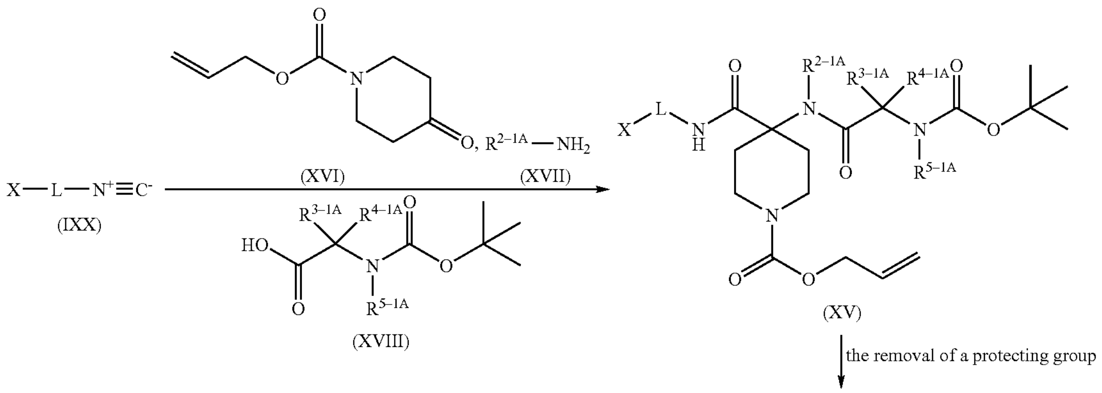

-continued

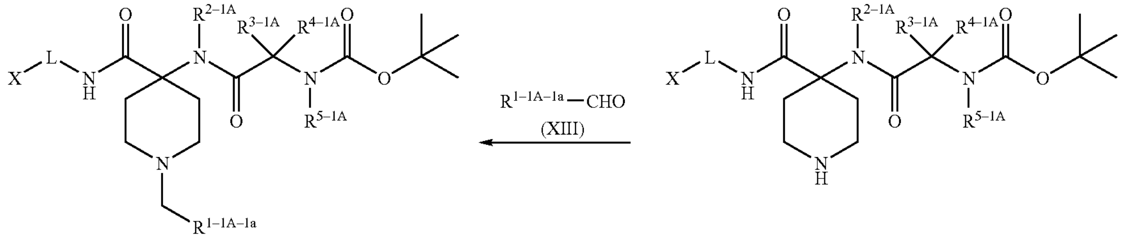

(XII-1) (XIV)

Scheme (2)

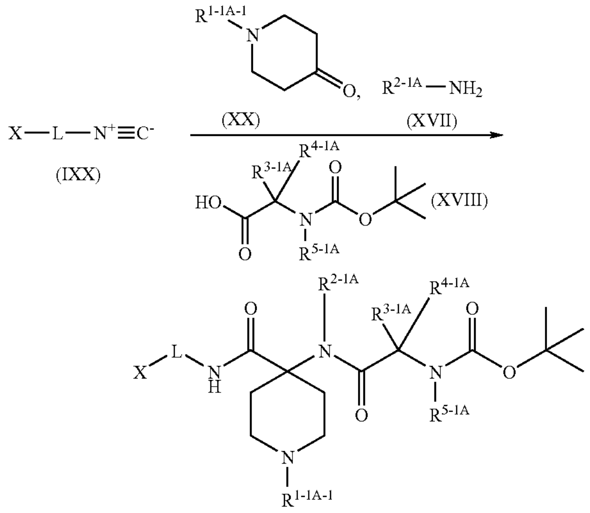

(XII)

Scheme (3)

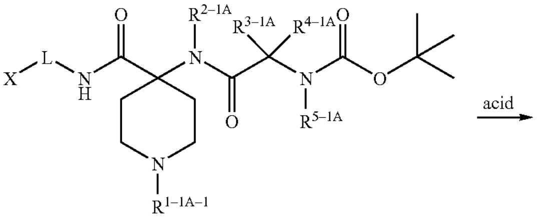

(XII)

-continued

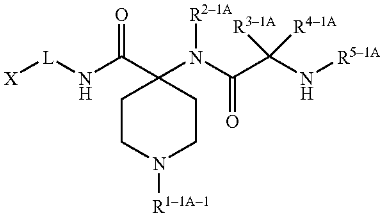

(II-1)

In Schemes, X is polystyrene resin, L is bivalent group, and the other symbols have the same meanings as defined hereinbefore.

Bivalent group represented by L is, though it depends on the type of the used resin, e.g. methylene or Rink. Rink is 4-(2,4-dimethoxybenzyl) phenoxymethyl.

In the present invention, e.g. aminomethylated polystyrene resin or 9-fluorenylmethyloxycarbonylamino-Rink resin etc. can be used as terminal amino polystyrene resin.

As shown the following reaction scheme, the resin of the formula (XVI) may be prepared from aminomethylated polystyrene resin or 9-fluorenylmethyloxycarbonylamino-Rink resin.

Scheme (4)

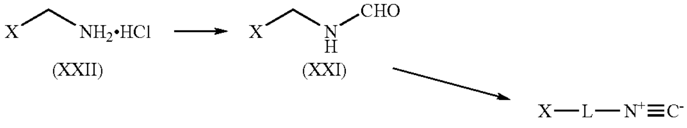

(IXX)

-continued

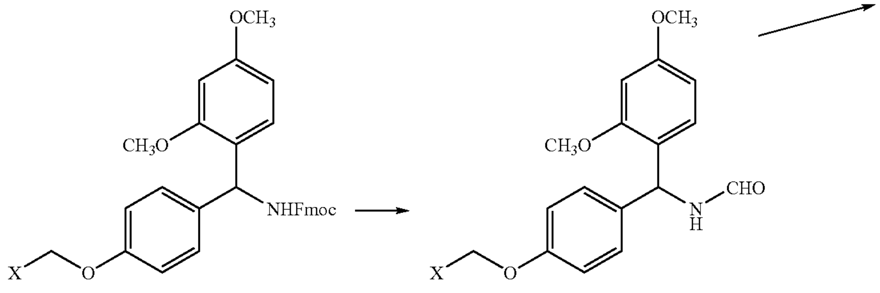

(XXIV) (XXIII)

In the reaction using polystyrene resin in the present invention, the reaction products may be purified by the conventional methods, for example, washing with a solvent (dimethylformamide, dichloromethane, methanol, tetrahydrofuran, toluene or acetic acid/toluene etc.) at several times. Moreover the obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization.

The compounds of the formula (II-2) may be prepared according to the following Scheme 5.

Scheme (5)

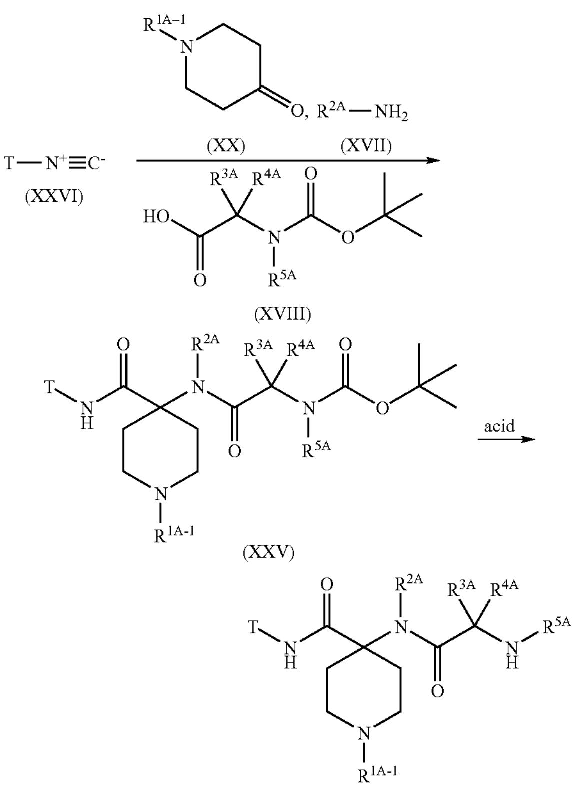

(XXVI) (XX) (XVII) (XVIII) (XXV) (II-2)

The other starting materials and each test compounds in t he present invention have been known per se or may be prepared by known methods.

[Pharmacological Activities]

Efficacy of the compounds of the invention represented by general formula (I) was confirmed, e.g., by the following tests.

As described in the foregoing, in order to carry out screening of a compound capable of inhibiting binding of HIV to CXCR4 or CCR5 which is a receptor on the CD4-postive cell, it is a more directive method to carry out it in an assay system that uses HIV virus. However, the use of a large amount of HIV virus in the screening is not practical due to a difficulty in handling it. On the other hand, since both the macrophage tropic (R5) HIV-1 and the ligands, that is, RANTES, MIP-1α and MIP-1β, bind to CCR5, it can be presumed that certain common characteristics are present in the CCR5 binding sites of the HIV side and the RANTES, MIP-1α and MIP-1β sides, and in the binding sides of CCR5 to the ligands, that is, RANTES, MIP-1α and MIP-1β, and HIV. Accordingly, in order to find a compound capable of inhibiting adsorption of HIV virus to cells, which has an inhibitory mechanism different from the current anti-AIDS drugs (reverse transcription inhibitors and protease inhibitors), it is possible to use an assay system that uses an endogeneous CCR5 ligand, RANTES, MIP-1α or MIP-1β instead of HIV.

Specifically, e.g., since CCR5 is a G protein-coupled seven transmembrane type receptor, an assay system in which the effect of RANTES on the transient increase of Ca ion induced via CCR5 is measured can be carried out as an assay system for screening a compound capable of inhibiting binding of RANTES to CCR5. Since both of the T cell tropic (X4) HIV and SDF-1 bind to CXCR4, similar idea can be considered.

[Test Methods]

(1) Isolation of Human CCR5 Gene

Human placental cDNA was prepared using Marathon cDNA amplification kit (Clontech). PCR primers hCCR5XbaI-F1: 5'-AGCTAGTCTAGATCCGTTC-CCCTACMGAAACTCTCC-3' (SEQ ID NO:1) and hCCR5XbaI-R1: 5'-AGCTAGTCTAGAGTGCA-CAACTCTGACTGGGTCACCA-3' (SEQ ID NO:2) were designed based on the sequence of GenBank U54994.

Using the human placental cDNA as the template and using Ex Taq (Takara), PCR reaction (2 minutes at 95° C.→(30 seconds at 95° C., 45 seconds at 60° C., 1 minute at 72° C.)×35 times) was carried out. The thus amplified PCR product was subjected to a 1% agarose gel electrophoresis, purified using QIAquick Gel Extraction Kit (QUIAGEN) and then digested with a restriction enzyme XbaI. The digested fragments were ligated to an expression vector pEF-BOS-bsr using DNA Ligation Kit Ver. 2 (Takara) and transformed into *Escherichia coli* DH5a. By preparing the resulting plasmid pEF-BOS-bsr/hCCR5, its DNA sequence was verified.

(2) Culturing of CHO Cell

CHO-dhfr(−) was cultured using Ham's F-12 (containing fetal bovine serum (10%), penicillin (50 U/ml) and streptomycin (50 mg/ml)). Also, the transduced cell was cultured by adding blasticidin (5 mg/ml) to the above medium.

(3) Transduction into CHO Cell

The plasmid pEF-BOS-bsr/hCCR5 was transduced into the CHO-dhfr(−) cell using DMRIE-C reagent (Gibco BRL). After 48 hours, the medium was replaced with a medium containing 5 mg/ml of blasticidin to carry out the selection, thereby establishing a stably over-expressing cell.

(4) Inhibition Test on the Binding of RANTES to CCR5 (Activity of RANTES to Induce Transient Increase of Ca Ion)

The thus established human CCR5 stably over-expressing CHO cell (CCR5/CHO cell) was suspended in Ham's F-12 medium containing FBS (10%) and dispensed in $3.0\times10^6$ cells/well portions into a 96 well plate. One day after culturing at 37° C., the culture supernatant was discarded, and Ham's F-12 medium (containing Fura-2AM (5 μM), Probenecid (2.5 mM) and HEPES (20 mM; pH 7.4)) was dispensed in 80 μl/well portions to carry out 1 hour of incubation at 37° C. under shaded condition. After washing twice with 1×Hanks/HEPES (20 mM; pH 7.4) solution, the same solution was dispensed in 100 μl/well portions. Each of the test compounds was added to the thus Fura-2AM-incorporated CCR5/CHO cell, and 3 minutes thereafter, a recombinant human RANTES (PeproTach) diluted with 1×Hanks/HEPES (20 mM; pH 7.4) solution was added thereto to a final concentration of 10 nM. Transient increase in the intracellular $Ca^{2+}$ concentration induced by the human RANTES was measured using a $Ca^{2+}$ detector for 96 well use (Hamamatsu Photonics), and inhibition ratio (%) of the test compound was calculated by the following calculation formula.

$$\text{Inhibition ratio}=(Ec-Ea)/Ec\times100$$

Ec: measured value of $Ca^{2+}$ transient increase by RANTES

Ea: measured value of $Ca^{2+}$ transient increase by RANTES when a test compound was added As a result, the compounds of the invention showed an inhibition ratio of 50% or more at 10 μM. For example, the compound of Example 2(1) showed an $IC_{50}$ value of 0.05 μM, and the compound of Example 2(2) an $IC_{50}$ value of 0.05 μM.

An assay system for finding a compound having adsorption inhibition effect on CCR5 directional HIV strain was described in the foregoing, and it is possible as a matter of course to find a compound capable of inhibiting the activity of CCR5 or a ligand thereof using this system. In the same manner, it is possible to find a compound capable of inhibiting the activity of other chemokine receptor or a ligand thereof. For example, a system for finding a compound capable of inhibiting the activity of CCR2 or a ligand thereof can be constructed. Since CCR2 is a G protein-coupled seven transmembrane type receptor similar to the case of CCR5, it can be carried out by measuring the effect of a ligand of CCR2, e.g., MCP-1 on the transient increase of Ca ion induced via CCR2.

(5) Inhibition Test on the Binding of MCP-1 to CCR2 (Activity of MCP-1 to Induce Transient Increase of Ca Ion)

A human CCR2-expressing cell, e.g., a human monocyte cell strain THP-1 (ATCC No. TIB-202), was suspended in RPMI 1640 medium containing FBS (10%), Fura-2AM (5 μM), Probenecid (2.5 mM) and HEPES (20 mM, pH 7.4) to a density of $5.0\times10^6$ cells/ml and incubated at 37° C. for 30 minutes under shaded condition. This was mixed with 4 to 8 volumes of 1× Hanks/HEPES (20 mM, pH 7.4)/Probenecid (2.5 mM) and further incubated at 37° C. for 30 minutes under shaded condition. After washing with 1× Hanks/HEPES (20 mM, pH 7.4)/Probenecid (2.5 mM) solution, the thus washed cells were re-suspended in the same solution to a density of $2.0\times10^6$ cells/ml and dispensed in 100 μl/well portions into a 96 well plate. Each of the test compound solutions was added thereto, and 3 minutes thereafter, a recombinant human MCP-1 (PeproTach) diluted with 1× Hanks/HEPES (20 mM, pH 7.4)/Probenecid (2.5 mM)was added thereto to a final concentration of 30 nM. Transient increase in the intracellular Ca 2+concentration induced by the human MCP-1 was measured using a $Ca^{2+}$ detector for 96 well use (Hamamatsu Photonics), and inhibition ratio (%) of the test compound was calculated by the following calculation formula.

$$\text{Inhibition ratio}=(Ec-Ea)/Ec\times100$$

Ec: measured value of $Ca^{2+}$ transient increase by MCP-1

Ea: measured value of $Ca^{2+}$ transient increase by MCP-1 when a test compound was added As a result, the compounds of the invention showed an inhibition ratio of 50% or more at 10 μM. For example, the compound of Example 5(2) showed an $IC_{50}$ value of 3 μM.

[Toxicity]

The toxicity of the compounds of the present invention is very low and therefore the compounds may be considered safe for pharmaceutical use.

INDUSTRIAL APPLICABILITY

[Application for Pharmaceuticals]

The compounds of the present invention of the formula (I) regulate the effect of chemokine/chemokine receptor in animal included human, especially human, so they are used for prevention and/or treatment of various inflammatory diseases, asthma, atopic dermatitis, urticaria, allergic diseases (allergic bronchopulmonary aspergillosis, allergic eosinophilic gastroenteritis est.), nephritis, nephropathy, hepatitis, arthritis, rheumatoid arthritis, psoriasis, rhinitis, conjunctivitis, ischemic reperfusion disorder, multiple sclerosis, ulcerative colitis, adult respiratory distress syndrome, cytotoxic shock, diabetes, autoimmune disease, multiple organ failure, immunosuppression, cancer metastasis and acquired immune deficiency syndrome.

For the purpose above described, the compounds of formula (I), non-toxic salts thereof, acid addition salts or hydrates thereof may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid forms for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se.

Sprays may comprise additional substances other than diluents, such as stabilizing agents (such as sodium sulfate), isotonic buffers (such as sodium chloride, sodium citrate or citric acid). For preparation of such sprays, for example, the method described in the U.S. Pat. Nos. 2,868,691 or 3,095,355 may be used.

BEST MODE FOR CARRYING OUT THE INVENTION

The following Reference Examples and Examples are intended to illustrate the present invention, but do not limit them.

In chromatographic separations and TLC, the solvents in parenthesis show the eluting and developing solvents and the ratios of the solvents used are by volume.

The solvents in parenthesis in NMR show the solvents used for measurement.

R* and S* do not represent the absolute position but the relative position.

REFERENCE EXAMPLE 1

Preparation of Resin (2)

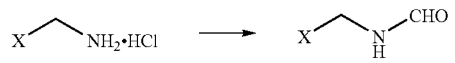

Resin (1) Resin (2)

Aminomethylpolystyrene resin hydrochloride (Resin (1); X is polystyrene resin.) (30.0 g) (1% divinylbenzene copolymer, Watanabe Kagaku, Catalog No A00062) was washed with dimethylformamide (300 ml), 10% diisopropylethylamine-dimethylformamide solution (300 ml) and dimethylformamide (300 ml) successively, and was suspended in dimethylformamide (200 ml). To the suspension were added formic acid (10.2 ml) and diisopropylcarbodiimide (42.3 ml) under cooling with ice, and it was stirred for 1 hour at room temperature. The resin was collected by filtration from the reaction solution, and was washed with dimethylformamide (250 ml×3), dichloromethane (250 ml×4), methanol (250 ml×2) and dichloromethane (250 ml×4) to give Resin (2).

IR (KBr): ν 1682 $cm^{-1}$.

REFERENCE EXAMPLE 2

Preparation of Resin (3)

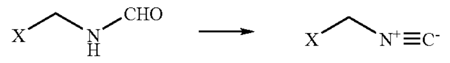

Resin (2) Resin (3)

To a suspension of Resin (2) prepared in Reference Example 1 in dichloromethane (300 ml) were added triethylamine (18.8 ml), carbon tetrachloride (13.0 ml) and triphenylphosphine (35.4 g), and it was refluxed for 1 hour. The reaction solution was cooled to room temperature, and the resin was collected by filtration. The resin was washed with dichloromethane (250 ml×3), methanol (250 ml×1) and dichloromethane (250 ml×2) and dried under reduced pressure to give Resin (3) 28.2 g).

IR (KBr): ν 2147 $cm^{-1}$.

REFERENCE EXAMPLE 3

Preparation of Compound (1)

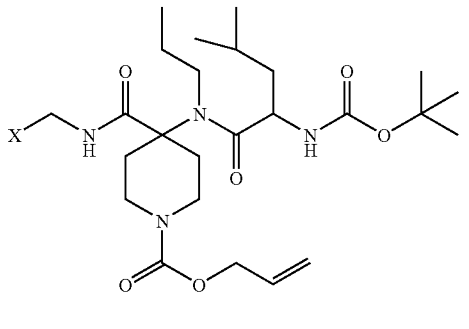

To a suspension of Resin (3) prepared in Reference Example 2 (2.5 g) in tetrahydrofuran/methanol (1:1; 25 ml) were added N-allyloxycarbonyl-4-piperidone (2.15 g), n-propylamine (0.97 ml) and N-(t-butyloxycarbonyl) leucine (2.93 g), and it was stirred for 16 hours at 65° C. The reaction solution was cooled to room temperature, and the resin was collected by filtration. The obtained resin was washed with tetrahydrofuran (25 ml×2), methanol (25 ml×2) and dichloromethane (25 ml×2) to give compound (1).

REFERENCE EXAMPLE 4

Preparation of Compound (2)

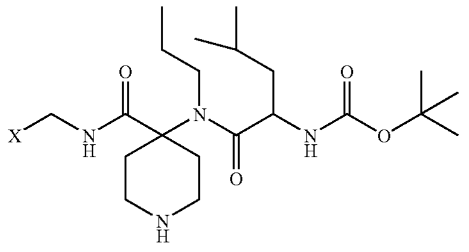

To a suspension of the compound (1) prepared in Reference Example 3 in dichloromethane (25 ml) were added acetic acid (0.81 ml), tributyltin hydride (1.90 ml) and tetrakis(triphenylphosphine)palladium (0) complex (270 mg), and it was stirred for 6 hours at room temperature. The resin was collected by filtration from the reaction solution, and was washed with dichloromethane (25 ml×3), methanol (25 ml×2), dichloromethane (25 ml×2) and dimethylformamide (25 ml×3) to give compound (2).

REFERENCE EXAMPLE 5

Preparation of Compound (3)

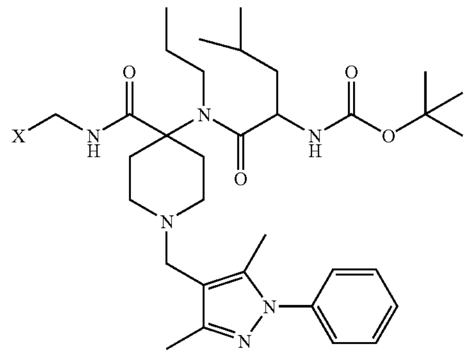

To a suspension of the compound (2) prepared in Reference Example 4 in dimethylformamide (25 ml) were added 3,5-dimethyl-1-phenyl-4-formylpyrazole (1.41 g), sodium triacetoxyborohydride (1.50 g) and acetic acid (0.2 ml), and it was stirred for 16 hours at room temperature. The resin was collected by filtration from the reaction solution, and was washed with dimethylformamide (20 ml×2), dichloromethane (20 ml×2), methanol (20 ml×2) and dichloromethane (20 ml×4) to give compound (3).

REFERENCE EXAMPLE 6

Preparation of Compound (4)

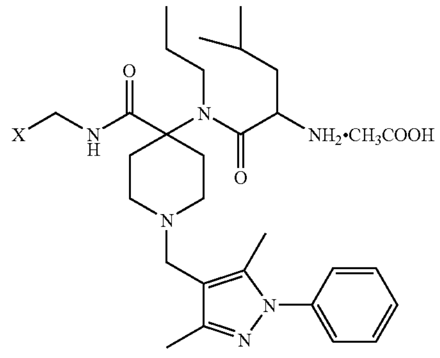

The compound (3) prepared in Reference Example 5 was suspended in 50% trifluoroacetic acid-dichloromethane solution (25 ml), and the suspension was stirred for 5 minutes at room temperature. The reaction solution was filtrated. The obtained resin was suspended in 50% trifluoroacetic acid-dichloromethane solution (25 ml), and it was stirred for 30 minutes at room temperature. The resin was collected by filtration from the reaction solution and was washed with dichloromethane (25 ml×4), toluene (25 ml×4), and 1.25 M acetic acid-toluene solution (25 ml×1) to give compound (4).

REFERENCE EXAMPLE 7

Preparation of Resin (5)

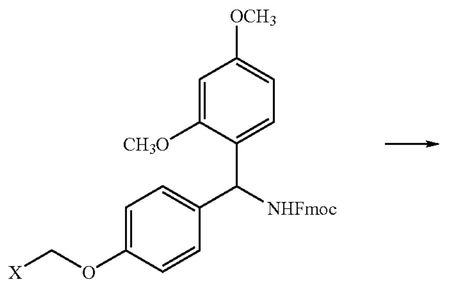

Resin (4)

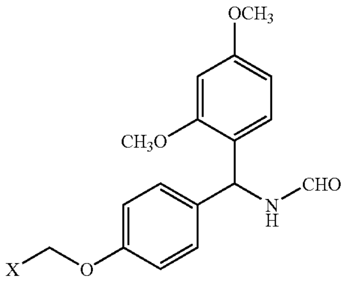

Resin (5)

9-fluorenylmethyloxycarbonylamino-Rink resin (Resin (4)) (5.0 g) (1% divinylbenzene copolymer, Watanabe Kagaku, Catalog No A00102) was washed with dimethylformamide (50 ml×3), and 20% piperidine-dimethylformamide solution (50 ml×2). The washed resin was suspended in 20% piperidine-dimethylformamide solution (50 ml), and the suspension was stirred for 30 minutes at room temperature. The reaction solution was filtrated. The obtained resin was washed with dimethylformamide (50 ml×5). To a suspension of the washed resin in dimethylformamide (20 ml) was added ethyl formate (30 ml), and it was refluxed for 6 hours. The reaction solution was cooled to room temperature and was filtrated. The filtrated resin was washed with dimethylformamide (50 ml×2), dichloromethane (50 ml×4), methanol (50 ml×4) and dichloromethane (50 ml×4), and dried under reduced pressure to give Resin (5) (4.34 g).

IR (KBr): ν 1693 $cm^{-1}$.

REFERENCE EXAMPLE 8

Preparation of Resin (6)

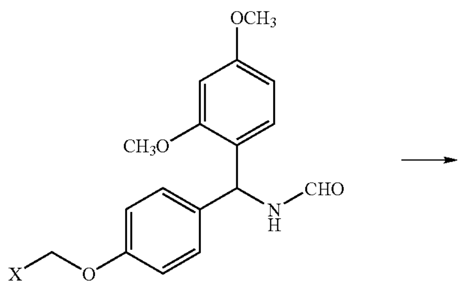

Resin (5)

-continued

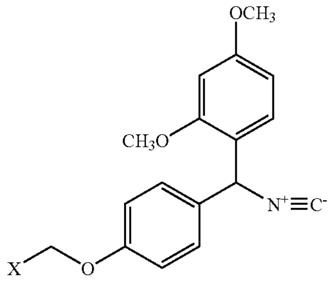

Resin (6)

By the same procedure as described in Reference Example 2 using Resin (4) prepared in Reference Example 7 (4.0 g), Resin (6) (3.56 g) was obtained.

IR (KBr): ν 2136 $cm^{-1}$.

REFERENCE EXAMPLE 9

Preparation of Compound (5)

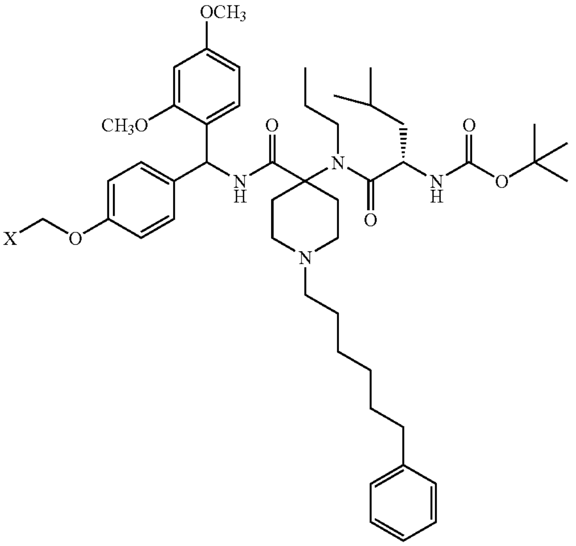

By the same procedure as described in Reference Example 3 using Resin (6) prepared in Reference Example 8 (1.0 g), N-(6-phenylhexyl)-4-piperidone (0.44 g), n-propylamine (0.14 ml) and N-(t-butyloxycarbonyl)-L-leucine (0.42 g), compound (5) was obtained.

REFERENCE EXAMPLE 10

Preparation of Compound (6)

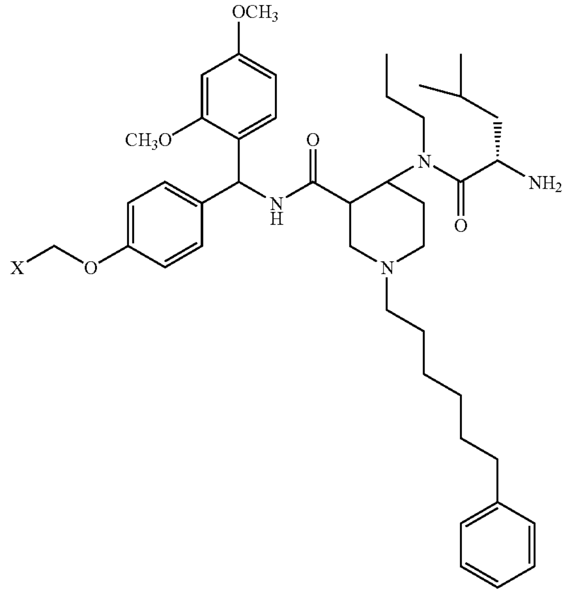

To a suspension of the compound (5) prepared in Reference Example 9 in 1.5 M 2,6-lutidine-dichloromethane (4 ml) was added 1M trimethylsilyl trifluoromethanesulfonate-dichloromethane solution (4 ml), and it was stirred for 30 minutes at room temperature. The resin was collected by filtration from the reaction solution. The obtained resin was again suspended in 1.5 M 2,6-lutidine-dichloromethane solution (4 ml), and 1M trimethylsilyl trifluoromethanesulfonate-dichloromethane solution (4 ml) was added thereto. It was stirred for 30 minutes at room temperature. The resin was collected by filtration from the reaction solution. The resin was washed with dichloromethane (6 ml×4), methanol (6 ml×4), and toluene (6 ml×5) to give compound (6).

EXAMPLE 1

9-(3,5-dimethyl-1-phenylpyrazol-4-ylmethyl)-2,5-dioxo-3-(2-methyl-1-propyl)-1-propyl-1,4,9-triazaspiro[5.5]undecane.2 hydrochloride

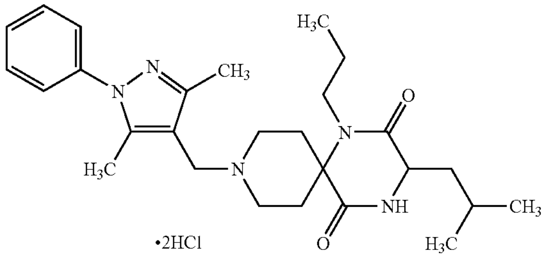

The compound (4) prepared in Reference Example 6 was suspended in 1.25 M acetic acid-toluene solution (25 ml), and the suspension was stirred for 24 hours at 90° C., and was stirred for 16 hours at room temperature. The reaction solution was filtrated. The obtained resin was washed with chloroform-methanol (1:1; 20 ml×2). The filtrate and the washings were concentrated. The residue was purified by column chromatography on silica gel (Fuji Silysia Chemical Ltd., FL60D; chloroform:methanol=30:1). A solution of the obtained residue in methanol was acidified by adding 1N hydrochloric acid, and was concentrated to give the title compound (703 mg) having the following physical data.

TLC: Rf 0.50 (chloroform:methanol=10:1);

NMR ($CD_3OD$): δ 7.68–7.50 (m, 5H), 4.36 (s, 2H), 4.03 (dd, J=7.8, 5.2 Hz, 1H), 3.83 (m, 2H), 3.64 (m, 2H), 3.47 (m, 2H), 2.64 (m, 2H), 2.49 (s, 3H), 2.44 (s, 3H), 2.20 (m, 2H), 1.81 (m, 1H), 1.68 (m, 2H), 1.60 (m, 2H), 1.05–0.90 (m, 9H);

IR (KBr): ν 3424, 3215, 2960, 2873, 2492, 1671, 1645, 1554, 1501, 1468, 1418, 1370, 1330, 1297, 1243, 1148, 958, 928, 754, 698 $cm^{-1}$;

MS (MALDI, Pos., α-CHCA): 488 $(M+Na)^+$, 466 $(M+H)^+$, 185.

elemental analysis: calculated ($C_{27}H_{39}N_5O_2$. 2HCl): C, 60.22%; H, 7.67%; N, 13.00%.

Found: C, 59.89%; H, 7.67%; N, 12.79%.

EXAMPLE 2(1)~2(3)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl)leucine, and furthermore by the same procedure as described in Reference Example 5→Reference Example 6→Example 1 using the corresponding compound instead of 3,5-dimethyl-1-phenyl-4-formylpyrazole, the following compounds of the present invention were obtained.

EXAMPLE 2(1)

9-(1,4-benzodioxan-6-ylmethyl)-1-butyl-3-cyclohexylmethyl-2,5-dioxo-1,4,9-triazaspiro[5.5]undecane.hydrochloride

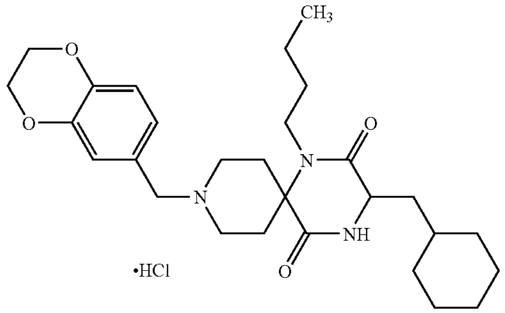

TLC: Rf 0.63 (chloroform:methanol=10:1);

NMR ($CD_3OD$): δ 7.08 (d, J=2.2 Hz, 1H), 6.99 (dd, J=8.0, 2.2 Hz, 1H), 6.92 (d, J=8.0 Hz, 1H), 4.27 (s, 4H), 4.23 (s, 2H), 4.04 (dd, J=7.6, 4.8 Hz, 1H), 3.74 (m, 2H), 3.60–3.35 (m, 4H), 2.43 (m, 2H), 2.15 (m, 2H), 1.90–1.60 (m, 7H), 1.60–1.45 (m, 2H), 1.45–1.30 (m, 2H), 1.30–1.10 (m, 4H), 1.10–0.80 (m, 5H);

IR (KBr): ν 3436, 2926, 2852, 2511, 1675, 1645, 1591, 1511, 1418, 1374, 1294, 1261, 1068, 1050, 930, 888 $cm^{-1}$;

MS (MALDI, Pos., α-CHCA): 484 $(M+H)^+$, 149.

elemental analysis: calculated ($C_{28}H_{41}N_3O_4$.HCl): C, 64.66%; H, 8.14%; N, 8.08%.

Found: C, 64.00%; H, 7.94%; N, 7.90%.

EXAMPLE 2(2)

1-butyl-3-cyclohexylmethyl-2,5-dioxo-9-(2-phenylimidazol-4-ylmethyl)-1,4,9-triazaspiro[5.5]undecane.2 hydrochloride

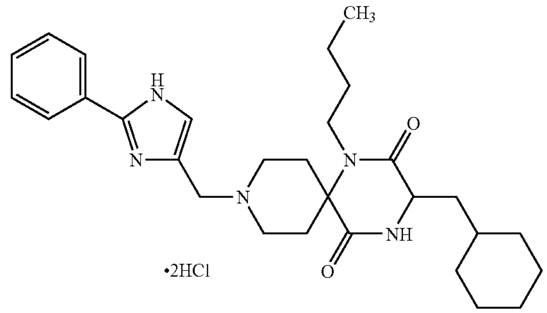

TLC: Rf 0.25 (chloroform:methanol=10:1);

NMR ($CD_3OD$): δ 8.05–7.94 (m, 3H), 7.75–7.60 (m, 3H), 4.59 (s, 2H), 4.05 (dd, J=7.4, 4.8 Hz, 1H), 3.88 (m, 2H), 3.65 (m, 2H), 3.51 (m, 2H), 2.68 (m, 2H), 2.19 (m, 2H), 1.90–1.60 (m, 6H), 1.60–1.45 (m, 3H), 1.45–1.30 (m, 3H), 1.30–1.10 (m, 3H), 1.10–0.80 (m, 5H);

IR (KBr): ν 3423, 2927, 2854, 2664, 1672, 1644, 1421, 1373, 1177, 775, 709, 688 $cm^{-1}$;

MS (MALDI, Pos., α-CHCA): 492 $(M+H)^+$.

elemental analysis: calculated ($C_{29}H_{41}N_5O_2$.2HCl 2.8$H_2O$): C, 56.63%; H, 7.96%; N, 11.39%.

Found: C, 56.90%; H, 7.23%; N, 10.78%.

EXAMPLE 2(3)

1-butyl-3-(2-methyl-1-propyl)-2,5-dioxo-9-(4-phenyloxyphenylmethyl)-1,4,9-triazaspiro[5.5]undecane.hydrochloride

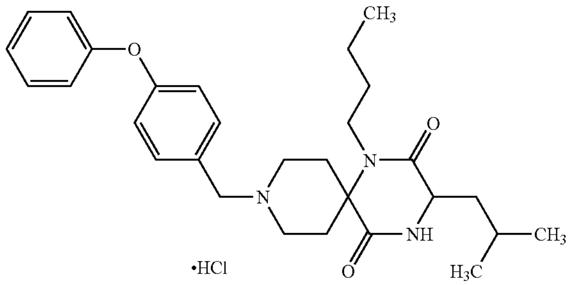

TLC: Rf 0.63 (chloroform:methanol=10:1);

NMR ($CD_3OD$): δ 7.54 (d, J=8.8 Hz, 2H), 7.40 (m, 2H), 7.18 (m, 1H), 7.11–7.00 (m, 4H), 4.33 (s, 2H), 4.01 (dd, J=7.6, 4.8 Hz, 1H), 3.80 (m, 2H), 3.60–3.35 (m, 4H), 2.46 (m, 2H), 2.18 (m, 2H), 1.80 (m, 1H), 1.70 (m, 1H), 1.54 (m, 2H), 1.37 (m, 3H), 1.00–0.90 (m, 9H);

IR (KBr): ν 3440, 3221, 3066, 2957, 2871, 2559, 1673, 1590, 1509, 1489, 1419, 1371, 1329, 1242, 1172, 873, 693 $cm^{-1}$;

MS (MALDI, Pos., α-CHCA): 478 $(M+H)^+$, 183.

elemental analysis: calculated ($C_{29}H_{39}N_3O_3$.HCl): C, 67.75%; H, 7.84%; N, 8.17%.

Found: C, 67.29%; H, 7.70%; N, 8.06%.

EXAMPLE 2(4)

(3S)-2,5-dioxo-3-(2-methylpropyl)-9-(6-phenylhexyl)-1-propyl-1,4,9-triazaspiro[5.5]undecane.hydrochloride

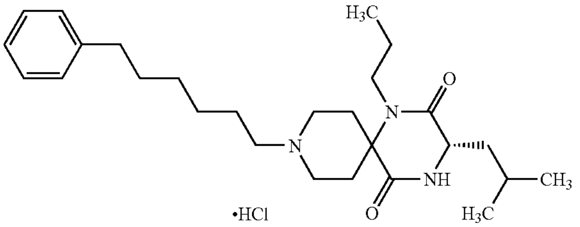

By the same procedure as described in Example 1 using the compound (6) prepared in Reference Example 10, the title compound (69 mg) having the following physical data was obtained.

TLC: Rf 0.46 (chloroform:methanol=10:1);

NMR ($CD_3OD$): δ 7.18 (m, 5H), 4.02 (dd, J=7.6, 4.8 Hz, 1H), 3.70 (m, 2H), 3.56 (m, 2H), 3.39 (m, 2H), 3.11 (m, 2H), 2.63 (dd, J=7.8, 7.2 Hz, 2H), 2.48 (m, 2H), 2.17 (m, 2H), 1.95–1.50 (m, 9H), 1.42 (m, 4H), 1.00–0.89 (m, 9H);

IR (KBr): ν 3435, 3205, 3082, 3026, 2935, 2870, 2493, 2361, 1674, 1454, 1417, 1370, 1331, 1155, 1071, 1004, 961, 750, 700 $cm^{-1}$;

MS (FAB, Pos., glycerin-m-nitrobenzyl alcohol): 442 $(M+H)^+$, 232, 171, 79 (base peak).

elemental analysis: calculated ($C_{27}H_{43}N_3O_2$.HCl): C, 67.83%; H, 9.28%; N, 8.79%.

Found: C, 67.56%; H, 9.50%; N, 8.71%.

EXAMPLE 2(5)

(3R)-2,5-dioxo-3-(2-methylpropyl)-9-(6-phenylhexyl)-1-propyl-1,4,9-triazaspiro[5.5]undecane.hydrochloride

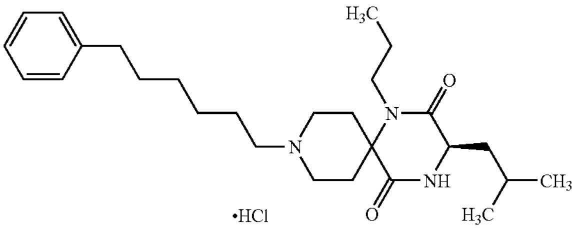

By the same procedure as described in Reference Example 9→Reference Example 10→Example 1 using Resin (6) prepared in Reference Example 8 (1.0 g), N-(6-phenylhexyl)-4-piperidone (0.44 g), n-propylamine (0.14 ml) and N-(t-butyloxycarbonyl)-D-leucine (0.42 g), the title compound (63 mg) having the following physical data was obtained.

TLC: Rf 0.46 (chloroform:methanol=10:1);

NMR ($CD_3OD$): δ 7.18 (m, 5H), 4.02 (dd, J=7.6, 4.6 Hz, 1H), 3.70 (m, 2H), 3.56 (m, 2H), 3.39 (m, 2H), 3.11 (m, 2H), 2.63 (dd, J=7.8, 7.2 Hz, 2H), 2.48 (m, 2H), 2.17 (m, 2H), 1.95–1.50 (m, 9H), 1.42 (m, 4H), 1.00–0.89 (m, 9H);

IR (KBr): ν 3441, 3204, 3082, 3026, 2935, 2870, 2660, 2499, 2413, 2361, 1674, 1455, 1417, 1370, 1330, 1267, 1205, 1154, 1070, 1003, 960, 928, 899, 750, 700 $cm^{-1}$;

MS (FAB, Pos., glycerin-m-nitrobenzyl alcohol): 442 $(M+H)^+$ (base peak), 294, 232, 202, 171, 79.

elemental analysis: calculated ($C_{27}H_{43}N_3O_2$.HCl): C, 67.83%; H, 9.28%; N, 8.79%.

Found: C, 67.52%; H, 9.51%; N, 8.70%.

EXAMPLE 3(1)~3(4)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl) leucine, and furthermore by the same procedure as described in Reference Example 5→Reference Example 6 Example 1 using the corresponding compound instead of 3,5-dimethyl-1-phenyl-4-formylpyrazole, the following compounds of the present invention were obtained.

EXAMPLE 3(1)

1-butyl-9-((3,5-dimethyl-1-phenyl)-4-pyrazolyl) methyl)-2,5-dioxo-3-(2-methyl-1-propyl)-1,4,9-triazaspiro[5.5]undecane.2 hydrochloride

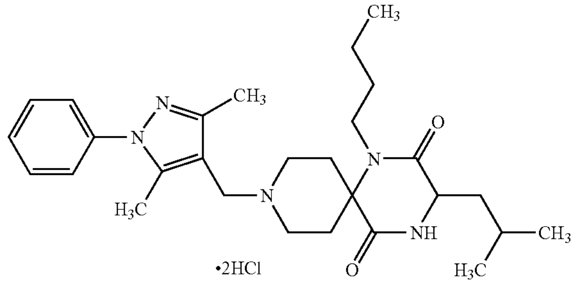

TLC: Rf 0.52 (chloroform:methanol=10:1);

NMR ($CD_3OD$): δ 7.70–7.48 (m, 5H), 4.35 (s, 2H), 4.03 (dd, J=7.8, 4.8 Hz, 1H), 3.83 (m, 2H), 3.63 (m, 2H), 3.51 (m, 2H), 2.64 (m, 2H), 2.48 (s, 3H), 2.43 (s, 3H), 2.20 (m, 2H), 1.81 (m, 2H), 1.71 (m, 2H), 1.55 (m, 2H), 1.50–1.35 (m, 4H), 1.05–0.90 (m, 6H).

EXAMPLE 3(2)

1-butyl-3-cyclohexylmethyl-2,5-dioxo-9-(4-phenyloxyphenylmethyl)-1,4,9-triazaspiro[5.5]undecane.hydrochloride

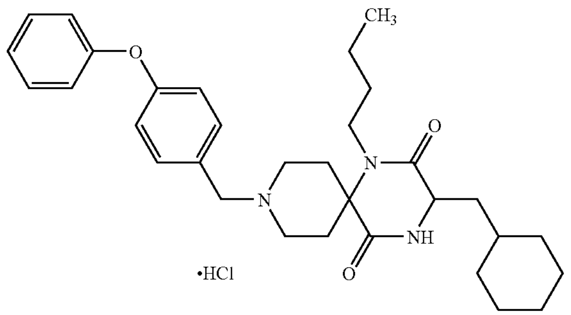

TLC: Rf 0.73 (chloroform:methanol=10:1);

NMR ($CD_3OD$): δ 7.74–7.56 (m, 1H), 7.53 (d, J=8.8 Hz, 2H), 7.40 (m, 2H), 7.18 (m, 1H), 7.10–7.00 (m, 3H), 4.33 (s, 2H), 4.04 (dd, J=7.4, 4.8 Hz, 1H), 3.80 (m, 2H), 3.60–3.35 (m, 4H), 2.43 (m, 2H), 2.17 (m, 2H), 1.90–1.60 (m, 7H), 1.60–1.45 (m, 2H), 1.45–1.30 (m, 2H), 1.30–1.15 (m, 4H), 1.10–0.80 (m, 5H).

EXAMPLE 3(3)

9-(1,4-benzodioxan-6-ylmethyl)-1-butyl-3-(2-methyl-1-propyl)-2,5-dioxo-1,4,9-triazaspiro[5.5]undecane.hydrochloride

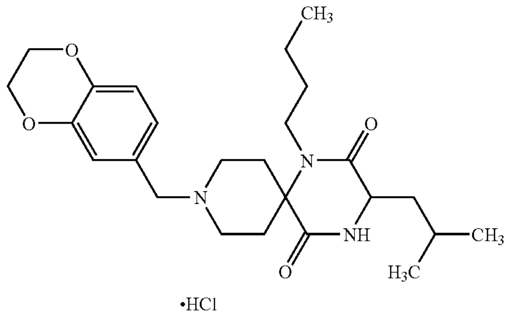

TLC: Rf 0.53 (chloroform:methanol=10:1);

NMR ($CD_3OD$): δ 7.08 (d, J=2.2 Hz, 1H), 7.01 (dd, J=8.2, 2.2 Hz, 1H), 6.93 (d, J=8.2 Hz, 1H), 4.27 (s, 4H), 4.23 (s, 2H), 4.01 (dd, J=7.8, 4.8 Hz, 1H), 3.72 (m, 2H), 3.55–3.35 (m, 4H), 2.43 (m, 2H), 2.16 (m, 2H), 1.80 (m, 1H), 1.67 (m, 2H), 1.55 (m, 2H), 1.37 (m, 2H), 1.00–0.90 (m, 9H).

EXAMPLE 3(4)

9-(4-benzyl oxyphenylmethyl)-1-butyl-2,5-dioxo-3-(2-methyl-1-propyl)-1,4,9-triazaspiro[5.5]undecane-.hydrochloride

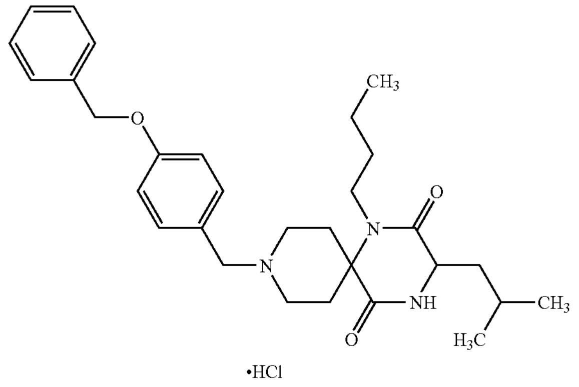

TLC: Rf 0.59 (chloroform:methanol=10:1);

NMR ($CD_3OD$): δ 7.54–7.25 (m, 7H), 7.10 (m, 2H), 5.13 (s, 2H), 4.27 (s, 2H), 4.00 (dd, J=8.2, 4.8 Hz, 1H), 3.72 (m, 2H), 3.55–3.35 (m, 4H), 2.42 (m, 2H), 2.16 (m, 2H), 1.90–1.25 (m, 7H), 1.00–0.90 (m, 9H).

EXAMPLE 4

1-butyl-2,5-dioxo-3-(2-methylpropyl)-9-(6-phenylhexyl)-1,4,9-triazaspiro[5.5]undecane.hydrochloride

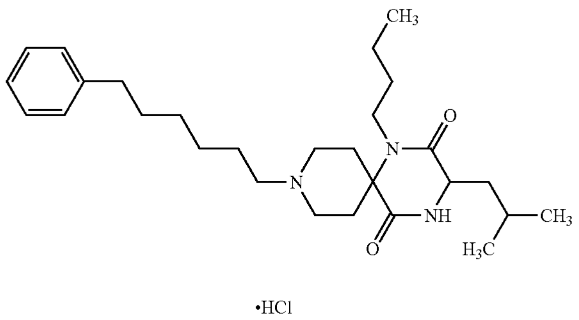

By the same procedure as described in Reference Example 3→Reference Example 6→Example 1 using Resin (3) prepared in Reference Example 2, N-(6-phenylhexyl)-4-piperidone, n-butylamine and N-(t-butyloxycarbonyl)leucine, the compound of the present invention having the following physical data was obtained.

TLC: Rf 0.62 (chloroform:methanol=10:1);

NMR ($CD_3OD$): δ 7.30–7.06 (m, 5H), 4.02 (dd, J=7.8, 4.8 Hz, 1H), 3.70 (m, 2H), 3.56 (m, 2H), 3.43 (m, 2H), 3.11 (m, 2H), 2.63 (t, J=7.8 Hz, 2H), 2.46 (m, 2H), 2.18 (m, 2H), 1.95–1.50 (m, 9H), 1.50–1.25 (m, 6H), 0.97 (m, 9H).

EXAMPLE 5(1)~5(12)

By the same procedure as described in Reference Example 9→Reference Example 10→Example 1 using the corresponding compounds respectively instead of N-(6-phenylhexyl)-4-piperidone, n-propylamine and N-(t-butyloxycarbonyl)-L-leucine, using Resin (6) prepared in Reference Example 8, the following compounds of the present invention were obtained.

EXAMPLE 5(1)

(3S)-1-(2-methylpropyl)-2,5-dioxo-3-(4-(N-benzyloxycarbonyl)aminobutyl)-9-(2-phenylethyl)-1,4,9-triazaspiro[5.5]undecane.hydrochloride

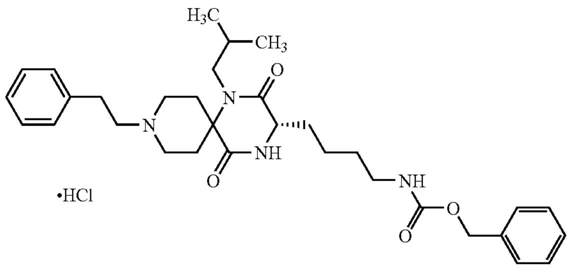

TLC: Rf 0.52 (chloroform:methanol=10:1);

NMR ($CD_3OD$): δ 7.33 (m, 10H), 5.07 (s, 2H), 4.12 (m, 1H), 3.94 (m, 1H), 3.61 (m, 5H), 3.39 (m, 2H), 3.13 (m, 4H), 2.31 (m, 4H), 1.92 (m, 3H), 1.51 (m, 2H), 1.39 (m, 2H), 0.93 (t, J=6.4 Hz, 6H).

EXAMPLE 5(2)

(3S)-1-propyl-2,5-dioxo-3-(4-(N-benzyloxycarbonyl)aminobutyl)-9-(2-phenylethyl)-1,4,9-triazaspiro[5.5]undecane.hydrochloride

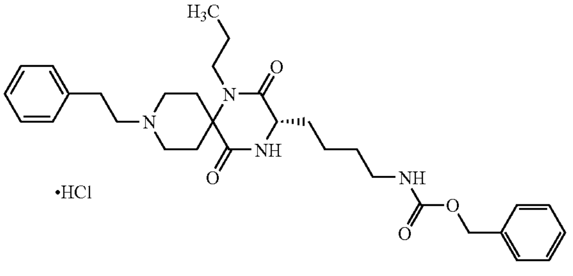

TLC: Rf 0.41 (chloroform:methanol=10:1);

NMR ($CD_3OD$): δ 7.33 (m, 10H), 5.06 (m, 2H), 4.07 (m, 1H), 3.86 (m, 1H), 3.76 (m, 1H), 3.63 (m, 2H), 3.37 (m, 4H), 3.12 (m, 4H), 2.43 (m, 2H), 2.21 (m, 2H), 1.86 (m, 2H), 1.55 (m, 4H), 1.37 (m, 2H), 0.95 (t, J=7.2 Hz, 3H).

EXAMPLE 5(3)

(3R)-1-propyl-2,5-dioxo-3-(4-(N-benzyloxycarbonyl) aminobutyl)-9-(2-phenylethyl)-1,4,9-triazaspiro [5.5]undecane.hydrochloride

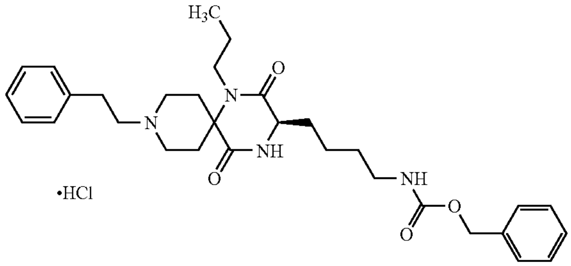

TLC: Rf 0.41 (chloroform:methanol=10:1);

NMR ($CD_3OD$): δ 7.33 (m, 10H), 5.06 (s, 2H), 4.07 (m, 1H), 3.86 (m, 1H), 3.76 (m, 1H), 3.63 (m, 2H), 3.37 (m, 4H), 3.12 (m, 4H), 2.43 (m, 2H), 2.21 (m, 2H), 1.86 (m, 2H), 1.55 (m, 4H), 1.37 (m, 2H), 0.95 (t, J=7.2 Hz, 3H).

EXAMPLE 5(4)

(3S)-1-propyl-2,5-dioxo-3-(4-(N-benzyloxycarbonyl)aminobutyl)-9-(3-phenylpropyl)-1,4,9-triazaspiro[5.5]undecane.hydrochloride

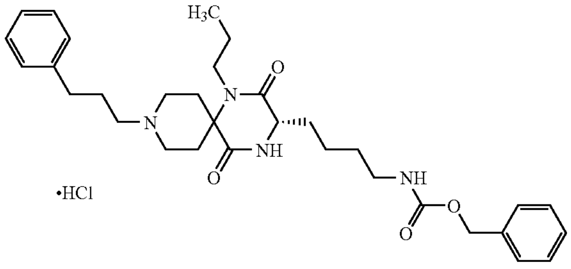

TLC: Rf 0.43 (chloroform:methanol=10:1);

NMR ($CD_3OD$): δ 7.33 (m, 5H), 7.26 (m, 5H), 5.05 (s, 2H), 4.05(m, 1H), 3.85–3.30 (m, 6H), 3.12 (m, 4H), 2.73 (t, J=7.6 Hz, 2H), 2.44 (m, 2H), 2.13 (m, 4H), 1.85 (m, 2H), 1.54 (m, 4H), 1.38 (m, 2H), 0.94 (t, J=7.2 Hz, 3H).

EXAMPLE 5(5)

(3R)-1-propyl-2,5-dioxo-3-(4-(N-benzyloxycarbonyl)aminobutyl)-9-(3-phenylpropyl)-1,4,9-triazaspiro[5.5]undecane.hydrochloride

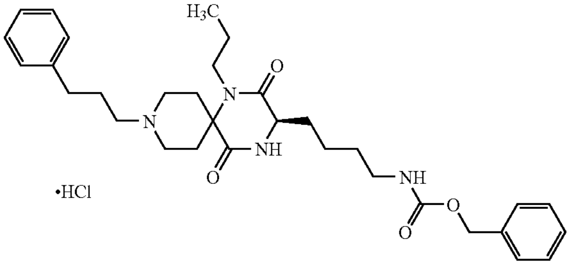

TLC: Rf 0.43 (chloroform:methanol=10:1);

NMR ($CD_3OD$): δ 7.33 (m, 5H), 7.26 (m, 5H), 5.05 (s, 2H), 4.05(m, 1H), 3.85–3.30 (m, 6H), 3.12 (m, 4H), 2.73 (t, J=7.2 Hz, 2H), 2.44 (m, 2H), 2.13 (m, 4H), 1.85 (m, 2H), 1.54 (m, 4H), 1.38 (m, 2H), 0.94 (t, J=7.2 Hz, 3H).

EXAMPLE 5(6)

(3S)-1-propyl-2,5-dioxo-3-(4-(N-benzyloxycarbonyl)aminobutyl)-9-(4-phenylbutyl)-1,4,9-triazaspiro [5.5]undecane.hydrochloride

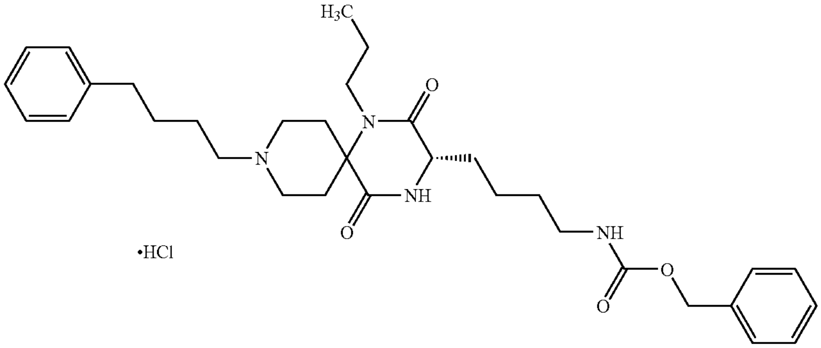

TLC: Rf 0.44 (chloroform:methanol=10:1);

NMR ($CD_3OD$): δ 7.33 (m, 5H), 7.22 (m, 5H), 5.06 (s, 2H), 4.05(m, 1H), 3.85–3.38 (m, 6H), 3.12 (m, 4H), 2.70 (m, 2H), 2.40 (m, 2H), 2.18 (m, 2H), 1.74 (m, 6H), 1.54 (m, 4H), 1.38 (m, 2H), 0.94 (t, J=7.0 Hz, 3H).

EXAMPLE 5(7)

(3R)-1-propyl-2,5-dioxo-3-(4-(N-benzyloxycarbonyl)aminobutyl)-9-(4-phenylbutyl)-1,4,9-triazaspiro[5.5]undecane.hydrochloride

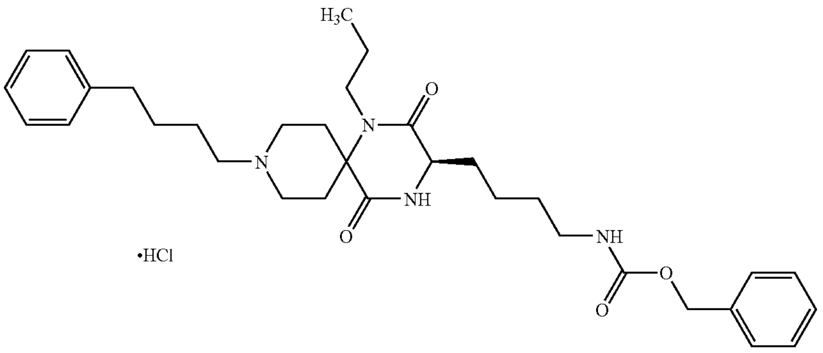

TLC: Rf 0.44 (chloroform:methanol=10:1);

NMR ($CD_3OD$): δ 7.33 (m, 5H), 7.22 (m, 5H), 5.06 (s, 2H), 4.05(m, 1H), 3.85–3.38 (m, 6H), 3.12 (m, 4H), 2.70 (m, 2H), 2.40 (m, 2H), 2.18 (m, 2H), 1.74 (m, 6H), 1.54 (m, 4H), 1.38 (m, 2H), 0.94 (t, J=7.0 Hz, 3H).

EXAMPLE 5(8)

(3S)-1-benzyl-2,5-dioxo-3-(2-methylpropyl)-9-benzyl-1,4,9-triazaspiro[5.5]undecane.hydrochloride

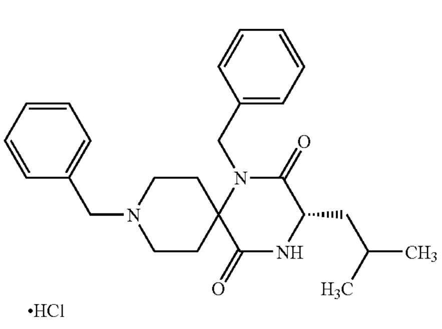

TLC: Rf 0.57 (chloroform:methanol=10:1);

NMR ($CD_3OD$): δ 7.48 (m, 5H), 7.23 (m, 5H), 4.82 (m, 2H), 4.31 (s, 2H), 4.17 (dd, J=8.0, 4.6 Hz, 1H), 3.72 (m, 2H), 3.40 (m, 2H), 2.52 (m, 2H), 2.08 (m, 2H), 2.00–1.60 (m, 3H), 0.98 (d, J=6.0 Hz, 6H).

EXAMPLE 5(9)

(3R)-1-benzyl-2,5-dioxo-3-(2-methylpropyl)-9-benzyl-1,4,9-triazaspiro[5.5]undecane.hydrochloride

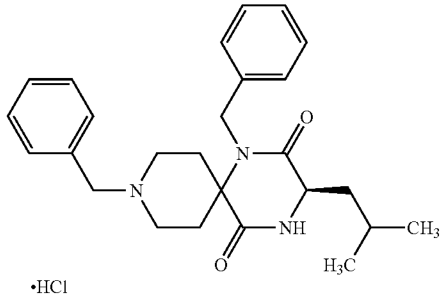

TLC: Rf 0.57 (chloroform:methanol=10:1);

NMR ($CD_3OD$): δ 7.48 (m, 5H), 7.23 (m, 5H), 4.82 (m, 2H), 4.31 (s, 2H), 4.17 (dd, J=8.0, 4.6 Hz, 1H), 3.72 (m, 2H), 3.40 (m, 2H), 2.52 (m, 2H), 2.08 (m, 2H), 2.00–1.60 (m, 3H), 0.98 (d, J=6.0 Hz, 6H).

EXAMPLE 5(10)

(3S)-1-propyl-2,5-dioxo-3-(4-(N-benzyloxycarbonyl)aminobutyl)-9-(2-(2-phenyl-5-methyloxazol-4-yl) ethyl)-1,4,9-triazaspiro[5.5]undecane.hydrochloride

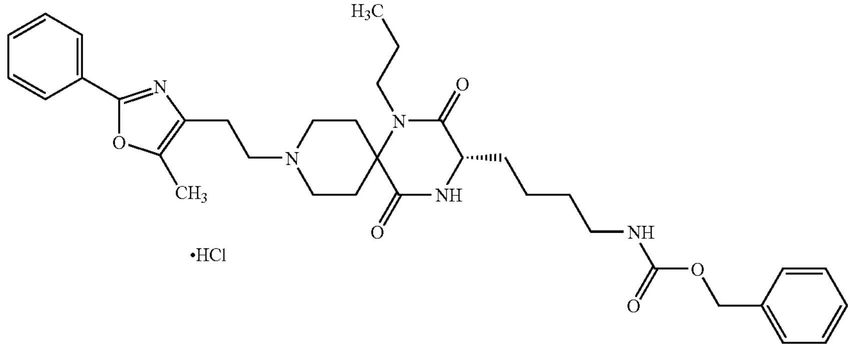

TLC: Rf 0.45 (chloroform:methanol=10:1);

NMR ($CD_3OD$): δ 8.01 (m, 2H), 7.53 (m, 3H), 7.34 (m, 5H), 5.07 (s, 2H), 4 .08 (dd, J=5.4, 4.4 Hz, 1H), 4.00–3.60 (m, 4H), 3.47 (m, 4H), 3.13 (m, 4H), 2.56 (m, 2H), 2.46 (s, 3H), 2.25 (m, 2H), 1.87 (m, 2H), 1.75–1.25 (m, 6H), 0.94 (t, J=7.2 Hz, 3H).

EXAMPLE 5(11)

(3S)-1-propyl-2,5-dioxo-3-(4-(N-(2-chlorophenylmethyl)oxycarbonyl)aminobutyl)-9-(2-phenylethyl)-1,4,9-triazaspiro[5.5]undecane.hydrochloride

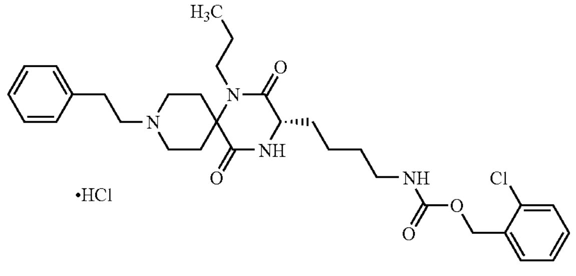

TLC: Rf 0.33 (chloroform:methanol=10:1);

NMR ($CD_3OD$): δ 7.33 (m, 9H), 5.17 (s, 2H), 4.08 (dd, J=5.2, 4.8 Hz, 1H), 3.80 (m, 2H), 3.65 (m, 3H), 3.39 (m, 3H), 3.14 (m, 4H), 2.50 (m, 2H), 2.22 (m, 2H), 1.85 (m, 2H), 1.70–1.20 (m, 6H), 0.95 (t, J=7.2 Hz, 3H).

EXAMPLE 5(12)

(3S)-1-propyl-2,5-dioxo-3-[3-(3-(2,4,6-trimethylphenylsulfonyl)guanidino)propyl]-9-(2-phenylethyl)-1,4,9-triazaspiro[5.5]undecane.hydrochloride

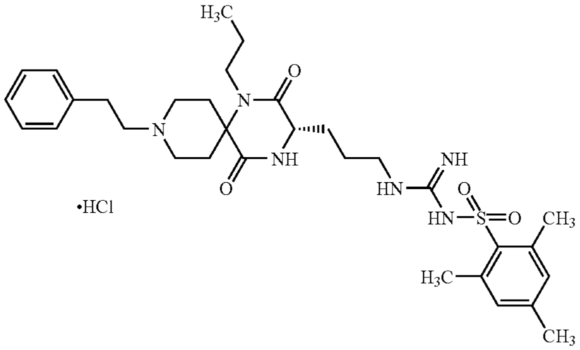

TLC: Rf 0.39 (chloroform:methanol=10:1);

NMR ($CD_3OD$): δ 7.32 (m, 5H), 7.05 (s, 2H), 4.10 (m, 1H), 3.88 (m, 1H), 3.67 (m, 3H), 3.40 (m, 4H), 3.18(m, 4H), 2.66 (s, 6H), 2.51 (m, 2H), 2.31 (s, 3H), 2.21 (m, 2H), 1.82 (m, 2H), 1.60 (m, 4H), 0.96 (t, J=7.2 Hz, 3H).

EXAMPLE 6(1)~6(32)

By the same procedure as described in Reference Example 3→Reference Example 4 using Resin (3) prepared in Reference Example 2, N-allyloxycarbonyl-4-piperidone, the corresponding amine derivatives and the corresponding amino acid derivatives, and furthermore by the same procedure as described in Reference Example 5→Reference Example 6→Example 1 using the corresponding aldehyde derivatives, the following compounds of the present invention were obtained.

EXAMPLE 6(1)

1-propyl-2,5-dioxo-3-(2-methylpropyl)-9-(4-phenyloxyphenylmethyl)-1,4,9-triazaspiro[5.5]undecane.hydrochloride

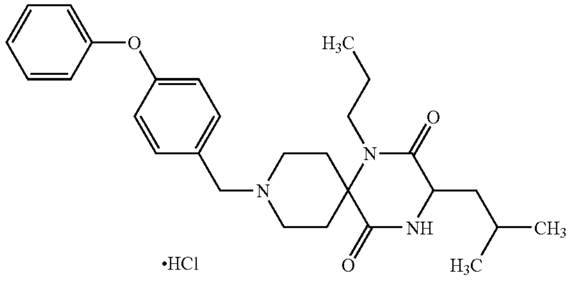

TLC: Rf 0.61 (chloroform:methanol=10:1);

NMR ($CD_3OD$): δ 7.55 (m, 2H), 7.40 (m, 2H), 7.18 (m, 1H), 7.05 (m, 4H), 4.33 (s, 2H), 4.01 (dd, J=7.6, 4.8 Hz, 1H), 3.79 (m, 2H), 3.60–3.30 (m, 4H), 2.46 (m, 2H), 2.17 (m, 2H), 1.95–1.40 (m, 5H), 0.94 (m, 9H).

EXAMPLE 6(2)

1-butyl-2,5-dioxo-3-cyclohexylmethyl-9-(4-methoxyphenylmethyl)-1,4,9-triazaspiro[5.5]undecane.hydrochloride

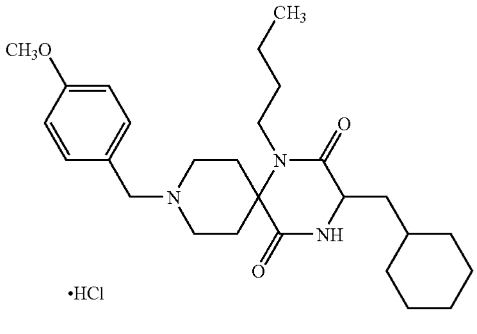

TLC: Rf 0.63 (chloroform:methanol=10:1);

NMR ($CD_3OD$): δ 7.47 (d, J=8.8 Hz, 2H), 7.03 (d, J=8.8 Hz, 2H), 4.29 (s, 2H), 4.04 (dd, J=7.6, 4.8 Hz, 1H), 3.83 (s, 3H), 3.74 (m, 2H), 3.55–3.35 (m, 4H), 2.41 (m, 2H), 2.15 (m, 2H), 1.85–1.55 (m, 7H), 1.55–1.42 (m, 3H), 1.42–1.30 (m, 3H), 1.30–1.10 (m, 2H), 1.08–0.80 (m, 5H).

EXAMPLE 6(3)

1-butyl-2,5-dioxo-3-cyclohexylmethyl-9-(4-allyloxyphenylmethyl)-1,4,9-triazaspiro[5.5]undecane.hydrochloride

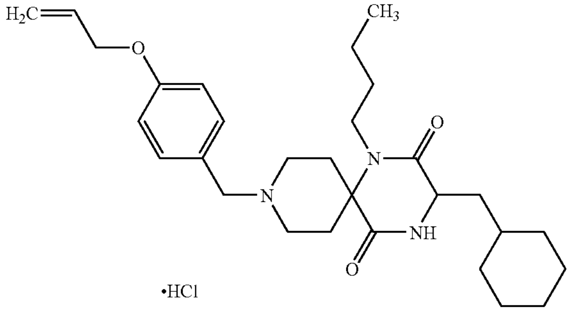

TLC: Rf 0.57 (chloroform:methanol=10:1);

NMR ($CD_3OD$): δ 7.46 (d, J=8.4 Hz, 2H), 7.04 (d, J=8.4 Hz, 2H), 6.06 (m, 1H), 5.41 (m, 1H), 5.28 (m, 2H), 4.59 (m, 2H), 4.28 (s, 2H), 4.04 (dd, J=7.2, 4.8 Hz, 1H), 3.77 (m, 2H), 3.55–3.35 (m, 4H), 2.39 (m, 2H), 2.16 (m, 2H), 1.90–1.60 (m, 7H), 1.60–1.45 (m, 2H), 1.45–1.30 (m, 2H), 1.30–1.10 (m, 3H), 1.10–0.80 (m, 5H).

EXAMPLE 6(4)

(3S)-1-propyl-9-(3,5-dimethyl-1-phenylpyrazol-4-ylmethyl)-2,5-dioxo-3-(2-methyl-1-propyl)-1,4,9-triazaspiro[5.5]undecane.2 Hydrochloride

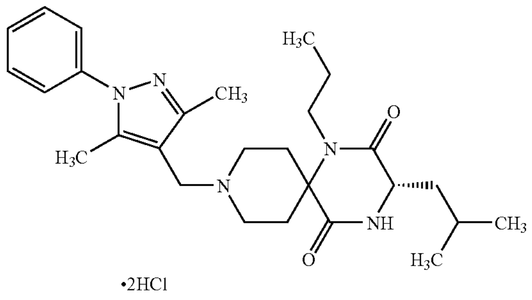

TLC: Rf 0.50 (chloroform:methanol=10:1);

NMR ($CD_3OD$): δ 7.65–7.45 (m, 5H), 4.33 (s, 2H), 4.03 (dd, J=7.8, 5.2 Hz, 1H), 3.85 (m, 2H), 3.62 (m, 2H), 3.44 (m, 2H), 2.59 (m, 2H), 2.43 (s, 3H), 2.41 (s, 3H), 2.20 (m, 2H), 1.81 (m, 1H), 1.71 (m, 2H), 1.64 (m, 2H), 1.00–0.90 (m, 9H).

EXAMPLE 6(5)

(3R)-1-propyl-9-(3,5-dimethyl-1-phenylpyrazol-4-ylmethyl)-2,5-dioxo-3-(2-methyl-1-propyl)-1,4,9-triazaspiro[5.5]undecane.2 hydrochloride

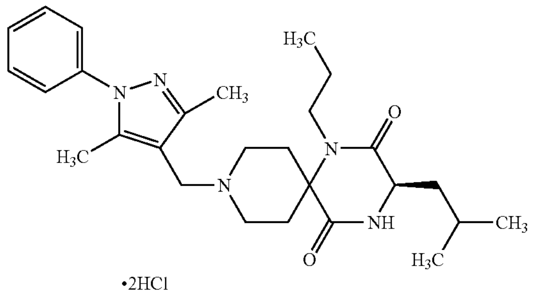

TLC: Rf 0.50 (chloroform:methanol=10:1);

NMR ($CD_3OD$): δ 7.65–7.45 (m, 5H), 4.33 (s, 2H), 4.03 (dd, J=7.8, 5.2 Hz, 1H), 3.85 (m, 2H), 3.62 (m, 2H), 3.44 (m, 2H), 2.59 (m, 2H), 2.43 (s, 3H), 2.41 (s, 3H), 2.20 (m, 2H), 1.81 (m, 1H), 1.71 (m, 2H), 1.64 (m, 2H), 1.00–0.90 (m, 9H).

EXAMPLE 6(6)

1-butyl-2,5-dioxo-3-(2-methylpropyl)-9-phenylmethyl-1,4,9-triazaspiro[5.5]undecane.hydrochloride

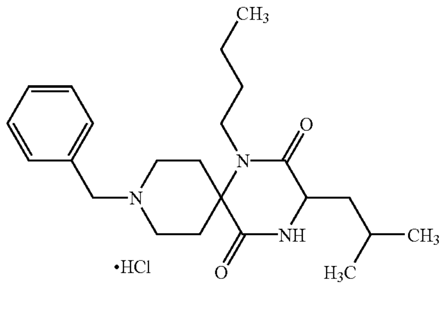

TLC: Rf 0.54 (chloroform:methanol=10:1);

NMR ($CD_3OD$): δ 7.64–7.44 (m, 5H), 4.36 (s, 2H), 4.01 (dd, J=7.8, 4.8 Hz, 1H), 3.77 (m, 2H), 3.55–3.35 (m, 4H), 2.60–2.30 (m, 2H), 2.17 (m, 2H), 1.95–1.75 (m, 1H), 1.75–1.60 (m, 2H), 1.60–1.45 (m, 2H), 1.45–1.20 (m, 2H), 1.10–0.80 (m, 9H).

EXAMPLE 6(7)

1-butyl-2,5-dioxo-3-(2-methylpropyl)-9-benzyloxycarbonyl-1,4,9-triazaspiro[5.5]undecane

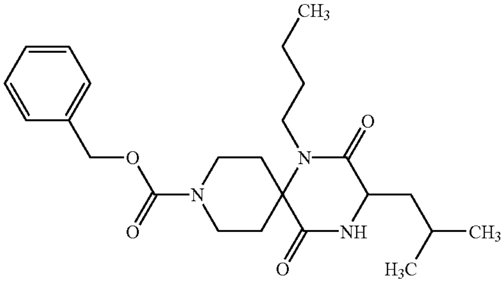

TLC: Rf 0.41 (chloroform:methanol=20:1);

NMR ($CDCl_3$): δ 7.45–7.28 (m, 5H), 6.31 (m, 1H), 5.15 (s, 2H), 4.14 (m, 2H), 3.96 (m, 1H), 3.63 (m, 1H), 3.44 (m, 1H), 3.26 (m, 2H), 1.99–1.14 (m, 11H), 1.02–0.88 (m, 9H).

EXAMPLE 6(8)

1-butyl-2,5-dioxo-3-cyclohexylmethyl-9-benzyloxycarbonyl-1,4,9-triazaspiro[5.5]undecane

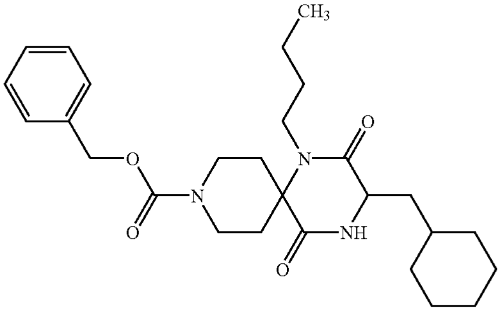

TLC: Rf 0.46 (chloroform:methanol=20:1);

NMR ($CDCl_3$): δ 7.40–7.29 (m, 5H), 5.98 (m, 1H), 5.15 (s, 2H), 4.14 (m, 2H), 4.00 (m, 1H), 3.65 (m, 1H), 3.43 (m, 1H), 3.26 (m, 2H), 2.03–1.81 (m, 4H), 1.80–1.60 (m, 5H), 1.60–1.10 (m, 10H), 1.10–0.85 (m, 5H).

EXAMPLE 6(9)

1-benzyl-2,5-dioxo-3-(2-methylpropyl)-9-(4-phenyloxyphenylmethyl)-1,4,9-triazaspiro[5.5]undecane-.hydrochloride

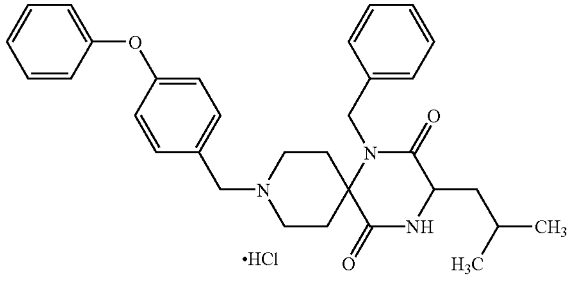

TLC: Rf 0.66 (chloroform:methanol=10:1);

NMR ($CD_3OD$): δ 7.50 (d, J=8.4 Hz, 2H), 7.45–7.12 (m, 8H), 7.10–6.98 (m, 4H), 4.82 (m, 2H), 4.29 (s, 2H), 4.18 (dd, J=8.0, 4.6 Hz, 1H), 3.73 (m, 2H), 3.42 (m, 2H), 2.65–2.30 (m, 2H), 2.20–2.05 (m, 2H), 2.00–1.60 (m, 3H), 0.98 (d, J=6.2 Hz, 6H).

EXAMPLE 6(10)

1-butyl-2,5-dioxo-3-propyl-9-(4-phenyloxyphenylmethyl)-1,4,9-triazaspiro[5.5]undecane.hydrochloride

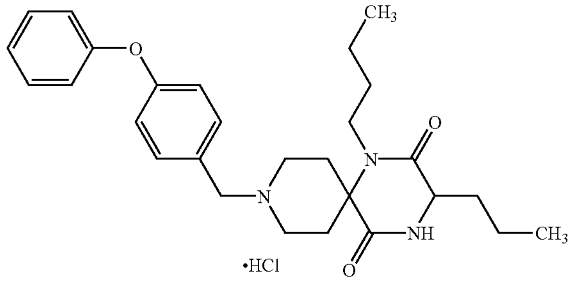

TLC: Rf 0.36 (chloroform:methanol=10:1);

NMR ($CD_3OD$): δ 7.51 (d, J=8.7 Hz, 2H), 7.39 (dd, J=8.7, 7.5 Hz, 2H), 7.18 (t, J=7.5 Hz, 1H), 7.10–7.00 (m, 4H), 4.33 (s, 2H), 4.04 (dd, J=5.7, 4.5 Hz, 1H), 3.93–3.66 (m, 2H), 3.55–3.31 (m, 4H), 2.47–2.09 (m, 4H), 1.92–1.68 (m, 2H), 1.61–1.21 (m, 6H), 1.01–0.90 (m, 6H).

EXAMPLE 6(11)

1-butyl-2,5-dioxo-3-methoxymethyl-9-(4-phenyloxyphenylmethyl)-1,4,9-triazaspiro[5.5]undecane.hydrochloride

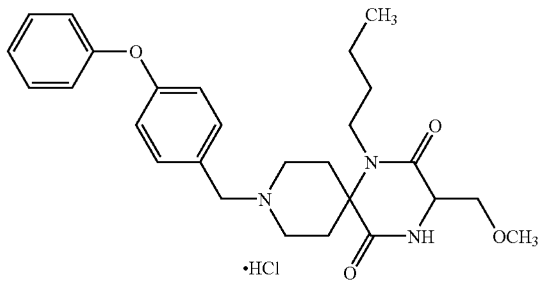

TLC: Rf 0.48 (chloroform:methanol=10:1);

NMR ($CD_3OD$): δ 7.51 (d, J=8.7 Hz, 2H), 7.39 (dd, J=8.7, 7.2 Hz, 2H), 7.17 (t, J=7.2 Hz, 1H), 7.09–6.99 (m, 4H), 4.30 (s, 2H), 4.07 (t, J=3.0 Hz, 1H), 3.91 (m, 1H), 3.77 (dd, J=9.0, 3.0 Hz, 1H), 3.67 (m, 1H), 3.58–3.39 (m, 4H), 3.31 (s, 3H), 3.26 (m, 1H), 2.48–2.13 (m, 4H), 1.65 (m, 1H), 1.53–1.28 (m, 3H), 0.95 (t, J=7.5 Hz, 3H).

EXAMPLE 6(12)

1-(1-methylpropyl)-2,5-dioxo-3-(2-methylpropyl)-9-(4-phenyloxyphenylmethyl)-1,4,9-triazaspiro[5.5]undecane.hydrochloride

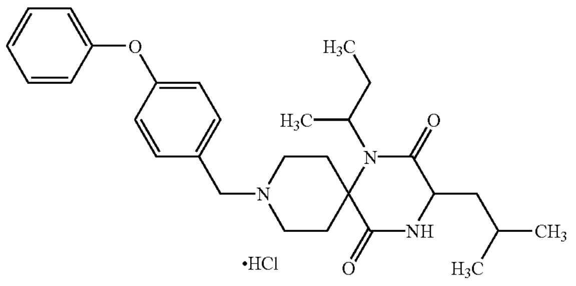

TLC: Rf 0.43 (chloroform:methanol=10:1);

NMR ($CD_3OD$): δ 7.46 (d, J=8.4 Hz, 2H), 7.38 (dd, J=8.4, 7.5 Hz, 2H), 7.16 (t, J=7.5 Hz, 1H), 7.08–6.99 (m, 4H), 4.15 (s, 2H), 3.91–3.82 (m, 1H), 3.81–3.65 (m, 1H), 3.64–3.44 (m, 1H), 3.44–3.15 (m, 3H), 2.42–2.00 (m, 4H), 1.88–1.56 (m, 5H), 1.46–1.37 (m, 3H), 0.99–0.85 (m, 9H).

EXAMPLE 6(13)

1-(2-methyl butyl)-2,5-dioxo-3-(2-methylpropyl)-9-(4-phenyloxyphenylmethyl)-1,4,9-triazaspiro[5.5]undecane.hydrochloride

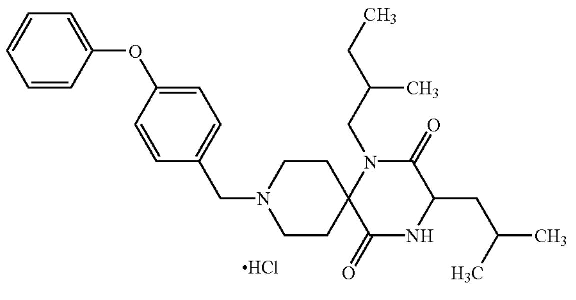

TLC: Rf 0.49 (chloroform:methanol=10:1);

NMR ($CD_3OD$): δ 7.49 (d, J=8.7 Hz, 2H), 7.39 (dd, J=8.7, 7.2 Hz, 2H), 7.17 (t, J=7.2 Hz, 1H), 7.08–6.94 (m, 4H), 4.27 (s, 2H), 4.04 (dd, J=8.4, 4.5 Hz, 1H), 3.83–3.21 (m, 6H), 2.45–2.12 (m, 4H), 1.92–1.56 (m, 4H), 1.42 (m, 1H), 1.14 (m, 1H), 1.00–0.83 (m, 12H).

EXAMPLE 6(14)

1-(2-methylpropyl)-2,5-dioxo-3-(2-methylpropyl)-9-(4-phenyloxyphenylmethyl)-1,4,9-triazaspiro[5.5]undecane.hydrochloride

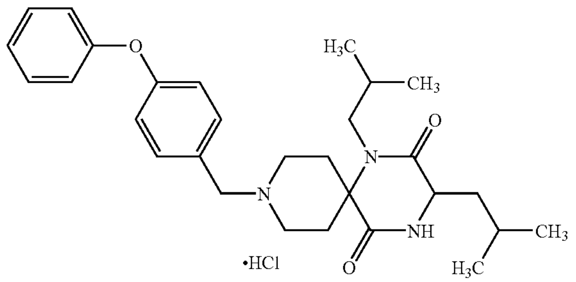

TLC: Rf 0.50 (chloroform:methanol=10:1);

NMR ($CD_3OD$): δ 7.50 (d, J=8.7 Hz, 2H), 7.39 (dd, J=8.7, 7.5 Hz, 2H), 7.17 (t, J=7.5 Hz, 1H), 7.13–7.04 (m, 4H), 4.28 (s, 2H), 4.04 (dd, J=8.1, 4.2 Hz, 1H), 3.81–3.54 (m, 2H), 3.52–3.21 (m, 4H), 2.46–2.11 (m, 4H), 2.00–1.57 (m, 4H), 0.94 (d, J=6.3 Hz, 6H), 0.90 (d, J=6.3 Hz, 3H), 0.90 (d, J=6.3 Hz, 3H).

EXAMPLE 6(15)

1-(2-dimethylaminoethyl)-2,5-dioxo-3-(2-methylpropyl)-9-(4-phenyloxyphenylmethyl)-1,4,9-triazaspiro[5.5]undecane.2 hydrochloride

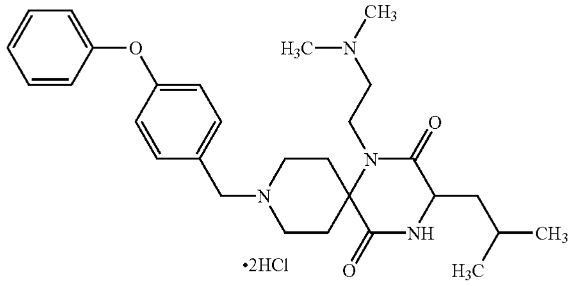

TLC: Rf 0.87 (chloroform:methanol:28% $NH_4OH$=80:10:1);

NMR ($CD_3OD$): δ 7.60 (d, J=8.7 Hz, 2H), 7.39 (dd, J=8.7, 7.5 Hz, 2H), 7.17 (t, J=7.5 Hz, 1H), 7.07–6.99 (m, 4H), 4.33 (s, 2H), 4.07 (dd, J=8.4, 4.8 Hz, 1H), 3.99–3.63 (m, 4H), 3.53–3.42 (m, 2H), 3.32–3.21 (m, 2H), 2.99 (s, 3H), 2.96 (s, 3H), 2.70–2.49 (m, 2H), 2.30–2.10 (m, 2H), 1.93–1.56 (m, 3H), 0.94 (d, J=6.6 Hz, 6H).

EXAMPLE 6(16)

1-(2-methoxyethyl)-2,5-dioxo-3-(2-methylpropyl)-9-(4-phenyloxyphenylmethyl)-1,4,9-triazaspiro[5.5]undecane.hydrochloride

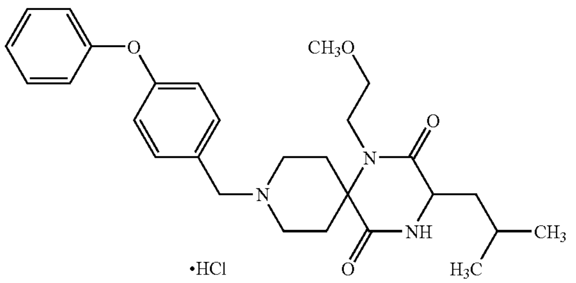

TLC: Rf 0.40 (chloroform:methanol=10:1);

NMR ($CD_3OD$): δ 7.47 (d, J=8.7 Hz, 2H), 7.39 (dd, J=8.7, 7.5 Hz, 2H), 7.17 (t, J=7.5 Hz, 1H), 7.09–6.99 (m, 4H), 4.25 (s, 2H), 4.03 (dd, J=7.8, 4.8 Hz, 1H), 3.75–3.34 (m, 8H), 3.31 (s, 3H), 2.48–2.28 (m, 2H), 2.25–2.06 (m, 2H), 1.90–1.57 (m, 3H), 0.94 (d, J=6.3 Hz, 3H), 0.93 (d, J=6.3 Hz, 3H).

EXAMPLE 6(17)

1-(2-methylthioethyl)-2,5-dioxo-3-(2-methylpropyl)-9-(4-phenyloxyphenylmethyl)-1,4,9-triazaspiro[5.5]undecane.hydrochloride

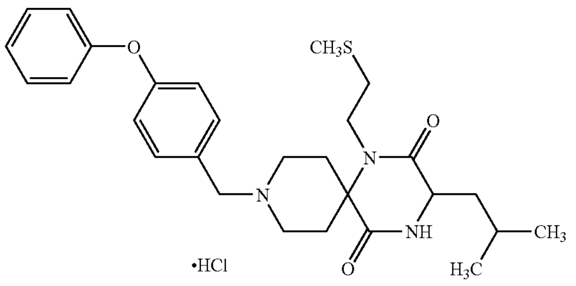

TLC: Rf 0.43 (chloroform:methanol=10:1);

NMR ($CD_3OD$): δ 7.48 (d, J=8.7 Hz, 2H), 7.39 (dd, J=8.7, 7.8 Hz, 2H), 7.17 (t, J=7.8 Hz, 1H), 7.08–6.99 (m, 4H), 4.25 (s, 2H), 4.02 (dd, J=7.8, 4.5 Hz, 1H), 3.81–3.49 (m, 4H), 3.48–3.33 (m, 2H), 2.74–2.51 (m, 2H), 2.39–2.10 (m, 7H), 1.90–1.56 (m, 3H), 0.94 (d, J=6.6 Hz, 3H), 0.93 (d, J=6.6 Hz, 3H).

EXAMPLE 6(18)

1-benzyl-2,5-dioxo-3-(2-methylpropyl)-9-(1,4-benzodioxan-6-ylmethyl)-1,4,9-triazaspiro[5.5]undecane.hydrochloride

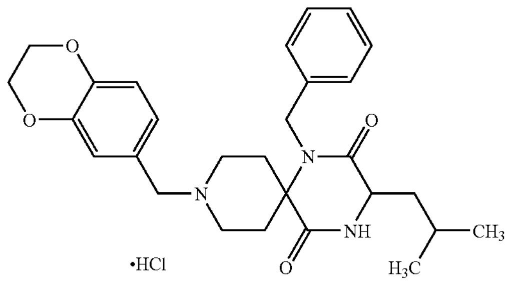

TLC: Rf 0.55 (chloroform:methanol=10:1);

NMR ($CD_3OD$): δ 7.40–7.15 (m, 5H), 7.03 (d, J=2.0 Hz, 1H), 6.96 (dd, J=8.2, 2.0 Hz, 1H), 6.90 (d, J=8.2 Hz, 1H), 4.80 (m, 2H), 4.25 (s, 4H), 4.21–4.10 (m, 3H), 3.80–3.55 (m, 2H), 3.50–3.30 (m, 2H), 2.60–2.25 (m, 2H), 2.20–2.00 (m, 2H), 2.00–1.60 (m, 3H), 0.98 (d, J=6.4 Hz, 6H).

EXAMPLE 6(19)

1-benzyl-2,5-dioxo-3-(2-methylpropyl)-9-(4-benzyloxyphenylmethyl)-1,4,9-triazaspiro[5.5]undecane.hydrochloride

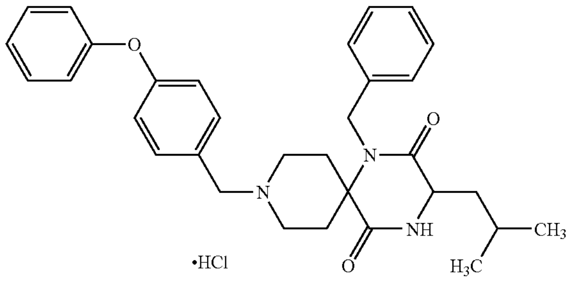

TLC: Rf 0.53 (chloroform:methanol=10:1);

NMR ($CD_3OD$): δ 7.50–7.15 (m, 12H), 7.07 (d, J=8.8 Hz, 2H), 5.12 (s, 2H), 4.81 (m, 2H), 4.24 (s, 2H), 4.17 (dd, J=8.4, 4.8 Hz, 1H), 3.70–3.55 (m, 2H), 3.50–3.35 (m, 2H), 2.60–2.25 (m, 2H), 2.20–2.00 (m, 2H), 2.00–1.60 (m, 3H), 0.98 (d, J=6.0 Hz, 6H).

EXAMPLE 6(20)

1-benzyl-2,5-dioxo-3-(2-methylpropyl)-9-(3,5-dimethyl-1-phenylpyrazol-4-ylmethyl)-1,4,9-triazaspiro[5.5]undecane.2 hydrochloride

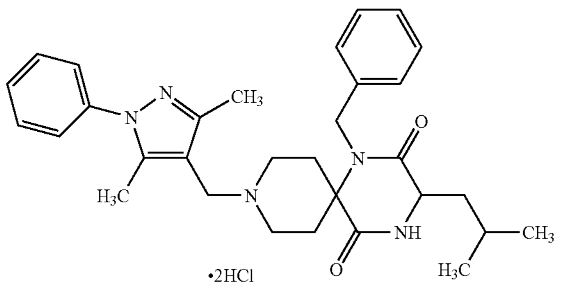

TLC: Rf 0.50 (chloroform:methanol=10:1);

NMR ($CD_3OD$): δ 7.70–7.45 (m, 5H), 7.40–7.15 (m, 5H), 4.92 (m, 2H), 4.29 (s, 2H), 4.20 (dd, J=8.4, 4.8 Hz, 1H), 3.90–3.65 (m, 2H), 3.65–3.45 (m, 2H), 2.85–2.50 (m, 2H), 2.44 (s, 3H), 2.39 (s, 3H), 2.20–2.00 (m, 2H), 2.00–1.60 (m, 3H), 1.00 (d, J=5.4 Hz, 6H).

EXAMPLE 6(21)

1-(3-methylphenylmethyl)-2,5-dioxo-3-(2-methylpropyl)-9-(1,4-benzodioxan-6-ylmethyl)-1,4,9-triazaspiro[5.5]undecane.hydrochloride

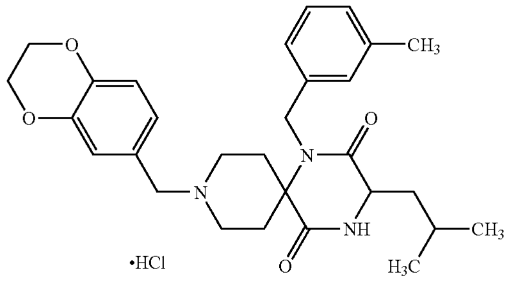

TLC: Rf 0.56 (chloroform:methanol=10:1);

NMR ($CD_3OD$): δ 7.18 (t, J=7.8 Hz, 1H), 7.10–6.85 (m, 6H), 4.77 (m, 2H), 4.25 (s, 4H), 4.19 (m, 3H), 3.68 (m, 2H), 3.40 (m, 2H), 2.60–2.30 (m, 2H), 2.29 (s, 3H), 2.20–2.00 (m, 2H), 2.00–1.60 (m, 3H), 0.99 (d, J=6.2 Hz, 6H).

EXAMPLE 6(22)

1-(3-methylphenylmethyl)-2,5-dioxo-3-(2-methylpropyl)-9-(3,5-dimethyl-1-phenylpyrazol-4-ylmethyl)-1,4,9-triazaspiro[5.5]undecane.2 hydrochloride

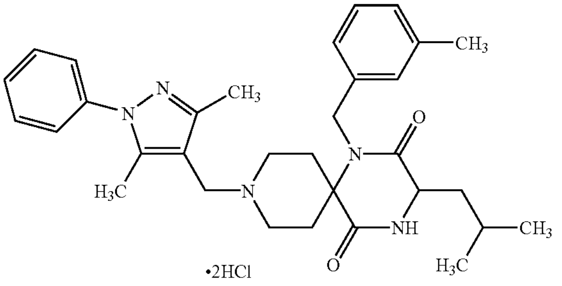

TLC: Rf 0.59 (chloroform:methanol=10:1);

NMR ($CD_3OD$): δ 7.70–7.45 (m, 5H), 7.18 (t, J=7.4 Hz, 1H), 7.10–7.00 (m, 3H), 4.88 (s, 2H), 4.31 (s, 2H), 4.20 (dd, J=8.2, 4.8 Hz, 1H), 3.76 (m, 2H), 3.60 (m, 2H), 2.90–2.50 (m, 2H), 2.47 (s, 3H), 2.41 (s, 3H), 2.30 (s, 3H), 2.10 (m, 2H), 1.88 (m, 1H), 1.85–1.65 (m, 2H), 1.00 (d, J=5.8 Hz, 6H).

EXAMPLE 6(23)

1-(1-methyl butyl)-2,5-dioxo-3-(2-methylpropyl)-9-(4-phenyloxyphenylmethyl)-1,4,9-triazaspiro[5.5]undecane.hydrochloride

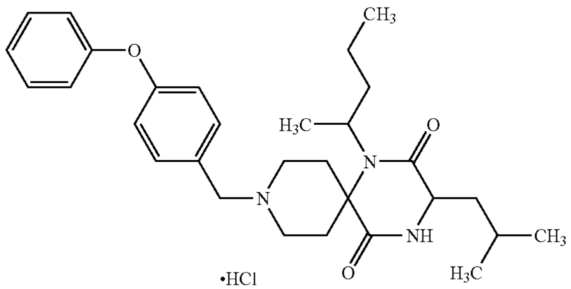

TLC: Rf 0.49, 0.56 (chloroform:methanol=10:1);

NMR ($CD_3OD$): δ 7.49 (d, J=8.7 Hz, 2H), 7.39 (dd, J=8.7, 7.5 Hz, 2H), 7.17 (t, J=7.5 Hz, 1H), 7.08–6.99 (m, 4H), 4.26 (s, 2H), 3.97–3.79 (m, 2H), 3.78–3.60 (m, 1H), 3.54–3.33 (m, 3H), 2.47–2.29 (m, 2H), 2.26–2.03 (m, 3H), 1.87–1.71 (m, 1H), 1.70–1.53 (m, 3H), 1.48–1.16 (m, 5H), 1.02–0.90 (m, 9H).

EXAMPLE 6(24)

1-(3-methylbutyl)-2,5-dioxo-3-(2-methylpropyl)-9-(4-phenyloxyphenylmethyl)-1,4,9-triazaspiro[5.5]undecane.hydrochloride

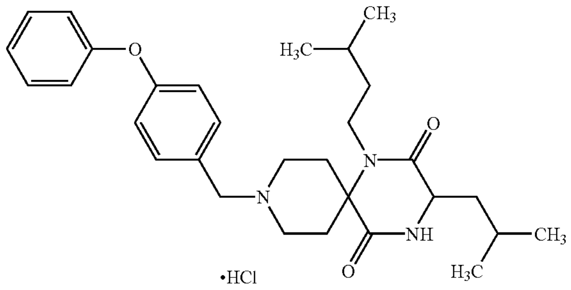

TLC: Rf 0.54 (chloroform:methanol=10:1);

NMR ($CD_3OD$): δ 7.51 (d, J=8.7 Hz, 2H), 7.39 (dd, J=8.7, 7.5 Hz, 2H), 7.18 (t, J=7.5 Hz, 1H), 7.10–7.00 (m, 4H), 4.33 (s, 2H), 4.00 (dd, J=8.1, 4.8 Hz, 1H), 3.90–3.71 (m, 2H), 3.56–3.34 (m, 4H), 2.46–2.29 (m, 2H), 2.28–2.10 (m, 2H), 1.90–1.56 (m, 4H), 1.55–1.32 (m, 2H), 1.04–0.85 (m, 12H).

EXAMPLE 6(25)

1-(2-methoxyphenylmethyl)-2,5-dioxo-3-(2-methylpropyl)-9-((3,5-dimethyl-1-phenyl)-4-pyrazolyl)methyl)-1,4,9-triazaspiro[5.5]undecane.2 hydrochloride

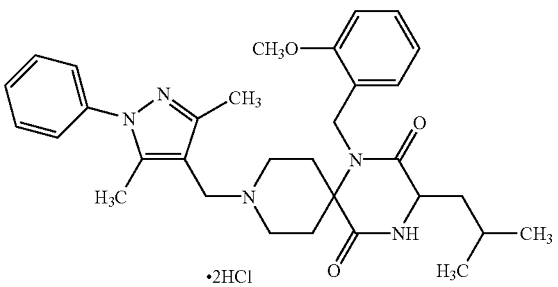

TLC: Rf 0.38 (chloroform:methanol=20:1);

NMR ($CD_3OD$): δ 7.59–7.41 (m, 5H), 7.26–7.17 (m, 1H), 6.99–6.84 (m, 3H), 4.74 (brs, 2H), 4.27 (s, 2H), 4.19 (dd, J=8.4, 4.5 Hz, 1H), 3.88 (s, 3H), 3.90–3.68 (m, 2H), 3.62–3.45 (m, 2H), 2.60–2.14 (m, 4H), 2.35 (s, 3H), 2.33 (s, 3H), 2.00–1.63 (m, 3H), 0.99 (d, J=6.3 Hz, 6H).

EXAMPLE 6(26)

1-(3-methoxyphenylmethyl)-2,5-dioxo-3-(2-methylpropyl)-9-((3,5-dimethyl-1-phenyl)-4-pyrazolyl)methyl)-1,4,9-triazaspiro[5.5]undecane.2 hydrochloride

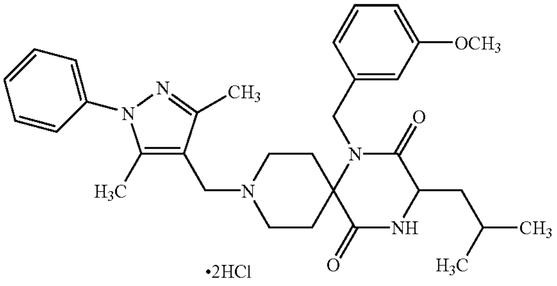

TLC: Rf 0.33 (chloroform:methanol=20:1);

NMR ($CD_3OD$): δ 7.65–7.48 (m, 5H), 7.20 (t, J=8.1 Hz, 1H), 6.85–6.80 (m, 2H), 6.77 (dd, J=7.8, 2.1 Hz, 1H), 4.90 (brs, 2H), 4.31 (s, 2H), 4.20 (dd, J=8.1, 4.8 Hz, 1H), 3.84–3.65 (m, 2H), 3.75 (s, 3H), 3.65–3.48 (m, 2H), 2.84–2.56 (m, 2H), 2.47 (s, 3H), 2.40 (s, 3H), 2.19–2.03 (m, 2H), 2.00–1.65 (m, 3H), 0.99 (d, J=6.3 Hz, 6H).

EXAMPLE 6(27)

1-(2-methylphenylmethyl)-2,5-dioxo-3-(2-methylpropyl)-9-(3,5-dimethyl-1-phenylpyrazol-4-ylmethyl)-1,4,9-triazaspiro[5.5]undecane.2 hydrochloride

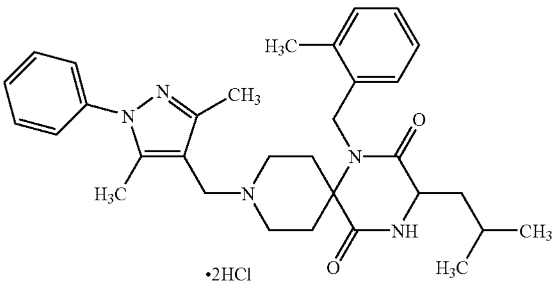

TLC: Rf 0.35 (chloroform:methanol=20:1);

NMR ($CD_3OD$): δ 7.63–7.46 (m, 5H), 7.18–7.06 (m, 3H), 6.99–6.91 (m, 1H), 4.81 (brs, 2H), 4.29 (s, 2H), 4.20 (dd, J=8.4, 4.5 Hz, 1H), 3.90–3.66 (m, 2H), 3.63–3.57 (m, 2H), 2.75–2.40 (m, 2H), 2.44 (s, 3H), 2.40 (s, 3H), 2.38 (s, 3H), 2.30–2.10 (m, 2H), 2.00–1.65 (m, 3H), 0.99 (d, J=6.3 Hz, 6H).

EXAMPLE 6(28)

1-(3-methylphenylmethyl)-2,5-dioxo-3-(2-methylpropyl)-9-(4-phenyloxyphenylmethyl)-1,4,9-triazaspiro[5.5]undecane.hydrochloride

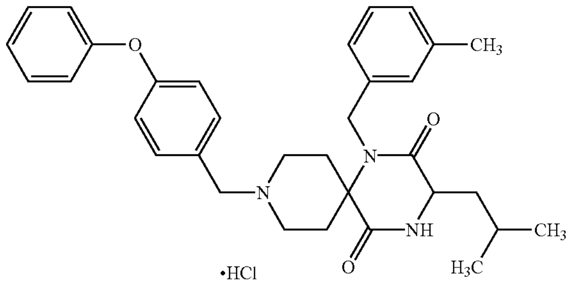

TLC: Rf 0.48 (chloroform:methanol=20:1);

NMR ($CD_3OD$): δ 7.53–7.46 (m, 2H), 7.42–7.36 (m, 2H), 7.22–7.14 (m, 2H), 7.06–6.96 (m, 7H), 4.85–4.65 (m, 2H), 4.28 (s, 2H), 4.18 (dd, J=8.1, 4.5 Hz, 1H), 3.80–3.62 (m, 2H), 3.50–3.30 (m, 2H), 2.58–2.25 (m, 2H), 2.29 (s, 3H), 2.18–2.04 (m, 2H), 1.95–1.62 (m, 3H), 0.98 (d, J=6.3 Hz, 6H).

EXAMPLE 6(29)

1-butyl-2,5-dioxo-3-cyclohexyl methyl-9-(5-ethylthiophen-2-ylmethyl)-1,4,9-triazaspiro[5.5]undecane-.hydrochloride

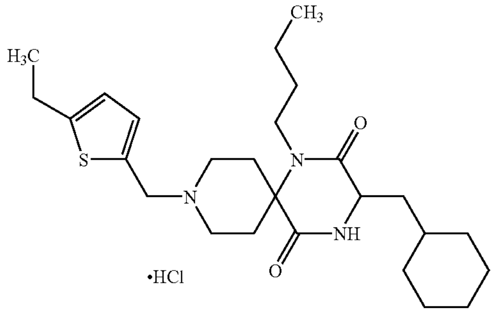

TLC: Rf 0.62 (chloroform:methanol=20:1);

NMR ($CD_3OD$): δ 7.17 (d, J=3.6 Hz, 1H), 6.85 (d, J=3.6 Hz, 1H), 4.53 (s, 2H), 4.04 (dd, J=7.8, 4.5 Hz, 1H), 3.88–3.72 (m, 2H), 3.58–3.45 (m, 2H), 3.43–3.33 (m, 2H), 2.87 (q, J=7.5 Hz, 2H), 2.50–2.30 (m, 2H), 2.30–2.08 (m, 2H), 1.83–1.10 (m, 17H), 1.31 (t, J=7.5 Hz, 3H), 1.05–0.85 (m, 2H), 0.95 (t, J=7.5 Hz, 3H).

EXAMPLE 6(30)

1-butyl-2,5-dioxo-3-cyclohexylmethyl-9-(5-ethylfuran-2-ylmethyl)-1,4,9-triazaspiro[5.5]undecane.hydrochloride

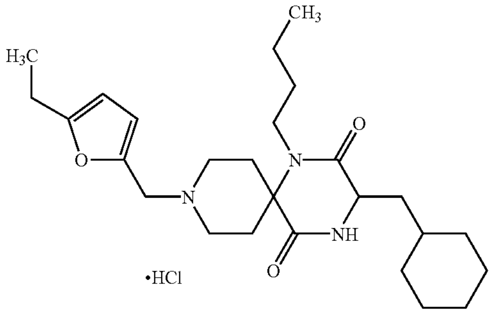

TLC: Rf 0.62 (chloroform:methanol=20:1);

NMR ($CD_3OD$): δ 6.63 (d, J=3.0 Hz, 1H), 6.14 (d, J=3.0 Hz, 1H), 4.39 (s, 2H), 4.04 (dd, J=7.5, 4.5 Hz, 1H), 3.90–3.70 (m, 2H), 3.55–3.40 (m, 2H), 3.40–3.35 (m, 2H), 2.69 (q, J=7.5 Hz, 2H), 2.50–2.30 (m, 2H), 2.30–2.10 (m, 2H), 1.85–1.05 (m, 17H), 1.25 (t, J=7.5 Hz, 3H), 1.05–0.85 (m, 2H), 0.96 (t, J=7.5 Hz, 3H).

EXAMPLE 6(31)

(3S)-1-butyl-2,5-dioxo-3-((1R)-1-hydroxy-2-methylpropyl)-9-(4-phenyloxyphenylmethyl)-1,4,9-triazaspiro[5.5]undecane.hydrochloride

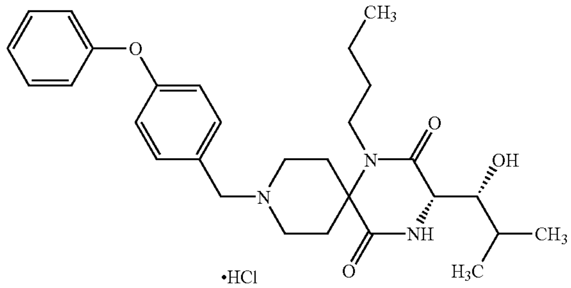

TLC: Rf 0.47 (chloroform:methanol=10:1);

NMR ($CD_3OD$): δ 7.52 (d, J=9.0 Hz, 2H), 7.44–7.35 (m, 2H), 7.18 (t, J=7.5 Hz, 1H), 7.10–7.00 (m, 4H), 4.33 (s, 2H), 4.16–4.00 (m, 2H), 3.75–3.40 (m, 5H), 3.26–3.09 (m, 1H), 2.56–2.08 (m, 4H), 1.82–1.60 (m, 2H), 1.50–1.30 (m, 3H), 1.05–0.89 (m, 9H).

EXAMPLE 6(32)

(3R)-1-butyl-2,5-dioxo-3-((1S)-1-hydroxy-2-methylpropyl)-9-(4-phenyloxyphenylmethyl)-1,4,9-triazaspiro[5.5]undecane.hydrochloride

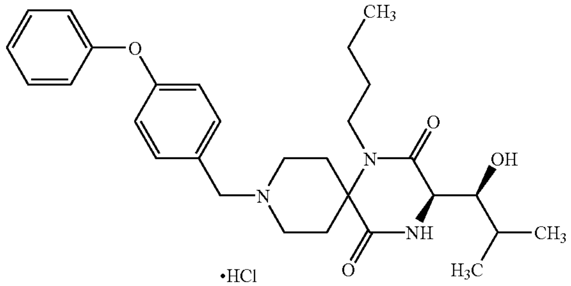

TLC: Rf 0.47 (chloroform:methanol=10:1);

NMR ($CD_3OD$): δ 7.52 (d, J=9.0 Hz, 2H), 7.44–7.35 (m, 2H), 7.18 (t, J=7.5 Hz, 1H), 7.10–7.00 (m, 4H), 4.33 (s, 2H), 4.16–4.00 (m, 2H), 3.75–3.40 (m, 5H), 3.26–3.09 (m, 1H), 2.56–2.08 (m, 4H), 1.82–1.60 (m, 2H), 1.50–1.30 (m, 3H), 1.05–0.89 (m, 9H).

EXAMPLE 7

(3S)-1-propyl-2,5-dioxo-3-(4-(N-benzyloxycarbonyl)aminobutyl)-9-allyloxycarbonyl-1,4,9-triazaspiro[5.5]undecane

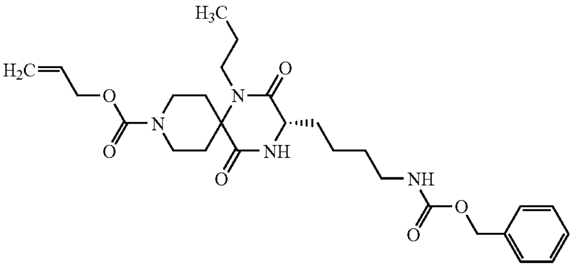

By the same procedure as described in Reference Example 9→Reference Example 10→Example 1 using Resin (6) prepared in Reference Example 8, N-allyloxycarbonyl-4-piperidone, n-propylamine and N-(t-butyloxycarbonyl)-N'-(benzyloxycarbonyl)-L-lysine, the compound of the present invention having the following physical data was obtained.

TLC: Rf 0.24 (ethyl acetate:hexane=4:1);

NMR ($CD_3OD$): δ 7.35 (m, 5H), 6.40 (m, 1H), 5.96 (ddt, J=17.2, 10.2, 5.6 Hz, 1H), 5.34 (m, 1H), 5.24 (m, 1H), 5.12 (s, 2H), 4.88 (m, 1H), 4.62 (m, 2H), 4.10 (m, 2H), 4.00 (m, 1H), 3.75 (m, 1H), 3.36 (m, 2H), 3.18 (m, 3H), 1.94 (m, 6H), 1.51 (m, 6H), 0.90 (t, J=7.2 Hz, 3H).

EXAMPLE 8

(3S)-1-propyl-2,5-dioxo-3-(4-(N-benzyloxycarbonyl)aminobutyl)-1,4,9-triazaspiro[5.5]undecane

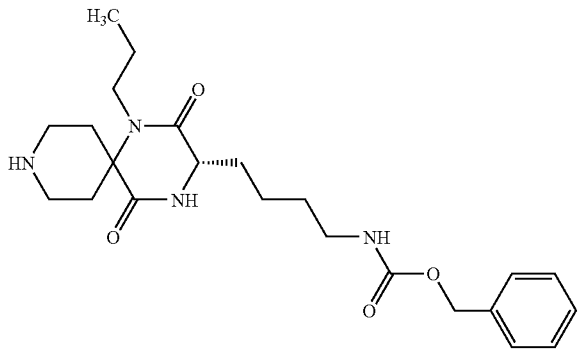

By the same procedure as described in Reference Example 4 using the compound prepared in Example 7, and furthermore, purification by cation-exchange resin and column chromatography on silica gel, the compound of the present invention having the following physical data was obtained.

TLC: Rf 0.56 (chloroform:methanol:28% $NH_4OH$=20:5:1);

NMR ($CD_3OD$): δ 7.40–7.20 (m, 10H), 5.06 (s, 2H), 4.03 (t, J=5.0 Hz, 1H), 3.55–3.18 (m, 4H), 3.12 (t, J=6.6 Hz, 2H), 3.08–2.98 (m, 2H), 2.20–1.70 (m, 6H), 1.70–1.20 (m, 6H), 0.93 (t, J=7.2 Hz, 3H).

EXAMPLE 8(1)

1-propyl-2,5-dioxo-3-(2-methylpropyl)-1,4,9-triazaspiro[5.5]undecane

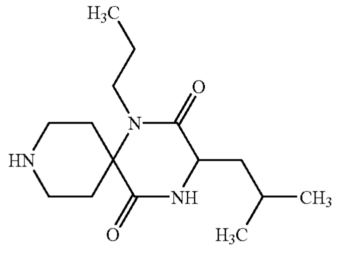

By the same procedure as described in Example 7→Example 8 using N-(t-butyloxycarbonyl)leucine instead of N-(t-butyloxycarbonyl)-N'-(benzyloxycarbonyl)-L-lysine, the compound of the present invention having the following physical data was obtained.

TLC: Rf 0.44 (chloroform:methanol:triethylamine=18:2:1);

NMR ($CD_3OD$): δ 3.99 (d, J=7.8, 4.4 Hz, 1H), 3.50–3.20 (m, 4H), 3.05–2.85 (m, 2H), 2.10–1.75 (m, 5H), 1.75–1.40 (m, 4H), 1.00–0.85 (m, 9H).

EXAMPLE 9

1-butyl-2,5-dioxo-3-(2-methylpropyl)-1,4,9-triazaspiro[5.5]undecane

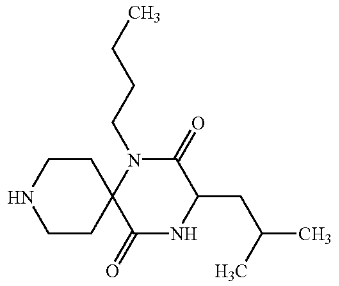

To a solution of the compound prepared in Example 6(7) (202 mg) in methanol (5 ml) was added 5% palladium on carbon (20 mg). Under an atmosphere of hydrogen, the reaction mixture was stirred for 3 hours at room temperature. The reaction mixture was filtrated through Celite (brand name). The filtrate was concentrated to give the compound of the present invention (127 mg) having the following physical data.

TLC: Rf 0.61 (chloroform:methanol:28% $NH_4OH$=20:5:1);

NMR ($CD_3OD$): δ 3.97 (dd, J=7.8 Hz, 4.5 Hz, 1H), 3.48–3.22 (m, 4H), 3.00–2.90 (m, 2H), 2.12–1.60 (m, 11H), 0.95 (t, J=7.2 Hz, 3H), 0.94 (d, J=6.6 Hz, 3H), 0.93 (d, J=6.6 Hz, 3H).

EXAMPLE 9(1)

1-butyl-2,5-dioxo-3-cyclohexylmethyl-1,4,9-triazaspiro[5.5]undecane

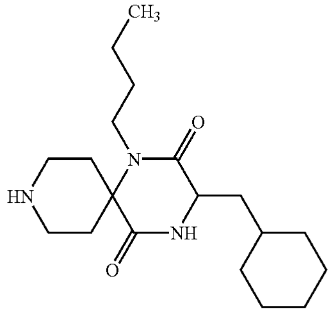

By the same procedure as described in Example 9 using the compound prepared in Example 6(8) instead of the compound prepared in Example 6(7), the compound of the present invention having the following physical data was obtained.

TLC: Rf 0.65 (chloroform:methanol:28% $NH_4OH$=20:5:1);

NMR ($CD_3OD$): δ 4.00 (dd, J=7.8 Hz, 4.5 Hz, 1H), 3.46–3.24 (m, 4H), 3.03–2.92 (m, 2H), 2.08–1.08 (m, 19H), 1.05–0.84 (m, 5H).

EXAMPLE 10

(3S)-1-propyl-2,5-dioxo-3-(4-(N-benzyloxycarbonyl) aminobutyl)-9-(4-dihydroxyboranephenylmethyl)-1,4,9-triazaspiro[5.5]undecane.hydrochloride

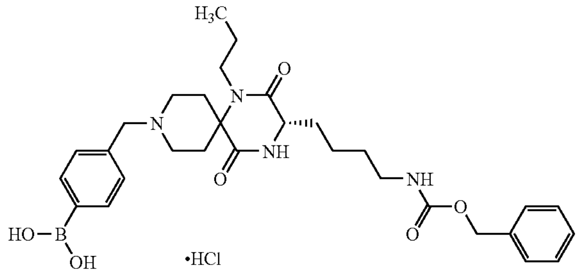

The compound prepared in Example 8 (70 mg) was dissolved in 1% acetic acid-dimethylformamide solution (2 ml). To this solution were added sodium triacetoxyborohydride (46 mg) and 4-formylphenylboronic acid (30 mg). The reaction mixture was stirred for 46 hours at room temperature. To the reaction mixture was added 10% acetic acid-methanol solution. This solution was loaded on cation-exchange resin (BondElut-SCX, Varian Co. Ltd., 0.6 mmol/g, 500 mg/3 ml), and the resin was washed with methanol, and furthermore, was eluted with 10% triethylamine-methanol solution. Only solution which was eluted with 10% triethylamine-methanol solution, was concentrated. The obtained residue was purified by column chromatography on silica gel (chloroform:methanol=1:0→30:1→10:1) to give the compound of the present invention (45 mg) having the following physical data.

TLC: Rf 0.24 (chloroform:methanol=10:1);

NMR ($CD_3OD$): δ 7.73 (br, 2H), 7.52 (br, 2H), 7.32 (m, 5H), 5.03 (s, 2H), 4.36 (s, 2H), 4.05 (t, J=4.8 Hz, 1H), 3.81 (m, 2H), 3.46 (m, 3H), 3.10 (t, J=6.6 Hz, 2H), 2.37 (br, 2H), 2.22 (br, 2H), 1.92–1.66 (m, 2H), 1.60–1.28 (m, 7H), 0.91 (t, J=7.5 Hz, 3H).

EXAMPLE 10(1)

(3S)-1-propyl-2,5-dioxo-3-(4-(N-benzyloxycarbonyl) aminobutyl)-9-(1,3-benzodioxalan-4-ylmethyl)-1,4,9-triazaspiro[5.5]undecane.hydrochloride

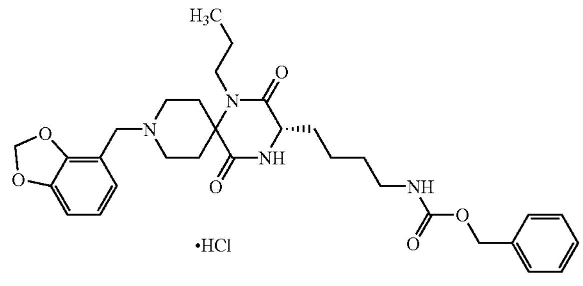

By the same procedure as described in Example 10 using 2,3-(methylenedioxy)benzaldehyde instead of 4-formylphenylboronic acid, the compound of the present invention having the following physical data was obtained.

TLC: Rf 0.25 (chloroform:methanol=10:1);

NMR ($CD_3OD$): δ 7.32 (m, 5H), 6.96 (m, 3H), 6.05 (s, 2H), 5.04 (s, 2H), 4.33 (s, 2H), 4.05 (t, J=4.5 Hz, 1H), 3.98–3.54 (m, 2H), 3.53 (m, 2H), 3.38 (m, 3H), 3.11 (t, J=6.6 Hz, 2H), 2.37 (br, 2H), 2.22 (br, 2H), 1.98–1.76 (m, 2H), 1.61–1.28 (m, 5H), 0.92 (t, J=7.2 Hz, 3H).

EXAMPLE 11

1-butyl-2,5-dioxo-3-(2-methylpropyl)-9-(1-(1,4-benzodioxan-6-yl)ethyl)-1,4,9-triazaspiro[5.5]undecane.hydrochloride

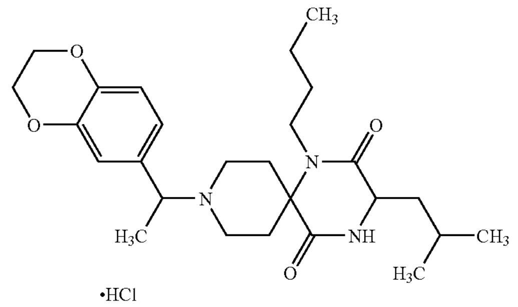

Under an atmosphere of argon, to a solution of the compound prepared in Example 9 (315 mg) in dichloromethane (5 ml) were added 1,4-benzodioxan-6-yl methyl ketone (285 mg), triethylamine (0.354 ml) and a solution of titanium tetrachloride in dichloromethane (1.0 M, 0.63 ml). The reaction mixture was stirred for 16 hours at room temperature. To the reaction mixture was added a solution of sodium cyanoborohydride (133 mg) in methanol (2 ml). The reaction mixture was stirred for 1 hour at room temperature. To the reaction mixture was added 2N aqueous solution of sodium hydroxide, and was extracted with ethyl acetate. The extract was dried over anhydrous magnesium sulfate and concentrated. The obtained residue was purified by column chromatography on silica gel (Fuji Silysia Chemical Ltd., BW235; chloroform:methanol=50:1). The obtained residue was dissolved in methanol. The solution was acidified by adding 1N hydrochloric acid, and was concentrated to give the compound of the present invention (176 mg) having the following physical data.

TLC: Rf 0.46 (chloroform:methanol=10:1);

NMR ($CD_3OD$): δ 7.04 (d, J=2.1 Hz, 1H), 6.98 (dd, J=8.4, 2.1 Hz, 1H), 6.92 (d, J=8.4 Hz, 1H), 4.40 (q, J=6.9 Hz, 1H), 4.26 (s, 4H), 3.98 (dd, J=8.1, 4.5 Hz, 1H), 3.82–3.17 (m, 6H), 2.55–2.04 (m, 4H), 1.87–1.28 (m, 10H), 1.04–0.85 (m, 9H).

EXAMPLE 11(1)

1-butyl-2,5-dioxo-3-(2-methylpropyl)-9-(1-(4-phenyloxyphenyl)ethyl)-1,4,9-triazaspiro[5.5]undecane-.hydrochloride

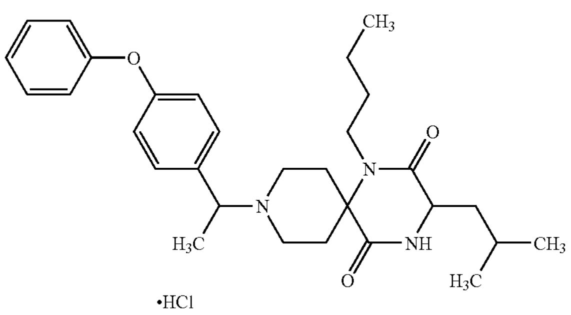

By the same procedure as described in Example 11 using 4-phenoxyacetophenone instead of 1,4-benzodioxan-6-yl methyl ketone, the compound of the present invention having the following physical data was obtained.

TLC: Rf 0.58, 0.62 (chloroform:methanol=10:1);

NMR ($CD_3OD$): δ 7.51 (d, J=8.7 Hz, 2H), 7.39 (dd, J=8.7, 7.5 Hz, 2H), 7.17 (t, J=7.5 Hz, 1H), 7.09–7.01 (m, 4H), 4.48 (m, 1H), 3.98 (dd, J=7.8, 4.8 Hz, 1H), 3.80–3.17 (m, 6H), 2.56–2.28 (m, 2H), 2.28–2.03 (m, 2H), 1.88–1.24 (m, 7H), 1.76 (d, J=6.9 Hz, 3H), 1.04–0.86 (m, 9H).

EXAMPLE 12

1-butyl-2,5-dioxo-3-cyclohexylmethyl-9-(1-(1,4-benzodioxan-6-yl)ethyl)-1,4,9-triazaspiro[5.5]undecane.hydrochloride

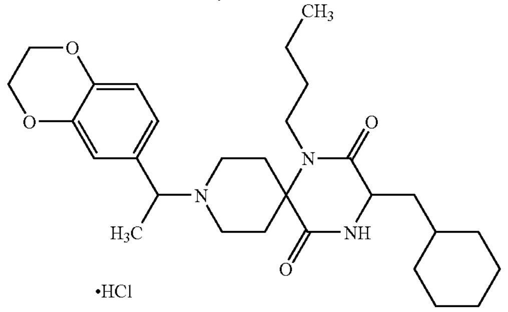

By the same procedure as described in Example 11 using the compound prepared in Example 9(1) instead of the compound prepared in Example 9, the compound of the present invention having the following physical data was obtained.

TLC: Rf 0.50 (chloroform:methanol=10:1);

NMR ($CD_3OD$): δ 7.02 (d, J=1.8 Hz, 1H), 6.96 (dd, J=8.4, 1.8 Hz, 1H), 6.92 (d, J=8.4 Hz, 1H), 4.39 (m, 1H), 4.26 (s, 4H), 4.01 (dd, J=7.5, 4.5 Hz, 1H), 3.80–3.20 (m, 6H), 2.50–2.02 (m, 4H), 1.82–1.13 (m, 18H), 1.04–0.83 (m, 5H).

EXAMPLE 13

(3S)-1-propyl-2,5-dioxo-3-(4-(N-benzyloxycarbonyl) aminobutyl)-9-allyl-1,4,9-triazaspiro[5.5]undecane.hydrochloride

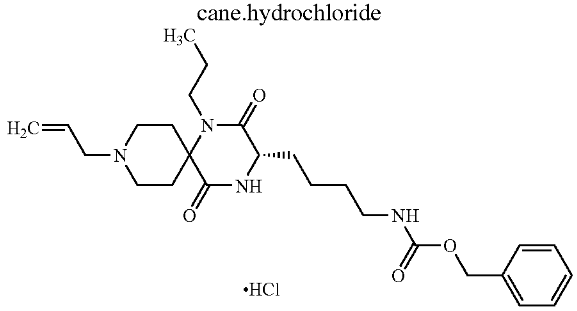

Under an atmosphere of argon, to a solution of the compound prepared in Example 7 (225 mg) in tetrahydrofuran (5 ml) was added tetrakis(triphenylphosphine)palladium (0) (51 mg) at room temperature. The reaction mixture was stirred for 16 hours at room temperature. The reaction mixture was loaded on cation-exchange resin (BondElut-SCX, Varian Co. Ltd., 0.6 mmol/g, 500 mg/3 ml), and the resin was washed with methanol, and furthermore, was eluted with 10% triethylamine-methanol solution (20 ml). Only solution which was eluted with 10% triethylamine-methanol solution, was concentrated. The obtained residue was purified by column chromatography on silica gel (chloroform:methanol=20:1) to give the compound of the present invention (122 mg) having the following physical data.

TLC: Rf 0.34 (chloroform:methanol=10:1);

NMR ($CD_3OD$): δ 7.34 (m, 5H), 6.00 (m, 1H), 5.62 (m, 1H), 5.61 (m, 1H), 5.06 (s, 2H), 4.07 (t, J=5.2 Hz, 1H), 3.77 (m, 4H), 3.44 (m, 4H), 3.12 (t, J=6.6 Hz, 2H), 2.39 (m, 2H), 2.20 (m, 2H), 1.84 (m, 2H), 1.54 (m, 4H), 1.37 (m, 2H), 0.94 (t, J=7.2 Hz, 3H).

EXAMPLE 14

(3S)-1-propyl-2,5-dioxo-3-(4-aminobutyl)-9-phenylethyl-1,4,9-triazaspiro[5.5]undecane

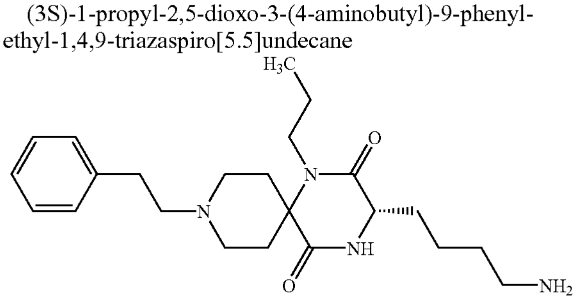

By the same procedure as described in Example 9 using the compound prepared in Example 5(11) instead of the compound prepared in Example 6(7), the compound of the present invention having the following physical data was obtained.

TLC: Rf 0.66 (chloroform:methanol:28% $NH_4OH$=20:5:1);

NMR ($CD_3OD$): δ 7.23 (m, 5H), 4.05 (t, J=5.2 Hz, 1H), 3.42 (m, 2H), 2.98 (m, 3H), 2.81 (m, 3H), 2.65 (m, 4H), 2.16 (m, 2H), 1.99 (m, 1H), 1.89 (m, 3H), 1.53 (m, 3H), 1.48 (m, 3H), 0.94 (t, J=7.2 Hz, 3H).

EXAMPLE 15

(3S)-1-propyl-2,5-dioxo-3-(4-(N-(4-phenyl)phenylcarbonyl)aminobutyl)-9-phenylethyl-1,4,9-triazaspiro[5.5]undecane.hydrochloride

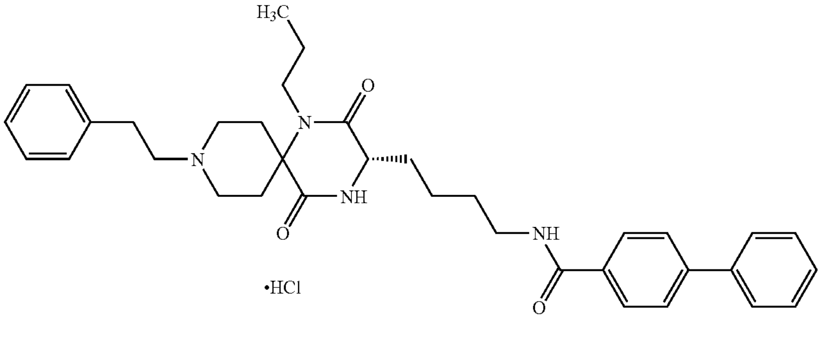

To a solution of the compound prepared in Example 14 (42 mg) in dichloroethane (2 ml) were added diisopropylethylamine (35 μl) and 4-phenylbenzoyl chloride (33 mg). The reaction mixture was stirred for 3 hours at room temperature. The reaction mixture was loaded on cation-exchange resin (BondElut-SCX, Varian Co. Ltd., 0.6 mmol/g, 500 mg/3 ml), and the resin was washed with methanol, and furthermore, was eluted with 10% triethylamine-methanol solution (20 ml). Only solution which was eluted with 10% triethylamine-methanol solution, was concentrated. The obtained residue was purified by column chromatography on silica gel (chloroform:methanol=10:0→10:1). To the obtained compound was added 4N hydrogen chloride-ethyl acetate solution to give the compound of the present invention (66 mg) having the following physical data.

TLC: Rf 0.50 (chloroform:methanol=10:1);

NMR ($CD_3OD$): δ 7.89 (d, J=8.1 Hz, 2H), 7.72 (d, J=8.1 Hz, 2H), 7.65 (d, J=7.2 Hz, 2H), 7.45 (t, J=7.2 Hz, 2H), 7.39–7.26 (m, 6H), 4.11 (m, 1H), 3.86–3.71 (m, 2H), 3.63–3.53 (m, 2H), 3.45–3.30 (m, 4H), 3.07 (m, 2H), 2.42 (br, 2H), 2.19 (m, 2H), 1.99–1.78 (m, 2H), 1.68–1.28 (m, 7H), 0.86 (t, J=7.5 Hz, 3H).

EXAMPLE 16

1-butyl-2,5-dioxo-3-cyclohexylmethyl-9-methyl-9-(1-(1,4-benzodioxan-6-yl)ethyl)-1,4,-diaza-9-azoniaspiro[5.5]undecane iodide

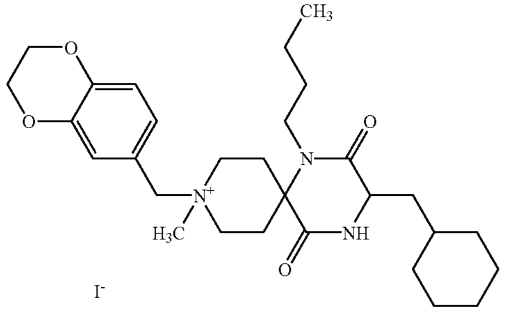

To a solution of the compound prepared in Example 2(1) (50 mg) in chloroform (2 ml) was added 1 N aqueous solution of sodium hydroxide (2 ml). The reaction mixture was stirred for 10 minutes at room temperature. The aqueous layer of the reaction mixture was removed. The organic layer was washed with water, dried over anhydrous magnesium sulfate and concentrated. To a solution of the obtained residue in acetone (2 ml) was added methyl iodide (118 μl). The reaction mixture was stirred for 18 hours at room temperature. The reaction mixture was concentrated. The obtained residue was solidified by diethyl ether to give the compound of the present invention (58 mg) having the following physical data.

TLC: Rf 0.23(ethyl acetate:acetic acid:water=8:1:1);

NMR ($CD_3OD$): δ 7.10–6.90 (m, 3H), 4.60+4.49 (s+s, 2H), 4.29 (s, 4H), 4.20–4.00 (m, 3H), 3.70–3.35 (m, 4H), 3.11+2.99 (s+s, 3H), 2.80–2.30 (m, 2H), 2.30–2.00 (m, 2H), 1.90–1.10 (m, 15H), 1.10–0.80 (m, 5H).

EXAMPLE 17

(3S)-3-(4-(N-benzyloxycarbonyl)aminobutyl)-2,5-dioxo-9-(2-hydroxy-2-phenylethyl)-1-propyl-1,4,9-triazaspiro[5.5]undecane

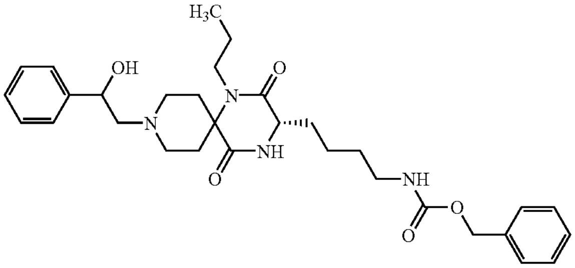

To a solution of the compound prepared in Example 8 (0.01 g) in 2-propanol (0.4 ml) was added styrene oxide (10 μl). The reaction mixture was refluxed for 4 hours. The reaction mixture was cooled to room temperature, and was loaded on ion exchange resin (OASIS MCX, Waters, 60 mg) washed with methanol (3 ml) prior to use. The resin was washed with methanol (2 ml), and was eluted with 10% triethylamine-methanol solution (2 ml). The elution was concentrated to give the compound of the present invention (13 mg) having the following physical data.

TLC: Rf 0.34 (chloroform:methanol=10:1);

NMR ($CD_3OD$): δ 7.40–7.20 (m, 10H), 5.06 (s, 2H), 4.03 (m, 1H), 3.40 (m, 2H), 3.12 (m, 2H), 3.10–2.60 (m, 6H), 2.50 (m, 1H), 2.40–2.00 (m, 2H), 2.00–1.70 (m, 4H), 1.70–1.20 (m, 6H), 0.93 (t, J=7.2 Hz, 3H).

EXAMPLE 18

(3S)-3-(4-(N-benzyloxycarbonyl) aminobutyl)-2,5-dioxo-9-(2-oxo-2-phenylethyl)-1-propyl-1,4,9-triazaspiro[5.5]undecane

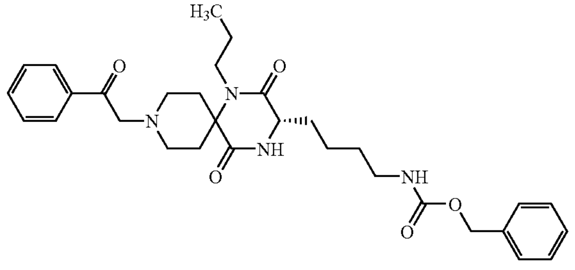

To a solution of the compound prepared in Example 8 (0.01 g) in dimethylformamide (0.4 ml) were added triethylamine (6 μl), and phenacyl bromide (9 mg). The reaction mixture was allowed to stand for 24 hours at room temperature. The reaction mixture was acidified by adding acetic acid (0.4 ml). The reaction mixture was loaded on ion exchange resin (OASIS MCX, Waters, 120 mg) washed with methanol (6 ml) prior to use. The resin was washed with methanol (2 ml), and was eluted with 10% triethylamine-methanol solution (4 ml). The elution was concentrated to give the compound of the present invention (12 mg) having the following physical data.

TLC: Rf 0.33 (chloroform:methanol=10:1);

NMR ($CD_3OD$): δ 8.01 (m, 2H), 7.54 (m, 3H), 7.33 (m, 5H), 5.05 (s, 2H), 4.02 (m, 1H), 4.00 (s, 2H), 3.44 (m, 2H), 3.12 (t, J=6.6 Hz, 2H), 2.95 (m, 2H), 2.40–2.10 (m, 2H), 2.00–1.70 (m, 5H), 1.68–1.20 (m, 7H), 0.94 (t, J=7.2 Hz, 3H).

EXAMPLE 19

(3S)-1-(2-methylpropyl)-2,5-dioxo-3-methyl-9-allyloxycarbonyl-1,4,9-triazaspiro[5.5]undecane

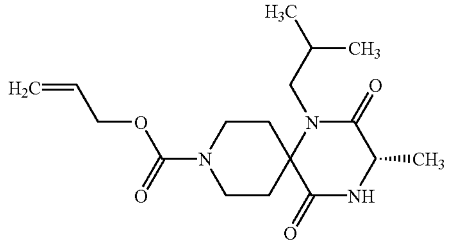

To a suspension of Resin (6) prepared in Reference Example 8 (300 mg) in tetrahydrofuran (1.5 ml) and methanol (1.5 ml) were added N-allyloxycarbonyl-4-piperidone (403 mg), isobutylamine (0.22 ml) and N-(t-butyloxycarbonyl)-L-alanine (381 mg) at room temperature. The reaction mixture was stirred for 20 hours at 65° C. The reaction mixture was cooled to room temperature and the resin was collected by filtration. The obtained resin was washed with tetrahydrofuran (3 ml×4) and dichloromethane (3 ml×5), and dried. The resin (384 mg) was obtained. To a suspension of the obtained resin (146 mg) in 1.5 M 2,6-lutidine-dichloromethane (2 ml) was added 1M trimethylsilyl trifluoromethanesulfonate-dichloromethane solution (2 ml). It was stirred for 30 minutes at room temperature. The reaction mixture was filtrated, and the resin was washed with dichloromethane (2 ml×3). The obtained resin was suspended in 1.5 M 2,6-lutidine-dichloromethane solution (2 ml) and 1 M trimethylsilyl trifluoromethanesulfonate-dichloromethane solution (2 ml) was added thereto. The reaction mixture was stirred for 30 minutes at room temperature. The resin was collected by filtration from the reaction solution, and was washed with dichloromethane (2 ml×4), methanol (2 ml×4) and dichloromethane (2 ml×4), dried and the resin was obtained. The obtained resin was suspended in 1.25M acetic acid-toluene solution (2 ml). The reaction mixture was stirred for 20 hours at 90° C. The reaction mixture was filtrated, and the resin was washed with toluene (2 ml×3) and methanol (2 ml×4). The filtrate was concentrated to give the compound of the present invention (19 mg) having the following physical data.

TLC: Rf 0.39 (chloroform:methanol=10:1);

MS (ESI, Pos., 20 V): 388 $(M+H)^+$;

HPLC condition: F;

HPLC retention time: 3.40 min;

NMR ($CD_3OD$): δ 5.98 (ddt, J=15.8, 10.4, 5.4 Hz, 1H), 5.30 (m, 1H), 5.21 (m, 1H), 4.59 (m, 2H), 4.20–4.00 (m, 3H), 3.85–3.60 (m, 2H), 3.41 (dd, J=14.2, 8.0 Hz, 1H), 3.18 (dd, J=14.2, 7.2 Hz, 1H), 2.10–1.70 (m, 5H), 1.43 (d, J=6.8 Hz, 3H), 0.89 (t, J=6.2 Hz, 6H).

EXAMPLE 19(1)

(3S)-1-(2-methylpropyl)-2,5-dioxo-3-methyl-9-(2-phenylethyl)-1,4,9-triazaspiro[5.5]undecane.acetate

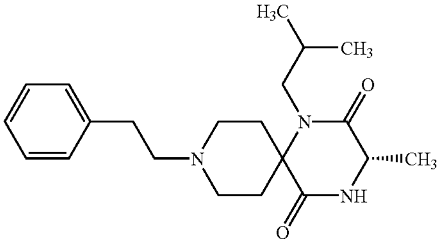

•$CH_3COOH$

By the same procedure as described in Example 19 using Resin (6) prepared in Reference Example 8 (200 mg), N-(2-phenylethyl)-4-piperidone (252 mg), isobutylamine (0.123 ml) and N-(t-butyloxycarbonyl)-L-alanine (235 mg), the compound of the present invention (50 mg) having the following physical data was obtained.

TLC: Rf 0.46 (chloroform:methanol=10:1);

MS (ESI, Pos., 20 V): 358 $(M+H)^+$;

HPLC condition: F;

HPLC retention time: 3.14 min;

NMR ($CD_3OD$): δ 7.40–7.20 (m, 5H), 4.15 (q, J=6.8 Hz, 1H), 3.65 (m, 1H), 3.55–3.35 (m, 3H), 3.25–3.05 (m, 3H), 3.05–2.90 (m, 3H), 2.50–2.05 (m, 4H), 1.98 (s, 3H), 1.92 (m, 1H), 1.43 (d, J=6.8 Hz, 3H), 0.92 (t, J=6.4 Hz, 6H).

EXAMPLE 19(2)

(3S)-1-(2-methylpropyl)-2,5-dioxo-3-(4-(N-benzyloxycarbonyl)aminobutyl)-9-(2-phenylethyl)-1,4,9-triazaspiro[5.5]undecane.acetate

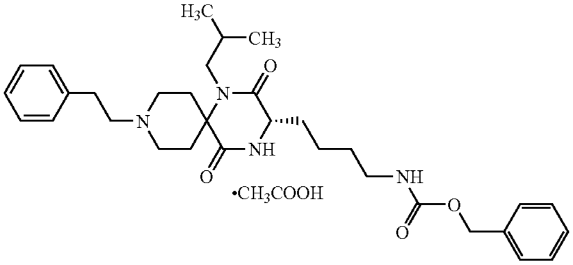

By the same procedure as described in Example 19 using Resin (6) prepared in Reference Example 8 (200 mg), N-(2-phenylethyl)-4-piperidone (252 mg), isobutylamine (0.123 ml) and N-(t-butyloxycarbonyl)-N'-(benzyloxycarbonyl)-L-lysine (472 mg), the compound of the present invention (71 mg) having the following physical data was obtained.

TLC: Rf 0.44 (chloroform:methanol=10:1);

MS (ESI, Pos., 20 V): 549 $(M+H)^+$;

HPLC condition: F;

HPLC retention time: 3.49 min;

NMR ($CD_3OD$): δ7.40–7.20 (m, 10H), 5.06 (s, 2H), 4.10 (m, 1H), 3.67 (m, 1H), 3.60–3.40 (m, 3H), 3.28–3.05 (m, 5H), 3.05–2.90 (m, 3H), 2.50–2.10 (m, 4H), 1.98 (s, 3H), 2.05–1.70 (m, 3H), 1.65–1.20 (m, 4H), 0.92 (t, J=6.2 Hz, 6H).

EXAMPLE 19(3)

(3S)-1-(1-benzyl piperidin-4-yl)-2,5-dioxo-3-methyl-9-(2-phenylethyl)-1,4,9-triazaspiro[5.5]undecane.2 acetate

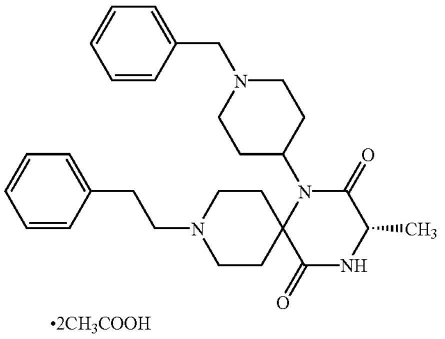

By the same procedure as described in Example 19 using Resin (6) prepared in Reference Example 8 (200 mg), N-(2-phenylethyl)-4-piperidone (252 mg), 4-amino-1-benzylpiperidine (0.253 ml) and N-(t-butyloxycarbonyl)-L-alanine (235 mg), the compound of the present invention (41 mg) having the following physical data was obtained.

TLC: Rf 0.10 (chloroform:methanol=10:1);

MS (ESI, Pos., 20 V): 475 $(M+H)^+$;

HPLC condition: F;

HPLC retention time: 3.09 min;

NMR ($CD_3OD$): δ 7.47 (m, 5H), 7.40–7.20 (m, 5H), 4.19 (s, 2H), 4.00 (q, J=6.8 Hz, 1H), 3.80–3.53 (m, 4H), 3.53–3, 35 (m, 4H), 3.30–3.15 (m, 2H), 3.15–2.90 (m, 3H), 2,55–2.30 (m, 3H), 2.30–2.00 (m, 2H), 1.98 (s, 6H), 1.85–1.70 (m, 3H), 1.42 (d, J=7.0 Hz, 3H).

EXAMPLE 19(4)

(3S)-1-(1-benzylpiperidin-4-yl)-2,5-dioxo-3-(4-(N-benzyloxycarbonyl)aminobutyl)-9-(2-phenylethyl)-1,4,9-triazaspiro[5.5]undecane.2 acetate

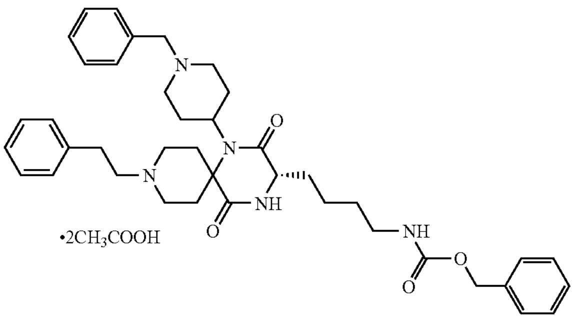

By the same procedure as described in Example 19 using Resin (6) prepared in Reference Example 8 (200 mg), N-(2-phenylethyl)-4-piperidone (252 mg), 4-amino-1-benzylpiperidine (0.253 ml) and N-(t-butyloxycarbonyl)-N'-(benzyloxycarbonyl)-L-lysine (472 mg), the compound of the present invention (33 mg) having the following physical data was obtained.

TLC: Rf 0.12 (chloroform:methanol=10:1);

MS (ESI, Pos., 20 V): 666 $(M+H)^+$;

HPLC condition: F;

HPLC retention time: 3.36 min;

NMR ($CD_3OD$): δ7.46 (m, 5H), 7.40–7.20 (m, 10H), 5.03 (s, 2H), 4.19 (s, 2H), 3.99 (m, 1H), 3.80–3.40 (m, 6H), 3.30–2.85 (m, 9H), 2.50–2.10 (m, 6H), 1.98 (s, 6H), 1.95–1.60 (m, 4H), 1.60–1.40 (m, 4H).

EXAMPLE 19(5)

(3S)1-(2,2-diphenylpropyl)-2,5-dioxo-3-methyl-9-(2-phenylethyl)-1,4,9-triazaspiro[5.5]undecane.acetate

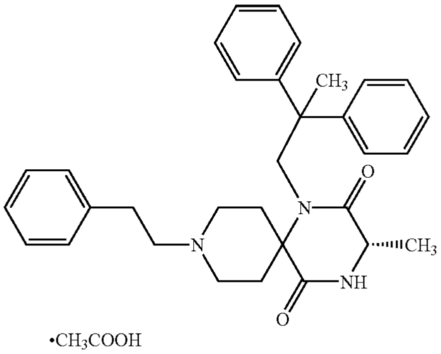

By the same procedure as described in Example 19 using Resin (6) prepared in Reference Example 8 (200 mg), N-(2-phenylethyl)-4-piperidone (252 mg), 2,2-diphenylpropylamine (307 mg) and N-(t-butyloxycarbonyl)-L-alanine (235 mg), the compound of the present invention (22 mg) having the following physical data was obtained.

TLC: Rf 0.42 (chloroform:methanol=10:1);

MS (ESI, Pos., 20 V): 496 $(M+H)^+$;

HPLC condition: F;

HPLC retention time: 3.58 min;

NMR ($CD_3OD$): δ 7.40–7.10 (m, 15H), 4.79 (m, 1H), 4.16 (m, 1H), 3.93 (m, 1H), 3.71 (s, 2H), 3.23 (m, 1H), 3.10–2.80 (m, 5H), 1.98 (s, 3H), 1.95–1.82 (m, 2H), 1.70–1.15 (m, 1H), 1.58 (s, 3H), 1.49 (d, J=6.8 Hz, 3H), 0.70 (m, 1H).

EXAMPLE 19(6)

(3S)-1-(2,2-diphenylpropyl)-2,5-dioxo-3-(4-(N-benzyloxycarbonyl)aminobutyl)-9-(2-phenylethyl)-1,4,9-triazaspiro[5.5]undecane.acetate

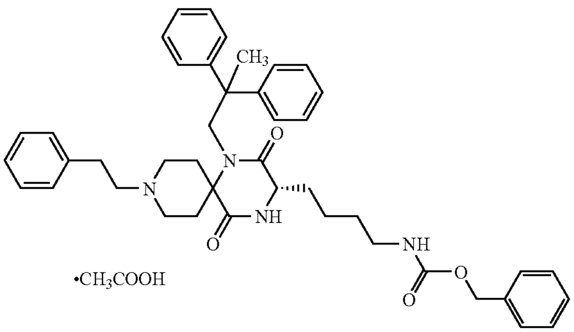

By the same procedure as described in Example 19 using Resin (6) prepared in Reference Example 8 (200 mg), N-(2-phenylethyl)-4-piperidone (252 mg), 2,2-diphenylpropylamine (307 mg) and N-(t-butyloxycarbonyl)-N'-(benzyloxycarbonyl)-L-lysine (472 mg), the compound of the present invention (18 mg) having the following physical data was obtained. MS (ESI, Pos., 20 V): 687 $(M+H)^+$;

HPLC condition: F;

HPLC retention time: 3.80 min;

TLC: Rf 0.46 (chloroform:methanol=10:1);

NMR ($CD_3OD$): δ 7.40–7.00 (m, 20H), 5.06 (s, 2H), 4.16 (m, 1H), 3.93 (m, 1H), 3.70 (s, 2H), 3.55 (m, 1H), 3.30–3.10 (m, 2H), 3.10–2.80 (m, 6H), 1.98 (s, 3H), 1.95–1.85 (m, 2H), 1.80 (s, 3H), 1.70–1.30 (m, 8H).

EXAMPLE 19(7)

(3S)-1-propyl-2,5-dioxo-3-(4-benzyloxyphenylmethyl)-9-(2-phenylethyl)-1,4,9-triazaspiro[5.5]undecane.acetate

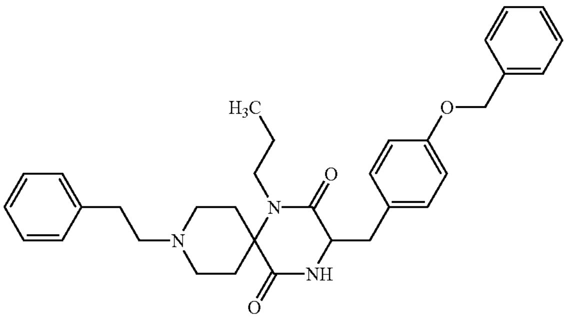

$\bullet CH_3COOH$

By the same procedure as described in Example 19 using Resin (6) prepared in Reference Example 8 (0.5 g), N-(2-phenylethyl)-4-piperidone (0.32 g), n-propylamine (0.13 ml) and N-(t-butyloxycarbonyl)-O-benzyl-L-tyrosine (0.58 g), the compound of the present invention (68 mg) having the following physical data was obtained.

TLC: Rf 0.51 (chloroform:methanol=10:1);

NMR ($CD_3OD$): δ 7.50–7.10 (m, 10H), 7.06 (d, J=8.8 Hz, 2H), 6.92 (d, J=8.8 Hz, 2H), 5.07 (s, 2H), 4.31 (m, 1H), 3.68 (m, 1H), 3.40 (m, 1H), 3.28–3.13 (m, 4H), 3.13–2.80 (m, 6H), 2.30–2.00 (m, 2H), 1.80–1.35 (m, 4H), 0.91 (t, J=7.2 Hz, 3H).

EXAMPLE 19(H1-1)~19(H13-62)

By the same procedure as described in Example 19 using Resin (6) prepared in Reference Example 8, the corresponding 4-piperidone derivatives, the corresponding amine derivatives and the corresponding amino acid derivatives, the compounds of the present invention, whose names were shown in the following Table 1A-1~13A-9, and whose structures were shown in the following Table 1B-1~13B-7, were obtained. Also, physical data of the above compounds were shown in the following Table 1C-1~13C-3.

In Tables in the present specification, $X_1$ is binding site of $R^1$, $X_2$ is binding site of $R^2$, $X_3$ is binding site of $R^3$, $X_4$ is binding site of $R^4$, $X_5$ is binding site of $R^5$.

For example, the structure of Example 19(H1-1) is shown as follows:

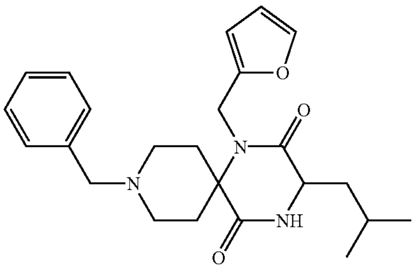

Furthermore, the conditions of high performance liquid chromatography (HPLC) in Tables in the present specification, were shown below:

Condition A
Column: YMC-Pack FL-ODS, 50×4.6 mm I.D., S-5um, 120A
Flow rate: 1 mL/min
Eluent
Component A: 0.1% trifluoroacetic acid aqueous solution
Component B: methanol The mixture ratio of A and B was fixed in 90/10 for 2 minutes from starting of measurement. The mixture ratio of A and B was linearly changed to 20/80 for 20 minutes. The mixture ratio of A and B was fixed in 20/80 for 5 minutes. The mixture ratio of A and B was linearly changed to 90/10 for 1 minute.

Condition B
Column: YMC-Pack FL-ODS, 50×4.6 mm I.D., S-5um, 120A
Flow rate: 1 mL/min
Eluent
Component A: 0.1% trifluoroacetic acid aqueous solution
Component B: methanol The mixture ratio of A and B was fixed in 80/20 for 2 minutes from starting of measurement. The mixture ratio of A and B was linearly changed to 20/80 for 20 minutes. The mixture ratio of A and B was fixed in 20/80 for 5 minutes. The mixture ratio of A and B was linearly changed to 80/20 for 1 minute.

Condition C
Column: YMC-Pack FL-ODS, 50×4.6 mm I.D., S-5um, 120A
Flow rate: 1 mL/min
Eluent
Component A: 0.1% trifluoroacetic acid aqueous solution
Component B: methanol The mixture ratio of A and B was fixed in 90/10 for 1 minute from starting of measurement. The mixture ratio of A and B was linearly changed to 10/90 for 16 minutes. The mixture ratio of A and B was fixed in 10/90 for 1 minute. The mixture ratio of A and B was linearly changed to 90/10 for 1 minute.

Condition D
Column: YMC-Pack FL-ODS, 50×4.6 mm I.D., S-5um, 120A
Flow rate: 1 mL/min
Eluent
Component A: 0.1% trifluoroacetic acid aqueous solution
Component B: methanol The mixture ratio of A and B was fixed in 90/10 at starting of measurement. The mixture ratio of A and B was linearly changed to 10/90 for 16 minutes. The mixture ratio of A and B was fixed in 10/90 for 0.5 minute. The mixture ratio of A and B was linearly changed to 90/10 for 0.5 minute.

Condition E

Column: YMC-Pack FL-ODS, 50×4.6 mm I.D., S-5um, 120A

Flow rate: 3 mL/min

Eluent

Component A: 0.1% trifluoroacetic acid aqueous solution

Component B: methanol

The mixture ratio of A and B was fixed in 90/10 at starting of measurement. The mixture ratio of A and B was linearly changed to 10/90 for 5 minutes. The mixture ratio of A and B was fixed in 10/90 for 0.5 minute. The mixture ratio of A and B was linearly changed to 90/10 for 0.1 minute.

Condition F

Column: Xterra™ MS $C_{18}$ 5 um, 4.6×50 mm I.D.

Flow rate: 3 mL/min

Eluent

Component A: 0.1% trifluoroacetic acid aqueous solution

Component B: 0.1% trifluoroacetic acid-acetonitrile solution

The mixture ratio of A and B was fixed in 95/5 for 0.5 minute from starting of measurement. The mixture ratio of A and B was linearly changed to 0/100 for 2.5 minute. The mixture ratio of A and B was fixed in 0/100 for 0.5 minute. The mixture ratio of A and B was linearly changed to 95/5 for 0.01 minute.

TABLE 1A-1

| Example No | Compound Name |
|---|---|
| 19(H1-1) | 1-(furan-2-ylmethyl)-2,5-dioxo-3-(2-methylpropyl)-9-benzyl-1,4,9-triazaspiro[5.5]undecane |
| 19(H1-2) | 1-(furan-2-ylmethyl)-2,5-dioxo-3-(indol-3-ylmethyl)-9-benzyl-1,4,9-triazaspiro[5.5]undecane |
| 19(H1-3) | 1-(furan-2-ylmethyl)-2,5-dioxo-3-benzyloxycarbonylmethyl-9-benzyl-1,4,9-triazaspiro[5.5]undecane |
| 19(H1-4) | 1-(tetrahydrofuran-2-ylmethyl)-2,5-dioxo-9-benzyl-1,4,9-triazaspiro[5.5]undecane |
| 19(H1-5) | 1-(tetrahydrofuran-2-ylmethyl)-2,5-dioxo-3-(2-methylpropyl)-9-benzyl-1,4,9-triazaspiro[5.5]undecane |
| 19(H1-6) | 1-(tetrahydrofuran-2-ylmethyl)-2,5-dioxo-3-phenylmethyl-9-benzyl-1,4,9-triazaspiro[5.5]undecane |
| 19(H1-7) | 1-(tetrahydrofuran-2-ylmethyl)-2,5-dioxo-3-(indol-3-ylmethyl)-9-benzyl-1,4,9-triazaspiro[5.5]undecane |
| 19(H1-8) | 1-(tetrahydrofuran-2-ylmethyl)-2,5-dioxo-3-benzyloxymethyl-9-benzyl-1,4,9-triazaspiro[5.5]undecane |
| 19(H1-9) | 1-(tetrahydrofuran-2-ylmethyl)-2,5-dioxo-3-benzyloxycarbonylmethyl-9-benzyl-1,4,9-triazaspiro[5.5]undecane |

TABLE 1A-2

| Example No | Compound Name |
|---|---|
| 19(H1-10) | 1-(tetrahydrofuran-2-ylmethyl)-2,5-dioxo-3-(4-(benzyloxycarbonylamino)butyl)-9-benzyl-1,4,9-triazaspiro[5.5]undecane |
| 19(H1-11) | 1-(2-(indol-3-yl)ethyl)-2,5-dioxo-3-(2-methylpropyl)-9-benzyl-1,4,9-triazaspiro[5.5]undecane |
| 19(H1-12) | 1(2-(indol-3-yl)ethyl)-2,5-dioxo-3-(indol-3-ylmethyl)-9-benzyl-1,4,9-triazaspiro[5.5]undecane |
| 19(H1-13) | 1-(2-(indol-3-yl)ethyl)-2,5-dioxo-3-benzyloxymethyl-9-benzyl-1,4,9-triazaspiro[5.5]undecane |
| 19(H1-14) | 1-benzyl-2,5-dioxo-9-benzyl-1,4,9-triazaspiro[5.5]undecane |
| 19(H1-15) | 1-benzyl-2,5-dioxo-3-(2-methylpropyl)-9-benzyl-1,4,9-triazaspiro[5.5]undecane |

TABLE 1A-2-continued

| Example No | Compound Name |
|---|---|
| 19(H1-16) | 1-benzyl-2,5-dioxo-3-phenylmethyl-9-benzyl-1,4,9-triazaspiro[5.5]undecane |
| 19(H1-17) | 1-benzyl-2,5-dioxo-3-(indol-3-ylmethyl)-9-benzyl-1,4,9-triazaspiro[5.5]undecane |
| 19(H1-18) | 1-benzyl-2,5-dioxo-3-benzyloxymethyl-9-benzyl-1,4,9-triazaspiro[5.5]undecane |

TABLE 1A-3

| Example No | Compound Name |
|---|---|
| 19(H1-19) | 1-benzyl-2,5-dioxo-3-benzyloxycarbonylmethyl-9-benzyl-1,4,9-triazaspiro[5.5]undecane |
| 19(H1-20) | 1-benzyl-2,5-dioxo-3-(4-(benzyloxycarbonylamino)butyl)-9-benzyl-1,4,9-triazaspiro[5.5]undecane |
| 19(H1-21) | 1-(2,2-diphenylethyl)-2,5-dioxo-9-benzyl-1,4,9-triazaspiro[5.5]undecane |
| 19(H1-22) | 1-(2,2-diphenylethyl)-2,5-dioxo-3-(2-methylpropyl)-9-benzyl-1,4,9-triazaspiro[5.5]undecane |
| 19(H1-23) | 1-(2,2-diphenylethyl)-2,5-dioxo-3-phenylmethyl-9-benzyl-1,4,9-triazaspiro[5.5]undecane |
| 19(H1-24) | 1-(2,2-diphenylethyl)-2,5-dioxo-3-(indol-3-ylmethyl)-9-benzyl-1,4,9-triazaspiro[5.5]undecane |
| 19(H1-25) | 1-(2,2-diphenylethyl)-2,5-dioxo-3-benzyloxymethyl-9-benzyl-1,4,9-triazaspiro[5.5]undecane |
| 19(H1-26) | 1-(2,2-diphenylethyl)-2,5-dioxo-3-benzyloxycarbonylmethyl-9-benzyl-1,4,9-triazaspiro[5.5]undecane |
| 19(H1-27) | 1-(2,2-diphenylethyl)-2,5-dioxo-3-(4-(benzyloxycarbonylamino)butyl)-9-benzyl-1,4,9-triazaspiro[5.5]undecane |

TABLE 1A-4

| Example No | Compound Name |
|---|---|
| 19(H1-28) | 1-(2-phenylethyl)-2,5-dioxo-9-benzyl-1,4,9-triazaspiro[5.5]undecane |
| 19(H1-29) | 1-(2-phenylethyl)-2,5-dioxo-3-(2-methylpropyl)-9-benzyl-1,4,9-triazaspiro[5.5]undecane |
| 19(H1-30) | 1-(2-phenylethyl)-2,5-dioxo-3-phenylmethyl-9-benzyl-1,4,9-triazaspiro[5.5]undecane |
| 19(H1-31) | 1-(2-phenylethyl)-2,5-dioxo-3-(indol-3-ylmethyl)-9-benzyl-1,4,9-triazaspiro[5.5 ]undecane |
| 19(H1-32) | 1-(2-phenylethyl)-2,5-dioxo-3-benzyloxymethyl-9-benzyl-1,4,9-triazaspiro[5.5]undecane |
| 19(H1-33) | 1-(2-phenylethyl)-2,5-dioxo-3-benzyloxycarbonylmethyl-9-benzyl-1,4,9-triazaspiro[5.5]undecane |
| 19(H1-34) | 1-(2-phenylethyl)-2,5-dioxo-3-(4-(benzyloxycarbonylamino)butyl)-9-benzyl-1,4,9-triazaspiro[5.5]undecane |
| 19(H1-35) | 1-propyl-2,5-dioxo-9-benzyl-1,4,9-triazaspiro[5.5]undecane |
| 19(H1-36) | 1-propyl-2,5-dioxo-3-(2-methylpropyl)-9-benzyl-1,4,9-triazaspiro[5.5]undecane |
| 19(H1-37) | 1-propyl-2,5-dioxo-3-phenylmethyl-9-benzyl-1,4,9-triazaspiro[5.5]undecane |

TABLE 1A-5

| Example No | Compound Name |
|---|---|
| 19(H1-38) | 1-propyl-2,5-dioxo-3-(indol-3-ylmethyl)-9-benzyl-1,4,9-triazaspiro[5.5]undecane |
| 19(H1-39) | 1-propyl-2,5-dioxo-3-benzyloxymethyl-9-benzyl-1,4,9-triazaspiro[5.5[undecane |
| 19(H1-40) | 1-propyl-2,5-dioxo-3-benzyloxycarbonylmethyl-9-benzyl-1,4,9-triazaspiro[5.5]undecane |

TABLE 1A-5-continued

| Example No | Compound Name |
|---|---|
| 19(H1-41) | 1-propyl-2,5-dioxo-3-(4-(benzyloxycarbonylamino)butyl)-9-benzyl-1,4,9-triazaspiro[5.5]undecane |
| 19(H1-42) | 1-(2-(t-butyloxycarbonyl)ethyl)-2,5-dioxo-9-benzyl-1,4,9-triazaspiro[5.5]undecane |
| 19(H1-43) | 1-(2-(t-butyloxycarbonyl)ethyl)-2,5-dioxo-3-(2-methyl-propyl)-9-benzyl-1,4,9-triazaspiro[5.5]undecane |
| 19(H1-44) | 1-(2-(t-butyloxycarbonyl)ethyl)-2,5-dioxo-3-phenylmethyl-9-benzyl-1,4,9-triazaspiro[5.5]undecane |
| 19(H1-45) | 1-(2-(t-butyloxycarbonyl)ethyl)-2,5-dioxo-3-(indol-3-yl-methyl)-9-benzyl-1,4,9-triazaspiro[5.5 ]undecane |
| 19(H1-46) | 1-(2-(t-butyloxycarbonyl)ethyl)-2,5-dioxo-3-benzyloxy-methyl-9-benzyl-1,4,9-triazaspiro[5.5]undecane |

TABLE 1A-6

| Example No | Compound Name |
|---|---|
| 19(H1-47) | 1-(2-(t-butyloxycarbonyl)ethyl)-2,5-dioxo-3-benzyloxycarbonylmethyl-9-benzyl-1,4,9-triazaspiro[5.5]undecane |
| 19(H1-48) | 1-(2-(t-butyloxycarbonyl)ethyl)-2,5-dioxo-3-(4-(benzyloxycarbonylamino)butyl)-9-benzyl-1,4,9-triazaspiro[5.5]undecane |
| 19(H1-49) | 1-(1-benzylpyrrolidin-3-yl)-2,5-dioxo-9-benzyl-1,4,9-triazaspiro[5.5]undecane |
| 19(H1-50) | 1-(1-benzylpyrrolidin-3-yl)-2,5-dioxo-3-(2-methylpropyl)-9-benzyl-1,4,9-triazaspiro[5.5]undecane |
| 19(H1-51) | 1-(1-benzylpyrrolidin-3-yl)-2,5-dioxo-3-phenylmethyl-9-benzyl-1,4,9-triazaspiro[5.5]undecane |
| 19(H1-52) | 1-(1-benzylpyrrolidin-3-yl)-2,5-dioxo-3-(indol-3-ylmethyl)-9-benzyl-1,4,9-triazaspiro[5.5]undecane |
| 19(H1-53) | 1-(1-benzylpyrrolidin-3-yl)-2,5-dioxo-3-benzyloxymethyl-9-benzyl-1,4,9-triazaspiro[5.5]undecane |
| 19(H1-54) | 1-(1-benzylpyrrolidin-3-yl)-2,5-dioxo-3-benzyloxycarbonylmethyl-9-benzyl-1,4,9-triazaspiro[5.5]undecane |

TABLE 1A-7

| Example No | Compound Name |
|---|---|
| 19(H1-55) | 1-(1-benzylpyrrolidin-3-yl)-2,5-dioxo-3-(4-benzyloxycarbonylamino)butyl)-9-benzyl-1,4,9-triazaspiro[5.5]undecane |

TABLE 2A-1

| Example No | Compound Name |
|---|---|
| 19(H2-1) | 1-(furan-2-ylmethyl)-2,5-dioxo-9-(2-phenylethyl)-1,4,9-triazaspiro[5.5]undecane |
| 19(H2-2) | 1-(furan-2-ylmethyl)-2,5-dioxo-3-(indol-3-ylmethyl)-9-(2-phenylethyl)-1,4,9-triazaspiro[5.5]undecane |
| 19(H2-3) | 1-(furan-2-ylmethyl)-2,5-dioxo-3-benzyloxymethyl-9-(2-phenylethyl)-1,4,9-triazaspiro[5.5]undecane |
| 19(H2-4) | 1-(furan-2-ylmethyl)-2,5-dioxo-3-benzyloxycarbonylmethyl-9-(2-phenylethyl)-1,4,9-triazaspiro[5.5]undecane |
| 19(H2-5) | 1-(furan-2-ylmethyl)-2,5-dioxo-3-(4-(benzyloxycarbonylamino)butyl)-9-(2-phenylethyl)-1,4,9-triazaspiro[5.5]undecane |
| 19(H2-6) | 1-(tetrahydrofuran-2-ylmethyl)-2,5-dioxo-9-(2-phenylethyl)-1,4,9-triazaspiro[5.5]undecane |

TABLE 2A-1-continued

| Example No | Compound Name |
|---|---|
| 19(H2-7) | 1-(tetrahydrofuran-2-ylmethyl)-2,5-dioxo-3-(2-methylpropyl)-9-(2-phenylethyl)-1,4,9-triazaspiro[5.5]undecane |
| 19(H2-8) | 1-(tetrahydrofuran-2-ylmethyl)-2,5-dioxo-3-phenylmethyl-9-(2-phenylethyl)-1,4,9-triazaspiro[5.5]undecane |

TABLE 2A-2

| Example No | Compound Name |
|---|---|
| 19(H2-9) | 1-(tetrahydrofuran-2-ylmethyl)-2,5-dioxo-3-(indol-3-ylmethyl)-9-(2-phenylethyl)-1,4,9-triazaspiro[5.5] undecane |
| 19(H2-10) | 1-(tetrahydrofuran-2-ylmethyl)-2,5-dioxo-3-benzyloxymethyl-9-(2-phenylethyl)-1,4,9-triazaspiro[5.5]undecane |
| 19(H2-11) | 1-(tetrahydrofuran-2-ylmethyl)-2,5-dioxo-3-benzyloxycarbonylmethyl-9-(2-phenylethyl)-1,4,9-triazaspiro[5.5]undecane |
| 19(H2-12) | 1-(tetrahydrofuran-2-ylmethyl)-2,5-dioxo-3-(4-(benzyloxycarbonylamino)butyl)-9-(2-phenylethyl)-1,4,9-triazaspiro[5.5]undecane |
| 19(H2-13) | 1-(2-(indol-3-yl)ethyl)-2,5-dioxo-9-(2-phenylethyl)-1,4,9-triazaspiro[5.5]undecane |
| 19(H2-14) | 1-(2-(indol-3-yl)ethyl)-2,5-dioxo-3-(2-methylpropyl)-9-(2-phenylethyl)-1,4,9-triazaspiro[5.5]undecane |
| 19(H2-15) | 1-(2-(indol-3-yl)ethyl)-2,5-dioxo-3-phenylmethyl-9-(2-phenylethyl)-1,4,9-triazaspiro[5.5]undecane |
| 19(H2-16) | 1-(2-(indol-3-yl)ethyl)-2,5-dioxo-3-(indol-3-ylmethyl)-9-(2-phenylethyl)-1,4,9-triazaspiro[5.5]undecane |

TABLE 2A-3

| Example No | Compound Name |
|---|---|
| 19(H2-17) | 1-(2-(indol-3-yl)ethyl)-2,5-dioxo-3-benzyloxymethyl-9-(2-phenylethyl)-1,4,9-triazaspiro[5.5]undecane |
| 19(H2-18) | 1-(2-(indol-3-yl)ethyl)-2,5-dioxo-3-benzyloxycarbonylmethyl-9-(2-phenylethyl)-1,4,9-triazaspiro[5.5]undecane |
| 19(H2-19) | 1-(2-(indol-3-yl)ethyl)-2,5-dioxo-3-(4-(benzyloxycarbonylamino)butyl)-9-(2-phenylethyl)-1,4,9-triazaspiro[5.5]undecane |
| 19(H2-20) | 1-benzyl-2,5-dioxo-9-(2-phenylethyl)-1,4,9-triazaspiro[5.5]undecane |
| 19(H2-21) | 1-benzyl-2,5-dioxo-3-(2-methylpropyl)-9-(2-phenylethyl)-1,4,9-triazaspiro[5.5]undecane |
| 19(H2-22) | 1-benzyl-2,5-dioxo-3-phenylmethyl-9-(2-phenylethyl)-1,4,9-triazaspiro[5.5]undecane |
| 19(H2-23) | 1-benzyl-2,5-dioxo-3-(indol-3-ylmethyl)-9-(2-phenylethyl)-1,4,9-triazaspiro[5.5]undecane |
| 19(H2-24) | 1-benzyl-2,5-dioxo-3-benzyloxymethyl-9-(2-phenylethyl)-1,4,9-triazaspiro[5.5]undecane |
| 19(H2-25) | 1-benzyl-2,5-dioxo-3-benzyloxycarbonylmethyl-9-(2-phenylethyl)-1,4,9-triazaspiro[5.5]undecane |

TABLE 2A-4

| Example No | Compound Name |
|---|---|
| 19(H2-26) | 1-benzyl-2,5-dioxo-3-(4-(benzyloxycarbonylamino)butyl)-9-(2-phenylethyl)-1,4,9-triazaspiro[5.5]undecane |
| 19(H2-27) | 1-(2,2-diphenylethyl)-2,5-dioxo-9-(2-phenylethyl)-1,4,9-triazaspiro[5.5]undecane |

TABLE 2A-4-continued

| Example No | Compound Name |
|---|---|
| 19(H2-28) | 1-(2,2-diphenylethyl)-2,5-dioxo-3-(2-methylpropyl)-9-(2-phenylethyl)-1,4,9-triazaspiro[5.5]undecane |
| 19(H2-29) | 1-(2,2-diphenylethyl)-2,5-dioxo-3-phenylmethyl-9-(2-phenylethyl)-1,4,9-triazaspiro[5.5]undecane |
| 19(H2-30) | 1-(2,2-diphenylethyl)-2,5-dioxo-3-(indol-3-ylmethyl)-9-(2-phenylethyl)-1,4,9-triazaspiro[5.5]undecane |
| 19(H2-31) | 1-(2,2-diphenylethyl)-2,5-dioxo-3-benzyloxymethyl-9-(2-phenylethyl)-1,4,9-triazaspiro[5.5]undecane |
| 19(H2-32) | 1-(2,2-diphenylethyl)-2,5-dioxo-3-benzyloxycarbonylmethyl-9-(2-phenylethyl)-1,4,9-triazaspiro[5.5]undecane |
| 19(H2-33) | 1-(2,2-diphenylethyl)-2,5-dioxo-3-(4-(benzyloxycarbonylamino)butyl)-9-(2-phenylethyl)-1,4,9-triazaspiro[5.5]undecane |
| 19(H2-34) | 1-(2-phenylethyl)-2,5-dioxo-9-(2-phenylethyl)-1,4,9-triazaspiro[5.5]undecane |

TABLE 2A-5

| Example No | Compound Name |
|---|---|
| 19(H2-35) | 1-(2-phenylethyl)-2,5-dioxo-3-(2-methylpropyl)-9-(2-phenylethyl)-1,4,9-triazaspiro[5.5]undecane |
| 19(H2-36) | 1-(2-phenylethyl)-2,5-dioxo-3-phenylmethyl-9-(2-phenylethyl)-1,4,9-triazaspiro[5.5]undecane |
| 19(H2-37) | 1-(2-phenylethyl)-2,5-dioxo-3-(indol-3-ylmethyl)-9-(2-phenylethyl)-1,4,9-triazaspiro[5.5]undecane |
| 19(H2-38) | 1-(2-phenylethyl)-2,5-dioxo-3-benzyloxymethyl-9-(2-phenylethyl)-1,4,9-triazaspiro[5.5]undecane |
| 19(H2-39) | 1-(2-phenylethyl)-2,5-dioxo-3-benzyloxycarbonylmethyl-9-(2-phenylethyl)-1,4,9-triazaspiro[5.5]undecane |
| 19(H2-40) | 1-(2-phenylethyl)-2,5-dioxo-3-(4-(benzyloxycarbonylamino)butyl)-9-(2-phenylethyl)-1,4,9-triazaspiro[5.5]undecane |
| 19(H2-41) | 1-propyl-2,5-dioxo-9-(2-phenylethyl)-1,4,9-triazaspiro[5.5]undecane |
| 19(H2-42) | 1-propyl-2,5-dioxo-3-(2-methylpropyl)-9-(2-phenylethyl)-1,4,9-triazaspiro[5.5]undecane |
| 19(H2-43) | 1-propyl-2,5-dioxo-3-phenylmethyl-9-(2-phenylethyl)-1,4,9-triazaspiro[5.5]undecane |

TABLE 2A-6

| Example No | Compound Name |
|---|---|
| 19(H2-44) | 1-propyl-2,5-dioxo-3-(indol-3-ylmethyl)-9-(2-phenylethyl)-1,4,9-triazaspiro[5.5]undecane |
| 19(H2-45) | 1-propyl-2,5-dioxo-3-benzyloxymethyl-9-(2-phenylethyl)-1,4,9-triazaspiro[5.5]undecane |
| 19(H2-46) | 1-propyl-2,5-dioxo-3-benzyloxycarbonylmethyl-9-(2-phenylethyl)-1,4,9-triazaspiro[5.5]undecane |
| 19(H2-47) | 1-propyl-2,5-dioxo-3-(4-(benzyloxycarbonylamino)butyl)-9-(2-phenylethyl)-1,4,9-triazaspiro[5.5]undecane |
| 19(H2-48) | 1-(2-(t-butyloxycarbonyl)ethyl)-2,5-dioxo-9-(2-phenylethyl)-1,4,9-triazaspiro[5.5]undecane |
| 19(H2-49) | 1-(2-(t-butyloxycarbonyl)ethyl)-2,5-dioxo-3-(2-methylpropyl)-9-(2-phenylethyl)-1,4,9-triazaspiro[5.5]undecane |
| 19(H2-50) | 1-(2-(t-butyloxycarbonyl)ethyl)-2,5-dioxo-3-phenylmethyl-9-(2-phenylethyl)-1,4,9-triazaspiro[5.5]undecane |
| 19(H2-51) | 1-(2-(t-butyloxycarbonyl)ethyl)-2,5-dioxo-3-(indol-3-ylmethyl)-9-(2-phenylethyl)-1,4,9-triazaspiro[5.5] undecane |

TABLE 2A-7

| Example No | Compound Name |
|---|---|
| 19(H2-52) | 1-(2-(t-butyloxycarbonyl)ethyl)-2,5-dioxo-3-benzyloxymethyl-9-(2-phenylethyl)-1,4,9-triazaspiro[5.5]undecane |
| 19(H2-53) | 1-(2-(t-butyloxycarbonyl)ethyl)-2,5-dioxo-3-benzyloxycarbonylmethyl-9-(2-phenylethyl)-1,4,9-triazaspiro[5.5]undecane |
| 19(H2-54) | 1-(2-(t-butyloxycarbonyl)ethyl)-2,5-dioxo-3-(4-(benzyloxycarbonylamino)butyl)-9-(2-phenylethyl)-1,4,9-triazaspiro[5.5]undecane |
| 19(H2-55) | 1-(1-benzylpyrrolidin-3-yl)-2,5-dioxo-9-(2-phenylethyl)-1,4,9-triazaspiro[5.5]undecane |
| 19(H2-56) | 1-(1-benzylpyrrolidin-3-yl)-2,5-dioxo-3-(2-methylpropyl)-9-(2-phenylethyl)-1,4,9-triazaspiro[5.5]undecane |
| 19(H2-57) | 1-(1-benzylpyrrolidin-3-yl)-2,5-dioxo-3-phenylmethyl-9-(2-phenylethyl)-1,4,9-triazaspiro[5.5]undecane |
| 19(H2-58) | 1-(1-benzylpyrrolidin-3-yl)-2,5-dioxo-3-(indol-3-ylmethyl)-9-(2-phenylethyl)-1,4,9-triazaspiro[5.5]undecane |
| 19(H2-59) | 1-(1-benzylpyrrolidin-3-yl)-2,5-dioxo-3-benzyloxymethyl-9-(2-phenylethyl)-1,4,9-triazaspiro[5.5]undecane |

TABLE 2A-8

| Example No | Compound Name |
|---|---|
| 19(H2-60) | 1-(1-benzylpyrrolidin-3-yl)-2,5-dioxo-3-benzyloxycarbonylmethyl-9-(2-phenylethyl)-1,4,9-triazaspiro[5.5]undecane |
| 19(H2-61) | 1-(1-benzylpyrrolidin-3-yl)-2,5-dioxo-3-(4-(benzyloxycarbonylamino)butyl)-9-(2-phenylethyl)-1,4,9-triazaspiro[5.5]undecane |

TABLE 3A-1

| Example No | Compound Name |
|---|---|
| 19(H3-1) | 1-(furan-2-ylmethyl)-2,5-dioxo-9-(3-phenylpropyl)-1,4,9-triazaspiro[5.5]undecane |
| 19(H3-2) | 1-(furan-2-ylmethyl)-2,5-dioxo-3-(2-methylpropyl)-9-(3-phenylpropyl)-1,4,9-triazaspiro[5.5]undecane |
| 19(H3-3) | 1-(furan-2-ylmethyl)-2,5-dioxo-3-benzyl-9-(3-phenylpropyl)-1,4,9-triazaspiro[5.5]undecane |
| 19(H3-4) | 1-(furan-2-ylmethyl)-2,5-dioxo-3-(indol-3-ylmethyl)-9-(3-phenylpropyl)-1,4,9-triazaspiro[5.5]undecane |
| 19(H3-5) | 1-(furan-2-ylmethyl)-2,5-dioxo-3-benzyloxymethyl-9-(3-phenylpropyl)-1,4,9-triazaspiro[5.5]undecane |
| 19(H3-6) | 1-(furan-2-ylmethyl)-2,5-dioxo-3-benzyloxycarbonylmethyl-9-(3-phenylpropyl)-1,4,9-triazaspiro[5.5]undecane |
| 19(H3-7) | 1-(furan-2-ylmethyl)-2,5-dioxo-3-(4-(benzyloxycarbonylamino)butyl)-9-(3-phenylpropyl)-1,4,9-triazaspiro[5.5]undecane |
| 19(H3-8) | 1-(tetrahydrofuran-2-ylmethyl)-2,5-dioxo-9-(3-phenylpropyl)-1,4,9-triazaspiro[5.5]undecane |
| 19(H3-9) | 1-(tetrahydrofuran-2-ylmethyl)-2,5-dioxo-3-(2-methylpropyl)-9-(3-phenylpropyl)-1,4,9-triazaspiro[5.5]undecane |

TABLE 3A-2

| Example No | Compound Name |
|---|---|
| 19(H3-10) | 1-(tetrahydrofuran-2-ylmethyl)-2,5-dioxo-3-phenylmethyl-9-(3-phenylpropyl)-1,4,9-triazaspiro[5.5]undecane |
| 19(H3-11) | 1-(tetrahydrofuran-2-ylmethyl)-2,5-dioxo-3-(indol-3-ylmethyl)-9-(3-phenylpropyl)-1,4,9-triazaspiro[5.5]undecane |

TABLE 3A-2-continued

| Example No | Compound Name |
|---|---|
| 19(H3-12) | 1-(tetrahydrofuran-2-ylmethyl)-2,5-dioxo-3-benzyloxymethyl-9-(3-phenylpropyl)-1,4,9-triazaspiro[5.5]undecane |
| 19(H3-13) | 1-(tetrahydrofuran-2-ylmethyl)-2,5-dioxo-3-benzyloxycarbonylmethyl-9-(3-phenylpropyl)-1,4,9-triazaspiro[5.5]undecane |
| 19(H3-14) | 1-(tetrahydrofuran-2-ylmethyl)-2,5-dioxo-3-(4-(benzyloxycarbonylamino)butyl)-9-(3-phenylpropyl)-1,4,9-triazaspiro[5.5]undecane |
| 19(H3-15) | 1-(2-(indol-3-yl)ethyl)-2,5-dioxo-9-(3-phenylpropyl)-1,4,9-triazaspiro[5.5]undecane |
| 19(H3-16) | 1-(2-(indol-3-yl)ethyl)-2,5-dioxo-3-(2-methylpropyl)-9-(3-phenylpropyl)-1,4,9-triazaspiro[5.5]undecane |
| 19(H3-17) | 1-(2-(indol-3-yl)ethyl)-2,5-dioxo-3-phenylmethyl-9-(3-phenylpropyl)-1,4,9-triazaspiro[5.5]undecane |

TABLE 3A-3

| Example No | Compound Name |
|---|---|
| 19(H3-18) | 1-(2-indol-3-yl)ethyl)-2,5-dioxo-3-(indol-3-ylmethyl)-9-(3-phenylpropyl)-1,4,9-triazaspiro[5.5]undecane |
| 19(H3-19) | 1-(2-(indol-3-yl)ethyl)-2,5-dioxo-3-benzyloxymethyl-9-(3-phenylpropyl)-1,4,9-triazaspiro[5.5]undecane |
| 19(H3-20) | 1-(2-(indol-3-yl)ethyl)-2,5-dioxo-3-benzyloxycarbonylmethyl-9-(3-phenylpropyl)-1,4,9-triazaspiro[5.5]undecane |
| 19(H3-21) | 1-(2-(indol-3-yl)ethyl)-2,5-dioxo-3-(4-(benzyloxycarbonylamino)butyl)-9-(3-phenylpropyl)-1,4,9-triazaspiro[5.5]undecane |
| 19(H3-22) | 1-benzyl-2,5-dioxo-9-(3-phenylpropyl)-1,4,9-triazaspiro[5.5]undecane |
| 19(H3-23) | 1-benzyl-2,5-dioxo-3-(2-methylpropyl)-9-(3-phenylpropyl)-1,4,9-triazaspiro[5.5]undecane |
| 19(H3-24) | 1-benzyl-2,5-dioxo-3-phenylmethyl-9-(3-phenylpropyl)-1,4,9-triazaspiro[5.5]undecane |
| 19(H3-25) | 1-benzyl-2,5-dioxo-3-(indol-3-ylmethyl)-9-(3-phenylpropyl)-1,4,9-triazaspiro[5.5]undecane |

TABLE 3A-4

| Example No | Compound Name |
|---|---|
| 19(H3-26) | 1-benzyl-2,5-dioxo-3-benzyloxymethyl-9-(3-phenylpropyl)-1,4,9-triazaspiro[5.5]undecane |
| 19(H3-27) | 1-benzyl-2,5-dioxo-3-benzyloxycarbonylmethyl-9-(3-phenylpropyl)-1,4,9-triazaspiro[5.5]undecane |
| 19(H3-28) | 1-benzyl-2,5-dioxo-3-(4-(benzyloxycarbonylamino)butyl)-9-(3-phenylpropyl)-1,4,9-triazaspiro[5.5]undecane |
| 19(H3-29) | 1-(2,2-diphenylethyl)-2,5-dioxo-9-(3-phenylpropyl)-1,4,9-triazaspiro[5.5]undecane |
| 19(H3-30) | 1-(2,2-diphenylethyl)-2,5-dioxo-3-(2-methylpropyl)-9-(3-phenylpropyl)-1,4,9-triazaspiro[5.5]undecane |
| 19(H3-31) | 1-(2,2-diphenylethl)-2,5-dioxo-3-phenylmethyl-9-(3-phenylpropyl)-1,4,9-triazaspiro[5.5]undecane |
| 19(H3-32) | 1-(2,2-diphenylethyl)-2,5-dioxo-3-(indol-3-ylmethyl)-9-(3-phenylpropyl)-1,4,9-triazaspiro[5.5]undecane |
| 19(H3-33) | 1-(2,2-diphenylethyl)-2,5-dioxo-3-benzyloxymethyl-9-(3-phenylpropyl)-1,4,9-triazaspiro[5.5]undecane |
| 19(H3-34) | 1-(2,2-diphenylethyl)-2,5-dioxo-3-benzyloxycarbonylmethyl-9-(3-phenylpropyl)-1,4,9-triazaspiro[5.5]undecane |

TABLE 3A-5

| Example No | Compound Name |
|---|---|
| 19(H3-35) | 1-(2,2-diphenylethyl)-2,5-dioxo-3-(4-(benzyloxycarbonylamino)butyl)-9-(3-phenylpropyl)-1,4,9-triazaspiro[5.5]undecane |
| 19(H3-36) | 1-(2-phenylethyl)-2,5-dioxo-9-(3-phenylpropyl)-1,4,9-triazaspiro[5.5]undecane |
| 19(H3-37) | 1-(2-phenylethyl)-2,5-dioxo-3-(2-methylpropyl)-9-(3-phenylpropyl)-1,4,9-triazaspiro[5.5]undecane |
| 19(H3-38) | 1-(2-phenylethyl)-2,5-dioxo-3-phenylmethyl-9-(3-phenylpropyl)-1,4,9-triazaspiro[5.5]undecane |
| 19(H3-39) | 1-(2-phenylethyl)-2,5-dioxo-3-(indol-3-ylmethyl)-9-(3-phenylpropyl)-1,4,9-triazaspiro[5.5]undecane |
| 19(H3-40) | 1-(2-phenylethyl)-2,5-dioxo-3-benzyloxymethyl-9-(3-phenylpropyl)-1,4,9-triazaspiro[5.5]undecane |
| 19(H3-41) | 1-(2-phenylethyl)-2,5-dioxo-3-benzyloxycarbonylmethyl-9-(3-phenylpropyl)-1,4,9-triazaspiro[5.5]undecane |
| 19(H3-42) | 1-(2-phenylethyl)-2,5-dioxo-3-(4-(benzyloxycarbonylamino)butyl)-9-(3-phenylpropyl)-1,4,9-triazaspiro[5.5]undecane |
| 19(H3-43) | 1-propyl-2,5-dioxo-9-(3-phenylpropyl)-1,4,9-triazaspiro[5.5]undecane |

TABLE 3A-6

| Example No | Compound Name |
|---|---|
| 19(H3-44) | 1-propyl-2,5-dioxo-3-(2-methylpropyl)-9-(3-phenylpropyl)-1,4,9-triazaspiro[5.5]undecane |
| 19(H3-45) | 1-propyl-2,5-dioxo-3-phenylmethyl-9-(3-phenylpropyl)-1,4,9-triazaspiro[5.5]undecane |
| 19(H3-46) | 1-propyl-2,5-dioxo-3-(indol-3-ylmethyl)-9-(3-phenylpropyl)-1,4,9-triazaspiro[5.5]undecane |
| 19(H3-47) | 1-propyl-2,5-dioxo-3-benzyloxymethyl-9-(3-phenylpropyl)-1,4,9-triazaspiro[5.5]undecane |
| 19(H3-48) | 1-propyl-2,5-dioxo-3-benzyloxycarbonylmethyl-9-(3-phenylpropyl)-1,4,9-triazaspiro[5.5]undecane |
| 19(H3-49) | 1-propyl-2,5-dioxo-3-(4-benzyloxycarbonylamino)butyl)-9-(3-phenylpropyl)-1,4,9-triazaspiro[5.5]undecane |
| 19(H3-50) | 1-(2-(t-butyloxycarbonyl)ethyl)-2,5-dioxo-9-(3-phenylpropyl)-1,4,9-triazaspiro[5.5]undecane |
| 19(H3-51) | 1-(2-(t-butyloxycarbonyl)ethyl)-2,5-dioxo-3-(2-methylpropyl)-9-(3-phenylpropyl)-1,4,9-triazaspiro[5.5]undecane |
| 19(H3-52) | 1-(2-(t-butyloxycarbonyl)ethyl)-2,5-dioxo-3-phenylmethyl-9-(3-phenylpropyl)-1,4,9-triazaspiro[5.5]undecane |

TABLE 3A-7

| Example No | Compound Name |
|---|---|
| 19(H3-53) | 1-(2-(t-butyloxycarbonyl)ethyl)-2,5-dioxo-3-(indol-3-ylmethyl)-9-(3-phenylpropyl)-1,4,9-triazaspiro[5.5]undecane |
| 19(H3-54) | 1-(2-(t-butyloxycarbonyl)ethyl)-2,5-dioxo-3-benzyloxymethyl-9-(3-phenylpropyl)-1,4,9-triazaspiro[5.5]undecane |
| 19(H3-55) | 1-(2-(t-butyloxycarbonyl)ethyl)-2,5-dioxo-3-benzyloxycarbonylmethyl-9-(3-phenylpropyl)-1,4,9-triazaspiro[5.5]undecane |
| 19(H3-56) | 1-(2-(t-butyloxycarbonyl)ethyl)-2,5-dioxo-3-(4-(benzyloxycarbonylamino)butyl)-9-(3-phenylpropyl)-1,4,9-triazaspiro[5.5]undecane |
| 19(H3-57) | 1-(1-benzylpyrrolidin-3-yl)-2,5-dioxo-9-(3-phenylpropyl)-1,4,9-triazaspiro[5.5]undecane |
| 19(H3-58) | 1-(1-benzylpyrrolidin-3-yl)-2,5-dioxo-3-(2-methylpropyl)-9-(3-phenylpropyl)-1,4,9-triazaspiro[5.5]undecane |
| 19(H3-59) | 1-(1-benzylpyrrolidin-3-yl)-2,5-dioxo-3-phenylmethyl-9-(3-phenylpropyl)-1,4,9-triazaspiro[5.5]undecane |

TABLE 3A-7-continued

| Example No | Compound Name |
|---|---|
| 19(H3-60) | 1-(1-benzylpyrrolidin-3-yl)-2,5-dioxo-3-(indol-3-ylmethyl)-9-(3-phenylpropyl)-1,4,9-triazaspiro[5.5]undecane |

TABLE 3A-8

| Example No | Compound Name |
|---|---|
| 19(H3-61) | 1-(1-benzylpyrrolidin-3-yl)-2,5-dioxo-3-benzyloxymethyl-9-(3-phenylpropyl)-1,4,9-triazaspiro[5.5]undecane |
| 19(H3-62) | 1-(1-benzylpyrrolidin-3-yl)-2,5-dioxo-3-benzyloxycarbonylmethyl-9-(3-phenylpropyl)-1,4,9-triazaspiro[5.5]undecane |
| 19(H3-63) | 1-(1-benzylpyrrolidin-3-yl)-2,5-dioxo-3-(4-(benzyloxycarbonylamino)butyl)-9-(3-phenylpropyl)-1,4,9-triazaspiro[5.5]undecane |

TABLE 4A-1

| Example No | Compound Name |
|---|---|
| 19(H4-1) | 1-(furan-2-ylmethyl)-2,5-dioxo-9-(4-phenylbutyl)-1,4,9-triazaspiro[5.5]undecane |
| 19(H4-2) | 1-(furan-2-ylmethyl)-2,5-dioxo-3-(2-methylpropyl)-9-(4-phenylbutyl)-1,4,9-triazaspiro[5.5]undecane |
| 19(H4-3) | 1-(furan-2-ylmethyl)-2,5-dioxo-3-benzyl-9-(4-phenylbutyl)-1,4,9-triazaspiro[5.5]undecane |
| 19(H4-4) | 1-(furan-2-ylmethyl)-2,5-dioxo-3-(indol-3-ylmethyl)-9-(4-phenylbutyl)-1,4,9-triazaspiro[5.5]undecane |
| 19(H4-5) | 1-(furan-2-ylmethyl)-2,5-dioxo-3-benzyloxymethyl-9-(4-phenylbutyl)-1,4,9-triazaspiro[5.5]undecane |
| 19(H4-6) | 1-(furan-2-ylmethyl)-2,5-dioxo-3-benzyloxycarbonylmethyl-9-(4-phenylbutyl)-1,4,9-triazaspiro[5.5]undecane |
| 19(H4-7) | 1-(furan-2-ylmethyl)-2,5-dioxo-3-(4-(benzyloxycarbonylamino)butyl)-9-(4-phenylbutyl)-1,4,9-triazaspiro[5.5]undecane |
| 19(H4-8) | 1-(tetrahydrofuran-2-ylmethyl)-2,5-dioxo-9-(4-phenylbutyl)-1,4,9-triazaspiro[5.5]undecane |
| 19(H4-9) | 1-(tetrahydrofuran-2-ylmethyl)-2,5-dioxo-3-(2-methylpropyl)-9-(4-phenylbutyl)-1,4,9-triazaspiro[5.5]undecane |

TABLE 4A-2

| Example No | Compound Name |
|---|---|
| 19(H4-10) | 1-(tetrahydrofuran-2-ylmethyl)-2,5-dioxo-3-phenylmethyl-9-(4-phenylbutyl)-1,4,9-triazaspiro[5.5]undecane |
| 19(H4-11) | 1-(tetrahydrofuran-2-ylmethyl)-2,5-dioxo-3-(indol-3-ylmethyl)-9-(4-phenylbutyl)-1,4,9-triazaspiro[5.5]undecane |
| 19(H4-12) | 1-(tetrahydrofuran-2-ylmethyl)-2,5-dioxo-3-benzyloxymethyl-9-(4-phenylbutyl)-1,4,9-triazaspiro[5.5]undecane |
| 19(H4-13) | 1-(tetrahydrofuran-2-ylmethyl)-2,5-dioxo-3-benzyloxycarbonylmethyl-9-(4-phenylbutyl)-1,4,9-triazaspiro[5.5]undecane |
| 19(H4-14) | 1-(tetrahydrofuran-2-ylmethyl)-2,5-dioxo-3-(4-(benzyloxycarbonylamino)butyl)-9-(4-phenylbutyl)-1,4,9-triazaspiro[5.5]undecane |
| 19(H4-15) | 1-(2-(indol-3-yl)ethyl)-2,5-dioxo-9-(4-phenylbutyl)-1,4,9-triazaspiro[5.5]undecane |
| 19(H4-16) | 1-(2-(indol-3-yl)ethyl)-2,5-dioxo-3-(2-methylpropyl)-9-(4-phenylbutyl)-1,4,9-triazaspiro[5.5]undecane |

TABLE 4A-2-continued

| Example No | Compound Name |
|---|---|
| 19(H4-17) | 1-(2-(indol-3-yl)ethyl)-2,5-dioxo-3-phenylmethyl-9-(4-phenylbutyl)-1,4,9-triazaspiro[5.5]undecane |

TABLE 4A-3

| Example No | Compound Name |
|---|---|
| 19(H4-18) | 1-(2-(indol-3-yl)ethyl)-2,5-dioxo-3-(indol-3-ylmethyl)-9-(4-phenylbutyl)-1,4,9-triazaspiro[5.5]undecane |
| 19(H4-19) | 1-(2-(indol-3-yl)ethyl)-2,5-dioxo-3-benzyloxymethyl-9-(4-phenylbutyl)-1,4,9-triazaspiro[5.5]undecane |
| 19(H4-20) | 1-(2-(indol-3-yl)ethyl)-2,5-dioxo-3-benzyloxycarbonylmethyl-9-(4-phenylbutyl)-1,4,9-triazaspiro[5.5]undecane |
| 19(H4-21) | 1-(2-(indol-3-yl)ethyl)-2,5-dioxo-3-(4-(benzyloxycarbonylamino)butyl)-9-(4-phenylbutyl)-1,4,9-triazaspiro[5.5]undecane |
| 19(H4-22) | 1-benzyl-2,5-dioxo-9-(4-phenylbutyl)-1,4, 9-triazaspiro[5.5]undecane |
| 19(H4-23) | 1-benzyl-2,5-dioxo-3-(2-methylpropyl)-9-(4-phenylbutyl)-1,4,9-triazaspiro[5.5]undecane |
| 19(H4-24) | 1-benzyl-2,5-dioxo-3-phenylmethyl-9-(4-phenylbutyl)-1,4,9-triazaspiro[5.5]undecane |
| 19(H4-25) | 1-benzyl-2,5-dioxo-3-(indol-3-ylmethyl)-9-(4-phenylbutyl)-1,4,9-triazaspiro[5.5]undecane |
| 19(H4-26) | 1-benzyl-2,5-dioxo-3-benzyloxymethyl-9-(4-phenylbutyl)-1,4,9-triazaspiro[5.5]undecane |

TABLE 4A-4

| Example No | Compound Name |
|---|---|
| 19(H4-27) | 1-benzyl-2,5-dioxo-3-benzyloxycarbonylmethyl-9-(4-phenylbutyl)-1,4,9-triazaspiro[5.5]undecane |
| 19(H4-28) | 1-benzyl-2,5-dioxo-3-(4-(benzyloxycarbonylamino)butyl)-9-(4-phenylbutyl)-1,4,9-triazaspiro[5.5]undecane |
| 19(H4-29) | 1-(2,2-diphenylethyl)-2,5-dioxo-9-(4-phenylbutyl)-1,4,9-triazaspiro[5.5]undecane |
| 19(H4-30) | 1-(2,2-diphenylethyl)-2,5-dioxo-3-(2-methylpropyl)-9-(4-phenylbutyl)-1,4,9-triazaspiro[5.5]undecane |
| 19(H4-31) | 1-(2,2-diphenylethyl)-2,5-dioxo-3-phenylmethyl-9-(4-phenylbutyl)-1,4,9-triazaspiro[5.5]undecane |
| 19(H4-32) | 1-(2,2-diphenylethyl)-2,5-dioxo-3-(indol-3-ylmethyl)-9-(4-phenylbutyl)-1,4,9-triazaspiro[5.5]undecane |
| 19(H4-33) | 1-(2,2-diphenylethyl)-2,5-dioxo-3-benzyloxymethyl-9-(4-phenylbutyl)-1,4,9-triazaspiro[5.5]undecane |
| 19(H4-34) | 1-(2,2-diphenylethyl)-2,5-dioxo-3-benzyloxycarbonylmethyl-9-(4-phenylbutyl)-1,4,9-triazaspiro[5.5]undecane |
| 19(H4-35) | 1-(2,2-diphenylethyl)-2,5-dioxo-3-(4-(benzyloxycarbonylamino)butyl)-9-(4-phenylbutyl)-1,4,9-triazaspiro[5.5]undecane |

TABLE 4A-5

| Example No | Compound Name |
|---|---|
| 19(H4-36) | 1-(2-phenylethyl)-2,5-dioxo-9-(4-phenylbutyl)-1,4,9-triazaspiro[5.5]undecane |

TABLE 4A-5-continued

| Example No | Compound Name |
|---|---|
| 19(H4-37) | 1-(2-phenylethyl)-2,5-dioxo-3-(2-methylpropyl)-9-(4-phenylbutyl)-1,4,9-triazaspiro[5.5]undecane |
| 19(H4-38) | 1-(2-phenylethyl)-2,5-dioxo-3-phenylmethyl-9-(4-phenylbutyl)-1,4,9-triazaspiro[5.5]undecane |
| 19(H4-39) | 1-(2-phenylethyl)-2,5-dioxo-3-(indol-3-ylmethyl)-9-(4-phenylbutyl)-1,4,9-triazaspiro[5.5]undecane |
| 19(H4-40) | 1-(2-phenylethyl)-2,5-dioxo-3-benzyloxymethyl-9-(4-phenylbutyl)-1,4,9-triazaspiro[5.5]undecane |
| 19(H4-41) | 1-(2-phenylethyl)-2,5-dioxo-3-benzyloxycarbonylmethyl-9-(4-phenylbutyl)-1,4,9-triazaspiro[5.5]undecane |
| 19(H4-42) | 1-(2-phenylethyl)-2,5-dioxo-3-(4-(benzyloxycarbonylamino)butyl)-9-(4-phenylbutyl)-1,4,9-triazaspiro[5.5]undecane |
| 19(H4-43) | 1-propyl-2,5-dioxo-9-(4-phenylbutyl)-1,4,9-triazaspiro[5.5]undecane |
| 19(H4-44) | 1-propyl-2,5-dioxo-3-(2-methylpropyl)-9-(4-phenylbutyl)-1,4,9-triazaspiro[5.5]undecane |

TABLE 4A-6

| Example No | Compound Name |
|---|---|
| 19(H4-45) | 1-propyl-2,5-dioxo-3-phenylmethyl-9-(4-phenylbutyl)-1,4,9-triazaspiro[5.5]undecane |
| 19(H4-46) | 1-propyl-2,5-dioxo-3-(indol-3-ylmethyl)-9-(4-phenylbutyl)-1,4,9-triazaspiro[5.5]undecane |
| 19(H4-47) | 1-propyl-2,5-dioxo-3-benzyloxymethyl-9-(4-phenylbutyl)-1,4,9-triazaspiro[5.5]undecane |
| 19(H4-48) | 1-propyl-2,5-dioxo-3-benzyloxycarbonylmethyl-9-(4-phenylbutyl)-1,4,9-triazaspiro[5.5]undecane |
| 19(H4-49) | 1-propyl-2,5-dioxo-3-(4-(benzyloxycarbonylamino)butyl)-9-(4-phenylbutyl)-1,4,9-triazaspiro[5.5]undecane |
| 19(H4-50) | 1-(2-(t-butyloxycarbonyl)ethyl)-2,5-dioxo-9-(4-phenylbutyl)-1,4,9-triazaspiro[5.5]undecane |
| 19(H4-51) | 1-(2-(t-butyloxycarbonyl)ethyl)-2,5-dioxo-3-(2-methylpropyl)-9-(4-phenylbutyl)-1,4,9-triazaspiro[5.5]undecane |
| 19(H4-52) | 1-(2-(t-butyloxycarbonyl)ethyl)-2,5-dioxo-3-phenylmethyl-9-(4-phenylbutyl)-1,4,9-triazaspiro[5.5]undecane |
| 19(H4-53) | 1-(2-(t-butyloxycarbonyl)ethyl)-2,5-dioxo-3-(indol-3-ylmethyl)-9-(4-phenylbutyl)-1,4,9-triazaspiro[5.5]undecane |

TABLE 4A-7

| Example No | Compound Name |
|---|---|
| 19(H4-54) | 1-(2-(t-butyloxycarbonyl)ethyl)-2,5-dioxo-3-benzyloxymethyl-9-(4-phenylbutyl)-1,4,9-triazaspiro[5.5]undecane |
| 19(H4-55) | 1-(2-(t-butyloxycarbonyl)ethyl)-2,5-dioxo-3-benzyloxycarbonylmethyl-9-(4-phenylbutyl)-1,4,9-triazaspiro[5.5]undecane |
| 19(H4-56) | 1-(2-(t-butyloxycarbonyl)ethyl)-2,5-dioxo-3-(4-(benzyloxycarbonylamino)butyl)-9-(4-phenylbutyl)-1,4,9-triazaspiro[5.5]undecane |
| 19(H4-57) | 1-(1-benzylpyrrolidin-3-yl)-2,5-dioxo-9-(4-phenylbutyl)-1,4,9-triazaspiro[5.5]undecane |
| 19(H4-58) | 1-(1-benzylpyrrolidin-3-yl)-2,5-dioxo-3-(2-methylpropyl)-9-(4-phenylbutyl)-1,4,9-triazaspiro[5.5]undecane |
| 19(H4-59) | 1-(1-benzylpyrrolidin-3-yl)-2,5-dioxo-3-phenylmethyl-9-(4-phenylbutyl)-1,4,9-triazaspiro[5.5]undecane |
| 19(H4-60) | 1-(1-benzylpyrrolidin-3-yl)-2,5-dioxo-3-(indol-3-ylmethyl)-9-(4-phenylbutyl)-1,4,9-triazaspiro[5.5]undecane |
| 19(H4-61) | 1-(1-benzylpyrrolidin-3-yl)-2,5-dioxo-3-benzyloxymethyl-9-(4-phenylbutyl)-1,4,9-triazaspiro[5.5]undecane |

TABLE 4A-8

| Example No | Compound Name |
|---|---|
| 19(H4-62) | 1-(1-benzylpyrrolidin-3-yl)-2,5-dioxo-3-benzyloxycarbonylmethyl-9-(4-phenylbutyl)-1,4,9-triazaspiro[5.5]undecane |
| 19(H4-63) | 1-(1-benzylpyrrolidin-3-yl)-2,5-dioxo-3-(4-(benzyloxycarbonylamino)butyl)-9-(4-phenylbutyl)-1,4,9-triazaspiro[5.5]undecane |

TABLE 5A-1

| Example No | Compound Name |
|---|---|
| 19(H5-1) | 1-(furan-2-ylmethyl)-2,5-dioxo-9-phenyl-1,4,9-triazaspiro[5.5]undecane |
| 19(H5-2) | 1-(furan-2-ylmethyl)-2,5-dioxo-3-(2-methylpropyl)-9-phenyl-1,4,9-triazaspiro[5.5]undecane |
| 19(H5-3) | 1-(furan-2-ylmethyl)-2,5-dioxo-3-benzyl-9-phenyl-1,4,9-triazaspiro[5.5]undecane |
| 19(H5-4) | 1-(furan-2-ylmethyl)-2,5-dioxo-3-(indol-3-ylmethyl)-9-phenyl-1,4,9-triazaspiro[5.5]undecane |
| 19(H5-5) | 1-(furan-2-ylmethyl)-2,5-dioxo-3-benzyloxymethyl-9-phenyl-1,4,9-triazaspiro[5.5]undecane |
| 19(H5-6) | 1-(furan-2-ylmethyl)-2,5-dioxo-3-benzyloxycarbonylmethyl-9-phenyl-1,4,9-triazaspiro[5.5]undecane |
| 19(H5-7) | 1-(furan-2-ylmethyl)-2,5-dioxo-3-(4-(benzyloxycarbonylamino)butyl)-9-phenyl-1,4,9-triazaspiro[5.5]undecane |
| 19(H5-8) | 1-(tetrahydrofuran-2-ylmethyl)-2,5-dioxo-9-phenyl-1,4,9-triazaspiro[5.5]undecane |
| 19(H5-9) | 1-(tetrahydrofuran-2-ylmethyl)-2,5-dioxo-3-(2-methylpropyl)-9-phenyl-1,4,9-triazaspiro[5.5]undecane |

TABLE 5A-2

| Example No | Compound Name |
|---|---|
| 19(H5-10) | 1-(tetrahydrofuran-2-ylmethyl)-2,5-dioxo-3-phenylmethyl-9-phenyl-1,4,9-triazaspiro[5.5]undecane |
| 19(H5-11) | 1-(tetrahydrofuran-2-ylmethyl)-2,5-dioxo-3-(indol-3-ylmethyl)-9-phenyl-1,4,9-triazaspiro[5.5]undecane |
| 19(H5-12) | 1-(tetrahydrofuran-2-ylmethyl)-2,5-dioxo-3-benzyloxymethyl-9-phenyl-1,4,9-triazaspiro[5.5]undecane |
| 19(H5-13) | 1-(tetrahydrofuran-2-ylmethyl)-2,5-dioxo-3-benzyloxycarbonylmethyl-9-phenyl-1,4,9-triazaspiro[5.5]undecane |
| 19(H5-14) | 1-(tetrahydrofuran-2-ylmethyl)-2,5-dioxo-3-(4-(benzyloxycarbonylamino)butyl)-9-phenyl-1,4,9-triazaspiro[5.5]undecane |
| 19(H5-15) | 1-(2-(indol-3-yl) ethyl)-2,5-dioxo-9-phenyl-1,4,9-triazaspiro[5.5]undecane |
| 19(H5-16) | 1-(2-(indol-3-yl)ethyl)-2,5-dioxo-3-(2-methylpropyl)-9-phenyl-1,4,9-triazaspiro[5.5]undecane |
| 19(H5-17) | 1-(2-(indol-3-yl)ethyl)-2,5-dioxo-3-phenylmethyl-9-phenyl-1,4,9-triazaspiro[5.5]undecane |
| 19(H5-18) | 1-(2-(indol-3-yl)ethyl)-2,5-dioxo-3-(indol-3-ylmethyl)-9-phenyl-1,4,9-triazaspiro[5.5]undecane |

TABLE 5A-3

| Example No | Compound Name |
| --- | --- |
| 19(H5-19) | 1-(2-(indol-3-yl)ethyl)-2,5-dioxo-3-benzyloxymethyl-9-phenyl-1,4,9-triazaspiro[5.5]undecane |
| 19(H5-20) | 1-(2-(indol-3-yl)ethyl)-2,5-dioxo-3-benzyloxycarbonylmethyl-9-phenyl-1,4,9-triazaspiro[5.5]undecane |
| 19(H5-21) | 1-(2-(indol-3-yl)ethyl)-2,5-dioxo-3-(4-(benzyloxycarbonylamino)butyl)-9-phenyl-1,4,9-triazaspiro[5.5]undecane |
| 19(H5-22) | 1-benzyl-2,5-dioxo-9-phenyl-1,4,9-triazaspiro[5.5]undecane |
| 19(H5-23) | 1-benzyl-2,5-dioxo-3-(2-methylpropyl)-9-phenyl-1,4,9-triazaspiro[5.5]undecane |
| 19(H5-24) | 1-benzyl-2,5-dioxo-3-phenylmethyl-9-phenyl-1,4,9-triazaspiro[5.5]undecane |
| 19(H5-25) | 1-benzyl-2,5-dioxo-3-(indol-3-ylmethyl)-9-phenyl-1,4,9-triazaspiro[5.5]undecane |
| 19(H5-26) | 1-benzyl-2,5-dioxo-3-benzyloxymethyl-9-phenyl-1,4,9-triazaspiro[5.5]undecane |
| 19(H5-27) | 1-benzyl-2,5-dioxo-3-benzyloxycarbonylmethyl-9-phenyl-1,4,9-triazaspiro[5.5]undecane |

TABLE 5A-4

| Example No | Compound Name |
| --- | --- |
| 19(H5-28) | 1-benzyl-2,5-dioxo-3-(4-(benzyloxycarbonylamino)butyl)-9-phenyl-1,4,9-triazaspiro[5.5]undecane |
| 19(H5-29) | 1-(2,2-diphenylethyl)-2,5-dioxo-9-phenyl-1,4,9-triazaspiro[5.5]undecane |
| 19(H5-30) | 1-(2,2-diphenylethyl)-2,5-dioxo-3-(2-methylpropyl)-9-phenyl-1,4,9-triazaspiro[5.5]undecane |
| 19(H5-31) | 1-(2,2-diphenylethyl)-2,5-dioxo-3-phenylmethyl-9-phenyl-1,4,9-triazaspiro[5.5]undecane |
| 19(H5-32) | 1-(2,2-diphenylethyl)-2,5-dioxo-3-(indol-3-ylmethyl)-9-phenyl-1,4,9-triazaspiro[5.5]undecane |
| 19(H5-33) | 1-(2,2-diphenylethyl)-2,5-dioxo-3-benzyloxymethyl-9-phenyl-1,4,9-triazaspiro[5.5]undecane |
| 19(H5-34) | 1-(2,2-diphenylethyl)-2,5-dioxo-3-benzyloxycarbonylmethyl-9-phenyl-1,4,9-triazaspiro[5.5]undecane |
| 19(H5-35) | 1-(2,2-diphenylethyl)-2,5-dioxo-3-(4-(benzyloxycarbonylamino)butyl)-9-phenyl-1,4,9-triazaspiro[5.5]undecane |
| 19(H5-36) | 1-(2-phenylethyl)-2,5-dioxo-9-phenyl-1,4,9-triazaspiro[5.5]undecane |

TABLE 5A-5

| Example No | Compound Name |
| --- | --- |
| 19(H5-37) | 1-(2-phenylethyl)-2,5-dioxo-3-(2-methylpropyl)-9-phenyl-1,4,9-triazaspiro[5.5]undecane |
| 19(H5-38) | 1-(2-phenylethyl)-2,5-dioxo-3-phenylmethyl-9-phenyl-1,4,9-triazaspiro[5.5]undecane |
| 19(H5-39) | 1-(2-phenylethyl)-2,5-dioxo-3-(indol-3-ylmethyl)-9-phenyl-1,4,9-triazaspiro[5.5]undecane |
| 19(H5-40) | 1-(2-phenylethyl)-2,5-dioxo-3-benzyloxymethyl-9-phenyl-1,4,9-triazaspiro[5.5]undecane |
| 19(H5-41) | 1-(2-phenylethyl)-2,5-dioxo-3-benzyloxycarbonylmethyl-9-phenyl-1,4,9-triazaspiro[5.5]undecane |
| 19(H5-42) | 1-(2-phenylethyl)-2,5-dioxo-3-(4-(benzyloxycarbonylamino)butyl)-9-phenyl-1,4,9-triazaspiro[5.5]undecane |
| 19(H5-43) | 1-propyl-2,5-dioxo-9-phenyl-1,4,9-triazaspiro[5.5]undecane |
| 19(H5-44) | 1-propyl-2,5-dioxo-3-(2-methylpropyl)-9-phenyl-1,4,9-triazaspiro[5.5]undecane |
| 19(H5-45) | 1-propyl-2,5-dioxo-3-phenylmethyl-9-phenyl-1,4,9-triazaspiro[5.5]undecane |

TABLE 5A-6

| Example No | Compound Name |
| --- | --- |
| 19(H5-46) | 1-propyl-2,5-dioxo-3-(indol-3-ylmethyl)-9-phenyl-1,4,9-triazaspiro[5.5]undecane |
| 19(H5-47) | 1-propyl-2,5-dioxo-3-benzyloxymethyl-9-phenyl-1,4,9-triazaspiro[5.5]undecane |
| 19(H5-48) | 1-propyl-2,5-dioxo-3-benzyloxycarbonylmethyl-9-phenyl-1,4,9-triazaspiro[5.5]undecane |
| 19(H5-49) | 1-propyl-2,5-dioxo-3-(4-(benzyloxycarbonylamino)butyl)-9-phenyl-1,4,9-triazaspiro[5.5]undecane |
| 19(H5-50) | 1-(2-(t-butyloxycarbonyl)ethyl)-2,5-dioxo-9-phenyl-1,4,9-triazaspiro[5.5]undecane |
| 19(H5-51) | 1-(2-(t-butyloxycarbonyl)ethyl)-2,5-dioxo-3-(2-methylpropyl)-9-phenyl-1,4,9-triazaspiro[5.5]undecane |
| 19(H5-52) | 1-(2-(t-butyloxycarbonyl)ethyl)-2,5-dioxo-3-phenylmethyl-9-phenyl-1,4,9-triazaspiro[5.5]undecane |
| 19(H5-53) | 1-(2-(t-butyloxycarbonyl)ethyl)-2,5-dioxo-3-(indol-3-ylmethyl)-9-phenyl-1,4,9-triazaspiro[5.5]undecane |
| 19(H5-54) | 1-(2-(t-butyloxycarbonyl)ethyl)-2,5-dioxo-3-benzyloxymethyl-9-phenyl-1,4,9-triazaspiro[5.5]undecane |

TABLE 5A-7

| Example No | Compound Name |
| --- | --- |
| 19(H5-55) | 1-(2-(t-butyloxycarbonyl)ethyl)-2,5-dioxo-3-benzyloxycarbonylmethyl-9-phenyl-1,4,9-triazaspiro[5.5]undecane |
| 19(H5-56) | 1-(2-(t-butyloxycarbonyl)ethyl)-2,5-dioxo-3-(4-(benzyloxycarbonylamino)butyl)-9-phenyl-1,4,9-triazaspiro[5.5]undecane |
| 19(H5-57) | 1-(1-benzylpyrrolidin-3-yl)-2,5-dioxo-3-(2-methylpropyl)-9-phenyl-1,4,9-triazaspiro[5.5]undecane |
| 19(H5-58) | 1-(1-benzylpyrrolidin-3-yl)-2,5-dioxo-3-phenylmethyl-9-phenyl-1,4,9-triazaspiro[5.5]undecane |
| 19(H5-59) | 1-(1-benzylpyrrolidin-3-yl)-2,5-dioxo-3-(indol-3-ylmethyl)-9-phenyl-1,4,9-triazaspiro[5.5]undecane |
| 19(H5-60) | 1-(1-benzylpyrrolidin-3-yl)-2,5-dioxo-3-benzyloxymethyl-9-phenyl-1,4,9-triazaspiro[5.5]undecane |
| 19(H5-61) | 1-(1-benzylpyrrolidin-3-yl)-2,5-dioxo-3-benzyloxycarbonylmethyl-9-phenyl-1,4,9-triazaspiro[5.5]undecane |
| 19(H5-62) | 1-(1-benzylpyrrolidin-3-yl)-2,5-dioxo-3-(4-(benzyloxycarbonylamino)butyl)-9-phenyl-1,4,9-triazaspiro[5.5]undecane |

TABLE 6A-1

| Example No | Compound Name |
| --- | --- |
| 19(H6-1) | 1-(furan-2-ylmethyl)-2,5-dioxo-9-(5-phenylpentyl)-1,4,9-triazaspiro[5.5]undecane |
| 19(H6-2) | 1-(furan-2-ylmethyl)-2,5-dioxo-3-benzyloxymethyl-9-(5-phenylpentyl)-1,4,9-triazaspiro[5.5]undecane |
| 19(H6-3) | 1-(tetrahydrofuran-2-ylmethyl)-2,5-dioxo-9-(5-phenylpentyl)-1,4,9-triazaspiro[5.5]undecane |
| 19(H6-4) | 1-(tetrahydrofuran-2-ylmethyl)-2,5-dioxo-3-(2-methylpropyl)-9-(5-phenylpentyl)-1,4,9-triazaspiro[5.5]undecane |
| 19(H6-5) | 1-(tetrahydrofuran-2-ylmethyl)-2,5-dioxo-3-phenylmethyl-9-(5-phenylpentyl)-1,4,9-triazaspiro[5.5]undecane |
| 19(H6-6) | 1-(tetrahydrofuran-2-ylmethyl)-2,5-dioxo-3-(indol-3-ylmethyl)-9-(5-phenylpentyl)-1,4,9-triazaspiro[5.5]undecane |
| 19(H6-7) | 1-(tetrahydrofuran-2-ylmethyl)-2,5-dioxo-3-benzyloxymethyl-9-(5-phenylpentyl)-1,4,9-triazaspiro[5.5]undecane |
| 19(H6-8) | 1-(tetrahydrofuran-2-ylmethyl)-2,5-dioxo-3-benzyloxycarbonylmethyl-9-(5-phenylpentyl)-1,4,9-triazaspiro[5.5]undecane |

TABLE 6A-2

| Example No | Compound Name |
|---|---|
| 19(H6-9) | 1-(tetrahydrofuran-2-ylmethyl)-2,5-dioxo-3-(4-(benzyloxycarbonylamino)butyl)-9-(5-phenylpentyl)-1,4,9-triazaspiro[5.5]undecane |
| 19(H6-10) | 1-(2-(indol-3-yl)ethyl)-2,5-dioxo-9-(5-phenylpentyl)-1,4,9-triazaspiro[5.5]undecane |
| 19(H6-11) | 1-(2-(indol-3-yl)ethyl)-2,5-dioxo-3-(2-methylpropyl)-9-(5-phenylpentyl)-1,4,9-triazaspiro[5.5]undecane |
| 19(H6-12) | 1-(2-(indol-3-yl)ethyl)-2,5-dioxo-3-phenylmethyl-9-(5-phenylpentyl)-1,4,9-triazaspiro[5.5]undecane |
| 19(H6-13) | 1-(2-(indol-3-yl)ethyl)-2,5-dioxo-3-(indol-3-ylmethyl)-9-(5-phenylpentyl)-1,4,9-triazaspiro[5.5]undecane |
| 19(H6-14) | 1-(2-(indol-3-yl)ethyl)-2,5-dioxo-3-benzyloxymethyl-9-(5-phenylpentyl)-1,4,9-triazaspiro[5.5]undecane |
| 19(H6-15) | 1-(2-(indol-3-yl)ethyl)-2,5-dioxo-3-benzyloxycarbonylmethyl-9-(5-phenylpentyl)-1,4,9-triazaspiro[5.5]undecane |
| 19(H6-16) | 1-(2-(indol-3-yl)ethyl)-2,5-dioxo-3-(4-(benzyloxycarbonylamino)butyl)-9-(5-phenylpentyl)-1,4,9-triazaspiro[5.5]undecane |

TABLE 6A-3

| Example No | Compound Name |
|---|---|
| 19(H6-17) | 1-benzyl-2,5-dioxo-9-(5-phenylpentyl)-1,4,9-triazaspiro[5.5]undecane |
| 19(H6-18) | 1-benzyl-2,5-dioxo-3-(2-methylpropyl)-9-(5-phenylpentyl)-1,4,9-triazaspiro[5.5]undecane |
| 19(H6-19) | 1-benzyl-2,5-dioxo-3-phenylmethyl-9-(5-phenylpentyl)-1,4,9-triazaspiro[5.5]undecane |
| 19(H6-20) | 1-benzyl-2,5-dioxo-3-indol-3-ylmethyl)-9-(5-phenylpentyl)-1,4,9-triazaspiro[5.5]undecane |
| 19(H6-21) | 1-benzyl-2,5-dioxo-3-benzyloxymethyl-9-(5-phenylpentyl)-1,4,9-triazaspiro[5.5]undecane |
| 19(H6-22) | 1-benzyl-2,5-dioxo-3-benzyloxycarbonylmethyl-9-(5-phenylpentyl)-1,4,9-triazaspiro[5.5]undecane |
| 19(H6-23) | 1-benzyl-2,5-dioxo-3-(4-(benzyloxycarbonylamino)butyl)-9-(5-phenylpentyl)-1,4,9-triazaspiro[5.5]undecane |
| 19(H6-24) | 1-(2,2-diphenylethyl)-2,5-dioxo-9-(5-phenylpentyl)-1,4,9-triazaspiro[5.5]undecane |
| 19(H6-25) | 1-(2,2-diphenylethyl)-2,5-dioxo-3-(2-methylpropyl)-9-(5-phenylpentyl)-1,4,9-triazaspiro[5.5]undecane |

TABLE 6A-4

| Example No | Compound Name |
|---|---|
| 19(H6-26) | 1-(2,2-diphenylethyl)-2,5-dioxo-3-phenylmethyl-9-(5-phenylpentyl)-1,4,9-triazaspiro[5.5]undecane |
| 19(H6-27) | 1-(2,2-diphenylethyl)-2,5-dioxo-3-(indol-3-ylmethyl)-9-(5-phenylpentyl)-1,4,9-triazaspiro[5.5]undecane |
| 19(H6-28) | 1-(2,2-diphenylethyl)-2,5-dioxo-3-benzyloxymethyl-9-(5-phenylpentyl)-1,4,9-triazaspiro[5.5]undecane |
| 19(H6-29) | 1-(2,2-diphenylethyl)-2,5-dioxo-3-benzyloxycarbonylmethyl-9-(5-phenylpentyl)-1,4,9-triazaspiro[5.5]undecane |
| 19(H6-30) | 1-(2,2-diphenylethyl)-2,5-dioxo-3-(4-(benzyloxycarbonylamino)butyl)-9-(5-phenylpentyl)-1,4,9-triazaspiro[5.5]undecane |
| 19(H6-31) | 1-(2-phenylethyl)-2,5-dioxo-9-(5-phenylpentyl)-1,4,9-triazaspiro[5.5]undecane |
| 19(H6-32) | (1-(2-phenylethyl)-2,5-dioxo-3-(2-methylpropyl)-9-(5-phenylpentyl)-1,4,9-triazaspiro[5.5]undecane |
| 19(H6-33) | 1-(2-phenylethyl)-2,5-dioxo-3-phenylmethyl-9-(5-phenylpentyl)-1,4,9-triazaspiro[5.5]undecane |

TABLE 6A-5

| Example No | Compound Name |
|---|---|
| 19(H6-34) | 1-(2-phenylethyl)-2,5-dioxo-3-(indol-3-ylmethyl)-9-(5-phenylpentyl)-1,4,9-triazaspiro[5.5]undecane |
| 19(H6-35) | 1-(2-phenylethyl)-2,5-dioxo-3-benzyloxymethyl-9-(5-phenylpentyl)-1,4,9-triazaspiro[5.5]undecane |
| 19(H6-36) | 1-(2-phenylethyl)-2,5-dioxo-3-benzyloxycarbonylmethyl-9-(5-phenylpentyl)-1,4,9-triazaspiro[5.5]undecane |
| 19(H6-37) | 1-(2-phenylethyl)-2,5-dioxo-3-(4-(benzyloxycarbonylamino)butyl)-9-(5-phenylpentyl)-1,4,9-triazaspiro[5.5]undecane |
| 19(H6-38) | 1-propyl-2,5-dioxo-9-(5-phenylpentyl)-1,4,9-triazaspiro[5.5]undecane |
| 19(H6-39) | 1-propyl-2,5-dioxo-3-(2-methylpropyl)-9-(5-phenylpentyl)-1,4,9-triazaspiro[5.5]undecane |
| 19(H6-40) | 1-propyl-2,5-dioxo-3-phenylmethyl-9-(5-phenylpentyl)-1,4,9-triazaspiro[5.5]undecane |
| 19(H6-41) | 1-propyl-2,5-dioxo-3-(indol-3-ylmethyl)-9-(5-phenylpentyl)-1,4,9-triazaspiro[5.5]undecane |
| 19(H6-42) | 1-propyl-2,5-dioxo-3-benzyloxymethyl-9-(5-phenylpentyl)-1,4,9-triazaspiro[5.5]undecane |

TABLE 6A-6

| Example No | Compound Name |
|---|---|
| 19(H6-43) | 1-propyl-2,5-dioxo-3-benzyloxycarbonylmethyl-9-(5-phenylpentyl)-1,4,9-triazaspiro[5.5]undecane |
| 19(H6-44) | 1-propyl-2,5-dioxo-3-(4-(benzyloxycarbonylamino)butyl)-9-(5-phenylpentyl)-1,4,9-triazaspiro[5.5]undecane |
| 19(H6-45) | 1-(2-(t-butyloxycarbonyl)ethyl)-2,5-dioxo-9-(5-phenylpentyl)-1,4,9-triazaspiro[5.5]undecane |
| 19(H6-46) | 1-(2-(t-butyloxycarbonyl)ethyl)-2,5-dioxo-3-(2-methylpropyl)-9-(5-phenylpentyl)-1,4,9-triazaspiro[5.5]undecane |
| 19(H6-47) | 1-(2-(t-butyloxycarbonyl)ethyl)-2,5-dioxo-3-phenylmethyl-9-(5-phenylpentyl)-1,4,9-triazaspiro[5.5]undecane |
| 19(H6-48) | 1-(2-(t-butyloxycarbonyl)ethyl)-2,5-dioxo-3-(indol-3-ylmethyl)-9-(5-phenylpentyl)-1,4,9-triazaspiro[5.5]undecane |
| 19(H6-49) | 1-(2-(t-butyloxycarbonyl)ethyl)-2,5-dioxo-3-benzyloxymethyl-9-(5-phenylpentyl)-1,4,9-triazaspiro[5.5]undecane |
| 19(H6-50) | 1-(2-(t-butyloxycarbonyl)ethyl)-2,5-dioxo-3-benzyloxycarbonylmethyl-9-(5-phenylpentyl)-1,4,9-triazaspiro[5.5]undecane |

TABLE 6A-7

| Example No | Compound Name |
|---|---|
| 19(H6-51) | 1-(2-(t-butyloxycarbonyl)ethyl)-2,5-dioxo-3-(4-(benzyloxycarbonylamino)butyl)-9-(5-phenylpentyl)-1,4,9-triazaspiro[5.5]undecane |
| 19(H6-52) | 1-(1-benzylpyrrolidin-3-yl)-2,5-dioxo-9-(5-phenylpentyl)-1,4,9-triazaspiro[5.5]undecane |
| 19(H6-53) | 1-(1-benzylpyrrolidin-3-yl)-2,5-dioxo-3-(2-methylpropyl)-9-(5-phenylpentyl)-1,4,9-triazaspiro[5.5]undecane |
| 19(H6-54) | 1-(1-benzylpyrrolidin-3-yl)-2,5-dioxo-3-phenylmethyl-9-(5-phenylpentyl)-1,4,9-triazaspiro[5.5]undecane |
| 19(H6-55) | 1-(1-benzylpyrrolidin-3-yl)-2,5-dioxo-3-(indol-3-ylmethyl)-9-(5-phenylpentyl)-1,4,9-triazaspiro[5.5]undecane |
| 19(H6-56) | 1-(1-benzylpyrrolidin-3-yl)-2,5-dioxo-3-benzyloxymethyl-9-(5-phenylpentyl)-1,4,9-triazaspiro[5.5]undecane |
| 19(H6-57) | 1-(1-benzylpyrrolidin-3-yl)-2,5-dioxo-3-benzyloxycarbonylmethyl-9-(5-phenylpentyl)-1,4,9-triazaspiro[5.5]undecane |
| 19(H6-58) | 1-(1-benzylpyrrolidin-3-yl)-2,5-dioxo-3-(4-(benzyloxycarbonylamino)butyl)-9-(5-phenylpentyl)-1,4,9-triazaspiro[5.5]undecane |

TABLE 7A-1

| Example No | Compound Name |
|---|---|
| 19(H7-1) | 1-(furan-2-ylmethyl)-2,5-dioxo-9-(6-phenylhexyl)-1,4,9-triazaspiro[5.5]undecane |
| 19(H7-2) | 1-(furan-2-ylmethyl)-2,5-dioxo-3-(2-methylpropyl)-9-(6-phenylhexyl)-1,4,9-triazaspiro[5.5]undecane |
| 19(H7-3) | 1-(furan-2-ylmethyl)-2,5-dioxo-3-benzyl-9-(6-phenylhexyl)-1,4,9-triazaspiro[5.5]undecane |
| 19(H7-4) | 1-(furan-2-ylmethyl)-2,5-dioxo-3-(indol-3-ylmethyl)-9-(6-phenylhexyl)-1,4,9-triazaspiro[5.5]undecane |
| 19(H7-5) | 1-(furan-2-ylmethyl)-2,5-dioxo-3-benzyloxymethyl-9-(6-phenylhexyl)-1,4,9-triazaspiro[5.5]undecane |
| 19(H7-6) | 1-(tetrahydrofuran-2-ylmethyl)-2,5-dioxo-9-(6-phenylhexyl)-1,4,9-triazaspiro[5.5]undecane |
| 19(H7-7) | 1-(tetrahydrofuran-2-ylmethyl)-2,5-dioxo-3-(2-methylpropyl)-9-(6-phenylhexyl)-1,4,9-triazaspiro[5.5]undecane |
| 19(H7-8) | 1-(tetrahydrofuran-2-ylmethyl)-2,5-dioxo-3-phenylmethyl-9-(6-phenylhexyl)-1,4,9-triazaspiro[5.5]undecane |
| 19(H7-9) | 1-(tetrahydrofuran-2-ylmethyl)-2,5-dioxo-3-(indol-3-ylmethyl)-9-(6-phenylhexyl)-1,4,9-triazaspiro[5.5]undecane |

TABLE 7A-2

| Example No | Compound Name |
|---|---|
| 19(H7-10) | 1-(tetrahydrofuran-2-ylmethyl)-2,5-dioxo-3-benzyloxymethyl-9-(6-phenylhexyl)-1,4,9-triazaspiro[5.5]undecane |
| 19(H7-11) | 1-(tetrahydrofuran-2-ylmethyl)-2,5-dioxo-3-benzyloxycarbonylmethyl-9-(6-phenylhexyl)-1,4,9-triazaspiro[5.5]undecane |
| 19(H7-12) | 1-(tetrahydrofuran-2-ylmethyl)-2,5-dioxo-3-(4-(benzyloxycarbonylamino)butyl)-9-(6-phenylhexyl)-1,4,9-triazaspiro[5.5]undecane |
| 19(H7-13) | 1-(2-(indol-3-yl)ethyl)-2,5-dioxo-9-(6-phenylhexyl)-1,4,9-triazaspiro[5.5]undecane |
| 19(H7-14) | 1-(2-(indol-3-yl)ethyl)-2,5-dioxo-3-(2-methylpropyl)-9-(6-phenylhexyl)-1,4,9-triazaspiro[5.5]undecane |
| 19(H7-15) | 1-(2-(indol-3-yl)ethyl)-2,5-dioxo-3-phenylmethyl-9-(6-phenylhexyl)-1,4,9-triazaspiro[5.5]undecane |
| 19(H7-16) | 1-(2-(indol-3-yl)ethyl)-2,5-dioxo-3-(indol-3-ylmethyl)-9-(6-phenylhexyl)-1,4,9-triazaspiro[5.5]undecane |
| 19(H7-17) | 1-(2-(indol-3-yl) ethyl)-2,5-dioxo-3-benzyloxymethyl-9-(6-phenylhexyl)-1,4,9-triazaspiro[5.5]undecane |

TABLE 7A-3

| Example No | Compound Name |
|---|---|
| 19(H7-18) | 1-(2-(indol-3-yl)ethyl)-2,5-dioxo-3-benzyloxycarbonylmethyl-9-(6-phenylhexyl)-1,4,9-triazaspiro[5.5]undecane |
| 19(H7-19) | 1-(2-(indol-3-yl)ethyl)-2,5-dioxo-3-(4-(benzyloxycarbonylamino)butyl)-9-(6-phenylhexyl)-1,4,9-triazaspiro[5.5]undecane |
| 19(H7-20) | 1-benzyl-2,5-dioxo-9-(6-phenylhexyl)-1,4,9-triazaspiro[5.5]undecane |
| 19(H7-21) | 1-benzyl-2,5-dioxo-3-(2-methylpropyl)-9-(6-phenylhexyl)-1,4,9-triazaspiro[5.5]undecane |
| 19(H7-22) | 1-benzyl-2,5-dioxo-3-phenylmethyl-9-(6-phenylhexyl)-1,4,9-triazaspiro[5.5]undecane |
| 19(H7-23) | 1-benzyl-2,5-dioxo-3-(indol-3-ylmethyl)-9-(6-phenylhexyl)-1,4,9-triazaspiro[5.5]undecane |
| 19(H7-24) | 1-benzyl-2,5-dioxo-3-benzyloxymethyl-9-(6-phenylhexyl)-1,4,9-triazaspiro[5.5]undecane |
| 19(H7-25) | 1-benzyl-2,5-dioxo-3-benzyloxycarbonylmethyl-9-(6-phenylhexyl)-1,4,9-triazaspiro[5.5]undecane |
| 19(H7-26) | 1-benzyl-2,5-dioxo-3-(4-(benzyloxycarbonylamino)butyl)-9-(6-phenylhexyl)-1,4,9-triazaspiro[5.5]undecane |

TABLE 7A-4

| Example No | Compound Name |
|---|---|
| 19(H7-27) | 1-(2,2-diphenylethyl)-2,5-dioxo-9-(6-phenylhexyl)-1,4,9-triazaspiro[5.5]undecane |
| 19(H7-28) | 1-(2,2-diphenylethyl)-2,5-dioxo-3-(2-methylpropyl)-9-(6-phenylhexyl)-1,4,9-triazaspiro[5.5]undecane |
| 19(H7-29) | 1-(2,2-diphenylethyl)-2,5-dioxo-3-phenylmethyl-9-(6-phenylhexyl)-1,4,9-triazaspiro[5.5]undecane |
| 19(H7-30) | 1-(2,2-diphenylethyl)-2,5-dioxo-3-(indol-3-ylmethyl)-9-(6-phenylhexyl)-1,4,9-triazaspiro[5.5]undecane |
| 19(H7-31) | 1-(2,2-diphenylethyl)-2,5-dioxo-3-benzyloxymethyl-9-(6-phenylhexyl)-1,4,9-triazaspiro[5.5]undecane |
| 19(H7-32) | 1-(2,2-diphenylethyl)-2,5-dioxo-3-benzyloxycarbonylmethyl-9-(6-phenylhexyl)-1,4,9-triazaspiro[5.5]undecane |
| 19(H7-33) | 1-(2,2-diphenylethyl)-2,5-dioxo-3-(4-(benzyloxycarbonylamino)butyl)-9-(6-phenylhexyl)-1,4,9-triazaspiro[5.5]undecane |
| 19(H7-34) | 1-(2-phenylethyl)-2,5-dioxo-3-(2-methylpropyl)-9-(6-phenylhexyl)-1,4,9-triazaspiro[5.5]undecane |

TABLE 7A-5

| Example No | Compound Name |
|---|---|
| 19(H7-35) | 1-(2-phenylethyl)-2,5-dioxo-3-phenylmethyl-9-(6-phenylhexyl)-1,4,9-triazaspiro[5.5]undecane |
| 19(H7-36) | 1-(2-phenylethyl)-2,5-dioxo-3-(indol-3-ylmethyl)-9-(6-phenylhexyl)-1,4,9-triazaspiro[5.5]undecane |
| 19(H7-37) | 1-(2-phenylethyl)-2,5-dioxo-3-benzyloxymethyl-9-(6-phenylhexyl)-1,4,9-triazaspiro[5.5]undecane |
| 19(H7-38) | 1-(2-phenylethyl)-2,5-dioxo-3-benzyloxycarbonylmethyl-9-(6-phenylhexyl)-1,4,9-triazaspiro[5.5]undecane |
| 19(H7-39) | 1-(2-phenylethyl)-2,5-dioxo-3-(4-(benzyloxycarbonylamino)butyl)-9-(6-phenylhexyl)-1,4,9-triazaspiro[5.5]undecane |
| 19(H7-40) | 1-propyl-2,5-dioxo-9-(6-phenylhexyl)-1,4,9-triazaspiro[5.5]undecane |
| 19(H7-41) | 1-propyl-2,5-dioxo-3-(2-methylpropyl)-9-(6-phenylhexyl)-1,4,9-triazaspiro[5.5]undecane |
| 19(H7-42) | 1-propyl-2,5-dioxo-3-phenylmethyl-9-(6-phenylhexyl)-1,4,9-triazaspiro[5.5]undecane |
| 19(H7-43) | 1-propyl-2,5-dioxo-3-(indol-3-ylmethyl)-9-(6-phenylhexyl)-1,4,9-triazaspiro[5.5]undecane |

TABLE 7A-6

| Example No | Compound Name |
|---|---|
| 19(H7-44) | 1-propyl-2,5-dioxo-3-benzyloxymethyl-9-(6-phenylhexyl)-1,4,9-triazaspiro[5.5]undecane |
| 19(H7-45) | 1-propyl-2,5-dioxo-3-benzyloxycarbonylmethyl-9-(6-phenylhexyl)-1,4,9-triazaspiro[5.5]undecane |
| 19(H7-46) | 1-propyl-2,5-dioxo-3-(4-(benzyloxycarbonylamino)butyl)-9-(6-phenylhexyl)-1,4,9-triazaspiro[5.5]undecane |
| 19(H7-47) | 1-(2-(t-butyloxycarbonyl)ethyl)-2,5-dioxo-9-(6-phenylhexyl)-1,4,9-triazaspiro[5.5]undecane |
| 19(H7-48) | 1-(2-(t-butyloxycarbonyl)ethyl)-2,5-dioxo-3-(2-methylpropyl)-9-(6-phenylhexyl)-1,4,9-triazaspiro[5.5]undecane |
| 19(H7-49) | 1-(2-(t-butyloxycarbonyl)ethyl)-2,5-dioxo-3-phenylmethyl-9-(6-phenylhexyl)-1,4,9-triazaspiro[5.5]undecane |
| 19(H7-50) | 1-(2-(t-butyloxycarbonyl)ethyl)-2,5-dioxo-3-(indol-3-ylmethyl)-9-(6-phenylhexyl)-1,4,9-triazaspiro[5.5]undecane |
| 19(H7-51) | 1-(2-(t-butyloxycarbonyl)ethyl)-2,5-dioxo-3-benzyloxymethyl-9-(6-phenylhexyl)-1,4,9-triazaspiro[5.5]undecane |

TABLE 7A-7

| Example No | Compound Name |
|---|---|
| 19(H7-52) | 1-(2-(t-butyloxycarbonyl)ethyl)-2,5-dioxo-3-benzyloxycarbonylmethyl-9-(6-phenylhexyl)-1,4,9-triazaspiro[5.5]undecane |
| 19(H7-53) | 1-(2-(t-butyloxycarbonyl)ethyl)-2,5-dioxo-3-(4-(benzyloxycarbonylamino)butyl)-9-(6-phenylhexyl)-1,4,9-triazaspiro[5.5]undecane |
| 19(H7-54) | 1-(1-benzylpyrrolidin-3-yl)-2,5-dioxo-9-(6-phenylhexyl)-1,4,9-triazaspiro[5.5]undecane |
| 19(H7-55) | 1-(1-benzylpyrrolidin-3-yl)-2,5-dioxo-3-(2-methylpropyl)-9-(6-phenylhexyl)-1,4,9-triazaspiro[5.5]undecane |
| 19(H7-56) | 1-(1-benzylpyrrolidin-3-yl)-2,5-dioxo-3-phenylmethyl-9-(6-phenylhexyl)-1,4,9-triazaspiro[5.5]undecane |
| 19(H7-57) | 1-(1-benzylpyrrolidin-3-yl)-2,5-dioxo-3-(indol-3-ylmethyl)-9-(6-phenylhexyl)-1,4,9-triazaspiro[5.5]undecane |
| 19(H7-58) | 1-(1-benzylpyrrolidin-3-yl)-2,5-dioxo-3-benzyloxymethyl-9-(6-phenylhexyl)-1,4,9-triazaspiro[5.5]undecane |
| 19(H7-59) | 1-(1-benzylpyrrolidin-3-yl)-2,5-dioxo-3-benzyloxycarbonylmethyl-9-(6-phenylhexyl)-1,4,9-triazaspiro[5.5]undecane |

TABLE 7A-8

| Example No | Compound Name |
|---|---|
| 19(H7-60) | 1-(1-benzylpyrrolidin-3-yl)-2,5-dioxo-3-(4-(benzyloxycarbonylamino)butyl)-9-(6-phenylhexyl)-1,4,9-triazaspiro[5.5]undecane |

TABLE 8A-1

| Example No | Compound Name |
|---|---|
| 19(H8-1) | 1-(furan-2-ylmethyl)-2,5-dioxo-3-benzyl-9-methyl-1,4,9-triazaspiro[5.5]undecane |
| 19(H8-2) | 1-(furan-2-ylmethyl)-2,5-dioxo-3-(indol-3-ylmethyl)-9-methyl-1,4,9-triazaspiro[5.5]undecane |
| 19(H8-3) | 1-(tetrahydrofuran-2-ylmethyl)-2,5-dioxo-9-methyl-1,4,9-triazaspiro[5.5]undecane |
| 19(H8-4) | 1-(tetrahydrofuran-2-ylmethyl)-2,5-dioxo-3-(2-methylpropyl)-9-methyl-1,4,9-triazaspiro[5.5]undecane |
| 19(H8-5) | 1-(tetrahydrofuran-2-ylmethyl)-2,5-dioxo-3-phenylmethyl-9-methyl-1,4,9-triazaspiro[5.5]undecane |
| 19(H8-6) | 1-(tetrahydrofuran-2-ylmethyl)-2,5-dioxo-3-(indol-3-ylmethyl)-9-methyl-1,4,9-triazaspiro[5.5]undecane |
| 19(H8-7) | 1-(tetrahydrofuran-2-ylmethyl)-2,5-dioxo-3-benzyloxymethyl-9-methyl-1,4,9-triazaspiro[5.5]undecane |
| 19(H8-8) | 1-(tetrahydrofuran-2-ylmethyl)-2,5-dioxo-3-benzyloxycarbonylmethyl-9-methyl-1,4,9-triazaspiro[5.5]undecane |
| 19(H8-9) | 1-(tetrahydrofuran-2-ylmethyl)-2,5-dioxo-3-(4-(benzyloxycarbonylamino)butyl)-9-methyl-1,4,9-triazaspiro[5.5]undecane |

TABLE 8A-2

| Example No | Compound Name |
|---|---|
| 19(H8-10) | 1-(2-(indol-3-yl)ethyl)-2,5-dioxo-9-methyl-1,4,9-triazaspiro[5.5]undecane |
| 19(H8-11) | 1-(2-(indol-3-yl)ethyl)-2,5-dioxo-3-(2-methylpropyl)-9-methyl-1,4,9-triazaspiro[5.5]undecane |

TABLE 8A-2-continued

| Example No | Compound Name |
|---|---|
| 19(H8-12) | 1-(2-(indol-3-yl)ethyl)-2,5-dioxo-3-phenylmethyl-9-methyl-1,4,9-triazaspiro[5.5]undecane |
| 19(H8-13) | 1-(2-(indol-3-yl)ethyl)-2,5-dioxo-3-(indol-3-ylmethyl)-9-methyl-1,4,9-triazaspiro[5.5]undecane |
| 19(H8-14) | 1-(2-(indol-3-yl)ethyl)-2,5-dioxo-3-benzyloxymethyl-9-methyl-1,4,9-triazaspiro[5.5]undecane |
| 19(H8-15) | 1-(2-(indol-3-yl)ethyl)-2,5-dioxo-3-benzyloxycarbonylmethyl-9-methyl-1,4,9-triazaspiro[5.5]undecane |
| 19(H8-16) | 1-(2-(indol-3-yl)ethyl)-2,5-dioxo-3-(4-(benzyloxycarbonylamino)butyl)-9-methyl-1,4,9-triazaspiro[5.5]undecane |
| 19(H8-17) | 1-benzyl-2,5-dioxo-9-methyl-1,4,9-triazaspiro[5.5]undecane |
| 19(H8-18) | 1-benzyl-2,5-dioxo-3-(2-methylpropyl)-9-methyl-1,4,9-triazaspiro[5.5]undecane |

TABLE 8A-3

| Example No | Compound Name |
|---|---|
| 19(H8-19) | 1-benzyl-2,5-dioxo-3-phenylmethyl-9-methyl-1,4,9-triazaspiro[5.5]undecane |
| 19(H8-20) | 1-benzyl-2,5-dioxo-3-(indol-3-ylmethyl)-9-methyl-1,4,9-triazaspiro[5.5]undecane |
| 19(H8-21) | 1-benzyl-2,5-dioxo-3-benzyloxymethyl-9-methyl-1,4,9-triazaspiro[5.5]undecane |
| 19(H8-22) | 1-benzyl-2,5-dioxo-3-benzyloxycarbonylmethyl-9-methyl-1,4,9-triazaspiro[5.5]undecane |
| 19(H8-23) | 1-benzyl-2,5-dioxo-3-(4-(benzyloxycarbonylamino)butyl)-9-methyl-1,4,9-triazaspiro[5.5]undecane |
| 19(H8-24) | 1-(2,2-diphenylethyl)-2,5-dioxo-9-methyl-1,4,9-triazaspiro[5.5]undecane |
| 19(H8-25) | 1-(2,2-diphenylethyl)-2,5-dioxo-3-(2-methylpropyl)-9-methyl-1,4,9-triazaspiro[5.5]undecane |
| 19(H8-26) | 1-(2,2-diphenylethyl)-2,5-dioxo-3-phenylmethyl-9-methyl-1,4,9-triazaspiro[5.5]undecane |
| 19(H8-27) | 1-(2,2-diphenylethyl)-2,5-dioxo-3-(indol-3-ylmethyl)-9-methyl-1,4,9-triazaspiro[5.5]undecane |

TABLE 8A-4

| Example No | Compound Name |
|---|---|
| 19(H8-28) | 1-(2,2-diphenylethyl)-2,5-dioxo-3-benzyloxymethyl-9-methyl-1,4,9-triazaspiro[5.5]undecane |
| 19(H8-29) | 1-(2,2-diphenylethyl)-2,5-dioxo-3-benzyloxycarbonylmethyl-9-methyl-1,4,9-triazaspiro[5.5]undecane |
| 19(H8-30) | 1-(2,2-diphenylethyl)-2,5-dioxo-3-(4-(benzyloxycarbonylamino)butyl)-9-methyl-1,4,9-triazaspiro[5.5]undecane |
| 19(H8-31) | 1-(2-phenylethyl)-2,5-dioxo-9-methyl-1,4,9-triazaspiro[5.5]undecane |
| 19(H8-32) | 1-(2-phenylethyl)-2,5-dioxo-3-(2-methylpropyl)-9-methyl-1,4,9-triazaspiro[5.5]undecane |
| 19(H8-33) | 1-(2-phenylethyl)-2,5-dioxo-3-phenylmethyl-9-methyl-1,4,9-triazaspiro[5.5]undecane |
| 19(H8-34) | 1-(2-phenylethyl)-2,5-dioxo-3-(indol-3-ylmethyl)-9-methyl-1,4,9-triazaspiro[5.5]undecane |
| 19(H8-35) | 1-(2-phenylethyl)-2,5-dioxo-3-benzyloxymethyl-9-methyl-1,4,9-triazaspiro[5.5]undecane |
| 19(H8-36) | 1-(2-phenylethyl)-2,5-dioxo-3-benzyloxycarbonylmethyl-9-methyl-1,4,9-triazaspiro[5.5]undecane |

TABLE 8A-5

| Example No | Compound Name |
|---|---|
| 19(H8-37) | 1-(2-phenylethyl)-2,5-dioxo-3-(4-(benzyloxycarbonylamino)butyl)-9-methyl-1,4,9-triazaspiro[5.5]undecane |
| 19(H8-38) | 1-propyl-2,5-dioxo-9-methyl-1,4,9-triazaspiro[5.5]undecane |
| 19(H8-39) | 1-propyl-2,5-dioxo-3-(2-methylpropyl)-9-methyl-1,4,9-triazaspiro[5.5]undecane |
| 19(H8-40) | 1-propyl-2,5-dioxo-3-phenylmethyl-9-methyl-1,4,9-triazaspiro[5.5]undecane |
| 19(H8-41) | 1-propyl-2,5-dioxo-3-(indol-3-ylmethyl)-9-methyl-1,4,9-triazaspiro[5.5]undecane |
| 19(H8-42) | 1-propyl-2,5-dioxo-3-benzyloxymethyl-9-methyl-1,4,9-triazaspiro[5.5]undecane |
| 19(H8-43) | 1-propyl-2,5-dioxo-3-benzyloxycarbonylmethyl-9-methyl-1,4,9-triazaspiro[5.5]undecane |
| 19(H8-44) | 1-propyl-2,5-dioxo-3-(4-(benzyloxycarbonylamino)butyl)-9-methyl-1,4,9-triazaspiro[5.5]undecane |
| 19(H8-45) | 1-(2-(t-butyloxycarbonyl)ethyl)-2,5-dioxo-9-methyl-1,4,9-triazaspiro[5.5]undecane |

TABLE 8A-6

| Example No | Compound Name |
|---|---|
| 19(H8-46) | 1-(2-(t-butyloxycarbonyl)ethyl)-2,5-dioxo-3-phenylmethyl-9-methyl-1,4,9-triazaspiro[5.5]undecane |
| 19(H8-47) | 1-(2-(t-butyloxycarbonyl)ethyl)-2,5-dioxo-3-(indol-3-ylmethyl)-9-methyl-1,4,9-triazaspiro[5.5]undecane |
| 19(H8-48) | 1-(2-(t-butyloxycarbonyl)ethyl)-2,5-dioxo-3-benzyloxymethyl-9-methyl-1,4,9-triazaspiro[5.5]undecane |
| 19(H8-49) | 1-(2-(t-butyloxycarbonyl)ethyl)-2,5-dioxo-3-benzyloxycarbonylmethyl-9-methyl-1,4,9-triazaspiro[5.5]undecane |
| 19(H8-50) | 1-(2-(t-butyloxycarbonyl)ethyl)-2,5-dioxo-3-(4-(benzyloxycarbonylamino)butyl)-9-methyl-1,4,9-triazaspiro[5.5]undecane |
| 19(H8-51) | 1-(1-benzylpyrrolidin-3-yl)-2,5-dioxo-9-methyl-1,4,9-triazaspiro[5.5]undecane |
| 19(H8-52) | 1-(1-benzylpyrrolidin-3-yl)-2,5-dioxo-3-(2-methylpropyl)-9-methyl-1,4,9-triazaspiro[5.5]undecane |
| 19(H8-53) | 1-(1-benzylpyrrolidin-3-yl)-2,5-dioxo-3-phenylmethyl-9-methyl-1,4,9-triazaspiro[5.5]undecane |
| 19(H8-54) | 1-(1-benzylpyrrolidin-3-yl)-2,5-dioxo-3-(indol-3-ylmethyl)-9-methyl-1,4,9-triazaspiro[5.5]undecane |

TABLE 8A-7

| Example No | Compound Name |
|---|---|
| 19(H8-55) | 1-(1-benzylpyrrolidin-3-yl)-2,5-dioxo-3-benzyloxymethyl-9-methyl-1,4,9-triazaspiro[5.5]undecane |
| 19(H8-56) | 1-(1-benzylpyrrolidin-3-yl)-2,5-dioxo-3-benzyloxycarbonylmethyl-9-methyl-1,4,9-triazaspiro[5.5]undecane |
| 19(H8-57) | 1-(1-benzylpyrrolidin-3-yl)-2,5-dioxo-3-(4-(benzyloxycarbonylamino)butyl)-9-methyl-1,4,9-triazaspiro[5.5]undecane |

TABLE 9A-1

| Example No | Compound Name |
|---|---|
| 19(H9-1) | (3S)-1-cyclopropyl-2,5-dioxo-3-(4-(benzyloxycarbonylamino)butyl)-9-(2-phenylethyl)-1,4,9-triazaspiro[5.5]undecane |
| 19(H9-2) | (3S)-1-cyclobutyl-2,5-dioxo-3-(4-(benzyloxycarbonylamino)butyl)-9-(2-phenylethyl)-1,4,9-triazaspiro[5.5]undecane |
| 19(H9-3) | (3S)-1-((1S,2S,5S)-6,6-dimethylbicyclo[3.1.1]heptan-2-ylmethyl)-2,5-dioxo-3-(4-(benzyloxycarbonylamino)butyl)-9-(2-phenylethyl)-1,4,9-triazaspiro[5.5]undecane |
| 19(H9-4) | (3S)-1-cyclopentyl-2,5-dioxo-3-(4-(benzyloxycarbonylamino)butyl)-9-(2-phenylethyl)-1,4,9-triazaspiro[5.5]undecane |
| 19(H9-5) | (3S)-1-cyclohexyl-2,5-dioxo-3-(4-(benzyloxycarbonylamino)butyl)-9-(2-phenylethyl)-1,4,9-triazaspiro[5.5]undecane |
| 19(H9-6) | (3S)-1-(cyclohexylmethyl)-2,5-dioxo-3-(4-(benzyloxycarbonylamino)butyl)-9-(2-phenylethyl)-1,4,9-triazaspiro[5.5]undecane |
| 19(H9-7) | (3S)-1-(2-(1-methylpyrrolidin-2-yl)ethyl)-2,5-dioxo-3-(4-(benzyloxycarbonylamino)butyl)-9-(2-phenylethyl)-1,4,9-triazaspiro[5.5]undecane |

TABLE 9A-2

| Example No | Compound Name |
|---|---|
| 19(H9-8) | (3S)-1-((1-ethylpyrrolidin-2-yl)methyl)-2,5-dioxo-3-(4-(benzyloxycarbonylamino)butyl)-9-(2-phenylethyl)-1,4,9-triazaspiro[5.5]undecane |
| 19(H9-9) | (3S)-1-(indan-5-yl)-2,5-dioxo-3-(4-(benzyloxycarbonylamino)butyl)-9-(2-phenylethyl)-1,4,9-triazaspiro[5.5]undecane |
| 19(H9-10) | (3S)-1-cycloheptyl-2,5-dioxo-3-(4-(benzyloxycarbonylamino)butyl)-9-(2-phenylethyl)-1,4,9-triazaspiro[5.5]undecane |
| 19(H9-11) | (3S)-1-(thiophen-2-ylmethyl)-2,5-dioxo-3-(4-(benzyloxycarbonylamino)butyl)-9-(2-phenylethyl)-1,4,9-triazaspiro[5.5]undecane |
| 19(H9-12) | (3S)-1-(2-(morpholin-4-yl)ethyl)-2,5-dioxo-3-(4-(benzyloxycarbonylamino)butyl)-9-(2-phenylethyl)-1,4,9-triazaspiro[5.5]undecane |
| 19(H9-13) | (3S)-1-(3-(morpholin-4-yl)propyl)-2,5-dioxo-3-(4-(benzyloxycarbonylamino)butyl)-9-(2-phenylethyl)-1,4,9-triazaspiro[5.5]undecane |
| 19(H9-14) | (3S)-1-(2-(pyridin-2-yl)ethyl)-2,5-dioxo-3-(4-(benzyloxycarbonylamino)butyl)-9-(2-phenylethyl)-1,4,9-triazaspiro[5.5]undecane |

TABLE 9A-3

| Example No | Compound Name |
|---|---|
| 19(H9-15) | (3S)-1-(pyridin-3-ylmethyl)-2,5-dioxo-3-(4-(benzyloxycarbonylamino)butyl)-9-(2-phenylethyl)-1,4,9-triazaspiro[5.5]undecane |
| 19(H9-16) | (3S)-1-(pyridin-4-ylmethyl)-2,5-dioxo-3-(4-(benzyloxycarbonylamino)butyl)-9-(2-phenylethyl)-1,4,9-triazaspiro[5.5]undecane |
| 19(H9-17) | (3S)-1-(1-(ethoxycarbonyl)piperidin-4-yl)-2,5-dioxo-3-(4-(benzyloxycarbonylamino)butyl)-9-(2-phenylethyl)-1,4,9-triazaspiro[5.5]undecane |
| 19(H9-18) | (3S)-1-(2-(piperidin-1-yl)ethyl)-2,5-dioxo-3-(4-(benzyloxycarbonylamino)butyl)-9-(2-phenylethyl)-1,4,9-triazaspiro[5.5]undecane |
| 19(H9-19) | (3S)-1-(1-phenylethyl)-2,5-dioxo-3-(4-(benzyloxycarbonylamino)butyl)-9-(2-phenylethyl)-1,4,9-triazaspiro[5.5]undecane |

TABLE 9A-3-continued

| Example No | Compound Name |
|---|---|
| 19(H9-20) | (3S)-1-(1-methylethyl)-2,5-dioxo-3-(4-(benzyloxycarbonylamino)butyl)-9-(2-phenylethyl)-1,4,9-triazaspiro[5.5]undecane |
| 19(H9-21) | (3S)-1-(1,3-dimethylbutyl)-2,5-dioxo-3-(4 (benzyloxycarbonylamino)butyl)-9-(2-phenylethyl)-1,4,9-triazaspiro[5.5]undecane |

TABLE 9A-4

| Example No | Compound Name |
|---|---|
| 19(H9-22) | (3S)-1-(1-methyl-3-phenylpropyl)-2,5-dioxo-3-(4-(benzyloxycarbonylamino)butyl)-9-(2-phenylethyl)-1,4,9-triazaspiro[5.5]undecane |
| 19(H9-23) | (3S)-1-(1-methylpropyl)-2,5-dioxo-3-(4-(benzyloxycarbonylamino)butyl)-9-(2-phenylethyl)-1,4,9-triazaspiro[5.5]undecane |
| 19(H9-24) | (3S)-1-(1-methylbutyl)-2,5-dioxo-3-(4-(benzyloxycarbonylamino)butyl)-9-(2-phenylethyl)-1,4,9-triazaspiro[5.5]undecane |
| 19(H9-25) | (3S)-1-((2-fluorophenyl)methyl)-2,5-dioxo-3-(4-(benzyloxycarbonylamino)butyl)-9-(2-phenylethyl)-1,4,9-triazaspiro[5.5]undecane |
| 19(H9-26) | (3S)-1-((2-methoxyphenyl)methyl)-2,5-dioxo-3-(4-(benzyloxycarbonylamino)butyl)-9-(2-phenylethyl)-1,4,9-triazaspiro[5.5]undecane |
| 19(H9-27) | (3S)-1-((3-fluorophenyl)methyl)-2,5-dioxo-3-(4-(benzyloxycarbonylamino)butyl)-9-(2-phenylethyl)-1,4,9-triazaspiro[5.5]undecane |
| 19(H9-28) | (3S)-1-((3-methoxyphenyl)methyl)-2,5-dioxo-3-(4-(benzyloxycarbonylamino)butyl)-9-(2-phenylethyl)-1,4,9-triazaspiro[5.5]undecane |

TABLE 9A-5

| Example No | Compound Name |
|---|---|
| 19(H9-29) | (3S)-1-((4-fluorophenyl)methyl)-2,5-dioxo-3-(4-(benzyloxycarbonylamino)butyl)-9-(2-phenylethyl)-1,4,9-triazaspiro[5.5]undecane |
| 19(H9-30) | (3S)-1-((4-methoxyphenyl)methyl)-2,5-dioxo-3-(4-(benzyloxycarbonylamino)butyl)-9-(2-phenylethyl)-1,4,9-triazaspiro[5.5]undecane |
| 19(H9-31) | (3S)-1-((4-methylphenyl)methyl)-2,5-dioxo-3-(4-(benzyloxycarbonylamino)butyl)-9-(2-phenylethyl)-1,4,9-triazaspiro[5.5]undecane |
| 19(H9-32) | (3S)-1-(2,2-dimethylpropyl)-2,5-dioxo-3-(4-(benzyloxycarbonylamino)butyl)-9-(2-phenylethyl)-1,4,9-triazaspiro[5.5]undecane |
| 19(H9-33) | (3S)-1-(2-phenylpropyl)-2,5-dioxo-3-(4-(benzyloxycarbonylamino)butyl)-9-(2-phenylethyl)-1,4,9-triazaspiro[5.5]undecane |
| 19(H9-34) | (3S)-1-(2-methylpropyl)-2,5-dioxo-3-(4-(benzyloxycarbonylamino)butyl)-9-(2-phenylethyl)-1,4,9-triazaspiro[5.5]undecane |
| 19(H9-35) | (3S)-1-(2-methylbutyl)-2,5-dioxo-3-(4-(benzyloxycarbonylamino)butyl)-9-(2-phenylethyl)-1,4,9-triazaspiro[5.5]undecane |

TABLE 9A-6

| Example No | Compound Name |
|---|---|
| 19(H9-36) | (3S)-1-benzyl-2,5-dioxo-3-(4-(benzyloxycarbonylamino)butyl)-9-(2-phenylethyl)-1,4,9-triazaspiro[5.5]undecane |
| 19(H9-37) | (3S)-1-(2-(N,N-dimethylamino)ethyl)-2,5-dioxo-3-(4-(benzyloxycarbonylamino)butyl)-9-(2-phenylethyl)-1,4,9-triazaspiro[5.5]undecane |
| 19(H9-38) | (3S)-1-(2-methoxyethyl)-2,5-dioxo-3-(4-(benzyloxycarbonylamino)butyl)-9-(2-phenylethyl)-1,4,9-triazaspiro[5.5]undecane |
| 19(H9-39) | (3S)-1-(2-propynyl)-2,5-dioxo-3-(4-(benzyloxycarbonylamino)butyl)-9-(2-phenylethyl)-1,4,9-triazaspiro[5.5]undecane |
| 19(H9-40) | (3S)-1-(2-propenyl)-2,5-dioxo-3-(4-(benzyloxycarbonylamino)butyl)-9-(2-phenylethyl)-1,4,9-triazaspiro[5.5]undecane |
| 19(H9-41) | (3S)-1-(3-hydroxypropyl)-2,5-dioxo-3-(4-(benzyloxycarbonylamino)butyl)-9-(2-phenylethyl)-1,4,9-triazaspiro[5.5]undecane |
| 19(H9-42) | (3S)-1-(3-methylbutyl)-2,5-dioxo-3-(4-(benzyloxycarbonylamino)butyl)-9-(2-phenylethyl)-1,4,9-triazaspiro[5.5]undecane |

TABLE 9A-7

| Example No | Compound Name |
|---|---|
| 19(H9-43) | (3S)-1-propyl-2,5-dioxo-3-(4-(benzyloxycarbonylamino)butyl)-9-(2-phenylethyl)-1,4,9-triazaspiro[5.5]undecane |
| 19(H9-44) | (3S)-1-(3-(N,N-dimethylamino)propyl)-2,5-dioxo-3-(4-(benzyloxycarbonylamino)butyl)-9-(2-phenylethyl)-1,4,9-triazaspiro[5.5]undecane |
| 19(H9-45) | (3S)-1-(3-ethoxypropyl)-2,5-dioxo-3-(4-(benzyloxycarbonylamino)butyl)-9-(2-phenylethyl)-1,4,9-triazaspiro[5.5]undecane |
| 19(H9-46) | (3S)-1-(3-phenylpropyl)-2,5-dioxo-3-(4-(benzyloxycarbonylamino)butyl)-9-(2-phenylethyl)-1,4,9-triazaspiro[5.5]undecane |
| 19(H9-47) | (3S)-1-(4-phenylbutyl)-2,5-dioxo-3-(4-(benzyloxycarbonylamino)butyl)-9-(2-phenylethyl)-1,4,9-triazaspiro[5.5]undecane |
| 19(H9-48) | (3S)-1-pentyl-2,5-dioxo-3-(4-(benzyloxycarbonylamino)butyl)-9-(2-phenylethyl)-1,4,9-triazaspiro[5.5]undecane |
| 19(H9-49) | (3S)-1-(3-(imidazol-1-yl)propyl)-2,5-dioxo-3-(4-(benzyloxycarbonylamino)butyl)-9-(2-phenylethyl)-1,4,9-triazaspiro[5.5]undecane |

TABLE 9A-8

| Example No | Compound Name |
|---|---|
| 19(H9-50) | (3S)-1-butyl-2,5-dioxo-3-(4-(benzyloxycarbonylamino)butyl)-9-(2-phenylethyl)-1,4,9-triazaspiro[5.5]undecane |
| 19(H9-51) | (3S)-1-(2-(1-cyclohexenyl)ethyl)-2,5-dioxo-3-(4-(benzyloxycarbonylamino)butyl)-9-(2-phenylethyl)-1,4,9-triazaspiro[5.5]undecane |
| 19(H9-52) | (3S)-1-(cyclopropylmethyl)-2,5-dioxo-3-(4-(benzyloxycarbonylamino)butyl)-9-(2-phenylethyl)-1,4,9-triazaspiro[5.5]undecane |
| 19(H9-53) | (3S)-1-ethyl-2,5-dioxo-3-(4-(benzyloxycarbonylamino)butyl)-9-(2-phenylethyl)-1,4,9-triazaspiro[5.5]undecane |
| 19(H9-54) | (3S)-1-(3-methoxypropyl)-2,5-dioxo-3-(4-(benzyloxycarbonylamino)butyl)-9-(2-phenylethyl)-1,4,9-triazaspiro[5.5]undecane |
| 19(H9-55) | (3S)-1-(2-(pyridin-4-yl)ethyl)-2,5-dioxo-3-(4-(benzyloxycarbonylamino)butyl)-9-(2-phenylethyl)-1,4,9-triazaspiro[5.5]undecane |

TABLE 9A-8-continued

| Example No | Compound Name |
|---|---|
| 19(H9-56) | (3S)-1-((3-chlorophenyl)methyl)-2,5-dioxo-3-(4-(benzyloxycarbonylamino)butyl)-9-(2-phenylethyl)-1,4,9-triazaspiro[5.5]undecane |

TABLE 9A-9

| Example No | Compound Name |
|---|---|
| 19(H9-57) | (3S)-1-(3-methylthiopropyl)-2,5-dioxo-3-(4-(benzyloxycarbonylamino)butyl)-9-(2-phenylethyl)-1,4,9-triazaspiro[5.5]undecane |
| 19(H9-58) | (3S)-1-(2-(thiophen-2-yl)ethyl)-2,5-dioxo-3-(4-(benzyloxycarbonylamino)butyl)-9-(2-phenylethyl)-1,4,9-triazaspiro[5.5]undecane |
| 19(H9-59) | (3S)-1-(2-(1,1-dimethylethylthio)ethyl)-2,5-dioxo-3-(4-(benzyloxycarbonylamino)butyl)-9-(2-phenylethyl)-1,4,9-triazaspiro[5.5]undecane |
| 19(H9-60) | (3S)-1-((t-butoxycarbonyl)methyl)-2,5-dioxo-3-(4-(benzyloxycarbonylamino)butyl)-9-(2-phenylethyl)-1,4,9-triazaspiro[5.5]undecane |
| 19(H9-61) | (3S)-1-((5-methylfuran-2-yl)methyl)-2,5-dioxo-3-(4-(benzyloxycarbonylamino)butyl)-9-(2-phenylethyl)-1,4,9-triazaspiro[5.5]undecane |
| 19(H9-62) | (3S)-1-(2-(pyridin-3-yl)ethyl)-2,5-dioxo-3-(4-(benzyloxycarbonylamino)butyl)-9-(2-phenylethyl)-1,4,9-triazaspiro[5.5]undecane |

TABLE 10A-1

| Example No | Compound Name |
|---|---|
| 19(H10-1) | (3S)-1-cyclopropyl-2,5-dioxo-3-(3-(benzyloxycarbonylamino)propyl)-9-(2-phenylethyl)-1,4,9-triazaspiro[5.5]undecane |
| 19(H10-2) | (3S)-1-cyclobutyl-2,5-dioxo-3-(3-(benzyloxycarbonylamino)propyl)-9-(2-phenylethyl)-1,4,9-triazaspiro[5.5]undecane |
| 19(H10-3) | (3S)-1-((1S,2S,5S)-6,6-dimethylbicyclo[3.1.1]heptan-2-ylmethyl)-2,5-dioxo-3-(3-(benzyloxycarbonylamino)propyl)-9-(2-phenylethyl)-1,4,9-triazaspiro[5.5]undecane |
| 19(H10-4) | (3S)-1-cyclopentyl-2,5-dioxo-3-(3-(benzyloxycarbonylamino)propyl)-9-(2-phenylethyl)-1,4,9-triazaspiro[5.5]undecane |
| 19(H10-5) | (3S)-1-cyclohexyl-2,5-dioxo-3-(3-(benzyloxycarbonylamino)propyl)-9-(2-phenylethyl)-1,4,9-triazaspiro[5.5]undecane |
| 19(H10-6) | (3S)-1-(cyclohexylmethyl)-2,5-dioxo-3-(3-(benzyloxycarbonylamino)propyl)-9-(2-phenylethyl)-1,4,9-triazaspiro[5.5]undecane |
| 19(H10-7) | (3S)-1-cyclooctyl-2,5-dioxo-3-(3-(benzyloxycarbonylamino)propyl)-9-(2-phenylethyl)-1,4,9-triazaspiro[5.5]undecane |

TABLE 10A-2

| Example No | Compound Name |
|---|---|
| 19(H10-8) | (3S)-1-(2-(1-methylpyrrolidin-2-yl)ethyl)-2,5-dioxo-3-(3-(benzyloxycarbonylamino)propyl)-9-(2-phenylethyl)-1,4,9-triazaspiro[5.5]undecane |

TABLE 10A-2-continued

| Example No | Compound Name |
|---|---|
| 19(H10-9) | (3S)-1-((1-ethylpyrrolidin-2-yl)methyl)-2,5-dioxo-3-(3-(benzyloxycarbonylamino)propyl)-9-(2-phenylethyl)-1,4,9-triazaspiro[5.5]undecane |
| 19(H10-10) | (3S)-1-(indan-5-yl)-2,5-dioxo-3-(3-(benzyloxycarbonylamino)propyl)-9-(2-phenylethyl)-1,4,9-triazaspiro[5.5]undecane |
| 19(H10-11) | (3S)-1-cycloheptyl-2,5-dioxo-3-(3-(benzyloxycarbonylamino)propyl)-9-(2-phenylethyl)-1,4,9-triazaspiro[5.5]undecane |
| 19(H10-12) | (3S)-1-(thiophen-2-ylmethyl)-2,5-dioxo-3-(3-(benzyloxycarbonylamino)propyl)-9-(2-phenylethyl)-1,4,9-triazaspiro[5.5]undecane |
| 19(H10-13) | (3S)-1-(2-(morpholin-4-yl)ethyl)-2,5-dioxo-3-(3-(benzyloxycarbonylamino)propyl)-9-(2-phenylethyl)-1,4,9-triazaspiro[5.5]undecane |
| 19(H10-14) | (3S)-1-(3-(morpholin-4-yl)propyl)-2,5-dioxo-3-(3-(benzyloxycarbonylamino)propyl)-9-(2-phenylethyl)-1,4,9-triazaspiro[5.5]undecane |

TABLE 10A-3

| Example No | Compound Name |
|---|---|
| 19(H10-15) | (3S)-1-(2-(pyridin-2-yl)ethyl)-2,5-dioxo-3-(3-(benzyloxycarbonylamino)propyl)-9-(2-phenylethyl)-1,4,9-triazaspiro[5.5]undecane |
| 19(H10-16) | (3S)-1-(pyridin-3-ylmethyl)-2,5-dioxo-3-(3-(benzyloxycarbonylamino)propyl)-9-(2-phenylethyl)-1,4,9-triazaspiro[5.5]undecane |
| 19(H10-17) | (3S)-1-(pyridin-4-ylmethyl)-2,5-dioxo-3-(3-(benzyloxycarbonylamino)propyl)-9-(2-phenylethyl)-1,4,9-triazaspiro[5.5]undecane |
| 19(H10-18) | (3S)-1-(1-(ethoxycarbonyl)piperidin-4-yl)-2,5-dioxo-3-(3-(benzyloxycarbonylamino)propyl)-9-(2-phenylethyl)-1,4,9-triazaspiro[5.5]undecane |
| 19(H10-19) | (3S)-1-(2-(piperidin-1-yl)ethyl)-2,5-dioxo-3-(3-(benzyloxycarbonylamino)propyl)-9-(2-phenylethyl)-1,4,9-triazaspiro[5.5]undecane |
| 19(H10-20) | (3S)-1-phenyl-2,5-dioxo-3-(3-(benzyloxycarbonylamino)propyl)-9-(2-phenylethyl)-1,4,9-triazaspiro[5.5]undecane |
| 19(H10-21) | (3S)-1-(1-phenylethyl)-2,5-dioxo-3-(3-(benzyloxycarbonylamino)propyl)-9-(2-phenylethyl)-1,4,9-triazaspiro[5.5]undecane |

TABLE 10A-4

| Example No | Compound Name |
|---|---|
| 19(H10-22) | (3S)-1-(1-methylethyl)-2,5-dioxo-3-(3-(benzyloxycarbonylamino)propyl)-9-(2-phenylethyl)-1,4,9-triazaspiro[5.5]undecane |
| 19(H10-23) | (3S)-1-(1,3-dimethylbutyl)-2,5-dioxo-3-(3-(benzyloxycarbonylamino)propyl)-9-(2-phenylethyl)-1,4,9-triazaspiro[5.5]undecane |
| 19(H10-24) | (3S)-1-(1-methyl-3-phenylpropyl)-2,5-dioxo-3-(3-(benzyloxycarbonylamnio)propyl)-9-(2-phenylethyl)-1,4,9-triazaspiro[5.5]undecane |
| 19(H10-25) | (3S)-1-(1-methylpropyl)-2,5-dioxo-3-(3-(benzyloxycarbonylamino)propyl)-9-(2-phenylethyl)-1,4,9-triazaspiro[5.5]undecane |
| 19(H10-26) | (3S)-1-(1-ethylpropyl)-2,5-dioxo-3-(3-(benzyloxycarbonylamino)propyl)-9-(2-phenylethyl)-1,4,9-triazaspiro[5.5]undecane |
| 19(H10-27) | (3S)-1-(1-methylbutyl)-2,5-dioxo-3-(3-(benzyloxycarbonylamino)propyl)-9-(2-phenylethyl)-1,4,9-triazaspiro[5.5]undecane |

TABLE 10A-4-continued

| Example No | Compound Name |
|---|---|
| 19(H10-28) | (3S)-1-((2-fluorophenyl)methyl)-2,5-dioxo-3-(3-(benzyloxycarbonylamino)propyl)-9-(2-phenylethyl)-1,4,9-triazaspiro[5.5]undecane |

TABLE 10A-5

| Example No | Compound Name |
|---|---|
| 19(H10-29) | (3S)-1-((2-methoxyphenyl)methyl)-2,5-dioxo-3-(3-(benzyloxycarbonylamino)propyl)-9-(2-phenylethyl)-1,4,9-triazaspiro[5.5]undecane |
| 19(H10-30) | (3S)-1-((3-fluorophenyl)methyl)-2,5-dioxo-3-(3-(benzyloxycarbonylamino)propyl)-9-(2-phenylethyl)-1,4,9-triazaspiro[5.5]undecane |
| 19(H10-31) | (3S)-1-((3-methoxyphenyl)methyl)-2,5-dioxo-3-(3-(benzyloxycarbonylamino)propyl)-9-(2-phenylethyl)-1,4,9-triazaspiro[5.5]undecane |
| 19(H10-32) | (3S)-1-((4-fluorophenyl)methyl)-2,5-dioxo-3-(3-(benzyloxycarbonylamino)propyl)-9-(2-phenylethyl)-1,4,9-triazaspiro[5.5]undecane |
| 19(H10-33) | (3S)-1-((4-methoxyphenyl)methyl)-2,5-dioxo-3-(3-(benzyloxycarbonylamino)propyl)-9-(2-phenylethyl)-1,4,9-triazaspiro[5.5]undecane |
| 19(H10-34) | (3S)-1-((4-methylphenyl)methyl)-2,5-dioxo-3-(3-(benzyloxycarbonylamino)propyl)-9-(2-phenylethyl)-1,4,9-triazaspiro[5.5]undecane |
| 19(H10-35) | (3S)-1-(2,2-dimethylpropyl)-2,5-dioxo-3-(3-(benzyloxycarbonylamino)propyl)-9-(2-phenylethyl)-1,4,9-triazaspiro[5.5]undecane |

TABLE 10A-6

| Example No | Compound Name |
|---|---|
| 19(H10-36) | (3S)-1-(2-phenylpropyl)-2,5-dioxo-3-(3-(benzyloxycarbonylamino)propyl)-9-(2-phenylethyl)-1,4,9-triazaspiro[5.5]undecane |
| 19(H10-37) | (3S)-1-(2-methylpropyl)-2,5-dioxo-3-(3-(benzyloxycarbonylamino)propyl)-9-(2-phenylethyl)-1,4,9-triazaspiro[5.5]undecane |
| 19(H10-38) | (3S)-1-(2-methylbutyl)-2,5-dioxo-3-(3-(benzyloxycarbonylamino)propyl)-9-(2-phenylethyl)-1,4,9-triazaspiro[5.5]undecane |
| 19(H10-39) | (3S)-1-benzyl-2,5-dioxo-3-(3-(benzyloxycarbonylamino)propyl)-9-(2-phenylethyl)-1,4,9-triazaspiro[5.5]undecane |
| 19(H10-40) | (3S)-1-(2-(N,N-dimethylamino)ethyl)-2,5-dioxo-3-(3-(benzyloxycarbonylamino)propyl)-9-(2-phenylethyl)-1,4,9-triazaspiro[5.5]undecane |
| 19(H10-41) | (3S)-1-(2-methoxyethyl)-2,5-dioxo-3-(3-(benzyloxycarbonylamino)propyl)-9-(2-phenylethyl)-1,4,9-triazaspiro[5.5]undecane |
| 19(H10-42) | (3S)-1-(2-propynyl)-2,5-dioxo-3-(3-(benzyloxycarbonylamino)propyl)-9-(2-phenylethyl)-1,4,9-triazaspiro[5.5]undecane |

TABLE 10A-7

| Example No | Compound Name |
|---|---|
| 19(H10-43) | (3S)-1-(2-propenyl)-2,5-dioxo-3-(3-(benzyloxycarbonylamino)propyl)-9-(2-phenylethyl)-1,4,9-triazaspiro[5.5]undecane |

TABLE 10A-7-continued

| Example No | Compound Name |
|---|---|
| 19(H10-44) | (3S)-1-(3-hydroxypropyl)-2,5-dioxo-3-(3-(benzyloxycarbonylamino)propyl)-9-(2-phenylethyl)-1,4,9-triazaspiro[5.5]undecane |
| 19(H10-45) | (3S)-1-(3-methylbutyl)-2,5-dioxo-3-(3-(benzyloxycarbonylamino)propyl)-9-(2-phenylethyl)-1,4,9-triazaspiro[5.5]undecane |
| 19(H10-46) | (3S)-1-propyl-2,5-dioxo-3-(3-(benzyloxycarbonylamino)propyl)-9-(2-phenylethyl)-1,4,9-triazaspiro[5.5]undecane |
| 19(H10-47) | (3S)-1-(3-(N,N-dimethylamino)propyl)-2,5-dioxo-3-(3-(benzyloxycarbonylamino)propyl)-9-(2-phenylethyl)-1,4,9-triazaspiro[5.5]undecane |
| 19(H10-48) | (3S)-1-(3-ethoxypropyl)-2,5-dioxo-3-(3-(benzyloxycarbonylamino)propyl)-9-(2-phenylethyl)-1,4,9-triazaspiro[5.5]undecane |
| 19(H10-49) | (3S)-1-(3-phenylpropyl)-2,5-dioxo-3-(3-(benzyloxycarbonylamino)propyl)-9-(2-phenylethyl)-1,4,9-triazaspiro[5.5]undecane |

TABLE 10A-8

| Example No | Compound Name |
|---|---|
| 19(H10-50) | (3S)-1-(4-phenylbutyl)-2,5-dioxo-3-(3-(benzyloxycarbonylamino)propyl)-9-(2-phenylethyl)-1,4,9-triazaspiro[5.5]undecane |
| 19(H10-51) | (3S)-1-pentyl-2,5-dioxo-3-(3-(benzyloxycarbonylamino)propyl)-9-(2-phenylethyl)-1,4,9-triazaspiro[5.5]undecane |
| 19(H10-52) | (3S)-1-(3-(imidazol-1-yl)propyl)-2,5-dioxo-3-(3-(benzyloxycarbonylamino)propyl)-9-(2-phenylethyl)-1,4,9-triazaspiro[5.5]undecane |
| 19(H10-53) | (3S)-1-butyl-2,5-dioxo-3-(3-(benzyloxycarbonylamino) propyl)-9-(2-phenylethyl)-1,4,9-triazaspiro[5.5]undecane |
| 19(H10-54) | (3S)-1-(2-(1-cyclohexenyl)ethyl)-2,5-dioxo-3-(3-(benzyloxycarbonylamino)propyl)-9-(2-phenylethyl)-1,4,9-triazaspiro[5.5]undecane |
| 19(H10-55) | (3S)-1-(cyclopropylmethyl)-2,5-dioxo-3-(3-(benzyloxycarbonylamino)propyl)-9-(2-phenylethyl)-1,4,9-triazaspiro[5.5]undecane |
| 19(H10-56) | (3S)-1-ethyl-2,5-dioxo-3-(3-(benzyloxycarbonylamino) propyl)-9-(2-phenylethyl)-1,4,9-triazaspiro[5.5]undecane |

TABLE 10A-9

| Example No | Compound Name |
|---|---|
| 19(H10-57) | (3S)-1-(3-methoxypropyl)-2,5-dioxo-3-(3-(benzyloxycarbonylamino)propyl)-9-(2-phenylethyl)-1,4,9-triazaspiro[5.5]undecane |
| 19(H10-58) | (3S)-1-(2-(N-ethyl-N-(3-methylphenyl)amino)ethyl)-2,5-dioxo-3-(3-(benzyloxycarbonylamino)propyl)-9-(2-phenylethyl)-1,4,9-triazaspiro[5.5]undecane |
| 19(H10-59) | (3S)-1-(2-(pyridin-4-yl)ethyl)-2,5-dioxo-3-(3-(benzyloxycarbonylamino)propyl)-9-(2-phenylethyl)-1,4,9-triazaspiro[5.5]undecane |
| 19(H10-60) | (3S)-1-((3-chlorophenyl)methyl)-2,5-dioxo-3-(3-(benzyloxycarbonylamino)propyl)-9-(2-phenylethyl)-1,4,9-triazaspiro[5.5]undecane |
| 19(H10-61) | (3S)-1-(3-methylthiopropyl)-2,5-dioxo-3-(3-(benzyloxycarbonylamino)propyl)-9-(2-phenylethyl)-1,4,9-triazaspiro[5.5]undecane |
| 19(H10-62) | (3S)-1-(2-(thiophen-2-yl)ethyl)-2,5-dioxo-3-(3-(benzyloxycarbonylamino)propyl)-9-(2-phenylethyl)-1,4,9-triazaspiro[5.5]undecane |

TABLE 10A-9-continued

| Example No | Compound Name |
|---|---|
| 19(H10-63) | (3S)-1-(2-(1,1-dimethylethylthio)ethyl)-2,5-dioxo-3-(3-(benzyloxycarbonylamino)propyl)-9-(2-phenylethyl)-1,4,9-triazaspiro[5.5]undecane |

TABLE 10A-10

| Example No | Compound Name |
|---|---|
| 19(H10-64) | (3S)-1-((t-butoxycarbonyl)methyl)-2,5-dioxo-3-(3-(benzyloxycarbonylamino)propyl)-9-(2-phenylethyl)-1,4,9-triazaspiro[5.5]undecane |
| 19(H10-65) | (3S)-1-((2S)-2-hydroxypropyl)-2,5-dioxo-3-(3-(benzyloxycarbonylamino)propyl)-9-(2-phenylethyl)-1,4,9-triazaspiro[5.5]undecane |
| 19(H10-66) | (3S)-1-((5-methylfuran-2-yl)methyl)-2,5-dioxo-3-(3-(benzyloxycarbonylamino)propyl)-9-(2-phenylethyl)-1,4,9-triazaspiro[5.5]undecane |
| 19(H10-67) | (3S)-1-((1R)-1-(4-methylphenyl)ethyl)-2,5-dioxo-3-(3-(benzyloxycarbonylamino)propyl)-9-(2-phenylethyl)-1,4,9-triazaspiro[5.5]undecane |
| 19(H10-68) | (3S)-1-(2-(pyridin-3-yl)ethyl)-2,5-dioxo-3-(3-(benzyloxycarbonylamino)propyl)-9-(2-phenylethyl)-1,4,9-triazaspiro[5.5]undecane |

TABLE 11A-1

| Example No | Compound Name |
|---|---|
| 19(H11-1) | (3S)-1-cyclopropyl-2,5-dioxo-3-(2-methylpropyl)-9-(4-phenylbutyl)-1,4,9-triazaspiro[5.5]undecane |
| 19(H11-2) | (3S)-1-cyclobutyl-2,5-dioxo-3-(2-methylpropyl)-9-(4-phenylbutyl)-1,4,9-triazaspiro[5.5]undecane |
| 19(H11-3) | (3S)-1-((1S,2S,5S)-6,6-dimethylbicyclo[3.1.1]heptan-2-ylmethyl)-2,5-dioxo-3-(2-methylpropyl)-9-(4-phenylbutyl)-1,4,9-triazaspiro[5.5]undecane |
| 19(H11-4) | (3S)-1-cyclopentyl-2,5-dioxo-3-(2-methylpropyl)-9-(4-phenylbutyl)-1,4,9-triazaspiro[5.5]undecane |
| 19(H11-5) | (3S)-1-cyclohexyl-2,5-dioxo-3-(2-methylpropyl)-9-(4-phenylbutyl)-1,4,9-triazaspiro[5.5]undecane |
| 19(H11-6) | (3S)-1-(cyclohexylmethyl)-2,5-dioxo-3-(2-methylpropyl)-9-(4-phenylbutyl)-1,4,9-triazaspiro[5.5]undecane |
| 19(H11-7) | (3S)-1-(2-(1-methylpyrrolidin-2-yl)ethyl)-2,5-dioxo-3-(2-methylpropyl)-9-(4-phenylbutyl)-1,4,9-triazaspiro[5.5]undecane |
| 19(H11-8) | (3S)-1-((1-ethylpyrrolidin-2-yl)methyl)-2,5-dioxo-3-(2-methylpropyl)-9-(4-phenylbutyl)-1,4,9-triazaspiro[5.5]undecane |

TABLE 11A-2

| Example No | Compound Name |
|---|---|
| 19(H11-9) | (3S)-1-(indan-5-yl)-2,5-dioxo-3-(2-methylpropyl)-9-(4-phenylbutyl)-1,4,9-triazaspiro[5.5]undecane |
| 19(H11-10) | (3S)-1-cycloheptyl-2,5-dioxo-3-(2-methylpropyl)-9-(4-phenylbutyl)-1,4,9-triazaspiro[5.5]undecane |
| 19(H11-11) | (3S)-1-(thiophen-2-ylmethyl)-2,5-dioxo-3-(2-methylpropyl)-9-(4-phenylbutyl)-1,4,9-triazaspiro[5.5]undecane |
| 19(H11-12) | (3S)-1-(2-(morpholin-4-yl)ethyl)-2,5-dioxo-3-(2-methylpropyl)-9-(4-phenylbutyl)-1,4,9-triazaspiro[5.5]undecane |

TABLE 11A-2-continued

| Example No | Compound Name |
|---|---|
| 19(H11-13) | (3S)-1-(3-(morpholin-4-yl)propyl)-2,5-dioxo-3-(2-methylpropyl)-9-(4-phenylbutyl)-1,4,9-triazaspiro[5.5]undecane |
| 19(H11-14) | (3S)-1-(2-(pyridin-2-yl)ethyl)-2,5-dioxo-3-(2-methylpropyl)-9-(4-phenylbutyl)-1,4,9-triazaspiro[5.5]undecane |
| 19(H11-15) | (3S)-1-(pyridin-3-ylmethyl)-2,5-dioxo-3-(2-methylpropyl)-9-(4-phenylbutyl)-1,4,9-triazaspiro[5.5]undecane |

TABLE 11A-3

| Example No | Compound Name |
|---|---|
| 19(H11-16) | (3S)-1-(pyridin-4-ylmethyl)-2,5-dioxo-3-(2-methylpropyl)-9-(4-phenylbutyl)-1,4,9-triazaspiro[5.5]undecane |
| 19(H11-17) | (3S)-1-(1-(ethoxycarbonyl)piperidin-4-yl)-2,5-dioxo-3-(2-methylpropyl)-9-(4-phenylbutyl)-1,4,9-triazaspiro[5.5]undecane |
| 19(H11-18) | (3S)-1-(2-(piperidin-1-yl)ethyl)-2,5-dioxo-3-(2-methylpropyl)-9-(4-phenylbutyl)-1,4,9-triazaspiro[5.5]undecane |
| 19(H11-19) | (3S)-1-(1-phenylethyl)-2,5-dioxo-3-(2-methylpropyl)-9-(4-phenylbutyl)-1,4,9-triazaspiro[5.5]undecane |
| 19(H11-20) | (3S)-1-(1-methylethyl)-2,5-dioxo-3-(2-methylpropyl)-9-(4-phenylbutyl)-1,4,9-triazaspiro[5.5]undecane |
| 19(H11-21) | (3S)-1-((2-fluorophenyl)methyl)-2,5-dioxo-3-(2-methylpropyl)-9-(4-phenylbutyl)-1,4,9-triazaspiro[5.5]undecane |
| 19(H11-22) | (3S)-1-((2-methoxyphenyl)methyl)-2,5-dioxo-3-(2-methylpropyl)-9-(4-phenylbutyl)-1,4,9-triazaspiro[5.5]undecane |

TABLE 11A-4

| Example No | Compound Name |
|---|---|
| 19(H11-23) | (3S)-1-((3-fluorophenyl)methyl)-2,5-dioxo-3-(2-methylpropyl)-9-(4-phenylbutyl)-1,4,9-triazaspiro[5.5]undecane |
| 19(H11-24) | (3S)-1-((3-methoxyphenyl)methyl)-2,5-dioxo-3-(2-methylpropyl)-9-(4-phenylbutyl)-1,4,9-triazaspiro[5.5]undecane |
| 19(H11-25) | (3S)-1-((4-fluorophenyl)methyl)-2,5-dioxo-3-(2-methylpropyl)-9-(4-phenylbutyl)-1,4,9-triazaspiro[5.5]undecane |
| 19(H11-26) | (3S)-1-((4-methoxyphenyl)methyl)-2,5-dioxo-3-(2-methylpropyl)-9-(4-phenylbutyl)-1,4,9-triazaspiro[5.5]undecane |
| 19(H11-27) | (3S)-1-((4-methylphenyl)methyl)-2,5-dioxo-3-(2-methylpropyl)-9-(4-phenylbutyl)-1,4,9-triazaspiro[5.5]undecane |
| 19(H11-28) | (3S)-1-(2,2-dimethylpropyl)-2,5-dioxo-3-(2-methylpropyl)-9-(4-phenylbutyl)-1,4,9-triazaspiro[5.5]undecane |
| 19(H11-29) | (3S)-1-(2-phenylpropyl)-2,5-dioxo-3-(2-methylpropyl)-9-(4-phenylbutyl)-1,4,9-triazaspiro[5.5]undecane |

TABLE 11A-5

| Example No | Compound Name |
|---|---|
| 19(H11-30) | (3S)-1-(2-methylpropyl)-2,5-dioxo-3-(2-methylpropyl)-9-(4-phenylbutyl)-1,4,9-triazaspiro[5.5]undecane |
| 19(H11-31) | (3S)-1-(2-methylbutyl)-2,5-dioxo-3-(2-methylpropyl)-9-(4-phenylbutyl)-1,4,9-triazaspiro[5.5]undecane |
| 19(H11-32) | (3S)-1-benzyl-2,5-dioxo-3-(2-methylpropyl)-9-(4-phenylbutyl)-1,4,9-triazaspiro[5.5]undecane |
| 19(H11-33) | (3S)-1-(2-(N,N-dimethylamino)ethyl)-2,5-dioxo-3-(2-methylpropyl)-9-(4-phenylbutyl)-1,4,9-triazaspiro[5.5]undecane |
| 19(H11-34) | (3S)-1-(2-methoxyethyl)-2,5-dioxo-3-(2-methylpropyl)-9-(4-phenylbutyl)-1,4,9-triazaspiro[5.5]undecane |
| 19(H11-35) | (3S)-1-(2-propynyl)-2,5-dioxo-3-(2-methylpropyl)-9-(4-phenylbutyl)-1,4,9-triazaspiro[5.5]undecane |
| 19(H11-36) | (3S)-1-(2-propenyl)-2,5-dioxo-3-(2-methylpropyl)-9-(4-phenylbutyl)-1,4,9-triazaspiro[5.5]undecane |
| 19(H11-37) | (3S)-1-(3-hydroxypropyl)-2,5-dioxo-3-(2-methylpropyl)-9-(4-phenylbutyl)-1,4,9-triazaspiro[5.5]undecane |

TABLE 11A-6

| Example No | Compound Name |
|---|---|
| 19(H11-38) | (3S)-1-(3-methylbutyl)-2,5-dioxo-3-(2-methylpropyl)-9-(4-phenylbutyl)-1,4,9-triazaspiro[5.5]undecane |
| 19(H11-39) | (3S)-1-propyl-2,5-dioxo-3-(2-methylpropyl)-9-(4-phenylbutyl)-1,4,9-triazaspiro[5.5]undecane |
| 19(H11-40) | (3S)-1-(3-(N,N-dimethylamino)propyl)-2,5-dioxo-3-(2-methylpropyl)-9-(4-phenylbutyl)-1,4,9-triazaspiro[5.5]undecane |
| 19(H11-41) | (3S)-1-(3-ethoxypropyl)-2,5-dioxo-3-(2-methylpropyl)-9-(4-phenylbutyl)-1,4,9-triazaspiro[5.5]undecane |
| 19(H11-42) | (3S)-1-(3-phenylpropyl)-2,5-dioxo-3-(2-methylpropyl)-9-(4-phenylbutyl)-1,4,9-triazaspiro[5.5]undecane |
| 19(H11-43) | (3S)-1-(4-phenylbutyl)-2,5-dioxo-3-(2-methylpropyl)-9-(4-phenylbutyl)-1,4,9-triazaspiro[5.5]undecane |
| 19(H11-44) | (3S)-1-pentyl-2,5-dioxo-3-(2-methylpropyl)-9-(4-phenylbutyl)-1,4,9-triazaspiro[5.5]undecane |
| 19(H11-45) | (3S)-1-(3-(imidazol-1-yl)propyl)-2,5-dioxo-3-(2-methylpropyl)-9-(4-phenylbutyl)-1,4,9-triazaspiro[5.5]undecane |

TABLE 11A-7

| Example No | Compound Name |
|---|---|
| 19(H11-46) | (3S)-1-butyl-2,5-dioxo-3-(2-methylpropyl)-9-(4-phenylbutyl)-1,4,9-triazaspiro[5.5]undecane |
| 19(H11-47) | (3S)-1-(2-(1-cyclohexenyl)ethyl)-2,5-dioxo-3-(2-methylpropyl)-9-(4-phenylbutyl)-1,4,9-triazaspiro[5.5]undecane |
| 19(H11-48) | (3S)-1-(cyclopropylmethyl)-2,5-dioxo-3-(2-methylpropyl)-9-(4-phenylbutyl)-1,4,9-triazaspiro[5.5]undecane |
| 19(H11-49) | (3S)-1-ethyl-2,5-dioxo-3-(2-methylpropyl)-9-(4-phenylbutyl)-1,4,9-triazaspiro[5.5]undecane |
| 19(H11-50) | (3S)-1-(3-methoxypropyl)-2,5-dioxo-3-(2-methylpropyl)-9-(4-phenylbutyl)-1,4,9-triazaspiro[5.5]undecane |
| 19(H11-51) | (3S)-1-(2-(pyridin-4-yl)ethyl)-2,5-dioxo-3-(2-methylpropyl)-9-(4-phenylbutyl)-1,4,9-triazaspiro[5.5]undecane |
| 19(H11-52) | (3S)-1-((3-chlorophenyl)methyl)-2,5-dioxo-3-(2-methylpropyl)-9-(4-phenylbutyl)-1,4,9-triazaspiro[5.5]undecane |
| 19(H11-53) | (3S)-1-(3-methylthiopropyl)-2,5-dioxo-3-(2-methylpropyl)-9-(4-phenylbutyl)-1,4,9-triazaspiro[5.5]undecane |

TABLE 11A-8

| Example No | Compound Name |
|---|---|
| 19(H11-54) | (3S)-1-(2-(thiophen-2-yl)ethyl)-2,5-dioxo-3-(2-methylpropyl)-9-(4-phenylbutyl)-1,4,9-triazaspiro[5.5]undecane |
| 19(H11-55) | (3S)-1-(2-(1,1-dimethylethylthio)ethyl)-2,5-dioxo-3-(2-methylpropyl)-9-(4-phenylbutyl)-1,4,9-triazaspiro[5.5]undecane |
| 19(H11-56) | (3S)-1-((t-butoxycarbonyl)methyl)-2,5-dioxo-3-(2-methylpropyl)-9-(4-phenlybutyl)-1,4,9-triazaspiro[5.5]undecane |
| 19(H11-57) | (3S)-1-((5-methylfuran-2-yl)methyl)-2,5-dioxo-3-(2-methylpropyl)-9-(4-phenylbutyl)-1,4,9-triazaspiro[5.5]undecane |
| 19(H11-58) | (3S)-1-(2-(pyridin-3-yl)ethyl)-2,5-dioxo-3-(2-methylpropyl)-9-(4-phenylbutyl)-1,4,9-triazaspiro[5.5]undecane |

TABLE 12A-1

| Example No | Compound Name |
|---|---|
| 19(H12-1) | (3S)-1-cyclopropyl-2,5-dioxo-3-(2-methylpropyl)-9-(5-phenylpentyl)-1,4,9-triazaspiro[5.5]undecane |
| 19(H12-2) | (3S)-1-cyclobutyl-2,5-dioxo-3-(2-methylpropyl)-9-(5-phenylpentyl)-1,4,9-triazaspiro[5.5]undecane |
| 19(H12-3) | (3S)-1-((1S,2S,5S)-6,6-dimethylbicyclo[3.1.1]heptan-2-ylmethyl)-2,5-dioxo-3-(2-methylpropyl)-9-(5-phenylpentyl)-1,4,9-triazaspiro[5.5]undecane |
| 19(H12-4) | (3S)-1-cyclopentyl-2,5-dioxo-3-(2-methylpropyl)-9-(5-phenylpentyl)-1,4,9-triazaspiro[5.5]undecane |
| 19(H12-5) | (3S)-1-cyclohexyl-2,5-dioxo-3-(2-methylpropyl)-9-(5-phenylpentyl)-1,4,9-triazaspiro[5.5]undecane |
| 19(H12-6) | (3S)-1-(cyclohexylmethyl)-2,5-dioxo-3-(2-methylpropyl)-9-(5-phenylpentyl)-1,4,9-triazaspiro[5.5]undecane |
| 19(H12-7) | (3S)-1-(1,2,3,4-tetrahydronaphthyl)-2,5-dioxo-3-(2-methylpropyl)-9-(5-phenylpentyl)-1,4,9-triazaspiro[5.5]undecane |
| 19(H12-8) | (3S)-1-cyclooctyl-2,5-dioxo-3-(2-methylpropyl)-9-(5-phenylpentyl)-1,4,9-triazaspiro[5.5]undecane |

TABLE 12A-2

| Example No | Compound Name |
|---|---|
| 19(H12-9) | (3S)-1-(2-(1-methylpyrrolidin-2-yl)ethyl)-2,5-dioxo-3-(2-methylpropyl)-9-(5-phenylpentyl)-1,4,9-triazaspiro[5.5]undecane |
| 19(H12-10) | (3S)-1-((1-ethylpyrrolidin-2-yl)methyl)-2,5-dioxo-3-(2-methylpropyl)-9-(5-phenylpentyl)-1,4,9-triazaspiro[5.5]undecane |
| 19(H12-11) | (3S)-1-(indan-5-yl)-2,5-dioxo-3-(2-methylpropyl)-9-(5-phenylpentyl)-1,4,9-triazaspiro[5.5]undecane |
| 19(H12-12) | (3S)-1-cycloheptyl-2,5-dioxo-3-(2-methylpropyl)-9-(5-phenylpentyl)-1,4,9-triazaspiro[5.5]undecane |
| 19(H12-13) | (3S)-1-(thiophen-2-ylmethyl)-2,5-dioxo-3-(2-methylpropyl)-9-(5-phenylpentyl)-1,4,9-triazaspiro[5.5]undecane |
| 19(H12-14) | (3S)-1-(2-(morpholin-4-yl)ethyl)-2,5-dioxo-3-(2-methylpropyl)-9-(5-phenylpentyl)-1,4,9-triazaspiro[5.5]undecane |
| 19(H12-15) | (3S)-1-(3-(morpholin-4-yl)propyl)-2,5-dioxo-3-(2-methylpropyl)-9-(5-phenylpentyl)-1,4,9-triazaspiro[5.5]undecane |

TABLE 12A-3

| Example No | Compound Name |
|---|---|
| 19(H12-16) | (3S)-1-(2-(pyridin-2-yl)ethyl)-2,5-dioxo-3-(2-methylpropyl)-9-(5-phenylpentyl)-1,4,9-triazaspiro[5.5]undecane |
| 19(H12-17) | (3S)-1-(pyridin-3-ylmethyl)-2,5-dioxo-3-(2-methyipropyl)-9-(5-phenylpentyl)-1,4,9-triazaspiro[5.5]undecane |
| 19(H12-18) | (3S)-1-(pyridin-4-ylmethyl)-2,5-dioxo-3-(2-methylpropyl)-9-(5-phenylpentyl)-1,4,9-triazaspiro[5.5]undecane |
| 19(H12-19) | (3S)-1-(2-(piperidin-1-yl)ethyl)-2,5-dioxo-3-(2-methylpropyl)-9-(5-phenylpentyl)-1,4,9-triazaspiro[5.5]undecane |
| 19(H12-20) | (3S)-1-phenyl-2,5-dioxo-3-(2-methylpropyl)-9-(5-phenylpentyl)-1,4,9-triazaspiro[5.5]undecane |
| 19(H12-21) | (3S)-1-(1-phenylethyl)-2,5-dioxo-3-(2-methylpropyl)-9-(5-phenylpentyl)-1,4,9-triazaspiro[5.5]undecane |
| 19(H12-22) | (3S)-1-(1-methylethyl)-2,5-dioxo-3-(2-methylpropyl)-9-(5-phenylpentyl)-1,4,9-triazaspiro[5.5]undecane |

TABLE 12A-4

| Example No | Compound Name |
|---|---|
| 19(H12-23) | (3S)-1-(1,3-dimethylbutyl)-2,5-dioxo-3-(2-methylpropyl)-9-(5-phenylpentyl)-1,4,9-triazaspiro[5.5]undecane |
| 19(H12-24) | (3S)-1-(1-methyl-3-phenylpropyl)-2,5-dioxo-3-(2-methylpropyl)-9-(5-phenylpentyl)-1,4,9-triazaspiro[5.5]undecane |
| 19(H12-25) | (3S)-1-(1-methylpropyl)-2,5-dioxo-3-(2-methylpropyl)-9-(5-phenylpentyl)-1,4,9-triazaspiro[5.5]undecane |
| 19(H12-26) | (3S)-1-(1-ethylpropyl)-2,5-dioxo-3-(2-methylpropyl)-9-(5-phenylpentyl)-1,4,9-triazaspiro[5.5]undecane |
| 19(H12-27) | (3S)-1-(1-methylbutyl)-2,5-dioxo-3-(2-methylpropyl)-9-(5-phenylpentyl)-1,4,9-triazaspiro[5.5]undecane |
| 19(H12-28) | (3S)-1-((2-fluorophenyl)methyl)-2,5-dioxo-3-(2-methylpropyl)-9-(5-phenylpentyl)-1,4,9-triazaspiro[5.5]undecane |
| 19(H12-29) | (3S)-1-((2-methoxyphenyl)methyl)-2,5-dioxo-3-(2-methylpropyl)-9-(5-phenylpentyl)-1,4,9-triazaspiro[5.5]undecane |

TABLE 12A-5

| Example No | Compound Name |
|---|---|
| 19(H12-30) | (3S)-1-((3-fluorophenyl)methyl)-2,5-dioxo-3-(2-methylpropyl)-9-(5-phenylpentyl)-1,4,9-triazaspiro[5.5]undecane |
| 19(H12-31) | (3S)-1-((3-methoxyphenyl)methyl)-2,5-dioxo-3-(2-methylpropyl)-9-(5-phenylpentyl)-1,4,9-triazaspiro[5.5]undecane |
| 19(H12-32) | (3S)-1-((4-fluorophenyl)methyl)-2,5-dioxo-3-(2-methylpropyl)-9-(5-phenylpentyl)-1,4,9-triazaspiro[5.5]undecane |
| 19(H12-33) | (3S)-1-((4-methoxyphenyl)methyl)-2,5-dioxo-3-(2-methylpropyl)-9-(5-phenylpentyl)-1,4,9-triazaspiro[5.5]undecane |
| 19(H12-34) | (3S)-1-((4-methylphenyl)methyl)-2,5-dioxo-3-(2-methylpropyl)-9-(5-phenylpentyl)-1,4,9-triazaspiro[5.5]undecane |
| 19(H12-35) | (3S)-1-(2,2-dimethylpropyl)-2,5-dioxo-3-(2-methylpropyl)-9-(5-phenylpentyl)-1,4,9-triazaspiro[5.5]undecane |
| 19(H12-36) | (3S)-1-(2-phenylpropyl)-2,5-dioxo-3-(2-methylpropyl)-9-(5-phenylpentyl)-1,4,9-triazaspiro[5.5]undecane |

TABLE 12A-6

| Example No | Compound Name |
|---|---|
| 19(H12-37) | (3S)-1-(2-methylpropyl)-2,5-dioxo-3-(2-methylpropyl)-9-(5-phenylpentyl)-1,4,9-triazaspiro[5.5]undecane |
| 19(H12-38) | (3S)-1-(2-methylbutyl)-2,5-dioxo-3-(2-methylpropyl)-9-(5-phenylpentyl-1,4,9-triazaspiro[5.5]undecane |
| 19(H12-39) | (3S)-1-benzyl-2,5-dioxo-3-(2-methylpropyl)-9-(5-phenylpentyl)-1,4,9-triazaspiro[5.5]undecane |
| 19(H12-40) | (3S)-1-(2-(N,N-dimethylamino)ethyl)-2,5-dioxo-3-(2-methylpropyl)-9-(5-phenylpentyl)-1,4,9-triazaspiro[5.5]undecane |
| 19(H12-41) | (3S)-1-(2-methoxyethyl)-2,5-dioxo-3-(2-methylpropyl)-9-(5-phenylpentyl)-1,4,9-triazaspiro[5.5]undecane |
| 19(H12-42) | (3S)-1-(2-propynyl)-2,5-dioxo-3-(2-methylpropyl)-9-(5-phenylpentyl)-1,4,9-triazaspiro[5.5]undecane |
| 19(H12-43) | (3S)-1-(2-propenyl)-2,5-dioxo-3-(2-methylpropyl)-9-(5-phenylpentyl-1,4,9-triazaspiro[5.5]undecane |
| 19(H12-44) | (3S)-1-(3-hydroxypropyl)-2,5-dioxo-3-(2-methylpropyl)-9-(5-penylpentyl)-1,4,9-triazaspiro[5.5]undecane |

TABLE 12A-7

| Example No | Compound Name |
|---|---|
| 19(H12-45) | (3S)-1-(3-methylbutyl)-2,5-dioxo-3-(2-methylpropyl)-9-(5-phenylpentyl)-1,4,9-triazaspiro[5.5]undecane |
| 19(H12-46) | (3S)-1-propyl-2,5-dioxo-3-(2-methylpropyl)-9-(5-phenylpentyl)-1,4,9-triazaspiro[5.5]undecane |
| 19(H12-47) | (3S)-1-(3-(N,N-dimethylamino)propyl)-2,5-dioxo-3-(2-methylpropyl)-9-(5-phenylpentyl)-1,4,9-triazaspiro[5.5]undecane |
| 19(H12-48) | (3S)-1-(3-ethoxypropyl)-2,5-dioxo-3-(2-methylpropyl)-9-(5-phenylpentyl)-1,4,9-triazaspiro[5.5]undecane |
| 19(H12-49) | (3S)-1-(3-phenylpropyl)-2,5-dioxo-3-(2-methylpropyl)-9-(5-phenylpentyl)-1,4,9-triazaspiro[5.5]undecane |
| 19(H12-50) | (3S)-1-(4-phenylbutyl)-2,5-dioxo-3-(2-methylpropyl)-9-(5-phenylpentyl)-1,4,9-triazaspiro[5.5]undecane |
| 19(H12-51) | (3S)-1-pentyl-2,5-dioxo-3-(2-methylpropyl)-9-(5-phenylpentyl)-1,4,9-triazaspiro[5.5]undecane |
| 19(H12-52) | (3S)-1-(3-(imidazol-1-yl)propyl)-2,5-dioxo-3-(2-methylpropyl)-9-(5-phenylpentyl)-1,4,9-triazaspiro[5.5]undecane |

TABLE 12A-8

| Example No | Compound Name |
|---|---|
| 19(H12-53) | (3S)-1-butyl-2,5-dioxo-3-(2-methylpropyl)-9-(5-phenylpentyl)-1,4,9-triazaspiro[5.5]undecane |
| 19(H12-54) | (3S)-1-(2-(1-cyclohexenyl)ethyl)-2,5-dioxo-3-(2-methylpropyl)-9-(5-phenylpentyl)-1,4,9-triazaspiro[5.5]undecane |
| 19(H12-55) | (3S)-1-(cyclopropylmethyl)-2,5-dioxo-3-(2-methylpropyl)-9-(5-phenylpentyl)-1,4,9-triazaspiro[5.5]undecane |
| 19(H12-56) | (3S)-1-ethyl-2,5-dioxo-3-(2-methylpropyl)-9-(5-phenylpentyl)-1,4,9-triazaspiro[5.5]undecane |
| 19(H12-57) | (3S)-1-(1-propylbutyl)-2,5-dioxo-3-(2-methylpropyl)-9-(5-phenylpentyl)-1,4,9-triazaspiro[5.5]undecane |
| 19(H12-58) | (3S)-1-(3-methoxypropyl)-2,5-dioxo-3-(2-methylpropyl)-9-(5-phenylpentyl)-1,4,9-triazaspiro[5.5]undecane |
| 19(H12-59) | (3S)-1-(2-(pyridin-4-yl)ethyl)-2,5-dioxo-3-(2-methylpropyl)-9-(5-phenylpentyl)-1,4,9-triazaspiro[5.5]undecane |
| 19(H12-60) | (3S)-1-((3-chlorophenyl)methyl)-2,5-dioxo-3-(2-methylpropyl)-9-(5-phenylpentyl)-1,4,9-triazaspiro[5.5]undecane |

TABLE 12A-9

| Example No | Compound Name |
|---|---|
| 19(H12-61) | (3S)-1-(3-methylthiopropyl)-2,5-dioxo-3-(2-methylpropyl)-9-(5-phenylpentyl)-1,4,9-triazaspiro[5.5]undecane |
| 19(H12-62) | (3S)-1-(2-(thiophen-2-yl)ethyl)-2,5-dioxo-3-(2-methylpropyl)-9-(5-phenylpentyl)-1,4,9-triazaspiro[5.5]undecane |
| 19(H12-63) | (3S)-1-(2-(1,1-dimethylethylthio)ethyl)-2,5-dioxo-3-(2-methylpropyl)-9-(5-phenylpentyl)-1,4,9-triazaspiro[5.5]undecane |
| 19(H12-64) | (3S)-1-((t-butoxycarbonyl)methyl)-2,5-dioxo-3-(2-methylpropyl)-9-(5-phenylpentyl)-1,4,9-triazaspiro[5.5]undecane |
| 19(H12-65) | (3S)-1-((2R)-2-hydroxypropyl)-2,5-dioxo-3-(2-methylpropyl)-9-(5-phenylpentyl)-1,4,9-triazaspiro[5.5]undecane |
| 19(H12-66) | (3S)-1-((2S)-2-hydroxypropyl)-2,5-dioxo-3-(2-methylpropyl)-9-(5-phenylpentyl)-1,4,9-triazaspiro[5.5]undecane |
| 19(H12-67) | (3S)-1-((5-methylfuran-2-yl)methyl)-2,5-dioxo-3-(2-methylpropyl)-9-(5-phenylpentyl)-1,4,9-triazaspiro[5.5]undecane |

TABLE 12A-10

| Example No | Compound Name |
|---|---|
| 19(H12-68) | (3S)-1-((1R)-1-(4-methylphenyl)ethyl)-2,5-dioxo-3-(2-methylpropyl)-9-(5-phenylpentyl)-1,4,9-triazaspiro[5.5]undecane |
| 19(H12-69) | (3S)-1-(2-(pyridin-3-yl)ethyl)-2,5-dioxo-3-(2-methylpropyl)-9-(5-phenylpentyl)-1,4,9-triazaspiro-[5.5]undecane |

TABLE 13A-1

| Example No | Compound Name |
|---|---|
| 19(H13-1) | (3S)-1-cyclopropyl-2,5-dioxo-3-(2-methylpropyl)-9-(6-phenylhexyl)-1,4,9-triazaspiro[5.5]undecane |
| 19(H13-2) | (3S)-1-cyclobutyl-2,5-dioxo-3-(2-methylpropyl)-9-(6-phenylhexyl)-1,4,9-triazaspiro[5.5]undecane |
| 19(H13-3) | (3S)-1-((1S,2S,5S)-6,6-dimethylbicyclo[3.1.1]heptan-2-ylmethyl)-2,5-dioxo-3-(2-methylpropyl)-9-(6-phenylhexyl)-1,4,9-triazaspiro[5.5]undecane |
| 19(H13-4) | (3S)-1-cyclopentyl-2,5-dioxo-3-(2-methylpropyl)-9-(6-phenylhexyl)-1,4,9-triazaspiro[5.5]undecane |
| 19(H13-5) | (3S)-1-cyclohexyl-2,5-dioxo-3-(2-methylpropyl)-9-(6-phenylhexyl)-1,4,9-triazaspiro[5.5]undecane |
| 19(H13-6) | (3S)-1-(cyclohexylmethyl)-2,5-dioxo-3-(2-methylpropyl)-9-(6-phenylhexyl)-1,4,9-triazaspiro[5.5]undecane |
| 19(H13-7) | (3S)-1-(1,2,3,4-tetrahydronaphthyl)-2,5-dioxo-3-(2-methylpropyl)-9-(6-phenylhexyl)-1,4,9-triazaspiro[5.5]undecane |
| 19(H13-8) | (3S)-1-cyclooctyl-2,5-dioxo-3-(2-methylpropyl)-9-(6-phenylhexyl)-1,4,9-triazaspiro[5.5]undecane |

TABLE 13A-2

| Example No | Compound Name |
|---|---|
| 19(H13-9) | (3S)-1-(2-(1-methylpyrrolidin-2-yl)ethyl)-2,5-dioxo-3-(2-methylpropyl)-9-(6-phenylhexyl)-1,4,9-triazaspiro[5.5]undecane |
| 19(H13-10) | (3S)-1-((1-ethylpyrrolidin-2-yl)methyl)-2,5-dioxo-3-(2-methylpropyl)-9-(6-phenylhexyl)-1,4,9-triazaspiro[5.5]undecane |
| 19(H13-11) | (3S)-1-(indan-5-yl)-2,5-dioxo-3-(2-methylpropyl)-9-(6-phenylhexyl)-1,4,9-triazaspiro[5.5]undecane |
| 19(H13-12) | (3S)-1-cycloheptyl-2,5-dioxo-3-(2-methylpropyl)-9-(6-phenylhexyl)-1,4,9-triazaspiro[5.5]undecane |
| 19(H13-13) | (3S)-1-(thiophen-2-ylmethyl)-2,5-dioxo-3-(2-methylpropyl)-9-(6-phenylhexyl)-1,4,9-triazaspiro[5.5]undecane |
| 19(H13-14) | (3S)-1-(2-(morpholin-4-yl)ethyl)-2,5-dioxo-3-(2-methylpropyl)-9-(6-phenylhexyl)-1,4,9-triazaspiro[5.5]undecane |
| 19(H13-15) | (3S)-1-(3-(morpholin-4-yl)propyl)-2,5-dioxo-3-(2-methylpropyl)-9-(6-phenylhexyl)-1,4,9-triazaspiro[5.5]undecane |

TABLE 13A-3

| Example No | Compound Name |
|---|---|
| 19(H13-16) | (3S)-1-(2-(pyridin-2-yl)ethyl)-2,5-dioxo-3-(2-methylpropyl)-9-(6-phenylhexyl)-1,4,9-triazaspiro[5.5]undecane |
| 19(H13-17) | (3S)-1-(pyridin-3-ylmethyl)-2,5-dioxo-3-(2-methylpropyl)-9-(6-phenylhexyl)-1,4,9-triazaspiro[5.5]undecane |
| 19(H13-18) | (3S)-1-(1-(ethoxycarbonyl)piperidin-4-yl)-2,5-dioxo-3-(2-methylpropyl)-9-(6-phenylhexyl)-1,4,9-triazaspiro[5.5]undecane |
| 19(H13-19) | (3S)-1-(2-(piperidin-1-yl)ethyl)-2,5-dioxo-3-(2-methylpropyl)-9-(6-phenylhexyl)-1,4,9-triazaspiro[5.5]undecane |
| 19(H13-20) | (3S)-1-(1-phenylethyl)-2,5-dioxo-3-(2-methylpropyl)-9-(6-phenylhexyl)-1,4,9-triazaspiro[5.5]undecane |
| 19(H13-21) | (3S)-1-(1,2-dimethylpropyl)-2,5-dioxo-3-(2-methylpropyl)-9-(6-phenylhexyl)-1,4,9-triazaspiro[5.5]undecane |
| 19(H13-22) | (3S)-1-(1,3-dimethylbutyl)-2,5-dioxo-3-(2-methylpropyl)-9-(6-phenylhexyl)-1,4,9-triazaspiro[5.5]undecane |

TABLE 13A-4

| Example No | Compound Name |
|---|---|
| 19(H13-23) | (3S)-1-(1-ethylpropyl)-2,5-dioxo-3-(2-methylpropyl)-9-(6-phenylhexyl)-1,4,9-triazaspiro[5.5]undecane |
| 19(H13-24) | (3S)-1-((2-fluorophenyl)methyl)-2,5-dioxo-3-(2-methylpropyl)-9-(6-phenylhexyl)-1,4,9-triazaspiro[5.5]undecane |
| 19(H13-25) | (3S)-1-((2-methoxyphenyl)methyl)-2,5-dioxo-3-(2-methylpropyl)-9-(6-phenylhexyl)-1,4,9-triazaspiro[5.5]undecane |
| 19(H13-26) | (3S)-1-((3-fluorophenyl)methyl)-2,5-dioxo-3-(2-methylpropyl)-9-(6-phenylhexyl)-1,4,9-triazaspiro[5.5]undecane |
| 19(H13-27) | (3S)-1-((3-methoxyphenyl)methyl)-2,5-dioxo-3-(2-methylpropyl)-9-(6-phenylhexyl)-1,4,9-triazaspiro[5.5]undecane |
| 19(H13-28) | (3S)-1-((4-fluorophenyl)methyl)-2,5-dioxo-3-(2-methylpropyl)-9-(6-phenylhexyl)-1,4,9-triazaspiro[5.5]undecane |

TABLE 13A-4-continued

| Example No | Compound Name |
|---|---|
| 19(H13-29) | (3S)-1-((4-methoxyphenyl)methyl)-2,5-dioxo-3-(2-methylpropyl)-9-(6-phenylhexyl)-1,4,9-triazaspiro[5.5]undecane |

TABLE 13A-5

| Example No | Compound Name |
|---|---|
| 19(H13-30) | (3S)-1-((4-methylphenyl)methyl)-2,5-dioxo-3-(2-methylpropyl)-9-(6-phenylhexyl)-1,4,9-triazaspiro[5.5]undecane |
| 19(H13-31) | (3S)-1-(2,2-dimethylpropyl)-2,5-dioxo-3-(2-methylpropyl)-9-(6-phenylhexyl)-1,4,9-triazaspiro[5.5]undecane |
| 19(H13-32) | (3S)-1-(2-phenylpropyl)-2,5-dioxo-3-(2-methylpropyl)-9-(6-phenylhexyl)-1,4,9-triazaspiro[5.5]undecane |
| 19(H13-33) | (3S)-1-(2-methylpropyl)-2,5-dioxo-3-(2-methylpropyl)-9-(6-phenylhexyl)-1,4,9-triazaspiro[5.5]undecane |
| 19(H13-34) | (3S)-1-(2-methylbutyl)-2,5-dioxo-3-(2-methylpropyl)-9-(6-phenylhexyl)-1,4,9-triazaspiro[5.5]undecane |
| 19(H13-35) | (3S)-1-benzyl-2,5-dioxo-3-(2-methylpropyl)-9-(6-phenylhexyl)-1,4,9-triazaspiro[5.5]undecane |
| 19(H13-36) | (3S)-1-(2-(N,N-dimethylamino)ethyl)-2,5-dioxo-3-(2-methylpropyl)-9-(6-phenylhexyl)-1,4,9-triazaspiro[5.5]undecane |
| 19(H13-37) | (3S)-1-(2-methoxyethyl)-2,5-dioxo-3-(2-methylpropyl)-9-(6-phenylhexyl)-1,4,9-triazaspiro[5.5]undecane |

TABLE 13A-6

| Example No | Compound Name |
|---|---|
| 19(H13-38) | (3S)-1-(2-propynyl)-2,5-dioxo-3-(2-methylpropyl)-9-(6-phenylhexyl)-1,4,9-triazaspiro[5.5]undecane |
| 19(H13-39) | (3S)-1-(2-propenyl)-2,5-dioxo-3-(2-methylpropyl)-9-(6-phenylhexyl)-1,4,9-triazaspiro[5.5]undecane |
| 19(H13-40) | (3S)-1-(3-hydroxypropyl)-2,5-dioxo-3-(2-methylpropyl)-9-(6-phenylhexyl)-1,4,9-triazaspiro[5.5]undecane |
| 19(H13-41) | (3S)-1-(3-methylbutyl)-2,5-dioxo-3-(2-methylpropyl)-9-(6-phenylhexyl)-1,4,9-triazaspiro[5.5]undecane |
| 19(H13-42) | (3S)-1-propyl-2,5-dioxo-3-(2-methylpropyl)-9-(6-phenylhexyl)-1,4,9-triazaspiro[5.5]undecane |
| 19(H13-43) | (3S)-1-(3-(N,N-dimethylamino)propyl)-2,5-dioxo-3-(2-methylpropyl)-9-(6-phenylhexyl)-1,4,9-triazaspiro[5.5]undecane |
| 19(H13-44) | (3S)-1-(3-ethoxypropyl)-2,5-dioxo-3-(2-methylpropyl)-9-(6-phenylhexyl)-1,4,9-triazaspiro[5.5]undecane |
| 19(H13-45) | (3S)-1-(3-phenylpropyl)-2,5-dioxo-3-(2-methylpropyl)-9-(6-phenylhexyl)-1,4,9-triazaspiro[5.5]undecane |

TABLE 13A-7

| Example No | Compound Name |
|---|---|
| 19(H13-46) | (3S)-1-(4-phenylbutyl)-2,5-dioxo-3-(2-methylpropyl)-9-(6-phenylhexyl)-1,4,9-triazaspiro[5.5]undecane |
| 19(H13-47) | (3S)-1-pentyl-2,5-dioxo-3-(2-methylpropyl)-9-(6-phenylhexyl)-1,4,9-triazaspiro[5.5]undecane |

TABLE 13A-7-continued

| Example No | Compound Name |
|---|---|
| 19(H13-48) | (3S)-1-(3-(imidazol-1-yl)propyl)-2,5-dioxo-3-(2-methylpropyl)-9-(6-phenylhexyl)-1,4,9-triazaspiro[5.5]undecane |
| 19(H13-49) | (3S)-1-butyl-2,5-dioxo-3-(2-methylpropyl)-9-(6-phenylhexyl)-1,4,9-triazaspiro[5.5]undecane |
| 19(H13-50) | (3S)-1-(2-(1-cyclohexenyl)ethyl)-2,5-dioxo-3-(2-methylpropyl)-9-(6-phenylhexyl)-1,4,9-triazaspiro[5.5]undecane |
| 19(H13-51) | (3S)-1-(cyclopropylmethyl)-2,5-dioxo-3-(2-methylpropyl)-9-(6-phenylhexyl)-1,4,9-triazaspiro[5.5]undecane |
| 19(H13-52) | (3S)-1-ethyl-2,5-dioxo-3-(2-methylpropyl)-9-(6-phenylhexyl)-1,4,9-triazaspiro[5.5]undecane |
| 19(H13-53) | (3S)-1-(1-propylbutyl)-2,5-dioxo-3-(2-methylpropyl)-9-(6-phenylhexyl)-1,4,9-triazaspiro[5.5]undecane |

TABLE 13A-8

| Example No | Compound Name |
|---|---|
| 19(H13-54) | (3S)-1-(3-methoxypropyl)-2,5-dioxo-3-(2-methylpropyl)-9-(6-phenylhexyl)-1,4,9-triazaspiro[5.5]undecane |
| 19(H13-55) | (3S)-1-(2-(pyridin-4-yl)ethyl)-2,5-dioxo-3-(2-methylpropyl)-9-(6-phenylhexyl)-1,4,9-triazaspiro[5.5]undecane |
| 19(H13-56) | (3S)-1-((3-chlorophenyl)methyl)-2,5-dioxo-3-(2-methylpropyl)-9-(6-phenylhexyl)-1,4,9-triazaspiro[5.5]undecane |
| 19(H13-57) | (3S)-1-(3-methylthiopropyl)-2,5-dioxo-3-(2-methylpropyl)-9-(6-phenylhexyl)-1,4,9-triazaspiro[5.5]-undecane |
| 19(H13-58) | (3S)-1-(2-(thiophen-2-yl)ethyl)-2,5-dioxo-3-(2-methylpropyl)-9-(6-phenylhexyl)-1,4,9-triazaspiro[5.5]undecane |
| 19(H13-59) | (3S)-1-(2-(1,1-dimethylethylthio)ethyl)-2,5-dioxo-3-(2-methylpropyl)-9-(6-phenylhexyl)-1,4,9-triazaspiro[5.5]undecane |
| 19(H13-6O) | (3S)-1-((t-butoxycarbonyl)methyl)-2,5-dioxo-3-(2-methylpropyl)-9-(6-phenylhexyl)-1,4,9-triazaspiro[5.5]undecane |

TABLE 13A-9

| Example No | Compound Name |
|---|---|
| 19(H13-61) | (3S)-1-((5-methylfuran-2-yl)methyl)-2,5-dioxo-3-(2-methylpropyl)-9-(6-phenylhexyl)-1,4,9-triazaspiro[5.5]undecane |
| 19(H13-62) | (3S)-1-(2-(pyridin-3-yl)ethyl)-2,5-dioxo-3-(2-methylpropyl)-9-(6-phenylhexyl)-1,4,9-triazaspiro[5.5]undecane |

TABLE 1B-1
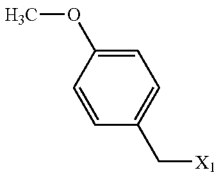
| Example No | $R^2$ | $R^3$ | $R^4$ | $R^5$ |
|---|---|---|---|---|
| 19(H1-1) | 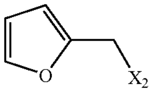 | H | 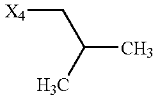 | H |
| 19(H1-2) | 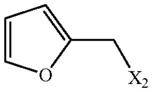 | H | 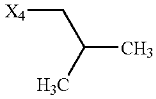 | H |
| 19(H1-3) | 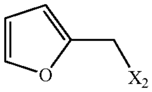 | H | 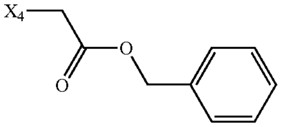 | H |
| 19(H1-4) | 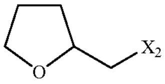 | H | H | H |
| 19(H1-5) | 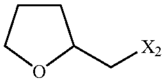 | H | 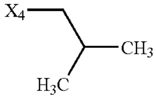 | H |
| 19(H1-6) | 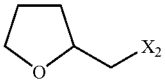 | H | 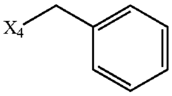 | H |
| 19(H1-7) | 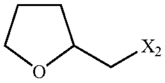 | H | 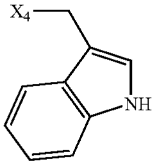 | H |
| 19(H1-8) | 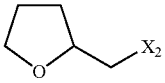 | H | 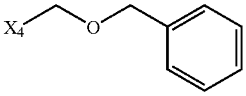 | H |

TABLE 1B-2
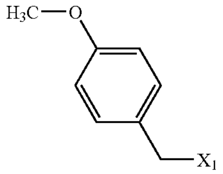
| Example No | $R^2$ | $R^3$ | $R^4$ | $R^5$ |
|---|---|---|---|---|
| 19(H1-9) | 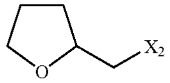 | H | 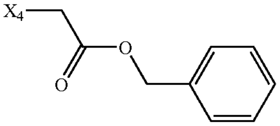 | H |
| 19(H1-10) | 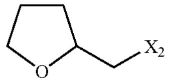 | H | 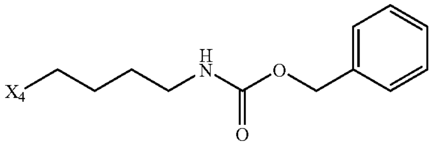 | H |
| 19(H1-11) | 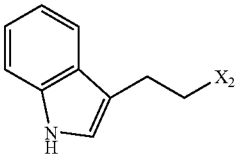 | H | 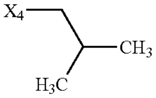 | H |
| 19(H1-12) | 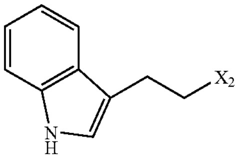 | H | 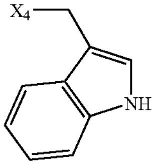 | H |
| 19(H1-13) | 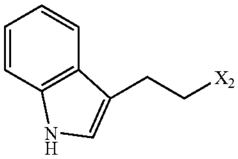 | H | 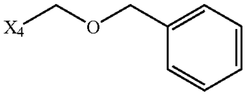 | H |
| 19(H1-14) | 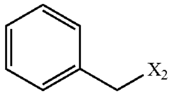 | H | H | H |
| 19(H1-15) | 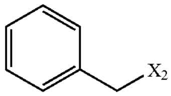 | H | 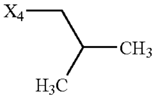 | H |
| 19(H1-16) | 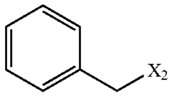 | H | 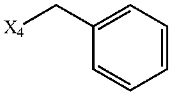 | H |

TABLE 1B-3
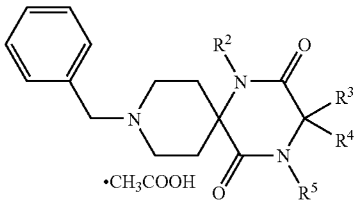
•$CH_3COOH$
| Example No | $R^2$ | $R^3$ | $R^4$ | $R^5$ |
|---|---|---|---|---|
| 19(H1-17) | 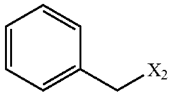 | H | 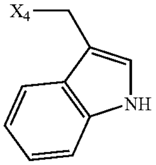 | H |
| 19(H1-18) | 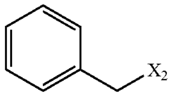 | H | 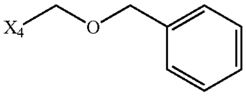 | H |
| 19(H1-19) | 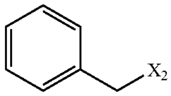 | H | 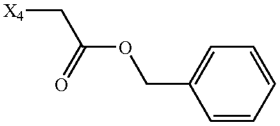 | H |
| 19(H1-20) | 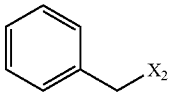 | H | 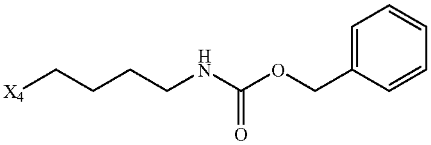 | H |
| 19(H1-21) | 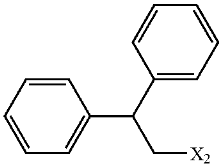 | H | H | H |
| 19(H1-22) | 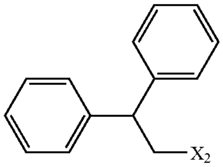 | H | 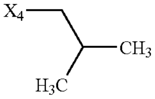 | H |
| 19(H1-23) | 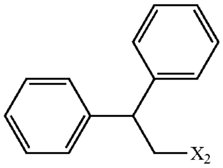 | H | 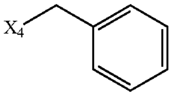 | H |

TABLE 1B-4
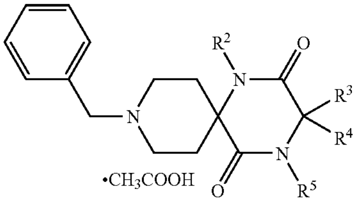
•$CH_3COOH$
| Example No | $R^2$ | $R^3$ | $R^4$ | $R^5$ |
|---|---|---|---|---|
| 19(H1-24) | 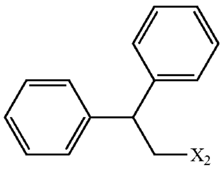 | H | 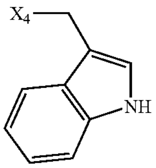 | H |
| 19(H1-25) | 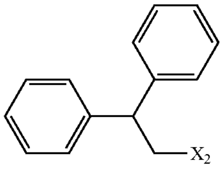 | H | 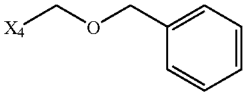 | H |
| 19(H1-26) | 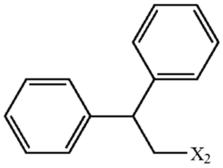 | H | 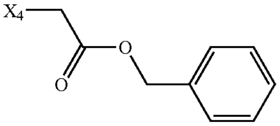 | H |
| 19(H1-27) | 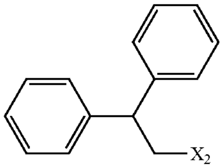 | H | 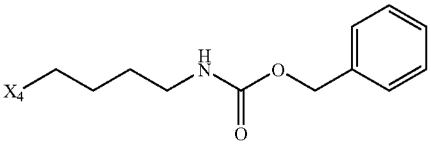 | H |
| 19(H1-28) | 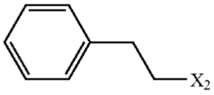 | H | H | H |
| 19(H1-29) | 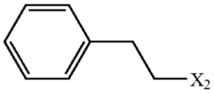 | H | 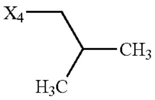 | H |
| 19(H1-30) | 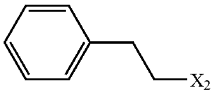 | H | 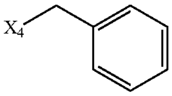 | H |
| 19(H1-31) | 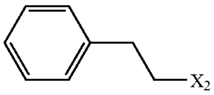 | H | 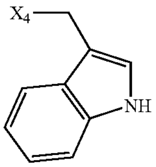 | H |

TABLE 1B-5
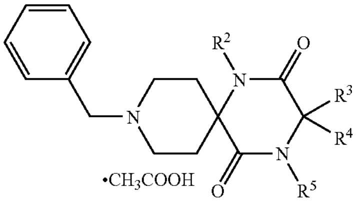
•$CH_3COOH$
| Example No | $R^2$ | $R^3$ | $R^4$ | $R^5$ |
|---|---|---|---|---|
| 19(H1-32) | 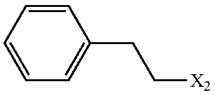 | H | 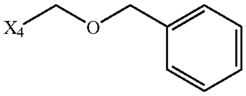 | H |
| 19(H1-33) | 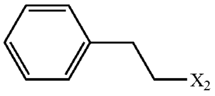 | H | 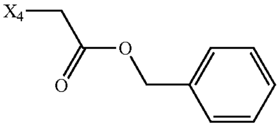 | H |
| 19(H1-34) | 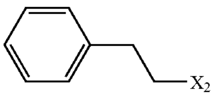 | H | 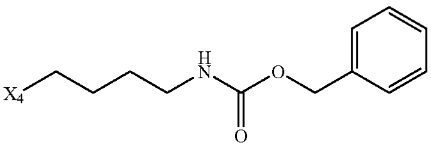 | H |
| 19(H1-35) | 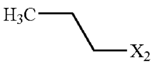 | H | H | H |
| 19(H1-36) | 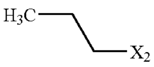 | H | 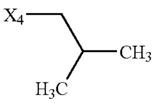 | H |
| 19(H1-37) | 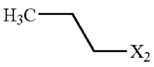 | H | 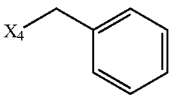 | H |
| 19(H1-38) | 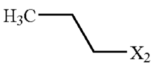 | H | 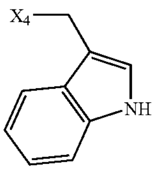 | H |
| 19(H1-39) | 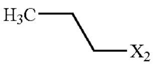 | H | 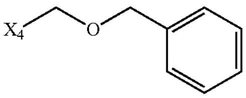 | H |
| 19(H1-40) | 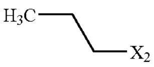 | H | 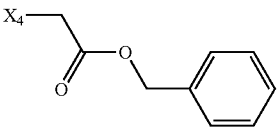 | H |

TABLE 1B-6
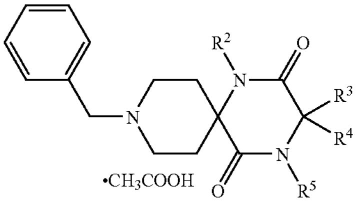
•$CH_3COOH$
| Example No | $R^2$ | $R^3$ | $R^4$ | $R^5$ |
|---|---|---|---|---|
| 19(H1-41) | 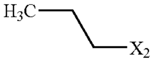 | H | 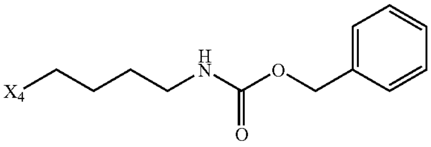 | H |
| 19(H1-42) | 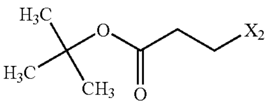 | H | H | H |
| 19(H1-43) | 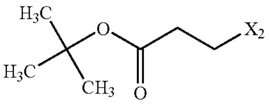 | H | 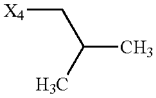 | H |
| 19(H1-44) | 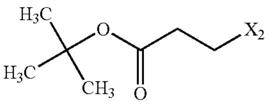 | H | 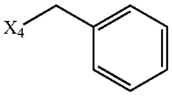 | H |
| 19(H1-45) | 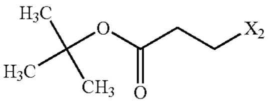 | H | 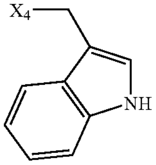 | H |
| 19(H1-46) | 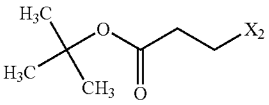 | H | 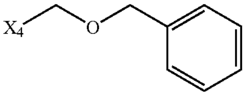 | H |
| 19(H1-47) | 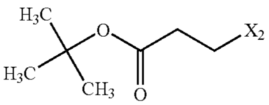 | H | 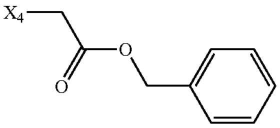 | H |
| 19(H1-48) | 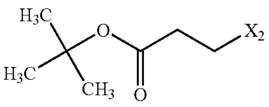 | H | 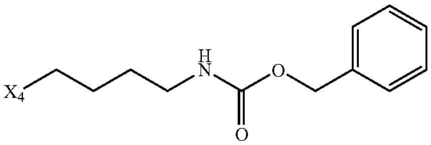 | H |

TABLE 1B-7
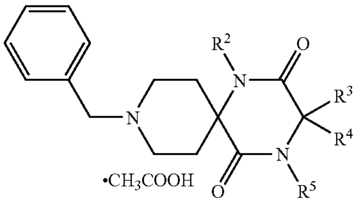
•$CH_3COOH$
| Example No | $R^2$ | $R^3$ | $R^4$ | $R^5$ |
| --- | --- | --- | --- | --- |
| 19(H1-49) | 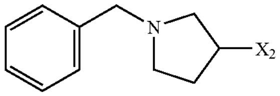 | H | H | H |
| 19(H1-50) | 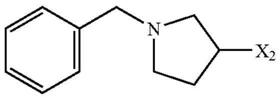 | H | 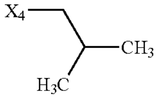 | H |
| 19(H1-51) | 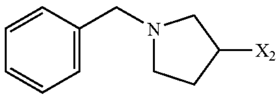 | H | 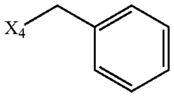 | H |
| 19(H1-52) | 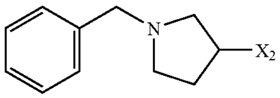 | H | 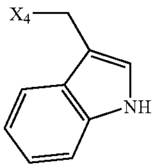 | H |
| 19(H1-53) | 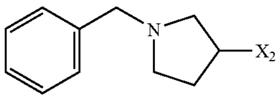 | H | 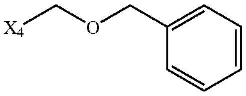 | H |
| 19(H1-54) | 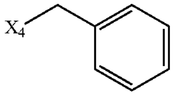 | H | 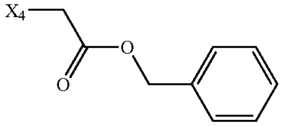 | H |
| 19(H1-55) | 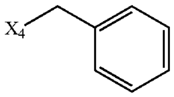 | H | 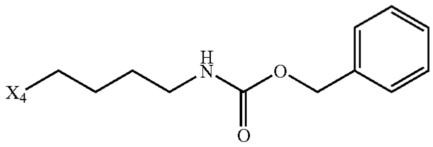 | H |
TABLE 2B-1
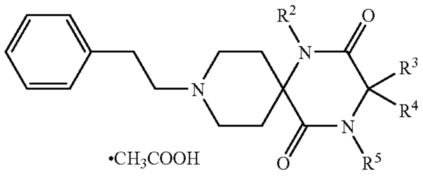
•$CH_3COOH$
| Example No | $R^2$ | $R^3$ | $R^4$ | $R^5$ |
| --- | --- | --- | --- | --- |
| 19(H2-1) | 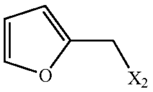 | H | H | H |

TABLE 2B-1-continued
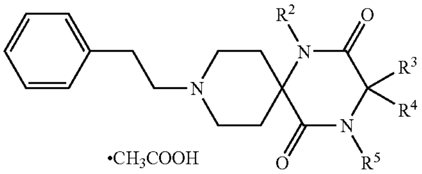
•$CH_3COOH$
| Example No | $R^2$ | $R^3$ | $R^4$ | $R^5$ |
|---|---|---|---|---|
| 19(H2-2) | 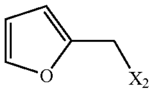 | H | 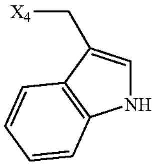 | H |
| 19(H2-3) | 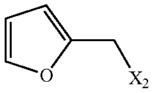 | H | 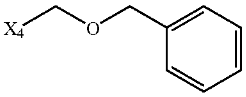 | H |
| 19(H2-4) | 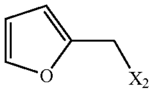 | H | 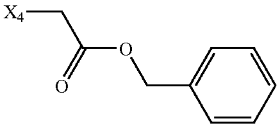 | H |
| 19(H2-5) | 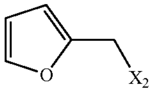 | H | 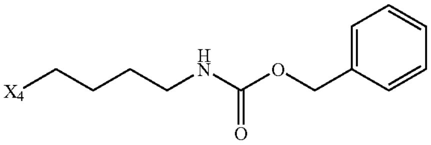 | H |
| 19(H2-6) | 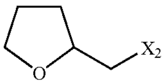 | H | H | H |
| 19(H2-7) | 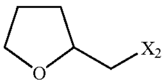 | H | 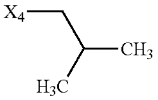 | H |
| 19(H2-8) | 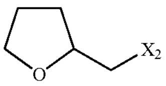 | H | 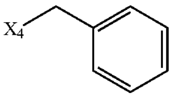 | H |

TABLE 2B-2
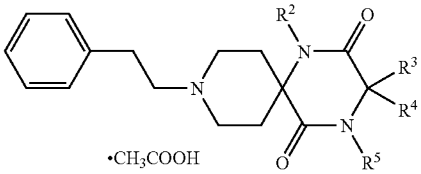
•$CH_3COOH$
| Example No | $R^2$ | $R^3$ | $R^4$ | $R^5$ |
|---|---|---|---|---|
| 19(H2-9) | 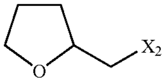 | H | 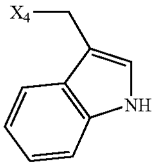 | H |
| 19(H2-10) | 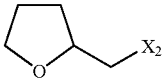 | H | 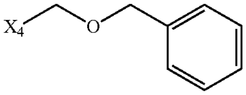 | H |
| 19(H2-11) | 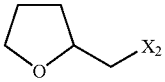 | H | 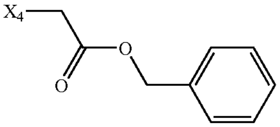 | H |
| 19(H2-12) | 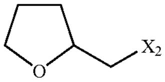 | H | 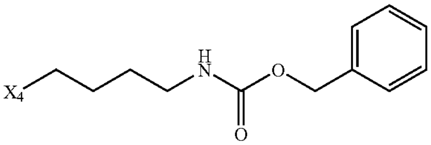 | H |
| 19(H2-13) | 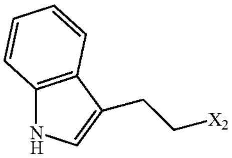 | H | H | H |
| 19(H2-14) | 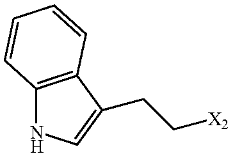 | H | 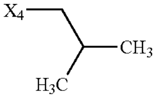 | H |
| 19(H2-15) | 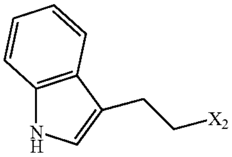 | H | 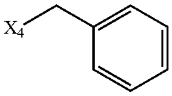 | H |

TABLE 2B-3
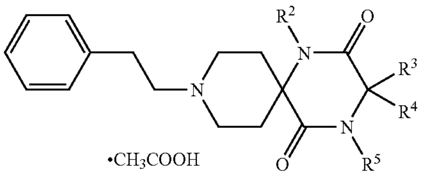
•$CH_3COOH$
| Example No | $R^2$ | $R^3$ | $R^4$ | $R^5$ |
|---|---|---|---|---|
| 19(H2-16) | 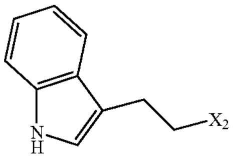 | H | 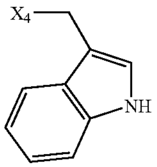 | H |
| 19(H2-17) | 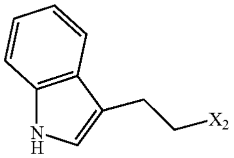 | H | 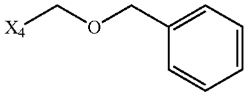 | H |
| 19(H2-18) | 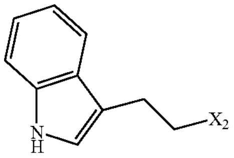 | H | 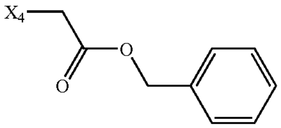 | H |
| 19(H2-19) | 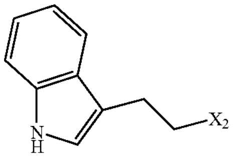 | H | 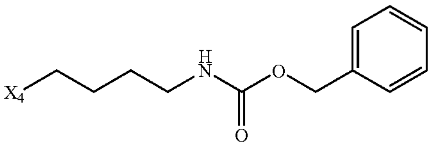 | H |
| 19(H2-20) | 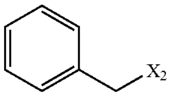 | H | H | H |
| 19(H2-21) | 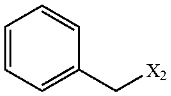 | H | 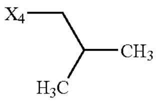 | H |
| 19(H2-22) | 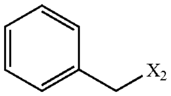 | H | 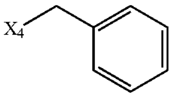 | H |
| 19(H2-23) | 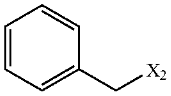 | H | 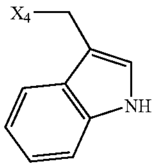 | H |

TABLE 2B-4
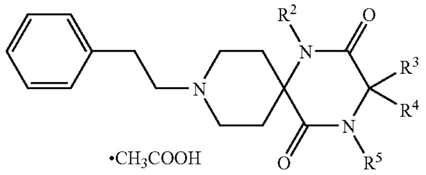
•$CH_3COOH$
| Example No | $R^2$ | $R^3$ | $R^4$ | $R^5$ |
| --- | --- | --- | --- | --- |
| 19(H2-24) | 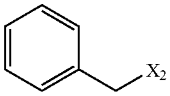 | H | 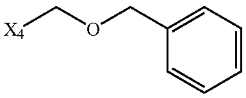 | H |
| 19(H2-25) | 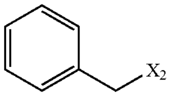 | H | 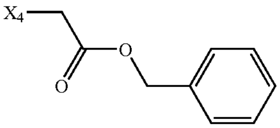 | H |
| 19(H2-26) | 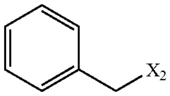 | H | 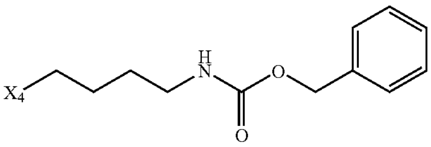 | H |
| 19(H2-27) | 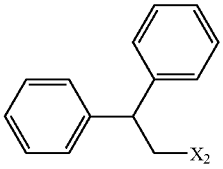 | H | H | H |
| 19(H2-28) | 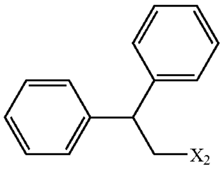 | H | 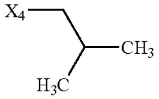 | H |
| 19(H2-29) | 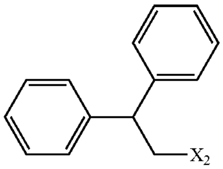 | H | 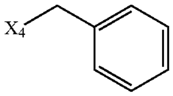 | H |
| 19(H2-30) | 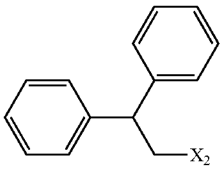 | H | 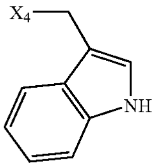 | H |
| 19(H2-31) | 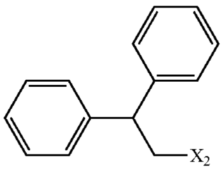 | H | 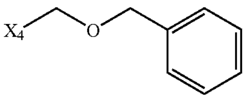 | H |

TABLE 2B-5
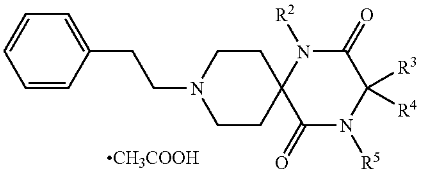
•$CH_3COOH$
| Example No | $R^2$ | $R^3$ | $R^4$ | $R^5$ |
| --- | --- | --- | --- | --- |
| 19(H2-32) | 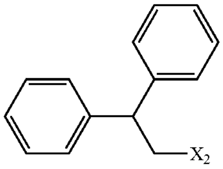 | H | 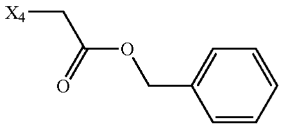 | H |
| 19(H2-33) | 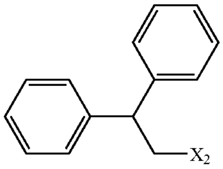 | H | 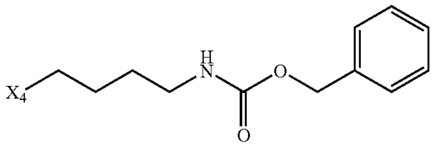 | H |
| 19(H2-34) | 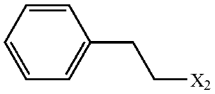 | H | H | H |
| 19(H2-35) | 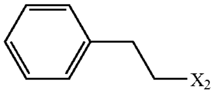 | H | 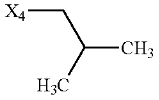 | H |
| 19(H2-36) | 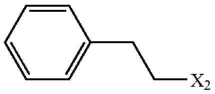 | H | 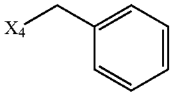 | H |
| 19(H2-37) | 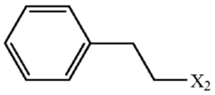 | H | 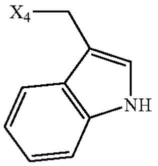 | H |
| 19(H2-38) | 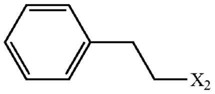 | H | 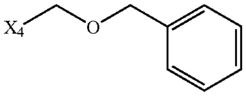 | H |
| 19(H2-39) | 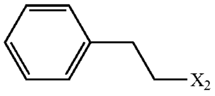 | H | 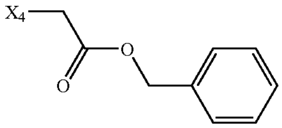 | H |

TABLE 2B-6
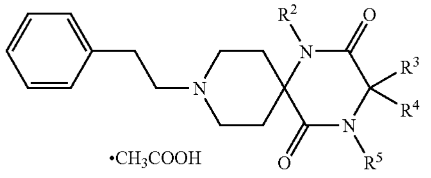
•$CH_3COOH$
| Example No | $R^2$ | $R^3$ | $R^4$ | $R^5$ |
|---|---|---|---|---|
| 19(H2-40) | 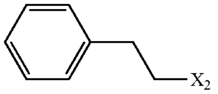 | H | 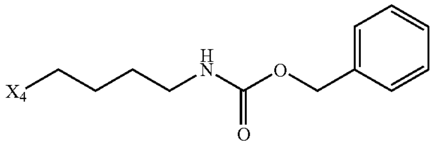 | H |
| 19(H2-41) | 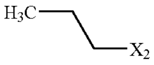 | H | H | H |
| 19(H2-42) | 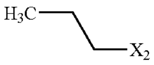 | H | 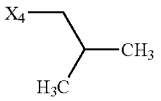 | H |
| 19(H2-43) | 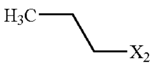 | H | 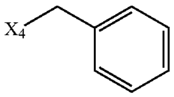 | H |
| 19(H2-44) | 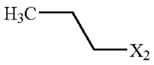 | H | 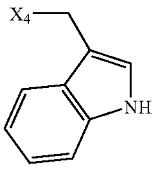 | H |
| 19(H2-45) | 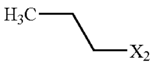 | H | 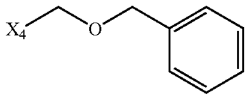 | H |
| 19(H2-46) | 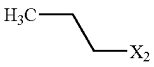 | H | 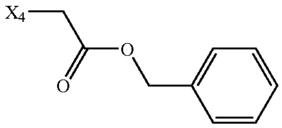 | H |
| 19(H2-47) | 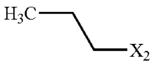 | H | 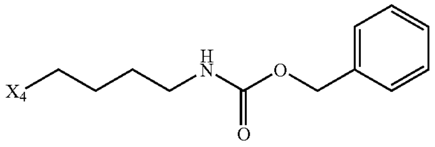 | H |
| 19(H2-48) | 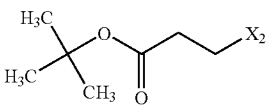 | H | H | H |

TABLE 2B-7
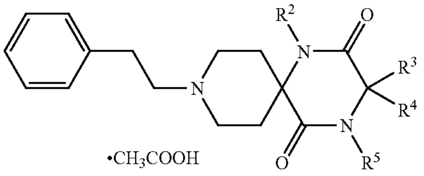
•$CH_3COOH$
| Example No | $R^2$ | $R^3$ | $R^4$ | $R^5$ |
|---|---|---|---|---|
| 19(H2-49) | 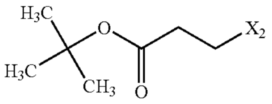 | H | 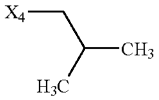 | H |
| 19(H2-50) | 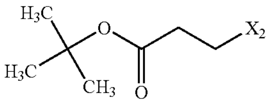 | H | 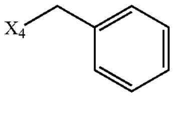 | H |
| 19(H2-51) | 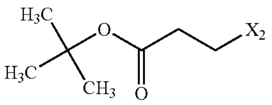 | H | 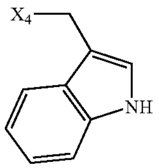 | H |
| 19(H2-52) | 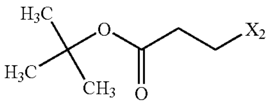 | H | 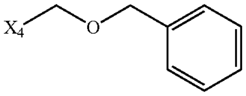 | H |
| 19(H2-53) | 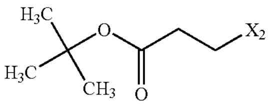 | H | 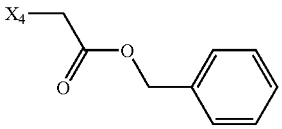 | H |
| 19(H2-54) | 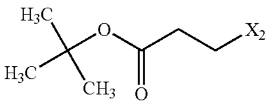 | H | 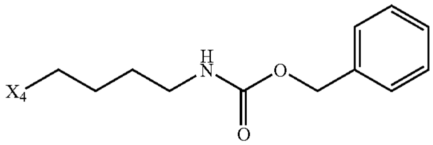 | H |
| 19(H2-55) | 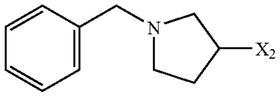 | H | H | H |
| 19(H2-56) | 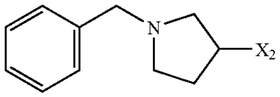 | H | 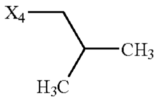 | H |

TABLE 2B-8
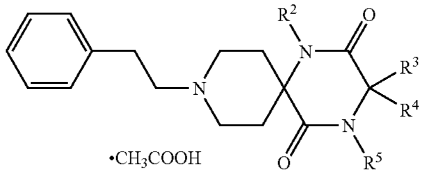
$\bullet CH_3COOH$
| Example No | $R^2$ | $R^3$ | $R^4$ | $R^5$ |
|---|---|---|---|---|
| 19(H2-57) | 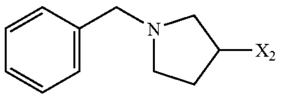 | H | 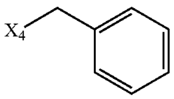 | H |
| 19(H2-58) | 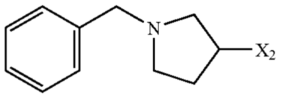 | H | 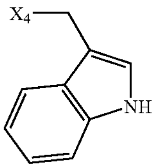 | H |
| 19(H2-59) | 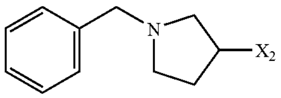 | H | 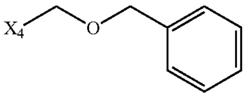 | H |
| 19(H2-60) | 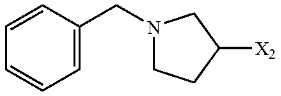 | H | 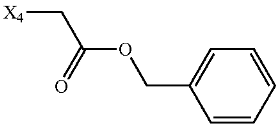 | H |
| 19(H2-61) | 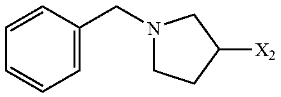 | H | 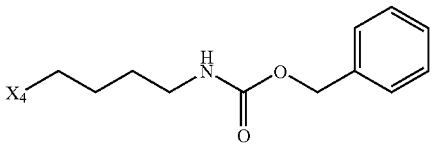 | H |
TABLE 3B-1
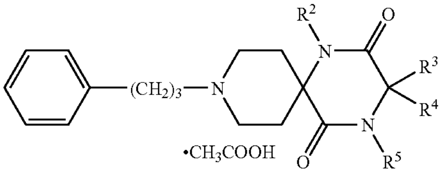
$\bullet CH_3COOH$
| Example No | $R^2$ | $R^3$ | $R^4$ | $R^5$ |
|---|---|---|---|---|
| 19(H3-1) | 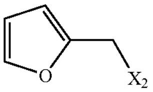 | H | H | H |
| 19(H3-2) | 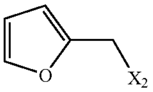 | H | 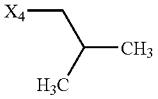 | H |

TABLE 3B-1-continued
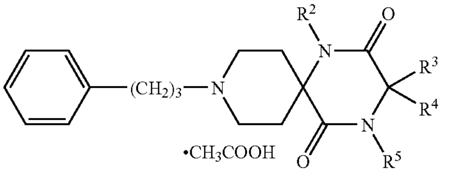
•$CH_3COOH$
| Example No | $R^2$ | $R^3$ | $R^4$ | $R^5$ |
|---|---|---|---|---|
| 19(H3-3) | 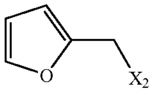 | H | 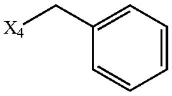 | H |
| 19(H3-4) | 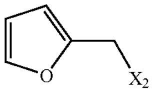 | H | 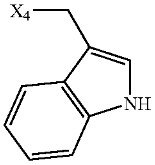 | H |
| 19(H3-5) | 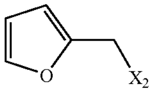 | H | 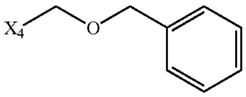 | H |
| 19(H3-6) | 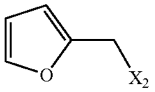 | H | 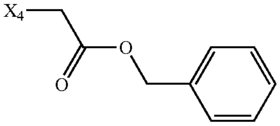 | H |
| 19(H3-7) | 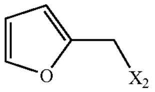 | H | 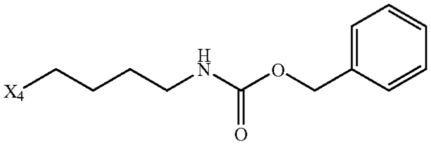 | H |
| 19(H3-8) | 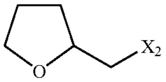 | H | H | H |
TABLE 3B-2
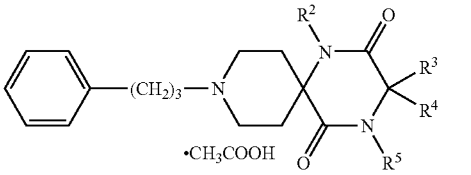
•$CH_3COOH$
| Example No | $R^2$ | $R^3$ | $R^4$ | $R^5$ |
|---|---|---|---|---|
| 19(H3-9) | 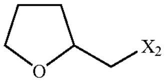 | H | 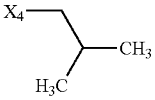 | H |
| 19(H3-10) | 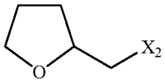 | H | 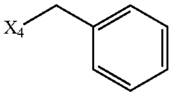 | H |

TABLE 3B-2-continued
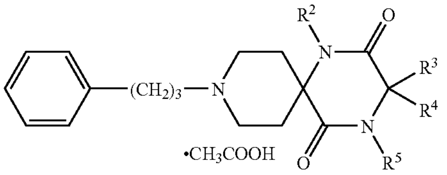
| Example No | $R^2$ | $R^3$ | $R^4$ | $R^5$ |
| --- | --- | --- | --- | --- |
| 19(H3-11) | 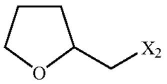 | H | 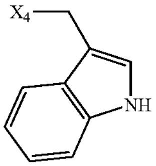 | H |
| 19(H3-12) | 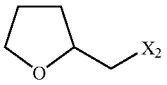 | H | 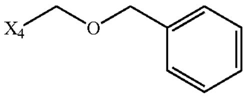 | H |
| 19(H3-13) | 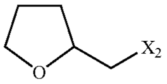 | H | 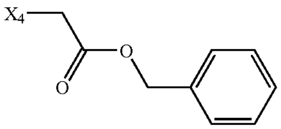 | H |
| 19(H3-14) | 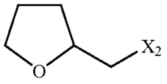 | H | 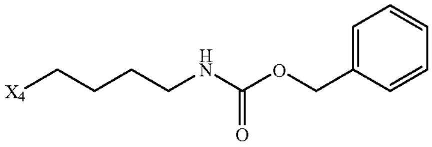 | H |
| 19(H3-15) | 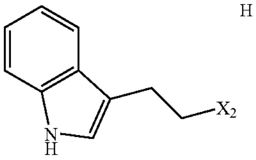 | H | H | H |
| 19(H3-16) | 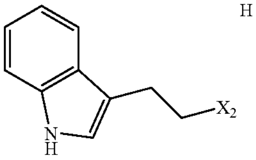 | H | 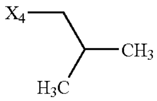 | H |

TABLE 3B-3
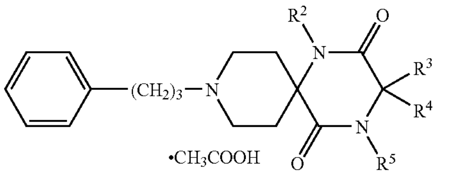
•$CH_3COOH$
| Example No | $R^2$ | $R^3$ | $R^4$ | $R^5$ |
|---|---|---|---|---|
| 19(H3-17) | 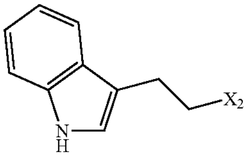 | H | 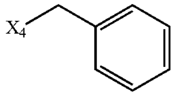 | H |
| 19(H3-18) | 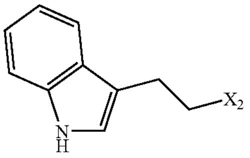 | H | 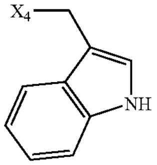 | H |
| 19(H3-19) | 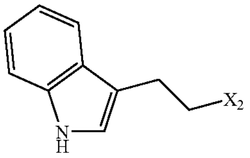 | H | 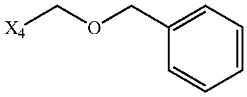 | H |
| 19(H3-20) | 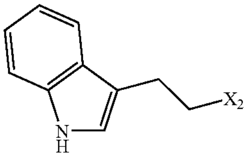 | H | 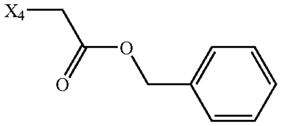 | H |
| 19(H3-21) | 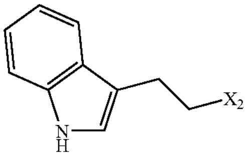 | H | 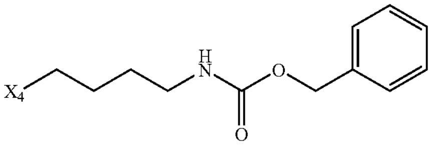 | H |
| 19(H3-22) | 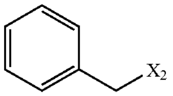 | H | H | H |
| 19(H3-23) | 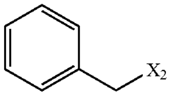 | H | 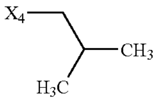 | H |
| 19(H3-24) | 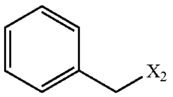 | H | 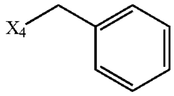 | H |

TABLE 3B-4
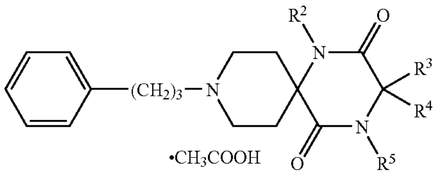
•$CH_3COOH$
| Example No | $R^2$ | $R^3$ | $R^4$ | $R^5$ |
|---|---|---|---|---|
| 19(H3-25) | 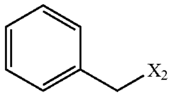 | H | 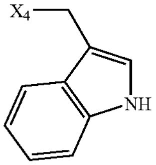 | H |
| 19(H3-26) | 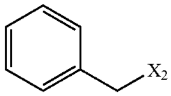 | H | 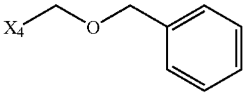 | H |
| 19(H3-27) | 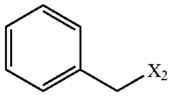 | H | 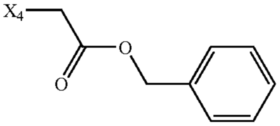 | H |
| 19(H3-28) | 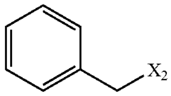 | H | 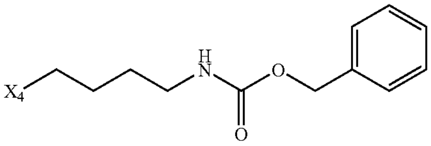 | H |
| 19(H3-29) | 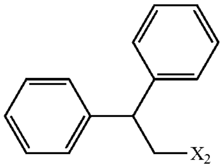 | H | H | H |
| 19(H3-30) | 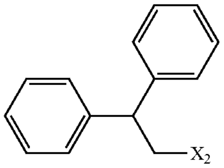 | H | 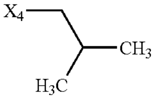 | H |
| 19(H3-31) | 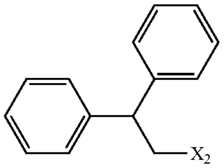 | H | 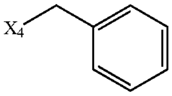 | H |

TABLE 3B-5
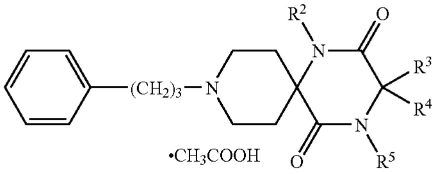
$\cdot CH_3COOH$
| Example No | $R^2$ | $R^3$ | $R^4$ | $R^5$ |
|---|---|---|---|---|
| 19(H3-32) | 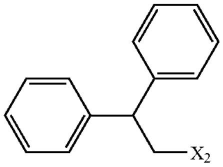 | H | 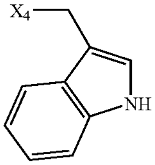 | H |
| 19(H3-33) | 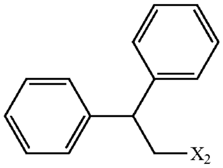 | H | 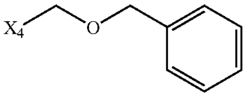 | H |
| 19(H3-34) | 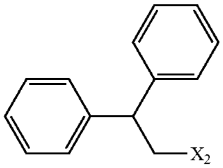 | H | 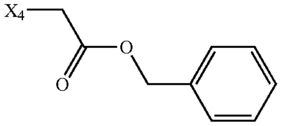 | H |
| 19(H3-35) | 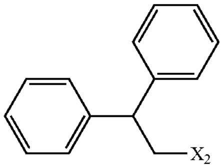 | H | 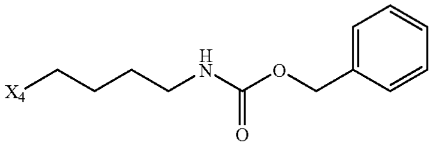 | H |
| 19(H3-36) | 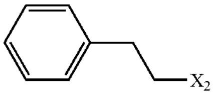 | H | H | H |
| 19(H3-37) | 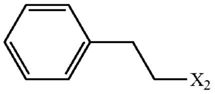 | H | 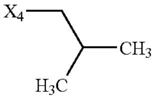 | H |
| 19(H3-38) | 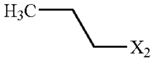 | H | 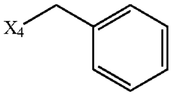 | H |
| 19(H3-39) | 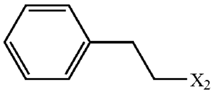 | H | 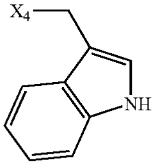 | H |

TABLE 3B-6
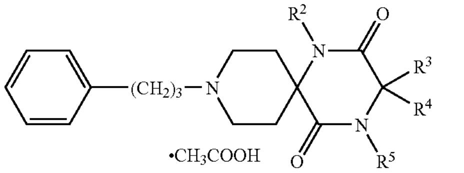
•$CH_3COOH$
| Example No | $R^2$ | $R^3$ | $R^4$ | $R^5$ |
|---|---|---|---|---|
| 19(H3-40) | 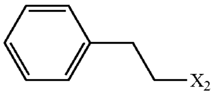 | H | 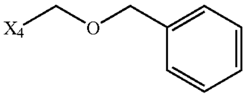 | H |
| 19(H3-41) | 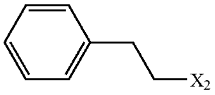 | H | 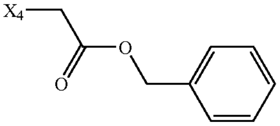 | H |
| 19(H3-42) | 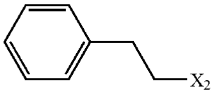 | H | 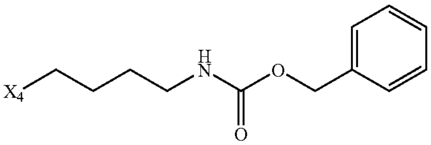 | H |
| 19(H3-43) | 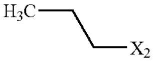 | H | H | H |
| 19(H3-44) | 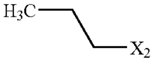 | H | 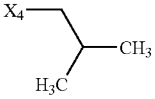 | H |
| 19(H3-45) | 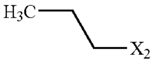 | H | 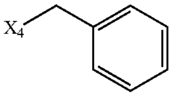 | H |
| 19(H3-46) | 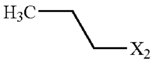 | H | 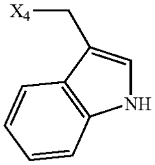 | H |
| 19(H3-47) | 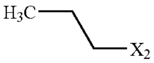 | H | 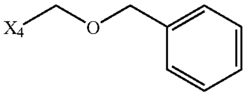 | H |
| 19(H3-48) | 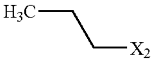 | H | 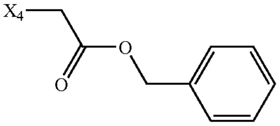 | H |

TABLE 3B-7
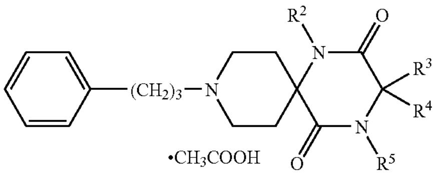
$\cdot CH_3COOH$
| Example No | $R^2$ | $R^3$ | $R^4$ | $R^5$ |
|---|---|---|---|---|
| 19(H3-49) | 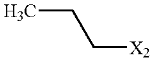 | H | 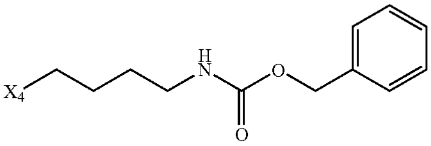 | H |
| 19(H3-50) | 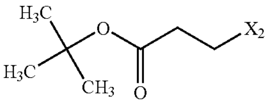 | H | H | H |
| 19(H3-51) | 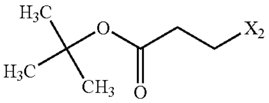 | H | 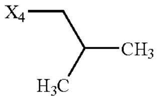 | H |
| 19(H3-52) | 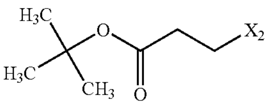 | H | 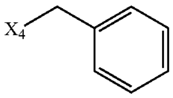 | H |
| 19(H3-53) | 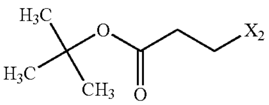 | H | 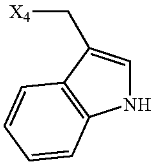 | H |
| 19(H3-54) | 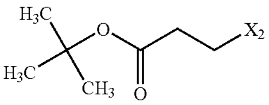 | H | 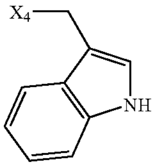 | H |
| 19(H3-55) | 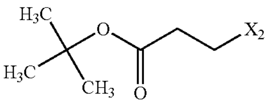 | H | 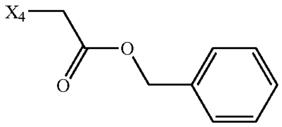 | H |
| 19(H3-56) | 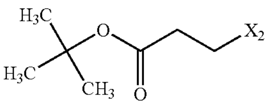 | H | 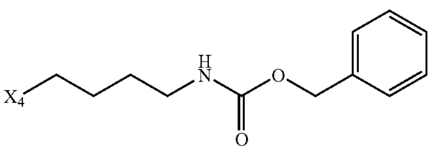 | H |

TABLE 3B-8
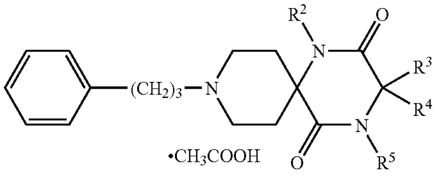
•$CH_3COOH$
| Example No | $R^2$ | $R^3$ | $R^4$ | $R^5$ |
|---|---|---|---|---|
| 19(H3-57) | 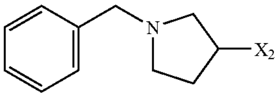 | H | H | H |
| 19(H3-58) | 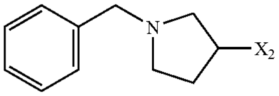 | H | 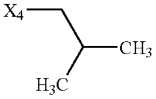 | H |
| 19(H3-59) | 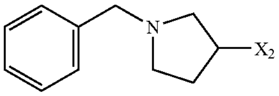 | H | 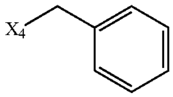 | H |
| 19(H3-60) | 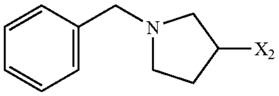 | H | 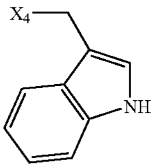 | H |
| 19(H3-61) | 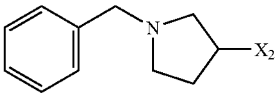 | H | 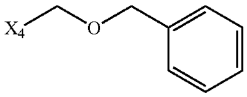 | H |
| 19(H3-62) | 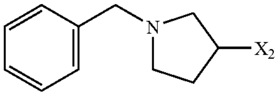 | H | 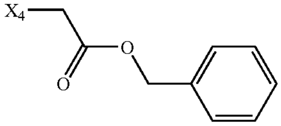 | H |
| 19(H3-63) | 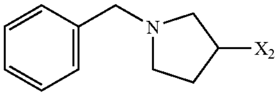 | H | 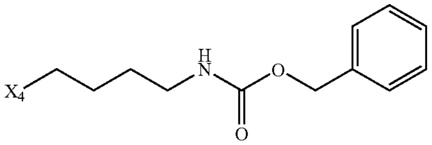 | H |
TABLE 4B-1
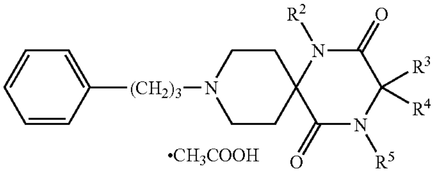
•$CH_3COOH$
| Example No | $R^2$ | $R^3$ | $R^4$ | $R^5$ |
|---|---|---|---|---|
| 19(H4-1) | 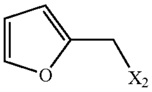 | H | H | H |

TABLE 4B-1-continued
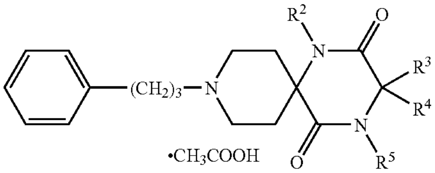
$\bullet CH_3COOH$
| Example No | $R^2$ | $R^3$ | $R^4$ | $R^5$ |
|---|---|---|---|---|
| 19(H4-2) | 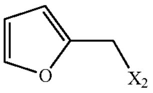 | H | 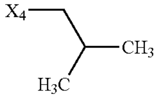 | H |
| 19(H4-3) | 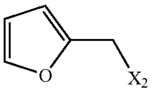 | H | 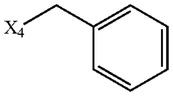 | H |
| 19(H4-4) | 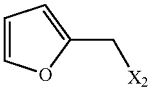 | H | 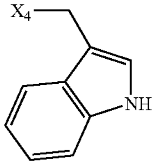 | H |
| 19(H4-5) | 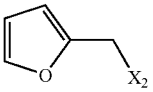 | H | 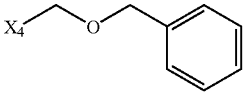 | H |
| 19(H4-6) | 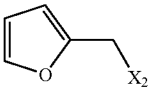 | H | 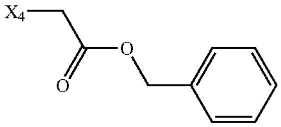 | H |
| 19(H4-7) | 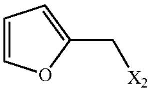 | H | 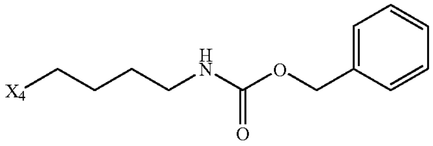 | H |
| 19(H4-8) | 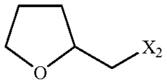 | H | H | H |
TABLE 4B-2
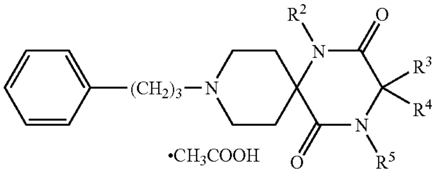
$\bullet CH_3COOH$
| Example No | $R^2$ | $R^3$ | $R^4$ | $R^5$ |
|---|---|---|---|---|
| 19(H4-9) | 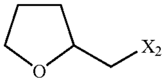 | H | 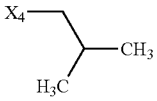 | H |

TABLE 4B-2-continued
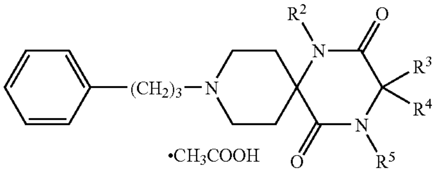
•$CH_3COOH$
| Example No | $R^2$ | $R^3$ | $R^4$ | $R^5$ |
|---|---|---|---|---|
| 19(H4-10) | 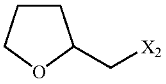 | H | 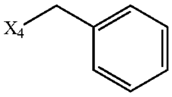 | H |
| 19(H4-11) | 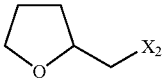 | H | 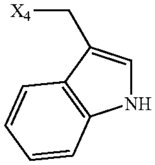 | H |
| 19(H4-12) | 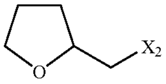 | H | 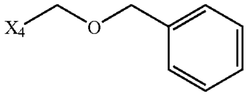 | H |
| 19(H4-13) | 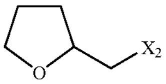 | H | 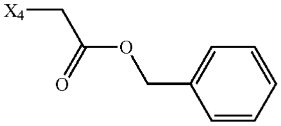 | H |
| 19(H4-14) | 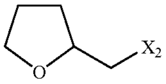 | H | 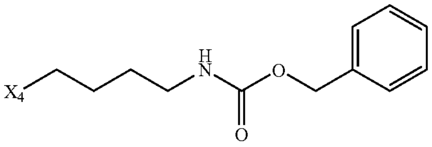 | H |
| 19(H4-15) | 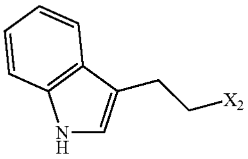 | H | H | H |
| 19(H4-16) | 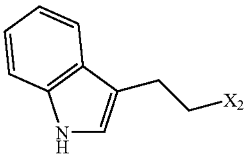 | H | 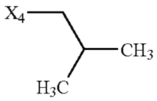 | H |

TABLE 4B-3
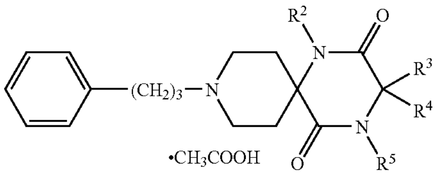
•$CH_3COOH$
| Example No | $R^2$ | $R^3$ | $R^4$ | $R^5$ |
|---|---|---|---|---|
| 19(H4-17) | 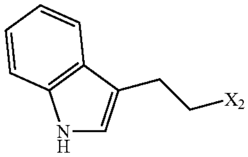 | H | 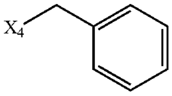 | H |
| 19(H4-18) | 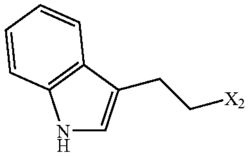 | H | 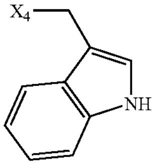 | H |
| 19(H4-19) | 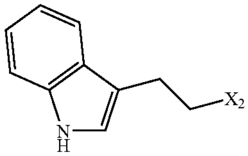 | H | 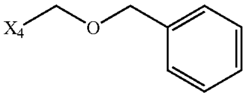 | H |
| 19(H4-20) | 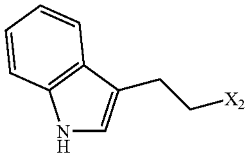 | H | 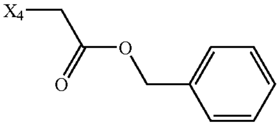 | H |
| 19(H4-21) | 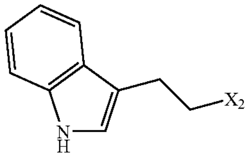 | H | 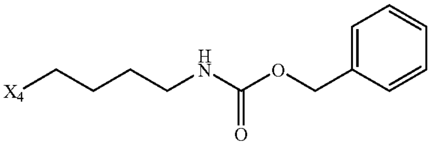 | H |
| 19(H4-22) | 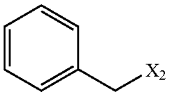 | H | H | H |
| 19(H4-23) | 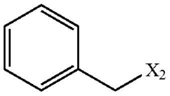 | H | 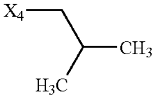 | H |
| 19(H4-24) | 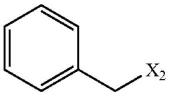 | H | 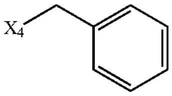 | H |

TABLE 4B-4
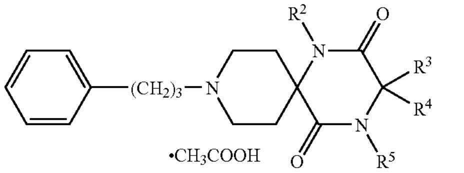
$\cdot CH_3COOH$
| Example No | $R^2$ | $R^3$ | $R^4$ | $R^5$ |
|---|---|---|---|---|
| 19(H4-25) | 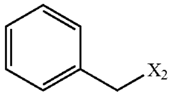 | H | 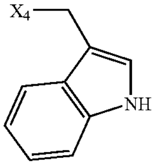 | H |
| 19(H4-26) | 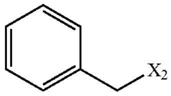 | H | 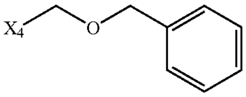 | H |
| 19(H4-27) | 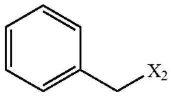 | H | 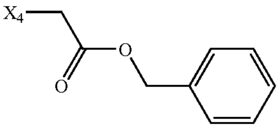 | H |
| 19(H4-28) | 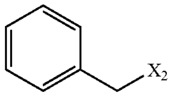 | H | 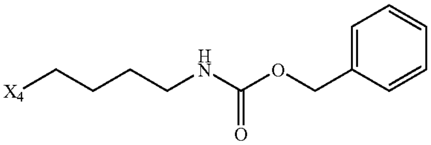 | H |
| 19(H4-29) | 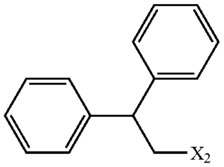 | H | H | H |
| 19(H4-30) | 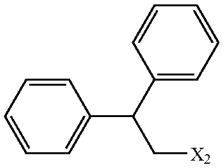 | H | 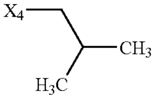 | H |
| 19(H4-31) | 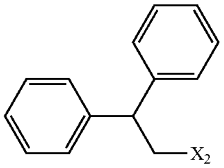 | H | 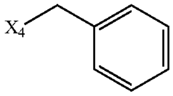 | H |

TABLE 4B-5
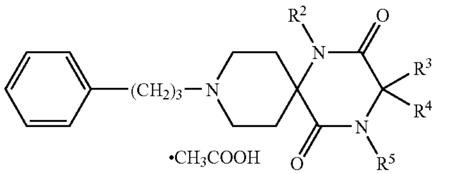
$\cdot CH_3COOH$
| Example No | $R^2$ | $R^3$ | $R^4$ | $R^5$ |
|---|---|---|---|---|
| 19(H4-32) | 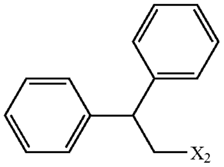 | H | 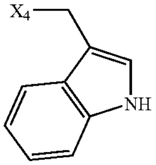 | H |
| 19(H4-33) | 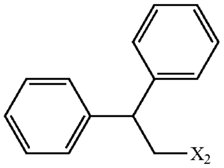 | H | 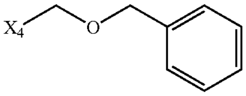 | H |
| 19(H4-34) | 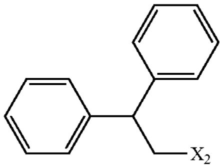 | H | 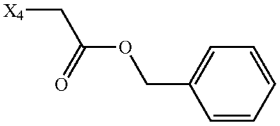 | H |
| 19(H4-35) | 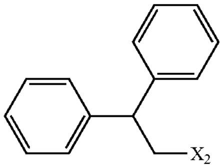 | H | 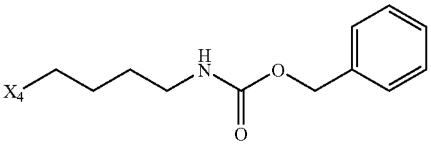 | H |
| 19(H4-36) | 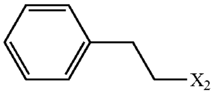 | H | H | H |
| 19(H4-37) | 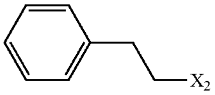 | H | 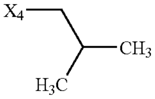 | H |
| 19(H4-38) | 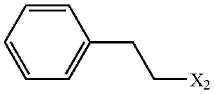 | H | 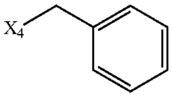 | H |
| 19(H4-39) | 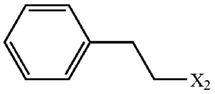 | H | 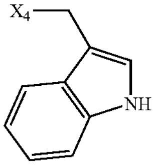 | H |

TABLE 4B-6
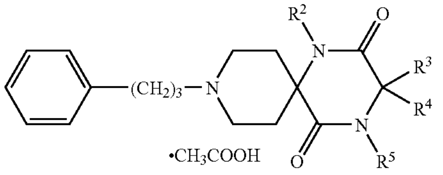
•$CH_3COOH$
| Example No | $R^2$ | $R^3$ | $R^4$ | $R^5$ |
|---|---|---|---|---|
| 19(H4-40) | 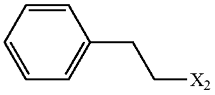 | H | 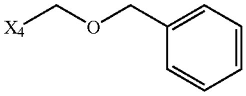 | H |
| 19(H4-41) | 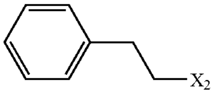 | H | 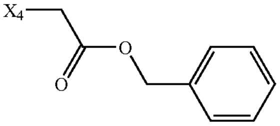 | H |
| 19(H4-42) | 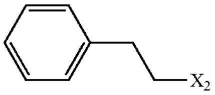 | H | 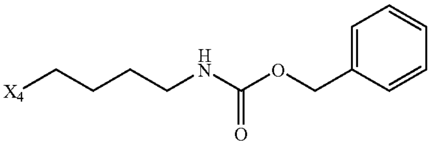 | H |
| 19(H4-43) | 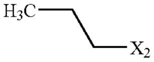 | H | H | H |
| 19(H4-44) | 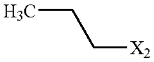 | H | 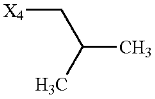 | H |
| 19(H4-45) | 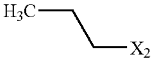 | H | 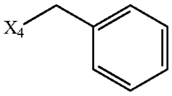 | H |
| 19(H4-46) | 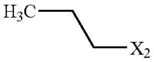 | H | 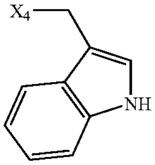 | H |
| 19(H4-47) | 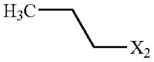 | H | 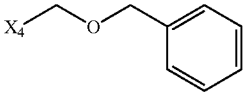 | H |
| 19(H4-48) | 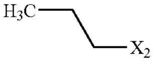 | H | 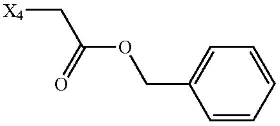 | H |

TABLE 4B-7
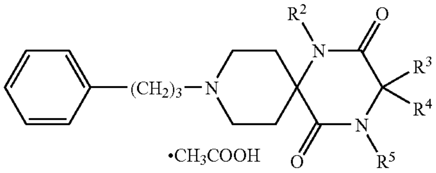
•$CH_3COOH$
| Example No | $R^2$ | $R^3$ | $R^4$ | $R^5$ |
|---|---|---|---|---|
| 19(H4-49) | 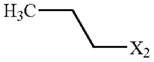 | H | 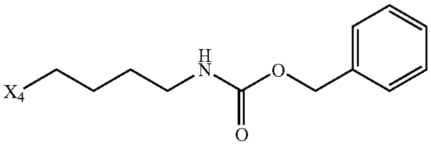 | H |
| 19(H4-50) | 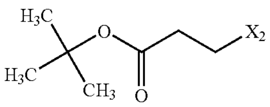 | H | H | H |
| 19(H4-51) | 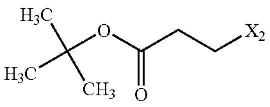 | H | 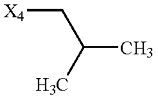 | H |
| 19(H4-52) | 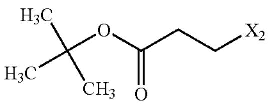 | H | 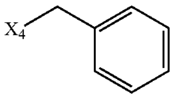 | H |
| 19(H4-53) | 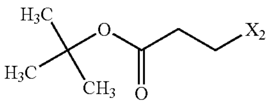 | H | 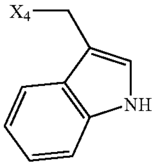 | H |
| 19(H4-54) | 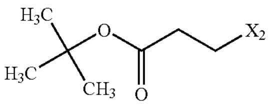 | H | 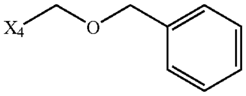 | H |
| 19(H4-55) | 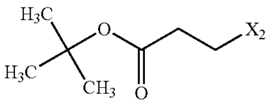 | H | 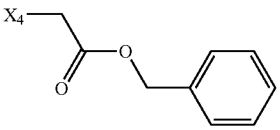 | H |
| 19(H4-56) | 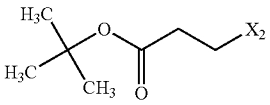 | H | 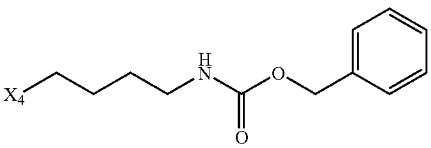 | H |

TABLE 4B-8
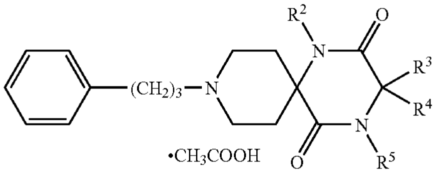
•$CH_3COOH$
| Example No | $R^2$ | $R^3$ | $R^4$ | $R^5$ |
|---|---|---|---|---|
| 19(H4-57) | 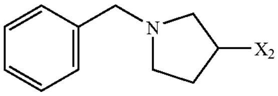 | H | H | H |
| 19(H4-58) | 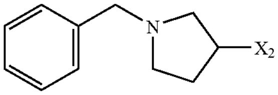 | H | 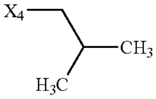 | H |
| 19(H4-59) | 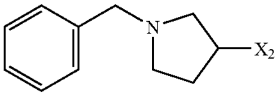 | H | 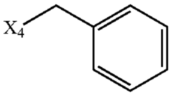 | H |
| 19(H4-60) | 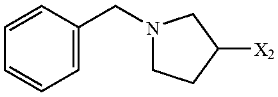 | H | 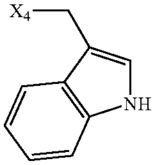 | H |
| 19(H4-61) | 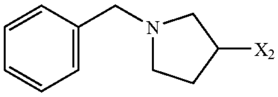 | H | 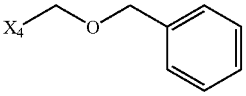 | H |
| 19(H4-62) | 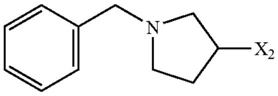 | H | 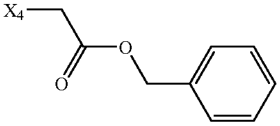 | H |
| 19(H4-63) | 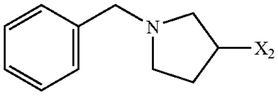 | H | 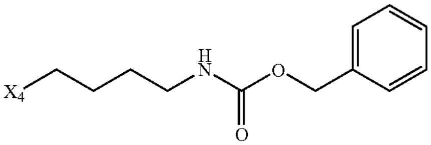 | H |
TABLE 5B-1
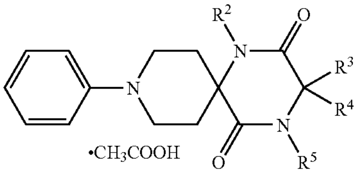
•$CH_3COOH$
| Example No | $R^2$ | $R^3$ | $R^4$ | $R^5$ |
|---|---|---|---|---|
| 19(H5-1) | 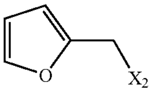 | H | H | H |

TABLE 5B-1-continued
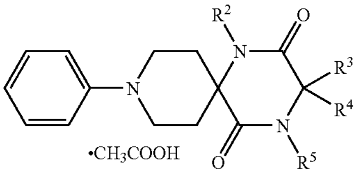
•$CH_3COOH$
| Example No | $R^2$ | $R^3$ | $R^4$ | $R^5$ |
|---|---|---|---|---|
| 19(H5-2) | 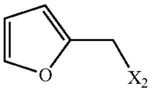 | H | 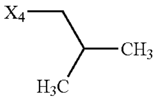 | H |
| 19(H5-3) | 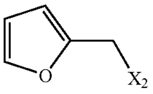 | H | 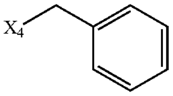 | H |
| 19(H5-4) | 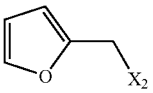 | H | 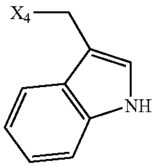 | H |
| 19(H5-5) | 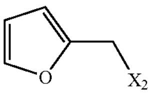 | H | 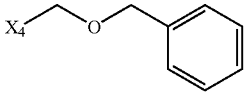 | H |
| 19(H5-6) | 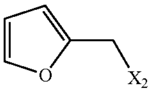 | H | 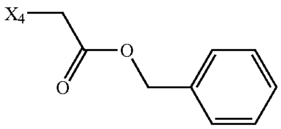 | H |
| 19(H5-7) | 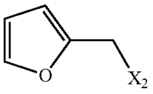 | H | 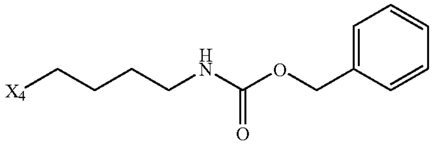 | H |
| 19(H5-8) | 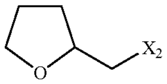 | H | H | H |
TABLE 5B-2
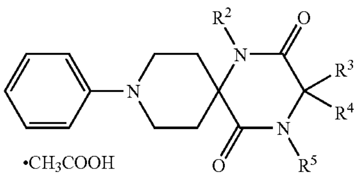
•$CH_3COOH$
| Example No | $R^2$ | $R^3$ | $R^4$ | $R^5$ |
|---|---|---|---|---|
| 19(H5-9) | 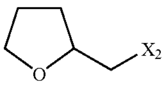 | H | 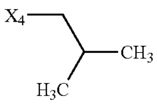 | H |

TABLE 5B-2-continued
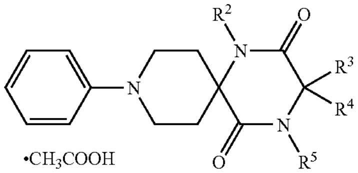
$\bullet CH_3COOH$
| Example No | $R^2$ | $R^3$ | $R^4$ | $R^5$ |
|---|---|---|---|---|
| 19(H5-10) | 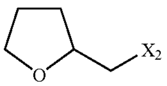 | H | 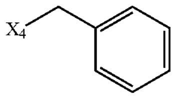 | H |
| 19(H5-11) | 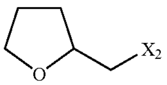 | H | 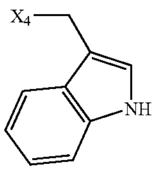 | H |
| 19(H5-12) | 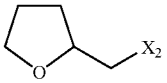 | H | 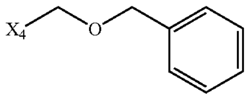 | H |
| 19(H5-13) | 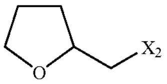 | H | 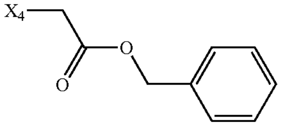 | H |
| 19(H5-14) | 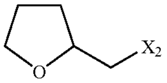 | H | 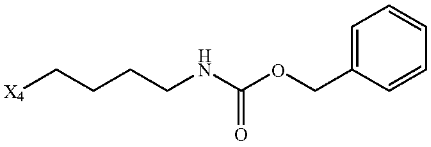 | H |
| 19(H5-15) | 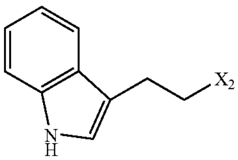 | H | H | H |
| 19(H5-16) | 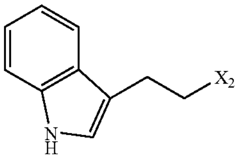 | H | 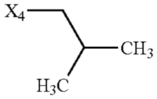 | H |

TABLE 5B-3
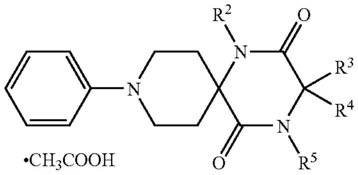
•$CH_3COOH$
| Example No | $R^2$ | $R^3$ | $R^4$ | $R^5$ |
|---|---|---|---|---|
| 19(H5-17) | 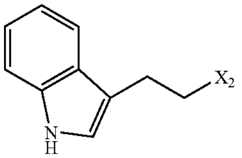 | H | 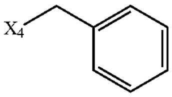 | H |
| 19(H5-18) | 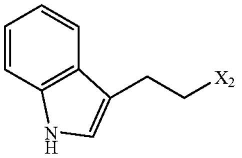 | H | 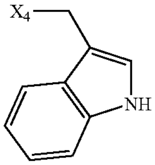 | H |
| 19(H5-19) | 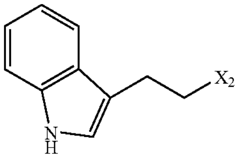 | H | 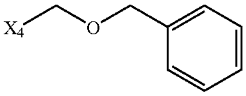 | H |
| 19(H5-20) | 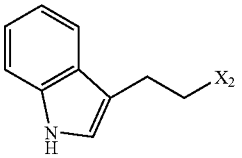 | H | 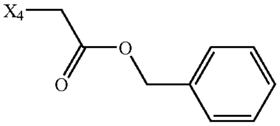 | H |
| 19(H5-21) | 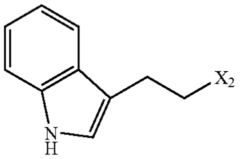 | H | 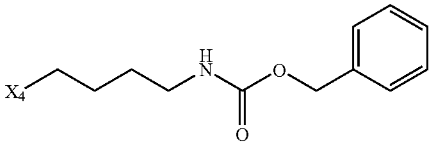 | H |
| 19(H5-22) | 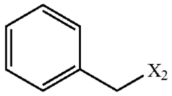 | H | H | H |
| 19(H5-23) | 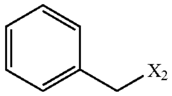 | H | 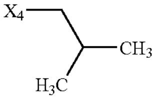 | H |
| 19(H5-24) | 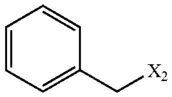 | H | 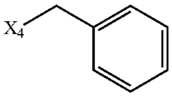 | H |

TABLE 5B-4
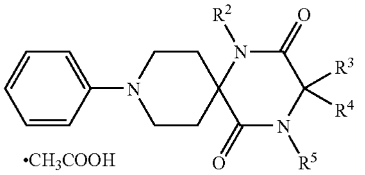
•$CH_3COOH$
| Example No | $R^2$ | $R^3$ | $R^4$ | $R^5$ |
|---|---|---|---|---|
| 19(H5-25) | 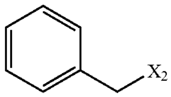 | H | 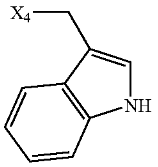 | H |
| 19(H5-26) | 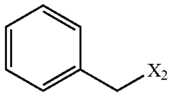 | H | 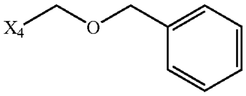 | H |
| 19(H5-27) | 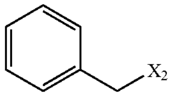 | H | 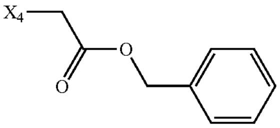 | H |
| 19(H5-28) | 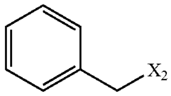 | H | 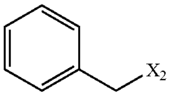 | H |
| 19(H5-29) | 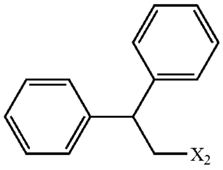 | H | H | H |
| 19(H5-30) | 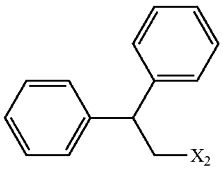 | H | 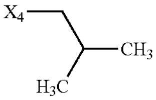 | H |
| 19(H5-31) | 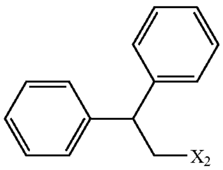 | H | 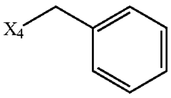 | H |

TABLE 5B-5
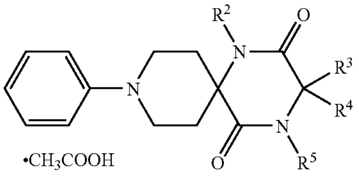
•$CH_3COOH$
| Example No | $R^2$ | $R^3$ | $R^4$ | $R^5$ |
|---|---|---|---|---|
| 19(H5-32) | 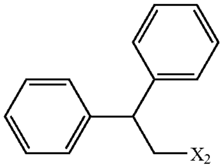 | H | 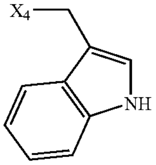 | H |
| 19(H5-33) | 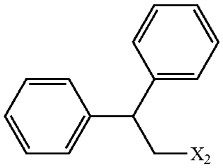 | H | 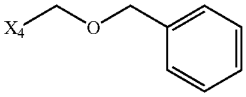 | H |
| 19(H5-34) | 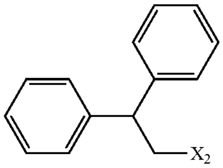 | H | 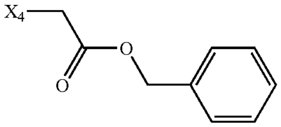 | H |
| 19(H5-35) | 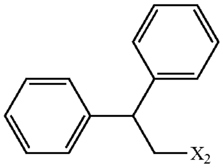 | H | 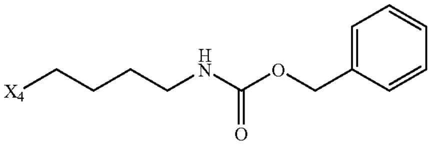 | H |
| 19(H5-36) | 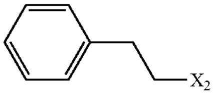 | H | H | H |
| 19(H5-37) | 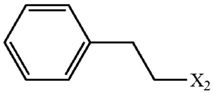 | H | 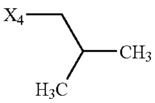 | H |
| 19(H5-38) | 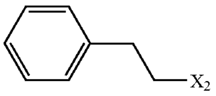 | H | 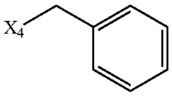 | H |
| 19(H5-39) | 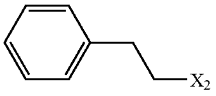 | H | 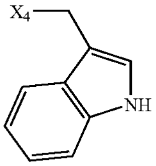 | H |

TABLE 5B-6
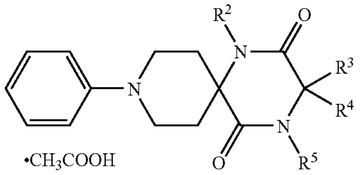
$\cdot CH_3COOH$
| Example No | $R^2$ | $R^3$ | $R^4$ | $R^5$ |
| --- | --- | --- | --- | --- |
| 19(H5-40) | 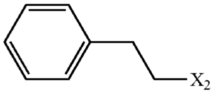 | H | 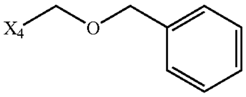 | H |
| 19(H5-41) | 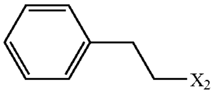 | H | 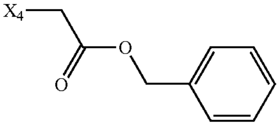 | H |
| 19(H5-42) | 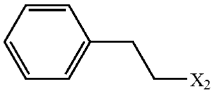 | H | 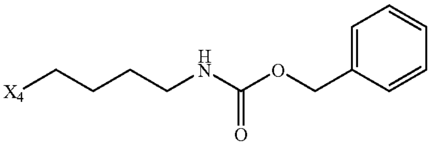 | H |
| 19(H5-43) | 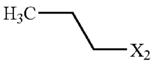 | H | H | H |
| 19(H5-44) | 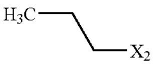 | H | 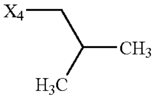 | H |
| 19(H5-45) | 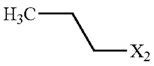 | H | 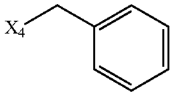 | H |
| 19(H5-46) | 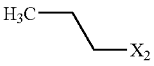 | H | 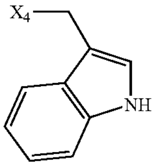 | H |
| 19(H5-47) | 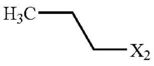 | H | 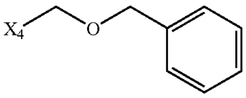 | H |
| 19(H5-48) | 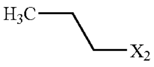 | H | 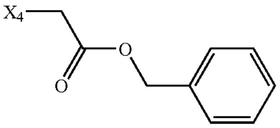 | H |

TABLE 5B-7
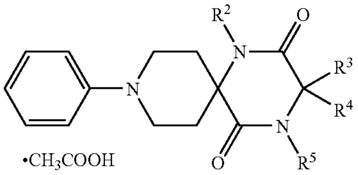
•$CH_3COOH$
| Example No | $R^2$ | $R^3$ | $R^4$ | $R^5$ |
| --- | --- | --- | --- | --- |
| 19(H5-49) | 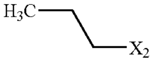 | H | 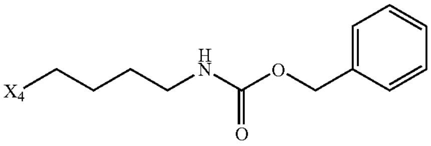 | H |
| 19(H5-50) | 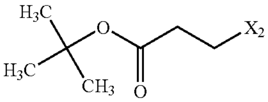 | H | H | H |
| 19(H5-51) | 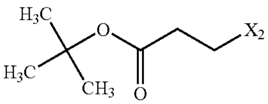 | H | 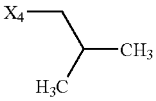 | H |
| 19(H5-52) | 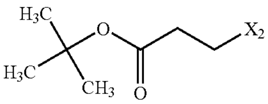 | H | 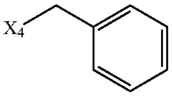 | H |
| 19(H5-53) | 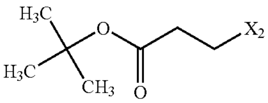 | H | 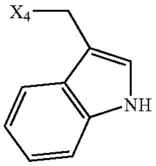 | H |
| 19(H5-54) | 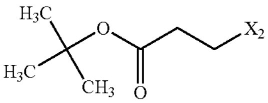 | H | 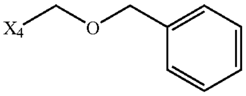 | H |
| 19(H5-55) | 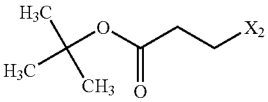 | H | 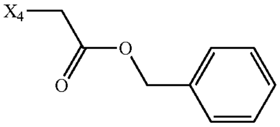 | H |
| 19(H5-56) | 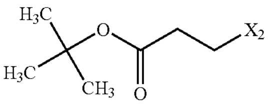 | H | 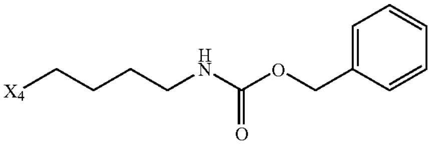 | H |

TABLE 5B-8
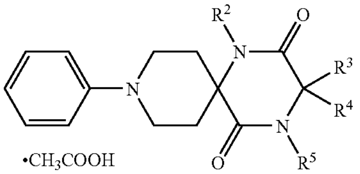
•$CH_3COOH$
| Example No | $R^2$ | $R^3$ | $R^4$ | $R^5$ |
|---|---|---|---|---|
| 19(H5-57) | 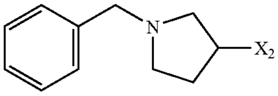 | H | 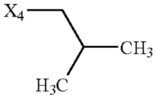 | H |
| 19(H5-58) | 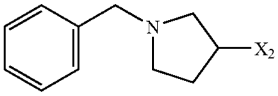 | H | 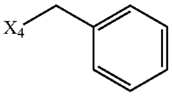 | H |
| 19(H5-59) | 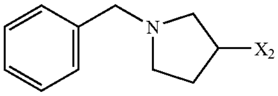 | H | 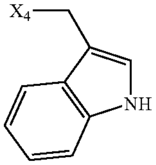 | H |
| 19(H5-60) | 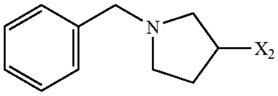 | H | 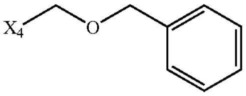 | H |
| 19(H5-61) | 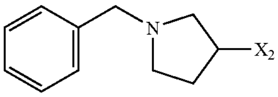 | H | 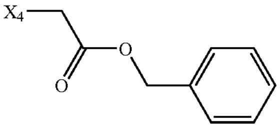 | H |
| 19(H5-62) | 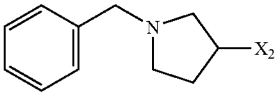 | H | 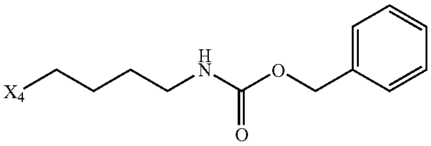 | H |
TABLE 6B-1
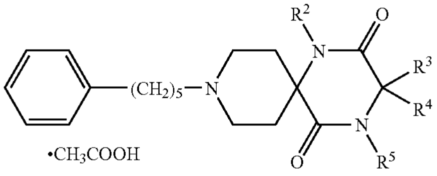
•$CH_3COOH$
| Example No | $R^2$ | $R^3$ | $R^4$ | $R^5$ |
|---|---|---|---|---|
| 19(H6-1) | 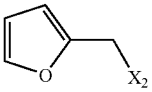 | H | H | H |

TABLE 6B-1-continued
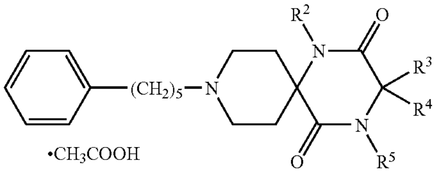
•$CH_3COOH$
| Example No | $R^2$ | $R^3$ | $R^4$ | $R^5$ |
|---|---|---|---|---|
| 19(H6-2) | 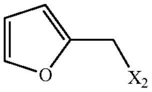 | H | 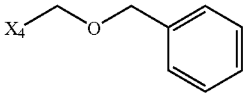 | H |
| 19(H6-3) | 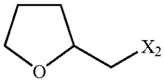 | H | H | H |
| 19(H6-4) | 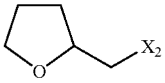 | H | 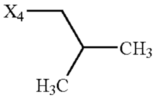 | H |
| 19(H6-5) | 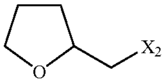 | H | 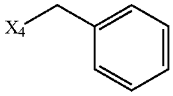 | H |
| 19(H6-6) | 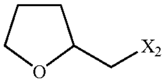 | H | 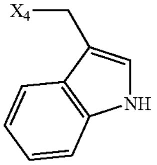 | H |
| 19(H6-7) | 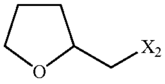 | H | 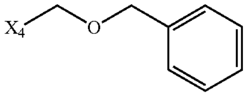 | H |
| 19(H6-8) | 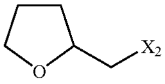 | H | 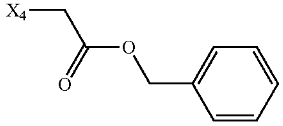 | H |
TABLE 6B-2
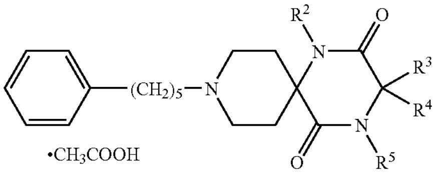
•$CH_3COOH$
| Example No | $R^2$ | $R^3$ | $R^4$ | $R^5$ |
|---|---|---|---|---|
| 19(H6-9) | 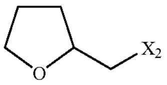 | H | 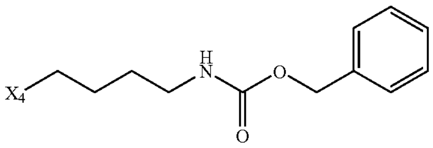 | H |

TABLE 6B-2-continued
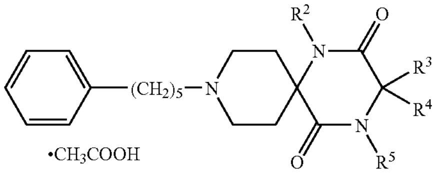
•$CH_3COOH$
| Example No | $R^2$ | $R^3$ | $R^4$ | $R^5$ |
|---|---|---|---|---|
| 19(H6-10) | 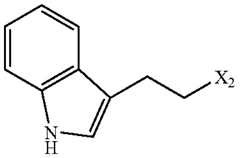 | H | H | H |
| 19(H6-11) | 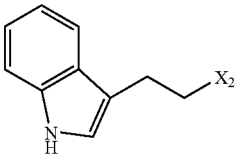 | H | 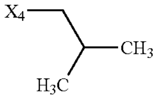 | H |
| 19(H6-12) | 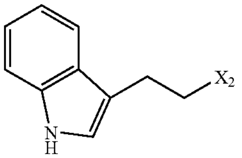 | H | 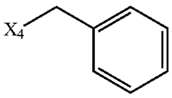 | H |
| 19(H6-13) | 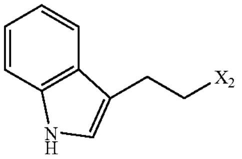 | H | 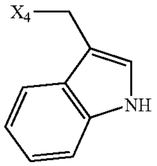 | H |
| 19(H6-14) | 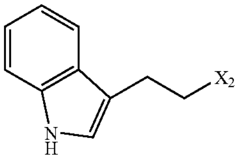 | H | 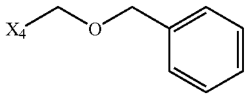 | H |
| 19(H6-15) | 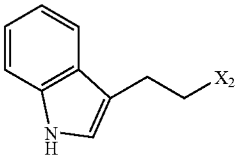 | H | 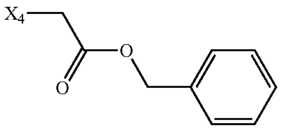 | H |
| 19(H6-16) | 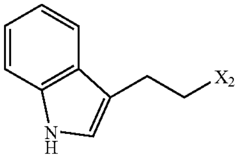 | H | 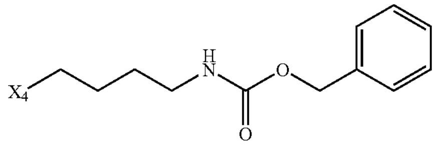 | H |

TABLE 6B-3
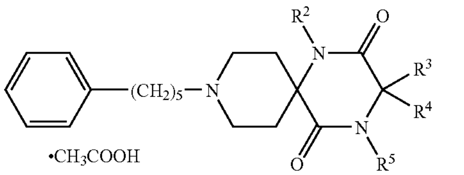
•$CH_3COOH$
| Example No | $R^2$ | $R^3$ | $R^4$ | $R^5$ |
| --- | --- | --- | --- | --- |
| 19(H6-17) | 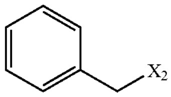 | H | H | H |
| 19(H6-18) | 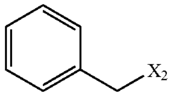 | H | 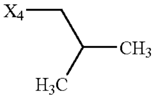 | H |
| 19(H6-19) | 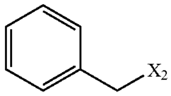 | H | 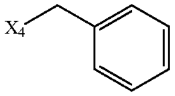 | H |
| 19(H6-20) | 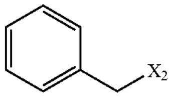 | H | 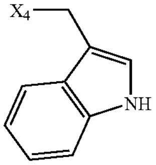 | H |
| 19(H6-21) | 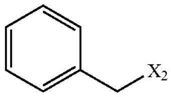 | H | 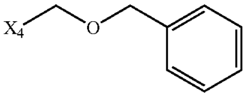 | H |
| 19(H6-22) | 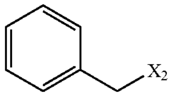 | H | 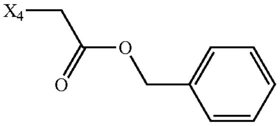 | H |
| 19(H6-23) | 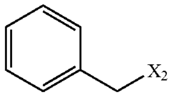 | H | 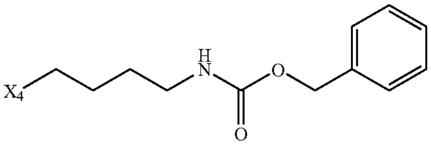 | H |
| 19(H6-24) | 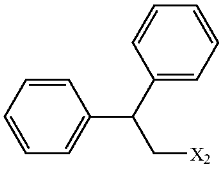 | H | H | H |

TABLE 6B-4
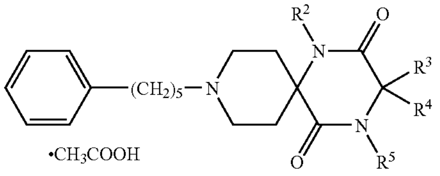
$\bullet CH_3COOH$
| Example No | $R^2$ | $R^3$ | $R^4$ | $R^5$ |
|---|---|---|---|---|
| 19(H6-25) | 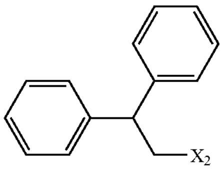 | H | 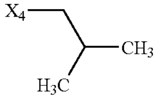 | H |
| 19(H6-26) | 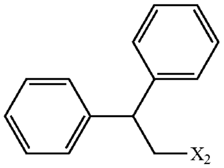 | H | 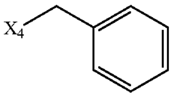 | H |
| 19(H6-27) | 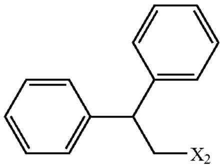 | H | 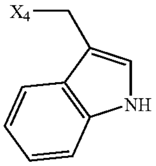 | H |
| 19(H6-28) | 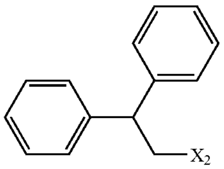 | H | 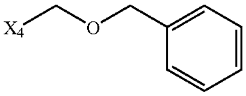 | H |
| 19(H6-29) | 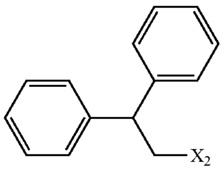 | H | 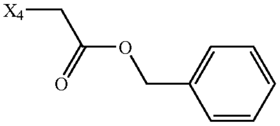 | H |
| 19(H6-30) | 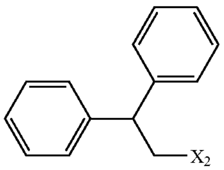 | H | 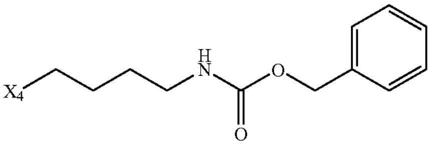 | H |
| 19(H6-31) | 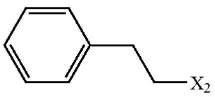 | H | H | H |
| 19(H6-32) | 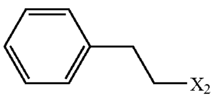 | H | 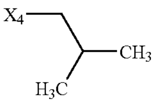 | H |

TABLE 6B-5
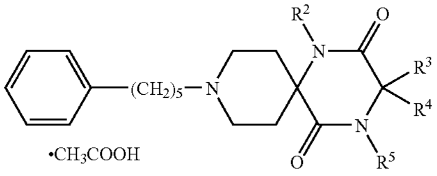
•$CH_3COOH$
| Example No | $R^2$ | $R^3$ | $R^4$ | $R^5$ |
|---|---|---|---|---|
| 19(H6-33) | 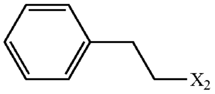 | H | 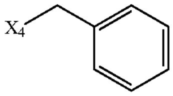 | H |
| 19(H6-34) | 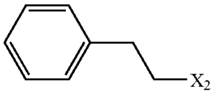 | H | 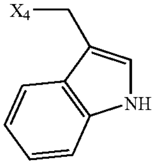 | H |
| 19(H6-35) | 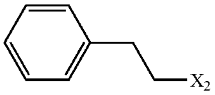 | H | 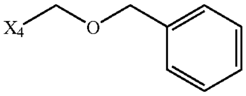 | H |
| 19(H6-36) | 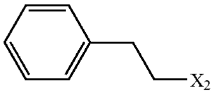 | H | 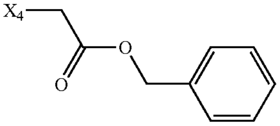 | H |
| 19(H6-37) | 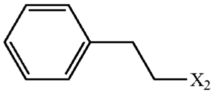 | H | 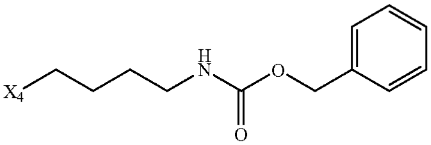 | H |
| 19(H6-38) | 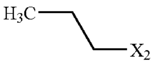 | H | H | H |
| 19(H6-39) | 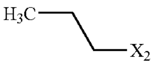 | H | 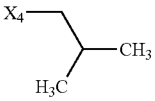 | H |
| 19(H6-40) | 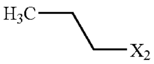 | H | 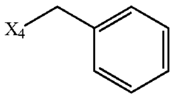 | H |

TABLE 6B-6
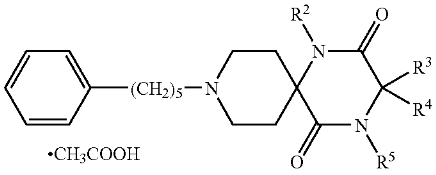
•$CH_3COOH$
| Example No | $R^2$ | $R^3$ | $R^4$ | $R^5$ |
|---|---|---|---|---|
| 19(H6-41) | 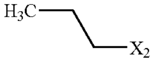 | H | 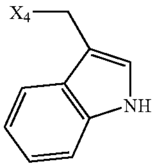 | H |
| 19(H6-42) | 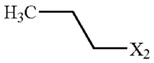 | H | 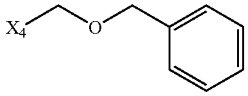 | H |
| 19(H6-43) | 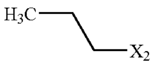 | H | 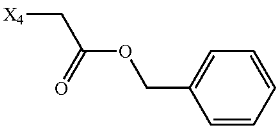 | H |
| 19(H6-44) | 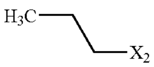 | H | 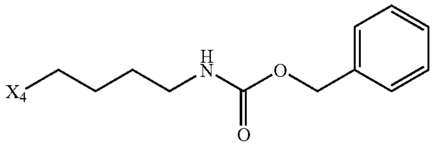 | H |
| 19(H6-45) | 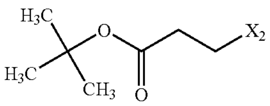 | H | H | H |
| 19(H6-46) | 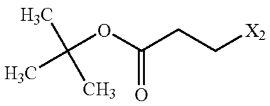 | H | 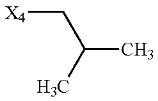 | H |
| 19(H6-47) | 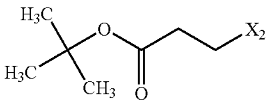 | H | 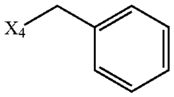 | H |
| 19(H6-48) | 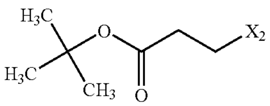 | H | 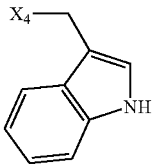 | H |

TABLE 6B-7
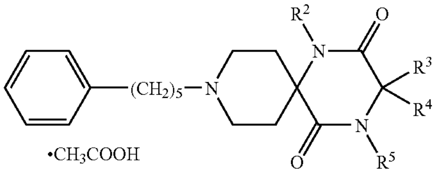
$\bullet CH_3COOH$
| Example No | $R^2$ | $R^3$ | $R^4$ | $R^5$ |
|---|---|---|---|---|
| 19(H6-49) | 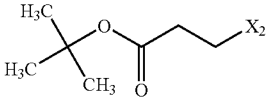 | H | 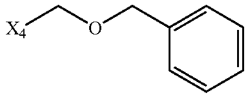 | H |
| 19(H6-50) | 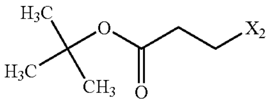 | H | 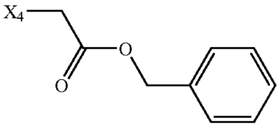 | H |
| 19(H6-51) | 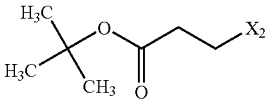 | H | 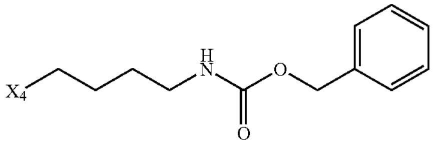 | H |
| 19(H6-52) | 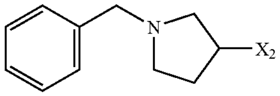 | H | H | H |
| 19(H6-53) | 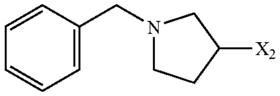 | H | 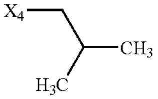 | H |
| 19(H6-54) | 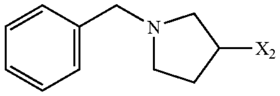 | H | 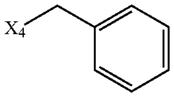 | H |
| 19(H6-55) | 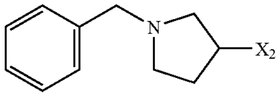 | H | 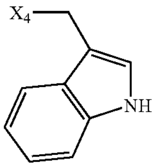 | H |
| 19(H6-56) | 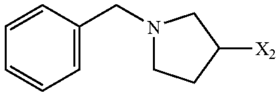 | H | 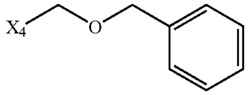 | H |

TABLE 6B-8
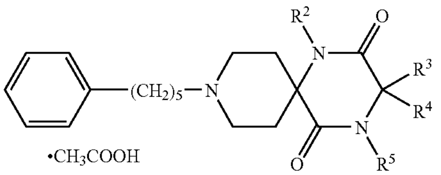
•$CH_3COOH$
| Example No | $R^2$ | $R^3$ | $R^4$ | $R^5$ |
|---|---|---|---|---|
| 19(H6-57) | 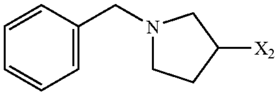 | H | 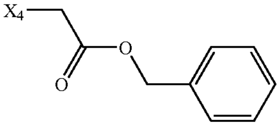 | H |
| 19(H6-58) | 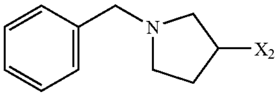 | H | 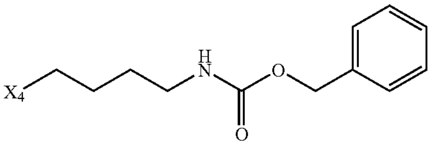 | H |
TABLE 7B-1
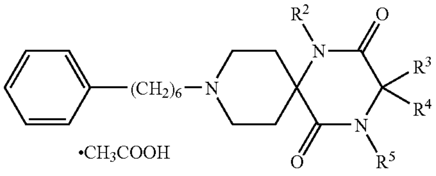
•$CH_3COOH$
| Example No | $R^2$ | $R^3$ | $R^4$ | $R^5$ |
|---|---|---|---|---|
| 19(H7-1) | 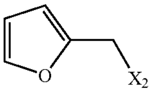 | H | H | H |
| 19(H7-2) | 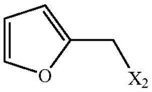 | H | 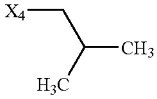 | H |
| 19(H7-3) | 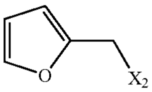 | H | 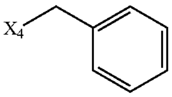 | H |
| 19(H7-4) | 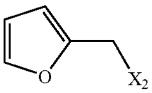 | H | 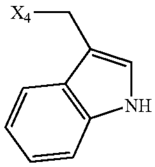 | H |
TABLE 7B-1-continued
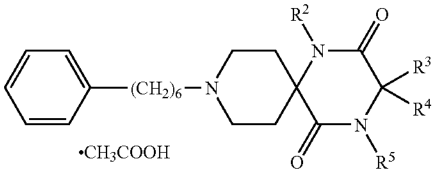
•$CH_3COOH$
| Example No | $R^2$ | $R^3$ | $R^4$ | $R^5$ |
|---|---|---|---|---|
| 19(H7-5) | 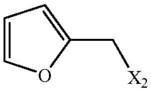 | H | 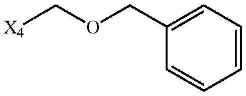 | H |
| 19(H7-6) | 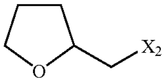 | H | H | H |
| 19(H7-7) | 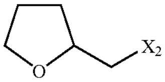 | H | 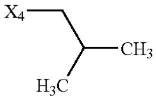 | H |
| 19(H7-8) | 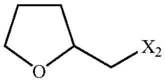 | H | 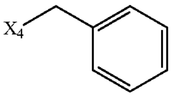 | H |

TABLE 7B-2
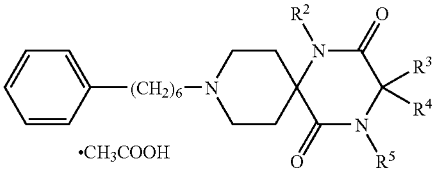
•$CH_3COOH$
| Example No | $R^2$ | $R^3$ | $R^4$ | $R^5$ |
| --- | --- | --- | --- | --- |
| 19(H7-9) | 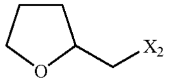 | H | 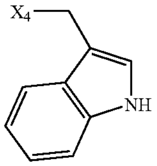 | H |
| 19(H7-10) | 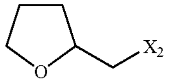 | H | 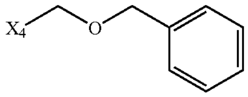 | H |
| 19(H7-11) | 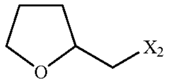 | H | 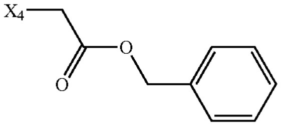 | H |
| 19(H7-12) | 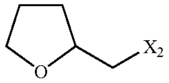 | H | 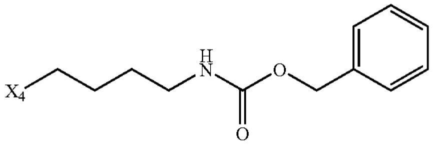 | H |
| 19(H7-13) | 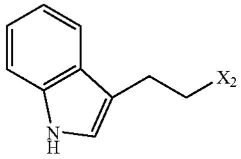 | H | H | H |
| 19(H7-14) | 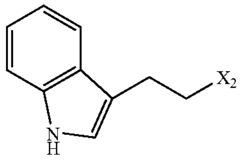 | H | 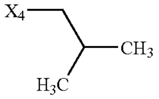 | H |
| 19(H7-15) | 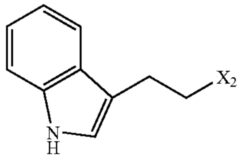 | H | 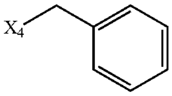 | H |

TABLE 7B-3
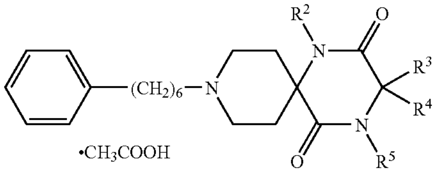
•$CH_3COOH$
| Example No | $R^2$ | $R^3$ | $R^4$ | $R^5$ |
|---|---|---|---|---|
| 19(H7-16) | 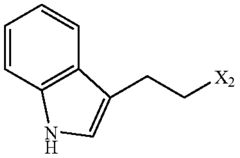 | H | 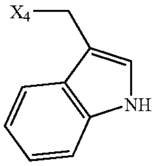 | H |
| 19(H7-17) | 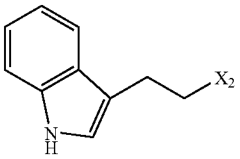 | H | 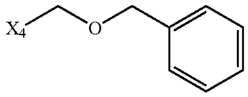 | H |
| 19(H7-18) | 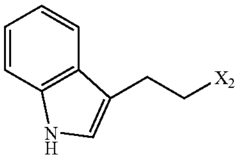 | H | 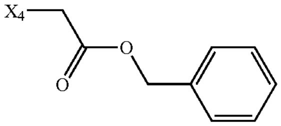 | H |
| 19(H7-19) | 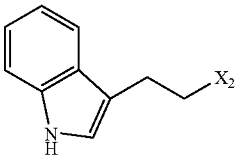 | H | 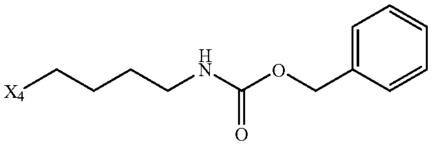 | H |
| 19(H7-20) | 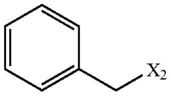 | H | H | H |
| 19(H7-21) | 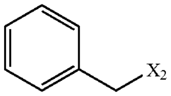 | H | 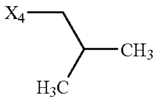 | H |
| 19(H7-22) | 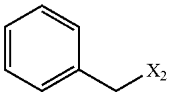 | H | 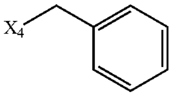 | H |
| 19(H7-23) | 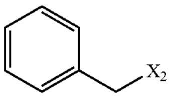 | H | 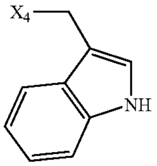 | H |

TABLE 7B-4
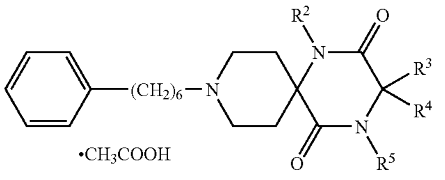
•$CH_3COOH$
| Example No | $R^2$ | $R^3$ | $R^4$ | $R^5$ |
| --- | --- | --- | --- | --- |
| 19(H7-24) | 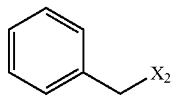 | H | 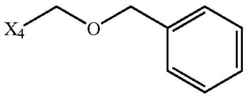 | H |
| 19(H7-25) | 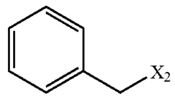 | H | 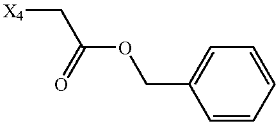 | H |
| 19(H7-26) | 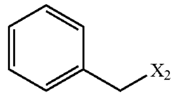 | H | 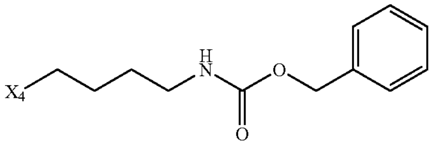 | H |
| 19(H7-27) | 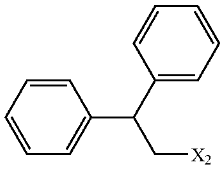 | H | H | H |
| 19(H7-28) | 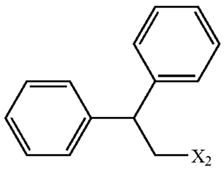 | H | 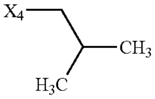 | H |
| 19(H7-29) | 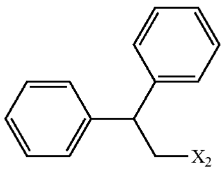 | H | 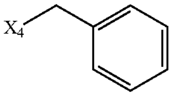 | H |
| 19(H7-30) | 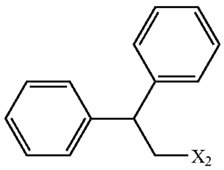 | H | 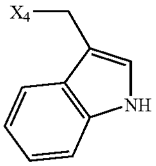 | H |
| 19(H7-31) | 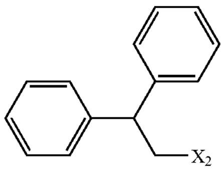 | H | 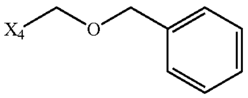 | H |

TABLE 7B-5
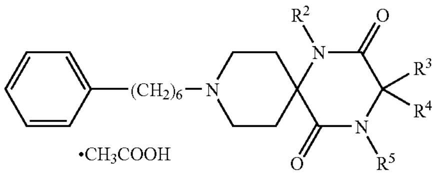
•$CH_3COOH$
| Example No | $R^2$ | $R^3$ | $R^4$ | $R^5$ |
|---|---|---|---|---|
| 19(H7-32) | 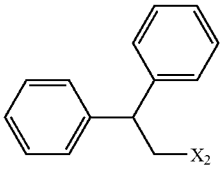 | H | 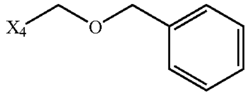 | H |
| 19(H7-33) | 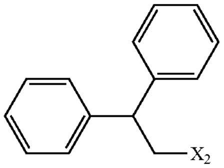 | H | 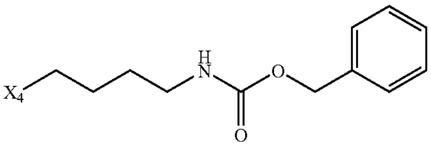 | H |
| 19(H7-34) | 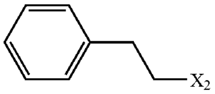 | H | 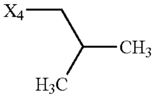 | H |
| 19(H7-35) | 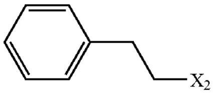 | H | 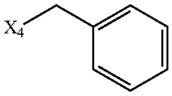 | H |
| 19(H7-36) | 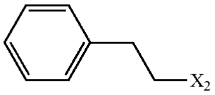 | H | 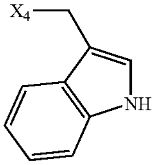 | H |
| 19(H7-37) | 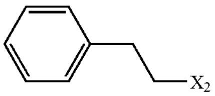 | H | 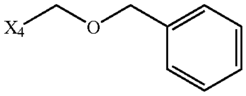 | H |
| 19(H7-38) | 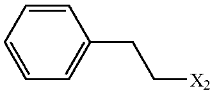 | H | 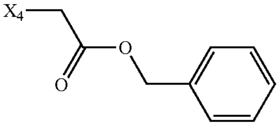 | H |
| 19(H7-39) | 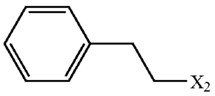 | H | 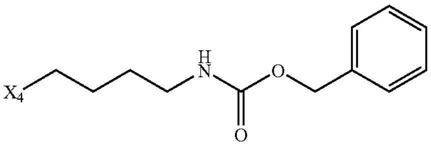 | H |

TABLE 7B-6
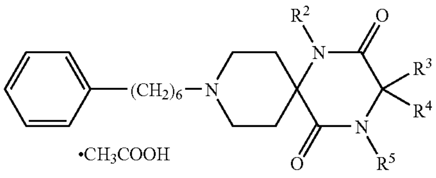
$\cdot CH_3COOH$
| Example No | $R^2$ | $R^3$ | $R^4$ | $R^5$ |
|---|---|---|---|---|
| 19(H7-40) | 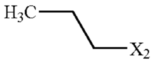 | H | H | H |
| 19(H7-41) | 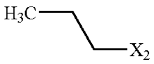 | H | 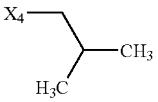 | H |
| 19(H7-42) | 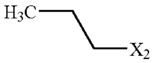 | H | 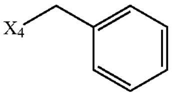 | H |
| 19(H7-43) | 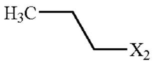 | H | 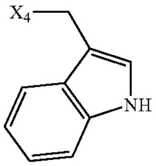 | H |
| 19(H7-44) | 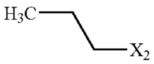 | H | 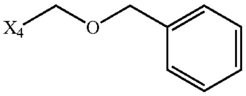 | H |
| 19(H7-45) | 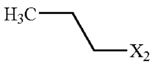 | H | 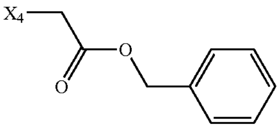 | H |
| 19(H7-46) | 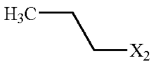 | H | 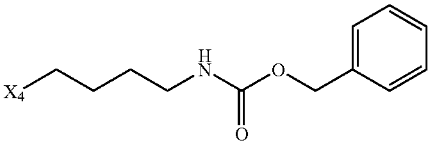 | H |
| 19(H7-47) | 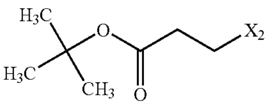 | H | H | H |
| 19(H7-48) | 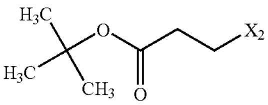 | H | 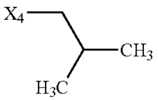 | H |

TABLE 7B-7
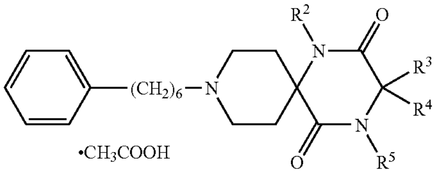
| Example No | $R^2$ | $R^3$ | $R^4$ | $R^5$ |
|---|---|---|---|---|
| 19(H7-49) | 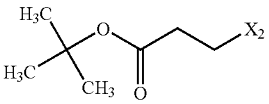 | H | 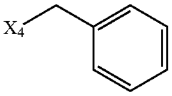 | H |
| 19(H7-50) | 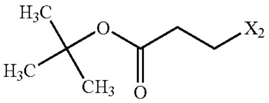 | H | 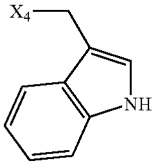 | H |
| 19(H7-51) | 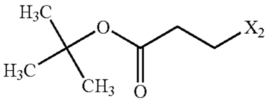 | H | 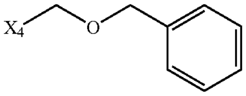 | H |
| 19(H7-52) | 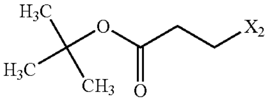 | H | 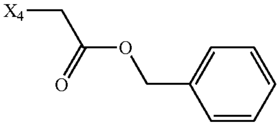 | H |
| 19(H7-53) | 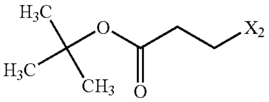 | H | 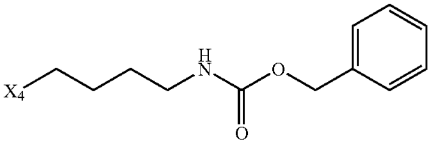 | H |
| 19(H7-54) | 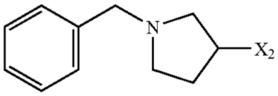 | H | H | H |
| 19(H7-55) | 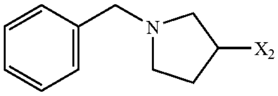 | H | 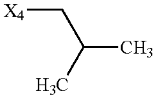 | H |
| 19(H7-56) | 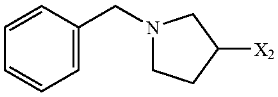 | H | 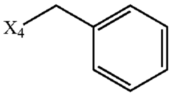 | H |

TABLE 7B-8
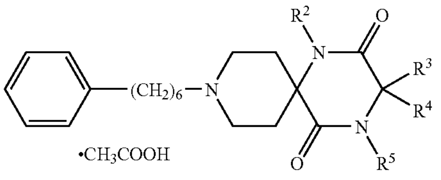
•$CH_3COOH$
| Example No | $R^2$ | $R^3$ | $R^4$ | $R^5$ |
|---|---|---|---|---|
| 19(H7-57) | 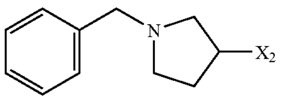 | H | 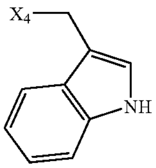 | H |
| 19(H7-58) | 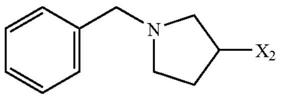 | H | 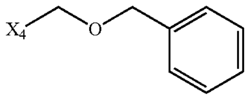 | H |
| 19(H7-59) | 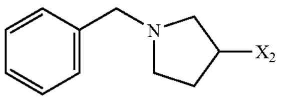 | H | 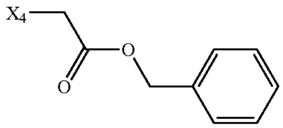 | H |
| 19(H7-60) | 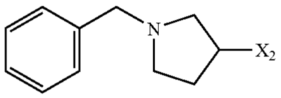 | H | 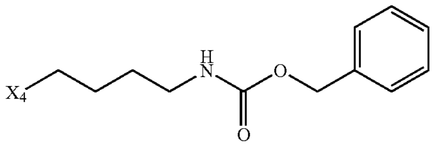 | H |
TABLE 8B-1
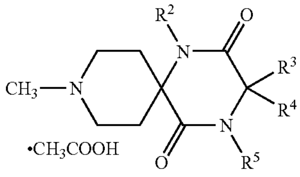
•$CH_3COOH$
| Example No | $R^2$ | $R^3$ | $R^4$ | $R^5$ |
|---|---|---|---|---|
| 19(H8-1) | 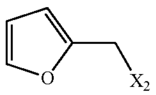 | H | 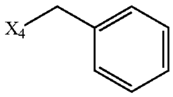 | H |
| 19(H8-2) | 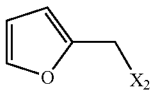 | H | 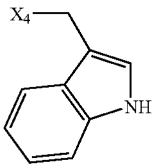 | H |
| 19(H8-3) | 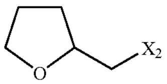 | H | H | H |

TABLE 8B-1-continued
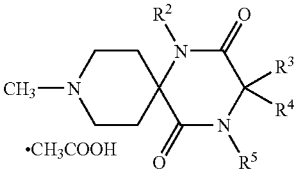
•$CH_3COOH$
| Example No | $R^2$ | $R^3$ | $R^4$ | $R^5$ |
|---|---|---|---|---|
| 19(H8-4) | 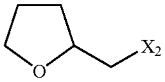 | H | 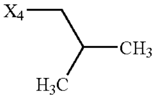 | H |
| 19(H8-5) | 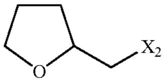 | H | 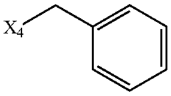 | H |
| 19(H8-6) | 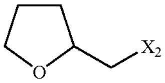 | H | 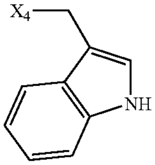 | H |
| 19(H8-7) | 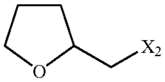 | H | 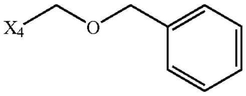 | H |
| 19(H8-8) | 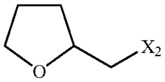 | H | 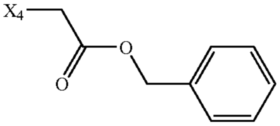 | H |
TABLE 8B-2
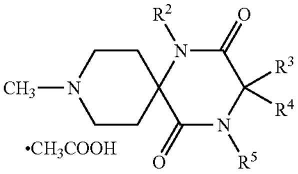
•$CH_3COOH$
| Example No | $R^2$ | $R^3$ | $R^4$ | $R^5$ |
|---|---|---|---|---|
| 19(H8-9) | 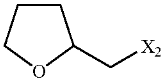 | H | 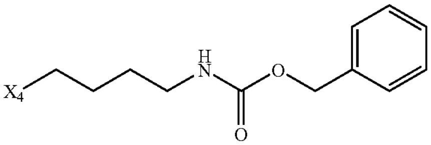 | H |
| 19(H8-10) | 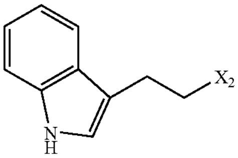 | H | H | H |

TABLE 8B-2-continued
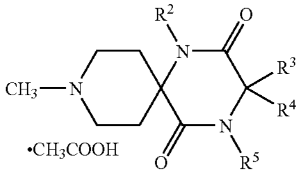
| Example No | $R^2$ | $R^3$ | $R^4$ | $R^5$ |
| --- | --- | --- | --- | --- |
| 19(H8-11) | 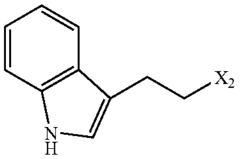 | H | 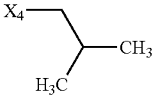 | H |
| 19(H8-12) | 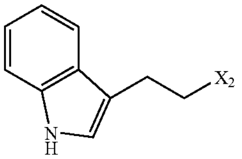 | H | 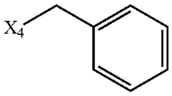 | H |
| 19(H8-13) | 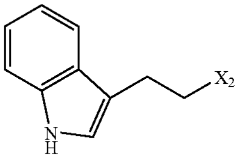 | H | 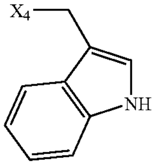 | H |
| 19(H8-14) | 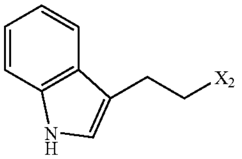 | H | 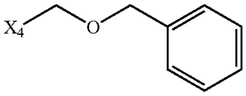 | H |
| 19(H8-15) | 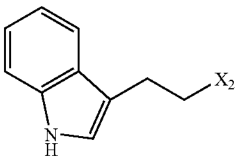 | H | 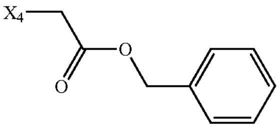 | H |
| 19(H8-16) | 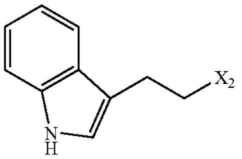 | H | 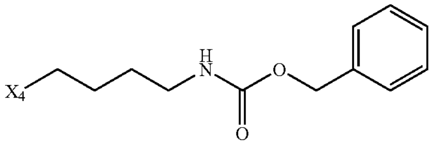 | H |

TABLE 8B-3
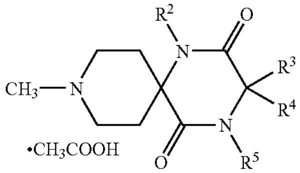
$\cdot CH_3COOH$
| Example No | $R^2$ | $R^3$ | $R^4$ | $R^5$ |
|---|---|---|---|---|
| 19(H8-17) | 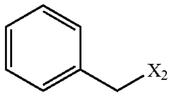 | H | H | H |
| 19(H8-18) | 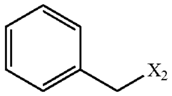 | H | 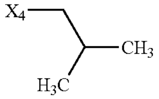 | H |
| 19(H8-19) | 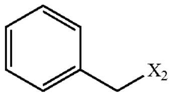 | H | 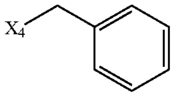 | H |
| 19(H8-20) | 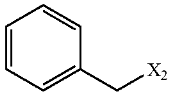 | H | 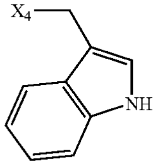 | H |
| 19(H8-21) | 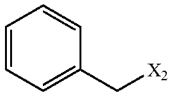 | H | 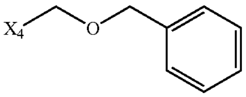 | H |
| 19(H8-22) | 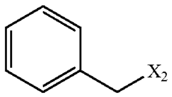 | H | 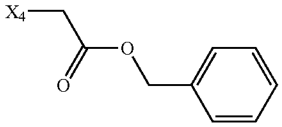 | H |
| 19(H8-23) | 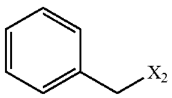 | H | 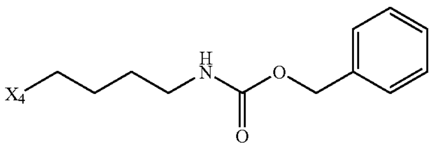 | H |
| 19(H8-24) | 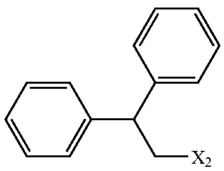 | H | H | H |

TABLE 8B-4
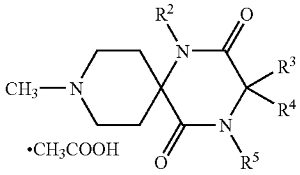
$\cdot CH_3COOH$
| Example No | $R^2$ | $R^3$ | $R^4$ | $R^5$ |
|---|---|---|---|---|
| 19(H8-25) | 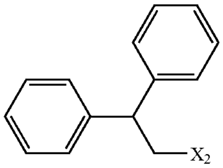 | H | 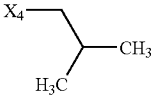 | H |
| 19(H8-26) | 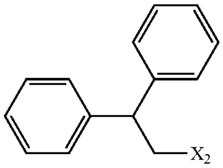 | H | 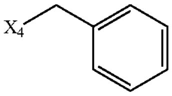 | H |
| 19(H8-27) | 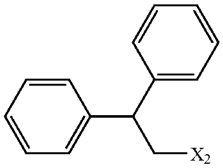 | H | 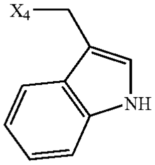 | H |
| 19(H8-28) | 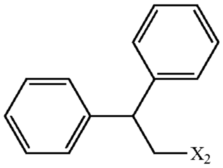 | H | 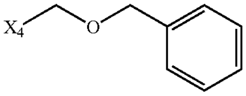 | H |
| 19(H8-29) | 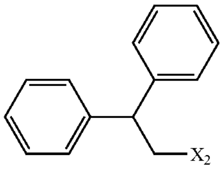 | H | 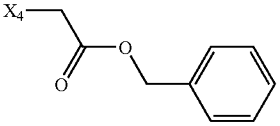 | H |
| 19(H8-30) | 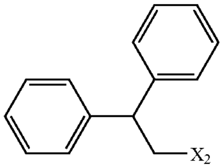 | H | 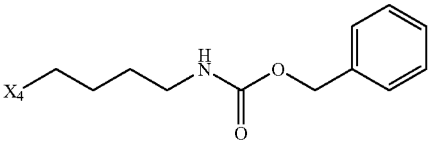 | H |
| 19(H8-31) | 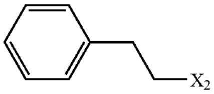 | H | H | H |
| 19(H8-32) | 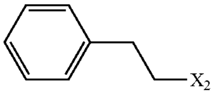 | H | 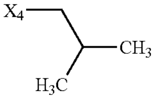 | H |

TABLE 8B-5
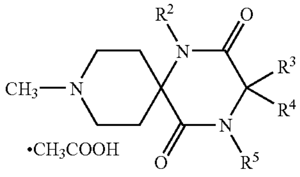
•$CH_3COOH$
| Example No | $R^2$ | $R^3$ | $R^4$ | $R^5$ |
|---|---|---|---|---|
| 19(H8-33) | 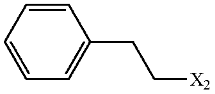 | H | 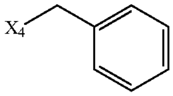 | H |
| 19(H8-34) | 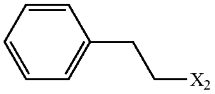 | H | 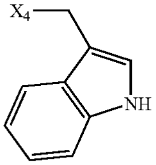 | H |
| 19(H8-35) | 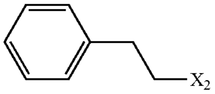 | H | 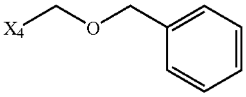 | H |
| 19(H8-36) | 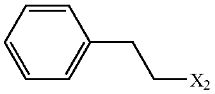 | H | 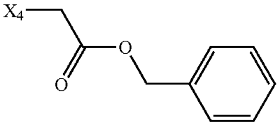 | H |
| 19(H8-37) | 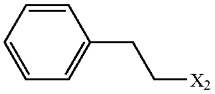 | H | 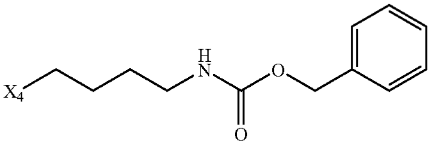 | H |
| 19(H8-38) | 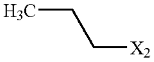 | H | H | H |
| 19(H8-39) | 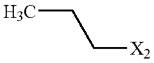 | H | 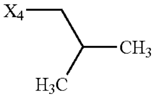 | H |
| 19(H8-40) | 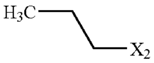 | H | 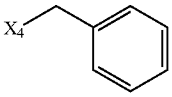 | H |

TABLE 8B-6
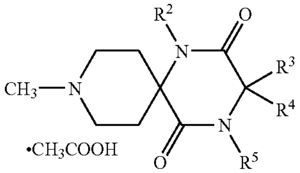
•$CH_3COOH$
| Example No | $R^2$ | $R^3$ | $R^4$ | $R^5$ |
| --- | --- | --- | --- | --- |
| 19(H8-41) | 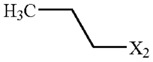 | H | 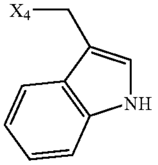 | H |
| 19(H8-42) | 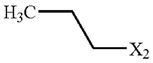 | H | 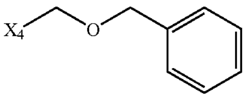 | H |
| 19(H8-43) | 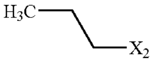 | H | 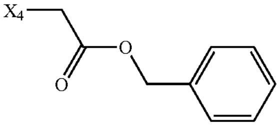 | H |
| 19(H8-44) | 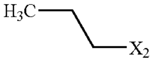 | H | 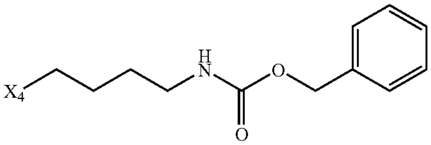 | H |
| 19(H8-45) | 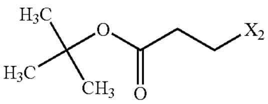 | H | H | H |
| 19(H8-46) | 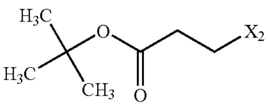 | H | 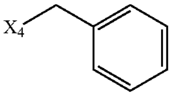 | H |
| 19(H8-47) | 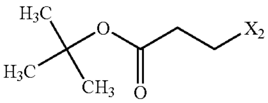 | H | 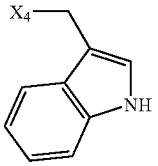 | H |
| 19(H8-48) | 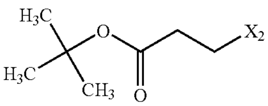 | H | 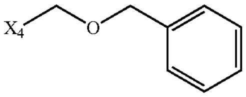 | H |

TABLE 8B-7
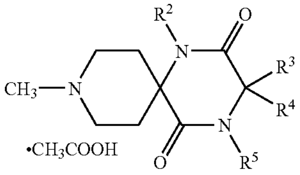
$\cdot CH_3COOH$
| Example No | $R^2$ | $R^3$ | $R^4$ | $R^5$ |
|---|---|---|---|---|
| 19(H8-49) | 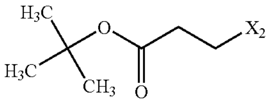 | H | 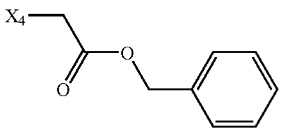 | H |
| 19(H8-50) | 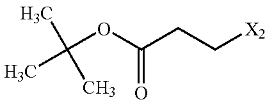 | H | 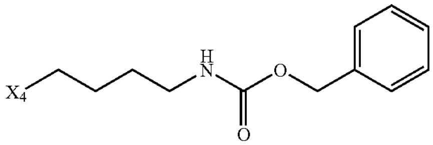 | H |
| 19(H8-51) | 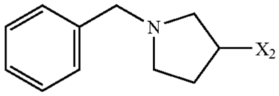 | H | H | H |
| 19(H8-52) | 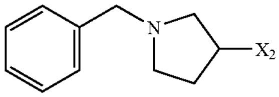 | H | 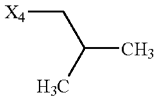 | H |
| 19(H8-53) | 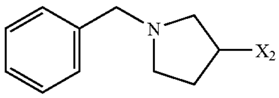 | H | 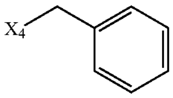 | H |
| 19(H8-54) | 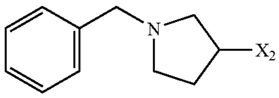 | H | 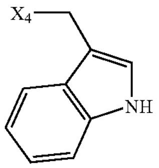 | H |
| 19(H8-55) | 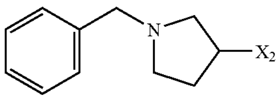 | H | 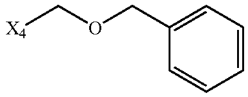 | H |
| 19(H8-56) | 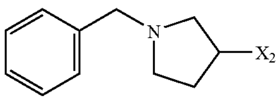 | H | 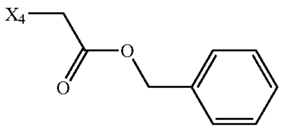 | H |

TABLE 8B-8
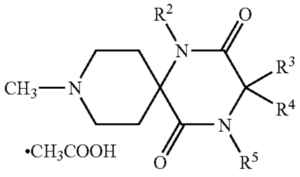
•$CH_3COOH$
| Example No | $R^2$ | $R^3$ | $R^4$ | $R^5$ |
|---|---|---|---|---|
| 19(H8-57) | 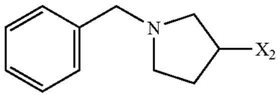 | H | 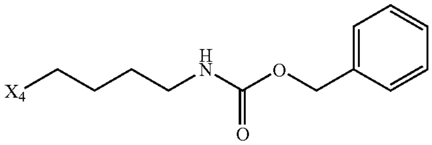 | H |
TABLE 9B-1
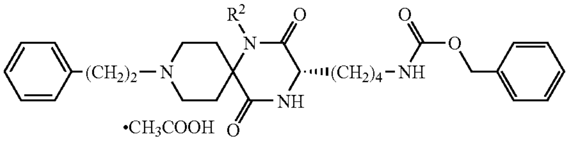
•$CH_3COOH$
| Example No | $R^2$ |
|---|---|
| 19(H9-1) | 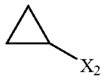 |
| 19(H9-2) | 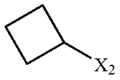 |
| 19(H9-3) | 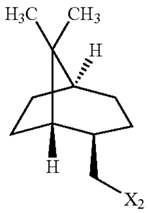 |
| 19(H9-4) | 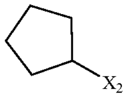 |
| 19(H9-5) | 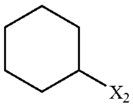 |
| 19(H9-6) | 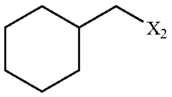 |
| 19(H9-7) | 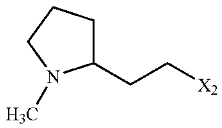 |
TABLE 9B-1-continued
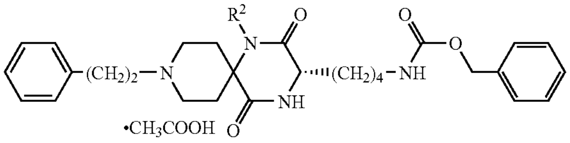
•$CH_3COOH$
| Example No | $R^2$ |
|---|---|
| 19(H9-8) | 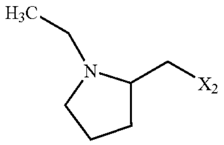 |
TABLE 9B-2
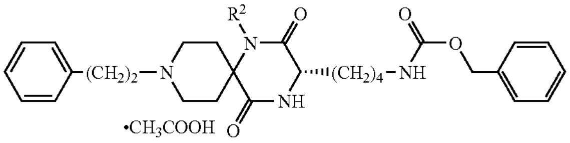
•$CH_3COOH$
| Example No | $R^2$ |
|---|---|
| 19(H9-9) | 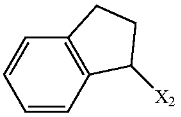 |
| 19(H9-10) | 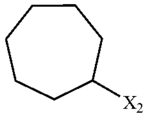 |
| 19(H9-11) | 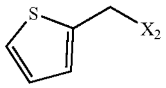 |
| 19(H9-12) | 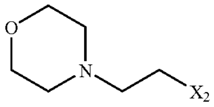 |

TABLE 9B-2-continued
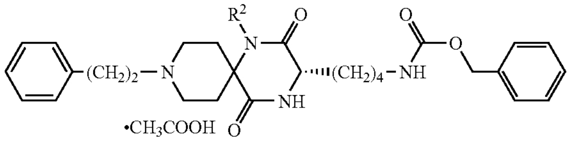
$\cdot CH_3COOH$
| Example No | $R^2$ |
|---|---|
| 19(H9-13) | 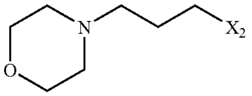 |
| 19(H9-14) | 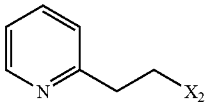 |
| 19(H9-15) | 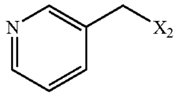 |
| 19(H9-16) | 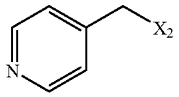 |
TABLE 9B-3
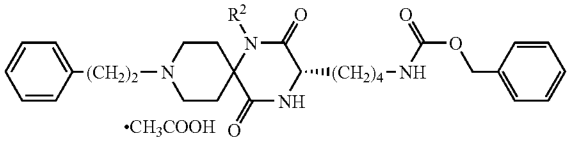
$\cdot CH_3COOH$
| Example No | $R^2$ |
|---|---|
| 19(H9-17) | 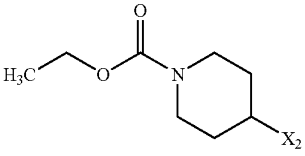 |
| 19(H9-18) | 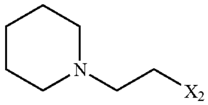 |
| 19(H9-19) | 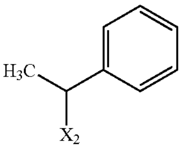 |
| 19(H9-20) | 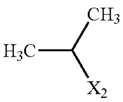 |
TABLE 9B-3-continued
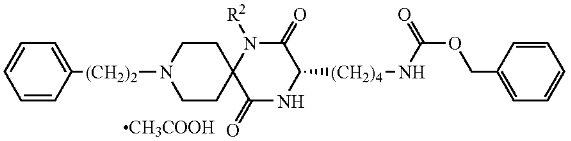
$\cdot CH_3COOH$
| Example No | $R^2$ |
|---|---|
| 19(H9-21) | 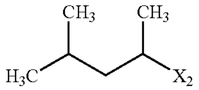 |
| 19(H9-22) | 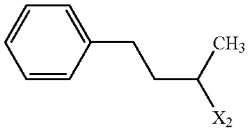 |
| 19(H9-23) | 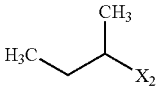 |
| 19(H9-24) | 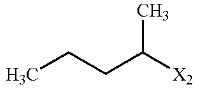 |
TABLE 9B-4
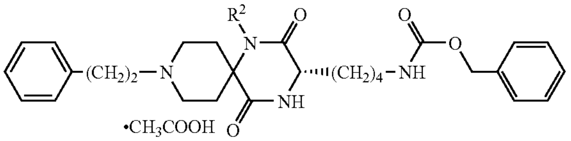
$\cdot CH_3COOH$
| Example No | $R^2$ |
|---|---|
| 19(H9-25) | 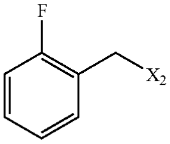 |
| 19(H9-26) | 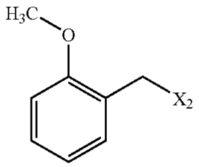 |
| 19(H9-27) | 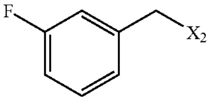 |
| 19(H9-28) | 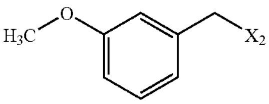 |

TABLE 9B-4-continued
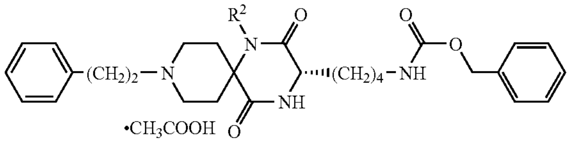
| Example No | $R^2$ |
| --- | --- |
| 19(H9-29) | 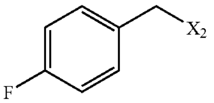 |
| 19(H9-30) | 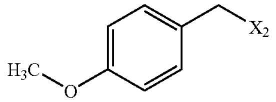 |
| 19(H9-31) | 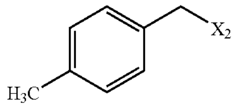 |
| 19(H9-32) | 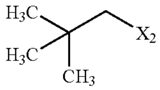 |
TABLE 9B-5
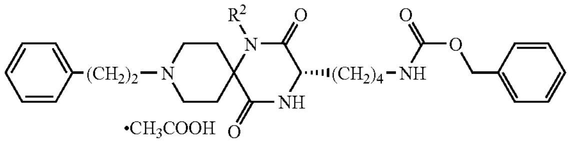
| Example No | $R^2$ |
| --- | --- |
| 19(H9-33) | 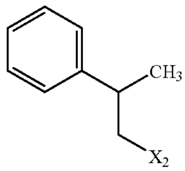 |
| 19(H9-34) | 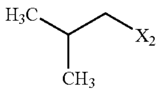 |
| 19(H9-35) | 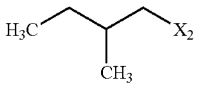 |
| 19(H9-36) | 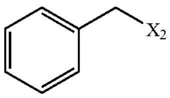 |
| 19(H9-37) | 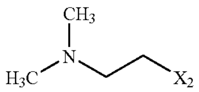 |
TABLE 9B-5-continued
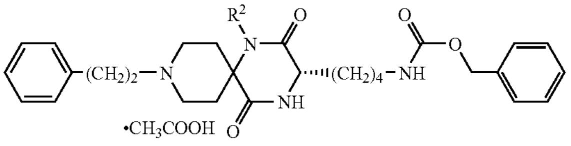
| Example No | $R^2$ |
| --- | --- |
| 19(H9-38) | 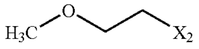 |
| 19(H9-39) | 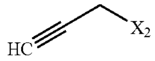 |
| 19(H9-40) | 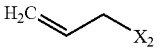 |
| 19(H9-41) | 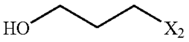 |
| 19(H9-42) | 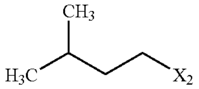 |
| 19(H9-43) | 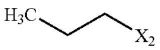 |
TABLE 9B-6
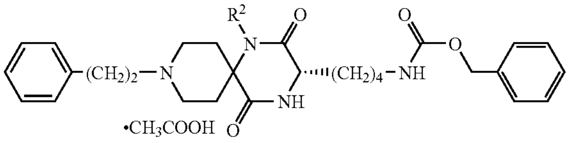
| Example No | $R^2$ |
| --- | --- |
| 19(H9-44) | 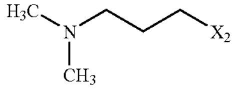 |
| 19(H9-45) | 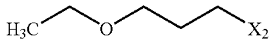 |
| 19(H9-46) | 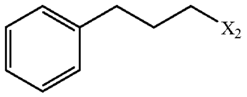 |
| 19(H9-47) | 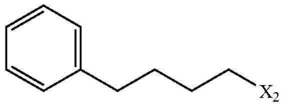 |
| 19(H9-48) | 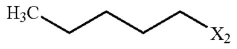 |
| 19(H9-49) | 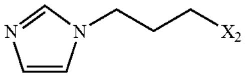 |
| 19(H9-50) | 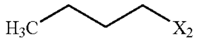 |

TABLE 9B-6-continued
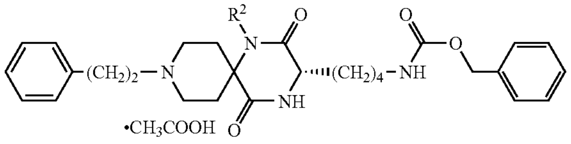
| Example No | $R^2$ |
|---|---|
| 19(H9-51) | 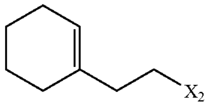 |
| 19(H9-52) | 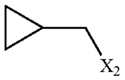 |
| 19(H9-53) | 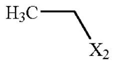 |
| 19(H9-54) | 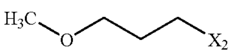 |
TABLE 9B-7
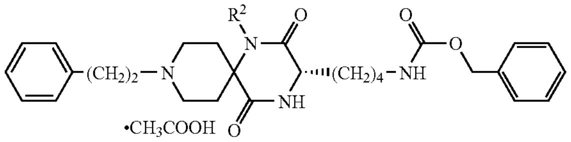
| Example No | $R^2$ |
|---|---|
| 19(H9-55) | 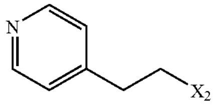 |
| 19(H9-56) | 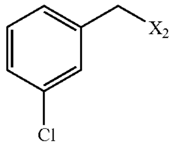 |
| 19(H9-57) | 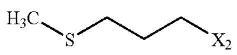 |
| 19(H9-58) | 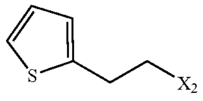 |
| 19(H9-59) | 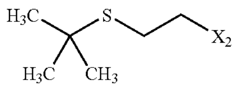 |
| 19(H9-60) | 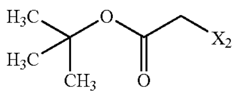 |
TABLE 9B-7-continued
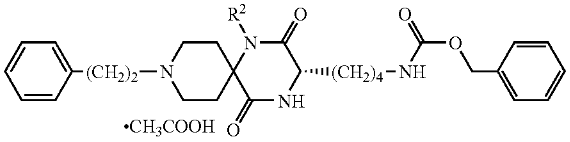
| Example No | $R^2$ |
|---|---|
| 19(H9-61) | 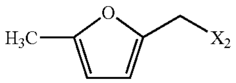 |
| 19(H9-62) | 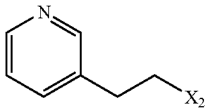 |
TABLE 10B-1
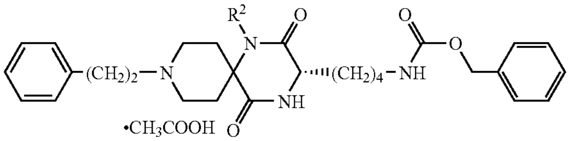
| Example No | $R^2$ |
|---|---|
| 19(H10-1) | 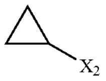 |
| 19(H10-2) | 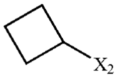 |
| 19(H10-3) | 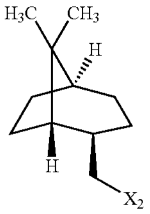 |
| 19(H10-4) | 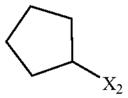 |
| 19(H10-5) | 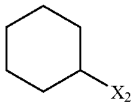 |
| 19(H10-6) | 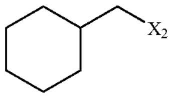 |

TABLE 10B-1-continued
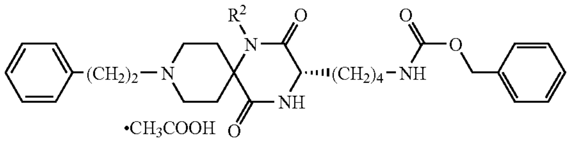
| Example No | $R^2$ |
|---|---|
| 19(H10-7) | 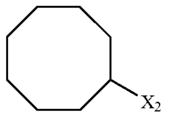 |
| 19(H10-8) | 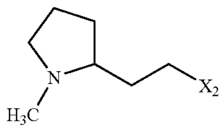 |
TABLE 10B-2
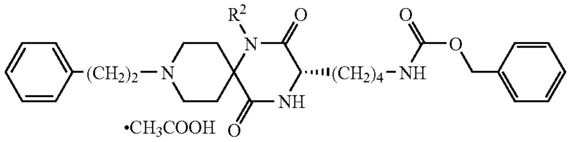
| Example No | $R^2$ |
|---|---|
| 19(H10-9) | 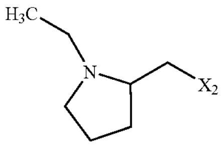 |
| 19(H10-10) | 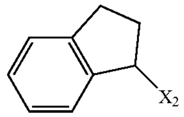 |
| 19(H10-11) | 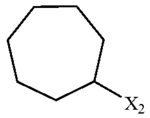 |
| 19(H10-12) | 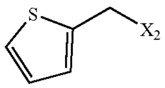 |
| 19(H10-13) | 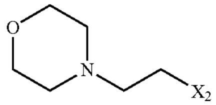 |
| 19(H10-14) | 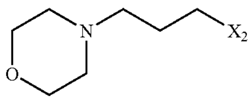 |
TABLE 10B-2-continued
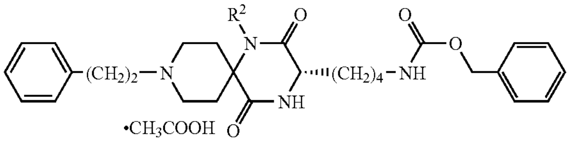
| Example No | $R^2$ |
|---|---|
| 19(H10-15) | 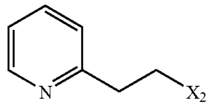 |
| 19(H10-16) | 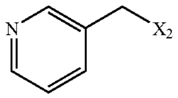 |
TABLE 10B-3
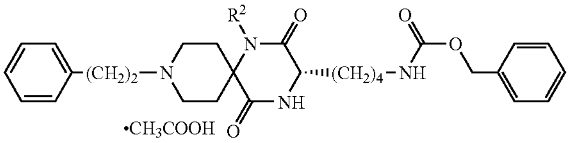
| Example No | $R^2$ |
|---|---|
| 19(H10-17) | 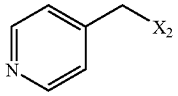 |
| 19(H10-18) | 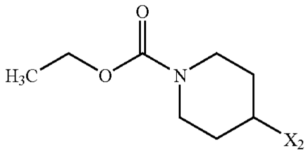 |
| 19(H10-19) | 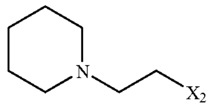 |
| 19(H10-20) | 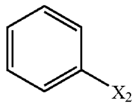 |
| 19(H10-21) | 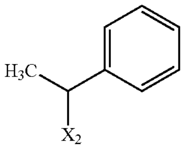 |
| 19(H10-22) | 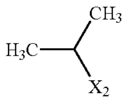 |

TABLE 10B-3-continued
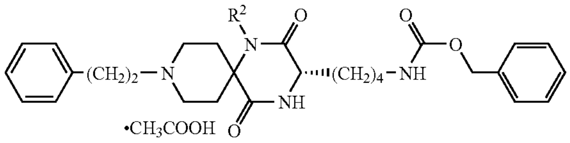
•$CH_3COOH$
| Example No | $R^2$ |
|---|---|
| 19(H10-23) | 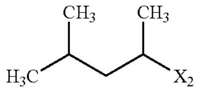 |
| 19(H10-24) | 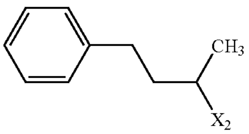 |
TABLE 10B-4
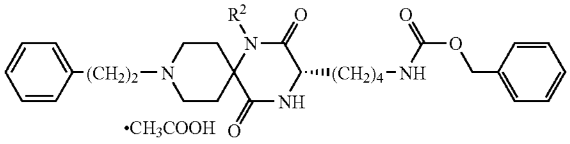
•$CH_3COOH$
| Example No | $R^2$ |
|---|---|
| 19(H10-25) | 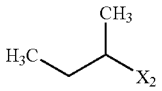 |
| 19(H10-26) | 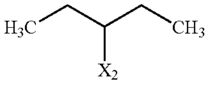 |
| 19(H10-27) | 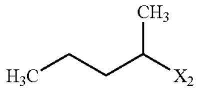 |
| 19(H10-28) | 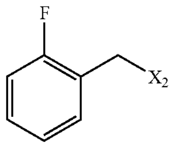 |
| 19(H10-29) | 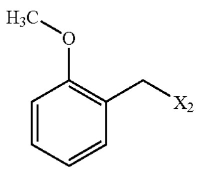 |
| 19(H10-30) | 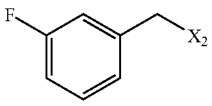 |
TABLE 10B-4-continued
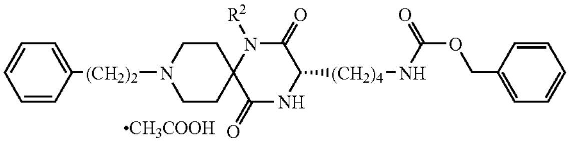
•$CH_3COOH$
| Example No | $R^2$ |
|---|---|
| 19(H10-31) | 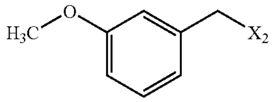 |
| 19(H10-32) | 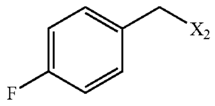 |
TABLE 10B-5
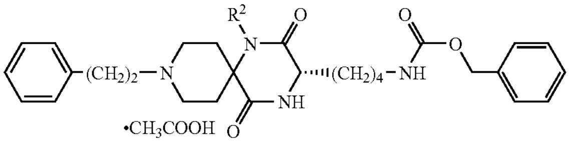
•$CH_3COOH$
| Example No | $R^2$ |
|---|---|
| 19(H10-33) | 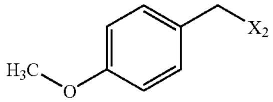 |
| 19(H10-34) | 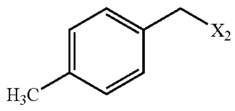 |
| 19(H10-35) | 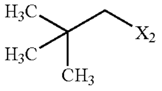 |
| 19(H10-36) | 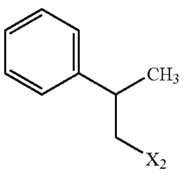 |
| 19(H10-37) | 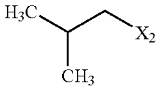 |
| 19(H10-38) | 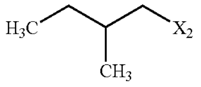 |
| 19(H10-39) | 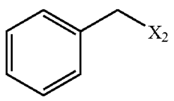 |

TABLE 10B-5-continued
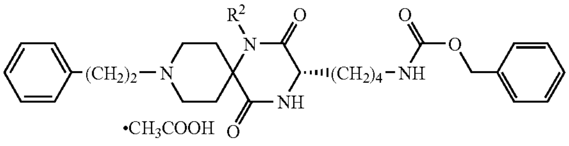
•$CH_3COOH$
| Example No | $R^2$ |
|---|---|
| 19(H10-40) | 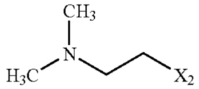 |
| 19(H10-41) | 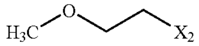 |
TABLE 10B-6
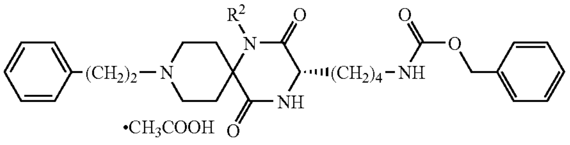
•$CH_3COOH$
| Example No | $R^2$ |
|---|---|
| 19(H10-42) | 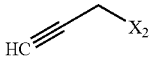 |
| 19(H10-43) | 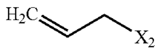 |
| 19(H10-44) | 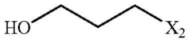 |
| 19(H10-45) | 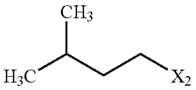 |
| 19(H10-46) | 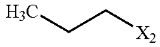 |
| 19(H10-47) | 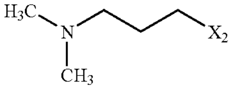 |
| 19(H10-48) | 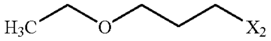 |
| 19(H10-49) | 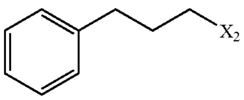 |
| 19(H10-50) | 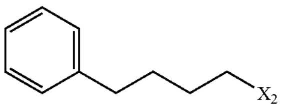 |
| 19(H10-51) | 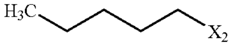 |
| 19(H10-52) | 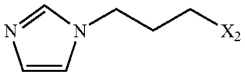 |
TABLE 10B-6-continued
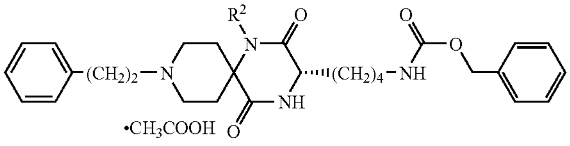
•$CH_3COOH$
| Example No | $R^2$ |
|---|---|
| 19(H10-53) | 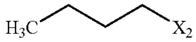 |
TABLE 10B-7
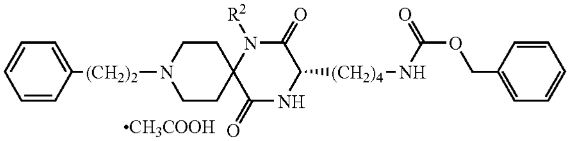
•$CH_3COOH$
| Example No | $R^2$ |
|---|---|
| 19(H10-54) | 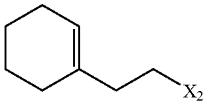 |
| 19(H10-55) | 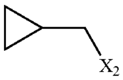 |
| 19(H10-56) | 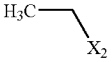 |
| 19(H10-57) | 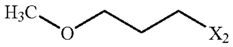 |
| 19(H10-58) | 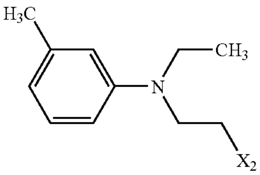 |
| 19(H10-59) | 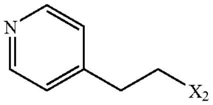 |
| 19(H10-60) | 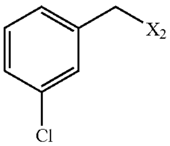 |
| 19(H10-61) | 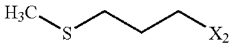 |
| 19(H10-62) | 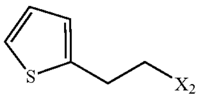 |

TABLE 10B-8
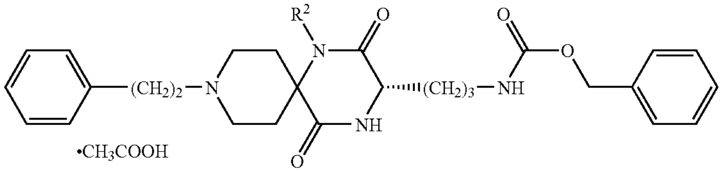
•$CH_3COOH$
| Example No | $R^2$ |
|---|---|
| 19(H10-63) | 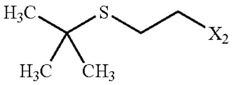 |
| 19(H10-64) | 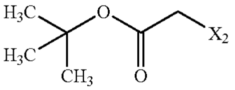 |
| 19(H10-65) | 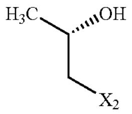 |
| 19(H10-66) | 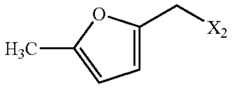 |
| 19(H10-67) | 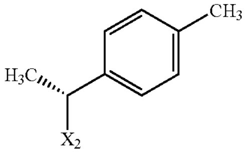 |
| 19(H10-68) | 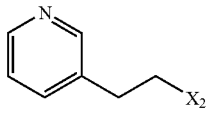 |
TABLE 11B-1
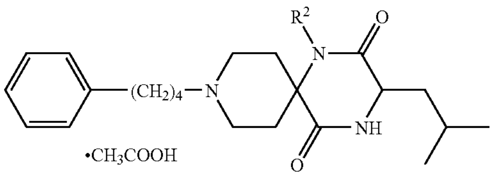
•$CH_3COOH$
| Example No | $R^2$ |
|---|---|
| 19(H11-1) | 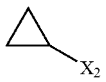 |
| 19(H11-2) | 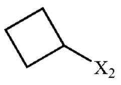 |
TABLE 11B-1-continued
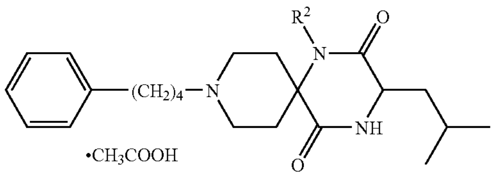
•$CH_3COOH$
| Example No | $R^2$ |
|---|---|
| 19(H11-3) | 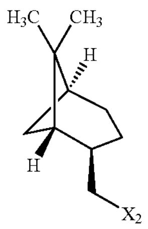 |

TABLE 11B-1-continued
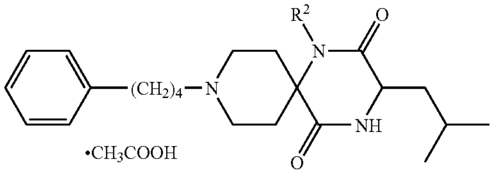
•$CH_3COOH$
| Example No | $R^2$ |
|---|---|
| 19(H11-4) | 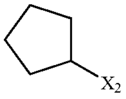 |
| 19(H11-5) | 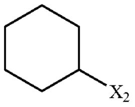 |
| 19(H11-6) | 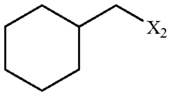 |
| 19(H11-7) | 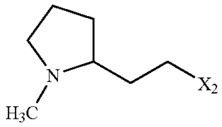 |
| 19(H11-8) | 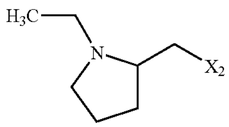 |
TABLE 11B-2
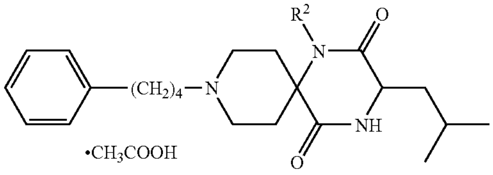
•$CH_3COOH$
| Example No | $R^2$ |
|---|---|
| 19(H11-9) | 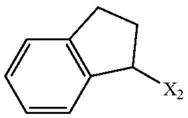 |
| 19(H11-10) | 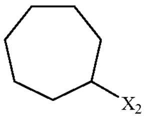 |
| 19(H11-11) | 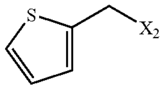 |
TABLE 11B-2-continued
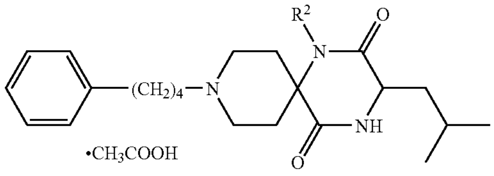
•$CH_3COOH$
| Example No | $R^2$ |
|---|---|
| 19(H11-12) | 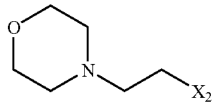 |
| 19(H11-13) | 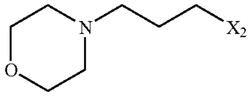 |
| 19(H11-14) | 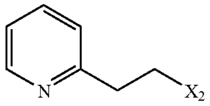 |
| 19(H11-15) | 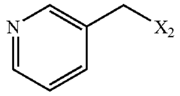 |
| 19(H11-16) | 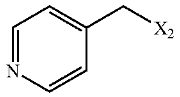 |
TABLE 11B-3
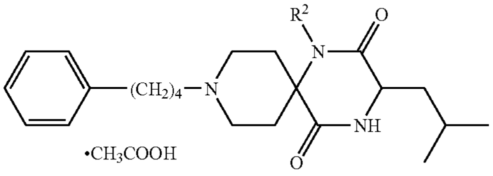
•$CH_3COOH$
| Example No | $R^2$ |
|---|---|
| 19(H11-17) | 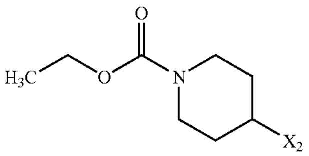 |
| 19(H11-18) | 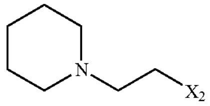 |
| 19(H11-19) | 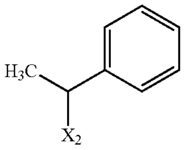 |

TABLE 11B-3-continued
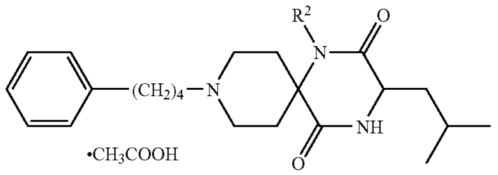
$\bullet CH_3COOH$
| Example No | $R^2$ |
|---|---|
| 19(H11-20) | 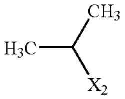 |
| 19(H11-21) | 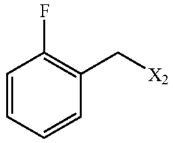 |
| 19(H11-22) | 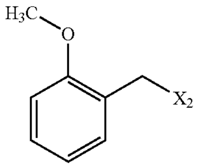 |
| 19(H11-23) | 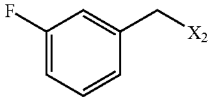 |
| 19(H11-24) | 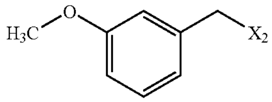 |
TABLE 11B-4
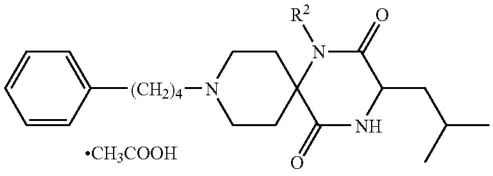
$\bullet CH_3COOH$
| Example No | $R^2$ |
|---|---|
| 19(H11-25) | 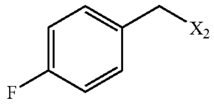 |
| 19(H11-26) | 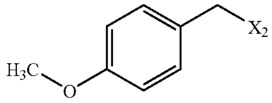 |
| 19(H11-27) | 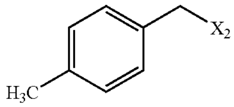 |
TABLE 11B-4-continued
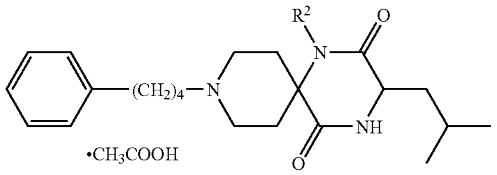
$\bullet CH_3COOH$
| Example No | $R^2$ |
|---|---|
| 19(H11-28) | 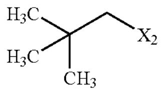 |
| 19(H11-29) | 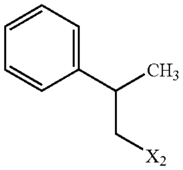 |
| 19(H11-30) | 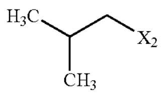 |
| 19(H11-31) | 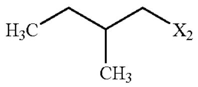 |
| 19(H11-32) | 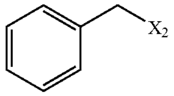 |
| 19(H11-33) | 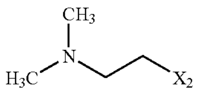 |
TABLE 11B-5
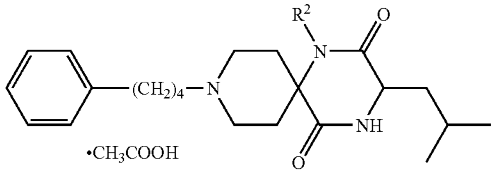
$\bullet CH_3COOH$
| Example No | $R^2$ |
|---|---|
| 19(H11-34) | 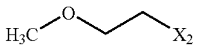 |
| 19(H11-35) | 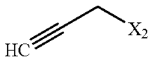 |
| 19(H11-36) | 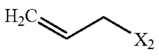 |
| 19(H11-37) | 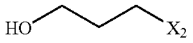 |

TABLE 11B-5-continued
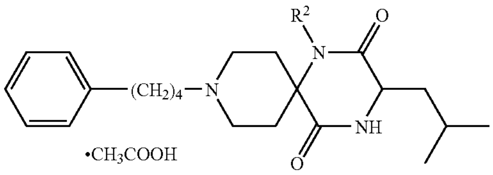
•$CH_3COOH$
| Example No | $R^2$ |
| --- | --- |
| 19(H11-38) | 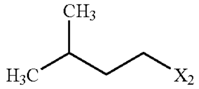 |
| 19(H11-39) | 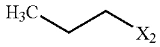 |
| 19(H11-40) | 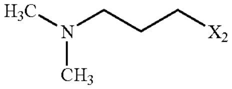 |
| 19(H11-41) | 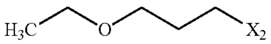 |
| 19(H11-42) | 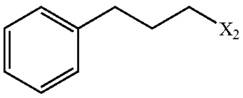 |
| 19(H11-43) | 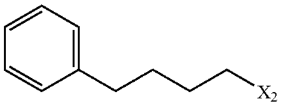 |
| 19(H11-44) | 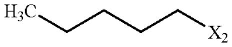 |
| 19(H11-45) | 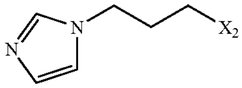 |
TABLE 11B-6
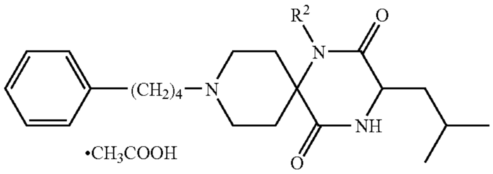
•$CH_3COOH$
| Example No | $R^2$ |
| --- | --- |
| 19(H11-46) | 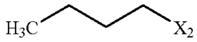 |
| 19(H11-47) | 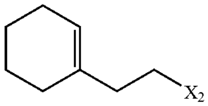 |
| 19(H11-48) | 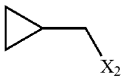 |
TABLE 11B-6-continued
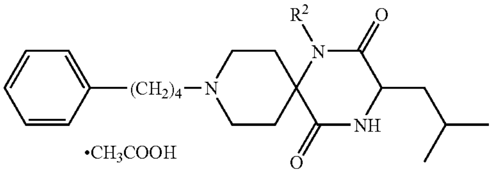
•$CH_3COOH$
| Example No | $R^2$ |
| --- | --- |
| 19(H11-49) | 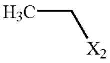 |
| 19(H11-50) | 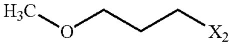 |
| 19(H11-51) | 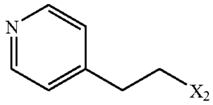 |
| 19(H11-52) | 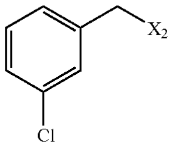 |
| 19(H11-53) | 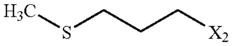 |
| 19(H11-54) | 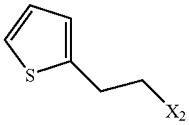 |
| 19(H11-55) | 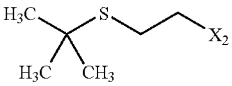 |
TABLE 11B-7
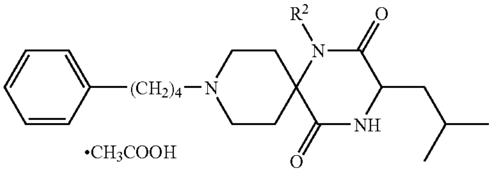
•$CH_3COOH$
| Example No | $R^2$ |
| --- | --- |
| 19(H11-56) | 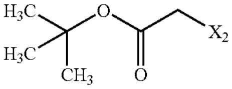 |
| 19(H11-57) | 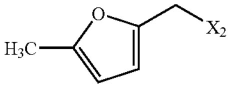 |

TABLE 11B-7-continued
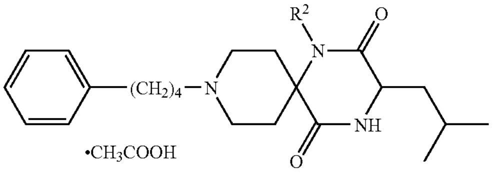
$\bullet CH_3COOH$
| Example No | $R^2$ |
| --- | --- |
| 19(H11-58) | 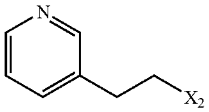 |
TABLE 12B-1
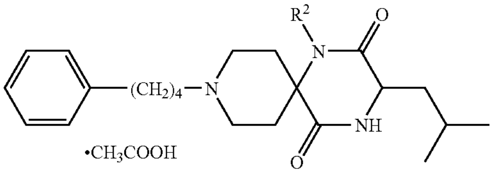
$\bullet CH_3COOH$
| Example No | $R^2$ |
| --- | --- |
| 19(H12-1) | 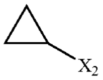 |
| 19(H12-2) | 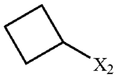 |
| 19(H12-3) | 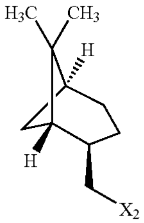 |
| 19(H12-4) | 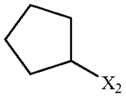 |
| 19(H12-5) | 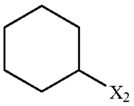 |
| 19(H12-6) | 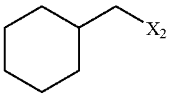 |
| 19(H12-7) | 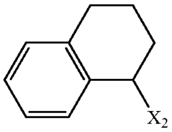 |
TABLE 12B-1-continued
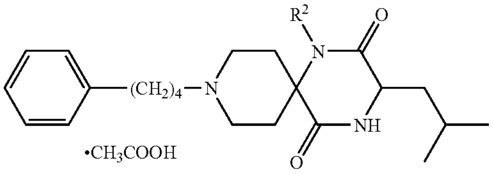
$\bullet CH_3COOH$
| Example No | $R^2$ |
| --- | --- |
| 19(H12-8) | 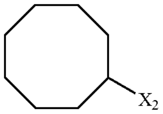 |
TABLE 12B-2
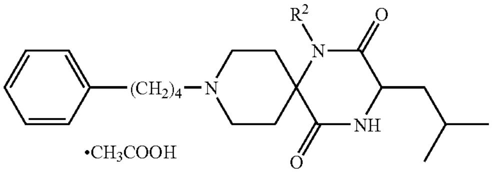
$\bullet CH_3COOH$
| Example No | $R^2$ |
| --- | --- |
| 19(H12-9) | 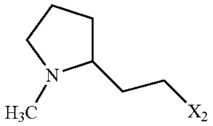 |
| 19(H12-9) | 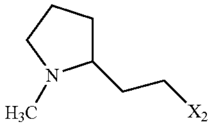 |
| 19(H12-9) | 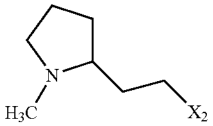 |
| 19(H12-9) | 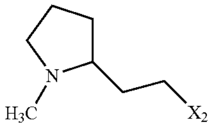 |
| 19(H12-9) | 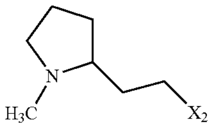 |
| 19(H12-9) | 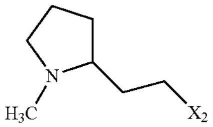 |

TABLE 12B-2-continued
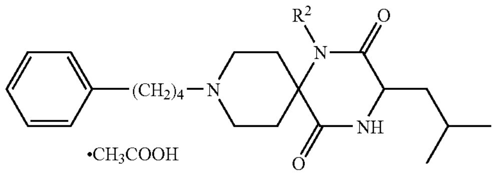
•$CH_3COOH$
| Example No | $R^2$ |
| --- | --- |
| 19(H12-9) | 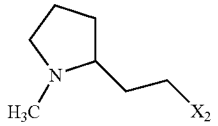 |
| 19(H12-9) | 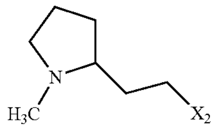 |
TABLE 12B-3
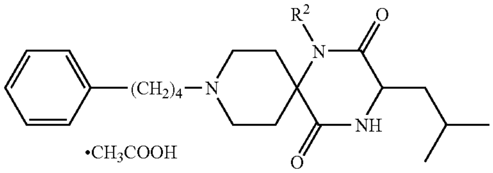
•$CH_3COOH$
| Example No | $R^2$ |
| --- | --- |
| 19(H12-17) | 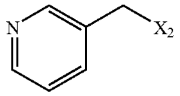 |
| 19(H12-18) | 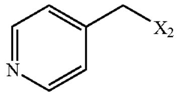 |
| 19(H12-19) | 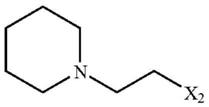 |
| 19(H12-20) | 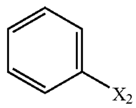 |
| 19(H12-21) | 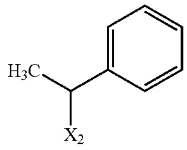 |
| 19(H12-22) | 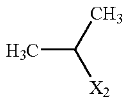 |
TABLE 12B-3-continued
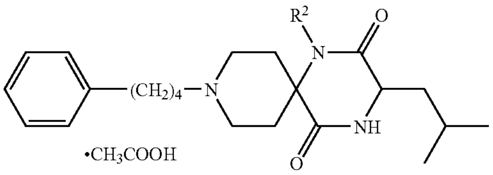
•$CH_3COOH$
| Example No | $R^2$ |
| --- | --- |
| 19(H12-23) | 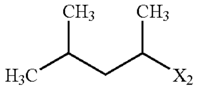 |
| 19(H12-24) | 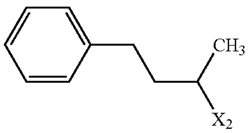 |
TABLE 12B-4
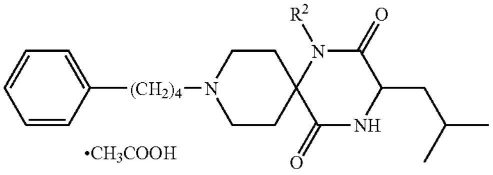
•$CH_3COOH$
| Example No | $R^2$ |
| --- | --- |
| 19(H12-25) | 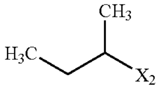 |
| 19(H12-26) | 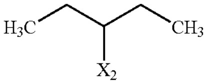 |
| 19(H12-27) | 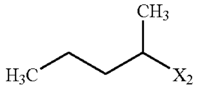 |
| 19(H12-28) | 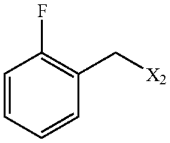 |
| 19(H12-29) | 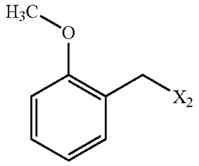 |
| 19(H12-30) | 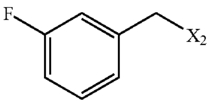 |

TABLE 12B-4-continued
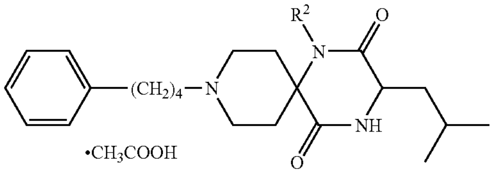
$\bullet CH_3COOH$
| Example No | $R^2$ |
|---|---|
| 19(H12-31) | 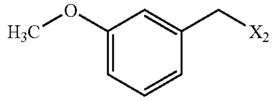 |
| 19(H12-32) | 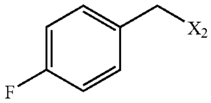 |
TABLE 12B-5
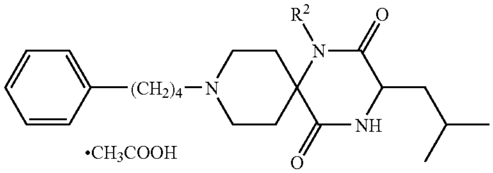
$\bullet CH_3COOH$
| Example No | $R^2$ |
|---|---|
| 19(H12-33) | 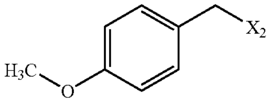 |
| 19(H12-34) | 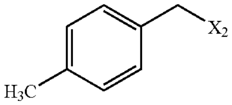 |
| 19(H12-35) | 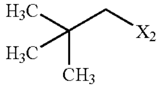 |
| 19(H12-36) | 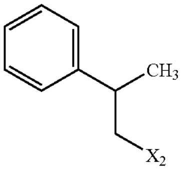 |
| 19(H12-37) | 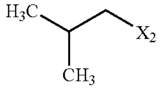 |
| 19(H12-38) | 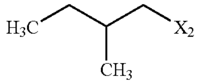 |
TABLE 12B-5-continued
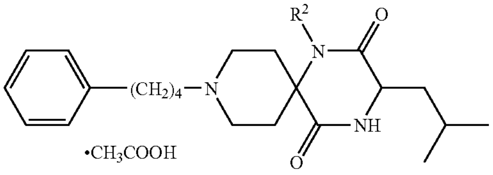
$\bullet CH_3COOH$
| Example No | $R^2$ |
|---|---|
| 19(H12-39) | 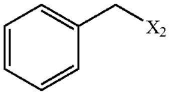 |
| 19(H12-40) | 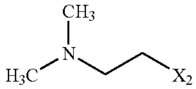 |
| 19(H12-41) | 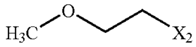 |
TABLE 12B-6
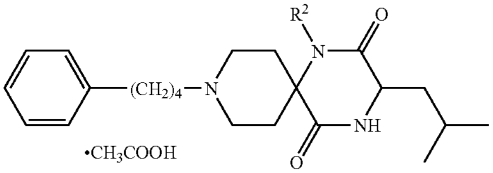
$\bullet CH_3COOH$
| Example No | $R^2$ |
|---|---|
| 19(H12-42) | 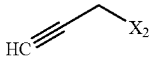 |
| 19(H12-43) | 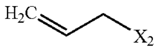 |
| 19(H12-44) | 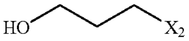 |
| 19(H12-45) | 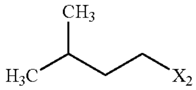 |
| 19(H12-46) | 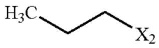 |
| 19(H12-47) | 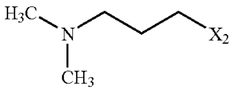 |
| 19(H12-48) | 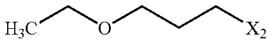 |
| 19(H12-49) | 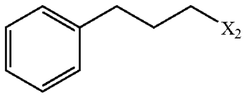 |

TABLE 12B-6-continued
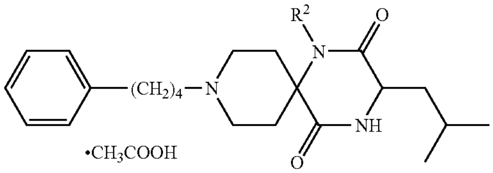
•$CH_3COOH$
| Example No | $R^2$ |
|---|---|
| 19(H12-50) | 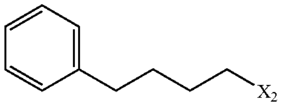 |
| 19(H12-51) | 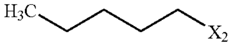 |
| 19(H12-52) | 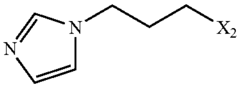 |
| 19(H12-53) | 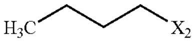 |
TABLE 12B-7
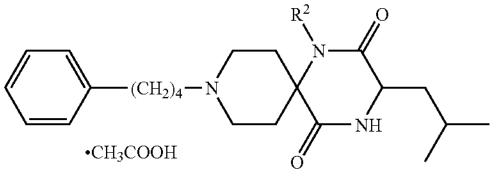
•$CH_3COOH$
| Example No | $R^2$ |
|---|---|
| 19(H12-54) | 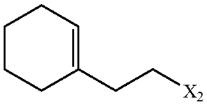 |
| 19(H12-54) | 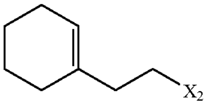 |
| 19(H12-54) | 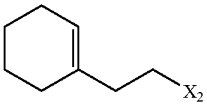 |
| 19(H12-54) | 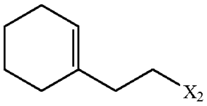 |
| 19(H12-54) | 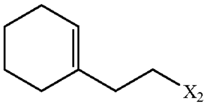 |
TABLE 12B-7-continued
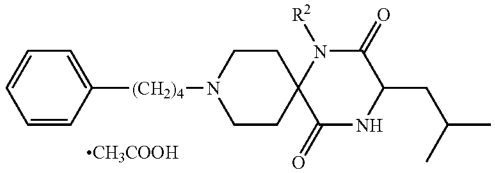
•$CH_3COOH$
| Example No | $R^2$ |
|---|---|
| 19(H12-54) | 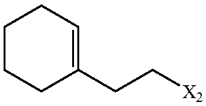 |
| 19(H12-54) | 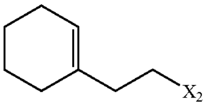 |
| 19(H12-54) | 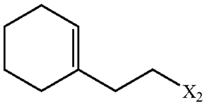 |
| 19(H12-54) | 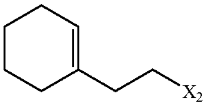 |
| 19(H12-54) | 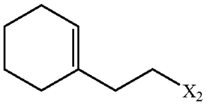 |
TABLE 12B-8
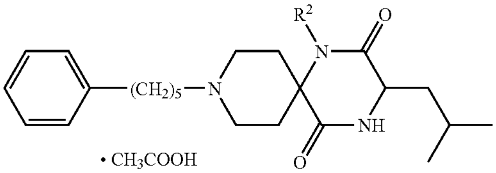
• $CH_3COOH$
| Example No | $R^2$ |
|---|---|
| 19(H12-64) | 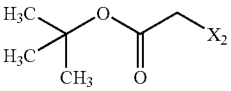 |
| 19(H12-65) | 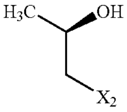 |
| 19(H12-66) | 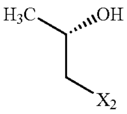 |

TABLE 12B-8-continued
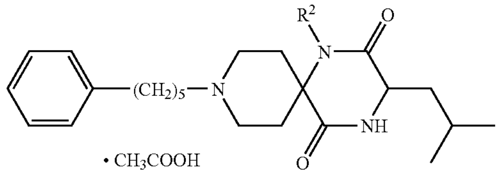
• $CH_3COOH$
| Example No | $R^2$ |
|---|---|
| 19(H12-67) | 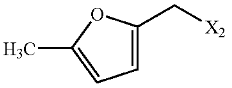 |
| 19(H12-68 | 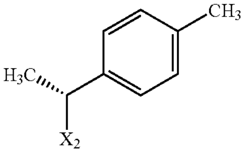 |
| 19(H12-69) | 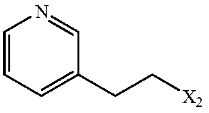 |
TABLE 13B-1
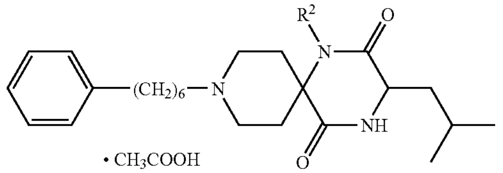
• $CH_3COOH$
| Example No | $R^2$ |
|---|---|
| 19(H13-1) | 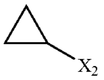 |
| 19(H13-2) | 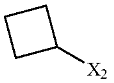 |
| 19(H13-3) | 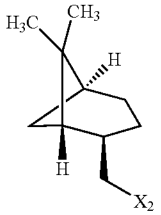 |
| 19(H13-4) | 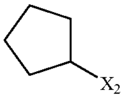 |
TABLE 13B-1-continued
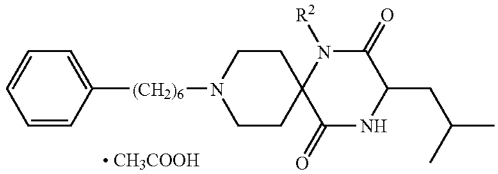
• $CH_3COOH$
| Example No | $R^2$ |
|---|---|
| 19(H13-5) | 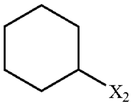 |
| 19(H13-6) | 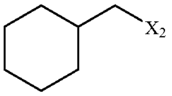 |
| 19(H13-7) | 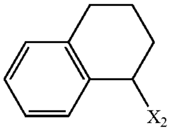 |
| 19(H13-8) | 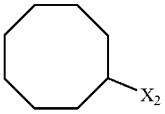 |
TABLE 13B-2
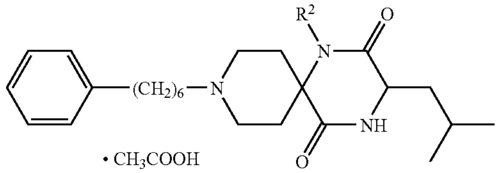
• $CH_3COOH$
| Example No | $R^2$ |
|---|---|
| 19(H13-9) | 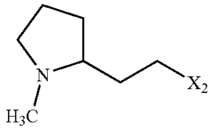 |
| 19(H13-10) | 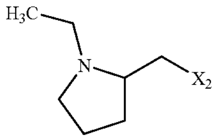 |
| 19(H13-11) | 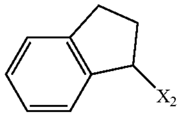 |

TABLE 13B-2-continued
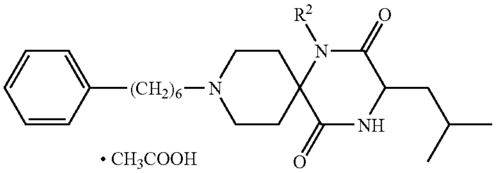
• $CH_3COOH$
| Example No | $R^2$ |
|---|---|
| 19(H13-12) | 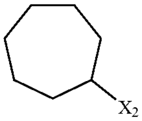 |
| 19(H13-13) | 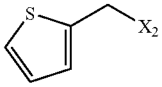 |
| 19(H13-14) | 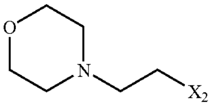 |
| 19(H13-15) | 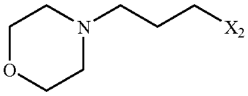 |
| 19(H13-16) | 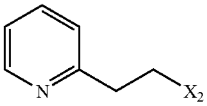 |
TABLE 13B-3
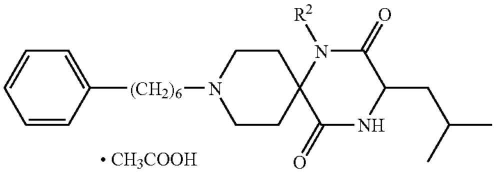
• $CH_3COOH$
| Example No | $R^2$ |
|---|---|
| 19(H13-17) | 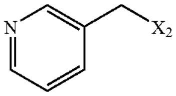 |
| 19(H13-18) | 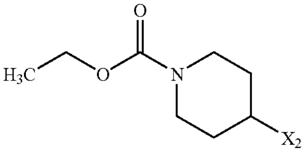 |
| 19(H13-19) | 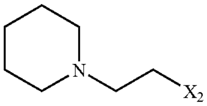 |
TABLE 13B-3-continued
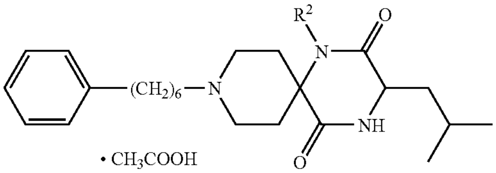
• $CH_3COOH$
| Example No | $R^2$ |
|---|---|
| 19(H13-20) | 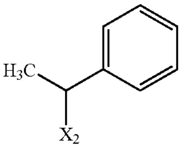 |
| 19(H13-21) | 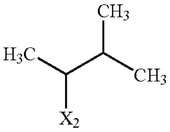 |
| 19(H13-22) | 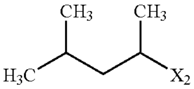 |
| 19(H13-23) | 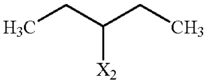 |
| 19(H13-24) | 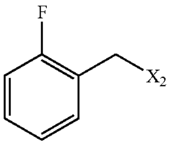 |
TABLE 13B-4
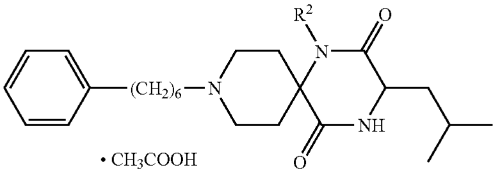
• $CH_3COOH$
| Example No | $R^2$ |
|---|---|
| 19(H13-25) | 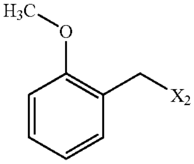 |
| 19(H13-26) | 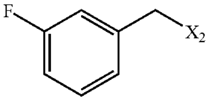 |

TABLE 13B-4-continued
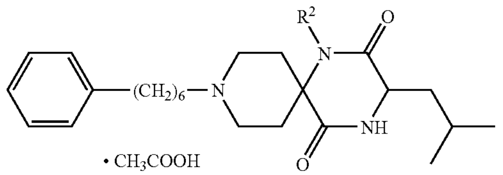
• $CH_3COOH$
| Example No | $R^2$ |
|---|---|
| 19(H13-27) | 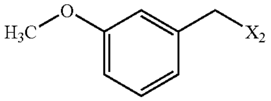 |
| 19(H13-28) | 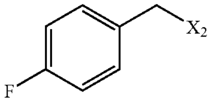 |
| 19(H13-29) | 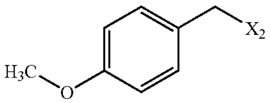 |
| 19(H13-31) | 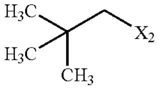 |
| 19(H13-32) | 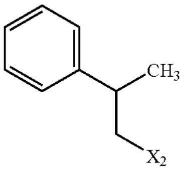 |
TABLE 13B-5
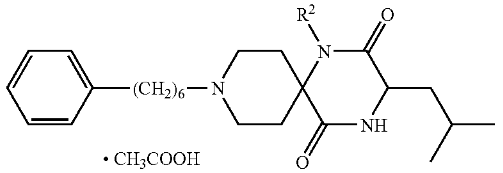
• $CH_3COOH$
| Example No | $R^2$ |
|---|---|
| 19(H13-33) | 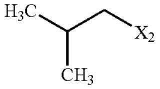 |
| 19(H13-34) | 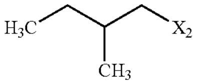 |
| 19(H13-35) | 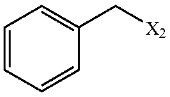 |
TABLE 13B-5-continued
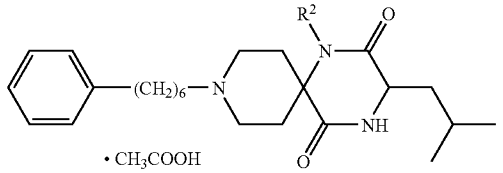
• $CH_3COOH$
| Example No | $R^2$ |
|---|---|
| 19(H13-36) | 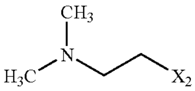 |
| 19(H13-37) | 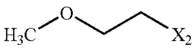 |
| 19(H13-38) | 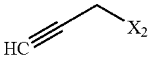 |
| 19(H13-39) | 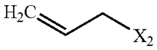 |
| 19(H13-40) | 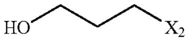 |
| 19(H13-41) | 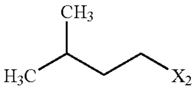 |
| 19(H13-42) | 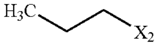 |
| 19(H13-43) | 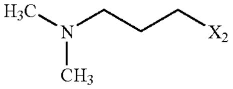 |
| 19(H13-44) | 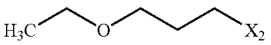 |
TABLE 13B-6
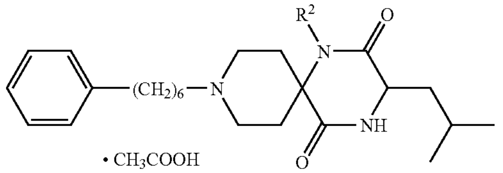
• $CH_3COOH$
| Example No | $R^2$ |
|---|---|
| 19(H13-45) | 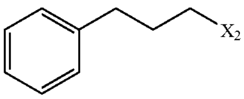 |
| 19(H13-46) | 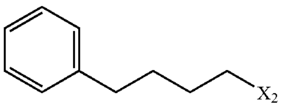 |
| 19(H13-47) | 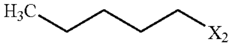 |

TABLE 13B-6-continued

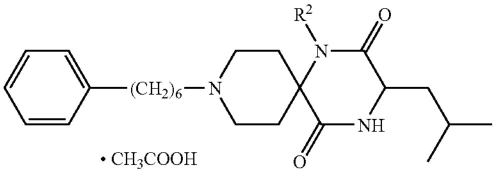

• $CH_3COOH$

| Example No | $R^2$ |
|---|---|
| 19(H13-48) | 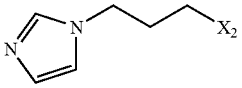 |
| 19(H13-49) | 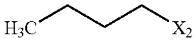 |
| 19(H13-50) | 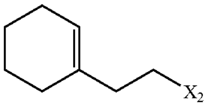 |
| 19(H13-51) | 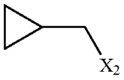 |
| 19(H13-52) | 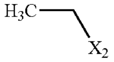 |
| 19(H13-53) | 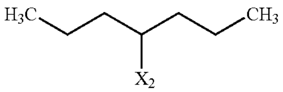 |
| 19(H13-54) | 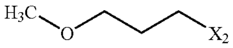 |

TABLE 13B-7

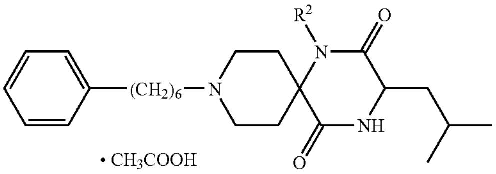

• $CH_3COOH$

| Example No | $R^2$ |
|---|---|
| 19(H13-55) | 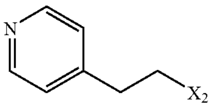 |
| 19(H13-56) | 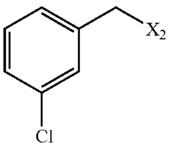 |
| 19(H13-57) | 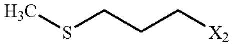 |

TABLE 13B-7-continued

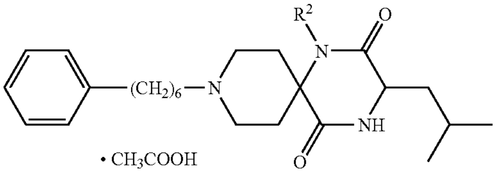

• $CH_3COOH$

| Example No | $R^2$ |
|---|---|
| 19(H13-58) | 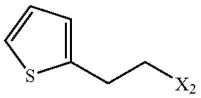 |
| 19(H13-59) | 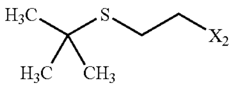 |
| 19(H13-60) | 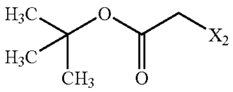 |
| 19(H13-61) | 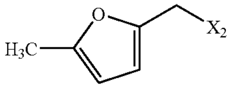 |
| 19(H13-62) | 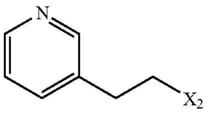 |

TABLE 1C-1

| Example No | HPLC condition | Retention time (min) | Mass data | Mass condition |
|---|---|---|---|---|
| 19(H1-1) | F | 3.16 | 410 $(M + H)^+$. | ESI (Pos., 20 V) |
| 19(H1-2) | F | 3.17 | 483 $(M + H)^+$. | ESI (Pos., 20 V) |
| 19(H1-3) | F | 4.24 | 502 $(M + H)^+$. | ESI (Pos., 20 V) |
| 19(H1-4) | F | 2.83 | 358 $(M + H)^+$. | ESI (Pos., 20 V) |
| 19(H1-5) | F | 3.09 | 415 $(M + H)^+$. | ESI (Pos., 20 V) |
| 19(H1-6) | F | 3.11 | 448 $(M + H)^+$. | ESI (Pos., 20 V) |
| 19(H1-7) | F | 3.11 | 487 $(M + H)^+$. | ESI (Pos., 20 V) |
| 19(H1-8) | F | 3.17 | 478 $(M + H)^+$. | ESI (Pos., 20 V) |
| 19(H1-9) | F | 3.23 | 506 $(M + H)^+$. | ESI (Pos., 20 V) |
| 19(H1-10) | F | 3.25 | 563 $(M + H)^+$. | ESI (Pos., 20 V) |
| 19(H1-11) | F | 3.35 | 473 $(M + H)^+$. | ESI (Pos., 20 V) |
| 19(H1-12) | F | 3.32 | 546 $(M + H)^+$. | ESI (Pos., 20 V) |
| 19(H1-13) | F | 3.37 | 537 $(M + H)^+$. | ESI (Pos., 20 V) |
| 19(H1-14) | F | 3.01 | 364 $(M + H)^+$. | ESI (Pos., 20 V) |
| 19(H1-15) | F | 3.25 | 420 $(M + H)^+$. | ESI (Pos., 20 V) |
| 19(H1-16) | F | 3.24 | 454 $(M + H)^+$. | ESI (Pos., 20 V) |
| 19(H1-17) | F | 3.23 | 493 $(M + H)^+$. | ESI (Pos., 20 V) |
| 19(H1-18) | F | 3.29 | 484 $(M + H)^+$. | ESI (Pos., 20 V) |
| 19(H1-19) | F | 3.36 | 512 $(M + H)^+$. | ESI (Pos., 20 V) |
| 19(H1-20) | F | 3.38 | 569 $(M + H)^+$. | ESI (Pos., 20 V) |
| 19(H1-21) | F | 3.26 | 454 $(M + H)^+$. | ESI (Pos., 20 V) |
| 19(H1-22) | F | 3.52 | 510 $(M + H)^+$. | ESI (Pos., 20 V) |
| 19(H1-23) | F | 3.51 | 544 $(M + H)^+$. | ESI (Pos., 20 V) |
| 19(H1-24) | F | 3.48 | 583 $(M + H)^+$. | ESI (Pos., 20 V) |
| 19(H1-25) | F | 3.53 | 574 $(M + H)^+$. | ESI (Pos., 20 V) |
| 19(H1-26) | F | 3.59 | 602 $(M + H)^+$. | ESI (Pos., 20 V) |

TABLE 1C-2

| Example No | HPLC condition | Retention time (min) | Mass data | Mass condition |
|---|---|---|---|---|
| 19(H1-27) | F | 3.56 | 659 $(M + H)^+$. | ESI (Pos., 20 V) |
| 19(H1-28) | F | 3.07 | 378 $(M + H)^+$. | ESI (Pos., 20 V) |
| 19(H1-29) | F | 3.31 | 434 $(M + H)^+$. | ESI (Pos., 20 V) |
| 19(H1-30) | F | 3.30 | 468 $(M + H)^+$. | ESI (Pos., 20 V) |
| 19(H1-31) | F | 3.29 | 507 $(M + H)^+$. | ESI (Pos., 20 V) |
| 19(H1-32) | F | 3.35 | 498 $(M + H)^+$. | ESI (Pos., 20 V) |
| 19(H1-33) | F | 3.40 | 526 $(M + H)^+$. | ESI (Pos., 20 V) |
| 19(H1-34) | F | 3.41 | 583 $(M + H)^+$. | ESI (Pos., 20 V) |
| 19(H1-35) | F | 2.84 | 316 $(M + H)^+$. | ESI (Pos., 20 V) |
| 19(H1-36) | F | 3.11 | 372 $(M + H)^+$. | ESI (Pos., 20 V) |
| 19(H1-37) | F | 3.11 | 406 $(M + H)^+$. | ESI (Pos., 20 V) |
| 19(H1-38) | F | 3.09 | 445 $(M + H)^+$. | ESI (Pos., 20 V) |
| 19(H1-39) | F | 3.18 | 436 $(M + H)^+$. | ESI (Pos., 20 V) |
| 19(H1-40) | F | 3.22 | 464 $(M + H)^+$. | ESI (Pos., 20 V) |
| 19(H1-41) | F | 3.26 | 521 $(M + H)^+$. | ESI (Pos., 20 V) |
| 19(H1-42) | F | 3.04 | 402 $(M + H)^+$. | ESI (Pos., 20 V) |
| 19(H1-43) | F | 3.34 | 458 $(M + H)^+$. | ESI (Pos., 20 V) |
| 19(H1-44) | F | 3.36 | 492 $(M + H)^+$. | ESI (Pos., 20 V) |
| 19(H1-45) | F | 3.30 | 531 $(M + H)^+$. | ESI (Pos., 20 V) |
| 19(H1-46) | F | 3.35 | 522 $(M + H)^+$. | ESI (Pos., 20 V) |
| 19(H1-47) | F | 3.39 | 550 $(M + H)^+$. | ESI (Pos., 20 V) |
| 19(H1-48) | F | 3.40 | 607 $(M + H)^+$. | ESI (Pos., 20 V) |
| 19(H1-49) | F | 2.85 | 433 $(M + H)^+$. | ESI (Pos., 20 V) |
| 19(H1-50) | F | 3.03 | 489 $(M + H)^+$. | ESI (Pos., 20 V) |
| 19(H1-51) | F | 3.05 | 523 $(M + H)^+$. | ESI (Pos., 20 V) |
| 19(H1-52) | F | 3.06 | 562 $(M + H)^+$. | ESI (Pos., 20 V) |

TABLE 1C-3

| Example No | HPLC condition | Retention time (min) | Mass data | Mass condition |
|---|---|---|---|---|
| 19(H1-53) | F | 3.11 | 553 $(M + H)^+$. | ESI (Pos., 20 V) |
| 19(H1-54) | F | 3.14 | 581 $(M + H)^+$. | ESI (Pos., 20 V) |
| 19(H1-55) | F | 3.16 | 638 $(M + H)^+$. | ESI (Pos., 20 V) |

TABLE 2C-1

| Example No | HPLC condition | Retention time (min) | Mass data | Mass condition |
|---|---|---|---|---|
| 19(H2-1) | B | 10.20 | 368 $(M + H)^+$. | APCI (Pos., 40 V) |
| 19(H2-2) | F | 3.23 | 497 $(M + H)^+$. | ESI (Pos., 20 V) |
| 19(H2-3) | F | 3.73 | 488 $(M + H)^+$. | ESI (Pos., 20 V) |
| 19(H2-4) | F | 3.72 | 516 $(M + H)^+$. | ESI (Pos., 20 V) |
| 19(H2-5) | C | 14.80 | 573 $(M + H)^+$, 465. | APCI (Pos., 40 V) |
| 19(H2-6) | F | 2.91 | 372 $(M + H)^+$. | ESI (Pos., 20 V) |
| 19(H2-7) | F | 3.15 | 428 $(M + H)^+$. | ESI (Pos., 20 V) |
| 19(H2-8) | F | 3.17 | 462 $(M + H)^+$. | ESI (Pos., 20 V) |
| 19(H2-9) | F | 3.17 | 501 $(M + H)^+$. | ESI (Pos., 20 V) |
| 19(H2-10) | F | 3.24 | 492 $(M + H)^+$. | ESI (Pos., 20 V) |
| 19(H2-11) | F | 3.26 | 520 $(M + H)^+$. | ESI (Pos., 20 V) |
| 19(H2-12) | F | 3.30 | 577 $(M + H)^+$. | ESI (Pos., 20 V) |
| 19(H2-13) | F | 3.16 | 431 $(M + H)^+$. | ESI (Pos., 20 V) |
| 19(H2-14) | F | 3.37 | 487 $(M + H)^+$. | ESI (Pos., 20 V) |
| 19(H2-15) | B | 17.50 | 521 $(M + H)^+$, 144. | APCI (Pos., 40 V) |
| 19(H2-16) | F | 3.34 | 560 $(M + H)^+$. | ESI (Pos., 20 V) |
| 19(H2-17) | F | 3.41 | 551 $(M + H)^+$. | ESI (Pos., 20 V) |
| 19(H2-18) | F | 3.44 | 579 $(M + H)^+$. | ESI (Pos., 20 V) |
| 19(H2-19) | C | 15.70 | 636 $(M + H)^+$, 528, 279. | APCI (Pos., 40 V) |
| 19(H2-20) | F | 3.07 | 378 $(M + H)^+$. | ESI (Pos., 20 V) |

TABLE 2C-1-continued

| Example No | HPLC condition | Retention time (min) | Mass data | Mass condition |
|---|---|---|---|---|
| 19(H2-21) | F | 3.30 | 434 $(M + H)^+$. | ESI (Pos., 20 V) |
| 19(H2-22) | F | 3.31 | 468 $(M + H)^+$. | ESI (Pos., 20 V) |
| 19(H2-23) | F | 3.30 | 507 $(M + H)^+$. | ESI (Pos., 20 V) |
| 19(H2-24) | F | 3.36 | 498 $(M + H)^+$. | ESI (Pos., 20 V) |
| 19(H2-25) | F | 3.41 | 526 $(M + H)^+$. | ESI (Pos., 20 V) |
| 19(H2-26) | F | 3.42 | 583 $(M + H)^+$. | ESI (Pos.. 20 V) |

TABLE 2C-2

| Example No | HPLC condition | Retention time (min) | Mass data | Mass condition |
|---|---|---|---|---|
| 19(H2-27) | F | 3.33 | 468 $(M + H)^+$. | ESI (Pos., 20 V) |
| 19(H2-28) | F | 3.57 | 524 $(M + H)^+$. | ESI (Pos., 20 V) |
| 19(H2-29) | F | 3.55 | 558 $(M + H)^+$. | ESI (Pos., 20 V) |
| 19(H2-30) | F | 3.54 | 597 $(M + H)^+$. | ESI (Pos., 20 V) |
| 19(H2-31) | F | 3.60 | 588 $(M + H)^+$. | ESI (Pos., 20 V) |
| 19(H2-32) | F | 3.65 | 616 $(M + H)^+$. | ESI (Pos., 20 V) |
| 19(H2-33) | F | 3.60 | 673 $(M + H)^+$. | ESI (Pos., 20 V) |
| 19(H2-34) | F | 3.13 | 392 $(M + H)^+$. | ESI (Pos., 20 V) |
| 19(H2-35) | F | 3.37 | 448 $(M + H)^+$. | ESI (Pos., 20 V) |
| 19(H2-36) | F | 3.37 | 482 $(M + H)^+$. | ESI (Pos., 20 V) |
| 19(H2-37) | F | 3.35 | 521 $(M + H)^+$. | ESI (Pos., 20 V) |
| 19(H2-38) | F | 3.42 | 512 $(M + H)^+$. | ESI (Pos., 20 V) |
| 19(H2-39) | F | 3.46 | 540 $(M + H)^+$. | ESI (Pos., 20 V) |
| 19(H2-40) | F | 3.50 | 597 $(M + H)^+$. | ESI (Pos., 20 V) |
| 19(H2-41) | F | 2.92 | 330 $(M + H)^+$. | ESI (Pos., 20 V) |
| 19(H2-42) | F | 3.20 | 386 $(M + H)^+$. | ESI (Pos., 20 V) |
| 19(H2-43) | F | 3.17 | 420 $(M + H)^+$. | ESI (Pos., 20 V) |
| 19(H2-44) | F | 3.17 | 459 $(M + H)^+$. | ESI (Pos., 20 V) |
| 19(H2-45) | F | 3.26 | 450 $(M + H)^+$. | ESI (Pos., 20 V) |
| 19(H2-46) | F | 3.30 | 478 $(M + H)^+$. | ESI (Pos., 20 V) |
| 19(H2-47) | F | 3.32 | 535 $(M + H)^+$. | ESI (Pos., 20 V) |
| 19(H2-48) | F | 3.11 | 416 $(M + H)^+$. | ESI (Pos., 20 V) |
| 19(H2-49) | F | 3.36 | 472 $(M + H)^+$. | ESI (Pos., 20 V) |
| 19(H2-50) | F | 3.34 | 506 $(M + H)^+$. | ESI (Pos., 20 V) |
| 19(H2-51) | F | 3.33 | 545 $(M + H)^+$. | ESI (Pos., 20 V) |
| 19(H2-52) | F | 3.41 | 536 $(M + H)^+$. | ESI (Pos., 20 V) |

TABLE 2C-3

| Example No | HPLC condition | Retention time (min) | Mass data | Mass condition |
|---|---|---|---|---|
| 19(H2-53) | F | 3.50 | 564 $(M + H)^+$. | ESI (Pos., 20 V) |
| 19(H2-54) | F | 3.50 | 621 $(M + H)^+$. | ESI (Pos., 20 V) |
| 19(H2-55) | F | 2.92 | 447 $(M + H)^+$. | ESI (Pos., 20 V) |
| 19(H2-56) | F | 3.09 | 503 $(M + H)^+$. | ESI (Pos., 20 V) |
| 19(H2-57) | F | 3.09 | 537 $(M + H)^+$. | ESI (Pos., 20 V) |
| 19(H2-58) | F | 3.11 | 576 $(M + H)^+$. | ESI (Pos., 20 V) |
| 19(H2-59) | F | 3.18 | 567 $(M + H)^+$. | ESI (Pos., 20 V) |
| 19(H2-60) | F | 3.20 | 595 $(M + H)^+$. | ESI (Pos., 20 V) |
| 19(H2-61) | F | 3.24 | 652 $(M + H)^+$. | ESI (Pos., 20 V) |

TABLE 3C-1

| Example No | HPLC condition | Retention time (min) | Mass data | Mass condition |
|---|---|---|---|---|
| 19(H3-1) | B | 10.80 | 382 (M + H)+. | APCI (Pos., 40 V) |
| 19(H3-2) | F | 3.27 | 438 (M + H)+. | ESI (Pos., 20 V) |
| 19(H3-3) | F | 3.28 | 472 (M + H)+. | ESI (Pos., 20 V) |
| 19(H3-4) | F | 3.27 | 511 (M + H)+. | ESI (Pos., 20 V) |
| 19(H3-5) | F | 3.35 | 502 (M + H)+. | ESI (Pos., 20 V) |
| 19(H3-6) | F | 3.37 | 530 (M + H)+. | ESI (Pos., 20 V) |
| 19(H3-7) | F | 2.98 | 386 (M + H)+. | ESI (Pos., 20 V) |
| 19(H3-8) | F | 3.22 | 442 (M + H)+. | ESI (Pos., 20 V) |
| 19(H3-9) | F | 3.23 | 476 (M + H)+. | ESI (Pos., 20 V) |
| 19(H3-10) | F | 3.23 | 476 (M + H)+. | ESI (Pos., 20 V) |
| 19(H3-11) | F | 3.22 | 515 (M + H)+. | ESI (Pos., 20 V) |
| 19(H3-12) | F | 3.29 | 506 (M + H)+. | ESI (Pos., 20 V) |
| 19(H3-13) | F | 3.31 | 534 (M + H)+. | ESI (Pos., 20 V) |
| 19(H3-14) | F | 3.34 | 591 (M + H)+. | ESI (Pos., 20 V) |
| 19(H3-15) | F | 3.20 | 445 (M + H)+. | ESI (Pos., 20 V) |
| 19(H3-16) | F | 3.43 | 501 (M + H)+. | ESI (Pos., 20 V) |
| 19(H3-17) | F | 3.40 | 535 (M + H)+. | ESI (Pos., 20 V) |
| 19(H3-18) | F | 3.39 | 571 (M + H)+. | ESI (Pos., 20 V) |
| 19(H3-19) | F | 3.45 | 565 (M + H)+. | ESI (Pos., 20 V) |
| 19(H3-20) | F | 3.49 | 593 (M + H)+. | ESI (Pos., 20 V) |
| 19(H3-21) | F | 3.49 | 650 (M + H)+. | ESI (Pos., 20 V) |
| 19(H3-22) | F | 3.13 | 392 (M + H)+. | ESI (Pos., 20 V) |
| 19(H3-23) | F | 3.35 | 448 (M + H)+. | ESI (Pos., 20 V) |
| 19(H3-24) | F | 3.34 | 482 (M + H)+. | ESI (Pos., 20 V) |
| 19(H3-25) | F | 3.34 | 521 (M + H)+. | ESI (Pos., 20 V) |
| 19(H3-26) | F | 3.42 | 512 (M + H)+. | ESI (Pos., 20 V) |

TABLE 3C-2

| Example No | HPLC condition | Retention time (min) | Mass data | Mass condition |
|---|---|---|---|---|
| 19(H3-27) | F | 3.45 | 540 (M + H)+. | ESI (Pos., 20 V) |
| 19(H3-28) | F | 3.46 | 597 (M + H)+. | ESI (Pos., 20 V) |
| 19(H3-29) | F | 3.37 | 482 (M + H)+. | ESI (Pos., 20 V) |
| 19(H3-30) | F | 3.61 | 538 (M + H)+. | ESI (Pos., 20 V) |
| 19(H3-31) | F | 3.61 | 572 (M + H)+. | ESI (Pos., 20 V) |
| 19(H3-32) | F | 3.57 | 611 (M + H)+. | ESI (Pos., 20 V) |
| 19(H3-33) | F | 3.64 | 602 (M + H)+. | ESI (Pos., 20 V) |
| 19(H3-34) | F | 3.68 | 630 (M + H)+. | ESI (Pos., 20 V) |
| 19(H3-35) | F | 3.66 | 687 (M + H)+. | ESI (Pos., 20 V) |
| 19(H3-36) | F | 3.20 | 406 (M + H)+. | ESI (Pos., 20 V) |
| 19(H3-37) | F | 3.43 | 462 (M + H)+. | ESI (Pos., 20 V) |
| 19(H3-38) | F | 3.42 | 496 (M + H)+. | ESI (Pos., 20 V) |
| 19(H3-39) | F | 3.40 | 535 (M + H)+. | ESI (Pos., 20 V) |
| 19(H3-40) | F | 3.48 | 526 (M + H)+. | ESI (Pos., 20 V) |
| 19(H3-41) | F | 3.50 | 554 (M + H)+. | ESI (Pos., 20 V) |
| 19(H3-42) | F | 3.51 | 611 (M + H)+. | ESI (Pos., 20 V) |
| 19(H3-43) | F | 3.01 | 344 (M + H)+. | ESI (Pos., 20 V) |
| 19(H3-44) | F | 3.23 | 400 (M + H)+. | ESI (Pos., 20 V) |
| 19(H3-45) | F | 3.24 | 434 (M + H)+. | ESI (Pos., 20 V) |
| 19(H3-46) | F | 3.25 | 473 (M + H)+. | ESI (Pos., 20 V) |
| 19(H3-47) | F | 3.30 | 464 (M + H)+. | ESI (Pos., 20 V) |
| 19(H3-48) | F | 3.33 | 492 (M + H)+. | ESI (Pos., 20 V) |
| 19(H3-49) | F | 3.37 | 549 (M + H)+. | ESI (Pos., 20 V) |
| 19(H3-50) | F | 3.18 | 430 (M + H)+. | ESI (Pos., 20 V) |
| 19(H3-51) | F | 3.40 | 486 (M + H)+. | ESI (Pos., 20 V) |
| 19(H3-52) | F | 3.40 | 520 (M + H)+. | ESI (Pos., 20 V) |

TABLE 3C-3

| Example No | HPLC condition | Retention time (min) | Mass data | Mass condition |
|---|---|---|---|---|
| 19(H3-53) | F | 3.40 | 559 (M + H)+. | ESI (Pos., 20 V) |
| 19(H3-54) | F | 3.45 | 550 (M + H)+. | ESI (Pos., 20 V) |
| 19(H3-55) | F | 3.49 | 578 (M + H)+. | ESI (Pos., 20 V) |
| 19(H3-56) | F | 3.51 | 635 (M + H)+. | ESI (Pos., 20 V) |
| 19(H3-57) | F | 2.98 | 461 (M + H)+. | ESI (Pos., 20 V) |
| 19(H3-58) | F | 3.14 | 517 (M + H)+. | ESI (Pos., 20 V) |
| 19(H3-59) | F | 3.14 | 551 (M + H)+. | ESI (Pos., 20 V) |
| 19(H3-60) | F | 3.15 | 590 (M + H)+. | ESI (Pos., 20 V) |
| 19(H3-61) | F | 3.21 | 581 (M + H)+. | ESI (Pos., 20 V) |
| 19(H3-62) | F | 3.24 | 609 (M + H)+. | ESI (Pos., 20 V) |
| 19(H3-63) | F | 3.27 | 666 (M + H)+. | ESI (Pos., 20 V) |

TABLE 4C-1

| Example No | HPLC condition | Retention time (min) | Mass data | Mass condition |
|---|---|---|---|---|
| 19(H4-1) | F | 3.14 | 396 (M + H)+. | ESI (Pos., 20 V) |
| 19(H4-2) | F | 3.36 | 453 (M + H)+. | ESI (Pos., 20 V) |
| 19(H4-3) | F | 3.35 | 486 (M + H)+. | ESI (Pos., 20 V) |
| 19(H4-4) | F | 3.36 | 525 (M + H)+. | ESI (Pos., 20 V) |
| 19(H4-5) | F | 3.41 | 516 (M + H)+. | ESI (Pos., 20 V) |
| 19(H4-6) | F | 3.45 | 544 (M + H)+. | ESI (Pos., 20 V) |
| 19(H4-7) | F | 3.45 | 601 (M + H)+. | ESI (Pos., 20 V) |
| 19(H4-8) | F | 3.05 | 400 (M + H)+. | ESI (Pos., 20 V) |
| 19(H4-9) | F | 3.29 | 456 (M + H)+. | ESI (Pos., 20 V) |
| 19(H4-10) | F | 3.29 | 490 (M + H)+. | ESI (Pos., 20 V) |
| 19(H4-11) | F | 3.29 | 529 (M + H)+. | ESI (Pos., 20 V) |
| 19(H4-12) | F | 3.36 | 520 (M + H)+. | ESI (Pos., 20 V) |
| 19(H4-13) | F | 3.38 | 548 (M + H)+. | ESI (Pos., 20 V) |
| 19(H4-14) | F | 3.42 | 605 (M + H)+. | ESI (Pos., 20 V) |
| 19(H4-15) | F | 3.26 | 459 (M + H)+. | ESI (Pos., 20 V) |
| 19(H4-16) | F | 3.47 | 515 (M + H)+. | ESI (Pos., 20 V) |
| 19(H4-17) | F | 3.47 | 549 (M + H)+. | ESI (Pos., 20 V) |
| 19(H4-18) | F | 3.44 | 588 (M + H)+. | ESI (Pos., 20 V) |
| 19(H4-19) | F | 3.51 | 579 (M + H)+. | ESI (Pos., 20 V) |
| 19(H4-20) | F | 3.54 | 607 (M + H)+. | ESI (Pos., 20 V) |
| 19(H4-21) | F | 3.55 | 664 (M + H)+. | ESI (Pos., 20 V) |
| 19(H4-22) | F | 3.20 | 406 (M + H)+. | ESI (Pos., 20 V) |
| 19(H4-23) | F | 3.44 | 462 (M + H)+. | ESI (Pos., 20 V) |
| 19(H4-24) | F | 3.42 | 496 (M + H)+. | ESI (Pos., 20 V) |
| 19(H4-25) | F | 3.42 | 535 (M + H)+. | ESI (Pos., 20 V) |
| 19(H4-26) | F | 3.47 | 526 (M + H)+. | ESI (Pos., 20 V) |

TABLE 4C-2

| Example No | HPLC condition | Retention time (min) | Mass data | Mass condition |
|---|---|---|---|---|
| 19(H4-27) | F | 3.51 | 554 (M + H)+. | ESI (Pos., 20 V) |
| 19(H4-28) | F | 3.52 | 611 (M + H)+. | ESI (Pos., 20 V) |
| 19(H4-29) | F | 3.42 | 496 (M + H)+. | ESI (Pos., 20 V) |
| 19(H4-30) | F | 3.66 | 552 (M + H)+. | ESI (Pos., 20 V) |
| 19(H4-31) | F | 3.66 | 586 (M + H)+. | ESI (Pos., 20 V) |
| 19(H4-32) | F | 3.62 | 625 (M + H)+. | ESI (Pos., 20 V) |
| 19(H4-33) | F | 3.68 | 616 (M + H)+. | ESI (Pos., 20 V) |
| 19(H4-34) | F | 3.72 | 644 (M + H)+. | ESI (Pos., 20 V) |
| 19(H4-35) | F | 3.69 | 701 (M + H)+. | ESI (Pos., 20 V) |
| 19(H4-36) | F | 3.26 | 420 (M + H)+. | ESI (Pos., 20 V) |
| 19(H4-37) | F | 3.48 | 476 (M + H)+. | ESI (Pos., 20 V) |
| 19(H4-38) | F | 3.46 | 510 (M + H)+. | ESI (Pos., 20 V) |
| 19(H4-39) | F | 3.46 | 549 (M + H)+. | ESI (Pos., 20 V) |
| 19(H4-40) | F | 3.55 | 540 (M + H)+. | ESI (Pos., 20 V) |
| 19(H4-41) | F | 3.56 | 568 (M + H)+. | ESI (Pos., 20 V) |

TABLE 4C-2-continued

| Example No | HPLC condition | Retention time (min) | Mass data | Mass condition |
|---|---|---|---|---|
| 19(H4-42) | F | 3.57 | 625 (M + H)+. | ESI (Pos., 20 V) |
| 19(H4-43) | F | 3.09 | 358 (M + H)+. | ESI (Pos., 20 V) |
| 19(H4-44) | F | 3.31 | 414 (M + H)+. | ESI (Pos., 20 V) |
| 19(H4-45) | F | 3.31 | 448 (M + H)+. | ESI (Pos., 20 V) |
| 19(H4-46) | F | 3.31 | 487 (M + H)+. | ESI (Pos., 20 V) |
| 19(H4-47) | F | 3.38 | 478 (M + H)+. | ESI (Pos., 20 V) |
| 19(H4-48) | F | 3.40 | 506 (M + H)+. | ESI (Pos., 20 V) |
| 19(H4-49) | F | 3.43 | 563 (M + H)+. | ESI (Pos., 20 V) |
| 19(H4-50) | F | 3.25 | 444 (M + H)+. | ESI (Pos., 20 V) |
| 19(H4-51) | F | 3.50 | 500 (M + H)+. | ESI (Pos., 20 V) |
| 19(H4-52) | F | 3.47 | 534 (M + H)+. | ESI (Pos., 20 V) |

TABLE 4C-3

| Example No | HPLC condition | Retention time (min) | Mass data | Mass condition |
|---|---|---|---|---|
| 19(H4-53) | F | 3.46 | 573 (M + H)+. | ESI (Pos., 20 V) |
| 19(H4-54) | F | 3.53 | 564 (M + H)+. | ESI (Pos., 20 V) |
| 19(H4-55) | F | 3.55 | 592 (M + H)+. | ESI (Pos., 20 V) |
| 19(H4-56) | F | 3.56 | 649 (M + H)+. | ESI (Pos., 20 V) |
| 19(H4-57) | F | 3.05 | 475 (M + H)+. | ESI (Pos., 20 V) |
| 19(H4-58) | F | 3.19 | 531 (M + H)+. | ESI (Pos., 20 V) |
| 19(H4-59) | F | 3.20 | 565 (M + H)+. | ESI (Pos., 20 V) |
| 19(H4-60) | F | 3.22 | 604 (M + H)+. | ESI (Pos., 20 V) |
| 19(H4-61) | F | 3.27 | 595 (M + H)+. | ESI (Pos., 20 V) |
| 19(H4-62) | F | 3.30 | 623 (M + H)+. | ESI (Pos., 20 V) |
| 19(H4-63) | F | 3.33 | 680 (M + H)+. | ESI (Pos., 20 V) |

TABLE 5C-1

| Example No | HPLC condition | Retention time (min) | Mass data | Mass condition |
|---|---|---|---|---|
| 19(H5-1) | F | 2.89 | 340 (M + H)+. | ESI (Pos., 20 V) |
| 19(H5-2) | F | 3.17 | 396 (M + H)+. | ESI (Pos., 20 V) |
| 19(H5-3) | F | 3.16 | 430 (M + H)+. | ESI (Pos., 20 V) |
| 19(H5-4) | F | 3.14 | 469 (M + H)+. | ESI (Pos., 20 V) |
| 19(H5-5) | F | 3.23 | 460 (M + H)+. | ESI (Pos., 20 V) |
| 19(H5-6) | F | 3.29 | 488 (M + H)+. | ESI (Pos., 20 V) |
| 19(H5-7) | F | 3.31 | 545 (M + H)+. | ESI (Pos., 20 V) |
| 19(H5-8) | F | 2.79 | 344 (M + H)+. | ESI (Pos., 20 V) |
| 19(H5-9) | F | 3.07 | 400 (M + H)+. | ESI (Pos., 20 V) |
| 19(H5-10) | F | 3.09 | 434 (M + H)+. | ESI (Pos., 20 V) |
| 19(H5-11) | F | 3.07 | 473 (M + H)+. | ESI (Pos., 20 V) |
| 19(H5-12) | F | 3.16 | 464 (M + H)+. | ESI (Pos., 20 V) |
| 19(H5-13) | F | 3.20 | 492 (M + H)+. | ESI (Pos., 20 V) |
| 19(H5-14) | F | 3.22 | 549 (M + H)+. | ESI (Pos., 20 V) |
| 19(H5-15) | F | 3.08 | 403 (M + H)+. | ESI (Pos., 20 V) |
| 19(H5-16) | F | 3.34 | 459 (M + H)+. | ESI (Pos., 20 V) |
| 19(H5-17) | F | 3.31 | 493 (M + H)+. | ESI (Pos., 20 V) |
| 19(H5-18) | F | 3.29 | 532 (M + H)+. | ESI (Pos., 20 V) |
| 19(H5-19) | F | 3.36 | 523 (M + H)+. | ESI (Pos., 20 V) |
| 19(H5-20) | F | 3.42 | 551 (M + H)+. | ESI (Pos., 20 V) |
| 19(H5-21) | F | 3.42 | 608 (M + H)+. | ESI (Pos., 20 V) |
| 19(H5-22) | F | 3.00 | 350 (M + H)+. | ESI (Pos., 20 V) |
| 19(H5-23) | F | 3.27 | 406 (M + H)+. | ESI (Pos., 20 V) |
| 19(H5-24) | F | 3.25 | 440 (M + H)+. | ESI (Pos., 20 V) |
| 19(H5-25) | F | 3.23 | 479 (M + H)+. | ESI (Pos., 20 V) |
| 19(H5-26) | F | 3.31 | 470 (M + H)+. | ESI (Pos., 20 V) |

TABLE 5C-2

| Example No | HPLC condition | Retention time (min) | Mass data | Mass condition |
|---|---|---|---|---|
| 19(H5-27) | F | 3.38 | 498 (M + H)+· | ESI (Pos., 20 V) |
| 19(H5-28) | F | 3.38 | 555 (M + H)+· | ESI (Pos., 20 V) |
| 19(H5-29) | F | 3.31 | 440 (M + H)+· | ESI (Pos., 20 V) |
| 19(H5-30) | F | 3.61 | 496 (M + H)+· | ESI (Pos., 20 V) |
| 19(H5-31) | F | 3.57 | 530 (M + H)+· | ESI (Pos., 20 V) |
| 19(H5-32) | F | 3.51 | 569 (M + H)+· | ESI (Pos., 20 V) |
| 19(H5-33) | F | 3.61 | 560 (M + H)+· | ESI (Pos., 20 V) |
| 19(HS-34) | F | 3.66 | 588 (M + H)+· | ESI (Pos., 20 V) |
| 19(H5-35) | F | 3.62 | 645 (M + H)+· | ESI (Pos., 20 V) |
| 19(H5-36) | F | 3.07 | 364 (M + H)+· | ESI (Pos., 20 V) |
| 19(H5-37) | F | 3.36 | 420 (M + H)+· | ESI (Pos., 20 V) |
| 19(H5-38) | F | 3.33 | 454 (M + H)+· | ESI (Pos., 20 V) |
| 19(H5-39) | F | 3.29 | 493 (M + H)+· | ESI (Pos., 20 V) |
| 19(H5-40) | F | 3.38 | 484 (M + H)+· | ESI (Pos., 20 V) |
| 19(H5-41) | F | 3.44 | 512 (M + H)+· | ESI (Pos., 20 V) |
| 19(H5-42) | F | 3.44 | 569 (M + H)+· | ESI (Pos., 20 V) |
| 19(H5-43) | F | 2.81 | 302 (M + H)+· | ESI (Pos., 20 V) |
| 19(H5-44) | F | 3.11 | 358 (M + H)+· | ESI (Pos., 20 V) |
| 19(H5-45) | F | 3.09 | 392 (M + H)+· | ESI (Pos., 20 V) |
| 19(H5-46) | F | 3.09 | 431 (M + H)+· | ESI (Pos., 20 V) |
| 19(H5-47) | F | 3.18 | 422 (M + H)+· | ESI (Pos., 20 V) |
| 19(H5-48) | F | 3.22 | 450 (M + H)+· | ESI (Pos., 20 V) |
| 19(H5-49) | F | 3.25 | 507 (M + H)+· | ESI (Pos., 20 V) |
| 19(H5-50) | F | 3.03 | 388 (M + H)+· | ESI (Pos., 20 V) |
| 19(H5-51) | F | 3.33 | 444 (M + H)+· | ESI (Pos., 20 V) |
| 19(H5-52) | F | 3.29 | 478 (M + H)+· | ESI (Pos., 20 V) |

TABLE 5C-3

| Example No | HPLC condition | Retention time (min) | Mass data | Mass condition |
|---|---|---|---|---|
| 19(H5-53) | F | 3.27 | 517 (M + H)+. | ESI (Pos., 20 V) |
| 19(H5-54) | F | 3.36 | 508 (M + H)+. | ESI (Pos., 20 V) |
| 19(H5-55) | F | 3.42 | 536 (M + H)+. | ESI (Pos., 20 V) |
| 19(H5-56) | F | 3.42 | 593 (M + H)+. | ESI (Pos., 20 V) |
| 19(H5-57) | F | 3.05 | 475 (M + H)+. | ESI (Pos., 20 V) |
| 19(H5-58) | A | 3.07 | 509 (M + H)+. | APCI (Pos., 40 V) |
| 19(H5-59) | F | 3.11 | 548 (M + H)+. | ESI (Pos., 20 V) |
| 19(H5-60) | F | 3.11 | 539 (M + H)+. | ESI (Pos., 20 V) |
| 19(H5-61) | F | 3.18 | 566 (M + H)+. | ESI (Pos., 20 V) |
| 19(H5-62) | F | 3.46 | 624 (M + H)+. | ESI (Pos., 20 V) |

TABLE 6C-1

| Example No | HPLC condition | Retention time (min) | Mass data | Mass condition |
|---|---|---|---|---|
| 19(H6-1) | C | 14.10 | 410 (M + H)+. | APCI (Pos., 40 V) |
| 19(H6-2) | D | 15.20 | 530 (M + H)+, 279. | APCI (Pos., 40 V) |
| 19(H6-3) | D | 12.60 | 414 (M + H)+, 264. | ARCI (Pos., 40 V) |
| 19(H6-4) | C | 15.40 | 470 (M + H)+, 215. | APCI (Pos., 40 V) |
| 19(H6-5) | D | 15.00 | 504 (M + H)+, 354. | APCI (Pos., 40 V) |
| 19(H6-6) | D | 14.60 | 543 (M + H)+, 279. | APCI (Pos., 40 V) |
| 19(H6-7) | D | 15.30 | 534 (M + H)+, 426, 279. | APCI (Pos., 40 V) |
| 19(H6-8) | D | 15.30 | 562 (M + H)+, 244. | APCI (Pos., 40 V) |
| 19(H6-9) | D | 15.50 | 619 (M + H)+, 511, 281. | APCI (Pos., 40 V) |
| 19(H6-10) | F | 3.38 | 473 (M + H)+. | ESI (Pos., 20 V) |
| 19(H6-11) | F | 3.59 | 529 (M + H)+. | ESI (Pos., 20 V) |
| 19(H6-12) | C | 16.50 | 563 (M + H)+, 144. | APCI (Pos., 40 V) |
| 19(H6-13) | F | 3.55 | 602 (M + H)+. | ESI (Pos., 20 V) |

TABLE 6C-1-continued

| Example No | HPLC condition | Retention time (min) | Mass data | Mass condition |
|---|---|---|---|---|
| 19(H6-14) | D | 15.80 | 593 (M + H)+. | APCI (Pos., 40 V) |
| 19(H6-15) | F | 3.64 | 621 (M + H)+. | ESI (Pos., 20 V) |
| 19(H6-16) | F | 3.65 | 678 (M + H)+. | ESI (Pos., 20 V) |
| 19(H6-17) | C | 14.90 | 420 (M + H)+, 270. | APCI (Pos., 40 V) |
| 19(H6-18) | F | 3.55 | 476 (M + H)+. | ESI (Pos., 20 V) |
| 19(H6-19) | F | 3.55 | 510 (M + H)+. | ESI (Pos., 20 V) |
| 19(H6-20) | C | 15.80 | 549 (M + H)+, 279. | APCI (Pos., 40 V) |
| 19(H6-21) | D | 15.70 | 540 (M + H)+. | ARCI (Pos., 40 V) |
| 19(H6-22) | F | 3.62 | 568 (M + H)+. | ESI (Pos., 20 V) |
| 19(H6-23) | F | 3.62 | 625 (M + H)+. | ESI (Pos., 20 V) |
| 19(H6-24) | F | 3.55 | 510 (M + H)+. | ESI (Pos., 20 V) |
| 19(H6-25) | F | 3.79 | 566 (M + H)+. | ESI (Pos., 20 V) |
| 19(H6-26) | F | 3.78 | 600 (M + H)+. | ESI (Pos., 20 V) |

TABLE 6C-2

| Example No | HPLC condi-tion | Retention time (min) | Mass data | Mass condition |
|---|---|---|---|---|
| 19(H6-27) | F | 3.74 | 639 (M + H)+. | ESI (Pos., 20 V) |
| 19(H6-28) | D | 17.20 | 630 (M + H)+, 480, 279. | APCI (Pos., 40 V) |
| 19(H6-29) | F | 3.84 | 658 (M + H)+. | ESI (Pos., 20 V) |
| 19(H6-30) | F | 3.80 | 715 (M + H)+. | ESI (Pos., 20 V) |
| 19(H6-31) | C | 15.50 | 434 (M + H)+, 284. | APCI (Pos., 40 V) |
| 19(H6-32) | F | 3.60 | 490 (M + H)+. | ESI (Pos., 20 V) |
| 19(H6-33) | F | 3.60 | 524 (M + H)+. | ESI (Pos., 20 V) |
| 19(H6-34) | F | 3.56 | 563 (M + H)+. | ESI (Pos., 20 V) |
| 19(H6-35) | C | 17.20 | 554 (M + H)+, 446. | APCI (Pos., 40 V) |
| 19(H6-36) | F | 3.67 | 582 (M + H)+. | ESI (Pos., 20 V) |
| 19(H6-37) | F | 3.67 | 639 (M + H)+. | ESI (Pos., 20 V) |
| 19(H6-38) | F | 3.22 | 372 (M + H)+. | ESI (Pos., 20 V) |
| 19(H6-39) | D | 14.30 | 428 (M + H)+, 279. | APCI (Pos., 40 V) |
| 19(H6-40) | F | 3.44 | 462 (M + H)+. | ESI (Pos., 20 V) |
| 19(H6-41) | F | 3.42 | 501 (M + H)+. | ESI (Pos., 20 V) |
| 19(H6-42) | D | 15.20 | 492 (M + H)+, 384, 279 | APCI (Pos., 40 V) |
| 19(H6-43) | C | 16.20 | 520 (M + H)+, 224. | APCI (Pos., 40 V) |
| 19(H6-44) | C | 16.40 | 577 (M + H)+, 469, 281. | APCI (Pos., 40 V) |
| 19(H6-45) | F | 3.36 | 458 (M + H)+. | ESI (Pos., 20 V) |
| 19(H6-46) | F | 3.60 | 514 (M + H)+. | ESI (Pos., 20 V) |
| 19(H6-47) | F | 3.59 | 548 (M + H)+. | ESI (Pos., 20 V) |
| 19(H6-48) | F | 3.57 | 587 (M + H)+. | ESI (Pos., 20 V) |
| 19(H6-49) | D | 16.20 | 578 (M + H)+, 522. | APCI (Pos., 40 V) |
| 19(H6-50) | C | 17.20 | 606 (M + H)+, 550. | APCI (Pos., 40 V) |
| 19(H6-51) | F | 3.66 | 663 (M + H)+. | ESI (Pos., 20 V) |
| 19(H6-52) | F | 3.16 | 489 (M + H)+. | ESI (Pos., 20 V) |

TABLE 6C-3

| Example No | HPLC condi-tion | Retention time (min) | Mass data | Mass condition |
|---|---|---|---|---|
| 19(H6-53) | F | 3.33 | 545 (M + H)+. | ESI (Pos., 20 V) |
| 19(H6-54) | C | 15.20<br>15.70 | 579 (M + H)+,<br>420, 158. | APCI (Pos., 40 V) |

TABLE 6C-3-continued

| Example No | HPLC condi-tion | Retention time (min) | Mass data | Mass condition |
|---|---|---|---|---|
| 19(H6-55) | F | 3.33 | 618 (M + H)+. | ESI (Pos., 20 V) |
| 19(H6-56) | C | 15.60<br>16.00 | 609 (M + H)+,<br>501, 279, 158. | APCI (Pos., 40 V) |
| 19(H6-57) | F | 3.40 | 637 (M + H)+. | ESI (Pos., 20 V) |
| 19(H6-58) | F | 3.44 | 694 (M + H)+. | ESI (Pos., 20 V) |

TABLE 7C-1

| Example No | HPLC condition | Retention time (min) | Mass data | Mass condition |
|---|---|---|---|---|
| 19(H7-1) | C | 15.20 | 424 (M + H)+. | APCI (Pos., 40 V) |
| 19(H7-2) | D | 14.90 | 480 (M + H)+. | APCI (Pos., 40 V) |
| 19(H7-3) | F | 3.57 | 514 (M + H)+. | ESI (Pos., 20 V) |
| 19(H7-4) | F | 3.55 | 553 (M + H)+. | ESI (Pos., 20 V) |
| 19(H7-5) | C | 17.10 | 544 (M + H)+. | APCI (Pos., 40 V) |
| 19(H7-6) | C | 15.20 | 428 (M + H)+, 264. | APCI (Pos., 40 V) |
| 19(H7-7) | D | 15.00 | 484 (M + H)+. | APCI (Pos., 40 V) |
| 19(H7-8) | F | 3.51 | 518 (M + H)+. | ESI (Pos., 20 V) |
| 19(H7-9) | F | 3.49 | 557 (M + H)+. | ESI (Pos., 20 V) |
| 19(H7-10) | F | 3.56 | 548 (M + H)+. | ESI (Pos., 20 V) |
| 19(H7-11) | C | 17.20 | 576 (M + H)+, 197. | APCI (Pos., 40 V) |
| 19(H7-12) | F | 3.59 | 633 (M + H)+. | ESI (Pos., 20 V) |
| 19(H7-13) | C | 16.20 | 487 (M + H)+, 279. | APCI (Pos., 40 V) |
| 19(H7-14) | D | 15.70 | 543 (M + H)+, 274. | APCI (Pos., 40 V) |
| 19(H7-15) | F | 3.64 | 577 (M + H)+. | ESI (Pos., 20 V) |
| 19(H7-16) | F | 3.62 | 616 (M + H)+. | ESI (Pos., 20 V) |
| 19(H7-17) | F | 3.68 | 607 (M + H)+. | ESI (Pos., 20 V) |
| 19(H7-18) | F | 3.72 | 635 (M + H)+. | ESI (Pos., 20 V) |
| 19(H7-19) | C | 17.70 | 692 (M + H)+, 584. | APCI (Pos., 40 V) |
| 19(H7-20) | C | 15.60 | 434 (M + H)+, 270. | APCI (Pos., 40 V) |
| 19(H7-21) | C | 17.20 | 490 (M + H)+, 326, 221. | APCI (Pos., 40 V) |
| 19(H7-22) | C | 17.20 | 524 (M + H)+, 360, 255. | APCI (Pos., 40 V) |
| 19(H7-23) | C | 16.90 | 563 (M + H)+. | APCI (Pos., 40 V) |
| 19(H7-24) | C | 17.50 | 554 (M + H)+, 285. | APCI (Pos., 40 V) |
| 19(H7-25) | C | 17.70 | 582 (M + H)+, 313, 149. | APCI (Pos., 40 V) |
| 19(H7-26) | C | 17.70 | 639 (M + H)+, 531, 370, 213. | APCI (Pos., 40 V) |

TABLE 7C-2

| Example No | HPLC condi-tion | Retention time (min) | Mass data | Mass condition |
|---|---|---|---|---|
| 19(H7-27) | C | 17.70 | 524 (M + H)+, 360, 255, 181. | APCI (Pos., 40 V) |
| 19(H7-28) | D | 17.10 | 580 (M + H)+, 416, 181. | APCI (Pos., 40 V) |
| 19(H7-29) | F | 3.86 | 614 (M + H)+. | ESI (Pos., 20 V) |
| 19(H7-30) | F | 3.80 | 653 (M + H)+. | ESI (Pos., 20 V) |
| 19(H7-31) | C | 19.00 | 644 (M + H)+, 149. | APCI (Pos., 40 V) |
| 19(H7-32) | F | 3.91 | 672 (M + H)+. | ESI (Pos., 20 V) |
| 19(H7-33) | F | 3.87 | 729 (M + H)+. | ESI (Pos., 20 V) |
| 19(H7-34) | D | 16.10 | 504 (M + H)+, 235. | APCI (Pos., 40 V) |

TABLE 7C-2-continued

| Example No | HPLC condi-tion | Retention time (min) | Mass data | Mass condition |
|---|---|---|---|---|
| 19(H7-35) | F | 3.67 | 538 $(M + H)^+$. | ESI (Pos., 20 V) |
| 19(H7-36) | F | 3.66 | 577 $(M + H)^+$. | ESI (Pos., 20 V) |
| 19(H7-37) | F | 3.73 | 568 $(M + H)^+$. | ESI (Pos., 20 V) |
| 19(H7-38) | F | 3.76 | 596 $(M + H)^+$. | ESI (Pos., 20 V) |
| 19(H7-39) | F | 3.72 | 653 $(M + H)^+$. | ESI (Pos., 20 V) |
| 19(H7-40) | C | 15.20 | 386 $(M + H)^+$, 222. | APCI (Pos., 40 V) |
| 19(H7-41) | D | 14.90 | 442 $(M + H)^+$, 278. | APCI (Pos., 40 V) |
| 19(H7-42) | D | 15.20 | 476 $(M + H)^+$, 312. | APCI (Pos., 40 V) |
| 19(H7-43) | C | 16.40 | 515 $(M + H)^+$, 488, 404, 351, 256, 220, 146, 130. | APCI (Pos., 40 V) |
| 19(H7-44) | D | 15.50 | 506 $(M + H)^+$, 398. | APCI (Pos., 40 V) |
| 19(H7-45) | D | 15.50 | 534 $(M + H)^+$. | APCI (Pos., 40 V) |
| 19(H7-46) | D | 15.80 | 591 $(M + H)^+$, 483. | APCI (Pos., 40 V) |
| 19(H7-47) | C | 16.60 | 472 $(M + H)^+$, 416, 279 | APCI (Pos., 40 V) |
| 19(H7-48) | C | 17.40 | 528 $(M + H)^+$, 499, 473, 452, 415, 247, 203, 149. | APCI (Pos., 40 V) |
| 19(H7-49) | F | 3.69 | 562 $(M + H)^+$. | ESI (Pos., 20 V) |
| 19(H7-50) | F | 3.66 | 601 $(M + H)^+$. | ESI (Pos., 20 V) |
| 19(H7-51) | F | 3.71 | 592 $(M + H)^+$. | ESI (Pos., 20 V) |

TABLE 7C-3

| Example No | HPLC condi-tion | Retention time (min) | Mass data | Mass condition |
|---|---|---|---|---|
| 19(H7-52) | F | 3.74 | 620 $(M + H)^+$. | ESI (Pos., 20 V) |
| 19(H7-53) | F | 3.75 | 677 $(M + H)^+$. | ESI (Pos., 20 V) |
| 19(H7-54) | C | 14.70 | 503 $(M + H)^+$, 344. | APCI (Pos., 40 V) |
| 19(H7-55) | D | 14.20 | 559 $(M + H)^+$, 400, 279, 158. | APCI (Pos., 40 V) |
| 19(H7-56) | F | 3.39 | 593 $(M + H)^+$. | ESI (Pos., 20 V) |
| 19(H7-57) | F | 3.39 | 632 $(M + H)^+$. | ESI (Pos., 20 V) |
| 19(H7-58) | F | 3.46 | 623 $(M + H)^+$. | ESI (Pos., 20 V) |
| 19(H7-59) | F | 3.48 | 651 $(M + H)^+$. | ESI (Pos., 20 V) |
| 19(H7-60) | F | 3.51 | 708 $(M + H)^+$. | ESI (Pos., 20 V) |

TABLE 8C-1

| Example No | HPLC condi-tion | Retention time (min) | Mass data | Mass condition |
|---|---|---|---|---|
| 19(H8-1) | C | 10.70 | 368 $(M + H)^+$, 250. | APCI (Pos., 40 V) |
| 19(H8-2) | F | 2.98 | 407 $(M + H)^+$. | ESI (Pos., 20 V) |
| 19(H8-3) | F | 0.67 | 282 $(M + H)^+$. | ESI (Pos., 20 V) |
| 19(H8-4) | C | 9.60 10.30 | 338 $(M + H)^+$. | APCI (Pos., 40 V) |
| 19(H8-5) | F | 2.90 | 372 $(M + H)^+$. | ESI (Pos., 20 V) |
| 19(H8-6) | F | 2.92 | 411 $(M + H)^+$. | ESI (Pos., 20 V) |
| 19(H8-7) | F | 2.98 | 402 $(M + H)^+$. | ESI (Pos., 20 V) |
| 19(H8-8) | F | 3.03 | 452 $(M + Na)^+$, 430 $(M + H)^+$. | ESI (Pos., 20 V) |
| 19(H8-9) | F | 3.09 | 509 $(M + Na)^+$, 487 $(M + H)^+$. | ESI (Pos., 20 V) |
| 19(H8-10) | C | 9.20 | 341 $(M + H)^+$. | APCI (Pos., 40 V) |

TABLE 8C-1-continued

| Example No | HPLC condi-tion | Retention time (min) | Mass data | Mass condition |
|---|---|---|---|---|
| 19(H8-11) | F | 3.14 | 397 $(M + H)^+$. | ESI (Pos., 20 V) |
| 19(H8-12) | F | 3.12 | 431 $(M + H)^+$. | ESI (Pos., 20 V) |
| 19(H8-13) | F | 3.12 | 470 $(M + H)^+$. | ESI (Pos., 20 V) |
| 19(H8-14) | F | 3.18 | 461 $(M + H)^+$. | ESI (Pos., 20 V) |
| 19(H8-15) | F | 3.23 | 489 $(M + H)^+$. | ESI (Pos., 20 V) |
| 19(H8-16) | F | 3.27 | 546 $(M + H)^+$. | ESI (Pos., 20 V) |
| 19(H8-17) | F | 2.63 | 288 $(M + H)^+$. | ESI (Pos., 20 V) |
| 19(H8-18) | C | 12.00 | 344 $(M + H)^+$, 215, 124. | APCI (Pos., 40 V) |
| 19(H8-19) | F | 3.01 | 378 $(M + H)^+$. | ESI (Pos., 20 V) |
| 19(H8-20) | F | 3.03 | 417 (M + H)+. | ESI (Pos., 20 V) |
| 19(H8-21) | F | 3.10 | 408 $(M + H)^+$. | ESI (Pos., 20 V) |
| 19(H8-22) | F | 3.16 | 436 $(M + H)^+$. | ESI (Pos., 20 V) |
| 19(H8-23) | F | 3.20 | 493 $(M + H)^+$. | ESI (Pos., 20 V) |
| 19(H8-24) | F | 3.07 | 378 $(M + H)^+$. | ESI (Pos., 20 V) |
| 19(H8-25) | F | 3.34 | 434 $(M + H)^+$. | ESI (Pos., 20 V) |

TABLE 8C-2

| Example No | HPLC condi-tion | Retention time (min) | Mass data | Mass condition |
|---|---|---|---|---|
| 19(H8-26) | C | 16.00 | 468 $(M + H)^+$. | APCI (Pos., 40 V) |
| 19(H8-27) | F | 3.33 | 507 $(M + H)^+$. | ESI (Pos., 20 V) |
| 19(H8-28) | F | 3.38 | 498 $(M + H)^+$. | ESI (Pos., 20 V) |
| 19(H8-29) | F | 3.44 | 526 $(M + H)^+$. | ESI (Pos., 20 V) |
| 19(H8-30) | F | 3.42 | 583 $(M + H)^+$. | ESI (Pos., 20 V) |
| 19(H8-31) | C | 8.90 | 302 $(M + H)^+$, 123. | APCI (Pos., 40 V) |
| 19(H8-32) | F | 3.12 | 358 $(M + H)^+$. | ESI (Pos., 20 V) |
| 19(H8-33) | F | 3.11 | 392 $(M + H)^+$. | ESI (Pos., 20 V) |
| 19(H8-34) | C | 13.40 | 431 $(M + H)^+$. | APCI (Pos., 40 V) |
| 19(H8-35) | F | 3.18 | 422 $(M + H)^+$. | ESI (Pos., 20 V) |
| 19(H8-36) | F | 3.23 | 450 $(M + H)^+$. | ESI (Pos., 20 V) |
| 19(H8-37) | F | 3.23 | 507 $(M + H)^+$. | ESI (Pos., 20V) |
| 19(H8-38) | F | 0.65 | 240 $(M + H)^+$. | ESI (Pos., 20 V) |
| 19(H8-39) | D | 8.60 | 296 $(M + H)^+$. | APCI (Pos., 40 V) |
| 19(H8-40) | F | 2.87 | 330 $(M + H)^+$. | ESI (Pos., 20 V) |
| 19(H8-41) | F | 2.89 | 369 $(M + H)^+$. | ESI (Pos., 20 V) |
| 19(H8-42) | F | 2.94 | 360 $(M + H)^+$. | ESI (Pos., 20V) |
| 19(H8-43) | F | 3.01 | 388 $(M + H)^+$. | ESI (Pos., 20V) |
| 19(H8-44) | F | 3.07 | 445 $(M + H)^+$. | ESI (Pos., 20V) |
| 19(H8-45) | F | 2.79 | 326 $(M + H)^+$. | ESI (Pos., 20 V) |
| 19(H8-46) | F | 3.09 | 416 $(M + H)^+$. | ESI (Pos., 20 V) |
| 19(H8-47) | F | 3.11 | 455 $(M + H)^+$. | ESI (Pos., 20 V) |
| 19(H8-48) | F | 3.16 | 446 $(M + H)^+$. | ESI (Pos., 20 V) |
| 19(H8-49) | C | 14.60 | 474 $(M + H)^+$, 418. | APCI (Pos., 40 V) |
| 19(H8-50) | F | 3.23 | 531 $(M + H)^+$. | ESI (Pos., 20 V) |
| 19(H8-51) | F | 1.95 | 357 $(M + H)^+$. | ESI (Pos., 20 V) |

TABLE 8C-3

| Example No | HPLC condi-tion | Retention time (min) | Mass data | Mass condition |
|---|---|---|---|---|
| 19(H8-52) | F | 3.01 | 413 $(M + H)^+$. | ESI (Pos., 20 V) |
| 19(H8-53) | F | 3.00 | 447 $(M + H)^+$. | ESI (Pos., 20 V) |
| 19(H8-54) | F | 3.03 | 486 $(M + H)^+$. | ESI (Pos., 20 V) |
| 19(H8-55) | F | 3.07 | 477 $(M + H)^+$. | ESI (Pos., 20 V) |
| 19(H8-56) | F | 3.12 | 505 $(M + H)^+$. | ESI (Pos., 20 V) |
| 19(H8-57) | C | 12.50 | 562 $(M + H)^+$, 454. | APCI (Pos., 40 V) |

TABLE 9C-1

| Example No | HPLC condi-tion | Retention time (min) | Mass data | Mass condition |
|---|---|---|---|---|
| 19(H9-1) | D | 12.30 | 533 $(M + H)^+$, 388. | APCI(Pos., 40 V) |
| 19(H9-2) | D | 13.36 | 547 $(M + H)^+$, 439, 181. | APCI (Pos., 40 V) |
| 19(H9-3) | D | 16.15 | 629 $(M + H)^+$, 521. | APCI (Pos., 40 V) |
| 19(H9-4) | D | 13.78 | 561 $(M + H)^+$, | APCI (Pos., 40 V) |
| 19(H9-5) | D | 14.20 | 575 $(M + H)^+$, 460. | APCI (Pos., 40 V) |
| 19(H9-6) | D | 14.90 | 589 $(M + H)^+$. | APCI (Pos., 40 V) |
| 19(H9-7) | D | 11.36 | 604 $(M + H)^+$. | APCI (Pos., 40 V) |
| 19(H9-8) | D | 11.26 | 604 $(M + H)^+$, 496. | APCI (Pos., 40 V) |
| 19(H9-9) | D | 13.90 | 609 $(M + H)^+$. | APCI (Pos., 40 V) |
| 19(H9-10) | D | 14.40 | 589 $(M + H)^+$, 474. | APCI (Pos., 40 V) |
| 19(H9-11) | D | 13.52 | 589 $(M + H)^+$, 481. | APCI (Pos., 40 V) |
| 19(H9-12) | D | 11.05 | 606 $(M + H)^+$, 498. | APCI (Pos., 40 V) |
| 19(H9-13) | D | 11.06 | 620 $(M + H)^+$, 512. | APCI (Pos., 40 V) |
| 19(H9-14) | D | 11.31 | 598 $(M + H)^+$, 490. | APCI (Pos., 40 V) |
| 19(H9-15) | D | 11.05 | 584 $(M + H)^+$, 476. | APCI (Pos., 40 V) |
| 19(H9-16) | D | 10.99 | 584 $(M + H)^+$. | APCI (Pos., 40 V) |
| 19(H9-17) | D | 13.62 | 648 $(M + H)^+$. | APCI (Pos., 40 V) |
| 19(H9-18) | D | 11.68 | 604 $(M + H)^+$, 496. | APCI (Pos., 40 V) |
| 19(H9-19) | D | 14.41 | 597 $(M + H)^+$. | APCI (Pos., 40 V) |
| 19(H9-20) | D | 12.89 | 535 $(M + H)^+$. | APCI (Pos., 40 V) |
| 19(H9-21) | D | 14.41 | 577 $(M + H)^+$. | APCI (Pos., 40 V) |
| 19(H9-22) | D | 14.05 | 625 $(M + H)^+$. | APCI (Pos., 40 V) |
| 19(H9-23) | D | 13.68 | 549 $(M + H)^+$. | APCI (Pos., 40 V) |
| 19(H9-24) | D | 14.05 | 563 $(M + H)^+$. | APCI (Pos., 40 V) |
| 19(H9-25) | D | 13.73 | 601 $(M + H)^+$, 493. | APCI (Pos., 40 V) |
| 19(H9-26) | D | 13.89 | 613 $(M + H)^+$, 505. | APCI (Pos., 40 V) |

TABLE 9C-2

| Example No | HPLC condi-tion | Retention time (min) | Mass data | Mass condition |
|---|---|---|---|---|
| 19(H9-27) | D | 13.99 | 601 $(M + H)^+$, 493. | APCI (Pos., 40 V) |
| 19(H9-28) | D | 13.89 | 613 $(M + H)^+$, 505. | APCI (Pos., 40 V) |
| 19(H9-29) | D | 14.05 | 601 $(M + H)^+$, 493. | APCI (Pos., 40 V) |
| 19(H9-30) | D | 13.73 | 613 $(M + H)^+$, 505. | APCI (Pos., 40 V) |
| 19(H9-31) | D | 14.41 | 597 $(M + H)^+$, 489. | APCI (Pos., 40 V) |
| 19(H9-32) | D | 14.31 | 563 $(M + H)^+$, 455. | APCI (Pos., 40 V) |
| 19(H9-33) | D | 14.68 14.95 | 611 $(M + H)^+$, 503. | APCI (Pos., 40 V) |
| 19(H9-34) | D | 13.57 | 549 $(M + H)^+$, 441. | APCI (Pos., 40 V) |
| 19(H9-35) | D | 14.20 | 563 $(M + H)^+$, 455. | APCI (Pos., 40 V) |
| 19(H9-36) | D | 13.84 | 583 $(M + H)^+$, 475. | APCI (Pos., 40 V) |
| 19(H9-37) | D | 11.10 | 564 $(M + H)^+$, 456. | APCI (Pos., 40 V) |
| 19(H9-38) | D | 12.35 | 551 $(M + H)^+$, 443. | APCI (Pos., 40 V) |

TABLE 9C-2-continued

| Example No | HPLC condi-tion | Retention time (min) | Mass data | Mass condition |
|---|---|---|---|---|
| 19(H9-39) | D | 12.04 | 531 $(M + H)^+$, 423. | APCI (Pos., 40 V) |
| 19(H9-40) | D | 12.56 | 533 $(M + H)^+$, 425. | APCI (Pos., 40 V) |
| 19(H9-41) | D | 11.78 | 551 $(M + H)^+$, 443. | APCI (Pos., 40 V) |
| 19(H9-42) | D | 14.20 | 563 $(M + H)^+$, 455. | APCI (Pos., 40 V) |
| 19(H9-43) | D | 12.99 | 535 $(M + H)^+$, 427. | APCI (Pos., 40 V) |
| 19(H9-44) | D | 11.21 | 578 $(M + H)^+$, 470. | APCI (Pos., 40 V) |
| 19(H9-45) | D | 13.20 | 579 $(M + H)^+$, 471. | APCI (Pos., 40 V) |
| 19(H9-46) | D | 14.83 | 611 $(M + H)^+$, 503. | APCI (Pos., 40 V) |
| 19(H9-47) | D | 15.31 | 625 $(M + H)^+$, 517. | APCI (Pos., 40 V) |
| 19(H9-48) | D | 14.36 | 563 $(M + H)^+$, 563. | APCI (Pos., 40 V) |
| 19(H9-49) | D | 11.04 | 601 $(M + H)^+$, 493. | APCI (Pos., 40 V) |
| 19(H9-50) | D | 13.56 | 549 $(M + H)^+$, 441. | APCI (Pos., 40 V) |
| 19(H9-51) | D | 15.26 | 601 $(M + H)^+$, 493. | APCI (Pos., 40 V) |

TABLE 9C-3

| Example No | HPLC condi-tion | Retention time (min) | Mass data | Mass condition |
|---|---|---|---|---|
| 19(H9-52) | D | 13.15 | 547 $(M + H)^+$, 439. | APCI (Pos., 40 V) |
| 19(H9-53) | D | 12.19 | 521 $(M + H)^+$, 413. | APCI (Pos., 40 V) |
| 19(H9-54) | D | 12.63 | 565 $(M + H)^+$, 457. | APCI (Pos., 40 V) |
| 19(H9-55) | D | 11.00 | 598 $(M + H)^+$, 493. | APCI (Pos., 40 V) |
| 19(H9-56) | D | 14.57 | 617 $(M + H)^+$, 509. | APCI (Pos., 40 V) |
| 19(H9-57) | D | 13.36 | 581 $(M + H)^+$, 473. | APCI (Pos., 40 V) |
| 19(H9-58) | D | 13.98 | 603 $(M + H)^+$, 495. | APCI (Pos., 40 V) |
| 19(H9-59) | D | 14.57 | 609 $(M + H)^+$, 501. | APCI (Pos., 40 V) |
| 19(H9-60) | D | 14.05 | 607 $(M + H)^+$. | APCI (Pos., 40 V) |
| 19(H9-61) | D | 13.68 | 587 $(M + H)^+$. | APCI (Pos., 40 V) |
| 19(H9-62) | D | 11.21 | 598 $(M + H)^+$, 490. | APCI (Pos., 40 V) |

TABLE 10C-1

| Example No | HPLC condi-tion | Retention time (min) | Mass data | Mass condition |
|---|---|---|---|---|
| 19(H10-1) | F | 3.39 | 519 $(M + H)^+$. | ESI (Pos., 20 V) |
| 19(H10-2) | F | 3.47 | 532 $(M + H)^+$. | ESI (Pos., 20 V) |
| 19(H10-3) | F | 3.79 | 615 $(M + H)^+$. | ESI (Pos., 20 V) |
| 19(H10-4) | F | 3.49 | 547 $(M + H)^+$. | ESI (Pos., 20 V) |
| 19(H10-5) | F | 3.55 | 561 $(M + H)^+$. | ESI (Pos., 20 V) |
| 19(H10-6) | F | 3.62 | 575 $(M + H)^+$. | ESI (Pos., 20 V) |

TABLE 10C-1-continued

| Example No | HPLC condi-tion | Retention time (min) | Mass data | Mass condition |
|---|---|---|---|---|
| 19(H10-7) | F | 3.64 | 589 $(M + H)^+$. | ESI (Pos., 20 V) |
| 19(H10-8) | F | 3.22 | 590 $(M + H)^+$. | ESI (Pos., 20 V) |
| 19(H10-9) | F | 3.22 | 590 $(M + H)^+$. | ESI (Pos., 20 V) |
| 19(H10-10) | F | 3.58 | 595 $(M + H)^+$. | ESI (Pos., 20 V) |
| 19(H10-11) | F | 3.58 | 575 $(M + H)^+$. | ESI (Pos., 20 V) |
| 19(H10-12) | F | 3.49 | 575 $(M + H)^+$. | ESI (Pos., 20 V) |
| 19(H10-13) | F | 3.20 | 592 $(M + H)^+$. | ESI (Pos., 20 V) |
| 19(H10-14) | F | 3.20 | 606 $(M + H)^+$. | ESI (Pos., 20 V) |
| 19(H10-15) | F | 3.20 | 584 $(M + H)^+$. | ESI (Pos., 20 V) |
| 19(H10-16) | F | 3.18 | 570 $(M + H)^+$. | ESI (Pos., 20 V) |
| 19(H10-17) | F | 3.18 | 570 $(M + H)^+$. | ESI (Pos., 20 V) |
| 19(H10-18) | F | 3.45 | 634 $(M + H)^+$. | ESI (Pos., 20 V) |
| 19(H10-19) | F | 3.23 | 590 $(M + H)^+$. | ESI (Pos., 20 V) |
| 19(H10-20) | F | 3.44 | 555 $(M + H)^+$. | ESI (Pos., 20 V) |
| 19(H10-21) | F | 3.57 | 583 $(M + H)^+$. | ESI (Pos., 20 V) |
| 19(H10-22) | F | 3.40 | 521 $(M + H)^+$. | ESI (Pos., 20 V) |
| 19(H10-23) | F | 3.58 | 563 $(M + H)^+$. | ESI (Pos., 20 V) |
| 19(H10-24) | F | 3.66 | 611 $(M + H)^+$. | ESI (Pos., 20 V) |
| 19(H10-25) | F | 3.47 | 535 $(M + H)^+$. | ESI (Pos., 20 V) |
| 19(H10-26) | D | 13.62 | 549 $(M + H)^+$. | APCI (Pos., 40 V) |

TABLE 10C-2

| Example No | HPLC condi-tion | Retention time (min) | Mass data | Mass condition |
|---|---|---|---|---|
| 19(H10-27) | F | 3.55 | 549 $(M + H)^+$. | ESI (Pos., 20 V) |
| 19(H10-28) | F | 3.53 | 587 $(M + H)^+$. | ESI (Pos., 20 V) |
| 19(H10-29) | F | 3.53 | 599 $(M + H)^+$. | ESI (Pos., 20 V) |
| 19(H10-30) | F | 3.55 | 587 $(M + H)^+$. | ESI (Pos., 20 V) |
| 19(H10-31) | F | 3.53 | 599 $(M + H)^+$. | ESI (Pos., 20 V) |
| 19(H10-32) | F | 3.55 | 587 $(M + H)^+$. | ESI (Pos., 20 V) |
| 19(H10-33) | F | 3.53 | 599 $(M + H)^+$. | ESI (Pos., 20 V) |
| 19(H10-34) | F | 3.58 | 583 $(M + H)^+$. | ESI (Pos., 20 V) |
| 19(H10-35) | F | 3.56 | 549 $(M + H)^+$. | ESI (Pos., 20 V) |
| 19(H10-36) | F | 3.60 | 597 $(M + H)^+$. | ESI (Pos., 20 V) |
| 19(H10-37) | F | 3.45 | 535 $(M + H)^+$. | ESI (Pos., 20 V) |
| 19(H10-38) | F | 3.53 | 549 $(M + H)^+$. | ESI (Pos., 20 V) |
| 19(H10-39) | F | 3.51 | 569 $(M + H)^+$. | ESI (Pos., 20 V) |
| 19(H10-40) | F | 3.18 | 550 $(M + H)^+$. | ESI (Pos., 20 V) |
| 19(H10-41) | F | 3.34 | 537 $(M + H)^+$. | ESI (Pos., 20 V) |
| 19(H10-42) | F | 3.36 | 517 $(M + H)^+$. | ESI (Pos., 20 V) |
| 19(H10-43) | F | 3.40 | 519 $(M + H)^+$. | ESI (Pos., 20 V) |
| 19(H10-44) | F | 3.27 | 537 $(M + H)^+$. | ESI (Pos., 20 V) |
| 19(H10-45) | F | 3.53 | 549 $(M + H)^+$. | ESI (Pos., 20 V) |
| 19(H10-46) | F | 3.40 | 521 $(M + H)^+$. | ESI (Pos., 20 V) |
| 19(H10-47) | F | 3.18 | 564 $(M + H)^+$. | ESI (Pos., 20 V) |
| 19(H10-48) | F | 3.40 | 565 $(M + H)^+$. | ESI (Pos., 20 V) |
| 19(H10-49) | F | 3.60 | 597 $(M + H)^+$. | ESI (Pos., 20 V) |
| 19(H10-50) | F | 3.67 | 611 $(M + H)^+$. | ESI (Pos., 20 V) |
| 19(H10-51) | F | 3.53 | 549 $(M + H)^+$. | ESI (Pos., 20 V) |
| 19(H10-52) | F | 3.18 | 587 $(M + H)^+$. | ESI (Pos., 20 V) |

TABLE 10C-3

| Example No | HPLC condi-tion | Retention time (min) | Mass data | Mass condition |
|---|---|---|---|---|
| 19(H10-53) | F | 3.47 | 535 $(M + H)^+$. | ESI (Pos., 20 V) |
| 19(H10-54) | F | 3.64 | 587 $(M + H)^+$. | ESI (Pos., 20 V) |
| 19(H10-55) | F | 3.44 | 533 $(M + H)^+$. | ESI (Pos., 20 V) |
| 19(H10-56) | F | 3.34 | 507 $(M + H)^+$. | ESI (Pos., 20 V) |
| 19(H10-57) | F | 3.36 | 551 $(M + H)^+$. | ESI (Pos., 20 V) |
| 19(H10-58) | F | 3.45 | 640 $(M + H)^+$. | ESI (Pos., 20 V) |

TABLE 10C-3-continued

| Example No | HPLC condi-tion | Retention time (min) | Mass data | Mass condition |
|---|---|---|---|---|
| 19(H10-59) | F | 3.18 | 584 $(M + H)^+$. | ESI (Pos., 20 V) |
| 19(H10-60) | F | 3.60 | 603 $(M + H)^+$. | ESI (Pos., 20 V) |
| 19(H10-61) | F | 3.45 | 567 $(M + H)^+$. | ESI (Pos., 20 V) |
| 19(H10-62) | F | 3.53 | 589 $(M + H)^+$. | ESI (Pos., 20 V) |
| 19(H10-63) | F | 3.60 | 595 $(M + H)^+$. | ESI (Pos., 20 V) |
| 19(H10-64) | F | 3.53 | 593 $(M + H)^+$. | ESI (Pos., 20 V) |
| 19(H10-65) | F | 3.29 | 537 $(M + H)^+$. | ESI (Pos., 20 V) |
| 19(H10-66) | F | 3.49 | 573 $(M + H)^+$. | ESI (Pos., 20 V) |
| 19(H10-67) | F | 3.60 | 597 $(M + H)^+$. | ESI (Pos., 20 V) |
| 19(H10-68) | F | 3.20 | 584 $(M + H)^+$. | ESI (Pos., 20 V) |

TABLE 11C-1

| Example No | HPLC condi-tion | Retention time (min) | Mass data | Mass condition |
|---|---|---|---|---|
| 19(H11-1) | D | 12.10 | 412 $(M + H)^+$. | APCI (Pos., 40 V) |
| 19(H11-2) | D | 13.52 | 426 $(M + H)^+$. | APCI (Pos., 40 V) |
| 19(H11-3) | D | 16.47 | 508 $(M + H)^+$. | APCI (Pos., 40 V) |
| 19(H11-4) | D | 14.03 | 440 $(M + H)^+$. | APCI (Pos., 40 V) |
| 19(H11-5) | D | 14.36 | 454 $(M + H)^+$. | APCI (Pos., 40 V) |
| 19(H11-6) | D | 15.15 | 468 $(M + H)^+$. | APCI (Pos., 40 V) |
| 19(H11-7) | D | 10.66 | 483 $(M + H)^+$. | APCI (Pos., 40 V) |
| 19(H11-8) | D | 10.52 | 483 $(M + H)^+$. | APCI (Pos., 40 V) |
| 19(H11-9) | D | 13.94 | 488 $(M + H)^+$. | APCI (Pos., 40 V) |
| 19(H11-10) | D | 15.02 | 468 $(M + H)^+$. | APCI (Pos., 40 V) |
| 19(H11-11) | D | 13.36 | 468 $(M + H)^+$. | APCI (Pos., 40 V) |
| 19(H11-12) | D | 10.31 | 485 $(M + H)^+$. | APCI (Pos., 40 V) |
| 19(H11-13) | D | 10.52 | 499 $(M + H)^+$. | APCI (Pos., 40 V) |
| 19(H11-14) | D | 10.73 | 477 $(M + H)^+$. | APCI (Pos., 40 V) |
| 19(H11-15) | D | 10.36 | 463 $(M + H)^+$. | APCI (Pos., 40 V) |
| 19(H11-16) | D | 10.26 | 463 $(M + H)^+$. | APCI (Pos., 40 V) |
| 19(H11-17) | D | 13.76 | 527 $(M + H)^+$. | APCI (Pos., 40 V) |
| 19(H11-18) | D | 10.89 | 483 $(M + H)^+$. | APCI (Pos., 40 V) |
| 19(H11-19) | D | 13.92 | 476 $(M + H)^+$. | APCI (Pos., 40 V) |
| 19(H11-20) | D | 12.78 | 414 $(M + H)^+$. | APCI (Pos., 40 V) |
| 19(H11-21) | D | 13.47 | 480 $(M + H)^+$. | APCI (Pos., 40 V) |
| 19(H11-22) | D | 13.84 | 492 $(M + H)^+$. | APCI (Pos., 40 V) |
| 19(H11-23) | D | 13.84 | 480 $(M + H)^+$. | APCI (Pos., 40 V) |
| 19(H11-24) | D | 13.84 | 492 $(M + H)^+$. | APCI (Pos., 40 V) |
| 19(H11-25) | D | 14.05 | 480 $(M + H)^+$. | APCI (Pos., 40 V) |
| 19(H11-26) | D | 13.57 | 492 $(M + H)^+$. | APCI (Pos., 40 V) |

TABLE 11C-2

| Example No | HPLC condi-tion | Retention time (min) | Mass data | Mass condition |
|---|---|---|---|---|
| 19(H11-27) | D | 14.52 | 476 $(M + H)^+$. | APCI (Pos., 40 V) |
| 19(H11-28) | D | 14.41 | 442 $(M + H)^+$. | APCI (Pos., 40 V) |
| 19(H11-29) | D | 14.92<br>15.50 | 490 $(M + H)^+$. | APCI (Pos., 40 V) |
| 19(H11-30) | D | 13.62 | 428 $(M + H)^+$. | APCI (Pos., 40 V) |
| 19(H11-31) | D | 14.36 | 442 $(M + H)^+$. | APCI (Pos., 40 V) |
| 19(H11-32) | D | 13.78 | 462 $(M + H)^+$. | APCI (Pos., 40 V) |
| 19(H11-33) | D | 10.31 | 443 $(M + H)^+$. | APCI (Pos., 40 V) |
| 19(H11-34) | D | 12.10 | 430 $(M + H)^+$. | APCI (Pos., 40 V) |
| 19(H11-35) | D | 11.63 | 410 $(M + H)^+$. | APCI (Pos., 40 V) |
| 19(H11-36) | D | 12.42 | 412 $(M + H)^+$. | APCI (Pos., 40 V) |
| 19(H11-37) | D | 11.31 | 430 $(M + H)^+$. | APCI (Pos., 40 V) |
| 19(H11-38) | D | 14.26 | 442 $(M + H)^+$. | APCI (Pos., 40 V) |
| 19(H11-39) | D | 12.89 | 414 $(M + H)^+$. | APCI (Pos., 40 V) |
| 19(H11-40) | D | 10.52 | 457 $(M + H)^+$. | APCI (Pos., 40 V) |
| 19(H11-41) | D | 13.10 | 458 $(M + H)^+$. | APCI (Pos., 40 V) |

TABLE 11C-2-continued

| Example No | HPLC condition | Retention time (min) | Mass data | Mass condition |
|---|---|---|---|---|
| 19(H11-42) | D | 15.04 | 490 (M + H)+. | APCI (Pos., 40 V) |
| 19(H11-43) | D | 15.57 | 504 (M + H)+. | APCI (Pos., 40 V) |
| 19(H11-44) | D | 14.57 | 442 (M + H)+. | APCI (Pos., 40 V) |
| 19(H11-45) | D | 10.52 | 480 (M + H)+. | APCI (Pos., 40 V) |
| 19(H11-46) | D | 13.73 | 428 (M + H)+. | APCI (Pos., 40 V) |
| 19(H11-47) | D | 15.47 | 480 (M + H)+. | APCI (Pos., 40 V) |
| 19(H11-48) | D | 13.10 | 426 (M + H)+. | APCI (Pos., 40 V) |
| 19(H11-49) | D | 11.94 | 400 (M + H)+. | APCI (Pos., 40 V) |
| 19(H11-50) | D | 12.36 | 444 (M + H)+. | APCI (Pos., 40 V) |
| 19(H11-51) | D | 10.63 | 477 (M + H)+. | APCI (Pos., 40 V) |

TABLE 11C-3

| Example No | HPLC condition | Retention time (min) | Mass data | Mass condition |
|---|---|---|---|---|
| 19(H11-52) | D | 14.57 | 496 (M + H)+. | APCI (Pos., 40 V) |
| 19(H11-53) | D | 13.15 | 460 (M + H)+. | APCI (Pos., 40 V) |
| 19(H11-54) | D | 13.99 | 482 (M + H)+. | APCI (Pos., 40 V) |
| 19(H11-55) | D | 14.73 | 488 (M + H)+. | APCI (Pos., 40 V) |
| 19(H11-56) | D | 14.05 | 486 (M + H)+. | APCI (Pos., 40 V) |
| 19(H11-57) | D | 13.68 | 466 (M + H)+. | APCI (Pos., 40 V) |
| 19(H11-58) | D | 10.73 | 477 (M + H)+. | APCI (Pos., 40 V) |

TABLE 12C-1

| Example No | HPLC condition | Retention time (min) | Mass data | Mass condition |
|---|---|---|---|---|
| 19(H12-1) | F | 3.45 | 426 (M + H)+. | ESI (Pos., 20 V) |
| 19(H12-2) | F | 3.56 | 440 (M + H)+. | ESI (Pos., 20 V) |
| 19(H12-3) | F | 3.93 | 522 (M + H)+. | ESI (Pos., 20 V) |
| 19(H12-4) | F | 3.60 | 454 (M + H)+. | ESI (Pos., 20 V) |
| 19(H12-5) | F | 3.66 | 468 (M + H)+. | ESI (Pos., 20 V) |
| 19(H12-6) | F | 3.75 | 482 (M + H)+. | ESI (Pos., 20 V) |
| 19(H12-7) | F | 3.71 | 516 (M + H)+. | ESI (Pos., 20 V) |
| 19(H12-8) | F | 3.77 | 496 (M + H)+. | ESI (Pos., 20 V) |
| 19(H12-9) | F | 3.25 | 497 (M + H)+. | ESI (Pos., 20 V) |
| 19(H12-10) | F | 3.27 | 497 (M + H)+. | ESI (Pos., 20 V) |
| 19(H12-11) | F | 3.67 | 502 (M + H)+. | ESI (Pos., 20 V) |
| 19(H12-12) | F | 3.69 | 482 (M + H)+. | ESI (Pos., 20 V) |
| 19(H12-13) | F | 3.60 | 482 (M + H)+. | ESI (Pos., 20 V) |
| 19(H12-14) | F | 3.23 | 499 (M + H)+. | ESI (Pos., 20 V) |
| 19(H12-15) | F | 3.23 | 513 (M + H)+. | ESI (Pos., 20 V) |
| 19(H12-16) | F | 3.23 | 491 (M + H)+. | ESI (Pos., 20 V) |
| 19(H12-17) | F | 3.22 | 477 (M + H)+. | ESI (Pos., 20 V) |
| 19(H12-18) | F | 3.22 | 477 (M + H)+. | ESI (Pos., 20 V) |
| 19(H12-19) | F | 3.27 | 497 (M + H)+. | ESI (Pos., 20 V) |
| 19(H12-20) | F | 3.49 | 462 (M + H)+. | ESI (Pos., 20 V) |
| 19(H12-21) | F | 3.64 | 490 (M + H)+. | ESI (Pos., 20 V) |
| 19(H12-22) | F | 3.49 | 428 (M + H)+. | ESI (Pos., 20 V) |
| 19(H12-23) | F | 3.69 | 470 (M + H)+. | ESI (Pos., 20 V) |
| 19(H12-24) | F | 3.77 | 518 (M + H)+. | ESI (Pos., 20 V) |
| 19(H12-25) | F | 3.54 | 442 (M + H)+. | ESI (Pos., 20 V) |
| 19(H12-26) | F | 3.62 | 456 (M + H)+. | ESI (Pos., 20 V) |

TABLE 12C-2

| Example No | HPLC condition | Retention time (min) | Mass data | Mass condition |
|---|---|---|---|---|
| 19(H12-27) | F | 3.64 | 456 (M + H)+. | ESI (Pos., 20 V) |
| 19(H12-28) | F | 3.62 | 494 (M + H)+. | ESI (Pos., 20 V) |
| 19(H12-29) | F | 3.62 | 506 (M + H)+. | ESI (Pos., 20 V) |
| 19(H12-30) | F | 3.62 | 494 (M + H)+. | ESI (Pos., 20 V) |
| 19(H12-31) | F | 3.61 | 506 (M + H)+. | ESI (Pos., 20 V) |
| 19(H12-32) | F | 3.64 | 494 (M + H)+. | ESI (Pos., 20 V) |
| 19(H12-33) | F | 3.60 | 506 (M + H)+. | ESI (Pos., 20 V) |
| 19(H12-34) | F | 3.66 | 490 (M + H)+. | ESI (Pos., 20 V) |
| 19(H12-35) | F | 3.64 | 456 (M + H)+. | ESI (Pos., 20 V) |
| 19(H12-36) | F | 3.71 | 504 (M + H)+. | ESI (Pos., 20 V) |
| 19(H12-37) | F | 3.57 | 442 (M + H)+. | ESI (Pos., 20 V) |
| 19(H12-38) | F | 3.63 | 456 (M + H)+. | ESI (Pos., 20 V) |
| 19(H12-39) | F | 3.60 | 476 (M + H)+. | ESI (Pos., 20 V) |
| 19(H12-40) | F | 3.19 | 457 (M + H)+. | ESI (Pos., 20 V) |
| 19(H12-41) | F | 3.42 | 444 (M + H)+. | ESI (Pos., 20 V) |
| 19(H12-42) | F | 3.43 | 424 (M + H)+. | ESI (Pos., 20 V) |
| 19(H12-43) | F | 3.45 | 426 (M + H)+. | ESI (Pos., 20 V) |
| 19(H12-44) | F | 3.32 | 444 (M + H)+. | ESI (Pos., 20 V) |
| 19(H12-45) | F | 3.62 | 456 (M + H)+. | ESI (Pos., 20 V) |
| 19(H12-46) | F | 3.49 | 428 (M + H)+. | ESI (Pos., 20 V) |
| 19(H12-47) | F | 3.20 | 471 (M + H)+. | ESI (Pos., 20 V) |
| 19(H12-48) | F | 3.49 | 472 (M + H)+. | ESI (Pos., 20 V) |
| 19(H12-49) | F | 3.70 | 504 (M + H)+. | ESI (Pos., 20 V) |
| 19(H12-50) | F | 3.77 | 518 (M + H)+. | ESI (Pos., 20 V) |
| 19(H12-51) | F | 3.62 | 456 (M + H)+. | ESI (Pos., 20 V) |
| 19(H12-52) | F | 3.21 | 494 (M + H)+. | ESI (Pos., 20 V) |

TABLE 12C-4

| Example No | HPLC condition | Retention time (min) | Mass data | Mass condition |
|---|---|---|---|---|
| 19(H12-53) | F | 3.56 | 442 (M + H)+. | ESI (Pos., 20 V) |
| 19(H12-54) | F | 3.75 | 494 (M + H)+. | ESI (Pos., 20 V) |
| 19(H12-55) | F | 3.51 | 440 (M + H)+. | ESI (Pos., 20 V) |
| 19(H12-56) | F | 3.40 | 414 (M + H)+. | ESI (Pos., 20 V) |
| 19(H12-57) | F | 3.75 | 484 (M + H)+. | ESI (Pos., 20 V) |
| 19(H12-58) | F | 3.42 | 458 (M + H)+. | ESI (Pos., 20 V) |
| 19(H12-59) | F | 3.20 | 491 (M + H)+. | ESI (Pos., 20 V) |
| 19(H12-60) | F | 3.68 | 510 (M + H)+. | ESI (Pos., 20 V) |
| 19(H12-61) | F | 3.52 | 474 (M + H)+. | ESI (Pos., 20 V) |
| 19(H12-62) | F | 3.62 | 496 (M + H)+. | ESI (Pos., 20 V) |
| 19(H12-63) | F | 3.67 | 502 (M + H)+. | ESI (Pos., 20 V) |
| 19(H12-64) | F | 3.60 | 500 (M + H)+. | ESI (Pos., 20 V) |
| 19(H12-65) | F | 3.33 | 444 (M + H)+. | ESI (Pos., 20 V) |
| 19(H12-66) | F | 3.33 | 444 (M + H)+. | ESI (Pos., 20 V) |
| 19(H12-67) | F | 3.57 | 480 (M + H)+. | ESI (Pos., 20 V) |
| 19(H12-68) | F | 3.68 | 504 (M + H)+. | ESI (Pos., 20 V) |
| 19(H12-69) | F | 3.20 | 491 (M + H)+. | ESI (Pos., 20 V) |

TABLE 13C-1

| Example No | HPLC condition | Retention time (min) | Mass data | Mass condition |
|---|---|---|---|---|
| 19(H13-1) | F | 3.48 | 440 (M + H)+. | ESI (Pos., 20 V) |
| 19(H13-2) | F | 3.60 | 454 (M + H)+. | ESI (Pos., 20 V) |
| 19(H13-3) | F | 3.94 | 536 (M + H)+. | ESI (Pos., 20 V) |
| 19(H13-4) | F | 3.64 | 468 (M + H)+. | ESI (Pos., 20 V) |
| 19(H13-5) | F | 3.69 | 482 (M + H)+. | ESI (Pos., 20 V) |
| 19(H13-6) | F | 3.78 | 496 (M + H)+. | ESI (Pos., 20 V) |
| 19(H13-7) | F | 3.74 | 530 (M + H)+. | ESI (Pos., 20 V) |
| 19(H13-8) | F | 3.79 | 510 (M + H)+. | ESI (Pos., 20 V) |
| 19(H13-9) | F | 3.29 | 511 (M + H)+. | ESI (Pos., 20 V) |
| 19(H13-10) | F | 3.32 | 511 (M + H)+. | ESI (Pos., 20 V) |
| 19(H13-11) | F | 3.72 | 516 (M + H)+. | ESI (Pos., 20 V) |
| 19(H13-12) | F | 3.73 | 496 (M + H)+. | ESI (Pos., 20 V) |
| 19(H13-13) | F | 3.64 | 496 (M + H)+. | ESI (Pos., 20 V) |

TABLE 13C-1-continued

| Example No | HPLC condition | Retention time (min) | Mass data | Mass condition |
|---|---|---|---|---|
| 19(H13-14) | F | 3.26 | 513 $(M + H)^+$. | ESI (Pos., 20 V) |
| 19(H13-15) | F | 3.28 | 527 $(M + H)^+$. | ESI (Pos., 20 V) |
| 19(H13-16) | F | 3.28 | 505 $(M + H)^+$. | ESI (Pos., 20 V) |
| 19(H13-17) | F | 3.27 | 491 $(M + H)^+$. | ESI (Pos., 20 V) |
| 19(H13-18) | F | 3.58 | 555 $(M + H)^+$. | ESI (Pos., 20 V) |
| 19(H13-19) | F | 3.32 | 511 $(M + H)^+$. | ESI (Pos., 20 V) |
| 19(H13-20) | F | 3.66 | 504 $(M + H)^+$. | ESI (Pos., 20 V) |
| 19(H13-21) | F | 3.66 | 470 $(M + H)^+$. | ESI (Pos., 20 V) |
| 19(H13-22) | F | 3.74 | 484 $(M + H)^+$. | ESI (Pos., 20 V) |
| 19(H13-23) | F | 3.67 | 470 $(M + H)^+$. | ESI (Pos., 20 V) |
| 19(H13-24) | F | 3.66 | 508 $(M + H)^+$. | ESI (Pos., 20 V) |
| 19(H13-25) | F | 3.67 | 520 $(M + H)^+$. | ESI (Pos., 20 V) |
| 19(H13-26) | F | 3.69 | 508 $(M + H)^+$. | ESI (Pos., 20 V) |

TABLE 13C-2

| Example No | HPLC condition | Retention time (min) | Mass data | Mass condition |
|---|---|---|---|---|
| 19(H13-27) | F | 3.64 | 520 $(M + H)^+$. | ESI (Pos., 20 V) |
| 19(H13-28) | F | 3.68 | 508 $(M + H)^+$. | ESI (Pos., 20 V) |
| 19(H13-29) | F | 3.64 | 520 $(M + H)^+$. | ESI (Pos., 20 V) |
| 19(H13-30) | F | 3.72 | 504 $(M + H)^+$. | ESI (Pos., 20 V) |
| 19(H13-31) | F | 3.70 | 470 $(M + H)^+$. | ESI (Pos., 20 V) |
| 19(H13-32) | F | 3.76 | 518 $(M + H)^+$. | ESI (Pos,, 20 V) |
| 19(H13-33) | F | 3.61 | 456 $(M + H)^+$. | ESI (Pos., 20 V) |
| 19(H13-34) | F | 3.68 | 470 $(M + H)^+$. | ESI (Pos., 20 V) |
| 19(H13-35) | F | 3.65 | 490 $(M + H)^+$. | ESI (Pos., 20 V) |
| 19(H13-36) | F | 3.24 | 471 $(M + H)^+$. | ESI (Pos., 20 V) |
| 19(H13-37) | F | 3.47 | 458 $(M + H)^+$. | ESI (Pos., 20 V) |
| 19(H13-38) | F | 3.51 | 438 $(M + H)^+$. | ESI (Pos., 20 V) |
| 19(H13-39) | F | 3.51 | 440 $(M + H)^+$. | ESI (Pos., 20 V) |
| 19(H13-40) | F | 3.39 | 458 $(M + H)^+$. | ESI (Pos., 20 V) |
| 19(H13-41) | F | 3.67 | 470 $(M + H)^+$. | ESI (Pos., 20 V) |
| 19(H13-42) | F | 3.54 | 442 $(M + H)^+$. | ESI (Pos., 20 V) |
| 19(H13-43) | F | 3.25 | 485 $(M + H)^+$. | ESI (Pos., 20 V) |
| 19(H13-44) | F | 3.55 | 486 $(M + H)^+$. | ESI (Pos., 20 V) |
| 19(H13-45) | F | 3.75 | 518 $(M + H)^+$. | ESI (Pos., 20 V) |
| 19(H13-46) | F | 3.80 | 532 $(M + H)^+$. | ESI (Pos., 20 V) |
| 19(H13-47) | F | 3.69 | 470 $(M + H)^+$. | ESI (Pos., 20 V) |
| 19(H13-48) | F | 3.25 | 508 $(M + H)^+$. | ESI (Pos., 20 V) |
| 19(H13-49) | F | 3.62 | 456 $(M + H)^+$. | ESI (Pos., 20 V) |
| 19(H13-50) | F | 3.80 | 508 $(M + H)^+$. | ESI (Pos., 20 V) |
| 19(H13-51) | F | 3.58 | 454 $(M + H)^+$. | ESI (Pos., 20 V) |
| 19(H13-52) | F | 3.46 | 428 $(M + H)^+$. | ESI (Pos., 20 V) |

TABLE 13C-3

| Example No | HPLC condition | Retention time (min) | Mass data | Mass condition |
|---|---|---|---|---|
| 19(H13-53) | F | 3.80 | 498 $(M + H)^+$. | ESI (Pos., 20 V) |
| 19(H13-54) | F | 3.47 | 472 $(M + H)^+$. | ESI (Pos., 20 V) |
| 19(H13-55) | F | 3.26 | 505 $(M + H)^+$. | ESI (Pos., 20 V) |
| 19(H13-56) | F | 3.73 | 524 $(M + H)^+$. | ESI (Pos., 20 V) |
| 19(H13-57) | F | 3.58 | 488 $(M + H)^+$. | ESI (Pos., 20 V) |
| 19(H13-58) | F | 3.67 | 510 $(M + H)^+$. | ESI (Pos., 20 V) |
| 19(H13-59) | F | 3.73 | 516 $(M + H)^+$. | ESI (Pos., 20 V) |
| 19(H13-60) | F | 3.64 | 514 $(M + H)^+$. | ESI (Pos., 20 V) |
| 19(H13-61) | F | 3.62 | 494 $(M + H)^+$. | ESI (Pos., 20 V) |
| 19(H13-62) | F | 3.25 | 505 $(M + H)^+$. | ESI (Pos., 20 V) |

EXAMPLE 20

(3S)-1-propyl-2,5-dioxo-3-(4-(benzylcarbonylamino)butyl)-9-(2,4,6-trimethoxybenzyl)-1,4,9-triazaspiro[5.5]undecane

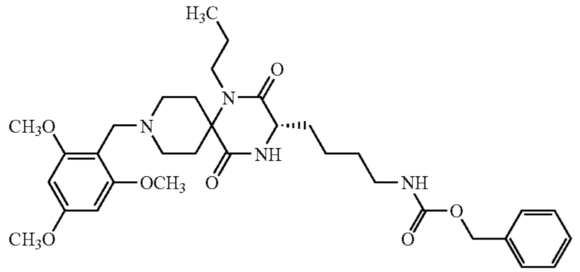

To a solution of the compound prepared in Example 8 (0.01 g) in dichloroethane (0.2 ml) were added 2,4,6-trimethoxybenzaldehyde (0.013 g), sodium triacetoxyborohydride (0.015 g) and dimethylformamide (0.2 ml). The reaction mixture was stirred for 50 hours at room temperature. The reaction mixture was loaded on ion exchange resin (OASIS MCX, Waters, 60 mg) washed with methanol (3 ml) prior to use. The resin was washed with methanol (2 ml), and was eluted with 10% triethylamine-methanol solution (2 ml). The elution was concentrated to give the compound of the present invention (4.4 mg) having the following physical data.

TLC: Rf 0.33 (chloroform:methanol=10:1);

NMR ($CD_3OD$): δ 7.33 (m, 5H), 6.21 (s, 2H), 5.05 (s, 2H), 4.00 (m, 1H), 3.80 (s, 9H), 3.59 (s, 2H), 3.40 (m, 2H), 3.11 (t, J=6.6 Hz, 2H), 3.05–2.75 (m, 4H), 2.40–2.00 (m, 2H), 2.00–1.70 (m, 4H), 1.65–1.25 (m, 6H), 0.90 (t, J=7.2 Hz, 3H).

EXAMPLE 20(1)

(3S)-1-propyl-2,5-dioxo-3-(4-(benzylcarbonylamino)butyl)-9-(2,2-dimethylpropyl)-1,4,9-triazaspiro[5.5]undecane

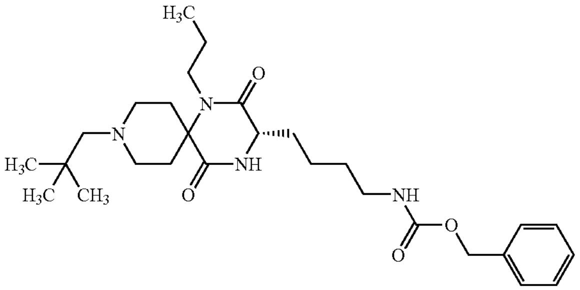

By the same procedure as described in Example 20 using the compound prepared in Example 8 (0.01 g) and pivalaldehyde (8 μl), the compound of the present invention (2.5 mg) having the following physical data was obtained.

TLC: Rf 0.53 (chloroform:methanol=10:1);

NMR ($CD_3OD$): δ 7.33 (m, 5H), 5.06 (s, 2H), 4.02 (m, 1H), 3.50–3.30 (m, 2H), 3.20–3.00 (m, 4H), 3.00–2.60 (m, 4H), 2.20–2.00 (m, 2H), 1.90–1.70 (m, 3H), 1.70–1.20 (m, 7H), 0.92 (t, J=7.4 Hz, 3H), 0.90 (s, 9H).

EXAMPLE 20(H14-1)~20(H15-77)

By the same procedure as described in Example 20 using the compound prepared in Example 8 or 8(1) and the corresponding aldehyde derivatives, the compounds of the present invention, whose names were shown in the following Table 14A-1~15A-10, and whose structures were shown in the following Table 14B-1~15B-12, were obtained. Also, physical data of the above compounds were shown in the following Table 14C-1~15C-3.

TABLE 14A-1

| Example No | Compound Name |
|---|---|
| 20(H14-1) | (3S)-1-propyl-2,5-dioxo-3-(4-(benzyloxycarbonylamino)-butyl)-9-(2,4,6-trimethoxyphenylmethyl)-1,4,9-triazaspiro[5.5]undecane |
| 20(H14-2) | (3S)-1-propyl-2,5-dioxo-3-(4-(benzyloxycarbonylamino)-butyl)-9-(3-cyanophenylmethyl)-1,4,9-triazaspiro-[5.5]undecane |
| 20(H14-3) | (3S)-1-propyl-2,5-dioxo-3-(4-(benzyloxycarbonylamino)-butyl)-9-(3-methylbutyl)-1,4,9-triazaspiro-[5.5]undecane |
| 20(H14-4) | (3S)-1-propyl-2,5-dioxo-3-(4-(benzyloxycarbonylamino)-butyl)-9-(2-(1-carboxymethyloxy)phenylmethyl)-1,4,9-triazaspiro[5.5]undecane |
| 20(H14-5) | (3S)-1-propyl-2,5-dioxo-3-(4-(benzyloxycarbonylamino)-butyl)-9-(4-dimethylaminophenylmethyl)-1,4,9-triazaspiro[5.5]undecane |
| 20(H14-6) | (3S)-1-propyl-2,5-dioxo-3-(4-(benzyloxycarbonylamino)-butyl)-9-(3-phenoxyphenylmethyl)-1,4,9-triazaspiro-[5.5]undecane |
| 20(H14-7) | (3S)-1-propyl-2,5-dioxo-3-(4-(benzyloxycarbonylamino)-butyl)-9-((2E)-2-methylbutenyl)-1,4,9-triazaspiro-[5.5]undecane |

TABLE 14A-2

| Example No | Compound Name |
|---|---|
| 20(H14-8) | (3S)-1-propyl-2,5-dioxo-3-(4-(benzyloxycarbonylamino)-butyl)-9-((1S,5S)-6,6-dimethylbicyclo[3.3.1]-2-hepten-2-ylmethyl)-1,4,9-triazaspiro[5.5]-undecane |
| 20(H14-9) | (3S)-1-propyl-2,5-dioxo-3-(4-(benzyloxycarbonylamino)-butyl)-9-(1-carboxymethyl)-1,4,9-triazaspiro[5.5]-undecane |
| 20(H14-10) | (3S)-1-propyl-2,5-dioxo-3-(4-(benzyloxycarbonylamino)-butyl)-9-cyclopropylmethyl-1,4,9-triazaspiro[5.5]-undecane |
| 20(H14-11) | (3S)-1-propyl-2,5-dioxo-3-(4-(benzyloxycarbonylamino)-butyl)-9-(3-methylthiopropyl)-1,4,9-triazaspiro[5.5]-undecane |
| 20(H14-12) | (3S)-1-propyl-2,5-dioxo-3-(4-(benzyloxycarbonylamino)-butyl)-9-(3-carboxypropyl)-1,4,9-triazaspiro[5.5]-undecane |
| 20(H14-13) | (3S)-1-propyl-2,5-dioxo-3-(4-(benzyloxycarbonylamino)-butyl)-9-(2,6-dimethyl-5-heptenyl)-1,4,9-triazaspiro-[5.5]undecane |
| 20(H14-14) | (3S)-1-propyl-2,5-dioxo-3-(4-(benzyloxycarbonylamino)-butyl)-9-(quinolin-2-yl)-1,4,9-triazaspiro[5.5]-undecane |

TABLE 14A-3

| Example No | Compound Name |
|---|---|
| 20(H14-15) | (3S)-1-propyl-2,5-dioxo-3-(4-(benzyloxycarbonylamino)-butyl)-9-((2S,3R,4R,5R)-2-acetylamino-3,4,5,6-tetrahydroxyhexanyl)-1,4,9-triazaspiro[5.5]-undecane |
| 20(H14-16) | (3S)-1-propyl-2,5-dioxo-3-(4-(benzyloxycarbonylamino)-butyl)-9-(2,2-dimethylpropyl)-1,4,9-triazaspiro[5.5]-undecane |
| 20(H14-17) | (3S)-1-propyl-2,5-dioxo-3-(4-(benzyloxycarbonylamino)-butyl)-9-((4Z)-decenyl)-1,4,9-triazaspiro[5.5]-undecane |
| 20(H14-18) | (3S)-1-propyl-2,5-dioxo-3-(4-(benzyloxycarbonylamino)-butyl)-9-(3-phenylpropyl)-1,4,9-triazaspiro[5.5]-undecane |
| 20(H14-19) | (3S)-1-propyl-2,5-dioxo-3-(4-(benzyloxycarbonylamino)-butyl)-9-butyl-1,4,9-triazaspiro[5.5]undecane |
| 20(H14-20) | (3S)-1-propyl-2,5-dioxo-3-(4-(benzyloxycarbonylamino)-butyl)-9-benzyl-1,4,9-triazaspiro[5.5]undecane |
| 20(H14-21) | (3S)-1-propyl-2,5-dioxo-3-(4-(benzyloxycarbonylamino)-butyl)-9-((2E)-3-(4-dimethylaminophenyl)propenyl)-1,4,9-triazaspiro[5.5]undecane |

TABLE 14A-4

| Example No | Compound Name |
|---|---|
| 20(H14-22) | (3S)-1-propyl-2,5-dioxo-3-(4-(benzyloxycarbonylamino)-butyl)9-((2E)-3-(furan-2-yl)propenyl)-1,4,9-triazaspiro[5.5]undecane |
| 20(H14-23) | (3S)-1-propyl-2,5-dioxo-3-(4-(benzyloxycarbonylamino)-butyl)-9-(3-hydroxyphenylmethyl)-1,4,9-triazaspiro-[5.5]undecane |
| 20(H14-24) | (3S)-1-propyl-2,5-dioxo-3-(4-(benzyloxycarbonylamino)-butyl)-9-(2-hydroxyphenylmethyl)-1,4,9-triazaspiro-[5.5]undecane |
| 20(H14-25) | (3S)-1-propyl-2,5-dioxo-3-(4-(benzyloxycarbonylamino)-butyl)-9-(4-dihydroxyboranephenylmethyl)-1,4,9-triazaspiro[5.5]undecane |
| 20(H14-26) | (3S)-1-propyl-2,5-dioxo-3-(4-(benzyloxycarbonylamino)-butyl)-9-(4-heptyloxyphenylmethyl)-1,4,9-triazaspiro-[5.5]undecane |
| 20(H14-27) | (3S)-1-propyl-2,5-dioxo-3-(4-(benzyloxycarbonylamino)-butyl)-9-(benzofuran-2-ylmethyl)-1,4,9-triazaspiro-[5.5]undecane |
| 20(H14-28) | (3S)-1-propyl-2,5-dioxo-3-(4-(benzyloxycarbonylamino)-butyl)-9-(3-methylbenzothiophen-2-ylmethyl)-1,4,9-triazaspiro[5.5]undecane |

TABLE 14A-5

| Example No | Compound Name |
|---|---|
| 20(H14-29) | (3S)-1-propyl-2,5-dioxo-3-(4-(benzyloxycarbonylamino)-butyl)-9-(2-(4-chlorophenylthio)phenylmethyl)-1,4,9-triazaspiro[5.5]undecane |
| 20(H14-30) | (3S)-1-propyl-2,5-dioxo-3-(4-(benzyloxycarbonylamino)-butyl)-9-(3,7-dimethyl-6-octenyl)-1,4,9-triazaspiro-[5.5]undecane |
| 20(H14-31) | (3S)-1-propyl-2,5-dioxo-3-(4-(benzyloxycarbonylamino)-butyl)-9-(4-(pyrrolidin-1-yl)phenylmethyl)-1,4,9-triazaspiro[5.5]undecane |
| 20(H14-32) | (3S)-1-propyl-2,5-dioxo-3-(4-(benzyloxycarbonylamino)-butyl)-9-(2-methyl-3-(4-(2,2-dimethylpropyl)phenyl)-propyl)-1,4,9-triazaspiro[5.5]undecane |
| 20(H14-33) | (3S)-1-propyl-2,5-dioxo-3-(4-(benzyloxycarbonylamino)-butyl)-9-(2-benzyloxyphenylmethyl)-1,4,9-triazaspiro-[5.5]undecane |

TABLE 14A-5-continued

| Example No | Compound Name |
|---|---|
| 20(H14-34) | (3S)-1-propyl-2,5-dioxo-3-(4-(benzyloxycarbonylamino)-butyl)-9-(4-hydroxy-3,5-bis(1,1-dimethylethyl)-phenylmethyl)-1,4,9-triazaspiro[5.5]undecane |

TABLE 14A-6

| Example No | Compound Name |
|---|---|
| 20(H14-35) | (3S)-1-propyl-2,5-dioxo-3-(4-(benzyloxycarbonylamino)-butyl)-9-(2-methyl-3-(4-(1-methylethyl)phenyl)propyl)-1,4,9-triazaspiro[5.5]undecane |
| 20(H14-36) | (3S)-1-propyl-2,5-dioxo-3-(4-(benzyloxycarbonylamino)-butyl)-9-(3,4-di-(benzyloxy)phenylmethyl)-1,4,9-triazaspiro[5.5]undecane |
| 20(H14-37) | (3S)-1-propyl-2,5-dioxo-3-(4-(benzyloxycarbonylamino)-butyl)-9-(4-octyloxyphenylmethyl)-1,4,9-triazaspiro-[5.5]undecane |
| 20(H14-38) | (3S)-1-propyl-2,5-dioxo-3-(4-(benzyloxycarbonylamino)-butyl)-9-(3,5,5-trimethylhexyl)-1,4,9-triazaspiro-[5.5]undecane |
| 20(H14-39) | (3S)-1-propyl-2,5-dioxo-3-(4-(benzyloxycarbonylamino)-butyl)-9-butyloxycarbonylmethyl-1,4,9-triazaspiro-[5.5]undecane |
| 20(H14-40) | (3S)-1-propyl-2,5-dioxo-3-(4-(benzyloxycarbonylamino)-butyl)-9-(4-(4-hydroxy-4-methylpentyl)-3-cyclohexenyl-methyl)-1,4,9-triazaspiro[5.5]undecane |
| 20(H14-41) | (3S)-1-propyl-2,5-dioxo-3-(4-(benzyloxycarbonylamino)-butyl)-9-(5-hydroxypentyl)-1,4,9-triazaspiro[5.5]-undecane |

TABLE 14A-7

| Example No | Compound Name |
|---|---|
| 20(H14-42) | (3S)-1-propyl-2,5-dioxo-3-(4-(benzyloxycarbonylamino)-butyl)-9-(2-((1R,2S,3R,5R)-2-hydroxy-4,6,8-trioxaspiro-[bicyclo[3.3.0]octan-7,1'-cyclohexan]-3-ylmethyl)-1,4,9-triazaspiro[5.5]undecane |
| 20(H14-43) | (3S)-1-propyl-2,5-dioxo-3-(4-(benzyloxycarbonylamino)-butyl)-9-(3-phenylpyrazol-4-ylmethyl)-1,4,9-triazaspiro[5.5]undecane |
| 20(H14-44) | (3S)-1-propyl-2,5-dioxo-3-(4-(benzyloxycarbonylamino)-butyl)-9-(4-(1,1-dimethylethyl)phenylmethyl)-1,4,9-triazaspiro[5.5]undecane |
| 20(H14-45) | (3S)-1-propyl-2,5-dioxo-3-(4-(benzyloxycarbonylamino)-butyl)-9-(1,4-benzodioxan-6-ylmethyl)-1,4,9-triazaspiro[5.5]undecane |
| 20(H14-46) | (3S)-1-propyl-2,5-dioxo-3-(4-(benzyloxycarbonylamino)-butyl)-9-(2-(2,2,6-trimethyl-1-cyclohexenyl)ethyl)-1,4,9-triazaspiro[5.5]undecane |
| 20(H14-47) | (3S)-1-propyl-2,5-dioxo-3-(4-(benzyloxycarbonylamino)-butyl)-9-(4-(3-dimethylaminopropyloxy)phenylmethyl)-1,4,9-triazaspiro[5.5]undecane |

TABLE 14A-8

| Example No | Compound Name |
|---|---|
| 20(H14-48) | (3S)-1-propyl-2,5-dioxo-3-(4-(benzyloxycarbonylamino)-butyl)-9-(furan-2-ylmethyl)-1,4,9-triazaspiro[5.5]-undecane |

TABLE 14A-8-continued

| Example No | Compound Name |
|---|---|
| 20(H14-49) | (3S)-1-propyl-2,5-dioxo-3-(4-(benzyloxycarbonylamino)-butyl)-9-(2-methylpropyl)-1,4,9-triazaspiro[5.5]undecane |
| 20(H14-50) | (3S)-1-propyl-2,5-dioxo-3-(4-(benzyloxycarbonylamino)-butyl)-9-cyclohexylmethyl-1,4,9-triazaspiro[5.5]undecane |
| 20(H14-51) | (3S)-1-propyl-2,5-dioxo-3-(4-(benzyloxycarbonylamino)-butyl)-9-(thiazol-2-ylmethyl)-1,4,9-triazaspiro[5.5]undecane |
| 20(H14-52) | (3S)-1-propyl-2,5-dioxo-3-(4-(benzyloxycarbonylamino)-butyl)-9-(4-acetylaminophenylmethyl)-1,4,9-triazaspiro[5.5]undecane |
| 20(H14-53) | (3S)-1-propyl-2,5-dioxo-3-(4-(benzyloxycarbonylamino)-butyl)-9-(2-methoxyphenylmethyl)-1,4,9-triazaspiro[5.5]undecane |
| 20(H14-54) | (3S)-1-propyl-2,5-dioxo-3-(4-(benzyloxycarbonylamino)-butyl)-9-(4-methoxyphenylmethyl)-1,4,9-triazaspiro[5.5]undecane |

TABLE 14A-9

| Example No | Compound Name |
|---|---|
| 20(H14-55) | (3S)-1-propyl-2,5-dioxo-3-(4-(benzyloxycarbonylamino)-butyl)-9-(4-biphenylmethyl)-1,4,9-triazaspiro[5.5]undecane |
| 20(H14-56) | (3S)-1-propyl-2,5-dioxo-3-(4-(benzyloxycarbonylamino)-butyl)-9-((2E,6E)-3,7-dimethyl-2,6-octadienyl)-1,4,9-triazaspiro[5.5]undecane |
| 20(H14-57) | (3S)-1-propyl-2,5-dioxo-3-(4-(benzyloxycarbonylamino)-butyl)-9-(4-dimethylaminophenylmethyl)-1,4,9-triazaspiro[5.5]undecane |
| 20(H14-58) | (3S)-1-propyl-2,5-dioxo-3-(4-(benzyloxycarbonylamino)-butyl)-9-(2-ethylhexyl)-1,4,9-triazaspiro[5.5]undecane |
| 20(H14-59) | (3S)-1-propyl-2,5-dioxo-3-(4-(benzyloxycarbonylamino)-butyl)-9-(3-fluorophenylmethyl)-1,4,9-triazaspiro[5.5]undecane |
| 20(H14-60) | (3S)-1-propyl-2,5-dioxo-3-(4-(benzyloxycarbonylamino)-butyl)-9-(2-hydroxyethyl)-1,4,9-triazaspiro[5.5]undecane |
| 20(H14-61) | (3S)-1-propyl-2,5-dioxo-3-(4-(benzyloxycarbonylamino)-butyl)-9-(naphthalen-1-ylmethyl)-1,4,9-triazaspiro[5.5]undecane |

TABLE 14A-10

| Example No | Compound Name |
|---|---|
| 20(H14-62) | (3S)-1-propyl-2,5-dioxo-3-(4-(benzyloxycarbonylamino)-butyl)-9-propyl-1,4,9-triazaspiro[5.5]undecane |
| 20(H14-63) | (3S)-1-propyl-2,5-dioxo-3-(4-(benzyloxycarbonylamino)-butyl)-9-((2S,3S,4R)-2,3,4,5-tetrahydroxypentyl)-1,4,9-triazaspiro[5.5]undecane |
| 20(H14-64) | (3S)-1-propyl-2,5-dioxo-3-(4-(benzyloxycarbonylamino)-butyl)-9-(thiophen-2-ylmethyl)-1,4,9-triazaspiro[5.5]undecane |
| 20(H14-65) | (3S)-1-propyl-2,5-dioxo-3-(4-(benzyloxycarbonylamino)-butyl)-9-((2E)-decenyl)-1,4,9-triazaspiro[5.5]undecane |
| 20(H14-66) | (3S)-1-propyl-2,5-dioxo-3-(4-(benzyloxycarbonylamino)-butyl)-9-(4-chlorophenylmethyl)-1,4,9-triazaspiro[5.5]undecane |
| 20(H14-67) | (3S)-1-propyl-2,5-dioxo-3-(4-(benzyloxycarbonylamino)-butyl)-9-(1,3-benzodioxolen-4-ylmethyl)-1,4,9-triazaspiro[5.5]undecane |
| 20(H14-68) | (3S)-1-propyl-2,5-dioxo-3-(4-(benzyloxycarbonylamino)-butyl)-9-((3S,4R)-3,4,5-trihydroxypentyl)-1,4,9-triazaspiro[5.5]undecane |

TABLE 14A-11

| Example No | Compound Name |
|---|---|
| 20(H14-69) | (3S)-1-propyl-2,5-dioxo-3-(4-(benzyloxycarbonylamino)-butyl)-9-(2,3-dimethyl-5-oxo-1-phenyl-3-pyrazolin-4-ylmethyl)-1,4,9-triazaspiro[5.5]undecane |
| 20(H14-70) | (3S)-1-propyl-2,5-dioxo-3-(4-(benzyloxycarbonylamino)-butyl)-9-(4-((2E)-4-methylpentenyl)-3-cyclohexenyl-methyl)-1,4,9-triazaspiro[5.5]undecane |
| 20(H14-71) | (3S)-1-propyl-2,5-dioxo-3-(4-(benzyloxycarbonylamino)-butyl)-9-(3-methoxy-4-hexyloxyphenylmethyl)-1,4,9-triazaspiro[5.5]undecane |
| 20(H14-72) | (3S)-1-propyl-2,5-dioxo-3-(4-(benzyloxycarbonylamino)-butyl)-9-(4-fluorophenylmethyl)-1,4,9-triazaspiro[5.5]undecane |
| 20(H14-73) | (3S)-1-propyl-2,5-dioxo-3-(4-(benzyloxycarbonylamino)-butyl)-9-(3,5,6-trimethyl-3-cyclohexenylmethyl)-1,4,9-triazaspiro[5.5]undecane |
| 20(H14-74) | (3S)-1-propyl-2,5-dioxo-3-(4-(benzyloxycarbonylamino)-butyl)-9-(3,5-dimethyl-1-phenylpyrazol-4-ylmethyl)-1,4,9-triazaspiro[5.5]undecane |
| 20(H14-75) | (3S)-1-propyl-2,5-dioxo-3-(4-(benzyloxycarbonylamino)-butyl)-9-(2-benzyloxyethyl)-1,4,9-triazaspiro[5.5]-undecane |

TABLE 14A-12

| Example No | Compound Name |
|---|---|
| 20(H14-76) | (3S)-1-propyl-2,5-dioxo-3-(4-(benzyloxycarbonylamino)-butyl)-9-(3-methoxy-4-benzyloxyphenylmethyl)-1,4,9-triazaspiro[5.5]undecane |
| 20(H14-77) | (3S)-1-propyl-2,5-dioxo-3-(4-(benzyloxycarbonylamino)-butyl)-9-(3-benzyloxyphenylmethyl)-1,4,9-triazaspiro[5.5]undecane |
| 20(H14-78) | (3S)-1-propyl-2,5-dioxo-3-(4-(benzyloxycarbonylamino)-butyl)-9-(4-benzyloxyphenylmethyl)-1,4,9-triazaspiro[5.5]undecane |
| 20(H14-79) | (3S)-1-propyl-2,5-dioxo-3-(4-(benzyloxycarbonylamino)-butyl)-9-(4-phenyloxyphenylmethyl)-1,4,9-triazaspiro[5.5]undecane |
| 20(H14-80) | (3S)-1-propyl-2,5-dioxo-3-(4-(benzyloxycarbonylamino)-butyl)-9-(4-allyloxyphenylmethyl)-1,4,9-triazaspiro[5.5]undecane |

TABLE 15A-1

| Example No | Compound Name |
|---|---|
| 20(H15-1) | 1-propyl-2,5-dioxo-3-(2-methylpropyl)-9-(2,4,6-trimethoxyphenylmethyl)-1,4,9-triazaspiro[5.5]undecane |
| 20(H15-2) | 1-propyl-2,5-dioxo-3-(2-methylpropyl)-9-(3-cyanophenylmethyl)-1,4,9-triazaspiro[5.5]undecane |
| 20(H15-3) | 1-propyl-2,5-dioxo-3-(2-methylpropyl)-9-(3-methylbutyl)-1,4,9-triazaspiro[5.5]undecane |
| 20(H15-4) | 1-propyl-2,5-dioxo-3-(2-methylpropyl)-9-(2-(1-carboxymethyloxy)phenylmethyl)-1,4,9-triazaspiro[5.5]undecane |
| 20(H15-5) | 1-propyl-2,5-dioxo-3-(2-methylpropyl)-9-(4-dimethylaminophenylmethyl)-1,4,9-triazaspiro[5.5]undecane |
| 20(H15-6) | 1-propyl-2,5-dioxo-3-(2-methylpropyl)-9-(3-phenoxyphenylmethyl)-1,4,9-triazaspiro[5.5]undecane |
| 20(H15-7) | 1-propyl-2,5-dioxo-3-(2-methylpropyl)-9-((2E)-2-methylbutenyl)-1,4,9-triazaspiro[5.5]undecane |
| 20(H15-8) | 1-propyl-2,5-dioxo-3-(2-methylpropyl)-9-((1S,5S)-6,6-dimethylbicyclo[3.3.1]-2-hepten-2-ylmethyl)-1,4,9-triazaspiro[5.5]undecane |

TABLE 15A-2

| Example No | Compound Name |
|---|---|
| 20(H15-9) | 1-propyl-2,5-dioxo-3-(2-methylpropyl)-9-(1-carboxymethyl)-1,4,9-triazaspiro[5.5]undecane |
| 20(H15-10) | 1-propyl-2,5-dioxo-3-(2-methylpropyl)-9-cyclopropylmethyl-1,4,9-triazaspiro[5.5]undecane |
| 20(H15-11) | 1-propyl-2,5-dioxo-3-(2-methylpropyl)-9-(3-methylthiopropyl)-1,4,9-triazaspiro[5.5]undecane |
| 20(H15-12) | 1-propyl-2,5-dioxo-3-(2-methylpropyl)-9-(3-carboxypropyl)-1,4,9-triazaspiro[5.5]undecane |
| 20(H15-13) | 1-propyl-2,5-dioxo-3-(2-methylpropyl)-9-(2,6-dimethyl-5-heptenyl)-1,4,9-triazaspiro[5.5]undecane |
| 20(H15-14) | 1-propyl-2,5-dioxo-3-(2-methylpropyl)-9-(quinolin-2-yl)-1,4,9-triazaspiro[5.5]undecane |
| 20(H15-15) | 1-propyl-2,5-dioxo-3-(2-methylpropyl)-9-((2S,3R,4R,5R)-2-acetylamino-3,4,5,6-tetrahydroxyhexanyl)-1,4,9-triazaspiro[5.5]undecane |
| 20(H15-16) | 1-propyl-2,5-dioxo-3-(2-methylpropyl)-9-(2,2-dimethylpropyl)-1,4,9-triazaspiro[5.5]undecane |
| 20(H15-17) | 1-propyl-2,5-dioxo-3-(2-methylpropyl)-9-((4Z)-decenyl)-1,4,9-triazaspiro[5.5]undecane |

TABLE 15A-3

| Example No | Compound Name |
|---|---|
| 20(H15-18) | 1-propyl-2,5-dioxo-3-(2-methylpropyl)-9-(3-phenylpropyl)-1,4,9-triazaspiro[5.5]undecane |
| 20(H15-19) | 1-propyl-2,5-dioxo-3-(2-methylpropyl)-9-butyl-1,4,9-triazaspiro[5.5]undecane |
| 20(H15-20) | 1-propyl-2,5-dioxo-3-(2-methylpropyl)-9-benzyl-1,4,9-triazaspiro[5.5]undecane |
| 20(H15-21) | 1-propyl-2,5-dioxo-3-(2-methylpropyl)-9-((2E)-3-(furan-2-yl)propenyl)-1,4,9-triazaspiro[5.5]undecane |
| 20(H15-22) | 1-propyl-2,5-dioxo-3-(2-methylpropyl)-9-(3-hydroxyphenylmethyl)-1,4,9-triazaspiro[5.5]undecane |
| 20(H15-23) | 1-propyl-2,5-dioxo-3-(2-methylpropyl)-9-(2-hydroxyphenylmethyl)-1,4,9-triazaspiro[5.5]undecane |
| 20(H15-24) | 1-propyl-2,5-dioxo-3-(2-methylpropyl)-9-(4-dihydroxyboranephenylmethyl)-1,4,9-triazaspiro[5.5]undecane |
| 20(H15-25) | 1-propyl-2,5-dioxo-3-(2-methylpropyl)-9-(4-heptyloxyphenylmethyl)-1,4,9-triazaspiro[5.5]undecane |
| 20(H15-26) | 1-propyl-2,5-dioxo-3-(2-methylpropyl)-9-(benzofuran-2-ylmethyl)-1,4,9-triazaspiro[5.5]undecane |

TABLE 15A-4

| Example No | Compound Name |
|---|---|
| 20(H15-27) | 1-propyl-2,5-dioxo-3-(2-methylpropyl)-9-(3-methylbenzothiophen-2-ylmethyl)-1,4,9-triazaspiro[5.5]undecane |
| 20(H15-28) | 1-propyl-2,5-dioxo-3-(2-methylpropyl)-9-(2-(4-chlorophenylthio)phenylmethyl)-1,4,9-triazaspiro[5.5]undecane |
| 20(H15-29) | 1-propyl-2,5-dioxo-3-(2-methylpropyl)-9-(3,7-dimethyl-6-octenyl)-1,4,9-triazaspiro[5.5]undecane |
| 20(H15-30) | 1-propyl-2,5-dioxo-3-(2-methylpropyl)-9-(4-(pyrrolidin-1-yl)phenylmethyl)-1,4,9-triazaspiro[5.5]undecane |
| 20(H15-31) | 1-propyl-2,5-dioxo-3-(2-methylpropyl)-9-(2-methyl-3-(4-(2,2-dimethylpropyl)phenyl)propyl)-1,4,9-triazaspiro[5.5]undecane |
| 20(H15-32) | 1-propyl-2,5-dioxo-3-(2-methylpropyl)-9-(2-benzyloxyphenylmethyl)-1,4,9-triazaspiro[5.5]undecane |

TABLE 15A-4-continued

| Example No | Compound Name |
|---|---|
| 20(H15-33) | 1-propyl-2,5-dioxo-3-(2-methylpropyl)-9-(4-hydroxy-3,5-di-(1,1-dimethylethyl)phenylmethyl)-1,4,9-triazaspiro[5.5]undecane |
| 20(H15-34) | 1-propyl-2,5-dioxo-3-(2-methylpropyl)-9-(2-methyl-3-(4-(1-methylethyl)phenyl)propyl)-1,4,9-triazaspiro[5.5]undecane |

TABLE 15A-5

| Example No | Compound Name |
|---|---|
| 20(H15-35) | 1-propyl-2,5-dioxo-3-(2-methylpropyl)-9-(3,4-di-(benzyloxy)phenylmethyl)-1,4,9-triazaspiro[5.5]undecane |
| 20(H15-36) | 1-propyl-2,5-dioxo-3-(2-methylpropyl)-9-(4-octyloxyphenylmethyl)-1,4,9-triazaspiro[5.5]undecane |
| 20(H15-37) | 1-propyl-2,5-dioxo-3-(2-methylpropyl)-9-(3,5,5-trimethylhexyl)-1,4,9-triazaspiro[5.5]undecane |
| 20(H15-38) | 1-propyl-2,5-dioxo-3-(2-methylpropyl)-9-butyloxycarbonylmethyl-1,4,9-triazaspiro[5.5]undecane |
| 20(H15-39) | 1-propyl-2,5-dioxo-3-(2-methylpropyl)-9-(4-(4-hydroxy-4-methylpentyl)-3-cyclohexenylmethyl)-1,4,9-triazaspiro[5.5]undecane |
| 20(H15-40) | 1-propyl-2,5-dioxo-3-(2-methylpropyl)-9-(5-hydroxypentyl)-1,4,9-triazaspiro[5.5]undecane |
| 20(H15-41) | 1-propyl-2,5-dioxo-3-(2-methylpropyl)-9-(2-((1R,2S,3R,5R)-2-hydroxy-4,6,8-trioxaspiro[bicyclo[3.3.0]octan-7,1'-cyclohexan]-3-ylmethyl)-1,4,9-triazaspiro[5.5]undecane |
| 20(H15-42) | 1-propyl-2,5-dioxo-3-(2-methylpropyl)-9-(3-phenylpyrazol-4-ylmethyl)-1,4,9-triazaspiro[5.5]undecane |

TABLE 15A-6

| Example No | Compound Name |
|---|---|
| 20(H15-43) | 1-propyl-2,5-dioxo-3-(2-methylpropyl)-9-(4-(1,1-dimethylethyl)phenylmethyl)-1,4,9-triazaspiro[5.5]undecane |
| 20(H15-44) | 1-propyl-2,5-dioxo-3-(2-methylpropyl)-9-(1,4-benzodioxan-6-ylmethyl)-1,4,9-triazaspiro[5.5]undecane |
| 20(H15-45) | 1-propyl-2,5-dioxo-3-(2-methylpropyl)-9-(2-(2,2,6-trimethyl-1-cyclohexenyl)ethyl)-1,4,9-triazaspiro[5.5]undecane |
| 20(H15-46) | 1-propyl-2,5-dioxo-3-(2-methylpropyl)-9-(4-(3-dimethylaminopropyloxy)phenylmethyl)-1,4,9-triazaspiro[5.5]undecane |
| 20(H15-47) | 1-propyl-2,5-dioxo-3-(2-methylpropyl)-9-(furan-2-ylmethyl)-1,4,9-triazaspiro[5.5]undecane |
| 20(H15-48) | 1-propyl-2,5-dioxo-3-(2-methylpropyl)-9-(2-methylpropyl)-1,4,9-triazaspiro[5.5]undecane |
| 20(H15-49) | 1-propyl-2,5-dioxo-3-(2-methylpropyl)-9-cyclohexylmethyl-1,4,9-triazaspiro[5.5]undecane |
| 20(H15-50) | 1-propyl-2,5-dioxo-3-(2-methylpropyl)-9-(thiazol-2-ylmethyl)-1,4,9-triazaspiro[5.5]undecane |

TABLE 15A-7

| Example No | Compound Name |
|---|---|
| 20(H15-51) | 1-propyl-2,5-dioxo-3-(2-methylpropyl)-9-(4-acetylaminophenylmethyl)-1,4,9-triazaspiro[5.5]undecane |

TABLE 15A-7-continued

| Example No | Compound Name |
|---|---|
| 20(H15-52) | 1-propyl-2,5-dioxo-3-(2-methylpropyl)-9-(2-methoxyphenylmethyl)-1,4,9-triazaspiro[5.5]undecane |
| 20(H15-53) | 1-propyl-2,5-dioxo-3-(2-methylpropyl)-9-(4-methoxyphenylmethyl)-1,4,9-triazaspiro[5.5]undecane |
| 20(H15-54) | 1-propyl-2,5-dioxo-3-(2-methylpropyl)-9-(4-biphenylmethyl)-1,4,9-triazaspiro[5.5]undecane |
| 20(H15-55) | 1-propyl-2,5-dioxo-3-(2-methylpropyl)-9-(2-ethylhexyl)-1,4,9-triazaspiro[5.5]undecane |
| 20(H15-56) | 1-propyl-2,5-dioxo-3-(2-methylpropyl)-9-(3-fluorophenylmethyl)-1,4,9-triazaspiro[5.5]undecane |
| 20(H15-57) | 1-propyl-2,5-dioxo-3-(2-methylpropyl)-9-(2-hydroxyethyl)-1,4,9-triazaspiro[5.5]undecane |
| 20(H15-58) | 1-propyl-2,5-dioxo-3-(2-methylpropyl)-9-(naphthalen-1-ylmethyl)-1,4,9-triazaspiro[5.5]undecane |
| 20(H15-59) | 1-propyl-2,5-dioxo-3-(2-methylpropyl)-9-propyl-1,4,9-triazaspiro[5.5]undecane |

TABLE 15A-8

| Example No | Compound Name |
|---|---|
| 20(H15-60) | 1-propyl-2,5-dioxo-3-(2-methylpropyl)-9-((2S,3S,4R)-2,3,4,5-tetrahydroxypentyl)-1,4,9-triazaspiro[5.5]undecane |
| 20(H15-61) | 1-propyl-2,5-dioxo-3-(2-methylpropyl)-9-(thiophen-2-ylmethyl)-1,4,9-triazaspiro[5.5]undecane |
| 20(H15-62) | 1-propyl-2,5-dioxo-3-(2-methylpropyl)-9-((2E)-decenyl)-1,4,9-triazaspiro[5.5]undecane |
| 20(H15-63) | 1-propyl-2,5-dioxo-3-(2-methylpropyl)-9-(4-chlorophenylmethyl)-1,4,9-triazaspiro[5.5]undecane |
| 20(H15-64) | 1-propyl-2,5-dioxo-3-(2-methylpropyl)-9-(1,3-benzodioxolen-4-ylmethyl)-1,4,9-triazaspiro[5.5]undecane |
| 20(H15-65) | 1-propyl-2,5-dioxo-3-(2-methylpropyl)-9-((3S,4R)-3,4,5-trihydroxypentyl)-1,4,9-triazaspiro[5.5]undecane |
| 20(H15-66) | 1-propyl-2,5-dioxo-3-(2-methylpropyl)-9-(2,3-dimethyl-5-oxo-1-phenyl-3-pyrazolin-4-ylmethyl)-1,4,9-triazaspiro[5.5]undecane |
| 20(H15-67) | 1-propyl-2,5-dioxo-3-(2-methylpropyl)-9-(4-((2E)-4-methylpentenyl)-3-cyclohexenylmethyl)-1,4,9-triazaspiro[5.5]undecane |

TABLE 15A-9

| Example No | Compound Name |
|---|---|
| 20(H15-68) | 1-propyl-2,5-dioxo-3-(2-methylpropyl)-9-(3-methoxy-4-hexyloxyphenylmethyl)-1,4,9-triazaspiro[5.5]undecane |
| 20(H15-69) | 1-propyl-2,5-dioxo-3-(2-methylpropyl)-9-(4-fluorophenylmethyl)-1,4,9-triazaspiro[5.5]undecane |
| 20(H15-70) | 1-propyl-2,5-dioxo-3-(2-methylpropyl)-9-(3,5,6-trimethyl-3-cyclohexenylmethyl)-1,4,9-triazaspiro[5.5]undecane |
| 20(H15-71) | 1-propyl-2,5-dioxo-3-(2-methylpropyl)-9-(3,5-dimethyl-1-phenylpyrazol-4-ylmethyl)-1,4,9-triazaspiro[5.5]undecane |
| 20(H15-72) | 1-propyl-2,5-dioxo-3-(2-methylpropyl)-9-(2-benzyloxyethyl)-1,4,9-triazaspiro[5.5]undecane |
| 20(H15-73) | 1-propyl-2,5-dioxo-3-(2-methylpropyl)-9-(3-methoxy-4-benzyloxyphenylmethyl)-1,4,9-triazaspiro[5.5]undecane |

TABLE 15A-9-continued

| Example No | Compound Name |
|---|---|
| 20(H15-74) | 1-propyl-2,5-dioxo-3-(2-methylpropyl)-9-(3-benzyloxyphenylmethyl)-1,4,9-triazaspiro[5.5]undecane |
| 20(H15-75) | 1-propyl-2,5-dioxo-3-(2-methylpropyl)-9-(4-benzyloxyphenylmethyl)-1,4,9-triazaspiro[5.5]undecane |

TABLE 15A-10

| Example No | Compound Name |
|---|---|
| 20(H15-76) | 1-propyl-2,5-dioxo-3-(2-methylpropyl)-9-(4-phenyloxyphenylmethyl)-1,4,9-triazaspiro[5.5]undecane |
| 20(H15-77) | 1-propyl-2,5-dioxo-3-(2-methylpropyl)-9-(4-allyloxyphenylmethyl)-1,4,9-triazaspiro[5.5]undecane |

TABLE 14B-1

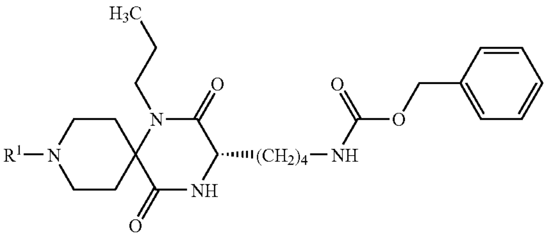

| Example No | $R^1$ |
|---|---|
| 20(H14-1) | 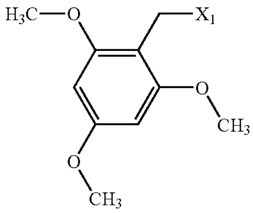 |
| 20(H14-2) | 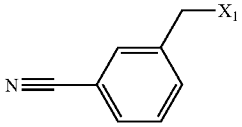 |
| 20(H14-3) | 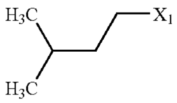 |
| 20(H14-4) | 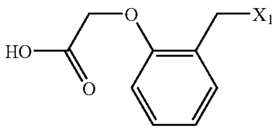 |

TABLE 14B-1-continued

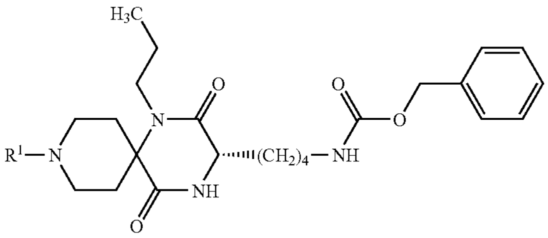

| Example No | $R^1$ |
|---|---|
| 20(H14-5) | 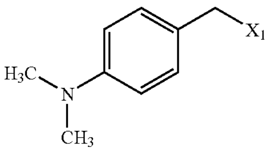 |
| 20(H14-6) | 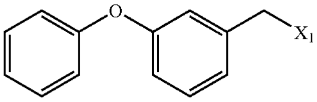 |

TABLE 14B-2

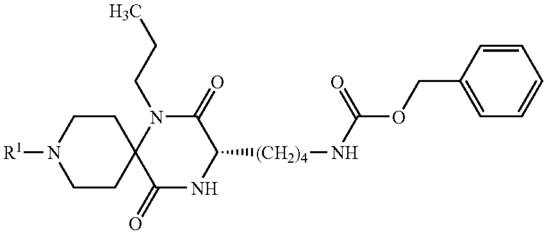

| Example No | $R^1$ |
|---|---|
| 20(H14-7) | 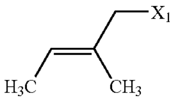 |
| 20(H14-8) | 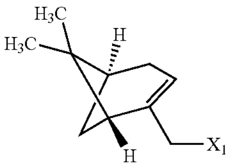 |
| 20(H14-9) | 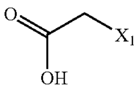 |
| 20(H14-10) | 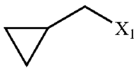 |
| 20(H14-11) | 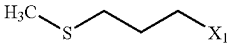 |
| 20(H14-12) | 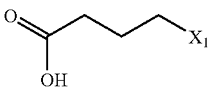 |

TABLE 14B-2-continued
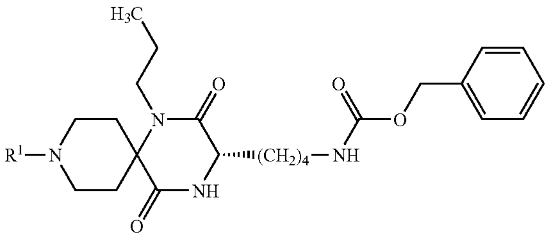
| Example No | $R^1$ |
|---|---|
| 20(H14-13) | 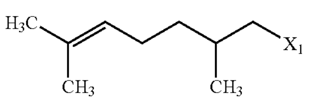 |
| 20(H14-14) | 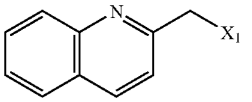 |
TABLE 14B-3
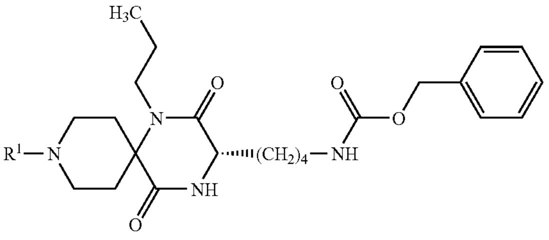
| Example No | $R^1$ |
|---|---|
| 20(H14-15) | 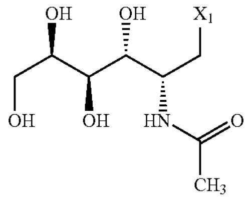 |
| 20(H14-16) | 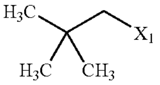 |
| 20(H14-17) | 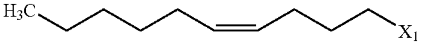 |
| 20(H14-18) | 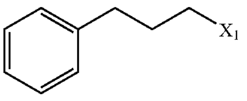 |
| 20(H14-19) | 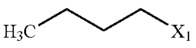 |
| 20(H14-20) | 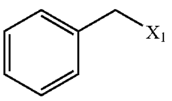 |
TABLE 14B-3-continued
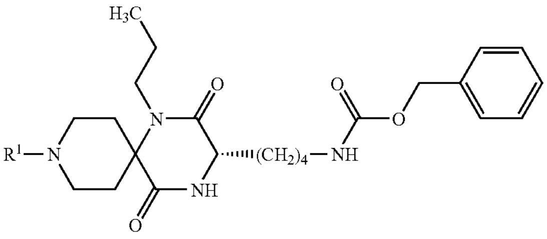
| Example No | $R^1$ |
|---|---|
| 20(H14-21) | 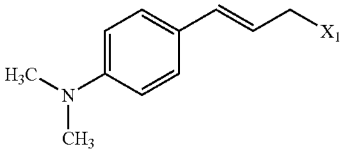 |
| 20(H14-22) | 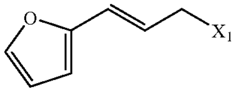 |
TABLE 14B-4
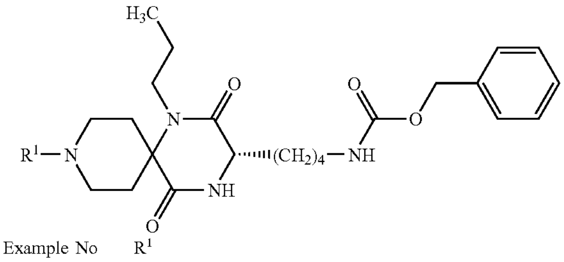
| Example No | $R^1$ |
|---|---|
| 20(H14-23) | 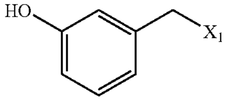 |
| 20(H14-24) | 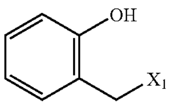 |
| 20(H14-25) | 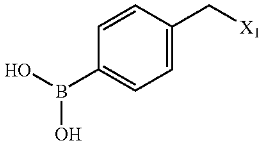 |
| 20(H14-26) | 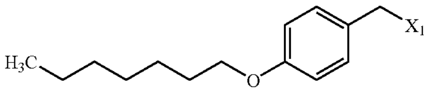 |
| 20(H14-27) | 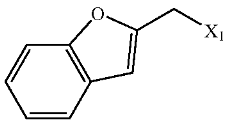 |

TABLE 14B-4-continued
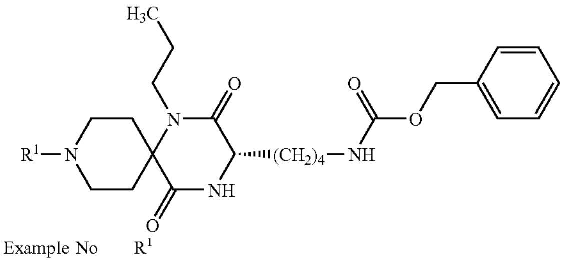
| Example No | $R^1$ |
|---|---|
| 20(H14-28) | 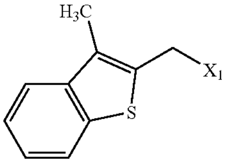 |
| 20(H14-29) | 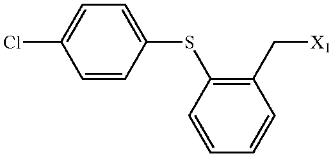 |
TABLE 14B-5
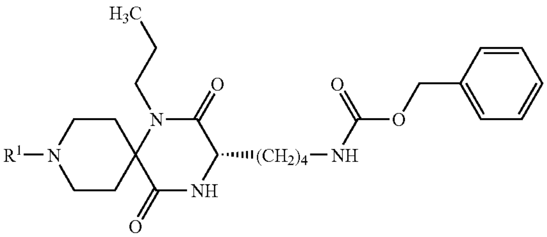
| Example No | $R^1$ |
|---|---|
| 20(H14-30) | 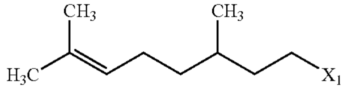 |
| 20(H14-31) | 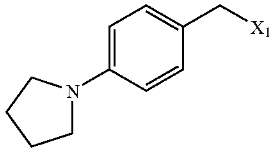 |
| 20(H14-32) | 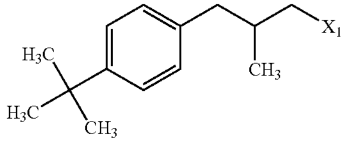 |
| 20(H14-33) | 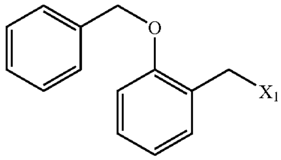 |
TABLE 14B-5-continued
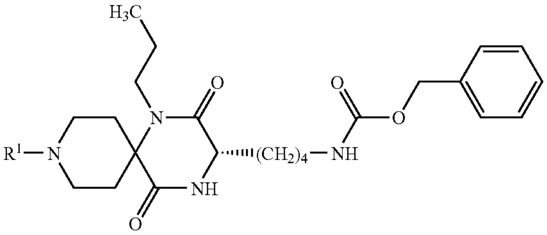
| Example No | $R^1$ |
|---|---|
| 20(H14-34) | 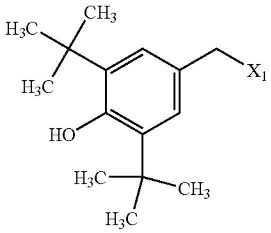 |
| 20(H14-35) | 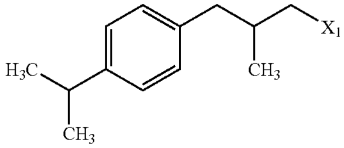 |
TABLE 14B-6
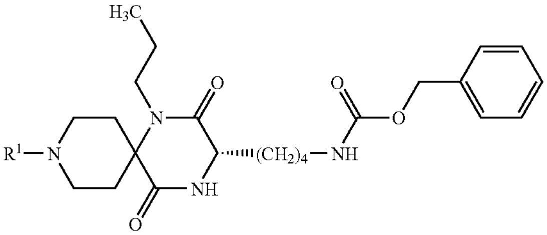
| Example No | $R^1$ |
|---|---|
| 20(H14-36) | 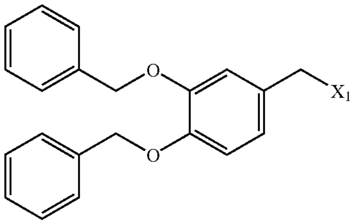 |
| 20(H14-37) | 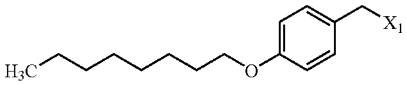 |
| 20(H14-38) | 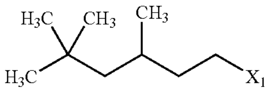 |

TABLE 14B-6-continued
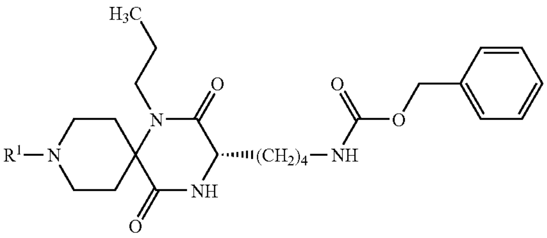
| Example No | $R^1$ |
|---|---|
| 20(H14-39) | 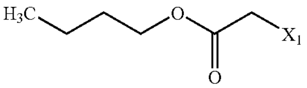 |
| 20(H14-40) | 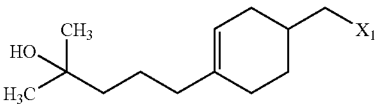 |
| 20(H14-41) | 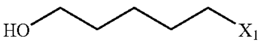 |
| 20(H14-42) | 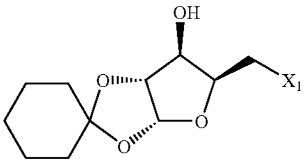 |
TABLE 14B-7
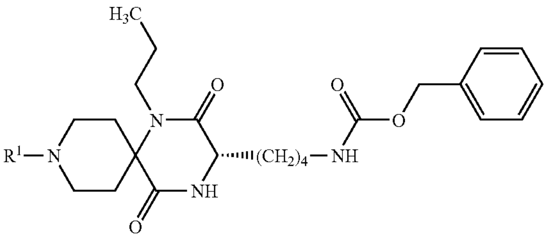
| Example No | $R^1$ |
|---|---|
| 20(H14-43) | 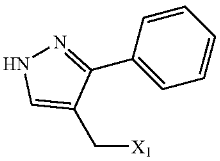 |
| 20(H14-44) | 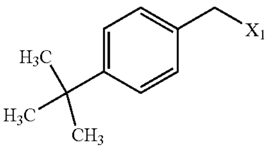 |
| 20(H14-45) | 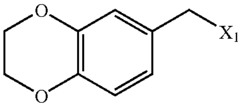 |
TABLE 14B-7-continued
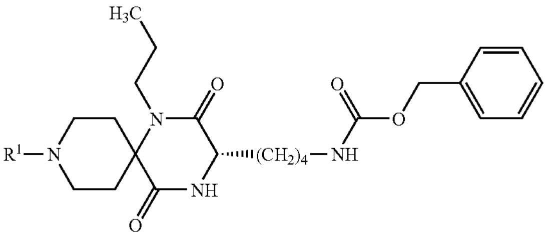
| Example No | $R^1$ |
|---|---|
| 20(H14-46) | 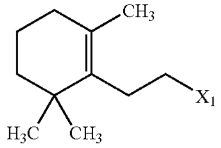 |
| 20(H14-48) | 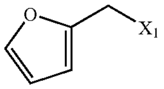 |
| 20(H14-49) | 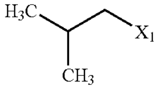 |
TABLE 14B-8
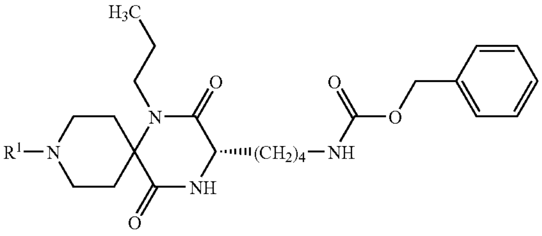
| Example No | $R^1$ |
|---|---|
| 20(H14-50) | 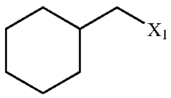 |
| 20(H14-51) | 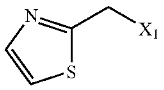 |
| 20(H14-52) | 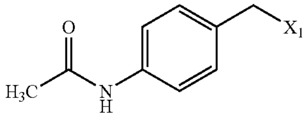 |
| 20(H14-53) | 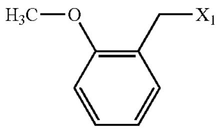 |

TABLE 14B-8-continued
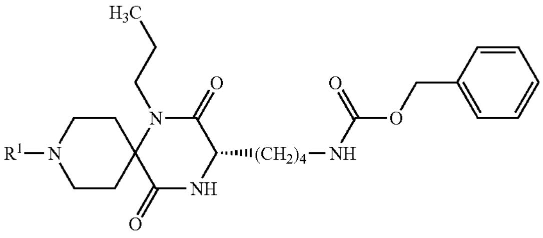
| Example No | $R^1$ |
|---|---|
| 20(H14-54) | 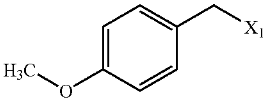 |
| 20(H14-55) | 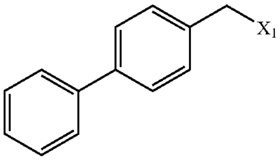 |
| 20(H14-56) | 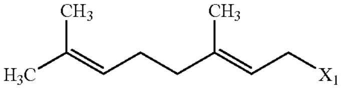 |
| 20(H14-57) | 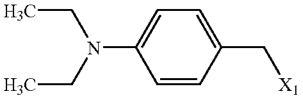 |
TABLE 14B-9
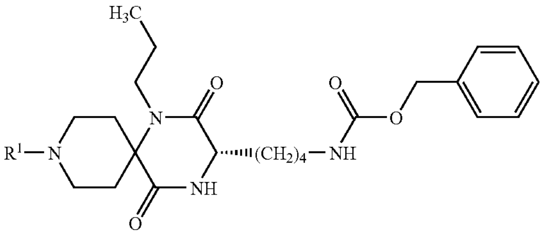
| Example No | $R^1$ |
|---|---|
| 20(H14-58) | 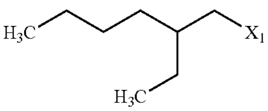 |
| 20(H14-59) | 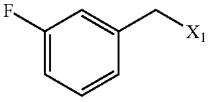 |
| 20(H14-60) | 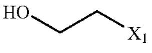 |
TABLE 14B-9-continued
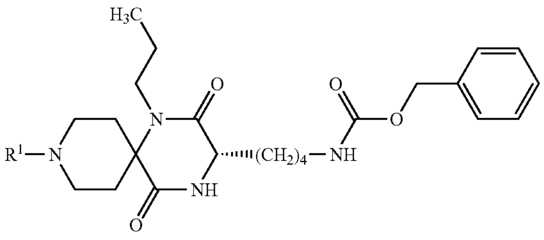
| Example No | $R^1$ |
|---|---|
| 20(H14-61) | 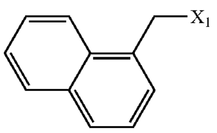 |
| 20(H14-62) | 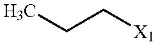 |
| 20(H14-63) | 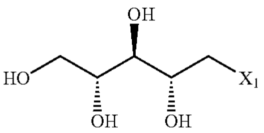 |
| 20(H14-64) | 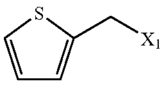 |
| 20(H14-65) | 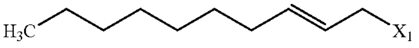 |
| 20(H14-66) | 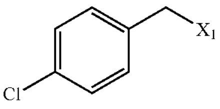 |
TABLE 14B-10
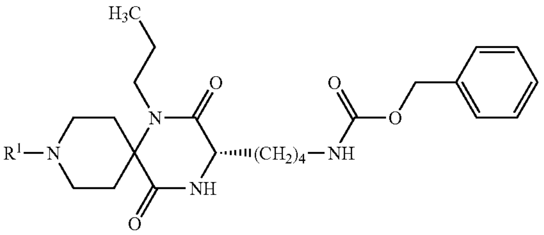
| Example No | $R^1$ |
|---|---|
| 20(H14-67) | 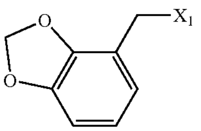 |
| 20(H14-68) | 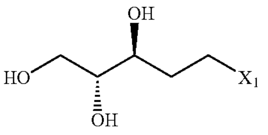 |

TABLE 14B-10-continued
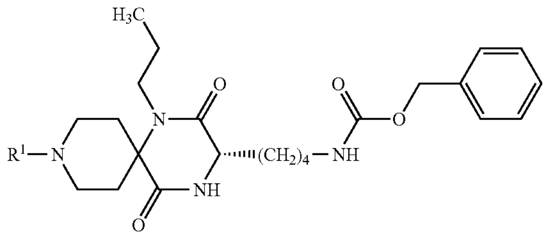
| Example No | $R^1$ |
|---|---|
| 20(H14-69) | 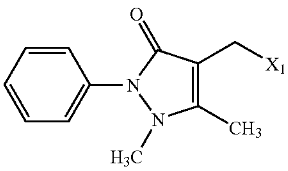 |
| 20(H14-70) | 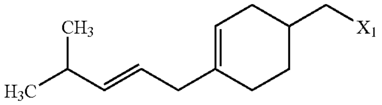 |
| 20(H14-71) | 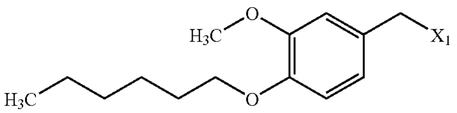 |
| 20(H14-72) | 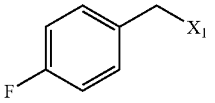 |
| 20(H14-73) | 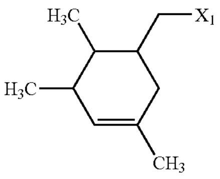 |
TABLE 14B-11
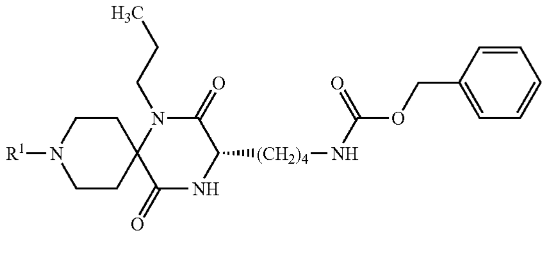
| Example No | $R^1$ |
|---|---|
| 20(H14-74) | 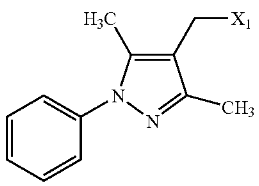 |
TABLE 14B-11-continued
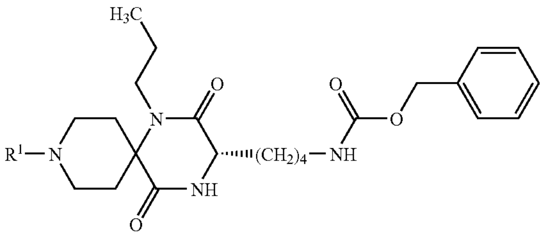
| Example No | $R^1$ |
|---|---|
| 20(H14-75) | 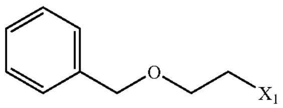 |
| 20(H14-76) | 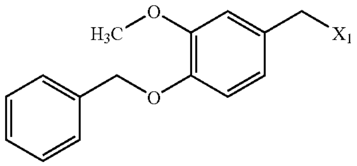 |
| 20(H14-77) | 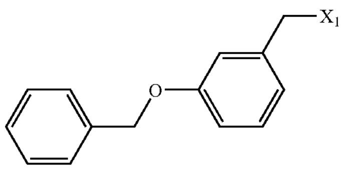 |
| 20(H14-78) | 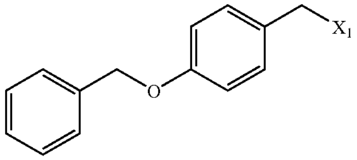 |
| 20(H14-79) | 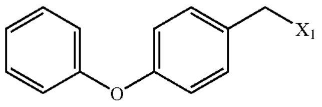 |
| 20(H14-80) | 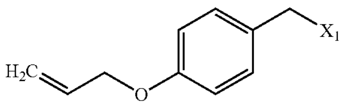 |

TABLE 15B-1
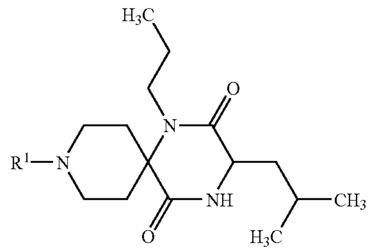
| Example No | $R^1$ |
| --- | --- |
| 20(H15-1) | 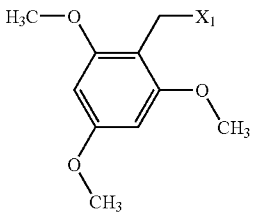 |
| 20(H15-2) | 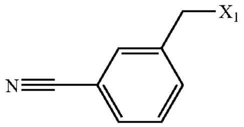 |
| 20(H15-3) | 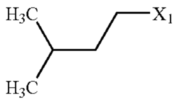 |
| 20(H15-4) | 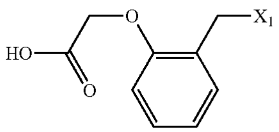 |
| 20(H15-5) | 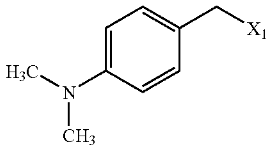 |
| 20(H15-6) | 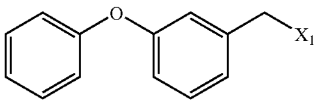 |
TABLE 15B-2
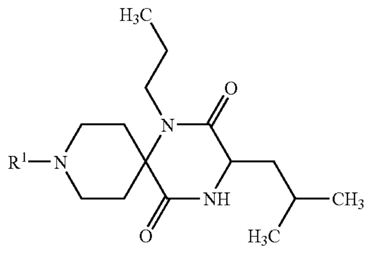
| Example No | $R^1$ |
| --- | --- |
| 20(H15-7) | 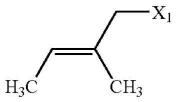 |
| 20(H15-8) | 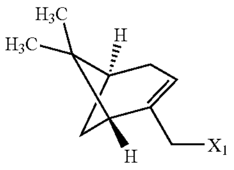 |
| 20(H15-9) | 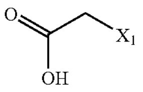 |
| 20(H15-10) | 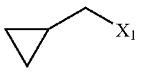 |
| 20(H15-11) | 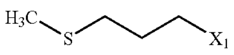 |
| 20(H15-12) | 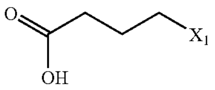 |
| 20(H15-13) | 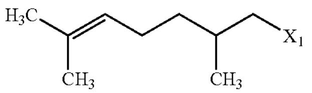 |
| 20(H15-14) | 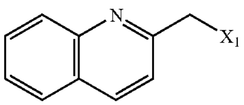 |

TABLE 15B-3
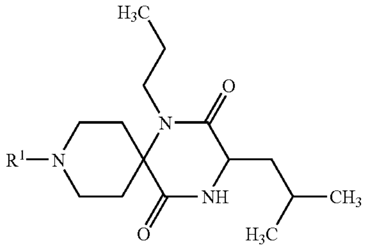
| Example No | $R^1$ |
| --- | --- |
| 20(H15-15) | 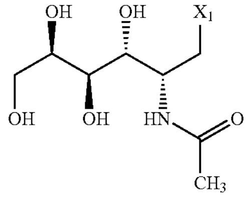 |
| 20(H15-16) | 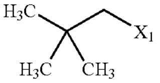 |
| 20(H15-17) | 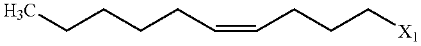 |
| 20(H15-18) | 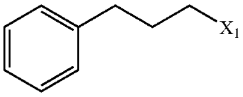 |
| 20(H15-19) | 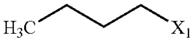 |
| 20(H15-20) | 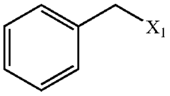 |
| 20(H15-21) | 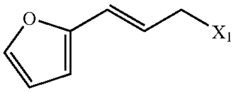 |
| 20(H15-22) | 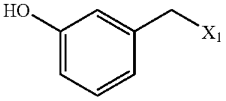 |
TABLE 15B-4
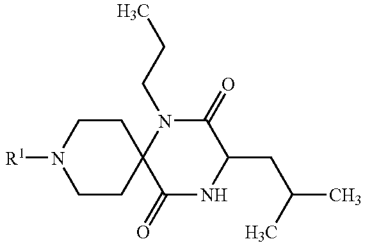
| Example No | $R^1$ |
| --- | --- |
| 20(H15-23) | 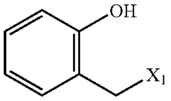 |
| 20(H15-24) | 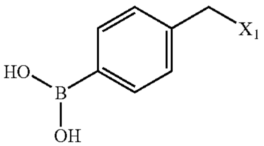 |
| 20(H15-25) | 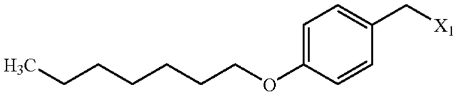 |
| 20(H15-26) | 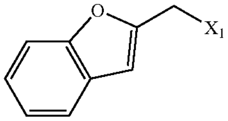 |
| 20(H15-27) | 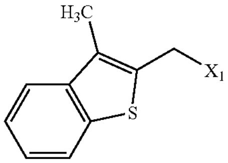 |
| 20(H15-28) | 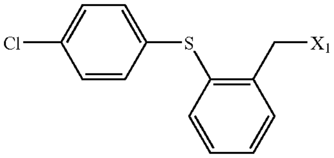 |
| 20(H15-29) | 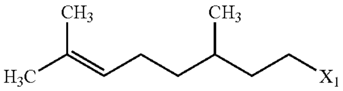 |

TABLE 15B-5
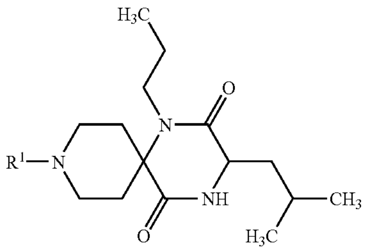
| Example No | $R^1$ |
| --- | --- |
| 20(H15-30) | 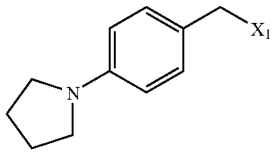 |
| 20(H15-31) | 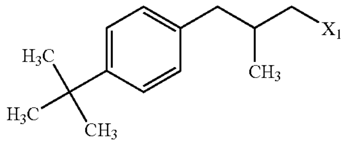 |
| 20(H15-32) | 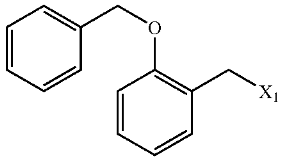 |
| 20(H15-33) | 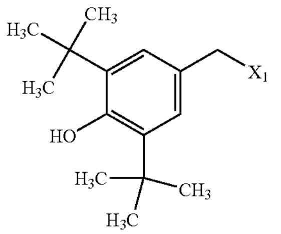 |
| 20(H15-34) | 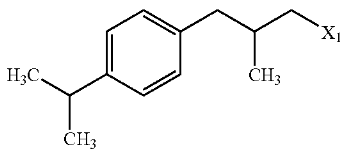 |
TABLE 15B-6
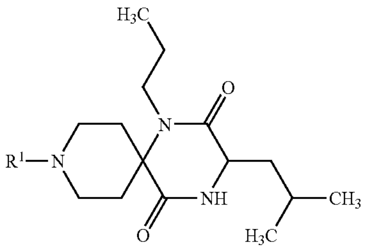
| Example No | $R^1$ |
| --- | --- |
| 20(H15-35) | 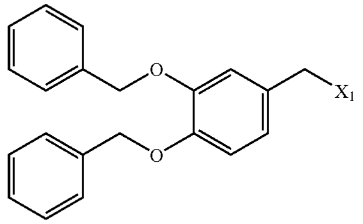 |
| 20(H15-36) | 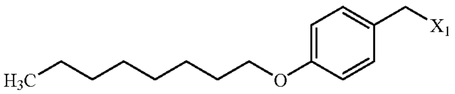 |
| 20(H15-37) | 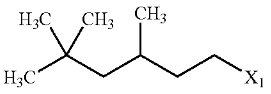 |
| 20(H15-38) | 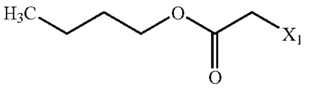 |
| 20(H15-39) | 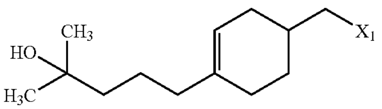 |
| 20(H15-40) | 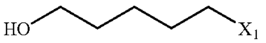 |
| 20(H15-41) | 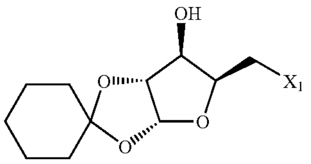 |

TABLE 15B-7
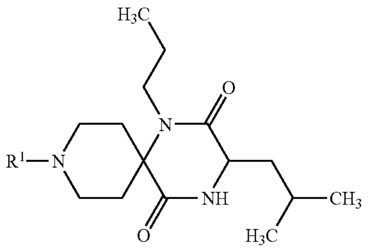
| Example No | $R^1$ |
|---|---|
| 20(H15-42) | 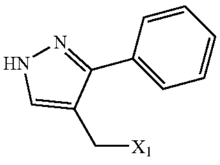 |
| 20(H15-43) | 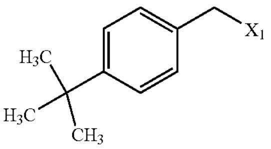 |
| 20(H15-44) | 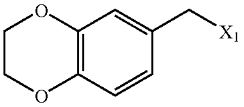 |
| 20(H15-45) | 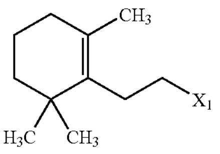 |
| 20(H15-46) | 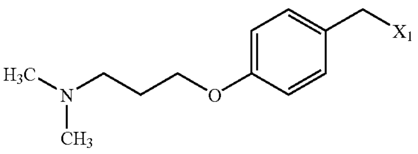 |
| 20(H15-47) | 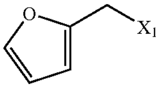 |
| 20(H15-48) | 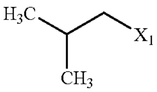 |
TABLE 15B-8
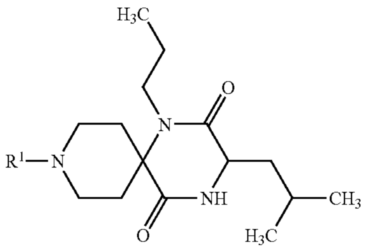
| Example No | $R^1$ |
|---|---|
| 20(H15-49) | 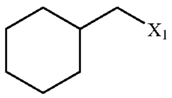 |
| 20(H15-50) | 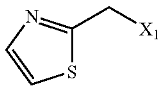 |
| 20(H15-51) | 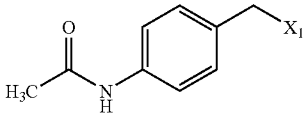 |
| 20(H15-52) | 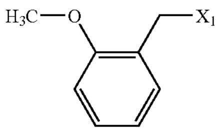 |
| 20(H15-53) | 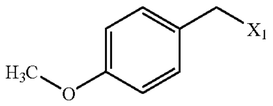 |
| 20(H15-54) | 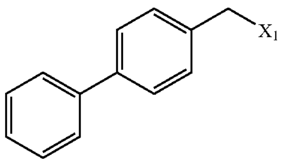 |
| 20(H15-55) | 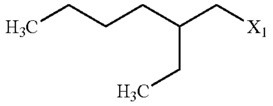 |

TABLE 15B-9
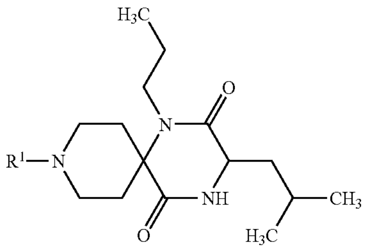
| Example No | $R^1$ |
|---|---|
| 20(H15-56) | 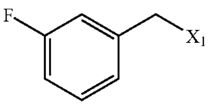 |
| 20(H15-57) | 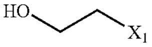 |
| 20(H15-58) | 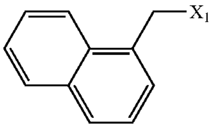 |
| 20(H15-59) | 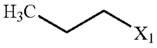 |
| 20(H15-60) | 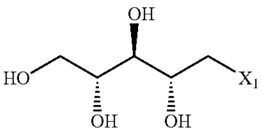 |
| 20(H15-61) | 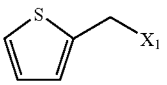 |
| 20(H15-62) | 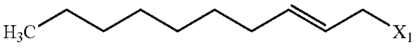 |
| 20(H15-63) | 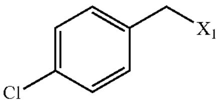 |
| 20(H15-64) | 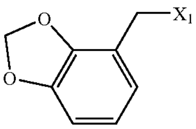 |
TABLE 15B-10
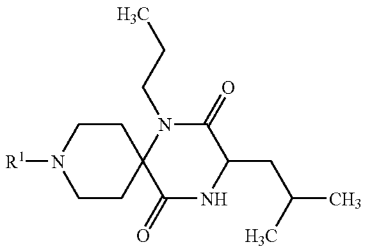
| Example No | $R^1$ |
|---|---|
| 20(H15-65) | 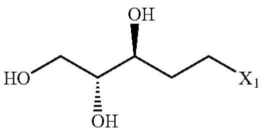 |
| 20(H15-66) | 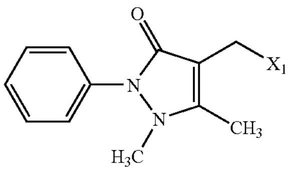 |
| 20(H15-67) | 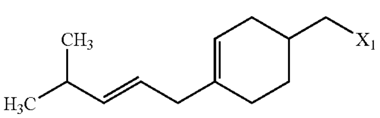 |
| 20(H15-68) | 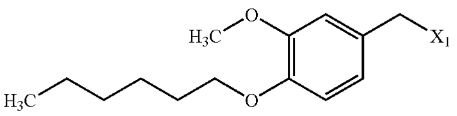 |
| 20(H15-69) | 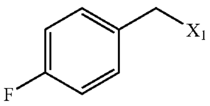 |
| 20(H15-70) | 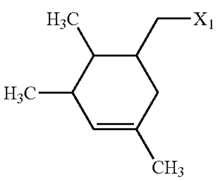 |

TABLE 15B-11

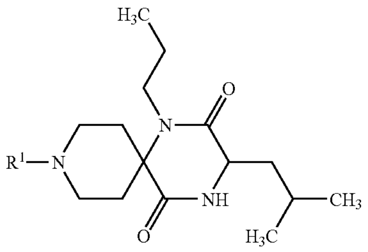

| Example No | $R^1$ |
|---|---|
| 20(H15-71) | 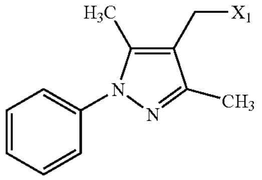 |
| 20(H15-72) | 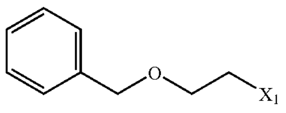 |
| 20(H15-73) | 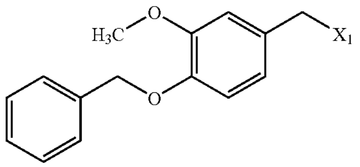 |
| 20(H15-74) | 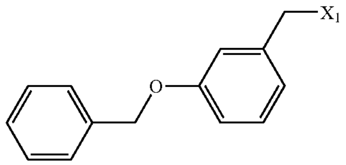 |
| 20(H15-75) | 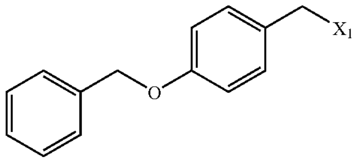 |
| 20(H15-76) | 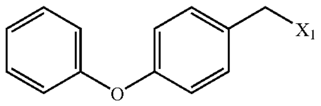 |

TABLE 15B-12

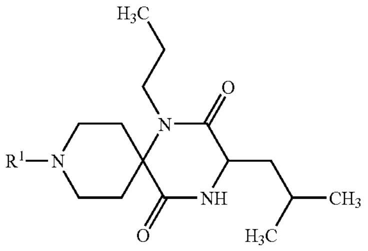

| Example No | $R^1$ |
|---|---|
| 20(H15-77) | 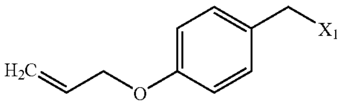 |

TABLE 14C-1

| Example No | HPLC condition | Retention time (min) | Mass data | Mass condition |
|---|---|---|---|---|
| 20(H14-1) | F | 3.40 | 611 $(M + H)^+$. | ESI (Pos., 20 V) |
| 20(H14-2) | F | 3.27 | 546 $(M + H)^+$. | ESI (Pos., 20 V) |
| 20(H14-3) | F | 3.29 | 501 $(M + H)^+$. | ESI (Pos., 20 V) |
| 20(H14-4) | F | 3.25 | 595 $(M + H)^+$. | ESI (Pos., 20 V) |
| 20(H14-5) | F | 3.12 | 564 $(M + H)^+$. | ESI (Pos., 20 V) |
| 20(H14-6) | F | 3.52 | 613 $(M + H)^+$. | ESI (Pos., 20 V) |
| 20(H14-7) | F | 3.25 | 499 $(M + H)^+$. | ESI (Pos., 20 V) |
| 20(H14-8) | F | 3.49 | 565 $(M + H)^+$. | ESI (Pos., 20 V) |
| 20(H14-9) | F | 3.09 | 489 $(M + H)^+$. | ESI (Pos., 20 V) |
| 20(H14-10) | F | 3.18 | 485 $(M + H)^+$. | ESI (Pos., 20 V) |
| 20(H14-11) | F | 3.23 | 519 $(M + H)^+$. | ESI (Pos., 20 V) |
| 20(H14-12) | F | 3.12 | 517 $(M + H)^+$. | ESI (Pos., 20 V) |
| 20(H14-13) | F | 3.53 | 555 $(M + H)^+$. | ESI (Pos., 20 V) |
| 20(H14-14) | F | 3.33 | 572 $(M + H)^+$. | ESI (Pos., 20 V) |
| 20(H14-15) | F | 3.03 | 636 $(M + H)^+$. | ESI (Pos., 20 V) |
| 20(H14-16) | F | 3.25 | 501 $(M + H)^+$. | ESI (Pos., 20 V) |
| 20(H14-17) | F | 3.66 | 569 $(M + H)^+$. | ESI (Pos., 20 V) |
| 20(H14-18) | F | 3.38 | 549 $(M + H)^+$. | ESI (Pos., 20 V) |
| 20(H14-19) | F | 3.22 | 487 $(M + H)^+$. | ESI (Pos., 20 V) |
| 20(H14-20) | F | 3.29 | 521 $(M + H)^+$. | ESI (Pos., 20 V) |
| 20(H14-21) | F | 3.11 | 590 $(M + H)^+$. | ESI (Pos., 20 V) |
| 20(H14-22) | F | 3.31 | 537 $(M + H)^+$. | ESI (Pos., 20 V) |
| 20(H14-23) | F | 3.20 | 537 $(M + H)^+$. | ESI (Pos., 20 V) |
| 20(H14-24) | F | 3.23 | 537 $(M + H)^+$. | ESI (Pos., 20 V) |
| 20(H14-25) | F | 3.16 | 565 $(M + H)^+$. | ESI (Pos., 20 V) |
| 20(H14-26) | F | 3.82 | 635 $(M + H)^+$. | ESI (Pos., 20 V) |

TABLE 14C-2

| Example No | HPLC condition | Retention time (min) | Mass data | Mass condition |
|---|---|---|---|---|
| 20(H14-27) | F | 3.36 | 561 $(M + H)^+$. | ESI (Pos., 20 V) |
| 20(H14-28) | F | 3.44 | 591 $(M + H)^+$. | ESI (Pos., 20 V) |
| 20(H14-29) | F | 3.62 | 663 $(M + H)^+$. | ESI (Pos., 20 V) |
| 20(H14-30) | F | 3.60 | 569 $(M + H)^+$. | ESI (Pos., 20 V) |
| 20(H14-31) | F | 3.40 | 590 $(M + H)^+$. | ESI (Pos., 20 V) |
| 20(H14-32) | F | 3.67 | 619 $(M + H)^+$. | ESI (Pos., 20 V) |
| 20(H14-33) | F | 3.51 | 627 $(M + H)^+$. | ESI (Pos., 20 V) |
| 20(H14-34) | F | 3.66 | 649 $(M + H)^+$. | ESI (Pos., 20 V) |
| 20(H14-35) | F | 3.64 | 605 $(M + H)^+$. | ESI (Pos., 20 V) |
| 20(H14-36) | F | 3.71 | 733 $(M + H)^+$. | ESI (Pos., 20 V) |
| 20(H14-37) | F | 3.91 | 649 $(M + H)^+$. | ESI (Pos., 20 V) |
| 20(H14-38) | F | 3.56 | 557 $(M + H)^+$. | ESI (Pos., 20 V) |
| 20(H14-39) | F | 3.33 | 545 $(M + H)^+$. | ESI (Pos., 20 V) |
| 20(H14-40) | F | 3.38 | 625 $(M + H)^+$. | ESI (Pos., 20 V) |
| 20(H14-41) | F | 3.12 | 517 $(M + H)^+$. | ESI (Pos., 20 V) |

TABLE 14C-2-continued

| Example No | HPLC condi-tion | Retention time (min) | Mass data | Mass condition |
|---|---|---|---|---|
| 20(H14-42) | F | 3.34 | 643 $(M + H)^+$. | ESI (Pos., 20 V) |
| 20(H14-43) | F | 3.23 | 587 $(M + H)^+$. | ESI (Pos., 20 V) |
| 20(H14-44) | F | 3.53 | 577 $(M + H)^+$. | ESI (Pos., 20 V) |
| 20(H14-45) | F | 3.31 | 579 $(M + H)^+$. | ESI (Pos., 20 V) |
| 20(H14-46) | F | 3.60 | 581 $(M + H)^+$. | ESI (Pos., 20 V) |
| 20(H14-47) | F | 3.09 | 622 $(M + H)^+$. | ESI (Pos., 20 V) |
| 20(H14-48) | F | 3.22 | 511 $(M + H)^+$. | ESI (Pos., 20 V) |
| 20(H14-49) | F | 3.20 | 487 $(M + H)^+$. | ESI (Pos., 20 V) |
| 20(H14-50) | F | 3.36 | 527 $(M + H)^+$. | ESI (Pos., 20 V) |
| 20(H14-51) | F | 3.14 | 528 $(M + H)^+$. | ESI (Pos., 20 V) |
| 20(H14-52) | F | 3.16 | 578 $(M + H)^+$. | ESI (Pos., 20 V) |

TABLE 14C-3

| Example No | HPLC condi-tion | Retention time (min) | Mass data | Mass condition |
|---|---|---|---|---|
| 20(H14-53) | F | 3.31 | 551 $(M + H)^+$. | ESI (Pos., 20 V) |
| 20(H14-54) | F | 3.31 | 551 $(M + H)^+$. | ESI (Pos., 20 V) |
| 20(H14-55) | F | 3.51 | 597 $(M + H)^+$. | ESI (Pos., 20 V) |
| 20(H14-56) | F | 3.55 | 567 $(M + H)^+$. | ESI (Pos., 20 V) |
| 20(H14-57) | F | 3.09 | 592 $(M + H)^+$. | ESI (Pos., 20 V) |
| 20(H14-58) | F | 3.51 | 543 $(M + H)^+$. | ESI (Pos., 20 V) |
| 20(H14-59) | F | 3.31 | 539 $(M + H)^+$. | ESI (Pos., 20 V) |
| 20(H14-60) | F | 3.07 | 475 $(M + H)^+$. | ESI (Pos., 20 V) |
| 20(H14-61) | F | 3.40 | 571 $(M + H)^+$. | ESI (Pos., 20 V) |
| 20(H14-62) | F | 3.15 | 473 $(M + H)^+$. | ESI (Pos., 20 V) |
| 20(H14-63) | F | 3.04 | 565 $(M + H)^+$. | ESI (Pos., 20 V) |
| 20(H14-64) | F | 3.25 | 527 $(M + H)^+$. | ESI (Pos., 20 V) |
| 20(H14-65) | F | 3.69 | 569 $(M + H)^+$. | ESI (Pos., 20 V) |
| 20(H14-66) | F | 3.38 | 555 $(M + H)^+$. | ESI (Pos., 20 V) |
| 20(H14-67) | F | 3.29 | 565 $(M + H)^+$. | ESI (Pos., 20 V) |
| 20(H14-68) | F | 3.03 | 549 $(M + H)^+$. | ESI (Pos., 20 V) |
| 20(H14-69) | F | 3.22 | 631 $(M + H)^+$. | ESI (Pos., 20 V) |
| 20(H14-70) | F | 3.69 | 607 $(M + H)^+$. | ESI (Pos., 20 V) |
| 20(H14-71) | F | 3.66 | 651 $(M + H)^+$. | ESI (Pos., 20 V) |
| 20(H14-72) | F | 3.31 | 539 $(M + H)^+$. | ESI (Pos., 20 V) |
| 20(H14-73) | F | 3.50 | 567 $(M + H)^+$. | ESI (Pos., 20 V) |
| 20(H14-74) | F | 3.31 | 615 $(M + H)^+$. | ESI (Pos., 20 V) |
| 20(H14-75) | F | 3.35 | 565 $(M + H)^+$. | ESI (Pos., 20 V) |
| 20(H14-76) | F | 3.51 | 657 $(M + H)^+$. | ESI (Pos., 20 V) |
| 20(H14-77) | F | 3.55 | 627 $(M + H)^+$. | ESI (Pos., 20 V) |
| 20(H14-78) | F | 3.55 | 627 $(M + H)^+$. | ESI (Pos., 20 V) |

TABLE 14C-4

| Example No | HPLC condi-tion | Retention time (min) | Mass data | Mass condition |
|---|---|---|---|---|
| 20(H14-79) | F | 3.53 | 613 $(M + H)^+$. | ESI (Pos., 20 V) |
| 20(H14-80) | F | 3.42 | 577 $(M + H)^+$. | ESI (Pos., 20 V) |

TABLE 15C-1

| Example No | HPLC condi-tion | Retention time (min) | Mass data | Mass condition |
|---|---|---|---|---|
| 20(H15-1) | D | 12.20 | 462 $(M + H)^+$, 282, 181. | APCI (Pos., 40 V) |
| 20(H15-2) | D | 10.20 | 397 $(M + H)^+$. | APCI (Pos., 40 V) |

TABLE 15C-1-continued

| Example No | HPLC condi-tion | Retention time (min) | Mass data | Mass condition |
|---|---|---|---|---|
| 20(H15-3) | D | 10.50 | 352 $(M + H)^+$. | APCI (Pos., 40 V) |
| 20(H15-4) | D | 10.90 | 446 $(M + H)^+$. | APCI (Pos., 40 V) |
| 20(H15-5) | D | 9.47 | 415 $(M + H)^+$, 282, 150. | APCI (Pos., 40 V) |
| 20(H15-6) | D | 13.90 | 464 $(M + H)^+$. | APCI (Pos., 40 V) |
| 20(H15-7) | D | 10.50 | 350 $(M + H)^+$. | APCI (Pos., 40 V) |
| 20(H15-8) | D | 13.70 | 416 $(M + H)^+$. | APCI (Pos., 40 V) |
| 20(H15-9) | D | 8.05 | 340 $(M + H)^+$, 282. | APCI (Pos., 40 V) |
| 20(H15-10) | D | 9.26 | 336 $(M + H)^+$. | APCI (Pos., 40 V) |
| 20(H15-11) | D | 9.73 | 370 $(M + H)^+$, 282. | APCI (Pos., 40 V) |
| 20(H15-12) | D | 8.36 | 368 $(M + H)^+$, 310, 282. | APCI (Pos., 40 V) |
| 20(H15-13) | D | 13.70 | 406 $(M + H)^+$. | APCI (Pos., 40 V) |
| 20(H15-14) | D | 12.40 | 423 $(M + H)^+$, 158. | APCI (Pos., 40 V) |
| 20(H15-15) | D | 7.94 | 487 $(M + H)^+$, 310, 282. | APCI (Pos., 40 V) |
| 20(H15-16) | D | 9.94 | 352 $(M + H)^+$, 310. | APCI (Pos., 40 V) |
| 20(H15-17) | D | 15.10 | 420 $(M + H)^+$. | APCI (Pos., 40 V) |
| 20(H15-18) | D | 11.80 | 400 $(M + H)^+$. | APCI (Pos., 40 V) |
| 20(H15-19) | D | 9.80 | 338 $(M + H)^+$. | APCI (Pos., 40 V) |
| 20(H15-20) | D | 10.80 | 372 $(M + H)^+$. | APCI (Pos., 40 V) |
| 20(H15-21) | D | 11.20 | 388 $(M + H)^+$. | APCI (Pos., 40 V) |
| 20(H15-22) | D | 10.10 | 388 $(M + H)^+$. | APCI (Pos., 40 V) |
| 20(H15-23) | D | 10.70 | 388 $(M + H)^+$, 282. | APCI (Pos., 40 V) |
| 20(H15-24) | D | 9.80 | 416 $(M + H)^+$, 372, 310, 282. | APCI (Pos., 40 V) |
| 20(H15-25) | D | 16.40 | 486 $(M + H)^+$. | APCI (Pos., 40 V) |
| 20(H15-26) | D | 12.30 | 412 $(M + H)^+$. | APCI (Pos., 40 V) |

TABLE 15C-2

| Example No | HPLC condi-tion | Retention time (min) | Mass data | Mass condition |
|---|---|---|---|---|
| 20(H15-27) | D | 13.20 | 442 $(M + H)^+$. | APCI (Pos., 40 V) |
| 20(H15-28) | D | 14.90 | 514 $(M + H)^+$. | APCI (Pos., 40 V) |
| 20(H15-29) | D | 14.40 | 420 $(M + H)^+$. | APCI (Pos., 40 V) |
| 20(H15-30) | D | 13.20 | 441 $(M + H)^+$, 282, 160. | APCI (Pos., 40 V) |
| 20(H15-31) | D | 15.40 | 470 $(M + H)^+$. | APCI (Pos., 40 V) |
| 20(H15-32) | D | 13.80 | 478 $(M + H)^+$. | APCI (Pos., 40 V) |
| 20(H15-33) | D | 15.10 | 500 $(M + H)^+$, 282, 219. | APCI (Pos., 40 V) |
| 20(H15-34) | D | 14.90 | 456 $(M + H)^+$. | APCI (Pos., 40 V) |
| 20(H15-35) | D | 15.60 | 584 $(M + H)^+$. | APCI (Pos., 40 V) |
| 20(H15-36) | D | 17.10 | 500 $(M + H)^+$. | APCI (Pos., 40 V) |
| 20(H15-37) | D | 14.30 | 408 $(M + H)^+$. | APCI (Pos., 40 V) |
| 20(H15-38) | D | 11.60 | 396 $(M + H)^+$. | APCI (Pos., 40 V) |
| 20(H15-39) | D | 13.30 | 476 $(M + H)^+$, 458. | APCI (Pos., 40 V) |
| 20(H15-40) | D | 8.94 | 368 $(M + H)^+$, 310, 282. | APCI (Pos., 40 V) |
| 20(H15-41) | D | 13.30 | 516 $(M + Na)^+$, 494 $(M + H)^+$. | APCI (Pos., 40 V) |
| 20(H15-42) | D | 11.10 | 438 $(M + H)^+$, 282, 189, 173. | APCI (Pos., 40 V) |
| 20(H15-43) | D | 14.40 | 428 $(M + H)^+$. | APCI (Pos., 40 V) |
| 20(H15-44) | D | 11.10 | 430 $(M + H)^+$. | APCI (Pos., 40 V) |
| 20(H15-45) | D | 14.50 | 432 $(M + H)^+$. | APCI (Pos., 40 V) |
| 20(H15-46) | D | 9.21 | 473 $(M + H)^+$. | APCI (Pos., 40 V) |
| 20(H15-47) | D | 9.84 | 362 $(M + H)^+$. | APCI (Pos., 40 V) |
| 20(H15-48) | D | 9.57 | 338 $(M + H)^+$. | APCI (Pos., 40 V) |
| 20(H15-49) | D | 11.70 | 378 $(M + H)^+$. | APCI (Pos., 40 V) |
| 20(H15-50) | D | 9.42 | 379 $(M + H)^+$. | APCI (Pos., 40 V) |

TABLE 15C-2-continued

| Example No | HPLC condi-tion | Retention time (min) | Mass data | Mass condition |
|---|---|---|---|---|
| 20(H15-51) | D | 10.00 | 429 (M + H)+. | APCI (Pos., 40 V) |
| 20(H15-52) | D | 11.40 | 402 (M + H)+. | APCI (Pos., 40 V) |

TABLE 15C-3

| Example No | HPLC condi-tion | Retention time (min) | Mass data | Mass condition |
|---|---|---|---|---|
| 20(H15-53) | D | 11.30 | 402 (M + H)+. | APCI (Pos., 40 V) |
| 20(H15-54) | D | 14.00 | 448 (M + H)+. | APCI (Pos., 40 V) |
| 20(H15-55) | D | 13.50 | 394 (M + H)+. | APCI (Pos., 40 V) |
| 20(H15-56) | D | 11.10 | 390 (M + H)+. | APCI (Pos., 40 V) |
| 20(H15-57) | D | 8.00 | 326 (M + H)+, 296. | APCI (Pos., 40 V) |
| 20(H15-58) | D | 12.90 | 422 (M + H)+. | APCI (Pos., 40 V) |
| 20(H15-59) | D | 9.05 | 324 (M + H)+. | APCI (Pos., 40 V) |
| 20(H15-60) | D | 8.00 | 414 (M + H)+, 340, 310, 282. | APCI (Pos., 40 V) |
| 20(H15-61) | D | 10.40 | 378 (M + H)+, 310. | APCI (Pos., 40 V) |
| 20(H15-62) | D | 15.70 | 420 (M + H)+. | APCI (Pos., 40 V) |
| 20(H15-63) | D | 12.30 | 406 (M + H)+. | APCI (Pos., 40 V) |
| 20(H15-64) | D | 11.10 | 416 (M + H)+. | APCI (Pos., 40 V) |
| 20(H15-65) | D | 7.79 | 400 (M + H)+, 310, 282. | APCI (Pos., 40 V) |
| 20(H15-66) | D | 10.60 | 482 (M + H)+, 282. | APCI (Pos., 40 V) |
| 20(H15-67) | D | 15.60 | 458 (M + H)+. | APCI (Pos., 40 V) |
| 20(H15-68) | D | 15.40 | 502 (M + H)+, 137. | APCI (Pos., 40 V) |
| 20(H15-69) | D | 11.20 | 390 (M + H)+. | APCI (Pos., 40 V) |
| 20(H15-70) | D | 13.60 | 418 (M + H)+. | APCI (Pos., 40 V) |
| 20(H15-71) | D | 11.40 | 466 (M + H)+, 217. | APCI (Pos., 40 V) |
| 20(H15-72) | D | 12.40 | 416 (M + H)+. | APCI (Pos., 40 V) |
| 20(H15-73) | D | 13.70 | 508 (M + H)+. | APCI (Pos., 40 V) |
| 20(H15-74) | D | 14.20 | 478 (M + H)+. | APCI (Pos., 40 V) |
| 20(H15-75) | D | 14.20 | 478 (M + H)+. | APCI (Pos., 40 V) |
| 20(H15-76) | D | 13.70 | 464 (M + H)+, 205. | APCI (Pos., 40 V) |
| 20(H15-77) | D | 12.60 | 428 (M + H)+. | APCI (Pos., 40 V) |

EXAMPLE 21

(3S)-1-propyl-2,5-dioxo-3-(4-(benzylcarbonylamino) butyl)-9-(3-phenylpropanoyl)-1,4,9-triazaspiro[5.5]undecane

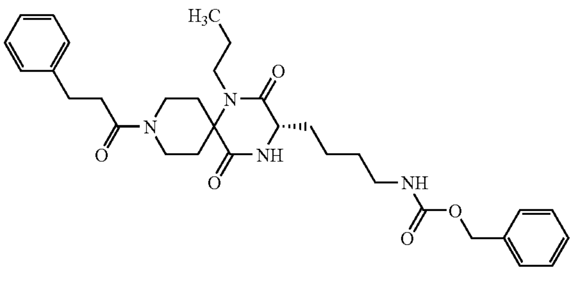

To a solution of the compound prepared in Example 8 (0.01 g) in dichloroethane (0.2 ml) were added diisopropylethylamine (6 μl), 3-phenylpropanoyl chloride (5 μl). The reaction mixture was stirred for 1 hour at room temperature. The reaction mixture was passed through the column with aminomethylated polystyrene-2% divinylbenzene copolymer resin (NovaBiochem, AM Resin, 50 mg). The resin was washed with dichloroethane and filtrated. The filtrate was concentrated to give the compound of the present invention (14 mg) having the following physical data.

TLC: Rf 0.55 (chloroform:methanol=10:1);

NMR ($CD_3OD$): δ 7.40–7.10 (m, 10H), 5.06 (s, 2H), 4.03 (m, 1H), 3.70–3.55 (m, 2H), 3.28–3.00 (m, 5H), 3.00–2.80 (m, 3H), 2.80–2.60 (m, 2H), 2.00–1.65 (m, 6H), 1.65–1.40 (m, 6H), 0.90 (t, J=7.2 Hz, 3H).

EXAMPLE 21(1)

(3S)-1-propyl-2,5-dioxo-3-(4-(benzylcarbonylamino)butyl)-9-benzenesulfonyl-1,4,9-triazaspiro[5.5]undecane

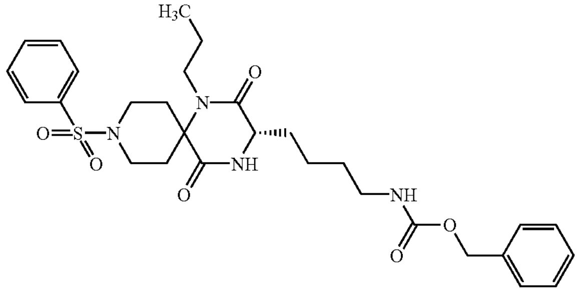

By the same procedure as described in Example 21 using the compound prepared in Example 8 (0.01 g), diisopropylethylamine (6 μl) and benzenesulfonyl chloride (4.5 μl), the compound of the present invention (16 mg) having the following physical data was obtained.

TLC: Rf 0.58 (chloroform:methanol=10:1);

NMR ($CD_3OD$): δ 7.80 (m, 2H), 7.63 (m, 3H), 7.33 (m, 5H), 5.04 (s, 2H), 3.98 (t, J=4.8 Hz, 1H), 3.60–3.35 (m, 2H), 3.28–2.90 (m, 6H), 2.20–1.65 (m, 6H), 1.65–1.20 (m, 6H), 0.89 (t, J=7.2 Hz, 3H).

EXAMPLE 21(2)

(3S)-1-propyl-2,5-dioxo-3-(4-(benzylcarbonylamino) butyl)-9-benzylaminocarbonyl-1,4,9-triazaspiro[5.5]undecane

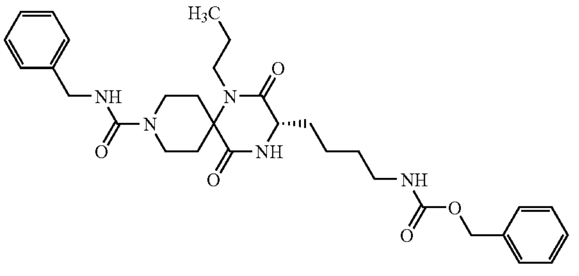

By the same procedure as described in Example 21 using the compound prepared in Example 8 (0.01 g) and benzyl isocyanate (4 μl), the compound of the present invention (16 mg) having the following physical data was obtained.

TLC: Rf 0.45 (chloroform:methanol=10:1);

NMR ($CD_3OD$): δ 7.40–7.10 (m, 10H), 5.05 (s, 2H), 4.37 (s, 2H), 4.10–3.90 (m, 3H), 3.60–3.45 (m, 2H), 3.30–3.00 (m, 4H), 2.10–1.70 (m, 6H), 1.65–1.20 (m, 6H), 0.87 (t, J=7.4 Hz, 3H).

EXAMPLE 21 (H16-1)~21 (H19-71)

By the same procedure as described in Example 21, 21(1) or 21(2), using the compound prepared in Example 8 or 8(1) and the corresponding acid chloride derivatives, sulfonyl chloride derivatives or isocyanate derivatives, the compounds of the present invention, whose names were shown in the following Table 16A-1~19A-9, and whose structures were shown in the following Table 16B-1~19B-11, were obtained. Also, physical data of the above compounds were shown in the following Table 16C-1~19C-3.

TABLE 16A-1

| Example No | Compound Name |
|---|---|
| 21(H16-1) | (3S)-1-propyl-2,5-dioxo-3-(4-(benzyloxycarbonylamino)-butyl)-9-((4-phenylphenyl)carbonyl)-1,4,9-triazaspiro[5.5]undecane |
| 21(H16-2) | (3S)-1-propyl-2,5-dioxo-3-(4-(benzyloxycarbonylamino)-butyl)-9-((4-dimethylaminophenyl)carbonyl)-1,4,9-triazaspiro[5.5]undecane |
| 21(H16-3) | (3S)-1-propyl-2,5-dioxo-3-(4-(benzyloxycarbonylamino)-butyl)-9-((3-(2-chlorophenyl)-5-methylisooxazol-4-yl)carbonyl)-1,4,9-triazaspiro[5.5]undecane |
| 21(H16-4) | (3S)-1-propyl-2,5-dioxo-3-(4-(benzyloxycarbonylamino)-butyl)-9-((4-fluorophenyl)carbonyl)-1,4,9-triazaspiro[5.5]undecane |
| 21(H16-5) | (3S)-1-propyl-2,5-dioxo-3-(4-(benzyloxycarbonylamino)-butyl)-9-((3-fluorophenyl)carbonyl)-1,4,9-triazaspiro[5.5]undecane |
| 21(H16-6) | (3S)-1-propyl-2,5-dioxo-3-(4-(benzyloxycarbonylamino)-butyl)-9-((2-fluorophenyl)carbonyl)-1,4,9-triazaspiro[5.5]undecane |
| 21(H16-7) | (3S)-1-propyl-2,5-dioxo-3-(4-(benzyloxycarbonylamino)-butyl)-9-(cyclopentylcarbonyl)-1,4,9-triazaspiro[5.5]undecane |

TABLE 16A-2

| Example No | Compound Name |
|---|---|
| 21(H16-8) | (3S)-1-propyl-2,5-dioxo-3-(4-(benzyloxycarbonylamino)-butyl)-9-((3-methylphenyl)carbonyl)-1,4,9-triazaspiro[5.5]undecane |
| 21(H16-9) | (3S)-1-propyl-2,5-dioxo-3-(4-(benzyloxycarbonylamino)-butyl)-9-((3-methoxyphenyl)carbonyl)-1,4,9-triazaspiro[5.5]undecane |
| 21(H16-10) | (3S)-1-propyl-2,5-dioxo-3-(4-(benzyloxycarbonylamino)-butyl)-9-(2,2-dimethylpropanoyl)-1,4,9-triazaspiro[5.5]undecane |
| 21(H16-11) | (3S)-1-propyl-2,5-dioxo-3-(4-(benzyloxycarbonylamino)-butyl)-9-(pyridin-3-ylcarbonyl)-1,4,9-triazaspiro[5.5]undecane |
| 21(H16-12) | (3S)-1-propyl-2,5-dioxo-3-(4-(benzyloxycarbonylamino)-butyl)-9-(pyridin-4-ylcarbonyl)-1,4,9-triazaspiro[5.5]undecane |
| 21(H16-13) | (3S)-1-propyl-2,5-dioxo-3-(4-(benzyloxycarbonylamino)-butyl)-9-(pyridin-2-ylcarbonyl)-1,4,9-triazaspiro[5.5]undecane |

TABLE 16A-2-continued

| Example No | Compound Name |
|---|---|
| 21(H16-14) | (3S)-1-propyl-2,5-dioxo-3-(4-(benzyloxycarbonylamino)-butyl)-9-(2-phenylacetyl)-1,4,9-triazaspiro[5.5]undecane |

TABLE 16A-3

| Example No | Compound Name |
|---|---|
| 21(H16-15) | (3S)-1-propyl-2,5-dioxo-3-(4-(benzyloxycarbonylamino)-butyl)-9-(2-phenyloxyacetyl)-1,4,9-triazaspiro[5.5]undecane |
| 21(H16-16) | (3S)-1-propyl-2,5-dioxo-3-(4-(benzyloxycarbonylamino)-butyl)-9-((4-ethyl-2,3-dioxopiperazinyl)carbonyl)-1,4,9-triazaspiro[5.5]undecane |
| 21(H16-17) | (3S)-1-propyl-2,5-dioxo-3-(4-(benzyloxycarbonylamino)-butyl)-9-((2-phenylthiopyridin-3-yl)carbonyl)-1,4,9-triazaspiro[5.5]undecane |
| 21(H16-18) | (3S)-1-propyl-2,5-dioxo-3-(4-(benzyloxycarbonylamino)-butyl)-9-((2-phenyloxypyridin-3-yl)carbonyl)-1,4,9-triazaspiro[5.5]undecane |
| 21(H16-19) | (3S)-1-propyl-2,5-dioxo-3-(4-(benzyloxycarbonylamino)-butyl)-9-((2-methoxyphenyl)carbonyl)-1,4,9-triazaspiro[5.5]undecane |
| 21(H16-20) | (3S)-1-propyl-2,5-dioxo-3-(4-(benzyloxycarbonylamino)-butyl)-9-(2-(thiophen-2-yl)acetyl)-1,4,9-triazaspiro[5.5]undecane |
| 21(H16-21) | (3S)-1-propyl-2,5-dioxo-3-(4-(benzyloxycarbonylamino)-butyl)-9-hexanoyl-1,4,9-triazaspiro[5.5]undecane |

TABLE 16A-4

| Example No | Compound Name |
|---|---|
| 21(H16-22) | (3S)-1-propyl-2,5-dioxo-3-(4-(benzyloxycarbonylamino)-butyl)-9-((4-methylphenyl)carbonyl)-1,4,9-triazaspiro[5.5]undecane |
| 21(H16-23) | (3S)-1-propyl-2,5-dioxo-3-(4-(benzyloxycarbonylamino)-butyl)-9-(2-methylpropanoyl)-1,4,9-triazaspiro[5.5]undecane |
| 21(H16-24) | (3S)-1-propyl-2,5-dioxo-3-(4-(benzyloxycarbonylamino)-butyl)-9-(3-cyclopentylpropanoyl)-1,4,9-triazaspiro[5.5]undecane |
| 21(H16-25) | (3S)-1-propyl-2,5-dioxo-3-(4-(benzyloxycarbonylamino)-butyl)-9-((2E)3-phenyl-2-propenoyl)-1,4,9-triazaspiro[5.5]undecane |
| 21(H16-26) | (3S)-1-propyl-2,5-dioxo-3-(4-(benzyloxycarbonylamino)-butyl)-9-((2-methylphenyl)carbonyl)-1,4,9-triazaspiro[5.5]undecane |
| 21(H16-27) | (3S)-1-propyl-2,5-dioxo-3-(4-(benzyloxycarbonylamino)-butyl)-9-(3,3-dimethylbutenoyl)-1,4,9-triazaspiro[5.5]undecane |
| 21(H16-28) | (3S)-1-propyl-2,5-dioxo-3-(4-(benzyloxycarbonylamino)-butyl)-9-(cyclohexylcarbonyl)-1,4,9-triazaspiro[5.5]undecane |

TABLE 16A-5

| Example No | Compound Name |
|---|---|
| 21(H16-29) | (3S)-1-propyl-2,5-dioxo-3-(4-(benzyloxycarbonylamino)-butyl)-9-(phenylcarbonyl)-1,4,9-triazaspiro[5.5]undecane |

TABLE 16A-5-continued

| Example No | Compound Name |
|---|---|
| 21(H16-30) | (3S)-1-propyl-2,5-dioxo-3-(4-(benzyloxycarbonylamino)-butyl)-9-(thiophen-2-ylcarbonyl)-1,4,9-triazaspiro[5.5]undecane |
| 21(H16-31) | (3S)-1-propyl-2,5-dioxo-3-(4-(benzyloxycarbonylamino)-butyl)-9-((2,6,6-trimethyl-1-cyclohexenyl)carbonyl)-1,4,9-triazaspiro[5.5]undecane |
| 21(H16-32) | (3S)-1-propyl-2,5-dioxo-3-(4-(benzyloxycarbonylamino)-butyl)-9-(ethoxyoxalyl)-1,4,9-triazaspiro[5.5]undecane |
| 21(H16-33) | (3S)-1-propyl-2,5-dioxo-3-(4-(benzyloxycarbonylamino)-butyl)-9-((3-phenyl-5-methylisooxazol-4-yl)carbonyl)-1,4,9-triazaspiro[5.5]undecane |
| 21(H16-34) | (3S)-1-propyl-2,5-dioxo-3-(4-(benzyloxycarbonylamino)-butyl)-9-((5-methyl-2-phenyl-1,2,3-triazol-4-yl)carbonyl)-1,4,9-triazaspiro[5.5]undecane |
| 21(H16-35) | (3S)-1-propyl-2,5-dioxo-3-(4-(benzyloxycarbonylamino)-butyl)-9-(2-(3-methoxyphenyl)acetyl)-1,4,9-triazaspiro[5.5]undecane |

TABLE 16A-6

| Example No | Compound Name |
|---|---|
| 21(H16-36) | (3S)-1-propyl-2,5-dioxo-3-(4-(benzyloxycarbonylamino)-butyl)-9-(4-methoxyphenylcarbonyl)-1,4,9-triazaspiro[5.5]undecane |
| 21(H16-37) | (3S)-1-propyl-2,5-dioxo-3-(4-(benzyloxycarbonylamino)-butyl)-9-((furan-2-yl)carbonyl)-1,4,9-triazaspiro[5.5]undecane |
| 21(H16-38) | (3S)-1-propyl-2,5-dioxo-3-(4-(benzyloxycarbonylamino)-butyl)-9-(2-benzyloxyacetyl)-1,4,9-triazaspiro[5.5]undecane |
| 21(H16-39) | (3S)-1-propyl-2,5-dioxo-3-(4-(benzyloxycarbonylamino)-butyl)-9-(cyclobutylcarbonyl)-1,4,9-triazaspiro[5.5]undecane |
| 21(H16-40) | (3S)-1-propyl-2,5-dioxo-3-(4-(benzyloxycarbonylamino)-butyl)-9-(2-(4-methoxyphenyl)acetyl)-1,4,9-triazaspiro[5.5]undecane |
| 21(H16-41) | (3S)-1-propyl-2,5-dioxo-3-(4-(benzyloxycarbonylamino)-butyl)-9-acetyl-1,4,9-triazaspiro[5.5]undecane |
| 21(H16-42) | (3S)-1-propyl-2,5-dioxo-3-(4-(benzyloxycarbonylamino)-butyl)-9-(4-methylpentanoyl)-1,4,9-triazaspiro[5.5]undecane |

TABLE 16A-7

| Example No | Compound Name |
|---|---|
| 21(H16-43) | (3S)-1-propyl-2,5-dioxo-3-(4-(benzyloxycarbonylamino)-butyl)-9-(2-methoxyacetyl)-1,4,9-triazaspiro[5.5]undecane |
| 21(H16-44) | (3S)-1-propyl-2,5-dioxo-3-(4-(benzyloxycarbonylamino)-butyl)-9-(3-methylthiopropanoyl)-1,4,9-triazaspiro[5.5]undecane |
| 21(H16-45) | (3S)-1-propyl-2,5-dioxo-3-(4-(benzyloxycarbonylamino)-butyl)-9-((isooxazol-5-yl)carbonyl)-1,4,9-triazaspiro[5.5]undecane |
| 21(H16-46) | (3S)-1-propyl-2,5-dioxo-3-(4-(benzyloxycarbonylamino)-butyl)-9-(2-cyclopentylacetyl)-1,4,9-triazaspiro[5.5]undecane |
| 21(H16-47) | (3S)-1-propyl-2,5-dioxo-3-(4-(benzyloxycarbonylamino)-butyl)-9-pentanoyl-1,4,9-triazaspiro[5.5]undecane |
| 21(H16-48) | (3S)-1-propyl-2,5-dioxo-3-(4-(benzyloxycarbonylamino)-butyl)-9-(3-methylbutanoyl)-1,4,9-triazaspiro[5.5]undecane |

TABLE 16A-7-continued

| Example No | Compound Name |
|---|---|
| 21(H16-49) | (3S)-1-propyl-2,5-dioxo-3-(4-(benzyloxycarbonylamino)-butyl)-9-(2-phenylthioacetyl)-1,4,9-triazaspiro[5.5]undecane |

TABLE 16A-8

| Example No | Compound Name |
|---|---|
| 21(H16-50) | (3S)-1-propyl-2,5-dioxo-3-(4-(benzyloxycarbonylamino)-butyl)-9-((4-methyl-1,2,3-thiadiazol-5-yl)carbonyl)-1,4,9-triazaspiro[5.5]undecane |
| 21(H16-51) | (3S)-1-propyl-2,5-dioxo-3-(4-(benzyloxycarbonylamino)-butyl)-9-((3-cyanophenyl)carbonyl)-1,4,9-triazaspiro[5.5]undecane |
| 21(H16-52) | (3S)-1-propyl-2,5-dioxo-3-(4-(benzyloxycarbonylamino)-butyl)-9-butanoyl-1,4,9-triazaspiro[5.5]undecane |
| 21(H16-53) | (3S)-1-propyl-2,5-dioxo-3-(4-(benzyloxycarbonylamino)-butyl)-9-propanoyl-1,4,9-triazaspiro[5.5]undecane |
| 21(H16-54) | (3S)-1-propyl-2,5-dioxo-3-(4-(benzyloxycarbonylamino)-butyl)-9-(cyclopropylcarbonyl)-1,4,9-triazaspiro[5.5]undecane |
| 21(H16-55) | (3S)-1-propyl-2,5-dioxo-3-(4-(benzyloxycarbonylamino)-butyl)-9-(2H-benzo[3,4-d]1,3-dioxolan-5-ylcarbonyl)-1,4,9-triazaspiro[5.5]undecane |
| 21(H16-56) | (3S)-1-propyl-2,5-dioxo-3-(4-(benzyloxycarbonylamino)-butyl)-9-((1-phenyl-5-propylpyrazol-4-yl)carbonyl)-1,4,9-triazaspiro[5.5]undecane |

TABLE 16A-9

| Example No | Compound Name |
|---|---|
| 21(H16-57) | (3S)-1-propyl-2,5-dioxo-3-(4-(benzyloxycarbonylamino)-butyl)-9-((5-(1,1-dimethylethyl)-2-methylfuran-3-yl)-carbonyl)-1,4,9-triazaspiro[5.5]undecane |
| 21(H16-58) | (3S)-1-propyl-2,5-dioxo-3-(4-(benzyloxycarbonylamino)-butyl)-9-((1-(1,1-dimethylethyl)-3-methylpyrazol-5-yl)-carbonyl)-1,4,9-triazaspiro[5.5]undecane |
| 21(H16-59) | (3S)-1-propyl-2,5-dioxo-3-(4-(benzyloxycarbonylamino)-butyl)-9-methylsulfonyl-1,4,9-triazaspiro[5.5]undecane |
| 21(H16-60) | (3S)-1-propyl-2,5-dioxo-3-(4-(benzyloxycarbonylamino)-butyl)-9-pentylsulfonyl-1,4,9-triazaspiro[5.5]undecane |
| 21(H16-61) | (3S)-1-propyl-2,5-dioxo-3-(4-(benzyloxycarbonylamino)-butyl)-9-((1-methylethyl)sulfonyl)-1,4,9-triazaspiro[5.5]-undecane |
| 21(H16-62) | (3S)-1-propyl-2,5-dioxo-3-(4-(benzyloxycarbonylamino)-butyl)-9-((4-chlorophenyl)sulfonyl)-1,4,9-triazaspiro[5.5]-undecane |
| 21(H16-63) | (3S)-1-propyl-2,5-dioxo-3-(4-(benzyloxycarbonylamino)-butyl)-9-((2-iodophenyl)sulfonyl)-1,4,9-triazaspiro[5.5]-undecane |

TABLE 16A-10

| Example No | Compound Name |
|---|---|
| 21(H16-64) | (3S)-1-propyl-2,5-dioxo-3-(4-(benzyloxycarbonylamino)-butyl)-9-((4-nitrophenyl)sulfonyl)-1,4,9-triazaspiro[5.5]-undecane |

TABLE 16A-10-continued

| Example No | Compound Name |
|---|---|
| 21(H16-65) | (3S)-1-propyl-2,5-dioxo-3-(4-(benzyloxycarbonylamino)-butyl)-9-((4-methylsulfonylphenyl)sulfonyl)-1,4,9-triazaspiro[5.5]undecane |
| 21(H16-66) | (3S)-1-propyl-2,5-dioxo-3-(4-(benzyloxycarbonylamino)-butyl)-9-((4-trifluoromethylphenyl)sulfonyl)-1,4,9-triazaspiro[5.5]undecane |
| 21(H16-67) | (3S)-1-propyl-2,5-dioxo-3-(4-(benzyloxycarbonylamino)-butyl)-9-((4-biphenyl)sulfonyl)-1,4,9-triazaspiro[5.5]-undecane |
| 21(H16-68) | (3S)-1-propyl-2,5-dioxo-3-(4-(benzyloxycarbonylamino)-butyl)-9-((2-biphenyl)sulfonyl)-1,4,9-triazaspiro[5.5]-undecane |
| 21(H16-69) | (3S)-1-propyl-2,5-dioxo-3-(4-(benzyloxycarbonylamino)-butyl)-9-((2-methoxycarbonylphenyl)sulfonyl)-1,4,9-triazaspiro[5.5]undecane |
| 21(H16-70) | (3S)-1-propyl-2,5-dioxo-3-(4-(benzyloxycarbonylamino)-butyl)-9-((3,4-difluorophenyl)sulfonyl)-1,4,9-triazaspiro[5.5]undecane |

TABLE 16A-11

| Example No | Compound Name |
|---|---|
| 21(H16-71) | (3S)-1-propyl-2,5-dioxo-3-(4-(benzyloxycarbonylamino)-butyl)-9-((2,6-difluorophenyl)sulfonyl)-1,4,9-triazaspiro[5.5]undecane |
| 21(H16-72) | (3S)-1-propyl-2,5-dioxo-3-(4-(benzyloxycarbonylamino)-butyl)-9-((2,5-difluorophenyl)sulfonyl)-1,4,9-triazaspiro[5.5]undecane |
| 21(H16-73) | (3S)-1-propyl-2,5-dioxo-3-(4-(benzyloxycarbonylamino)-butyl)-9-((2,5-dimethoxyphenyl)sulfonyl)-1,4,9-triazaspiro[5.5]undecane |
| 21(H16-74) | (3S)-1-propyl-2,5-dioxo-3-(4-(benzyloxycarbonylamino)-butyl)-9-((2-chloro-4-trifluoromethylphenyl)sulfonyl)-1,4,9-triazaspiro[5.5]undecane |
| 21(H16-75) | (3S)-1-propyl-2,5-dioxo-3-(4-(benzyloxycarbonylamino)-butyl)-9-(2-naphthylsulfonyl)-1,4,9-triazaspiro[5.5]-undecane |
| 21(H16-76) | (3S)-1-propyl-2,5-dioxo-3-(4-(benzyloxycarbonylamino)-butyl)-9-(((1E)-2-phenylvinyl)sulfonyl)-1,4,9-triazaspiro[5.5]undecane |
| 21(H16-77) | (3S)-1-propyl-2,5-dioxo-3-(4-(benzyloxycarbonylamino)-butyl)-9-((furan-2-yl)sulfonyl)-1,4,9-triazaspiro[5.5]-undecane |

TABLE 16A-12

| Example No | Compound Name |
|---|---|
| 21(H16-78) | (3S)-1-propyl-2,5-dioxo-3-(4-(benzyloxycarbonylamino)-butyl)-9-((thiophen-2-yl)sulfonyl)-1,4,9-triazaspiro[5.5]-undecane |

TABLE 17A-1

| Example No | Compound Name |
|---|---|
| 21(H17-1) | (3S)-1-propyl-2,5-dioxo-3-(4-(benzyloxycarbonylamino)-butyl)-9-((4-bromo-2,5-dichlorothiophen-3-yl)sulfonyl)-1,4,9-triazaspiro[5.5]undecane |

TABLE 17A-1-continued

| Example No | Compound Name |
|---|---|
| 21(H17-2) | (3S)-1-propyl-2,5-dioxo-3-(4-(benzyloxycarbonylamino)-butyl)-9-((5-phenylsulfonylthiophen-2-yl)sulfonyl)-1,4,9-triazaspiro[5.5]undecane |
| 21(H17-3) | (3S)-1-propyl-2,5-dioxo-3-(4-(benzyloxycarbonylamino)-butyl)-9-((7-chlorobenzofurazan-4-yl)sulfonyl)-1,4,9-triazaspiro[5.5]undecane |
| 21(H17-4) | (3S)-1-propyl-2,5-dioxo-3-(4-(benzyloxycarbonylamino)-butyl)-9-((4-methyl-2-acetylaminothiazol-5-yl)sulfonyl)-1,4,9-triazaspiro[5.5]undecane |
| 21(H17-5) | (3S)-1-propyl-2,5-dioxo-3-(4-(benzyloxycarbonylamino)-butyl)-9-((2-methoxy-dibenzofuran-3-yl)sulfonyl)-1,4,9-triazaspiro[5.5]undecane |
| 21(H17-6) | (3S)-1-propyl-2,5-dioxo-3-(4-(benzyloxycarbonylamino)-butyl)-9-((3,4-dichlorophenyl)sulfonyl)-1,4,9-triazaspiro[5.5]-undecane |
| 21(H17-7) | (3S)-1-propyl-2,5-dioxo-3-(4-(benzyloxycarbonylamino)-butyl)-9-((4-methoxyphenyl)sulfonyl)-1,4,9-triazaspiro[5.5]-undecane |

TABLE 17A-2

| Example No | Compound Name |
|---|---|
| 21(H17-8) | (3S)-1-propyl-2,5-dioxo-3-(4-(benzyloxycarbonylamino)-butyl)-9-benzylsulfonyl-1,4,9-triazaspiro[5.5]undecane |
| 21(H17-9) | (3S)-1-propyl-2,5-dioxo-3-(4-(benzyloxycarbonylamino)-butyl)-9-((ethylamino)carbonyl)-1,4,9-triazaspiro[5.5]-undecane |
| 21(H17-10) | (3S)-1-propyl-2,5-dioxo-3-(4-(benzyloxycarbonylamino)-butyl)-9-((propylamino)carbonyl)-1,4,9-triazaspiro[5.5]-undecane |
| 21(H17-11) | (3S)-1-propyl-2,5-dioxo-3-(4-(benzyloxycarbonylamino)-butyl)-9-((1-methylethylamino)carbonyl)-1,4,9-triazaspiro[5.5]undecane |
| 21(H17-12) | (3S)-1-propyl-2,5-dioxo-3-(4-(benzyloxycarbonylamino)-butyl)-9-((ethoxycarbonylmethylamino)carbonyl)-1,4,9-triazaspiro[5.5]undecane |
| 21(H17-13) | (3S)-1-propyl-2,5-dioxo-3-(4-(benzyloxycarbonylamino)-butyl)-9-((butylamino)carbonyl)-1,4,9-triazaspiro[5.5]-undecane |
| 21(H17-14) | (3S)-1-propyl-2,5-dioxo-3-(4-(benzyloxycarbonylamino)-butyl)-9-((4-chlorophenylamino)carbonyl)-1,4,9-triazaspiro[5.5]undecane |

TABLE 17A-3

| Example No | Compound Name |
|---|---|
| 21(H17-15) | (3S)-1-propyl-2,5-dioxo-3-(4-(benzyloxycarbonylamino)-butyl)-9-((phenylamino)carbonyl)-1,4,9-triazaspiro[5.5]-undecane |
| 21(H17-16) | (3S)-1-propyl-2,5-dioxo-3-(4-(benzyloxycarbonylamino)-butyl)-9-((4-methylphenylamino)carbonyl)-1,4,9-triazaspiro[5.5]undecane |
| 21(H17-17) | (3S)-1-propyl-2,5-dioxo-3-(4-(benzyloxycarbonylamino)-butyl)-9-((hexylamino)carbonyl)-1,4,9-triazaspiro[5.5]-undecane |
| 21(H17-18) | (3S)-1-propyl-2,5-dioxo-3-(4-(benzyloxycarbonylamino)-butyl)-9-((4-fluorophenylamino)carbonyl)-1,4,9-triazaspiro[5.5]undecane |
| 21(H17-19) | (3S)-1-propyl-2,5-dioxo-3-(4-(benzyloxycarbonylamino)-butyl)-9-((benzylamino)carbonyl)-1,4,9-triazaspiro[5.5]-undecane |
| 21(H17-20) | (3S)-1-propyl-2,5-dioxo-3-(4-(benzyloxycarbonylamino)-butyl)-9-((cyclohexylamino)carbonyl)-1,4,9-triazaspiro[5.5]undecane |

TABLE 17A-3-continued

| Example No | Compound Name |
|---|---|
| 21(H17-21) | (3S)-1-propyl-2,5-dioxo-3-(4-(benzyloxycarbonylamino)-butyl)-9-((3-methylphenylamino)carbonyl)-1,4,9-triazaspiro[5.5]undecane |

TABLE 17A-4

| Example No | Compound Name |
|---|---|
| 21(H17-22) | (3S)-1-propyl-2,5-dioxo-3-(4-(benzyloxycarbonylamino)-butyl)-9-((octylamino)carbonyl)-1,4,9-triazaspiro[5.5]-undecane |
| 21(H17-23) | (3S)-1-propyl-2,5-dioxo-3-(4-(benzyloxycarbonylamino)-butyl)-9-((4-bromophenylamino)carbonyl)-1,4,9-triazaspiro[5.5]undecane |
| 21(H17-24) | (3S)-1-propyl-2,5-dioxo-3-(4-(benzyloxycarbonylamino)-butyl)-9-((2-(thiophen-2-yl)ethylamino)carbonyl)-1,4,9-triazaspiro[5.5]undecane |
| 21(H17-25) | (3S)-1-propyl-2,5-dioxo-3-(4-(benzyloxycarbonylamino)-butyl)-9-((4-(1-methylethyl)phenylamino)carbonyl)-1,4,9-triazaspiro[5.5]undecane |
| 21(H17-26) | (3S)-1-propyl-2,5-dioxo-3-(4-(benzyloxycarbonylamino)-butyl)-9-((3-chlorophenylamino)carbonyl)-1,4,9-triazaspiro[5.5]undecane |
| 21(H17-27) | (3S)-1-propyl-2,5-dioxo-3-(4-(benzyloxycarbonylamino)-butyl)-9-((2,4,5-trimethylphenylamino)carbonyl)-1,4,9-triazaspiro[5.5]undecane |
| 21(H17-28) | (3S)-1-propyl-2,5-dioxo-3-(4-(benzyloxycarbonylamino)-butyl)-9-((2,4,6-trimethylphenylamino)carbonyl)-1,4,9-triazaspiro[5.5]undecane |

TABLE 17A-5

| Example No | Compound Name |
|---|---|
| 21(H17-29) | (3S)-1-propyl-2,5-dioxo-3-(4-(benzyloxycarbonylamino)-butyl)-9-((4-phenyloxyphenylamino)carbonyl)-1,4,9-triazaspiro[5.5]undecane |
| 21(H17-30) | (3S)-1-propyl-2,5-dioxo-3-(4-(benzyloxycarbonylamino)-butyl)-9-((4-butyloxyphenylamino)carbonyl)-1,4,9-triazaspiro[5.5]undecane |
| 21(H17-31) | (3S)-1-propyl-2,5-dioxo-3-(4-(benzyloxycarbonylamino)-butyl)-9-((4-phenylphenylamino)carbonyl)-1,4,9-triazaspiro[5.5]undecane |
| 21(H17-32) | (3S)-1-propyl-2,5-dioxo-3-(4-(benzyloxycarbonylamino)-butyl)-9-((2-phenylphenylamino)carbonyl)-1,4,9-triazaspiro[5.5]undecane |
| 21(H17-33) | (3S)-1-propyl-2,5-dioxo-3-(4-(benzyloxycarbonylamino)-butyl)-9-((4-trifluoromethylphenylamino)carbonyl)-1,4,9-triazaspiro[5.5]undecane |
| 21(H17-34) | (3S)-1-propyl-2,5-dioxo-3-(4-(benzyloxycarbonylamino)-butyl)-9-((3,4-dichlorophenylamino)carbonyl)-1,4,9-triazaspiro[5.5]undecane |
| 21(H17-35) | (3S)-1-propyl-2,5-dioxo-3-(4-(benzyloxycarbonylamino)-butyl)-9-((4-butyloxycarbonylphenylamino)carbonyl)-1,4,9-triazaspiro[5.5]undecane |

TABLE 17A-6

| Example No | Compound Name |
|---|---|
| 21(H17-36) | (3S)-1-propyl-2,5-dioxo-3-(4-(benzyloxycarbonylamino)-butyl)-9-((2,6-di(1-methylethyl)phenylamino)carbonyl)-1,4,9-triazaspiro[5.5]undecane |

TABLE 17A-6-continued

| Example No | Compound Name |
|---|---|
| 21(H17-37) | (3S)-1-propyl-2,5-dioxo-3-(4-(benzyloxycarbonylamino)-butyl)-9-((2,5-dimethylphenylamino)carbonyl)-1,4,9-triazaspiro[5.5]undecane |
| 21(H17-38) | (3S)-1-propyl-2,5-dioxo-3-(4-(benzyloxycarbonylamino)-butyl)-9-((2-ethyl-6-(1-methylethyl)phenylamino)carbonyl)-1,4,9-triazaspiro[5.5]undecane |
| 21(H17-39) | (3S)-1-propyl-2,5-dioxo-3-(4-(benzyloxycarbonylamino)-butyl)-9-((2,4,6-trichlorophenylamino)carbonyl)-1,4,9-triazaspiro[5.5]undecane |
| 21(H17-40) | (3S)-1-propyl-2,5-dioxo-3-(4-(benzyloxycarbonylamino)-butyl)-9-((3,4-dimethylphenylamino)carbonyl)-1,4,9-triazaspiro[5.5]undecane |
| 21(H17-41) | (3S)-1-propyl-2,5-dioxo-3-(4-(benzyloxycarbonylamino)-butyl)-9-((2-methylthiophenylamino)carbonyl)-1,4,9-triazaspiro[5.5]undecane |
| 21(H17-42) | (3S)-1-propyl-2,5-dioxo-3-(4-(benzyloxycarbonylamino)-butyl)-9-((4-methylthiophenylamino)carbonyl)-1,4,9-triazaspiro[5.5]undecane |

TABLE 17A-7

| Example No | Compound Name |
|---|---|
| 21(H17-43) | (3S)-1-propyl-2,5-dioxo-3-(4-(benzyloxycarbonylamino)-butyl)-9-((4-butylphenylamino)carbonyl)-1,4,9-triazaspiro[5.5]undecane |
| 21(H17-44) | (3S)-1-propyl-2,5-dioxo-3-(4-(benzyloxycarbonylamino)-butyl)-9-((2-chloro-5-trifluoromethylphenylamino)carbonyl)-1,4,9-triazaspiro[5.5]undecane |
| 21(H17-45) | (3S)-1-propyl-2,5-dioxo-3-(4-(benzyloxycarbonylamino)-butyl)-9-((2,6-dibromo-4-ethylphenylamino)carbonyl)-1,4,9-triazaspiro[5.5]undecane |
| 21(H17-46) | (3S)-1-propyl-2,5-dioxo-3-(4-(benzyloxycarbonylamino)-butyl)-9-((1-ethoxycarbonyl-2-methylpropylamino)carbonyl)-1,4,9-triazaspiro[5.5]undecane |
| 21(H17-47) | (3S)-1-propyl-2,5-dioxo-3-(4-(benzyloxycarbonylamino)-butyl)-9-((phenylcarbonylamino)carbonyl)-1,4,9-triazaspiro[5.5]undecane |
| 21(H17-48) | (3S)-1-propyl-2,5-dioxo-3-(4-(benzyloxycarbonylamino)-butyl)-9-((2,4,6-tribromophenylamino)carbonyl)-1,4,9-triazaspiro[5.5]undecane |
| 21(H17-49) | (3S)-1-propyl-2,5-dioxo-3-(4-(benzyloxycarbonylamino)-butyl)-9-((2,5-difluorophenylamino)carbonyl)-1,4,9-triazaspiro[5.5]undecane |

TABLE 17A-8

| Example No | Compound Name |
|---|---|
| 21(H17-50) | (3S)-1-propyl-2,5-dioxo-3-(4-(benzyloxycarbonylamino)-butyl)-9-((3,5-bis(methoxycarbonyl)phenylamino)carbonyl)-1,4,9-triazaspiro[5.5]undecane |
| 21(H17-51) | (3S)-1-propyl-2,5-dioxo-3-(4-(benzyloxycarbonylamino)-butyl)-9-((6,7-methylenedioxycoumarin-4-ylmethylamino)-carbonyl)-1,4,9-triazaspiro[5.5]undecane |
| 21(H17-52) | (3S)-1-propyl-2,5-dioxo-3-(4-(benzyloxycarbonylamino)-butyl)-9-((2,6-dimethylphenylamino)carbonyl)-1,4,9-triazaspiro[5.5]undecane |
| 21(H17-53) | (3S)-1-propyl-2,5-dioxo-3-(4-(benzyloxycarbonylamino)-butyl)-9-((2-methylpropyloxy)carbonyl)-1,4,9-triazaspiro[5.5]undecane |
| 21(H17-54) | (3S)-1-propyl-2,5-dioxo-3-(4-(benzyloxycarbonylamino)-butyl)-9-((2-ethylhexyloxy)carbonyl)-1,4,9-triazaspiro[5.5]-undecane |
| 21(H17-55) | (3S)-1-propyl-2,5-dioxo-3-(4-(benzyloxycarbonylamino)-butyl)-9-(ethoxycarbonyl)-1,4,9-triazaspiro[5.5]undecane |

TABLE 17A-8-continued

| Example No | Compound Name |
|---|---|
| 21(H17-56) | (3S)-1-propyl-2,5-dioxo-3-(4-(benzyloxycarbonylamino)-butyl)-9-(allyloxycarbonyl)-1,4,9-triazaspiro[5.5]undecane |

TABLE 17A-9

| Example No | Compound Name |
|---|---|
| 21(H17-57) | (3S)-1-propyl-2,5-dioxo-3-(4-(benzyloxycarbonylamino)-butyl)-9-(propyloxycarbonyl)-1,4,9-triazaspiro[5.5]-undecane |
| 21(H17-58) | (3S)-1-propyl-2,5-dioxo-3-(4-(benzyloxycarbonylamino)-butyl)-9-(butyloxycarbonyl)-1,4,9-triazaspiro[5.5]undecane |
| 21(H17-59) | (3S)-1-propyl-2,5-dioxo-3-(4-(benzyloxycarbonylamino)-butyl)-9-(hexyloxycarbonyl)-1,4,9-triazaspiro[5.5]undecane |
| 21(H17-60) | (3S)-1-propyl-2,5-dioxo-3-(4-(benzyloxycarbonylamino)-butyl)-9-((2,2,2-trichloroethyloxy)carbonyl)-1,4,9-triazaspiro[5.5]undecane |
| 21(H17-61) | (3S)-1-propyl-2,5-dioxo-3-(4-(benzyloxycarbonylamino)-butyl)-9-((fluoren-9-ylmethyloxy)carbonyl)-1,4,9-triazaspiro[5.5]undecane |
| 21(H17-62) | (3S)-1-propyl-2,5-dioxo-3-(4-(benzyloxycarbonylamino)-butyl)-9-((1R,5R,2S)-5-methyl-2-(1-methylethyl)cyclohex-yloxycarbonyl)-1,4,9-triazaspiro[5.5]undecane |
| 21(H17-63) | (3S)-1-propyl-2,5-dioxo-3-(4-(benzyloxycarbonylamino)-butyl)-9-((2-methoxyethoxy)carbonyl)-1,4,9-triazaspiro[5.5]undecane |

TABLE 17A-10

| Example No | Compound Name |
|---|---|
| 21(H17-64) | (3S)-1-propyl-2,5-dioxo-3-(4-(benzyloxycarbonylamino)-butyl)-9-(pentyloxycarbonyl)-1,4,9-triazaspiro[5.5]undecane |
| 21(H17-65) | (3S)-1-propyl-2,5-dioxo-3-(4-(benzyloxycarbonylamino)-butyl)-9-((1-methylethyloxy)carbonyl)-1,4,9-triazaspiro[5.5]undecane |
| 21(H17-66) | (3S)-1-propyl-2,5-dioxo-3-(4-(benzyloxycarbonylamino)-butyl)-9-((3-butenyloxy)carbonyl)-1,4,9-triazaspiro[5.5]-undecane |
| 21(H17-67) | (3S)-1-propyl-2,5-dioxo-3-(4-(benzyloxycarbonylamino)-butyl)-9-((2R,1S,5S)-methyl-2-(1-methylethyl)cyclohexyl-oxycarbonyl)-1,4,9-triazaspiro[5.5]undecane |
| 21(H17-68) | (3S)-1-propyl-2,5-dioxo-3-(4-(benzyloxycarbonylamino)-butyl)-9-(cyclopentyloxycarbonyl)-1,4,9-triazaspiro[5.5]-undecane |
| 21(H17-69) | (3S)-1-propyl-2,5-dioxo-3-(4-(benzyloxycarbonylamino)-butyl)-9-((1,1-dimethylethyloxy)carbonyl)-1,4,9-triazaspiro[5.5]undecane |
| 21(H17-70) | (3S)-1-propyl-2,5-dioxo-3-(4-(benzyloxycarbonylamino)-butyl)-9-(benzyloxycarbonyl)-1,4,9-triazaspiro[5.5]-undecane |

TABLE 17A-11

| Example No | Compound Name |
|---|---|
| 21(H17-71) | (3S)-1-propyl-2,5-dioxo-3-(4-(benzyloxycarbonylamino)-butyl)-9-((N,N-diphenylamino)carbonyl)-1,4,9-triazaspiro[5.5]undecane |
| 21(H17-72) | (3S)-1-propyl-2,5-dioxo-3-(4-(benzyloxycarbonylamino)-butyl)-9-((N-phenyl-N-methylamino)carbonyl)-1,4,9-triazaspiro[5.5]undecane |

TABLE 17A-11-continued

| Example No | Compound Name |
|---|---|
| 21(H17-73) | (3S)-1-propyl-2,5-dioxo-3-(4-(benzyloxycarbonylamino)-butyl)-9-((N,N-dimethylamino)carbonyl)-1,4,9-triazaspiro[5.5]undecane |
| 21(H17-74) | (3S)-1-propyl-2,5-dioxo-3-(4-(benzyloxycarbonylamino)-butyl)-9-((N,N-diethylamino)carbonyl)-1,4,9-triazaspiro[5.5]undecane |
| 21(H17-75) | (3S)-1-propyl-2,5-dioxo-3-(4-(benzyloxycarbonylamino)-butyl)-9-((N,N-bis(1-methylethyl)amino)carbonyl)-1,4,9-triazaspiro[5.5]undecane |
| 21(H17-76) | (3S)-1-propyl-2,5-dioxo-3-(4-(benzyloxycarbonylamino)-butyl)-9-(morpholin-4-ylcarbonyl)-1,4,9-triazaspiro[5.5]-undecane |
| 21(H17-77) | (3S)-1-propyl-2,5-dioxo-3-(4-(benzyloxycarbonylamino)-butyl)-9-(carbazol-9-ylcarbonyl)-1,4,9-triazaspiro[5.5]-undecane |

TABLE 17A-12

| Example No | Compound Name |
|---|---|
| 21(H17-78) | (3S)-1-propyl-2,5-dioxo-3-(4-(benzyloxycarbonylamino)-butyl)-9-(pyrrolidin-1-ylcarbonyl)-1,4,9-triazaspiro[5.5]undecane |

TABLE 18A-1

| Example No | Compound Name |
|---|---|
| 21(H18-1) | 1-propyl-2,5-dioxo-3-(2-methylpropyl)-9-((4-biphenyl)carbonyl)-1,4,9-triazaspiro[5.5]undecane |
| 21(H18-2) | 1-propyl-2,5-dioxo-3-(2-methylpropyl)-9-((4,7,7-trimethyl-2-oxa-3-oxobicyclo[2.2.1]heptan-1-yl)-carbonyl)-1,4,9-triazaspiro[5.5]undecane |
| 21(H18-3) | 1-propyl-2,5-dioxo-3-(2-methylpropyl)-9-((4-dimethylaminophenyl)carbonyl)-1,4,9-triazaspiro[5.5]undecane |
| 21(H18-4) | 1-propyl-2,5-dioxo-3-(2-methylpropyl)-9-((3-(2-chlorophenyl)-5-methylisooxazol-4-yl)carbonyl)-1,4,9-triazaspiro[5.5]undecane |
| 21(H18-5) | 1-propyl-2,5-dioxo-3-(2-methylpropyl)-9-((4-fluorophenyl)carbonyl)-1,4,9-triazaspiro[5.5]undecane |
| 21(H18-6) | 1-propyl-2,5-dioxo-3-(2-methylpropyl)-9-((3-fluorophenyl)carbonyl)-1,4,9-triazaspiro[5.5]undecane |
| 21(H18-7) | 1-propyl-2,5-dioxo-3-(2-methylpropyl)-9-((2-fluorophenyl)carbonyl)-1,4,9-triazaspiro[5.5]undecane |
| 21(H18-8) | 1-propyl-2,5-dioxo-3-(2-methylpropyl)-9-(cyclopentylcarbonyl)-1,4,9-triazaspiro[5.5]undecane |

TABLE 18A-2

| Example No | Compound Name |
|---|---|
| 21(H18-9) | 1-propyl-2,5-dioxo-3-(2-methylpropyl)-9-((3-methylphenyl)carbonyl)-1,4,9-triazaspiro[5.5]undecane |

TABLE 18A-2-continued

| Example No | Compound Name |
|---|---|
| 21(H18-10) | 1-propyl-2,5-dioxo-3-(2-methylpropyl)-9-((3-methoxyphenyl)carbonyl)-1,4,9-triazaspiro[5.5]undecane |
| 21(H18-11) | 1-propyl-2,5-dioxo-3-(2-methylpropyl)-9-(2,2-dimethylpropanoyl)-1,4,9-triazaspiro[5.5]undecane |
| 21(H18-12) | 1-propyl-2,5-dioxo-3-(2-methylpropyl)-9-(pyridin-3-ylcarbonyl)-1,4,9-triazaspiro[5.5]undecane |
| 21(H18-13) | 1-propyl-2,5-dioxo-3-(2-methylpropyl)-9-(pyridin-2-ylcarbonyl)-1,4,9-triazaspiro[5.5]undecane |
| 21(H18-14) | 1-propyl-2,5-dioxo-3-(2-methylpropyl)-9-(2-phenylacetyl)-1,4,9-triazaspiro[5.5]undecane |
| 21(H18-15) | 1-propyl-2,5-dioxo-3-(2-methylpropyl)-9-(2-phenyloxyacetyl)-1,4,9-triazaspiro[5.5]undecane |
| 21(H18-16) | 1-propyl-2,5-dioxo-3-(2-methylpropyl)-9-((4-ethyl-2,3-dioxopiperazinyl)carbonyl)-1,4,9-triazaspiro[5.5]undecane |
| 21(H18-17) | 1-propyl-2,5-dioxo-3-(2-methylpropyl)-9-((2-phenylthiopyridin-3-yl)carbonyl)-1,4,9-triazaspiro[5.5]undecane |

TABLE 18A-3

| Example No | Compound Name |
|---|---|
| 21(H18-18) | 1-propyl-2,5-dioxo-3-(2-methylpropyl)-9-((2-phenyloxypyridin-3-yl)carbonyl)-1,4,9-triazaspiro[5.5]undecane |
| 21(H18-19) | 1-propyl-2,5-dioxo-3-(2-methylpropyl)-9-((2-methoxyphenyl)carbonyl)-1,4,9-triazaspiro[5.5]undecane |
| 21(H18-20) | 1-propyl-2,5-dioxo-3-(2-methylpropyl)-9-(2-(thiophen-2-yl)acetyl)-1,4,9-triazaspiro[5.5]undecane |
| 21(H18-21) | 1-propyl-2,5-dioxo-3-(2-methylpropyl)-9-hexanoyl-1,4,9-triazaspiro[5.5]undecane |
| 21(H18-22) | 1-propyl-2,5-dioxo-3-(2-methylpropyl)-9-((4-methylphenyl)carbonyl)-1,4,9-triazaspiro[5.5]undecane |
| 21(H18-23) | 1-propyl-2,5-dioxo-3-(2-methylpropyl)-9-(2-methylpropanoyl)-1,4,9-triazaspiro[5.5]undecane |
| 21(H18-24) | 1-propyl-2,5-dioxo-3-(2-methylpropyl)-9-(3-cyclopentylpropanoyl)-1,4,9-triazaspiro[5.5]undecane |
| 21(H18-25) | 1-propyl-2,5-dioxo-3-(2-methylpropyl)-9-((2E)-3-phenyl-2-propenoyl)-1,4,9-triazaspiro[5.5]undecane |
| 21(H18-26) | 1-propyl-2,5-dioxo-3-(2-methylpropyl)-9-((2-methylphenyl)carbonyl)-1,4,9-triazaspiro[5.5]undecane |

TABLE 18A-4

| Example No | Compound Name |
|---|---|
| 21(H18-27) | 1-propyl-2,5-dioxo-3-(2-methylpropyl)-9-(3,3-dimethylbutanoyl)-1,4,9-triazaspiro[5.5]undecane |
| 21(H18-28) | 1-propyl-2,5-dioxo-3-(2-methylpropyl)-9-cyclohexylcarbonyl-1,4,9-triazaspiro[5.5]undecane |
| 21(H18-29) | 1-propyl-2,5-dioxo-3-(2-methylpropyl)-9-phenylcarbonyl-1,4,9-triazaspiro[5.5]undecane |
| 21(H18-30) | 1-propyl-2,5-dioxo-3-(2-methylpropyl)-9-(thiophen-2-ylcarbonyl)-1,4,9-triazaspiro[5.5]undecane |
| 21(H18-31) | 1-propyl-2,5-dioxo-3-(2-methylpropyl)-9-((2,6,6-trimethyl-1-cyclohexenyl)carbonyl)-1,4,9-triazaspiro[5.5]undecane |
| 21(H18-32) | 1-propyl-2,5-dioxo-3-(2-methylpropyl)-9-((ethoxycarbonyl)carbonyl)-1,4,9-triazaspiro[5.5]undecane |
| 21(H18-33) | 1-propyl-2,5-dioxo-3-(2-methylpropyl)-9-((3-phenyl-5-methylisooxazol-4-yl)carbonyl)-1,4,9-triazaspiro[5.5]undecane |

TABLE 18A-4-continued

| Example No | Compound Name |
|---|---|
| 21(H18-34) | 1-propyl-2,5-dioxo-3-(2-methylpropyl)-9-((5-methyl-2-phenyl-1,2,3-triazol-4-yl)carbonyl)-1,4,9-triazaspiro[5.5]undecane |

TABLE 18A-5

| Example No | Compound Name |
|---|---|
| 21(H18-35) | 1-propyl-2,5-dioxo-3-(2-methylpropyl)-9-(2-(3-methoxyphenyl)acetyl)-1,4,9-triazaspiro[5.5]undecane |
| 21(H18-36) | 1-propyl-2,5-dioxo-3-(2-methylpropyl)-9-(4-methoxyphenylcarbonyl)-1,4,9-triazaspiro[5.5]undecane |
| 21(H18-37) | 1-propyl-2,5-dioxo-3-(2-methylpropyl)-9-((furan-2-yl)carbonyl)-1,4,9-triazaspiro[5.5]undecane |
| 21(H18-38) | 1-propyl-2,5-dioxo-3-(2-methylpropyl)-9-(2-benzyloxyacetyl)-1,4,9-triazaspiro[5.5]undecane |
| 21(H18-39) | 1-propyl-2,5-dioxo-3-(2-methylpropyl)-9-(cyclobutylcarbonyl)-1,4,9-triazaspiro[5.5]undecane |
| 21(H18-40) | 1-propyl-2,5-dioxo-3-(2-methylpropyl)-9-(2-(4-methoxyphenyl)acetyl)-1,4,9-triazaspiro[5.5]undecane |
| 21(H18-41) | 1-propyl-2,5-dioxo-3-(2-methylpropyl)-9-acetyl-1,4,9-triazaspiro[5.5]undecane |
| 21(H18-42) | 1-propyl-2,5-dioxo-3-(2-methylpropyl)-9-(4-methylpentanoyl)-1,4,9-triazaspiro[5.5]undecane |
| 21(H18-43) | 1-propyl-2,5-dioxo-3-(2-methylpropyl)-9-(2-methoxyacetyl)-1,4,9-triazaspiro[5.5]undecane |

TABLE 18A-6

| Example No | Compound Name |
|---|---|
| 2l(H18-44) | 1-propyl-2,5-dioxo-3-(2-methylpropyl)-9-(3-methylthiopropanoyl)-1,4,9-triazaspiro[5.5]undecane |
| 21(H18-45) | 1-propyl-2,5-dioxo-3-(2-methylpropyl)-9-((isooxazol-5-yl)carbonyl)-1,4,9-triazaspiro[5.5]undecane |
| 21(H18-46) | 1-propyl-2,5-dioxo-3-(2-methylpropyl)-9-(2-cyclopentylacetyl)-1,4,9-triazaspiro[5.5]-undecane |
| 21(H18-47) | 1-propyl-2,5-dioxo-3-(2-methylpropyl)-9-pentanoyl-1,4,9-triazaspiro[5.5]undecane |
| 21(H18-48) | 1-propyl-2,5-dioxo-3-(2-methylpropyl)-9-(3-methylpropanoyl)-1,4,9-triazaspiro[5.5]undecane |
| 21(H18-49) | 1-propyl-2,5-dioxo-3-(2-methylpropyl)-9-(2-phenylthioacetyl)-1,4,9-triazaspiro[5.5]undecane |
| 21(H18-50) | 1-propyl-2,5-dioxo-3-(2-methylpropyl)-9-((4-methyl-1,2,3-thiadiazol-5-yl)carbonyl)-1,4,9-triazaspiro[5.5]undecane |
| 21(H18-51) | 1-propyl-2,5-dioxo-3-(2-methylpropyl)-9-((3-cyanophenyl)carbonyl)-1,4,9-triazaspiro[5.5]-undecane |
| 21(H18-52) | 1-propyl-2,5-dioxo-3-(2-methylpropyl)-9-butanoyl-1,4,9-triazaspiro[5.5]undecane |

TABLE 18A-7

| Example No | Compound Name |
|---|---|
| 21(H18-53) | 1-propyl-2,5-dioxo-3-(2-methylpropyl)-9-propanoyl-1,4,9-triazaspiro[5.5]undecane |
| 21(H18-54) | 1-propyl-2,5-dioxo-3-(2-methylpropyl)-9-cyclopropylcarbonyl-1,4,9-triazaspiro[5.5]undecane |
| 21(H18-55) | 1-propyl-2,5-dioxo-3-(2-methylpropyl)-9-(2H-benzo[3,4-d]1,3-dioxolan-5-ylcarbonyl)-1,4,9-triazaspiro[5.5]undecane |

TABLE 18A-7-continued

| Example No | Compound Name |
|---|---|
| 21(H18-56) | 1-propyl-2,5-dioxo-3-(2-methylpropyl)-9-((1-phenyl-5-propylpyrazol-4-yl)carbonyl)-1,4,9-triazaspiro[5.5]undecane |
| 21(H18-57) | 1-propyl-2,5-dioxo-3-(2-methylpropyl)-9-((5-(1,1-dimethylethyl)-2-methylfuran-3-yl)carbonyl)-1,4,9-triazaspiro[5.5]undecane |
| 21(H18-58) | 1-propyl-2,5-dioxo-3-(2-methylpropyl)-9-((1-(1,1-dimethylethyl)-3-methylpyrazol-5-yl)carbonyl)-1,4,9-triazaspiro[5.5]undecane |
| 21(H18-59) | 1-propyl-2,5-dioxo-3-(2-methylpropyl)-9-methylsulfonyl-1,4,9-triazaspiro[5.5]undecane |
| 21(H18-60) | 1-propyl-2,5-dioxo-3-(2-methylpropyl)-9-pentylsulfonyl-1,4,9-triazaspiro[5.5]undecane |

TABLE 18A-8

| Example No | Compound Name |
|---|---|
| 21(H18-61) | 1-propyl-2,5-dioxo-3-(2-methylpropyl)-9-((1-methylethyl)sulfonyl)-1,4,9-triazaspiro[5.5]undecane |
| 21(H18-62) | 1-propyl-2,5-dioxo-3-(2-methylpropyl)-9-((2-iodophenyl)sulfonyl)-1,4,9-triazaspiro[5.5]undecane |
| 21(H18-63) | 1-propyl-2,5-dioxo-3-(2-methylpropyl)-9-((4-methylsulfonylphenyl)sulfonyl)-1,4,9-triazaspiro[5.5]undecane |
| 21(H18-64) | 1-propyl-2,5-dioxo-3-(2-methylpropyl)-9-((4-trifluoromethylphenyl)sulfonyl)-1,4,9-triazaspiro[5.5]undecane |
| 21(H18-65) | 1-propyl-2,5-dioxo-3-(2-methylpropyl)-9-((4-phenylphenyl)sulfonyl)-1,4,9-triazaspiro[5.5]undecane |
| 21(H18-66) | 1-propyl-2,5-dioxo-3-(2-methylpropyl)-9-((2-phenylphenyl)sulfonyl)-1,4,9-triazaspiro[5.5]undecane |
| 21(H18-67) | 1-propyl-2,5-dioxo-3-(2-methylpropyl)-9-((2-methoxycarbonylphenyl)sulfonyl)-1,4,9-triazaspiro[5.5]undecane |
| 21(H18-68) | 1-propyl-2,5-dioxo-3-(2-methylpropyl)-9-((3,4-difluorophenyl)sulfonyl)-1,4,9-triazaspiro[5.5]undecane |
| 21(H18-69) | 1-propyl-2,5-dioxo-3-(2-methylpropyl)-9-((2,6-difluorophenyl)sulfonyl)-1,4,9-triazaspiro[5.5]undecane |

TABLE 18A-9

| Example No | Compound Name |
|---|---|
| 21(H18-70) | 1-propyl-2,5-dioxo-3-(2-methylpropyl)-9-((2,5-difluorophenyl)sulfonyl)-1,4,9-triazaspiro[5.5]undecane |
| 21(H18-71) | 1-propyl-2,5-dioxo-3-(2-methylpropyl)-9-((2,5-dimethoxyphenyl)sulfonyl)-1,4,9-triazaspiro[5.5]undecane |
| 21(H18-72) | 1-propyl-2,5-dioxo-3-(2-methylpropyl)-9-(2-naphthylsulfonyl)-1,4,9-triazaspiro[5.5]undecane |
| 21(H18-73) | 1-propyl-2,5-dioxo-3-(2-methylpropyl)-9-(((1E)-2-phenylvinyl)sulfonyl)-1,4,9-triazaspiro[5.5]undecane |
| 21(H18-74) | 1-propyl-2,5-dioxo-3-(2-methylpropyl)-9-((furan-2-yl)-sulfonyl)-1,4,9-triazaspiro[5.5]undecane |
| 21(H18-75) | 1-propyl-2,5-dioxo-3-(2-methylpropyl)-9-((thiophen-2-yl)sulfonyl)-1,4,9-triazaspiro[5.5]undecane |

TABLE 19A-1

| Example No | Compound Name |
|---|---|
| 21(H19-1) | 1-propyl-2,5-dioxo-3-(2-methylpropyl)-9-((4-methyl-2-acetylaminothiazol-5-yl)sulfonyl)-1,4,9-triazaspiro[5.5]undecane |
| 21(H19-2) | 1-propyl-2,5-dioxo-3-(2-methylpropyl)-9-((2-methoxy-dibenzofuran-3-yl)sulfonyl)-1,4,9-triazaspiro[5.5]-undecane |
| 21(H19-3) | 1-propyl-2,5-dioxo-3-(2-methylpropyl)-9-((4-methoxyphenyl)sulfonyl)-1,4,9-triazaspiro[5.5]undecane |
| 21(H19-4) | 1-propyl-2,5-dioxo-3-(2-methylpropyl)-9-benzylsulfonyl-1,4,9-triazaspiro[5.5]undecane |
| 21(H19-5) | 1-propyl-2,5-dioxo-3-(2-methylpropyl)-9-((ethylamino)carbonyl)-1,4,9-triazaspiro[5.5]undecane |
| 21(H19-6) | 1-propyl-2,5-dioxo-3-(2-methylpropyl)-9-((propylamino)carbonyl)-1,4,9-triazaspiro[5.5]undecane |
| 21(H19-7) | 1-propyl-2,5-dioxo-3-(2-methylpropyl)-9-((1-methylethylamino)carbonyl)-1,4,9-triazaspiro[5.5]undecane |
| 21(H19-8) | 1-propyl-2,5-dioxo-3-(2-methylpropyl)-9-((ethoxycarbonylmethylamino)carbonyl)-1,4,9-triazaspiro[5.5]undecane |

TABLE 19A-2

| Example No | Compound Name |
|---|---|
| 21(H19-9) | 1-propyl-2,5-dioxo-3-(2-methylpropyl)-9-((butylamino)carbonyl)-1,4,9-triazaspiro[5.5]undecane |
| 21(H19-10) | 1-propyl-2,5-dioxo-3-(2-methylpropyl)-9-((4-chlorophenylamino)carbonyl)-1,4,9-triazaspiro[5.5]undecane |
| 21(H19-11) | 1-propyl-2,5-dioxo-3-(2-methylpropyl)-9-((phenylamino)carbonyl)-1,4,9-triazaspiro[5.5]undecane |
| 21(H19-12) | 1-propyl-2,5-dioxo-3-(2-methylpropyl)-9-((4-methylphenylamino)carbonyl)-1,4,9-triazaspiro[5.5]undecane |
| 21(H19-13) | 1-propyl-2,5-dioxo-3-(2-methylpropyl)-9-((hexylamino)carbonyl)-1,4,9-triazaspiro[5.5]undecane |
| 21(H19-14) | 1-propyl-2,5-dioxo-3-(2-methylpropyl)-9-((4-fluorophenylamino)carbonyl)-1,4,9-triazaspiro[5.5]undecane |
| 21(H19-15) | 1-propyl-2,5-dioxo-3-(2-methylpropyl)-9-((benzylamino)carbonyl)-1,4,9-triazaspiro[5.5]undecane |
| 21(H19-16) | 1-propyl-2,5-dioxo-3-(2-methylpropyl)-9-((cyclohexylamino)carbonyl)-1,4,9-triazaspiro[5.5]undecane |
| 21(H19-17) | 1-propyl-2,5-dioxo-3-(2-methylpropyl)-9-((3-methylphenylamino)carbonyl)-1,4,9-triazaspiro[5.5]undecane |

TABLE 19A-3

| Example No | Compound Name |
|---|---|
| 21(H19-18) | 1-propyl-2,5-dioxo-3-(2-methylpropyl)-9-((octylamino)carbonyl)-1,4,9-triazaspiro[5.5]undecane |
| 21(H19-19) | 1-propyl-2,5-dioxo-3-(2-methylpropyl)-9-((4-bromophenylamino)carbonyl)-1,4,9-triazaspiro[5.5]undecane |

TABLE 19A-3-continued

| Example No | Compound Name |
|---|---|
| 21(H19-20) | 1-propyl-2,5-dioxo-3-(2-methylpropyl)-9-((2-(thiophen-2-yl)ethylamino)carbonyl)-1,4,9-triazaspiro[5.5]undecane |
| 21(H19-21) | 1-propyl-2,5-dioxo-3-(2-methylpropyl)-9-((4-(1-methylethyl)phenylamino)carbonyl)-1,4,9-triazaspiro[5.5]undecane |
| 21(H19-22) | 1-propyl-2,5-dioxo-3-(2-methylpropyl)-9-((3-chlorophenylamino)carbonyl)-1,4,9-triazaspiro[5.5]undecane |
| 21(H19-23) | 1-propyl-2,5-dioxo-3-(2-methylpropyl)-9-((2,4,5-trimethylphenylamino)carbonyl)-1,4,9-triazaspiro[5.5]undecane |
| 21(H19-24) | 1-propyl-2,5-dioxo-3-(2-methylpropyl)-9-((2,4,6-trimethylphenylamino)carbonyl)-1,4,9-triazaspiro[5.5]undecane |
| 21(H19-25) | 1-propyl-2,5-dioxo-3-(2-methylpropyl)-9-((4-phenyloxyphenylamino)carbonyl)-1,4,9-triazaspiro[5.5]undecane |

TABLE 19A-4

| Example No | Compound Name |
|---|---|
| 21(H19-26) | 1-propyl-2,5-dioxo-3-(2-methylpropyl)-9-((4-butyloxyphenylamino)carbonyl)-1,4,9-triazaspiro[5.5]undecane |
| 21(H19-27) | 1-propyl-2,5-dioxo-3-(2-methylpropyl)-9-((4-phenylphenylamino)carbonyl)-1,4,9-triazaspiro[5.5]undecane |
| 21(H19-28) | 1-propyl-2,5-dioxo-3-(2-methylpropyl)-9-((2-phenylphenylamino)carbonyl)-1,4,9-triazaspiro[5.5]undecane |
| 21(H19-29) | 1-propyl-2,5-dioxo-3-(2-methylpropyl)-9-((4-trifluoromethylphenylamino)carbonyl)-1,4,9-triazaspiro[5.5]undecane |
| 21(H19-30) | 1-propyl-2,5-dioxo-3-(2-methylpropyl)-9-((3,4-dichlorophenylamino)carbonyl)-1,4,9-triazaspiro[5.5]undecane |
| 21(H19-31) | 1-propyl-2,5-dioxo-3-(2-methylpropyl)-9-((4-butyloxycarbonylphenylamino)carbonyl)-1,4,9-triazaspiro[5.5]undecane |
| 21(H19-32) | 1-propyl-2,5-dioxo-3-(2-methylpropyl)-9-((2,6-bis(1-methylethyl)phenylamino)carbonyl)-1,4,9-triazaspiro[5.5]undecane |
| 21(H19-33) | 1-propyl-2,5-dioxo-3-(2-methylpropyl)-9-((2,5-dimethylphenylamino)carbonyl)-1,4,9-triazaspiro[5.5]undecane |

TABLE 19A-5

| Example No | Compound Name |
|---|---|
| 21(H19-34) | 1-propyl-2,5-dioxo-3-(2-methylpropyl)-9-((2-ethyl-6-(1-methylethyl)phenylamino)carbonyl)-1,4,9-triazaspiro[5.5]undecane |
| 21(H19-35) | 1-propyl-2,5-dioxo-3-(2-methylpropyl)-9-((2,4,6-trichlorophenylamino)carbonyl)-1,4,9-triazaspiro[5.5]undecane |
| 21(H19-36) | 1-propyl-2,5-dioxo-3-(2-methylpropyl)-9-((3,4-dimethylphenylamino)carbonyl)-1,4,9-triazaspiro[5.5]undecane |
| 21(H19-37) | 1-propyl-2,5-dioxo-3-(2-methylpropyl)-9-((2-methylthiophenylamino)carbonyl)-1,4,9-triazaspiro[5.5]undecane |
| 21(H19-38) | 1-propyl-2,5-dioxo-3-(2-methylpropyl)-9-((4-methylthiophenylamino)carbonyl)-1,4,9-triazaspiro[5.5]undecane |

TABLE 19A-5-continued

| Example No | Compound Name |
|---|---|
| 21(H19-39) | 1-propyl-2,5-dioxo-3-(2-methylpropyl)-9-((4-butylphenylamino)carbonyl)-1,4,9-triazaspiro[5.5]undecane |
| 21(H19-40) | 1-propyl-2,5-dioxo-3-(2-methylpropyl)-9-((2,6-dibromo-4-ethylphenylamino)carbonyl)-1,4,9-triazaspiro[5.5]undecane |
| 21(H19-41) | 1-propyl-2,5-dioxo-3-(2-methylpropyl)-9-((1-ethoxycarbonyl-2-methylpropylamino)carbonyl)-1,4,9-triazaspiro[5.5]undecane |

TABLE 19A-6

| Example No | Compound Name |
|---|---|
| 21(H19-42) | 1-propyl-2,5-dioxo-3-(2-methylpropyl)-9-((phenylcarbonylamino)carbonyl)-1,4,9-triazaspiro[5.5]undecane |
| 21(H19-43) | 1-propyl-2,5-dioxo-3-(2-methylpropyl)-9-((2,4,6-tribromophenylamino)carbonyl)-1,4,9-triazaspiro[5.5]undecane |
| 21(H19-44) | 1-propyl-2,5-dioxo-3-(2-methylpropyl)-9-((2,5-difluorophenylamino)carbonyl)-1,4,9-triazaspiro[5.5]undecane |
| 21(H19-45) | 1-propyl-2,5-dioxo-3-(2-methylpropyl)-9-((3,5-bis(methoxycarbonyl)phenylamino)carbonyl)-1,4,9-triazaspiro[5.5]undecane |
| 21(H19-46) | 1-propyl-2,5-dioxo-3-(2-methylpropyl)-9-((6,7-methylenedioxycoumarin-4-ylmethylamino)carbonyl)-1,4,9-triazaspiro[5.5]undecane |
| 21(H19-47) | 1-propyl-2,5-dioxo-3-(2-methylpropyl)-9-((2,6-dimethylphenylamino)carbonyl)-1,4,9-triazaspiro[5.5]undecane |
| 21(H19-48) | 1-propyl-2,5-dioxo-3-(2-methylpropyl)-9-((2-methylpropyloxy)carbonyl)-1,4,9-triazaspiro[5.5]undecane |
| 21(H19-49) | 1-propyl-2,5-dioxo-3-(2-methylpropyl)-9-((2-ethylhexyloxy)carbonyl)-1,4,9-triazaspiro[5.5]undecane |

TABLE 19A-7

| Example No | Compound Name |
|---|---|
| 21(H19-50) | 1-propyl-2,5-dioxo-3-(2-methylpropyl)-9-ethoxy-carbonyl-1,4,9-triazaspiro[5.5]undecane |
| 21(H19-51) | 1-propyl-2,5-dioxo-3-(2-methylpropyl)-9-allyloxy-carbonyl-1,4,9-triazaspiro[5.5]undecane |
| 21(H19-52) | 1-propyl-2,5-dioxo-3-(2-methylpropyl)-9-propyloxy-carbonyl-1,4,9-triazaspiro[5.5]undecane |
| 21(H19-53) | 1-propyl-2,5-dioxo-3-(2-methylpropyl)-9-butyloxy-carbonyl-1,4,9-triazaspiro[5.5]undecane |
| 21(H19-54) | 1-propyl-2,5-dioxo-3-(2-methylpropyl)-9-hexyloxy-carbonyl-1,4,9-triazaspiro[5.5]undecane |
| 21(H19-55) | 1-propyl-2,5-dioxo-3-(2-methylpropyl)-9-((fluoren-9-ylmethyloxy)carbonyl)-1,4,9-triazaspiro[5.5]undecane |
| 21(H19-56) | 1-propyl-2,5-dioxo-3-(2-methylpropyl)-9-((1R,5R,2S)-5-methyl-2-(1-methylethyl)cyclohexyloxycarbonyl)-1,4,9-triazaspiro[5.5]undecane |
| 21(H19-57) | 1-propyl-2,5-dioxo-3-(2-methylpropyl)-9-((2-methoxyethoxy)carbonyl)-1,4,9-triazaspiro[5.5]undecane |
| 21(H19-58) | 1-propyl-2,5-dioxo-3-(2-methylpropyl)-9-pentyloxy-carbonyl-1,4,9-triazaspiro[5.5]undecane |

TABLE 19A-8

| Example No | Compound Name |
|---|---|
| 21(H19-59) | 1-propyl-2,5-dioxo-3-(2-methylpropyl)-9-((1-methylethyloxy)carbonyl)-1,4,9-triazaspiro[5.5]undecane |
| 21(H19-60) | 1-propyl-2,5-dioxo-3-(2-methylpropyl)-9-((3-butenyloxy)carbonyl)-1,4,9-triazaspiro[5.5]undecane |
| 21(H19-61) | 1-propyl-2,5-dioxo-3-(2-methylpropyl)-9-((2R,1S,5S)-methyl-2-(1-methylethyl)cyclohexyloxycarbonyl)-1,4,9-triazaspiro[5.5]undecane |
| 21(H19-62) | 1-propyl-2,5-dioxo-3-(2-methylpropyl)-9-cyclopentyloxycarbonyl-1,4,9-triazaspiro[5.5]undecane |
| 21(H19-63) | 1-propyl-2,5-dioxo-3-(2-methylpropyl)-9-benzyloxy-carbonyl-1,4,9-triazaspiro[5.5]undecane |
| 21(H19-64) | 1-propyl-2,5-dioxo-3-(2-methylpropyl)-9-((N,N-diphenylamino)carbonyl)-1,4,9-triazaspiro[5.5]undecane |
| 21(H19-65) | 1-propyl-2,5-dioxo-3-(2-methylpropyl)-9-((N-phenyl-N-methylamino)carbonyl)-1,4,9-triazaspiro[5.5]undecane |
| 21(H19-66) | 1-propyl-2,5-dioxo-3-(2-methylpropyl)-9-((N,N-dimethylamino)carbonyl)-1,4,9-triazaspiro[5.5]undecane |
| 21(H19-67) | 1-propyl-2,5-dioxo-3-(2-methylpropyl)-9-((N,N-diethylamino)carbonyl)-1,4,9-triazaspiro[5.5]undecane |

TABLE 19A-9

| Example No | Compound Name |
|---|---|
| 21(H19-68) | 1-propyl-2,5-dioxo-3-(2-methylpropyl)-9-((N,N-bis(1-methylethyl)amino)carbonyl)-1,4,9-triazaspiro[5.5]undecane |
| 21(H19-69) | 1-propyl-2,5-dioxo-3-(2-methylpropyl)-9-(morpholin-4-ylcarbonyl)-1,4,9-triazaspiro[5.5]undecane |
| 21(H19-70) | 1-propyl-2,5-dioxo-3-(2-methylpropyl)-9-(carbazol-9-ylcarbonyl)-1,4,9-triazaspiro[5.5]undecane |
| 21(H19-71) | 1-propyl-2,5-dioxo-3-(2-methylpropyl)-9-(pyrrolidin-1-ylcarbonyl)-1,4,9-triazaspiro[5.5]undecane |

TABLE 16B-1

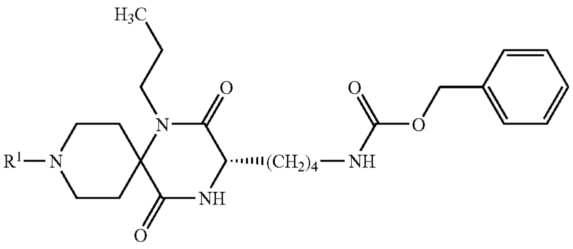

| Example No | $R^1$ |
|---|---|
| 21(H16-1) | 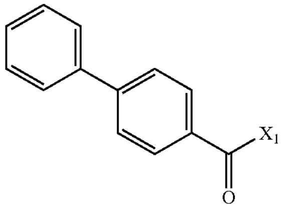 |
| 21(H16-2) | 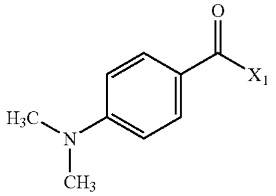 |
| 21(H16-3) | 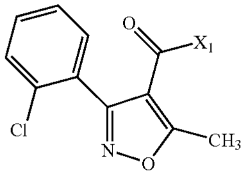 |
| 21(H16-4) | 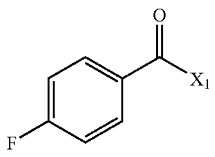 |
| 21(H16-5) | 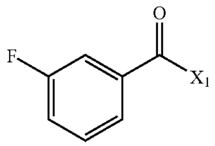 |

TABLE 16B-2
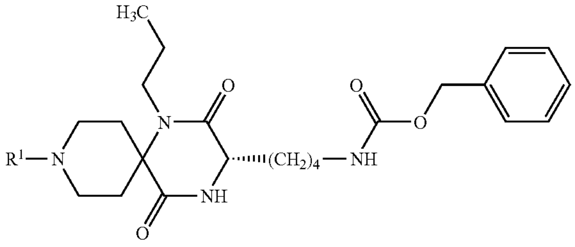
| Example No | $R^1$ |
| --- | --- |
| 21(H16-6) | 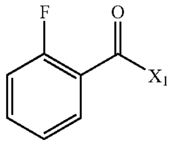 |
| 21(H16-7) | 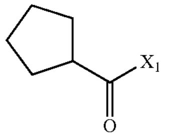 |
| 21(H16-8) | 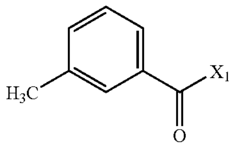 |
| 21(H16-9) | 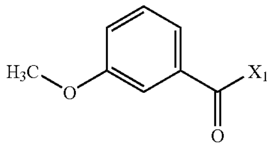 |
| 21(H16-10) | 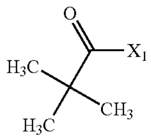 |
| 21(H16-11) | 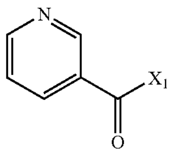 |
TABLE 16B-3
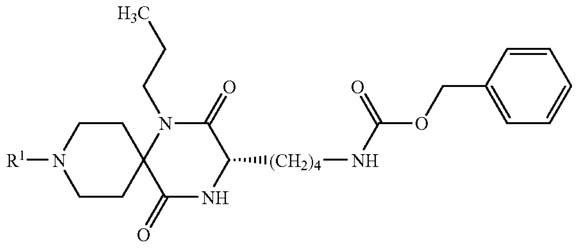
| Example No | $R^1$ |
| --- | --- |
| 21(H16-12) | 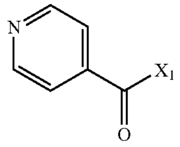 |
| 21(H16-13) | 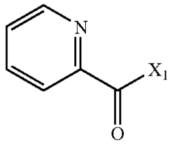 |
| 21(H16-14) | 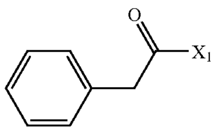 |
| 21(H16-15) | 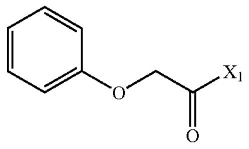 |
| 21(H16-16) | 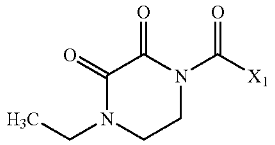 |
| 21(H16-17) | 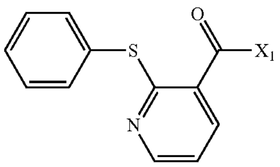 |

TABLE 16B-4
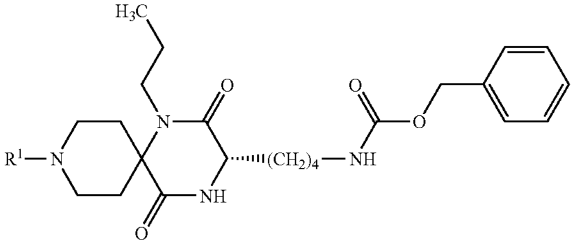
| Example No | $R^1$ |
|---|---|
| 21(H16-18) | 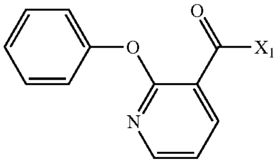 |
| 21(H16-19) | 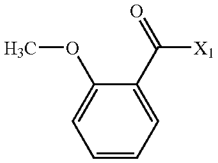 |
| 21(H16-20) | 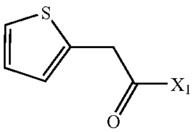 |
| 21(H16-21) | 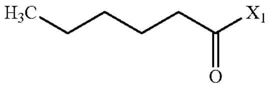 |
| 21(H16-22) | 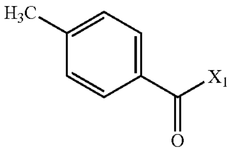 |
| 21(H16-23) | 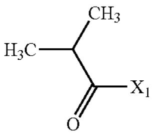 |
| 21(H16-24) | 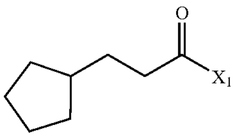 |
TABLE 16B-5
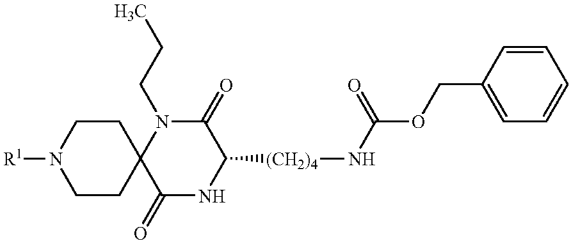
| Example No | $R^1$ |
|---|---|
| 21(H16-25) | 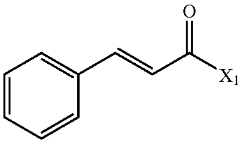 |
| 21(H16-26) | 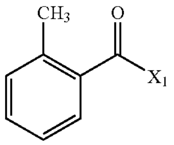 |
| 21(H16-27) | 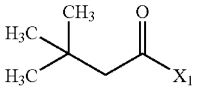 |
| 21(H16-28) | 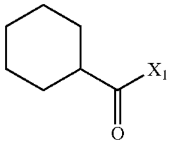 |
| 21(H16-29) | 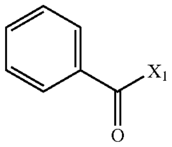 |
| 21(H16-30) | 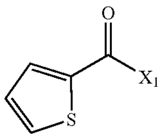 |
| 21(H16-31) | 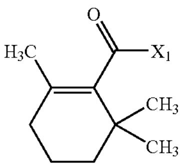 |

TABLE 16B-6
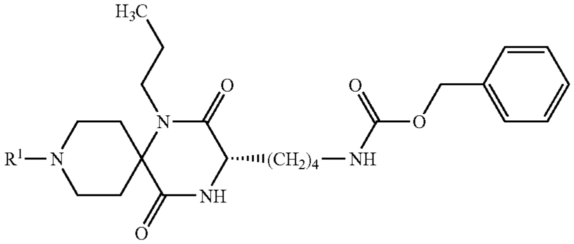
| Example No | $R^1$ |
|---|---|
| 21(H16-32) | 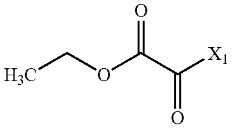 |
| 21(H16-33) | 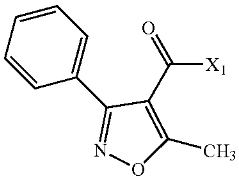 |
| 21(H16-34) | 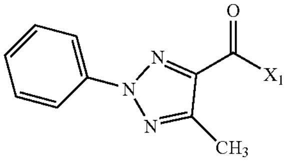 |
| 21(H16-35) | 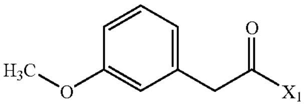 |
| 21(H16-36) | 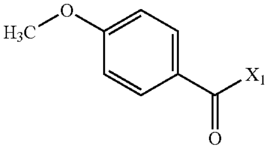 |
| 21(H16-37) | 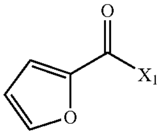 |
| 21(H16-38) | 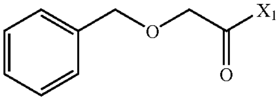 |
TABLE 16B-7
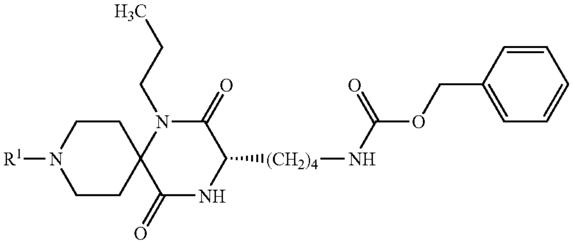
| Example No | $R^1$ |
|---|---|
| 21(H16-39) | 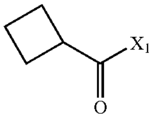 |
| 21(H16-40) | 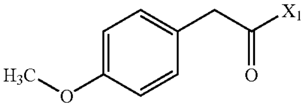 |
| 21(H16-41) | 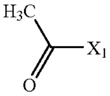 |
| 21(H16-42) | 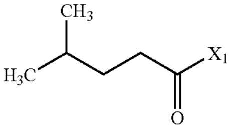 |
| 21(H16-43) | 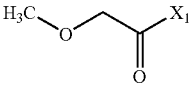 |
| 21(H16-44) | 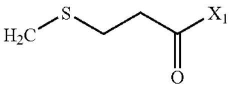 |
| 21(H16-45) | 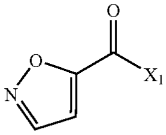 |
| 21(H16-46) | 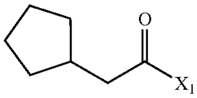 |

TABLE 16B-8
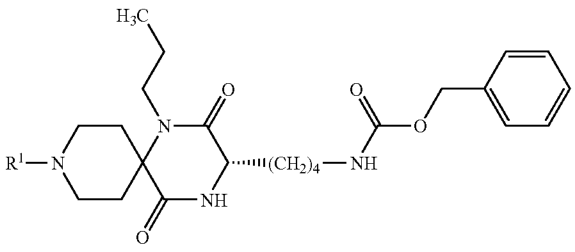
| Example No | $R^1$ |
|---|---|
| 21(H16-47) | 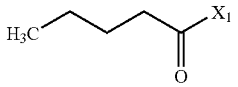 |
| 21(H16-48) | 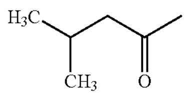 |
| 21(H16-49) | 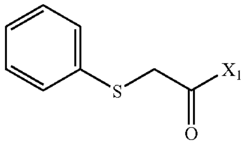 |
| 21(H16-50) | 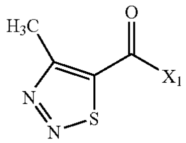 |
| 21(H16-51) | 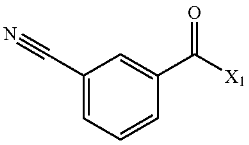 |
| 21(H16-52) | 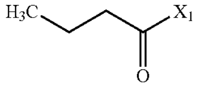 |
| 21(H16-53) | 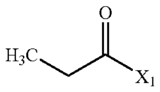 |
| 21(H16-54) | 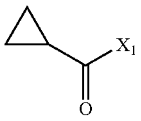 |
TABLE 16B-9
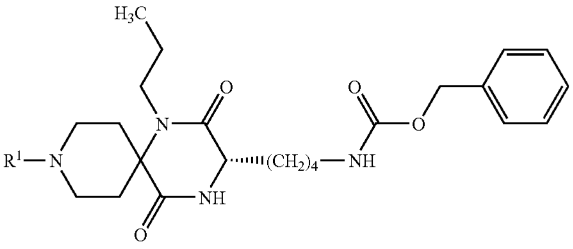
| Example No | $R^1$ |
|---|---|
| 21(H16-55) | 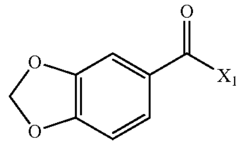 |
| 21(H16-56) | 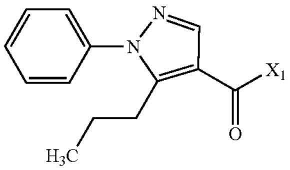 |
| 21(H16-57) | 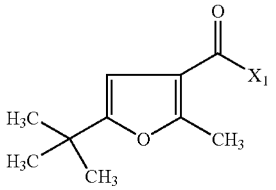 |
| 21(H16-58) | 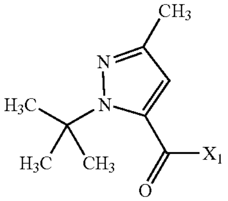 |
| 21(H16-59) | 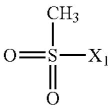 |
| 21(H16-60) | 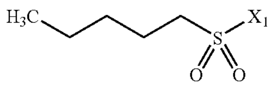 |

TABLE 16B-10
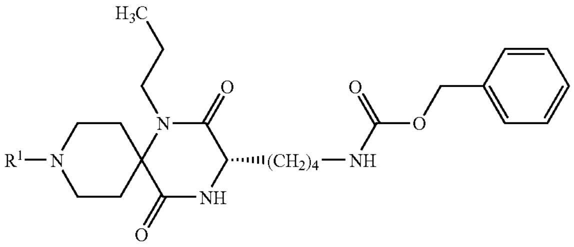
| Example No | $R^1$ |
|---|---|
| 21(H16-61) | 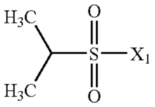 |
| 21(H16-62) | 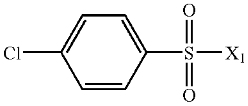 |
| 21(H16-63) | 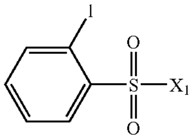 |
| 21(H16-64) | 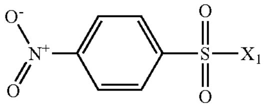 |
| 21(H16-65) | 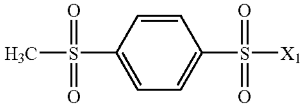 |
| 21(H16-66) | 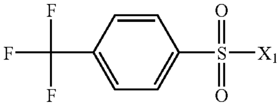 |
| 21(H16-67) | 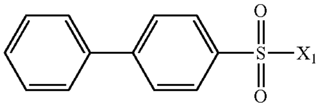 |
| 21(H16-68) | 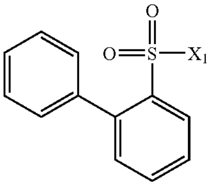 |
TABLE 16B-11
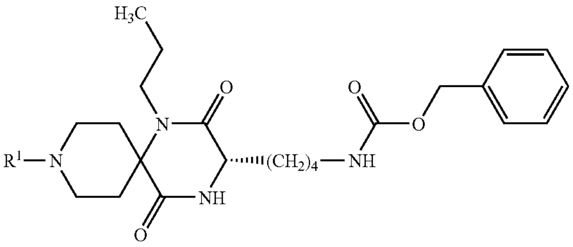
| Example No | $R^1$ |
|---|---|
| 21(H16-69) | 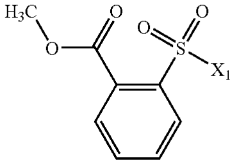 |
| 21(H16-70) | 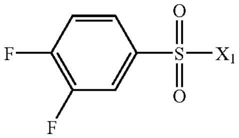 |
| 21(H16-71) | 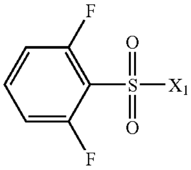 |
| 21(H16-72) | 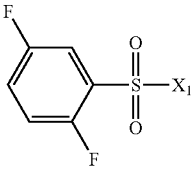 |
| 21(H16-73) | 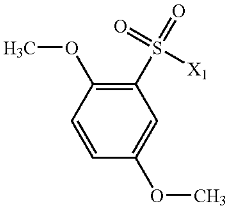 |
| 21(H16-74) | 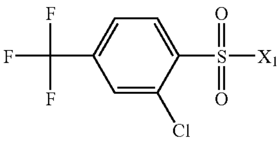 |

TABLE 16B-12
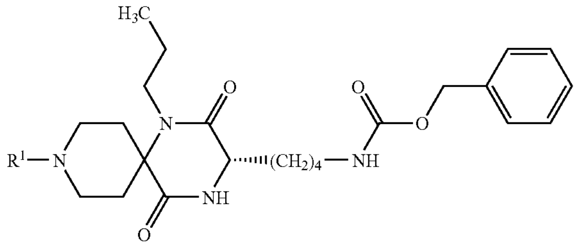
| Example No | $R^1$ |
|---|---|
| 21(H16-75) | 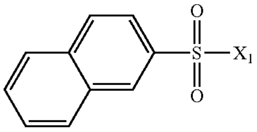 |
| 21(H16-76) | 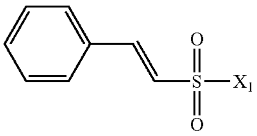 |
| 21(H16-77) | 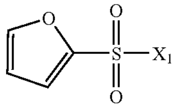 |
| 21(H16-78) | 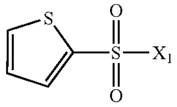 |
TABLE 17B-1
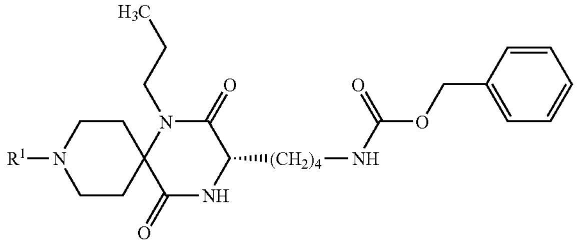
| Example No | $R^1$ |
|---|---|
| 21(H17-1) | 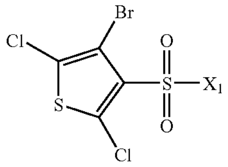 |
TABLE 17B-1-continued
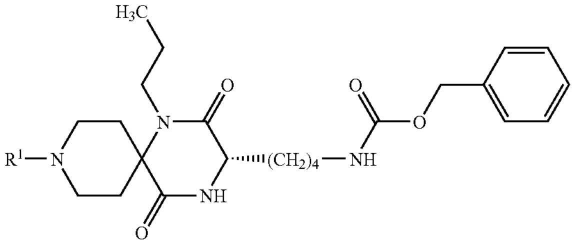
| Example No | $R^1$ |
|---|---|
| 21(H17-2) | 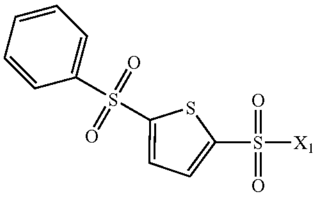 |
| 21(H17-3) | 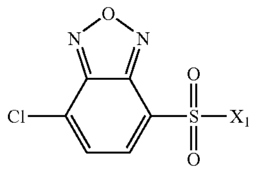 |
| 21(H17-4) | 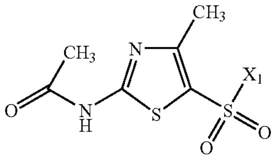 |
| 21(H17-5) | 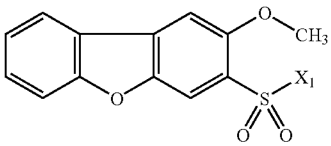 |
| 21(H17-6) | 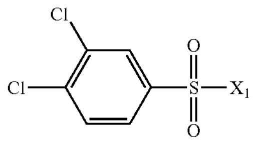 |

TABLE 17B-2
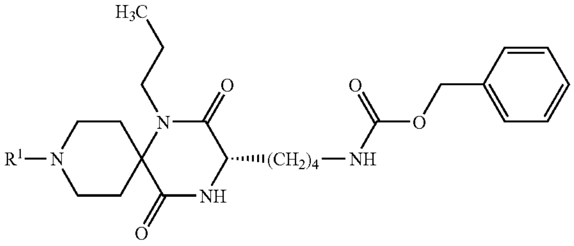
| Example No | $R^1$ |
|---|---|
| 21(H17-7) | 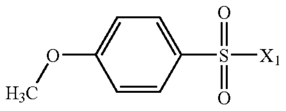 |
| 21(H17-8) | 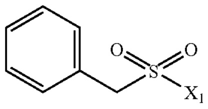 |
| 21(H17-9) | 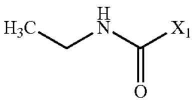 |
| 21(H17-10) | 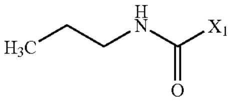 |
| 21(H17-11) | 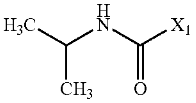 |
| 21(H17-12) | 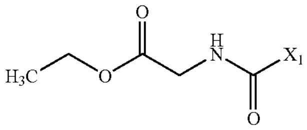 |
| 21(H17-13) | 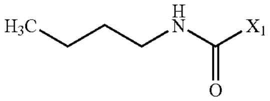 |
| 21(H17-14) | 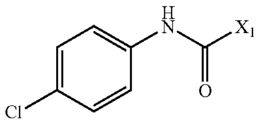 |
TABLE 17B-3
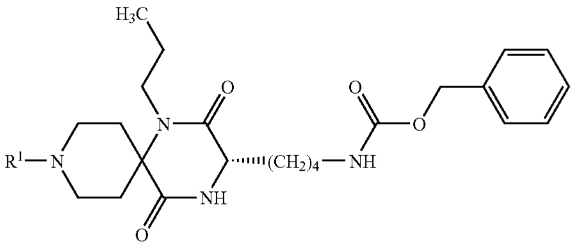
| Example No | $R^1$ |
|---|---|
| 21(H17-15) | 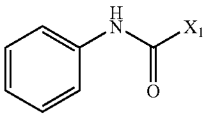 |
| 21(H17-16) | 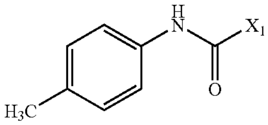 |
| 21(H17-17) | 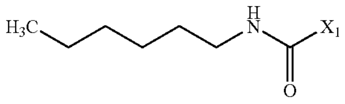 |
| 21(H17-18) | 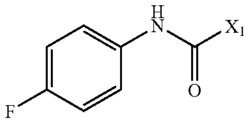 |
| 21(H17-19) | 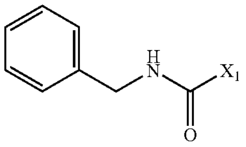 |
| 21(H17-20) | 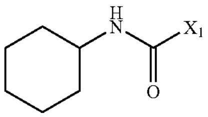 |
| 21(H17-21) | 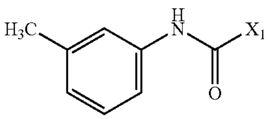 |

TABLE 17B-4
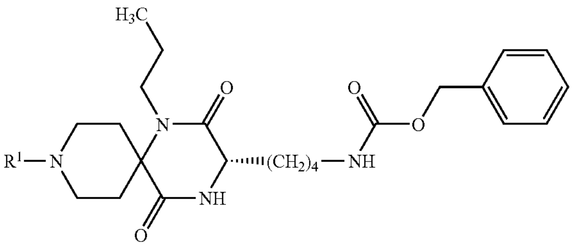
| Example No | $R^1$ |
| --- | --- |
| 21(H17-22) | 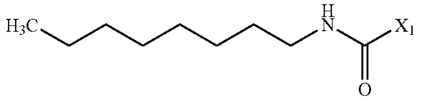 |
| 21(H17-23) | 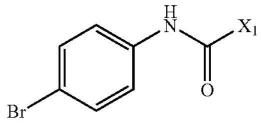 |
| 21(H17-24) | 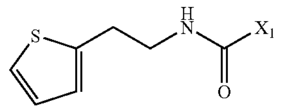 |
| 21(H17-25) | 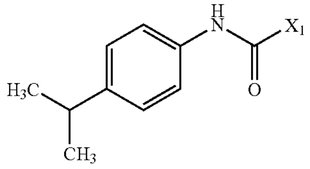 |
| 21(H17-26) | 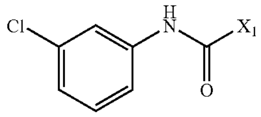 |
| 21(H17-27) | 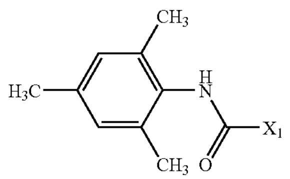 |
| 21(H17-28) | 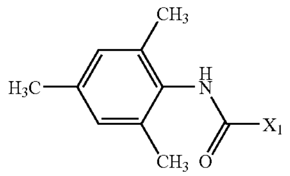 |
TABLE 17B-5
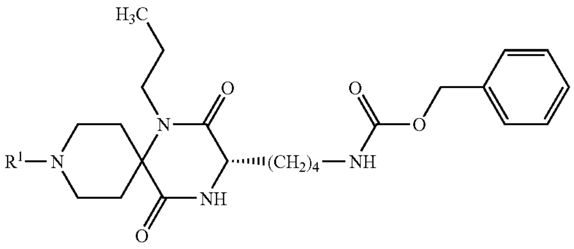
| Example No | $R^1$ |
| --- | --- |
| 21(H17-29) | 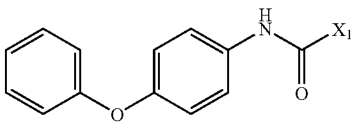 |
| 21(H17-30) | 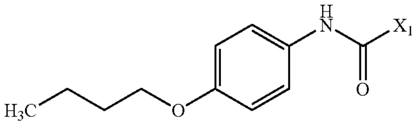 |
| 21(H17-31) | 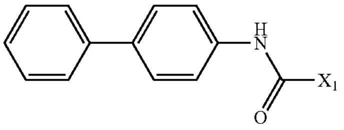 |
| 21(H17-32) | 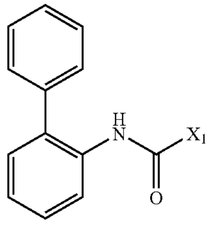 |
| 21(H17-33) | 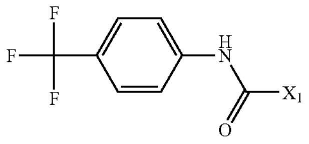 |
| 21(H17-34) | 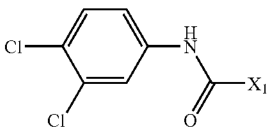 |

TABLE 17B-6
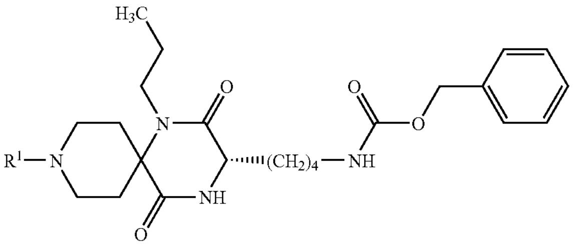
| Example No | $R^1$ |
| --- | --- |
| 21(H17-35) | 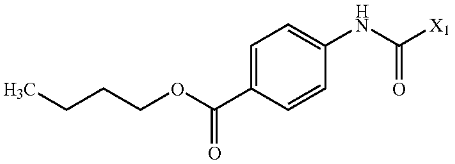 |
| 21(H17-36) | 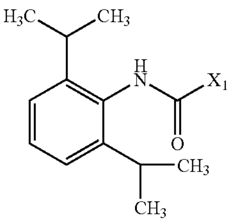 |
| 21(H17-37) | 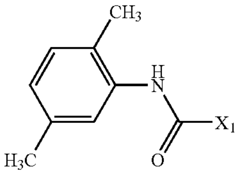 |
| 21(H17-38) | 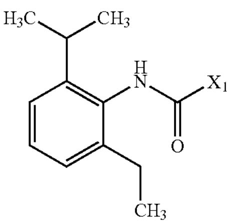 |
| 21(H17-39) | 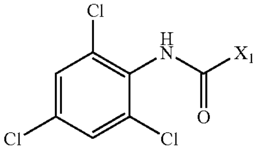 |
TABLE 17B-7
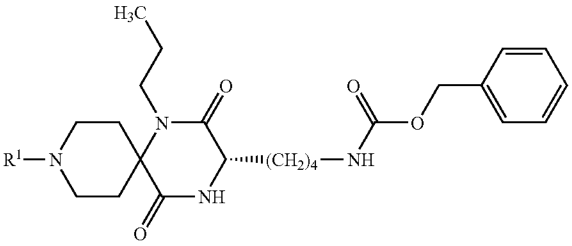
| Example No | $R^1$ |
| --- | --- |
| 21(H17-40) | 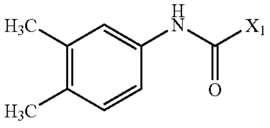 |
| 21(H17-41) | 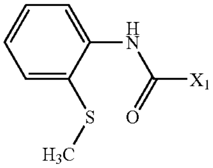 |
| 21(H17-42) | 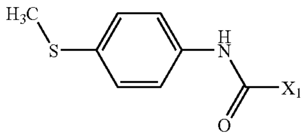 |
| 21(H17-43) | 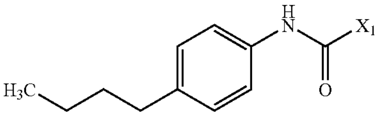 |
| 21(H17-44) | 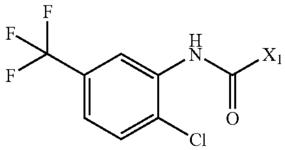 |
| 21(H17-45) | 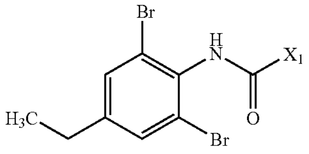 |

TABLE 17B-8
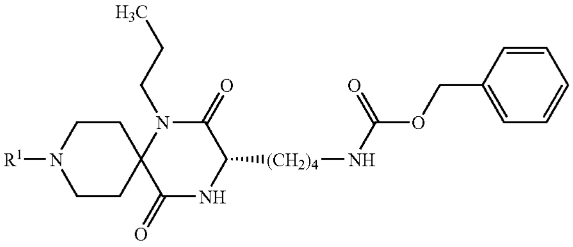
| Example No | R¹ |
|---|---|
| 21(H17-46) | 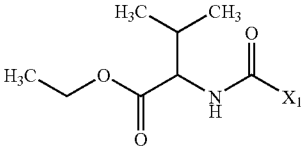 |
| 21(H17-47) | 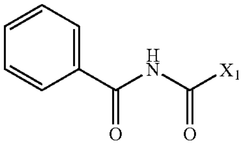 |
| 21(H17-48) | 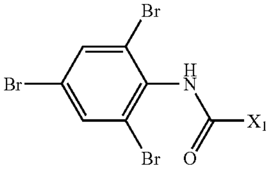 |
| 21(H17-49) | 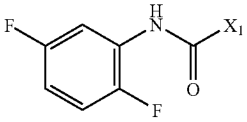 |
| 21(H17-50) | 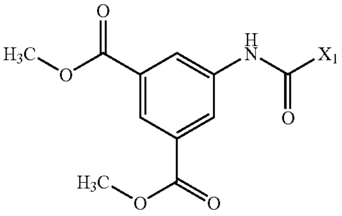 |
| 21(H17-51) | 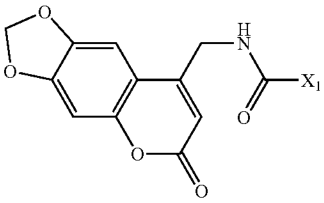 |
TABLE 17B-9
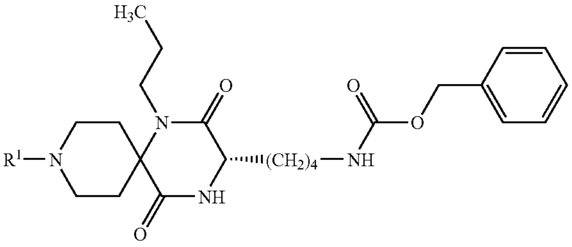
| Example No | R¹ |
|---|---|
| 21(H17-52) | 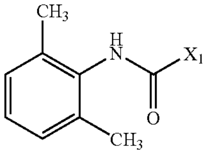 |
| 21(H17-53) | 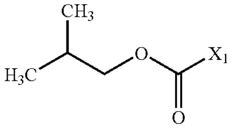 |
| 21(H17-54) | 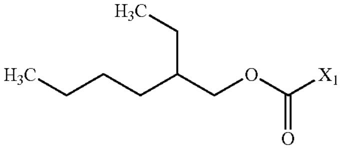 |
| 21(H17-55) | 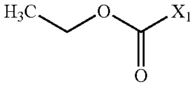 |
| 21(H17-56) | 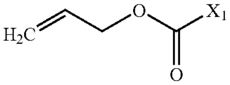 |
| 21(H17-57) | 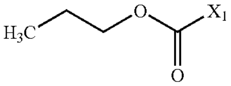 |
| 21(H17-58) | 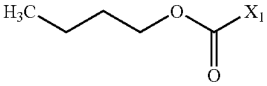 |
| 21(H17-59) | 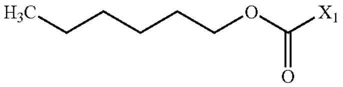 |

TABLE 17B-10
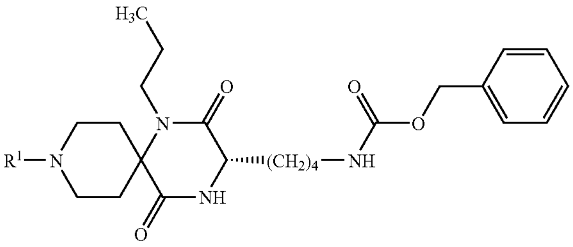
| Example No | $R^1$ |
|---|---|
| 21(H17-60) | 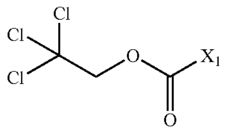 |
| 21(H17-61) | 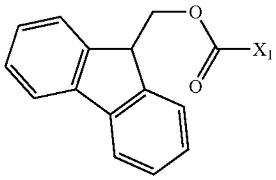 |
| 21(H17-62) | 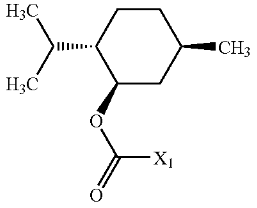 |
| 21(H17-63) | 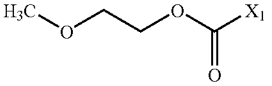 |
| 21(H17-64) | 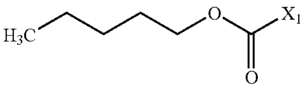 |
| 21(H17-65) | 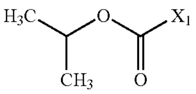 |
| 21(H17-66) | 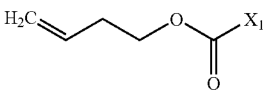 |
TABLE 17B-11
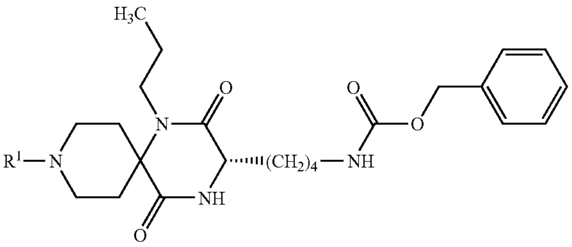
| Example No | $R^1$ |
|---|---|
| 21(H17-67) | 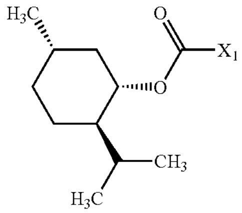 |
| 21(H17-68) | 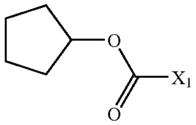 |
| 21(H17-69) | 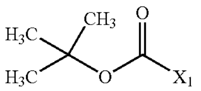 |
| 21(H17-70) | 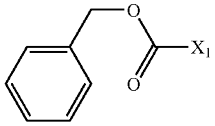 |
| 21(H17-71) | 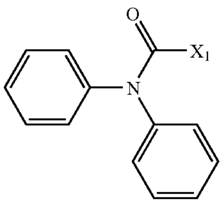 |
| 21(H17-72) | 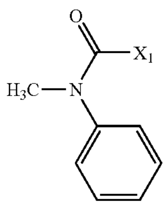 |

TABLE 17B-12
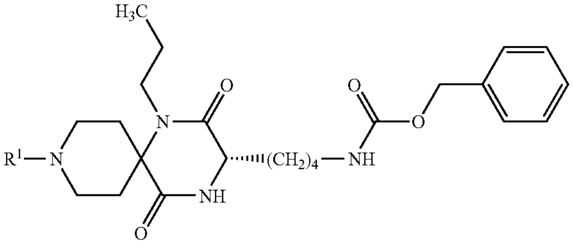
| Example No | $R^1$ |
| --- | --- |
| 21(H17-73) | 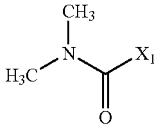 |
| 21(H17-74) | 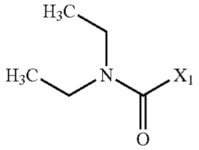 |
| 21(H17-75) | 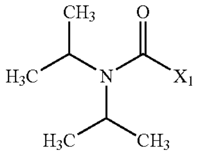 |
| 21(H17-76) | 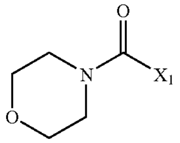 |
| 21(H17-77) | 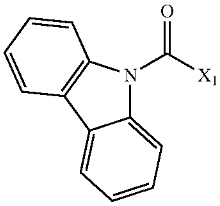 |
| 21(H17-78) | 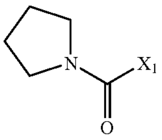 |
TABLE 18B-1
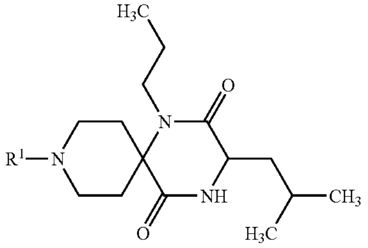
| Example No | $R^1$ |
| --- | --- |
| 21(H18-1) | 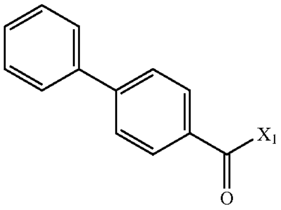 |
| 21(H18-2) | 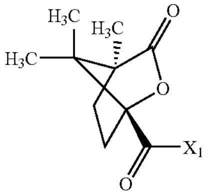 |
| 21(H18-3) | 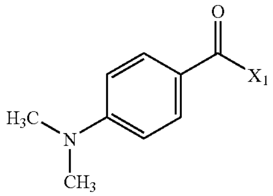 |
| 21(H18-4) | 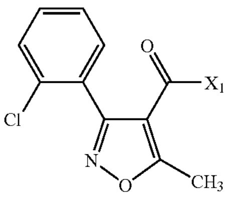 |
| 21(H18-5) | 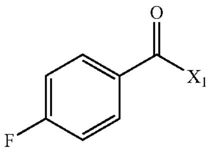 |

TABLE 18B-2
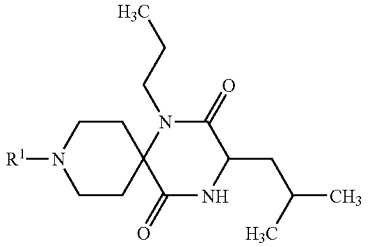
| Example No | $R^1$ |
|---|---|
| 21(H18-6) | 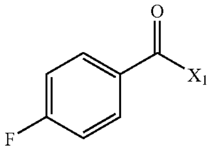 |
| 21(H18-7) | 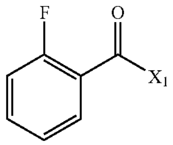 |
| 21(H18-8) | 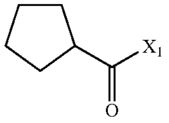 |
| 21(H18-9) | 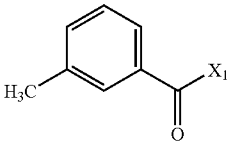 |
| 21(H18-10) | 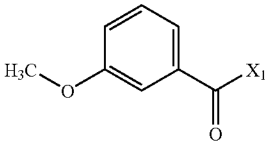 |
| 21(H18-11) | 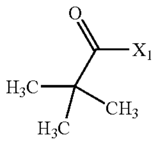 |
| 21(H18-12) | 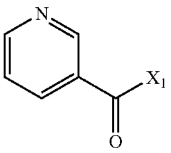 |
TABLE 18B-3
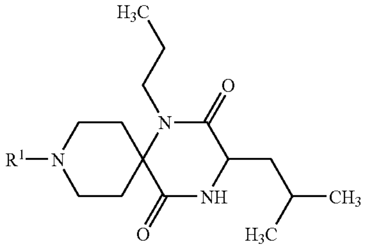
| Example No | $R^1$ |
|---|---|
| 21(H18-13) | 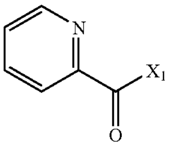 |
| 21(H18-14) | 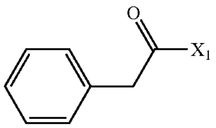 |
| 21(H18-15) | 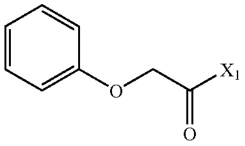 |
| 21(H18-16) | 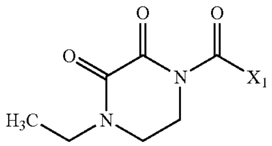 |
| 21(H18-17) | 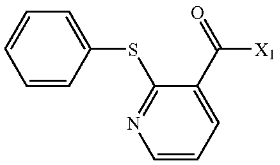 |
| 21(H18-18) | 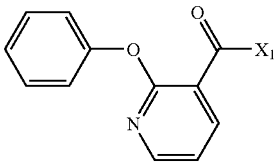 |

TABLE18B-4
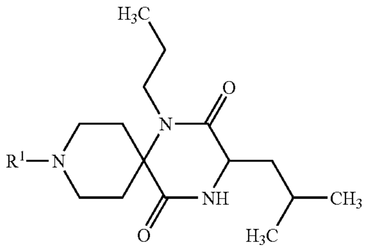
| Example No | $R^1$ |
|---|---|
| 21(H18-19) | 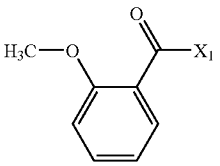 |
| 21(H18-20) | 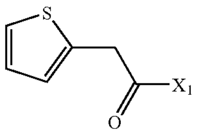 |
| 21(H18-21) | 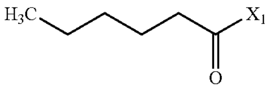 |
| 21(H18-22) | 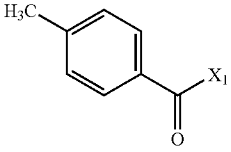 |
| 21(H18-23) | 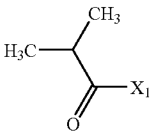 |
| 21(H18-24) | 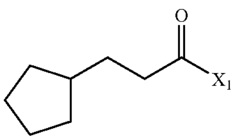 |
| 21(H18-25) | 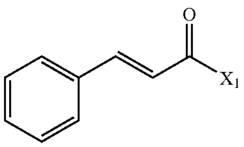 |
TABLE 18B-5
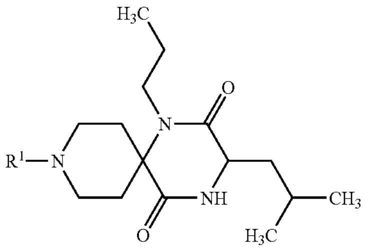
| Example No | $R^1$ |
|---|---|
| 21(H18-26) | 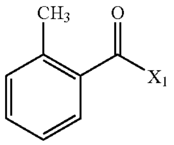 |
| 21(H18-27) | 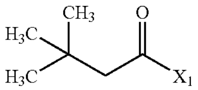 |
| 21(H18-28) | 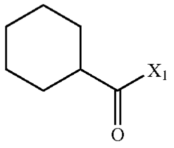 |
| 21(H18-29) | 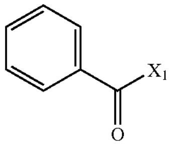 |
| 21(H18-30) | 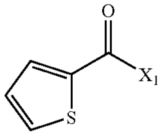 |
| 21(H18-31) | 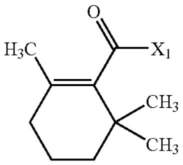 |
| 21(H18-32) | 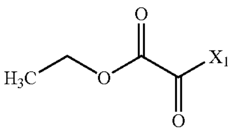 |

TABLE 18B-6
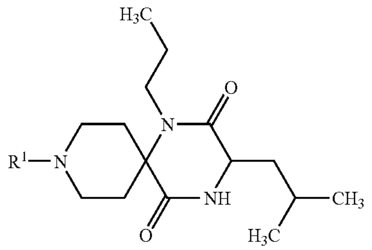
| Example No | $R^1$ |
|---|---|
| 21(H18-33) | 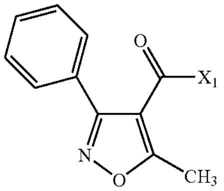 |
| 21(H18-34) | 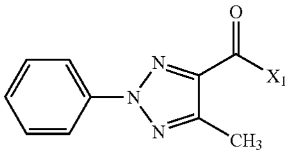 |
| 21(H18-35) | 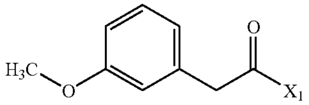 |
| 21(H18-36) | 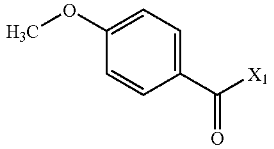 |
| 21(H18-37) | 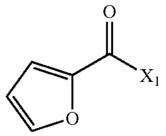 |
| 21(H18-38) | 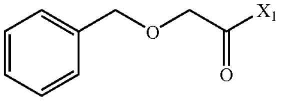 |
| 21(H18-39) | 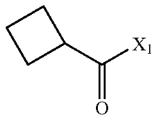 |
TABLE 18B-7
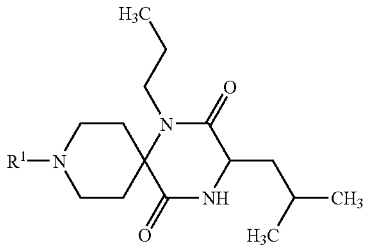
| Example No | c $R^1$ |
|---|---|
| 21(H18-40) | 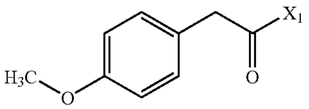 |
| 21(H18-41) | 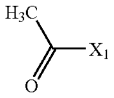 |
| 21(H18-42) | 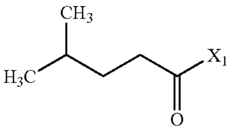 |
| 21(H18-43) | 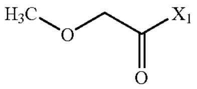 |
| 21(H18-44) | 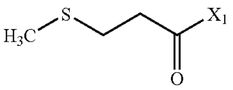 |
| 21(H18-45) | 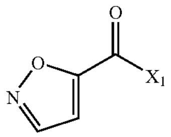 |
| 21(H18-46) | 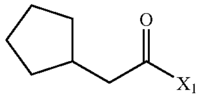 |
| 21(H18-47) | 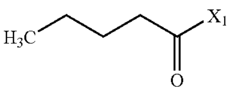 |
| 21(H18-48) | 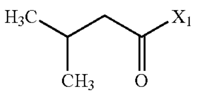 |

TABLE 18B-8
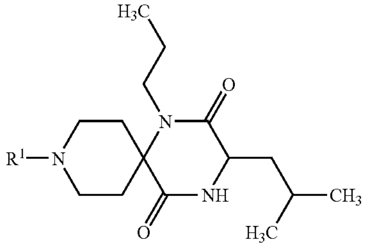
| Example No | $R^1$ |
| --- | --- |
| 21(H18-49) | 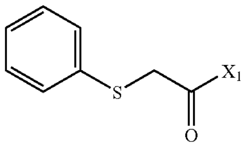 |
| 21(H18-50) | 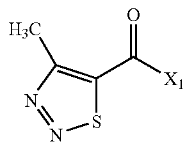 |
| 21(H18-51) | 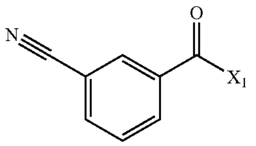 |
| 21(H18-52) | 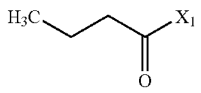 |
| 21(H18-53) | 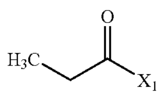 |
| 21(H18-54) | 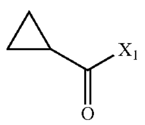 |
| 21(H18-55) | 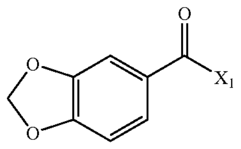 |
TABLE 18B-9
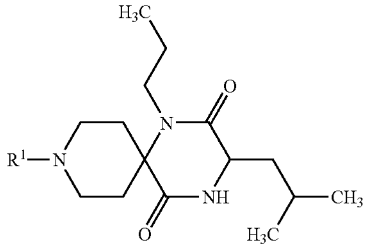
| Example No | $R^1$ |
| --- | --- |
| 21(H18-56) | 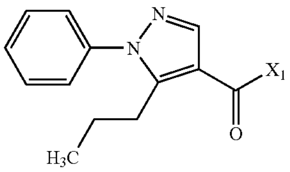 |
| 21(H18-57) | 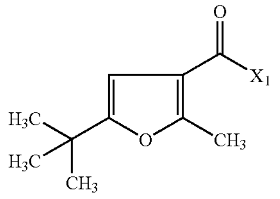 |
| 21(H18-58) | 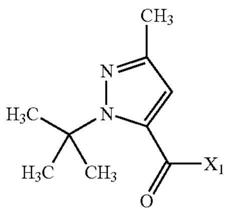 |
| 21(H18-59) | 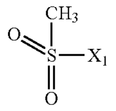 |
| 21(H18-60) | 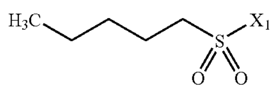 |
| 21(H18-61) | 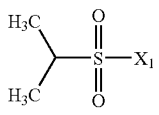 |
| 21(H18-62) | 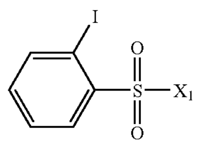 |

TABLE 18D-10
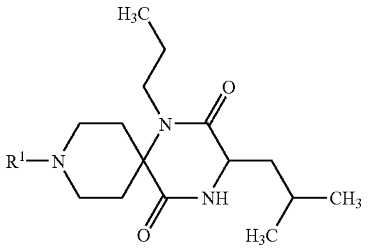
| Example No | $R^1$ |
|---|---|
| 21(H18-63) | 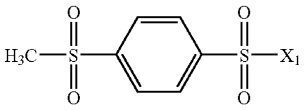 |
| 21(H18-64) | 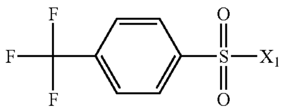 |
| 21(H18-65) | 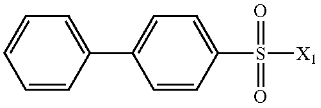 |
| 21(H18-66) | 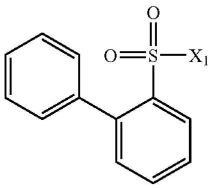 |
| 21(H18-67) | 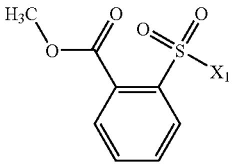 |
| 21(H18-68) | 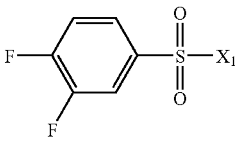 |
| 21(H18-69) | 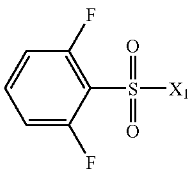 |
TABLE 18B-11
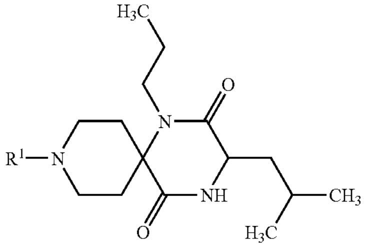
| Example No | $R^1$ |
|---|---|
| 21(H18-70) | 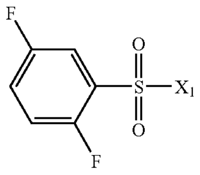 |
| 21(H18-71) | 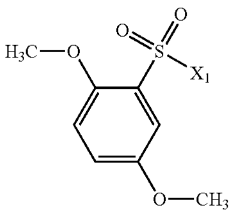 |
| 21(H18-72) | 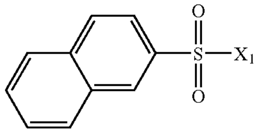 |
| 21(H18-73) | 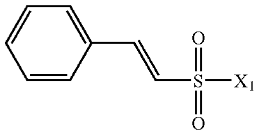 |
| 21(H18-74) | 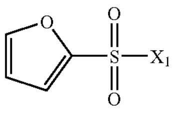 |
| 21(H18-75) | 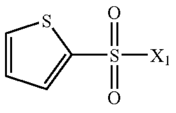 |

TABLE 19B-1
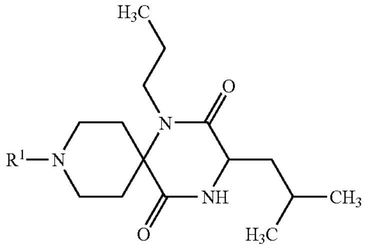
| Example No | $R^1$ |
| --- | --- |
| 21(H19-1) | 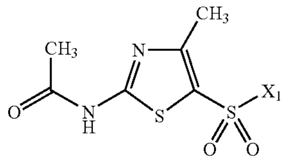 |
| 21(H19-2) | 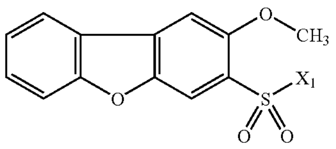 |
| 21(H19-3) | 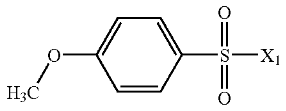 |
| 21(H19-4) | 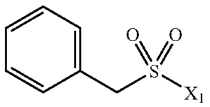 |
| 21(H19-5) | 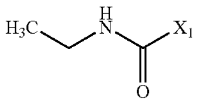 |
| 21(H19-6) | 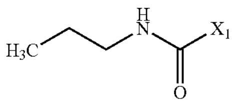 |
| 21(H19-7) | 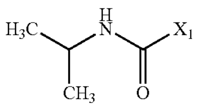 |
| 21(H19-8) | 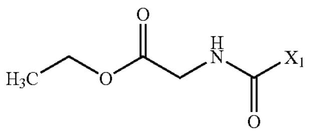 |
TABLE 19B-2
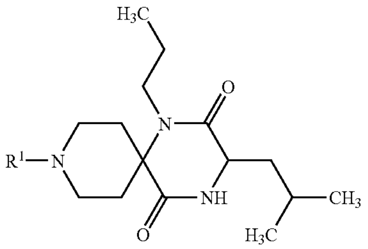
| Example No | $R^1$ |
| --- | --- |
| 21(H19-9) | 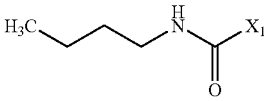 |
| 21(H19-10) | 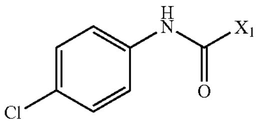 |
| 21(H19-11) | 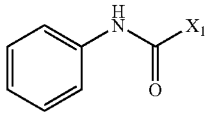 |
| 21(H19-12) | 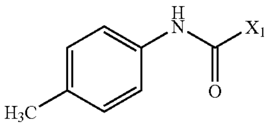 |
| 21(H19-13) | 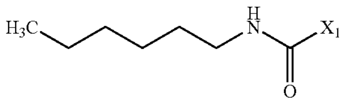 |
| 21(H19-14) | 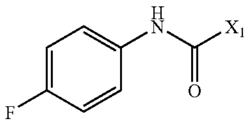 |
| 21(H19-15) | 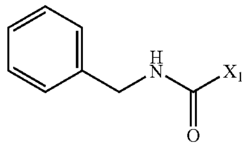 |

TABLE 19B-3
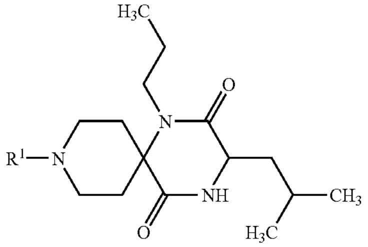
| Example No | $R^1$ |
|---|---|
| 21(H19-16) | 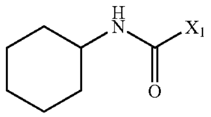 |
| 21(H19-17) | 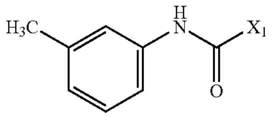 |
| 21(H19-18) | 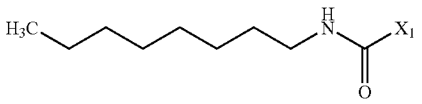 |
| 21(H19-19) | 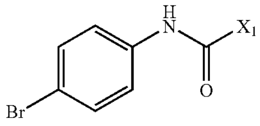 |
| 21(H19-20) | 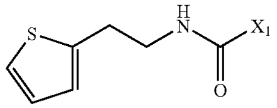 |
| 21(H19-21) | 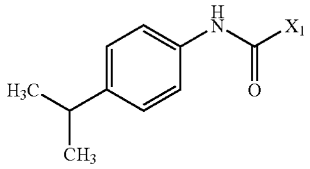 |
| 21(H19-22) | 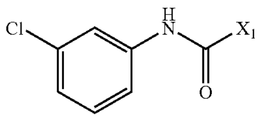 |
TABLE 19B-4
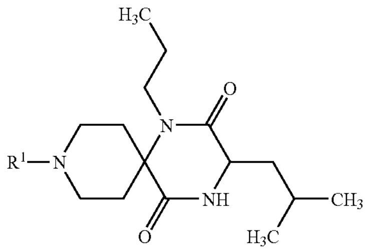
| Example No | $R^1$ |
|---|---|
| 21(H19-23) | 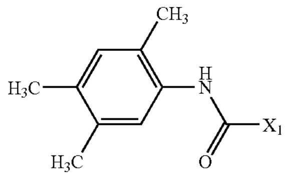 |
| 21(H19-24) | 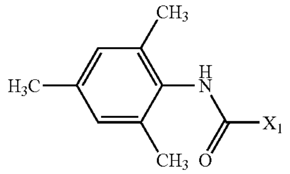 |
| 21(H19-25) | 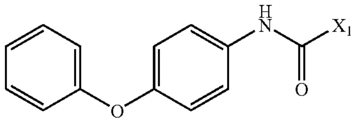 |
| 21(H19-26) | 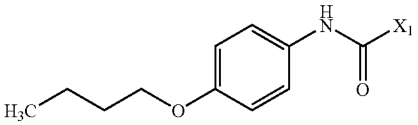 |
| 21(H19-27) | 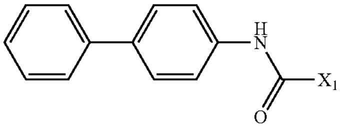 |
| 21(H19-28) | 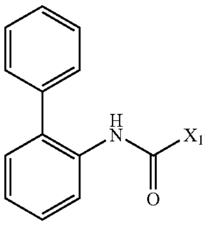 |

TABLE 19B-5
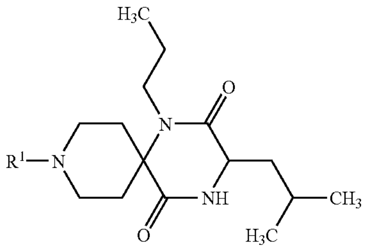
| Example No | $R^1$ |
| --- | --- |
| 21(H19-29) | 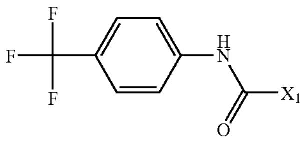 |
| 21(H19-30) | 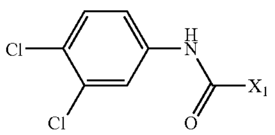 |
| 21(H19-31) | 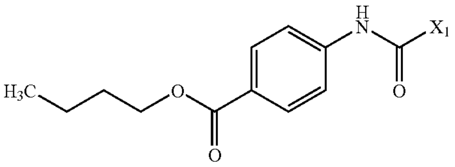 |
| 21(H19-32) | 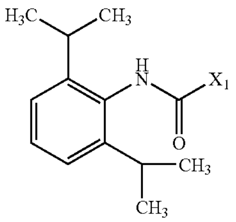 |
| 21(H19-33) | 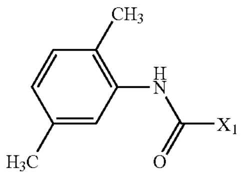 |
TABLE 19B-6
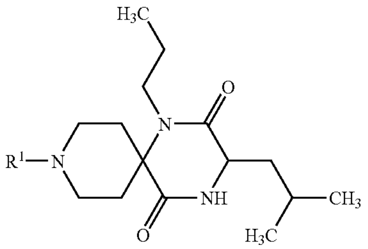
| Example No | $R^1$ |
| --- | --- |
| 21(H19-34) | 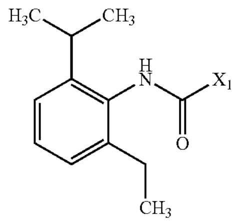 |
| 21(H19-35) | 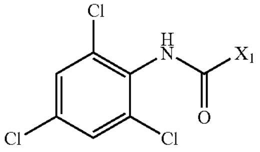 |
| 21(H19-36) | 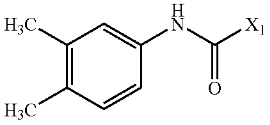 |
| 21(H19-37) | 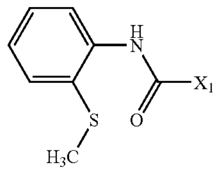 |
| 21(H19-38) | 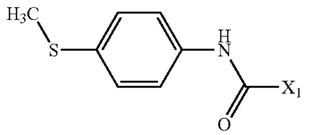 |
| 21(H19-39) | 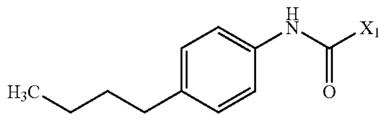 |

TABLE 19B-7
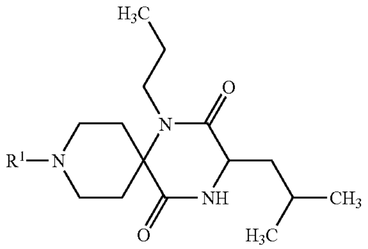
| Example No | $R^1$ |
|---|---|
| 21(H19-40) | 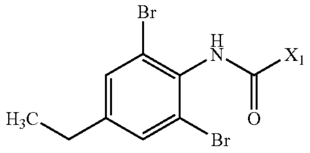 |
| 21(H19-41) | 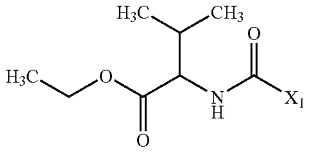 |
| 21(H19-42) | 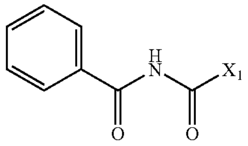 |
TABLE 19B-7-continued
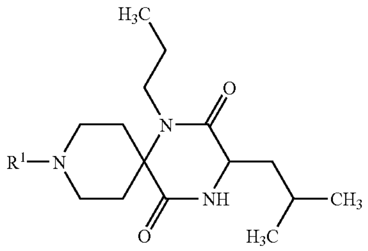
| Example No | $R^1$ |
|---|---|
| 21(H19-43) | 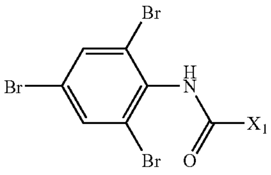 |
| 21(H19-44) | 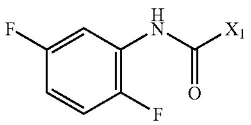 |
| 21(H19-45) | 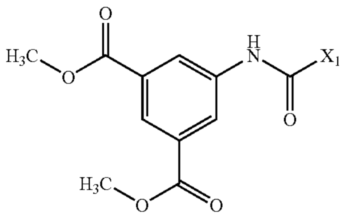 |
TABLE 19B-8
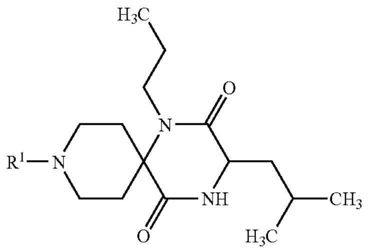
| Example No | $R^1$ |
|---|---|
| 21(H19-46) | 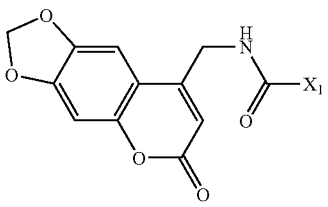 |

TABLE 19B-8-continued
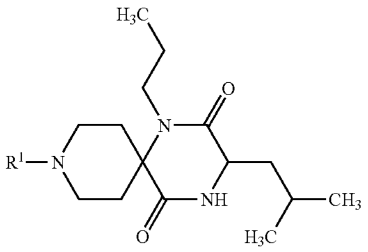
| Example No | $R^1$ |
|---|---|
| 21(H19-47) | 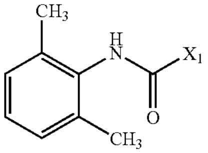 |
| 21(H19-48) | 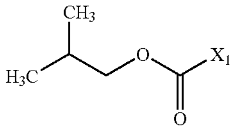 |
| 21(H19-49) | 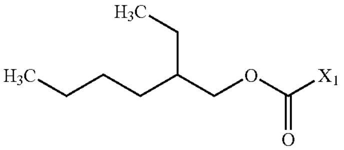 |
| 21(H19-50) | 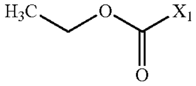 |
| 21(H19-51) | 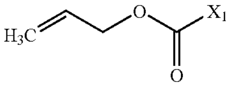 |
| 21(H19-52) | 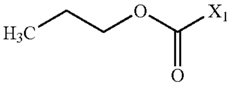 |
| 21(H19-53) | 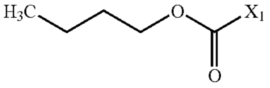 |

TABLE 19B-9
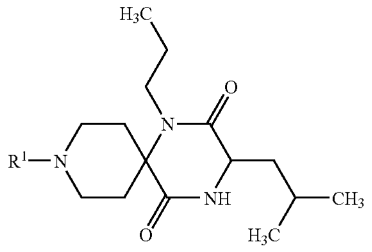
| Example No | $R^1$ |
|---|---|
| 21(H19-54) | 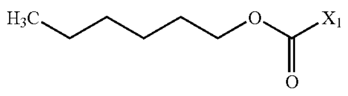 |
| 21(H19-55) | 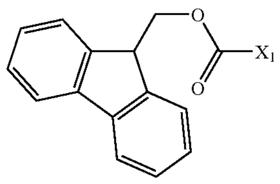 |
| 21(H19-56) | 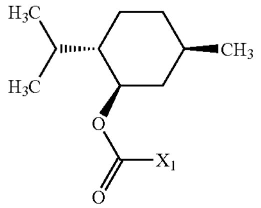 |
| 21(H19-57) | 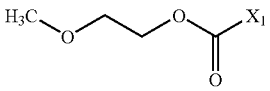 |
| 21(H19-58) | 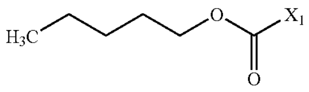 |
| 21(H19-59) | 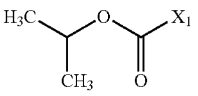 |
| 21(H19-60) | 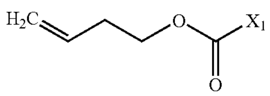 |
TABLE 19B-10
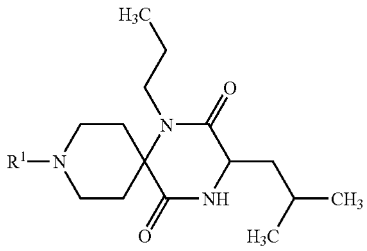
| Example No | $R^1$ |
|---|---|
| 21(H19-61) | 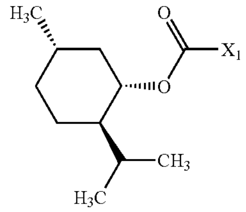 |
| 21(H19-62) | 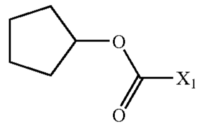 |
| 21(H19-63) | 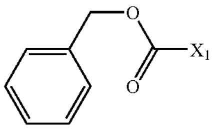 |
| 21(H19-64) | 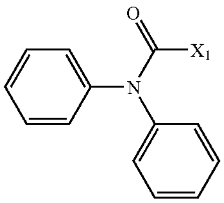 |
| 21(H19-65) | 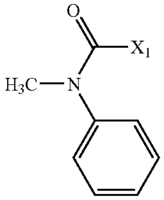 |
| 21(H19-66) | 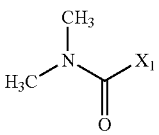 |

TABLE 19B-11

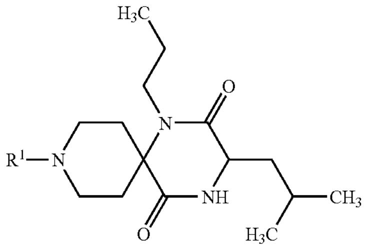

| Example No | $R^1$ |
|---|---|
| 21(H19-67) | 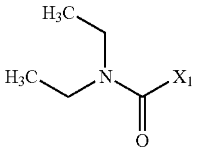 |
| 21(H19-68) | 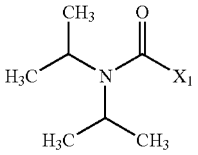 |
| 21(H19-69) | 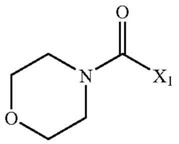 |
| 21(H19-70) | 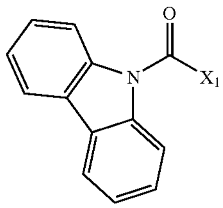 |
| 21(H19-71) | 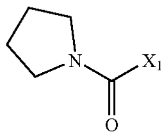 |

TABLE 16C-1

| Example No | HPLC condi-tion | Retention time (min) | Mass data | Mass condition |
|---|---|---|---|---|
| 21(H16-1) | F | 3.84 | 611 $(M + H)^+$. | ESI (Pos., 20 V) |
| 21(H16-2) | F | 3.28 | 578 $(M + H)^+$. | ESI (Pos., 20 V) |
| 21(H16-3) | F | 3.70 | 651 $(M + H)^+$. | ESI (Pos., 20 V) |
| 21(H16-4) | F | 3.59 | 553 $(M + H)^+$. | ESI (Pos., 20 V) |
| 21(H16-5) | F | 3.59 | 553 $(M + H)^+$. | ESI (Pos., 20 V) |
| 21(H16-6) | F | 3.57 | 553 $(M + H)^+$. | ESI (Pos., 20 V) |
| 21(H16-7) | F | 3.60 | 527 $(M + H)^+$. | ESI (Pos., 20 V) |
| 21(H16-8) | F | 3.63 | 549 $(M + H)^+$. | ESI (Pos., 20 V) |
| 21(H16-9) | F | 3.56 | 565 $(M + H)^+$. | ESI (Pos., 20 V) |
| 21(H16-10) | F | 3.59 | 515 $(M + H)^+$. | ESI (Pos., 20 V) |
| 21(H16-11) | F | 3.16 | 536 $(M + H)^+$, 431. | ESI (Pos., 20 V) |

TABLE 16C-1-continued

| Example No | HPLC condi-tion | Retention time (min) | Mass data | Mass condition |
|---|---|---|---|---|
| 21(H16-12) | F | 3.15 | 536 $(M + H)^+$, 431. | ESI (Pos., 20 V) |
| 21(H16-13) | F | 3.32 | 536 $(M + H)^+$. | ESI (Pos., 20 V) |
| 21(H16-14) | F | 3.60 | 549 $(M + H)^+$. | ESI (Pos., 20 V) |
| 21(H16-15) | F | 3.62 | 565 $(M + H)^+$. | ESI (Pos., 20 V) |
| 21(H16-16) | F | 3.29 | 599 $(M + H)^+$. | ESI (Pos., 20 V) |
| 21(H16-17) | F | 3.63 | 644 $(M + H)^+$. | ESI (Pos., 20 V) |
| 21(H16-18) | F | 3.59 | 628 $(M + H)^+$. | ESI (Pos., 20 V) |
| 21(H16-19) | F | 3.53 | 565 $(M + H)^+$. | ESI (Pos., 20 V) |
| 21(H16-20) | F | 3.56 | 555 $(M + H)^+$. | ESI (Pos., 20 V) |
| 21(H16-21) | F | 3.68 | 529 $(M + H)^+$. | ESI (Pos., 20 V) |
| 21(H16-22) | F | 3.64 | 549 $(M + H)^+$. | ESI (Pos., 20 V) |
| 21(H16-23) | F | 3.47 | 501 $(M + H)^+$. | ESI (Pos., 20 V) |
| 21(H16-24) | F | 3.81 | 555 $(M + H)^+$. | ESI (Pos., 20 V) |
| 21(H16-25) | F | 3.67 | 561 $(M + H)^+$. | ESI (Pos., 20 V) |
| 21(H16-26) | F | 3.59 | 549 $(M + H)^+$. | ESI (Pos., 20 V) |

TABLE 16C-2

| Example No | HPLC condi-tion | Retention time (min) | Mass data | Mass condition |
|---|---|---|---|---|
| 21(H16-27) | F | 3.64 | 529 $(M + H)^+$. | ESI (Pos., 20 V) |
| 21(H16-28) | F | 3.68 | 541 $(M + H)^+$. | ESI (Pos., 20 V) |
| 21(H16-29) | F | 3.53 | 535 $(M + H)^+$. | ESI (Pos., 20 V) |
| 21(H16-30) | F | 3.54 | 541 $(M + H)^+$. | ESI (Pos., 20 V) |
| 21(H16-31) | F | 3.84 | 581 $(M + H)^+$. | ESI (Pos., 20 V) |
| 21(H16-32) | F | 3.52 | 531 $(M + H)^+$. | ESI (Pos., 20 V) |
| 21(H16-33) | F | 3.67 | 616 $(M + H)^+$. | ESI (Pos., 20 V) |
| 21(H16-34) | F | 3.84 | 616 $(M + H)^+$. | ESI (Pos., 20 V) |
| 21(H16-35) | F | 3.59 | 579 $(M + H)^+$. | ESI (Pos., 20 V) |
| 21(H16-36) | F | 3.55 | 565 $(M + H)^+$. | ESI (Pos., 20 V) |
| 21(H16-37) | F | 3.45 | 525 $(M + H)^+$. | ESI (Pos., 20 V) |
| 21(H16-38) | F | 3.63 | 579 $(M + H)^+$. | ESI (Pos., 20 V) |
| 21(H16-39) | F | 3.52 | 513 $(M + H)^+$. | ESI (Pos., 20 V) |
| 21(H16-40) | F | 3.57 | 579 $(M + H)^+$. | ESI (Pos., 20 V) |
| 21(H16-41) | F | 3.30 | 473 $(M + H)^+$. | ESI (Pos., 20 V) |
| 21(H16-42) | F | 3.65 | 529 $(M + H)^+$. | ESI (Pos., 20 V) |
| 21(H16-43) | F | 3.28 | 503 $(M + H)^+$. | ESI (Pos., 20 V) |
| 21(H16-44) | F | 3.49 | 533 $(M + H)^+$. | ESI (Pos., 20 V) |
| 21(H16-45) | F | 3.43 | 526 $(M + H)^+$. | ESI (Pos., 20 V) |
| 21(H16-46) | F | 3.70 | 541 $(M + H)^+$. | ESI (Pos., 20 V) |
| 21(H16-47) | F | 3.58 | 515 $(M + H)^+$. | ESI (Pos., 20 V) |
| 21(H16-48) | F | 3.55 | 515 $(M + H)^+$. | ESI (Pos., 20 V) |
| 21(H16-49) | F | 3.69 | 581 $(M + H)^+$. | ESI (Pos., 20 V) |
| 21(H16-50) | F | 3.47 | 557 $(M + H)^+$. | ESI (Pos., 20 V) |
| 21(H16-51) | F | 3.53 | 560 $(M + H)^+$. | ESI (Pos., 20 V) |
| 21(H16-52) | F | 3.46 | 501 $(M + H)^+$. | ESI (Pos., 20 V) |

TABLE 16C-3

| Example No | HPLC condi-tion | Retention time (min) | Mass data | Mass condition |
|---|---|---|---|---|
| 21(H16-53) | F | 3.37 | 487 $(M + H)^+$. | ESI (Pos., 20 V) |
| 21(H16-54) | F | 3.42 | 499 $(M + H)^+$. | ESI (Pos., 20 V) |
| 21(H16-55) | F | 3.54 | 579 $(M + H)^+$. | ESI (Pos., 20 V) |
| 21(H16-56) | F | 3.71 | 643 $(M + H)^+$. | ESI (Pos., 20 V) |
| 21(H16-57) | F | 3.89 | 595 $(M + H)^+$. | ESI (Pos., 20 V) |
| 21(H16-58) | F | 3.60 | 595 $(M + H)^+$. | ESI (Pos., 20 V) |
| 21(H16-59) | F | 3.45 | 509 $(M + H)^+$. | ESI (Pos., 20 V) |
| 21(H16-60) | F | 3.81 | 565 $(M + H)^+$. | ESI (Pos., 20 V) |
| 21(H16-61) | F | 3.56 | 537 $(M + H)^+$. | ESI (Pos., 20 V) |
| 21(H16-62) | F | 3.87 | 605 $(M + H)^+$. | ESI (Pos., 20 V) |

TABLE 16C-3-continued

| Example No | HPLC condi-tion | Retention time (min) | Mass data | Mass condition |
|---|---|---|---|---|
| 21(H16-63) | F | 3.86 | 697 (M + H)+. | ESI (Pos., 20 V) |
| 21(H16-64) | F | 3.79 | 616 (M + H)+. | ESI (Pos., 20 V) |
| 21(H16-65) | F | 3.63 | 649 (M + H)+. | ESI (Pos., 20 V) |
| 21(H16-66) | F | 3.93 | 639 (M + H)+. | ESI (Pos., 20 V) |
| 21(H16-67) | F | 4.00 | 647 (M + H)+. | ESI (Pos., 20 V) |
| 21(H16-68) | F | 3.97 | 647 (M + H)+. | ESI (Pos., 20 V) |
| 21(H16-69) | F | 3.71 | 629 (M + H)+. | ESI (Pos., 20 V) |
| 21(H16-70) | F | 3.82 | 607 (M + H)+. | ESI (Pos., 20 V) |
| 21(H16-71) | F | 3.76 | 607 (M + H)+. | ESI (Pos., 20 V) |
| 21(H16-72) | F | 3.81 | 607 (M + H)+. | ESI (Pos., 20 V) |
| 21(H16-73) | F | 3.71 | 631 (M + H)+. | ESI (Pos., 20 V) |
| 21(H16-74) | F | 4.01 | 673 (M + H)+. | ESI (Pos., 20 V) |
| 21(H16-75) | F | 3.91 | 621 (M + H)+. | ESI (Pos., 20 V) |
| 21(H16-76) | F | 3.82 | 597 (M + H)+. | ESI (Pos., 20 V) |
| 21(H16-77) | F | 3.67 | 561 (M + H)+. | ESI (Pos., 20 V) |
| 21(H16-78) | F | 3.73 | 577 (M + H)+. | ESI (Pos., 20 V) |

TABLE 17C-1

| Example No | HPLC condi-tion | Retention time (min) | Mass data | Mass condition |
|---|---|---|---|---|
| 21(H17-1) | F | 4.08 | 724 (M + H)+. | ESI (Pos., 20 V) |
| 21(H17-2) | F | 3.90 | 717 (M + H)+. | ESI (Pos., 20 V) |
| 21(H17-3) | F | 3.87 | 647 (M + H)+. | ESI (Pos., 20 V) |
| 21(H17-4) | F | 3.59 | 649 (M + H)+. | ESI (Pos., 20 V) |
| 21(H17-5) | F | 3.98 | 691 (M + H)+. | ESI (Pos., 20 V) |
| 21(H17-6) | F | 4.01 | 639 (M + H)+. | ESI (Pos., 20 V) |
| 21(H17-7) | F | 3.76 | 601 (M + H)+. | ESI (Pos., 20 V) |
| 21(H17-8) | F | 3.72 | 585 (M + H)+. | ESI (Pos., 20 V) |
| 21(H17-9) | F | 3.33 | 502 (M + H)+. | ESI (Pos., 20 V) |
| 21(H17-10) | F | 3.42 | 516 (M + H)+. | ESI (Pos., 20 V) |
| 21(H17-11) | F | 3.43 | 516 (M + H)+. | ESI (Pos., 20 V) |
| 21(H17-12) | F | 3.40 | 560 (M + H)+. | ESI (Pos., 20 V) |
| 21(H17-13) | F | 3.54 | 530 (M + H)+. | ESI (Pos., 20 V) |
| 21(H17-14) | F | 3.72 | 584 (M + H)+. | ESI (Pos., 20 V) |
| 21(H17-15) | F | 3.59 | 550 (M + H)+. | ESI (Pos., 20 V) |
| 21(H17-16) | F | 3.66 | 564 (M + H)+. | ESI (Pos., 20 V) |
| 21(H17-17) | F | 3.73 | 558 (M + H)+. | ESI (Pos., 20 V) |
| 21(H17-18) | F | 3.60 | 568 (M + H)+. | ESI (Pos., 20 V) |
| 21(H17-19) | F | 3.57 | 564 (M + H)+. | ESI (Pos., 20 V) |
| 21(H17-20) | F | 3.62 | 556 (M + H)+. | ESI (Pos., 20 V) |
| 21(H17-21) | F | 3.66 | 564 (M + H)+. | ESI (Pos., 20 V) |
| 21(H17-22) | F | 3.96 | 586 (M + H)+. | ESI (Pos., 20 V) |
| 21(H17-23) | F | 3.76 | 628 (M + H)+. | ESI (Pos., 20 V) |
| 21(H17-24) | F | 3.59 | 584 (M + H)+. | ESI (Pos., 20 V) |
| 21(H17-25) | F | 3.85 | 592 (M + H)+. | ESI (Pos., 20 V) |
| 21(H17-26) | F | 3.75 | 584 (M + H)+. | ESI (Pos., 20 V) |

TABLE 17C-2

| Example No | HPLC condi-tion | Retention time (min) | Mass data | Mass condition |
|---|---|---|---|---|
| 21(H17-27) | F | 3.74 | 592 (M + H)+. | ESI (Pos., 20 V) |
| 21(H17-28) | F | 3.69 | 592 (M + H)+. | ESI (Pos., 20 V) |
| 21(H17-29) | F | 3.85 | 642 (M + H)+. | ESI (Pos., 20 V) |
| 21(H17-30) | F | 3.86 | 622 (M + H)+. | ESI (Pos., 20 V) |
| 21(H17-31) | F | 3.86 | 626 (M + H)+. | ESI (Pos., 20 V) |
| 21(H17-32) | F | 3.78 | 626 (M + H)+. | ESI (Pos., 20 V) |
| 21(H17-33) | F | 3.82 | 618 (M + H)+. | ESI (Pos., 20 V) |
| 21(H17-34) | F | 3.86 | 618 (M + H)+. | ESI (Pos., 20 V) |
| 21(H17-35) | F | 3.90 | 650 (M + H)+. | ESI (Pos., 20 V) |
| 21(H17-36) | F | 3.89 | 634 (M + H)+. | ESI (Pos., 20 V) |

TABLE 17C-2-continued

| Example No | HPLC condi-tion | Retention time (min) | Mass data | Mass condition |
|---|---|---|---|---|
| 21(H17-37) | F | 3.66 | 578 (M + H)+. | ESI (Pos., 20 V) |
| 21(H17-38) | F | 3.80 | 620 (M + H)+. | ESI (Pos., 20 V) |
| 21(H17-39) | F | 3.76 | 652 (M + H)+. | ESI (Pos., 20 V) |
| 21(H17-40) | F | 3.72 | 578 (M + H)+. | ESI (Pos., 20 V) |
| 21(H17-41) | F | 3.64 | 596 (M + H)+. | ESI (Pos., 20 V) |
| 21(H17-42) | F | 3.68 | 596 (M + H)+. | ESI (Pos., 20 V) |
| 21(H17-43) | F | 3.97 | 606 (M + H)+. | ESI (Pos., 20 V) |
| 21(H17-44) | F | 3.90 | 652 (M + H)+. | ESI (Pos., 20 V) |
| 21(H17-45) | F | 3.83 | 736 (M + H)+. | ESI (Pos., 20 V) |
| 21(H17-46) | F | 3.65 | 602 (M + H)+. | ESI (Pos., 20 V) |
| 21(H17-47) | F | 3.48 | 578 (M + H)+. | ESI (Pos., 20 V) |
| 21(H17-48) | F | 3.80 | 785 (M + H)+. | ESI (Pos., 20 V) |
| 21(H17-49) | F | 3.64 | 586 (M + H)+. | ESI (Pos., 20 V) |
| 21(H17-50) | F | 3.68 | 666 (M + H)+. | ESI (Pos., 20 V) |
| 21(H17-51) | F | 3.51 | 676 (M + H)+. | ESI (Pos., 20 V) |
| 21(H17-52) | F | 3.61 | 578 (M + H)+. | ESI (Pos., 20 V) |

TABLE 17C-3

| Example No | HPLC condi-tion | Retention time (min) | Mass data | Mass condition |
|---|---|---|---|---|
| 21(H17-53) | F | 3.79 | 531 (M + H)+. | ESI (Pos., 20 V) |
| 21(H17-54) | F | 4.24 | 587 (M + H)+. | ESI (Pos., 20 V) |
| 21(H17-55) | F | 3.57 | 503 (M + H)+. | ESI (Pos., 20 V) |
| 21(H17-56) | F | 3.62 | 515 (M + H)+. | ESI (Pos., 20 V) |
| 21(H17-57) | F | 3.67 | 517 (M + H)+. | ESI (Pos., 20 V) |
| 21(H17-58) | F | 3.79 | 531 (M + H)+. | ESI (Pos., 20 V) |
| 21(H17-59) | F | 4.03 | 559 (M + H)+. | ESI (Pos., 20 V) |
| 21(H17-60) | F | 3.89 | 605 (M + H)+. | ESI (Pos., 20 V) |
| 21(H17-61) | F | 4.06 | 653 (M + H)+. | ESI (Pos., 20 V) |
| 21(H17-62) | F | 4.35 | 613 (M + H)+. | ESI (Pos., 20 V) |
| 21(H17-63) | F | 3.44 | 533 (M + H)+. | ESI (Pos., 20 V) |
| 21(H17-64) | F | 3.90 | 545 (M + H)+. | ESI (Pos., 20 V) |
| 21(H17-65) | F | 3.67 | 517 (M + H)+. | ESI (Pos., 20 V) |
| 21(H17-66) | F | 3.72 | 529 (M + H)+. | ESI (Pos., 20 V) |
| 21(H17-67) | F | 4.35 | 613 (M + H)+. | ESI (Pos., 20 V) |
| 21(H17-68) | F | 3.78 | 543 (M + H)+. | ESI (Pos., 20 V) |
| 21(H17-69) | F | 3.79 | 531 (M + H)+. | ESI (Pos., 20 V) |
| 21(H17-70) | F | 3.81 | 565 (M + H)+. | ESI (Pos., 20 V) |
| 21(H17-71) | F | 3.86 | 626 (M + H)+. | ESI (Pos., 20 V) |
| 21(H17-72) | F | 3.65 | 564 (M + H)+. | ESI (Pos., 20 V) |
| 21(H17-73) | F | 3.39 | 502 (M + H)+. | ESI (Pos., 20 V) |
| 21(H17-74) | F | 3.58 | 530 (M + H)+. | ESI (Pos., 20 V) |
| 21(H17-75) | F | 3.79 | 558 (M + H)+. | ESI (Pos., 20 V) |
| 21(H17-76) | F | 3.34 | 544 (M + H)+. | ESI (Pos., 20 V) |
| 21(H17-77) | F | 4.03 | 624 (M + H)+. | ESI (Pos., 20 V) |
| 21(H17-78) | F | 3.49 | 528 (M + H)+. | ESI (Pos., 20 V) |

TABLE 18C-1

| Example No | HPLC condi-tion | Retention time (min) | Mass data | Mass condition |
|---|---|---|---|---|
| 21(H18-1) | F | 3.82 | 923 (2M + H)+, 462 (M + H)+. | ESI (Pos., 20 V) |
| 21(H18-2) | F | 3.81 | 462 (M + H)+. | ESI (Pos., 20 V) |
| 21(H18-3) | F | 3.12 | 857 (2M + H)+, 429 (M + H)+. | ESI (Pos., 20 V) |
| 21(H18-4) | F | 3.62 | 501 (M + H)+. | ESI (Pos., 20 V) |
| 21(H18-5) | F | 3.49 | 807 (2M + H)+, 404 (M + H)+. | ESI (Pos., 20 V) |
| 21(H18-6) | F | 3.51 | 807 (2M + H)+, 404 (M + H)+. | ESI (Pos., 20 V) |

TABLE 18C-1-continued

| Example No | HPLC condition | Retention time (min) | Mass data | Mass condition |
|---|---|---|---|---|
| 21(H18-7) | F | 3.49 | 807 (2M + H)$^+$, 404 (M + H)$^+$. | ESI (Pos., 20 V) |
| 21(H18-8) | F | 3.51 | 755 (2M + H)$^+$, 378 (M + H)$^+$. | ESI (Pos., 20 V) |
| 21(H18-9) | F | 3.56 | 799 (2M + H)$^+$, 400 (M + H)$^+$. | ESI (Pos., 20 V) |
| 21(H18-10) | F | 3.49 | 831 (2M + H)$^+$, 416 (M + H)$^+$. | ESI (Pos., 20 V) |
| 21(H18-11) | F | 3.49 | 753 (2M + H)$^+$, 366 (M + H)$^+$. | ESI (Pos., 20 V) |
| 21(H18-12) | F | 3.00 | 773 (2M + H)$^+$, 387 (M + H)$^+$. | ESI (Pos., 20 V) |
| 21(H18-13) | F | 3.16 | 387 (M + H)$^+$. | ESI (Pos., 20 V) |
| 21(H18-14) | F | 3.50 | 799 (2M + H)$^+$, 400 (M + H)$^+$. | ESI (Pos., 20 V) |
| 21(H18-15) | F | 3.53 | 831 (2M + H)$^+$, 416 (M + H)$^+$. | ESI (Pos., 20 V) |
| 21(H18-16) | F | 3.13 | 450 (M + H)$^+$. | ESI (Pos., 20 V) |
| 21(H18-17) | F | 3.57 | 989 (2M + H)$^+$, 495 (M + H)$^+$. | ESI (Pos., 20 V) |
| 21(H18-18) | F | 3.53 | 957 (2M + H)$^+$, 479 (M + H)$^+$. | ESI (Pos., 20 V) |
| 21(H18-19) | F | 3.44 | 831 (2M + H)$^+$, 416 (M + H)$^+$. | ESI (Pos., 20 V) |
| 21(H18-20) | F | 3.45 | 811 (2M + H)$^+$, 406 (M + H)$^+$. | ESI (Pos., 20 V) |
| 21(H18-21) | F | 3.61 | 759 (2M + H)$^+$, 380 (M + H)$^+$. | ESI (Pos., 20 V) |
| 21(H18-22) | F | 3.56 | 799 (2M + H)$^+$, 400 (M + H)$^+$. | ESI (Pos., 20 V) |
| 21(H18-23) | F | 3.32 | 703 (2M + H)$^+$, 352 (M + H)$^+$. | ESI (Pos., 20 V) |
| 21(H18-24) | F | 3.75 | 811 (2M + H)$^+$, 406 (M + H)$^+$. | ESI (Pos., 20 V) |
| 21(H18-25) | F | 3.60 | 823 (2M + H)$^+$, 412 (M + H)$^+$. | ESI (Pos., 20 V) |
| 21(H18-26) | F | 3.51 | 799 (2M + H)$^+$, 400 (M + H)$^+$. | ESI (Pos., 20 V) |

TABLE 18C-2

| Example No | HPLC condition | Retention time (min) | Mass data | Mass condition |
|---|---|---|---|---|
| 21(H18-27) | F | 3.55 | 759 (2M + H)$^+$, 380 (M + H)$^+$. | ESI (Pos., 20 V) |
| 21(H18-28) | F | 3.58 | 783 (2M + H)$^+$, 392 (M + H)$^+$. | ESI (Pos., 20 V) |
| 21(H18-29) | F | 3.45 | 771 (2M + H)$^+$, 386 (M + H)$^+$. | ESI (Pos., 20 V) |
| 21(H18-30) | F | 3.44 | 783 (2M + H)$^+$, 392 (M + H)$^+$. | ESI (Pos., 20 V) |
| 21(H18-31) | F | 3.79 | 432 (M + H)$^+$. | ESI (Pos., 20 V) |
| 21(H18-32) | F | 3.41 | 382 (M + H)$^+$. | ESI (Pos., 20 V) |
| 21(H18-33) | F | 3.61 | 933 (2M + H)$^+$, 467 (M + H)$^+$. | ESI (Pos., 20 V) |
| 21(H18-34) | F | 3.80 | 933 (2M + H)$^+$, 467 (M + H)$^+$. | ESI (Pos., 20 V) |
| 21(H18-35) | F | 3.48 | 859 (2M + H)$^+$, 430 (M + H)$^+$. | ESI (Pos., 20 V) |
| 21(H18-36) | F | 3.46 | 831 (2M + H)$^+$, 416 (M + H)$^+$. | ESI (Pos., 20 V) |
| 21(H18-37) | F | 3.35 | 751 (2M + H)$^+$, 376 (M + H)$^+$. | ESI (Pos., 20 V) |
| 21(H18-38) | F | 3.53 | 430 (M + H)$^+$. | ESI (Pos., 20 V) |
| 21(H18-39) | F | 3.40 | 727 (2M + H)$^+$, 364 (M + H)$^+$. | ESI (Pos., 20 V) |
| 21(H18-40) | F | 3.48 | 859 (2M + H)$^+$, 430 (M + H)$^+$. | ESI (Pos., 20 V) |

TABLE 18C-2-continued

| Example No | HPLC condition | Retention time (min) | Mass data | Mass condition |
|---|---|---|---|---|
| 21(H18-41) | F | 3.11 | 647 (2M + H)$^+$, 324 (M + H)$^+$. | ESI (Pos., 20 V) |
| 21(H18-42) | F | 3.60 | 759 (2M + H)$^+$, 380 (M + H)$^+$. | ESI (Pos., 20 V) |
| 21(H18-43) | F | 3.13 | 354 (M + H)$^+$. | ESI (Pos., 20 V) |
| 21(H18-44) | F | 3.35 | 767 (2M + H)$^+$, 384 (M + H)$^+$. | ESI (Pos., 20 V) |
| 21(H18-45) | F | 3.28 | 753 (2M + H)$^+$, 377 (M + H)$^+$. | ESI (Pos., 20 V) |
| 21(H18-46) | F | 3.60 | 783 (2M + H)$^+$, 392 (M + H)$^+$. | ESI (Pos., 20 V) |
| 21(H18-47) | F | 3.47 | 731 (2M + H)$^+$, 366 (M + H)$^+$. | ESI (Pos., 20 V) |
| 21(H18-48) | F | 3.44 | 731 (2M + H)$^+$, 366 (M + H)$^+$. | ESI (Pos., 20 V) |
| 21(H18-49) | F | 3.62 | 863 (2M + H)$^+$, 432 (M + H)$^+$. | ESI (Pos., 20 V) |
| 21(H18-50) | F | 3.34 | 815 (2M + H)$^+$, 408 (M + H)$^+$. | ESI (Pos., 20 V) |
| 21(H18-51) | F | 3.42 | 821 (2M + H)$^+$, 411 (M + H)$^+$. | ESI (Pos., 20 V) |
| 21(H18-52) | F | 3.33 | 703 (2M + H)$^+$, 352 (M + H)$^+$. | ESI (Pos., 20 V) |

TABLE 18C-3

| Example No | HPLC condition | Retention time (min) | Mass data | Mass condition |
|---|---|---|---|---|
| 21(H18-53) | F | 3.22 | 675 (2M + H)$^+$, 338 (M + H)$^+$. | ESI (Pos., 20 V) |
| 21(H18-54) | F | 3.27 | 699 (2M + H)$^+$, 350 (M + H)$^+$. | ESI (Pos., 20 V) |
| 21(H18-55) | F | 3.45 | 859 (2M + H)$^+$, 430 (M + H)$^+$. | ESI (Pos., 20 V) |
| 21(H18-56) | F | 3.64 | 987 (2M + H)$^+$, 494 (M + H)$^+$. | ESI (Pos., 20 V) |
| 21(H18-57) | F | 3.86 | 891 (2M + H)$^+$, 446 (M + H)$^+$. | ESI (Pos., 20 V) |
| 21(H18-58) | F | 3.51 | 446 (M + H)$^+$. | ESI (Pos., 20 V) |
| 21(H18-59) | F | 3.29 | 360 (M + H)$^+$. | ESI (Pos., 20 V) |
| 21(H18-60) | F | 3.76 | 416 (M + H)$^+$. | ESI (Pos., 20 V) |
| 21(H18-61) | F | 3.45 | 797 (2M + Na)$^+$, 388 (M + H)$^+$. | ESI (Pos., 20 V) |
| 21(H18-62) | F | 3.82 | 548 (M + H)$^+$. | ESI (Pos., 20 V) |
| 21(H18-63) | F | 3.55 | 500 (M + H)$^+$. | ESI (Pos., 20 V) |
| 21(H18-64) | F | 3.90 | 490 (M + H)$^+$. | ESI (Pos., 20 V) |
| 21(H18-65) | F | 3.99 | 498 (M + H)$^+$. | ESI (Pos., 20 V) |
| 21(H18-66) | F | 3.97 | 498 (M + H)$^+$. | ESI (Pos., 20 V) |
| 21(H18-67) | F | 3.62 | 480 (M + H)$^+$. | ESI (Pos., 20 V) |
| 21(H18-68) | F | 3.77 | 458 (M + H)$^+$. | ESI (Pos., 20 V) |
| 21(H18-69) | F | 3.70 | 458 (M + H)$^+$. | ESI (Pos., 20 V) |
| 21(H18-70) | F | 3.76 | 458 (M + H)$^+$. | ESI (Pos., 20 V) |
| 21(H18-71) | F | 3.62 | 985 (2M + Na)$^+$, 482 (M + H)$^+$. | ESI (Pos., 20 V) |
| 21(H18-72) | F | 3.89 | 472 (M + H)$^+$. | ESI (Pos., 20 V) |
| 21(H18-73) | F | 3.79 | 448 (M + H)$^+$. | ESI (Pos., 20 V) |
| 21(H18-74) | F | 3.58 | 412 (M + H)$^+$. | ESI (Pos., 20 V) |
| 21(H18-75) | F | 3.65 | 428 (M + H)$^+$. | ESI (Pos., 20 V) |

TABLE 19C-1

| Example No | HPLC condition | Retention time (min) | Mass data | Mass condition |
|---|---|---|---|---|
| 21(H19-1) | F | 3.48 | 500 (M + H)+ | ESI (Pos., 20 V) |
| 21(H19-2) | F | 3.96 | 542 (M + H)+ | ESI (Pos., 20 V) |
| 21(H19-3) | F | 3.68 | 452 (M + H)+ | ESI (Pos., 20 V) |
| 21(H19-4) | F | 3.64 | 436 (M + H)+ | ESI (Pos., 20 V) |
| 21(H19-5) | F | 3.13 | 353 (M + H)+ | ESI (Pos., 20 V) |
| 21(H19-6) | F | 3.25 | 367 (M + H)+ | ESI (Pos., 20 V) |
| 21(H19-7) | F | 3.26 | 367 (M + H)+ | ESI (Pos., 20 V) |
| 21(H19-8) | F | 3.21 | 411 (M + H)+ | ESI (Pos., 20 V) |
| 21(H19-9) | F | 3.37 | 381 (M + H)+ | ESI (Pos., 20 V) |
| 21(H19-10) | F | 3.63 | 435 (M + H)+ | ESI (Pos., 20 V) |
| 21(H19-11) | F | 3.45 | 401 (M + H)+ | ESI (Pos., 20 V) |
| 21(H19-12) | F | 3.55 | 415 (M + H)+ | ESI (Pos., 20 V) |
| 21(H19-13) | F | 3.65 | 409 (M + H)+ | ESI (Pos., 20 V) |
| 21(H19-14) | F | 3.49 | 419 (M + H)+ | ESI (Pos., 20 V) |
| 21(H19-15) | F | 3.43 | 415 (M + H)+ | ESI (Pos., 20 V) |
| 21(H19-16) | F | 3.50 | 407 (M + H)+ | ESI (Pos., 20 V) |
| 21(H19-17) | F | 3.54 | 415 (M + H)+ | ESI (Pos., 20 V) |
| 21(H19-18) | F | 3.90 | 437 (M + H)+ | ESI (Pos., 20 V) |
| 21(H19-19) | F | 3.67 | 481 (M + H)+ | ESI (Pos., 20 V) |
| 21(H19-20) | F | 3.46 | 435 (M + H)+ | ESI (Pos., 20 V) |
| 21(H19-21) | F | 3.77 | 443 (M + H)+ | ESI (Pos., 20 V) |
| 21(H19-22) | F | 3.64 | 435 (M + H)+ | ESI (Pos., 20 V) |
| 21(H19-23) | F | 3.64 | 443 (M + H)+ | ESI (Pos., 20 V) |
| 21(H19-24) | F | 3.58 | 443 (M + H)+ | ESI (Pos., 20 V) |
| 21(H19-25) | F | 3.79 | 493 (M + H)+ | ESI (Pos., 20 V) |
| 21(H19-26) | F | 3.78 | 473 (M + H)+ | ESI (Pos., 20 V) |

TABLE 19C-2

| Example No | HPLC condition | Retention time (min) | Mass data | Mass condition |
|---|---|---|---|---|
| 21(H19-27) | F | 3.80 | 477 (M + H)+ | ESI (Pos., 20 V) |
| 21(H19-28) | F | 3.70 | 477 (M + H)+ | ESI (Pos., 20 V) |
| 21(H19-29) | F | 3.74 | 469 (M + H)+ | ESI (Pos., 20 V) |
| 21(H19-30) | F | 3.79 | 469 (M + H)+ | ESI (Pos., 20 V) |
| 21(H19-31) | F | 3.85 | 501 (M + H)+ | ESI (Pos., 20 V) |
| 21(H19-32) | F | 3.81 | 485 (M + H)+ | ESI (Pos., 20 V) |
| 21(H19-33) | F | 3.56 | 429 (M + H)+ | ESI (Pos., 20 V) |
| 21(H19-34) | F | 3.72 | 471 (M + H)+ | ESI (Pos., 20 V) |
| 21(H19-35) | F | 3.67 | 505 (M + H)+ | ESI (Pos., 20 V) |
| 21(H19-36) | F | 3.63 | 429 (M + H)+ | ESI (Pos., 20 V) |
| 21(H19-37) | F | 3.57 | 447 (M + H)+ | ESI (Pos., 20 V) |
| 21(H19-38) | F | 3.59 | 447 (M + H)+ | ESI (Pos., 20 V) |
| 21(H19-39) | F | 3.91 | 457 (M + H)+ | ESI (Pos., 20 V) |
| 21(H19-40) | F | 3.77 | 587 (M + H)+ | ESI (Pos., 20 V) |
| 21(H19-41) | F | 3.50 | 453 (M + H)+ | ESI (Pos., 20 V) |
| 21(H19-42) | F | 3.34 | 429 (M + H)+ | ESI (Pos., 20 V) |
| 21(H19-43) | F | 3.75 | 638 (M + H)+ | ESI (Pos., 20 V) |
| 21(H19-44) | F | 3.54 | 437 (M + H)+ | ESI (Pos., 20 V) |
| 21(H19-45) | F | 3.58 | 517 (M + H)+ | ESI (Pos., 20 V) |
| 21(H19-46) | F | 3.35 | 527 (M + H)+ | ESI (Pos., 20 V) |
| 21(H19-47) | F | 3.47 | 429 (M + H)+ | ESI (Pos., 20 V) |
| 21(H19-48) | F | 3.70 | 382 (M + H)+ | ESI (Pos., 20 V) |
| 21(H19-49) | F | 4.22 | 438 (M + H)+ | ESI (Pos., 20 V) |
| 21(H19-50) | F | 3.43 | 354 (M + H)+ | ESI (Pos., 20 V) |
| 21(H19-51) | F | 3.50 | 366 (M + H)+ | ESI (Pos., 20 V) |
| 21(H19-52) | F | 3.57 | 368 (M + H)+ | ESI (Pos., 20 V) |

TABLE 19C-3

| Example No | HPLC condition | Retention time (min) | Mass data | Mass condition |
|---|---|---|---|---|
| 21(H19-53) | F | 3.72 | 382 (M + H)+ | ESI (Pos., 20 V) |
| 21(H19-54) | F | 3.99 | 410 (M + H)+ | ESI (Pos., 20 V) |
| 21(H19-55) | F | 4.03 | 504 (M + H)+ | ESI (Pos., 20 V) |
| 21(H19-56) | F | 4.37 | 464 (M + H)+ | ESI (Pos., 20 V) |
| 21(H19-57) | F | 3.28 | 384 (M + H)+ | ESI (Pos., 20 V) |
| 21(H19-58) | F | 3.86 | 396 (M + H)+ | ESI (Pos., 20 V) |
| 21(H19-59) | F | 3.56 | 368 (M + H)+ | ESI (Pos., 20 V) |
| 21(H19-60) | F | 3.60 | 380 (M + H)+ | ESI (Pos., 20 V) |
| 21(H19-61) | F | 4.39 | 464 (M + H)+ | ESI (Pos., 20 V) |
| 21(H19-62) | F | 3.71 | 394 (M + H)+ | ESI (Pos., 20 V) |
| 21(H19-63) | F | 3.74 | 416 (M + H)+ | ESI (Pos., 20 V) |
| 21(H19-64) | F | 3.81 | 477 (M + H)+ | ESI (Pos., 20 V) |
| 21(H19-65) | F | 3.55 | 415 (M + H)+ | ESI (Pos., 20 V) |
| 21(H19-66) | F | 3.22 | 353 (M + H)+ | ESI (Pos., 20 V) |
| 21(H19-67) | F | 3.46 | 381 (M + H)+ | ESI (Pos., 20 V) |
| 21(H19-68) | F | 3.71 | 409 (M + H)+ | ESI (Pos., 20 V) |
| 21(H19-69) | F | 3.17 | 395 (M + H)+ | ESI (Pos., 20 V) |
| 21(H19-70) | F | 3.97 | 475 (M + H)+ | ESI (Pos., 20 V) |
| 21(H19-71) | F | 3.34 | 379 (M + H)+ | ESI (Pos., 20 V) |

EXAMPLE 22

(3S)-1-propyl-2,5-dioxo-3-(4-(3-phenylpropanoyl) aminobutyl)-9-(2-phenylethyl)-1,4,9-triazaspiro[5.5] undecane

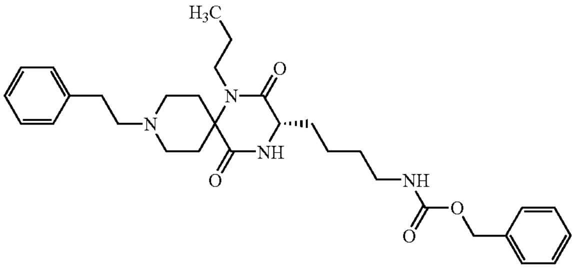

To a solution of the compound prepared in Example 14 (5 mg) in dichloroethane (0.5 ml) were added pyridine (2 μl), 3-phenylpropanoyl chloride (4 μl). The reaction mixture was stirred for 3 hours at room temperature. To the reaction mixture was added methanol, and it was loaded on ion exchange resin (OASIS MCX, Waters, 60 mg) washed with methanol (3 ml) prior to use. The resin was washed with methanol (2 ml), and was eluted with 10% triethylamine-methanol solution (2 ml). The elution was concentrated to give the compound of the present invention (1.6 mg) having the following physical data.

TLC: Rf 0.49 (chloroform:methanol=10:1);

NMR (CD$_3$OD): 67.40–7.10 (m, 10H), 4.03 (m, 1H), 3.60–3.30 (m, 2H), 3.14 (m, 2H), 3.06–2.90 (m, 3H), 2.90–2.75 (m, 4H), 2.75–2.60 (m, 3H), 2.45 (t, J=7.4 Hz, 2H), 2.30–2.00 (m, 2H), 2.00–1.70 (m, 4H), 1.70–1.20 (m, 6H), 0.93 (t, J=7.2 Hz, 3H).

EXAMPLE 22(1)

(3S)-1-propyl-2,5-dioxo-3-(4-benzenesulfonylaminobutyl)-9-(2-phenylethyl)-1,4,9-triazaspiro[5.5] undecane

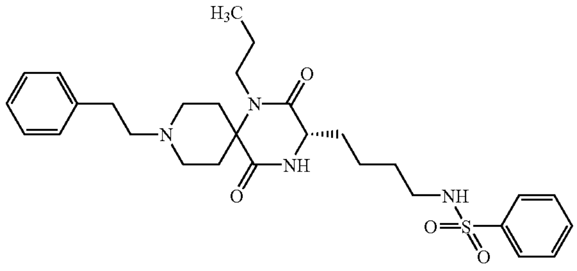

By the same procedure as described in Example 22 using the compound prepared in Example 14 (5 mg), pyridine (2 μl), benzenesulfonyl chloride (3 μl), the compound of the present invention (4.4 mg) having the following physical data was obtained.

TLC: Rf 0.49 (chloroform:methanol=10:1);

NMR ($CD_3OD$): δ 7.84 (m, 2H), 7.59 (m, 3H), 7.34–7.10 (m, 5H), 4.01 (t, J=5.0 Hz, 1H), 3.55–3.30 (m, 2H), 3.05–2.90 (m, 3H), 2.90–2.75 (m, 4H), 2.75 –2.60 (m, 3H), 2.30–2.00 (m, 2H), 1.96 (m, 2H), 1.88–1.70 (m, 2H), 1.70–1.20 (m, 6H), 0.94 (t, J=7.4 Hz, 3H).

EXAMPLE 22(2)

(3S)-1-propyl-2,5-dioxo-3-(4-(N-benzylcarbamoyl) aminobutyl)-9-(2-phenylethyl)-1,4,9-triazaspiro[5.5] undecane

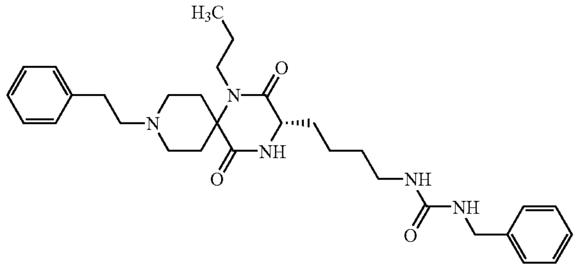

By the same procedure as described in Example 22 using the compound prepared in Example 14 (5 mg), and benzyl isocyanate (3 μl), the compound of the present invention (7 mg) having the following physical data was obtained.

TLC: Rf 0.46 (chloroform:methanol=10:1);

NMR ($CD_3OD$): δ 7.40–7.10 (m, 10H), 4.30 (s, 2H), 4.04 (t, J=5.0 Hz, 1H), 3.55–3.30 (m, 2H), 3.15 (t, J=6.6 Hz, 3H), 3.05–2.90 (m, 3H), 2.90–2.75 (m, 3H), 2.75–2.60 (m, 2H), 2.35–2.05 (m, 2H), 2.02–1.70 (m, 4H), 1.70–1.20 (m, 6H), 0.93 (t, J=7.4 Hz, 3H).

EXAMPLE 22(H20-1)~22(H21-77)

By the same procedure as described in Example 22, 22(1) or 22(2) using the compound prepared in Example 14 and the corresponding acid chloride derivatives, sulfonyl chloride derivatives or isocyanate derivatives, the compounds of the present invention, whose names were shown in the following Table 20A-1~21A-11, and whose structures were shown in the following Table 20B-1~21B-12, were obtained. Also, physical data of the above compounds were shown in the following Table 20C-1~21C-3.

TABLE 20A-1

| Example No | Compound Name |
|---|---|
| 22(H20-1) | (3S)-1-propyl-2,5-dioxo-3-(4-((4-biphenyl)carbonylamino)butyl)-9-(2-phenylethyl)-1,4,9-triazaspiro[5.5]undecane |
| 22(H20-2) | (3S)-1-propyl-2,5-dioxo-3-(4-((4,7,7-trimethyl-2-oxa-3-oxobicyclo[2.2.1]heptan-1-yl)carbonylamino)butyl)-9-(2-phenylethyl)-1,4,9-triazaspiro[5.5]undecane |
| 22(H20-3) | (3S)-1-propyl-2,5-dioxo-3-(4-((4-dimethylaminophenyl)carbonylamino)butyl)-9-(2-phenylethyl)-1,4,9-triazaspiro[5.5]undecane |
| 22(H20-4) | (3S)-1-propyl-2,5-dioxo-3-(4-((3-(2-chlorophenyl)-5-methylisooxazol-4-yl)carbonylamino)butyl)-9-(2-phenylethyl)-1,4,9-triazaspiro[5.5]undecane |
| 22(H20-5) | (3S)-1-propyl-2,5-dioxo-3-(4-((4-fluorophenyl)carbonylamino)butyl)-9-(2-phenylethyl)-1,4,9-triazaspiro[5.5]undecane |
| 22(H20-6) | (3S)-1-propyl-2,5-dioxo-3-(4-((3-fluorophenyl)carbonylamino)butyl)-9-(2-phenylethyl)-1,4,9-triazaspiro[5.5]undecane |
| 22(H20-7) | (3S)-1-propyl-2,5-dioxo-3-(4-((2-fluorophenyl)carbonylamino)butyl)-9-(2-phenylethyl)-1,4,9-triazaspiro[5.5]undecane |

TABLE 20A-2

| Example No | Compound Name |
|---|---|
| 22(H20-8) | (3S)-1-propyl-2,5-dioxo-3-(4-(cyclopentylcarbonylamino)butyl)-9-(2-phenylethyl)-1,4,9-triazaspiro[5.5]undecane |
| 22(H20-9) | (3S)-1-propyl-2,5-dioxo-3-(4-((3-methylphenyl)carbonylamino)butyl)-9-(2-phenylethyl)-1,4,9-triazaspiro[5.5]undecane |
| 22(H20-10) | (3S)-1-propyl-2,5-dioxo-3-(4-((3-methoxyphenyl)carbonylamino)butyl)-9-(2-phenylethyl)-1,4,9-triazaspiro[5.5]undecane |
| 22(H20-11) | (3S)-1-propyl-2,5-dioxo-3-(4-(2,2-dimethylpropanoylamino)butyl)-9-(2-phenylethyl)-1,4,9-triazaspiro[5.5]undecane |
| 22(H20-12) | (3S)-1-propyl-2,5-dioxo-3-(4-(pyridin-3-ylcarbonylamino)butyl)-9-(2-phenylethyl)-1,4,9-triazaspiro[5.5]undecane |
| 22(H20-13) | (3S)-1-propyl-2,5-dioxo-3-(4-(pyridin-2-ylcarbonylamino)butyl)-9-(2-phenylethyl)-1,4,9-triazaspiro[5.5]undecane |
| 22(H20-14) | (3S)-1-propyl-2,5-dioxo-3-(4-(2-phenylacetylamino)butyl)-9-(2-phenylethyl)-1,4,9-triazaspiro[5.5]undecane |

TABLE 20A-3

| Example No | Compound Name |
|---|---|
| 22(H20-15) | (3S)-1-propyl-2,5-dioxo-3-(4-(2-phenyloxyacetylamino)butyl)-9-(2-phenylethyl)-1,4,9-triazaspiro[5.5]undecane |
| 22(H20-16) | (3S)-1-propyl-2,5-dioxo-3-(4-((4-ethyl-2,3-dioxopiperazinyl)carbonylamino)butyl)-9-(2-phenylethyl)-1,4,9-triazaspiro[5.5]undecane |

TABLE 20A-3-continued

| Example No | Compound Name |
|---|---|
| 22(H20-17) | (3S)-1-propyl-2,5-dioxo-3-(4-((2-phenylthiopyridin-3-yl)carbonylamino)butyl)-9-(2-phenylethyl)-1,4,9-triazaspiro[5.5]undecane |
| 22(H20-18) | (3S)-1-propyl-2,5-dioxo-3-(4-((2-phenyloxypyridin-3-yl)carbonylamino)butyl)-9-(2-phenylethyl)-1,4,9-triazaspiro[5.5]undecane |
| 22(H20-19) | (3S)-1-propyl-2,5-dioxo-3-(4-((2-methoxyphenyl)carbonylamino)butyl)-9-(2-phenylethyl)-1,4,9-triazaspiro[5.5]undecane |
| 22(H20-20) | (3S)-1-propyl-2,5-dioxo-3-(4-(2-(thiophen-2-yl)acetylamino)butyl)-9-(2-phenylethyl)-1,4,9-triazaspiro[5.5]undecane |
| 22(H20-21) | (3S)-1-propyl-2,5-dioxo-3-(4-(hexanoylamino)butyl)-9-(2-phenylethyl)-1,4,9-triazaspiro[5.5]undecane |

TABLE 20A-4

| Example No | Compound Name |
|---|---|
| 22(H20-22) | (3S)-1-propyl-2,5-dioxo-3-(4-((4-methylphenyl)carbonylamino)butyl)-9-(2-phenylethyl)-1,4,9-triazaspiro[5.5]undecane |
| 22(H20-23) | (3S)-1-propyl-2,5-dioxo-3-(4-(2-methylpropanoylamino)butyl)-9-(2-phenylethyl)-1,4,9-triazaspiro[5.5]undecane |
| 22(H20-24) | (3S)-1-propyl-2,5-dioxo-3-(4-(3-cyclopentylpropanoylamino)butyl)-9-(2-phenylethyl)-1,4,9-triazaspiro[5.5]undecane |
| 22(H20-25) | (3S)-1-propyl-2,5-dioxo-3-(4-((2E)-3-phenyl-2-propenoylamino)butyl)-9-(2-phenylethyl)-1,4,9-triazaspiro[5.5]undecane |
| 22(H20-26) | (3S)-1-propyl-2,5-dioxo-3-(4-((2-methylphenyl)carbonylamino)butyl)-9-(2-phenylethyl)-1,4,9-triazaspiro[5.5]undecane |
| 22(H20-27) | (3S)-1-propyl-2,5-dioxo-3-(4-(3,3-dimethylbutanoylamino)butyl)-9-(2-phenylethyl)-1,4,9-triazaspiro[5.5]undecane |
| 22(H20-28) | (3S)-1-propyl-2,5-dioxo-3-(4-(cyclohexylcarbonylamino)butyl)-9-(2-phenylethyl)-1,4,9-triazaspiro[5.5]undecane |

TABLE 20A-5

| Example No | Compound Name |
|---|---|
| 22(H20-29) | (3S)-1-propyl-2,5-dioxo-3-(4-(phenylcarbonylamino)butyl)-9-(2-phenylethyl)-1,4,9-triazaspiro[5.5]undecane |
| 22(H20-30) | (3S)-1-propyl-2,5-dioxo-3-(4-(thiophen-2-ylcarbonylamino)butyl)-9-(2-phenylethyl)-1,4,9-triazaspiro[5.5]undecane |
| 22(H20-31) | (3S)-1-propyl-2,5-dioxo-3-(4-((2,6,6-trimethyl-1-cyclohexenyl)carbonylamino)butyl)-9-(2-phenylethyl)-1,4,9-triazaspiro[5.5]undecane |
| 22(H20-32) | (3S)-1-propyl-2,5-dioxo-3-(4-((3-phenyl-5-methyl-isooxazol-4-yl)carbonylamino)butyl)-9-(2-phenylethyl)-1,4,9-triazaspiro[5.5]undecane |
| 22(H20-33) | (3S)-1-propyl-2,5-dioxo-3-(4-((5-methyl-2-phenyl-1,2,3-triazol-4-yl)carbonylamino)butyl)-9-(2-phenylethyl)-1,4,9-triazaspiro[5.5]undecane |
| 22(H20-34) | (3S)-1-propyl-2,5-dioxo-3-(4-(2-(3-methoxyphenyl)acetylamino)butyl)-9-(2-phenylethyl)-1,4,9-triazaspiro[5.5]undecane |
| 22(H20-35) | (3S)-1-propyl-2,5-dioxo-3-(4-(4-methoxyphenylcarbonylamino)butyl)-9-(2-phenylethyl)-1,4,9-triazaspiro[5.5]undecane |

TABLE 20A-6

| Example No | Compound Name |
|---|---|
| 22(H20-36) | (3S)-1-propyl-2,5-dioxo-3-(4-((furan-2-yl)carbonylamino)butyl)-9-(2-phenylethyl)-1,4,9-triazaspiro[5.5]undecane |
| 22(H20-37) | (3S)-1-propyl-2,5-dioxo-3-(4-(2-benzyloxyacetylamino)butyl)-9-(2-phenylethyl)-1,4,9-triazaspiro[5.5]undecane |
| 22(H20-38) | (3S)-1-propyl-2,5-dioxo-3-(4-(cyclobutylcarbonylamino)butyl)-9-(2-phenylethyl)-1,4,9-triazaspiro[5.5]undecane |
| 22(H20-39) | (3S)-1-propyl-2,5-dioxo-3-(4-(2-(4-methoxyphenyl)acetylamino)butyl)-9-(2-phenylethyl)-1,4,9-triazaspiro[5.5]undecane |
| 22(H20-40) | (3S)-1-propyl-2,5-dioxo-3-(4-(acetylamino)butyl)-9-(2-phenylethyl)-1,4,9-triazaspiro[5.5]undecane |
| 22(H20-41) | (3S)-1-propyl-2,5-dioxo-3-(4-(4-methylpentanoylamino)butyl)-9-(2-phenylethyl)-1,4,9-triazaspiro[5.5]undecane |
| 22(H20-42) | (3S)-1-propyl-2,5-dioxo-3-(4-(2-methoxyacetylamino)butyl)-9-(2-phenylethyl)-1,4,9-triazaspiro[5.5]undecane |

TABLE 20A-7

| Example No | Compound Name |
|---|---|
| 22(H20-43) | (3S)-1-propyl-2,5-dioxo-3-(4-(3-methylthiopropanoylamino)butyl)-9-(2-phenylethyl)-1,4,9-triazaspiro[5.5]undecane |
| 22(H20-44) | (3S)-1-propyl-2,5-dioxo-3-(4-(2-cyclopentylacetylamino)butyl)-9-(2-phenylethyl)-1,4,9-triazaspiro[5.5]undecane |
| 22(H20-45) | (3S)-1-propyl-2,5-dioxo-3-(4-(pentanoylamino)butyl)-9-(2-phenylethyl)-1,4,9-triazaspiro[5.5]undecane |
| 22(H20-46) | (3S)-1-propyl-2,5-dioxo-3-(4-(3-methylpropanoylamino)butyl)-9-(2-phenylethyl)-1,4,9-triazaspiro[5.5]undecane |
| 22(H20-47) | (3S)-1-propyl-2,5-dioxo-3-(4-(2-phenylthioacetylamino)butyl)-9-(2-phenylethyl)-1,4,9-triazaspiro[5.5]undecane |
| 22(H20-48) | (3S)-1-propyl-2,5-dioxo-3-(4-((4-methyl-1,2,3-thiadiazol-5-yl)carbonylamino)butyl)-9-(2-phenylethyl)-1,4,9-triazaspiro[5.5]undecane |
| 22(H20-49) | (3S)-1-propyl-2,5-dioxo-3-(4-((3-cyanophenyl)carbonylamino)butyl)-9-(2-phenylethyl)-1,4,9-triazaspiro[5.5]undecane |

TABLE 20A-8

| Example No | Compound Name |
|---|---|
| 22(H20-50) | (3S)-1-propyl-2,5-dioxo-3-(4-(butanoylamino)butyl)-9-(2-phenylethyl)-1,4,9-triazaspiro[5.5]undecane |
| 22(H20-51) | (3S)-1-propyl-2,5-dioxo-3-(4-(propanoylamino)butyl)-9-(2-phenylethyl)-1,4,9-triazaspiro[5.5]undecane |
| 22(H20-52) | (3S)-1-propyl-2,5-dioxo-3-(4-(cyclopropylcarbonylamino)butyl)-9-(2-phenylethyl)-1,4,9-triazaspiro[5.5]undecane |
| 22(H20-53) | (3S)-1-propyl-2,5-dioxo-3-(4-(2H-benzo[3,4-d]1,3-dioxolan-5-ylcarbonylamino)butyl)-9-(2-phenylethyl)-1,4,9-triazaspiro[5.5]undecane |

TABLE 20A-8-continued

| Example No | Compound Name |
|---|---|
| 22(H20-54) | (3S)-1-propyl-2,5-dioxo-3-(4-((1-phenyl-5-propylpyrazol-4-yl)carbonylamino)butyl)-9-(2-phenylethyl)-1,4,9-triazaspiro[5.5]undecane |
| 22(H20-55) | (3S)-1-propyl-2,5-dioxo-3-(4-((5-(1,1-dimethylethyl)-2-methylfuran-3-yl)carbonylamino)butyl)-9-(2-phenylethyl)-1,4,9-triazaspiro[5.5]undecane |
| 22(H20-56) | (3S)-1-propyl-2,5-dioxo-3-(4-((1-(1,1-dimethylethyl)-3-methylpyrazol-5-yl)carbonylamino)butyl)-9-(2-phenylethyl)-1,4,9-triazaspiro[5.5]undecane |

TABLE 20A-9

| Example No | Compound Name |
|---|---|
| 22(H20-57) | (3S)-1-propyl-2,5-dioxo-3-(4-(methylsulfonylamino)butyl)-9-(2-phenylethyl)-1,4,9-triazaspiro[5.5]undecane |
| 22(H20-58) | (3S)-1-propyl-2,5-dioxo-3-(4-(pentylsulfonylamino)butyl)-9-(2-phenylethyl)-1,4,9-triazaspiro[5.5]undecane |
| 22(H20-59) | (3S)-1-propyl-2,5-dioxo-3-(4-(1-methylethylsulfonylamino)butyl)-9-(2-phenylethyl)-1,4,9-triazaspiro[5.5]undecane |
| 22(H20-60) | (3S)-1-propyl-2,5-dioxo-3-(4-(4-chlorophenylsulfonyl)butyl)-9-(2-phenylethyl)-1,4,9-triazaspiro[5.5]undecane |
| 22(H20-61) | (3S)-1-propyl-2,5-dioxo-3-(4-(2-iodophenylsulfonylamino)butyl)-9-(2-phenylethyl)-1,4,9-triazaspiro[5.5]undecane |
| 22(H20-62) | (3S)-1-propyl-2,5-dioxo-3-(4-(4-nitrophenylsulfonylamino)butyl)-9-(2-phenylethyl)-1,4,9-triazaspiro[5.5]undecane |
| 22(H20-63) | (3S)-1-propyl-2,5-dioxo-3-(4-(4-(methylsulfonyl)phenylsulfonylamino)butyl)-9-(2-phenylethyl)-1,4,9-triazaspiro[5.5]undecane |

TABLE 20A-10

| Example No | Compound Name |
|---|---|
| 22(H20-64) | (3S)-1-propyl-2,5-dioxo-3-(4-(4-trifluoromethylphenylsulfonylamino)butyl)-9-(2-phenylethyl)-1,4,9-triazaspiro[5.5]undecane |
| 22(H20-65) | (3S)-1-propyl-2,5-dioxo-3-(4-(4-phenylphenylsulfonylamino)butyl)-9-(2-phenylethyl)-1,4,9-triazaspiro[5.5]undecane |
| 22(H20-66) | (3S)-1-propyl-2,5-dioxo-3-(4-(2-phenylphenylsulfonylamino)butyl)-9-(2-phenylethyl)-1,4,9-triazaspiro[5.5]undecane |
| 22(H20-67) | (3S)-1-propyl-2,5-dioxo-3-(4-(3,4-difluorophenylsulfonylamino)butyl)-9-(2-phenylethyl)-1,4,9-triazaspiro[5.5]undecane |
| 22(H20-68) | (3S)-1-propyl-2,5-dioxo-3-(4-(2,6-difluorophenylsulfonylamino)butyl)-9-(2-phenylethyl)-1,4,9-triazaspiro[5.5]undecane |
| 22(H20-69) | (3S)-1-propyl-2,5-dioxo-3-(4-(2,5-difluorophenylsulfonylamino)butyl)-9-(2-phenylethyl)-1,4,9-triazaspiro[5.5]undecane |
| 22(H20-70) | (3S)-1-propyl-2,5-dioxo-3-(4-(2,5-dimethoxyphenylsulfonylamino)butyl)-9-(2-phenylethyl)-1,4,9-triazaspiro[5.5]undecane |

TABLE 20A-11

| Example No | Compound Name |
|---|---|
| 22(H20-71) | (3S)-1-propyl-2,5-dioxo-3-(4-(2-chloro-4-trifluoromethylphenylsulfonylamino)butyl)-9-(2-phenylethyl)-1,4,9-triazaspiro[5.5]undecane |
| 22(H20-72) | (3S)-1-propyl-2,5-dioxo-3-(4-(2-naphthylsulfonylamino)butyl)-9-(2-phenylethyl)-1,4,9-triazaspiro[5.5]undecane |
| 22(H20-73) | (3S)-1-propyl-2,5-dioxo-3-(4-((1E)-2-phenylvinylsulfonylamino)butyl)-9-(2-phenylethyl)-1,4,9-triazaspiro[5.5]undecane |
| 22(H20-74) | (3S)-1-propyl-2,5-dioxo-3-(4-(furan-2-ylsulfonylamino)butyl)-9-(2-phenylethyl)-1,4,9-triazaspiro[5.5]undecane |
| 22(H20-75) | (3S)-1-propyl-2,5-dioxo-3-(4-(thiophen-2-ylsulfonylamino)butyl)-9-(2-phenylethyl)-1,4,9-triazaspiro[5.5]undecane |

TABLE 21A-1

| Example No | Compound Name |
|---|---|
| 22(H21-1) | (3S)-1-propyl-2,5-dioxo-3-(4-(4-bromo-2,5-dichlorothiophen-3-ylsulfonylamino)butyl)-9-(2-phenylethyl)-1,4,9-triazaspiro[5.5]undecane |
| 22(H21-2) | (3S)-1-propyl-2,5-dioxo-3-(4-(5-phenylsulfonylthiophen-2-ylsulfonylamino)butyl)-9-(2-phenylethyl)-1,4,9-triazaspiro[5.5]undecane |
| 22(H21-3) | (3S)-1-propyl-2,5-dioxo-3-(4-(7-chlorobenzofurazan-4-ylsulfonylamino)butyl)-9-(2-phenylethyl)-1,4,9-triazaspiro[5.5]undecane |
| 22(H21-4) | (3S)-1-propyl-2,5-dioxo-3-(4-(4-methyl-2-acetylamino-thiazol-5-ylsulfonylamino)butyl)-9-(2-phenylethyl)-1,4,9-triazaspiro[5.5]undecane |
| 22(H21-5) | (3S)-1-propyl-2,5-dioxo-3-(4-(2-methoxy-dibenzofuran-3-ylsulfonylamino)butyl)-9-(2-phenylethyl)-1,4,9-triazaspiro[5.5]undecane |
| 22(H21-6) | (3S)-1-propyl-2,5-dioxo-3-(4-(3,4-dichlorophenylsulfonylamino)butyl)-9-(2-phenylethyl)-1,4,9-triazaspiro[5.5]undecane |
| 22(H21-7) | (3S)-1-propyl-2,5-dioxo-3-(4-(4-methoxyphenylsulfonylamino)butyl)-9-(2-phenylethyl)-1,4,9-triazaspiro[5.5]undecane |

TABLE 21A-2

| Example No | Compound Name |
|---|---|
| 22(H21-8) | (3S)-1-propyl-2,5-dioxo-3-(4-(benzylsulfonylamino)butyl)-9-(2-phenylethyl)-1,4,9-triazaspiro[5.5]undecane |
| 22(H21-9) | (3S)-1-propyl-2,5-dioxo-3-(4-((ethylamino)carbonylamino)butyl)-9-(2-phenylethyl)-1,4,9-triazaspiro[5.5]undecane |
| 22(H21-10) | (3S)-1-propyl-2,5-dioxo-3-(4-((propylamino)carbonylamino)butyl)-9-(2-phenylethyl)-1,4,9-triazaspiro[5.5]undecane |
| 22(H21-11) | (3S)-1-propyl-2,5-dioxo-3-(4-((1-methylethylamino)carbonylamino)butyl)-9-(2-phenylethyl)-1,4,9-triazaspiro[5.5]undecane |
| 22(H21-12) | (3S)-1-propyl-2,5-dioxo-3-(4-((butylamino)carbonylamino)butyl)-9-(2-phenylethyl)-1,4,9-triazaspiro[5.5]undecane |
| 22(H21-13) | (3S)-1-propyl-2,5-dioxo-3-(4-((4-chlorophenylamino)carbonylamino)butyl)-9-(2-phenylethyl)-1,4,9-triazaspiro[5.5]undecane |
| 22(H21-14) | (3S)-1-propyl-2,5-dioxo-3-(4-((phenylamino)carbonylamino)butyl)-9-(2-phenylethyl)-1,4,9-triazaspiro[5.5]undecane |

TABLE 21A-3

| Example No | Compound Name |
|---|---|
| 22(H21-15) | (3S)-1-propyl-2,5-dioxo-3-(4-((4-methylphenylamino)carbonylamino)butyl)-9-(2-phenylethyl)-1,4,9-triazaspiro[5.5]undecane |
| 22(H21-16) | (3S)-1-propyl-2,5-dioxo-3-(4-((hexylamino)carbonylamino)butyl)-9-(2-phenylethyl)-1,4,9-triazaspiro[5.5]undecane |
| 22(H21-17) | (3S)-1-propyl-2,5-dioxo-3-(4-((4-fluorophenylamino)carbonylamino)butyl)-9-(2-phenylethyl)-1,4,9-triazaspiro[5.5]undecane |
| 22(H21-18) | (3S)-1-propyl-2,5-dioxo-3-(4-((benzylamino)carbonylamino)butyl)-9-(2-phenylethyl)-1,4,9-triazaspiro[5.5]undecane |
| 22(H21-19) | (3S)-1-propyl-2,5-dioxo-3-(4-((cyclohexylamino)carbonylamino)butyl)-9-(2-phenylethyl)-1,4,9-triazaspiro[5.5]undecane |
| 22(H21-20) | (3S)-1-propyl-2,5-dioxo-3-(4-((3-methylphenylamino)carbonylamino)butyl)-9-(2-phenylethyl)-1,4,9-triazaspiro[5.5]undecane |
| 22(H21-21) | (3S)-1-propyl-2,5-dioxo-3-(4-((octylamino)carbonylamino)butyl)-9-(2-phenylethyl)-1,4,9-triazaspiro[5.5]undecane |

TABLE 21A-4

| Example No | Compound Name |
|---|---|
| 22(H21-22) | (3S)-1-propyl-2,5-dioxo-3-(4-((4-bromophenylamino)carbonylamino)butyl)-9-(2-phenylethyl)-1,4,9-triazaspiro[5.5]undecane |
| 22(H21-23) | (3S)-1-propyl-2,5-dioxo-3-(4-((2-(thiophen-2-yl)ethylamino)carbonylamino)butyl)-9-(2-phenylethyl)-1,4,9-triazaspiro[5.5]undecane |
| 22(H21-24) | (3S)-1-propyl-2,5-dioxo-3-(4-((4-(1-methylethyl)phenylamino)carbonylamino)butyl)-9-(2-phenylethyl)-1,4,9-triazaspiro[5.5]undecane |
| 22(H21-25) | (3S)-1-propyl-2,5-dioxo-3-(4-((3-chlorophenylamino)carbonylamino)butyl)-9-(2-phenylethyl)-1,4,9-triazaspiro[5.5]undecane |
| 22(H21-26) | (3S)-1-propyl-2,5-dioxo-3-(4-((2,4,5-trimethylphenylamino)carbonylamino)butyl)-9-(2-phenylethyl)-1,4,9-triazaspiro[5.5]undecane |
| 22(H21-27) | (3S)-1-propyl-2,5-dioxo-3-(4-((2,4,6-trimethylphenylamino)carbonylamino)butyl)-9-(2-phenylethyl)-1,4,9-triazaspiro[5.5]undecane |
| 22(H21-28) | (3S)-1-propyl-2,5-dioxo-3-(4-((4-phenyloxyphenylamino)carbonylamino)butyl)-9-(2-phenylethyl)-1,4,9-triazaspiro[5.5]undecane |

TABLE 21A-5

| Example No | Compound Name |
|---|---|
| 22(H21-29) | (3S)-1-propyl-2,5-dioxo-3-(4-((4-butyloxyphenylamino)carbonylamino)butyl)-9-(2-phenylethyl)-1,4,9-triazaspiro[5.5]undecane |
| 22(H21-30) | (3S)-1-propyl-2,5-dioxo-3-(4-((4-phenylphenylamino)carbonylamino)butyl)-9-(2-phenylethyl)-1,4,9-triazaspiro[5.5]undecane |
| 22(H21-31) | (3S)-1-propyl-2,5-dioxo-3-(4-((2-phenylphenylamino)carbonylamino)butyl)-9-(2-phenylethyl)-1,4,9-triazaspiro[5.5]undecane |

TABLE 21A-5-continued

| Example No | Compound Name |
|---|---|
| 22(H21-32) | (3S)-1-propyl-2,5-dioxo-3-(4-((4-trifluoromethylphenylamino)carbonylamino)butyl)-9-(2-phenylethyl)-1,4,9-triazaspiro[5.5]undecane |
| 22(H21-33) | (3S)-1-propyl-2,5-dioxo-3-(4-((3,4-dichlorophenylamino)carbonylamino)butyl)-9-(2-phenylethyl)-1,4,9-triazaspiro[5.5]undecane |
| 22(H21-34) | (3S)-1-propyl-2,5-dioxo-3-(4-((4-butyloxycarbonylphenylamino)carbonylamino)butyl)-9-(2-phenylethyl)-1,4,9-triazaspiro[5.5]undecane |
| 22(H21-35) | (3S)-1-propyl-2,5-dioxo-3-(4-((2,6-bis(1-methylethyl)phenylamino)carbonylamino)butyl)-9-(2-phenylethyl)-1,4,9-triazaspiro[5.5]undecane |

TABLE 21A-6

| Example No | Compound Name |
|---|---|
| 22(H21-36) | (3S)-1-propyl-2,5-dioxo-3-(4-((2,5-dimethylphenylamino)carbonylamino)butyl)-9-(2-phenylethyl)-1,4,9-triazaspiro[5.5]undecane |
| 22(H21-37) | (3S)-1-propyl-2,5-dioxo-3-(4-((2-ethyl-6-(1-methylethyl)phenylamino)carbonylamino)butyl)-9-(2-phenylethyl)-1,4,9-triazaspiro[5.5]undecane |
| 22(H21-38) | (3S)-1-propyl-2,5-dioxo-3-(4-((2,4,6-trichlorophenylamino)carbonylamino)butyl)-9-(2-phenylethyl)-1,4,9-triazaspiro[5.5]undecane |
| 22(H21-39) | (3S)-1-propyl-2,5-dioxo-3-(4-((3,4-dimethylphenylamino)carbonylamino)butyl)-9-(2-phenylethyl)-1,4,9-triazaspiro[5.5]undecane |
| 22(H21-40) | (3S)-1-propyl-2,5-dioxo-3-(4-((2-methylthiophenylamino)carbonylamino)butyl)-9-(2-phenylethyl)-1,4,9-triazaspiro[5.5]undecane |
| 22(H21-41) | (3S)-1-propyl-2,5-dioxo-3-(4-((4-methylthiophenylamino)carbonylamino)butyl)-9-(2-phenylethyl)-1,4,9-triazaspiro[5.5]undecane |
| 22(H21-42) | (3S)-1-propyl-2,5-dioxo-3-(4-((4-butylphenylamino)carbonylamino)butyl)-9-(2-phenylethyl)-1,4,9-triazaspiro[5.5]undecane |

TABLE 21A-7

| Example No | Compound Name |
|---|---|
| 22(H21-43) | (3S)-1-propyl-2,5-dioxo-3-(4-((2-chloro-5-trifluoromethylphenylamino)carbonylamino)butyl)-9-(2-phenylethyl)-1,4,9-triazaspiro[5.5]undecane |
| 22(H21-44) | (3S)-1-propyl-2,5-dioxo-3-(4-((2,6-dibromo-4-ethylphenylamino)carbonylamino)butyl)-9-(2-phenylethyl)-1,4,9-triazaspiro[5.5]undecane |
| 22(H21-45) | (3S)-1-propyl-2,5-dioxo-3-(4-((1-ethoxycarbonyl-2-methylpropylamino)carbonylamino)butyl)-9-(2-phenylethyl)-1,4,9-triazaspiro[5.5]undecane |
| 22(H21-46) | (3S)-1-propyl-2,5-dioxo-3-(4-((phenylcarbonylamino)carbonylamino)butyl)-9-(2-phenylethyl)-1,4,9-triazaspiro[5.5]undecane |
| 22(H21-47) | (3S)-1-propyl-2,5-dioxo-3-(4-((2,4,6-tribromophenylamino)carbonylamino)butyl)-9-(2-phenylethyl)-1,4,9-triazaspiro[5.5]undecane |
| 22(H21-48) | (3S)-1-propyl-2,5-dioxo-3-(4-((2,5-difluorophenylamino)carbonylamino)butyl)-9-(2-phenylethyl)-1,4,9-triazaspiro[5.5]undecane |

TABLE 21A-7-continued

| Example No | Compound Name |
|---|---|
| 22(H21-49) | (3S)-1-propyl-2,5-dioxo-3-(4-((3,5-bis(methoxycarbonyl)phenylamino)carbonylamino)butyl)-9-(2-phenylethyl)-1,4,9-triazaspiro[5.5]undecane |

TABLE 21A-8

| Example No | Compound Name |
|---|---|
| 22(H21-50) | (3S)-1-propyl-2,5-dioxo-3-(4-((6,7-methylenedioxycoumarin-4-ylmethylamino)carbonylamino)butyl)-9-(2-phenylethyl)-1,4,9-triazaspiro[5.5]undecane |
| 22(H21-51) | (3S)-1-propyl-2,5-dioxo-3-(4-((2,6-dimethylphenylamino)carbonylamino)butyl)-9-(2-phenylethyl)-1,4,9-triazaspiro[5.5]undecane |
| 22(H21-52) | (3S)-1-propyl-2,5-dioxo-3-(4-((2-methylpropyloxy)carbonylamino)butyl)-9-(2-phenylethyl)-1,4,9-triazaspiro[5.5]undecane |
| 22(H21-53) | (3S)-1-propyl-2,5-dioxo-3-(4-((2-ethylhexyloxy)carbonylamino)butyl)-9-(2-phenylethyl)-1,4,9-triazaspiro[5.5]undecane |
| 22(H21-54) | (3S)-1-propyl-2,5-dioxo-3-(4-(ethoxycarbonylamino)butyl)-9-(2-phenylethyl)-1,4,9-triazaspiro[5.5]undecane |
| 22(H21-55) | (3S)-1-propyl-2,5-dioxo-3-(4-(allyloxycarbonylamino)butyl)-9-(2-phenylethyl)-1,4,9-triazaspiro[5.5]undecane |
| 22(H21-56) | (3S)-1-propyl-2,5-dioxo-3-(4-(propyloxycarbonylamino)butyl)-9-(2-phenylethyl)-1,4,9-triazaspiro[5.5]undecane |

TABLE 21A-9

| Example No | Compound Name |
|---|---|
| 22(H21-57) | (3S)-1-propyl-2,5-dioxo-3-(4-(butyloxycarbonylamino)butyl)-9-(2-phenylethyl)-1,4,9-triazaspiro[5.5]undecane |
| 22(H21-58) | (3S)-1-propyl-2,5-dioxo-3-(4-(hexyloxycarbonylamino)butyl)-9-(2-phenylethyl)-1,4,9-triazaspiro[5.5]undecane |
| 22(H21-59) | (3S)-1-propyl-2,5-dioxo-3-(4-((2,2,2-trichloroethyloxy)carbonylamino)butyl)-9-(2-phenylethyl)-1,4,9-triazaspiro[5.5]undecane |
| 22(H21-60) | (3S)-1-propyl-2,5-dioxo-3-(4-((fluoren-9-ylmethyloxy)carbonylamino)butyl)-9-(2-phenylethyl)-1,4,9-triazaspiro[5.5]undecane |
| 22(H21-61) | (3S)-1-propyl-2,5-dioxo-3-(4-((1S,5S,2R)-5-methyl-2-(1-methylethyl)cyclohexyloxycarbonylamino)butyl)-9-(2-phenylethyl)-1,4,9-triazaspiro[5.5]undecane |
| 22(H21-62) | (3S)-1-propyl-2,5-dioxo-3-(4-((2-methoxyethoxy)carbonylamino)butyl)-9-(2-phenylethyl)-1,4,9-triazaspiro[5.5]undecane |

TABLE 21A-9-continued

| Example No | Compound Name |
|---|---|
| 22(H21-63) | (3S)-1-propyl-2,5-dioxo-3-(4-(pentyloxycarbonylamino)butyl)-9-(2-phenylethyl)-1,4,9-triazaspiro[5.5]undecane |

TABLE 21A-10

| Example No | Compound Name |
|---|---|
| 22(H21-64) | (3S)-1-propyl-2,5-dioxo-3-(4-((1-methylethyloxy)carbonylamino)butyl)-9-(2-phenylethyl)-1,4,9-triazaspiro[5.5]undecane |
| 22(H21-65) | (3S)-1-propyl-2,5-dioxo-3-(4-((3-butenyloxy)carbonylamino)butyl)-9-(2-phenylethyl)-1,4,9-triazaspiro[5.5]undecane |
| 22(H21-66) | (3S)-1-propyl-2,5-dioxo-3-(4-((2S,1R,5R)-methyl-2-(1-methylethyl)cyclohexyloxycarbonylamino)butyl)-9-(2-phenylethyl)-1,4,9-triazaspiro[5.5]undecane |
| 22(H21-67) | (3S)-1-propyl-2,5-dioxo-3-(4-(cyclopentyloxycarbonylamino)butyl)-9-(2-phenylethyl)-1,4,9-triazaspiro[5.5]undecane |
| 22(H21-68) | (3S)-1-propyl-2,5-dioxo-3-(4-((1,1-dimethylethyloxy)carbonylamino)butyl)-9-(2-phenylethyl)-1,4,9-triazaspiro[5.5]undecane |
| 22(H21-69) | (3S)-1-propyl-2,5-dioxo-3-(4-(benzyloxycarbonylamino)butyl)-9-(2-phenylethyl)-1,4,9-triazaspiro[5.5]undecane |
| 22(H21-70) | (3S)-1-propyl-2,5-dioxo-3-(4-((N,N-diphenylamino)carbonylamino)butyl)-9-(2-phenylethyl)-1,4,9-triazaspiro[5.5]undecane |

TABLE 21A-11

| Example No | Compound Name |
|---|---|
| 22(H21-71) | (3S)-1-propyl-2,5-dioxo-3-(4-((N-phenyl-N-methylamino)carbonylamino)butyl)-9-(2-phenylethyl)-1,4,9-triazaspiro[5.5]undecane |
| 22(H21-72) | (3S)-1-propyl-2,5-dioxo-3-(4-((N,N-dimethylamino)carbonylamino)butyl)-9-(2-phenylethyl)-1,4,9-triazaspiro[5.5]undecane |
| 22(H21-73) | (3S)-1-propyl-2,5-dioxo-3-(4-((N,N-diethylamino)carbonylamino)butyl)-9-(2-phenylethyl)-1,4,9-triazaspiro[5.5]undecane |
| 22(H21-74) | (3S)-1-propyl-2,5-dioxo-3-(4-((N,N-bis(1-methylethyl)amino)carbonylamino)butyl)-9-(2-phenylethyl)-1,4,9-triazaspiro[5.5]undecane |
| 22(H21-75) | (3S)-1-propyl-2,5-dioxo-3-(4-(morpholin-4-ylcarbonylamino)butyl)-9-(2-phenylethyl)-1,4,9-triazaspiro[5.5]undecane |
| 22(H21-76) | (3S)-1-propyl-2,5-dioxo-3-(4-(carbazol-9-ylcarbonylamino)butyl)-9-(2-phenylethyl)-1,4,9-triazaspiro[5.5]undecane |
| 22(H21-77) | (3S)-1-propyl-2,5-dioxo-3-(4-(pyrrolidin-1-ylcarbonylamino)butyl)-9-(2-phenylethyl)-1,4,9-triazaspiro[5.5]undecane |

TABLE 20B-1
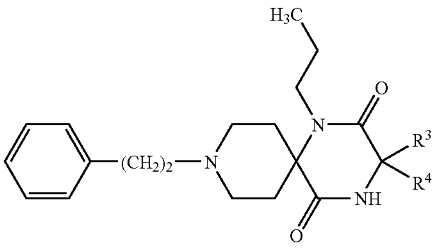
| Example No | $R^3$ | $R^4$ |
|---|---|---|
| 22(H20-1) | H | 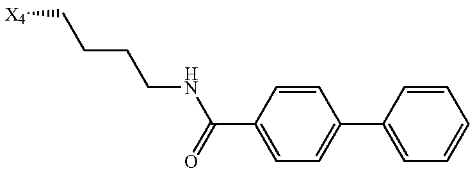 |
| 22(H20-2) | H | 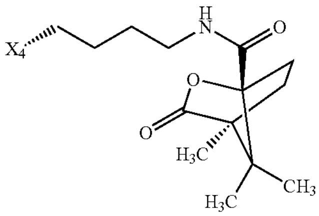 |
| 22(H20-3) | H | 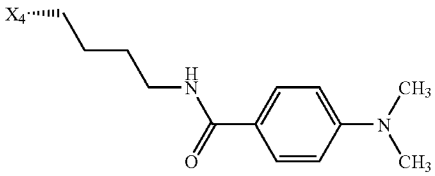 |
| 22(H20-4) | H | 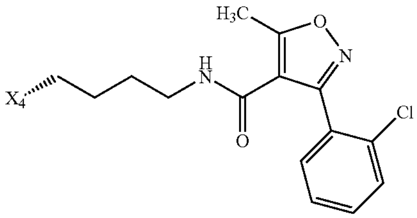 |
| 22(H20-5) | H | 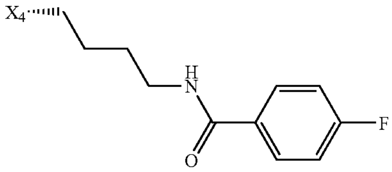 |

TABLE 20B-2
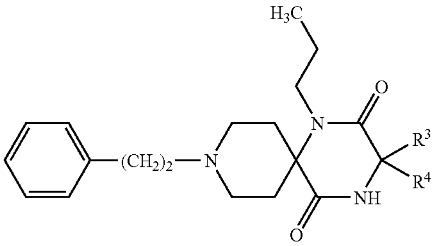
| Example No | $R^3$ | $R^4$ |
|---|---|---|
| 22(H20-6) | H | 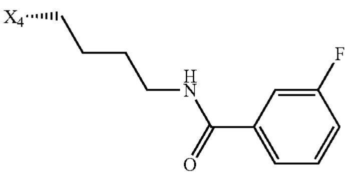 |
| 22(H20-7) | H | 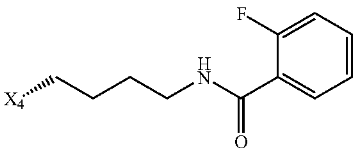 |
| 22(H20-8) | H | 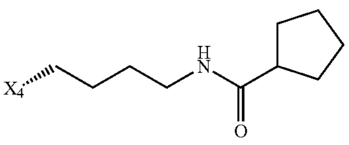 |
| 22(H20-9) | H | 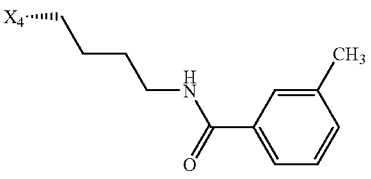 |
| 22(H20-10) | H | 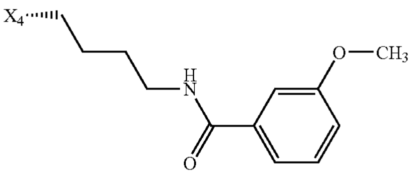 |
| 22(H20-11) | H | 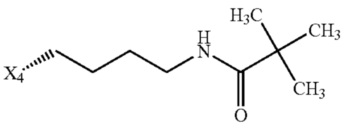 |
TABLE 20B-3
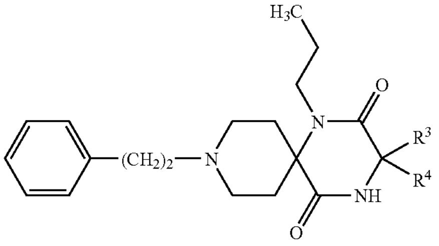
| Example No | $R^3$ | $R^4$ |
|---|---|---|
| 22(H20-12) | H | 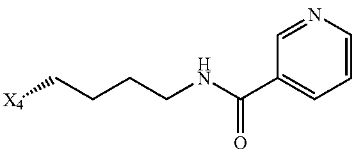 |
| 22(H20-13) | H | 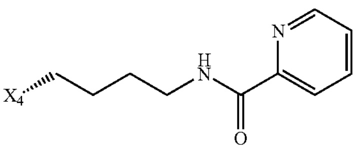 |
| 22(H20-14) | H | 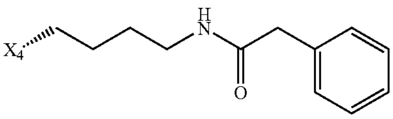 |
| 22(H20-15) | H | 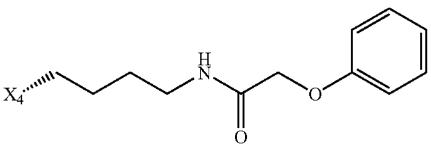 |
| 22(H20-16) | H | 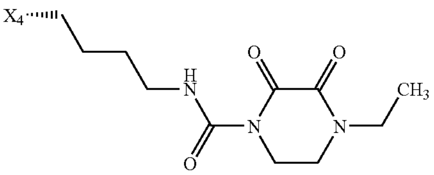 |
| 22(H20-17) | H | 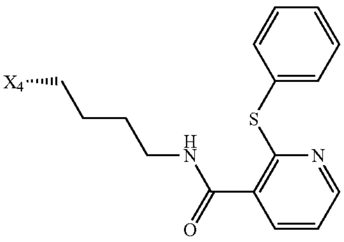 |

TABLE 20B-4
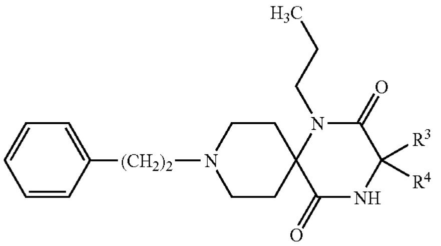
| Example No | $R^3$ | $R^4$ |
|---|---|---|
| 22(H20-18) | H | 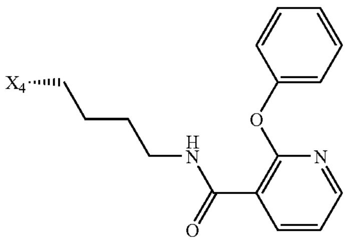 |
| 22(H20-19) | H | 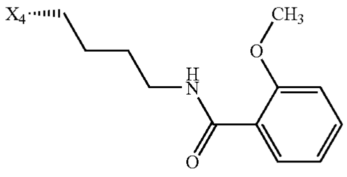 |
| 22(H20-20) | H | 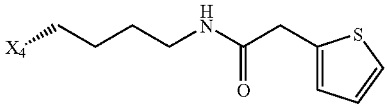 |
| 22(H20-21) | H | 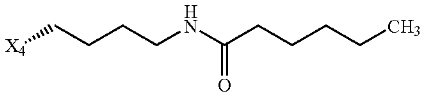 |
| 22(H20-22) | H | 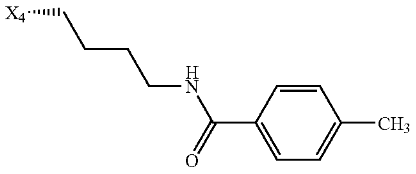 |
| 22(H20-23) | H | 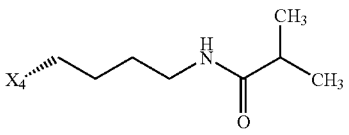 |
TABLE 20B-5
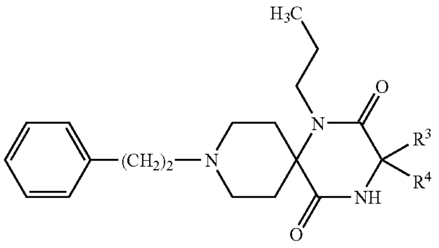
| Example No | $R^3$ | $R^4$ |
|---|---|---|
| 22(H20-24) | H | 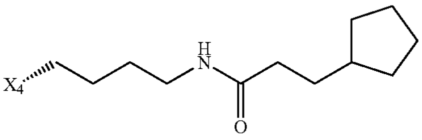 |
| 22(H20-25) | H | 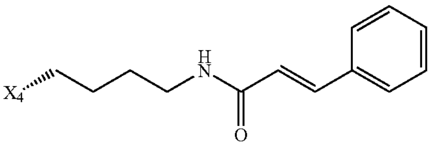 |
| 22(H20-26) | H | 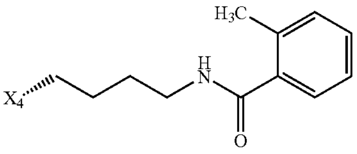 |
| 22(H20-27) | H | 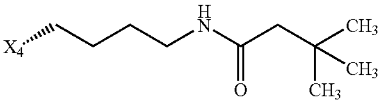 |
| 22(H20-28) | H | 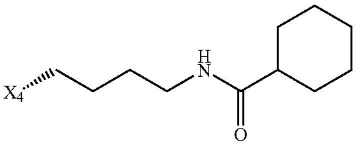 |
| 22(H20-29) | H | 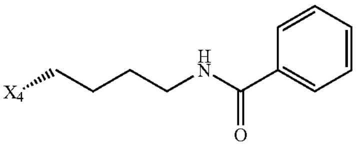 |
| 22(H20-30) | H | 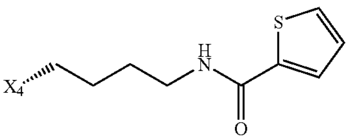 |

TABLE 20B-6
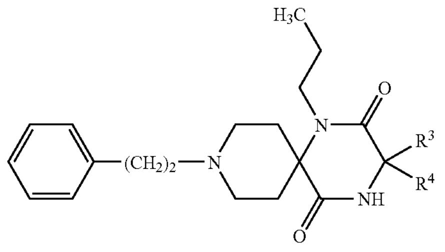
| Example No | $R^3$ | $R^4$ |
|---|---|---|
| 22(H20-31) | H | 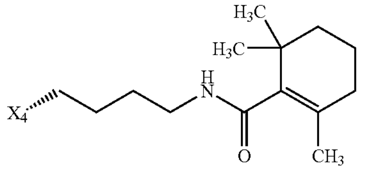 |
| 22(H20-32) | H | 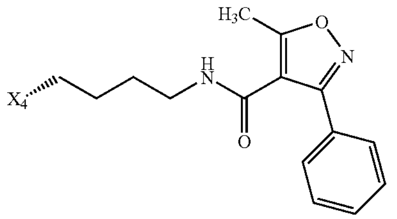 |
| 22(H20-33) | H | 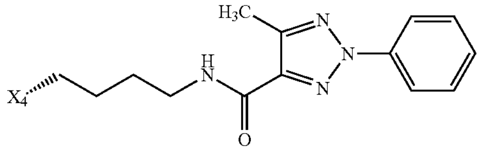 |
| 22(H20-34) | H | 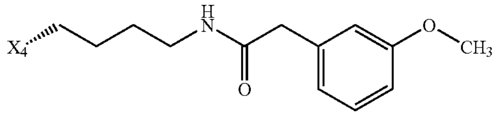 |
| 22(H20-35) | H | 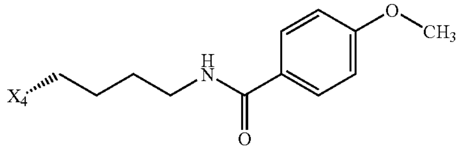 |
| 22(H20-36) | H | 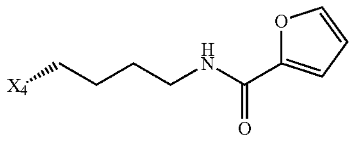 |

TABLE 20B-7
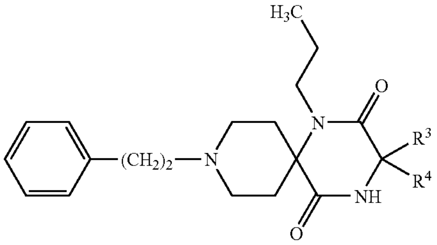
| Example No | $R^3$ | $R^4$ |
|---|---|---|
| 22(H20-37) | H | 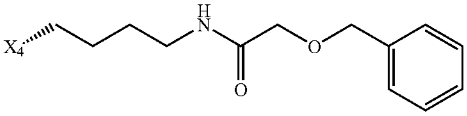 |
| 22(H20-38) | H | 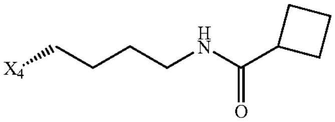 |
| 22(H20-39) | H | 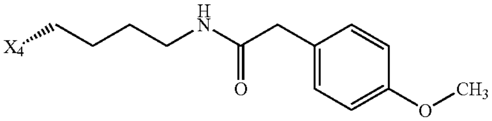 |
| 22(H20-40) | H | 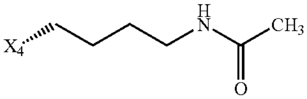 |
| 22(H20-41) | H | 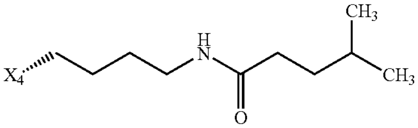 |
| 22(H20-42) | H | 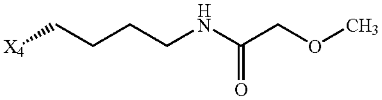 |
| 22(H20-43) | H | 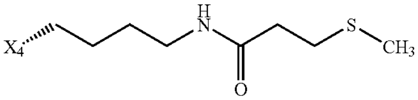 |
| 22(H20-44) | H | 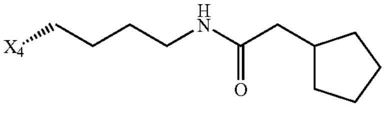 |

TABLE 20B-8
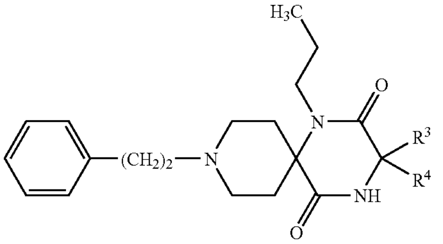
| Example No | $R^3$ | $R^4$ |
| --- | --- | --- |
| 22(H20-45) | H | 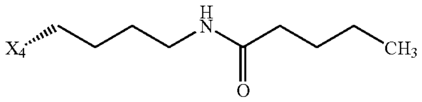 |
| 22(H20-46) | H | 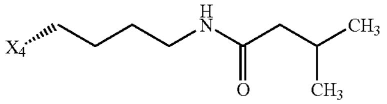 |
| 22(H20-47) | H | 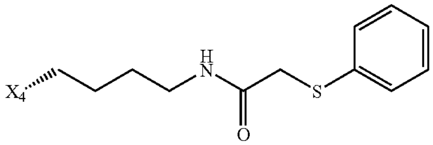 |
| 22(H20-48) | H | 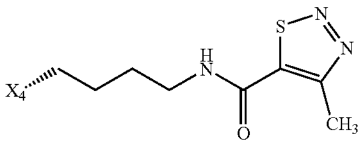 |
| 22(H20-49) | H | 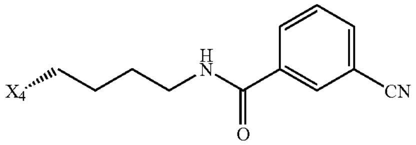 |
| 22(H20-50) | H | 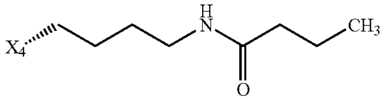 |
| 22(H20-51) | H | 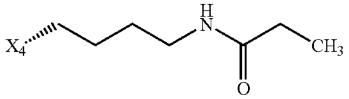 |
| 22(H20-52) | H | 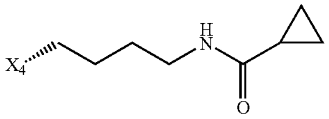 |
TABLE 20B-9
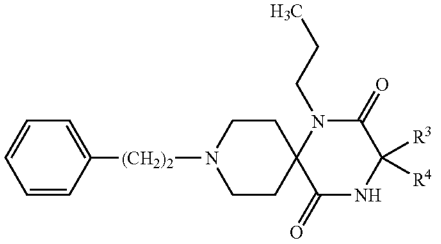
| Example No | $R^3$ | $R^4$ |
| --- | --- | --- |
| 22(H20-53) | H | 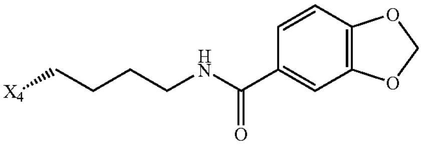 |
| 22(H20-54) | H | 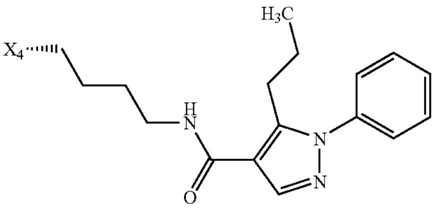 |
| 22(H20-55) | H | 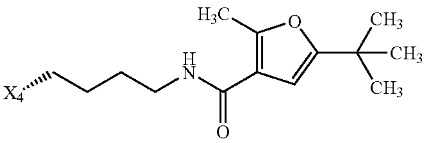 |
| 22(H20-56) | H | 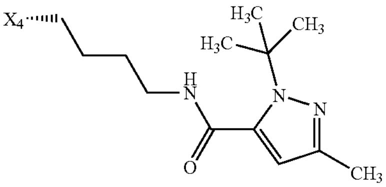 |
| 22(H20-57) | H | 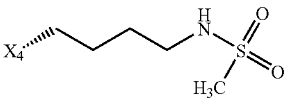 |
| 22(H20-58) | H | 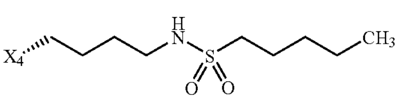 |
| 22(H20-59) | H | 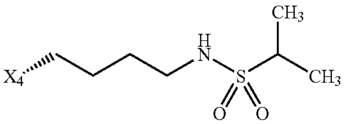 |

TABLE 20B-10
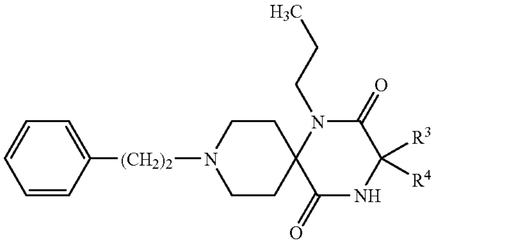
| Example No | $R^3$ | $R^4$ |
| --- | --- | --- |
| 22(H20-60) | H | 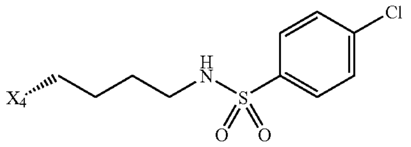 |
| 22(H20-61) | H | 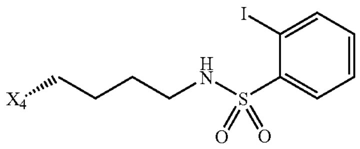 |
| 22(H20-62) | H | 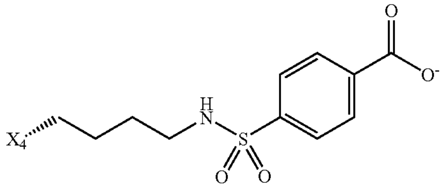 |
| 22(H20-63) | H | 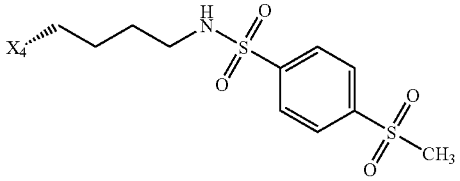 |
| 22(H20-64) | H | 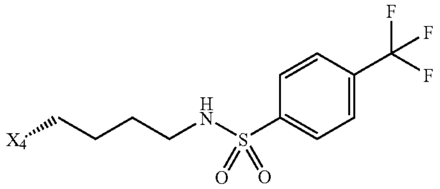 |
| 22(H20-65) | H | 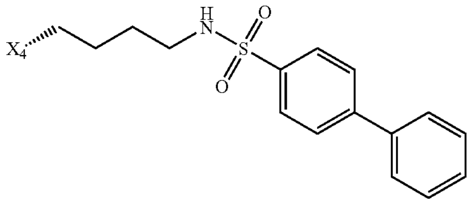 |

TABLE 20B-11
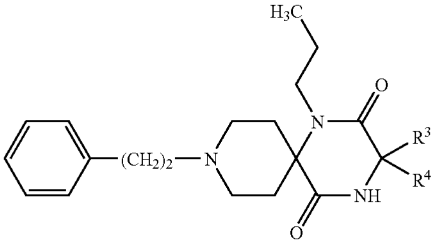
| Example No | $R^3$ | $R^4$ |
|---|---|---|
| 22(H20-66) | H | 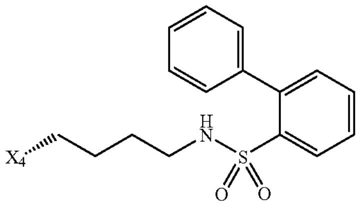 |
| 22(H20-67) | H | 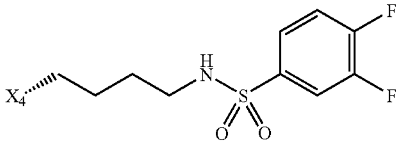 |
| 22(H20-68) | H | 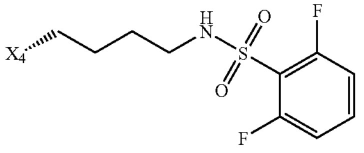 |
| 22(H20-69) | H | 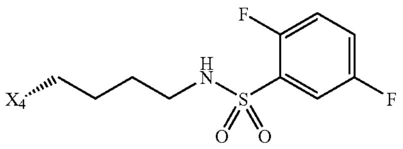 |
| 22(H20-70) | H | 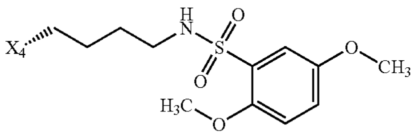 |
TABLE 20B-11-continued
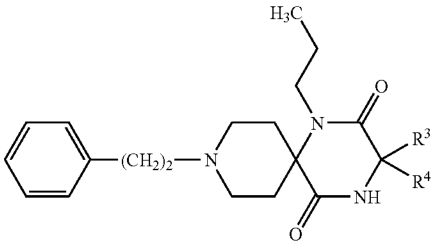
| Example No | $R^3$ | $R^4$ |
|---|---|---|
| 22(H20-71) | H | 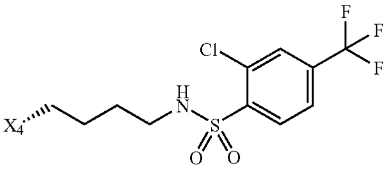 |
TABLE 20B-12
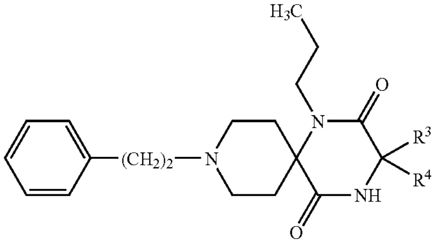
| Example No | $R^3$ | $R^4$ |
|---|---|---|
| 22(H20-72) | H | 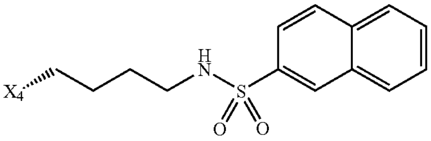 |
| 22(H20-73) | H | 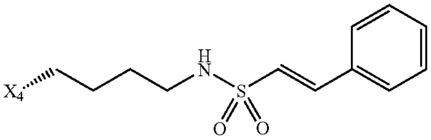 |
| 22(H20-74) | H | 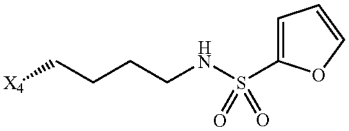 |
| 22(H20-75) | H | 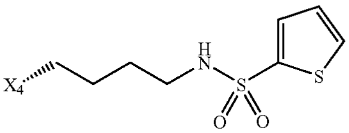 |

TABLE 21B-1
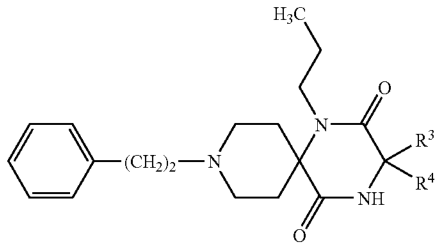
| Example No | $R^3$ | $R^4$ |
| --- | --- | --- |
| 22(H21-1) | H | 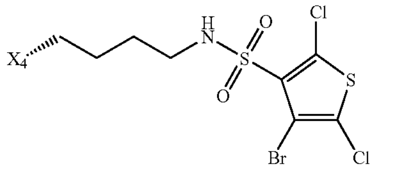 |
| 22(H21-2) | H | 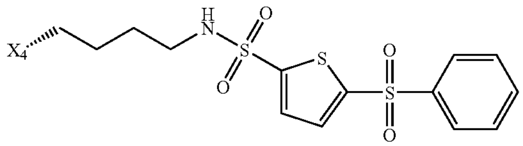 |
| 22(H21-3) | H | 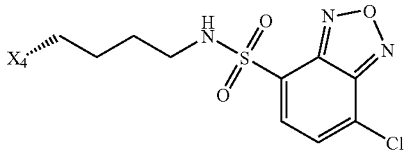 |
| 22(H21-4) | H | 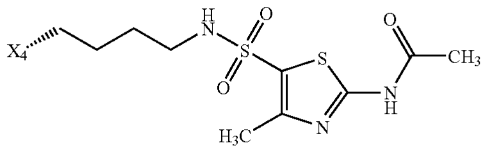 |
| 22(H21-5) | H | 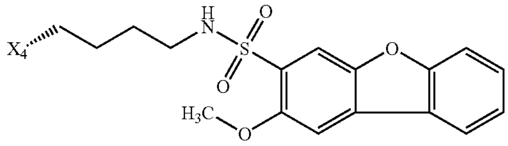 |
| 22(H21-6) | H | 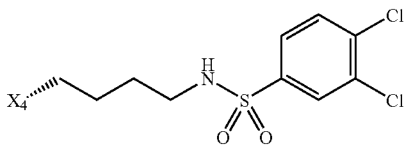 |
| 22(H21-7) | H | 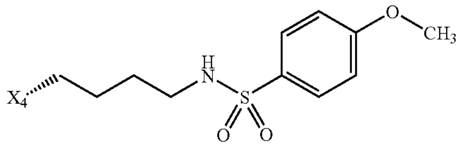 |

TABLE 21B-2
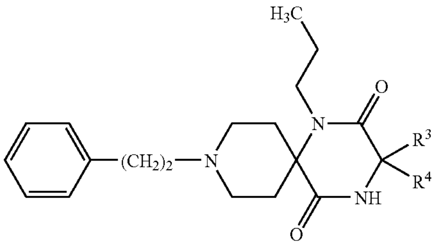
| Example No | $R^3$ | $R^4$ |
|---|---|---|
| 22(H21-8) | H | 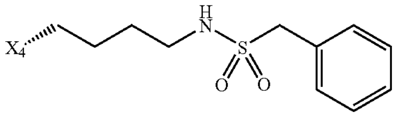 |
| 22(H21-9) | H | 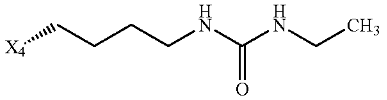 |
| 22(H21-10) | H | 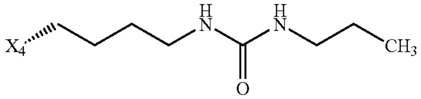 |
| 22(H21-11) | H | 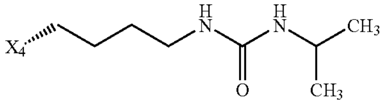 |
| 22(H21-12) | H | 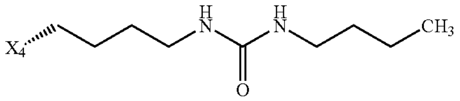 |
| 22(H21-13) | H | 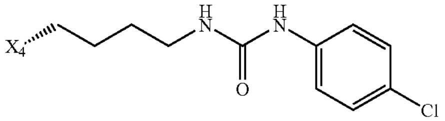 |
| 22(H21-14) | H | 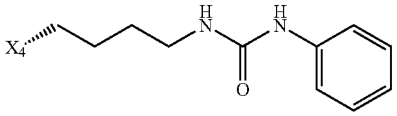 |
| 22(H21-15) | H | 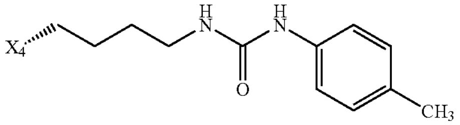 |

TABLE 21B-3
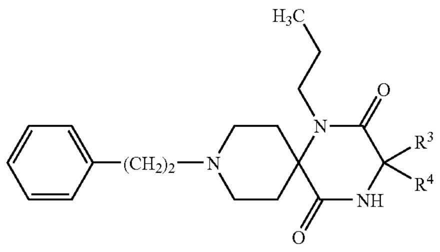
| Example No | $R^3$ | $R^4$ |
|---|---|---|
| 22(H21-16) | H | 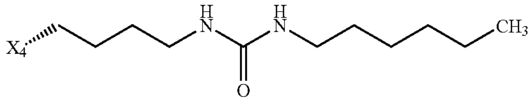 |
| 22(H21-17) | H | 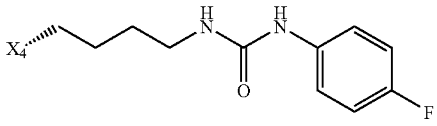 |
| 22(H21-18) | H | 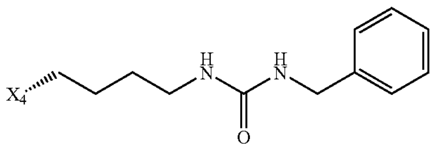 |
| 22(H21-19) | H | 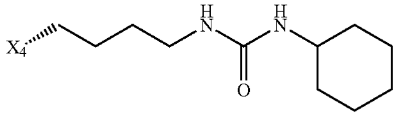 |
| 22(H21-20) | H | 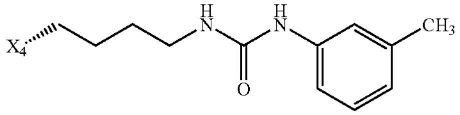 |
| 22(H21-21) | H | 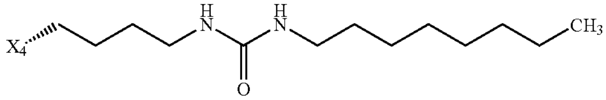 |
| 22(H21-22) | H | 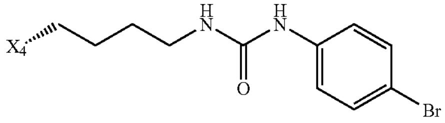 |
| 22(H21-23) | H | 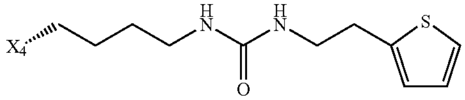 |

TABLE 21B-4
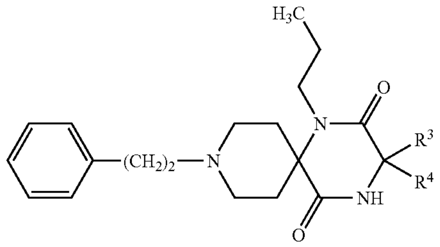
| Example No | $R^3$ | $R^4$ |
|---|---|---|
| 22(H21-24) | H | 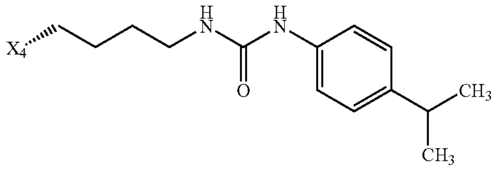 |
| 22(H21-25) | H | 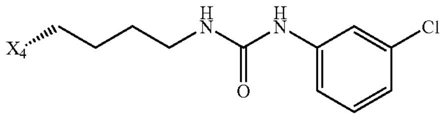 |
| 22(H21-26) | H | 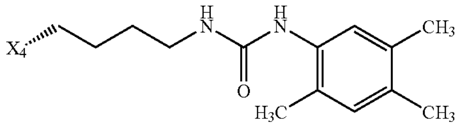 |
| 22(H21-27) | H | 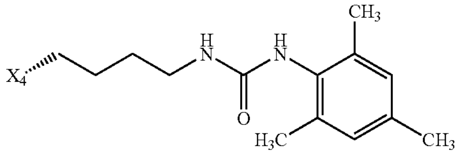 |
| 22(H21-28) | H | 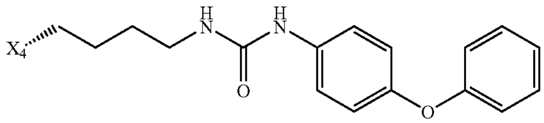 |
| 22(H21-29) | H | 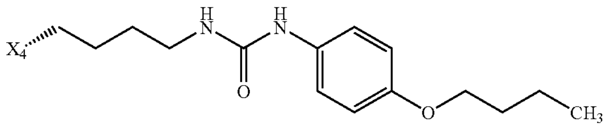 |
| 22(H21-30) | H | 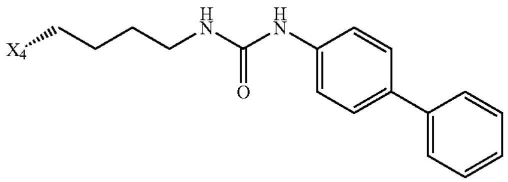 |

TABLE 21B-5
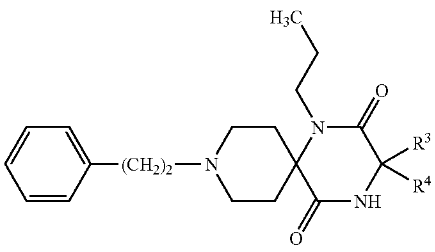
| Example No | $R^3$ | $R^4$ |
|---|---|---|
| 22(H21-31) | H | 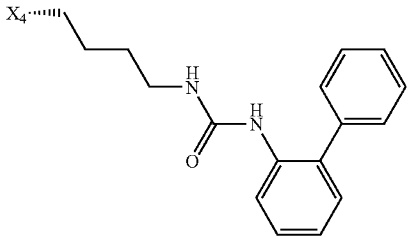 |
| 22(H21-32) | H | 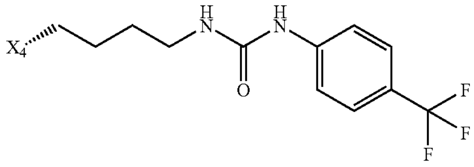 |
| 22(H21-33) | H | 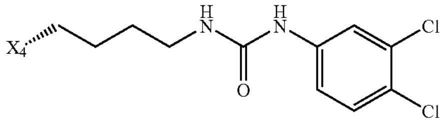 |
| 22(H21-34) | H | 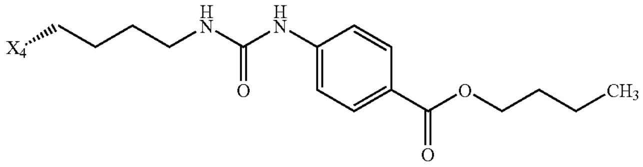 |
| 22(H21-35) | H | 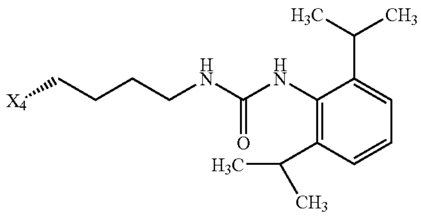 |
| 22(H21-36) | H | 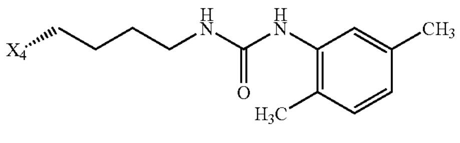 |

TABLE 21B-6
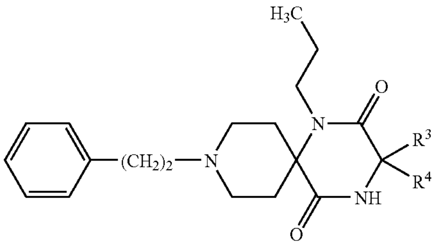
| Example No | $R^3$ | $R^4$ |
| --- | --- | --- |
| 22(H21-37) | H | 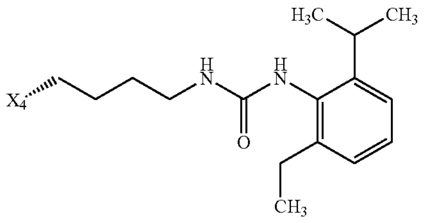 |
| 22(H21-38) | H | 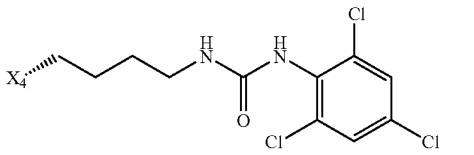 |
| 22(H21-39) | H | 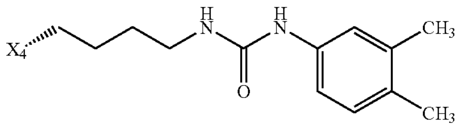 |
| 22(H21-40) | H | 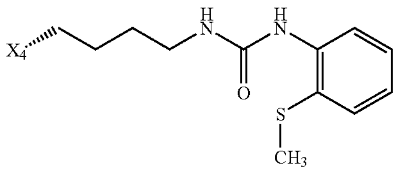 |
| 22(H21-41) | H | 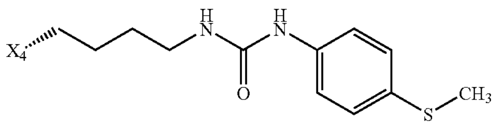 |
| 22(H21-42) | H | 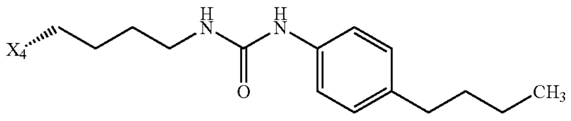 |

TABLE 21B-7
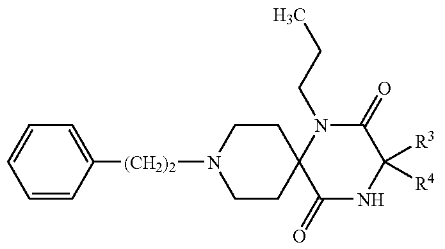
| Example No | $R^3$ | $R^4$ |
| --- | --- | --- |
| 22(H21-43) | H | 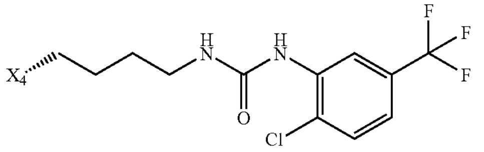 |
| 22(H21-44) | H | 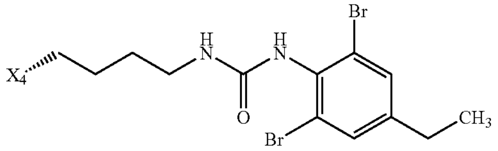 |
| 22(H21-45) | H | 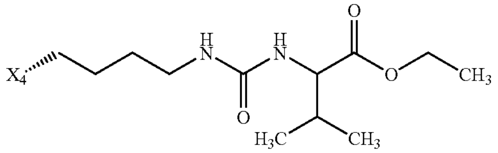 |
| 22(H21-46) | H | 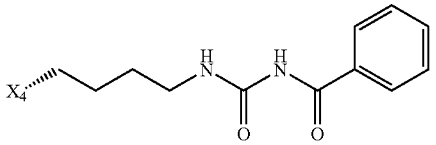 |
| 22(H21-47) | H | 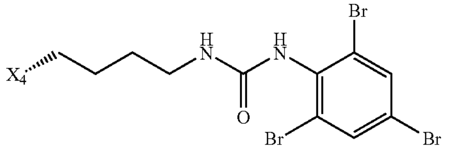 |
| 22(H21-48) | H | 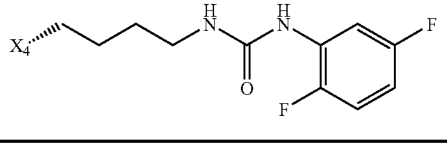 |

TABLE 21B-8
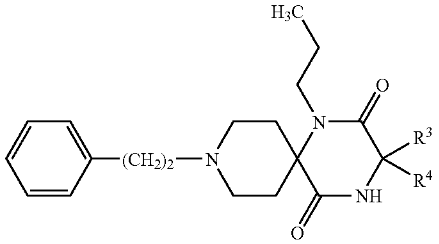
| Example No | $R^3$ | $R^4$ |
| --- | --- | --- |
| 22(H21-49) | H | 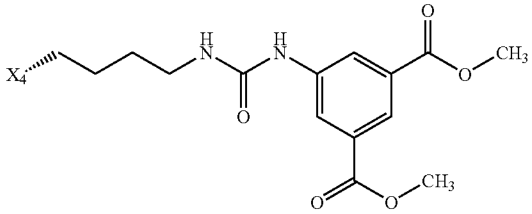 |
| 22(H21-50) | H | 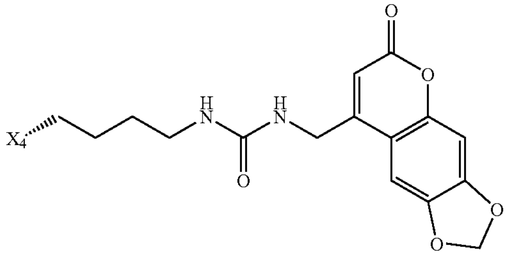 |
| 22(H21-51) | H | 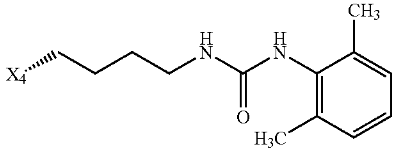 |
| 22(H21-52) | H | 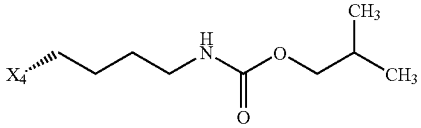 |
| 22(H21-53) | H | 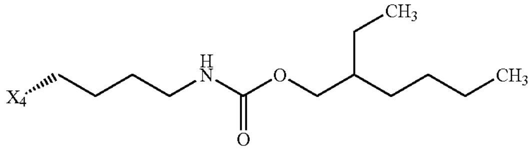 |
| 22(H21-54) | H | 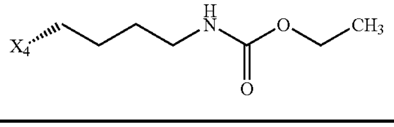 |

TABLE 21B-9
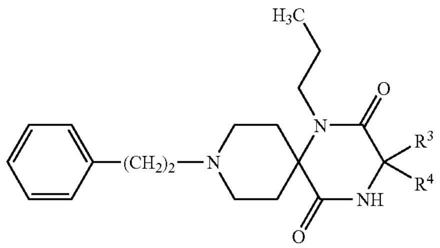
| Example No | $R^3$ | $R^4$ |
|---|---|---|
| 22(H21-55) | H | 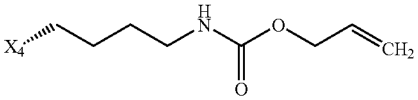 |
| 22(H21-56) | H | 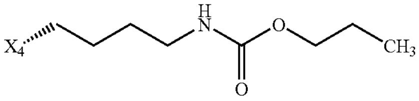 |
| 22(H21-57) | H | 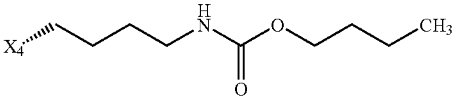 |
| 22(H21-58) | H | 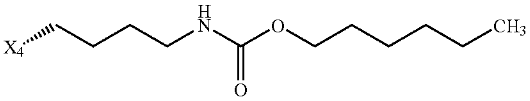 |
| 22(H21-59) | H | 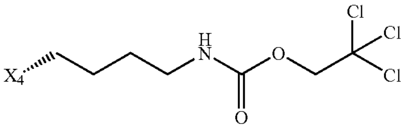 |
| 22(H21-60) | H | 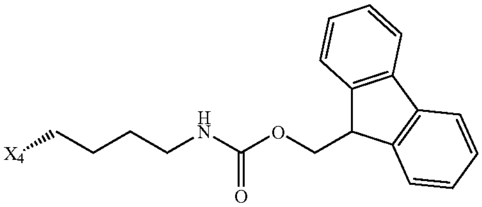 |
| 22(H21-61) | H | 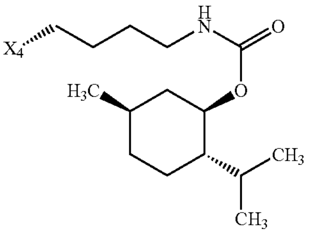 |

TABLE 21B-10
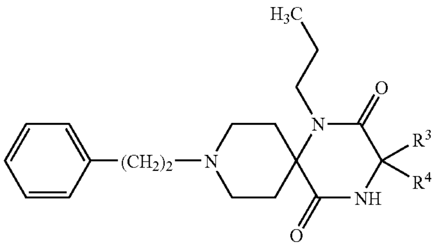
| Example No | $R^3$ | $R^4$ |
|---|---|---|
| 22(H21-62) | H | 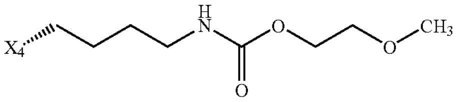 |
| 22(H21-63) | H | 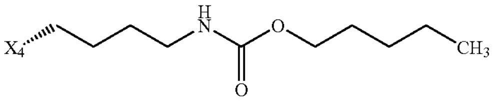 |
| 22(H21-64) | H | 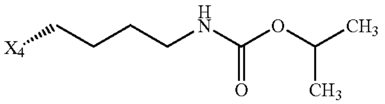 |
| 22(H21-65) | H | 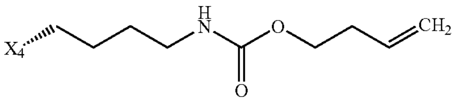 |
| 22(H21-66) | H | 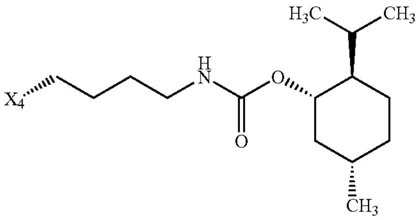 |
| 22(H21-67) | H | 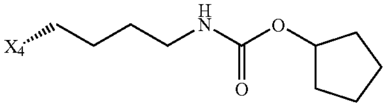 |
| 22(H21-68) | H | 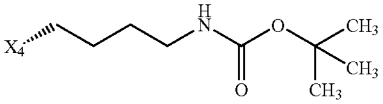 |

TABLE 21B-11

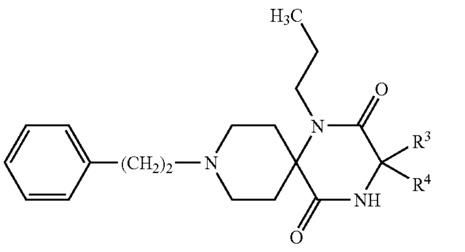

| Example No | $R^3$ | $R^4$ |
|---|---|---|
| 22(H21-69) | H | 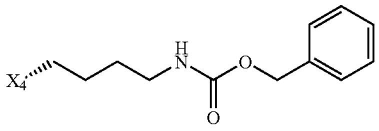 |
| 22(H21-70) | H | 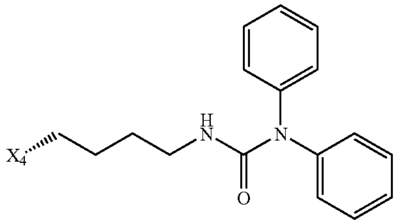 |
| 22(H21-71) | H | 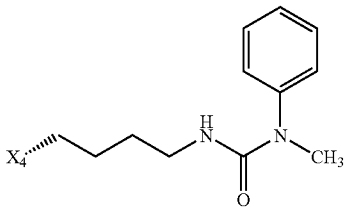 |
| 22(H21-72) | H | 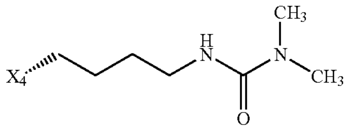 |
| 22(H21-73) | H | 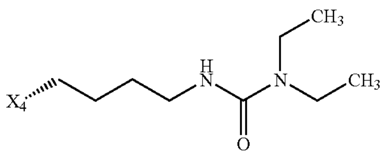 |
| 22(H21-74) | H | 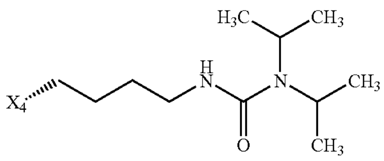 |

TABLE 21B-12

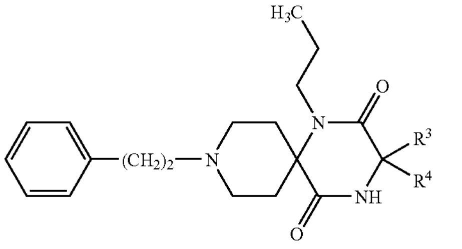

| Example No | $R^3$ | $R^4$ |
|---|---|---|
| 22(H21-75) | H | 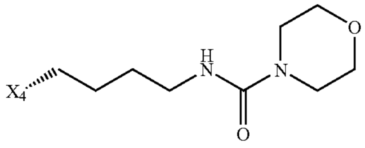 |
| 22(H21-76) | H | 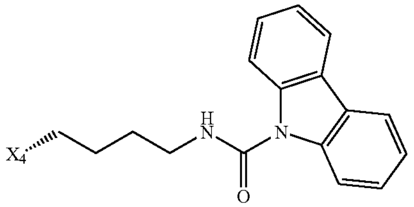 |
| 22(H21-77) | H | 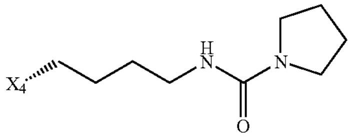 |

TABLE 20C-1

| Example No | HPLC condition | Retention time (min) | Mass data | Mass condition |
|---|---|---|---|---|
| 22(H20-1) | F | 3.43 | 581 $(M + H)^+$. | ESI (Pos., 20 V) |
| 22(H20-2) | F | 3.43 | 581 $(M + H)^+$. | ESI (Pos., 20 V) |
| 22(H20-3) | F | 3.09 | 548 $(M + H)^+$. | ESI (Pos., 20 V) |
| 22(H20-4) | F | 3.32 | 620 $(M + H)^+$. | ESI (Pos., 20 V) |
| 22(H20-5) | F | 3.24 | 523 $(M + H)^+$. | ESI (Pos., 20 V) |
| 22(H20-6) | F | 3.23 | 523 $(M + H)^+$. | ESI (Pos., 20 V) |
| 22(H20-7) | F | 3.20 | 523 $(M + H)^+$. | ESI (Pos., 20 V) |
| 22(H20-8) | F | 3.17 | 497 $(M + H)^+$. | ESI (Pos., 20 V) |
| 22(H20-9) | F | 3.26 | 519 $(M + H)^+$. | ESI (Pos., 20 V) |
| 22(H20-10) | F | 3.20 | 535 $(M + H)^+$. | ESI (Pos., 20 V) |
| 22(H20-11) | F | 3.16 | 485 $(M + H)^+$. | ESI (Pos., 20 V) |
| 22(H20-12) | F | 2.95 | 506 $(M + H)^+$. | ESI (Pos., 20 V) |
| 22(H20-13) | F | 3.11 | 506 $(M + H)^+$. | ESI (Pos., 20 V) |
| 22(H20-14) | F | 3.20 | 519 $(M + H)^+$. | ESI (Pos., 20 V) |
| 22(H20-15) | F | 3.25 | 535 $(M + H)^+$. | ESI (Pos., 20 V) |
| 22(H20-16) | F | 3.05 | 569 $(M + H)^+$. | ESI (Pos., 20 V) |
| 22(H20-17) | F | 3.25 | 614 $(M + H)^+$. | ESI (Pos., 20 V) |
| 22(H20-18) | F | 3.31 | 598 $(M + H)^+$. | ESI (Pos., 20 V) |
| 22(H20-19) | F | 3.23 | 535 $(M + H)^+$. | ESI (Pos., 20 V) |
| 22(H20-20) | F | 3.17 | 525 $(M + H)^+$. | ESI (Pos., 20 V) |
| 22(H20-21) | F | 3.24 | 499 $(M + H)^+$. | ESI (Pos., 20 V) |
| 22(H20-22) | F | 3.25 | 519 $(M + H)^+$. | ESI (Pos., 20 V) |
| 22(H20-23) | F | 3.06 | 471 $(M + H)^+$. | ESI (Pos., 20 V) |
| 22(H20-24) | F | 3.33 | 525 $(M + H)^+$. | ESI (Pos., 20 V) |
| 22(H20-25) | F | 3.28 | 531 $(M + H)^+$. | ESI (Pos., 20 V) |
| 22(H20-26) | F | 3.20 | 519 $(M + H)^+$. | ESI (Pos., 20 V) |

TABLE 20C-2

| Example No | HPLC condition | Retention time (min) | Mass data | Mass condition |
|---|---|---|---|---|
| 22(H20-27) | F | 3.20 | 499 (M + H)+. | ESI (Pos., 20 V) |
| 22(H20-28) | F | 3.23 | 511 (M + H)+. | ESI (Pos., 20 V) |
| 22(H20-29) | F | 3.18 | 505 (M + H)+. | ESI (Pos., 20 V) |
| 22(H20-30) | F | 3.16 | 511 (M + H)+. | ESI (Pos., 20 V) |
| 22(H20-31) | F | 3.36 | 551 (M + H)+. | ESI (Pos., 20 V) |
| 22(H20-32) | F | 3.27 | 586 (M + H)+. | ESI (Pos., 20 V) |
| 22(H20-33) | F | 3.42 | 586 (M + H)+. | ESI (Pos., 20 V) |
| 22(H20-34) | F | 3.20 | 549 (M + H)+. | ESI (Pos., 20 V) |
| 22(H20-35) | F | 3.20 | 535 (M + H)+. | ESI (Pos., 20 V) |
| 22(H20-36) | F | 3.09 | 495 (M + H)+. | ESI (Pos., 20 V) |
| 22(H20-37) | F | 3.27 | 549 (M + H)+. | ESI (Pos., 20 V) |
| 22(H20-38) | F | 3.11 | 483 (M + H)+. | ESI (Pos., 20 V) |
| 22(H20-39) | F | 3.20 | 549 (M + H)+. | ESI (Pos., 20 V) |
| 22(H20-40) | F | 2.96 | 443 (M + H)+. | ESI (Pos., 20 V) |
| 22(H20-41) | F | 3.22 | 499 (M + H)+. | ESI (Pos., 20 V) |
| 22(H20-42) | F | 3.00 | 473 (M + H)+. | ESI (Pos., 20 V) |
| 22(H20-43) | F | 3.07 | 503 (M + H)+. | ESI (Pos., 20 V) |
| 22(H20-44) | F | 3.23 | 511 (M + H)+. | ESI (Pos., 20 V) |
| 22(H20-45) | F | 3.16 | 485 (M + H)+. | ESI (Pos., 20 V) |
| 22(H20-46) | F | 3.12 | 485 (M + H)+. | ESI (Pos., 20 V) |
| 22(H20-47) | F | 3.27 | 551 (M + H)+. | ESI (Pos., 20 V) |
| 22(H20-48) | F | 3.11 | 527 (M + H)+. | ESI (Pos., 20 V) |
| 22(H20-49) | F | 3.20 | 530 (M + H)+. | ESI (Pos., 20 V) |
| 22(H20-50) | F | 3.07 | 471 (M + H)+. | ESI (Pos., 20 V) |
| 22(H20-51) | F | 3.01 | 457 (M + H)+. | ESI (Pos., 20 V) |
| 22(H20-52) | F | 3.07 | 469 (M + H)+. | ESI (Pos., 20 V) |

TABLE 20C-3

| Example No | HPLC condition | Retention time (min) | Mass data | Mass condition |
|---|---|---|---|---|
| 22(H20-53) | F | 3.18 | 549 (M + H)+. | ESI (Pos., 20 V) |
| 22(H20-54) | F | 3.34 | 613 (M + H)+. | ESI (Pos., 20 V) |
| 22(H20-55) | F | 3.49 | 565 (M + H)+. | ESI (Pos., 20 V) |
| 22(H20-56) | F | 3.22 | 565 (M + H)+. | ESI (Pos., 20 V) |
| 22(H20-57) | F | 3.03 | 479 (M + H)+. | ESI (Pos., 20 V) |
| 22(H20-58) | F | 3.34 | 535 (M + H)+. | ESI (Pos., 20 V) |
| 22(H20-59) | F | 3.14 | 507 (M + H)+. | ESI (Pos., 20 V) |
| 22(H20-60) | F | 3.40 | 575 (M + H)+. | ESI (Pos., 20 V) |
| 22(H20-61) | F | 3.38 | 667 (M + H)+. | ESI (Pos., 20 V) |
| 22(H20-62) | F | 3.35 | 586 (M + H)+. | ESI (Pos., 20 V) |
| 22(H20-63) | F | 3.22 | 619 (M + H)+. | ESI (Pos., 20 V) |
| 22(H20-64) | F | 3.45 | 609 (M + H)+. | ESI (Pos., 20 V) |
| 22(H20-65) | F | 3.51 | 617 (M + H)+. | ESI (Pos., 20 V) |
| 22(H20-66) | F | 3.49 | 617 (M + H)+. | ESI (Pos., 20 V) |
| 22(H20-67) | F | 3.38 | 557 (M + H)+. | ESI (Pos., 20 V) |
| 22(H20-68) | F | 3.29 | 577 (M + H)+. | ESI (Pos., 20 V) |
| 22(H20-69) | F | 3.33 | 577 (M + H)+. | ESI (Pos., 20 V) |
| 22(H20-70) | F | 3.29 | 601 (M + H)+. | ESI (Pos., 20 V) |
| 22(H20-71) | F | 3.51 | 643 (M + H)+. | ESI (Pos., 20 V) |
| 22(H20-72) | F | 3.42 | 591 (M + H)+. | ESI (Pos., 20 V) |
| 22(H20-73) | F | 3.39 | 567 (M + H)+. | ESI (Pos., 20 V) |
| 22(H20-74) | F | 3.22 | 531 (M + H)+. | ESI (Pos., 20 V) |
| 22(H20-75) | F | 3.23 | 547 (M + H)+. | ESI (Pos., 20 V) |

TABLE 21C-1

| Example No | HPLC condition | Retention time (min) | Mass data | Mass condition |
|---|---|---|---|---|
| 22(H21-1) | F | 3.51 | 694 (M + H)+. | ESI (Pos., 20 V) |
| 22(H21-2) | F | 3.45 | 687 (M + H)+. | ESI (Pos., 20 V) |
| 22(H21-3) | F | 3.40 | 617 (M + H)+. | ESI (Pos., 20 V) |

TABLE 21C-1-continued

| Example No | HPLC condition | Retention time (min) | Mass data | Mass condition |
|---|---|---|---|---|
| 22(H21-4) | F | 3.17 | 619 (M + H)+. | ESI (Pos., 20 V) |
| 22(H21-5) | F | 3.52 | 661 (M + H)+. | ESI (Pos., 20 V) |
| 22(H21-6) | F | 3.47 | 609 (M + H)+. | ESI (Pos., 20 V) |
| 22(H21-7) | F | 3.28 | 571 (M + H)+. | ESI (Pos., 20 V) |
| 22(H21-8) | F | 3.29 | 555 (M + H)+. | ESI (Pos., 20 V) |
| 22(H21-9) | F | 3.03 | 472 (M + H)+. | ESI (Pos., 20 V) |
| 22(H21-10) | F | 3.09 | 486 (M + H)+. | ESI (Pos., 20 V) |
| 22(H21-11) | F | 3.07 | 486 (M + H)+. | ESI (Pos., 20 V) |
| 22(H21-12) | F | 3.16 | 500 (M + H)+. | ESI (Pos., 20 V) |
| 22(H21-13) | F | 3.33 | 554 (M + H)+. | ESI (Pos., 20 V) |
| 22(H21-14) | F | 3.22 | 520 (M + H)+. | ESI (Pos., 20 V) |
| 22(H21-15) | F | 3.27 | 534 (M + H)+. | ESI (Pos., 20 V) |
| 22(H21-16) | F | 3.34 | 528 (M + H)+. | ESI (Pos., 20 V) |
| 22(H21-17) | F | 3.25 | 538 (M + H)+. | ESI (Pos., 20 V) |
| 22(H21-18) | F | 3.22 | 534 (M + H)+. | ESI (Pos., 20 V) |
| 22(H21-19) | F | 3.25 | 526 (M + H)+. | ESI (Pos., 20 V) |
| 22(H21-20) | F | 3.29 | 534 (M + H)+. | ESI (Pos., 20 V) |
| 22(H21-21) | F | 3.52 | 556 (M + H)+. | ESI (Pos., 20 V) |
| 22(H21-22) | F | 3.37 | 600 (M + H)+. | ESI (Pos., 20 V) |
| 22(H21-23) | F | 3.24 | 554 (M + H)+. | ESI (Pos., 20 V) |
| 22(H21-24) | F | 3.44 | 562 (M + H)+. | ESI (Pos., 20 V) |
| 22(H21-25) | F | 3.34 | 554 (M + H)+. | ESI (Pos., 20 V) |
| 22(H21-26) | F | 3.36 | 562 (M + H)+. | ESI (Pos., 20 V) |

TABLE 21C-2

| Example No | HPLC condition | Retention time (min) | Mass data | Mass condition |
|---|---|---|---|---|
| 22(H21-27) | F | 3.31 | 562(M + H)+. | ESI (Pos., 20 V) |
| 22(H21-28) | F | 3.47 | 612(M + H)+. | ESI (Pos., 20 V) |
| 22(H21-29) | F | 3.47 | 592(M + H)+. | ESI (Pos., 20 V) |
| 22(H21-30) | F | 3.47 | 596(M + H)+. | ESI (Pos., 20 V) |
| 22(H21-31) | F | 3.40 | 596(M + H)+. | ESI (Pos., 20 V) |
| 22(H21-32) | F | 3.42 | 588(M + H)+. | ESI (Pos., 20 V) |
| 22(H21-33) | F | 3.44 | 588(M + H)+. | ESI (Pos., 20 V) |
| 22(H21-34) | F | 3.49 | 620(M + H)+. | ESI (Pos., 20 V) |
| 22(H21-35) | F | 3.47 | 604(M + H)+. | ESI (Pos., 20 V) |
| 22(H21-36) | F | 3.31 | 548(M + H)+. | ESI (Pos., 20 V) |
| 22(H21-37) | F | 3.42 | 590(M + H)+. | ESI (Pos., 20 V) |
| 22(H21-38) | F | 3.36 | 623(M + H)+. | ESI (Pos., 20 V) |
| 22(H21-39) | F | 3.33 | 548(M + H)+. | ESI (Pos., 20 V) |
| 22(H21-40) | F | 3.29 | 566(M + H)+. | ESI (Pos., 20 V) |
| 22(H21-41) | F | 3.31 | 566(M + H)+. | ESI (Pos., 20 V) |
| 22(H21-42) | F | 3.53 | 576(M + H)+. | ESI (Pos., 20 V) |
| 22(H21-43) | F | 3.49 | 622(M + H)+. | ESI (Pos., 20 V) |
| 22(H21-44) | F | 3.42 | 706(M + H)+. | ESI (Pos., 20 V) |
| 22(H21-45) | F | 3.25 | 572(M + H)+. | ESI (Pos., 20 V) |
| 22(H21-46) | F | 3.23 | 548(M + H)+. | ESI (Pos., 20 V) |
| 22(H21-47) | F | 3.40 | 757(M + H)+. | ESI (Pos., 20 V) |
| 22(H21-48) | F | 3.33 | 556(M + H)+. | ESI (Pos., 20 V) |
| 22(H21-49) | F | 3.33 | 636(M + H)+. | ESI (Pos., 20 V) |
| 22(H21-50) | F | 3.18 | 646(M + H)+. | ESI (Pos., 20 V) |
| 22(H21-51) | F | 3.23 | 548(M + H)+. | ESI (Pos., 20 V) |
| 22(H21-52) | F | 3.30 | 501(M + H)+. | ESI (Pos., 20 V) |

TABLE 21C-3

| Example No | HPLC condition | Retention time (min) | Mass data | Mass condition |
|---|---|---|---|---|
| 22(H21-53) | F | 3.64 | 557 (M + H)+. | ESI (Pos., 20 V) |
| 22(H21-54) | F | 3.13 | 473 (M + H)+. | ESI (Pos., 20 V) |
| 22(H21-55) | F | 3.20 | 485 (M + H)+. | ESI (Pos., 20 V) |

TABLE 21C-3-continued

| Example No | HPLC condition | Retention time (min) | Mass data | Mass condition |
|---|---|---|---|---|
| 22(H21-56) | F | 3.21 | 487 (M + H)+. | ESI (Pos., 20 V) |
| 22(H21-57) | F | 3.31 | 501 (M + H)+. | ESI (Pos., 20 V) |
| 22(H21-58) | F | 3.49 | 529 (M + H)+. | ESI (Pos., 20 V) |
| 22(H21-59) | F | 3.38 | 575 (M + H)+. | ESI (Pos., 20 V) |
| 22(H21-60) | F | 3.57 | 623 (M + H)+. | ESI (Pos., 20 V) |
| 22(H21-61) | F | 3.69 | 583 (M + H)+. | ESI (Pos., 20 V) |
| 22(H21-62) | F | 3.09 | 503 (M + H)+. | ESI (Pos., 20 V) |
| 22(H21-63) | F | 3.40 | 515 (M + H)+. | ESI (Pos., 20 V) |
| 22(H21-64) | F | 3.22 | 487 (M + H)+. | ESI (Pos., 20 V) |
| 22(H21-65) | F | 3.25 | 499 (M + H)+. | ESI (Pos., 20 V) |
| 22(H21-66) | F | 3.69 | 583 (M + H)+. | ESI (Pos., 20 V) |
| 22(H21-67) | F | 3.31 | 513 (M + H)+. | ESI (Pos., 20 V) |
| 22(H21-68) | F | 3.28 | 501 (M + H)+. | ESI (Pos., 20 V) |
| 22(H21-69) | F | 3.34 | 535 (M + H)+. | ESI (Pos., 20 V) |
| 22(H21-70) | F | 3.40 | 596 (M + H)+. | ESI (Pos., 20 V) |
| 22(H21-71) | F | 3.23 | 534 (M + H)+. | ESI (Pos., 20 V) |
| 22(H21-72) | F | 3.01 | 472 (M + H)+. | ESI (Pos., 20 V) |
| 22(H21-73) | F | 3.12 | 500 (M + H)+. | ESI (Pos., 20 V) |
| 22(H21-74) | F | 3.27 | 528 (M + H)+. | ESI (Pos., 20 V) |
| 22(H21-75) | F | 3.01 | 514 (M + H)+. | ESI (Pos., 20 V) |
| 22(H21-76) | F | 3.49 | 574 (M + H)+. | ESI (Pos., 20 V) |
| 22(H21-77) | F | 3.07 | 498 (M + H)+. | ESI (Pos., 20 V) |

EXAMPLE 23

1-cyclopropylmethyl-2,5-dioxo-3-(2-methylpropyl)-9-(4-phenoxyphenyl)-1,3,9-triazaspiro[5.5]undecane.acetate

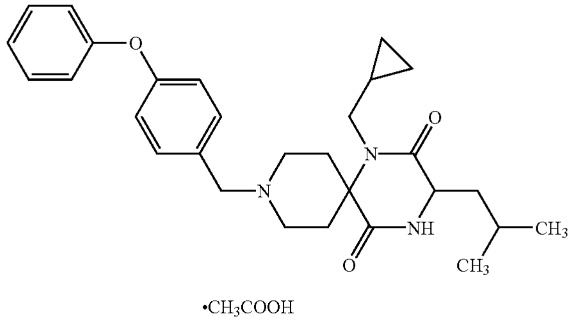

To a suspension of Resin (3) prepared in Reference Example 2 (0.5 g) in tetrahydrofuran/methanol (1:1; 5 ml) were added N-allyloxycarbonyl-4-piperidone (0.396 g), cyclopropylmethylamine (0.189 ml) and N-(t-butyloxycarbonyl)leucine (0.542 g), and it was stirred for 18 hours at 65° C. The reaction solution was cooled to room temperature and the resin was collected by filtration. The obtained resin was washed with dimethylformamide (5 ml×2), dichloromethane (5 ml×2), methanol (5 ml×2) and dichloromethane (5 ml×2). To a suspension of the obtained resin in dichloromethane (5 ml) were added acetic acid (0.149 ml), tributyltin hydride (0.351 ml) and tetrakis(triphenylphosphine)palladium (0) complex (50 mg), and it was stirred for 6 hours at room temperature. The resin was collected by filtration from the reaction solution, and was washed with dichloromethane (5 ml×4) and dimethylformamide (5 ml×3). The obtained resin was suspended in 1% acetic acid-dimethylformamide solution (5 ml), and 4-phenyloxybenzaldehyde (0.252 g), and sodium triacetoxyborohydride (0.277 g) were added thereto. It was stirred for 15 hours at room temperature. The resin was collected by filtration from reaction mixture, and was washed with methanol (5 ml×1), dimethylformamide (5 ml×3), methanol (5 ml×4) and dichloromethane (5 ml×4). The obtained resin was suspended in 50% trifluoroacetic acid-dichloromethane solution (5 ml), and it was stirred for 5 minutes at room temperature. The reaction solution was filtrated, and the obtained resin was suspended in 50% trifluoroacetic acid-dichloromethane solution (5 ml), and it was stirred for 30 minutes at room temperature. The obtained resin by filtration from the reaction solution was washed with dichloromethane (5 ml×3) and 1.25M acetic acid-toluene solution (5 ml×3). The obtained resin was suspended in 1.25M acetic acid-toluene solution (5 ml), and it was stirred for 23 hours at 90° C. The reaction solution was filtrated. The obtained resin was washed with chloroform-methanol (1:1; 2 ml×2). The filtrate and the washings were concentrated to give the compound of the present invention (274 mg) having the following physical data.

TLC: Rf 0.40 (chloroform:methanol=20:1);

NMR ($CD_3OD$): δ 7.49 (m, 2H), 7.40 (m, 2H), 7.18 (m, 2H), 7.04 (m, 3H), 4.33 (s, 2H), 4.04 (dd, J=8.1, 4.8 Hz, 1H), 3.78 (m, 2H), 3.52 (m, 2H), 3.35 (m, 2H), 2.45–2.10 (m, 4H), 1.98 (s, 3H, $CH_3COOH$), 1.97–1.58 (m, 4H), 0.94 (d, J=6.0 Hz, 6H), 0.51 (m, 2H), 0.36 (m, 2H).

EXAMPLE 23(1)

1-(thiophen-2-ylmethyl)-2,5-dioxo-3-(2-methylpropyl)-9-(4-phenoxyphenyl)-1,3,9-triazaspiro[5.5]undecane.acetate

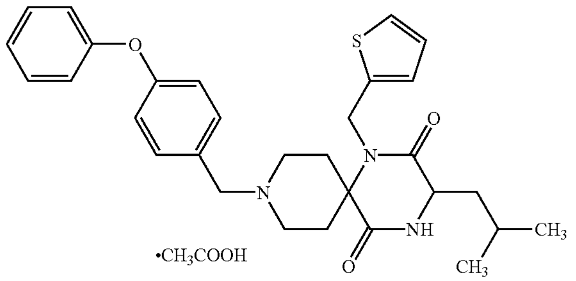

By the same procedure as described in Example 23 using Resin (3) prepared in Reference Example 2 (0.5 g), N-allyloxycarbonyl-4-piperidone (0.396 g), thiophen-2-ylmethylamine (0.205 ml) and N-(t-butyloxycarbonyl)leucine (0.542 g), 4-phenoxybenzaldehyde (0.252 g), the compound of the present invention (274 mg) having the following physical data was obtained.

TLC: Rf 0.39 (chloroform:methanol=20:1);

NMR ($CD_3OD$): δ 7.48 (m, 2H), 7.39 (m, 2H), 7.28 (m, 1H), 7.18 (m, 2H), 7.04 (m, 4H), 6.91 (m, 1H), 4.86 (s, 2H), 4.32 (s, 2H), 4.12 (dd, J=8.1, 4.5 Hz, 1H), 3.77 (m, 2H), 3.49 (m, 2H), 2.60–2.30 (m, 2H), 2.19 (m, 2H), 1.98 (s, 3H), 1.97–1.58 (m, 3H), 0.94 (d, J=6.0 Hz, 6H).

EXAMPLE 23(H22-1)~23(H31-31)

By the same procedure as described in Example 23 or 23(1), using Resin (3) prepared in Reference Example 2, the corresponding 4-piperidone derivatives, the corresponding amine derivatives, the corresponding amino acid derivatives, and the corresponding aldehyde derivatives, the compounds of the present invention, whose names were shown in the following Table 22A-1~31A-4, and whose structures were shown in the following Table 22B-1~31B-5, were obtained. Also, physical data of the above compound were shown in the followings Table 22C-1~31C-2.

TABLE 22A-1

| Example No | Compound Name |
|---|---|
| 23(H22-1) | (3S)-1-propyl-2,5-dioxo-3-(2-methylpropyl)-9-(6-phenylhexyl)-1,4,9-triazaspiro[5.5]undecane |
| 23(H22-2) | (3R)-1-propyl-2,5-dioxo-3-(2-methylpropyl)-9-(6-phenylhexyl)-1,4,9-triazaspiro[5.5]undecane |
| 23(H22-3) | (3S)-1-propyl-2,5-dioxo-3-methyl-9-(6-phenylhexyl)-1,4,9-triazaspiro[5.5]undecane |
| 23(H22-4) | (3S)-1-propyl-2,5-dioxo-3-benzyl-9-(6-phenylhexyl)-1,4,9-triazaspiro[5.5]undecane |
| 23(H22-5) | (3S)-1-propyl-2,5-dioxo-3-(1-(benzyloxymethyl)imidazol-5-ylmethyl)-9-(6-phenylhexyl)-1,4,9-triazaspiro[5.5]undecane |
| 23(H22-6) | (3S)-1-propyl-2,5-dioxo-3-(benzyloxymethyl)-9-(6-phenylhexyl)-1,4,9-triazaspiro[5.5]undecane |
| 23(H22-7) | (3S)-1-propyl-2,5-dioxo-3-(4-methoxyphenylmethyl)-9-(6-phenylhexyl)-1,4,9-triazaspiro[5.5]undecane |
| 23(H22-8) | (3S)-1-propyl-2,5-dioxo-3-((1R)-1-(benzyloxy)ethyl)-9-(6-phenylhexyl)-1,4,9-triazaspiro[5.5]undecane |

TABLE 22A-2

| Example No | Compound Name |
|---|---|
| 23(H22-9) | (3S)-1-propyl-2,5-dioxo-3-(pyridin-3-ylmethyl)-9-(6-phenylnexyl)-1,4,9-triazaspiro[5.5]undecane |
| 23(H22-10) | (3S)-1-propyl-2,5-dioxo-3-butyl-9-(6-phenylhexyl)-1,4,9-triazaspiro[5.5]undecane |
| 23(H22-11) | (3S)-1-propyl-2,5-dioxo-3-(cyclohexyloxycarbonylmethyl)-9-(6-phenylhexyl)-1,4,9-triazaspiro[5.5]undecane |
| 23(H22-12) | (3S)-1-propyl-2,5-dioxo-3-(cyclohexylmethyl)-9-(6-phenylhexyl)-1,4,9-triazaspiro[5.5]undecane |
| 23(H22-13) | (3R)-1-propyl-2,5-dioxo-3-(cyclohexyloxycarbonylmethyl)-9-(6-phenylhexyl)-1,4,9-triazaspiro[5.5]undecane |
| 23(H22-14) | (3R)-1-propyl-2,5-dioxo-3-(2-(cyclohexyloxycarbonyl)ethyl)-9-(6-phenylhexyl)-1,4,9-triazaspiro[5.5]undecane |
| 23(H22-15) | (3R)-1-propyl-2,5-dioxo-3-(4-(benzyloxy)phenylmethyl)-9-(6-phenylhexyl)-1,4,9-triazaspiro[5.5]undecane |
| 23(H22-16) | (3S)-1-propyl-2,5-dioxo-3-hydroxymethyl-9-(6-phenylhexyl)-1,4,9-triazaspiro[5.5]undecane |

TABLE 22A-3

| Example No | Compound Name |
|---|---|
| 23(H22-17) | (3S)-1-propyl-2,5-dioxo-3-(4-(benzyloxy)phenylmethyl)-9-(6-phenylhexyl)-1,4,9-triazaspiro[5.5]undecane |
| 23(H22-18) | (3R)-1-propyl-2,5-dioxo-3-butyl-9-(6-phenylhexyl)-1,4,9-triazaspiro[5.5]undecane |
| 23(H22-19) | (3R)-1-propyl-2,5-dioxo-3-(cyclohexylmethyl)-9-(6-phenylhexyl)-1,4,9-triazaspiro[5.5]undecane |
| 23(H22-20) | (3R)-1-propyl-2,5-dioxo-3-((1S)-1-(benzyloxy)ethyl)-9-(6-phenylhexyl)-1,4,9-triazaspiro[5.5]undecane |
| 23(H22-21) | (3R)-1-propyl-2,5-dioxo-3-(benzyloxymethyl)-9-(6-phenylhexyl)-1,4,9-triazaspiro[5.5]undecane |
| 23(H22-22) | (3R)-1-propyl-2,5-dioxo-3-((4-methoxyphenylmethylthio)methyl)-9-(6-phenylhexyl)-1,4,9-triazaspiro[5.5]undecane |
| 23(H22-23) | (3R)-1-propyl-2,5-dioxo-3-(benzylthiomethyl)-9-(6-phenylhexyl)-1,4,9-triazaspiro[5.5]undecane |
| 23(H22-24) | (3S)-1-propyl-2,5-dioxo-9-(6-phenylhexyl)-1,4,9-triazaspiro[5.5]undecane |

TABLE 22A-4

| Example No | Compound Name |
|---|---|
| 23(H22-25) | (3S)-1-propyl-2,5-dioxo-3-(imidazol-4-ylmethyl)-9-(6-phenylhexyl)-1,4,9-triazaspiro[5.5]undecane |
| 23(H22-26) | (3S)-1-propyl-2,5-dioxo-3-hydroxymethyl-9-(6-phenylhexyl)-1,4,9-triazaspiro[5.5]undecane |
| 23(H22-27) | (3R)-1-propyl-2,5-dioxo-3-((3-nitropyridin-2-yl)disulfanylmethyl)-9-(6-phenylhexyl)-1,4,9-triazaspiro[5.5]undecane |
| 23(H22-28) | (3S)-1-propyl-2,5-dioxo-3-(1-benzylimidazol-4-ylmethyl)-9-(6-phenylhexyl)-1,4,9-triazaspiro[5.5]undecane |
| 23(H22-29) | (3R)-1-propyl-2,5-dioxo-3-(4-hydroxyphenylmethyl)-9-(6-phenylhexyl)-1,4,9-triazaspiro[5.5]undecane |
| 23(H22-30) | (3S)-1-propyl-2,5-dioxo-3-(4-(benzyloxycarbonylamino)phenylmethyl)-9-(6-phenylhexyl)-1,4,9-triazaspiro[5.5]undecane |
| 23(H22-31) | (3R)-1-propyl-2,5-dioxo-3-(3-(aminocarbonylamino)propyl)-9-(6-phenylhexyl)-1,4,9-triazaspiro[5.5]undecane |
| 23(H22-32) | (3R)-1-propyl-2,5-dioxo-3-(1-naphthylmethyl)-9-(6-phenylhexyl)-1,4,9-triazaspiro[5.5]undecane |

TABLE 22A-5

| Example No | Compound Name |
|---|---|
| 23(H22-33) | (3S)-1-propyl-2,5-dioxo-3-(3,4-dichlorophenylmethyl)-9-(6-phenylhexyl)-1,4,9-triazaspiro[5.5]undecane |
| 23(H22-34) | (3R)-1-propyl-2,5-dioxo-3-((1,1-dimethylethylthio)methyl)-9-(6-phenylhexyl)-1,4,9-triazaspiro[5.5]undecane |
| 23(H22-35) | (3S)-1-propyl-2,5-dioxo-3-(2-methylpropyl)-4-methyl-9-(6-phenylhexyl)-1,4,9-triazaspiro[5.5]undecane |
| 23(H22-36) | (3S)-1-propyl-2,5-dioxo-3-propyl-9-(6-phenylhexyl)-1,4,9-triazaspiro[5.5]undecane |
| 23(H22-37) | (3S)-1-propyl-2,5-dioxo-3-(4-benzyloxyphenylmethyl)-4-methyl-9-(6-phenylhexyl)-1,4,9-triazaspiro[5.5]undecane |
| 23(H22-38) | (3S)-1-propyl-2,5-dioxo-3-((1R)-1-hydroxyethyl)-9-(6-phenylhexyl)-1,4,9-triazaspiro[5.5]undecane |
| 23(H22-39) | (3S)-1-propyl-2,5-dioxo-3-(aminocarbonylmethyl)-9-(6-phenylhexyl)-1,4,9-triazaspiro[5.5]undecane |
| 23(H22-40) | (3S)-1-propyl-2,5-dioxo-3-((1R)-1-hydroxyethyl)-9-(6-phenylhexyl)-1,4,9-triazaspiro[5.5]undecane |
| 23(H22-41) | (3R)-1-propyl-2,5-dioxo-3-methyl-9-(6-phenylhexyl)-1,4,9-triazaspiro[5.5]undecane |

TABLE 22A-6

| Example No | Compound Name |
|---|---|
| 23(H22-42) | (3R)-1-propyl-2,5-dioxo-3-(pyridin-3-ylmethyl)-9-(6-phenylhexyl)-1,4,9-triazaspiro[5.5]undecane |
| 23(H22-43) | (3S)-1-propyl-2,5-dioxo-3-(carboxymethyl)-9-(6-phenylhexyl)-1,4,9-triazaspiro[5.5]undecane |
| 23(H22-44) | (3S)-1-propyl-2,5-dioxo-3-(4-hydroxyphenylmethyl)-9-(6-phenylhexyl)-1,4,9-triazaspiro[5.5]undecane |
| 23(H22-45) | (3S)-1-propyl-2,5-dioxo-3-(2-methylthioethyl)-9-(6-phenylnexyl)-1,4,9-triazaspiro[5.5]undecane |
| 23(H22-46) | (3R)-1-propyl-2,5-dioxo-3-((methylcarbonylamino)-methylthiomethyl)-9-(6-phenylhexyl)-1,4,9-triazaspiro[5.5]undecane |
| 23(H22-47) | (3R)-1-propyl-2,5-dioxo-3-((1S)-1-hydroxyethyl)-9-(6-phenylhexyl)-1,4,9-triazaspiro[5.5]undecane |
| 23(H22-48) | (3S)-1-propyl-2,5-dioxo-3-(2-chlorophenylmethyl)-9-(6-phenylhexyl)-1,4,9-triazaspiro[5.5]undecane |
| 23(H22-49) | (3S)-1-propyl-2,5-dioxo-3-(1-naphthylmethyl)-9-(6- |

TABLE 22A-6-continued

| Example No | Compound Name |
|---|---|
| | phenylhexyl)-1,4,9-triazaspiro[5.5]undecane |
| 23(H22-50) | (3S)-1-propyl-2,5-dioxo-3-(4-fluorophenylmethyl)-9-(6-phenylhexyl)-1,4,9-triazaspiro[5.5]undecane |

TABLE 22A-7

| Example No | Compound Name |
|---|---|
| 23(H22-51) | (3S)-1-propyl-2,5-dioxo-3-(cyanomethyl)-9-(6-phenylhexyl)-1,4,9-triazaspiro[5.5]undecane |
| 23(H22-52) | (3R)-1-propyl-2,5-dioxo-3-(indol-3-ylmethyl)-9-(6-phenylhexyl)-1,4,9-triazaspiro[5.5]undecane |
| 23(H22-53) | (3S)-1-propyl-2,5-dioxo-3-(4-(2-chlorophenylmethyloxycarbonylamino)-butyl)-9-(6-phenylhexyl)-1,4,9-triazaspiro[5.5]undecane |
| 23(H22-54) | (3R)-1-propyl-2,5-dioxo-3-(benzyloxycarbonylmethyl)-9-(6-phenylhexyl)-1,4,9-triazaspiro[5.5]undecane |
| 23(H22-55) | (3S)-1-propyl-2,5-dioxo-3-(3-(1-imino-1-(2,4,6-trimethylphenylsulfonylamino)-methylamino)propyl)-9-(6-phenylhexyl)-1,4,9-triazaspiro[5.5]undecane |
| 23(H22-56) | (3S)-1-propyl-2,5-dioxo-3-(benzyloxycarbonylmethyl)-9-(6-phenylhexyl)-1,4,9-triazaspiro[5.5]undecane |
| 23(H22-57) | (3S)-1-propyl-2,5-dioxo-3-(4-(benzyloxycarbonylamino)butyl)-9-(6-phenylhexyl)-1,4,9-triazaspiro[5.5]undecane |
| 23(H22-58) | (3R)-1-propyl-2,5-dioxo-3-(4-methoxyphenylmethyl)-9-(6-phenylhexyl)-1,4,9-triazaspiro[5.5]undecane |

TABLE 22A-8

| Example No | Compound Name |
|---|---|
| 23(H22-59) | (3R)-1-propyl-2,5-dioxo-3-(4-(benzyloxycarbonylamino)butyl)-9-(6-phenylhexyl)-1,4,9-triazaspiro[5.5]undecane |
| 23(H22-60) | (3S)-1-propyl-2,5-dioxo-3-(3-(benzyloxycarbonylamino)propyl)-9-(6-phenylhexyl)-1,4,9-triazaspiro[5.5]undecane |
| 23(H22-61) | (3R)-1-propyl-2,5-dioxo-3-(1-(benzyloxymethyl)imidazol-4-ylmethyl)-9-(6-phenylhexyl)-1,4,9-triazaspiro[5.5]undecane |
| 23(H22-62) | (3R)-1-propyl-2,5-dioxo-3-(4-ethoxyphenylmethyl)-9-(6-phenylhexyl)-1,4,9-triazaspiro[5.5]undecane |
| 23(H22-63) | (3S)-1-propyl-2,5-dioxo-3-(4-phenylphenylmethyl)-9-(6- |

TABLE 22A-8-continued

| Example No | Compound Name |
|---|---|
| | phenylhexyl)-1,4,9-triazaspiro[5.5]undecane |
| 23(H22-64) | (3S)-1-propyl-2,5-dioxo-3-(1,1-diphenylmethyl)-9-(6-phenylhexyl)-1,4,9-triazaspiro[5.5]undecane |

TABLE 23A-1

| Example No | Compound Name |
|---|---|
| 23(H23-1) | 1-butyl-2,5-dioxo-3-(2-methylpropyl)-9-(1,4-benzodioxan-6-ylmethyl)-1,4,9-triazaspiro[5.5]undecane |
| 23(H23-2) | 1-butyl-2,5-dioxo-3-(2-methylpropyl)-9-(4-methoxyphenylmethyl)-1,4,9-triazaspiro[5.5]undecane |
| 23(H23-3) | 1-butyl-2,5-dioxo-3-(2-methylpropyl)-9-(4-diethylaminophenylmethyl)-1,4,9-triazaspiro[5.5]undecane |
| 23(H23-4) | 1-butyl-2,5-dioxo-3-(2-methylpropyl)-9-(3,5-dimethyl-1-phenylpyrazol-4-ylmethyl)-1,4,9-triazaspiro[5.5]undecane |
| 23(H23-5) | 1-butyl-2,5-dioxo-3-(2-methylpropyl)-9-(4-benzyloxyphenylmethyl)-1,4,9-triazaspiro[5.5]undecane |
| 23(H23-6) | 1-butyl-2,5-dioxo-3-(2-methylpropyl)-9-(4-phenyloxyphenylmethyl)-1,4,9-triazaspiro[5.5]undecane |
| 23(H23-7) | 1-butyl-2,5-dioxo-3-(2-methylpropyl)-9-(4-allyloxyphenylmethyl)-1,4,9-triazaspiro[5.5]undecane |
| 23(H23-8) | 1-butyl-2,5-dioxo-3-(2-methylpropyl)-9-(dibenzofuran-2-ylmethyl)-1,4,9-triazaspiro[5.5]undecane |
| 23(H23-9) | 1-butyl-2,5-dioxo-3-(2-methylpropyl)-9-(2-phenylimidazol-4-ylmethyl)-1,4,9-triazaspiro[5.5]undecane |

TABLE 23A-2

| Example No | Compound Name |
|---|---|
| 23(H23-10) | 1-butyl-2,5-dioxo-3-cyclohexylmethyl-9-(1,4-benzodioxan-6-ylmethyl)-1,4,9-triazaspiro[5.5]undecane |
| 23(H23-11) | 1-butyl-2,5-dioxo-3-cyclohexylmethyl-9-(4-methoxyphenylmethyl)-1,4,9-triazaspiro[5.5]undecane |
| 23(H23-12) | 1-butyl-2,5-dioxo-3-cyclohexylmethyl-9-(4-diethylaminophenylmethyl)-1,4,9-triazaspiro[5.5]undecane |
| 23(H23-13) | 1-butyl-2,5-dioxo-3-cyclohexylmethyl-9-(3,5-dimethyl-1-phenylpyrazol-4-ylmethyl)-1,4,9-triazaspiro[5.5]undecane |
| 23(H23-14) | 1-butyl-2,5-dioxo-3-cyclohexylmethyl-9-(4-benzyloxyphenylmethyl)-1,4,9-triazaspiro[5.5]undecane |
| 23(H23-15) | 1-butyl-2,5-dioxo-3-cyclohexylmethyl-9-(4-phenyloxyphenylmethyl)-1,4,9-triazaspiro[5.5]undecane |
| 23(H23-16) | 1-butyl-2,5-dioxo-3-cyclohexylmethyl-9-(4-allyloxyphenylmethyl)-1,4,9-triazaspiro[5.5]undecane |

TABLE 23A-2-continued

| Example No | Compound Name |
|---|---|
| 23(H23-17) | 1-butyl-2,5-dioxo-3-cyclohexylmethyl-9-(dibenzofuran-2-ylmethyl)-1,4,9-triazaspiro[5.5]undecane |
| 23(H23-18) | 1-butyl-2,5-dioxo-3-cyclohexylmethyl-9-(2-phenylimidazol-4-ylmethyl)-1,4,9-triazaspiro[5.5]undecane |

TABLE 24A-1

| Example No | Compound Name |
|---|---|
| 23(H24-1) | 1-ethyl-2,5-dioxo-3-(2-methylpropyl)-9-(1,4-benzodioxan-6-ylmethyl)-1,4,9-triazaspiro[5.5]undecane |
| 23(H24-2) | 1-ethyl-2,5-dioxo-3-(2-methylpropyl)-9-(3,5-dimethyl-1-phenylpyrazol-4-ylmethyl)-1,4,9-triazaspiro[5.5]undecane |
| 23(H24-3) | 1-ethyl-2,5-dioxo-3-(2-methylpropyl)-9-(5-methylfuran-2-ylmethyl)-1,4,9-triazaspiro[5.5]undecane |
| 23(H24-4) | 1-ethyl-2,5-dioxo-3-(2-methylpropyl)-9-(5-bromothiophen-2-ylmethyl)-1,4,9-triazaspiro[5.5]undecane |
| 23(H24-5) | 1-ethyl-2,5-dioxo-3-(2-methylpropyl)-9-(3-methylthiophen-2-ylmethyl)-1,4,9-triazaspiro[5.5]undecane |
| 23(H24-6) | 1-ethyl-2,5-dioxo-3-(2-methylpropyl)-9-(5-ethylfuran-2-ylmethyl)-1,4,9-triazaspiro[5.5]undecane |
| 23(H24-7) | 1-ethyl-2,5-dioxo-3-(2-methylpropyl)-9-(pyridin-4-ylmethyl)-1,4,9-triazaspiro[5.5]undecane |
| 23(H24-8) | 1-ethyl-2,5-dioxo-3-(2-methylpropyl)-9-(1-methylindol-3-ylmethyl)-1,4,9-triazaspiro[5.5]undecane |
| 23(H24-9) | 1-ethyl-2,5-dioxo-3-(2-methylpropyl)-9-(4-methylimidazol-5-ylmethyl)-1,4,9-triazaspiro[5.5]undecane |

TABLE 24A-2

| Example No | Compound Name |
|---|---|
| 23(H24-10) | 1-ethyl-2,5-dioxo-3-(2-methylpropyl)-9-(2,4-dioxo-1,3-dihydropyrimidin-5-ylmethyl)-1,4,9-triazaspiro[5.5]undecane |
| 23(H24-11) | 1-ethyl-2,5-dioxo-3-(2-methylpropyl)-9-(5-(2-chlorophenyl)furan-2-ylmethyl)-1,4,9-triazaspiro[5.5]undecane |
| 23(H24-12) | 1-ethyl-2,5-dioxo-3-(2-methylpropyl)-9-(5-(3-chlorophenyl)furan-2-ylmethyl)-1,4,9-triazaspiro[5.5]undecane |
| 23(H24-13) | 1-ethyl-2,5-dioxo-3-(2-methylpropyl)-9-(indol-3-ylmethyl)-1,4,9-triazaspiro[5.5]undecane |
| 23(H24-14) | 1-ethyl-2,5-dioxo-3-(2-methylpropyl)-9-(5-(hydroxymethyl)furan-2-ylmethyl)-1,4,9-triazaspiro[5.5]undecane |
| 23(H24-15) | 1-ethyl-2,5-dioxo-3-(2-methylpropyl)-9-(5-(carboxy)thiophen-2-ylmethyl)-1,4,9-triazaspiro[5.5]undecane |
| 23(H24-16) | 1-ethyl-2,5-dioxo-3-(2-methylpropyl)-9-(5-(carboxy)furan-2-ylmethyl)-1,4,9-triazaspiro[5.5]undecane |
| 23(H24-17) | 1-ethyl-2,5-dioxo-3-(2-methylpropyl)-9-(5-ethylthiophen-2-ylmethyl)-1,4,9-triazaspiro[5.5]undecane |

TABLE 24A-2-continued

| Example No | Compound Name |
|---|---|
| 23(H24-18) | 1-ethyl-2,5-dioxo-3-(2-methylpropyl)-9-(1-methylbenzimidazol-2-ylmethyl)-1,4,9-triazaspiro[5.5]undecane |

TABLE 24A-3

| Example No | Compound Name |
|---|---|
| 23(H24-19) | 1-ethyl-2,5-dioxo-3-(2-methylpropyl)-9-(5-(2-trifluoromethoxyphenyl)furan-2-ylmethyl)-1,4,9-triazaspiro[5.5]undecane |
| 23(H24-20) | 1-ethyl-2,5-dioxo-3-(2-methylpropyl)-9-(6-(methoxycarbonyl)indol-3-ylmethyl)-1,4,9-triazaspiro[5.5]undecane |
| 23(H24-21) | 1-ethyl-2,5-dioxo-3-(2-methylpropyl)-9-(5-(2,6-dichloro-4-trifluoromethylphenyl) furan-2-ylmethyl)-1,4,9-triazaspiro[5.5]undecane |
| 23(H24-22) | 1-ethyl-2,5-dioxo-3-(2-methylpropyl)-9-(4-bromothiophen-2-ylmethyl)-1,4,9-triazaspiro[5.5]undecane |
| 23(H24-23) | 1-ethyl-2,5-dioxo-3-(2-methylpropyl)-9-(5-(2-chloro-5-trifluoromethylphenyl)furan-2-ylmethyl)-1,4,9-triazaspiro[5.5]undecane |
| 23(H24-24) | 1-ethyl-2,5-dioxo-3-(2-methylpropyl)-9-(5-(3-trifluoromethylphenyl)furan-2-ylmethyl)-1,4,9-triazaspiro[5.5]undecane |
| 23(H24-25) | 1-ethyl-2,5-dioxo-3-(2-methylpropyl)-9-(1-acetylindol-3-ylmethyl)-1,4,9-triazaspiro[5.5]undecane |

TABLE 24A-4

| Example No | Compound Name |
|---|---|
| 23(H24-26) | 1-ethyl-2,5-dioxo-3-(2-methylpropyl)-9-(5-(3,5-bis(trifluoromethyl)phenyl)furan-2-ylmethyl)-1,4,9-triazaspiro[5.5]undecane |
| 23(H24-27) | 1-ethyl-2,5-dioxo-3-(2-methylpropyl)-9-(5-chloro-3-methyl-1-phenylpyrazol-4-ylmethyl)-1,4,9-triazaspiro[5.5]undecane |
| 23(H24-28) | 1-ethyl-2,5-dioxo-3-(2-methylpropyl)-9-(5-(4-methoxyphenyl)thiophen-2-ylmethyl)-1,4,9-triazaspiro[5.5]undecane |
| 23(H24-29) | 1-ethyl-2,5-dioxo-3-(2-methylpropyl)-9-(5-(2-trifluoromethylphenyl)furan-2-ylmethyl)-1,4,9-triazaspiro[5.5]undecane |
| 23(H24-30) | 1-ethyl-2,5-dioxo-3-(2-methylpropyl)-9-(2,5-dimethyl-1-(4-carboxyphenyl)pyrrol-3-ylmethyl)-1,4,9-triazaspiro[5.5]undecane |
| 23(H24-31) | 1-ethyl-2,5-dioxo-3-(2-methylpropyl)-9-(5-(4-chlorophenyl)furan-2-ylmethyl)-1,4,9-triazaspiro[5.6]undecane |

TABLE 25A-1

| Example No | Compound Name |
|---|---|
| 23(H25-1) | 1-propyl-2,5-dioxo-3-(2-methylpropyl)-9-(1,4-benzodioxan-6-ylmethyl)-1,4,9-triazaspiro[5.5]undecane |
| 23(H25-2) | 1-propyl-2,5-dioxo-3-(2-methylpropyl)-9-(3,5-dimethyl-1-phenylpyrazol-4-ylmethyl)-1,4,9-triazaspiro[5.5]undecane |
| 23(H25-3) | 1-propyl-2,5-dioxo-3-(2-methylpropyl)-9-(5-methylfuran-2-ylmethyl)-1,4,9-triazaspiro[5.5]undecane |
| 23(H25-4) | 1-propyl-2,5-dioxo-3-(2-methylpropyl)-9-(5-bromothiophen-2-ylmethyl)-1,4,9-triazaspiro[5.5]undecane |
| 23(H25-5) | 1-propyl-2,5-dioxo-3-(2-methylpropyl)-9-(3-methylthiophen-2-ylmethyl)-1,4,9-triazaspiro[5.5]undecane |
| 23(H25-6) | 1-propyl-2,5-dioxo-3-(2-methylpropyl)-9-(5-ethylfuran-2-ylmethyl)-1,4,9-triazaspiro[5.5]undecane |
| 23(H25-7) | 1-propyl-2,5-dioxo-3-(2-methylpropyl)-9-(1-methylindol-3-ylmethyl)-1,4,9-triazaspiro[5.5]undecane |
| 23(H25-8) | 1-propyl-2,5-dioxo-3-(2-methylpropyl)-9-(4-methylimidazol-5-ylmethyl)-1,4,9-triazaspiro[5.5]undecane |

TABLE 25A-2

| Example No | Compound Name |
|---|---|
| 23(H25-9) | 1-propyl-2,5-dioxo-3-(2-methylpropyl)-9-(2,4-dioxo-1,3-dihydropyrimidin-5-ylmethyl)-1,4,9-triazaspiro[5.5]undecane |
| 23(H25-10) | 1-propyl-2,5-dioxo-3-(2-methylpropyl)-9-(5-(2-chlorophenyl)furan-2-ylmethyl)-1,4,9-triazaspiro[5.5]undecane |
| 23(H25-11) | 1-propyl-2,5-dioxo-3-(2-methylpropyl)-9-(indol-3-ylmethyl)-1,4,9-triazaspiro[5.5]undecane |
| 23(H25-12) | 1-propyl-2,5-dioxo-3-(2-methylpropyl)-9-(5-(hydroxymethyl)furan-2-ylmethyl)-1,4,9-triazaspiro[5.5]undecane |
| 23(H25-13) | 1-propyl-2,5-dioxo-3-(2-methylpropyl)-9-(5-(carboxy)furan-2-ylmethyl)-1,4,9-triazaspiro[5.5]undecane |
| 23(H25-14) | 1-propyl-2,5-dioxo-3-(2-methylpropyl)-9-(5-ethylthiophen-2-ylmethyl)-1,4,9-triazaspiro[5.5]undecane |
| 23(H25-15) | 1-propyl-2,5-dioxo-3-(2-methylpropyl)-9-(1-methylbenzimidazol-2-ylmethyl)-1,4,9-triazaspiro[5.5]undecane |
| 23(H25-16) | 1-propyl-2,5-dioxo-3-(2-methylpropyl)-9-(5-(2-trifluoromethoxyphenyl)furan-2-ylmethyl)-1,4,9-triazaspiro[5.5]undecane |

TABLE 25A-3

| Example No | Compound Name |
|---|---|
| 23(H25-17) | 1-propyl-2,5-dioxo-3-(2-methylpropyl)-9-(6-(methoxycarbonyl)indol-3-ylmethyl)-1,4,9-triazaspiro[5.5]undecane |
| 23(H25-18) | 1-propyl-2,5-dioxo-3-(2-methylpropyl)-9-(5-(2,6-dichloro-4-trifluoromethylphenyl)furan-2-ylmethyl)-1,4,9-triazaspiro[5.5]undecane |

TABLE 25A-3-continued

| Example No | Compound Name |
|---|---|
| 23(H25-19) | 1-propyl-2,5-dioxo-3-(2-methylpropyl)-9-(4-bromothiophen-2-ylmethyl)-1,4,9-triazaspiro[5.5]undecane |
| 23(H25-20) | 1-propyl-2,5-dioxo-3-(2-methylpropyl)-9-(5-(2-chloro-5-trifluoromethylphenyl)furan-2-ylmethyl)-1,4,9-triazaspiro[5.5]undecane |
| 23(H25-21) | 1-propyl-2,5-dioxo-3-(2-methylpropyl)-9-(5-(3-trifluoromethylphenyl)furan-2-ylmethyl)-1,4,9-triazaspiro[5.5]undecane |
| 23(H25-22) | 1-propyl-2,5-dioxo-3-(2-methylpropyl)-9-(1-acetylindol-3-ylmethyl)-1,4,9-triazaspiro[5.5]undecane |
| 23(H25-23) | 1-propyl-2,5-dioxo-3-(2-methylpropyl)-9-(5-(3,5-bis(trifluoromethyl)phenyl)furan-2-ylmethyl)-1,4,9-triazaspiro[5.5]undecane |

TABLE 25A-4

| Example No | Compound Name |
|---|---|
| 23(H25-24) | 1-propyl-2,5-dioxo-3-(2-methylpropyl)-9-(5-chloro-3-methyl-1-phenylpyrazol-4-ylmethyl)-1,4,9-triazaspiro[5.5]undecane |
| 23(H25-25) | 1-propyl-2,5-dioxo-3-(2-methylpropyl)-9-(5-(4-methoxyphenyl)thiophen-2-ylmethyl)-1,4,9-triazaspiro[5.5]undecane |
| 23(H25-26) | 1-propyl-2,5-dioxo-3-(2-methylpropyl)-9-(5-(2-trifluoromethylphenyl)furan-2-ylmethyl)-1,4,9-triazaspiro[5.5]undecane |
| 23(H25-27) | 1-propyl-2,5-dioxo-3-(2-methylpropyl)-9-(2,5-dimethyl-1-(4-carboxyphenyl)pyrrol-3-ylmethyl)-1,4,9-triazaspiro[5.5]undecane |
| 23(H25-28) | 1-propyl-2,5-dioxo-3-(2-methylpropyl)-9-(5-(4-chlorophenyl)furan-2-ylmethyl)-1,4,9-triazaspiro[5.6]undecane |

TABLE 26A-1

| Example No | Compound Name |
|---|---|
| 23(H26-1) | 1-butyl-2,5-dioxo-3-(2-methylpropyl)-9-(1,4-benzodioxan-6-ylmethyl)-1,4,9-triazaspiro[5.5]undecane |
| 23(H26-2) | 1-butyl-2,5-dioxo-3-(2-methylpropyl)-9-(3,5-dimethyl-1-phenylpyrazol-4-ylmethyl)-1,4,9-triazaspiro[5.5]undecane |
| 23(H26-3) | 1-butyl-2,5-dioxo-3-(2-methylpropyl)-9-(5-methylfuran-2-ylmethyl)-1,4,9-triazaspiro[5.5]undecane |
| 23(H26-4) | 1-butyl-2,5-dioxo-3-(2-methylpropyl)-9-(5-bromothiophen-2-ylmethyl)-1,4,9-triazaspiro[5.5]undecane |
| 23(H26-5) | 1-butyl-2,5-dioxo-3-(2-methylpropyl)-9-(3-methylthiophen-2-ylmethyl)-1,4,9-triazaspiro[5.5]undecane |
| 23(H26-6) | 1-butyl-2,5-dioxo-3-(2-methylpropyl)-9-(5-ethylfuran-2-ylmethyl)-1,4,9-triazaspiro[5.5]undecane |
| 23(H26-7) | 1-butyl-2,5-dioxo-3-(2-methylpropyl)-9-(pyridin-4-ylmethyl)-1,4,9-triazaspiro[5.5]undecane |

TABLE 26A-1-continued

| Example No | Compound Name |
|---|---|
| 23(H26-8) | 1-butyl-2,5-dioxo-3-(2-methylpropyl)-9-(1-methylindol-3-ylmethyl)-1,4,9-triazaspiro[5.5]undecane |
| 23(H26-9) | 1-butyl-2,5-dioxo-3-(2-methylpropyl)-9-(4-methylimidazol-5-ylmethyl)-1,4,9-triazaspiro[5.5]undecane |

TABLE 26A-2

| Example No | Compound Name |
|---|---|
| 23(H26-10) | 1-butyl-2,5-dioxo-3-(2-methylpropyl)-9-(2,4-dioxo-1,3-dihydropyrimidin-5-ylmethyl)-1,4,9-triazaspiro[5.5]undecane |
| 23(H26-11) | 1-butyl-2,5-dioxo-3-(2-methylpropyl)-9-(5-(2-chlorophenyl)furan-2-ylmethyl)-1,4,9-triazaspiro[5.5]undecane |
| 23(H26-12) | 1-butyl-2,5-dioxo-3-(2-methylpropyl)-9-(5-(3-chlorophenyl)furan-2-ylmethyl)-1,4,9-triazaspiro[5.5]undecane |
| 23(H26-13) | 1-butyl-2,5-dioxo-3-(2-methylpropyl)-9-(indol-3-ylmethyl)-1,4,9-triazaspiro[5.5]undecane |
| 23(H26-14) | 1-butyl-2,5-dioxo-3-(2-methylpropyl)-9-(5-(hydroxymethyl)furan-2-ylmethyl)-1,4,9-triazaspiro[5.5]undecane |
| 23(H26-15) | 1-butyl-2,5-dioxo-3-(2-methylpropyl)-9-(5-(carboxy)thiophen-2-ylmethyl)-1,4,9-triazaspiro[5.5]undecane |
| 23(H26-16) | 1-butyl-2,5-dioxo-3-(2-methylpropyl)-9-(5-(carboxy)furan-2-ylmethyl)-1,4,9-triazaspiro[5.5]undecane |
| 23(H26-17) | 1-butyl-2,5-dioxo-3-(2-methylpropyl)-9-(5-ethylthiophen-2-ylmethyl)-1,4,9-triazaspiro[5.5]undecane |
| 23(H26-18) | 1-butyl-2,5-dioxo-3-(2-methylpropyl)-9-(1-methylbenzimidazol-2-ylmethyl)-1,4,9-triazaspiro[5.5]undecane |

TABLE 26A-3

| Example No | Compound Name |
|---|---|
| 23(H26-19) | 1-butyl-2,5-dioxo-3-(2-methylpropyl)-9-(5-(2-trifluoromethoxyphenyl)furan-2-ylmethyl)-1,4,9-triazaspiro[5.5]undecane |
| 23(H26-20) | 1-butyl-2,5-dioxo-3-(2-methylpropyl)-9-(6-(methoxycarbonyl)indol-3-ylmethyl)-1,4,9-triazaspiro[5.5]undecane |
| 23(H26-21) | 1-butyl-2,5-dioxo-3-(2-methylpropyl)-9-(5-(2,6-dichloro-4-trifluoromethylphenyl)furan-2-ylmethyl)-1,4,9-triazaspiro[5.5]undecane |
| 23(H26-22) | 1-butyl-2,5-dioxo-3-(2-methylpropyl)-9-(4-bromothiophen-2-ylmethyl)-1,4,9-triazaspiro[5.5]undecane |
| 23(H26-23) | 1-butyl-2,5-dioxo-3-(2-methylpropyl)-9-(5-(2-chloro-5-trifluoromethylphenyl)furan-2-ylmethyl)-1,4,9-triazaspiro[5.5]undecane |
| 23(H26-24) | 1-butyl-2,5-dioxo-3-(2-methylpropyl)-9-(5-(3-trifluoromethylphenyl)furan-2-ylmethyl)-1,4,9-triazaspiro[5.5]undecane |
| 23(H26-25) | 1-butyl-2,5-dioxo-3-(2-methylpropyl)-9-(1-acetylindol-3-ylmethyl)-1,4,9-triazaspiro[5.5]undecane |

TABLE 26A-4

| Example No | Compound Name |
|---|---|
| 23(H26-26) | 1-butyl-2,5-dioxo-3-(2-methylpropyl)-9-(5-(3,5-bis(trifluoromethyl)phenyl)furan-2-ylmethyl)-1,4,9-triazaspiro[5.5]undecane |
| 23(H26-27) | 1-butyl-2,5-dioxo-3-(2-methylpropyl)-9-(5-chloro-3-methyl-1-phenylpyrazol-4-ylmethyl)-1,4,9-triazaspiro[5.5]undecane |
| 23(H26-28) | 1-butyl-2,5-dioxo-3-(2-methylpropyl)-9-(5-(4-methoxyphenyl)thiophen-2-ylmethyl)-1,4,9-triazaspiro[5.5]undecane |
| 23(H26-29) | 1-butyl-2,5-dioxo-3-(2-methylpropyl)-9-(5-(2-trifluoromethylphenyl)furan-2-ylmethyl)-1,4,9-triazaspiro[5.5]undecane |
| 23(H26-30) | 1-butyl-2,5-dioxo-3-(2-methylpropyl)-9-(2,5-dimethyl-1-(4-carboxyphenyl) pyrrol-3-ylmethyl)-1,4,9-triazaspiro[5.5]undecane |
| 23(H26-31) | 1-butyl-2,5-dioxo-3-(2-methylpropyl)-9-(5-(4-chlorophenyl)furan-2-ylmethyl)-1,4,9-triazaspiro[5.6]undecane |

TABLE 27A-1

| Example No | Compound Name |
|---|---|
| 23(H27-1) | 1-benzyl-2,5-dioxo-3-(2-methylpropyl)-9-benzyl-1,4,9-triazaspiro[5.5]undecane |
| 23(H27-2) | 1-benzyl-2,5-dioxo-3-(2-methylpropyl)-9-((4-methoxyphenyl)methyl)-1,4,9-triazaspiro[5.5]undecane |
| 23(H27-3) | 1-benzyl-2,5-dioxo-3-(2-methylpropyl)-9-(1,4-benzodioxan-6-ylmethyl)-1,4,9-triazaspiro[5.5]undecane |
| 23(H27-4) | 1-benzyl-2,5-dioxo-3-(2-methylpropyl)-9-((4-phenoxyphenyl)methyl)-1,4,9-triazaspiro[5.5]undecane |
| 23(H27-5) | 1-benzyl-2,5-dioxo-3-(2-methylpropyl)-9-((4-benzyloxyphenyl)methyl)-1,4,9-triazaspiro[5.5]undecane |
| 23(H27-6) | 1-benzyl-2,5-dioxo-3-(2-methylpropyl)-9-(3,5-dimethyl-1-phenylpyrazol-4-ylmethyl)-1,4,9-triazaspiro[5.5]undecane |
| 23(H27-7) | 1-benzyl-2,5-dioxo-3-(2-methylpropyl)-9-(2-phenylimidazol-5-ylmethyl)-1,4,9-triazaspiro[5.5]undecane |
| 23(H27-8) | 1-benzyl-2,5-dioxo-3-(2-methylpropyl)-9-((4-hydroxyphenyl)methyl)-1,4,9-triazaspiro[5.5]undecane |
| 23(H27-9) | 1-((2-methoxyphenyl)methyl)-2,5-dioxo-3-(2-methylpropyl)-9-benzyl-1,4,9-triazaspiro[5.5]undecane |

TABLE 27A-2

| Example No | Compound Name |
|---|---|
| 23(H27-10) | 1-((2-methoxyphenyl)methyl)-2,5-dioxo-3-(2-methylpropyl)-9-((4-methoxyphenyl)methyl)-1,4,9-triazaspiro[5.5]undecane |
| 23(H27-11) | 1-((2-methoxyphenyl)methyl)-2,5-dioxo-3-(2-methylpropyl)-9-(1,4-benzodioxan-6-ylmethyl)-1,4,9-triazaspiro[5.5]undecane |

TABLE 27A-2-continued

| Example No | Compound Name |
|---|---|
| 23(H27-12) | 1-((2-methoxyphenyl)methyl)-2,5-dioxo-3-(2-methylpropyl)-9-((4-phenoxyphenyl)methyl)-1,4,9-triazaspiro[5.5]undecane |
| 23(H27-13) | 1-((2-methoxyphenyl)methyl)-2,5-dioxo-3-(2-methylpropyl)-9-((4-benzyloxyphenyl)methyl)-1,4,9-triazaspiro[5.5]undecane |
| 23(H27-14) | 1-((2-methoxyphenyl)methyl)-2,5-dioxo-3-(2-methylpropyl)-9-(3,5-dimethyl-1-phenylpyrazol-4-ylmethyl)-1,4,9-triazaspiro[5.5]undecane |
| 23(H27-15) | 1-((2-methoxyphenyl)methyl)-2,5-dioxo-3-(2-methylpropyl)-9-(2-phenylimidazol-5-ylmethyl)-1,4,9-triazaspiro[5.5]undecane |
| 23(H27-16) | 1-((2-methoxyphenyl)methyl)-2,5-dioxo-3-(2-methylpropyl)-9-((4-hydroxyphenyl)methyl)-1,4,9-triazaspiro[5.5]undecane |

TABLE 27A-3

| Example No | Compound Name |
|---|---|
| 23(H27-17) | 1-((3-methoxyphenyl)methyl)-2,5-dioxo-3-(2-methylpropyl)-9-benzyl-1,4,9-triazaspiro[5.5]undecane |
| 23(H27-18) | 1-((3-methoxyphenyl)methyl)-2,5-dioxo-3-(2-methylpropyl)-9-((4-methoxyphenyl)methyl)-1,4,9-triazaspiro[5.5]undecane |
| 23(H27-19) | 1-((3-methoxyphenyl)methyl)-2,5-dioxo-3-(2-methylpropyl)-9-((4-phenoxyphenyl)methyl)-1,4,9-triazaspiro[5.5]undecane |
| 23(H27-20) | 1-((3-methoxyphenyl)methyl)-2,5-dioxo-3-(2-methylpropyl)-9-((4-benzyloxyphenyl)methyl)-1,4,9-triazaspiro[5.5]undecane |
| 23(H27-21) | 1-((3-methoxyphenyl)methyl)-2,5-dioxo-3-(2-methylpropyl)-9-(3,5-dimethyl-1-phenylpyrazol-4-ylmethyl)-1,4,9-triazaspiro[5.5]undecane |
| 23(H27-22) | 1-((3-methoxyphenyl)methyl)-2,5-dioxo-3-(2-methylpropyl)-9-(2-phenylimidazol-5-ylmethyl)-1,4,9-triazaspiro[5.5]undecane |
| 23(H27-23) | 1-((3-methoxyphenyl)methyl)-2,5-dioxo-3-(2-methylpropyl)-9-((4-hydroxyphenyl)methyl)-1,4,9-triazaspiro[5.5]undecane |

TABLE 27A-4

| Example No | Compound Name |
|---|---|
| 23(H27-24) | 1-((4-methoxyphenyl)methyl)-2,5-dioxo-3-(2-methylpropyl)-9-benzyl-1,4,9-triazaspiro[5.5]undecane |
| 23(H27-25) | 1-((4-methoxyphenyl)methyl)-2,5-dioxo-3-(2-methylpropyl)-9-(1,4-benzodioxan-6-ylmethyl)-1,4,9-triazaspiro[5.5]undecane |
| 23(H27-26) | 1-((4-methoxyphenyl)methyl)-2,5-dioxo-3-(2-methylpropyl)-9-((4-phenoxyphenyl)methyl)-1,4,9-triazaspiro[5.5]undecane |

TABLE 27A-4-continued

| Example No | Compound Name |
|---|---|
| 23(H27-27) | 1-((4-methoxyphenyl)methyl)-2,5-dioxo-3-(2-methylpropyl)-9-((4-benzyloxyphenyl)methyl)-1,4,9-triazaspiro[5.5]undecane |
| 23(H27-28) | 1-((4-methoxyphenyl)methyl)-2,5-dioxo-3-(2-methylpropyl)-9-(3,5-dimethyl-1-phenylpyrazol-4-ylmethyl)-1,4,9-triazaspiro[5.5]undecane |
| 23(H27-29) | 1-((4-methoxyphenyl)methyl)-2,5-dioxo-3-(2-methylpropyl)-9-(2-phenylimidazol-5-ylmethyl)-1,4,9-triazaspiro[5.5]undecane |
| 23(H27-30) | 1-((4-methoxyphenyl)methyl)-2,5-dioxo-3-(2-methylpropyl)-9-((4-hydroxyphenyl)methyl)-1,4,9-triazaspiro[5.5]undecane |

TABLE 27A-5

| Example No | Compound Name |
|---|---|
| 23(H27-31) | 1-(pyridin-2-ylmethyl)-2,5-dioxo-3-(2-methylpropyl)-9-benzyl-1,4,9-triazaspiro[5.5]undecane |
| 23(H27-32) | 1-(pyridin-2-ylmethyl)-2,5-dioxo-3-(2-methylpropyl)-9-((4-methoxyphenyl)methyl)-1,4,9-triazaspiro[5.5]undecane |
| 23(H27-33) | 1-(pyridin-2-ylmethyl)-2,5-dioxo-3-(2-methylpropyl)-9-(2H,3H-benzo[3,4-e]1,4-dioxan-6-ylmethyl)-1,4,9-triazaspiro[5.5]undecane |
| 23(H27-34) | 1-(pyridin-2-ylmethyl)-2,5-dioxo-3-(2-methylpropyl)-9-((4-phenoxyphenyl)methyl)-1,4,9-triazaspiro[5.5]undecane |
| 23(H27-35) | 1-(pyridin-2-ylmethyl)-2,5-dioxo-3-(2-methylpropyl)-9-((4-benzyloxyphenyl)methyl)-1,4,9-triazaspiro[5.5]undecane |
| 23(H27-36) | 1-(pyridin-2-ylmethyl)-2,5-dioxo-3-(2-methylpropyl)-9-(3,5-dimethyl-1-phenylpyrazol-4-ylmethyl)-1,4,9-triazaspiro[5.5]undecane |
| 23(H27-37) | 1-(pyridin-2-ylmethyl)-2,5-dioxo-3-(2-methylpropyl)-9-(2-phenylimidazol-5-ylmethyl)-1,4,9-triazaspiro[5.5]undecane |

TABLE 27A-6

| Example No | Compound Name |
|---|---|
| 23(H27-38) | 1-(pyridin-2-ylmethyl)-2,5-dioxo-3-(2-methylpropyl)-9-((4-hydroxyphenyl)methyl)-1,4,9-triazaspiro[5.5]undecane |
| 23(H27-39) | 1-(pyridin-3-ylmethyl)-2,5-dioxo-3-(2-methylpropyl)-9-benzyl-1,4,9-triazaspiro[5.5]undecane |
| 23(H27-40) | 1-(pyridin-3-ylmethyl)-2,5-dioxo-3-(2-methylpropyl)-9-((4-methoxyphenyl)methyl)-1,4,9-triazaspiro[5.5]undecane |

TABLE 27A-6-continued

| Example No | Compound Name |
|---|---|
| 23(H27-41) | 1-(pyridin-3-ylmethyl)-2,5-dioxo-3-(2-methylpropyl)-9-(1,4-benzodioxan-6-ylmethyl)-1,4,9-triazaspiro[5.5]undecane |
| 23(H27-42) | 1-(pyridin-3-ylmethyl)-2,5-dioxo-3-(2-methylpropyl)-9-((4-phenoxyphenyl)methyl)-1,4,9-triazaspiro[5.5]undecane |
| 23(H27-43) | 1-(pyridin-3-ylmethyl)-2,5-dioxo-3-(2-methylpropyl)-9-((4-benzyloxyphenyl)methyl)-1,4,9-triazaspiro[5.5]undecane |
| 23(H27-44) | 1-(pyridin-3-ylmethyl)-2,5-dioxo-3-(2-methylpropyl)-9-(3,5-dimethyl-1-phenylpyrazol-4-ylmethyl)-1,4,9-triazaspiro[5.5]undecane |

TABLE 27A-7

| Example No | Compound Name |
|---|---|
| 23(H27-45) | 1-(pyridin-3-ylmethyl)-2,5-dioxo-3-(2-methylpropyl)-9-(2-phenylimidazol-5-ylmethyl)-1,4,9-triazaspiro[5.5]undecane |
| 23(H27-46) | 1-(pyridin-3-ylmethyl)-2,5-dioxo-3-(2-methylpropyl)-9-((4-hydroxyphenyl)methyl)-1,4,9-triazaspiro[5.5]undecane |
| 23(H27-47) | 1-(pyridin-4-ylmethyl)-2,5-dioxo-3-(2-methylpropyl)-9-benzyl-1,4,9-triazaspiro[5.5]undecane |
| 23(H27-48) | 1-(pyridin-4-ylmethyl)-2,5-dioxo-3-(2-methylpropyl)-9-((4-methoxyphenyl)methyl)-1,4,9-triazaspiro[5.5]undecane |
| 23(H27-49) | 1-(pyridin-4-ylmethyl)-2,5-dioxo-3-(2-methylpropyl)-9-(1,4-benzodioxan-6-ylmethyl)-1,4,9-triazaspiro[5.5]undecane |
| 23(H27-50) | 1-(pyridin-4-ylmethyl)-2,5-dioxo-3-(2-methylpropyl)-9-((4-phenoxyphenyl)methyl)-1,4,9-triazaspiro[5.5]undecane |
| 23(H27-51) | 1-(pyridin-4-ylmethyl)-2,5-dioxo-3-(2-methylpropyl)-9-((4-benzyloxyphenyl)methyl)-1,4,9-triazaspiro[5.5]undecane |

TABLE 27A-8

| Example No | Compound Name |
|---|---|
| 23(H27-52) | 1-(pyridin-4-ylmethyl)-2,5-dioxo-3-(2-methylpropyl)-9-(3,5-dimethyl-1-phenylpyrazol-4-ylmethyl)-1,4,9-triazaspiro[5.5]undecane |
| 23(H27-53) | 1-(pyridin-4-ylmethyl)-2,5-dioxo-3-(2-methylpropyl)-9-(2-phenylimidazol-5-ylmethyl)-1,4,9-triazaspiro[5.5]undecane |
| 23(H27-54) | 1-(pyridin-4-ylmethyl)-2,5-dioxo-3-(2-methylpropyl)-9-((4-hydroxyphenyl)methyl)-1,4,9-triazaspiro[5.5]undecane |

TABLE 27A-8-continued

| Example No | Compound Name |
|---|---|
| 23(H27-55) | 1-((2-methylphenyl)methyl)-2,5-dioxo-3-(2-methylpropyl)-9-benzyl-1,4,9-triazaspiro[5.5]undecane |
| 23(H27-56) | 1-((2-methylphenyl)methyl)-2,5-dioxo-3-(2-methylpropyl)-9-((4-methoxyphenyl)methyl)-1,4,9-triazaspiro[5.5]undecane |
| 23(H27-57) | 1-((2-methylphenyl)methyl)-2,5-dioxo-3-(2-methylpropyl)-9-(1,4-benzodioxan-6-ylmethyl)-1,4,9-triazaspiro[5.5]undecane |
| 23(H27-58) | 1-((2-methylphenyl)methyl)-2,5-dioxo-3-(2-methylpropyl)-9-((4-phenoxyphenyl)methyl)-1,4,9-triazaspiro[5.5]undecane |

TABLE 27A-9

| Example No | Compound Name |
|---|---|
| 23(H27-59) | 1-((2-methylphenyl)methyl)-2,5-dioxo-3-(2-methylpropyl)-9-((4-benzyloxyphenyl)methyl)-1,4,9-triazaspiro[5.5]undecane |
| 23(H27-60) | 1-((2-methylphenyl)methyl)-2,5-dioxo-3-(2-methylpropyl)-9-(3,5-dimethyl-1-phenylpyrazol-4-ylmethyl)-1,4,9-triazaspiro[5.5]undecane |
| 23(H27-61) | 1-((2-methylphenyl)methyl)-2,5-dioxo-3-(2-methylpropyl)-9-(2-phenylimidazol-5-ylmethyl)-1,4,9-triazaspiro[5.5]undecane |
| 23(H27-62) | 1-((2-methylphenyl)methyl)-2,5-dioxo-3-(2-methylpropyl)-9-((4-hydroxyphenyl)methyl)-1,4,9-triazaspiro[5.5]undecane |
| 23(H27-63) | 1-((3-methylphenyl)methyl)-2,5-dioxo-3-(2-methylpropyl)-9-benzyl-1,4,9-triazaspiro[5.5]undecane |
| 23(H27-64) | 1-((3-methylphenyl)methyl)-2,5-dioxo-3-(2-methylpropyl)-9-((4-methoxyphenyl)methyl)-1,4,9-triazaspiro[5.5]undecane |
| 23(H27-65) | 1-((3-methylphenyl)methyl)-2,5-dioxo-3-(2-methylpropyl)-9-(1,4-benzodioxan-6-ylmethyl)-1,4,9-triazaspiro[5.5]undecane |

TABLE 27A-10

| Example No | Compound Name |
|---|---|
| 23(H27-66) | 1-((3-methylphenyl)methyl)-2,5-dioxo-3-(2-methylpropyl)-9-((4-phenoxyphenyl)methyl)-1,4,9-triazaspiro[5.5]undecane |
| 23(H27-67) | 1-((3-methylphenyl)methyl)-2,5-dioxo-3-(2-methylpropyl)-9-((4-benzyloxyphenyl)methyl)-1,4,9-triazaspiro[5.5]undecane |
| 23(H27-68) | 1-((3-methylphenyl)methyl)-2,5-dioxo-3-(2-methylpropyl)-9-(3,5-dimethyl-1-phenylpyrazol-4-ylmethyl)-1,4,9-triazaspiro[5.5]undecane |

TABLE 27A-10-continued

| Example No | Compound Name |
|---|---|
| 23(H27-69) | 1-((3-methylphenyl)methyl)-2,5-dioxo-3-(2-methylpropyl)-9-(2-phenylimidazol-5-ylmethyl)-1,4,9-triazaspiro[5.5]undecane |
| 23(H27-70) | 1-((3-methylphenyl)methyl)-2,5-dioxo-3-(2-methylpropyl)-9-((4-hydroxyphenyl)methyl)-1,4,9-triazaspiro[5.5]undecane |
| 23(H27-71) | 1-((4-methylphenyl)methyl)-2,5-dioxo-3-(2-methylpropyl)-9-benzyl-1,4,9-triazaspiro[5.5]undecane |
| 23(H27-72) | 1-((4-methylphenyl)methyl)-2,5-dioxo-3-(2-methylpropyl)-9-((4-methoxyphenyl)methyl)-1,4,9-triazaspiro[5.5]undecane |

TABLE 27A-11

| Example No | Compound Name |
|---|---|
| 23(H27-73) | 1-((4-methylphenyl)methyl)-2,5-dioxo-3-(2-methylpropyl)-9-(1,4-benzodioxan-6-ylmethyl)-1,4,9-triazaspiro[5.5]undecane |
| 23(H27-74) | 1-((4-methylphenyl)methyl)-2,5-dioxo-3-(2-methylpropyl)-9-((4-phenoxyphenyl)methyl)-1,4,9-triazaspiro[5.5]undecane |
| 23(H27-75) | 1-((4-methylphenyl)methyl)-2,5-dioxo-3-(2-methylpropyl)-9-((4-benzyloxyphenyl)methyl)-1,4,9-triazaspiro[5.5]undecane |
| 23(H27-76) | 1-((4-methylphenyl)methyl)-2,5-dioxo-3-(2-methylpropyl)-9-(3,5-dimethyl-1-phenylpyrazol-4-ylmethyl)-1,4,9-triazaspiro[5.5]undecane |
| 23(H27-77) | 1-((4-methylphenyl)methyl)-2,5-dioxo-3-(2-methylpropyl)-9-(2-phenylimidazol-5-ylmethyl)-1,4,9-triazaspiro[5.5]undecane |
| 23(H27-78) | 1-((4-methylphenyl)methyl)-2,5-dioxo-3-(2-methylpropyl)-9-((4-hydroxyphenyl)methyl)-1,4,9-triazaspiro[5.5]undecane |

TABLE 28A-1

| Example No | Compound Name |
|---|---|
| 23(H28-1) | 1-propyl-2,5-dioxo-3-cyclohexylmethyl-9-(1,4-benzodioxan-6-ylmethyl)-1,4,9-triazaspiro[5.5]undecane |
| 23(H28-2) | 1-propyl-2,5-dioxo-3-cyclohexylmethyl-9-(3,5-dimethyl-1-phenylpyrazol-4-ylmethyl)-1,4,9-triazaspiro[5.5]undecane |
| 23(H28-3) | 1-propyl-2,5-dioxo-3-cyclohexylmethyl-9-(5-methylfuran-2-ylmethyl)-1,4,9-triazaspiro[5.5]undecane |
| 23(H28-4) | 1-propyl-2,5-dioxo-3-cyclohexylmethyl-9-(5-bromothiophen-2-ylmethyl)-1,4,9-triazaspiro[5.5]undecane |
| 23(H28-5) | 1-propyl-2,5-dioxo-3-cyclohexylmethyl-9-(3-methylthiophen-2-ylmethyl)-1,4,9-triazaspiro[5.5]undecane |
| 23(H28-6) | 1-propyl-2,5-dioxo-3-cyclohexylmethyl-9-(5-ethylfuran-2-ylmethyl)-1,4,9-triazaspiro[5.5]undecane |

TABLE 28A-1-continued

| Example No | Compound Name |
|---|---|
| 23(H28-7) | 1-propyl-2,5-dioxo-3-cyclohexylmethyl-9-(pyridin-4-ylmethyl)-1,4,9-triazaspiro[5.5]undecane |
| 23(H28-8) | 1-propyl-2,5-dioxo-3-cyclohexylmethyl-9-(1-methylindol-3-ylmethyl)-1,4,9-triazaspiro[5.5]undecane |
| 23(H28-9) | 1-propyl-2,5-dioxo-3-cyclohexylmethyl-9-(4-methylimidazol-5-ylmethyl)-1,4,9-triazaspiro[5.5]undecane |

TABLE 28A-2

| Example No | Compound Name |
|---|---|
| 23(H28-10) | 1-propyl-2,5-dioxo-3-cyclohexylmethyl-9-(2,4-dioxo-1,3-dihydropyrimidin-5-ylmethyl)-1,4,9-triazaspiro[5.5]undecane |
| 23(H28-11) | 1-propyl-2,5-dioxo-3-cyclohexylmethyl-9-(5-(2-chlorophenyl)furan-2-ylmethyl)-1,4,9-triazaspiro[5.5]undecane |
| 23(H28-12) | 1-propyl-2,5-dioxo-3-cyclohexylmethyl-9-(5-(3-chlorophenyl)furan-2-ylmethyl)-1,4,9-triazaspiro[5.5]undecane |
| 23(H28-13) | 1-propyl-2,5-dioxo-3-cyclohexylmethyl-9-(5-(hydroxymethyl)furan-2-ylmethyl)-1,4,9-triazaspiro[5.5]undecane |
| 23(H28-14) | 1-propyl-2,5-dioxo-3-cyclohexylmethyl-9-(5-(carboxy)thiophen-2-ylmethyl)-1,4,9-triazaspiro[5.5]undecane |
| 23(H28-15) | 1-propyl-2,5-dioxo-3-cyclohexylmethyl-9-(5-(carboxy)furan-2-ylmethyl)-1,4,9-triazaspiro[5.5]undecane |
| 23(H28-16) | 1-propyl-2,5-dioxo-3-cyclohexylmethyl-9-(5-ethylthiophen-2-ylmethyl)-1,4,9-triazaspiro[5.5]undecane |
| 23(H28-17) | 1-propyl-2,5-dioxo-3-cyclohexylmethyl-9-(1-methylbenzimidazol-2-ylmethyl)-1,4,9-triazaspiro[5.5]undecane |

TABLE 28A-3

| Example No | Compound Name |
|---|---|
| 23(H28-18) | 1-propyl-2,5-dioxo-3-cyclohexylmethyl-9-(5-(2-trifluoromethoxyphenyl)furan-2-ylmethyl)-1,4,9-triazaspiro[5.5]undecane |
| 23(H28-19) | 1-propyl-2,5-dioxo-3-cyclohexylmethyl-9-(6-(methoxycarbonyl)indol-3-ylmethyl)-1,4,9-triazaspiro[5.5]undecane |
| 23(H28-20) | 1-propyl-2,5-dioxo-3-cyclohexylmethyl-9-(5-(2,6-dichloro-4-trifluoromethylphenyl)furan-2-ylmethyl)-1,4,9-triazaspiro[5.5]undecane |
| 23(H28-21) | 1-propyl-2,5-dioxo-3-cyclohexylmethyl-9-(4-bromothiophen-2-ylmethyl)-1,4,9-triazaspiro[5.5]undecane |
| 23(H28-22) | 1-propyl-2,5-dioxo-3-cyclohexylmethyl-9-(5-(2-chloro-5-trifluoromethylphenyl) furan-2-ylmethyl)-1,4,9-triazaspiro[5.5]undecane |
| 23(H28-23) | 1-propyl-2,5-dioxo-3-cyclohexylmethyl-9-(5-(3-trifluoromethylphenyl)furan-2-ylmethyl)-1,4,9-triazaspiro[5.5]undecane |

TABLE 28A-3-continued

| Example No | Compound Name |
|---|---|
| 23(H28-24) | 1-propyl-2,5-dioxo-3-cyclohexylmethyl-9-(1-acetylindol-3-ylmethyl)-1,4,9-triazaspiro[5.5]undecane |

TABLE 28A-4

| Example No | Compound Name |
|---|---|
| 23(H28-25) | 1-propyl-2,5-dioxo-3-cyclohexylmethyl-9-(5-(3,5-bis(trifluoromethyl)phenyl)furan-2-ylmethyl)-1,4,9-triazaspiro[5.5]undecane |
| 23(H28-26) | 1-propyl-2,5-dioxo-3-cyclohexylmethyl-9-(5-chloro-3-methyl-1-phenylpyrazol-4-ylmethyl)-1,4,9-triazaspiro[5.5]undecane |
| 23(H28-27) | 1-propyl-2,5-dioxo-3-cyclohexylmethyl-9-(5-(4-methoxyphenyl)thiophen-2-ylmethyl)-1,4,9-triazaspiro[5.5]undecane |
| 23(H28-28) | 1-propyl-2,5-dioxo-3-cyclohexylmethyl-9-(5-(2-trifluoromethylphenyl)furan-2-ylmethyl)-1,4,9-triazaspiro[5.5]undecane |
| 23(H28-29) | 1-propyl-2,5-dioxo-3-cyclohexylmethyl-9-(2,5-dimethyl-1-(4-carboxyphenyl)pyrrol-3-ylmethyl)-1,4,9-triazaspiro[5.5]undecane |
| 23(H28-30) | 1-propyl-2,5-dioxo-3-cyclohexylmethyl-9-(5-(4-chlorophenyl)furan-2-ylmethyl)-1,4,9-triazaspiro[5.6]undecane |

TABLE 29A-1

| Example No | Compound Name |
|---|---|
| 23(H29-1) | 1-butyl-2,5-dioxo-3-cyclohexylmethyl-9-(1,4-benzodioxan-6-ylmethyl)-1,4,9-triazaspiro[5.5]undecane |
| 23(H29-2) | 1-butyl-2,5-dioxo-3-cyclohexylmethyl-9-(3,5-dimethyl-1-phenylpyrazol-4-ylmethyl)-1,4,9-triazaspiro[5.5]undecane |
| 23(H29-3) | 1-butyl-2,5-dioxo-3-cyclohexylmethyl-9-(5-methylfuran-2-ylmethyl)-1,4,9-triazaspiro[5.5]undecane |
| 23(H29-4) | 1-butyl-2,5-dioxo-3-cyclohexylmethyl-9-(5-bromothiophen-2-ylmethyl)-1,4,9-triazaspiro[5.5]undecane |
| 23(H29-5) | 1-butyl-2,5-dioxo-3-cyclohexylmethyl-9-(3-methylthiophen-2-ylmethyl)-1,4,9-triazaspiro[5.5]undecane |
| 23(H29-6) | 1-butyl-2,5-dioxo-3-cyclohexylmethyl-9-(5-ethylfuran-2-ylmethyl)-1,4,9-triazaspiro[5.5]undecane |
| 23(H29-7) | 1-butyl-2,5-dioxo-3-cyclohexylmethyl-9-(pyridin-4-ylmethyl)-1,4,9-triazaspiro[5.5]undecane |
| 23(H29-8) | 1-butyl-2,5-dioxo-3-cyclohexylmethyl-9-(1-methylindol-3-ylmethyl)-1,4,9-triazaspiro[5.5]undecane |
| 23(H29-9) | 1-butyl-2,5-dioxo-3-cyclohexylmethyl-9-(4-methylimidazol-5-ylmethyl)-1,4,9-triazaspiro[5.5]undecane |

TABLE 29A-2

| Example No | Compound Name |
|---|---|
| 23(H29-10) | 1-butyl-2,5-dioxo-3-cyclohexylmethyl-9-(2,4-dioxo-1,3-dihydropyrimidin-5-ylmethyl)-1,4,9-triazaspiro[5.5]undecane |
| 23(H29-11) | 1-butyl-2,5-dioxo-3-cyclohexylmethyl-9-(5-(2-chlorophenyl)furan-2-ylmethyl)-1,4,9-triazaspiro[5.5]undecane |
| 23(H29-12) | 1-butyl-2,5-dioxo-3-cyclohexylmethyl-9-(5-(3-chlorophenyl)furan-2-ylmethyl)-1,4,9-triazaspiro[5.5]undecane |
| 23(H29-13) | 1-butyl-2,5-dioxo-3-cyclohexylmethyl-9-(indol-3-ylmethyl)-1,4,9-triazaspiro[5.5]undecane |
| 23(H29-14) | 1-butyl-2,5-dioxo-3-cyclohexylmethyl-9-(5-(hydroxymethyl)furan-2-ylmethyl)-1,4,9-triazaspiro[5.5]undecane |
| 23(H29-15) | 1-butyl-2,5-dioxo-3-cyclohexylmethyl-9-(5-(carboxy)thiophen-2-ylmethyl)-1,4,9-triazaspiro[5.5]undecane |
| 23(H29-16) | 1-butyl-2,5-dioxo-3-cyclohexylmethyl-9-(5-(carboxy)furan-2-ylmethyl)-1,4,9-triazaspiro[5.5]undecane |
| 23(H29-17) | 1-butyl-2,5-dioxo-3-cyclohexylmethyl-9-(5-ethylthiophen-2-ylmethyl)-1,4,9-triazaspiro[5.5]undecane |
| 23(H29-18) | 1-butyl-2,5-dioxo-3-cyclohexylmethyl-9-(1-methylbenzimidazol-2-ylmethyl)-1,4,9-triazaspiro[5.5]undecane |

TABLE 29A-3

| Example No | Compound Name |
|---|---|
| 23(H29-19) | 1-butyl-2,5-dioxo-3-cyclohexylmethyl-9-(5-(2-trifluoromethoxyphenyl)furan-2-ylmethyl)-1,4,9-triazaspiro[5.5]undecane |
| 23(H29-20) | 1-butyl-2,5-dioxo-3-cyclohexylmethyl-9-(6-(methoxycarbonyl)indol-3-ylmethyl)-1,4,9-triazaspiro[5.5]undecane |
| 23(H29-21) | 1-butyl-2,5-dioxo-3-cyclohexylmethyl-9-(5-(2,6-dichloro-4-trifluoromethylphenyl)furan-2-ylmethyl)-1,4,9-triazaspiro[5.5]undecane |
| 23(H29-22) | 1-butyl-2,5-dioxo-3-cyclohexylmethyl-9-(4-bromothiophen-2-ylmethyl)-1,4,9-triazaspiro[5.5]undecane |
| 23(H29-23) | 1-butyl-2,5-dioxo-3-cyclohexylmethyl-9-(5-(2-chloro-5-trifluoromethylphenyl)furan-2-ylmethyl)-1,4,9-triazaspiro[5.5]undecane |
| 23(H29-24) | 1-butyl-2,5-dioxo-3-cyclohexylmethyl-9-(5-(3-trifluoromethylphenyl)furan-2-ylmethyl)-1,4,9-triazaspiro[5.5]undecane |
| 23(H29-25) | 1-butyl-2,5-dioxo-3-cyclohexylmethyl-9-(1-acetylindol-3-ylmethyl)-1,4,9-triazaspiro[5.5]undecane |

TABLE 29A-4

| Example No | Compound Name |
|---|---|
| 23(H29-26) | 1-butyl-2,5-dioxo-3-cyclohexylmethyl-9-(5-(3,5-bis(trifluoromethylmethyl)phenyl)furan-2-ylmethyl)-1,4,9-triazaspiro[5.5]undecane |

TABLE 29A-4-continued

| Example No | Compound Name |
|---|---|
| 23(H29-27) | 1-butyl-2,5-dioxo-3-cyclohexylmethyl-9-(5-chloro-3-methyl-1-phenylpyrazol-4-ylmethyl)-1,4,9-triazaspiro[5.5]undecane |
| 23(H29-28) | 1-butyl-2,5-dioxo-3-cyclohexylmethyl-9-(5-(4-methoxyphenyl)thiophen-2-ylmethyl)-1,4,9-triazaspiro[5.5]undecane |
| 23(H29-29) | 1-butyl-2,5-dioxo-3-cyclohexylmethyl-9-(5-(2-trifluoromethylmethylphenyl)furan-2-ylmethyl)-1,4,9-triazaspiro[5.5]undecane |
| 23(H29-30) | 1-butyl-2,5-dioxo-3-cyclohexylmethyl-9-(2,5-dimethyl-1-(4-carboxyphenyl)pyrrol-3-ylmethyl)-1,4,9-triazaspiro[5.5]undecane |
| 23(H29-31) | 1-butyl-2,5-dioxo-3-cyclohexylmethyl-9-(5-(4-chlorophenyl)furan-2-ylmethyl)-1,4,9-triazaspiro[5.6]undecane |

TABLE 30A-1

| Example No | Compound Name |
|---|---|
| 23(H30-1) | 1-(2-methoxyethyl)-2,5-dioxo-3-cyclohexylmethyl-9-(1,4-benzodioxan-6-ylmethyl)-1,4,9-triazaspiro[5.5]undecane |
| 23(H30-2) | 1-(2-methoxyethyl)-2,5-dioxo-3-cyclohexylmethyl-9-(3,5-dimethyl-1-phenylpyrazol-4-ylmethyl)-1,4,9-triazaspiro[5.5]undecane |
| 23(H30-3) | 1-(2-methoxyethyl)-2,5-dioxo-3-cyclohexylmethyl-9-(5-methylfuran-2-ylmethyl)-1,4,9-triazaspiro[5.5]undecane |
| 23(H30-4) | 1-(2-methoxyethyl)-2,5-dioxo-3-cyclohexylmethyl-9-(5-bromothiophen-2-ylmethyl)-1,4,9-triazaspiro[5.5]undecane |
| 23(H30-5) | 1-(2-methoxyethyl)-2,5-dioxo-3-cyclohexylmethyl-9-(3-methylthiophen-2-ylmethyl)-1,4,9-triazaspiro[5.5]undecane |
| 23(H30-6) | 1-(2-methoxyethyl)-2,5-dioxo-3-cyclohexylmethyl-9-(5-ethylfuran-2-ylmethyl)-1,4,9-triazaspiro[5.5]undecane |
| 23(H30-7) | 1-(2-methoxyethyl)-2,5-dioxo-3-cyclohexylmethyl-9-(pyridin-4-ylmethyl)-1,4,9-triazaspiro[5.5]undecane |
| 23(H30-8) | 1-(2-methoxyethyl)-2,5-dioxo-3-cyclohexylmethyl-9-(1-methylindol-3-ylmethyl)-1,4,9-triazaspiro[5.5]undecane |

TABLE 30A-2

| Example No | Compound Name |
|---|---|
| 23(H30-9) | 1-(2-methoxyethyl)-2,5-dioxo-3-cyclohexylmethyl-9-(4-methylimidazol-5-ylmethyl)-1,4,9-triazaspiro[5.5]undecane |
| 23(H30-10) | 1-(2-methoxyethyl)-2,5-dioxo-3-cyclohexylmethyl-9-(2,4-dioxo-1,3-dihydropyrimidin-5-ylmethyl)-1,4,9-triazaspiro[5.5]undecane |

TABLE 30A-2-continued

| Example No | Compound Name |
|---|---|
| 23(H30-11) | 1-(2-methoxyethyl)-2,5-dioxo-3-cyclohexylmethyl-9-(5-(2-chlorophenyl)furan-2-ylmethyl)-1,4,9-triazaspiro[5.5]undecane |
| 23(H30-12) | 1-(2-methoxyethyl)-2,5-dioxo-3-cyclohexylmethyl-9-(5-(3-chlorophenyl)furan-2-ylmethyl)-1,4,9-triazaspiro[5.5]undecane |
| 23(H30-13) | 1-(2-methoxyethyl)-2,5-dioxo-3-cyclohexylmethyl-9-(indol-3-ylmethyl)-1,4,9-triazaspiro[5.5]undecane |
| 23(H30-14) | 1-(2-methoxyethyl)-2,5-dioxo-3-cyclohexylmethyl-9-(5-(hydroxymethyl)furan-2-ylmethyl)-1,4,9-triazaspiro[5.5]undecane |
| 23(H30-15) | 1-(2-methoxyethyl)-2,5-dioxo-3-cyclohexylmethyl-9-(5-(carboxy)thiophen-2-ylmethyl)-1,4,9-triazaspiro[5.5]undecane |

TABLE 30A-3

| Example No | Compound Name |
|---|---|
| 23(H30-16) | 1-(2-methoxyethyl)-2,5-dioxo-3-cyclohexylmethyl-9-(5-(carboxy)furan-2-ylmethyl)-1,4,9-triazaspiro[5.5]undecane |
| 23(H30-17) | 1-(2-methoxyethyl)-2,5-dioxo-3-cyclohexylmethyl-9-(5-ethylthiophen-2-ylmethyl)-1,4,9-triazaspiro[5.5]undecane |
| 23(H30-18) | 1-(2-methoxyethyl)-2,5-dioxo-3-cyclohexylmethyl-9-(1-methylbenzimidazol-2-ylmethyl)-1,4,9-triazaspiro[5.5]undecane |
| 23(H30-19) | 1-(2-methoxyethyl)-2,5-dioxo-3-cyclohexylmethyl-9-(5-(2-trifluoromethoxyphenyl)furan-2-ylmethyl)-1,4,9-triazaspiro[5.5]undecane |
| 23(H30-20) | 1-(2-methoxyethyl)-2,5-dioxo-3-cyclohexylmethyl-9-(6-(methoxycarbonyl)indol-3-ylmethyl)-1,4,9-triazaspiro[5.5]undecane |
| 23(H30-21) | 1-(2-methoxyethyl)-2,5-dioxo-3-cyclohexylmethyl-9-(5-(2,6-dichloro-4-trifluoromethylphenyl)furan-2-ylmethyl)-1,4,9-triazaspiro[5.5]undecane |
| 23(H30-22) | 1-(2-methoxyethyl)-2,5-dioxo-3-cyclohexylmethyl-9-(4-bromothiophen-2-ylmethyl)-1,4,9-triazaspiro[5.5]undecane |

TABLE 30A-4

| Example No | Compound Name |
|---|---|
| 23(H30-23) | 1-(2-methoxyethyl)-2,5-dioxo-3-cyclohexylmethyl-9-(5-(2-chloro-5-trifluoromethylphenyl)furan-2-ylmethyl)-1,4,9-triazaspiro[5.5]undecane |

TABLE 30A-4-continued

| Example No | Compound Name |
|---|---|
| 23(H30-24) | 1-(2-methoxyethyl)-2,5-dioxo-3-cyclohexylmethyl-9-(5-(3-trifluoromethylphenyl)furan-2-ylmethyl)-1,4,9-triazaspiro[5.5]undecane |
| 23(H30-25) | 1-(2-methoxyethyl)-2,5-dioxo-3-cyclohexylmethyl-9-(1-acetylindol-3-ylmethyl)-1,4,9-triazaspiro[5.5]undecane |
| 23(H30-26) | 1-(2-methoxyethyl)-2,5-dioxo-3-cyclohexylmethyl-9-(5-(3,5-bis(trifluoromethyl)phenyl)furan-2-ylmethyl)-1,4,9-triazaspiro[5.5]undecane |
| 23(H30-27) | 1-(2-methoxyethyl)-2,5-dioxo-3-cyclohexylmethyl-9-(5-chloro-3-methyl-1 -phenylpyrazol-4-ylmethyl)-1,4,9-triazaspiro[5.5]undecane |
| 23(H30-28) | 1-(2-methoxyethyl)-2,5-dioxo-3-cyclohexylmethyl-9-(5-(4-methoxyphenyl)thiophen-2-ylmethyl)-1,4,9-triazaspiro[5.5]undecane |
| 23(H30-29) | 1-(2-methoxyethyl)-2,5-dioxo-3-cyclohexylmethyl-9-(5-(2-trifluoromethylphenyl)furan-2-ylmethyl)-1,4,9-triazaspiro[5.5]undecane |

TABLE 30A-5

| Example No | Compound Name |
|---|---|
| 23(H30-30) | 1-(2-methoxyethyl)-2,5-dioxo-3-cyclohexylmethyl-9-(2,5-dimethyl-1-(4-carboxyphenyl)pyrrol-3-ylmethyl)-1,4,9-triazaspiro[5.5]undecane |
| 23(H30-31) | 1-(2-methoxyethyl)-2,5-dioxo-3-cyclohexylmethyl-9-(5-(4-chlorophenyl)furan-2-ylmethyl)-1,4,9-triazaspiro[5.6]undecane |

TABLE 31A-1

| Example No | Compound Name |
|---|---|
| 23(H31-1) | 1-benzyl-2,5-dioxo-3-cyclohexylmethyl-9-(1,4-benzodioxan-6-ylmethyl)-1,4,9-triazaspiro[5.5]undecane |
| 23(H31-2) | 1-benzyl-2,5-dioxo-3-cyclohexylmethyl-9-(3,5-dimethyl-1-phenylpyrazol-4-ylmethyl)-1,4,9-triazaspiro[5.5]undecane |
| 23(H31-3) | 1-benzyl-2,5-dioxo-3-cyclohexylmethyl-9-(5-methylfuran-2-ylmethyl)-1,4,9-triazaspiro[5.5]undecane |
| 23(H31-4) | 1-benzyl-2,5-dioxo-3-cyclohexylmethyl-9-(5-bromothiophen-2-ylmethyl)-1,4,9-triazaspiro[5.5]undecane |
| 23(H31-5) | 1-benzyl-2,5-dioxo-3-cyclohexylmethyl-9-(3-methylthiophen-2-ylmethyl)-1,4,9-triazaspiro[5.5]undecane |
| 23(H31-6) | 1-benzyl-2,5-dioxo-3-cyclohexylmethyl-9-(5-ethylfuran-2-ylmethyl)-1,4,9-triazaspiro[5.5]undecane |
| 23(H31-7) | 1-benzyl-2,5-dioxo-3-cyclohexylmethyl-9-(pyridin-4-ylmethyl)-1,4,9-triazaspiro[5.5]undecane |
| 23(H31-8) | 1-benzyl-2,5-dioxo-3-cyclohexylmethyl-9-(1-methylindol-3-ylmethyl)-1,4,9-triazaspiro[5.5]undecane |

TABLE 31A-1-continued

| Example No | Compound Name |
|---|---|
| 23(H31-9) | 1-benzyl-2,5-dioxo-3-cyclohexylmethyl-9-(4-methylimidazol-5-ylmethyl)-1,4,9-triazaspiro[5.5]undecane |

TABLE 31A-2

| Example No | Compound Name |
|---|---|
| 23(H31-10) | 1-benzyl-2,5-dioxo-3-cyclohexylmethyl-9-(2,4-dioxo-1,3-dihydropyrimidin-5-ylmethyl)-1,4,9-triazaspiro[5.5]undecane |
| 23(H31-11) | 1-benzyl-2,5-dioxo-3-cyclohexylmethyl-9-(5-(2-chlorophenyl)furan-2-ylmethyl)-1,4,9-triazaspiro[5.5]undecane |
| 23(H31-12) | 1-benzyl-2,5-dioxo-3-cyclohexylmethyl-9-(5-(3-chlorophenyl)furan-2-ylmethyl)-1,4,9-triazaspiro[5.5]undecane |
| 23(H31-13) | 1-benzyl-2,5-dioxo-3-cyclohexylmethyl-9-(indol-3-ylmethyl)-1,4,9-triazaspiro[5.5]undecane |
| 23(H31-14) | 1-benzyl-2,5-dioxo-3-cyclohexylmethyl-9-(5-(hydroxymethyl)furan-2-ylmethyl)-1,4,9-triazaspiro[5.5]undecane |
| 23(H31-15) | 1-benzyl-2,5-dioxo-3-cyclohexylmethyl-9-(5-(carboxy)thiophen-2-ylmethyl)-1,4,9-triazaspiro[5.5]undecane |
| 23(H31-16) | 1-benzyl-2,5-dioxo-3-cyclohexylmethyl-9-(5-(carboxy)furan-2-ylmethyl)-1,4,9-triazaspiro[5.5]undecane |
| 23(H31-17) | 1-benzyl-2,5-dioxo-3-cyclohexylmethyl-9-(5-ethylthiophen-2-ylmethyl)-1,4,9-triazaspiro[5.5]undecane |
| 23(H31-18) | 1-benzyl-2,5-dioxo-3-cyclohexylmethyl-9-(1-methylbenzimidazol-2-ylmethyl)-1,4,9-triazaspiro[5.5]undecane |

TABLE 31A-3

| Example No | Compound Name |
|---|---|
| 23(H31-19) | 1-benzyl-2,5-dioxo-3-cyclohexylmethyl-9-(5-(2-trifluoromethoxyphenyl)furan-2-ylmethyl)-1,4,9-triazaspiro[5.5]undecane |
| 23(H31-20) | 1-benzyl-2,5-dioxo-3-cyclohexylmethyl-9-(6-(methoxycarbonyl)indol-3-ylmethyl)-1,4,9-triazaspiro[5.5]undecane |
| 23(H31-21) | 1-benzyl-2,5-dioxo-3-cyclohexylmethyl-9-(5-(2,6-dichloro-4-trifluoromethylphenyl)furan-2-ylmethyl)-1,4,9-triazaspiro[5.5]undecane |
| 23(H31-22) | 1-benzyl-2,5-dioxo-3-cyclohexylmethyl-9-(4-bromothiophen-2-ylmethyl)-1,4,9-triazaspiro[5.5]undecane |
| 23(H31-23) | 1-benzyl-2,5-dioxo-3-cyclohexylmethyl-9-(5-(2-chloro-5-trifluoromethylphenyl)furan-2-ylmethyl)-1,4,9-triazaspiro[5.5]undecane |
| 23(H31-24) | 1-benzyl-2,5-dioxo-3-cyclohexylmethyl-9-(5-(3-trifluoromethylphenyl)furan-2-ylmethyl)-1,4,9-triazaspiro[5.5]undecane |
| 23(H31-25) | 1-benzyl-2,5-dioxo-3-cyclohexylmethyl-9-(1-acetylindol-3-ylmethyl)-1,4,9-triazaspiro[5.5]undecane |

TABLE 31A-4

| Example No | Compound Name |
|---|---|
| 23(H31-26) | 1-benzyl-2,5-dioxo-3-cyclohexylmethyl-9-(5-(3,5-bis(trifluoromethyl)phenyl)furan-2-ylmethyl)-1,4,9-triazaspiro[5.5]undecane |
| 23(H31-27) | 1-benzyl-2,5-dioxo-3-cyclohexylmethyl-9-(5-chloro-3-methyl-1-phenylpyrazol-4-ylmethyl)-1,4,9-triazaspiro[5.5]undecane |
| 23(H31-28) | 1-benzyl-2,5-dioxo-3-cyclohexylmethyl-9-(5-(4-methoxyphenyl)thiophen-2-ylmethyl)-1,4,9-triazaspiro[5.5]undecane |
| 23(H31-29) | 1-benzyl-2,5-dioxo-3-cyclohexylmethyl-9-(5-(2-trifluoromethylphenyl)furan-2-ylmethyl)-1,4,9-triazaspiro[5.5]undecane |
| 23(H31-30) | 1-benzyl-2,5-dioxo-3-cyclohexylmethyl-9-(2,5-dimethyl-1-(4-carboxyphenyl)pyrrol-3-ylmethyl)-1,4,9-triazaspiro[5.5]undecane |
| 23(H31-31) | 1-benzyl-2,5-dioxo-3-cyclohexylmethyl-9-(5-(4-chlorophenyl)furan-2-ylmethyl)-1,4,9-triazaspiro[5.6]undecane |

TABLE 22B-1

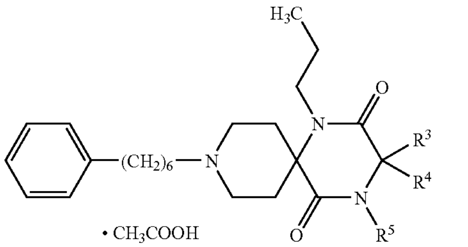

• $CH_3COOH$

| Example No | $R^3$ | $R^4$ | $R^5$ |
|---|---|---|---|
| 23(H22-1) | H | 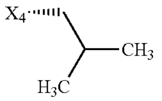 | H |
| 23(H22-2) | H | 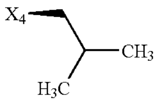 | H |
| 23(H22-3) | H | 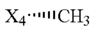 | H |
| 23(H22-4) | H | 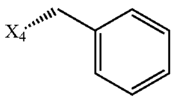 | H |
| 23(H22-5) | H | 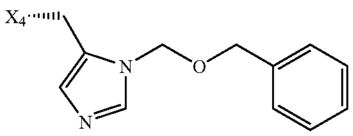 | H |

TABLE 22B-1-continued
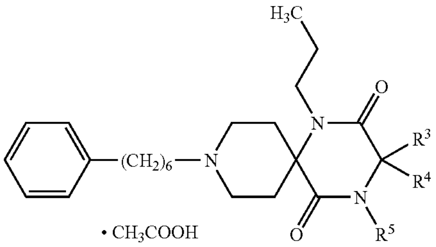
• $CH_3COOH$
| Example No | $R^3$ | $R^4$ | $R^5$ |
|---|---|---|---|
| 23(H22-6) | H | 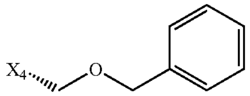 | H |
| 23(H22-7) | H | 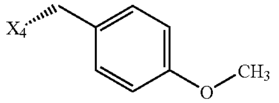 | H |
| 23(H22-8) | H | 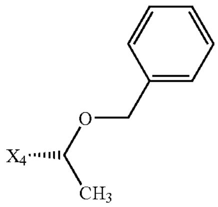 | H |
TABLE 22B-2
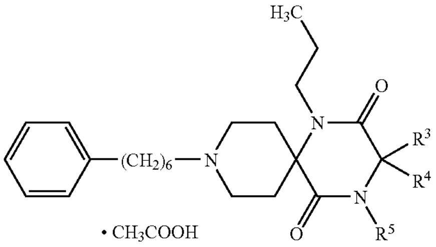
• $CH_3COOH$
| Example No | $R^3$ | $R^4$ | $R^5$ |
|---|---|---|---|
| 23(H22-9) | H | 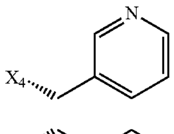 | H |
| 23(H22-10) | H | 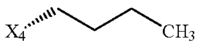 | H |
| 23(H22-11) | H | 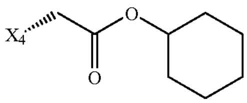 | H |
| 23(H22-12) | H | 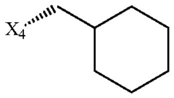 | H |
TABLE 22B-2-continued
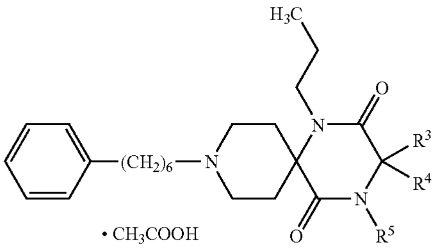
• $CH_3COOH$
| Example No | $R^3$ | $R^4$ | $R^5$ |
|---|---|---|---|
| 23(H22-13) | H | 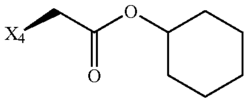 | H |
| 23(H22-14) | H | 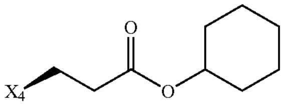 | H |
| 23(H22-15) | H | 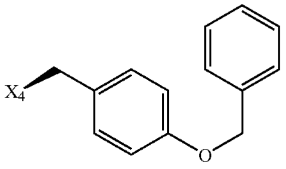 | H |
| 23(H22-16) | H | 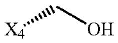 | H |
TABLE 22B-3
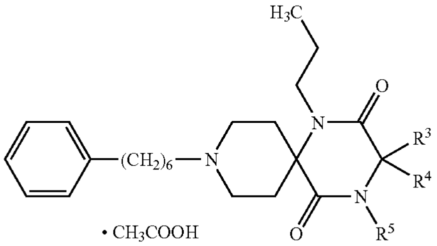
• $CH_3COOH$
| Example No | $R^3$ | $R^4$ | $R^5$ |
|---|---|---|---|
| 23(H22-17) | H | 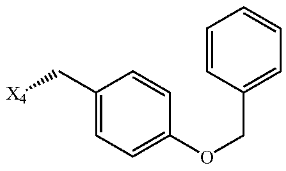 | H |
| 23(H22-18) | H | 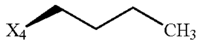 | H |
| 23(H22-19) | H | 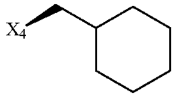 | H |

TABLE 22B-3-continued
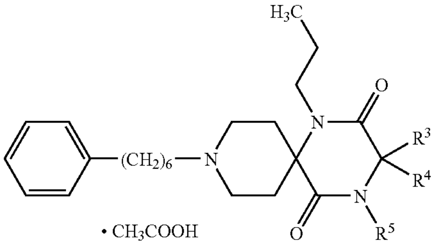
• $CH_3COOH$
| Example No | $R^3$ | $R^4$ | $R^5$ |
|---|---|---|---|
| 23(H22-20) | H | 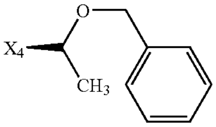 | H |
| 23(H22-21) | H | 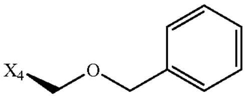 | H |
| 23(H22-22) | H | 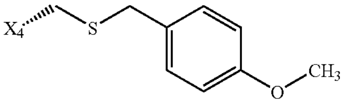 | H |
| 23(H22-23) | H | 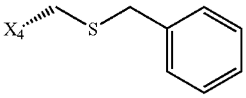 | H |
| 23(H22-24) | H | H | H |
TABLE 22B-4
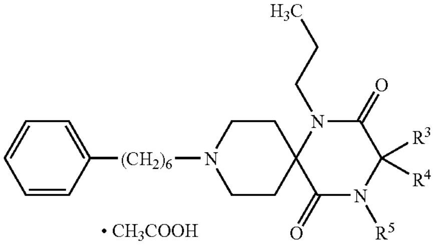
• $CH_3COOH$
| Example No | $R^3$ | $R^4$ | $R^5$ |
|---|---|---|---|
| 23(H22-25) | H | 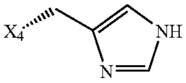 | H |
| 23(H22-26) | H | 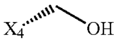 | H |
| 23(H22-27) | H | 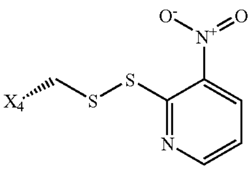 | H |
TABLE 22B-4-continued
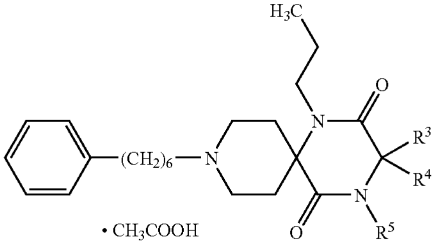
• $CH_3COOH$
| Example No | $R^3$ | $R^4$ | $R^5$ |
|---|---|---|---|
| 23(H22-28) | H | 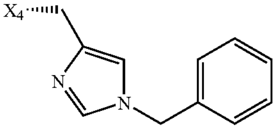 | H |
| 23(H22-29) | H | 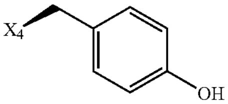 | H |
| 23(H22-30) | H | 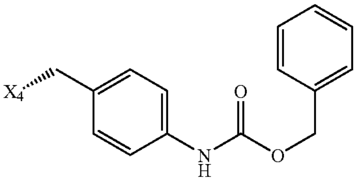 | H |
| 23(H22-31) | H | 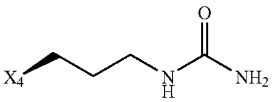 | H |
TABLE 22B-5
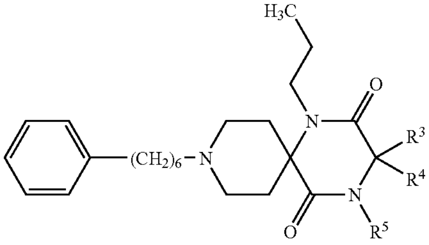
•$CH_3COOH$
| Example No | $R^3$ | $R^4$ | $R^5$ |
|---|---|---|---|
| 23(H22-32) | H | 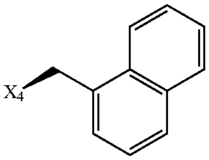 | H |

TABLE 22B-5-continued
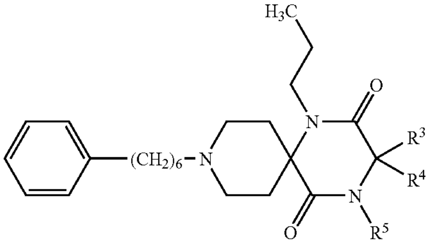
•$CH_3COOH$
| Example No | $R^3$ | $R^4$ | $R^5$ |
|---|---|---|---|
| 23(H22-33) | H | 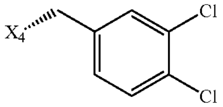 | H |
| 23(H22-34) | H | 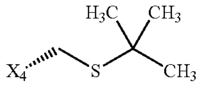 | H |
| 23(H22-35) | H | 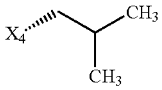 | $X_5$—$CH_3$ |
| 23(H22-36) | H | 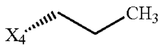 | H |
| 23(H22-37) | H | 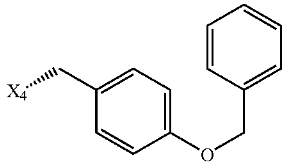 | $X_5$—$CH_3$ |
| 23(H22-38) | H | 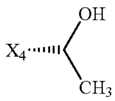 | H |
| 23(H22-39) | H | 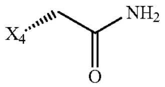 | H |
TABLE 22B-6
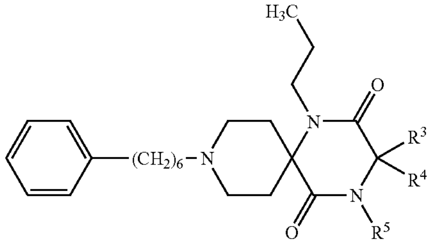
•$CH_3COOH$
| Example No | $R^3$ | $R^4$ | $R^5$ |
|---|---|---|---|
| 23(H22-40) | H | 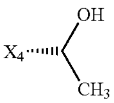 | H |
| 23(H22-41) | H | 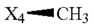 | H |
| 23(H22-42) | H | 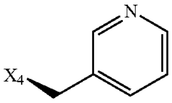 | H |
| 23(H22-43) | H | 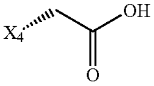 | H |
| 23(H22-44) | H | 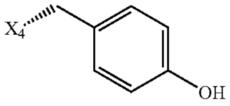 | H |
| 23(H22-45) | H | 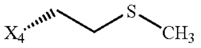 | H |
| 23(H22-46) | H | 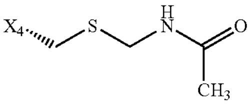 | H |
| 23(H22-47) | H | 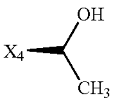 | H |
| 23(H22-48) | H | 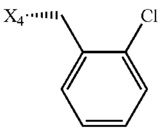 | H |

TABLE 22B-7
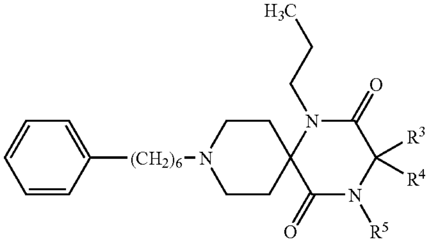
$\bullet CH_3COOH$
| Example No | $R^3$ | $R^4$ | $R^5$ |
|---|---|---|---|
| 23(H22-49) | H | 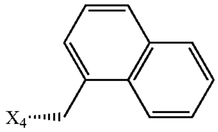 | H |
| 23(H22-50) | H | 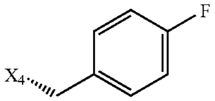 | H |
| 23(H22-51) | H | 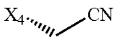 | H |
| 23(H22-52) | H | 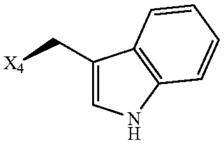 | H |
| 23(H22-53) | H | 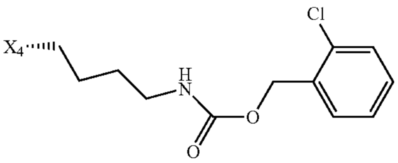 | H |
| 23(H22-54) | H | 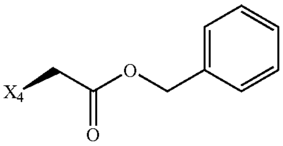 | H |
| 23(H22-55) | H | 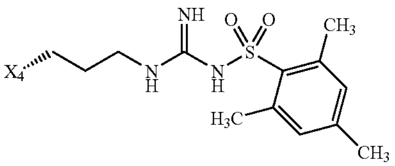 | H |
TABLE 22B-8
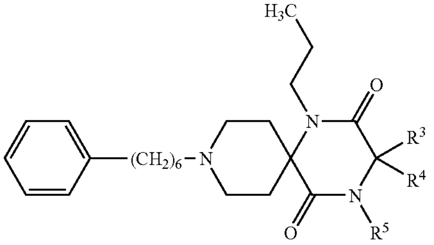
$\bullet CH_3COOH$
| Example No | $R^3$ | $R^4$ | $R^5$ |
|---|---|---|---|
| 23(H22-56) | H | 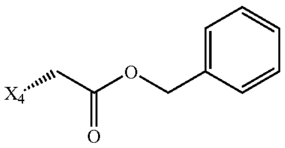 | H |
| 23(H22-57) | H | 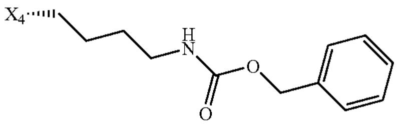 | H |
| 23(H22-58) | H | 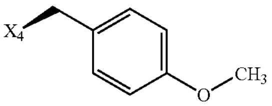 | H |
| 23(H22-59) | H | 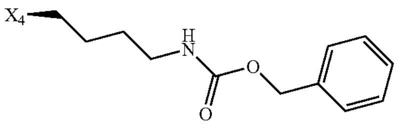 | H |
| 23(H22-60) | H | 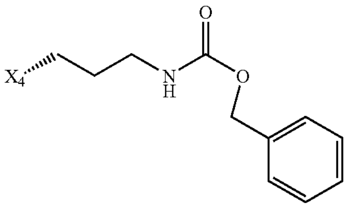 | H |
| 23(H22-61) | H | 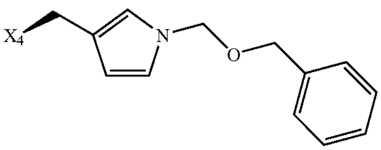 | H |

TABLE 22B-9
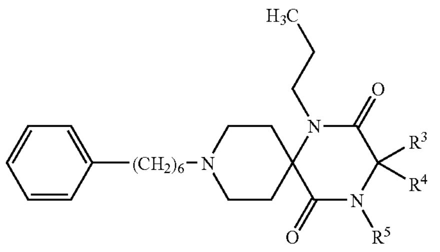
•$CH_3COOH$
| Example No | $R^3$ | $R^4$ | $R^5$ |
|---|---|---|---|
| 23(H22-62) | H | 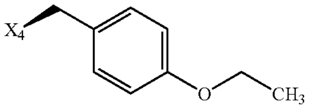 | H |
| 23(H22-63) | H | 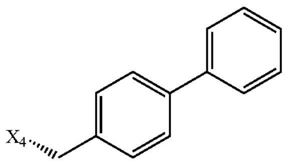 | H |
TABLE 22B-9-continued
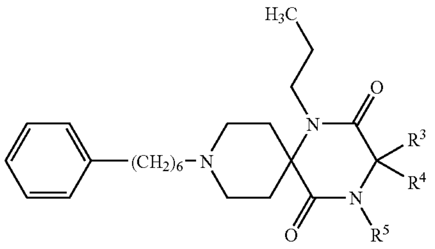
•$CH_3COOH$
| Example No | $R^3$ | $R^4$ | $R^5$ |
|---|---|---|---|
| 23(H22-64) | H | 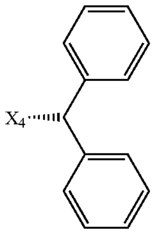 | H |
TABLE 23B-1
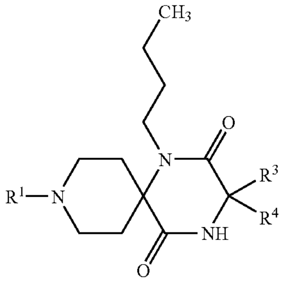
•$CH_3COOH$
| Example No | $R^1$ | $R^3$ | $R^4$ |
|---|---|---|---|
| 23(H23-1) | 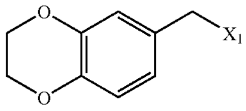 | H | 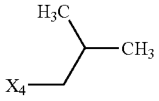 |
| 23(H23-2) | 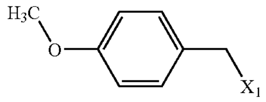 | H | 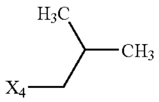 |
| 23(H23-3) | 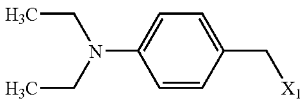 | H | 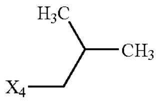 |

TABLE 23B-1-continued
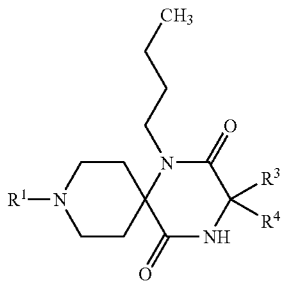
$\cdot CH_3COOH$
| Example No | $R^1$ | $R^3$ | $R^4$ |
| --- | --- | --- | --- |
| 23(H23-4) | 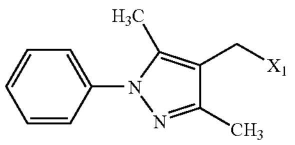 | H | 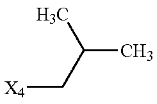 |
| 23(H23-5) | 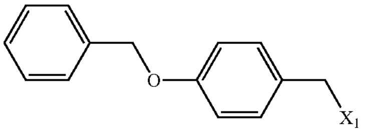 | H | 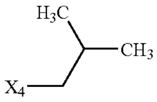 |
| 23(H23-6) | 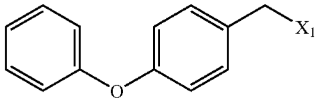 | H | 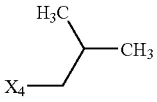 |
| 23(H23-7) | 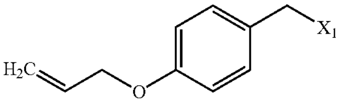 | H | 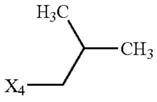 |
| 23(H23-8) | 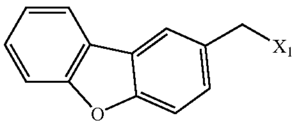 | H | 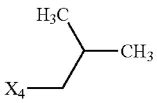 |

TABLE 23B-2
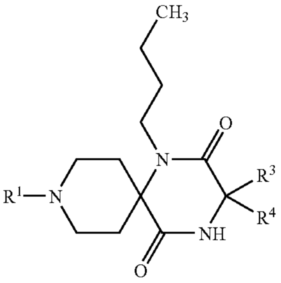
$\bullet CH_3COOH$
| Example No | $R^1$ | $R^3$ | $R^4$ |
| --- | --- | --- | --- |
| 23(H23-9) | 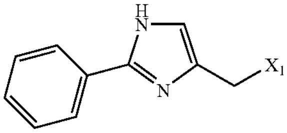 | H | 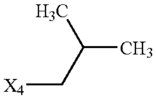 |
| 23(H23-10) | 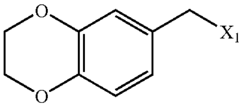 | H | 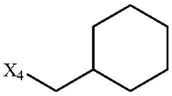 |
| 23(H23-11) | 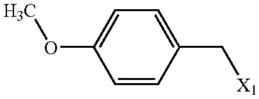 | H | 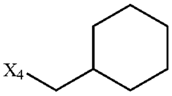 |
| 23(H23-12) | 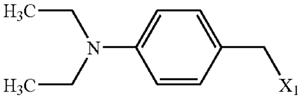 | H | 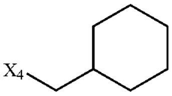 |
| 23(H23-13) | 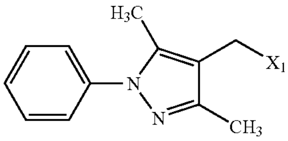 | H | 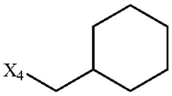 |
| 23(H23-14) | 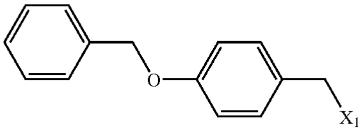 | H | 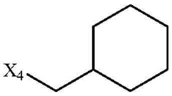 |
| 23(H23-15) | 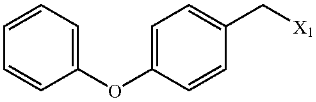 | H | 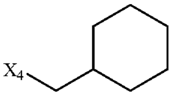 |

TABLE 23B-3
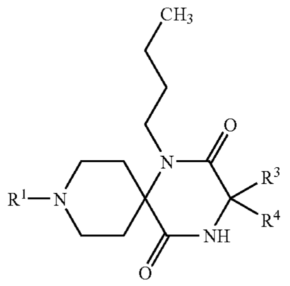
•$CH_3COOH$
| Example No | $R^1$ | $R^3$ | $R^4$ |
|---|---|---|---|
| 23(H23-16) | 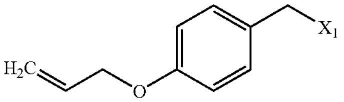 | H | 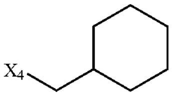 |
| 23(H23-17) | 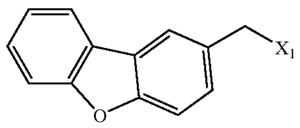 | H | 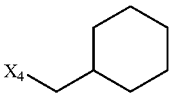 |
| 23(H23-18) | 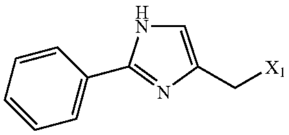 | H | 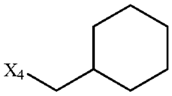 |
TABLE 24B-1
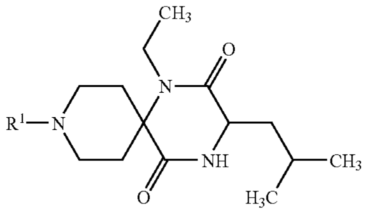
•$CH_3COOH$
| Example No | $R^1$ |
|---|---|
| 23(H24-1) | 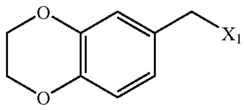 |
| 23(H24-2) | 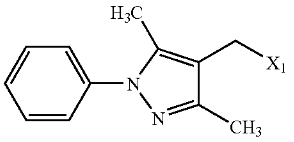 |
| 23(H24-3) | 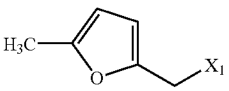 |
TABLE 24B-1-continued
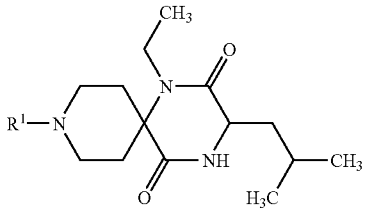
•$CH_3COOH$
| Example No | $R^1$ |
|---|---|
| 23(H24-4) | 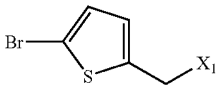 |
| 23(H24-5) | 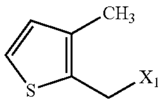 |
| 23(H24-6) | 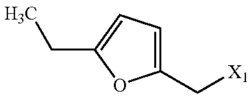 |

TABLE 24B-1-continued
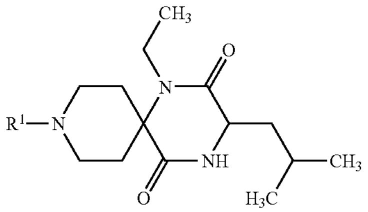
•$CH_3COOH$
| Example No | $R^1$ |
|---|---|
| 23(H24-7) | 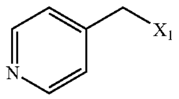 |
| 23(H24-8) | 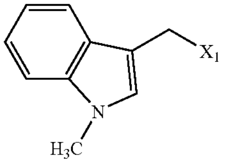 |
TABLE 24B-2
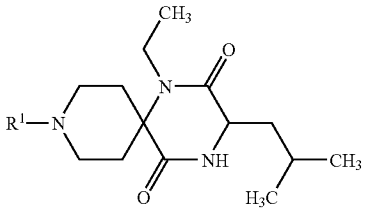
•$CH_3COOH$
| Example No | $R^1$ |
|---|---|
| 23(H24-9) | 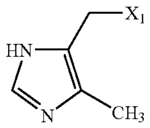 |
| 23(H24-10) | 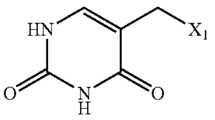 |
| 23(H24-11) | 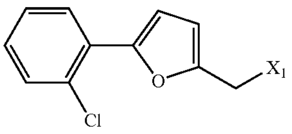 |
| 23(H24-12) | 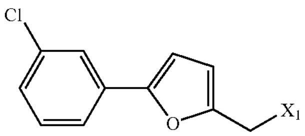 |
TABLE 24B-2-continued
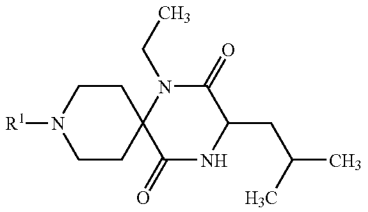
•$CH_3COOH$
| Example No | $R^1$ |
|---|---|
| 23(H24-13) | 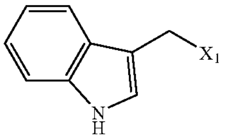 |
| 23(H24-14) | 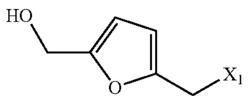 |
| 23(H24-15) | 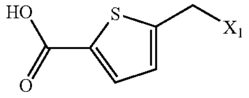 |
| 23(H24-16) | 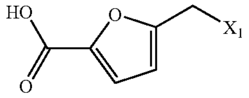 |
TABLE 24B-3
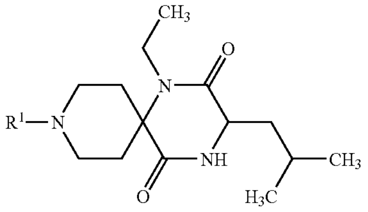
•$CH_3COOH$
| Example No | $R^1$ |
|---|---|
| 23(H24-17) | 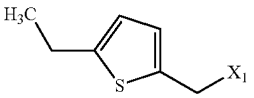 |
| 23(H24-18) | 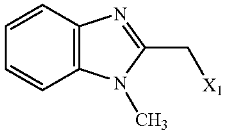 |

TABLE 24B-3-continued
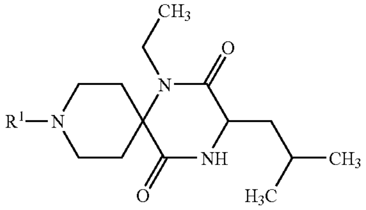
•$CH_3COOH$
| Example No | $R^1$ |
| --- | --- |
| 23(H24-19) | 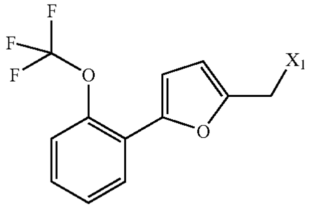 |
| 23(H24-20) | 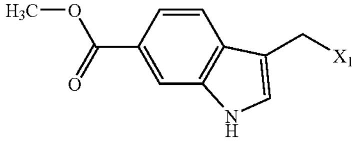 |
| 23(H24-21) | 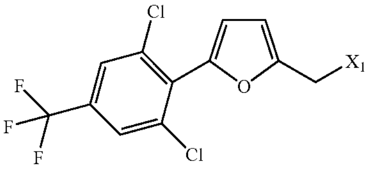 |
| 23(H24-22) | 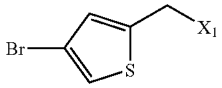 |
TABLE 24B-4
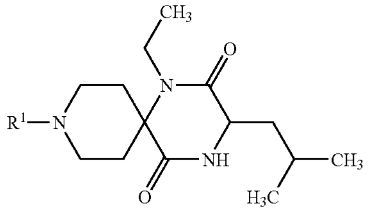
•$CH_3COOH$
| Example No | $R^1$ |
| --- | --- |
| 23(H24-23) | 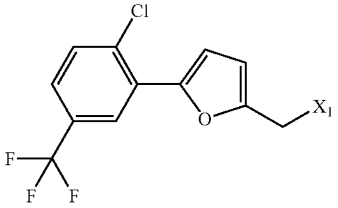 |
| 23(H24-24) | 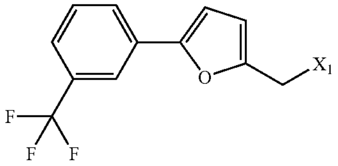 |
| 23(H24-25) | 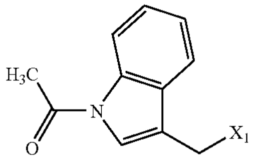 |
| 23(H24-26) | 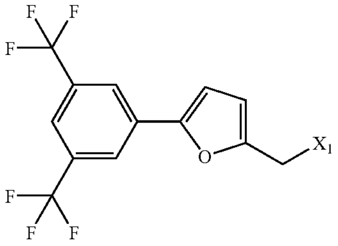 |
| 23(H24-27) | 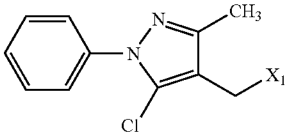 |
| 23(H24-28) | 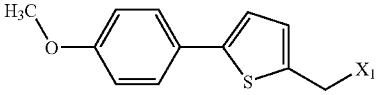 |

TABLE 24B-5
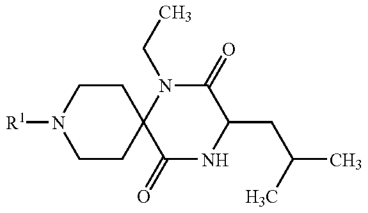
$\cdot CH_3COOH$
| Example No | $R^1$ |
|---|---|
| 23(H24-29) | 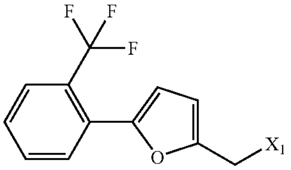 |
| 23(H24-30) | 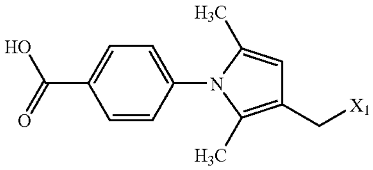 |
| 23(H24-31) | 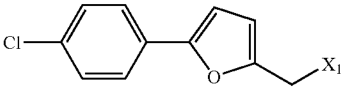 |
TABLE 25B-1
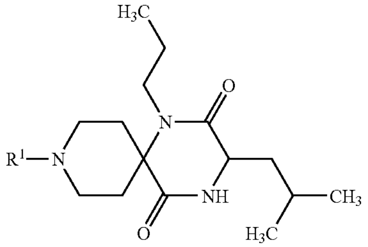
$\cdot CH_3COOH$
| Example No | $R^1$ |
|---|---|
| 23(H25-1) | 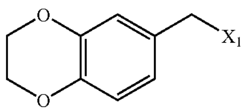 |
| 23(H25-2) | 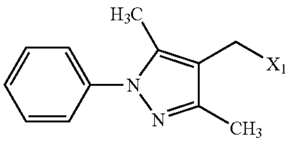 |
| 23(H25-3) | 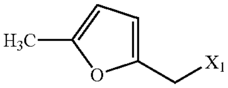 |
TABLE 25B-1-continued
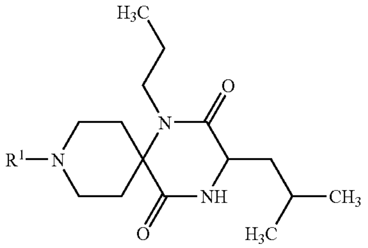
$\cdot CH_3COOH$
| Example No | $R^1$ |
|---|---|
| 23(H25-4) | 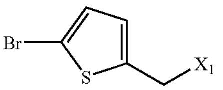 |
| 23(H25-5) | 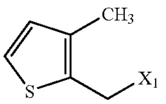 |
| 23(H25-6) | 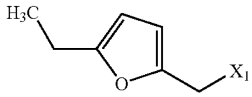 |
| 23(H25-7) | 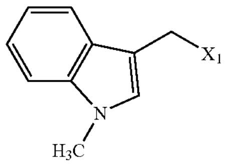 |
| 23(H25-8) | 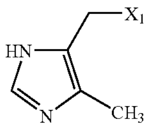 |
TABLE 25B-2
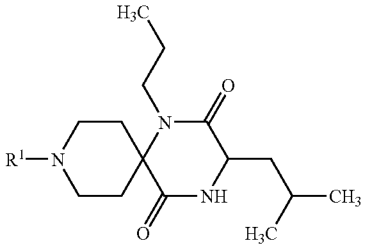
$\cdot CH_3COOH$
| Example No | $R^1$ |
|---|---|
| 23(H25-9) | 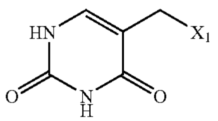 |

TABLE 25B-2-continued
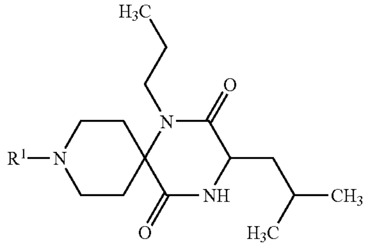
•$CH_3COOH$
| Example No | $R^1$ |
| --- | --- |
| 23(H25-10) | 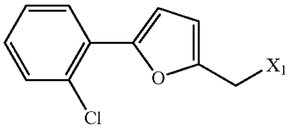 |
| 23(H25-11) | 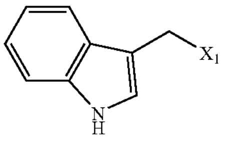 |
| 23(H25-12) | 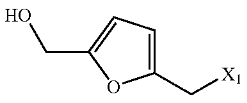 |
| 23(H25-13) | 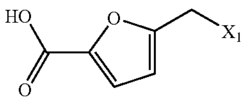 |
| 23(H25-14) | 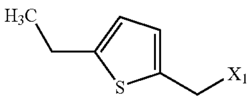 |
| 23(H25-15) | 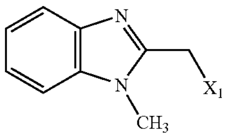 |
TABLE 25B-3
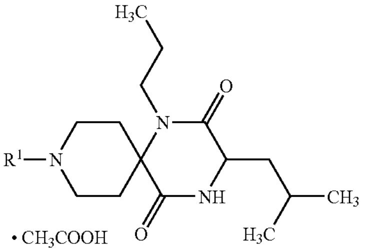
• $CH_3COOH$
| Example No | $R^1$ |
| --- | --- |
| 23(H25-16) | 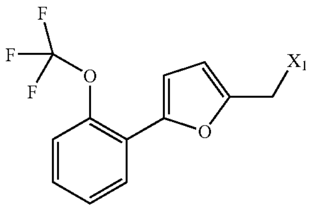 |
| 23(H25-17) | 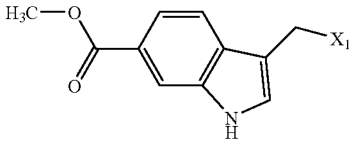 |
| 23(H25-18) | 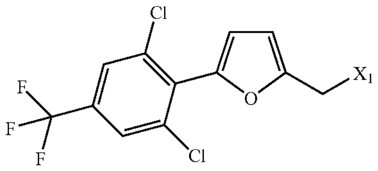 |
| 23(H25-19) | 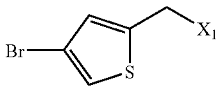 |
| 23(H25-20) | 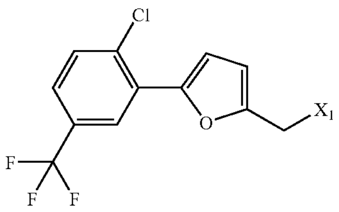 |
| 23(H25-21) | 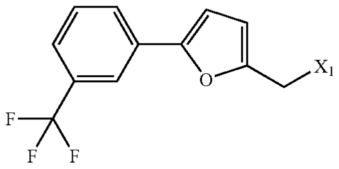 |

TABLE 25B-4
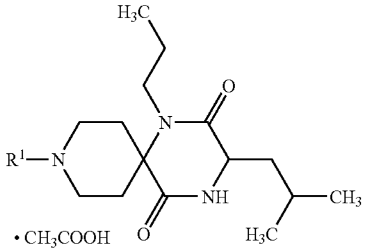
| Example No | $R^1$ |
| --- | --- |
| 23(H25-22) | 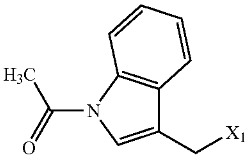 |
| 23(H25-23) | 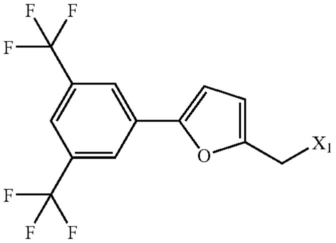 |
| 23(H25-24) | 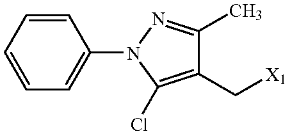 |
| 23(H25-25) | 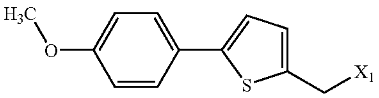 |
| 23(H25-26) | 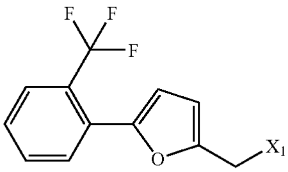 |
| 23(H25-27) | 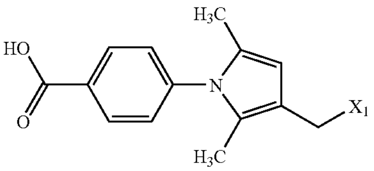 |
TABLE 25B-5
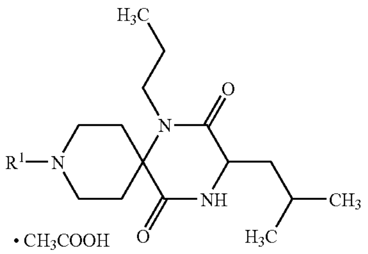
| Example No | $R^1$ |
| --- | --- |
| 23(H25-28) | 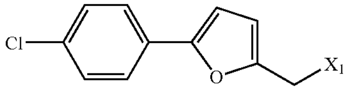 |
TABLE 26B-1
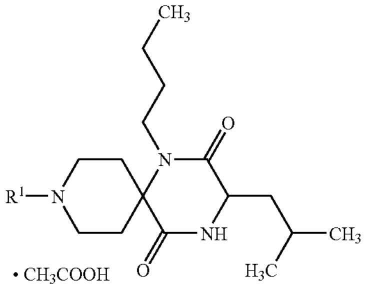
| Example No | $R^1$ |
| --- | --- |
| 23(H26-1) | 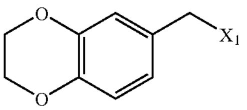 |
| 23(H26-2) | 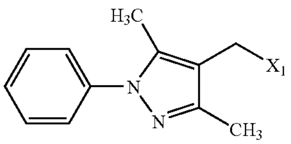 |
| 23(H26-3) | 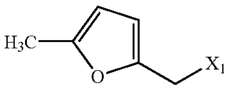 |
| 23(H26-4) | 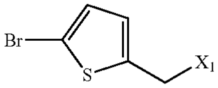 |
| 23(H26-5) | 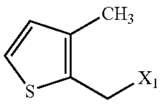 |
| 23(H26-6) | 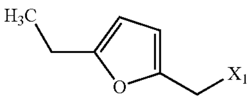 |

TABLE 26B-1-continued
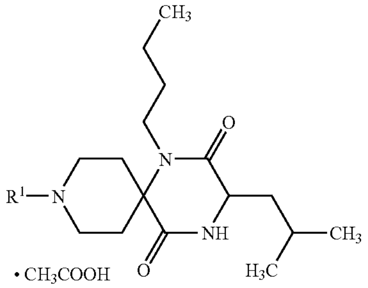
| Example No | $R^1$ |
|---|---|
| 23(H26-7) | 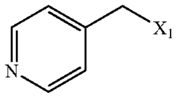 |
| 23(H26-8) | 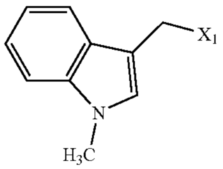 |
TABLE 26B-2
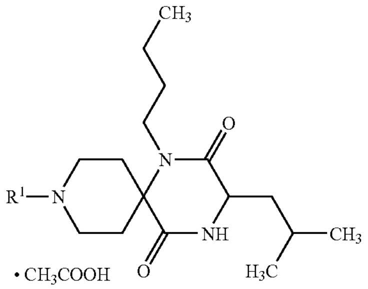
| Example No | $R^1$ |
|---|---|
| 23(H26-9) | 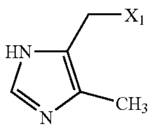 |
| 23(H26-10) | 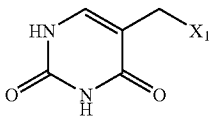 |
| 23(H26-11) | 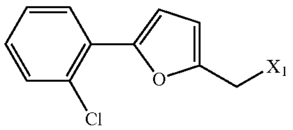 |
TABLE 26B-2-continued
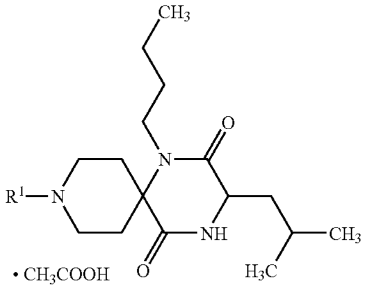
| Example No | $R^1$ |
|---|---|
| 23(H26-12) | 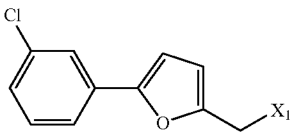 |
| 23(H26-13) | 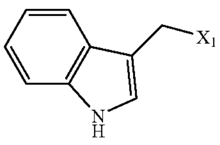 |
| 23(H26-14) | 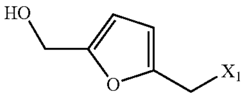 |
| 23(H26-15) | 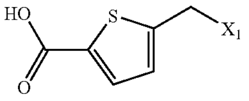 |
TABLE 26B-3
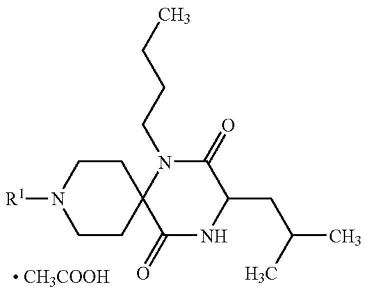
| Example No | $R^1$ |
|---|---|
| 23(H26-16) | 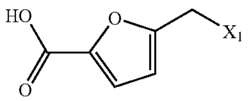 |
| 23(H26-17) | 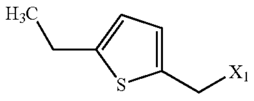 |

TABLE 26B-3-continued
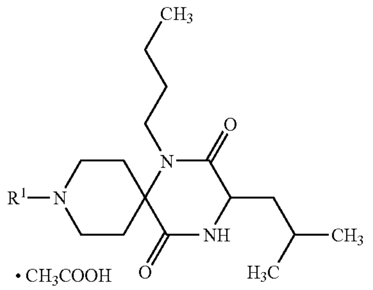
| Example No | $R^1$ |
|---|---|
| 23(H26-18) | 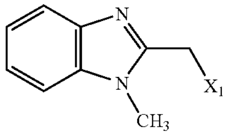 |
| 23(H26-19) | 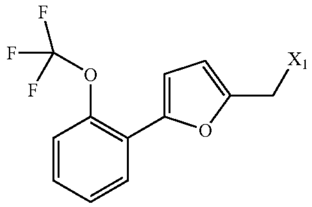 |
| 23(H26-20) | 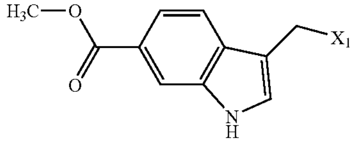 |
| 23(H26-21) | 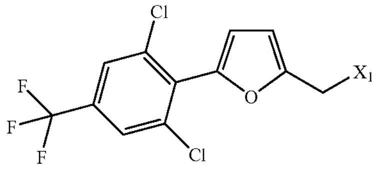 |
| 23(H26-22) | 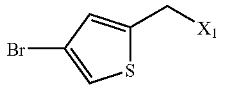 |
TABLE 26B-4
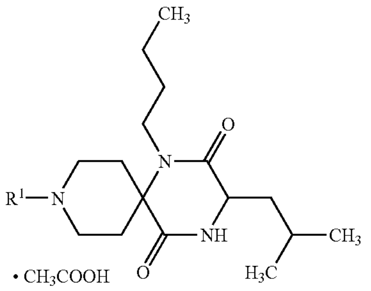
| Example No | $R^1$ |
|---|---|
| 23(H26-23) | 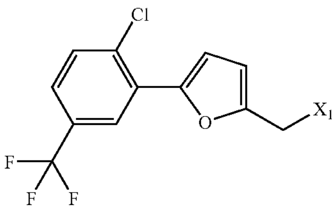 |
| 23(H26-24) | 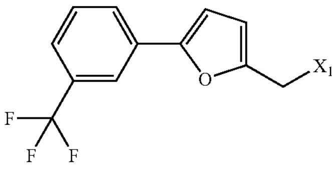 |
| 23(H26-25) | 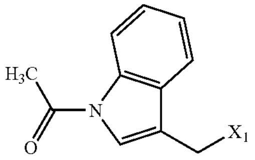 |
| 23(H26-26) | 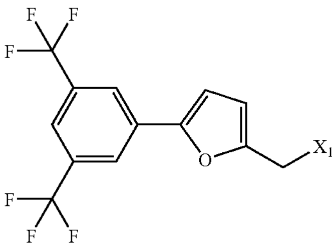 |
| 23(H26-27) | 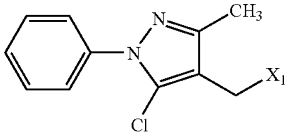 |

TABLE 26B-5
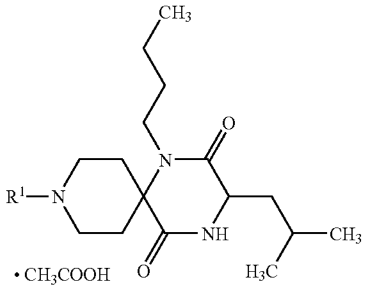
| Example No | $R^1$ |
|---|---|
| 23(H26-28) | 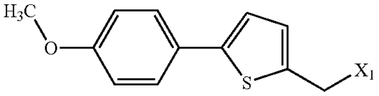 |
| 23(H26-29) | 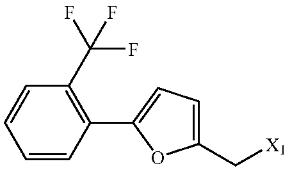 |
TABLE 26B-5-continued
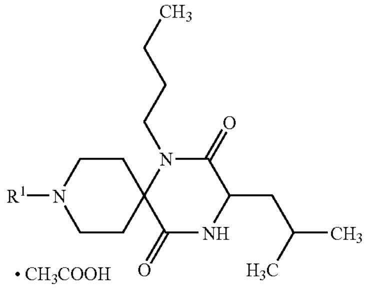
| Example No | $R^1$ |
|---|---|
| 23(H26-30) | 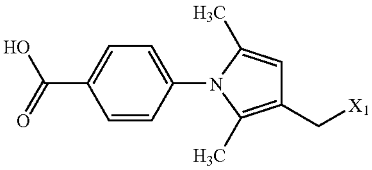 |
| 23(H26-31) | 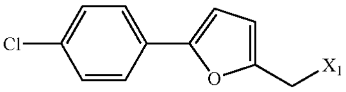 |
TABLE 27B-1
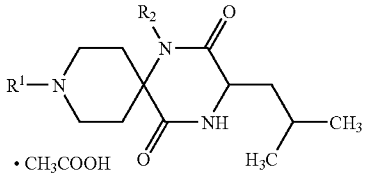
| Example No | $R^1$ | $R^2$ |
|---|---|---|
| 23(H27-1) | 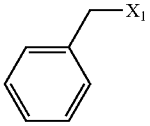 | 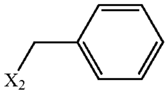 |
| 23(H27-2) | 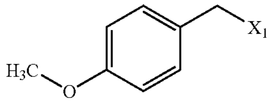 | 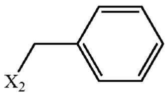 |
| 23(H27-3) | 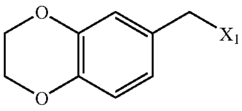 | 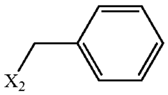 |
| 23(H27-4) | 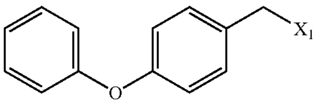 | 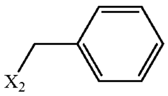 |

TABLE 27B-1-continued
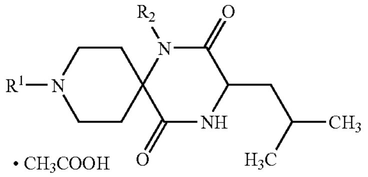
• $CH_3COOH$
| Example No | $R^1$ | $R^2$ |
|---|---|---|
| 23(H27-5) | 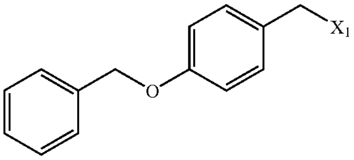 | 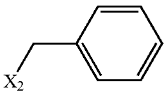 |
| 23(H27-6) | 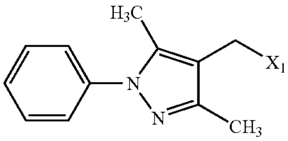 | 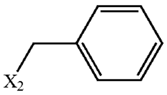 |
| 23(H27-7) | 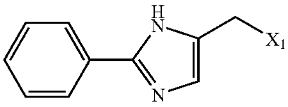 | 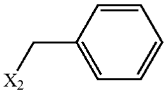 |
| 23(H27-8) | 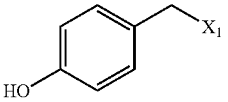 | 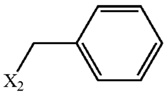 |
TABLE 27B-2
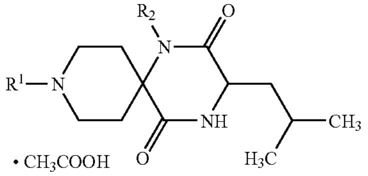
• $CH_3COOH$
| Example No | $R^1$ | $R^2$ |
|---|---|---|
| 23(H27-9) | 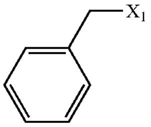 | 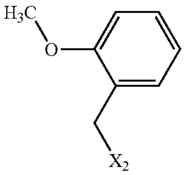 |
| 23(H27-10) | 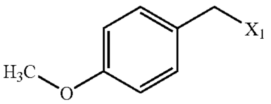 | 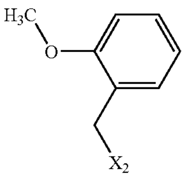 |

TABLE 27B-2-continued
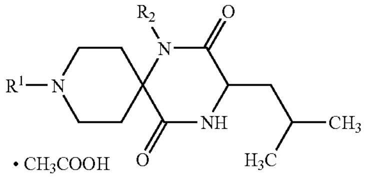
• $CH_3COOH$
| Example No | $R^1$ | $R^2$ |
| --- | --- | --- |
| 23(H27-11) | 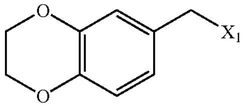 | 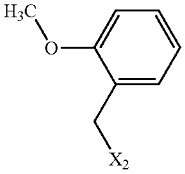 |
| 23(H27-12) | 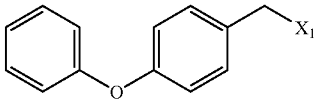 | 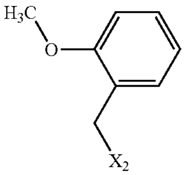 |
| 23(H27-13) | 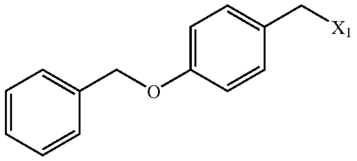 | 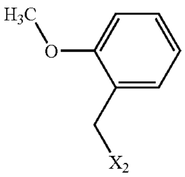 |
| 23(H27-14) | 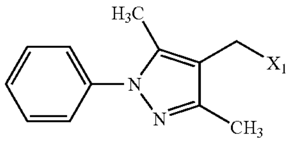 | 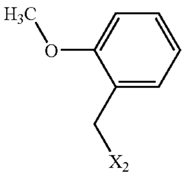 |
TABLE 27B-3
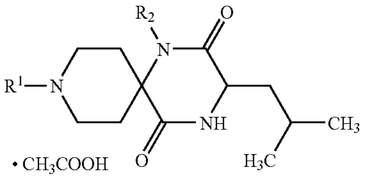
• $CH_3COOH$
| Example No | $R^1$ | $R^2$ |
| --- | --- | --- |
| 23(H27-15) | 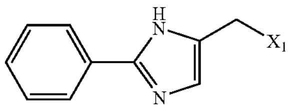 | 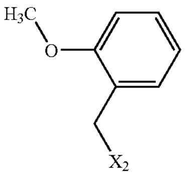 |

TABLE 27B-3-continued
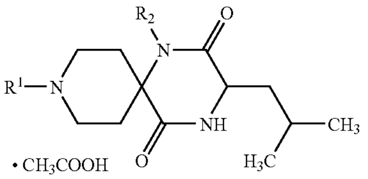
$\cdot CH_3COOH$
| Example No | $R^1$ | $R^2$ |
| --- | --- | --- |
| 23(H27-16) | 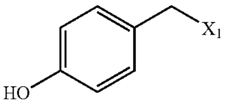 | 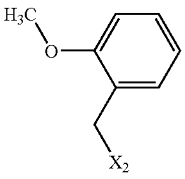 |
| 23(H27-17) | 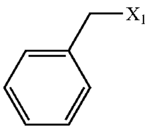 | 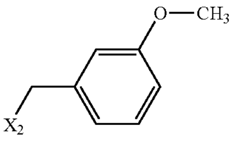 |
| 23(H27-18) | 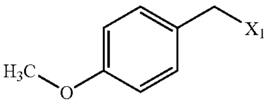 | 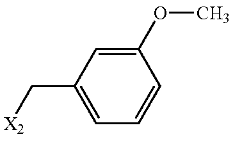 |
| 23(H27-19) | 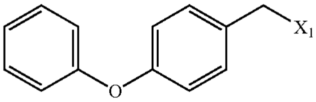 | 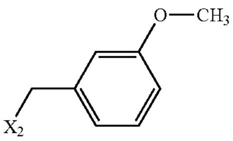 |
| 23(H27-20) | 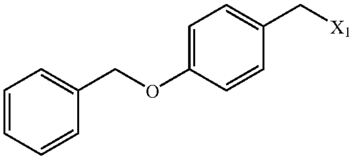 | 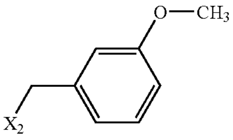 |
| 23(H27-21) | 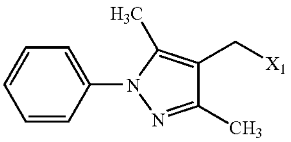 | 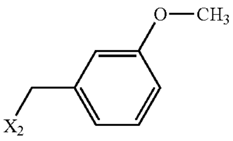 |

TABLE 27B-4
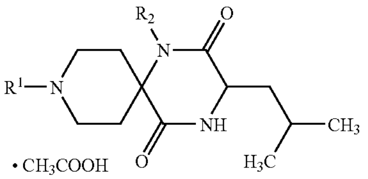
• $CH_3COOH$
| Example No | $R^1$ | $R^2$ |
| --- | --- | --- |
| 23(H27-22) | 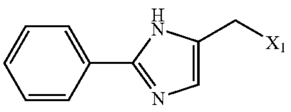 | 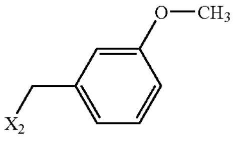 |
| 23(H27-23) | 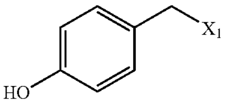 | 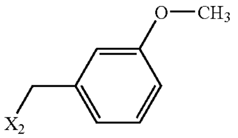 |
| 23(H27-24) | 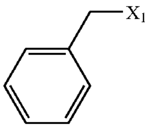 | 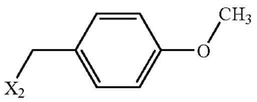 |
| 23(H27-25) | 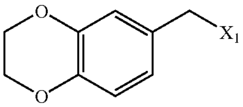 | 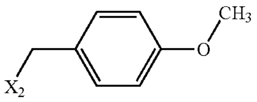 |
| 23(H27-26) | 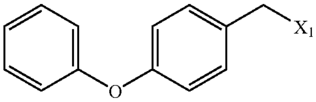 | 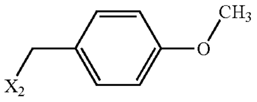 |
| 23(H27-27) | 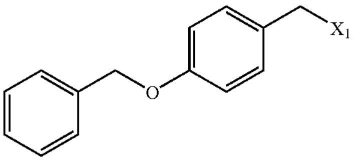 | 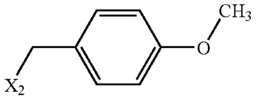 |
| 23(H27-28) | 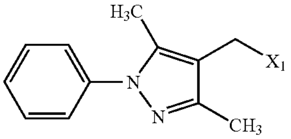 | 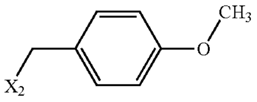 |
| 23(H27-29) | 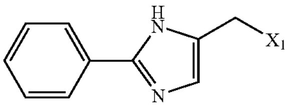 | 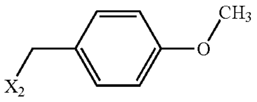 |

TABLE 27B-5
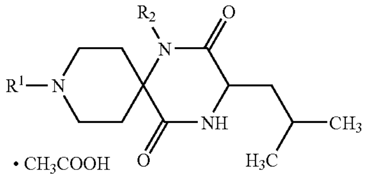
• $CH_3COOH$
| Example No | $R^1$ | $R^2$ |
|---|---|---|
| 23(H27-30) | 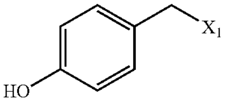 | 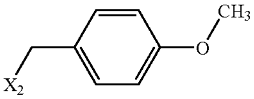 |
| 23(H27-31) | 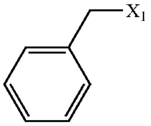 | 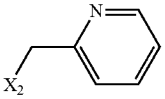 |
| 23(H27-32) | 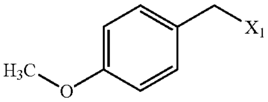 | 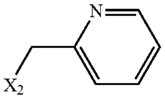 |
| 23(H27-33) | 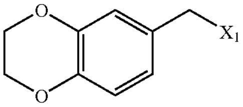 | 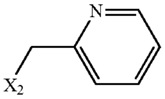 |
| 23(H27-34) | 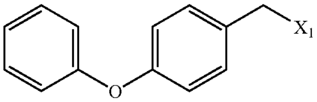 | 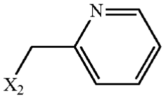 |
| 23(H27-35) | 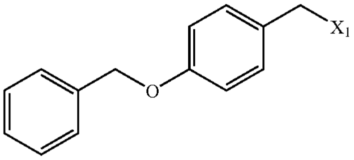 | 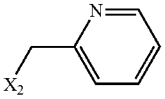 |
| 23(H27-36) | 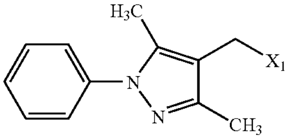 | 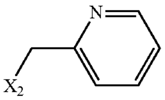 |
| 23(H27-37) | 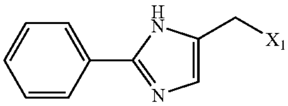 | 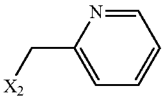 |

TABLE 27B-6
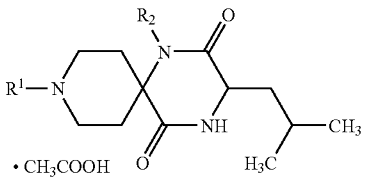
• $CH_3COOH$
| Example No | $R^1$ | $R^2$ |
|---|---|---|
| 23(H27-38) | 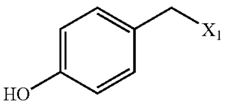 | 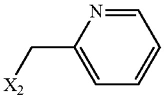 |
| 23(H27-39) | 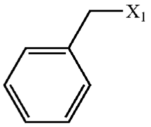 | 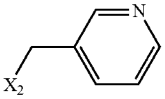 |
| 23(H27-40) | 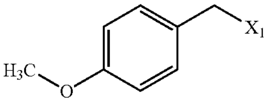 | 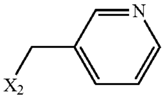 |
| 23(H27-41) | 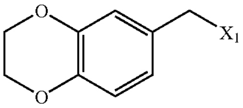 | 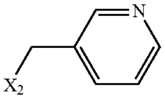 |
| 23(H27-42) | 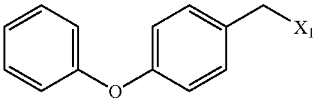 | 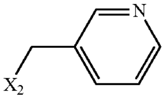 |
| 23(H27-43) | 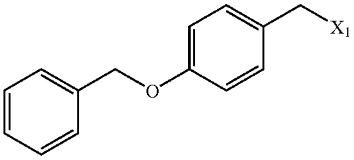 | 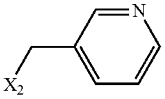 |
| 23(H27-44) | 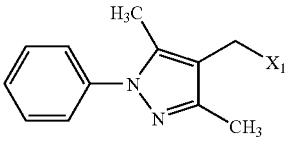 | 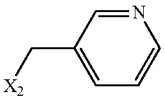 |
| 23(H27-45) | 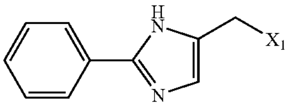 | 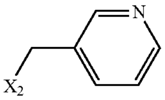 |

TABLE 27B-7
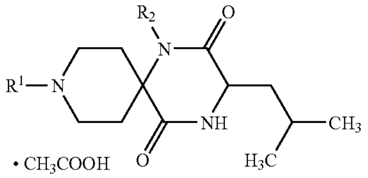
• $CH_3COOH$
| Example No | $R^1$ | $R^2$ |
|---|---|---|
| 23(H27-46) | 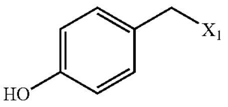 | 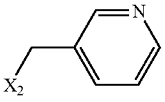 |
| 23(H27-47) | 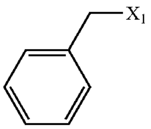 | 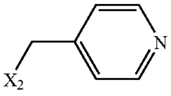 |
| 23(H27-48) | 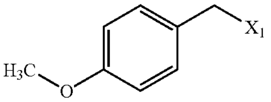 | 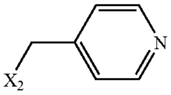 |
| 23(H27-49) | 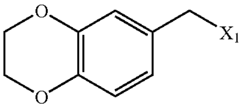 | 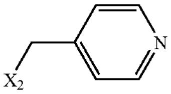 |
| 23(H27-50) | 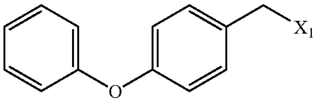 | 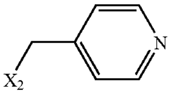 |
| 23(H27-51) | 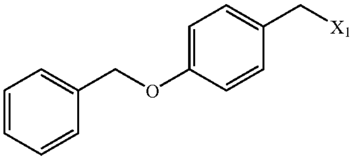 | 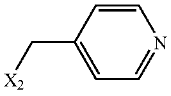 |
| 23(H27-52) | 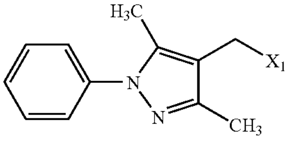 | 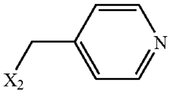 |
| 23(H27-53) | 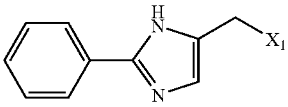 | 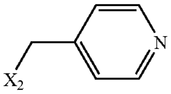 |

TABLE 27B-8
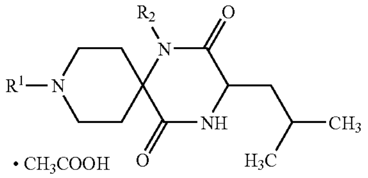
| Example No | $R^1$ | $R^2$ |
|---|---|---|
| 23(H27-54) | 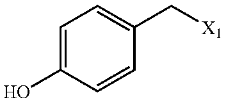 | 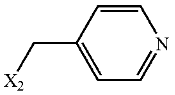 |
| 23(H27-55) | 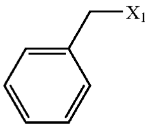 | 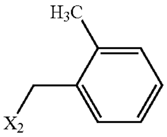 |
| 23(H27-56) | 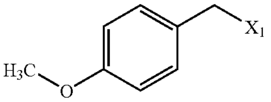 | 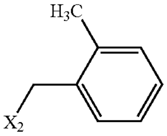 |
| 23(H27-57) | 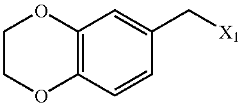 | 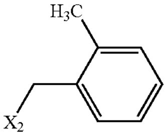 |
| 23(H27-58) | 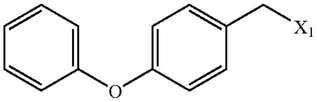 | 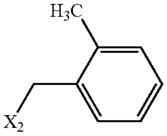 |
| 23(H27-59) | 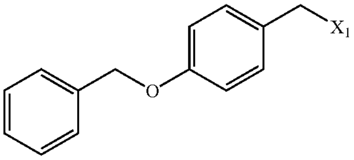 | 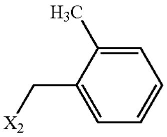 |
| 23(H27-60) | 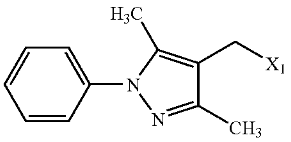 | 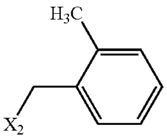 |

TABLE 27B-9
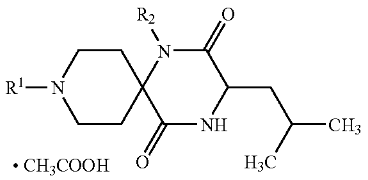
| Example No | $R^1$ | $R^2$ |
| --- | --- | --- |
| 23(H27-61) | 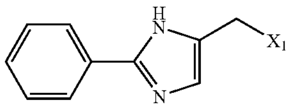 | 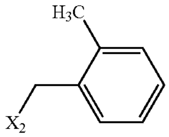 |
| 23(H27-62) | 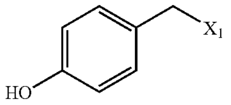 | 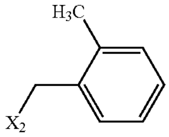 |
| 23(H27-63) | 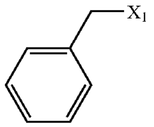 | 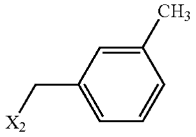 |
| 23(H27-64) | 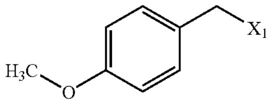 | 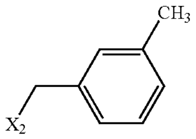 |
| 23(H27-65) | 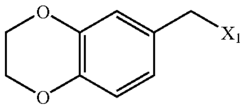 | 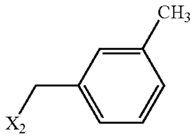 |
| 23(H27-66) | 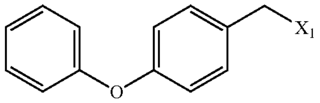 | 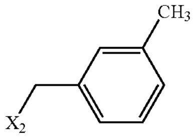 |
| 23(H27-67) | 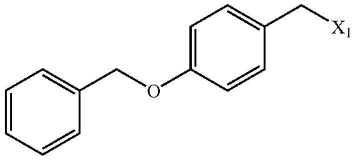 | 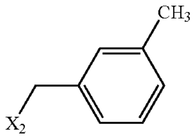 |

TABLE 27B-10
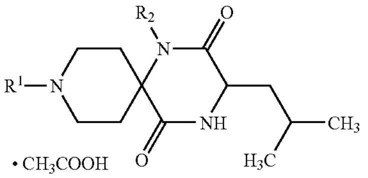
| Example No | $R^1$ | $R^2$ |
|---|---|---|
| 23(H27-68) | 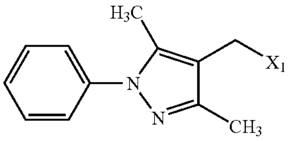 | 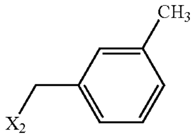 |
| 23(H27-69) | 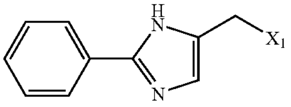 | 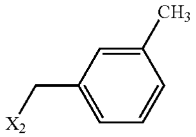 |
| 23(H27-70) | 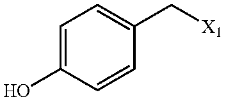 | 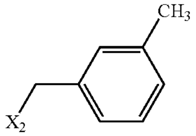 |
| 23(H27-71) | 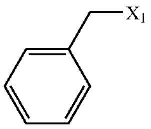 | 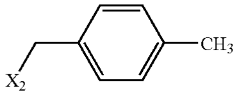 |
| 23(H27-72) | 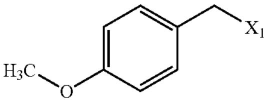 | 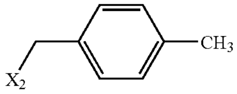 |
| 23(H27-73) | 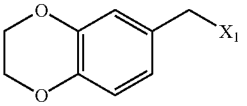 | 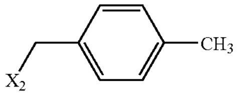 |
| 23(H27-74) | 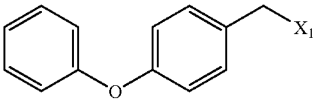 | 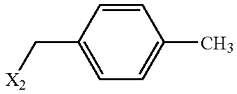 |
| 23(H27-75) | 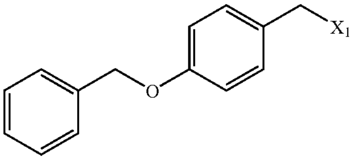 | 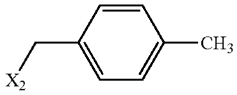 |

TABLE 27B-11
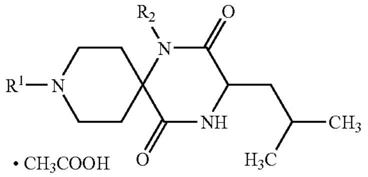
• $CH_3COOH$
| Example No | $R^1$ | $R^2$ |
|---|---|---|
| 23(H27-76) | 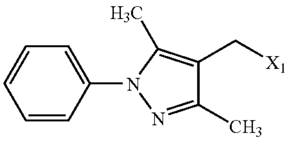 | 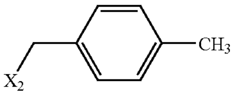 |
| 23(H27-77) | 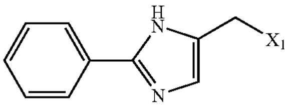 | 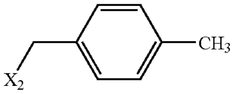 |
| 23(H27-78) | 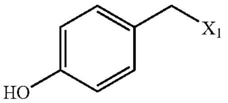 | 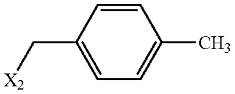 |
TABLE 28B-1
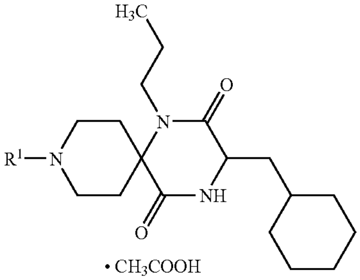
• $CH_3COOH$
| Example No | $R^1$ |
|---|---|
| 23(H28-2) | 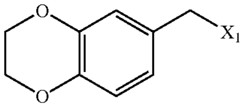 |
| 23(H28-2) | 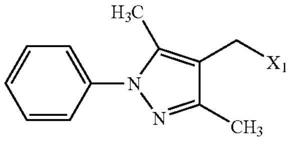 |
| 23(H28-3) | 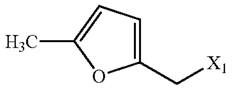 |
| 23(H28-4) | 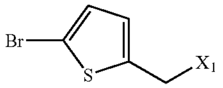 |
TABLE 28B-1-continued
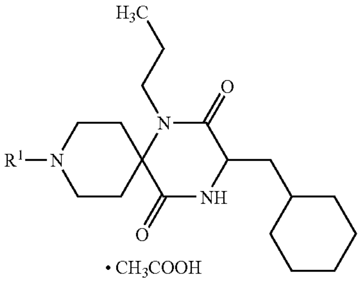
• $CH_3COOH$
| Example No | $R^1$ |
|---|---|
| 23(H28-5) | 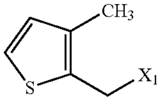 |
| 23(H28-6) | 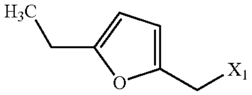 |
| 23(H28-7) | 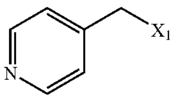 |
| 23(H28-8) | 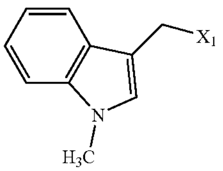 |

TABLE 28B-2
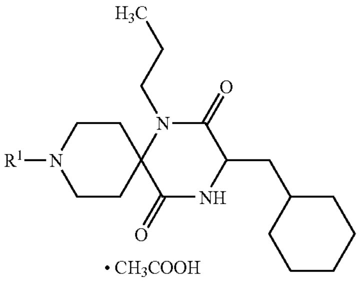
$\cdot CH_3COOH$
| Example No. | $R^1$ |
|---|---|
| 23(H28-9) | 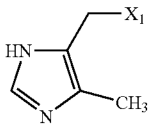 |
| 23(H28-10) | 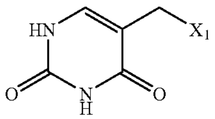 |
| 23(H28-11) | 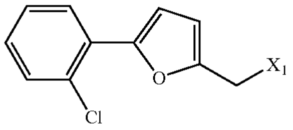 |
| 23(H28-12) | 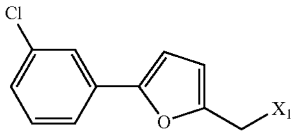 |
| 23(H28-13) | 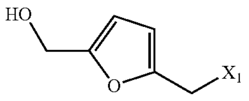 |
| 23(H28-14) | 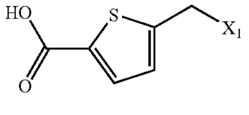 |
| 23(H28-15) | 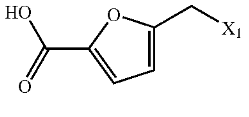 |
| 23(H28-16) | 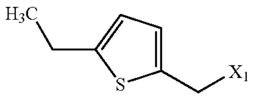 |
TABLE 28B-3
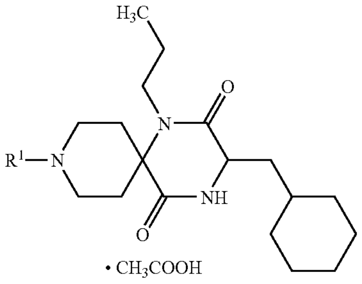
$\cdot CH_3COOH$
| Example No | $R^1$ |
|---|---|
| 23(H28-17) | 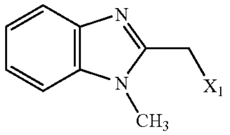 |
| 23(H28-18) | 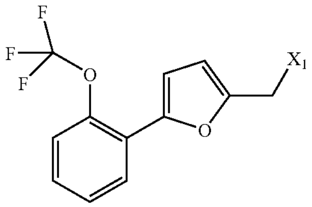 |
| 23(H28-19) | 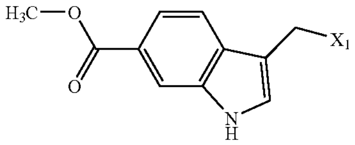 |
| 23(H28-20) | 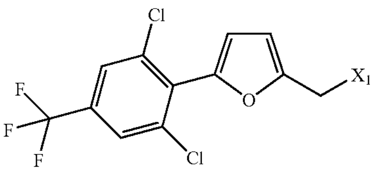 |
| 23(H28-21) | 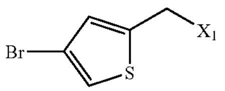 |
| 23(H28-22) | 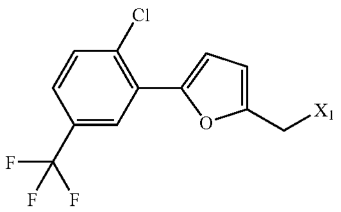 |

TABLE 28B-4
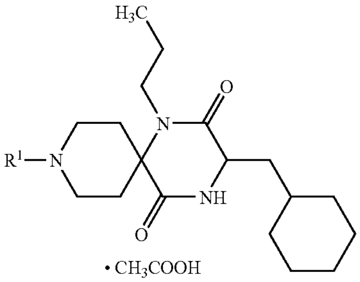
• $CH_3COOH$
| Example No | $R^1$ |
|---|---|
| 23(H28-23) | 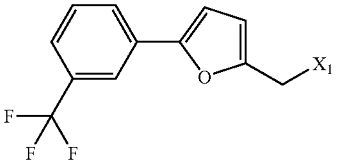 |
| 23(H28-24) | 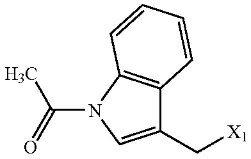 |
| 23(H28-25) | 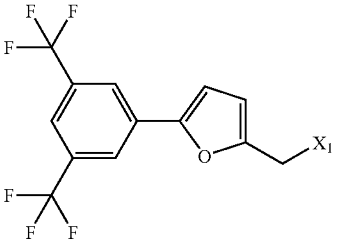 |
| 23(H28-26) | 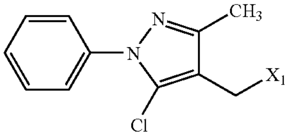 |
| 23(H28-27) | 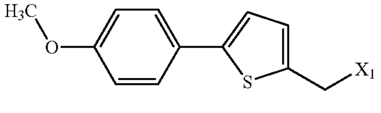 |
| 23(H28-28) | 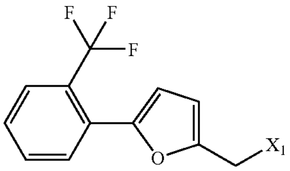 |
TABLE 28B-5
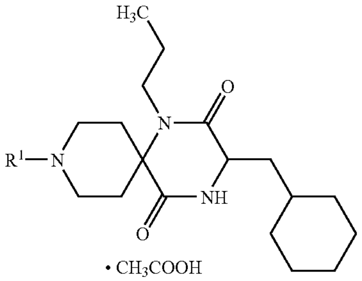
• $CH_3COOH$
| Example No | $R^1$ |
|---|---|
| 23(H28-29) | 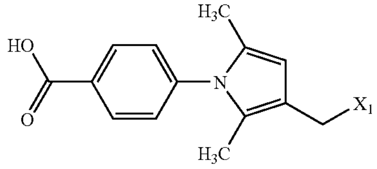 |
| 23(H28-30) | 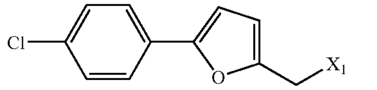 |
TABLE 29B-1
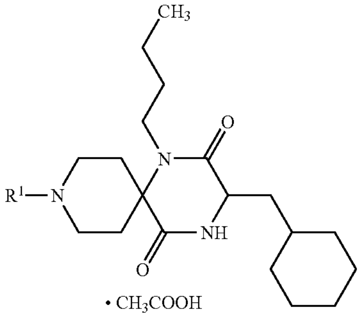
• $CH_3COOH$
| Example No | $R^1$ |
|---|---|
| 23(H29-1) | 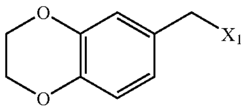 |
| 23(H29-2) | 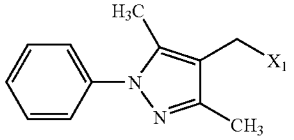 |
| 23(H29-3) | 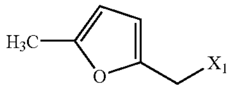 |
| 23(H29-4) | 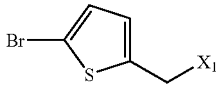 |

TABLE 29B-1-continued
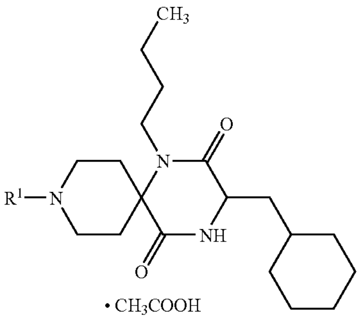
• $CH_3COOH$
| Example No | $R^1$ |
|---|---|
| 23(H29-5) | 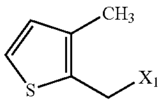 |
| 23(H29-6) | 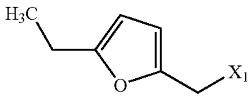 |
| 23(H29-7) | 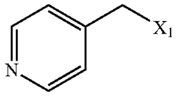 |
TABLE 29B-2
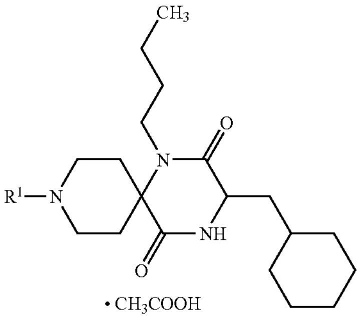
• $CH_3COOH$
| Example No | $R^1$ |
|---|---|
| 23(H29-8) | 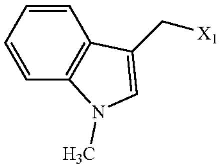 |
| 23(H29-9) | 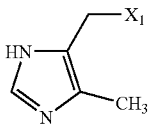 |
| 23(H29-10) | 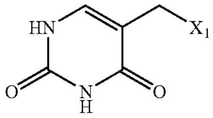 |
TABLE 29B-2-continued
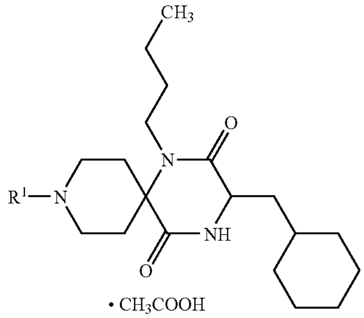
• $CH_3COOH$
| Example No | $R^1$ |
|---|---|
| 23(H29-11) | 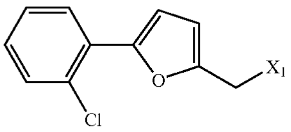 |
| 23(H29-12) | 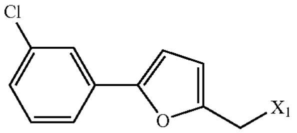 |
| 23(H29-13) | 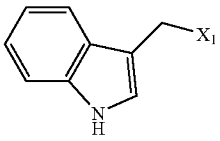 |
| 23(H29-14) | 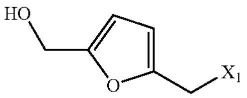 |
TABLE 29B-3
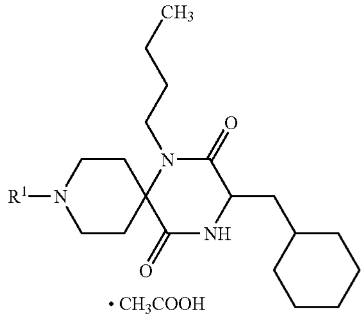
• $CH_3COOH$
| Example No | $R^1$ |
|---|---|
| 23(H29-15) | 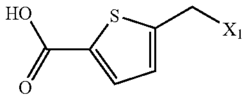 |
| 23(H29-16) | 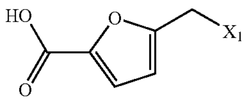 |

TABLE 29B-3-continued
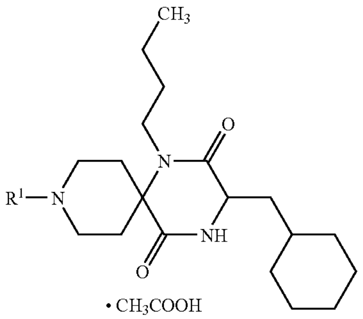
• $CH_3COOH$
| Example No | $R^1$ |
|---|---|
| 23(H29-17) | 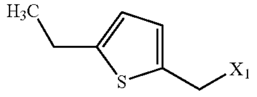 |
| 23(H29-18) | 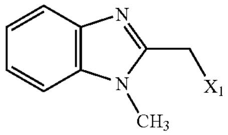 |
| 23(H29-19) | 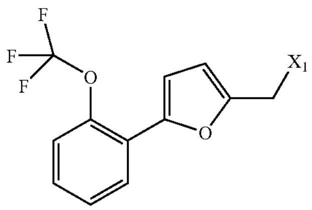 |
| 23(H29-20) | 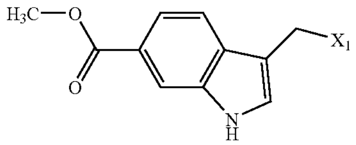 |
| 23(H29-21) | 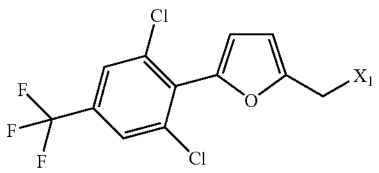 |
TABLE 29B-4
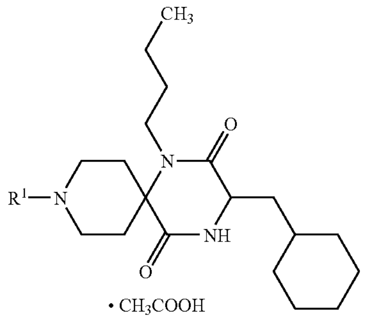
• $CH_3COOH$
| Example No | $R^1$ |
|---|---|
| 23(H29-22) | 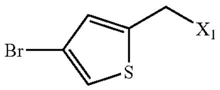 |
| 23(H29-23) | 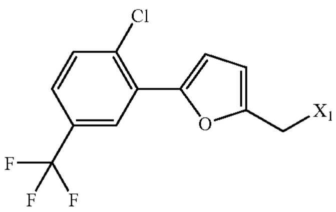 |
| 23(H29-24) | 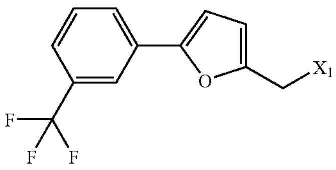 |
| 23(H29-25) | 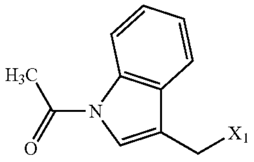 |
| 23(H29-26) | 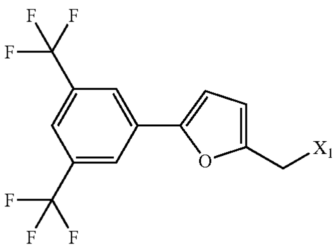 |

TABLE 29B-5
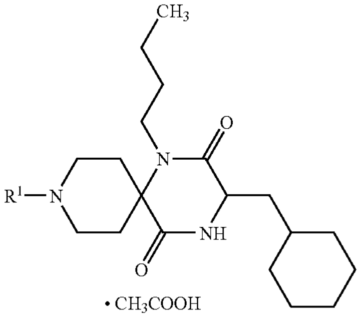
$\cdot CH_3COOH$
| Example No | $R^1$ |
|---|---|
| 23(H29-27) | 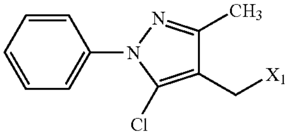 |
| 23(H29-28) | 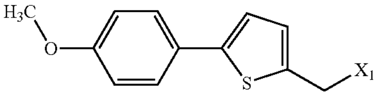 |
| 23(H29-29) | 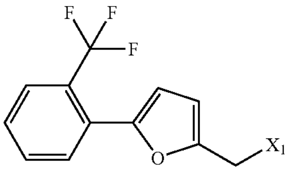 |
| 23(H29-30) | 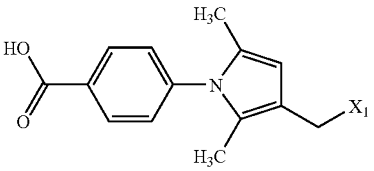 |
| 23(H29-31) | 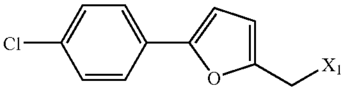 |
TABLE 30B-1
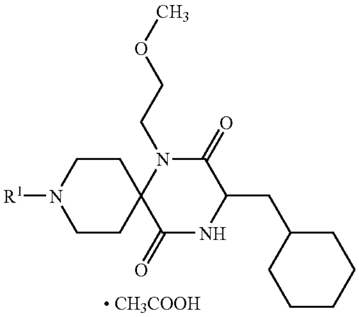
$\cdot CH_3COOH$
| Example No | $R^1$ |
|---|---|
| 23(H30-1) | 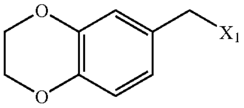 |
| 23(H30-2) | 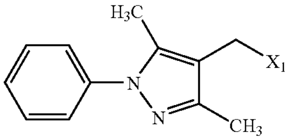 |
| 23(H30-3) | 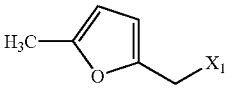 |
| 23(H30-4) | 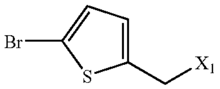 |
| 23(H30-5) | 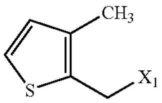 |
| 23(H30-6) | 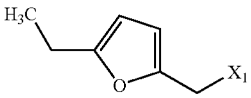 |
| 23(H30-7) | 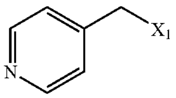 |

TABLE 30B-2
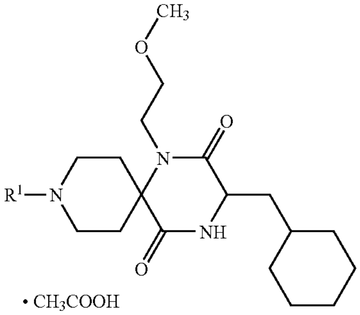
• $CH_3COOH$
| Example No | $R^1$ |
|---|---|
| 23(H30-8) | 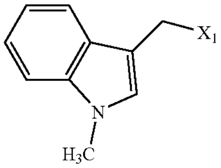 |
| 23(H30-9) | 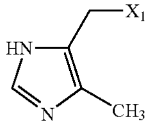 |
| 23(H30-10) | 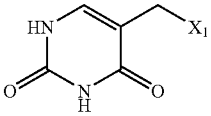 |
| 23(H30-11) | 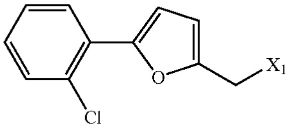 |
| 23(H30-12) | 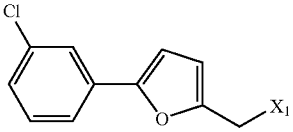 |
| 23(H30-13) | 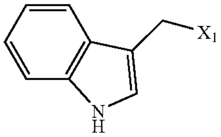 |
| 23(H30-14) | 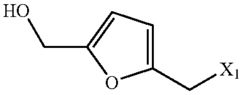 |
TABLE 30B-3
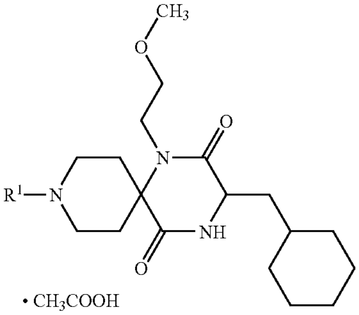
• $CH_3COOH$
| Example No | $R^1$ |
|---|---|
| 23(H30-15) | 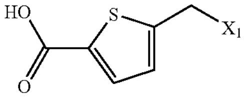 |
| 23(H30-16) | 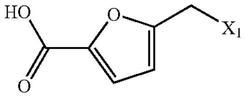 |
| 23(H30-17) | 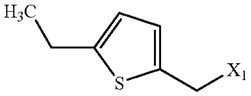 |
| 23(H30-18) | 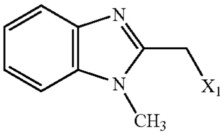 |
| 23(H30-19) | 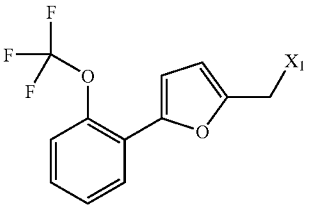 |
| 23(H30-20) | 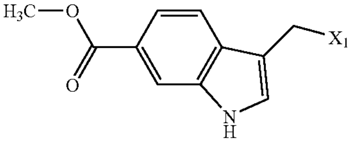 |

TABLE 30B-4
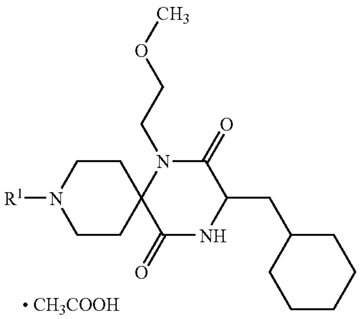
• $CH_3COOH$
| Example No | $R^1$ |
|---|---|
| 23(H30-21) | 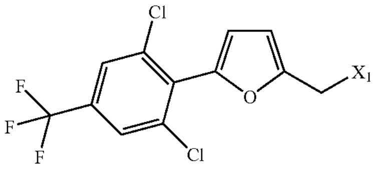 |
| 23(H30-22) | 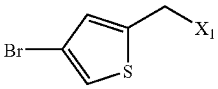 |
| 23(H30-23) | 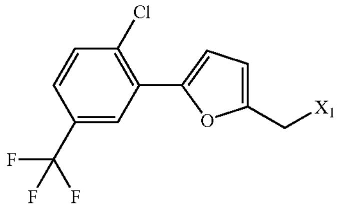 |
| 23(H30-24) | 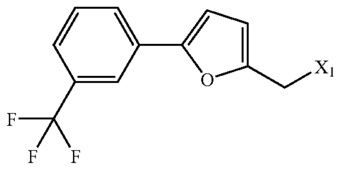 |
| 23(H30-25) | 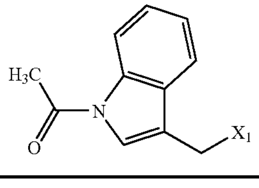 |
TABLE 30B-5
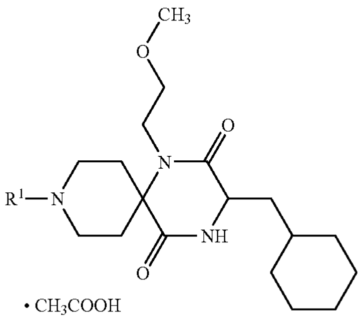
• $CH_3COOH$
| Example No | $R^1$ |
|---|---|
| 23(H30-26) | 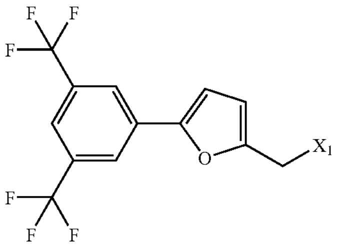 |
| 23(H30-27) | 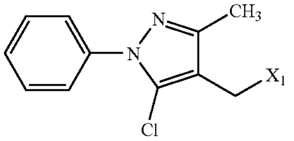 |
| 23(H30-28) | 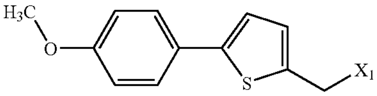 |
| 23(H30-29) | 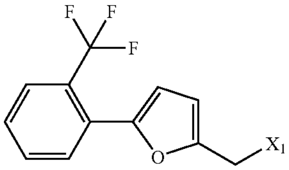 |
| 23(H30-30) | 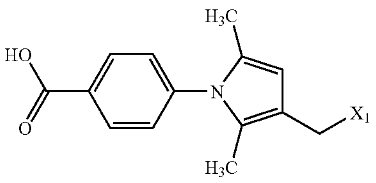 |
| 23(H30-31) | 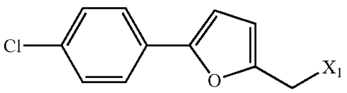 |

TABLE 31B-1
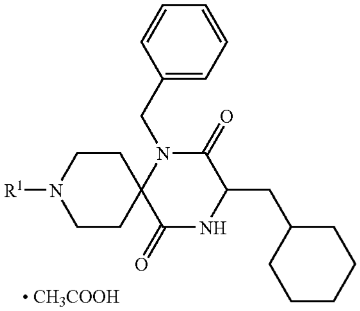
• $CH_3COOH$
| Example No | $R^1$ |
|---|---|
| 23(H31-1) | 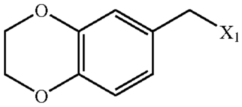 |
| 23(H31-2) | 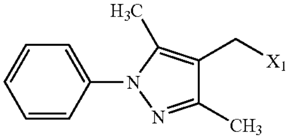 |
| 23(H31-3) | 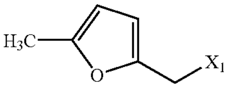 |
| 23(H31-4) | 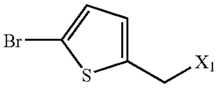 |
| 23(H31-5) | 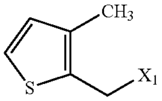 |
| 23(H31-6) | 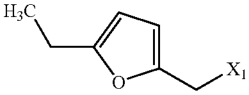 |
| 23(H31-7) | 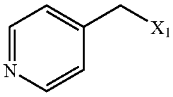 |
TABLE 31B-2
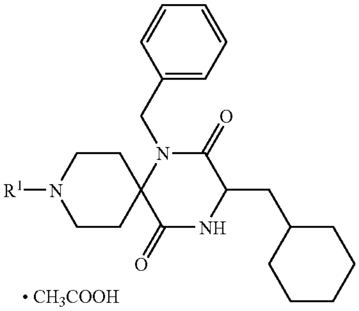
• $CH_3COOH$
| Example No | $R^1$ |
|---|---|
| 23(H31-8) | 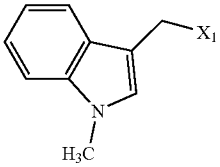 |
| 23(H31-9) | 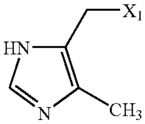 |
| 23(H31-10) | 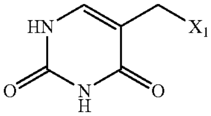 |
| 23(H31-11) | 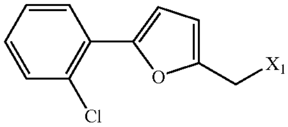 |
| 23(H31-12) | 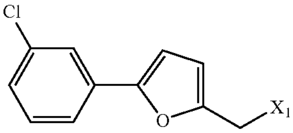 |
| 23(H31-13) | 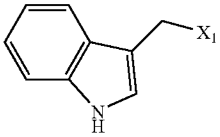 |
| 23(H31-14) | 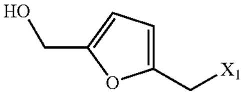 |

TABLE 31B-3
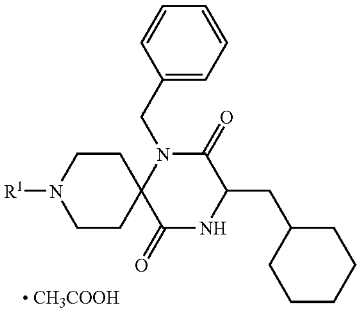
• $CH_3COOH$
| Example No | $R^1$ |
|---|---|
| 23(H31-15) | 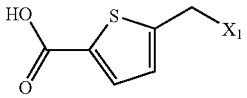 |
| 23(H31-16) | 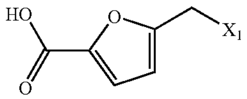 |
| 23(H31-17) | 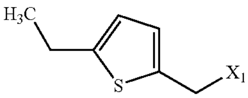 |
| 23(H31-18) | 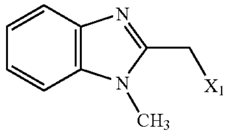 |
| 23(H31-19) | 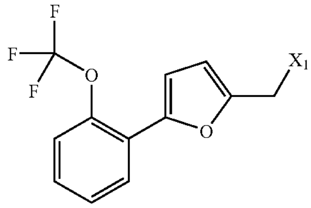 |
| 23(H31-20) | 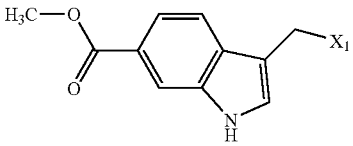 |
| 23(H31-21) | 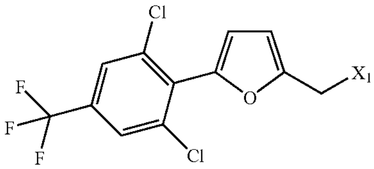 |
TABLE 31B-4
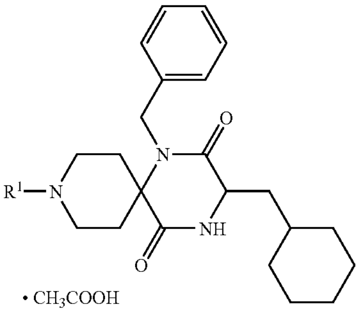
• $CH_3COOH$
| Example No | $R^1$ |
|---|---|
| 23(H31-22) | 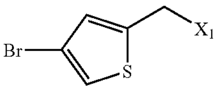 |
| 23(H31-23) | 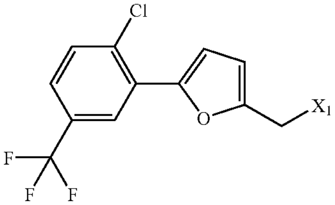 |
| 23(H31-24) | 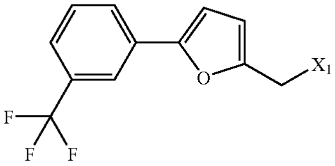 |
| 23(H31-25) | 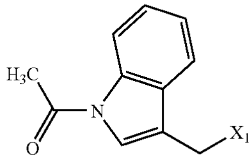 |
| 23(H31-26) | 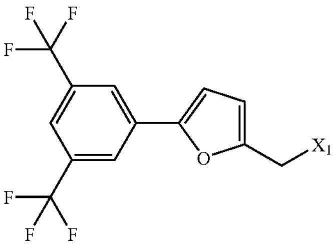 |

TABLE 31B-5

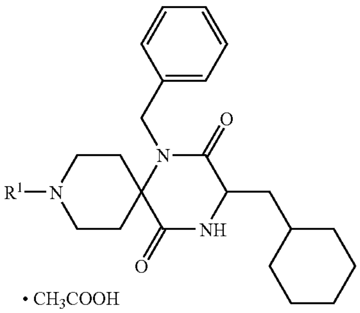

• $CH_3COOH$

| Example No | $R^1$ |
|---|---|
| 23(H31-27) | 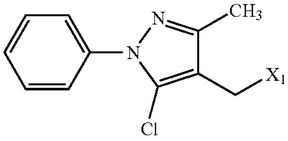 |
| 23(H31-28) | 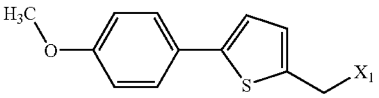 |
| 23(H31-29) | 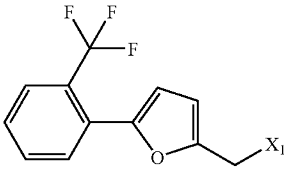 |
| 23(H31-30) | 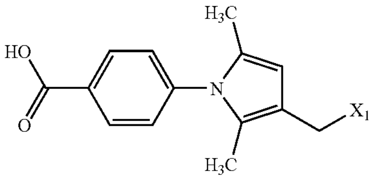 |
| 23(H31-31) | 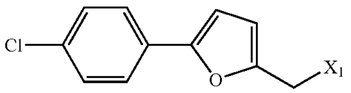 |

TABLE 22C-1

| Example No | HPLC condi-tion | Retention time (min) | Mass data | Mass condition |
|---|---|---|---|---|
| 23(H22-1) | E | 3.67 | 442 $(M + H)^+$, 369. | APCI (Pos., 40 V) |
| 23(H22-2) | E | 3.67 | 442 $(M + H)^+$, 440, 369. | APCI (Pos., 40 V) |
| 23(H22-3) | E | 3.22 | 400 $(M + H)^+$, 398, 370, 327. | APCI (Pos., 40 V) |
| 23(H22-4) | E | 3.76 | 476 $(M + H)^+$, 400. | APCI (Pos., 40 V) |
| 23(H22-5) | E | 3.36 | 586 $(M + H)^+$. | APCI (Pos., 40 V) |
| 23(H22-6) | E | 3.78 | 506 $(M + H)^+$, 398. | APCI (Pos., 40 V) |
| 23(H22-7) | E | 3.73 | 506 $(M + H)^+$. | APCI (Pos., 40 V) |
| 23(H22-8) | E | 3.97 | 520 $(M + H)^+$, 412, 356. | APCI (Pos., 40 V) |

TABLE 22C-1-continued

| Example No | HPLC condi-tion | Retention time (min) | Mass data | Mass condition |
|---|---|---|---|---|
| 23(H22-9) | E | 2.99 | 477 $(M + H)^+$, 400. | APCI (Pos., 40 V) |
| 23(H22-10) | E | 3.70 | 442 $(M + H)^+$, 412, 369. | APCI (Pos., 40 V) |
| 23(H22-11) | E | 4.03 | 526 $(M + H)^+$, 453, 372. | APCI (Pos., 40 V) |
| 23(H22-12) | E | 4.06 | 482 $(M + H)^+$, 409. | APCI (Pos., 40 V) |
| 23(H22-13) | E | 4.04 | 526 $(M + H)^+$, 453, 372. | APCI (Pos., 40 V) |
| 23(H22-14) | E | 4.10 | 540 $(M + H)^+$, 416. | APCI (Pos., 40 V) |
| 23(H22-15) | E | 4.29 | 582 $(M + H)^+$, 492. | APCI (Pos., 40 V) |
| 23(H22-16) | E | 3.15 | 416 $(M + H)^+$, 398. | APCI (Pos., 40 V) |
| 23(H22-17) | E | 4.29 | 582 $(M + H)^+$, 492. | APCI (Pos., 40 V) |
| 23(H22-18) | E | 3.71 | 442 $(M + H)^+$, 440, 412, 369. | APCI (Pos., 40 V) |
| 23(H22-19) | E | 4.05 | 482 $(M + H)^+$, 452, 409. | APCI (Pos., 40 V) |
| 23(H22-20) | E | 3.97 | 520 $(M + H)^+$, 478, 412. | APCI (Pos., 40 V) |
| 23(H22-21) | E | 3.89 | 506 $(M + H)^+$, 398. | APCI (Pos., 40 V) |
| 23(H22-22) | E | 4.02 | 552 $(M + H)^+$, 398. | APCI (Pos., 40 V) |
| 23(H22-23) | E | 4.03 | 522 $(M + H)^+$, 432, 398. | APCI (Pos., 40 V) |
| 23(H22-24) | E | 3.20 | 386 $(M + H)^+$. | APCI (Pos., 40 V) |
| 23(H22-25) | E | 2.93 | 466 $(M + H)^+$. | APCI (Pos., 40 V) |
| 23(H22-26) | E | 3.79 | 416 $(M + H)^+$. | APCI (Pos., 40 V) |

TABLE 22C-2

| Example No | HPLC condi-tion | Retention time (min) | Mass data | Mass condition |
|---|---|---|---|---|
| 23(H22-27) | E | 4.16 | 586 $(M + H)^+$, 432, 398, 295. | APCI (Pos., 40 V) |
| 23(H22-28) | E | 3.34 | 556 $(M + H)^+$. | APCI (Pos., 40 V) |
| 23(H22-29) | E | 3.33 | 492 $(M + H)^+$. | APCI (Pos., 40 V) |
| 23(H22-30) | E | 4.12 | 625 $(M + H)^+$, 491. | APCI (Pos., 40 V) |
| 23(H22-31) | E | 3.10 | 486 $(M + H)^+$, 484. | APCI (Pos., 40 V) |
| 23(H22-32) | E | 4.06 | 526 $(M + H)^+$. | APCI (Pos., 40 V) |
| 23(H22-33) | E | 4.22 | 544 $(M + H)^+$. | APCI (Pos., 40 V) |
| 23(H22-34) | E | 3.90 | 488 $(M + H)^+$, 398. | APCI (Pos., 40 V) |
| 23(H22-35) | E | 3.82 | 456 $(M + H)^+$. | APCI (Pos., 40 V) |
| 23(H22-36) | E | 3.11 | 428 $(M + H)^+$, 355. | APCI (Pos., 40 V) |
| 23(H22-37) | E | 4.39 | 596 $(M + H)^+$. | APCI (Pos., 40 V) |
| 23(H22-38) | E | 3.18 | 430 $(M + H)^+$, 386 | APCI (Pos., 40 V) |
| 23(H22-39) | E | 3.12 | 443 $(M + H)^+$. | APCI (Pos., 40 V) |
| 23(H22-40) | E | 3.18 | 430 $(M + H)^+$, 386, 356. | APCI (Pos., 40 V) |
| 23(H22-41) | E | 3.22 | 400 $(M + H)^+$, 398, 370, 327. | APCI (Pos., 40 V) |
| 23(H22-42) | E | 2.98 | 477 $(M + H)^+$. | APCI (Pos., 40 V) |
| 23(H22-43) | E | 3.17 | 444 $(M + H)^+$, 398. | APCI (Pos., 40 V) |
| 23(H22-44) | E | 3.32 | 492 $(M + H)^+$. | APCI (Pos., 40 V) |
| 23(H22-45) | E | 4.53 | 460 $(M + H)^+$. | APCI (Pos., 40 V) |
| 23(H22-46) | E | 2.26 | 503 $(M + H)^+$, 432, 398, 263. | APCI (Pos., 40 V) |

TABLE 22C-2-continued

| Example No | HPLC condition | Retention time (min) | Mass data | Mass condition |
|---|---|---|---|---|
| 23(H22-47) | E | 3.20 | 430 (M + H)+, 386. | APCI (Pos., 40 V) |
| 23(H22-48) | E | 3.87 | 510 (M + H)+, 472. | APCI (Pos., 40 V) |
| 23(H22-49) | E | 4.11 | 526 (M + H)+. | APCI (Pos., 40 V) |
| 23(H22-50) | E | 3.89 | 494 (M + H)+. | APCI (Pos., 40 V) |
| 23(H22-51) | E | 3.27 | 425 (M + H)+. | APCI (Pos., 40 V) |
| 23(H22-52) | E | 3.74 | 515 (M + H)+. | APCI (Pos., 40 V) |

TABLE 22C-3

| Example No | HPLC condition | Retention time (min) | Mass data | Mass condition |
|---|---|---|---|---|
| 23(H22-53) | E | 4.19 | 625 (M + H)+. | APCI (Pos., 40 V) |
| 23(H22-54) | E | 3.93 | 534 (M + H)+, 458. | APCI (Pos., 40 V) |
| 23(H22-55) | E | 4.08 | 667 (M + H)+. | APCI (Pos., 40 V) |
| 23(H22-56) | E | 3.94 | 534 (M + H)+, 458. | APCI (Pos., 40 V) |
| 23(H22-57) | E | 4.02 | 591 (M + H)+, 457. | APCI (Pos., 40 V) |
| 23(H22-58) | E | 3.79 | 506 (M + H)+. | APCI (Pos., 40 V) |
| 23(H22-59) | E | 4.01 | 591 (M + H)+. | APCI (Pos., 40 V) |
| 23(H22-60) | E | 3.91 | 577 (M + H)+. | APCI (Pos., 40 V) |
| 23(H22-61) | E | 3.47 | 586 (M + H)+. | APCI (Pos., 40 V) |
| 23(H22-62) | E | 3.94 | 520 (M + H)+. | APCI (Pos., 40 V) |
| 23(H22-63) | E | 4.33 | 552 (M + H)+. | APCI (Pos., 40 V) |
| 23(H22-64) | E | 4.21 | 552 (M + H)+. | APCI (Pos., 40 V) |

TABLE 23C

| Example No | HPLC condition | Retention time (min) | Mass data | Mass condition |
|---|---|---|---|---|
| 23(H23-1) | E | 3.00 | 444 (M + H)+. | APCI (Pos., 40 V) |
| 23(H23-2) | E | 3.07 | 416 (M + H)+. | APCI (Pos., 40 V) |
| 23(H23-3) | E | 2.52 | 457 (M + H)+, 296, 162. | APCI (Pos., 40 V) |
| 23(H23-4) | E | 3.17 | 480 (M + H)+, 296, 217, 185. | APCI (Pos., 40 V) |
| 23(H23-5) | E | 3.80 | 492 (M + H)+. | APCI (Pos., 40 V) |
| 23(H23-6) | E | 3.79 | 478 (M + H)+. | APCI (Pos., 40 V) |
| 23(H23-7) | E | 3.43 | 442 (M + H)+, 402, 336, 296. | APCI (Pos., 40 V) |
| 23(H23-8) | E | 3.86 | 498 (M + Na)+, 476 (M + H)+. | APCI (Pos., 40 V) |
| 23(H23-9) | E | 2.90 | 452 (M + H)+, 296. | APCI (Pos., 40 V) |
| 23(H23-10) | E | 3.57 | 484 (M + H)+, 332. | APCI (Pos., 40 V) |
| 23(H23-11) | E | 3.62 | 456 (M + H)+. | APCI (Pos., 40 V) |
| 23(H23-12) | E | 3.22 | 497 (M + H)+, 336, 162. | APCI (Pos., 40 V) |
| 23(H23-13) | E | 3.69 | 520 (M + H)+, 185. | APCI (Pos., 40 V) |
| 23(H23-14) | E | 4.16 | 532 (M + H)+. | APCI (Pos., 40 V) |
| 23(H23-15) | E | 4.16 | 518 (M + H)+. | APCI (Pos., 40 V) |
| 23(H23-16) | E | 3.89 | 482 (M + H)+, 442, 376, 336. | APCI (Pos., 40 V) |
| 23(H23-17) | E | 4.21 | 516 (M + H)+. | APCI (Pos., 40 V) |
| 23(H23-18) | E | 3.48 | 492 (M + H)+, 336, 189, 157. | APCI (Pos., 40 V) |

TABLE 24C-1

| Example No | HPLC condition | Retention time (min) | Mass data | Mass condition |
|---|---|---|---|---|
| 23(H24-1) | F | 3.07 | 416 (M + H)+. | ESI (Pos., 20 V) |
| 23(H24-2) | F | 3.11 | 452 (M + H)+. | ESI (Pos., 20 V) |
| 23(H24-3) | F | 3.04 | 362 (M + H)+. | ESI (Pos., 20 V) |
| 23(H24-4) | F | 3.16 | 442 (M + H)+. | ESI (Pos., 20 V) |
| 23(H24-5) | F | 3.07 | 378 (M + H)+. | ESI (Pos., 20 V) |
| 23(H24-6) | F | 3.12 | 376 (M + H)+. | ESI (Pos., 20 V) |
| 23(H24-7) | F | 2.74 | 359 (M + H)+. | ESI (Pos., 20 V) |
| 23(H24-8) | F | 3.18 | 411 (M + H)+. | ESI (Pos., 20 V) |
| 23(H24-9) | F | 2.76 | 362 (M + H)+. | ESI (Pos., 20 V) |
| 23(H24-10) | F | 2.76 | 392 (M + H)+. | ESI (Pos., 20 V) |
| 23(H24-11) | F | 3.35 | 458 (M + H)+. | ESI (Pos., 20 V) |
| 23(H24-12) | F | 3.38 | 458 (M + H)+. | ESI (Pos., 20 V) |
| 23(H24-13) | F | 3.12 | 397 (M + H)+. | ESI (Pos., 20 V) |
| 23(H24-14) | F | 2.87 | 378 (M + H)+. | ESI (Pos., 20 V) |
| 23(H24-15) | F | 2.92 | 408 (M + H)+. | ESI (Pos., 20 V) |
| 23(H24-16) | F | 2.89 | 392 (M + H)+. | ESI (Pos., 20 V) |
| 23(H24-17) | F | 3.18 | 392 (M + H)+. | ESI (Pos., 20 V) |
| 23(H24-18) | F | 3.01 | 412 (M + H)+. | ESI (Pos., 20 V) |
| 23(H24-19) | F | 3.44 | 508 (M + H)+. | ESI (Pos., 20 V) |
| 23(H24-20) | F | 3.11 | 455 (M + H)+. | ESI (Pos., 20 V) |
| 23(H24-21) | F | 3.53 | 560 (M + H)+. | ESI (Pos., 20 V) |
| 23(H24-22) | F | 3.12 | 442 (M + H)+. | ESI (Pos., 20 V) |
| 23(H24-23) | F | 3.49 | 526 (M + H)+. | ESI (Pos., 20 V) |
| 23(H24-24) | F | 3.42 | 492 (M + H)+. | ESI (Pos., 20 V) |
| 23(H24-25) | F | 3.16 | 439 (M + H)+. | ESI (Pos., 20 V) |
| 23(H24-26) | F | 3.57 | 560 (M + H)+. | ESI (Pos., 20 V) |

TABLE 24C-2

| Example No | HPLC condition | Retention time (min) | Mass data | Mass condition |
|---|---|---|---|---|
| 23(H24-27) | F | 3.18 | 472 (M + H)+. | ESI (Pos., 20 V) |
| 23(H24-28) | F | 3.33 | 470 (M + H)+. | ESI (Pos., 20 V) |
| 23(H24-29) | F | 3.38 | 492 (M + H)+. | ESI (Pos., 20 V) |
| 23(H24-30) | F | 3.16 | 495 (M + H)+. | ESI (Pos., 20 V) |
| 23(H24-31) | F | 3.38 | 458 (M + H)+. | ESI (Pos., 20 V) |

TABLE 25C-1

| Example No | HPLC condition | Retention time (min) | Mass data | Mass condition |
|---|---|---|---|---|
| 230H25-1) | F | 3.16 | 430 (M + H)+. | ESI (Pos., 20 V) |
| 23(H25-2) | F | 3.18 | 466 (M + H)+. | ESI (Pos., 20 V) |
| 23(H25-3) | F | 3.11 | 376 (M + H)+. | ESI (Pos., 20 V) |
| 23(H25-4) | F | 3.23 | 456 (M + H)+. | ESI (Pos., 20 V) |
| 23(H25-5) | F | 3.16 | 392 (M + H)+. | ESI (Pos., 20 V) |
| 23(H25-6) | F | 3.20 | 390 (M + H)+. | ESI (Pos., 20 V) |
| 23(H25-7) | F | 3.28 | 425 (M + H)+. | ESI (Pos., 20 V) |
| 23(H25-8) | F | 2.85 | 376 (M + H)+. | ESI (Pos., 20 V) |
| 23(H25-9) | F | 2.89 | 406 (M + H)+. | ESI (Pos., 20 V) |
| 23(H25-10) | F | 3.44 | 472 (M + H)+. | ESI (Pos., 20 V) |
| 23(H25-11) | F | 3.18 | 411 (M + H)+. | ESI (Pos., 20 V) |
| 23(H25-12) | F | 3.45 | 392 (M + H)+. | ESI (Pos., 20 V) |
| 23(H25-13) | F | 2.96 | 406 (M + H)+. | ESI (Pos., 20 V) |
| 23(H25-14) | F | 3.27 | 406 (M + H)+. | ESI (Pos., 20 V) |
| 23(H25-15) | F | 3.09 | 426 (M + H)+. | ESI (Pos., 20 V) |
| 23(H25-16) | F | 3.53 | 522 (M + H)+. | ESI (Pos., 20 V) |
| 23(H25-17) | F | 3.18 | 469 (M + H)+. | ESI (Pos., 20 V) |
| 23(H25-18) | F | 3.60 | 574 (M + H)+. | ESI (Pos., 20 V) |
| 23(H25-19) | F | 3.22 | 456 (M + H)+. | ESI (Pos., 20 V) |
| 23(H25-20) | F | 3.55 | 540 (M + H)+. | ESI (Pos., 20 V) |
| 23(H25-21) | F | 3.49 | 506 (M + H)+. | ESI (Pos., 20 V) |

TABLE 25C-1-continued

| Example No | HPLC condition | Retention time (min) | Mass data | Mass condition |
|---|---|---|---|---|
| 23(H25-22) | F | 3.25 | 453 $(M + H)^+$. | ESI (Pos., 20 V) |
| 23(H25-23) | F | 3.64 | 574 $(M + H)^+$. | ESI (Pos., 20 V) |
| 23(H25-24) | F | 3.25 | 486 $(M + H)^+$. | ESI (Pos., 20 V) |
| 23(H25-25) | F | 3.42 | 484 $(M + H)^+$. | ESI (Pos., 20 V) |
| 23(H25-26) | F | 3.47 | 506 $(M + H)^+$. | ESI (Pos., 20 V) |

TABLE 25C-2

| Example No | HPLC condition | Retention time (min) | Mass data | Mass condition |
|---|---|---|---|---|
| 23(H25-27) | F | 3.24 | 509 $(M + H)^+$. | ESI (Pos., 20 V) |
| 23(H25-28) | F | 3.47 | 472 $(M + H)^+$. | ESI (Pos., 20 V) |

TABLE 26C-1

| Example No | HPLC condition | Retention time (min) | Mass data | Mass condition |
|---|---|---|---|---|
| 23(H26-1) | F | 3.25 | 444 $(M + H)^+$. | ESI (Pos., 20 V) |
| 23(H26-2) | F | 3.26 | 480 $(M + H)^+$. | ESI (Pos., 20 V) |
| 23(H26-3) | F | 3.22 | 390 $(M + H)^+$. | ESI (Pos., 20 V) |
| 23(H26-4) | F | 3.33 | 470 $(M + H)^+$. | ESI (Pos., 20 V) |
| 23(H26-5) | F | 3.23 | 406 $(M + H)^+$. | ESI (Pos., 20 V) |
| 23(H26-6) | F | 3.29 | 404 $(M + H)^+$. | ESI (Pos., 20 V) |
| 23(H26-7) | F | 2.93 | 387 $(M + H)^+$. | ESI (Pos., 20 V) |
| 23(H26-8) | F | 3.34 | 439 $(M + H)^+$. | ESI (Pos., 20 V) |
| 23(H26-9) | F | 2.93 | 390 $(M + H)^+$. | ESI (Pos., 20 V) |
| 23(H26-10) | F | 2.97 | 420 $(M + H)^+$. | ESI (Pos., 20 V) |
| 23(H26-11) | F | 3.50 | 486 $(M + H)^+$. | ESI (Pos., 20 V) |
| 23(H26-12) | F | 3.52 | 486 $(M + H)^+$. | ESI (Pos., 20 V) |
| 23(H26-13) | F | 3.28 | 425 $(M + H)^+$. | ESI (Pos., 20 V) |
| 23(H26-14) | F | 3.04 | 406 $(M + H)^+$. | ESI (Pos., 20 V) |
| 23(H26-15) | F | 3.11 | 436 $(M + H)^+$. | ESI (Pos., 20 V) |
| 23(H26-16) | F | 3.04 | 420 $(M + H)^+$. | ESI (Pos., 20 V) |
| 23(H26-17) | F | 3.35 | 420 $(M + H)^+$. | ESI (Pos., 20 V) |
| 23(H26-18) | F | 3.20 | 440 $(M + H)^+$. | ESI (Pos., 20 V) |
| 23(H26-19) | F | 3.58 | 536 $(M + H)^+$. | ESI (Pos., 20 V) |
| 23(H26-20) | F | 3.25 | 483 $(M + H)^+$. | ESI (Pos., 20 V) |
| 23(H26-21) | F | 3.68 | 588 $(M + H)^+$. | ESI (Pos., 20 V) |
| 23(H26-22) | F | 3.30 | 472 $(M + H)^+$. | ESI (Pos., 20 V) |
| 23(H26-23) | F | 3.62 | 554 $(M + H)^+$. | ESI (Pos., 20 V) |
| 23(H26-24) | F | 3.57 | 520 $(M + H)^+$. | ESI (Pos., 20 V) |
| 23(H26-25) | F | 3.33 | 467 $(M + H)^+$. | ESI (Pos., 20 V) |
| 23(H26-26) | F | 3.71 | 588 $(M + H)^+$. | ESI (Pos., 20 V) |

TABLE 26C-2

| Example No | HPLC condition | Retention time (min) | Mass data | Mass condition |
|---|---|---|---|---|
| 23(H26-27) | F | 3.33 | 500 $(M + H)^+$. | ESI (Pos., 20 V) |
| 23(H26-28) | F | 3.49 | 498 $(M + H)^+$. | ESI (Pos., 20 V) |
| 23(H26-29) | F | 3.52 | 520 $(M + H)^+$. | ESI (Pos., 20 V) |
| 23(H26-30) | F | 3.32 | 523 $(M + H)^+$. | ESI (Pos., 20 V) |
| 23(H26-31) | F | 3.55 | 486 $(M + H)^+$. | ESI (Pos., 20 V) |

TABLE 27C-1

| Example No | HPLC condition | Retention time (min) | Mass data | Mass condition |
|---|---|---|---|---|
| 23(H27-1) | F | 3.31 | 420 $(M + H)^+$. | ESI (Pos., 20 V) |
| 23(H27-2) | F | 3.33 | 450 $(M + H)^+$. | ESI (Pos., 20 V) |
| 23(H27-3) | F | 3.31 | 478 $(M + H)^+$. | ESI (Pos., 20 V) |
| 23(H27-4) | F | 3.55 | 512 $(M + H)^+$. | ESI (Pos., 20 V) |
| 23(H27-5) | F | 3.58 | 526 $(M + H)^+$. | ESI (Pos., 20 V) |
| 23(H27-6) | F | 3.33 | 514 $(M + H)^+$. | ESI (Pos., 20 V) |
| 23(H27-7) | F | 3.16 | 486 $(M + H)^+$. | ESI (Pos., 20 V) |
| 23(H27-8) | F | 3.18 | 436 $(M + H)^+$. | ESI (Pos., 20 V) |
| 23(H27-9) | F | 3.31 | 450 $(M + H)^+$. | ESI (Pos., 20 V) |
| 23(H27-10) | F | 3.33 | 480 $(M + H)^+$. | ESI (Pos., 20 V) |
| 23(H27-11) | F | 3.33 | 508 $(M + H)^+$. | ESI (Pos., 20 V) |
| 23(H27-12) | F | 3.58 | 542 $(M + H)^+$. | ESI (Pos., 20 V) |
| 23(H27-13) | F | 3.60 | 556 $(M + H)^+$. | ESI (Pos., 20 V) |
| 23(H27-14) | F | 3.34 | 544 $(M + H)^+$. | ESI (Pos., 20 V) |
| 23(H27-15) | F | 3.18 | 516 $(M + H)^+$. | ESI (Pos., 20 V) |
| 23(H27-16) | F | 3.22 | 466 $(M + H)^+$. | ESI (Pos., 20 V) |
| 23(H27-17) | F | 3.29 | 450 $(M + H)^+$. | ESI (Pos., 20 V) |
| 23(H27-18) | F | 3.33 | 480 $(M + H)^+$. | ESI (Pos., 20 V) |
| 23(H27-19) | F | 3.56 | 542 $(M + H)^+$. | ESI (Pos., 20 V) |
| 23(H27-20) | F | 3.58 | 556 $(M + H)^+$. | ESI (Pos., 20 V) |
| 23(H27-21) | F | 3.33 | 544 $(M + H)^+$. | ESI (Pos., 20 V) |
| 23(H27-22) | F | 3.18 | 516 $(M + H)^+$. | ESI (Pos., 20 V) |
| 23(H27-23) | F | 3.20 | 466 $(M + H)^+$. | ESI (Pos., 20 V) |
| 23(H27-24) | F | 3.29 | 450 $(M + H)^+$. | ESI (Pos., 20 V) |
| 23(H27-25) | F | 3.31 | 508 $(M + H)^+$. | ESI (Pos., 20 V) |
| 23(H27-26) | F | 3.55 | 542 $(M + H)^+$. | ESI (Pos., 20 V) |

TABLE 27C-2

| Example No | HPLC condition | Retention time (min) | Mass data | Mass condition |
|---|---|---|---|---|
| 23(H27-27) | F | 3.56 | 556 $(M + H)^+$. | ESI (Pos., 20 V) |
| 23(H27-28) | F | 3.33 | 544 $(M + H)^+$. | ESI (Pos., 20 V) |
| 23(H27-29) | F | 3.17 | 516 $(M + H)^+$. | ESI (Pos., 20 V) |
| 23(H27-30) | F | 3.20 | 466 $(M + H)^+$. | ESI (Pos., 20 V) |
| 23(H27-31) | F | 2.92 | 421 $(M + H)^+$. | ESI (Pos., 20 V) |
| 23(H27-32) | F | 2.97 | 451 $(M + H)^+$. | ESI (Pos., 20 V) |
| 23(H27-33) | F | 2.96 | 479 $(M + H)^+$. | ESI (Pos., 20 V) |
| 23(H27-34) | F | 3.22 | 513 $(M + H)^+$. | ESI (Pos., 20 V) |
| 23(H27-35) | F | 3.25 | 527 $(M + H)^+$. | ESI (Pos., 20 V) |
| 23(H27-36) | F | 3.00 | 515 $(M + H)^+$. | ESI (Pos., 20 V) |
| 23(H27-37) | F | 2.87 | 487 $(M + H)^+$. | ESI (Pos., 20 V) |
| 23(H27-38) | F | 2.83 | 437 $(M + H)^+$. | ESI (Pos., 20 V) |
| 23(H27-39) | F | 2.90 | 421 $(M + H)^+$. | ESI (Pos., 20 V) |
| 23(H27-40) | F | 2.94 | 451 $(M + H)^+$. | ESI (Pos., 20 V) |
| 23(H27-41) | F | 2.92 | 479 $(M + H)^+$. | ESI (Pos., 20 V) |
| 23(H27-42) | F | 3.16 | 513 $(M + H)^+$. | ESI (Pos., 20 V) |
| 23(H27-43) | F | 3.20 | 527 $(M + H)^+$. | ESI (Pos., 20 V) |
| 23(H27-44) | F | 2.98 | 515 $(M + H)^+$. | ESI (Pos., 20 V) |
| 23(H27-45) | F | 2.85 | 487 $(M + H)^+$. | ESI (Pos., 20 V) |
| 23(H27-46) | F | 2.81 | 437 $(M + H)^+$. | ESI (Pos., 20 V) |
| 23(H27-47) | F | 2.89 | 421 $(M + H)^+$. | ESI (Pos., 20 V) |
| 23(H27-48) | F | 2.94 | 451 $(M + H)^+$. | ESI (Pos., 20 V) |
| 23(H27-49) | F | 2.92 | 479 $(M + H)^+$. | ESI (Pos., 20 V) |
| 23(H27-50) | F | 3.16 | 513 $(M + H)^+$. | ESI (Pos., 20 V) |
| 23(H27-51) | F | 3.18 | 527 $(M + H)^+$. | ESI (Pos., 20 V) |
| 23(H27-52) | F | 2.98 | 515 $(M + H)^+$. | ESI (Pos., 20 V) |

TABLE 27C-3

| Example No | HPLC condition | Retention time (min) | Mass data | Mass condition |
|---|---|---|---|---|
| 23(H27-53) | F | 2.83 | 487 $(M + H)^+$. | ESI (Pos., 20 V) |
| 23(H27-54) | F | 2.81 | 437 $(M + H)^+$. | ESI (Pos., 20 V) |
| 23(H27-55) | F | 3.33 | 434 $(M + H)^+$. | ESI (Pos., 20 V) |
| 23(H27-56) | F | 3.36 | 464 $(M + H)^+$. | ESI (Pos., 20 V) |
| 23(H27-57) | F | 3.34 | 492 $(M + H)^+$. | ESI (Pos., 20 V) |
| 23(H27-58) | F | 3.60 | 526 $(M + H)^+$. | ESI (Pos., 20 V) |
| 23(H27-59) | F | 3.62 | 540 $(M + H)^+$. | ESI (Pos., 20 V) |
| 23(H27-60) | F | 3.36 | 528 $(M + H)^+$. | ESI (Pos., 20 V) |
| 23(H27-61) | F | 3.20 | 500 $(M + H)^+$. | ESI (Pos., 20 V) |
| 23(H27-62) | F | 3.23 | 450 $(M + H)^+$. | ESI (Pos., 20 V) |
| 23(H27-63) | F | 3.36 | 434 $(M + H)^+$. | ESI (Pos., 20 V) |
| 23(H27-64) | F | 3.38 | 464 $(M + H)^+$. | ESI (Pos., 20 V) |
| 23(H27-65) | F | 3.36 | 492 $(M + H)^+$. | ESI (Pos., 20 V) |
| 23(H27-66) | F | 3.62 | 526 $(M + H)^+$. | ESI (Pos., 20 V) |
| 23(H27-67) | F | 3.62 | 540 $(M + H)^+$. | ESI (Pos., 20 V) |
| 23(H27-68) | F | 3.38 | 528 $(M + H)^+$. | ESI (Pos., 20 V) |
| 23(H27-69) | F | 3.23 | 500 $(M + H)^+$. | ESI (Pos., 20 V) |
| 23(H27-70) | F | 3.25 | 450 $(M + H)^+$. | ESI (Pos., 20 V) |
| 23(H27-71) | F | 3.36 | 434 $(M + H)^+$. | ESI (Pos., 20 V) |
| 23(H27-72) | F | 3.38 | 464 $(M + H)^+$. | ESI (Pos., 20 V) |
| 23(H27-73) | F | 3.36 | 492 $(M + H)^+$. | ESI (Pos., 20 V) |
| 23(H27-74) | F | 3.62 | 526 $(M + H)^+$. | ESI (Pos., 20 V) |
| 23(H27-75) | F | 3.62 | 540 $(M + H)^+$. | ESI (Pos., 20 V) |
| 23(H27-76) | F | 3.36 | 528 $(M + H)^+$. | ESI (Pos., 20 V) |
| 23(H27-77) | F | 3.22 | 500 $(M + H)^+$. | ESI (Pos., 20 V) |
| 23(H27-78) | F | 3.23 | 450 $(M + H)^+$. | ESI (Pos., 20 V) |

TABLE 28C-1

| Example No | HPLC condition | Retention time (min) | Mass data | Mass condition |
|---|---|---|---|---|
| 23(H28-1) | F | 3.36 | 470 $(M + H)^+$. | ESI (Pos., 20 V) |
| 23(H28-2) | F | 3.37 | 506 $(M + H)^+$. | ESI (Pos., 20 V) |
| 23(H28-3) | F | 3.31 | 416 $(M + H)^+$. | ESI (Pos., 20 V) |
| 23(H28-4) | F | 3.42 | 498 $(M + H)^+$. | ESI (Pos., 20 V) |
| 23(H28-5) | F | 3.35 | 432 $(M + H)^+$. | ESI (Pos., 20 V) |
| 23(H28-6) | F | 3.41 | 430 $(M + H)^+$. | ESI (Pos., 20 V) |
| 23(H28-7) | F | 3.04 | 413 $(M + H)^+$. | ESI (Pos., 20 V) |
| 23(H28-8) | F | 3.45 | 465 $(M + H)^+$. | ESI (Pos., 20 V) |
| 23(H28-9) | F | 3.03 | 416 $(M + H)^+$. | ESI (Pos., 20 V) |
| 23(H28-10) | F | 3.77 | 446 $(M + H)^+$. | ESI (Pos., 20 V) |
| 23(H28-11) | F | 3.61 | 512 $(M + H)^+$. | ESI (Pos., 20 V) |
| 23(H28-12) | F | 3.61 | 512 $(M + H)^+$. | ESI (Pos., 20 V) |
| 23(H28-13) | F | 3.15 | 432 $(M + H)^+$. | ESI (Pos., 20 V) |
| 23(H28-14) | F | 3.22 | 462 $(M + H)^+$. | ESI (Pos., 20 V) |
| 23(H28-15) | F | 3.16 | 446 $(M + H)^+$. | ESI (Pos., 20 V) |
| 23(H28-16) | F | 3.46 | 446 $(M + H)^+$. | ESI (Pos., 20 V) |
| 23(H28-17) | F | 3.29 | 466 $(M + H)^+$. | ESI (Pos., 20 V) |
| 23(H28-18) | F | 3.68 | 562 $(M + H)^+$. | ESI (Pos., 20 V) |
| 23(H28-19) | F | 3.36 | 509 $(M + H)^+$. | ESI (Pos., 20 V) |
| 23(H28-20) | F | 3.76 | 614 $(M + H)^+$. | ESI (Pos., 20 V) |
| 23(H28-21) | F | 3.42 | 498 $(M + H)^+$. | ESI (Pos., 20 V) |
| 23(H28-22) | F | 3.71 | 580 $(M + H)^+$. | ESI (Pos., 20 V) |
| 23(H28-23) | F | 3.66 | 546 $(M + H)^+$. | ESI (Pos., 20 V) |
| 23(H28-24) | F | 3.44 | 493 $(M + H)^+$. | ESI (Pos., 20 V) |
| 23(H28-25) | F | 3.79 | 614 $(M + H)^+$. | ESI (Pos., 20 V) |
| 23(H28-26) | F | 3.42 | 526 $(M + H)^+$. | ESI (Pos., 20 V) |

TABLE 28C-2

| Example No | HPLC condition | Retention time (min) | Mass data | Mass condition |
|---|---|---|---|---|
| 23(H28-27) | F | 3.58 | 524 $(M + H)^+$. | ESI (Pos., 20 V) |
| 23(H28-28) | F | 3.62 | 546 $(M + H)^+$. | ESI (Pos., 20 V) |
| 23(H28-29) | F | 3.42 | 549 $(M + H)^+$. | ESI (Pos., 20 V) |
| 23(H28-30) | F | 3.62 | 512 $(M + H)^+$. | ESI (Pos., 20 V) |

TABLE 29C-1

| Example No | HPLC condition | Retention time (min) | Mass data | Mass condition |
|---|---|---|---|---|
| 23(H29-1) | F | 3.44 | 484 $(M + H)^+$. | ESI (Pos., 20 V) |
| 23(H29-2) | F | 3.44 | 520 $(M + H)^+$. | ESI (Pos., 20 V) |
| 23(H29-3) | F | 3.42 | 430 $(M + H)^+$. | ESI (Pos., 20 V) |
| 23(H29-4) | F | 3.53 | 512 $(M + H)^+$. | ESI (Pos., 20 V) |
| 23(H29-5) | F | 3.44 | 446 $(M + H)^+$. | ESI (Pos., 20 V) |
| 23(H29-6) | F | 3.49 | 444 $(M + H)^+$. | ESI (Pos., 20 V) |
| 23(H29-7) | F | 3.09 | 427 $(M + H)^+$. | ESI (Pos., 20 V) |
| 23(H29-8) | F | 3.53 | 479 $(M + H)^+$. | ESI (Pos., 20 V) |
| 23(H29-9) | F | 3.11 | 430 $(M + H)^+$. | ESI (Pos., 20 V) |
| 23(H29-10) | F | 3.14 | 460 $(M + H)^+$. | ESI (Pos., 20 V) |
| 23(H29-11) | F | 3.67 | 526 $(M + H)^+$. | ESI (Pos., 20 V) |
| 23(H29-12) | F | 3.69 | 526 $(M + H)^+$. | ESI (Pos., 20 V) |
| 23(H29-13) | F | 3.47 | 465 $(M + H)^+$. | ESI (Pos., 20 V) |
| 23(H29-14) | F | 3.23 | 446 $(M + H)^+$. | ESI (Pos., 20 V) |
| 23(H29-15) | F | 3.29 | 476 $(M + H)^+$. | ESI (Pos., 20 V) |
| 23(H29-16) | F | 3.24 | 460 $(M + H)^+$. | ESI (Pos., 20 V) |
| 23(H29-17) | F | 3.55 | 460 $(M + H)^+$. | ESI (Pos., 20 V) |
| 23(H29-18) | F | 3.35 | 480 $(M + H)^+$. | ESI (Pos., 20 V) |
| 23(H29-19) | F | 3.73 | 576 $(M + H)^+$. | ESI (Pos., 20 V) |
| 23(H29-20) | F | 3.44 | 523 $(M + H)^+$. | ESI (Pos., 20 V) |
| 23(H29-21) | F | 3.83 | 628 $(M + H)^+$. | ESI (Pos., 20 V) |
| 23(H29-22) | F | 3.49 | 510 $(M + H)^+$. | ESI (Pos., 20 V) |
| 23(H29-23) | F | 3.77 | 594 $(M + H)^+$. | ESI (Pos., 20 V) |
| 23(H29-24) | F | 3.72 | 560 $(M + H)^+$. | ESI (Pos., 20 V) |
| 23(H29-25) | F | 3.52 | 507 $(M + H)^+$. | ESI (Pos., 20 V) |
| 23(H29-26) | F | 3.85 | 628 $(M + H)^+$. | ESI (Pos., 20 V) |

TABLE 29C-2

| Example No | HPLC condition | Retention time (min) | Mass data | Mass condition |
|---|---|---|---|---|
| 23(H29-27) | F | 3.51 | 540 $(M + H)^+$. | ESI (Pos., 20 V) |
| 23(H29-28) | F | 3.66 | 538 $(M + H)^+$. | ESI (Pos., 20 V) |
| 23(H29-29) | F | 3.69 | 560 $(M + H)^+$. | ESI (Pos., 20 V) |
| 23(H29-30) | F | 3.47 | 563 $(M + H)^+$. | ESI (Pos., 20 V) |
| 23(H29-31) | F | 3.68 | 526 $(M + H)^+$. | ESI (Pos., 20 V) |

TABLE 30C-1

| Example No | HPLC condition | Retention time (min) | Mass data | Mass condition |
|---|---|---|---|---|
| 23(H30-1) | F | 3.27 | 486 $(M + H)^+$. | ESI (Pos., 20 V) |
| 23(H30-2) | F | 3.31 | 522 $(M + H)^+$. | ESI (Pos., 20 V) |
| 23(H30-3) | F | 3.24 | 432 $(M + H)^+$. | ESI (Pos., 20 V) |
| 23(H30-4) | F | 3.34 | 512 $(M + H)^+$. | ESI (Pos., 20 V) |
| 23(H30-5) | F | 3.29 | 448 $(M + H)^+$. | ESI (Pos., 20 V) |
| 23(H30-6) | F | 3.33 | 446 $(M + H)^+$. | ESI (Pos., 20 V) |

TABLE 30C-1-continued

| Example No | HPLC condition | Retention time (min) | Mass data | Mass condition |
|---|---|---|---|---|
| 23(H30-7) | F | 2.98 | 429 $(M + H)^+$. | ESI (Pos., 20 V) |
| 23(H30-8) | F | 3.38 | 481 $(M + H)^+$. | ESI (Pos., 20 V) |
| 23(H30-9) | F | 2.98 | 432 $(M + H)^+$. | ESI (Pos., 20 V) |
| 23(H30-10) | F | 3.01 | 462 $(M + H)^+$. | ESI (Pos., 20 V) |
| 23(H30-11) | F | 3.51 | 528 $(M + H)^+$. | ESI (Pos., 20 V) |
| 23(H30-12) | F | 3.55 | 528 $(M + H)^+$. | ESI (Pos., 20 V) |
| 23(H30-13) | F | 3.33 | 467 $(M + H)^+$. | ESI (Pos., 20 V) |
| 23(H30-14) | F | 3.09 | 448 $(M + H)^+$. | ESI (Pos., 20 V) |
| 23(H30-15) | F | 3.16 | 478 $(M + H)^+$. | ESI (Pos., 20 V) |
| 23(H30-16) | F | 3.09 | 462 $(M + H)^+$. | ESI (Pos., 20 V) |
| 23(H30-17) | F | 3.36 | 462 $(M + H)^+$. | ESI (Pos., 20 V) |
| 23(H30-18) | F | 3.22 | 482 $(M + H)^+$. | ESI (Pos., 20 V) |
| 23(H30-19) | F | 3.60 | 578 $(M + H)^+$. | ESI (Pos., 20 V) |
| 23(H30-20) | F | 3.31 | 525 $(M + H)^+$. | ESI (Pos., 20 V) |
| 23(H30-21) | F | 3.69 | 630 $(M + H)^+$. | ESI (Pos., 20 V) |
| 23(H30-22) | F | 3.33 | 512 $(M + H)^+$. | ESI (Pos., 20 V) |
| 23(H30-23) | F | 3.64 | 596 $(M + H)^+$. | ESI (Pos., 20 V) |
| 23(H30-24) | F | 3.59 | 562 $(M + H)^+$. | ESI (Pos., 20 V) |
| 23(H30-25) | F | 3.34 | 509 $(M + H)^+$. | ESI (Pos., 20 V) |
| 23(H30-26) | F | 3.71 | 630 $(M + H)^+$. | ESI (Pos., 20 V) |

TABLE 30C-2

| Example No | HPLC condition | Retention time (min) | Mass data | Mass condition |
|---|---|---|---|---|
| 23(H30-27) | F | 3.34 | 542 $(M + H)^+$. | ESI (Pos., 20 V) |
| 23(H30-28) | F | 3.51 | 540 $(M + H)^+$. | ESI (Pos., 20 V) |
| 23(H30-29) | F | 3.53 | 562 $(M + H)^+$. | ESI (Pos., 20 V) |
| 23(H30-30) | F | 3.34 | 565 $(M + H)^+$. | ESI (Pos., 20 V) |
| 23(H30-31) | F | 3.55 | 528 $(M + H)^+$. | ESI (Pos., 20 V) |

TABLE 31C-1

| Example No | HPLC condition | Retention time (min) | Mass data | Mass condition |
|---|---|---|---|---|
| 23(H31-1) | F | 3.47 | 518 $(M + H)^+$. | ESI (Pos., 20 V) |
| 23(H31-2) | F | 3.47 | 554 $(M + H)^+$. | ESI (Pos., 20 V) |
| 23(H31-3) | F | 3.45 | 464 $(M + H)^+$. | ESI (Pos., 20 V) |
| 23(H31-4) | F | 3.55 | 544 $(M + H)^+$. | ESI (Pos., 20 V) |
| 23(H31-5) | F | 3.47 | 480 $(M + H)^+$. | ESI (Pos., 20 V) |
| 23(H31-6) | F | 3.53 | 478 $(M + H)^+$. | ESI (Pos., 20 V) |
| 23(H31-7) | F | 3.14 | 461 $(M + H)^+$. | ESI (Pos., 20 V) |
| 23(H31-8) | F | 3.56 | 513 $(M + H)^+$. | ESI (Pos., 20 V) |
| 23(H31-9) | F | 3.14 | 464 $(M + H)^+$. | ESI (Pos., 20 V) |
| 23(H31-10) | F | 3.20 | 494 $(M + H)^+$. | ESI (Pos., 20 V) |
| 23(H31-11) | F | 3.69 | 560 $(M + H)^+$. | ESI (Pos., 20 V) |
| 23(H31-12) | F | 3.71 | 560 $(M + H)^+$. | ESI (Pos., 20 V) |
| 23(H31-13) | F | 3.51 | 499 $(M + H)^+$. | ESI (Pos., 20 V) |
| 23(H31-14) | F | 3.27 | 480 $(M + H)^+$. | ESI (Pos., 20 V) |
| 23(H31-15) | F | 3.33 | 510 $(M + H)^+$. | ESI (Pos., 20 V) |
| 23(H31-16) | F | 3.29 | 494 $(M + H)^+$. | ESI (Pos., 20 V) |
| 23(H31-17) | F | 3.58 | 494 $(M + H)^+$. | ESI (Pos., 20 V) |
| 23(H31-18) | F | 3.40 | 514 $(M + H)^+$. | ESI (Pos., 20 V) |
| 23(H31-19) | F | 3.75 | 610 $(M + H)^+$. | ESI (Pos., 20 V) |
| 23(H31-20) | F | 3.49 | 557 $(M + H)^+$. | ESI (Pos., 20 V) |
| 23(H31-21) | F | 3.86 | 662 $(M + H)^+$. | ESI (Pos., 20 V) |
| 23(H31-22) | F | 3.53 | 544 $(M + H)^+$. | ESI (Pos., 20 V) |
| 23(H31-23) | F | 3.80 | 628 $(M + H)^+$. | ESI (Pos., 20 V) |
| 23(H31-24) | F | 3.75 | 594 $(M + H)^+$. | ESI (Pos., 20 V) |
| 23(H31-25) | F | 3.57 | 541 $(M + H)^+$. | ESI (Pos., 20 V) |
| 23(H31-26) | F | 3.86 | 662 $(M + H)^+$. | ESI (Pos., 20 V) |

TABLE 31C-2

| Example No | HPLC condition | Retention time (min) | Mass data | Mass condition |
|---|---|---|---|---|
| 23(H31-27) | F | 3.53 | 574 $(M + H)^+$. | ESI (Pos., 20 V) |
| 23(H31-28) | F | 3.67 | 572 $(M + H)^+$. | ESI (Pos., 20 V) |
| 23(H31-29) | F | 3.71 | 594 $(M + H)^+$. | ESI (Pos., 20 V) |
| 23(H31-30) | F | 3.51 | 597 $(M + H)^+$. | ESI (Pos., 20 V) |
| 23(H31-31) | F | 3.73 | 560 $(M + H)^+$. | ESI (Pos., 20 V) |

EXAMPLE 24(1)~24(119)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl) leucine, and furthermore by the same procedure as described in Reference Example 5→Reference Example 6→Example 1 using the corresponding compound instead of 3,5-dimethyl-1-phenyl-4-formylpyrazole, the following compounds of the present invention were obtained.

EXAMPLE 24(1)

(3S)-1-butyl-2,5-dioxo-3-(4-methoxyphenylmethyl)-9-cyclohexyl methyl-1,4,9-triazaspiro[5.5]undecane-.hydrochloride

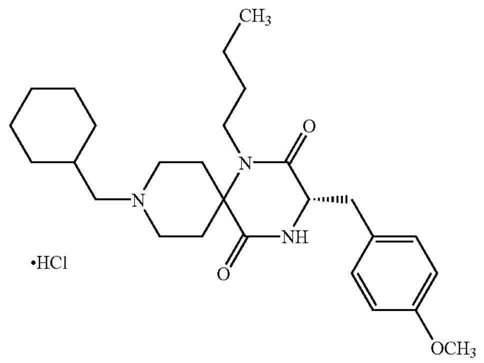

TLC: Rf 0.44 (chloroform:methanol=10:1);

NMR ($CD_3OD$): δ 7.06 (d, J=9.0 Hz, 2H), 6.84 (d, J=9.0 Hz, 2H), 4.31 (dd, J=4.5, 3.6 Hz, 1H), 3.82–3.67 (m, 4H), 3.49–3.30 (m, 3H), 3.25 (dd, J=13.8, 3.6 Hz, 1H), 3.23–3.10 (m, 2H), 2.95–2.87 (m, 2H), 2.87 (dd, J=13.8, 4.5 Hz, 1H), 2.31 (m, 1H), 2.05 (m, 1H), 1.91–1.64 (m, 7H), 1.56–1.14 (m, 7H), 1.09–0.91 (m, 5H), 0.26 (m, 1H).

EXAMPLE 24(2)

1-butyl-2,5-dioxo-3-(2-methylpropyl)-9-(2-(4-chlorophenyl)thiophen-5-ylmethyl)-1,4,9-triazaspiro[5.5] undecane.hydrochloride

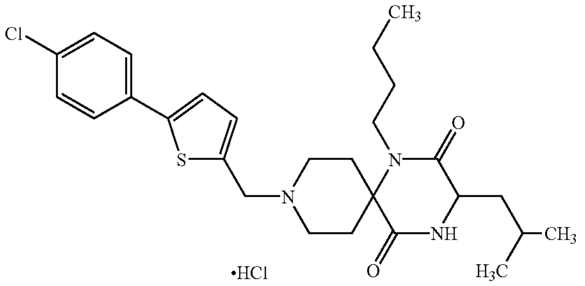

TLC: Rf 0.60 (chloroform:methanol=10:1);

NMR ($CD_3OD$): δ 7.65 (d, J=8.7 Hz, 2H), 7.42 (d, J=8.7 Hz, 2H), 7.42 (d, J=3.6 Hz, 1H), 7.34 (d, J=3.6 Hz, 1H), 4.61 (brs, 2H), 4.01 (dd, J=7.8, 4.5 Hz, 1H), 3.95–3.72 (m, 2H), 3.65–3.50 (m, 2H), 3.44–3.34 (m, 2H), 2.50–2.12 (m, 4H), 1.89–1.45 (m, 5H), 1.45–1.28 (m, 2H), 1.13–0.89 (m, 9H).

EXAMPLE 24(3)

1-butyl-2,5-dioxo-3-(2-methylpropyl)-9-(2-(4-methoxyphenyl)thiophen-5-ylmethyl)-1,4,9-triazaspiro [5.5]undecane.hydrochloride

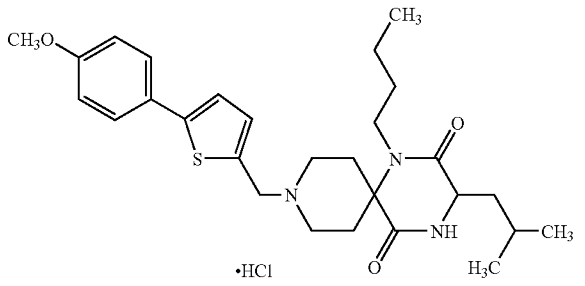

TLC: Rf 0.60 (chloroform:methanol=10:1);

NMR ($CD_3OD$): δ 7.57 (d, J=9.0 Hz, 2H), 7.33-7.26 (m, 2H), 6.97 (d, J=9.0 Hz, 2H), 4.58 (brs, 2H), 4.01 (dd, J=7.5, 4.5 Hz, 1H), 3.93-3.71 (m, 5H), 3.64–3.50 (m, 2H), 3.44–3.34 (m, 2H), 2.49–2.12 (m, 4H), 1.90–1.45 (m, 5H), 1.45–1.28 (m, 2H), 1.03–0.88 (m, 9H).

EXAMPLE 24(4)

1-((2E)-2-butenyl)-2,5-dioxo-3-(2-methylpropyl)-9-(4-phenyloxyphenylmethyl)-1,4,9-triazaspiro[5.5] undecane.hydrochloride

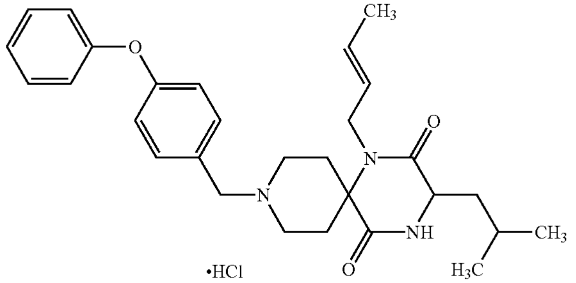

TLC: Rf 0.32 (chloroform:methanol=20:1);

NMR ($CD_3OD$): δ 7.52 (d, J=8.7 Hz, 2H), 7.44–7.35 (m, 2H), 7.22–7.14 (m, 1H), 7.06 (d, J=8.7 Hz, 2H), 7.10–7.00 (m, 2H), 5.75–5.60 (m, 1H), 5.52–5.38 (m, 1H), 4.33 (s, 2H), 4.15–3.93 (m, 2H), 4.03 (dd, J=7.8, 4.5 Hz, 1H), 3.88–3.66 (m, 2H), 3.55–3.42 (m, 2H), 2.52–2.35 (m, 2H), 2.28–2.08 (m, 2H), 1.90–1.57 (m, 3H), 1.65 (dd, J=6.3, 1.5 Hz, 3H), 0.95 (d, J=6.6 Hz, 3H), 0.94 (d, J=6.6 Hz, 3H).

EXAMPLE 24(5)

1-(furan-2-ylmethyl)-2,5-dioxo-3-(2-methylpropyl)-9-(4-phenyloxyphenylmethyl)-1,4,9-triazaspiro[5.5] undecane.hydrochloride

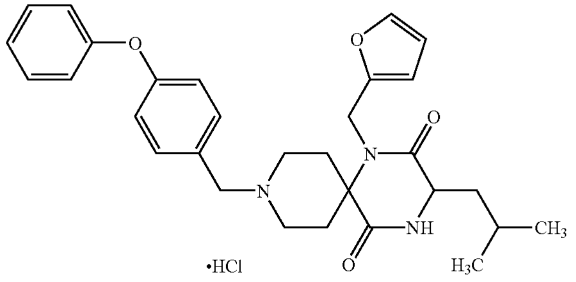

TLC: Rf 0.33 (chloroform:methanol=20:1);

NMR ($CD_3OD$): δ 7.52 (d, J=8.7 Hz, 2H), 7.43–7.36 (m, 3H), 7.18 (t, J=7.2 Hz, 1H), 7.09–6.99 (m, 4H), 6.33 (m, 1H), 6.28 (d, J=3.0 Hz, 1H), 4.69 (s, 2H), 4.33 (s, 2H), 4.08 (dd, J=7.8, 4.5 Hz, 1H), 3.87–3.72 (m, 2H), 3.57–3.42 (m, 2H), 2.65–2.38 (m, 2H), 2.30–2.12 (m, 2H), 1.90–1.56 (m, 3H), 0.93 (d, J=6.6 Hz, 3H), 0.91 (d, J=6.6 Hz, 3H).

EXAMPLE 24(6)

1-(thiophen-2-ylmethyl)-2,5-dioxo-3-(2-methylpropyl)-9-(4-phenyloxyphenylmethyl)-1,4,9-triazaspiro[5.5]undecane.hydrochloride

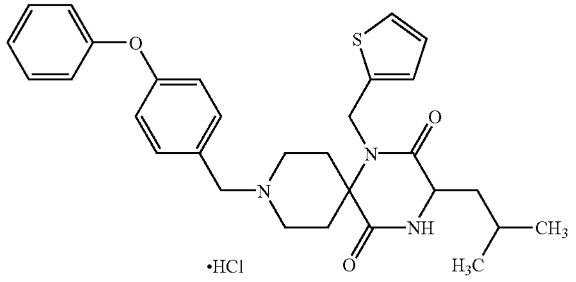

TLC: Rf 0.39 (chloroform:methanol=20:1);

NMR ($CD_3OD$): δ 7.53 (d, J=8.7 Hz, 2H), 7.43–7.34 (m, 2H), 7.27 (dd, J=5.1, 1.2 Hz, 1H), 7.18 (t, J=7.2 Hz, 1H), 7.09–7.00 (m, 5H), 6.91 (dd, J=5.1, 3.3 Hz, 1H), 4.92 (brs, 2H), 4.32 (s, 2H), 4.11 (dd, J=7.8, 4.5 Hz, 1H), 3.84–3.66 (m, 2H), 3.53–3.41 (m, 2H), 2.68–2.46 (m, 2H), 2.23–2.06 (m, 2H), 1.95–1.59 (m, 3H), 0.95 (d, J=6.6 Hz, 6H).

EXAMPLE 24(7)

1-cyclopropylmethyl-2,5-dioxo-3-(2-methylpropyl)-9-(4-phenyloxyphenylmethyl)-1,4,9-triazaspiro[5.5]undecane.hydrochloride

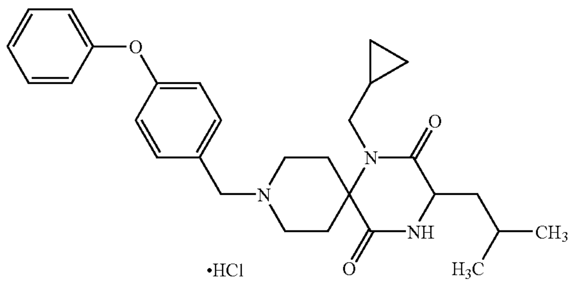

TLC: Rf 0.40 (chloroform:methanol=20:1);

NMR ($CD_3OD$): δ 7.53 (d, J=8.7 Hz, 2H), 7.43–7.35 (m, 2H), 7.18 (t, J=7.2 Hz, 1H), 7.08–7.00 (m, 4H), 4.33 (s, 2H), 4.04 (dd, J=7.8, 4.5 Hz, 1H), 3.87–3.68 (m, 2H), 3.56–3.43 (m, 2H), 3.46–3.35 (m 2H), 2.56–2.35 (m, 2H), 2.23–2.12 (m, 2H), 1.95–1.58 (m, 3H), 1.10–0.95 (m, 1H), 0.95 (d, J=6.6 Hz, 6H), 0.56–0.45 (m, 2H), 0.42–0.34 (m, 2H).

EXAMPLE 24(8)

1-(2-fluorophenylmethyl)-2,5-dioxo-3-(2-methylpropyl)-9-(4-phenyloxyphenylmethyl)-1,4,9-triazaspiro[5.5]undecane.hydrochloride

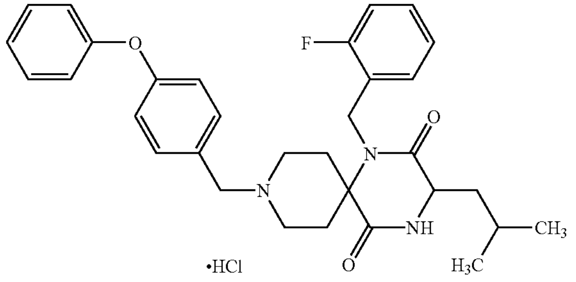

TLC: Rf 0.43 (chloroform:methanol=20:1);

NMR ($CD_3OD$): δ 7.48 (d, J=9.0 Hz, 2H), 7.42–7.34 (m, 2H), 7.32–7.21 (m, 1H), 7.17 (t, J=7.5 Hz, 1H), 7.14–7.06 (m, 3H), 7.06–6.98 (m, 4H), 4.80 (brs, 2H), 4.30 (s, 2H), 4.18 (dd, J=8.1, 4.8 Hz, 1H), 3.86–3.68 (m, 2H), 3.50–3.35 (m, 2H), 2.50–2.30 (m, 1H), 2.30–2.14 (m, 3H), 1.94–1.62 (m, 3H), 0.97 (d, J=6.3 Hz, 6H).

EXAMPLE 24(9)

1-(3-methyl-2-butenyl)-2,5-dioxo-3-(2-methylpropyl)-9-(4-phenyloxyphenylmethyl)-1,4,9-triazaspiro[5.5]undecane.hydrochloride

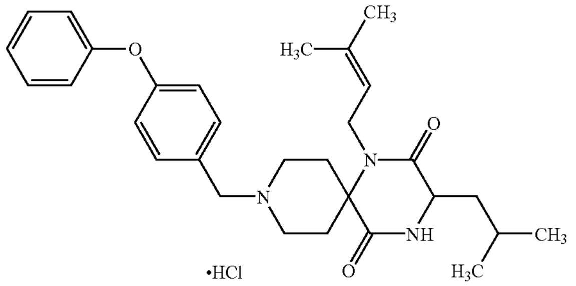

TLC: Rf 0.29 (chloroform:methanol=20:1);

NMR ($CD_3OD$): δ 7.52 (d, J=8.4 Hz, 2H), 7.43–7.35 (m, 2H), 7.18 (t, J=7.5 Hz, 1H), 7.09–7.00 (m, 4H), 4.97 (br, 1H), 4.32 (s, 2H), 4.20–4.00 (m, 2H), 4.02 (dd, J=7.8, 4.5 Hz, 1H), 3.90–3.68 (m, 2H), 3.55–3.45 (m, 2H), 2.52–2.32 (m, 2H), 2.30–2.08 (m, 2H), 1.90–1.56 (m, 3H), 1.74 (s, 3H), 1.69 (s, 3H), 0.94 (d, J=6.3 Hz, 3H), 0.94 (d, J=6.3 Hz, 3H).

EXAMPLE 24(10)

1-butyl-2,5-dioxo-3-(2-methylpropyl)-9-(quinolin-3-ylmethyl)-1,4,9-triazaspiro[5.5]undecane.2 hydrochloride

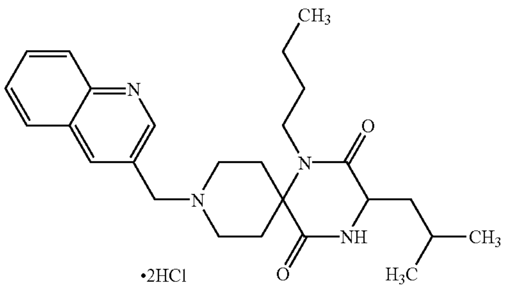

TLC: Rf 0.25 (chloroform:methanol=20:1);

NMR ($CD_3OD$): δ 9.52 (d, J=1.5 Hz, 1H), 9.35 (d, J=1.5 Hz, 1H), 8.35 (d, J=8.7 Hz, 1H), 8.27 (d, J=8.7 Hz, 1H), 8.24–8.16 (m, 1H), 8.04–7.96 (m, 1H), 4.76 (s, 2H), 4.03 (dd, J=7.5, 4.5 Hz, 1H), 4.00–3.85 (m, 2H), 3.68–3.55 (m, 2H), 3.55–3.43 (m, 2H), 2.76–2.56 (m, 2H), 2.27–2.05 (m, 2H), 1.82–1.10 (m, 15H), 1.05–0.83 (m, 2H), 0.92 (t, J=7.2 Hz, 3H).

EXAMPLE 24(11)

1-butyl-2,5-dioxo-3-(benzyloxycarbonylmethyl)-9-(4-phenyloxyphenylmethyl)-1,4,9-triazaspiro[5.5]undecane.hydrochloride

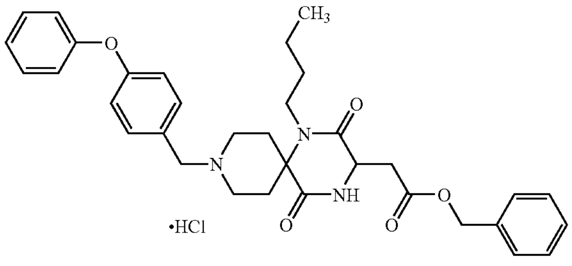

TLC: Rf 0.74 (chloroform:methanol=9:1);

NMR ($CD_3OD$): δ 7.52 (d, J=7.0 Hz, 2H), 7.40 (t, J=7.5 Hz, 2H), 7.33 (m, 5H), 7.18 (t, J=7.5 Hz, 1H), 7.05 (m, 4H), 5.12 (s, 2H), 4.33 (s, 2H), 4.31 (m, 1H), 3.88 (m, 1H), 3.66 (m, 1H), 3.50–3.35 (m, 4H), 3.08 (dd, J=17.7, 4.8 Hz, 1H), 2.86 (dd, J=17.7, 3.0 Hz, 1H), 2.34 (m, 2H), 2.25 (m, 2H), 1.50 (m, 2H), 1.36 (m, 2H), 0.94 (t, J=7.5 Hz, 3H).

EXAMPLE 24(12)

1-(3-methyl-2-butenyl)-2,5-dioxo-3-cyclohexylmethyl-9-(1,4-benzodioxan-6-ylmethyl)-1,4,9-triazaspiro[5.5]undecane.hydrochloride

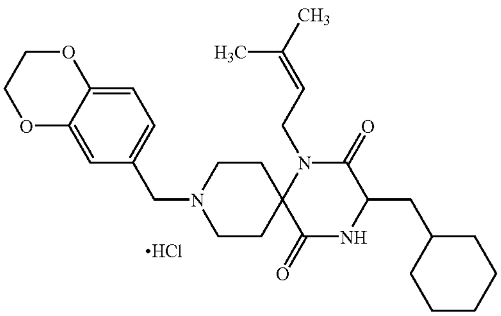

TLC: Rf 0.63 (chloroform:methanol=10:1);

NMR ($CD_3OD$): δ 7.04 (d, J=2.1 Hz, 1H), 6.96 (dd, J=8.1, 2.1 Hz, 1H), 6.92 (d, J=8.1 Hz, 1H), 4.96 (m, 1H), 4.26 (s, 4H), 4.22 (s, 2H), 4.10–4.00 (m, 3H), 3.84–3.68 (m, 2H), 3.52–3.40 (m, 2H), 2.43–2.08 (m, 4H), 1.84–1.42 (m, 13H), 1.38–1.12 (m, 4H), 1.04–0.85 (m, 2H).

EXAMPLE 24(13)

1-butyl-2,5-dioxo-3-cyclohexylmethyl-9-((2E)-3-phenyl-2-propenyl)-1,4,9-triazaspiro[5.5]undecane-.hydrochloride

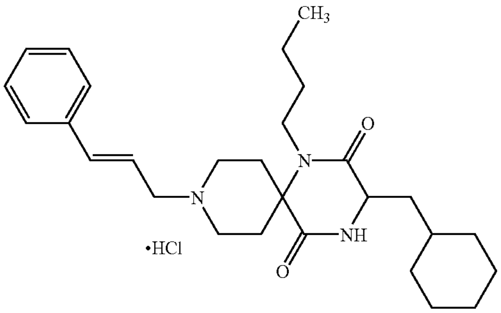

TLC: Rf 0.28 (chloroform:methanol=20:1);

NMR ($CD_3OD$): δ 7.53–7.48 (m, 2H), 7.30–7.40 (m, 3H), 6.95 (d, J=16.2 Hz, 1H), 6.36 (dd, J=16.2, 8.1 Hz, 1H), 4.07 (dd, J=7.5, 4.5 Hz, 1H), 3.96 (d, J=8.1 Hz, 2H), 3.86–3.75 (m, 2H), 3.60–3.52 (m, 2H), 3.42–3.34 (m, 2H), 2.42–2.18 (m, 4H), 1.82–1.14 (m, 15H), 0.96 (t, J=7.2 Hz, 3H), 0.96 (m, 2H).

EXAMPLE 24(14)

(3S)-1-butyl-2,5-dioxo-3-(1,1-dimethylethyl)-9-(4-phenyloxyphenylmethyl)-1,4,9-triazaspiro[5.5]undecane.hydrochloride

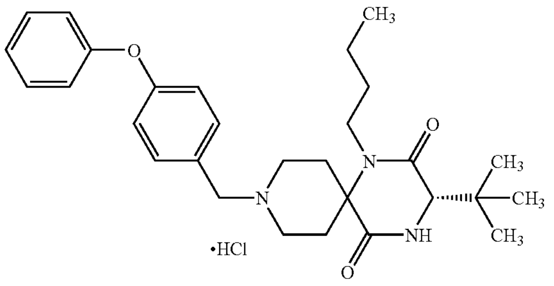

TLC: Rf 0.50 (chloroform:methanol=10:1);

NMR ($CD_3OD$): δ 7.54 (d, J=8.5 Hz, 2H), 7.39 (m, 2H), 7.18 (t, J=7.5 Hz, 1H), 7.08–7.02 (m, 4H), 4.34 (s, 2H), 3.88 (m, 2H), 3.62 (s, 1H), 3.46 (m, 4H), 2.45 (m, 2H), 2.13 (m, 2H), 1.66–1.47 (m, 2H), 1.36 (m, 2H), 1.02 (s, 9H), 0.95 (t, J=7.0 Hz, 3H).

EXAMPLE 24(15)

(3S)-1-butyl-2,5-dioxo-3-(1,1-dimethylethyl)-9-(1,4-benzodioxan-6-ylmethyl)-1,4,9-triazaspiro[5.5]undecane.hydrochloride

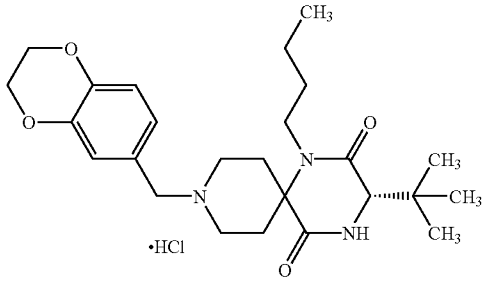

TLC: Rf 0.47 (chloroform:methanol=10:1);

NMR ($CD_3OD$): δ 7.07 (m, 1H), 6.99 (d, J=8.0 Hz, 1H), 6.91 (d, J=8.0 Hz, 1H), 4.26 (m, 4H), 4.24 (s, 2H), 3.83 (m, 2H), 3.62 (s, 1H), 3.45 (m, 4H), 2.42 (m, 2H), 2.11 (m, 2H), 1.64–1.5 (m, 2H), 1.38 (m, 2H), 1.01 (s, 9H), 0.95 (t, J=7.0 Hz, 3H).

EXAMPLE 24(16)

1-butyl-2,5-dioxo-3-(2-methylpropyl)-9-(4-methylthiazol-2-ylmethyl)-1,4,9-triazaspiro[5.5]undecane.hydrochloride

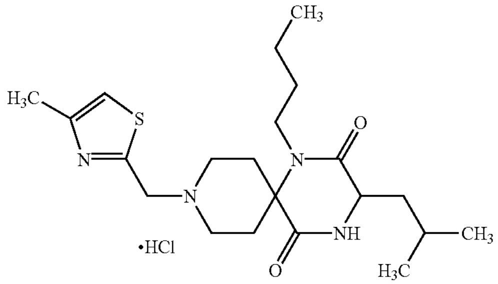

TLC: Rf 0.67 (chloroform:methanol=10:1);

NMR ($CD_3OD$): δ 7.34 (s, 1H), 4.73 (s, 2H), 4.01 (dd, J=8.0, 4.5 Hz, 1H), 3.93 (m, 2H), 3.65 (m, 2H), 3.41 (m, 2H), 2.53–2.41 (m, 2H), 2.48 (s, 3H), 2.23 (m, 2H), 1.85–1.52 (m, 5H), 1.38 (m, 2H), 0.96 (t, J=7.0 Hz, 3H), 0.94 (d, J=6.5 Hz, 3H), 0.93 (d, J=6.5 Hz, 3H).

EXAMPLE 24(17)

1-butyl-2,5-dioxo-3-cyclohexylmethyl-9-(5-methylthiazol-2-ylmethyl)-1,4,9-triazaspiro[5.5]undecane.hydrochloride

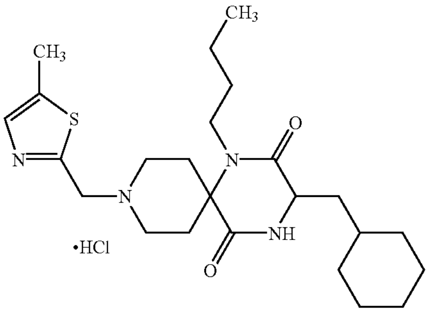

TLC: Rf 0.66 (chloroform:methanol=10:1);

NMR ($CD_3OD$): δ 7.34 (s, 1H), 4.72 (s, 2H), 4.04 (dd, J=7.5, 4.5 Hz, 1H), 3.98–3.86 (m, 2H), 3.67–3.63 (m, 2H), 3.44–3.38 (m, 2H), 2.56–2.42 (m, 2H), 2.48 (s, 3H), 2.30–2.14 (m, 2H), 1.84–1.18 (m, 15H), 0.96 (t, J=7.2 Hz, 3H), 0.96 (m, 2H).

EXAMPLE 24(18)

1-butyl-2,5-dioxo-3-cyclohexylmethyl-9-(4-methylthiazol-2-ylmethyl)-1,4,9-triazaspiro[5.5]undecane.hydrochloride

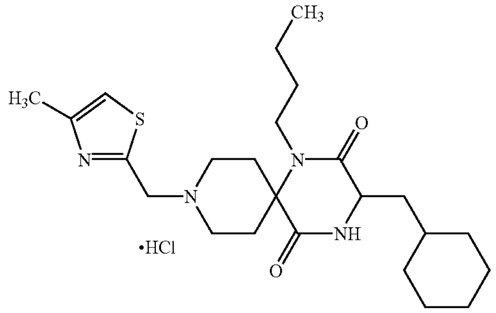

TLC: Rf 0.63 (chloroform:methanol=10:1);

NMR ($CD_3OD$): δ 7.63 (s, 1H), 4.69 (s, 2H), 4.03 (dd, J=7.3, 4.5 Hz, 1H), 3.96–3.82 (m, 2H), 3.72–3,58 (m, 2H), 3.42–3.37 (m, 2H), 2.52 (s, 3H), 2.56–2.36 (m, 2H), 2.28–2.12 (m, 2H), 1.80–1.12 (m, 15H), 0.96 (t, J=7.5 Hz, 3H), 0.96 (m, 2H).

EXAMPLE 24(19)

1-butyl-2,5-dioxo-3-(2-methylpropyl)-9-(5-methylthiazol-2-ylmethyl)-1,4,9-triazaspiro[5.5]undecane.hydrochloride

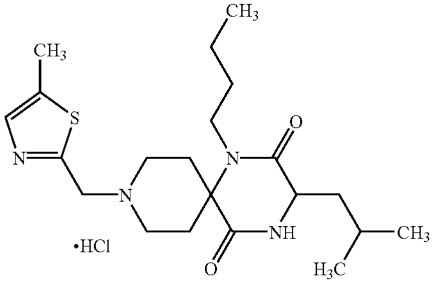

TLC: Rf 0.70 (chloroform:methanol=10:1);

NMR ($CD_3OD$): δ 7.63 (s, 1H), 4.69 (brs, 2H), 4.01 (dd, J=7.8, 4.5 Hz, 1H), 3.99–3.83 (m, 2H), 3.70–3.58 (m, 2H), 3.44–3.34 (m, 2H), 2.53 (s, 3H), 2.50–2.33 (m, 2H), 2.32–2.12 (m, 2H), 1.88–1.46 (m, 5H), 1.45–1.31 (m, 2H), 1.01–0.90 (m, 9H).

EXAMPLE 24(20)

(3R)-1-butyl-2,5-dioxo-3-cyclohexylmethyl-9-(1,4-benzodioxan-6-ylmethyl)-1,4,9-triazaspiro[5.5]undecane.hydrochloride

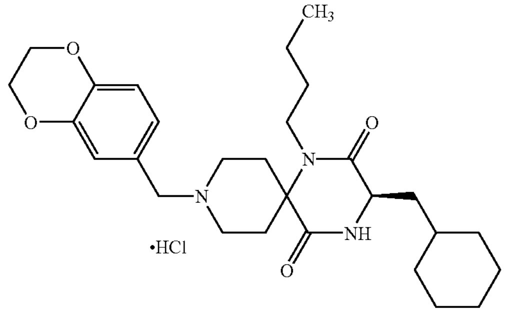

TLC: Rf 0.59 (chloroform:methanol=10:1);

NMR ($CD_3OD$): δ 7.04 (d, J=2.0 Hz, 1H), 6.97 (dd, J=8.5, 2.0 Hz, 1H), 6.93 (d, J=8.5 Hz, 1H), 4.26 (s, 4H), 4.24 (s, 2H), 4.04 (dd, J=7.5, 5.0 Hz, 1H), 3.76 (m, 2H), 3.46 (m, 4H), 2.39–2.11 (m, 4H), 1.78–1.17 (m, 15H), 0.95 (t, J=7.0 Hz, 3H), 0.95 (m, 2H).

HPLC condition

Column: YMC CHIRAL-CD BR, 0.46×25 cm, YMC, DB12S05-2546WTI;

Flow rate: 0.5 mL/min;

Eluent

Component A: 0.1 M potassium dihydrogenphosphate aqueous solution

Component B: acetonitrile

A:B=84:16;

UV: 235 nm;

Retention time: 18 min.

EXAMPLE 24(21)

(3S)-1-butyl-2,5-dioxo-3-cyclohexylmethyl-9-(1,4-benzodioxan-6-ylmethyl)-1,4,9-triazaspiro[5.5]undecane.hydrochloride

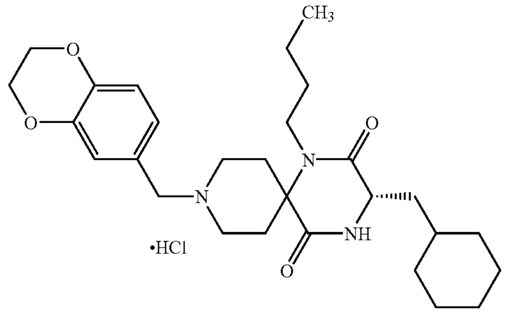

TLC: Rf 0.59 (chloroform:methanol=10:1);

NMR ($CD_3OD$): δ 7.04 (d, J=2.0 Hz, 1H), 6.97 (dd, J=8.5, 2.0 Hz, 1H), 6.93 (d, J=8.5 Hz, 1H), 4.26 (s, 4H), 4.24 (s, 2H), 4.04 (dd, J=7.5, 5.0 Hz, 1H), 3.76 (m, 2H), 3.46 (m,

4H), 2.39–2.11 (m, 4H), 1.78–1.17 (m, 15H), 0.95 (t, J=7.0 Hz, 3H), 0.95 (m, 2H).

HPLC condition

Column: YMC CHIRAL-CD BR, 0.46×25 cm, YMC, DB12S05-2546WTI;

Flow rate: 0.5 mL/min;

Eluent

Component A: 0.1 M potassium dihydrogenphosphate aqueous solution

Component B: acetonitrile

A: B=84:16;

UV: 235 nm;

Retention time: 20 min.

EXAMPLE 24(22)

(3R)-1-butyl-2,5-dioxo-3-((1R)-1-methylpropyl)-9-(4-phenyloxyphenylmethyl)-1,4,9-triazaspiro[5.5]undecane.hydrochloride

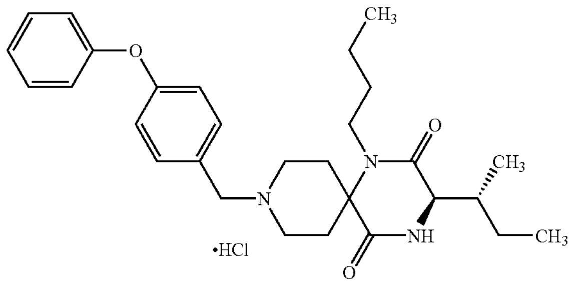

TLC: Rf 0.59 (chloroform:methanol=10:1);

NMR ($CD_3OD$): δ 7.53 (d, J=8.5 Hz, 2H), 7.39 (m, 2H), 7.18 (t, J=7.5 Hz, 1H), 7.08–7.01 (m, 4H), 4.33 (s, 2H), 3.96 (d, J=2.5 Hz, 1H), 3.92 (m, 1H), 3.75 (m, 1H), 3.53–3.44 (m, 4H), 2.49–2.32 (m, 2H), 2.16 (m, 2H), 2.06–1.98 (m, 1H), 1.61–1.21 (m, 6H), 1.00–0.89 (m, 9H).

EXAMPLE 24(23)

(3S)-1-butyl-2,5-dioxo-3-((1S)-1-methylpropyl)-9-(4-phenyloxyphenylmethyl)-1,4,9-triazaspiro[5.5]undecane.hydrochloride

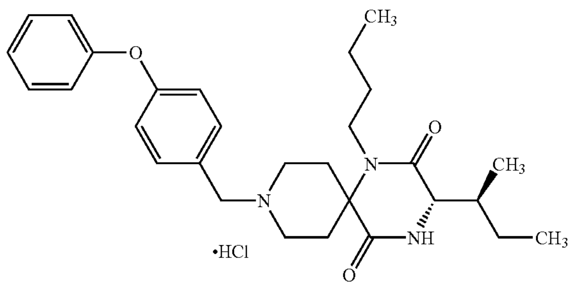

TLC: Rf 0.59 (chloroform:methanol=10:1);

NMR ($CD_3OD$): δ 7.53 (d, J=8.5 Hz, 2H), 7.39 (m, 2H), 7.18 (t, J=7.5 Hz, 1H), 7.08–7.01 (m, 4H), 4.33 (s, 2H), 3.96 (d, J=2.5 Hz, 1H), 3.92 (m, 1H), 3.75 (m, 1H), 3.53–3.44 (m, 4H), 2.49–2.32 (m, 2H), 2.16 (m, 2H), 2.06–1.98 (m, 1H), 1.61–1.21 (m, 6H), 1.00–0.89 (m, 9H).

EXAMPLE 24(24)

1-(2-butynyl)-2,5-dioxo-3-(2-methylpropyl)-9-(4-phenyloxyphenylmethyl)-1,4,9-triazaspiro[5.5]undecane.hydrochloride

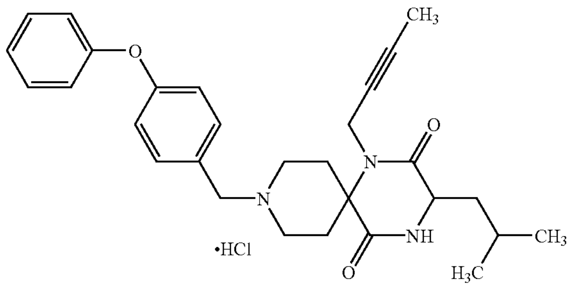

TLC: Rf 0.70 (chloroform:methanol=10:1);

NMR ($CD_3OD$): δ 7.51 (d, J=8.7 Hz, 2H), 7.39 (dd, J=8.7, 7.2 Hz, 2H), 7.18 (t, J=7.2 Hz, 1H), 7.09–7.00 (m, 4H), 4.33 (brs, 2H), 4.28–4.10 (m, 2H), 4.05 (dd, J=7.8, 4.5 Hz, 1H), 3.86–3.70 (m, 2H), 3.56–3.43 (m, 2H), 2.59–2.40 (m, 2H), 2.34–2.15 (m, 2H), 1.89–1.57 (m, 6H), 0.94 (d, J=6.6 Hz, 3H), 0.93 (d, J=6.6 Hz, 3H).

EXAMPLE 24(25)

1-(2-butynyl)-2,5-dioxo-3-cyclohexylmethyl-9-(1,4-benzodioxan-6-ylmethyl)-1,4,9-triazaspiro[5.5]undecane.hydrochloride

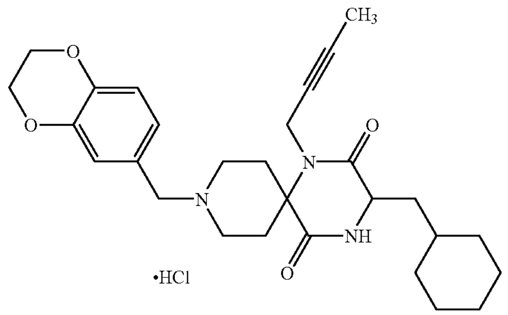

TLC: Rf 0.52 (chloroform:methanol=10:1);

NMR ($CD_3OD$): δ 7.04 (d, J=2.1 Hz, 1H), 6.97 (dd, J=8.4, 2.1 Hz, 1H), 6.93 (d, J=8.4 Hz, 1H), 4.26 (s, 4H), 4.23 (s, 2H), 4.18 (brs, 2H), 4.07 (dd, J=6.9, 4.8 Hz, 1H), 3.84–3.68 (m, 2H), 3.55–3.42 (m, 2H), 2.57–2.40 (m, 2H), 2.32–2.12 (m, 2H), 1.85–1.42 (m, 11H), 1.38–1.13 (m, 3H), 1.04–0.85 (m, 2H).

EXAMPLE 24(26)

1-pentyl-2,5-dioxo-3-cyclohexylmethyl-9-(1,4-benzodioxan-6-ylmethyl)-1,4,9-triazaspiro[5.5]undecane.hydrochloride

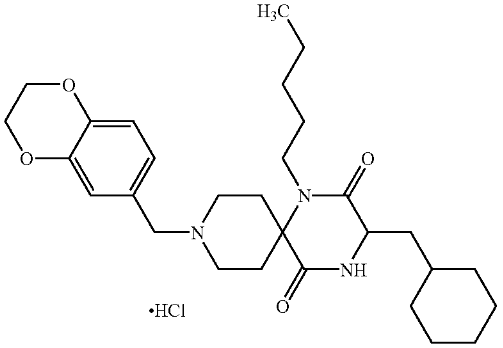

TLC: Rf 0.61 (chloroform:methanol=10:1);

NMR ($CD_3OD$): δ 7.04 (d, J=2.1 Hz, 1H), 6.97 (dd, J=8.4, 2.1 Hz, 1H), 6.92 (d, J=8.4 Hz, 1H), 4.26 (s, 4H), 4.22 (brs, 2H), 4.03 (dd, J=7.2, 4.5 Hz, 1H), 3.84–3.67 (m, 2H), 3.52–3.33 (m, 4H), 2.43–2.07 (m, 4H), 1.83–1.42 (m, 9H), 1.41–1.13 (m, 8H), 1.04–0.85 (m, 5H).

EXAMPLE 24(27)

1-(3-methoxyphenylmethyl)-2,5-dioxo-3-(benzyloxymethyl)-9-(3,5-dimethyl-1-phenylpyrazol-4-ylmethyl)-1,4,9-triazaspiro[5.5]undecane.2 hydrochloride

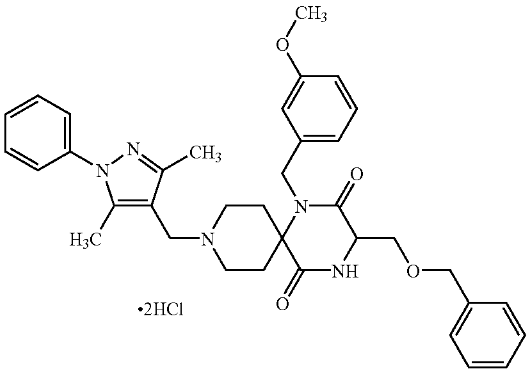

TLC: Rf 0.45 (chloroform:methanol=10:1);

NMR ($CD_3OD$): δ 7.60–7.43 (m, 5H), 7.38–7.24 (m, 5H), 7.14 (t, J=8.4 Hz, 1H), 6.83–6.72 (m, 3H), 4.96–4.70 (m, 2H), 4.60 (d, J=11.4 Hz, 1H), 4.50 (d, J=11.4 Hz, 1H), 4.29 (t, J=2.4 Hz, 1H), 4.24 (s, 2H), 4.02 (dd, J=9.6, 2.4 Hz, 1H), 3.93–3.79 (m, 1H), 3.72 (s, 3H), 3.70 (dd, J=9.6, 2.4 Hz, 1H), 3.70–3.60 (m, 1H), 3.55–3.44 (m, 1H), 3.35–3.23 (m, 1H), 2.58–2.05 (m, 10H).

EXAMPLE 24(28)

(3R)-1-butyl-2,5-dioxo-3-(2-methylpropyl)-9-(4-phenyloxyphenylmethyl)-1,4,9-triazaspiro[5.5]undecane.hydrochloride

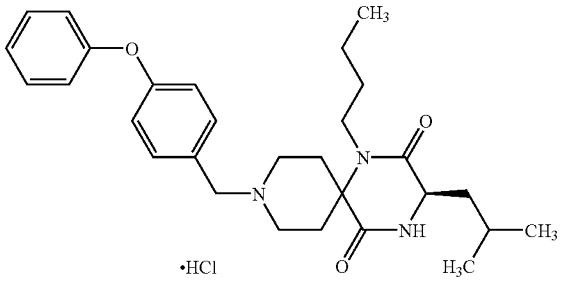

TLC: Rf 0.29 (chloroform:methanol=10:1);

NMR ($CD_3OD$): δ 7.54 (d, J=8.7 Hz, 2H), 7.42–7.36 (m, 2H), 7.18 (m, 1H), 7.05 (d, J=8.7 Hz, 2H), 7.05–7.02 (m, 2H), 4.32 (s, 2H), 4.01 (dd, J=7.8, 4.8 Hz, 1H), 3.85–3.72 (m, 2H), 3.50–3.39 (m, 4H), 2.52–2.38 (m, 2H), 2.24–2.11 (m, 2H), 1.84–1.20 (m, 7H), 0.95 (t, J=7.2 Hz, 3H), 0.95 (d, J=6.3 Hz, 3H), 0.93 (d, J=6.3 Hz, 3H).

HPLC condition

Column: CHIRALCEL OD-R, 0.46×25 cm, DAICEL, ODROCE-HD028;

Flow rate: 0.4 mL/min;

Eluent

Component A: 0.2M potassium dihydrogenphosphate aqueous solution

Component B: acetonitrile

A:B=64:36;

UV: 235 nm;

Retention time: 30 min.

EXAMPLE 24(29)

(3S)-1-butyl-2,5-dioxo-3-(2-methylpropyl)-9-(4-phenyloxyphenylmethyl)-1,4,9-triazaspiro[5.5]undecane.hydrochloride

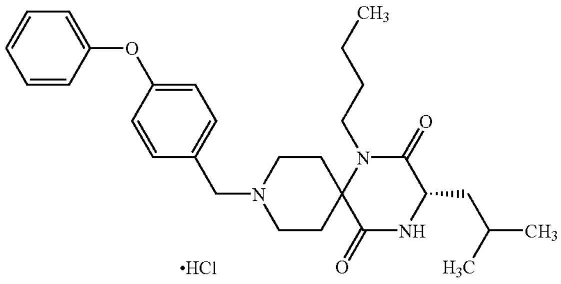

TLC: Rf 0.29 (chloroform:methanol=10:1);

NMR ($CD_3OD$): δ 7.54 (d, J=8.7 Hz, 2H), 7.42–7.36 (m, 2H), 7.18 (m, 1H), 7.05 (d, J=8.7 Hz, 2H), 7.05–7.02 (m, 2H), 4.33 (s, 2H), 3.98 (dd, J=8.1, 4.5 Hz, 1H), 3.86–3.72 (m, 2H), 3.53–3.37 (m, 4H), 2.47–2.36 (m, 2H), 2.24–2.12

(m, 2H), 1.80–1.30 (m, 7H), 0.95 (t, J=7.2 Hz, 3H), 0.95 (d, J=6.3 Hz, 3H), 0.93 (d, J=6.3 Hz, 3H).

HPLC condition

Column: CHIRALCEL OD-R, 0.46×25 cm, DAICEL, ODROCE-HD028;

Flow rate: 0.4 mL/min;

Eluent

Component A: 0.2M potassium dihydrogenphosphate aqueous solution

Component B: acetonitrile

A:B=64:36;

UV: 235 nm;

Retention time: 28 min.

EXAMPLE 24(30)

1-butyl-2,5-dioxo-3-cyclopentylmethyl-9-(1,4-benzodioxan-6-ylmethyl)-1,4,9-triazaspiro[5.5]undecane.hydrochloride

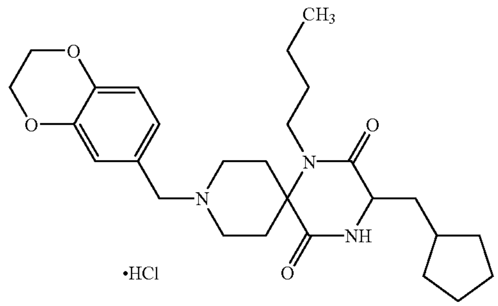

TLC: Rf 0.53 (chloroform:methanol=10:1);

NMR ($CD_3OD$): δ 7.05 (d, J=2.0 Hz, 1H), 6.98 (dd, J=8.5, 2.0 Hz, 1H), 6.93 (d, J=8.5 Hz, 1H), 4.26 (s, 4H), 4.23 (s, 2H), 3.99 (t, J=6.0 Hz, 1H), 3.77 (m, 2H), 3.46 (m, 2H), 3.37 (m, 2H), 2.36 (m, 2H), 2.15 (m, 2H), 1.96 (m, 1H), 1.81 (m, 4H), 1.59 (m, 6H), 1.36 (m, 2H), 1.15 (m, 2H), 0.95 (t, J=7.0 Hz, 3H).

EXAMPLE 24(31)

1-propyl-2,5-dioxo-3-(cyclohexylmethyloxymethyl)-9-(3,5-dimethyl-1-phenylpyrazol-4-ylmethyl)-1,4,9-triazaspiro[5.5]undecane.2 hydrochloride

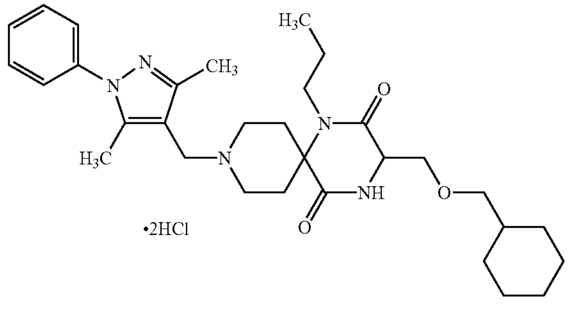

TLC: Rf 0.63 (chloroform:methanol=10:1);

NMR ($CD_3OD$): δ 7.59–7.46(m, 5H), 4.33 (s, 2H), 4.08 (m, 1H), 4.00 (m, 1H), 3.83 (m, 1H), 3.77 (m, 1H), 3.59 (m, 2H), 3.52 (m, 1H), 3.25 (d, J=6.5 Hz, 2H), 2.53 (m, 2H), 2.42 (m, 1H), 2.40 (s, 3H), 2.39 (s, 3H), 2.21 (m, 2H), 1.69 (m, 6H), 1.52 (m, 2H), 1.21 (m, 4H), 0.95 (t, J=7.0 Hz, 3H), 0.88 (m, 2H).

EXAMPLE 24(32)

(3S)-1-butyl-2,5-dioxo-3-(1-methylpropyl)-9-(1,4-benzodioxan-6-ylmethyl)-1,4,9-triazaspiro[5.5]undecane.hydrochloride

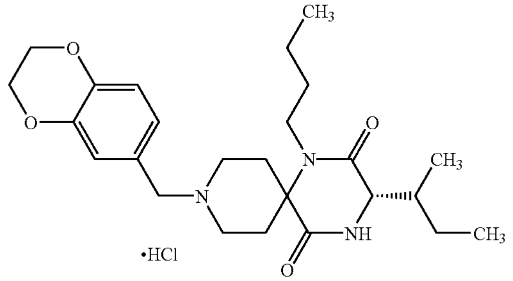

TLC: Rf 0.47 (chloroform:methanol=10:1);

NMR ($CD_3OD$): δ 7.06–6.90 (m, 3H), 4.26 (s, 4H), 4.23 (s, 2H), 3.95 (d, J=3.3 Hz, 1H), 3.87 (m, 1H), 3.70 (m, 1H), 3.58–3.42 (m, 4H), 2.56–2.30 (m, 2H), 2.20–1.98 (m, 2H), 1.54–1.00 (m, 7H), 0.99 (d, J=7.2 Hz, 3H), 0.95 (t, J=7.5 Hz, 3H), 0.91 (t, J=7.5 Hz, 3H).

EXAMPLE 24(33)

(3R)-1-butyl-2,5-dioxo-3-(1-methylpropyl)-9-(1,4-benzodioxan-6-ylmethyl)-1,4,9-triazaspiro[5.5]undecane.hydrochloride

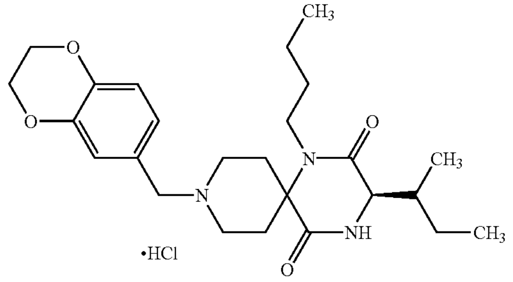

TLC: Rf 0.47 (chloroform:methanol=10:1);

NMR ($CD_3OD$): δ 7.06–6.91 (m, 3H), 4.26 (s, 4H), 4.23 (s, 2H), 3.95 (d, J=3.3 Hz, 1H), 3.87 (m, 1H), 3.70 (m, 1H), 3.56–3.40 (m, 4H), 2.50–2.32 (m, 2H), 2.18–1.96 (m, 2H), 1.62–1.17 (m, 7H), 0.99 (d, J=7.2 Hz, 3H), 0.95 (t, J=7.2 Hz, 3H), 0.91 (t, J=7.5 Hz, 3H).

EXAMPLE 24(34)

1-butyl-2,5-dioxo-3-(2-methylpropyl)-9-(5-phenylmethylthiophen-2-ylmethyl)-1,4,9-triazaspiro[5.5]undecane.hydrochloride

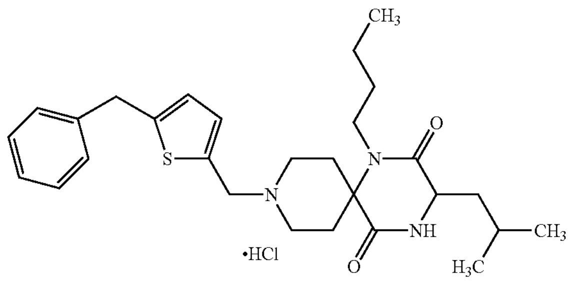

TLC: Rf 0.56 (chloroform:methanol=10:1);

NMR ($CD_3OD$): δ 7.32–7.21 (m, 5H), 7.17 (d, J=3.6 Hz, 1H), 6.89 (d, J=3.6 Hz, 1H), 4.51 (s, 2H), 4.17 (s, 2H), 4.00 (dd, J=7.8 Hz, 4.5 Hz, 1H), 3.84–3.72 (m, 2H), 3.56–3.44 (m, 2H), 3.38–3.32 (m, 2H), 2.42–2.14 (m, 4H), 1.84–1.30 (m, 7H), 0.95 (t, J=6.9 Hz, 3H), 0.94 (d, J=6.3 Hz, 3H), 0.92 (d, J=6.3 Hz, 3H).

EXAMPLE 24(35)

1-butyl-2,5-dioxo-3-cyclohexylmethyl-9-(2-phenylmethylthiophen-5-ylmethyl)-1,4,9-triazaspiro[5.5]undecane.hydrochloride

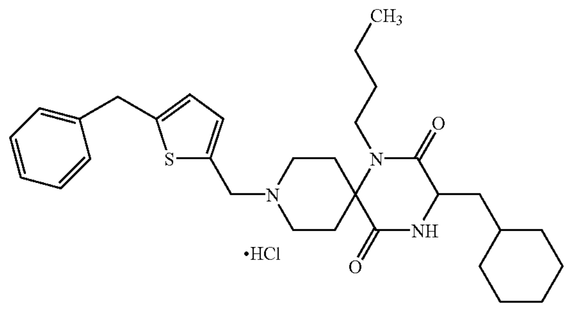

TLC: Rf 0.59 (chloroform:methanol=10:1);

NMR ($CD_3OD$): δ 7.32–7.21 (m, 5H), 7.18 (d, J=3.6 Hz, 1H), 6.89 (d, J=3.6 Hz, 1H), 4.51 (s, 2H), 4.17 (s, 2H), 4.03 (dd, J=7.8, 4.8 Hz, 1H), 3.84–3.72 (m, 2H), 3.58–3.44 (m, 2H), 3.40–3.36 (m, 2H), 2.44–2.08 (m, 4H), 1.81–1.07 (m, 15H), 0.95 (t, J=7.2 Hz, 3H), 0.95 (m, 2H).

EXAMPLE 24(36)

(3R)-1-butyl-2,5-dioxo-3-(2,2-dimethylpropyl)-9-(1,4-benzodioxan-6-ylmethyl)-1,4,9-triazaspiro[5.5]undecane.hydrochloride

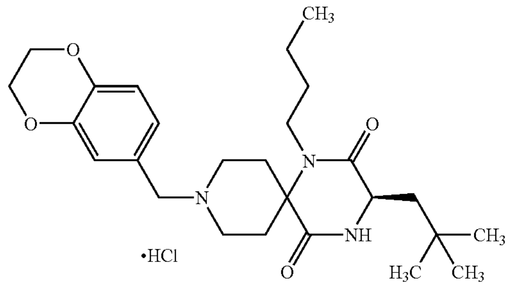

TLC: Rf 0.41 (chloroform:methanol=20:1);

NMR ($CD_3OD$): δ 7.05 (s, 1H), 6.98 (d, J=8.4 Hz, 1H), 6.92 (d, J=8.4 Hz, 1H), 4.26 (s, 4H), 4.23 (s, 2H), 4.00 (dd, J=7.0, 3.0 Hz, 1H), 3.83–3.64 (m, 2H), 3.50 (m, 2H), 3.38 (m, 2H), 2.35 (m, 2H), 2.25 (m, 2H), 1.99 (m, 1H), 1.55 (m, 1H), 1.50 (m, 2H), 1.35 (m, 2H), 0.99 (s, 9H), 0.95 (t, J=7.0 Hz, 3H).

EXAMPLE 24(37)

(3S)-1-butyl-2,5-dioxo-3-(2,2-dimethylpropyl)-9-(1,4-benzodioxan-6-ylmethyl)-1,4,9-triazaspiro[5.5]undecane.hydrochloride

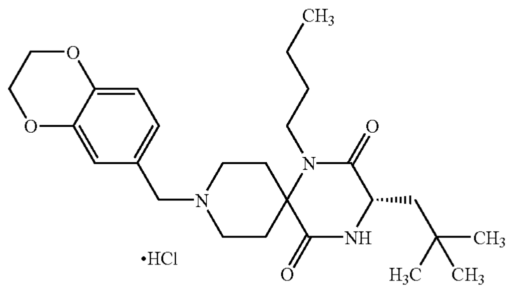

TLC: Rf 0.41 (chloroform:methanol=20:1);

NMR ($CD_3OD$): δ 7.05 (s, 1H), 6.98 (d, J=8.4 Hz, 1H), 6.92 (d, J=8.4 Hz, 1H), 4.26 (s, 4H), 4.23 (s, 2H), 4.00 (dd, J=7.0, 3.0 Hz, 1H), 3.83–3.63 (m, 2H), 3.50 (m, 2H), 3.38 (m, 2H), 2.35 (m, 2H), 2.25 (m, 2H), 1.99 (dd, J=14.0, 3.0 Hz, 1H), 1.55 (dd, J=14.0, 7.0 Hz, 1H), 1.50 (m, 2H), 1.35 (m, 2H), 0.99 (s, 9H), 0.95 (t, J=7.0 Hz, 3H).

EXAMPLE 24(38)

(3R)-1-(2-butynyl)-2,5-dioxo-3-(2,2-dimethylpropyl)-9-(4-phenyloxyphenylmethyl)-1,4,9-triazaspiro[5.5]undecane.hydrochloride

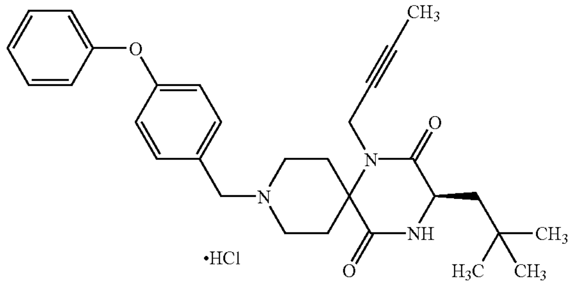

TLC: Rf 0.60 (chloroform:methanol=10:1);

NMR ($CD_3OD$): δ 7.51 (d, J=8.7 Hz, 2H), 7.39 (dd, J=8.7, 7.5 Hz, 2H), 7.18 (t, J=7.5 Hz, 1H), 7.10–7.00 (m, 4H), 4.33 (brs, 2H), 4.33–4.09 (m, 2H), 4.03 (dd, J=6.9, 3.3 Hz, 1H), 3.85–3.68 (m, 2H), 3.58–3.43 (m, 2H), 2.59–2.41 (m, 2H), 2.40–2.20 (m, 2H), 2.03 (dd, J=14.4, 3.3 Hz, 1H), 1.75 (brs, 3H), 1.56 (dd, J=14.4, 6.9 Hz, 1H), 0.99 (s, 9H).

EXAMPLE 24(39)

(3S)-1-(2-butynyl)-2,5-dioxo-3-(2,2-dimethylpropyl)-9-(4-phenyloxyphenylmethyl)-1,4,9-triazaspiro[5.5]undecane.hydrochloride

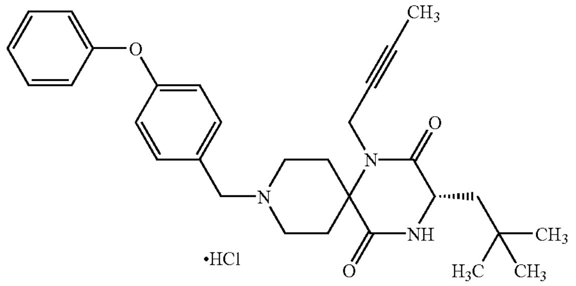

TLC: Rf 0.60 (chloroform:methanol=10:1);

NMR ($CD_3OD$): δ 7.51 (d, J=8.7 Hz, 2H), 7.39 (dd, J=8.7, 7.5 Hz, 2H), 7.18 (t, J=7.5 Hz, 1H), 7.10–7.00 (m, 4H), 4.33 (brs, 2H), 4.33–4.09 (m, 2H), 4.03 (dd, J=6.9, 3.3 Hz, 1H), 3.85–3.68 (m, 2H), 3.58–3.43 (m, 2H), 2.59–2.41 (m, 2H), 2.40–2.20 (m, 2H), 2.03 (dd, J=14.4, 3.3 Hz, 1H), 1.75 (brs, 3H), 1.56 (dd, J=14.4, 6.9 Hz, 1H), 0.99 (s, 9H).

EXAMPLE 24(40)

1-butyl-2,5-dioxo-3-cycloheptylmethyl-9-(1,4-benzodioxan-6-ylmethyl)-1,4,9-triazaspiro[5.5]undecane.hydrochloride

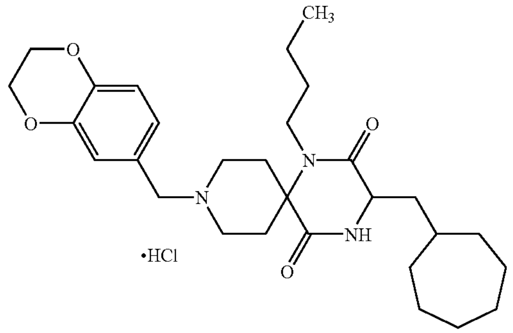

TLC: Rf 0.70 (chloroform:methanol=10:1);

NMR ($CD_3OD$): δ 7.04 (d, J=2.1 Hz, 1H), 6.97 (dd, J=8.4, 2.1 Hz, 1H), 6.93 (d, J=8.4 Hz, 1H), 4.26 (s, 4H), 4.24 (s, 2H), 3.99 (dd, J=8.1, 4.2 Hz, 1H), 3.84–3.70 (m, 2H), 3.45 (m, 2H), 3.36 (m, 2H), 2.37–2.11 (m, 4H), 1.80–1.49 (m, 15H), 1.36(m, 2H), 1.22 (m, 2H), 0.95 (t, J=7.5 Hz, 3H).

EXAMPLE 24(41)

1-butyl-2,5-dioxo-3-cyclohexylmethyl-9-(2,4,6-trimethoxyphenylmethyl)-1,4,9-triazaspiro[5.5]undecane.hydrochloride

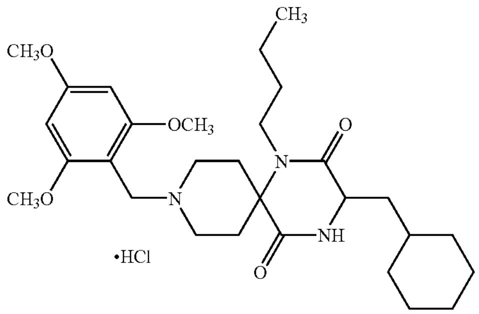

TLC: Rf 0.55 (chloroform:methanol=10:1);

NMR ($CD_3OD$): δ 6.31 (s, 2H), 4.26 (s, 2H), 4.03 (dd, J=7.8, 4.5 Hz, 1H), 3.89 (s, 6H), 3.84 (s, 3H), 3.84–3.73 (m, 2H), 3.54–3.33 (m, 4H), 2.44–2.25 (m, 2H), 2.24–2.03 (m, 2H), 1.84–1.12 (m, 15H), 1.06–0.85 (m, 5H).

EXAMPLE 24(42)

1-butyl-2,5-dioxo-3-(3-cyclohexylpropyl)-9-(1,4-benzodioxan-6-ylmethyl)-1,4,9-triazaspiro[5.5]undecane.hydrochloride

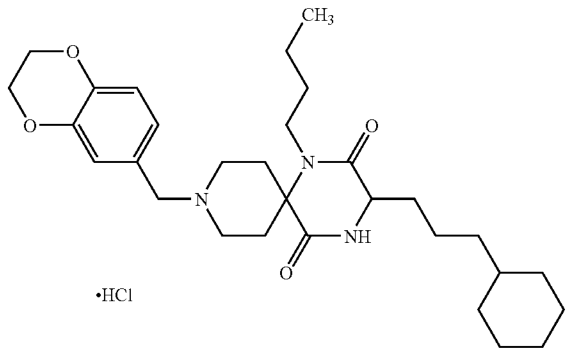

TLC: Rf 0.71 (chloroform:methanol=10:1);

NMR ($CD_3OD$): δ 7.05–6.91 (m, 3H), 4.26 (s, 4H), 4.22 (s, 2H), 4.04 (t, J=5.4 Hz, 1H), 3.84 (m, 1H), 3.67 (m, 1H), 3.54–3.40 (m, 3H), 3.35 (m, 1H), 2.44–2.08 (m, 4H), 1.90–1.16 (m, 19H), 0.95 (t, J=7.5 Hz, 3H), 0.95 (m, 2H).

EXAMPLE 24(43)

1-butyl-2,5-dioxo-3-(3-cyclohexylpropyl)-9-(4-phenyloxyphenylmethyl)-1,4,9-triazaspiro[5.5]undecane.hydrochloride

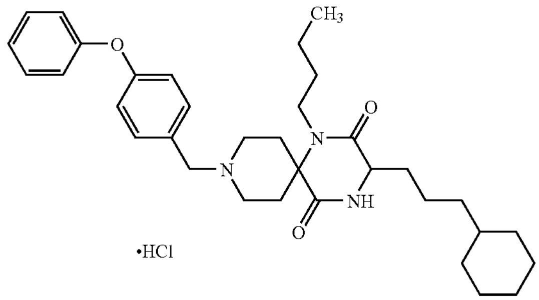

TLC: Rf 0.76 (chloroform:methanol=10:1);

NMR ($CD_3OD$): δ 7.53–7.49 (m, 2H), 7.42–7.36 (m, 2H), 7.18 (m, 1H), 7.10–7.02 (m, 4H), 4.32 (s, 2H), 4.04 (t, J=4.8 Hz, 1H), 3.87 (m, 1H), 3.71 (m, 1H), 3.56–3.40 (m, 3H), 3.35 (m, 1H), 2.48–2.12 (m, 4H), 1.86–1.10 (m, 19H), 0.95 (t, J=7.5 Hz, 3H), 0.95 (m, 2H).

EXAMPLE 24(44)

1-butyl-2,5-dioxo-3-(3-cyclohexylpropyl)-9-(3,5-dimethyl-1-phenylpyrazol-4-ylmethyl)-1,4,9-triazaspiro[5.5]undecane.2 hydrochloride

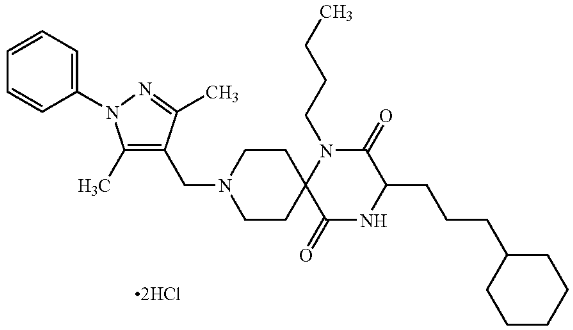

TLC: Rf 0.64 (chloroform:methanol=10:1);

NMR ($CD_3OD$): δ 7.59–7.45 (m, 5H), 4.31 (s, 2H), 4.06 (t, J=5.0 Hz, 1H), 3.92 (m, 1H), 3.77 (m, 1H), 3.63–3.37 (m, 4H), 2.44 (m, 2H), 2.39 (s, 3H), 2.38 (s, 3H), 2.21 (m, 2H), 1.85–1.68 (m, 7H), 1.54 (m, 2H), 1.39 (m, 4H), 1.23 (m, 6H), 0.96 (t, J=7.5 Hz, 3H), 0.89 (m, 2H).

EXAMPLE 24(45)

1-butyl-2,5-dioxo-3-(2-hydroxy-2-methylpropyl)-9-(4-phenyloxyphenylmethyl)-1,4,9-triazaspiro[5.5]undecane.hydrochloride

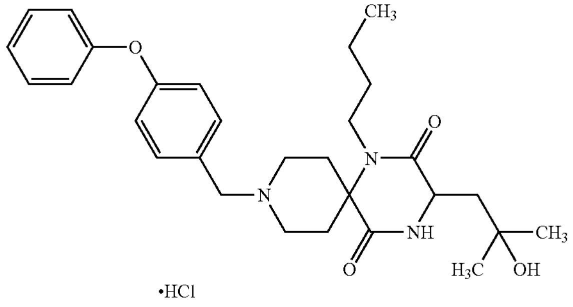

TLC: Rf 0.52 (chloroform:methanol=10:1);

NMR ($CD_3OD$): δ 7.50 (d, J=8.7 Hz, 2H), 7.39 (dd, J=8.7, 7.5 Hz, 2H), 7.18 (t, J=7.5 Hz, 1H), 7.09–7.00 (m, 4H), 4.32 (brs, 2H), 4.29 (dd, J=9.9, 3.0 Hz, 1H), 4.04–3.88 (m, 2H), 3.59–3.40 (m, 4H), 2.46–2.21 (m, 4H), 2.18 (dd, J=14.4, 3.0 Hz, 1H), 1.75 (dd, J=14.4, 9.9 Hz, 1H), 1.61–1.43 (m, 2H), 1.42–1.29 (m, 2H), 1.28 (s, 6H), 0.95 (t, J=7.5 Hz, 3H).

EXAMPLE 24(46)

1-(2-butynyl)-2,5-dioxo-3-(2-methylpropyl)-9-(3,5-dimethyl-1-phenylpyrazol-4-ylmethyl)-1,4,9-triazaspiro[5.5]undecane.2 hydrochloride

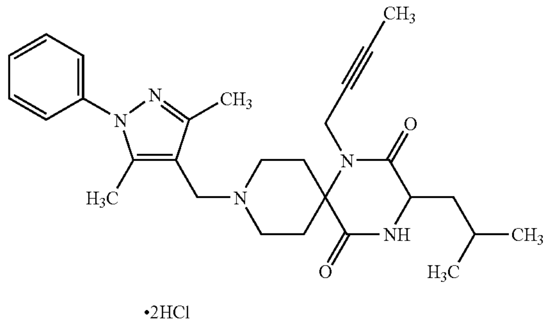

TLC: Rf 0.41 (chloroform:methanol=10:1);

NMR ($CD_3OD$): δ 7.61–7.45 (m, 5H), 4.32 (s, 2H), 4.31–4.18 (m, 2H), 4.06 (dd, J=7.8, 4.5 Hz, 1H), 3.93–3.77 (m, 2H), 3.68–3.57 (m, 2H), 2.72–2.57 (m, 2H), 2.40 (s, 3H), 2.38 (s, 3H), 2.36–2.16,(m, 2H), 1.92–1.59 (m, 6H), 0.95 (d, J=6.6 Hz, 3H), 0.94 (d, J=6.6 Hz, 3H).

EXAMPLE 24(47)

1-(2-butynyl)-2,5-dioxo-3-cyclohexylmethyl-9-(3,5-dimethyl-1-phenyl pyrazol-4-ylmethyl)-1,4,9-triazaspiro[5.5]undecane.2 hydrochloride

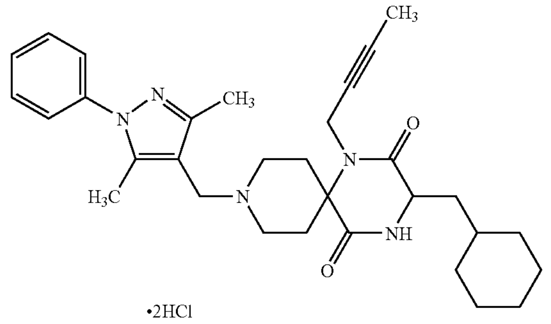

TLC: Rf 0.37 (chloroform:methanol=10:1);

NMR ($CD_3OD$): 7.60–7.43 (m, 5H), 4.32 (s, 2H), 4.23 (d, J=2.1 Hz, 2H), 4.09 (dd, J=7.2, 4.8 Hz, 1H), 3.92–3.78 (m, 2H), 3.68–3.56 (m, 2H), 2.66–2.51 (m, 2H), 2.38 (s, 3H), 2.36 (s, 3H), 2.36–2.16 (m, 2H), 1.83–1.60 (m, 10H), 1.59–1.43 (m, 1H), 1.38–1.12 (m, 3H), 1.06–0.87 (m, 2H).

EXAMPLE 24(48)

1-butyl-2,5-dioxo-3-cyclohexylmethyl-9-(3,5-dimethyl-1-phenylpyrazol-4-ylmethyl)-1,4,9-triazaspiro[5.5]undecane.2 hydrochloride

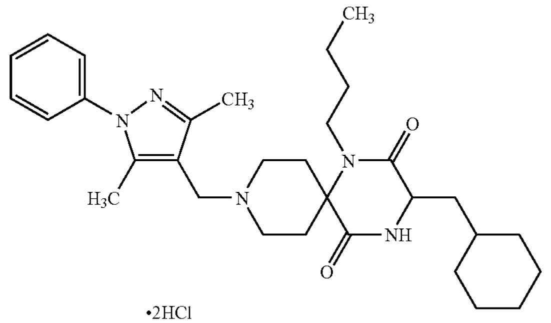

TLC: Rf 0.35 (chloroform:methanol=20:1);

NMR ($CD_3OD$): δ 7.63–7.48 (m, 5H), 4.33 (s, 2H), 4.05 (dd, J=7.8, 4.5 Hz, 1H), 3.95–3.74 (m, 2H), 3.67–3.56 (m, 2H), 3.48 (m, 2H), 2.72–2.58 (m, 2H), 2.45 (s, 3H), 2.41 (s, 3H), 2.30–2.07 (m, 2H), 1.84–1.10 (m, 15H), 1.02–0.92 (m, 2H), 0.96 (t, J=7.2 Hz, 3H).

EXAMPLE 24(49)

1-butyl-2,5-dioxo-3-(2-methylpropyl)-9-(2-phenyloxypyridin-3-ylmethyl)-1,4,9-triazaspiro[5.5]undecane.2 hydrochloride

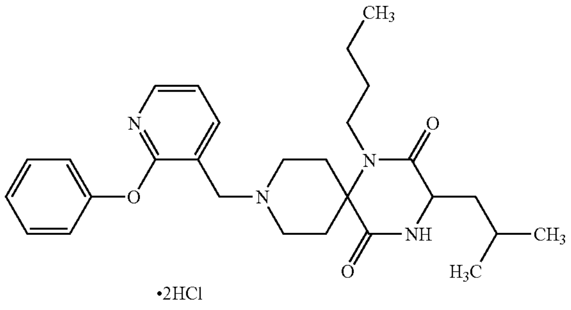

TLC: Rf 0.23 (chloroform:methanol=10:1);

NMR ($CD_3OD$): δ 8.19 (m, 1H), 8.07 (m, 1H), 7.47–7.42 (m, 2H), 7.29–7.19 (m, 4H), 4.55 (s, 2H), 4.03 (dd, J=7.8, 4.5 Hz, 1H), 3.94 (m, 2H), 3.64 (m, 2H), 3.38 (m, 2H), 2.54–2.16 (m, 4H), 1.90–1.28 (m, 7H), 0.96 (t, J=6.9 Hz, 3H), 0.96 (d, J=6.3 Hz, 3H), 0.94 (d, J=6.3 Hz, 3H).

EXAMPLE 24(50)

1-butyl-2,5-dioxo-3-cyclohexylmethyl-9-(2-phenyloxypyridin-3-ylmethyl)-1,4,9-triazaspiro[5.5]undecane.2 hydrochloride

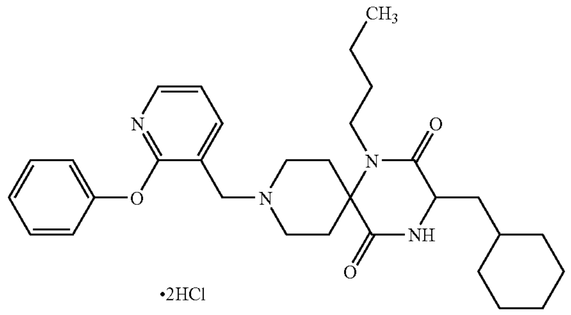

TLC: Rf 0.62 (chloroform:methanol=10:1);

NMR ($CD_3OD$): δ 8.19 (m, 1H), 8.09 (m, 1H), 7.47–7.42 (m, 2H), 7.29–7.19 (m, 4H), 4.55 (s, 2H), 4.05 (dd, J=7.8, 4.8 Hz, 1H), 3.96 (m, 2H), 3.64 (m, 2H), 3.42 (m, 2H), 2.48 (m, 2H), 2.36–2.16 (m, 2H), 1.82–1.14 (m, 15H), 0.96 (t, J=7.5 Hz, 3H), 0.95–0.84 (m, 2H).

EXAMPLE 24(51)

1-butyl-2,5-dioxo-3-cyclohexylmethyl-9-(4-methylbenzomorpholin-7-ylmethyl)-1,4,9-triazaspiro[5.5]undecane.2 hydrochloride

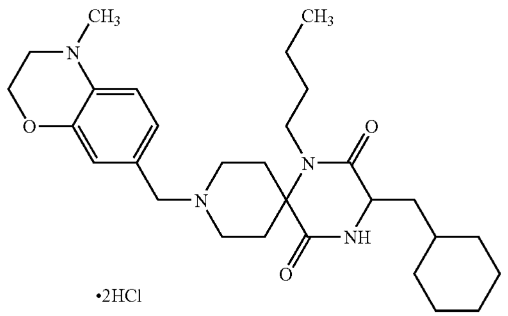

TLC: Rf 0.69 (chloroform:methanol=10:1);

NMR ($CDCl_3$): δ 6.93 (d, J=8.7 Hz, 1H), 6.86 (s, 1H), 6.75 (d, J=8.7 Hz, 1H), 4.28–4.25 (m, 2H), 4.17 (s, 2H), 4.03 (dd, J=7.5, 4.5 Hz, 1H), 3.80–3.65 (m, 2H), 3.50–3.40 (m, 2H), 3.40–3.30 (m, 2H), 2.91 (s, 3H), 2.38–2.06 (m, 4H), 1.78–1.63 (m, 8H), 1.63–1.42 (m, 3H), 1.40–1.18 (m, 6H), 1.05–0.90 (m, 2H), 0.95 (t, J=7.2 Hz, 3H).

EXAMPLE 24(52)

1-butyl-2,5-dioxo-3-(2-methylpropyl)-9-(4-methylbenzomorpholin-7-ylmethyl)-1,4,9-triazaspiro[5.5]undecane.2 hydrochloride

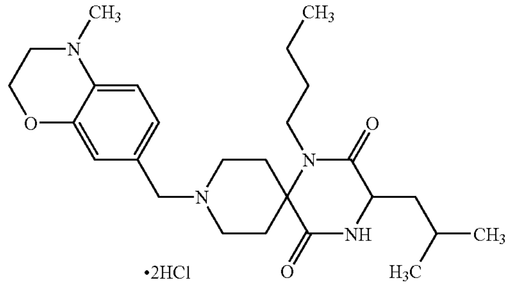

TLC: Rf 0.56 (chloroform:methanol=10:1);

NMR ($CDCl_3$): δ 7.00 (d, J=7.2 Hz, 1H), 6.94 (s, 1H), 6.85 (d, J=7.2 Hz, 1H), 4.31–4.29 (m, 2H), 4.19 (s, 2H), 4.00 (dd, J=7.8, 4.5 Hz, 1H), 3.79–3.66 (m, 2H), 3.47–3.34 (m, 6H), 2.97 (s, 3H), 2.45–2.34 (m, 2H), 2.22–2.10 (m, 2H), 1.84–1.75 (m, 1H), 1.71–1.46 (m, 4H), 1.42–1.32 (m, 2H), 0.97–0.92 (m, 9H).

EXAMPLE 24(53)

1-butyl-2,5-dioxo-3-(2-methylpropyl)-9-(4-(N-methyl-N-phenylamino)phenylmethyl)-1,4,9-triazaspiro[5.5]undecane.2 hydrochloride

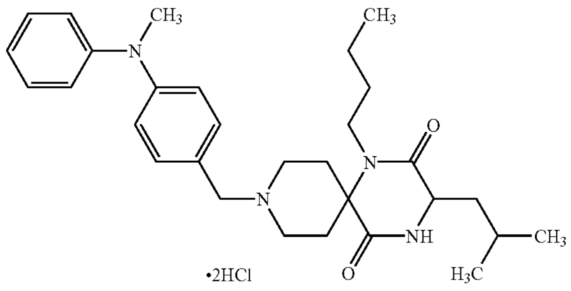

TLC: Rf 0.40 (chloroform:methanol=20:1);

NMR ($CD_3OD$): δ 7.40–7.28 (m, 4H), 7.19–7.10 (m, 3H), 6.94–6.86 (m, 2H), 4.23 (s, 2H), 4.00 (dd, J=7.8, 4.5 Hz, 1H), 3.86–3.63 (m, 2H), 3.55–3.30 (m, 4H), 3.31 (s, 3H), 2.46–2.27 (m, 2H), 2.26–2.06 (m, 2H), 1.90–1.42 (m, 5H), 1.44–1.26 (m, 2H), 0.98–0.91 (m, 9H).

EXAMPLE 24(54)

1-butyl-2,5-dioxo-3-cyclohexylmethyl-9-(4-(N-methyl-N-phenylamino) phenylmethyl)-1,4,9-triazaspiro[5.5]undecane.2 hydrochloride

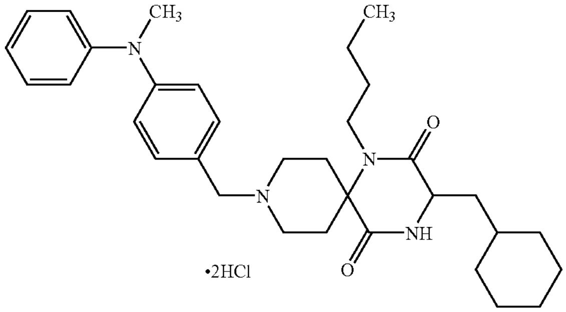

TLC: Rf 0.52 (chloroform:methanol=20:1);

NMR ($CD_3OD$): δ 7.40–7.28 (m, 4H), 7.20–7.12 (m, 3H), 6.93–6.86 (m, 2H), 4.24 (s, 2H), 4.03 (dd, J=7.5, 4.8 Hz, 1H), 3.85–3.66 (m, 2H), 3.55–3.40 (m, 2H), 3.40–3.30 (m, 2H), 3.32 (s, 3H), 2.44–2.07 (m, 4H), 1.84–1.40 (m, 10H), 1.40–1.10 (m, 5H), 1.06–0.85 (m, 2H), 0.95 (t, J=7.5 Hz, 3H).

EXAMPLE 24(55)

1-butyl-2,5-dioxo-3-(2-methylpropyl)-9-(2-(3,5-dimethylpyrazol-1-yl)-5-methoxyphenylmethyl)-1,4,9-triazaspiro[5.5]undecane.2 hydrochloride

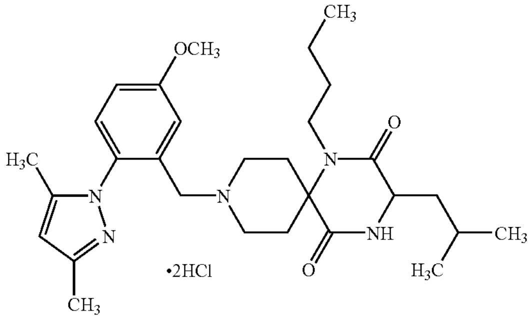

TLC: Rf 0.58 (chloroform:methanol=10:1);

NMR ($CD_3OD$): δ 7.53 (d, J=3.0 Hz, 1H), 7.44 (d, J=8.7 Hz, 1H), 7.22 (dd, J=8.7, 3.0 Hz, 1H), 6.29 (s, 1H), 4.09 (s, 2H), 4.02 (dd, J=7.5, 4.5 Hz, 1H), 3.94 (s, 3H), 3.74 (m, 2H), 3.42 (m, 4H), 2.44 (m, 2H), 2.37 (s, 3H), 2.22 (s, 3H), 2.22 (m, 2H), 1.86–1.30 (m, 7H), 0.96 (t, J=7.8 Hz, 3H), 0.95 (d, J=6.3 Hz, 3H), 0.94 (d, J=6.3 Hz, 3H).

EXAMPLE 24(56)

1-butyl-2,5-dioxo-3-cyclohexylmethyl-9-(2-(3,5-dimethylpyrazol-1-yl)-5-methoxyphenylmethyl)-1,4,9-triazaspiro[5.5]undecane.2 hydrochloride

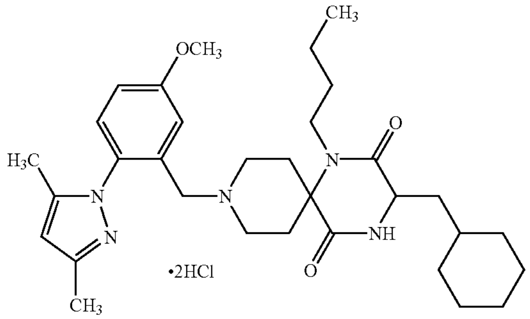

TLC: Rf 0.61 (chloroform:methanol=10:1);

NMR ($CD_3OD$): δ 7.43 (d, J=8.7 Hz, 1H), 7.40 (d, J=2.7 Hz, 1H), 7.22 (dd, J=8.7, 2.7 Hz, 1H), 6.22 (s, 1H), 4.09 (s, 2H), 4.06 (dd, J=7.5, 4.2 Hz, 1H), 3.93 (s, 3H), 3.80 (m, 2H), 3.42 (m, 4H), 2.38 (m, 2H), 2.34 (s, 3H), 2.22 (s, 3H), 2.20 (m, 2H), 1.80–1.16 (m, 15H), 0.96 (t, J=7.2 Hz, 3H), 0.96 (m, 2H).

EXAMPLE 24(57)

1-butyl-2,5-dioxo-3-(2-methylpropyl)-9-(3,5-diethyl-1-(4-chlorophenyl)pyrazol-4-ylmethyl)-1,4,9-triazaspiro[5.5]undecane.2 hydrochloride

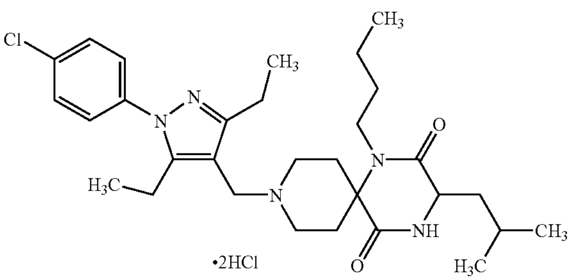

TLC: Rf 0.47 (chloroform:methanol=20:1);

NMR ($CD_3OD$): δ 7.53 (d, J=9.0 Hz, 2H), 7.49 (d, J=9.0 Hz, 2H), 4.31 (s, 2H), 4.02 (dd, J=7.8, 4.5 Hz, 1H), 3.94–3.73 (m, 2H), 3.65–3.54 (m, 2H), 3.49–3.38 (m, 2H), 2.88 (q, J=7.5 Hz, 2H), 2.77 (q, J=7.5 Hz, 2H), 2.58–2.38 (m, 2H), 2.30–2.12 (m, 2H), 1.90–1.56 (m, 5H), 1.55–1.30 (m, 2H), 1.31 (t, J=7.5 Hz, 3H), 0.99–0.94 (m, 12H).

EXAMPLE 24(58)

1-butyl-2,5-dioxo-3-cyclohexylmethyl-9-(3,5-diethyl-1-(4-chlorophenyl)pyrazol-4-ylmethyl)-1,4,9-triazaspiro[5.5]undecane.2 hydrochloride

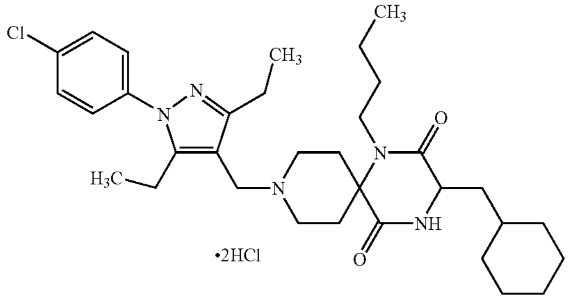

TLC: Rf 0.51 (chloroform:methanol=20:1);

NMR ($CD_3OD$): δ 7.58 (d, J=9.0 Hz, 2H), 7.48 (d, J=9.0 Hz, 2H), 4.31 (s, 2H), 4.05 (dd, J=7.5, 4.5 Hz, 1H), 3.94–3.73 (m, 2H), 3.65–3.54 (m, 2H), 3.50–3.38 (m, 2H), 2.88 (q, J=7.5 Hz, 2H), 2.77 (q, J=7.5 Hz, 2H), 2.60–2.60 (m, 2H), 2.28–2.09 (m, 2H), 1.85–1.10 (m, 15H), 1.31 (t, J=7.5 Hz, 3H), 1.04–0.85 (m, 2H), 0.96 (t, J=7.5 Hz, 3H), 0.94 (t, J=7.5 Hz, 3H).

EXAMPLE 24(59)

1-butyl-2,5-dioxo-3-(2-methylpropyl)-9-(6-phenyloxypyridin-3-ylmethyl)-1,4,9-triazaspiro[5.5]undecane.2 hydrochloride

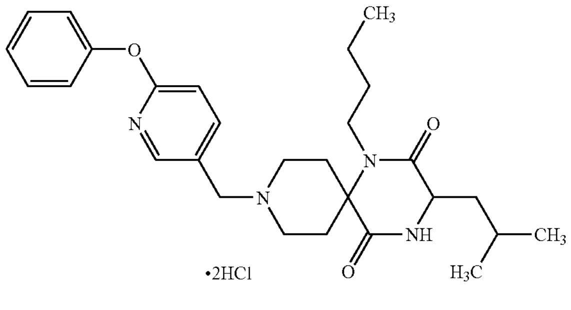

TLC: Rf 0.65 (chloroform:methanol=10:1);

NMR ($CD_3OD$): δ 8.32 (s, 1H), 8.06 (m, 1H), 7.44 (t, J=7.5 Hz, 2H), 7.26 (t, J=7.5 Hz, 1H), 7.14 (d, J=7.5 Hz, 2H), 7.06 (d, J=8.7 Hz, 1H), 4.39 (s, 2H), 4.01 (dd, J=7.5, 4.5 Hz, 1H), 3.90–3.70 (m, 2H), 3.53–3.41 (m, 4H), 2.45 (m, 2H), 2.25–2.12 (m, 2H), 1.78 (m, 1H), 1.72–1.50 (m, 4H), 1.36 (m, 2H), 0.97–0.93 (m, 9H).

EXAMPLE 24(60)

1-butyl-2,5-dioxo-3-cyclohexylmethyl-9-(6-phenyloxypyridin-3-ylmethyl)-1,4,9-triazaspiro[5.5]undecane.2 hydrochloride

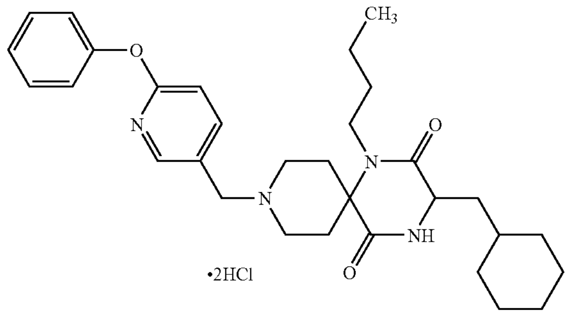

TLC: Rf 0.67 (chloroform:methanol=10:1);

NMR ($CD_3OD$): δ 8.31 (s, 1H), 8.07 (d, J=8.3 Hz, 1H), 7.44 (t, J=7.5 Hz, 2H), 7.26 (t, J=7.5 Hz, 1H), 7.14 (d, J=7.5 Hz, 2H), 7.06 (d, J=8.3 Hz, 1H), 4.39 (s, 2H), 4.04 (dd, J=7.8, 4.6 Hz, 1H), 3.90–3.76 (m, 2H), 3.52–3.38 (m, 4H), 2.58–2.36 (m, 2H), 2.25–2.11 (m, 2H), 1.80–1.42 (m, 10H), 1.42–1.17 (m, 5H), 1.05–0.85 (m, 2H), 0.95 (t, J=7.2 Hz, 3H).

EXAMPLE 24(61)

1-butyl-2,5-dioxo-3-(2-methylpropyl)-9-(1,3-benzodioxolan-5-ylmethyl)-1,4,9-triazaspiro[5.5]undecane.hydrochloride

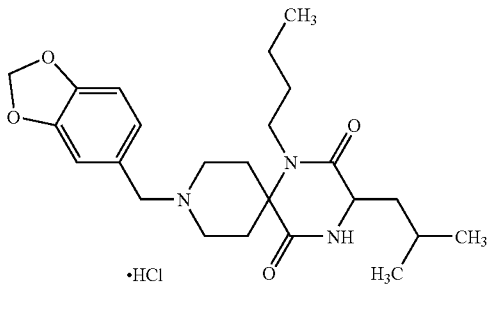

TLC: Rf 0.38 (chloroform:methanol=10:1);

NMR ($CD_3OD$): δ 7.05–7.00 (m, 2H), 6.92 (m, 1H), 6.03 (s, 2H), 4.26 (s, 2H), 4.02 (dd, J=7.5, 4.5 Hz, 1H), 3.84–3.68 (m, 2H), 3.52–3.36 (m, 4H), 2.42–2.10 (m, 4H), 1.88–1.32 (m, 7H), 0.96 (t, J=6.9 Hz, 3H), 0.95 (d, J=6.3 Hz, 3H), 0.94 (d, J=6.3 Hz, 3H).

EXAMPLE 24(62)

1-butyl-2,5-dioxo-3-cyclohexylmethyl-9-(1,3-benzodioxolan-5-ylmethyl)-1,4,9-triazaspiro[5.5]undecane.hydrochloride

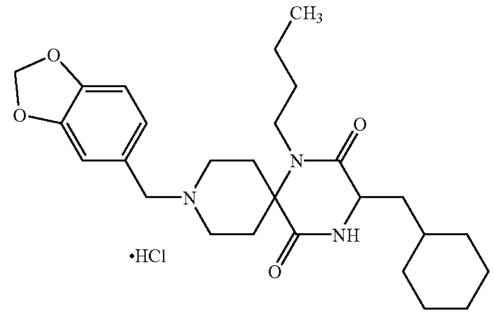

TLC: Rf 0.42 (chloroform:methanol=10:1);

NMR ($CD_3OD$): δ 7.06–7.01 (m, 2H), 6.92 (m, 1H), 6.03 (s, 2H), 4.27 (s, 2H), 4.04 (dd, J=7.5, 4.5 Hz, 1H), 3.82–3.70 (m, 2H), 3.56–3.36 (m, 4H), 2.48–2.10 (m, 4H), 1.82–1.16 (m, 15H), 0.96 (t, J=7.5 Hz, 3H), 0.96 (m, 2H).

EXAMPLE 24(63)

1-butyl-2,5-dioxo-3-cyclohexylmethyl-9-(2-hydroxy-4-methoxyphenylmethyl)-1,4,9-triazaspiro[5.5]undecane.hydrochloride

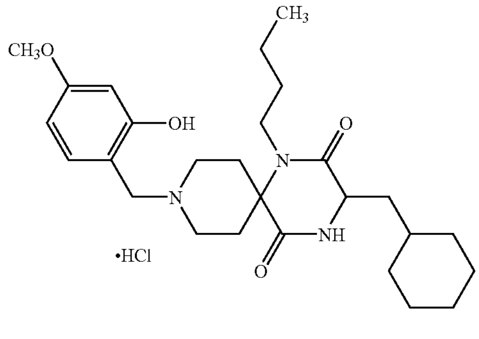

TLC: Rf 0.88 (chloroform:methanol=10:1);

NMR ($CD_3OD$): δ 7.26 (d, J=8.5 Hz, 1H), 6.51 (dd, J=8.5, 2.5 Hz, 1H), 6.48 (d, J=2.5 Hz, 1H), 4.26 (s, 2H), 4.03 (m, 1H), 3.77 (m, 5H), 3.47 (m, 2H), 3.37 (m, 2H), 2.34 (m, 2H), 2.15 (m, 2H), 1.69 (m, 6H), 1.52 (m, 4H), 1.31 (m,5H), 0.95 (m, 5H).

EXAMPLE 24(64)

1-butyl-2,5-dioxo-3-cyclohexylmethyl-9-(4-methylthiophenylmethyl)-1,4,9-triazaspiro[5.5]undecane-.hydrochloride

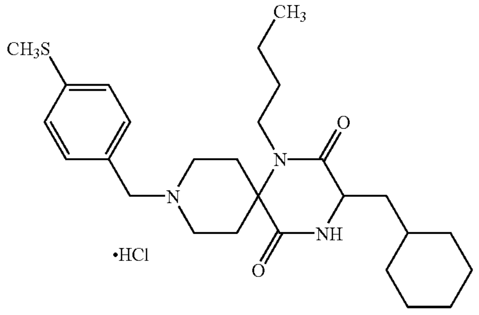

TLC: Rf 0.83 (chloroform:methanol=10:1);

NMR ($CD_3OD$): δ 7.44 (d, J=8.7 Hz, 2H), 7.36 (d, J=8.7 Hz, 2H), 4.32 (s, 2H), 4.03 (dd, J=7.5, 4.5 Hz, 1H), 3.80 (m, 2H), 3.49 (m, 2H), 3.34 (m, 2H), 2.50 (s, 3H), 2.36–2.11 (m, 4H), 1.69 (m, 10H), 1.39–1.23 (m, 5H), 0.95 (m, 5H).

EXAMPLE 24(65)

1-butyl-2,5-dioxo-3-(2-methylpropyl)-9-(4-(N,N-diphenylamino)phenylmethyl)-1,4,9-triazaspiro[5.5]undecane.hydrochloride

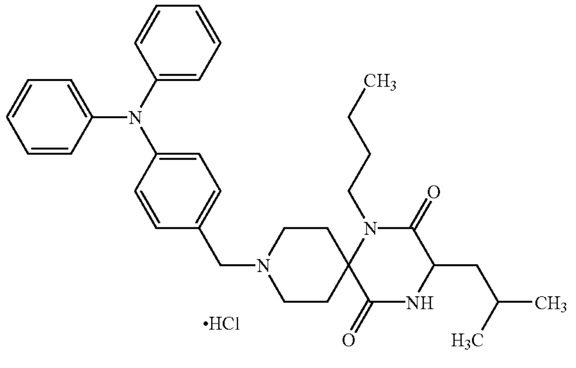

TLC: Rf 0.48 (chloroform:methanol=20:1);

NMR ($CD_3OD$): δ 7.40–7.25 (m, 6H), 7.13–7.01 (m, 8H), 4.27 (s, 2H), 4.01 (dd, J=7.8, 4.5 Hz, 1H), 3.87–3.68 (m, 2H), 3.56–3.44 (m, 2H), 3.44–3.32 (m, 2H), 2.48–2.32 (m, 2H), 2.29–2.10 (m, 2H), 1.90–1.44 (m, 5H), 1.44–1.30 (m, 2H), 0.96 (t, J=6.9 Hz, 3H), 0.94 (d, J=6.3 Hz, 3H), 0.94 (d, J=6.3 Hz, 3H).

EXAMPLE 24(66)

1-butyl-2,5-dioxo-3-cyclohexylmethyl-9-(4-(N,N-diphenylamino) phenylmethyl)-1,4,9-triazaspiro[5.5] undecane.hydrochloride

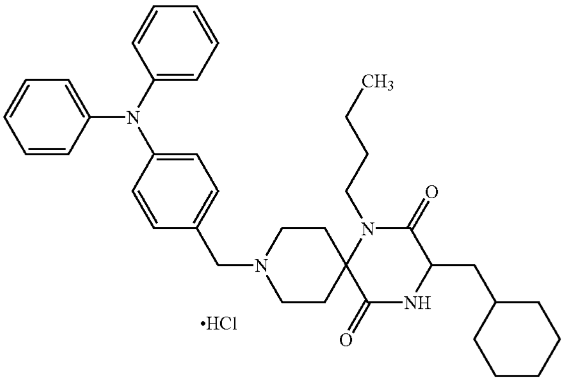

TLC: Rf 0.53 (chloroform:methanol=20:1);

NMR ($CD_3OD$): 67.41–7.26 (m, 6H), 7.14–7.00 (m, 8H), 4.27 (s, 2H), 4.04 (dd, J=7.5, 4.5 Hz, 1H), 3.88–3.68 (m, 2H), 3.57–3.45 (m, 2H), 3.44–3.36 (m, 2H), 2.48–2.32 (m, 2H), 2.28–2.07 (m, 2H), 1.84–1.44 (m, 10H), 1.44–1.14 (m, 5H), 1.00–0.90 (m, 2H), 0.96 (t, J=6.9 Hz, 3H).

EXAMPLE 24(67)

(3S)-1-(2-butynyl)-2,5-dioxo-3-cyclohexylmethyl-9-(3,5-dimethyl-1-phenyl pyrazol-4-ylmethyl)-1,4,9-triazaspiro[5.5]undecane.2 hydrochloride

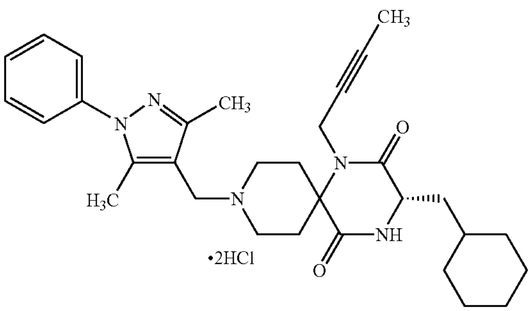

TLC: Rf 0.32 (chloroform:methanol=20:1);

NMR ($CD_3OD$): δ 7.59–7.46 (m, 5H), 4.32 (s, 2H), 4.24 (s, 2H), 4.09 (dd, J=7.5, 4.5 Hz, 1H), 3.86 (m, 2H), 3.65 (m, 2H), 2.60 (m, 2H), 2.39 (s, 3H), 2.38 (s, 3H), 2.26 (m, 2H), 1.88–1.66 (m, 10H), 1.53 (m, 1H), 1.25 (m, 3H), 0.96 (m, 2H).

EXAMPLE 24(68)

(3S)-1-(2-butynyl)-2,5-dioxo-3-(2-methylpropyl)-9-(3,5-dimethyl-1-phenylpyrazol-4-ylmethyl)-1,4,9-triazaspiro[5.5]undecane.2 hydrochloride

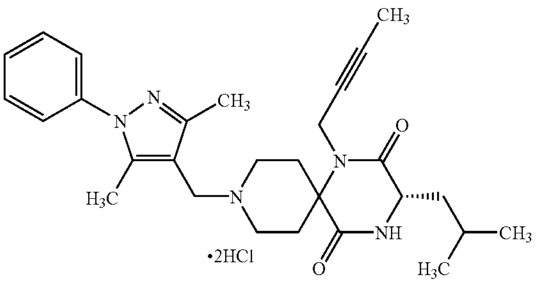

TLC: Rf 0.43 (chloroform:methanol=20:1);

NMR ($CD_3OD$): δ 7.60–7.46 (m, 5H), 4.32 (s, 2H), 4.26 (m, 2H), 4.06 (dd, J=7.5, 4.5 Hz, 1H), 3.85 (m, 2H), 3.62 (m, 2H), 2.60 (m, 2H), 2.39 (s, 3H), 2.38 (s, 3H), 2.27 (m, 2H), 1.89–1.61 (m, 6H), 0.95 (d, J=6.5 Hz, 3H), 0.94 (d, J=6.5 Hz, 3H).

EXAMPLE 24(69)

(3S)-1-butyl-2,5-dioxo-3-cyclohexylmethyl-9-(3,5-dimethyl-1-phenylpyrazol-4-ylmethyl)-1,4,9-triaza-spiro[5.5]undecane.2 hydrochloride

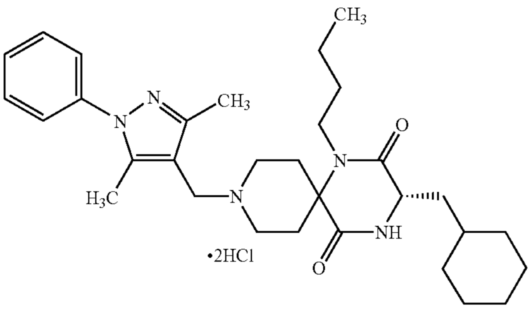

TLC: Rf 0.57 (chloroform:methanol=20:1);

NMR ($CD_3OD$): δ 7.59–7.45 (m, 5H), 4.32 (s, 2H), 4.06 (dd, J 7.8, 4.5 Hz, 1H), 3.85 (m, 2H), 3.60 (m, 2H), 3.43 (m, 2H), 2.53–2.44 (m, 2H), 2.45 (s,3H), 2.41 (s, 3H), 2.32–2.16 (m, 2H), 1.80–1.17 (m, 15H), 1.02–0.93 (m, 2H), 0.96 (d, J=7.0 Hz, 3H).

EXAMPLE 24(70)

1-butyl-2,5-dioxo-3-(2-methylpropyl)-9-(3,5-dimethyl-1-(4-methylphenyl)pyrazol-4-ylmethyl)-1,4,9-triazaspiro[5.5]undecane.2 hydrochloride

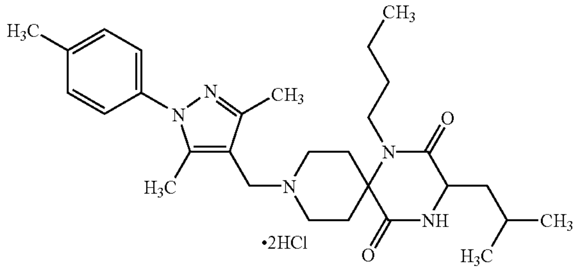

TLC: Rf 0.46 (chloroform:methanol=10:1);

NMR ($CD_3OD$): δ 7.36 (d, J=8.4 Hz, 2H), 7.31 (d, J=8.4 Hz, 2H), 4.30 (s, 2H), 4.02 (dd, J=7.8, 4.8 Hz, 1H), 3.84 (m, 2H), 3.60 (m, 2H), 3.38 (m, 2H), 2.42 (s, 3H), 2.37 (s, 3H), 2.35 (s, 3H), 2.52–2.18 (m, 4H), 1.90–1.32 (m, 7H), 0.96 (t, J=7.8 Hz, 3H), 0.95 (d, J=6.3 Hz, 3H), 0.94 (d, J=6.3 Hz, 3H).

EXAMPLE 24(71)

1-butyl-2,5-dioxo-3-cyclohexylmethyl-9-(3,5-dimethyl-1-(4-methylphenyl)pyrazol-4-ylmethyl)-1,4,9-triazaspiro[5.5]undecane.2 hydrochloride

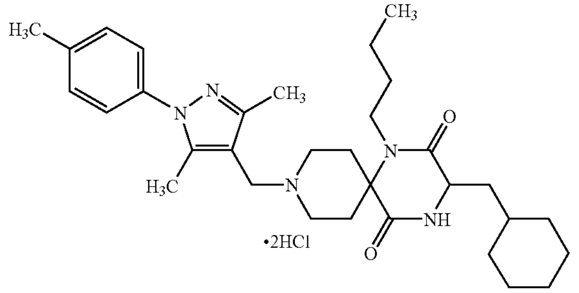

TLC: Rf 0.51 (chloroform:methanol=10:1);

NMR ($CD_3OD$): δ 7.38 (d, J=8.4 Hz, 2H), 7.33 (d, J=8.4 Hz, 2H), 4.31 (s, 2H), 4.06 (dd, J=7.5, 4.5 Hz, 1H), 3.82 (m, 2H), 3.60 (m, 2H), 3.42 (m, 2H), 2.43 (s, 3H), 2.38 (s, 3H), 2.36 (s, 3H), 2.56–2.14 (m, 3H), 1.84–1.16 (m, 15H), 0.97 (t, J=7.2 Hz, 3H), 0.97 (m, 2H).

EXAMPLE 24(72)

1-butyl-2,5-dioxo-3-(2-methylpropyl)-9-(3,5-dimethyl-1-(4-chlorophenyl)pyrazol-4-ylmethyl)-1,4,9-triazaspiro[5.5]undecane.2 hydrochloride

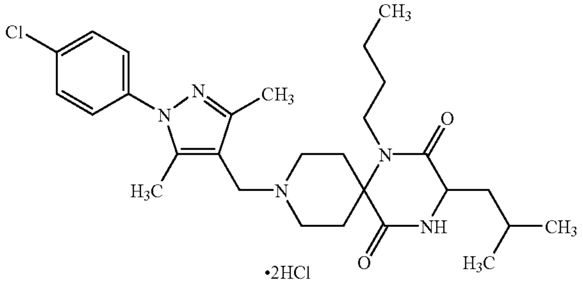

TLC: Rf 0.30 (chloroform:methanol=20:1);

NMR ($CD_3OD$): δ 7.57 (d, J=9.0 Hz, 2H), 7.49 (d, J=9.0 Hz, 2H), 4.31 (s, 2H), 4.02 (dd, J=7.8, 4.5 Hz, 1H), 3.91–3.80 (m, 2H), 3.60 (m, 2H), 3.46 (m, 2H), 2.52 (m, 2H), 2.40 (s, 3H), 2.39 (s, 3H), 2.27–2.15 (m, 2H), 1.86–1.81 (m, 1H), 1.76–1.51 (m, 4H), 1.44–1.32 (m, 2H), 0.96 (t, J=7.0 Hz, 3H), 0.95 (d, J=6.0 Hz, 3H), 0.94 (d, J=6.0 Hz, 3H).

EXAMPLE 24(73)

1-butyl-2,5-dioxo-3-cyclohexylmethyl-9-(3,5-dimethyl-1-(4-chlorophenyl)pyrazol-4-ylmethyl)-1,4,9-triazaspiro[5.5]undecane.2 hydrochloride

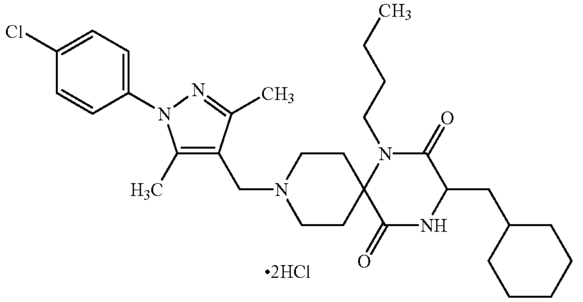

TLC: Rf 0.27 (chloroform:methanol=20:1);

NMR ($CD_3OD$): δ 7.57 (d, J=8.5 Hz, 2H), 7.48 (d, J=8.5 Hz, 2H), 4.31 (s, 2H), 4.04 (dd, J=7.8, 4.5 Hz, 1H), 3.91–3.77 (m, 2H), 3.60 (m, 2H), 3.45 (m, 2H), 2.50 (m, 2H), 2.39 (s, 6H), 2.27–2.14 (m, 2H), 1.80–1.51 (m, 9H), 1.44–1.17 (m, 6H), 1.03–0.89 (m, 5H).

EXAMPLE 24(74)

1-butyl-2,5-dioxo-3-(2-methylpropyl)-9-(3,5-dimethyl-1-(4-trifluoromethylphenyl)pyrazol-4-ylmethyl)-1,4,9-triazaspiro[5.5]undecane.2 hydrochloride

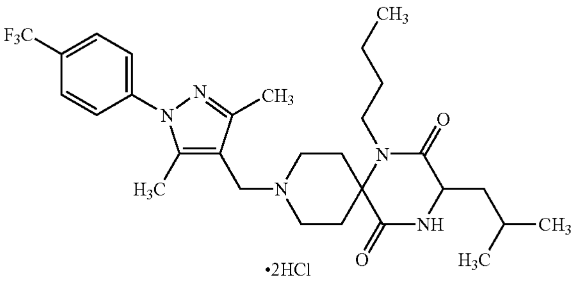

TLC: Rf 0.23 (chloroform:methanol=20:1);

NMR ($CD_3OD$): δ 7.87 (d, J=8.7 Hz, 2H), 7.72 (d, J=8.7 Hz, 2H), 4.32 (s, 2H), 4.02 (dd, J=7.8, 4.5 Hz, 1H), 3.93–3.78 (m, 2H), 3.60 (m, 2H), 3.43 (m, 2H), 2.50 (m, 2H), 2.45 (s, 3H), 2.40 (s, 3H), 2.29–2.16 (m, 2H), 1.86–1.77 (m, 1H), 1.74–1.54 (m, 4H), 1.44–1.34 (m, 2H), 0.96 (t, J=7.0 Hz, 3H), 0.95 (d, J=6.0 Hz, 3H), 0.94 (d, J=6.0 Hz, 3H).

EXAMPLE 24(75)

1-butyl-2,5-dioxo-3-cyclohexylmethyl-9-(3,5-dimethyl-1-(4-trifluoromethylphenyl)pyrazol-4-ylmethyl)-1,4,9-triazaspiro[5.5]undecane.2 hydrochloride

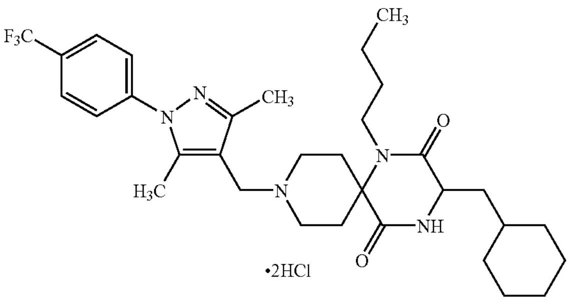

TLC: Rf 0.37 (chloroform:methanol=20:1);

NMR ($CD_3OD$): δ 7.87 (d, J=8.4 Hz, 2H), 7.72 (d, J=8.4 Hz, 2H), 4.32 (s, 2H), 4.05 (dd, J=7.8, 4.5 Hz, 1H), 3.92–3.78 (m, 2H), 3.60 (m, 2H), 3.45 (m, 2H), 2.50 (m, 2H), 2.45 (s, 3H), 2.40 (s, 3H), 2.28–2.15 (m, 2H), 1.80–1.51 (m, 9H), 1.44–1.21 (m, 6H), 1.03–0.93 (m, 5H).

EXAMPLE 24(76)

1-butyl-2,5-dioxo-3-(2-methylpropyl)-9-(3,5-diethyl-1-phenylpyrazol-4-ylmethyl)-1,4,9-triazaspiro[5.5]undecane.2 hydrochloride

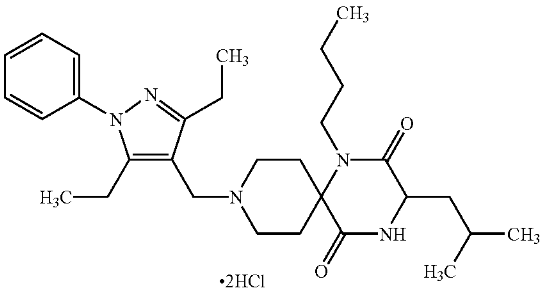

TLC: Rf 0.70 (chloroform:methanol=10:1);

NMR ($CD_3OD$): δ 7.61–7.53 (m, 3H), 7.53–7.46 (m, 2H), 4.32 (s, 2H), 4.03 (dd, J=7.5, 4.5 Hz, 1H), 3.95–3.79 (m, 2H), 3.65–3.58 (m, 2H), 3.50–3.38 (m, 2H), 2.85–2.75 (m, 4H), 2.47 (br, 2H), 2.28–2.16 (m, 2H), 1.83–1.46 (m, 3H), 1.41–1.29 (m, 4H), 0.98–0.91 (m, 15H).

EXAMPLE 24(77)

1-butyl-2,5-dioxo-3-cyclohexylmethyl-9-(3,5-diethyl-1-phenylpyrazol-4-ylmethyl)-1,4,9-triazaspiro[5.5]undecane.2 hydrochloride

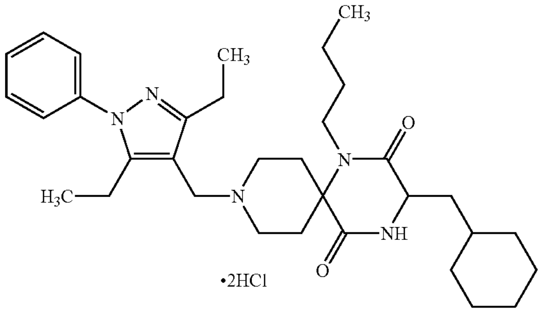

TLC: Rf 0.67 (chloroform:methanol=10:1);

NMR ($CD_3OD$): δ 7.61–7.53 (m, 3H), 7.53–7.46 (m, 2H), 4.32 (s, 2H), 4.05 (dd, J=7.5, 4.5 Hz, 1H), 3.95–3.79 (m, 2H), 3.70–3.55 (m, 2H), 3.47–3.31 (m, 2H), 2.91–2.75 (m, 4H), 2.60–2.45 (m, 2H), 2.30–2.14 (m, 2H), 1.80–1.43 (m, 9H), 1.43–1.15 (m, 8H), 0.98–0.91 (m, 9H).

EXAMPLE 24(78)

1-butyl-2,5-dioxo-3-cyclohexylmethyl-9-(2-phenylthiazol-4-ylmethyl)-1,4,9-triazaspiro[5.5]undecane.hydrochloride

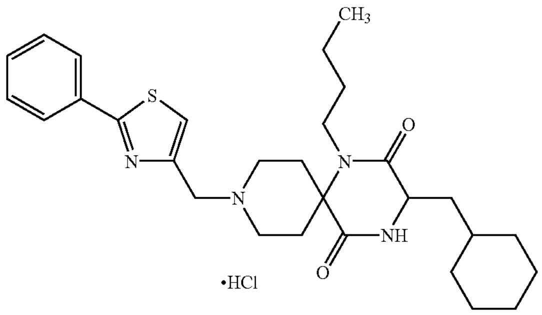

TLC: Rf 0.62 (chloroform:methanol=10:1);

NMR ($CD_3OD$): δ 8.03–8.00 (m, 2H), 7.87 (s, 1H), 7.52–7.49 (m, 3H), 4.54 (s, 2H), 4.04 (dd, J=7.6, 4.8 Hz, 1H), 4.04–3.87 (m, 2H), 3.70–3.58 (m, 2H), 3.51–3.39 (m, 2H), 2.58–2.38 (m, 2H), 2.26–2.13 (m, 2H), 1.78–1.43 (m, 9H), 1.40–1.15 (m, 6H), 1.10–0.90 (m, 5H).

EXAMPLE 24(79)

1-butyl-2,5-dioxo-3-(2-methylpropyl)-9-(2-phenylthiazol-4-ylmethyl)-1,4,9-triazaspiro[5.5]undecane.hydrochloride

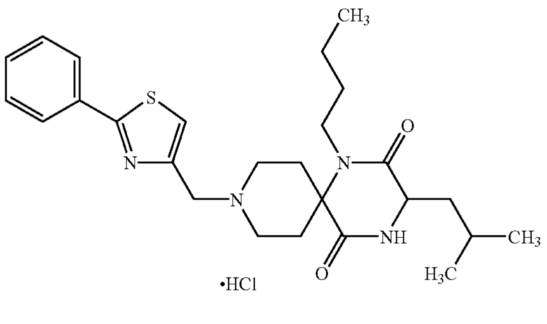

TLC: Rf 0.38 (chloroform:methanol=10:1);

NMR ($CD_3OD$): δ 8.02–8.01 (m, 2H), 7.85 (s, 1H), 7.51–7.50 (m, 3H), 4.55 (s, 2H), 4.03–3.86 (m, 3H), 3.68–3.59 (m, 2H), 3.45–3.36 (m, 2H), 2.50–2.34 (m, 2H), 2.29–2.16 (m, 2H), 1.88–1.45 (m, 5H), 1.36 (q, J=7.2 Hz, 2H), 0.97–0.93 (m, 9H).

EXAMPLE 24(80)

1-butyl-2,5-dioxo-3-(2-methylpropyl)-9-(2-(1,4-benzodioxan-2-yl)thiazol-4-ylmethyl)-1,4,9-triazaspiro[5.5]undecane.hydrochloride

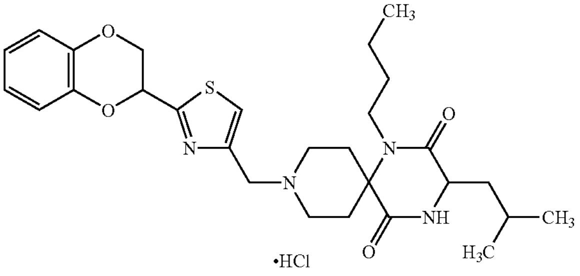

TLC: Rf 0.36 (chloroform:methanol=10:1);

NMR ($CD_3OD$): δ 7.88 (s, 1H), 7.00 (m, 1H), 6.94–6.87 (m, 3H), 5.66 (dd, J=6.0, 2.7 Hz, 1H), 4.62 (dd, J=11.7, 2.7 Hz, 1H), 4.51 (s, 2H), 4.42 (dd, J=11.7, 6.0 Hz, 1H), 4.02 (dd, J=7.5, 4.5 Hz, 1H), 3.88 (m, 2H), 3.58 (m, 2H), 3.40 (m, 2H), 2.48–2.16 (m, 4H), 1.90–1.28 (m, 7H), 0.97 (t, J=7.5 Hz, 3H), 0.95 (d, J=6.3 Hz, 3H), 0.94 (d, J=6.3 Hz, 3H).

EXAMPLE 24(81)

1-butyl-2,5-dioxo-3-(2-methylpropyl)-9-(4-trifluoromethyl-2-(morpholin-1-yl)thiazol-5-ylmethyl)-1,4,9-triazaspiro[5.5]undecane.2 hydrochloride

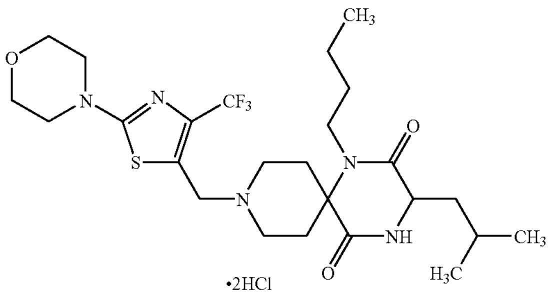

TLC: Rf 0.78 (chloroform:methanol=10:1);

NMR ($CD_3OD$): δ 4.63 (s, 2H), 4.03 (dd, J=7.8, 4,8 Hz, 1H), 3.86–3.78 (m, 6H), 3.58 (m, 6H), 3.40 (m, 2H), 2.44 (m, 2H), 2.22 (m, 2H), 1.88–1.32 (m, 8H), 0.97 (t, J=7.2 Hz, 3H), 0.95 (d, J=6.6 Hz, 3H), 0.94 (d, J=6.6 Hz, 3H).

EXAMPLE 24(82)

1-butyl-2,5-dioxo-3-(tetrahydropyran-4-ylmethyl)-9-(3,5-dimethyl-1-phenyl pyrazol-4-ylmethyl)-1,4,9-triazaspiro[5.5]undecane.2 hydrochloride

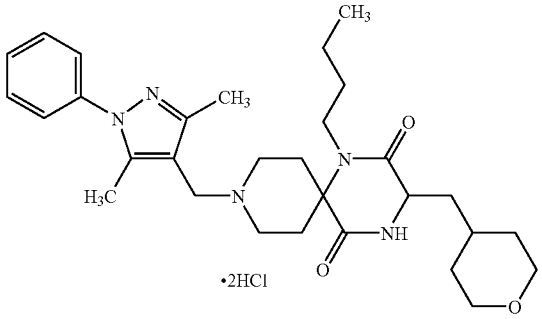

TLC: Rf 0.31 (chloroform:methanol=10:1);

NMR ($CD_3OD$): δ 7.60–7.46 (m, 5H), 4.33 (s, 2H), 4.09 (dd, J=7.5, 4.5 Hz, 1H), 3.98–3.78 (m, 4H), 3.68–3.56 (m, 2H), 3.50–3.36 (m, 4H), 2.58–2.16 (m, 4H), 2.40 (s, 3H), 2.39 (s, 3H), 1.84–1.20 (m, 11H), 0.97 (t, J=7.2 Hz, 3H).

EXAMPLE 24(83)

1-butyl-2,5-dioxo-3-(tetrahydropyran-4-ylmethyl)-9-(1,4-benzodioxan-6-ylmethyl)-1,4,9-triazaspiro[5.5]undecane.hydrochloride

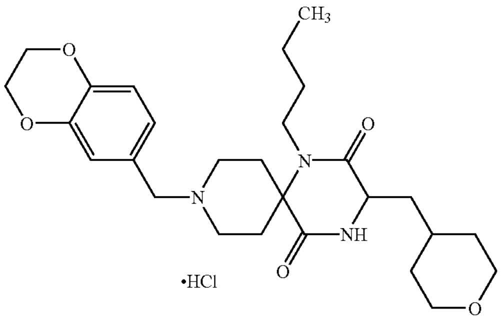

TLC: Rf 0.34 (chloroform:methanol=10:1);

NMR ($CD_3OD$): δ 7.06–6.92 (m, 3H), 4.27 (s, 4H), 4,24 (s, 2H), 4.07 (dd, J=7.5, 4.5 Hz, 1H), 3.96–3.86 (m, 2H), 3.84–3.68 (m, 2H), 3.52–3.36 (m, 6H), 2.44–2.10 (m, 4H), 1.82–1.22 (m, 11H), 0.96 (t, J=7.2 Hz, 3H).

EXAMPLE 24(84)

1-butyl-2,5-dioxo-3-cyclohexylmethyl-9-(4-carboxyphenylmethyl)-1,4,9-triazaspiro[5.5]undecane.hydrochloride

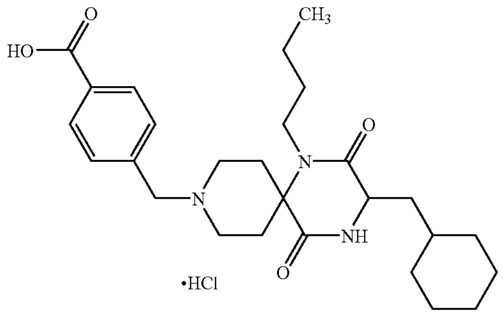

TLC: Rf 0.58 (chloroform:methanol:acetic acid=20:2:1);

NMR ($CD_3OD$): δ 8.14 (d, J=8.4 Hz, 2H), 7.68 (d, J=8.4 Hz, 2H), 4.45 (s, 2H), 4.04 (dd, J=7.5, 4.5 Hz, 1H), 3.94–3.76 (m, 2H), 3.56–3.43 (m, 2H), 3.43–3.34 (m, 2H), 2.50–2.31 (m, 2H), 2.28–2.08 (m, 2H), 1.84–1.12 (m, 15H), 1.06–0.90 (m, 2H), 0.95 (t, J=7.2 Hz, 3H).

EXAMPLE 24(85)

1-butyl-2,5-dioxo-3-(2-cyclohexylethyl)-9-(3,5-dimethyl-1-phenylpyrazol-4-ylmethyl)-1,4,9-triazaspiro[5.5]undecane.2 hydrochloride

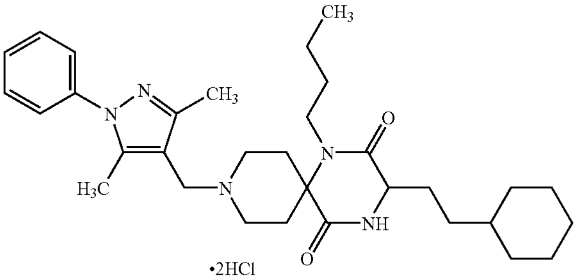

TLC: Rf 0.47 (chloroform:methanol=10:1);

NMR ($CD_3OD$): δ 7.56–7.45 (m, 5H), 4.32 (s, 2H), 4.02 (t, J=4.8 Hz, 1H), 3.98–3.85 (m, 1H), 3.85–3.70 (m, 1H), 3.65–3.56 (m, 2H), 3.56–3.42 (m, 1H), 3.42–3.30 (m, 1H), 2.55–2.37 (m, 2H), 2.38 (s, 3H), 2.37 (s, 3H), 2.30–2.13 (m, 2H), 1.92–1.78 (m, 2H), 1.78–1.60 (m, 5H), 1.60–1.48 (m, 2H), 1.48–1.32 (m, 2H), 1.32–1.08 (m, 6H), 0.96 (t, J=7.2 Hz, 3H), 0.96–0.85 (m, 2H).

EXAMPLE 24(86)

1-butyl-2,5-dioxo-3-(2-cyclohexylethyl)-9-(1,4-benzodioxan-6-ylmethyl)-1,4,9-triazaspiro[5.5]undecane.hydrochloride

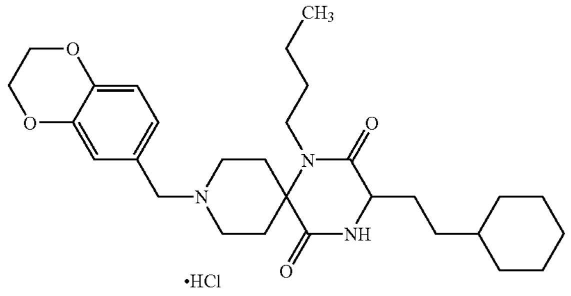

TLC: Rf 0.50 (chloroform:methanol=10:1);

NMR ($CD_3OD$): δ 7.05 (d, J=2.1 Hz, 1H), 6.98 (dd, J 8.1, 2.1 Hz, 1H), 6.92 (d, J=8.1 Hz, 1H), 4.26 (s, 4H), 4.23 (s, 2H), 4.03 (t, J=4.8 Hz, 1H), 3.90–3.79 (m, 1H), 3.76–3.62 (m, 1H), 3.50–3.38 (m, 3H), 3.38–3.30 (m, 1H), 2.43–2.06 (m, 4H), 1.92–1.78 (m, 2H), 1.78–1.60 (m, 5H), 1.60–1.45 (m, 2H), 1.42–1.30 (m, 2H), 1.30–1.08 (m, 6H), 0.95 (t, J=7.2 Hz, 3H), 0.97–0.88 (m, 2H).

EXAMPLE 24(87)

(3R)-1-butyl-2,5-dioxo-3-cyclohexylmethyl-9-(3,5-dimethyl-1-phenylpyrazol-4-ylmethyl)-1,4,9-triazaspiro[5.5]undecane.2 hydrochloride

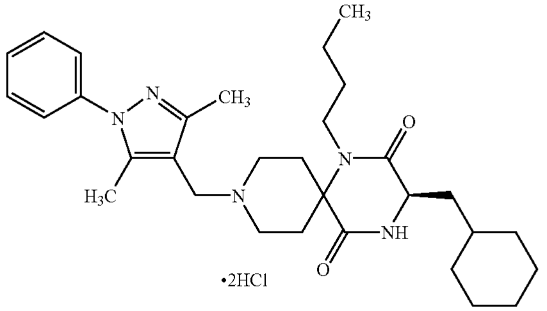

TLC: Rf 0.43 (chloroform:methanol=10:1);

NMR ($CD_3OD$): δ 7.61–7.48 (m, 5H), 4.33 (s, 2H), 4.06 (dd, J=7.5, 4.5 Hz, 1H), 3.95–3.78 (m, 2H), 3.68–3.58 (m, 2H), 3.50–3.40 (m, 2H), 2.62–2.45 (m, 2H), 2.42 (s, 3H), 2.40 (s, 3H), 2.30–2.12 (m, 2H), 1.82–1.12 (m, 15H), 0.97 (t, J=7.2 Hz, 3H), 0.97 (m, 2H).

EXAMPLE 24(88)

1-butyl-2,5-dioxo-3-(2-methylpropyl)-9-(4-methyl-2-phenylthiazol-5-ylmethyl)-1,4,9-triazaspiro[5.5]undecane.hydrochloride

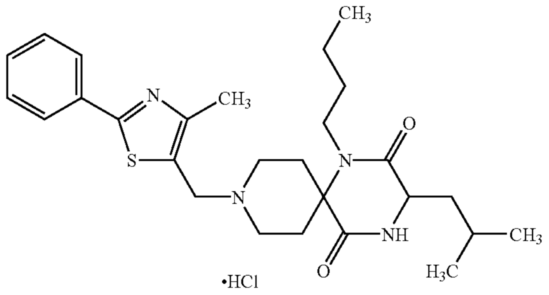

TLC: Rf 0.75 (chloroform:methanol=10:1);

NMR ($CD_3OD$): δ 7.98–7.95 (m, 2H), 7.55–7.50 (m, 3H), 4.69 (s, 2H), 4.01 (dd, J=7.5, 4.5 Hz, 1H), 3.98–3.78 (m, 2H), 3.65–3.56 (m, 2H), 3.50–3.40 (m, 2H), 2.58 (s, 3H), 2.60–2.48 (m, 2H), 2.27–2.14 (m, 2H), 1.88–1.48 (m, 5H), 1.48–1.30 (m, 2H), 0.97–0.93 (m, 9H).

EXAMPLE 24(89)

1-butyl-2,5-dioxo-3-(2-methylpropyl)-9-(2-(thiophen-1-yl)thiazol-4-ylmethyl)-1,4,9-triazaspiro[5.5]undecane.hydrochloride

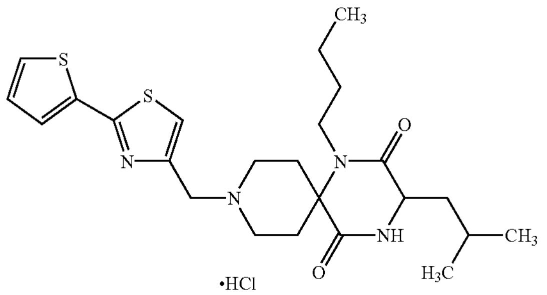

TLC: Rf 0.60 (chloroform:methanol=10:1);

NMR ($CD_3OD$): δ 7.81 (s, 1H), 7.67 (d, J=3.9 Hz, 1H), 7.60 (d, J=5.4 Hz, 1H), 7.14 (dd, J=5.4, 3.9 Hz, 1H), 4.49 (s, 2H), 4.00 (dd, J=7.8, 4.5 Hz, 1H), 3.98–3.82 (m, 2H), 3.62–3.55 (m, 2H), 3.42 (t, J=7.5 Hz, 2H), 2.58–2.40 (m, 2H), 2.28–2.10 (m, 2H), 1.86–1.42 (m, 5H), 1.46–1.30 (m, 2H), 0.97–0.93 (m, 9H).

EXAMPLE 24(90)

1-butyl-2,5-dioxo-3-(2-methylpropyl)-9-(2-(pyridin-4-yl)thiazol-4-ylmethyl)-1,4,9-triazaspiro[5.5]undecane.2 hydrochloride

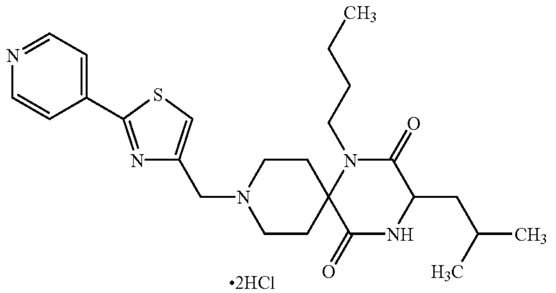

TLC: Rf 0.51 (chloroform:methanol=10:1);

NMR ($CD_3OD$): δ 8.98 (d, J=6.9 Hz, 2H), 8.71 (d, J=6.9 Hz, 2H), 8.37 (s, 1H), 4.66 (s, 2H), 4.01 (dd, J=7.8, 4.8 Hz, 1H), 4.00–3.87 (m, 2H), 3.70–3.59 (m, 2H), 3.50 (t, J=7.8 Hz, 2H), 2.72–2.58 (m, 2H), 2.25–2.08 (m, 2H), 1.88–1.46 (m, 5H), 1.46–1.35 (m, 2H), 0.97–0.92 (m, 9H).

EXAMPLE 24(91)

1-butyl-2,5-dioxo-3-cyclohexylmethyl-9-(3,4-dimethoxyphenylmethyl)-1,4,9-triazaspiro[5.5]undecane.hydrochloride

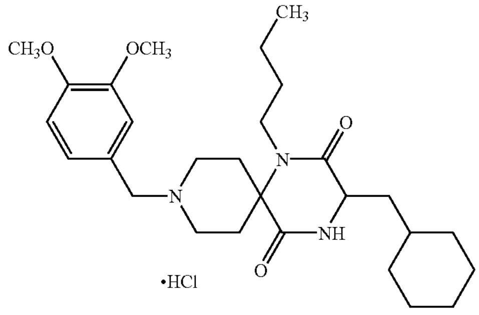

TLC: Rf 0.28 (chloroform:methanol=10:1);

NMR ($CD_3OD$): a 7.23 (s, 1H), 7.09 (d, J=8.4 Hz, 1H), 7.03 (d, J=8.4 Hz, 1H), 4.29 (s, 2H), 4.04 (dd, J=7.5, 4.8 Hz, 1H), 3.90 (s, 3H), 3.86 (s, 3H), 3.88–3.64 (m, 2H), 3.56–3.38 (m, 4H), 2.58–2.37 (m, 2H), 2.24–2.08 (m, 2H), 1.82–1.10 (m, 15H), 0.96 (t, J=7.2 Hz, 3H), 0.96 (m, 2H).

EXAMPLE 24(92)

1-butyl-2,5-dioxo-3-cyclohexylmethyl-9-(3,5-dimethoxyphenylmethyl)-1,4,9-triazaspiro[5.5]undecane.hydrochloride

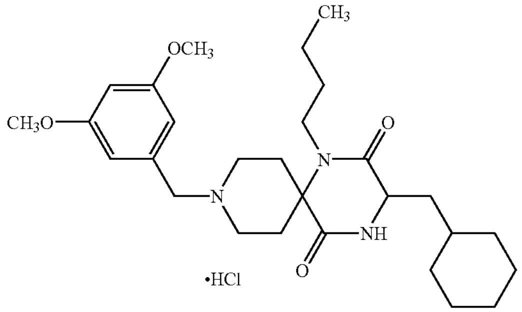

TLC: Rf 0.31 (chloroform:methanol=10:1);

NMR ($CD_3OD$): δ 6.74 (d, J=1.8 Hz, 2H), 6.60 (t, J=1.8 Hz, 1H), 4.28 (s, 2H), 4.04 (dd, J=7.8, 4.8 Hz, 1H), 3.86–3.70 (m, 2H), 3.83 (s, 6H), 3.58–3.36 (m, 4H), 2.52–2.36 (m, 2H), 2.24–2.08 (m, 2H), 1.82–1.10 (m, 15H), 0.96 (t, J=7.2 Hz, 3H), 0.96 (m, 2H).

EXAMPLE 24(93)

1-butyl-2,5-dioxo-3-(2-methylpropyl)-9-(5-(pyridin-2-yl)furan-2-ylmethyl)-1,4,9-triazaspiro[5.5]undecane.2 Hydrochloride

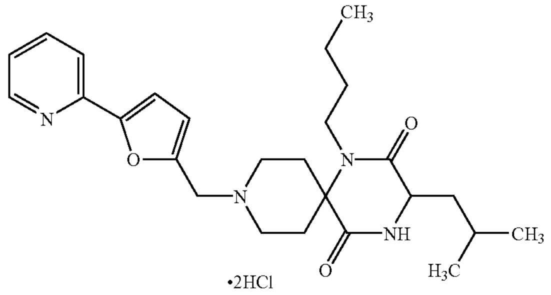

TLC: Rf 0.39 (chloroform:methanol=10:1);

NMR ($CD_3OD$): δ 8.76 (dd, J=5.4, 1.5 Hz, 1H), 8.51 (ddd, J=8.1, 7.5, 1.5 Hz, 1H), 8.39 (d, J=7.5 Hz, 1H), 7.85 (dd, J=8.1, 5.4 Hz, 1H), 7.61 (d, J=3.6 Hz, 1H), 7.08 (d, J=3.6 Hz, 1H), 4.63 (s, 2H), 4.00 (dd, J=7.8, 4.5 Hz, 1H), 3.98–3.81 (m, 2H), 3.65–3.55 (m, 2H), 3.49 (t, J=8.1 Hz, 2H), 2.72–2.55 (m, 2H), 2.28–2.10 (m, 2H), 1.90–1.27 (m, 7H), 1.00–0.89 (m, 9H).

EXAMPLE 24(94)

1-butyl-2,5-dioxo-3-(2-methylpropyl)-9-(5-(pyridin-3-yl)furan-2-ylmethyl)-1,4,9-triazaspiro[5.5]undecane.2 hydrochloride

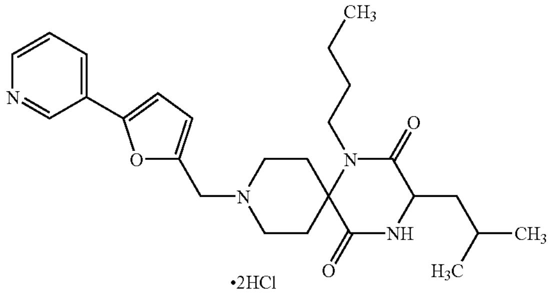

TLC: Rf 0.45 (chloroform:methanol=10:1);

NMR ($CD_3OD$): δ 9.34 (d, J=1.8 Hz, 1H), 8.94 (dd, J=8.1, 1.8 Hz, 1H), 8.75 (d, J=5.4 Hz, 1H), 8.10 (dd, J=8.1, 5.4 Hz, 1H), 7.34 (d, J=3.6 Hz, 1H), 6.98 (d, J=3.6 Hz, 1H), 4.57 (s, 2H), 4.00 (dd, J=7.8, 4.5 Hz, 1H), 3.98–3.77 (m, 2H), 3.63–3.43 (m, 4H), 2.73–2.55 (m, 2H), 2.28–2.09 (m, 2H), 1.89–1.27 (m, 7H), 1.00–0.89 (m, 9H).

EXAMPLE 24(95)

1-butyl-2,5-dioxo-3-(2-methylpropyl)-9-(4-(3,5-dimethylpyrazol-1-yl)phenylmethyl)-1,4,9-triazaspiro[5.5]undecane.2 hydrochloride

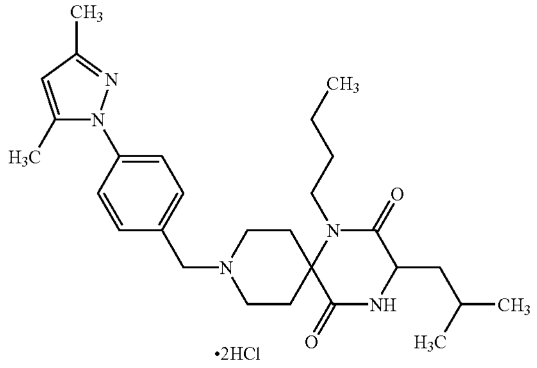

TLC: Rf 0.52 (chloroform:methanol=10:1);

NMR ($CD_3OD$): δ 7.94 (d, J=8.1 Hz, 2H), 7.71 (d, J=8.1 Hz, 2H), 6.51 (s, 1H), 4.49 (s, 2H), 4.01 (dd, J=7.8, 4.5 Hz, 1H), 3.85–3.76 (m, 2H), 3.58–3.48 (m, 4H), 2.72–2.58 (m, 2H), 2.45 (s, 3H), 2.39 (s, 3H), 2.23–2.06 (m, 2H), 1.88–1.45 (m, 5H), 1.45–1.34 (m, 2H), 0.97–0.92 (m, 9H).

EXAMPLE 24(96)

1-butyl-2,5-dioxo-3-(2-methylpropyl)-9-(4-(5-chloropyridin-3-yloxy)phenylmethyl)-1,4,9-triazaspiro[5.5]undecane.2 hydrochloride

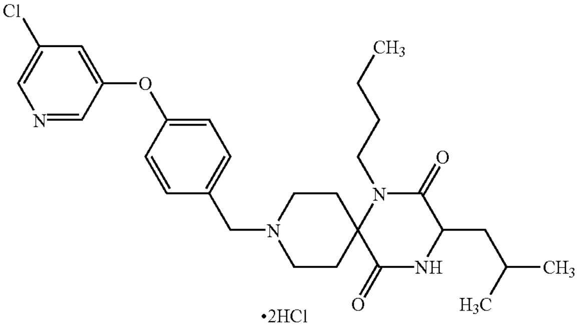

TLC: Rf 0.57 (chloroform:methanol=10:1);

NMR ($CD_3OD$): δ 8.54 (bs, 1H), 8.45 (bs, 1H), 7.87 (bs, 1H), 7.71 (d, J=8.4 Hz, 2H), 7.26 (d, J=8.4 Hz, 2H), 4.39 (s, 2H), 4.01 (dd, J=7.8, 4.8 Hz, 1H), 3.90–3.73 (m, 2H), 3.56–3.40 (m, 4H), 2.64–2.46 (m, 2H), 2.24–2.09 (m, 2H), 1.86–1.42 (m, 5H), 1.42–1.30 (m, 2H), 0.97–0.92 (m, 9H).

EXAMPLE 24(97)

1-butyl-2,5-dioxo-3-(2-methylpropyl)-9-(4-(pyrimidin-2-yloxy)phenylmethyl)-1,4,9-triazaspiro[5.5]undecane.2 hydrochloride

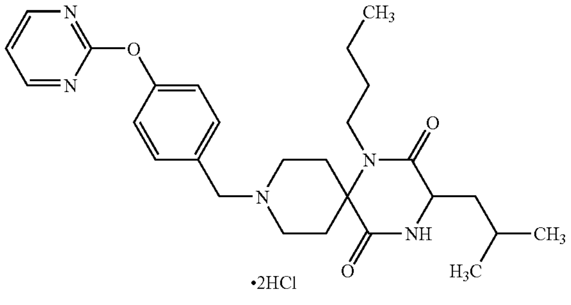

TLC: Rf 0.61 (chloroform:methanol=10:1);

NMR ($CD_3OD$): δ 8.62 (d, J=4.8 Hz, 2H), 7.68 (d, J=8.4 Hz, 2H), 7.32 (d, J=8.4 Hz, 2H), 7.26 (t, J=4.8 Hz, 1H), 4.40 (s, 2H), 4.02 (dd, J=7.5, 4.5 Hz, 1H), 3.93–3.72 (m, 2H), 3.60–3.35 (m, 4H), 2.58–2.40 (m, 2H), 2.28–2.07 (m, 2H), 1.90–1.45 (m, 5H), 1.45–1.36 (m, 2H), 0.98–0.90 (m, 9H).

EXAMPLE 24(98)

1-butyl-2,5-dioxo-3-(2-methylpropyl)-9-(4-(pyridin-3-yloxy)phenylmethyl)-1,4,9-triazaspiro[5.5]undecane.2 hydrochloride

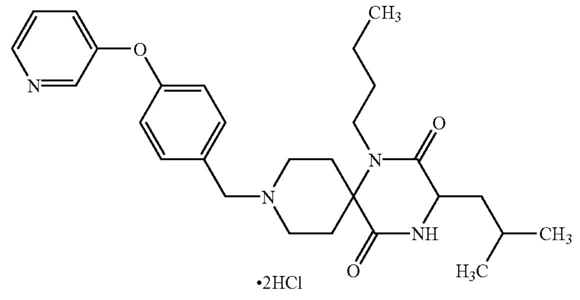

TLC: Rf 0.61 (chloroform:methanol=10:1);

NMR ($CD_3OD$): δ 8.76 (d, J=2.7 Hz, 1H), 8.63 (d, J=5.7 Hz, 1H), 8.28 (dd, J=8.7, 2.7 Hz, 1H), 8.07 (dd, J=8.7, 5.7 Hz, 1H), 7.78 (d, J=8.4 Hz, 2H), 7.35 (d, J=8.4 Hz, 2H), 4.41 (s, 2H), 4.02 (dd, J=7.8, 4.5 Hz, 1H), 3.93–3.72 (m, 2H), 3.58–3.40 (m, 4H), 2.68–2.48 (m, 2H), 2.26–2.06 (m, 2H), 1.90–1.46 (m, 5H), 1.46–1.30 (m, 2H), 0.98–0.91 (m, 9H).

EXAMPLE 24(99)

1-(2-butynyl)-2,5-dioxo-3-(2-methylpropyl)-9-(3,5-dimethyl-1-(4-methylphenyl)pyrazol-4-ylmethyl)-1,4,9-triazaspiro[5.5]undecane.2 hydrochloride

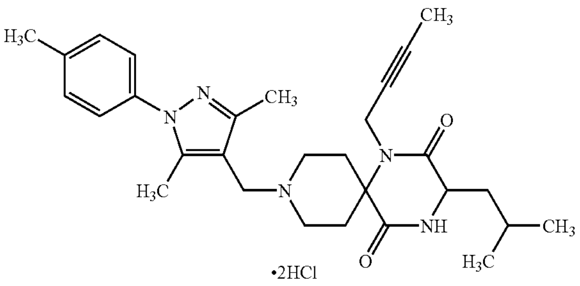

TLC: Rf 0.28 (chloroform:methanol=19:1);

NMR ($CD_3OD$): δ 7.39–7.29 (m, 4H), 4.31 (s, 2H), 4.27–4.20 (m, 2H), 4.06 (dd, J=7.5, 4.8 Hz, 1H), 3.84 (m, 2H), 3.62 (m, 2H), 2.59 (m, 2H), 2.42 (s, 3H), 2.37 (s, 3H), 2.34 (s, 3H), 2.28 (m, 2H), 1.92–1.60 (m, 6H), 0.96 (d, J=6.3 Hz, 3H), 0.95 (d, J=6.3 Hz, 3H).

EXAMPLE 24(100)

(3R)-1-(2-butynyl)-2,5-dioxo-3-cyclohexylmethyl-9-(3,5-dimethyl-1-phenylpyrazol-4-ylmethyl)-1,4,9-triazaspiro[5.5]undecane.2 hydrochloride

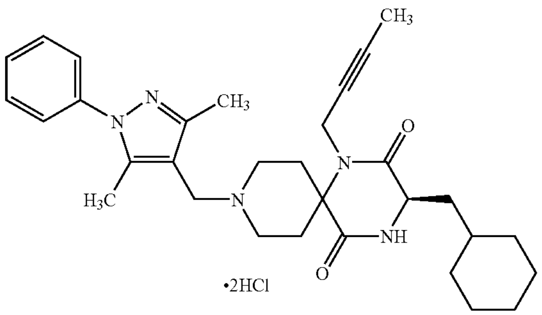

TLC: Rf 0.29 (chloroform:methanol=19:1);

NMR ($CD_3OD$): δ 7.59–7.43 (m, 5H), 4.31 (s, 2H), 4.25 (q, J=2.1 Hz, 2H), 4.09 (dd, J=7.2, 4.8 Hz, 1H), 3.85 (dt, J=3.0, 12.3 Hz, 2H), 3.68–3.56 (m, 2H), 2.61 (m, 2H), 2.38 (s, 3H), 2.37 (s, 3H), 2.26 (m, 2H), 1.83–1.43 (m, 8H), 1.75 (t, J=2.1 Hz, 3H), 1.38–1.12 (m, 3H), 0.96 (m, 2H).

EXAMPLE 24(101)

1-butyl-2,5-dioxo-3-(2-methylpropyl)-9-(4-(4-hydroxyphenyloxy)phenylmethyl)-1,4,9-triazaspiro[5.5]undecane.hydrochloride

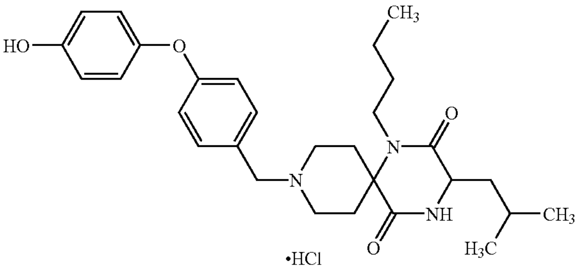

TLC: Rf 0.46 (chloroform:methanol=10:1);

NMR ($CD_3OD$): δ 7.47 (d, J=9.0 Hz, 2H), 6.97 (d, J=9.0 Hz, 2H), 6.88 (d, J=9.0 Hz, 2H), 6.80 (d, J=9.0 Hz, 2H), 4.30 (s, 2H), 4.00 (dd, J=7.5, 4.8 Hz, 1H), 3.86–3.70 (m, 2H), 3.52–3.34 (m, 4H), 2.48–2.30 (m, 2H), 2.28–2.10 (m, 2H), 1.88–1.44 (m, 5H), 1.44–1.28 (m, 2H), 0.97–0.92 (m, 9H).

EXAMPLE 24(102)

1-butyl-2,5-dioxo-3-(2-methylpropyl)-9-(4-(pyridin-2-yl)phenylmethyl)-1,4,9-triazaspiro[5.5]undecane.2 hydrochloride

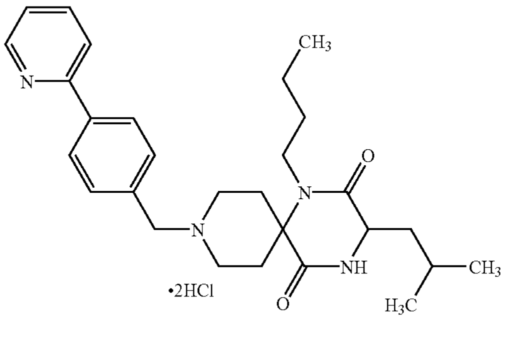

TLC: Rf 0.50 (chloroform:methanol=10:1);

NMR ($CD_3OD$): δ 8.89 (d, J=7.8 Hz, 1H), 8.70 (t, J=7.8 Hz, 1H), 8.43 (d, J=8.4 Hz, 1H), 8.10–8.06 (m, 3H), 7.98 (d, J=8.7 Hz, 2H), 4.51 (s, 2H), 4.01 (dd, J=7.8, 4.8 Hz, 1H), 3.96–3.78 (m, 2H), 3.56–3.45 (m, 4H), 2.72–2.58 (m, 2H), 2.24–2.08 (m, 2H), 1.84–1.44 (m, 5H), 1.44–1.34 (m, 2H), 0.97–0.92 (m, 9H).

EXAMPLE 24(103)

1-butyl-2,5-dioxo-3-(2-methylpropyl)-9-(4-(pyridin-3-yl) phenylmethyl)-1,4,9-triazaspiro[5.5]undecane.2 hydrochloride

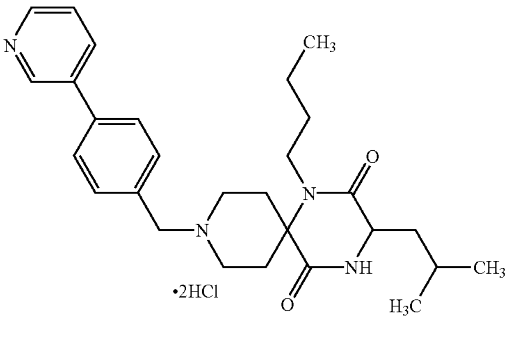

TLC: Rf 0.47 (chloroform:methanol=10:1);

NMR ($CD_3OD$): δ 9.24 (s, 1H), 8.98 (d, J=8.4 Hz, 1H), 8.88 (d, J=8.4 Hz, 1H), 8.21 (dd, J=8.4, 5.7 Hz, 1H), 7.96 (d, J=8.4 Hz, 2H), 7.87 (d, J=8.4 Hz, 2H), 4.47 (s, 2H), 4.01 (dd, J=7.5, 4.8 Hz, 1H), 3.96–3.75 (m, 2H), 3.58–3.44 (m, 4H), 2.64–2.50 (m, 2H), 2.25–2.08 (m, 2H), 1.88–1.48 (m, 5H), 1.48–1.32 (m, 2H), 0.97–0.92 (m, 9H).

EXAMPLE 24(104)

1-butyl-2,5-dioxo-3-(2-methylpropyl)-9-(3,5-dimethyl-1-(4-carboxyphenyl)pyrazol-4-ylmethyl)-1,4,9-triazaspiro[5.5]undecane.2 hydrochloride

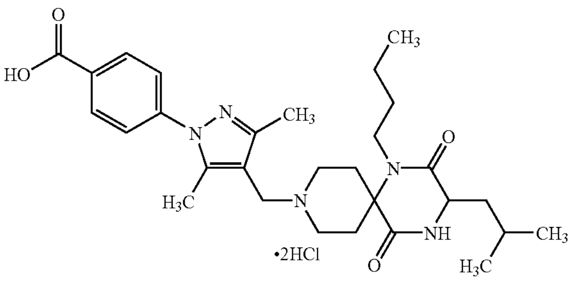

TLC: Rf 0.27 (chloroform:methanol=10:1);

NMR ($CD_3OD$): δ 8.19 (d, J=8.4 Hz, 2H), 7.61 (d, J=8.4 Hz, 2H), 4.32 (s, 2H), 4.03 dd, J=7.5, 4.5 Hz, 1H), 3.96–3.74 (m, 2H), 3.66–3.55 (m, 2H), 3.48–3.36 (m, 2H), 2.58–2.40 (m, 2H), 2.45 (s, 3H), 2.40 (s, 3H), 2.32–2.14 m, 2H), 1.90–1.46 (m, 5H), 1.46–1.30 (m, 2H), 0.99–0.95 (m, 9H).

EXAMPLE 24(105) 1-butyl-2,5-dioxo-3-(2-methylpropyl)-9-(4-(pyrazin-2-yloxy)phenylmethyl)-1,4,9-triazaspiro[5.5]undecane.2 hydrochloride

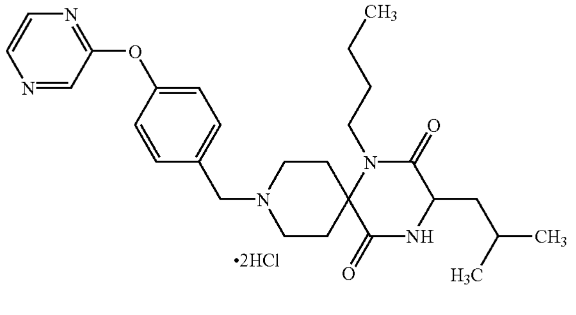

TLC: Rf 0.48 (chloroform:methanol=20:1);

NMR ($CD_3OD$): δ 8.47 d, J=1.5 Hz, 1H), 8.32 (d, J=2.7 Hz, 1H), 8.13 (dd, J=2.7, 1.5 Hz, 1H), 7.65 (d, J=8.4 Hz, 2H), 7.32 (d, J=8.4 Hz, 2H), 4.40 (s, 2H), 4.02 (dd, J=7.5, 4.5 Hz, 1H), 3.94–3.73 (m, 2H), 3.58–3.46 (m, 2H), 3.44–3.34 (m, 2H), 2.52–2.34 (m, 2H), 2.30–2.10 (m, 2H), 1.90–1.43 (m, 5H), 1.43–1.26 (m, 2H), 0.99–0.90 (m, 9H).

EXAMPLE 24(106)

1-butyl-2,5-dioxo-3-(2-methylpropyl)-9-(4-(4-carboxyphenyl)phenylmethyl)-1,4,9-triazaspiro[5.5]undecane.hydrochloride

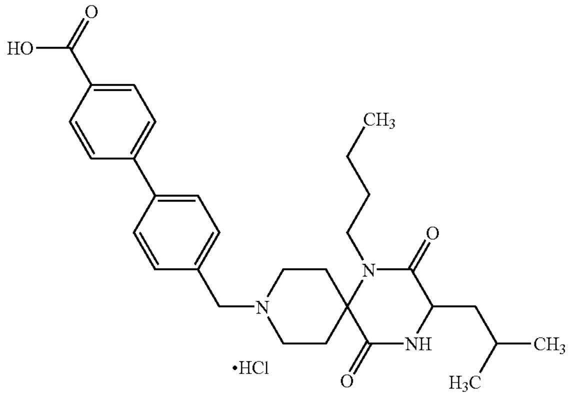

TLC: Rf 0.20 (chloroform:methanol=10:1);

NMR ($CD_3OD$): δ 8.11 (d, J=8.4 Hz, 2H), 7.83 (d, J=8.4 Hz, 2H), 7.77 (d, J=8.4 Hz, 2H), 7.69 (d, J=8.4 Hz, 2H), 4.43 (s, 2H), 4.01 (dd, J=7.8, 4.5 Hz, 1H), 3.96–3.74 (m, 2H), 3.58–3.36 (m, 4H), 2.55–2.38 (m, 2H), 2.28–2.10 (m, 2H), 1.88–1.44 (m, 5H), 1.44–1.30 (m, 2H), 0.97–0.92 (m, 9H).

EXAMPLE 24(107)

1-butyl-2,5-dioxo-3-(2-methylpropyl)-9-(4-(pyridin-4-yl)phenylmethyl)-1,4,9-triazaspiro[5.5]undecane.2 hydrochloride

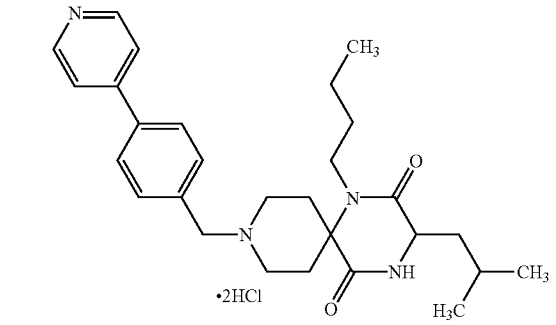

TLC: Rf 0.50 (chloroform:methanol=10:1);

NMR ($CD_3OD$): δ 8.91 (d, J=6.9 Hz, 2H), 8.45 (d, J=6.9 Hz, 2H), 8.11 (d, J=7.8 Hz, 2H), 7.91 (d, J=7.8 Hz, 2H), 4.49 (s, 2H), 4.01 (dd, J=7.8, 4.8 Hz, 1H), 3.96–3.78 (m, 2H), 3.58–3.40 (m, 4H), 2.64–2.48 (m, 2H), 2.26–2.08 (m, 2H), 1.90–1.28 (m, 7H), 0.96–0.93 (m, 9H).

EXAMPLE 24(108)

1-butyl-2,5-dioxo-3-(2-methylpropyl)-9-(4-(pyridin-2-yloxy)phenylmethyl)-1,4,9-triazaspiro[5.5]undecane.2 hydrochloride

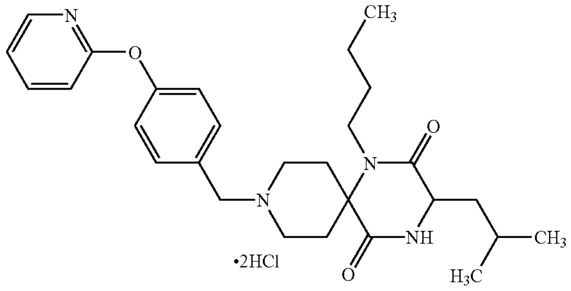

TLC: Rf 0.46 (chloroform:methanol=10:1);

NMR ($CD_3OD$): δ 8.44–8.15 (m, 2H), 7.82 (d, J=7.2 Hz, 2H), 7.60–7.40 (m, 1H), 7.42 (d, J=7.2 Hz, 2H), 7.27–7.24 (m, 1H), 4.43 (s, 2H), 4.02 (dd, J=7.5, 4.5 Hz, 1H), 3.92–3.70 (m, 2H), 3.58–3.40 (m, 4H), 2.64-2.42 (m, 2H), 2.28–2.06 (m, 2H), 1.92–1.28 (m, 7H), 0.97–0.94 (m, 9H).

EXAMPLE 24(109)

1-butyl-2,5-dioxo-3-cyclohexylmethyl-9-(naphthalen-2-ylmethyl)-1,4,9-triazaspiro[5.5]undecane.hydrochloride

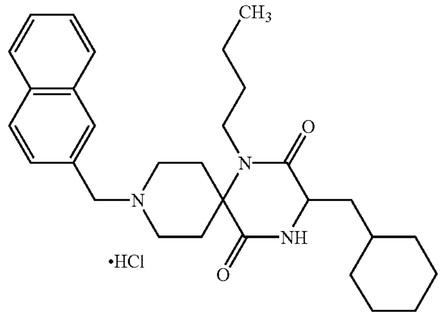

TLC: Rf 0.71 (chloroform:methanol=10:1);

NMR ($CD_3OD$): δ 8.08–7.93 (m, 4H), 7.64–7.57 (m, 3H), 4.54 (s, 2H), 4.04 (dd, J=7.5, 4.8 Hz, 1H), 3.96–3.80 (m, 2H), 3.60–3.44 (m, 2H), 3.42–3.36 (m, 2H), 2.42–2.08 (m, 4H), 1.82–1.16 (m, 15H), 0.95 (t, J=7.5 Hz, 3H), 0.95 (m, 2H).

EXAMPLE 24(110)

1-butyl-2,5-dioxo-3-cyclohexylmethyl-9-(6-methoxynaphthalen-2-ylmethyl)-1,4,9-triazaspiro[5.5]undecane.hydrochloride

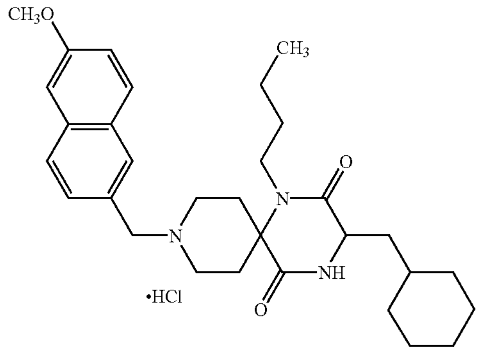

TLC: Rf 0.75 (chloroform:methanol=10:1);

NMR ($CD_3OD$): δ 7.98 (s, 1H), 7.91 (d, J=8.7 Hz, 1H), 7.85 (d, J=8.7 Hz, 1H), 7.58 (d, J=8.7 Hz, 1H), 7.31 (d, J=2.4 Hz, 1H), 7.22 (dd, J=8.7, 2.4 Hz, 1H), 4.48 (s, 2H), 4.04 (dd, J=7.8, 4.8 Hz, 1H), 3.94–3.78 (m, 2H), 3.93 (s, 3H), 3.58–3.44 (m, 2H), 3.42–3.36 (m, 2H), 2.48–2.30 (m, 2H), 2.24–2.08 (m, 2H), 1.82–1.10 (m, 15H), 0.95 (t, J=7.2 Hz, 3H), 0.95 (m, 2H).

EXAMPLE 24(111)

1-butyl-2,5-dioxo-3-(2-methylpropyl)-9-(4-(4-carboxyphenyloxy)phenylmethyl)-1,4,9-triazaspiro[5.5]undecane.hydrochloride

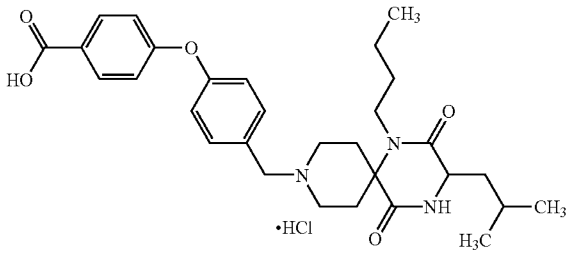

TLC: Rf 0.27 (chloroform:methanol=10:1);

NMR ($CD_3OD$): δ 8.03 (d, J=8.7 Hz, 2H), 7.63 (d, J=8.4 Hz, 2H), 7.17 (d, J=8.4 Hz, 2H), 7.07 (d, J=8.7 Hz, 2H), 4.37 (s, 2H), 4.01 (dd, J=7.5, 4.5 Hz, 1H), 3.90–3.70 (m, 2H), 3.56–3.36 (m, 4H), 2.56–2.38 (m, 2H), 2.25–2.10 (m, 2H), 1.84–1.44 (m, 5H), 1.44–1.39 (m, 2H), 0.98–0.93 (m, 9H).

EXAMPLE 24(112)

1-butyl-2,5-dioxo-3-(2-methylpropyl)-9-(5-(pyridin-4-yl)furan-2-ylmethyl)-1,4,9-triazaspiro[5.5]undecane.2hydrochloride

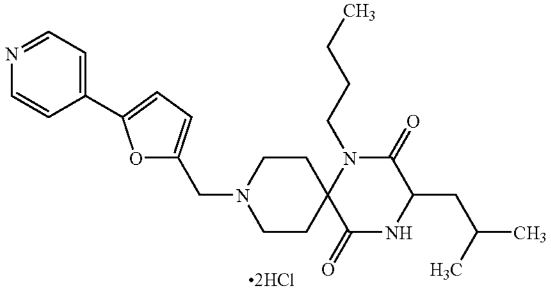

TLC: Rf 0.39 (chloroform:methanol=10:1);

NMR ($CD_3OD$): δ 8.80 (d, J=6.9 Hz, 2H), 8.39 (d, J=6.9 Hz, 2H), 7.69 (d, J=3.6 Hz, 1H), 7.08 (d, J=3.6 Hz, 1H), 4.62 (s, 2H), 4.00 (dd, J=7.8, 4.5, Hz, 1H), 3.99–3.79 (m, 2H), 3.65–3.43 (m, 4H), 2.72–2.54 (m, 2H), 2.30–2.10 (m, 2H), 1.88–1.26 (m, 7H), 1.00–0.84 (m, 9H).

EXAMPLE 24(113)

1-butyl-2,5-dioxo-3-cyclopentylmethyl-9-(4-phenyloxyphenylmethyl)-1,4,9-triazaspiro[5.5]undecane.hydrochloride

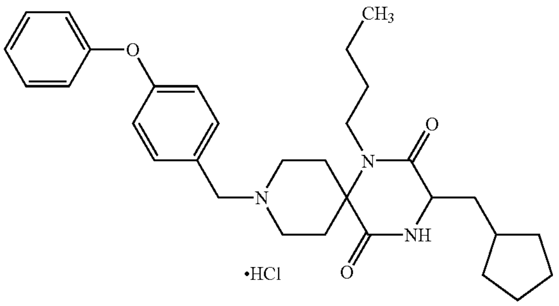

TLC: Rf 0.66 (chloroform:methanol=10:1);

NMR ($CD_3OD$): δ 7.52 (d, J=8.5 Hz, 2H), 7.40 (t, J=7.5 Hz, 2H), 7.18 (t, J=7.5 Hz, 1H), 7.05 (m, 4H), 4.34 (s, 2H), 4.00 (t, J=6.0 Hz, 1H), 3.82 (m, 2H), 3.49 (m, 2H), 3.39 (m, 2H), 2.37 (m, 2H), 2.17 (m, 2H), 1.96 (m, 1H), 1.81 (m, 4H), 1.58 (m, 6H), 1.38 (m, 2H), 1.17 (m, 2H), 0.95 (t, J=7.0 Hz, 3H).

EXAMPLE 24(114)

(3R)-1-butyl-2,5-dioxo-3-(2,2-dimethylpropyl)-9-(4-phenyloxyphenylmethyl)-1,4,9-triazaspiro[5.5]undecane.hydrochloride

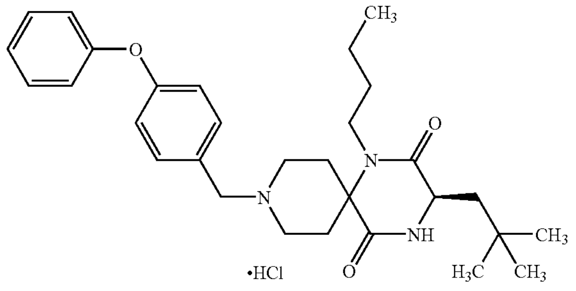

TLC: Rf 0.52 (chloroform:methanol=20:1);

NMR ($CD_3OD$): δ 7.52 (d, J=9.0 Hz, 2H), 7.40 (t, J=7.5 Hz, 2H), 7.18 (t, J=7.5 Hz, 1H), 7.04 (m, 4H), 4.33 (s, 2H), 4.01 (dd, J=7.2, 3.3 Hz, 1H), 3.82 (m, 1H), 3.71 (m, 1H), 3.50 (m, 2H), 3.43 (m, 2H), 2.38 (m, 2H), 2.24 (m, 2H), 2.00 (dd, J=14.0, 3.3 Hz, 1H), 1.55 (dd, J=14.0, 7.2 Hz, 1H), 1.50 (m, 2H), 1.36 (m, 2H), 0.99 (s, 9H), 0.95 (t, J=7.0 Hz, 3H).

EXAMPLE 24(115)

(3S)-1-butyl-2,5-dioxo-3-(2,2-dimethylpropyl)-9-(4-phenyloxyphenylmethyl)-1,4,9-triazaspiro[5.5]undecane.hydrochloride

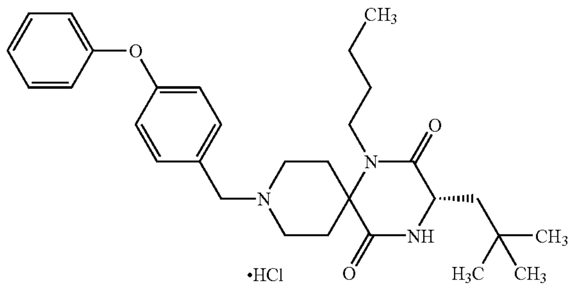

TLC: Rf 0.52 (chloroform:methanol=20:1);

NMR ($CD_3OD$): δ 7.52 (d, J=9.0 Hz, 2H), 7.40 (t, J=7.5 Hz, 2H), 7.18 (t, J=7.5 Hz, 1H), 7.04 (m, 4H), 4.33 (s, 2H), 4.01 (dd, J=7.2, 3.3 Hz, 1H), 3.82 (m, 1H), 3.71 (m, 1H), 3.50 (m, 2H), 3.43 (m, 2H), 2.38 (m, 2H), 2.24 (m, 2H), 2.00 (dd, J=14.0, 3.3 Hz, 1H), 1.55 (dd, J=14.0, 7.2 Hz, 1H), 1.50 (m, 2H), 1.36 (m, 2H), 0.99 (s, 9H), 0.95 (t, J=7.0 Hz, 3H).

EXAMPLE 24(116)

1-butyl-2,5-dioxo-3-cyclohexylmethyl-9-(4-nitrophenylmethyl)-1,4,9-triazaspiro[5.5]undecane.hydrochloride

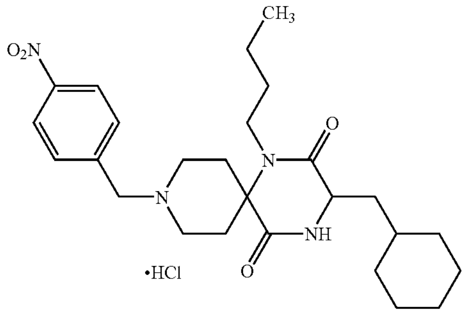

TLC: Rf 0.68 (chloroform:methanol=10:1);

NMR ($CD_3OD$): δ 8.33 (d, J=8.7 Hz, 2H), 7.78 (d, J=8.7 Hz, 2H), 4.49 (s, 2H), 4.03 (dd, J=7.5, 4.5 Hz, 1H), 3.93–3.76 (m, 2H), 3.55–3.43 (m, 2H), 3.40–3.31 (m, 2H), 2.45–2.28 (m, 2H), 2.27–2.08 (m, 2H), 1.83–1.14 (m, 15H), 1.04–0.86 (m, 5H).

EXAMPLE 24(117)

(3R)-1-(tetrahydrofuran-2-ylmethyl)-2,5-dioxo-3-phenylmethyl-9-(4-phenylbutyl)-1,4,9-triazaspiro[5.5]undecane.hydrochloride

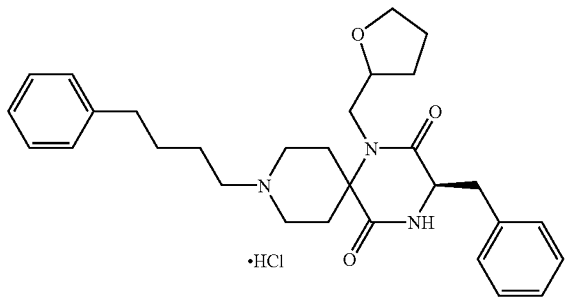

TLC: Rf 0.55 (chloroform:methanol=10:1);

NMR ($CDCl_3$): δ 7.38–7.14 (m, 10H), 6.00–5.75 (m, 1H), 4.40–4.15 (m, 2H), 3.92–3.58 (m, 3H), 3.58–2.25 (m, 13H), 2.18–1.45 (m, 10H).

EXAMPLE 24(118)

(3S)-1-(tetrahydrofuran-2-ylmethyl)-2,5-dioxo-3-phenylmethyl-9-(4-phenylbutyl)-1,4,9-triazaspiro[5.5]undecane.hydrochloride

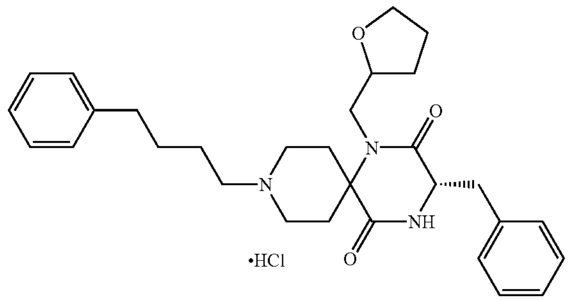

TLC: Rf 0.55 (chloroform:methanol=10:1);

NMR ($CDCl_3$): δ 7.40–7.15 (m, 10H), 6.05–5.80 (m, 1H), 4.40–4.10 (m, 2H), 3.90–3.55 (m, 3H), 3.55–2.20 (m, 13H), 2.18–1.45 (m, 10H).

EXAMPLE 24(119)

(3S)-1-propyl-2,5-dioxo-3-(3-(benzyloxycarbonyl amino) propyl)-9-(2-phenylethyl)-1,4,9-triazaspiro[5.5]undecane.hydrochloride

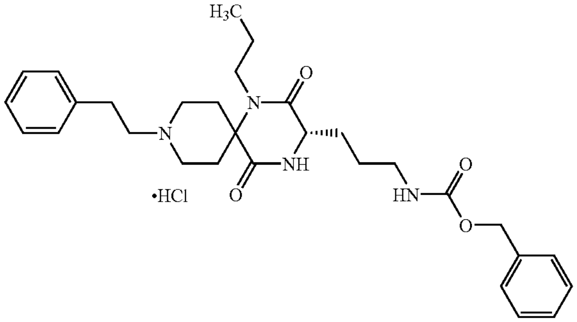

TLC: Rf 0.32 (chloroform:methanol=10:1);

NMR ($CD_3OD$): δ 7.40–7.20 (m, 10H), 5.06 (s, 2H), 4.09 (dd, J=5.2, 4.6 Hz, 1H), 4.00–3.70 (m, 2H), 3.70–3.55 (m, 2H), 3.50–3.30 (m, 4H), 3.20–3.00 (m, 4H), 2.65–2.35 (m, 2H), 2.30–2.10 (m, 2H), 2.00–1.75 (m, 2H), 1.70–1.40 (m, 4H), 0.96 (t, J=7.4 Hz, 3H).

EXAMPLE 25

1-butyl-2,5-dioxo-3-(carboxymethyl)-9-(4-phenyloxyphenylmethyl)-1,4,9-triazaspiro[5.5]undecane.hydrochloride

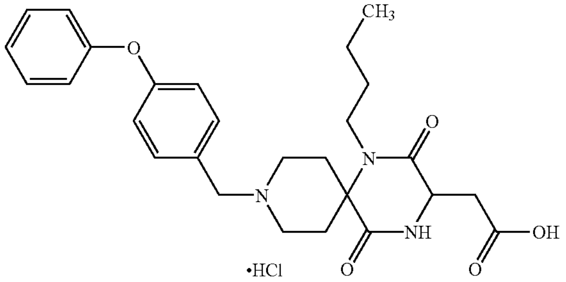

To a solution of the compound prepared in Example 24(11) (173 mg) in methanol (5 mL) was added 2N aqueous solution of sodium hydroxide (2 ml). The reaction mixture was stirred for 3 hours at room temperature. The reaction mixture was acidified to pH 4 by adding 2N hydrochloric acid, and was extracted with ethyl acetate. The extract was washed with a saturated aqueous solution of sodium chloride, dried over anhydrous sodium sulfate and concentrated. The obtained residue was dissolved in 1,4-dioxane, and 4N hydrogen chloride-1,4-dioxane solution was added thereto. The reaction mixture was concentrated. The obtained residue was washed with diethyl ether and dried to give the compound of the present invention (127 mg) having the following physical data.

TLC: Rf 0.51 (chloroform:methanol:acetic acid=20:4:1);

NMR ($CD_3OD$): 7.55–7.53 (m, 2H), 7.42–7.36 (m, 2H), 7.20–7.15 (m, 1H), 7.07–7.02 (m, 4H), 4.33 (s, 2H), 4.27 (t, J=4.5 Hz, 1H), 3.96–3.90 (m, 1H), 3.72–3.66 (m, 1H), 3.54–3.38 (m, 4H), 2.97 (dd, J=18.0,4.8Hz, 1H), 2.79 (dd, J=18.0, 4.8 Hz, 1H), 2.50–2.36 (m, 3H), 2.27–2.16 (m, 1H), 1.62–1.48 (m, 2H), 1.41–1.30 (m, 2H), 0.94 (t, J=7.2 Hz, 3H).

EXAMPLE 26(1)~26(3)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl) leucine, and furthermore by the same procedure as described in Reference Example 5→Reference Example 6→Example 1 using the corresponding compound instead of 3,5-dimethyl-1-phenyl-4-formylpyrazole, and furthermore by the same procedure as described in Example 25 because of acetylation of a part of hydroxy group, the following compounds of the present invention were obtained.

EXAMPLE 26(1)

1-(3-hydroxybutyl)-2,5-dioxo-3-(2-methylpropyl)-9-(4-phenyloxyphenylmethyl)-1,4,9-triazaspiro[5.5]undecane.hydrochloride

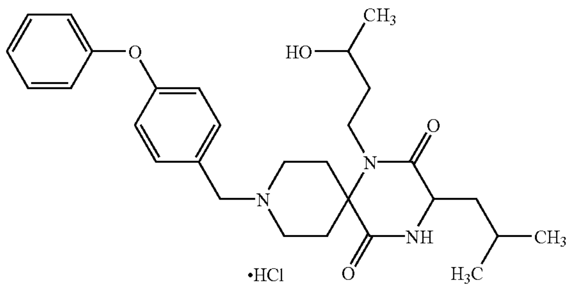

TLC: Rf 0.49 (chloroform:methanol=10:1);

NMR ($CD_3OD$): δ 7.54 (d, J=8.5 Hz, 2H), 7.39 (t, J=7.5 Hz, 2H), 7.18 (t, J=7.5 Hz, 1H), 7.04 (m, 4H), 4.33 (s, 2H), 4.02 (m, 1H), 3.80 (m, 3H), 3.51 (m, 4H), 2.46 (m, 2H), 2.19 (m, 2H), 1.85–1.57 (m, 5H), 1.17 (d, J=6.0 Hz, 3H), 0.94 (d, J=9.0 Hz, 6H).

EXAMPLE 26(2)

1-(3-hydroxypropyl)-2,5-dioxo-3-(2-methylpropyl)-9-(4-phenyloxyphenylmethyl)-1,4,9-triazaspiro[5.5]undecane.hydrochloride

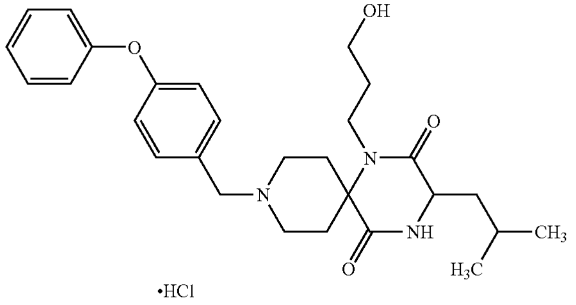

TLC: Rf 0.46 (chloroform:methanol=10:1);

NMR ($CD_3OD$): δ 7.51 (d, J=8.5 Hz, 2H), 7.40 (t, J=7.5 Hz, 2H), 7.18 (t, J=7.5 Hz, 1H), 7.04 (m, 4H), 4.34 (s, 2H), 4.02 (dd, J=7.5, 4.0 Hz, 1H), 3.80 (m, 2H), 3.60 (t, J=6.0 Hz, 2H), 3.48 (m, 4H), 2.40 (m, 2H), 2.20 (m, 2H), 1.82–1.58 (m, 5H), 0.94 (d, J=6.0 Hz, 3H), 0.93 (d, J=6.0 Hz, 3H).

EXAMPLE 26(3)

1-(2-hydroxybutyl)-2,5-dioxo-3-(2-methylpropyl)-9-(4-phenyloxyphenylmethyl)-1,4,9-triazaspiro[5.5]undecane.hydrochloride

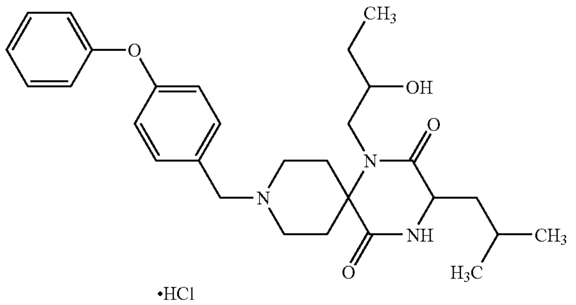

TLC: Rf 0.49 (chloroform:methanol=10:1);

NMR ($CD_3OD$): δ 7.50 (d, J=8.7 Hz, 2H), 7.39 (dd, J=8.7, 7.5 Hz, 2H), 7.18 (t, J=7.5 Hz, 1H), 7.10–7.00 (m, 4H), 4.32 (s, 2H), 4.03 (dd, J=8.1, 4.8 Hz, 1H), 3.96–3.41 (m, 6H), 3.27–3.14 (m, 1H), 2.68–2.53 (m, 1H), 2.37–2.26 (m, 3H), 1.94–1.24 (m, 5H), 1.08–0.82 (m, 9H).

EXAMPLE 27

1-butyl-2,5-dioxo-3-cyclohexylmethyl-9-(4-aminophenylmethyl)-1,4,9-triazaspiro[5.5]undecane.2hydrochloride

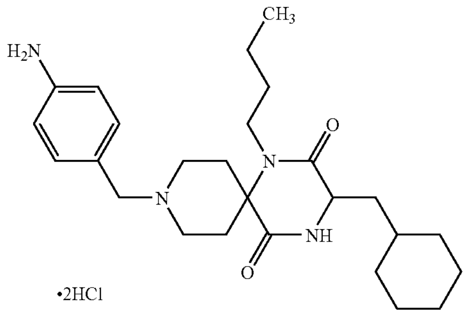

Under an atmosphere of argon, to a solution of the compound prepared in Example 24(116) (50 mg) in methanol was added 5% palladium on carbon (10 mg). Under an atmosphere of hydrogen, the reaction mixture was stirred for 20 minutes at room temperature. The reaction mixture was filtrated through Celite (brand name). The filtrate was concentrated. The residue was purified by column chromatography on silica gel (chloroform:methanol=50:1→30:1→20:1). The obtained compound was dissolved in methanol, and 4N-hydrogen chloride/ethyl acetate solution was added thereto. It was concentrated. The obtained residue was washed with diethyl ether and dried to give the compound of the present invention (34 mg) having the following physical data.

TLC: Rf 0.21 (chloroform:methanol=10:1);

NMR ($CD_3OD$): δ 7.80 (d, J=8.4 Hz, 2H), 7.47 (d, J=8.4 Hz, 2H), 4.41 (s, 2H), 4.03 (dd, J=7.5, 4.5 Hz, 1H), 3.86–3.74 (m, 2H), 3.52–3.45 (m, 4H), 2.65–2.52 (m, 2H), 2.24–2.08 (m, 2H), 1.80–1.16 (m, 15H), 0.94 (t, J=7.5 Hz, 3H), 0.94 (m, 2H).

EXAMPLE 28

1-butyl-2,5-dioxo-3-cyclohexylmethyl-9-(4-((4-methylphenyl)sulfonylamino)phenylmethyl)-1,4,9-triazaspiro[5.5]undecane.hydrochloride

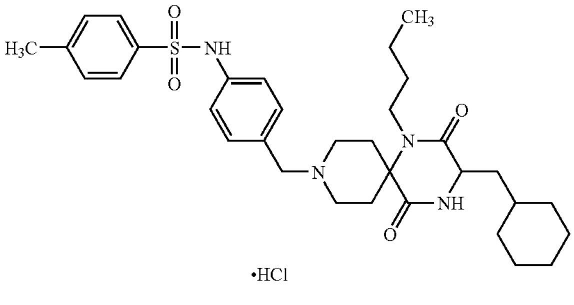

To a solution of the compound prepared in Example 28 (33 mg) in pyridine (2 ml) was added p-toluenesulfonyl chloride (21 mg). The reaction mixture was stirred for 27 hours at room temperature. The reaction mixture was concentrated, and saturated aqueous solution of sodium hydrogen carbonate was added thereto. It was extracted with ethyl acetate. The extract was washed with saturated aqueous solution of sodium chloride, dried over anhydrous sodium sulfate, and concentrated. The residue was purified by column chromatography on silica gel (chloroform:methanol=10:1). The obtained compound was dissolved in methanol, and 4N hydrogen chloride/ethyl acetate solution was added thereto, and it was concentrated. The residue was washed with diethyl ether and dried to give the compound of the present invention (27 mg) having the following physical data.

TLC: Rf 0.63 (chloroform:methanol=10:1);

NMR ($CD_3OD$): δ 7.70 (d, J=8.4 Hz, 2H), 7.41 (d, J=8.4 Hz, 2H), 7.30 (d, J=8.4 Hz, 2H), 7.22 (d, J=8.4 Hz, 2H), 4.25 (s, 2H), 4.03 (dd, J=7.2, 4.5 Hz, 1H), 3.78 (m, 2H), 3.42 (m, 4H), 2.42–2.06 (m, 4H), 2.37 (s, 3H), 1.82–1.10 (m, 15H), 0.95 (t, J=7.2 Hz, 3H), 0.95 (m, 2H).

EXAMPLE 28(1)

1-butyl-2,5-dioxo-3-cyclohexylmethyl-9-(4-(phenylcarbonylamino)phenylmethyl)-1,4,9-triazaspiro[5.5]undecane.2hydrochloride

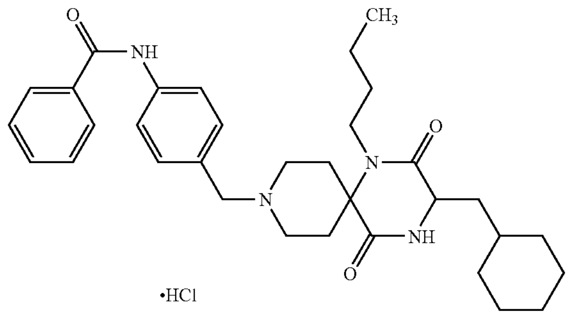

By the same procedure as described in Example 28 using benzoyl chloride instead of p-toluenesulfonyl chloride, the compound of the present invention having the following physical data was obtained.

TLC: Rf 0.43 (chloroform:methanol=10:1);

NMR ($CD_3OD$): δ 7.93 (d, J=8.4 Hz, 2H), 7.88 (d, J=8.4 Hz, 2H), 7.61–7.50 (m, 5H), 4.34 (s, 2H), 4.05 (dd, J=7.8, 4.5 Hz, 1H), 3.80 (m, 2H), 3.42 (m, 4H), 2.24 (m, 4H), 1.82–1.16 (m, 15H), 0.96 (t, J=7.2 Hz, 3H), 0.96 (m, 2H).

EXAMPLE 29

(3S)-1-butyl-2,5-dioxo-3-benzyloxymethyl-9-benzyloxycarbonyl-1,4,9-triazaspiro[5.5]undecane

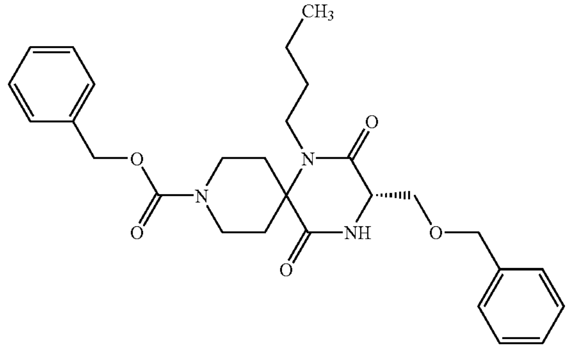

By the same procedure as described in Reference Example 3→Reference Example 6→Example 1 using Resin (3) prepared in Reference Example 2 and N-benzyloxycarbonyl-4-piperidone, O-benzyl-N-(t-butyloxycarbonyl)-L-serine, the compound of the present invention having the following physical data was obtained.

TLC: Rf 0.66 (chloroform:methanol=20:1);

NMR ($CDCl_3$): δ 7.40–7.25 (m, 10H), 6.09 (brs, 1H), 5.15 (s, 2H), 4.54 (s, 2H), 4.20–3.98 (br, 2H), 4.18(dd, J=8.4, 3.6 Hz, 1H), 3.93 (dd, J=9.3, 3.6 Hz, 1H), 3.80–3.56 (br, 1H), 3.66 (dd, J=9.3, 8.4, Hz, 1H), 3.45–3.12 (m, 3H), 2.02–1.75 (m, 4H), 1.57–1.39 (m, 2H), 1.38–1.20.(m, 2H), 0.91 (t, J=7.2 Hz, 3H).

EXAMPLE 30

(3S)-1-butyl-2,5-dioxo-3-hydroxymethyl-9-benzyloxycarbonyl-1,4,9-triazaspiro[5.5]undecane

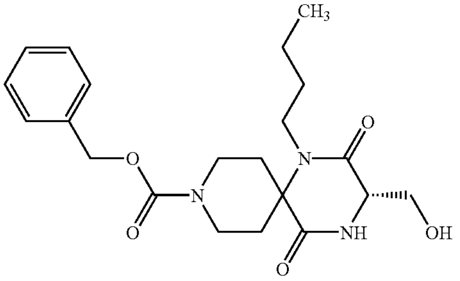

To a solution of the compound prepared in Example 29 (245 mg) in dichloromethane (5 ml) was added a 1 M solution of tribromoborane in dichloromethane (1.4 ml) at −40° C., and it was stirred for 3 hours at −20° C. To the reaction mixture were added water and saturated aqueous solution of sodium hydrogen carbonate, and it was extracted with ethyl acetate. The extract was washed with water and saturated aqueous solution of sodium chloride, dried over anhydrous sodium sulfate, and concentrated. The residue was purified by column chromatography on silica gel (chloroform:methanol=30:1) to give the compound of the present invention (173 mg) having the following physical data.

TLC: Rf 0.29 (chloroform:methanol=20:1);

NMR ($CDCl_3$): δ 7.42–7.27 (m, 5H), 6.26–6.15 (br, 1H), 5.16 (s, 2H), 4.26–4.00 (m, 2H), 3.98–3.82 (m, 2H), 3.84–3.60 (br, 1H), 3.43–3.13 (m, 4H), 2.80–2.68 (br, 1H), 2.05–1.75 (m, 4H), 1.58–1.40 (m, 2H), 1.40–1.20 (m, 2H), 0.92 (t, J=7.5 Hz, 3H).

EXAMPLE 31

(3S)-1-butyl-2,5-dioxo-3-hydroxymethyl-1,4,9-triazaspiro[5.5]undecane

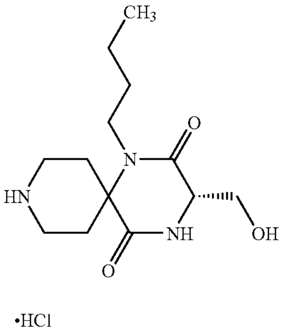

•HCl

By the same procedure as described in Example 9 using the compound prepared in Example 30, the compound of the present invention having the following physical data was obtained.

TLC: Rf 0.21 (chloroform: methanol: acetic acid=20:4:1);

NMR ($d_6$-DMSO): δ 7.83 (brs, 1H), 5.10–4.90 (br, 1H), 3.88–3.78 (m, 1H), 3.76–3.65 (m, 1H), 3.58–3.48 (m, 1H), 3.28–3.18 (m, 1H), 3.18–3.04 (m, 3H), 2.88–2.75 (m, 2H), 1.94–1.83 (m, 1H), 1.83–1.64 (m, 3H), 1.56–1.42 (m, 1H), 1.42–1.20 (m, 3H), 0.88 (t, J=7.2 Hz, 3H).

EXAMPLE 32(1)

(3S)-1-butyl-2,5-dioxo-3-hydroxymethyl-9-(4-phenyloxyphenylmethyl)-1,4,9-triazaspiro[5.5]undecane.hydrochloride

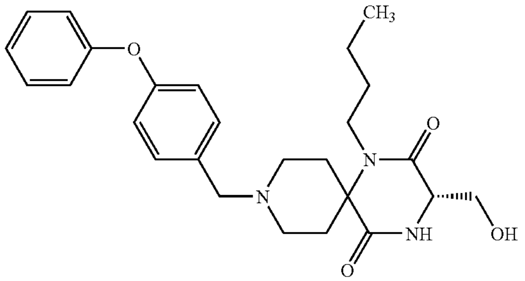

•HCl

By the same procedure as described in Example 10 using 4-phenyloxybenzaldehyde and the compound prepared in Example 31, the compound of the present invention having the following physical data was obtained.

TLC: Rf 0.49 (chloroform:methanol=10:1);

NMR ($CD_3OD$): δ 7.52 (d, J=8.7 Hz, 2H), 7.43–7.35 (m, 2H), 7.22–7.14 (m, 1H), 7.06 (d, J=8.7 Hz, 2H), 7.06–7.00 (m, 2H), 4.33 (s, 2H), 4.03–3.90 (m, 3H), 3.79–3.66 (m, 1H), 3.65 (dd, J=10.5, 2.4 Hz, 1H), 3.61–3.42 (m, 3H), 3.30–3.18 (m, 1H), 2.50–2.24 (m, 3H), 2.24–2.12 (m, 1H), 1.76–1.58 (m, 1H), 1.54–1.26 (m, 3H), 0.95 (t, J=7.5 Hz, 3H).

EXAMPLE 32(2)

(3S)-1-butyl-2,5-dioxo-3-hydroxymethyl-9-(3,5-dimethyl-1-phenylpyrazol-4-ylmethyl)-1,4,9-triazaspiro[5.5]undecane.2hydrochloride

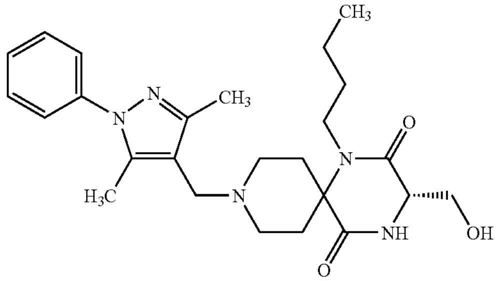

•2HCl

By the same procedure as described in Example 10 using 1-phenyl-3,5-dimethyl-4-formylpyrazole and the compound prepared in Example 31, the compound of the present invention having the following physical data was obtained.

TLC: Rf 0.47 (chloroform:methanol=10:1);

NMR ($CD_3OD$): δ 7.61–7.46 (m, 5H), 4.32 (s, 2H), 4.08–3.92 (m, 3H), 3.83–3.70 (m, 1H), 3.66 (dd, J=10.5, 2.4 Hz, 1H), 3.66–3.52 (m, 3H), 3.40–3.25 (m, 1H), 2.64–2.50 (m, 1H), 2.50–2.40 (m, 2H), 2.41 (s, 3H), 2.39 (s, 3H), 2.28–2.15 (m, 1H), 1.80–1.58 (m, 1H), 1.58–1.30 (m, 3H), 0.96 (t, J=7.5 Hz, 3H).

REFERENCE EXAMPLE 11

Preparation of Compound (7)

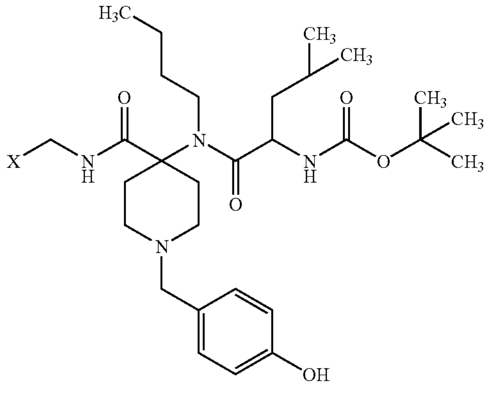

By the same procedure as described in Reference Example 3→Reference Example 4 using Resin (3) prepared in Reference Example 2 and N-allyloxycarbonyl-4-piperidone, n-butylamine and N-(t-butyloxycarbonyl)leucine, and furthermore by the same procedure as described in Reference Example 5 using 4-hydroxybenzaldehyde instead of 3,5-dimethyl-1-phenyl-4-formylpyrazole, compound (7) was obtained.

REFERENCE EXAMPLE 12

Preparation of Compound (8)

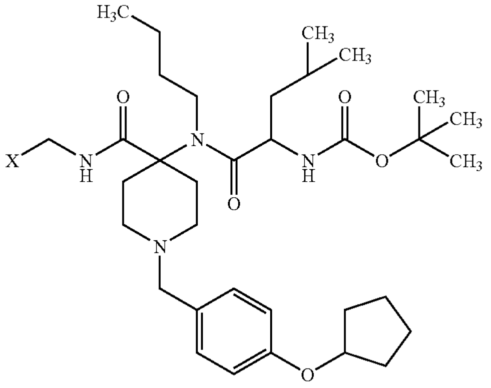

To a suspension of the compound prepared in Reference Example 11 (60 mg) in dichloromethane (2 ml) were added triphenylphosphine (80 mg), 1M cyclopentanol-dichloromethane solution (0.302 ml) and diethylazodicarboxylate (0.137 ml). The reaction mixture was stirred for 18 hours at room temperature. The reaction solution was filtrated. The obtained resin was washed with dichloromethane (2 ml×4), methanol (2 ml×3), and dichloromethane (3 ml×4) to give compound (8).

EXAMPLE 33

1-butyl-2,5-dioxo-3-(2-methylpropyl)-9-(4-cyclopentyloxyphenylmethyl)-1,4,9-triazaspiro[5.5]undecane.hydrochloride

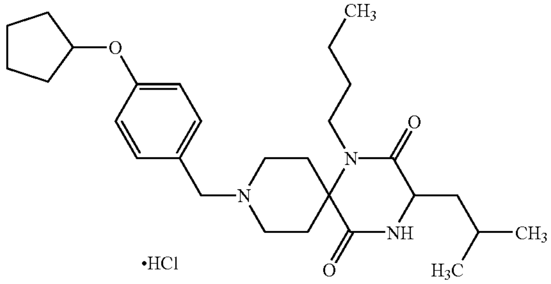

By the same procedure as described in Reference Example 6→Example 1 using the compound prepared in Reference Example 12, the compound of the present invention having the following physical data was obtained.

TLC: Rf 0.49 (chloroform:methanol=10:1);

NMR ($CD_3OD$): δ 7.41 (d, J=8.7 Hz, 2H), 6.98 (d, J=8.7 Hz, 2H), 4.83 (m, 1H), 4.25 (brs, 2H), 4.00 (dd, J=7.8, 4.5 Hz, 1H), 3.86–3.65 (m, 2H), 3.53–3.27 (m, 4H), 2.40–2.06 (m, 4H), 2.02–1.43 (m, 13H), 1.43–1.24 (m, 2H), 1.01–0.90 (m, 9H).

EXAMPLE 33(1)~33(6)

By the same procedure as described in Reference Example 11 using the corresponding compounds instead of n-butylamine and N-(t-butyloxycarbonyl)leucine, and by the same procedure as described in Reference Example 12→Example 33 using the corresponding compounds instead of cyclopentanol, the following compounds of the present invention were obtained.

EXAMPLE 33(1)

1-butyl-2,5-dioxo-3-cyclohexylmethyl-9-(4-(2-diethylaminoethyloxy)phenylmethyl)-1,4,9-triazaspiro[5.5]undecane.2hydrochloride

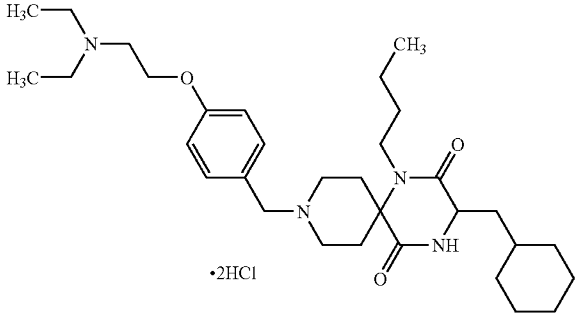

TLC: Rf 0.54 (chloroform:methanol: 28% $NH_4OH$=80:10:1);

NMR ($CD_3OD$): δ 7.57 (d, J=8.7 Hz, 2H), 7.12 (d, J=8.7 Hz, 2H), 4.40 (t, J=4.8 Hz, 2H), 4.30 (s, 2H), 4.03 (dd, J=7.5, 5.1 Hz, 1H), 3.84–3.67 (m, 2H), 3.63 (t, J=4.8 Hz, 2H), 3.50–3.40 (m, 4H), 3.40–3.31 (m, 4H), 2.58–2.41 (m, 2H), 2.23–2.04 (m, 2H), 1.82–1.42 (m, 10H), 1.41–1.12 (m, 11H), 1.04–0.87 (m, 5H).

EXAMPLE 33(2)

1-butyl-2,5-dioxo-3-cyclohexylmethyl-9-(4-(2-dimethylaminoethyloxy)phenylmethyl)-1,4,9-triazaspiro[5.5]undecane.2hydrochloride

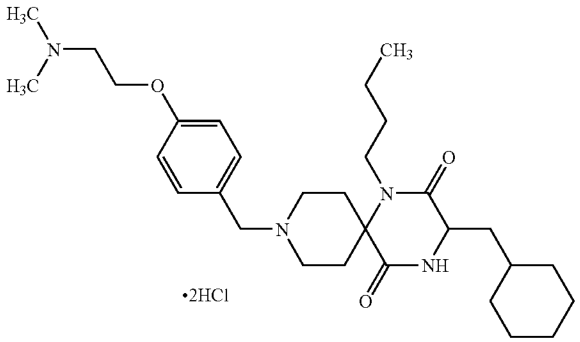

TLC: Rf 0.46 (chloroform:methanol: 28% $NH_4OH$=80:10:1);

NMR ($CD_3OD$): δ 7.57 (d, J=8.7 Hz, 2H), 7.13 (d, J=8.7 Hz, 2H), 4.39 (t, J=4.8 Hz, 2H), 4.30 (s, 2H), 4.02 (dd, J=7.5, 4.5 Hz, 1H), 3.84–3.67 (m, 2H), 3.61 (t, J=4.8 Hz, 2H), 3.50–3.38 (m, 4H), 2.98 (s, 6H), 2.59–2.42 (m, 2H), 2.24–2.03 (m, 2H), 1.83–1.12 (m, 15H), 1.04–0.86 (m, 5H).

EXAMPLE 33(3)

1-butyl-2,5-dioxo-3-cyclohexylmethyl-9-(4-propyloxyphenylmethyl)-1,4,9-triazaspiro[5.5]undecane.hydrochloride

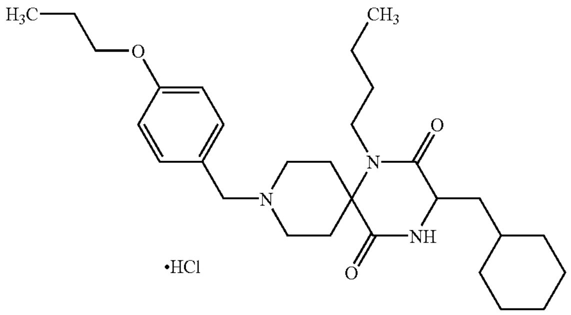

TLC: Rf 0.59 (chloroform:methanol=10:1);

NMR ($CD_3OD$): δ 7.43 (d, J=8.7 Hz, 2H), 7.01 (d, J=8.7 Hz, 2H), 4.27 (brs, 2H), 4.03 (dd, J=7.5, 4.5 Hz, 1H), 3.96 (t, J=6.6 Hz, 2H), 3.85–3.67 (m, 2H), 3.53–3.33 (m, 4H), 2.45–2.27 (m, 2H), 2.26–2.07 (m, 2H), 1.86–1.14 (m, 17H), 1.03 (t, J=7.2 Hz, 3H), 1.00–0.89 (m, 5H).

EXAMPLE 33(4)

1-(thiophen-2-ylmethyl)-2,5-dioxo-3-cyclohexylmethyl-9-(4-cyclopropylmethyloxyphenylmethyl)-1,4,9-triazaspiro[5.5]undecane.hydrochloride

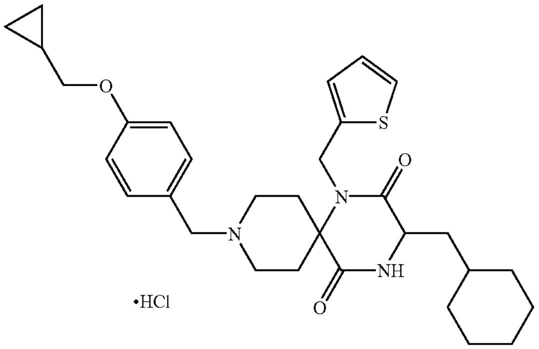

TLC: Rf 0.61 (chloroform:methanol=10:1);

NMR ($CD_3OD$): δ 7.42 (d, J=8.7 Hz, 2H), 7.27 (dd, J=5.4, 0.9 Hz, 1H), 7.06–6.97 (m, 3H), 6.91 (dd, J=5.4, 3.6 Hz, 1H), 4.95–4.85 (m, 2H), 4.27 (brs, 2H), 4.14 (dd, J=7.5, 4.5 Hz, 1H), 3.84 (d, J=6.6 Hz, 2H), 3.84–3.66 (m, 2H), 3.51–3.39 (m, 2H), 2.59–2.36 (m, 2H), 2.24–2.07 (m, 2H), 1.84–1.44 (m, 8H), 1.35–1.12 (m, 4H), 1.04–0.85 (m, 2H), 0.66–0.57 (m, 2H), 0.38–0.31 (m, 2H).

EXAMPLE 33(5)

1-butyl-2,5-dioxo-3-cyclohexylmethyl-9-(4-cyclopropylmethyloxyphenylmethyl)-1,4,9-triazaspiro[5.5]undecane.hydrochloride

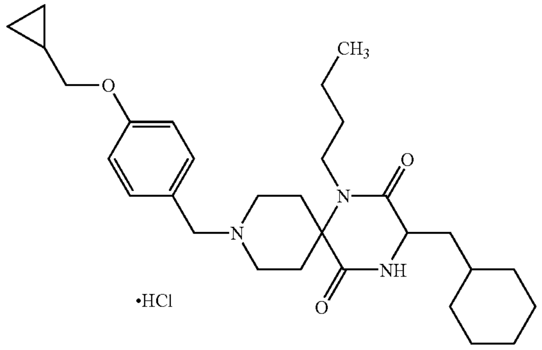

TLC: Rf 0.61 (chloroform:methanol=10:1);

NMR ($CD_3OD$): δ 7.42 (d, J=8.4 Hz, 2H), 7.01 (d, J=8.4 Hz, 2H), 4.26 (brs, 2H), 4.03 (dd, J=7.8, 4.8 Hz, 1H), 3.84 (d, J=6.9 Hz, 2H), 3.83–3.66 (m, 2H), 3.51–3.33 (m, 4H), 2.44–2.26 (m, 2H), 2.25–2.06 (m, 2H), 1.82–1.12 (m, 16H), 1.04–0.86 (m, 5H), 0.66–0.57 (m, 2H), 0.38–0.31 (m, 2H).

EXAMPLE 33(6)

1-butyl-2,5-dioxo-3-(2-methylpropyl)-9-(4-cyclopropylmethyloxyphenylmethyl)-1,4,9-triazaspiro[5.5]undecane.hydrochloride

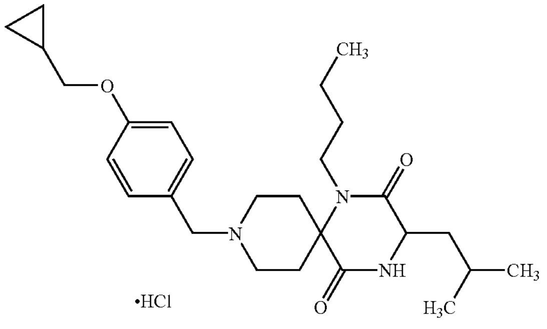

TLC: Rf 0.55 (chloroform:methanol=10:1);

NMR ($CD_3OD$): δ 7.42 (d, J=8.7 Hz, 2H), 7.01 (d, J=8.7 Hz, 2H), 4.26 (brs, 2H), 4.00 (dd, J=7.8, 4.5 Hz, 1H), 3.84 (d, J=6.9 Hz, 2H), 3.84–3.66 (m, 2H), 3.50–3.33 (m, 4H), 2.43–2.26 (m, 2H), 2.26–2.08 (m, 2H), 1.89–1.43 (m, 5H), 1.43–1.17 (m, 3H), 1.00–0.88 (m, 9H), 0.66–0.58 (m, 2H), 0.38–0.31 (m, 2H).

EXAMPLE 34

1-butyl-2,5-dioxo-3-cyclohexylmethyl-9-(4-(dimethylamino)phenylmethyl)-1,4,9-triazaspiro[5.5]undecane.2hydrochloride

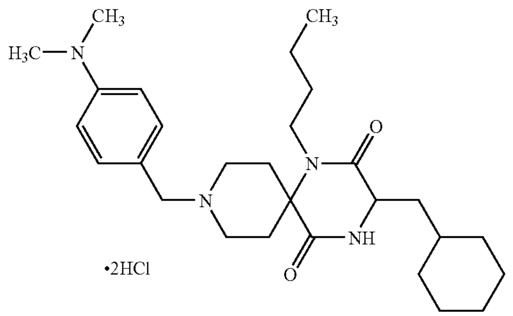

By the same procedure as described in Example 10 using 4-dimethylaminobenzaldehyde and the compound prepared in Example 9(1), the compound of the present invention having the following physical data was obtained.

TLC: Rf 0.26 (chloroform:methanol=10:1);

NMR ($CD_3OD$): δ 7.78 (d, J=8.7 Hz, 2H), 7.59 (d, J=8.7 Hz, 2H), 4.39 (s, 2H), 4.03 (dd, J=7.5, 4.8, Hz, 1H), 3.90–3.70 (m, 2H), 3.52–3.40 (m, 4H), 3.26 (s, 6H), 2.64–2.47 (m, 2H), 2.24–2.04 (m, 2H), 1.82–1.12 (m, 15H), 1.04–0.88 (m, 5H).

EXAMPLE 34(1)

1-butyl-2,5-dioxo-3-cyclohexyl methyl-9-(4-(diethylamino) phenylmethyl)-1,4,9-triazaspiro[5.5]undecane.2hydrochloride

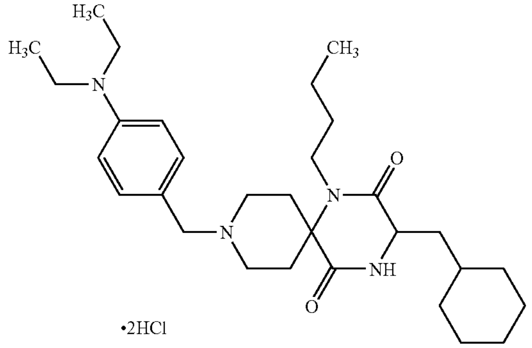

By the same procedure as described in Example 34 using 4-diethylaminobenzaldehyde instead of 4-dimethylaminobenzaldehyde, the compound of the present invention having the following physical data was obtained.

TLC: Rf 0.28 (chloroform:methanol: acetic acid=10:1);

NMR ($CD_3OD$): δ 7.94–7.78 (m, 2H), 7.72–7.52 (m, 2H), 4.43 (s, 2H), 4.03 (dd, J=7.5, 4.8, Hz, 1H), 3.92–3.73 (m, 2H), 3.73–3.60 (m, 4H), 3.54–3.40 (m, 4H), 2.63–2.45 (m, 2H), 2.25–2.05 (m, 2H), 1.82–1.10 (m, 21H), 1.04–0.86 (m, 5H).

EXAMPLE 35

(3S)-1-butyl-2,5-dioxo-3-(2-methylpropyl)-9-benzyloxycarbonyl-1,4,9-triazaspiro[5.5]undecane

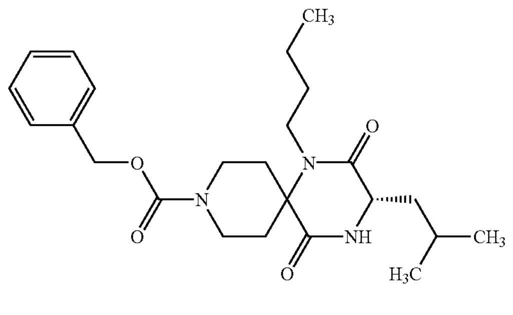

By the same procedure as described in Reference Example 3→Reference Example 6→Example 1 using Resin (3) prepared in Reference Example 2, N-benzyloxycarbonyl-4-piperidone, n-butylamine and N-(t-butyloxycarbonyl)-L-leucine, the compound of the present invention having the following physical data was obtained.

TLC: Rf 0.67 (chloroform:methanol=20:1);

NMR ($CD_3OD$): δ 7.35 (m, 5H), 6.50 (brs, 1H), 5.15 (s, 2H), 4.08 (m, 2H), 3.96 (m, 1H), 3.62 (brs, 1H), 3.44(brs, 1H), 3.26 (m, 2H), 1.95–1.76 (m, 4H), 1.61–1.45 (m, 5H), 1.31 (m, 2H), 0.96 (d, J=6.3 Hz, 3H), 0.93 (d, J=6.3 Hz, 3H), 0.91 (t, J=7.2 Hz, 3H).

EXAMPLE 36

(3S)-1-butyl-2,5-dioxo-3-(2-methylpropyl)-1,4,9-triazaspiro[5.5]undecane.hydrochloride

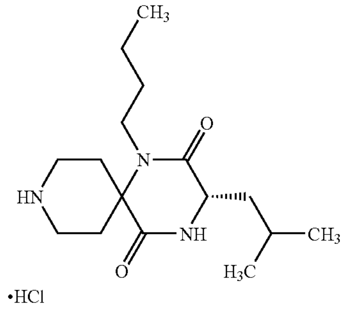

By the same procedure as described in Example 9 using the compound prepared in Example 35, the compound of the present invention having the following physical data was obtained.

TLC: Rf 0.18 (chloroform:methanol=4:1);

NMR ($CD_3OD$): δ 4.02 (dd, J=7.8, 4.6 Hz, 1H), 3.80 (dd, J=12.5, 4.0 Hz, 1H), 3.72 (dd, J=12.5, 4.0 Hz, 1H), 3.39 (m, 4H), 2.34–2.09 (m, 4H), 1.88–1.50 (m, 5H), 1.37 (m, 2H), 0.96 (t, J=7.5 Hz, 3H), 0.95 (d, J=6.5 Hz, 3H), 0.94 (d, J=6.5 Hz, 3H).

EXAMPLE 37(1)~37(88)

By the same procedure as described in Example 10 using the compound prepared in Example 36 and the corresponding aldehyde derivatives, the following compounds of the present invention were obtained.

EXAMPLE 37(1)

(3S)-1-butyl-2,5-dioxo-3-(2-methylpropyl)-9-(5-(3-methyl-4-chlorophenyl)-1-(4-methylphenylmethyl) pyrazol-3-ylmethyl)-1,4,9-triazaspiro[5.5] undecane.2hydrochloride

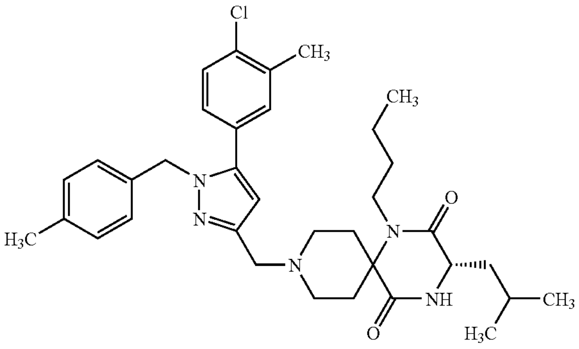

•2HCl

TLC: Rf 0.46 (chloroform:methanol=20:1);

NMR ($CD_3OD$): δ 7.42 (d, J=8.1 Hz, 1H), 7.28 (d, J=1.5 Hz, 1H), 7.19 (dd, J=8.1, 1.5 Hz, 1H), 7.11 (d, J=8.1 Hz, 2H), 6.92 (d, J=8.1 Hz, 2H), 6.65 (s, 1H), 5.35 (s, 2H), 4.40 (s, 2H), 4.02 (dd, J=7.5, 4.5 Hz, 1H), 3.97–3.76 (m, 2H), 3.64–3.52 (m, 2H), 3.46–3.35 (m, 2H), 2.56–2.38 (m, 2H), 2.35 (s, 3H), 2.28 (s, 3H), 2.30–2.10 (m, 2H), 1.91–1.46 (m, 5H), 1.46–1.30 (m, 2H), 0.96 (t, J=6.9 Hz, 3H), 0.95 (d, J=6.3 Hz, 6H).

EXAMPLE 37(2)

(3S)-1-butyl-2,5-dioxo-3-(2-methylpropyl)-9-(4-dimethylaminophenylmethyl)-1,4,9-triazaspiro[5.5] undecane.2hydrochloride

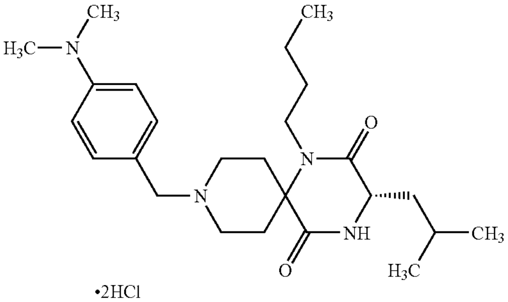

•2HCl

TLC: Rf 0.47 (chloroform:methanol=10:1);

NMR ($CD_3OD$): δ 7.78 (d, J=8.7 Hz, 2H), 7.58 (d, J=8.7 Hz, 2H), 4.40 (s, 2H), 4.01 (dd, J=7.8, 4.5 Hz, 1H), 3.82 (m, 2H), 3.42 (m, 4H), 3.26 (s, 6H), 2.56 (m, 2H), 2.18 (m, 2H), 1.88–1.30 (m, 7H), 0.95 (t, J=7.2 Hz, 3H), 0.95 (d, J=6.3 Hz, 3H), 0.94 (d, J=6.3 Hz, 3H).

EXAMPLE 37(3)

(3S)-1-butyl-2,5-dioxo-3-(2-methylpropyl)-9-(4-diethylaminophenylmethyl)-1,4,9-triazaspiro[5.5] undecane.2hydrochloride

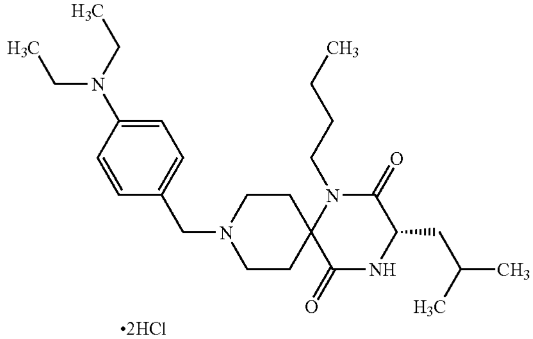

•2HCl

TLC: Rf 0.34 (chloroform:methanol=10:1);

NMR ($CD_3OD$): δ 7.96–7.82 (m, 2H), 7.74–7.55 (m, 2H), 4.40 (s, 2H), 4.00 (dd, J=7.5, 4.5 Hz, 1H), 3.93–3.60 (m, 6H), 3.55–3.40 (m, 4H), 2.65–2.48 (m, 2H), 2.25–2.06 (m, 2H), 1.89–1.26 (m, 7H), 1.15 (t, J=7.2 Hz, 6H), 1.00–0.87 (m, 9H).

EXAMPLE 37(4)

(3S)-1-butyl-2,5-dioxo-3-(2-methylpropyl)-9-(4-cyclohexyloxyphenylmethyl)-1,4,9-triazaspiro[5.5] undecane.hydrochloride

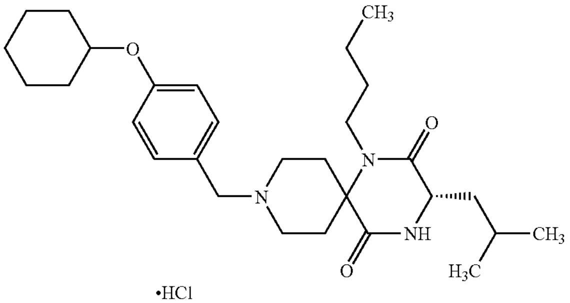

•HCl

TLC: Rf 0.61 (chloroform:methanol=10:1);

NMR ($CD_3OD$): δ 7.45–7.42 (m, 2H), 7.02–6.99 (m, 2H), 4.40–4.31 (m, 1H), 4.27 (s, 2H), 4.00 (dd, J=8.0, 4.5 Hz, 1H), 3.83–3.70 (m, 2H), 3.47 (brd, 2H), 3.42–3.35 (m, 2H), 2.43–2.32 (m, 2H), 2.24–2.11 (m, 2H), 2.00–1.93 (m, 2H), 1.86–1.32 (m, 15H), 0.97–0.92 (m, 9H).

EXAMPLE 37(5)

(3S)-1-butyl-2,5-dioxo-3-(2-methylpropyl)-9-(4-(4-methylphenyloxy)phenylmethyl)-1,4,9-triazaspiro[5.5]undecane.hydrochloride

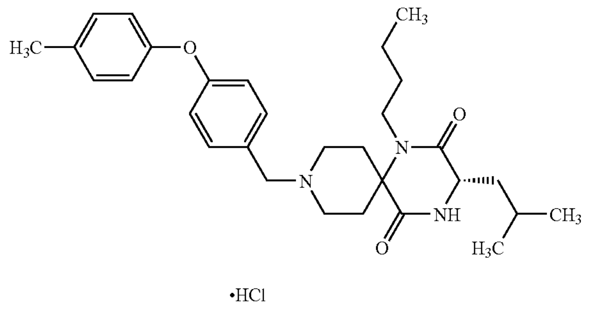

TLC: Rf 0.70 (chloroform:methanol=10:1);

NMR ($CD_3OD$): δ 7.52–7.47 (m, 2H), 7.22–7.19 (m, 2H), 7.04–7.00 (m, 2H), 6.94–6.90 (m, 2H), 4.32 (s, 2H), 4.01 (dd, J=8.0, 4.5 Hz, 1H), 3.86–3.73 (m, 2H), 3.48 (brd, 2H), 3.42–3.34 (m, 2H), 2.45–2.33 (m, 5H), 2.25–2.12 (m, 2H), 1.85–1.48 (m, 5H), 1.41–1.31 (m, 2H), 0.97–0.92 (m, 9H).

EXAMPLE 37(6)

(3S)-1-butyl-2,5-dioxo-3-(2-methylpropyl)-9-(4-(4-methoxyphenyloxy)phenylmethyl)-1,4,9-triazaspiro[5.5]undecane.hydrochloride

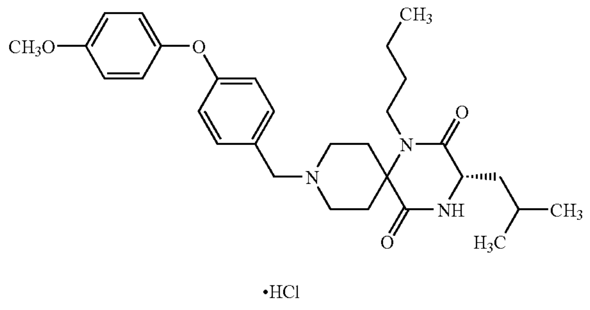

TLC: Rf 0.65 (chloroform:methanol=10:1);

NMR ($CD_3OD$): δ 7.49–7.46 (m, 2H), 7.00–6.94 (m, 6H), 4.31 (s, 2H), 4.01 (dd, J=8.0, 4.5 Hz, 1H), 3.84–3.71 (m, 5H), 3.48 (brd, 2H), 3.40–3.31 (m, 2H), 2.42–2.30 (m, 2H), 2.25–2.12 (m, 2H), 1.83–1.48 (m, 5H), 1.41–1.30 (m, 2H), 0.97–0.92 (m, 9H).

EXAMPLE 37(7)

(3S)-1-butyl-2,5-dioxo-3-(2-methylpropyl)-9-(4-butyl phenylmethyl)-1,4,9-triazaspiro[5.5]undecane-.hydrochloride

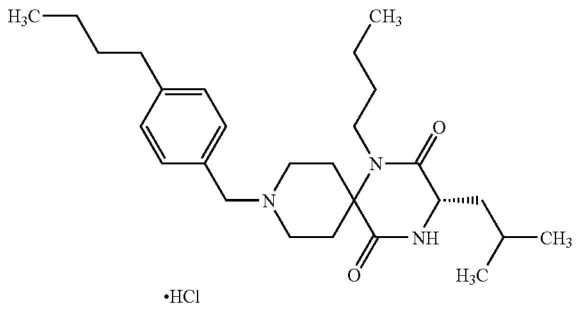

TLC: Rf 0.35 (chloroform:methanol=10:1);

NMR ($CD_3OD$): δ 7.46 (d, J=8.1 Hz, 2H), 7.32 (d, J=8.1 Hz, 2H), 4.31 (s, 2H), 4.01 (dd, J=7.8, 4.5 Hz, 1H), 3.84–3.68 (m, 2H), 3.54–3.36 (m, 4H), 2.67 (t, J=7.8 Hz, 2H), 2.48–2.30 (m, 2H), 2.26–2.08 (m, 2H), 1.90–1.28 (m, 11H), 0.96 (t, J=7.2 Hz, 3H), 0.95 (d, J=6.3 Hz, 3H), 0.94 (d, J=6.3 Hz, 3H), 0.94 (t, J=7.2 Hz, 3H).

EXAMPLE 37(8)

(3S)-1-butyl-2,5-dioxo-3-(2-methylpropyl)-9-(4-(2-methylpropyl)phenylmethyl)-1,4,9-triazaspiro[5.5]undecane.hydrochloride

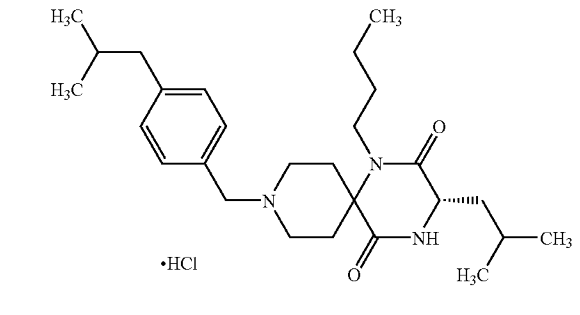

TLC: Rf 0.38 (chloroform:methanol=10:1);

NMR ($CD_3OD$): δ 7.47 (d, J=6.9 Hz, 2H), 7.30 (d, J=6.9 Hz, 2H), 4.33 (s, 2H), 4.01 (dd, J=7.5, 4.5 Hz, 1H), 3.90–3.70 (m, 2H), 3.56–3.34 (m, 4H), 2.53 (d, J=7.2 Hz, 2H), 2.53–2.30 (m, 2H), 2.24–2.08 (m, 2H), 1.96–1.26 (m, 8H), 0.95 (t, J=7.8 Hz, 3H), 0.95 (d, J=6.6 Hz, 3H), 0.94 (d, J=6.6 Hz, 3H), 0.91 (d, J=6.6 Hz, 6H).

EXAMPLE 37(9)

(3S)-1-butyl-2,5-dioxo-3-(2-methylpropyl)-9-(4-(4-fluorophenyloxy)phenylmethyl)-1,4,9-triazaspiro[5.5]undecane.hydrochloride

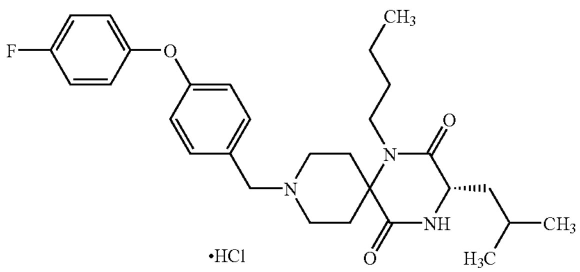

TLC: Rf 0.36 (chloroform:methanol=10:1);

NMR ($CD_3OD$): δ 7.53 (d, J=8.4 Hz, 2H), 7.17 (d, J=8.4 Hz, 2H), 7.16–7.04 (m, 4H), 4.33 (s, 2H), 4.02 (dd, J=7.8, 4.8 Hz, 1H), 3.88–3.68 (m, 2H), 3.58–3.36 (m, 4H), 2.46–2.10 (m, 4H), 1.90–1.24(m, 7H), 0.96 (t, J=6.9 Hz, 3H), 0.95 (d, J=6.6 Hz, 3H), 0.94 (d, J=6.6 Hz, 3H).

EXAMPLE 37(10)

(3S)-1-butyl-2,5-dioxo-3-(2-methylpropyl)-9-(3-hydroxy-4-methoxyphenylmethyl)-1,4,9-triazaspiro[5.5]undecane.hydrochloride

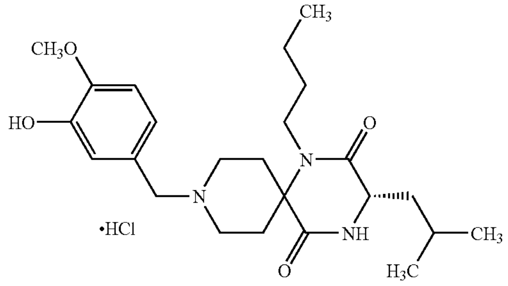

TLC: Rf 0.20 (chloroform:methanol=10:1);

NMR ($CD_3OD$): δ 7.03–6.94 (m, 3H), 4.23 (s, 2H), 4.01 (dd, J=7.8, 4.5 Hz, 1H), 3.89 (s, 3H), 3.84–3.68 (m, 2H), 3.56–3.36 (m, 4H), 2.42–2.08 (m, 4H), 1.88–1.24(m, 7H), 0.96 (t, J=7.2 Hz, 3H), 0.95 (d, J=6.3 Hz, 3H), 0.94 (d, J=6.3 Hz, 3H).

EXAMPLE 37(11)

(3S)-1-butyl-2,5-dioxo-3-(2-methylpropyl)-9-(2-fluorophenylmethyl)-1,4,9-triazaspiro[5.5]undecane-.hydrochloride

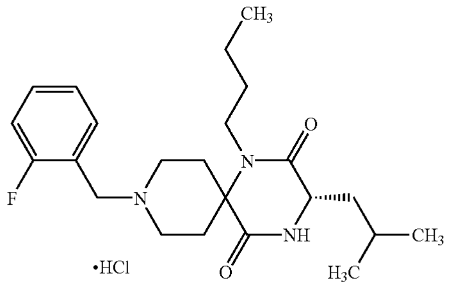

TLC: Rf 0.48 (hexane:ethyl acetate=1:1);

NMR ($CD_3OD$): δ 7.64–7.54 (m, 2H), 7.37–7.27 (m, 2H), 4.45 (s, 2H), 4.01 (dd, J=7.5, 4.5 Hz, 1H), 3.94–3.81 (m, 2H), 3.54 (m, 2H), 3.36 (m, 2H), 2.38 (m, 2H), 2.19 (m, 2H), 1.82–1.49 (m, 5H), 1.35 (m, 2H), 0.95 (t, J=7.5 Hz, 3H), 0.94 (d, J=6.5 Hz, 3H), 0.93 (d, J=6.5 Hz, 3H).

EXAMPLE 37(12)

(3S)-1-butyl-2,5-dioxo-3-(2-methylpropyl)-9-(3-fluorophenylmethyl)-1,4,9-triazaspiro[5.5]undecane-.hydrochloride

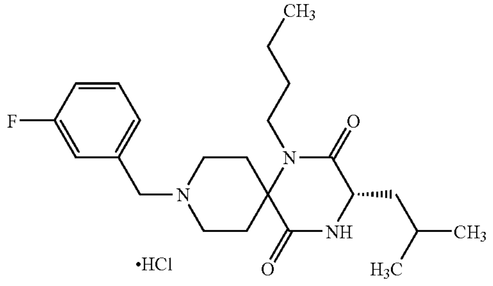

TLC: Rf 0.52 (hexane:ethyl acetate=1:1);

NMR ($CD_3OD$): δ 7.52 (dt, J=8.3, 6.0 Hz, 1H), 7.41–7.37 (m, 2H), 7.26 (t, J=8.3 Hz, 1H), 4.39 (s, 2H), 4.01 (dd, J=7.5, 4.5 Hz, 1H), 3.89–3.76 (m, 2H), 3.50–3.38 (m, 4H), 2.48–2.38 (m, 2H), 2.25–2.12 (m, 2H), 1.84–1.75 (m, 1H), 1.72–1.46 (m, 4H), 1.42–1.28 (m, 2H), 0.99–0.92 (m, 9H).

EXAMPLE 37(13)

(3S)-1-butyl-2,5-dioxo-3-(2-methylpropyl)-9-(4-fluorophenylmethyl)-1,4,9-triazaspiro[5.5]undecane-.hydrochloride

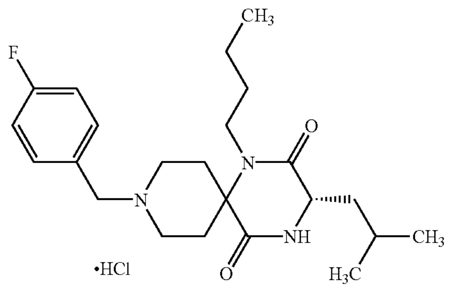

TLC: Rf 0.33 (hexane:ethyl acetate=1:1);

NMR ($CD_3OD$): δ 7.60 (dd, J=8.7, 5.4 Hz, 2H), 7.24 (t, J=8.7 Hz, 2H), 4.36 (s, 2H), 3.99 (dd, J=7.5, 4.5 Hz, 1H), 3.78 (m, 2H), 3.49–3.35 (m, 4H), 2.44–2.13 (m, 4H), 1.84–1.46 (m, 5H), 1.37 (m, 2H), 0.99–0.95 (m, 9H).

EXAMPLE 37(14)

(3S)-1-butyl-2,5-dioxo-3-(2-methylpropyl)-9-(2-chlorophenylmethyl)-1,4,9-triazaspiro[5.5]undecane-.hydrochloride

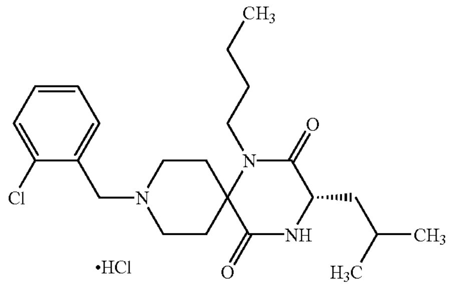

TLC: Rf 0.62 (hexane:ethyl acetate=1:1);

NMR ($CD_3OD$): δ 7.72 (d, J=7.0 Hz, 1H), 7.60 (dd, J=8.0, 1.5 Hz, 1H), 7.56–7.45 (m, 2H), 4.55 (s, 2H), 4.00 (dd, J=7.5, 4.5 Hz, 1H), 3.94 (m, 2H), 3.55 (m, 2H), 3.42–3.32 (m, 2H), 2.43–2.37 (m, 2H), 2.26–2.13 (m, 2H), 1.85–1.46 (m, 5H), 1.35 (m, 2H), 0.97–0.92 (m, 9H).

EXAMPLE 37(15)

(3S)-1-butyl-2,5-dioxo-3-(2-methylpropyl)-9-(4-chlorophenylmethyl)-1,4,9-triazaspiro[5.5]undecane-.hydrochloride

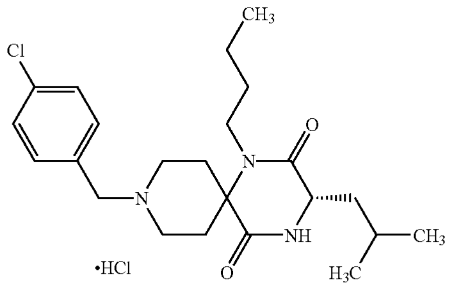

TLC: Rf 0.50 (chloroform:methanol=10:1);

NMR ($CD_3OD$): δ 7.55 (d, J=8.7 Hz, 2H), 7.51 (d, J=8.7 Hz, 2H), 4.34 (s, 2H), 4.00 (dd, J=7.8, 4.5, Hz, 1H), 3.88–3.68 (m, 2H), 3.51–3.34 (m, 4H), 2.49–2.52 (m, 2H), 2.26–2.08 (m, 2H), 1.90–1.44 (m, 5H), 1.44–1.29 (m, 2H), 1.00–0.89 (m, 9H).

EXAMPLE 37(16)

(3S)-1-butyl-2,5-dioxo-3-(2-methylpropyl)-9-(3-chlorophenylmethyl)-1,4,9-triazaspiro[5.5]undecane-.hydrochloride

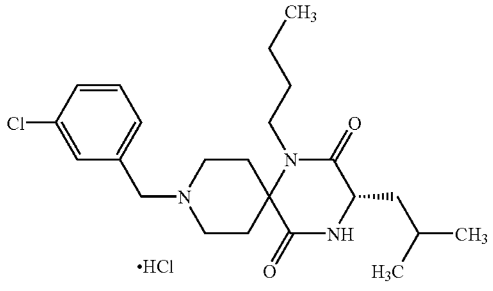

TLC: Rf 0.55 (chloroform:methanol=20:1);

NMR ($CD_3OD$): δ 7.68–7.64 (m, 1H), 7.56–7.45 (m, 3H), 4.37 (s, 2H), 4.00 (dd, J=7.8, 4.5 Hz, 1H), 3.91–3.72 (m, 2H), 3.54–3.32 (m, 4H), 2.53–2.34 (m, 2H), 2.27–2.08 (m, 2H), 1.90–1.44 (m, 5H), 1.44–1.27 (m, 2H), 0.99–0.89 (m, 9H).

EXAMPLE 37(17)

(3S)-1-butyl-2,5-dioxo-3-(2-methylpropyl)-9-(3-methyl-4-methoxyphenylmethyl)-1,4,9-triazaspiro[5.5]undecane.hydrochloride

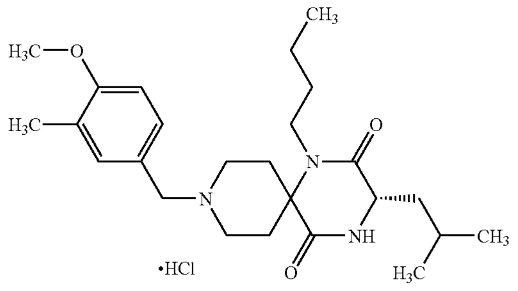

TLC: Rf 0.34 (chloroform:methanol=20:1);

NMR ($CD_3OD$): δ 7.38–7.30 (m, 2H), 6.99 (d, J=8.1 Hz, 1H), 4.25 (s, 2H), 4.00 (dd, J=7.8, 4.5 Hz, 1H), 3.85 (s, 3H), 3.85–3.65 (m, 2H), 3.52–3.33 (m, 4H), 2.50–2.30 (m, 2H), 2.22 (s, 3H), 2.20–2.07 (m, 2H), 1.90–1.43 (m, 5H), 1.43–1.28 (m, 2H), 0.99–0.88 (m, 9H).

EXAMPLE 37(18)

(3S)-1-butyl-2,5-dioxo-3-(2-methylpropyl)-9-(7-methoxy-1,3-benzodioxolan-5-ylmethyl)-1,4,9-triazaspiro[5.5]undecane.hydrochloride

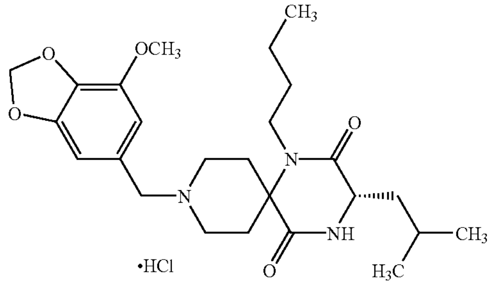

TLC: Rf 0.36 (chloroform:methanol=20:1);

NMR ($CD_3OD$): δ 6.85 (d, J=1.8 Hz, 1H), 6.74 (d, J=1.8 Hz, 1H), 5.99 (s, 2H), 4.25 (s, 2H), 4.01 (dd, J=7.8, 4.5 Hz, 1H), 3.92 (s, 3H), 3.87–3.66 (m, 2H), 3.52–3.32 (m, 4H), 2.52–2.34 (m, 2H), 2.26–2.08 (m, 2H), 1.90–1.43 (m, 5H), 1.43–1.29 (m, 2H), 0.99–0.90 (m, 9H).

EXAMPLE 37(19)

(3S)-1-butyl-2,5-dioxo-3-(2-methylpropyl)-9-(4-phenylthiophenylmethyl)-1,4,9-triazaspiro[5.5]undecane.hydrochloride

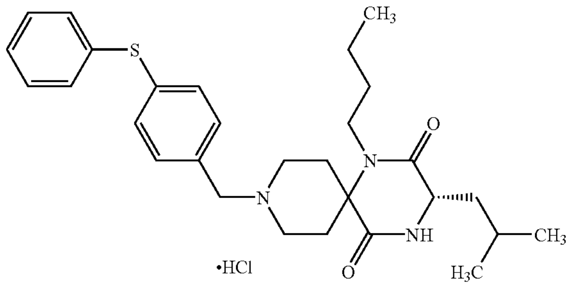

TLC: Rf 0.52 (chloroform:methanol=20:1);

NMR ($CD_3OD$): δ 7.50–7.36 (m, 7H), 7.30 (d, J=8.7 Hz, 2H), 4.31 (s, 2H), 4.00 (dd, J=7.8, 4.5 Hz, 1H), 3.88–3.68 (m, 2H), 3.53–3.32 (m, 4H), 2.50–2.30 (m, 2H), 2.26–2.06 (m, 2H), 1.90–1.42 (m, 5H), 1.42–1.27 (m, 2H), 0.98–0.89 (m, 9H).

EXAMPLE 37(20)

(3S)-1-butyl-2,5-dioxo-3-(2-methylpropyl)-9-(2-methylphenylmethyl)-1,4,9-triazaspiro[5.5]undecane.hydrochloride

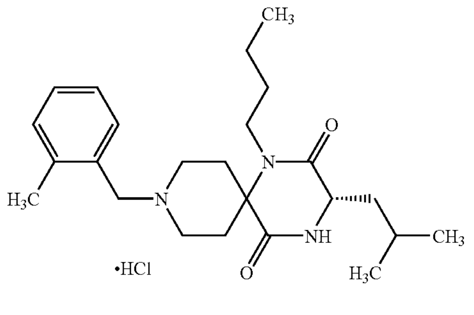

TLC: Rf 0.41 (chloroform:methanol=19:1);

NMR ($CD_3OD$): δ 7.57 (d, J=7.8 Hz, 1H), 7.42–7.28 (m, 3H), 4.41 (s, 2H), 4.01 (dd, J=7.8, 4.8 Hz, 1H), 3.89 (m, 2H), 3.53 (m, 2H), 3.42 (m, 2H), 2.48 (s, 3H), 2.48 (m, 2H), 2.16 (m, 2H), 1.90–1.42 (m, 5H), 1.36 (sextet, J=7.2 Hz, 2H), 0.94 (d, J=6.6 Hz, 3H), 0.94 (t, J=7.2 Hz, 3H), 0.93 (d, J=6.6 Hz, 3H).

EXAMPLE 37(21)

(3S)-1-butyl-2,5-dioxo-3-(2-methylpropyl)-9-(3-methylphenylmethyl)-1,4,9-triazaspiro[5.5]undecane.hydrochloride

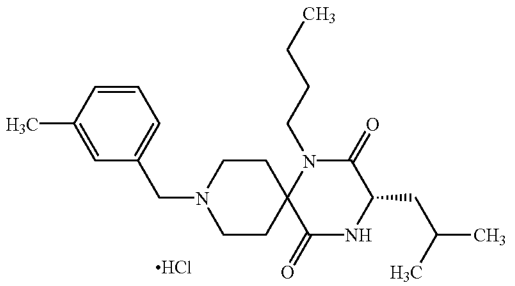

TLC: Rf 0.31 (chloroform:methanol=19:1);

NMR ($CD_3OD$): δ 7.41–7.29 (m, 4H), 4.31 (s, 2H), 4.00 (dd, J=7.8, 4.8 Hz, 1H), 3.79 (m, 2H), 3.52–3.34 (m, 4H), 2.40 (m, 2H), 2.40 (s, 3H), 2.17 (m, 2H), 1.90–1.44 (m, 5H), 1.36 (sextet, J=7.5 Hz, 2H), 0.94 (t, J=7.5 Hz, 3H), 0.94 (d, J=6.6 Hz, 3H), 0.93 (d, J=6.6 Hz, 3H).

EXAMPLE 37(22)

(3S)-1-butyl-2,5-dioxo-3-(2-methylpropyl)-9-(4-methylphenylmethyl)-1,4,9-triazaspiro[5.5]undecane.hydrochloride

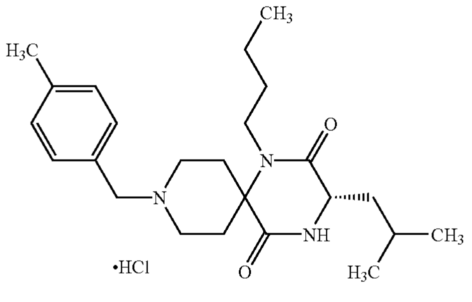

TLC: Rf 0.31 (chloroform:methanol=19:1);

NMR ($CD_3OD$): δ 7.43 (d, J=7.8 Hz, 2H), 7.31 (d, J=7.8 Hz, 2H), 4.31 (s, 2H), 4.00 (dd, J=7.8, 4.8 Hz, 1H), 3.78 (m, 2H), 3.52–3.35 (m, 4H), 2.40 (m, 2H), 2.37 (s, 3H), 2.17 (m, 2H), 1.88–1.44 (m, 5H), 1.36 (sextet, J=7.5 Hz, 2H), 0.94 (t, J=7.5 Hz, 3H), 0.94 (d, J=6.6 Hz, 3H), 0.93 (d, J=6.6 Hz, 3H).

EXAMPLE 37(23)

(3S)-1-butyl-2,5-dioxo-3-(2-methylpropyl)-9-(4-(1-methylethyl)phenylmethyl)-1,4,9-triazaspiro[5.5]undecane.hydrochloride

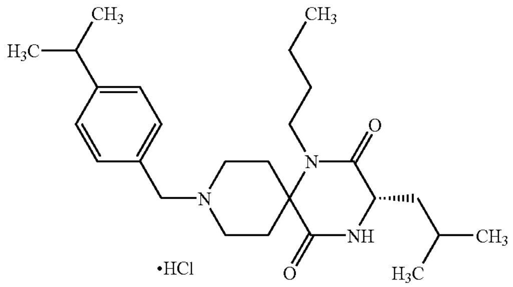

TLC: Rf 0.49 (chloroform:methanol=10:1);

NMR ($CD_3OD$): δ 7.48 (d, J=8.4 Hz, 2H), 7.38 (d, J=8.4 Hz, 2H), 4.32 (s, 2H), 4.01 (dd, J=7.8, 4.5 Hz, 1H), 3.88–3.70 (m, 2H), 3.54–3.36 (m, 4H), 3.04–2.88 (m, 1H), 2.48–2.30 (m, 2H), 2.28–2.08 (m, 2H), 1.90–1.28(m, 7H), 1.26 (d, J=6.9 Hz, 6H), 0.95 (t, J=7.2 Hz, 3H), 0.95 (d, J=6.9 Hz, 3H), 0.94 (d, J=6.9 Hz, 3H).

EXAMPLE 37(24)

(3S)-1-butyl-2,5-dioxo-3-(2-methylpropyl)-9-(3-fluoro-4-methoxyphenylmethyl)-1,4,9-triazaspiro[5.5]undecane.hydrochloride

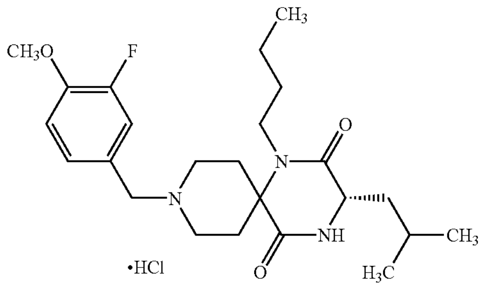

TLC: Rf 0.44 (chloroform:methanol=10:1);

NMR ($CD_3OD$): δ 7.40–7.32 (m, 2H), 7.21 (m, 1H), 4.31 (s, 2H), 4.01 (dd, J=7.5, 4.5 Hz, 1H), 3.92 (s, 3H), 3.86–3.64 (m, 2H), 3.58–3.36 (m, 4H), 2.56–2.32 (m, 2H), 2.28–2.08 (m, 2H), 1.90–1.26(m, 7H), 0.96 (t, J=7.2 Hz, 3H), 0.95 (d, J=6.6 Hz, 3H), 0.94 (d, J=6.6 Hz, 3H).

EXAMPLE 37(25)

(3S)-1-butyl-2,5-dioxo-3-(2-methylpropyl)-9-(4-(2-hydroxyethyloxy)phenylmethyl)-1,4,9-triazaspiro[5.5]undecane.hydrochloride

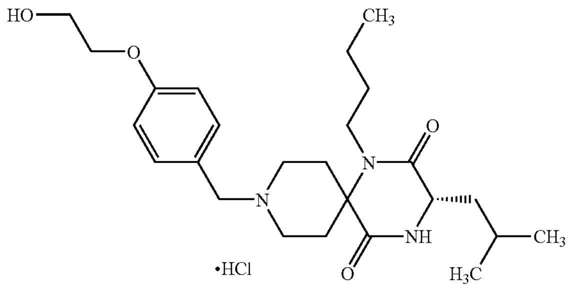

TLC: Rf 0.22 (chloroform:methanol=10:1);

NMR ($CD_3OD$): δ 7.48 (d, J=8.7 Hz, 2H), 7.07 (d, J=8.7 Hz, 2H), 4.29 (s, 2H), 4.09 (t, J=5.1 Hz, 2H), 4.01 (dd, J=7.5, 4.5 Hz, 1H), 3.88 (t, J=5.1 Hz, 2H), 3.86–3.64 (m, 2H), 3.54–3.36 (m, 4H), 2.50–2.30 (m, 2H), 2.26–2.08 (m, 2H), 1.90–1.24(m, 7H), 0.96 (t, J=7.2 Hz, 3H), 0.95 (d, J=6.6 Hz, 3H), 0.94 (d, J=6.6 Hz, 3H).

EXAMPLE 37(26)

(3S)-1-butyl-2,5-dioxo-3-(2-methylpropyl)-9-(2-hydroxy-3-methylphenylmethyl)-1,4,9-triazaspiro[5.5]undecane.hydrochloride

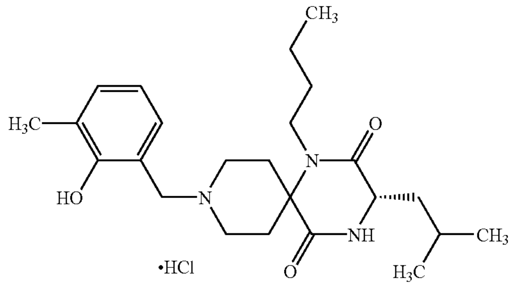

TLC: Rf 0.66 (chloroform:methanol=10:1);

NMR ($CD_3OD$): δ 7.24 (d, J=7.7 Hz, 2H), 6.89 (t, J=7.7 Hz, 1H), 4.36 (s, 2H), 4.02 (dd, J=7.5, 4.5 Hz, 1H), 3.95–3.76 (m, 2H), 3.58–3.36 (m, 4H), 2.44–2.08 (m, 4H), 2.89 (s, 3H), 1.90–1.24(m, 7H), 0.96 (t, J=7.2 Hz, 3H), 0.95 (d, J=6.6 Hz, 3H), 0.94 (d, J=6.6 Hz, 3H).

EXAMPLE 37(27)

(3S)-1-butyl-2,5-dioxo-3-(2-methylpropyl)-9-(4-trifluoromethyloxyphenylmethyl)-1,4,9-triazaspiro[5.5]undecane.hydrochloride

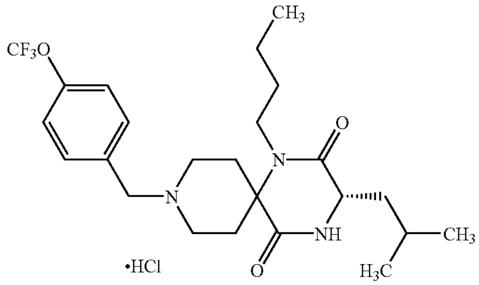

TLC: Rf 0.49 (chloroform:methanol=10:1);

NMR ($CD_3OD$): δ 7.71 (d, J=7.8 Hz, 2H), 7.42 (d, J=7.8 Hz, 2H), 4.41 (s, 2H), 4.01 (dd, J=7.8, 4.8 Hz, 1H), 3.90–3.72 (m, 2H), 3.56–3.36 (m, 4H), 2.56–2.36 (m, 2H), 2.26–2.08 (m, 2H), 1.90–1.28(m, 7H), 0.95 (t, J=7.5 Hz, 3H), 0.95 (d, J=6.3 Hz, 3H), 0.94 (d, J=6.3 Hz, 3H).

EXAMPLE 37(28)

(3S)-1-butyl-2,5-dioxo-3-(2-methylpropyl)-9-(3-methyl-5-chloro-1-phenyl pyrazol-4-ylmethyl)-1,4,9-triazaspiro[5.5]undecane.2hydrochloride

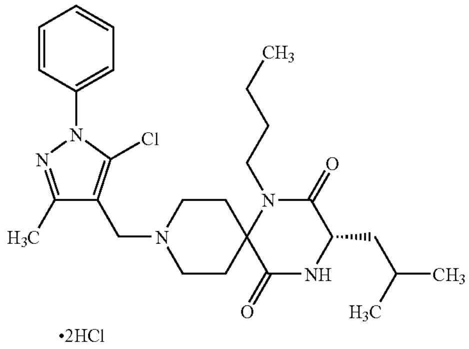

TLC: Rf 0.39 (chloroform:methanol=10:1);

NMR ($CD_3OD$): δ 7.59–7.50 (m, 5H), 4.35 (s, 2H), 4.03 (dd, J=7.8, 4.5 Hz, 1H), 3.98–3.80 (m, 2H), 3.72–3.58 (m, 2H), 3.46–3.38 (m, 2H), 2.58–2.38 (m, 2H), 2.45 (s, 3H), 2.36–2.18 (m, 2H), 1.92–1.24 (m, 7H), 0.97 (t, J=7.5 Hz, 3H), 0.96 (d, J=6.6 Hz, 3H), 0.95 (d, J=6.6 Hz, 3H).

EXAMPLE 37(29)

(3S)-1-butyl-2,5-dioxo-3-(2-methylpropyl)-9-(6-phenylpyridin-3-ylmethyl)-1,4,9-triazaspiro[5.5]undecane.hydrochloride

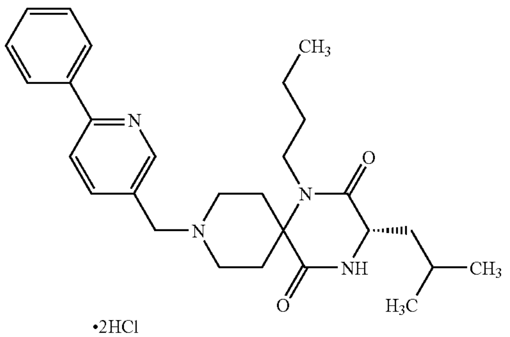

•2HCl

TLC: Rf 0.28 (chloroform:methanol=10:1);

NMR ($CD_3OD$): δ 9.17 (s, 1H), 8.80 (m, 1H), 8.39 (m, 1H), 8.03–7.97 (m, 2H), 7.73–7.65 (m, 3H), 4.65 (s, 2H), 4.03 (dd, J=7.2, 4.2 Hz, 1H), 4.02–3.82 (m, 2H), 3.64–3.42 (m, 2H), 3.78–3.56 (m, 2H), 2.30–2.08 (m, 2H), 1.88–1.24 (m, 7H), 0.96 (d, J=6.3 Hz, 3H), 0.95 (t, J=7.2 Hz, 3H), 0.95 (d, J=6.3 Hz, 3H).

EXAMPLE 37(30)

(3S)-1-butyl-2,5-dioxo-3-(2-methylpropyl)-9-(4-(4-methylsulfonylaminophenyloxy)phenylmethyl)-1,4,9-triazaspiro[5.5]undecane.hydrochloride

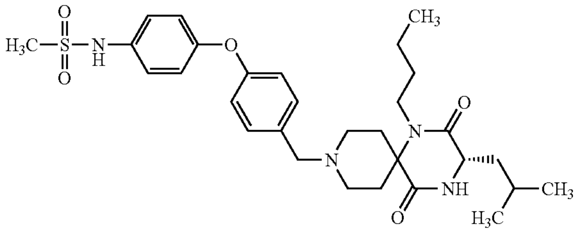

•HCl

TLC: Rf 0.18 (chloroform:methanol=10:1);

NMR ($CD_3OD$): δ 7.54 (d, J=8.7 Hz, 2H), 7.30 (d, J=9.0 Hz, 2H), 7.08 (d, J=8.7 Hz, 2H), 7.04 (d, J=9.0 Hz, 2H), 4.34 (s, 2H), 4.02 (dd, J 7.8, 4.5 Hz, 1H), 3.88–3.68 (m, 2H), 3.56–3.35 (m, 4H), 2.96 (s, 3H), 2.50–2.08 (m, 4H), 1.88–1.26 (m, 7H), 0.96 (t, J=6.9 Hz, 3H), 0.95 (d, J=6.6 Hz, 3H), 0.94 (d, J=6.6 Hz, 3H).

EXAMPLE 37(31)

(3S)-1-butyl-2,5-dioxo-3-(2-methylpropyl)-9-(3,5-dimethyl-1-(4-methylsulfonylaminophenyl)pyrazol-4-ylmethyl)-1,4,9-triazaspiro[5.5]undecane.2hydrochloride

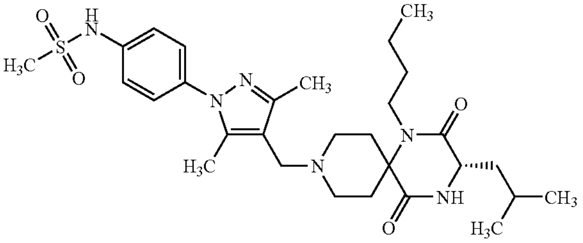

•2HCl

TLC: Rf 0.15 (chloroform:methanol=10:1);

NMR ($CD_3OD$): δ 7.49 (d, J=8.7 Hz, 2H), 7.43 (d, J=8.7 Hz, 2H), 4.33 (s, 2H), 4.03 (dd, J=7.8, 4.8 Hz, 1H), 3.96–3.76 (m, 2H), 3.66–3.58 (m, 2H), 3.56–3.42 (m, 2H), 3.05 (s, 3H), 2.68–2.46 (m, 2H), 2.44 (s, 3H), 2.41 (s, 3H), 2.32–2.10 (m, 2H), 1.90–1.28 (m, 7H), 0.97 (t, J=6.6 Hz, 3H), 0.96 (d, J=6.3 Hz, 3H), 0.95 (d, J=6.3 Hz, 3H).

EXAMPLE 37(32)

(3S)-1-butyl-2,5-dioxo-3-(2-methylpropyl)-9-(4-(5-methylpyridin-2-yloxy)phenylmethyl)-1,4,9-triaza-spiro[5.5]undecane.2hydrochloride

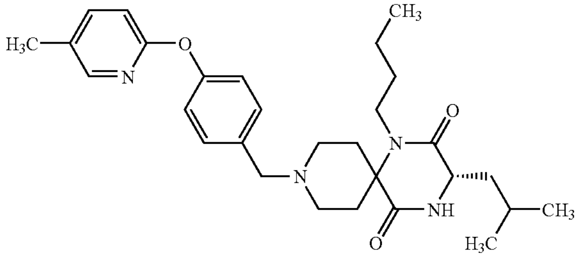

•2HCl

TLC: Rf 0.29 (chloroform:methanol=10:1);

NMR ($CD_3OD$): δ 8.12 (s, 1H), 7.93 (d, J=8.4 Hz, 1H), 7.68 (d, J=8.7 Hz, 2H), 7.30 (d, J=8.7 Hz, 2H), 7.06 (d, J=8.4 Hz, 1H), 4.40 (s, 2H), 4.03 (dd, J=7.8, 4.8 Hz, 1H), 3.94–3.76 (m, 2H), 3.58–3.40 (m, 4H), 2.56–2.36 (m, 2H), 2.38 (s, 3H), 2.30–2.08 (m, 2H), 1.88–1.24 (m, 7H), 0.96 (t, J=7.8 Hz, 3H), 0.96 (d, J=6.6 Hz, 3H), 0.95 (d, J=6.6 Hz, 3H).

EXAMPLE 37(33)

(3S)-1-butyl-2,5-dioxo-3-(2-methylpropyl)-9-(4-(6-methylpyridin-1-oxide-3-yloxy)phenylmethyl)-1,4,9-triazaspiro[5.5]undecane.hydrochloride

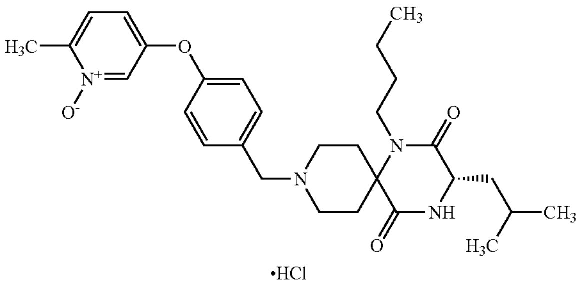

TLC: Rf 0.24 (chloroform:methanol=10:1);

NMR ($CD_3OD$): δ 8.47 (s, 1H), 7.71 (d, J=8.7 Hz, 2H), 7.62–7.48 (m, 2H), 7.29 (d, J=8.7 Hz, 2H), 4.40 (s, 2H), 4.02 (dd, J=7.8, 4.5 Hz, 1H), 3.92–3.72 (m, 2H), 3.58–3.38 (m, 4H), 2.64–2.40 (m, 2H), 2.60 (s, 3H), 2.28–2.10 (m, 2H), 1.90–1.28 (m, 7H), 0.96 (t, J=7.8 Hz, 3H), 0.95 (d, J=6.6 Hz, 3H), 0.94 (d, J=6.6 Hz, 3H).

EXAMPLE 37(34)

(3S)-1-butyl-2,5-dioxo-3-(2-methylpropyl)-9-(1-(2-methylpropyloxycarbonyl)indol-5-ylmethyl)-1,4,9-triazaspiro[5.5]undecane.hydrochloride

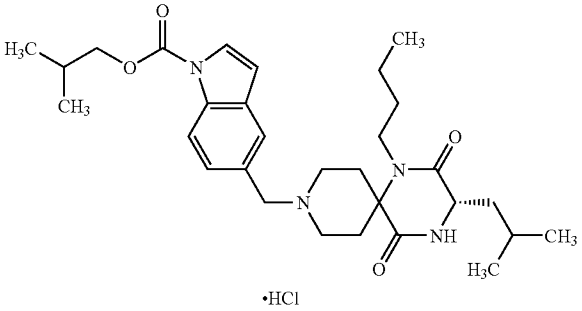

TLC: Rf 0.23 (chloroform:methanol=10:1);

NMR ($CD_3OD$): δ 8.16 (d, J=8.4 Hz, 1H), 7.82 (d, J=1.5 Hz, 1H), 7.78 (d, J=3.6 Hz, 1H), 7.50 (dd, J=8.4, 1.5 Hz, 1H), 6.75 (d, J=3.6 Hz, 1H), 4.46 (s, 2H), 4.27 (d, J=6.6 Hz, 2H), 4.01 (dd, J=7.8, 4.5 Hz, 1H), 3.82–3.74 (m, 2H), 3.58–3.36 (m, 4H), 2.48–2.30 (m, 2H), 2.26–2.08 (m, 3H), 1.88–1.24 (m, 7H), 1.09 (s, 3H), 1.06 (s, 3H), 0.95 (t, J=7.2 Hz, 3H), 0.95 (d, J=6.3 Hz, 3H), 0.94 (d, J=6.3 Hz, 3H).

EXAMPLE 37(35)

(3S)-1-butyl-2,5-dioxo-3-(2-methylpropyl)-9-(2-phenyl-5-methyloxazol-4-ylmethyl)-1,4,9-triazaspiro[5.5]undecane.hydrochloride

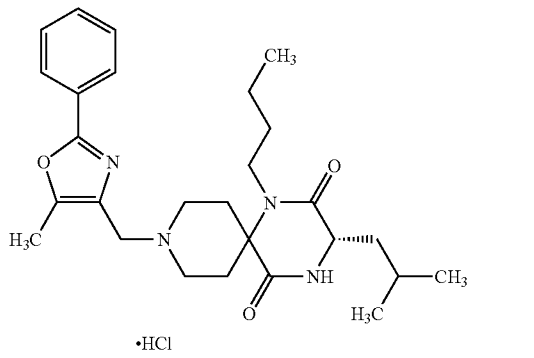

TLC: Rf 0.32 (chloroform:methanol=10:1);

NMR ($CD_3OD$): δ 8.05–8.02 (m, 2H), 7.52–7.50 (m, 3H), 4.35 (s, 2H), 4.02 (dd, J=7.8, 4.5 Hz, 1H), 3.98–3.80 (m, 2H), 3.70–3.58 (m, 2H), 3.44–3.38 (m, 2H), 2.53 (s, 3H), 2.53–2.36 (m, 2H), 2.34–2.14 (m, 2H), 1.90–1.26 (m, 7H), 0.96 (t, J=7.2 Hz, 3H), 0.95 (d, J=6.3 Hz, 3H), 0.94 (d, J=6.3 Hz, 3H).

EXAMPLE 37(36)

(3S)-1-butyl-2,5-dioxo-3-(2-methylpropyl)-9-(4-(tetrahydropyran-4-yloxy)phenylmethyl)-1,4,9-triazaspiro[5.5]undecane.hydrochloride

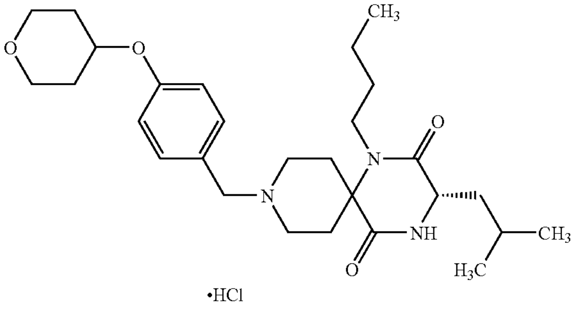

TLC: Rf 0.33 (chloroform:methanol=10:1);

NMR ($CD_3OD$): δ 7.47 (d, J=8.4 Hz, 2H), 7.07 (d, J=8.4 Hz, 2H), 4.64 (m, 1H), 4.29 (s, 2H), 4.01 (dd, J=7.5, 4.5 Hz, 1H), 3.98–3.91 (m, 2H), 3.84–3.68 (m, 2H), 3.64–3.56 (m, 2H), 3.50–3.37 (m, 4H), 2.50–2.30 (m, 2H), 2.24–1.98 (m, 4H), 1.88–1.26 (m, 9H), 0.95 (t, J=7.2 Hz, 3H), 0.95 (d, J=6.3 Hz, 3H), 0.94 (d, J=6.3 Hz, 3H).

EXAMPLE 37(37)

(3S)-1-butyl-2,5-dioxo-3-(2-methylpropyl)-9-(4-(6-methylpyridin-3-yloxy)phenylmethyl)-1,4,9-triazaspiro[5.5]undecane.2hydrochloride

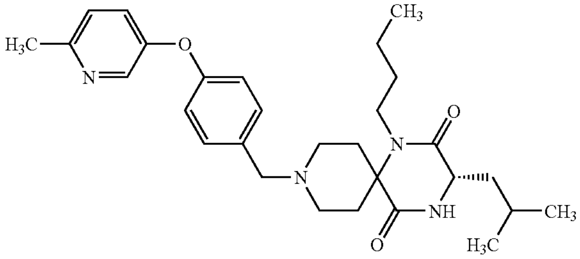

•2HCl

TLC: Rf 0.22 (chloroform:methanol=10:1);

NMR ($CD_3OD$): δ 8.55 (d, J=2.7 Hz, 1H), 8.10 (dd, J=9.0, 2.7 Hz, 1H), 7.84 (d, J=9.0 Hz, 1H), 7.72 (d, J=8.7 Hz, 2H), 7.29 (d, J=8.7 Hz, 2H), 4.40 (s, 2H), 4.02 (dd, J=7.8, 4.5 Hz, 1H), 3.94–3.70 (m, 2H), 3.58–3.38 (m, 4H), 2.74 (s, 3H), 2.60–2.42 (m, 2H), 2.28–2.08 (m, 2H), 1.90–1.26 (m, 7H), 0.96 (t, J=7.5 Hz, 3H), 0.96 (d, J=6.6 Hz, 3H), 0.95 (d, J=6.6 Hz, 3H).

EXAMPLE 37(38)

(3S)-1-butyl-2,5-dioxo-3-(2-methylpropyl)-9-(3,5-dimethyl-1-(4-fluorophenyl)pyrazol-4-ylmethyl)-1,4,9-triazaspiro[5.5]undecane.2hydrochloride

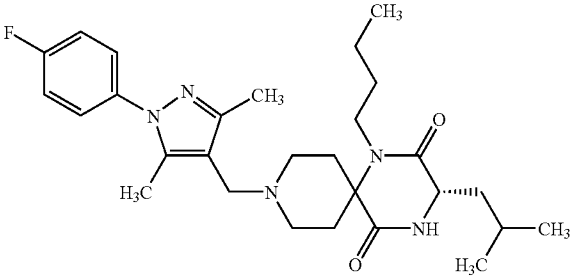

•2HCl

TLC: Rf 0.58 (chloroform:methanol=10:1);

NMR ($CD_3OD$): δ 7.55–7.46 (m, 2H), 7.36–7.25 (m, 2H), 4.30 (s, 2H), 4.02 (dd, J=7.8, 4.5 Hz, 1H), 3.95–3.73 (m, 2H), 3.66–3.55 (m, 2H), 3.52–3.40 (m, 2H), 2.63–2.45 (m, 2H), 2.39 (s, 3H), 2.37 (s, 3H), 2.30–2.10 (m, 2H), 1.90–1.43 (m, 5H), 1.43–1.30 (m, 2H), 0.99–0.91 (m, 9H).

EXAMPLE 37(39)

(3S)-1-butyl-2,5-dioxo-3-(2-methylpropyl)-9-(3,5-dimethyl-1-(pyridin-2-yl) pyrazol-4-ylmethyl)-1,4,9-triazaspiro[5.5]undecane.2hydrochloride

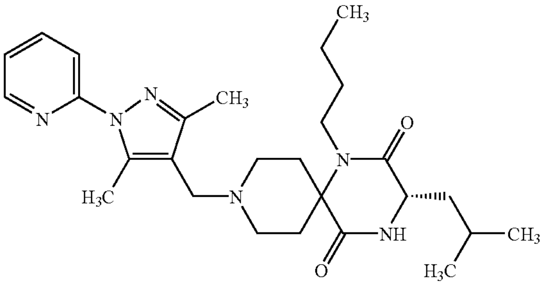

•2HCl

TLC: Rf 0.52 (chloroform:methanol=10:1);

NMR ($CD_3OD$): δ 8.55 (d, J=4.8 Hz, 1H), 8.12 (dd, J=8.4, 7.2 Hz, 1H), 7.87 (d, J=8.4 Hz, 1H), 7.50 (dd, J=7.2, 4.8 Hz, 1H), 4.32 (s, 2H), 4.02 (dd, J=7.8, 4.5 Hz, 1H), 3.96–3.73 (m, 2H), 3.67–3.55 (m, 2H), 3.54–3.40 (m, 2H), 2.69 (s, 3H), 2.70–2.48 (m, 2H), 2.44 (s, 3H), 2.28–2.08 (m, 2H), 1.92–1.43 (m, 5H), 1.43–1.26 (m, 2H), 0.99–0.90 (m, 9H).

EXAMPLE 37(40)

(3S)-1-butyl-2,5-dioxo-3-(2-methylpropyl)-9-(3,5-dimethyl-1-(4-hydroxyphenyl)pyrazol-4-ylmethyl)-1,4,9-triazaspiro[5.5]undecane.2hydrochloride

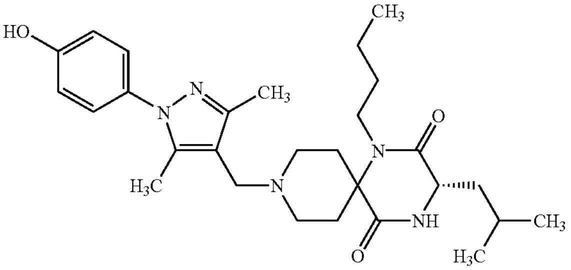

•2HCl

TLC: Rf 0.48 (chloroform:methanol=10:1);

NMR ($CD_3OD$): δ 7.30 (d, J=9.0 Hz, 2H), 6.95 (d, J=9.0 Hz, 2H), 4.33 (s, 2H), 4.02 (dd, J=7.5, 4.5 Hz, 1H), 3.92–3.77 (m, 2H), 3.61 (m, 2H), 3.47 (m, 2H), 2.58 (m, 2H), 2.45 (s, 3H), 2.36 (s, 3H), 2.20 (m, 2H), 1.88–1.76 (m, 1H), 1.73–1.32 (m, 6H), 0.96 (t, J=7.5 Hz, 3H), 0.95 (d, J=6.5 Hz, 3H), 0.94 (d, J=6.5 Hz, 3H).

EXAMPLE 37(41)

(3S)-1-butyl-2,5-dioxo-3-(2-methylpropyl)-9-(4-(2-carboxyethyl)phenylmethyl)-1,4,9-triazaspiro[5.5]undecane.hydrochloride

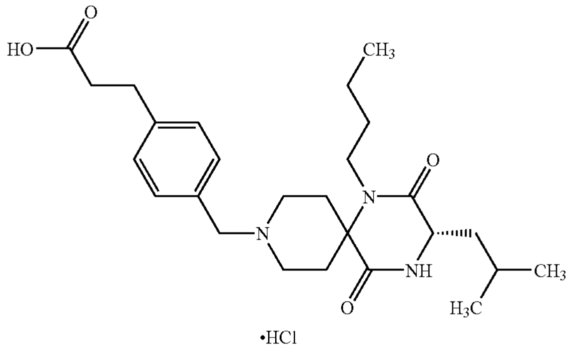

TLC: Rf 0.38 (chloroform:methanol=10:1);

NMR ($CD_3OD$): δ 7.47 (d, J=8.0 Hz, 2H), 7.37 (d, J=8.0 Hz, 2H), 4.31 (s, 2H), 4.00 (dd, J=7.5, 4.5 Hz, 1H), 3.86–3.73 (m, 2H), 3.49–3.35 (m, 4H), 2.96 (t, J=7.5 Hz, 2H), 2.62 (t, J=7.5 Hz, 2H), 2.44–2.33 (m, 2H), 2.23–2.11 (m, 2H), 1.84–1.32 (m, 7H), 0.94 (t, J=7.5 Hz, 3H), 0.94 (d, J=6.5 Hz, 3H), 0.93 (d, J=6.5 Hz, 3H).

EXAMPLE 37(42)

(3S)-1-butyl-2,5-dioxo-3-(2-methylpropyl)-9-(3,5-dimethyl-1-(4-(dimethylaminosulfonyl)phenyl)pyrazol-4-ylmethyl)-1,4,9-triazaspiro[5.5]undecane.2hydrochloride

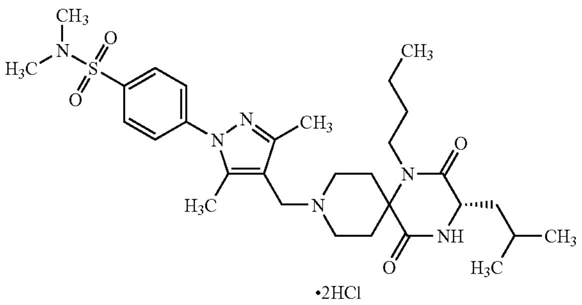

TLC: Rf 0.54 (chloroform:methanol=9:1);

NMR ($CD_3OD$): δ 7.96 (d, J=8.7 Hz, 2H), 7.77 (d, J=8.7 Hz, 2H), 4.32 (s, 2H), 4.02 (dd, J=7.8, 4.8 Hz, 1H), 3.95–3.75 (m, 2H), 3.66–3.56 (m, 2H), 3.47 (m, 2H), 2.74 (s, 6H), 2.56 (m, 2H), 2.48 (s, 3H), 2.41 (s, 3H), 2.30–2.12 (m, 2H), 1.90–1.46 (m, 5H), 1.38 (sextet, J=7.2 Hz, 2H), 0.98–0.93 (m, 9H).

EXAMPLE 37(43)

(3S)-1-butyl-2,5-dioxo-3-(2-methylpropyl)-9-(4-(5-methylpyridin-1-oxide-2-yloxy)phenylmethyl)-1,4,9-triazaspiro[5.5]undecane.hydrochloride

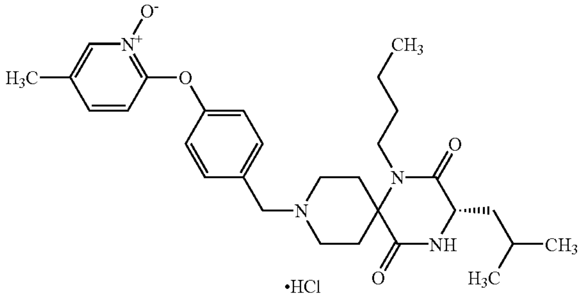

TLC: Rf 0.41 (chloroform:methanol=9:1);

NMR ($CD_3OD$): δ 7.77 (brs, 1H), 7.65–7.59 (m, 2H), 7.56 (dd, J=9.3, 2.4 Hz, 1H), 7.03–6.97 (m, 2H), 6.73 (d, J=9.3 Hz, 1H), 4.33 (s, 2H), 4.00 (dd, J=7.8, 4.8 Hz, 1H), 3.86–3.68 (m, 2H), 3.51–3.36 (m, 4H), 2.46 (m, 2H), 2.25–2.07 (m, 2H), 2.18 (s, 3H), 1.90–1.44 (m, 5H), 1.36 (sextet, J=7.2 Hz, 2H), 0.97–0.91 (m, 9H).

EXAMPLE 37(44)

(3S)-1-butyl-2,5-dioxo-3-(2-methylpropyl)-9-(4-(2-carboxy-1-ethenyl)phenylmethyl)-1,4,9-triazaspiro[5.5]undecane.hydrochloride

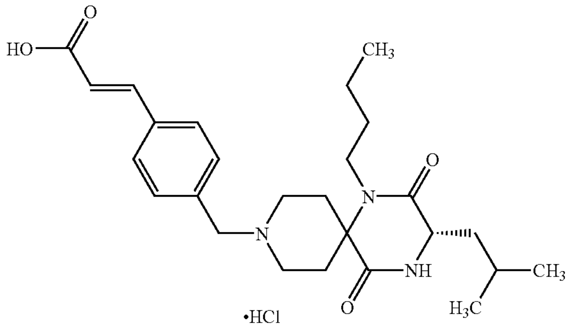

TLC: Rf 0.20 (chloroform:methanol=10:1);

NMR ($CD_3OD$): δ 7.75 (d, J=8.4 Hz, 2H), 7.70 (d, J=16.2 Hz, 1H), 7.61 (d, J=8.4 Hz, 2H), 6.58 (d, J=16.2 Hz, 2H), 4.39 (s, 2H), 4.02 (dd, J=7.8, 4.5 Hz, 1H), 3.92–3.74 (m, 2H), 3.58–3.36 (m, 4H), 2.50–2.32 (m, 2H), 2.30–2.10 (m, 2H), 1.90–1.24 (m, 7H), 0.96 (t, J=7.2 Hz, 3H), 0.95 (d, J=6.3 Hz, 3H), 0.94 (d, J=6.3 Hz, 3H).

EXAMPLE 37(45)

(3S)-1-butyl-2,5-dioxo-3-(2-methylpropyl)-9-(4-(4-(2-carboxy-1-ethenyl)phenyloxy)phenylmethyl)-1,4,9-triazaspiro[5.5]undecane.hydrochloride

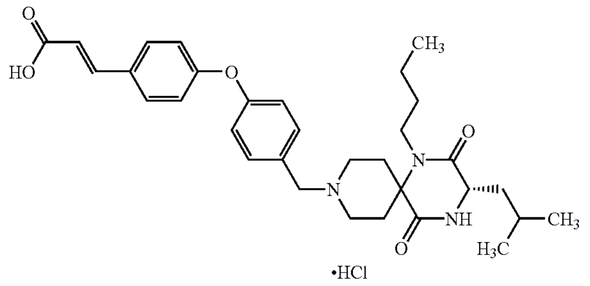

TLC: Rf 0.34 (chloroform:methanol=10:1);

NMR ($CD_3OD$): δ 7.69–7.57 (m, 5H), 7.14 (d, J=8.4 Hz, 2H), 7.05 (d, J=8.7 Hz, 2H), 6.42 (d, J=15.9 Hz, 1H), 4.36 (s, 2H), 4.01 (dd, J=7.8, 4.5 Hz, 1H), 3.92–3.70 (m, 2H), 3.56–3.35 (m, 4H), 2.48–2.30 (m, 2H), 2.30–2.12 (m, 2H), 1.88–1.25 (m, 7H), 0.98–0.88 (m, 9H).

EXAMPLE 37(46)

(3S)-1-butyl-2,5-dioxo-3-(2-methylpropyl)-9-(4-(4-aminocarbonylphenyloxy)phenylmethyl)-1,4,9-triazaspiro[5.5]undecane.hydrochloride

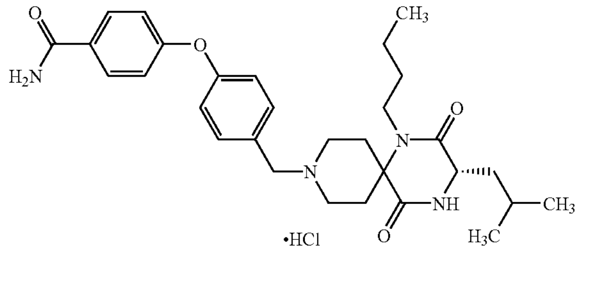

TLC: Rf 0.38 (chloroform:methanol=10:1);

NMR ($CD_3OD$): δ 7.90 (d, J=8.7 Hz, 2H), 7.60 (d, J=8.7 Hz, 2H), 7.15 (d, J=8.7 Hz, 2H), 7.07 (d, J=8.7 Hz, 2H), 4.36 (s, 2H), 4.01 (dd, J=7.8, 4.5, Hz, 1H), 3.90–3.70 (m, 2H), 3.58–3.35 (m, 4H), 2.54–2.36 (m, 2H), 2.30–2.10 (m, 2H), 1.90–1.26 (m, 7H), 1.00–0.86 (m, 9H).

EXAMPLE 37(47)

(3S)-1-butyl-2,5-dioxo-3-(2-methylpropyl)-9-(4-(4-aminosulfonylphenyloxy)phenylmethyl)-1,4,9-triazaspiro[5.5]undecane.hydrochloride

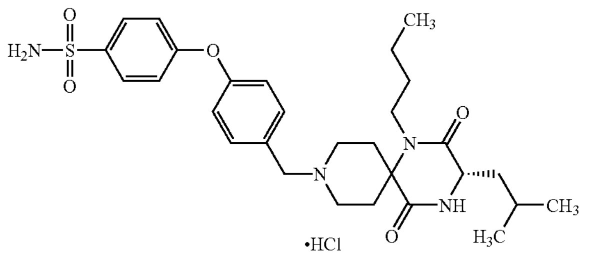

TLC: Rf 0.41 (chloroform:methanol=10:1);

NMR ($CD_3OD$): δ 7.90 (d, J=8.7 Hz, 2H), 7.57 (d, J=8.7 Hz, 2H), 7.17 (d, J=8.7 Hz, 2H), 7.13 (d, J=8.7 Hz, 2H), 4.28 (brs, 2H), 4.01 (dd, J=7.8, 4.5, Hz, 1H), 3.83–3.60 (m, 2H), 3.49–3.34 (m, 4H), 2.44–2.26 (m, 2H), 2.26–2.09 (m, 2H), 1.89–1.26 (m, 7H), 1.00–0.88 (m, 9H).

EXAMPLE 37(48)

(3S)-1-butyl-2,5-dioxo-3-(2-methylpropyl)-9-(3,5-dimethyl-1-benzylpyrazol-4-ylmethyl)-1,4,9-triazaspiro[5.5]undecane.2hydrochloride

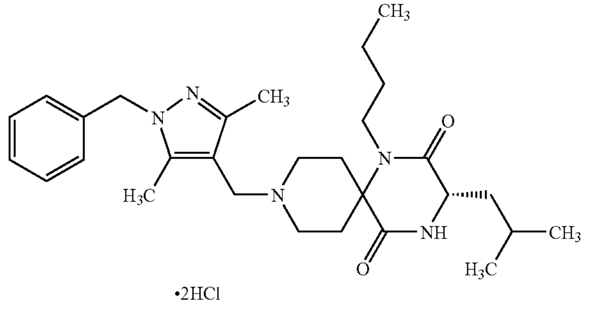

TLC: Rf 0.40 (chloroform:methanol=10:1);

NMR ($CD_3OD$): δ 7.41–7.33 (m, 3H), 7.21–7.19 (m, 2H), 5.45 (s, 2H), 4.30 (s, 2H), 4.01 (dd, J=7.5, 4.5 Hz, 1H), 3.89–3.73 (m, 2H), 3.60–3.46 (m, 4H), 2.61 (m, 2H), 2.48 (s, 3H), 2.46 (s, 3H), 2.23–2.11 (m, 2H), 1.87–1.31 (m, 7H), 0.95 (t, J=7.0 Hz, 3H), 0.94 (d, J=6.5 Hz, 3H), 0.93 (d, J=6.5 Hz, 3H).

EXAMPLE 37(49)

(3S)-1-butyl-2,5-dioxo-3-(2-methylpropyl)-9-(3,5-dimethyl-1-(2,4-difluorophenyl)pyrazol-4-ylmethyl)-1,4,9-triazaspiro[5.5]undecane.2hydrochloride

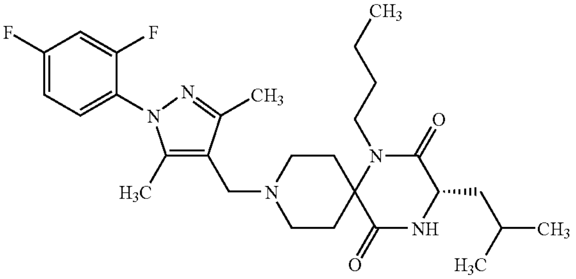

•2HCl

TLC: Rf 0.40 (chloroform:methanol=10:1);

NMR ($CD_3OD$): δ 7.61–7.53 (m, 1H), 7.33–7.26 (m, 1H), 7.23–7.16 (m, 1H), 4.31 (s, 2H), 4.02 (dd, J=7.5, 4.5 Hz, 1H), 3.92–3.76 (m, 2H), 3.63–3.56 (m, 2H), 3.49–3.45 (m, 2H), 2.57 (m, 2H), 2.40 (s, 3H), 2.29 (s, 3H), 2.19 (m, 2H), 1.86–1.34 (m, 7H), 0.96 (t, J=7.0 Hz, 3H), 0.95 (d, J=6.5 Hz, 3H), 0.94 (d, J=6.5 Hz, 3H).

EXAMPLE 37(50)

(3S)-1-butyl-2,5-dioxo-3-(2-methylpropyl)-9-(4-(pyrrolidin-1-ylmethyl)phenylmethyl)-1,4,9-triazaspiro[5.5]undecane.2hydrochloride

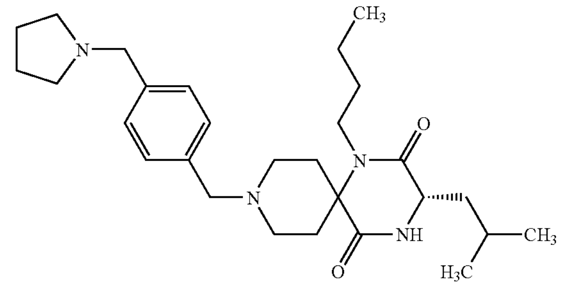

•2HCl

TLC: Rf 0.10 (chloroform:methanol=10:1);

NMR ($CD_3OD$): δ 7.75 (d, J=8.4 Hz, 2H), 7.65 (d, J=8.4 Hz, 2H), 4.43 (s, 2H), 4.40 (s, 2H), 4.00 (dd, J 7.5, 4.5 Hz, 1H), 3.92–3.70 (m, 2H), 3.56–3.40 (m, 6H), 3.25–3.12 (m, 2H), 2.68–2.48 (m, 2H), 2.28–1.95 (m, 6H), 1.88–1.42 (m, 5H), 1.42–1.30 (m, 2H), 0.98–0.90 (m, 9H).

EXAMPLE 37(51)

(3S)-1-butyl-2,5-dioxo-3-(2-methylpropyl)-9-(3,5-dimethyl-1-(4-(morpholin-4-ylsulfonyl)phenyl)pyrazol-4-ylmethyl)-1,4,9-triazaspiro[5.5]undecane.2hydrochloride

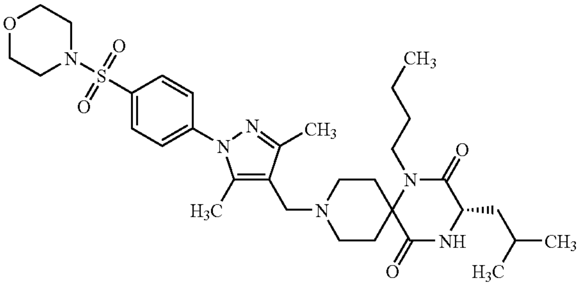

•2HCl

TLC: Rf 0.43 (chloroform:methanol=20:1);

NMR ($CD_3OD$): δ 7.95 (d, J=8.7 Hz, 2H), 7.80 (d, J=8.7 Hz, 2H), 4.32 (s, 2H), 4.02 (dd, J=7.8, 4.8 Hz, 1H), 3.95–3.72 (m, 2H), 3.76–3.67 (m, 4H), 3.66–3.57 (m, 2H), 3.56–3.42 (m, 2H), 3.08–2.95 (m, 4H), 2.70–2.50 (m, 2H), 2.50 (s, 3H), 2.42 (s, 3H), 2.31–2.10 (m, 2H), 1.90–1.44 (m, 5H), 1.44–1.30 (m, 2H), 1.00–0.91 (m, 9H).

EXAMPLE 37(52)

(3S)-1-butyl-2,5-dioxo-3-(2-methylpropyl)-9-(3,5-dimethyl-1-(4-(methylaminosulfonyl)phenyl)pyrazol-4-ylmethyl)-1,4,9-triazaspiro[5.5]undecane.2hydrochloride

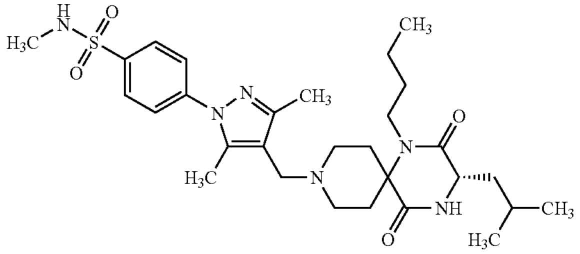

•2HCl

TLC: Rf 0.21 (chloroform:methanol=10:1);

NMR ($CD_3OD$): δ 8.01 (d, J=8.4 Hz, 2H), 7.73 (d, J=8.4 Hz, 2H), 4.34 (s, 2H), 4.04 (dd, J=7.8, 4.8 Hz, 1H), 3.98–3.78 (m, 2H), 3.66–3.58 (m, 2H), 3.44–3.30 (m, 2H), 2.59 (s, 3H), 2.54–2.38 (m, 2H), 2.47 (s, 3H), 2.40 (s, 3H), 2.36–2.16 (m, 2H), 1.90–1.26 (m, 7H), 0.97 (t, J=7.5 Hz, 3H), 0.96 (d, J=6.6 Hz, 6H).

EXAMPLE 37(53)

(3S)-1-butyl-2,5-dioxo-3-(2-methylpropyl)-9-(4-(4-cyanophenyloxy)phenylmethyl)-1,4,9-triazaspiro[5.5]undecane.hydrochloride

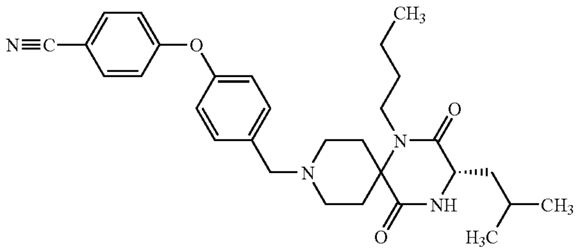

•HCl

TLC: Rf 0.30 (chloroform:methanol=10:1);

NMR ($CD_3OD$): δ 7.75 (d, J=8.4 Hz, 2H), 7.66 (d, J=8.7 Hz, 2H), 7.21 (d, J=8.4 Hz, 2H), 7.14 (d, J=8.7 Hz, 2H), 4.39 (s, 2H), 4.02 (dd, J=7.8, 4.5 Hz, 1H), 3.94–3.72 (m, 2H), 3.58–3.36 (m, 4H), 2.58–2.38 (m, 2H), 2.28–2.08 (m, 2H), 1.88–1.24 (m, 7H), 0.96 (t, J=7.2 Hz, 3H), 0.95 (d, J=6.3 Hz, 3H), 0.94 (d, J=6.3 Hz, 3H).

EXAMPLE 37(54)

(3S)-1-butyl-2,5-dioxo-3-(2-methylpropyl)-9-(4-(dimethylaminomethyl)phenylmethyl)-1,4,9-triazaspiro[5.5]undecane.2hydrochloride

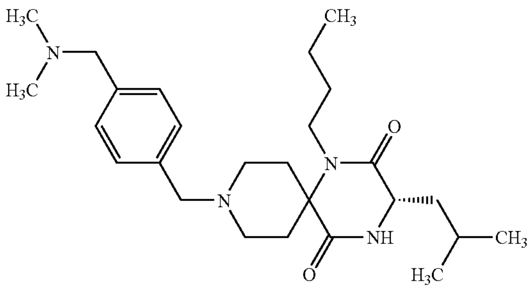

•2HCl

TLC: Rf 0.16 (chloroform:methanol=10:1);

NMR ($CD_3OD$): δ 7.76 (d, J=8.1 Hz, 2H), 7.63 (d, J=8.1 Hz, 2H), 4.41 (s, 2H), 4.37 (s, 2H), 4.00 (dd, J=7.8, 4.8 Hz, 1H), 3.90–3.72 (m, 2H), 3.50–3.42 (m, 4H), 2.87 (s, 6H), 2.65–2.50 (m, 2H), 2.22–2.04 (m, 2H), 1.88–1.32 (m, 7H), 0.97–0.92 (m, 9H).

EXAMPLE 37(55)

(3S)-1-butyl-2,5-dioxo-3-(2-methylpropyl)-9-(3,5-dimethyl-1-(4-(2-dimethylaminoethylaminosulfonyl)phenyl)pyrazol-4-ylmethyl)-1,4,9-triazaspiro[5.5]undecane.3hydrochloride

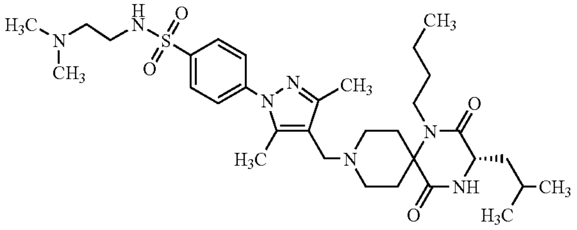

•3HCl

TLC: Rf 0.13 (chloroform:methanol=10:1);

NMR ($CD_3OD$): δ 8.07 (d, J=8.7 Hz, 2H), 7.78 (d, J=8.7 Hz, 2H), 4.31 (s, 2H), 4.01 (dd, J=8.1, 5.1 Hz, 1H), 3.95–3.74 (m, 2H), 3.68–3.45 (m, 4H), 3.40–3.20 (m, 4H), 2.95 (s, 6H), 2.70–2.50 (m, 2H), 2.49 (s, 3H), 2.41 (s, 3H), 2.28–2.12 (m, 2H), 1.88–1.34 (m, 7H), 0.98–0.92 (m, 9H).

EXAMPLE 37(56)

(3S)-1-butyl-2,5-dioxo-3-(2-methylpropyl)-9-(3-(4-hydroxyphenyl)phenylmethyl)-1,4,9-triazaspiro[5.5]undecane.hydrochloride

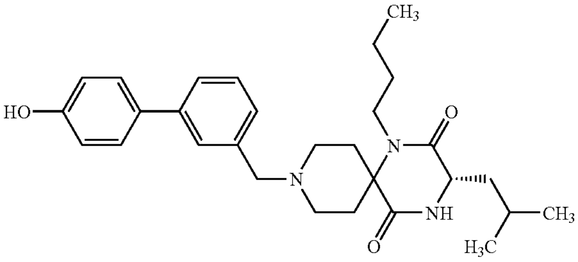

•HCl

TLC: Rf 0.53 (chloroform:methanol=10:1);

NMR ($CD_3OD$): δ 7.81 (s, 1H), 7.69 (d, J=7.5 Hz, 1H), 7.53 (d, J=9.0 Hz, 2H), 7.55–7.48 (m, 1H), 7.45 (d, J=7.5 Hz, 1H), 6.87 (d, J=9.0 Hz, 2H), 4.40 (s, 2H), 4.00 (dd, J=7.5, 4.5 Hz, 1H), 3.94–3.73 (m, 2H), 3.56–3.44 (m, 2H), 3.44–3.30 (m, 2H), 2.53–2.33 (m, 2H), 2.26–2.08 (m, 2H), 1.90–1.40 (m, 5H), 1.43–1.25 (m, 2H), 0.94 (d, J=6.3 Hz, 3H), 0.94 (t, J=7.2 Hz, 3H), 0.93 (d, J=6.3 Hz, 3H).

EXAMPLE 37(57)

(3S)-1-butyl-2,5-dioxo-3-(2-methylpropyl)-9-(4-(3-methoxyphenyloxy)phenylmethyl)-1,4,9-triazaspiro[5.5]undecane.hydrochloride

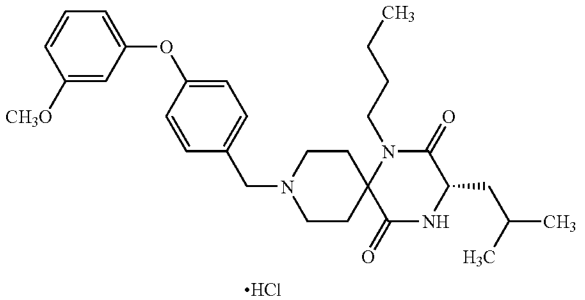

TLC: Rf 0.54 (chloroform:methanol=10:1);

NMR ($CD_3OD$): δ 7.53 (d, J=8.5 Hz, 2H), 7.28 (t, J=8.3 Hz, 1H), 7.07 (d, J=8.5 Hz, 2H), 6.75 (ddd, J=8.3, 2.3, 1.0 Hz, 1H), 6.60–6.57 (m, 2H), 4.33 (s, 2H), 4.01 (dd, J=7.5, 4.5 Hz, 1H), 3.86–3.73 (m, 2H), 3.77 (s, 3H), 3.51–3.34 (m, 4H), 2.41 (m, 2H), 2.42–2.12 (m, 2H), 1.84–1.33 (m, 7H), 0.95 (t, J=7.2 Hz, 3H), 0.94 (d, J=6.5 Hz, 3H), 0.93 (d, J=6.5 Hz, 3H).

EXAMPLE 37(58)

(3S)-1-butyl-2,5-dioxo-3-(2-methylpropyl)-9-(3,5-dimethyl-1-(quinoxalin-2-yl) pyrazol-4-ylmethyl)-1,4,9-triazaspiro[5.5]undecane.2hydrochloride

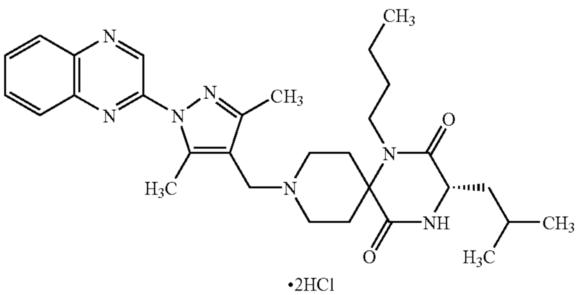

TLC: Rf 0.52 (chloroform:methanol=10:1);

NMR ($CD_3OD$): δ 9.51 (s, 1H), 8.12 (d, J=8.0 Hz, 1H), 8.04 (d, J=8.0 Hz, 1H), 7.90–7.80 (m, 2H), 4.37 (s, 2H), 4.02 (dd, J=7.5, 4.5 Hz, 1H), 3.96–3.81 (m, 2H), 3.63 (m, 2H), 3.44 (m, 2H), 2.92 (s, 3H), 2.47 (s, 3H), 2.47 (m, 2H), 2.29–2.17 (m, 2H), 1.86–1.33 (m, 7H), 0.95 (t, J=7.2 Hz, 3H), 0.95 (d, J=6.5 Hz, 3H), 0.94 (d, J=6.5 Hz, 3H).

EXAMPLE 37(59)

(3S)-1-butyl-2,5-dioxo-3-(2-methylpropyl)-9-(4-phenylcarbonylphenylmethyl)-1,4,9-triazaspiro[5.5]undecane.hydrochloride

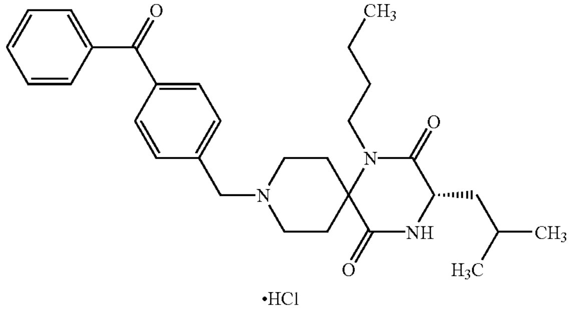

TLC: Rf 0.76 (chloroform:methanol=10:1);

NMR ($CD_3OD$): δ 7.88 (d, J=8.4 Hz, 2H), 7.81–7.67 (m, 5H), 7.57–7.52 (m, 2H), 4.49 (s, 2H), 4.01 (dd, J=8.1, 4.8 Hz, 1H), 4.00–3.78 (m, 2H), 3.59–3.48 (m, 2H), 3.44–3.35 (m, 2H), 2.50–2.32 (m, 2H), 2.32–2.14 (m, 2H), 1.88–1.24 (m, 7H), 1.02–0.88 (m, 9H).

EXAMPLE 37(60)

(3S)-1-butyl-2,5-dioxo-3-(2-methylpropyl)-9-(3,5-dimethyl-1-(4-(N-(2-hydroxyethyl)-N-methylaminosulfonyl)phenyl)pyrazol-4-ylmethyl)-1,4,9-triazaspiro[5.5]undecane.2hydrochloride

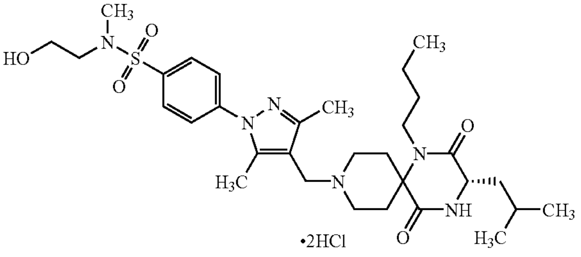

TLC: Rf 0.34 (chloroform:methanol=10:1);

NMR ($CD_3OD$): δ 8.00 (d, J=8.7 Hz, 2H), 7.76 (d, J=8.7 Hz, 2H), 4.34 (s, 2H), 4.04 (dd, J=7.8, 4.5 Hz, 1H), 3.98–3.76 (m, 2H), 3.70 (t, J=5.7 Hz, 2H), 3.68–3.58 (m, 2H), 3.50–3.38 (m, 2H), 3.20 (t, J=5.7 Hz, 2H), 2.88 (s, 3H), 2.58–2.38 (m, 2H), 2.48 (s, 3H), 2.41 (s, 3H), 2.36–2.16 (m, 2H), 1.90–1.24 (m, 7H), 0.97 (t, J=6.9 Hz, 3H), 0.96 (d, J=6.3 Hz, 3H), 0.95 (d, J=6.3 Hz, 3H).

EXAMPLE 37(61)

(3S)-1-butyl-2,5-dioxo-3-(2-methylpropyl)-9-(3,5-dimethyl-1-(2-phenylethyl) pyrazol-4-ylmethyl)-1,4,9-triazaspiro[5.5]undecane.2hydrochloride

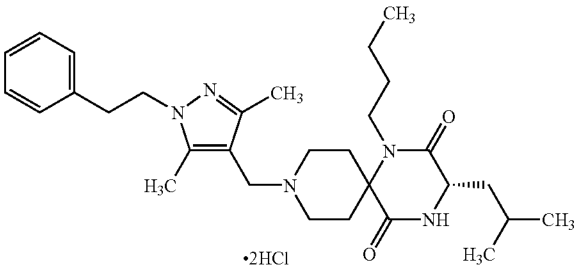

TLC: Rf 0.24 (chloroform:methanol=10:1);

NMR ($CD_3OD$): δ 7.31–7.23 (m, 3H), 7.10 (d, J=6.6 Hz, 2H), 4.44 (t, J=6.3 Hz, 2H), 4.21 (s, 2H), 4.03 (dd, J=7.8, 4.8 Hz, 1H), 3.82–3.60 (m, 2H), 3.58–3.32 (m, 4H), 3.13 (t, J=6.3 Hz, 2H), 2.72–2.52 (m, 2H), 2.50 (s, 3H), 2.24–2.04 (m, 2H), 1.99 (s, 3H), 1.90–1.36 (m, 7H), 0.97 (t, J=7.2 Hz, 3H), 0.96 (d, J=6.6 Hz, 3H), 0.95 (d, J=6.6 Hz, 3H).

EXAMPLE 37(62)

(3S)-1-butyl-2,5-dioxo-3-(2-methylpropyl)-9-(1,3,5-trimethylpyrazol-4-ylmethyl)-1,4,9-triazaspiro[5.5]undecane.2hydrochloride

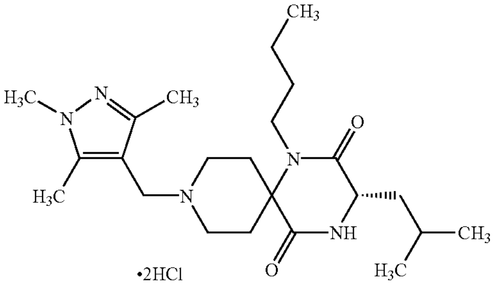

TLC: Rf 0.43 (chloroform:methanol=10:1);

NMR ($CD_3OD$): δ 4.28 (s, 2H), 4.00 (dd, J=7.8, 4.8 Hz, 1H), 3.87 (s, 3H), 3.87–3.69 (m, 2H), 3.60–3.43 (m, 4H), 2.69–2.50 (m, 2H), 2.46 (s, 3H), 2.44 (s, 3H), 2.26–2.08 (m, 2H), 1.90–1.28 (m, 7H), 0.98–0.85 (m, 9H).

EXAMPLE 37(63)

(3S)-1-butyl-2,5-dioxo-3-(2-methylpropyl)-9-(4-(morpholin-4-ylmethyl)phenylmethyl)-1,4,9-triazaspiro[5.5]undecane.2hydrochloride

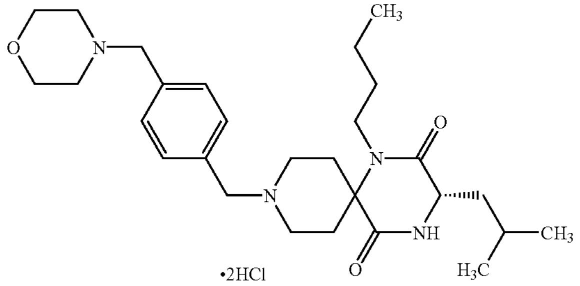

TLC: Rf 0.56 (chloroform:methanol=10:1);

NMR ($CD_3OD$): δ 7.74 (d, J=8.4 Hz, 2H), 7.66 (d, J=8.4 Hz, 2H), 4.40 (s, 4H), 4.00 (dd, J=7.5, 4.5 Hz, 1H), 4.10–3.70 (m, 6H), 3.54–3.42 (m, 4H), 3.40–3.16 (m, 4H), 2.65–2.46 (m, 2H), 2.24–2.03 (m, 2H), 1.88–1.28 (m, 7H), 1.02–0.88 (m, 9H).

EXAMPLE 37(64)

(3S)-1-butyl-2,5-dioxo-3-(2-methylpropyl)-9-(4-(4-methylpiperazin-1-ylmethyl)phenylmethyl)-1,4,9-triazaspiro[5.5]undecane.3hydrochloride

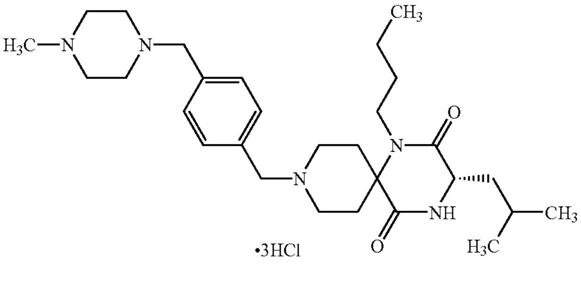

TLC: Rf 0.64 (chloroform:methanol=5:1);

NMR ($CD_3OD$): δ 7.45 (m, 4H), 4.55 (s, 2H), 4.42 (s, 2H), 4.01 (dd, J=7.5, 4.5 Hz, 1H), 3.88–3.56 (m, 10H), 3.53–3.43 (m, 4H), 3.01 (s, 3H), 2.59–2.47 (m, 2H), 2.22–2.09 (m, 2H), 1.85–1.33 (m, 7H), 0.94 (t, J=7.2 Hz, 3H), 0.94 (d, J=6.5 Hz, 3H), 0.93 (d, J=6.5 Hz, 3H).

EXAMPLE 37(65)

(3S)-1-butyl-2,5-dioxo-3-(2-methylpropyl)-9-(4-phenylsulfonylphenylmethyl)-1,4,9-triazaspiro[5.5] undecane.hydrochloride

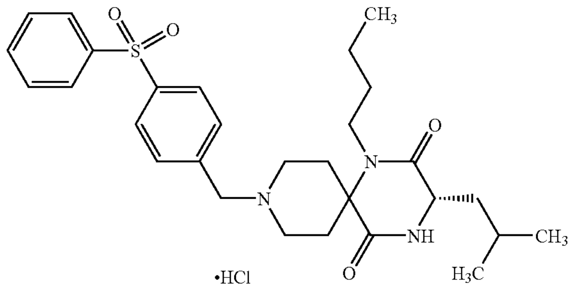

TLC: Rf 0.70 (ethyl acetate:methanol=9:1);

NMR ($CD_3OD$): δ 8.08 (d, J=8.4 Hz, 2H), 8.02–7.96 (m, 2H), 7.80 (d, J=8.4 Hz, 2H), 7.70–7.55 (m, 3H), 4.43 (s, 2H), 3.99 (dd, J=7.8, 4.8 Hz, 1H), 3.91–3.72 (m, 2H), 3.48–3.34 (m, 4H), 2.48–2.32 (m, 2H), 2.23–2.06 (m, 2H), 1.88–1.43 (m, 5H), 1.34 (sextet, J=7.2 Hz, 2H), 0.96–0.90 (m, 9H).

EXAMPLE 37(66)

(3S)-1-butyl-2,5-dioxo-3-(2-methylpropyl)-9-(3,5-dimethyl-1-cyclohexylpyrazol-4-ylmethyl)-1,4,9-triazaspiro[5.5]undecane.2hydrochloride

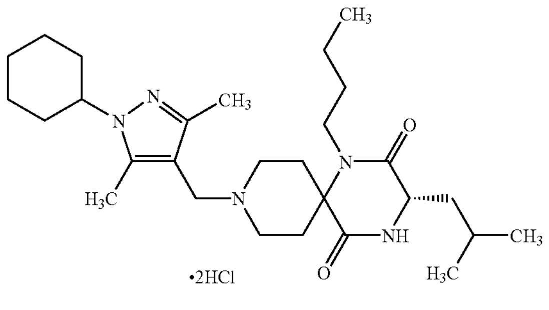

TLC: Rf 0.28 (ethyl acetate: methanol=9:1);

NMR ($CD_3OD$): δ 4.35–4.20 (m, 3H), 4.01 (dd, J=7.8, 4.8 Hz, 1H), 3.90–3.68 (m, 2H), 3.58–3.41 (m, 4H), 2.60–2.46 (m, 2H), 2.45 (s, 3H), 2.40 (s, 3H), 2.26–2.08 (m, 2H), 1.98–1.26 (m, 17H), 0.98–0.91 (m, 9H).

EXAMPLE 37(67)

(3S)-1-butyl-2,5-dioxo-3-(2-methylpropyl)-9-(4-(3-carboxyphenyloxy)phenylmethyl)-1,4,9-triazaspiro [5.5]undecane.hydrochloride

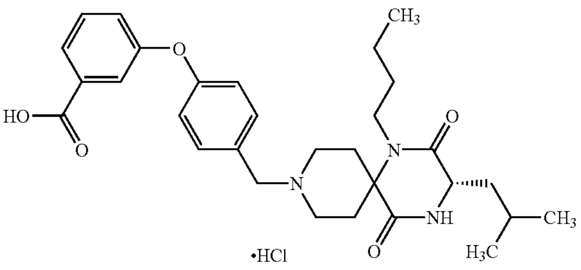

TLC: Rf 0.11 (ethyl acetate: methanol 9:1);

NMR ($CD_3OD$): δ 7.83 (ddd, J=7.8, 1.5, 0.9 Hz, 1H), 7.61 (dd, J=2.4, 1.5 Hz, 1H), 7.58 (d, J=8.7 Hz, 2H), 7.51 (t, J=7.8 Hz, 1H), 7.29 (ddd, J=7.8, 2.4, 0.9 Hz, 1H), 7.11 (d, J=8.7 Hz, 2H), 4.35 (s, 2H), 4.01 (dd, J=7.8, 4.8 Hz, 1H), 3.90–3.72 (m, 2H), 3.57–3.36 (m, 4H), 2.50–2.34 (m, 2H), 2.28–2.09 (m, 2H), 1.89–1.44 (m, 5H), 1.36 (sextet, J=7.2 Hz, 2H), 0.98–0.91 (m, 9H).

EXAMPLE 37(68)

(3S)-1-butyl-2,5-dioxo-3-(2-methylpropyl)-9-(4-(piperidin-1-ylmethyl)phenylmethyl)-1,4,9-triaza-spiro[5.5]undecane.2hydrochloride

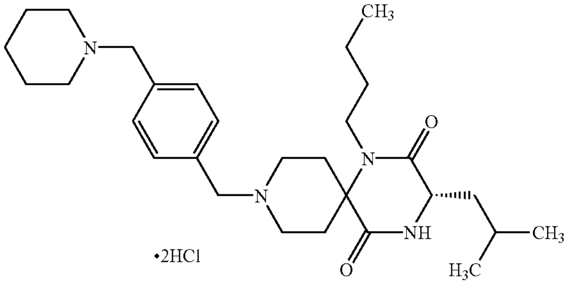

TLC: Rf 0.52 (chloroform:methanol=9:1);

NMR ($CD_3OD$): δ 7.75 (d, J=8.4 Hz, 2H), 7.65 (d, J=8.4 Hz, 2H), 4.41 (s, 2H), 4.34 (s, 2H), 4.00 (dd, J=7.8, 4.5 Hz, 1H), 3.91–3.71 (m, 2H), 3.54–3.41 (m, 6H), 3.05–2.91 (m, 2H), 2.67–2.49 (m, 2H), 2.25–2.05 (m, 2H), 2.00–1.28 (m, 13H), 0.98–0.91 (m, 9H).

EXAMPLE 37(69)

(3S)-1-butyl-2,5-dioxo-3-(2-methylpropyl)-9-(3,5-dimethyl-1-(4-(pyrrolidin-1-ylsulfonyl)phenyl)pyrazol-4-ylmethyl)-1,4,9-triazaspiro[5.5]undecane.2hydrochloride

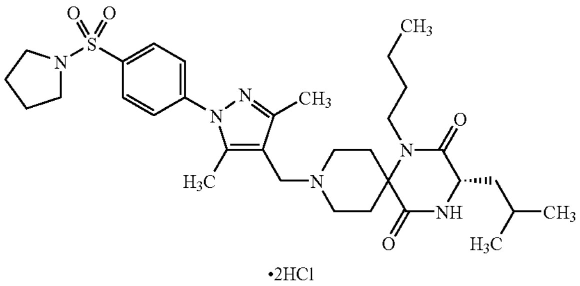

TLC: Rf 0.36 (ethyl acetate: methanol=9:1);

NMR ($CD_3OD$): δ 8.01 (d, J=8.7 Hz, 2H), 7.76 (d, J=8.7 Hz, 2H), 4.32 (s, 2H), 4.02 (dd, J=7.8, 4.8 Hz, 1H), 3.95–3.74 (m, 2H), 3.66–3.55 (m, 2H), 3.50–3.40 (m, 2H), 3.34–3.24 (m, 4H), 2.62–2.47 (m, 2H), 2.48 (s, 3H), 2.40 (s, 3H), 2.30–2.11 (m, 2H), 1.90–1.45 (m, 9H), 1.38 (sextet, J=7.2 Hz, 2H), 1.00–0.90 (m, 9H).

EXAMPLE 37(70)

(3S)-1-butyl-2,5-dioxo-3-(2-methylpropyl)-9-(2,3-dihydrobenzofuran-5-ylmethyl)-1,4,9-triazaspiro[5.5]undecane.hydrochloride

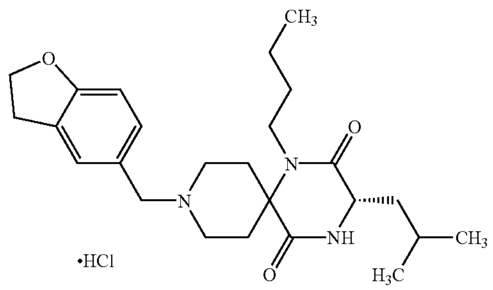

TLC: Rf 0.56 (ethyl acetate: methanol=9:1);

NMR ($CD_3OD$): δ 7.40 (brs, 1H), 7.26 (dd, J=8.1, 1.8 Hz, 1H), 6.80 (d, J=8.1 Hz, 1H), 4.59 (t, J=8.7 Hz, 2H), 4.26 (s, 2H), 4.00 (dd, J=7.8, 4.8 Hz, 1H), 3.84–3.66 (m, 2H), 3.52–3.36 (m, 4H), 3.24 (t, J=8.7 Hz, 2H), 2.49–2.35 (m, 2H), 2.25–2.08 (m, 2H), 1.89–1.43 (m, 5H), 1.36 (sextet, J=7.2 Hz, 2H), 0.98–0.91 (m, 9H).

EXAMPLE 37(71)

(3S)-1-butyl-2,5-dioxo-3-(2-methylpropyl)-9-(3,5-dimethyl-1-(4-(2-hydroxyethylaminosulfonyl)phenyl)pyrazol-4-ylmethyl)-1,4,9-triazaspiro[5.5]undecane.2hydrochloride

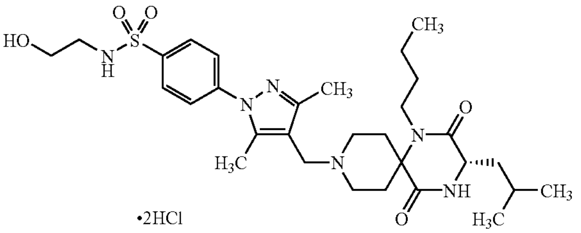

TLC: Rf 0.35 (chloroform:methanol=10:1);

NMR ($CD_3OD$): δ 8.03 (d, J=8.7 Hz, 2H), 7.72 (d, J=8.7 Hz, 2H), 4.32 (s, 2H), 4.02 (dd, J=7.5, 4.5 Hz, 1H), 3.95–3.73 (m, 2H), 3.67–3.57 (m, 2H), 3.56 (t, J=5.7 Hz, 2H), 3.51–3.40 (m, 2H), 3.01 (t, J=5.7 Hz, 2H), 2.63–2.42 (m, 2H), 2.47 (s, 3H), 2.41 (s, 3H), 2.32–2.12 (m, 2H), 1.92–1.44 (m, 5H), 1.44–1.30 (m, 2H), 1.00–0.91 (m, 9H).

EXAMPLE 37(72)

(3S)-1-butyl-2,5-dioxo-3-(2-methylpropyl)-9-(4-(carboxymethyloxy)phenylmethyl)-1,4,9-triazaspiro[5.5]undecane.hydrochloride

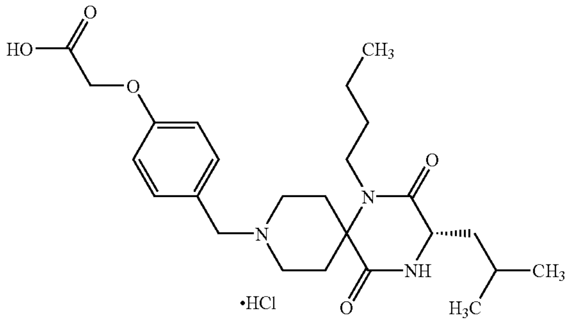

TLC: Rf 0.30 (chloroform:methanol=10:1);

NMR ($CD_3OD$): δ 7.47 (d, J=8.7 Hz, 2H), 7.04 (d, J=8.7 Hz, 2H), 4.71 (s, 2H), 4.29 (s, 2H), 4.00 (dd, J=7.8, 4.5 Hz, 1H), 3.88–3.67 (m, 2H), 3.53–3.33 (m, 4H), 2.46–2.28 (m, 2H), 2.26–2.08 (m, 2H), 1.90–1.27 (m, 7H), 0.99–0.90 (m, 9H).

EXAMPLE 37(73)

(3S)-1-butyl-2,5-dioxo-3-(2-methylpropyl)-9-(4-(1-phenyl-1-hydroxymethyl)phenylmethyl)-1,4,9-triazaspiro[5.5]undecane.hydrochloride

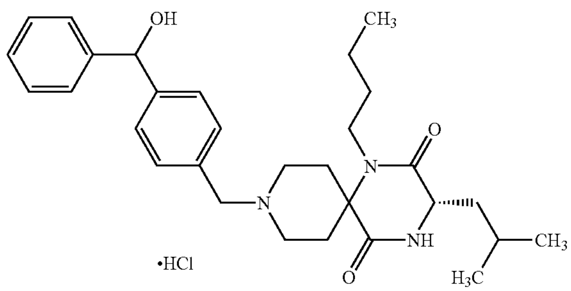

TLC: Rf 0.23 (chloroform:methanol=10:1);

NMR ($CD_3OD$): δ 7.62–7.18 (m, 9H), 5.82 (s, 1H), 4.33 (s, 2H), 4.00 (dd, J=7.8, 4.8 Hz, 1H), 3.88–3.68 (m, 2H), 3.56–3.36 (m, 4H), 2.48–2.28 (m, 2H), 2.24–2.06 (m, 2H), 1.88–1.24 (m, 7H), 0.95 (t, J=6.6 Hz, 3H), 0.94 (d, J=6.3 Hz, 3H), 0.93 (d, J=6.3 Hz, 3H).

EXAMPLE 37(74)

(3S)-1-butyl-2,5-dioxo-3-(2-methylpropyl)-9-(4-(4-hydroxypiperidin-1-ylmethyl)phenylmethyl)-1,4,9-triazaspiro[5.5]undecane.2hydrochloride

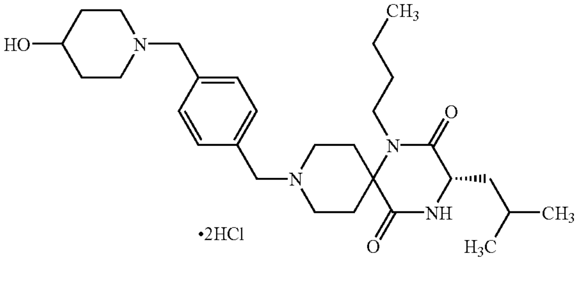

TLC: Rf 0.16 (chloroform:methanol=10:1);

NMR ($CD_3OD$): δ 7.73 (d, J=7.8 Hz, 2H), 7.69–7.61 (m, 2H), 4.42 (s, 2H), 4.40–4.34 (m, 2H), 4.11–4.05 (m, 1H), 4.00 (dd, J=7.5, 4.5 Hz, 1H), 3.93–3.72 (m, 2H), 3.55–3.38 (m, 4H), 3.16–3.00 (m, 1H), 2.60–2.38 (m, 2H), 2.26–2.06 (m, 3H), 2.00–1.88 (m, 2H), 1.88–1.43 (m, 9H), 1.43–1.14 (m, 2H), 0.98–0.90 (m, 9H).

EXAMPLE 37(75)

(3S)-1-butyl-2,5-dioxo-3-(2-methylpropyl)-9-(4-(3-carboxyphenylmethyloxy)phenylmethyl)-1,4,9-triazaspiro[5.5]undecane.hydrochloride

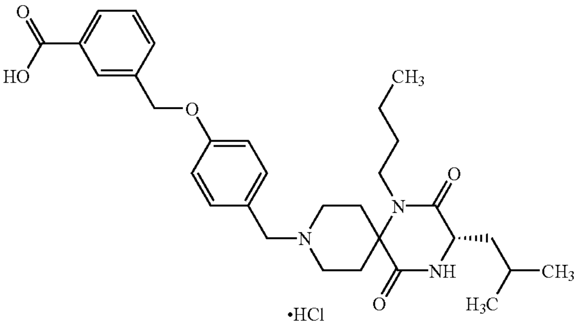

TLC: Rf 0.58 (chloroform:methanol=5:1);

NMR ($CD_3OD$): δ 8.10 (s, 1H), 7.98 (d, J=8.1 Hz, 1H), 7.68 (d, J=8.7 Hz, 1H), 7.50 (t, J=8.1 Hz, 1H), 7.47 (d, J=8.7 Hz, 2H), 7.13 (d, J=8.7 Hz, 2H), 5.22 (s, 2H), 4.29 (s, 2H), 4.01 (dd, J=7.5, 4.5 Hz, 1H), 3.86–3.68 (m, 2H), 3.54–3.32 (m, 4H), 2.42–2.08 (m, 4H), 1.90–1.28 (m, 7H), 0.95 (t, J=6.9 Hz, 3H), 0.95 (d, J=6.3 Hz, 3H), 0.94 (d, J=6.3 Hz, 3H).

EXAMPLE 37(76)

(3S)-1-butyl-2,5-dioxo-3-(2-methylpropyl)-9-(4-(bis(methylsulfonyl)amino)phenylmethyl)-1,4,9-triazaspiro[5.5]undecane.hydrochloride

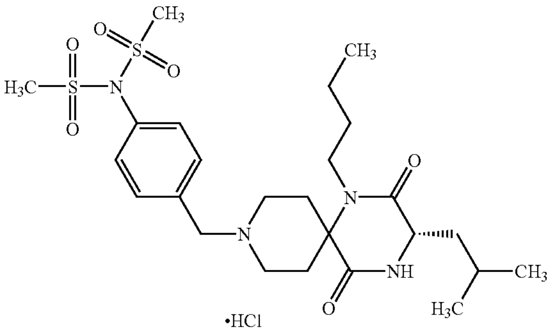

TLC: Rf 0.64 (chloroform:methanol=5:1);

NMR ($CD_3OD$): δ 7.72 (d, J=8.4 Hz, 2H), 7.61 (d, J=8.4 Hz, 2H), 4.44 (s, 2H), 4.03 (dd, J=7.5, 4.5 Hz, 1H), 3.96–3.78 (m, 2H), 3.58–3.36 (m, 4H), 3.47 (s, 6H), 2.50–2.12 (m, 4H), 1.92–1.28 (m, 7H), 0.96 (t, J=6.9 Hz, 3H), 0.95 (d, J=6.3 Hz, 3H), 0.94 (d, J=6.3 Hz, 3H).

EXAMPLE 37(77)

(3S)-1-butyl-2,5-dioxo-3-(2-methylpropyl)-9-(4-(1,4-benzodioxan-6-yloxy)phenylmethyl)-1,4,9-triazaspiro[5.5]undecane.hydrochloride

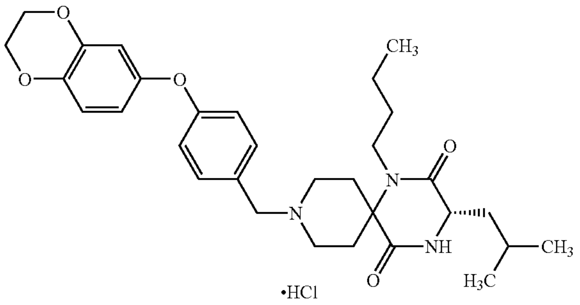

TLC: Rf 0.34 (chloroform:methanol=10:1);

NMR ($CD_3OD$): δ 7.49 (d, J=8.7 Hz, 2H), 7.02 (d, J=8.7 Hz, 2H), 6.85 (m, 1H), 6.55–6.51 (m, 2H), 4.33 (s, 2H), 4.24 (s, 4H), 4.02 (dd, J=7.5, 4.8 Hz, 1H), 3.88–3.70 (m, 2H), 3.56–3.32 (m, 4H), 2.42–2.10 (m, 4H), 1.92–1.24 (m, 7H), 0.96 (t, J=7.2 Hz, 3H), 0.95 (d, J=6.6 Hz, 3H), 0.94 (d, J=6.6 Hz, 3H).

EXAMPLE 37(78)

(3S)-1-butyl-2,5-dioxo-3-(2-methylpropyl)-9-(3-(3-hydroxyphenyl)phenylmethyl)-1,4,9-triazaspiro[5.5]undecane.hydrochloride

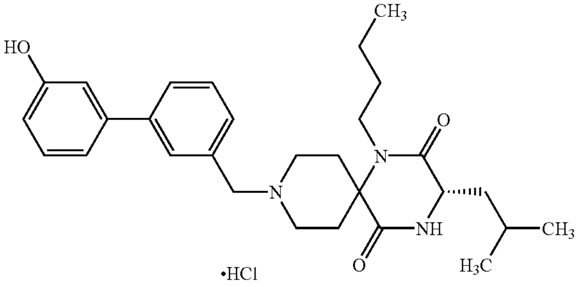

TLC: Rf 0.19 (chloroform:methanol=10:1);

NMR ($CD_3OD$): δ 7.83 (s, 1H), 7.74 (m, 1H), 7.59–7.51 (m, 2H), 7.28 (m, 1H), 7.16–7.09 (m, 2H), 6.81 (m, 1H), 4.44 (s, 2H), 4.01 (dd, J=7.8, 4.5 Hz, 1H), 3.94–3.76 (m, 2H), 3.58–3.32 (m, 4H), 2.50–2.32 (m, 2H), 2.28–2.08 (m, 2H), 1.88–1.26 (m, 7H), 0.95 (t, J=7.2 Hz, 3H), 0.95 (d, J=6.3 Hz, 3H), 0.94 (d, J=6.3 Hz, 3H).

EXAMPLE 37(79)

(3S)-1-butyl-2,5-dioxo-3-(2-methylpropyl)-9-(4-(methylsulfonylamino)phenylmethyl)-1,4,9-triazaspiro[5.5]undecane.hydrochloride

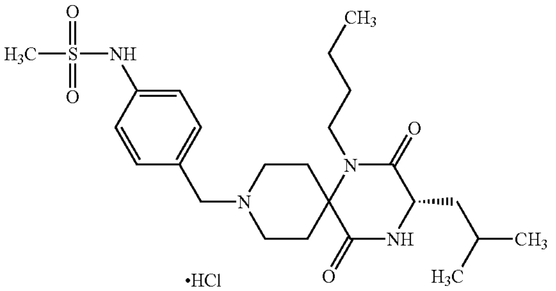

TLC: Rf 0.40 (chloroform:methanol=10:1);

NMR ($CD_3OD$): δ 7.52 (d, J=8.4 Hz, 2H), 7.34 (d, J=8.4 Hz, 2H), 4.32 (s, 2H), 4.01 (dd, J=7.8, 4.8 Hz, 1H), 3.88–3.72 (m, 2H), 3.52–3.14 (m, 4H), 3.01 (s, 3H), 2.46–2.30 (m, 2H), 2.28–2.10 (m, 2H), 1.88–1.10 (m, 7H), 0.98–0.90 (m, 9H).

EXAMPLE 37(80)

(3S)-1-butyl-2,5-dioxo-3-(2-methylpropyl)-9-(6-(4-methoxyphenyloxy)pyridin-3-ylmethyl)-1,4,9-triazaspiro[5.5]undecane.2hydrochloride

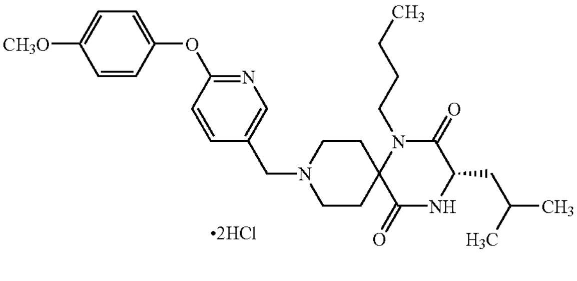

TLC: Rf 0.48 (chloroform:methanol=10:1);

NMR ($CD_3OD$): δ 8.30 (m, 1H), 8.05 (m, 1H), 7.10–6.86 (m, 5H), 4.39 (s, 2H), 4.01 (dd, J=7.8, 4.8 Hz, 1H), 3.90–3.74 (m, 2H), 3.81 (s, 3H), 3.54–3.32 (m, 4H), 2.54–2.32 (m, 2H), 2.28–2.05 (m, 2H), 1.88–1.26 (m, 7H), 0.98–0.90 (m, 9H).

EXAMPLE 37(81)

(3S)-1-butyl-2,5-dioxo-3-(2-methylpropyl)-9-(4-(4-methylaminocarbonylphenyloxy)phenylmethyl)-1,4,9-triazaspiro[5.5]undecane.hydrochloride

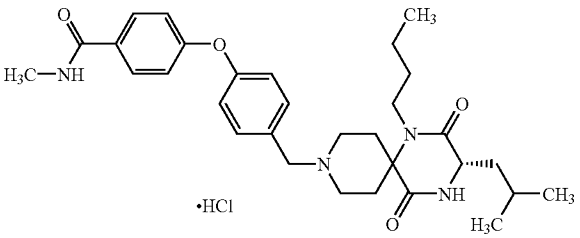

TLC: Rf 0.54 (chloroform:methanol=10:1);

NMR ($CD_3OD$): δ 8.39 (brd, J=4.5 Hz, 1H), 7.84 (d, J=9.0 Hz, 2H), 7.59 (d, J=9.0 Hz, 2H), 7.15 (d, J=9.0 Hz, 2H), 7.07 (d, J=9.0 Hz, 2H), 4.35 (s, 2H), 4.01 (m, 1H), 3.86–3.73 (m, 2H), 3.53–3.41 (m, 4H), 2.91 (d, J=4.5 Hz, 3H), 2.55–2.30 (m, 2H), 2.30–2.10 (m, 2H), 1.90–1.30 (m, 7H), 0.95 (t, J=6.9 Hz, 3H), 0.94 (d, J=6.6 Hz, 3H), 0.93 (d, J=6.6 Hz, 3H).

EXAMPLE 37(82)

(3S)-1-butyl-2,5-dioxo-3-(2-methylpropyl)-9-(4-(4-chlorophenyloxy)phenylmethyl)-1,4,9-triazaspiro[5.5]undecane.hydrochloride

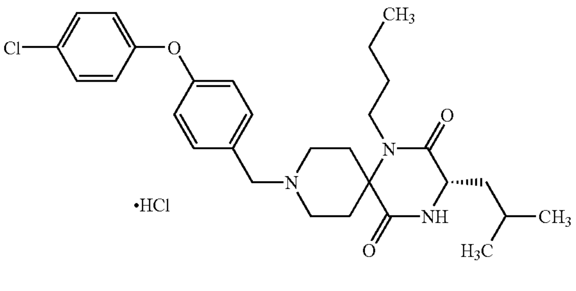

TLC: Rf 0.59 (chloroform:methanol=10:1);

NMR ($CD_3OD$): δ 7.53 (d, J=8.4 Hz, 2H), 7.38 (d, J=9.0 Hz, 2H), 7.08 (d, J=8.4 Hz, 2H), 7.02 (d, J=9.0 Hz, 2H), 4.31 (s, 2H), 4.01 (m, 1H), 3.90–3.70 (m, 2H), 3.60–3.30 (m, 4H), 2.50–2.10 (m, 4H), 1.90–1.30 (m, 7H), 0.95 (t, J=7.2 Hz, 3H), 0.94 (d, J=6.6 Hz, 3H), 0.93 (d, J=6.6 Hz, 3H).

EXAMPLE 37(83)

(3S)-1-butyl-2,5-dioxo-3-(2-methylpropyl)-9-(3-(4-carboxyphenyl)phenylmethyl)-1,4,9-triazaspiro[5.5]undecane.hydrochloride

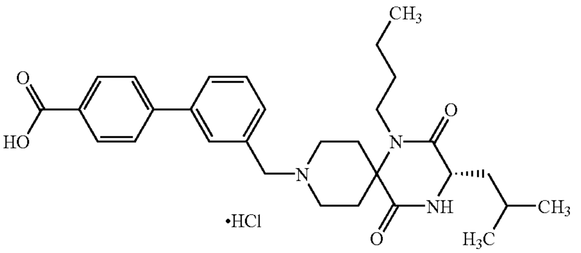

TLC: Rf 0.60 (chloroform:methanol=5:1);

NMR ($CD_3OD$): δ 8.13 (d, J=9.0 Hz, 2H), 7.93 (s, 1H), 7.84 (m, 1H), 7.81 (d, J=9.0 Hz, 2H), 7.66–7.56 (m, 2H), 4.46 (s, 2H), 4.02 (dd, J=7.5, 4.8 Hz, 1H), 3.96–3.74 (m, 2H), 3.58–3.36 (m, 4H), 2.48–2.08 (m, 4H), 1.88–1.24 (m, 7H), 0.95 (t, J=6.9 Hz, 3H), 0.95 (d, J=6.3 Hz, 3H), 0.94 (d, J=6.3 Hz, 3H).

EXAMPLE 37(84)

(3S)-1-butyl-2,5-dioxo-3-(2-methylpropyl)-9-(4-(phenylaminocarbonyl)phenylmethyl)-1,4,9-triazaspiro[5.5]undecane.hydrochloride

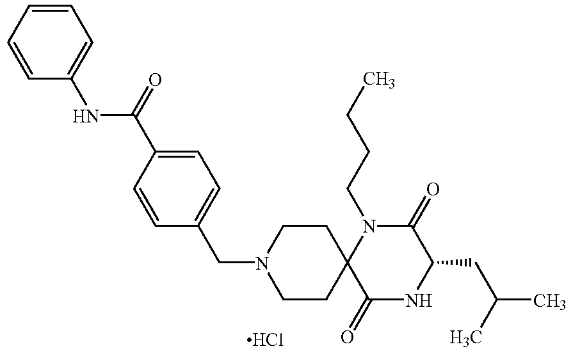

TLC: Rf 0.27 (chloroform:methanol=10:1);

NMR ($CD_3OD$): δ 8.07 (d, J=8.4 Hz, 2H), 7.74 (d, J=8.4 Hz, 2H), 7.72–7.67 (m, 2H), 7.38 (t, J=7.5 Hz, 2H), 7.17 (t, J=7.5 Hz, 1H), 4.47 (s, 2H), 4.02 (dd, J=7.8, 4.5 Hz, 1H), 3.96–3.76 (m, 2H), 3.58–3.36 (m, 4H), 2.54–2.36 (m, 2H), 2.28–2.12 (m, 2H), 1.90–1.24 (m, 7H), 0.96 (t, J=7.2 Hz, 3H), 0.95 (d, J=6.3 Hz, 3H), 0.94 (d, J=6.3 Hz, 3H).

EXAMPLE 37(85)

(3S)-1-butyl-2,5-dioxo-3-(2-methylpropyl)-9-(4-(4-methylthiophenyloxy)phenylmethyl)-1,4,9-triaza-spiro[5.5]undecane.hydrochloride

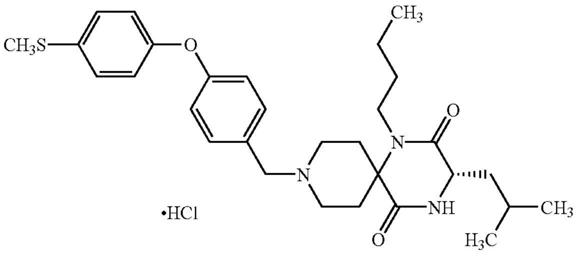

TLC: Rf 0.49 (chloroform:methanol=10:1);

NMR ($CD_3OD$): δ 7.53 (d, J=8.7 Hz, 2H), 7.33 (d, J=8.7 Hz, 2H), 7.07 (d, J=8.7 Hz, 2H), 7.00 (d, J=8.7 Hz, 2H), 4.34 (s, 2H), 4.02 (dd, J=7.8, 4.5 Hz, 1H), 3.88–3.68 (m, 2H), 3.56–3.36 (m, 4H), 2.48 (s, 3H), 2.48–2.32 (m, 2H), 2.28–2.08 (m, 2H), 1.90–1.28 (m, 7H), 0.96 (t, J=7.2 Hz, 3H), 0.95 (d, J=6.3 Hz, 3H), 0.94 (d, J=6.3 Hz, 3H).

EXAMPLE 37(86)

(3S)-1-butyl-2,5-dioxo-3-(2-methylpropyl)-9-(4-(4-(2-dimethylaminoethylaminocarbonyl)phenyloxy)phenylmethyl)-1,4,9-triazaspiro[5.5]undecane.2hydrochloride

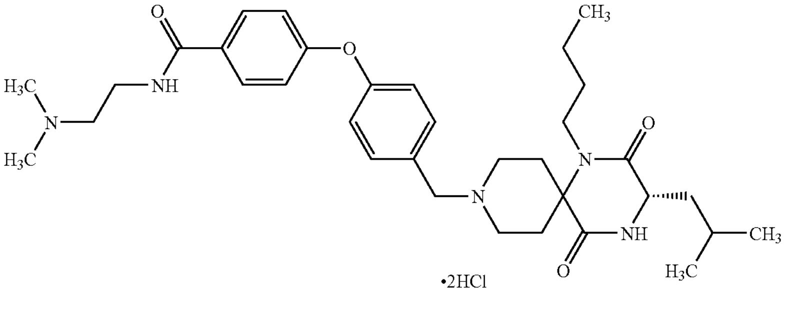

TLC: Rf 0.11 (chloroform:methanol=10:1);

NMR ($CD_3OD$): δ 7.93 (d, J=9.0 Hz, 2H), 7.64 (d, J=8.7 Hz, 2H), 7.15 (d, J=8.7 Hz, 2H), 7.10 (d, J=9.0 Hz, 2H), 4.36 (s, 2H), 4.01 (dd, J=7.8, 4.8 Hz, 1H), 3.88–3.70 (m, 4H), 3.54–3.36 (m, 6H), 2.98 (s, 6H), 2.62–2.44 (m, 2H), 2.24–2.08 (m, 2H), 1.88–1.30 (m, 7H), 0.98–0.90 (m, 9H).

EXAMPLE 37(87)

(3S)-1-butyl-2,5-dioxo-3-(2-methylpropyl)-9-(4-aminocarbonylphenylmethyl)-1,4,9-triazaspiro[5.5]undecane.hydrochloride

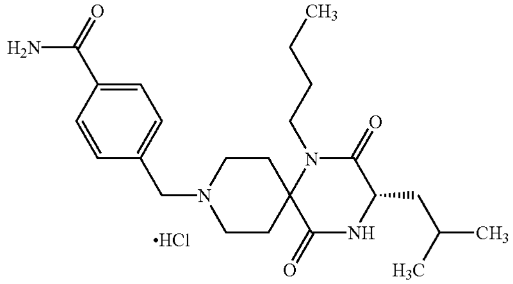

TLC: Rf 0.17 (chloroform:methanol=10:1);

NMR ($CD_3OD$): δ 7.98 (d, J=8.7 Hz, 2H), 7.70 (d, J=8.7 Hz, 2H), 4.43 (s, 2H), 4.00 (dd, J=7.5, 4.5 Hz, 1H), 3.92–3.74 (m, 2H), 3.52–3.36 (m, 4H), 2.58–2.40 (m, 2H), 2.26–2.08 (m, 2H), 1.88–1.28 (m, 7H), 0.98–0.88 (m, 9H).

EXAMPLE 37(88)

(3S)-1-butyl-2,5-dioxo-3-(2-methylpropyl)-9-(4-dimethylaminocarbonylphenylmethyl)-1,4,9-triaza-spiro[5.5]undecane.hydrochloride

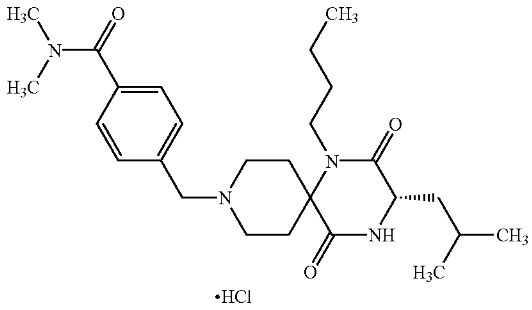

TLC: Rf 0.31 (chloroform:methanol=10:1);

NMR ($CD_3OD$): δ 7.68 (d, J=8.1 Hz, 2H), 7.54 (d, J=8.1 Hz, 2H), 4.41 (s, 2H), 4.01 (dd, J=7.8, 4.8 Hz, 1H), 3.92–3.82 (m, 2H), 3.54–3.36 (m, 4H), 3.11 (s, 3H), 2.99 (s, 3H), 2.56–2.38 (m, 2H), 2.26–2.08 (m, 2H), 1.86–1.28 (m, 7H), 1.00–0.86 (m, 9H).

EXAMPLE 38

(3S)-1-butyl-2,5-dioxo-3-cyclohexylmethyl-9-benzyloxycarbonyl-1,4,9-triazaspiro[5.5]undecane

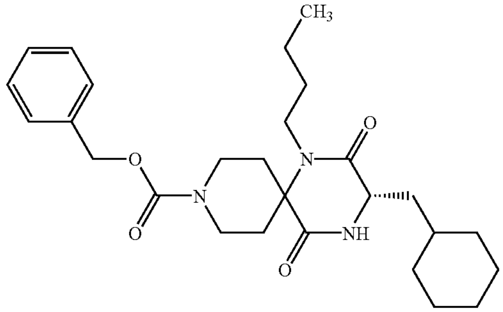

By the same procedure as described in Example 35 using N-(t-butyloxycarbonyl)-L-cyclohexylalanine instead of N-(t-butyloxycarbonyl-L-leucine, the compound of the present invention having the following physical data was obtained.

TLC: Rf 0.35 (hexane:ethyl acetate=1:1);

NMR ($CDCl_3$): δ 7.39–7.31 (m, 5H), 6.48 (brs, 1H), 5.16 (s, 2H), 4.15 (brs, 2H), 4.00 (ddd, J=9.6, 4.8, 1.5 Hz, 1H), 3.76–3.16 (m, 4H), 2.02–1.12 (m, 19H), 1.08–0.88 (m, 2H), 0.92 (t, J=7.2 Hz, 3H).

EXAMPLE 39

(3S)-1-butyl-2,5-dioxo-3-cyclohexyl methyl-1,4,9-triazaspiro[5.5]undecane.hydrochloride

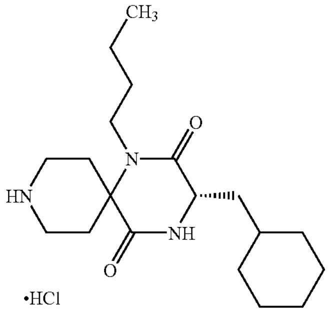

By the same procedure as described in Example 9 using the compound prepared in Example 38, the compound of the present invention having the following physical data was obtained.

TLC: Rf 0.08 (chloroform:methanol: acetic acid=90:10:1);

NMR ($CD_3OD$): δ 4.05 (dd, J=7.8, 4.8 Hz, 1H), 3.84–3.68 (m, 2H), 3.46–3.34 (m, 4H), 2.40–2.04 (m, 4H), 1.83–1.46 (m, 10H), 1.39 (sextet, J=7.5 Hz, 2H), 1.33–1.15 (m, 3H), 1.05–0.86 (m, 2H), 0.97 (t, J=7.2 Hz, 3H).

EXAMPLE 40(1)~40(90)

By the same procedure as described in Example 10 using the compound prepared in Example 39 and the corresponding aldehyde derivatives, the following compounds of the present invention were obtained.

EXAMPLE 40(1)

(3S)-1-butyl-2,5-dioxo-3-cyclohexylmethyl-9-(4-(4-methylphenyloxy)phenylmethyl)-1,4,9-triazaspiro[5.5]undecane.hydrochloride

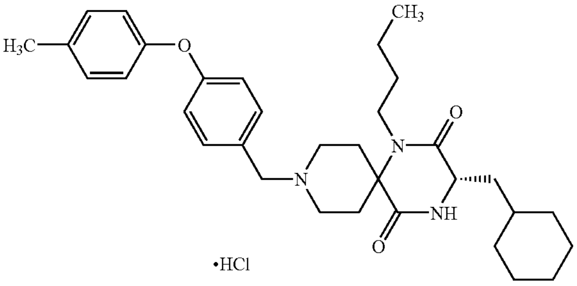

TLC: Rf 0.71 (ethyl acetate);

NMR ($CD_3OD$): δ 7.50 (d, J=8.7 Hz, 2H), 7.19 (d, J=8.7 Hz, 2H), 7.02 (d, J=8.7 Hz, 2H), 6.92 (d, J=8.7 Hz, 2H), 4.32 (s, 2H), 4.04 (dd, J=7.5, 4.5 Hz, 1H), 3.87–3.69 (m, 2H), 3.55–3.42 (m, 2H), 3.42–3.34 (m, 2H), 2.49–2.30 (m, 2H), 2.33 (s, 3H), 2.30–2.08 (m, 2H), 1.82–1.10 (m, 15H), 1.05–0.85 (m, 2H), 0.95 (t, J=7.2 Hz, 3H).

EXAMPLE 40(2)

(3S)-1-butyl-2,5-dioxo-3-cyclohexylmethyl-9-(4-(4-methoxyphenyloxy)phenylmethyl)-1,4,9-triazaspiro[5.5]undecane.hydrochloride

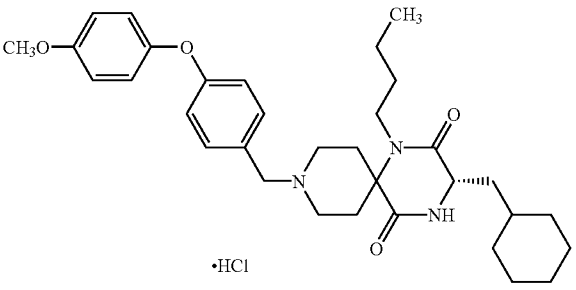

TLC: Rf 0.67 (ethyl acetate);

NMR ($CD_3OD$): δ 7.49 (d, J=8.4 Hz, 2H), 7.02–6.92 (m, 6H), 4.31 (s, 2H), 4.03 (dd, J=7.5, 4.5 Hz, 1H), 3.86–3.69 (m, 2H), 3.79 (s, 3H), 3.54–3.30 (m, 4H), 2.50–2.30 (m, 2H), 2.28–2.06 (m, 2H), 1.83–1.10 (m, 15H), 1.05–0.83 (m, 2H), 0.95 (t, J=7.2 Hz, 3H).

EXAMPLE 40(3)

(3S)-1-butyl-2,5-dioxo-3-cyclohexylmethyl-9-(2-fluorophenylmethyl)-1,4,9-triazaspiro[5.5]undecane-.hydrochloride

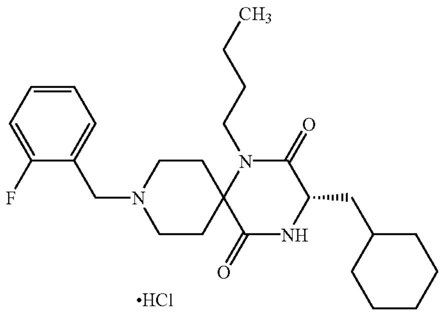

TLC: Rf 0.38 (hexane:ethyl acetate=1:1);

NMR ($CD_3OD$): δ 7.70–7.53 (m, 2H), 7.38–7.23 (m, 2H), 4.44 (s, 2H), 4.03 (dd, J=7.5, 4.5 Hz, 1H), 3.95–3.77 (m, 2H), 3.60–3.45 (m, 2H), 3.45–3.30 (m, 2H), 2.53–2.34 (m, 2H), 2.28–2.08 (m, 2H), 1.83–1.10 (m, 15H), 1.05–0.82 (m, 2H), 0.94 (t, J=7.2 Hz, 3H).

EXAMPLE 40(4)

(3S)-1-butyl-2,5-dioxo-3-cyclohexylmethyl-9-(3-fluorophenylmethyl)-1,4,9-triazaspiro[5.5]undecane-.hydrochloride

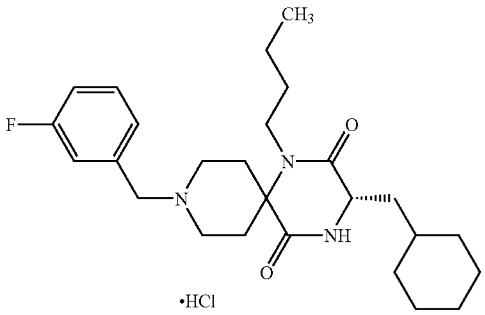

TLC: Rf 0.40 (hexane:ethyl acetate=1:1);

NMR ($CD_3OD$): δ 7.57–7.48 (m, 1H), 7.44–7.37 (m, 2H), 7.30–7.21 (m, 1H), 4.38 (s, 2H), 4.03 (dd, J=7.8, 4.8 Hz, 1H), 3.90–3.72 (m, 2H), 3.55–3.33 (m, 4H), 2.56–2.37 (m, 2H), 2.25–2.04 (m, 2H), 1.82–1.08 (m, 15H), 1.06–0.83 (m, 2H), 0.95 (t, J=7.2 Hz, 3H).

EXAMPLE 40(5)

(3S)-1-butyl-2,5-dioxo-3-cyclohexylmethyl-9-(4-fluorophenylmethyl)-1,4,9-triazaspiro[5.5]undecane-.hydrochloride

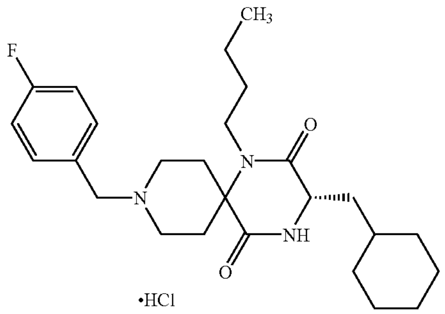

TLC: Rf 0.27 (hexane:ethyl acetate=1:1);

NMR ($CD_3OD$): δ 7.62 (dd, J=8.7, 5.1 Hz, 2H), 7.23 (dd, J=8.7, 8.7 Hz, 2H), 4.36 (s, 2H), 4.03 (dd, J=7.8, 4.8 Hz, 1H), 3.88–3.71 (m, 2H), 3.53–3.33 (m, 4H), 2.53–2.35 (m, 2H), 2.27–2.04 (m, 2H), 1.82–1.10 (m, 15H), 1.05–0.82 (m, 2H), 0.94 (t, J=7.2 Hz, 3H).

EXAMPLE 40(6)

(3S)-1-butyl-2,5-dioxo-3-cyclohexylmethyl-9-(3-chlorophenylmethyl)-1,4,9-triazaspiro[5.5]undecane-.hydrochloride

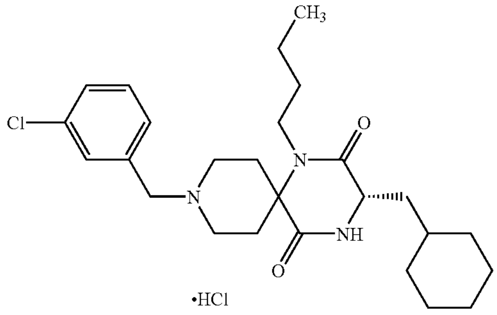

TLC: Rf 0.60 (hexane:ethyl acetate=1:1);

NMR ($CD_3OD$): δ 7.65 (m, 1H), 7.55–7.49 (m, 3H), 4.37 (s, 2H), 4.04 (dd, J=7.0, 4.5 Hz, 1H), 3.83 (m, 2H), 3.54–3.47 (m, 2H), 3.41–3.35 (m, 2H), 2.38 (m, 2H), 2.18 (m, 2H), 1.78–1.47 (m, 9H), 1.42–1.17 (m, 6H), 0.95 (t, J=7.5 Hz, 3H), 0.97–0.92 (m, 2H).

EXAMPLE 40(7)

(3S)-1-butyl-2,5-dioxo-3-cyclohexylmethyl-9-(4-cyclohexyloxyphenylmethyl)-1,4,9-triazaspiro[5.5]undecane.hydrochloride

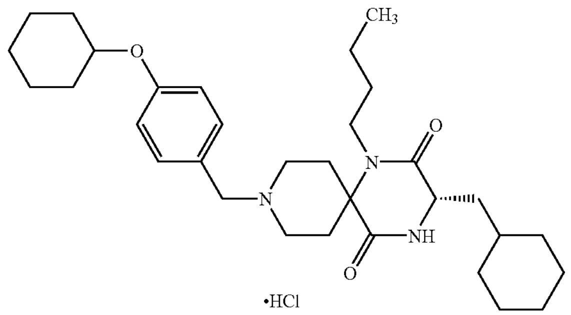

TLC: Rf 0.36 (chloroform:methanol=10:1);

NMR ($CD_3OD$): δ 7.41 (d, J=8.7 Hz, 2H), 7.00 (d, J=8.7 Hz, 2H), 4.36 (m, 1H), 4.24 (s, 2H), 4.03 (dd, J=7.8, 4.5 Hz, 1H), 3.82–3.65 (m, 2H), 3.50–3.30 (m, 4H), 2.42–2.25 (m, 2H), 2.25–2.06 (m, 2H), 2.02–1.92 (m, 2H), 1.84–1.14 (m, 23H), 1.04–0.89 (m, 5H).

EXAMPLE 40(8)

(3S)-1-butyl-2,5-dioxo-3-cyclohexylmethyl-9-(4-methoxy-3-hydroxyphenylmethyl)-1,4,9-triazaspiro[5.5]undecane.hydrochloride

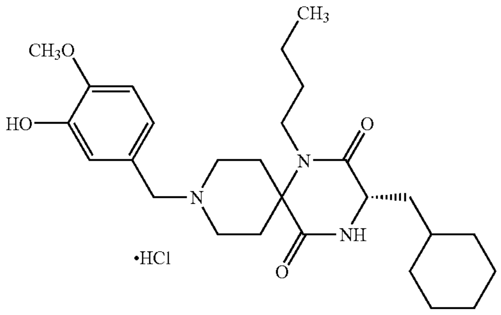

TLC: Rf 0.34 (chloroform:methanol=10:1);

NMR ($CD_3OD$): δ 7.01 (d, J=7.8 Hz, 1H), 6.99–6.93 (m, 2H), 4.22 (s, 2H), 4.03 (dd, J=7.5, 4.8 Hz, 1H), 3.87 (s, 3H), 3.83–3.67 (m, 2H), 3.52–3.42 (m, 2H), 3.42–3.33 (m, 2H), 2.44–2.27 (m, 2H), 2.26–2.07 (m, 2H), 1.83–1.12 (m, 15H), 1.04–0.89 (m, 5H).

EXAMPLE 40(9)

(3S)-1-butyl-2,5-dioxo-3-cyclohexylmethyl-9-(2-chlorophenylmethyl)-1,4,9-triazaspiro[5.5]undecane-.hydrochloride

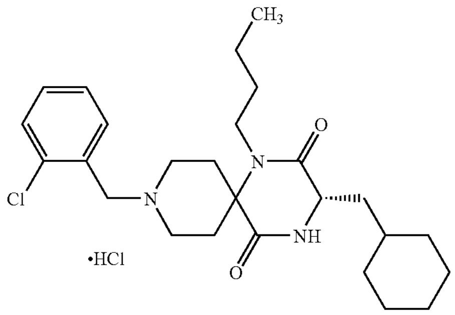

TLC: Rf 0.77 (chloroform:methanol=10:1);

NMR ($CD_3OD$): δ 7.69 (dd, J=7.5, 2.1 Hz, 1H), 7.60 (dd, J=7.5, 2.1 Hz, 1H), 7.51 (dt, J=2.1, 7.5 Hz, 1H), 7.47 (dt, J=2.1, 7.5 Hz, 1H), 4.52 (s, 2H), 4.04 (dd, J=7.8, 4.8 Hz, 1H), 4.00–3.82 (m, 2H), 3.60–3.48 (m, 2H), 3.43–3.34 (m, 2H), 2.48–2.29 (m, 2H), 2.28–2.07 (m, 2H), 1.83–1.44 (m, 10H), 1.43–1.12 (m, 5H), 1.04–0.88 (m, 5H).

EXAMPLE 40(10)

(3S)-1-butyl-2,5-dioxo-3-cyclohexyl methyl-9-(2-methylphenylmethyl)-1,4,9-triazaspiro[5.5]undecane.hydrochloride

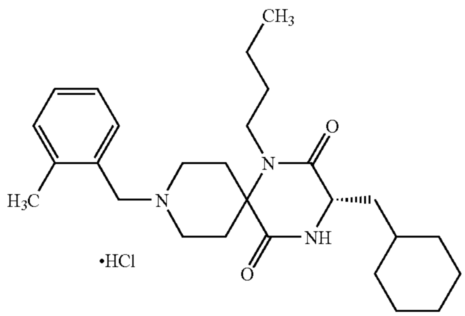

TLC: Rf 0.77 (chloroform:methanol=10:1);

NMR ($CD_3OD$): δ 7.56 (d, J=7.2 Hz, 1H), 7.41–7.30 (m, 3H), 4.41 (s, 2H), 4.04 (dd, J=7.5, 4.5 Hz, 1H), 3.98–3.79 (m, 2H), 3.57–3.48 (m, 2H), 3.44–3.39 (m, 2H), 2.56–2.38 (m, 2H), 2.48 (s, 3H), 2.26–2.06 (m, 2H), 1.82–1.15 (m, 15H), 1.02–0.84 (m, 5H).

EXAMPLE 40(11)

(3S)-1-butyl-2,5-dioxo-3-cyclohexylmethyl-9-(3-methylphenylmethyl)-1,4,9-triazaspiro[5.5]undecane.hydrochloride

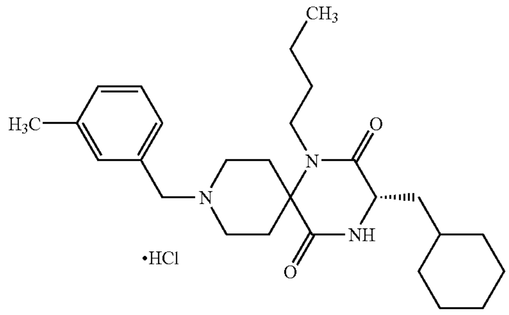

TLC: Rf 0.58 (chloroform:methanol=10:1);

NMR ($CD_3OD$): δ 7.40–7.28 (m, 4H), 4.31 (s, 2H), 4.03 (dd, J=7.5, 4.5 Hz, 1H), 3.84–3.70 (m, 2H), 3.52–3.46 (m, 4H), 2.51–2.30 (m, 2H), 2.39 (s, 3H), 2.24–2.04 (m, 2H), 1.80–1.12 (m, 15H), 1.02–0.84 (m, 5H).

EXAMPLE 40(12)

(3S)-1-butyl-2,5-dioxo-3-cyclohexylmethyl-9-(4-methylphenylmethyl)-1,4,9-triazaspiro[5.5]undecane.hydrochloride

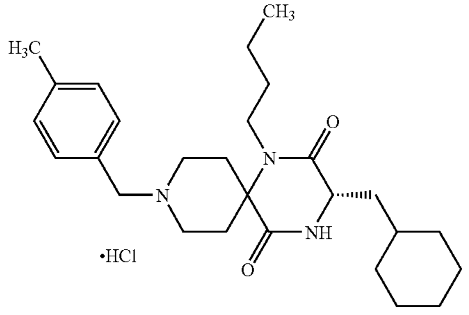

TLC: Rf 0.61 (chloroform:methanol=10:1);

NMR ($CD_3OD$): δ 7.44 (d, J=8.4 Hz, 2H), 7.31 (d, J=8.4 Hz, 2H), 4.31 (s, 2H), 4.03 (dd, J=7.5, 4.5 Hz, 1H), 3.88–3.70 (m, 2H), 3.52–3.36 (m, 4H), 2.48–2.30 (m, 2H), 2.38 (s, 3H), 2.30–2.08 (m, 2H), 1.81–1.10 (m, 15H), 1.04–0.82 (m, 5H).

EXAMPLE 40(13)

(3S)-1-butyl-2,5-dioxo-3-cyclohexylmethyl-9-(4-phenylthiophenylmethyl)-1,4,9-triazaspiro[5.5]undecane.hydrochloride

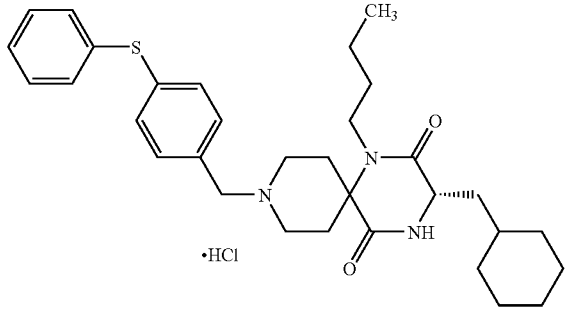

TLC: Rf 0.74 (chloroform:methanol=10:1);

NMR ($CD_3OD$): δ 7.50–7.37 (m, 7H), 7.29 (d, J=8.4 Hz, 2H), 4.31 (s, 2H), 4.03 (dd, J=7.5, 4.8 Hz, 1H), 3.84–3.70 (m, 2H), 3.50–3.32 (m, 4H), 2.56–2.38 (m, 2H), 2.24–2.05 (m, 2H), 1.81–1.06 (m, 15H), 1.02–0.84 (m, 5H).

EXAMPLE 40(14)

(3S)-1-butyl-2,5-dioxo-3-cyclohexylmethyl-9-(3-(2-methylpropyl)phenylmethyl)-1,4,9-triazaspiro[5.5]undecane.hydrochloride

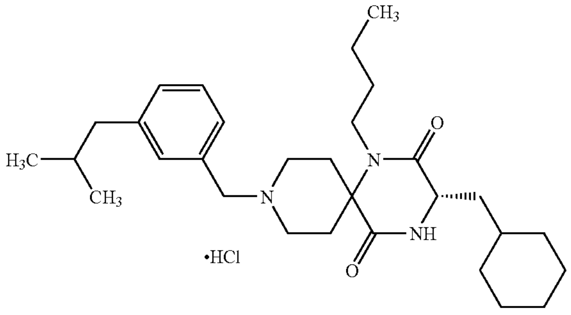

TLC: Rf 0.41 (chloroform:methanol=19:1);

NMR ($CD_3OD$): δ 7.47 (d, J=7.5 Hz, 2H), 7.29 (d, J=7.5 Hz, 2H), 4.32 (s, 2H), 4.03 (dd, J=7.8, 4.8 Hz, 1H), 3.80 (m, 2H), 3.56–3.36 (m, 4H), 2.52 (d, J=7.2 Hz, 2H), 2.45 (m, 2H), 2.16 (m, 2H), 1.96–1.14 (m, 16H), 0.97–0.89 (m, 11H).

EXAMPLE 40(15)

(3S)-1-butyl-2,5-dioxo-3-cyclohexylmethyl-9-(3-butylphenylmethyl)-1,4,9-triazaspiro[5.5]undecane-.hydrochloride

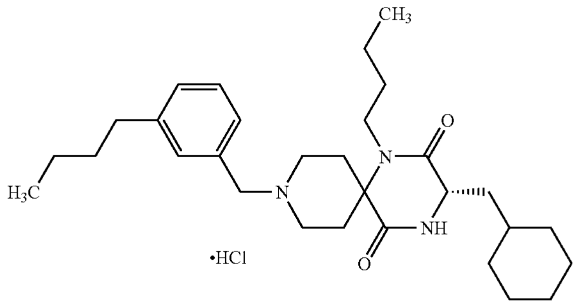

TLC: Rf 0.37 (chloroform:methanol=19:1);

NMR ($CD_3OD$): δ 7.46 (d, J=8.4 Hz, 2H), 7.32 (d, J=8.4 Hz, 2H), 4.31 (s, 2H), 4.03 (dd, J=7.2, 4.8 Hz, 1H), 3.79 (m, 2H), 3.56–3.36 (m, 4H), 2.66 (t, J=7.5 Hz, 2H), 2.41 (m, 2H), 2.16 (m, 2H), 1.82–1.20 (m, 19H), 1.00–0.89 (m, 2H), 0.94 (t, J=7.2 Hz, 3H), 0.93 (t, J=7.2 Hz, 3H).

EXAMPLE 40(16)

(3S)-1-butyl-2,5-dioxo-3-cyclohexylmethyl-9-(4-isopropylphenylmethyl)-1,4,9-triazaspiro[5.5]undecane.hydrochloride

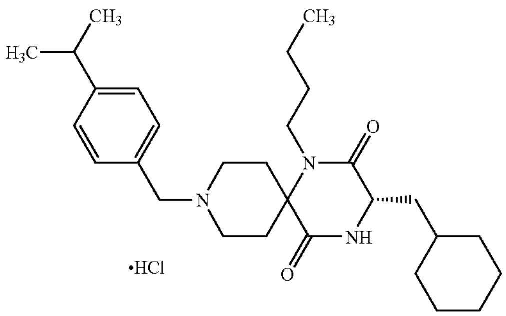

TLC: Rf 0.63 (chloroform:methanol=10:1);

NMR ($CD_3OD$): δ 7.46 (d, J=8.4 Hz, 2H), 7.37 (d, J=8.4 Hz, 2H), 4.32 (s, 2H), 4.03 (dd, J=7.8, 4.8 Hz, 1H), 3.88–3.74 (m, 2H), 3.52–3.43 (m, 2H), 3.43–3.32 (m, 2H), 3.02–2.90 (m, 1H), 2.45–2.25 (m, 2H), 2.25–2.08 (m, 2H), 1.80–1.12 (m, 21H), 1.04–0.88 (m, 5H).

EXAMPLE 40(17)

(3S)-1-butyl-2,5-dioxo-3-cyclohexylmethyl-9-(4-methoxy-3-fluorophenylmethyl)-1,4,9-triazaspiro[5.5]undecane.hydrochloride

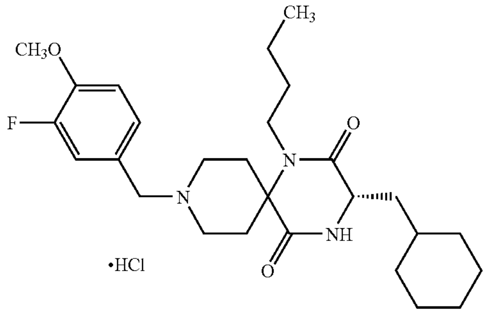

TLC: Rf 0.58 (chloroform:methanol=10:1);

NMR ($CD_3OD$): δ 7.40–7.31 (m, 2H), 7.22–7.17 (m, 1H), 4.30 (s, 2H), 4.03 (dd, J=7.8, 4.8 Hz, 1H), 3.90 (s, 3H), 3.86–3.70 (m, 2H), 3.50–3.38 (m, 4H), 2.52–2.32 (m, 2H), 2.26–2.05 (m, 2H), 1.80–1.15 (m, 15H), 1.01–0.88 (m, 5H).

EXAMPLE 40(18)

(3S)-1-butyl-2,5-dioxo-3-cyclohexylmethyl-9-(4-(2-hydroxyethoxy)phenylmethyl)-1,4,9-triazaspiro[5.5]undecane.hydrochloride

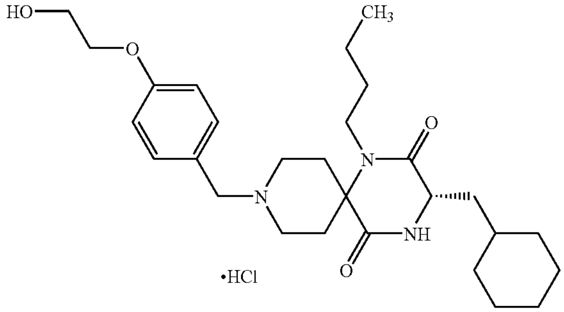

TLC: Rf 0.40 (chloroform:methanol=10:1);

NMR ($CD_3OD$): δ 7.47 (d, J=8.7 Hz, 2H), 7.06 (d, J=8.7 Hz, 2H), 4.29 (s, 2H), 4.08–4.00 (m, 3H), 3.89–3.84 (m, 2H), 3.84–3.68 (m, 2H), 3.52–3.36 (m, 4H), 2.48–2.30 (m, 2H), 2.25–2.08 (m, 2H), 1.80–1.10 (m, 15H), 1.04–0.86 (m, 5H).

EXAMPLE 40(19)

(3S)-1-butyl-2,5-dioxo-3-cyclohexylmethyl-9-(2-hydroxy-3-methyl phenylmethyl)-1,4,9-triazaspiro[5.5]undecane.hydrochloride

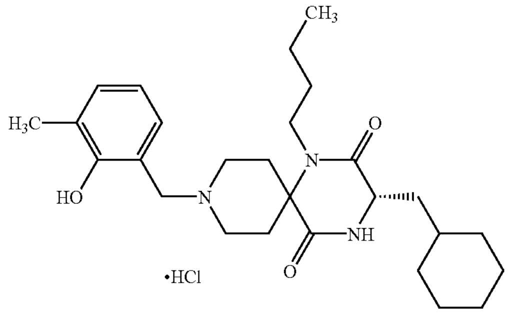

TLC: Rf 0.85 (chloroform:methanol=10:1);

NMR ($CD_3OD$): δ 7.30–7.21 (m, 2H), 6.88 (t, J=7.5 Hz, 1H), 4.36 (s, 2H), 4.03 (dd, J=7.8, 4.2 Hz, 1H), 3.94–3.78 (m, 2H), 3.56–3.46 (m, 2H), 3.42–3.32 (m, 2H), 2.50–2.30 (m, 2H), 2.28 (s, 3H), 2.28–2.06 (m, 2H), 1.82–1.01 (m, 15H), 1.00–0.87 (m, 5H).

EXAMPLE 40(20)

(3S)-1-butyl-2,5-dioxo-3-cyclohexylmethyl-9-(4-chlorophenylmethyl)-1,4,9-triazaspiro[5.5]undecane-.hydrochloride

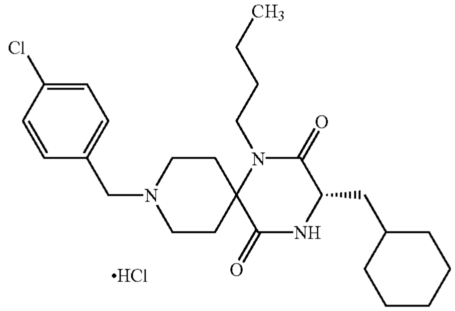

TLC: Rf 0.60 (chloroform:methanol=20:1);

NMR ($CD_3OD$): δ 7.57 (d, J=8.7 Hz, 2H), 7.51 (d, J=8.7 Hz, 2H), 4.36 (s, 2H), 4.03 (dd, J=7.5, 4.8 Hz, 1H), 3.89–3.71 (m, 2H), 3.53–3.33 (m, 4H), 2.52–2.32 (m, 2H), 2.26–2.07 (m, 2H), 1.83–1.06 (m, 15H), 1.04–0.84 (m, 2H), 0.95 (t, J=6.9 Hz, 3H).

EXAMPLE 40(21)

(3S)-1-butyl-2,5-dioxo-3-cyclohexylmethyl-9-(7-methoxy-1,3-benzodioxolan-5-ylmethyl)-1,4,9-triazaspiro[5.5]undecane.hydrochloride

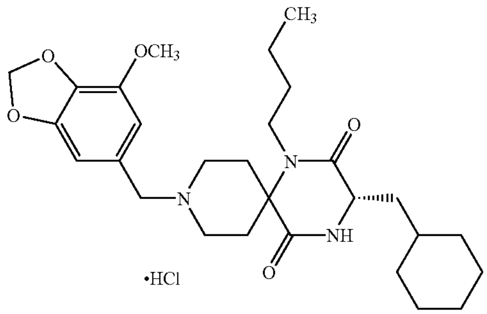

TLC: Rf 0.43 (chloroform:methanol=20:1);

NMR ($CD_3OD$): δ 6.85 (s, 1H), 6.74 (s, 1H), 5.99 (s, 2H), 4.25 (s, 2H), 4.03 (dd, J=7.5, 4.5 Hz, 1H), 3.92 (s, 3H), 3.87–3.67 (m, 2H), 3.54–3.34 (m, 4H), 2.53–2.30 (m, 2H), 2.25–2.05 (m, 2H), 1.83–1.10 (m, 15H), 1.06–0.83 (m, 2H), 0.95 (t, J=7.2 Hz, 3H).

EXAMPLE 40(22)

(3S)-1-butyl-2,5-dioxo-3-cyclohexylmethyl-9-(3-methyl-4-methoxyphenylmethyl)-1,4,9-triazaspiro[5.5]undecane.hydrochloride

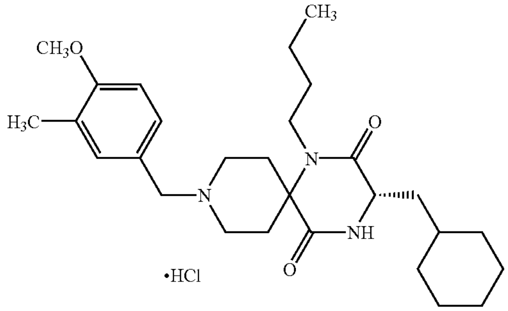

TLC: Rf 0.38 (chloroform:methanol=20:1);

NMR ($CD_3OD$): δ 7.37–7.28 (m, 2H), 6.99 (d, J=8.1 Hz, 1H), 4.25 (s, 2H), 4.03 (dd, J=7.5, 4.5 Hz, 1H), 3.85 (s, 3H), 3.84–3.66 (m, 2H), 3.52–3.32 (m, 4H), 2.48–2.28 (m, 2H), 2.22 (s, 3H), 2.22–2.05 (m, 2H), 1.83–1.10 (m, 15H), 1.06–0.83 (m, 2H), 0.94 (t, J=6.9 Hz, 3H).

EXAMPLE 40(23)

(3S)-1-butyl-2,5-dioxo-3-cyclohexylmethyl-9-(4-(4-fluorophenyloxy)phenylmethyl)-1,4,9-triazaspiro[5.5]undecane.hydrochloride

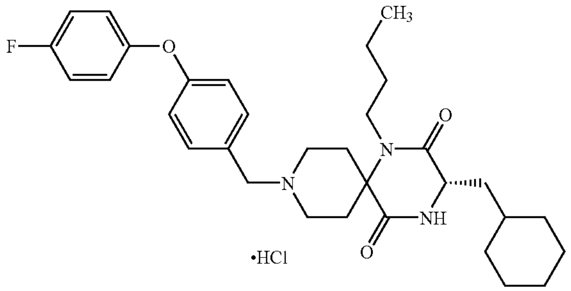

TLC: Rf 0.53 (chloroform:methanol=20:1);

NMR ($CD_3OD$): δ 7.53 (d, J=8.7 Hz, 2H), 7.18–7.00 (m, 6H), 4.33 (s, 2H), 4.04 (dd, J=7.5, 4.5 Hz, 1H), 3.87–3.69 (m, 2H), 3.55–3.32 (m, 4H), 2.52–2.32 (m, 2H), 2.28–2.08 (m, 2H), 1.83–1.12 (m, 15H), 1.06–0.83 (m, 2H), 0.95 (t, J=7.2 Hz, 3H).

EXAMPLE 40(24)

(3S)-1-butyl-2,5-dioxo-3-cyclohexylmethyl-9-(4-trifluoromethoxyphenylmethyl)-1,4,9-triazaspiro[5.5]undecane.hydrochloride

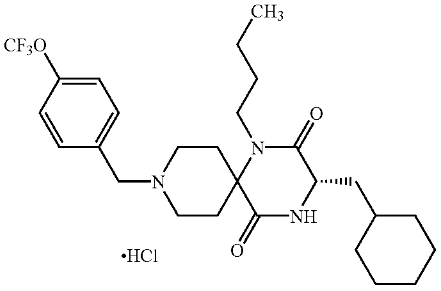

TLC: Rf 0.60 (chloroform:methanol=10:1);

NMR ($CD_3OD$): δ 7.72–7.69 (m, 2H), 7.41 (d, J=7.8 Hz, 2H), 4.40 (s, 2H), 4.03 (dd, J=7.5, 4.5 Hz, 1H), 3.90–3.75 (m, 2H), 3.52–3.38 (m, 4H), 2.54–2.32 (m, 2H), 2.28–2.10 (m, 2H), 1.80–1.10 (m, 15H), 1.02–0.88 (m, 5H).

EXAMPLE 40(25)

(3S)-1-butyl-2,5-dioxo-3-cyclohexyl methyl-9-(3-methyl-5-chloro-1-phenyl pyrazol-4-ylmethyl)-1,4,9-triazaspiro[5.5]undecane.2 hydrochloride

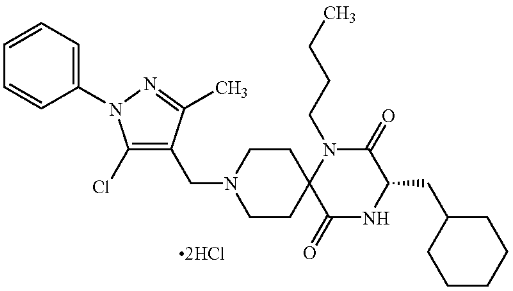

TLC: Rf 0.50 (chloroform:methanol=10:1);

NMR ($CD_3OD$): δ 7.56–7.50 (m, 5H), 4.33 (s, 2H), 4.05 (dd, J=7.8, 4.5 Hz, 1H), 3.98–3.80 (m, 2H), 3.70–3.59 (m, 2H), 3.50–3.40 (m, 2H), 2.60–2.38 (m, 2H), 2.45 (s, 3H), 2.32–2.14 (m, 2H), 1.82–1.14 (m, 15H), 1.02–0.86 (m, 5H),

EXAMPLE 40(26)

(3S)-1-butyl-2,5-dioxo-3-cyclohexylmethyl-9-(2,3-dimethyl-5-oxo-1-phenylpyrazolin-4-ylmethyl)-1,4,9-triazaspiro[5.5]undecane.2 hydrochloride

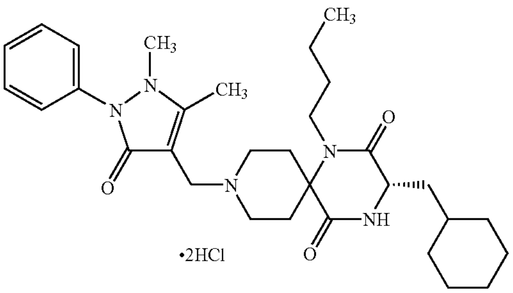

TLC: Rf 0.27 (chloroform:methanol=10:1);

NMR ($CD_3OD$): δ 7.62–7.48 (m, 3H), 7.44–7.38 (m, 2H), 4.13 (s, 2H), 4.04 (dd, J=7.5, 4.5 Hz, 1H), 3.88–3.72 (m, 2H), 3.64–3.52 (m, 2H), 3.50–3.38 (m, 2H), 3.35 (s, 3H), 2.60–2.40 (m, 2H), 2.48 (s, 3H), 2.28–2.10 (m, 2H), 1.82–1.10 (m, 15H), 1.02–0.84 (m, 5H).

EXAMPLE 40(27)

(3S)-1-butyl-2,5-dioxo-3-cyclohexylmethyl-9-(1-(2-methylpropyloxycarbonyl)indol-5-ylmethyl)-1,4,9-triazaspiro[5.5]undecane.hydrochloride

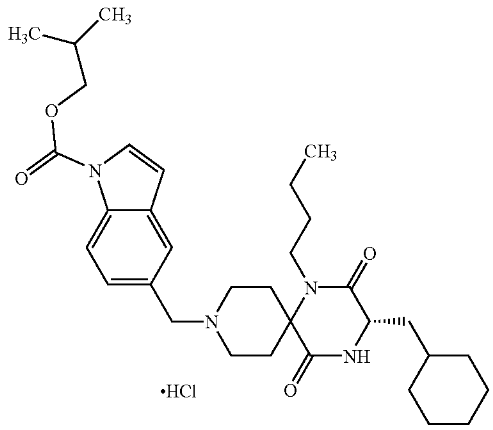

TLC: Rf 0.55 (chloroform:methanol=10:1);

NMR ($CD_3OD$): δ 8.26 (d, J=8.4 Hz, 1H), 7.82 (s, 1H), 7.76 (d, J=3.6 Hz, 1H), 7.50 (dd, J=8.4, 1.8 Hz, 1H), 6.74 (d, J=3.6 Hz, 1H), 4.44 (s, 2H), 4.25 (d, J=6.6 Hz, 2H), 4.03 (dd, J=7.8, 4.8 Hz, 1H), 3.86–3.72 (m, 2H), 3.52–3.40 (m, 4H), 2.52–2.36 (m, 2H), 2.25–2.06 (m, 3H), 1.80–1.10 (m, 15H), 1.07 (d, J=9.0 Hz, 6H), 1.00–0.84 (m, 5H).

EXAMPLE 40(28)

(3S)-1-butyl-2,5-dioxo-3-cyclohexylmethyl-9-(5-methyl-2-phenyloxazol-4-ylmethyl)-1,4,9-triazaspiro[5.5]undecane.hydrochloride

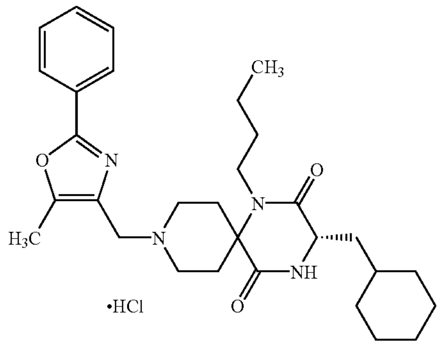

TLC: Rf 0.48 (chloroform:methanol=10:1);

NMR ($CD_3OD$): δ 8.04–8.00 (m, 2H), 7.51–7.49 (m, 3H), 4.34 (s, 2H), 4.04 (dd, J=7.8, 4.8 Hz, 1H), 3.98–3.82 (m, 2H), 3.70–3.60 (m, 2H), 3.44–3.38 (m, 2H), 2.52 (s, 3H), 2.50–2.36 (m, 2H), 2.28–2.12 (m, 2H), 1.80–1.12 (m, 15H), 1.00–0.86 (m, 5H).

EXAMPLE 40(29)

(3S)-1-butyl-2,5-dioxo-3-cyclohexylmethyl-9-(3,5-dimethyl-1-(4-methylsulfonylaminophenyl)pyrazol-4-ylmethyl)-1,4,9-triazaspiro[5.5]undecane.2 hydrochloride

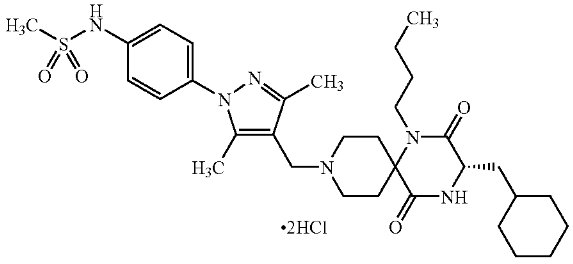

TLC: Rf 0.32 (chloroform:methanol=10:1);

NMR ($CD_3OD$): δ 7.47 (d, J=9.0 Hz, 2H), 7.41 (d, J=9.0 Hz, 2H), 4.32 (s, 2H), 4.04 (dd, J=7.8, 4.8 Hz, 1H), 3.92–3.76 (m, 2H), 3.65–3.58 (m, 2H), 3.52–3.45 (m, 2H), 3.04 (s, 3H), 2.64–2.50 (m, 2H), 2.43 (s, 3H), 2.40 (s, 3H), 2.28–2.12 (m, 2H), 1.82–1.10 (m, 15H), 1.00–0.88 (m, 5H).

EXAMPLE 40(30)

(3S)-1-butyl-2,5-dioxo-3-cyclohexylmethyl-9-(4-(4-methylsulfonylaminophenyloxy)phenylmethyl)-1,4,9-triazaspiro[5.5]undecane.hydrochloride

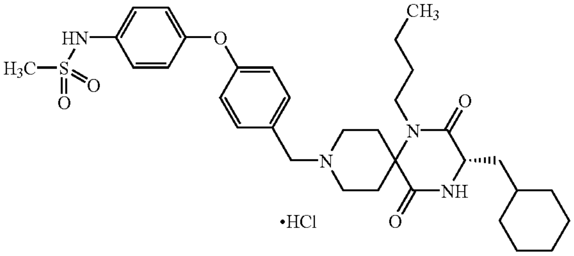

TLC: Rf 0.42 (chloroform:methanol=10:1);

NMR ($CD_3OD$): δ 7.53 (d, J=9.0 Hz, 2H), 7.29 (d, J=9.0 Hz, 2H), 7.08–7.00 (m, 4H), 4.33 (s, 2H), 4.03 (dd, J=7.5, 4.8 Hz, 1H), 3.85–3.72 (m, 2H), 3.54–3.36 (m, 4H), 2.95 (s, 3H), 2.48–2.34 (m, 2H), 2.25–2.08 (m, 2H), 1.80–1.14 (m, 15H), 0.98–0.88 (m, 5H).

EXAMPLE 40(31)

(3S)-1-butyl-2,5-dioxo-3-cyclohexylmethyl-9-(4-(6-methylpyridin-3-yloxy)phenylmethyl)-1,4,9-triazaspiro[5.5]undecane.2 hydrochloride

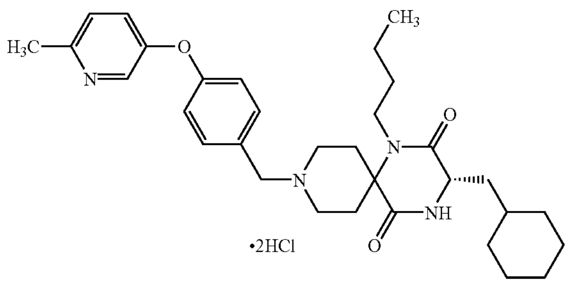

TLC: Rf 0.42 (chloroform:methanol=10:1);

NMR ($CD_3OD$): δ 8.58 (d, J=2.7 Hz, 1H), 8.17 (m, 1H), 7.90 (d, J=8.4 Hz, 1H), 7.75 (d, J=9.0 Hz, 2H), 7.30 (d, J=9.0 Hz, 2H), 4.39 (s, 2H), 4.03 (dd, J=7.5, 4.8 Hz, 1H), 3.88–3.72 (m, 2H), 3.56–3.44 (m, 4H), 2.76 (s, 3H), 2.68–2.50 (m, 2H), 2.24–2.06 (m, 2H), 1.82–1.14 (m, 15H), 1.02–0.88 (m, 5H).

EXAMPLE 40(32)

(3S)-1-butyl-2,5-dioxo-3-cyclohexylmethyl-9-(4-(6-methylpyridin-1-oxide-3-yloxy)phenylmethyl)-1,4,9-triazaspiro[5.5]undecane.hydrochloride

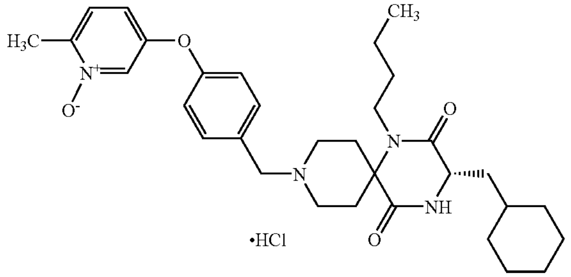

TLC: Rf 0.38 (chloroform:methanol=10:1);

NMR ($CD_3OD$): δ 8.40 (m, 1H), 7.69 (d, J=8.4 Hz, 2H), 7.69 (m, 1H), 7.54 (m, 1H), 7.27 (d, J=8.4 Hz, 2H), 4.39 (s, 2H), 4.04 (dd, J=7.5, 4.8 Hz, 1H), 3.88–3.72 (m, 2H), 3.58–3.39 (m, 4H), 2.59 (s, 3H), 2.58–2.40 (m, 2H), 2.28–2.06 (m, 2H), 1.82–1.10 (m, 15H), 1.02–0.84 (m, 5H).

EXAMPLE 40(33)

(3S)-1-butyl-2,5-dioxo-3-cyclohexyl methyl-9-(4-(tetrahydropyran-4-yloxy)phenylmethyl)-1,4,9-triazaspiro[5.5]undecane.hydrochloride

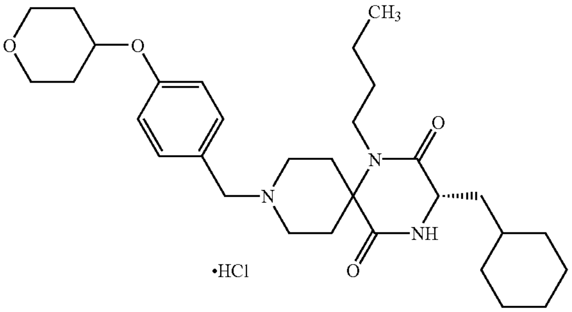

TLC: Rf 0.48 (chloroform:methanol=10:1);

NMR ($CD_3OD$): δ 7.49 (d, J=8.4 Hz, 2H), 7.05 (d, J=8.4 Hz, 2H), 4.63 (m, 1H), 4.27 (s, 2H), 4.02 (dd, J=7.8, 4.8 Hz, 1H), 3.97–3.90 (m, 2H), 3.84–3.66 (m, 2H), 3.62–3.52 (m, 2H), 3.50–3.38 (m, 3H), 2.54–2.38 (m, 2H), 2.22–1.98 (m, 4H), 1.80–1.10 (m, 18H), 1.00–0.86 (m, 5H).

EXAMPLE 40(34)

(3S)-1-butyl-2,5-dioxo-3-cyclohexylmethyl-9-(6-phenylpyridin-3-ylmethyl)-1,4,9-triazaspiro[5.5]undecane.2 hydrochloride

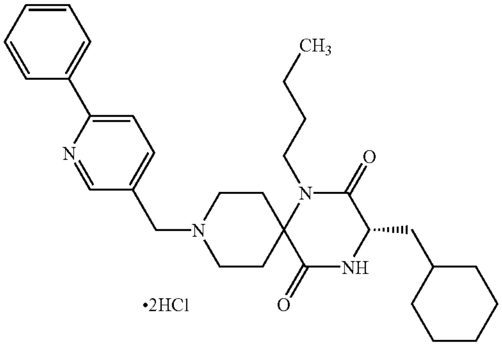

TLC: Rf 0.50 (chloroform:methanol=10:1);

NMR ($CD_3OD$): δ 9.14 (m, 1H), 8.75 (m, 1H), 8.36 (m, 1H), 8.02–7.99 (m, 2H) 7.68–7.62 (m, 3H), 4.63 (s, 2H), 4.05 (dd, J=7.5, 4.5 Hz, 1H), 4.02–3.94 (m, 2H), 3.64–3.42 (m, 4H), 2.72–2.56 (m, 2H), 2.25–2.06 (m, 2H), 1.80–1.10 (m, 15H), 1.00–0.86 (m, 5H).

EXAMPLE 40(35)

(3S)-1-butyl-2,5-dioxo-3-cyclohexylmethyl-9-(3,5-dimethyl-1-(4-fluorophenyl)pyrazol-4-ylmethyl)-1,4,9-triazaspiro[5.5]undecane.2 hydrochloride

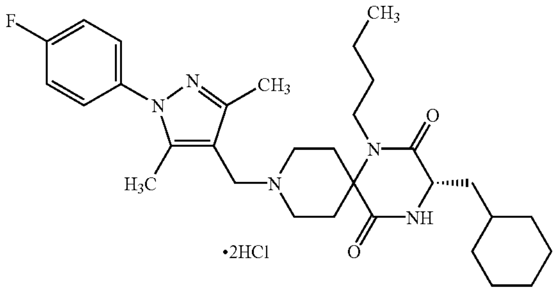

TLC: Rf 0.60 (chloroform:methanol=10:1);

NMR ($CD_3OD$): δ 7.58–7.50 (m, 2H), 7.37–7.28 (m, 2H), 4.32 (s, 2H), 4.05 (dd, J=7.5, 4.5 Hz, 1H), 3.94–3.73 (m, 2H), 3.67–3.55 (m, 2H), 3.53–3.42 (m, 2H, 2.70–2.48 (m, 2H), 2.43 (s, 3H), 2.39 (s, 3H), 2.30–2.08 (m, 2H), 1.84–1.10 (m, 15H), 1.08–0.93 (m, 2H), 0.95 (t, J=7.2 Hz, 3H).

EXAMPLE 40(36)

(3S)-1-butyl-2,5-dioxo-3-cyclohexyl methyl-9-(3,5-dimethyl-1-(pyridin-2-yl) pyrazol-4-ylmethyl)-1,4,9-triazaspiro[5.5]undecane.2 hydrochloride

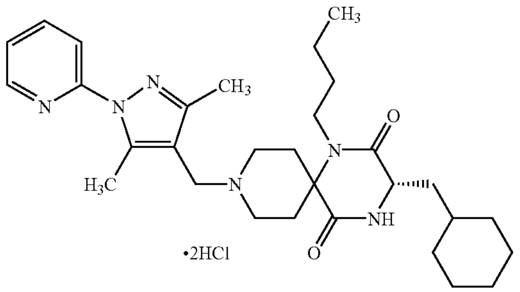

TLC: Rf 0.60 (chloroform:methanol=10:1);

NMR ($CD_3OD$): δ 8.53 (dd, J=4.8, 1.5 Hz, 1H), 8.11–8.00 (m, 1H), 7.84 (d, J=8.4 Hz, 1H), 7.49–7.41 (m, 1H), 4.32 (s, 2H), 4.05 (dd, J=7.5, 4.5 Hz, 1H), 3.95–3.74 (m, 2H), 3.66–3.54 (m, 2H), 3.50–3.37 (m, 2H), 2.68 (s, 3H), 2.64–2.40 (m, 2H), 2.43 (s, 3H), 2.30–2.08 (m, 2H), 1.93–1.10 (m, 15H), 1.08–0.92 (m, 2H), 0.95 (t, J=7.2 Hz, 3H).

EXAMPLE 40(37)

(3S)-1-butyl-2,5-dioxo-3-cyclohexylmethyl-9-(3,5-dimethyl-1-(4-hydroxyphenyl)pyrazol-4-ylmethyl)-1,4,9-triazaspiro[5.5]undecane.2 hydrochloride

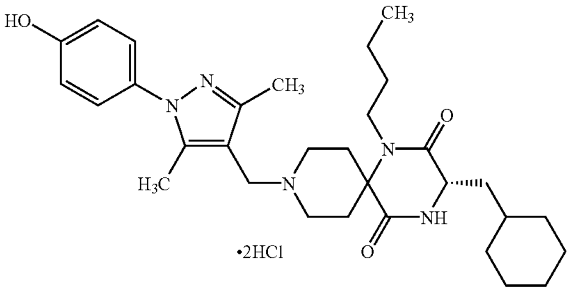

TLC: Rf 0.48 (chloroform:methanol=10:1);

NMR ($CD_3OD$): δ 7.34 (d, J=9.0 Hz, 2H), 6.96 (d, J=9.0 Hz, 2H),4.35 (s, 2H), 4.05 (dd, J=7.5, 4.5 Hz, 1H), 3.93–3.78 (m, 2H), 3.64–3.61 (m, 2H), 3.50 (t, J=8.0 Hz, 2H), 2.68–2.56 (m, 2H), 2.49 (s, 3H), 2.39 (s, 3H), 2.25–2.12 (m, 2H), 1.81–1.19 (m, 15H), 0.95 (t, J=7.5 Hz, 3H), 0.99–0.91 (m, 2H).

EXAMPLE 40(38)

(3S)-1-butyl-2,5-dioxo-3-cyclohexylmethyl-9-(4-(2-carboxyethyl)phenylmethyl)-1,4,9-triazaspiro[5.5]undecane.hydrochloride

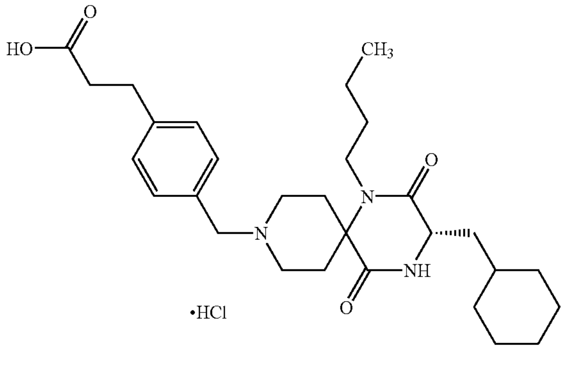

TLC: Rf 0.43 (chloroform:methanol=10:1);

NMR ($CD_8OD$): δ 7.46 (d, J=8.3 Hz, 2H), 7.38 (d, J=8.3 Hz, 2H),4.32 (s, 2H), 4.03 (dd, J=7.5, 4.5 Hz, 1H), 3.85–3.74 (m, 2H), 3.50–3.46 (m, 2H), 3.40–3.35 (m, 2H), 2.96 (t, J=7.2 Hz, 2H), 2.62 (t, J=7.2 Hz, 2H), 2.42–2.30 (m, 2H), 2.34–2.10 (m, 2H), 1.78–1.18 (m, 15H), 0.94 (t, J=7.2 Hz, 3H), 0.94 (m, 2H).

EXAMPLE 40(39)

(3S)-1-butyl-2,5-dioxo-3-cyclohexyl methyl-9-(4-(4-hydroxyphenyloxy)phenylmethyl)-1,4,9-triazaspiro[5.5]undecane.hydrochloride

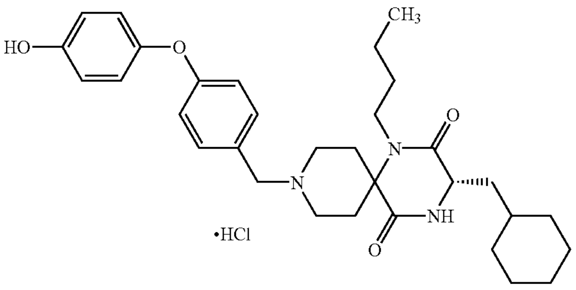

TLC: Rf 0.54 (chloroform:methanol=10:1);

NMR ($CD_3OD$): δ 7.47 (d, J=8.4 Hz, 2H), 6.97 (d, J=8.4 Hz, 2H), 6.88 (d, J=9.0 Hz, 2H), 6.80 (d, J=9.0 Hz, 2H), 4.30 (s, 2H), 4.03 (dd, J=7.5, 4.5 Hz, 1H), 3.83–3.72 (m, 2H), 3.49–3.34 (m, 4H), 2.38 (m, 2H), 2.23–2.10 (m, 2H), 1.78–1.16 (m, 15H), 1.02–0.92 (m, 2H), 0.95 (t, J=7.2 Hz, 3H).

EXAMPLE 40(40)

(3S)-1-butyl-2,5-dioxo-3-cyclohexylmethyl-9-(3,5-dimethyl-1-(4-carboxyphenyl)pyrazol-4-ylmethyl)-1,4,9-triazaspiro[5.5]undecane.2 hydrochloride

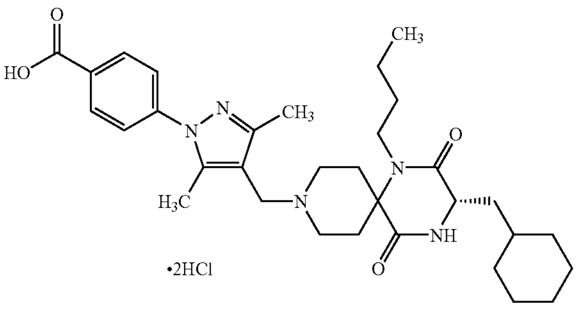

TLC: Rf 0.25 (chloroform:methanol=10:1);

NMR ($CD_3OD$): δ 8.19 (d, J=8.4 Hz, 2H), 7.61 (d, J=8.4 Hz, 2H), 4.33 (s, 2H), 4.06 (dd, J=7.5, 4.5 Hz, 1H), 3.93–3.80 (m, 2H), 3.61 (m, 2H), 3.43–3.38 (m, 2H), 2.44 (s, 3H), 2.40 (m, 2H), 2.39 (s, 3H), 2.21 (m, 2H), 1.75–1.18 (m, 15H), 0.96 (m, 2H), 0.96 (t, J=7.2 Hz, 3H).

EXAMPLE 40(41)

(3S)-1-butyl-2,5-dioxo-3-cyclohexylmethyl-9-(3,5-dimethyl-1-(4-(dimethylaminosulfonyl)phenyl)pyrazol-4-ylmethyl)-1,4,9-triazaspiro[5.5]undecane.2 hydrochloride

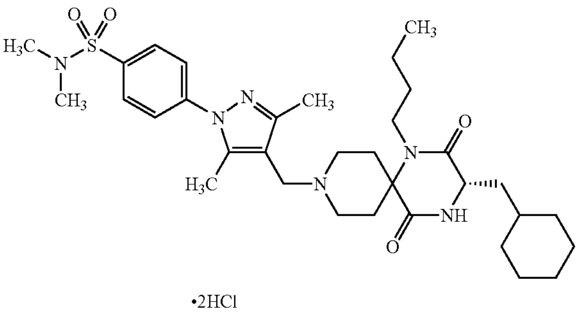

TLC: Rf 0.54 (chloroform:methanol=9:1);

NMR ($CD_3OD$): δ 7.96 (d, J=8.7 Hz, 2H), 7.78 (d, J=8.7 Hz, 2H), 4.31 (s, 2H), 4.05 (dd, J=7.8, 4.5 Hz, 1H), 3.94–3.74 (m, 2H), 3.66–3.56 (m, 2H), 3.48 (m, 2H), 2.74 (s, 6H), 2.59 (m, 2H), 2.49 (s, 3H), 2.41 (s, 3H), 2.29–2.10 (m, 2H), 1.84–1.16 (m, 13H), 1.06–0.86 (m, 5H).

EXAMPLE 40(42)

(3S)-1-butyl-2,5-dioxo-3-cyclohexylmethyl-9-(4-(5-methylpyridin-1-oxide-2-yloxy)phenylmethyl)-1,4,9-triazaspiro[5.5]undecane.hydrochloride

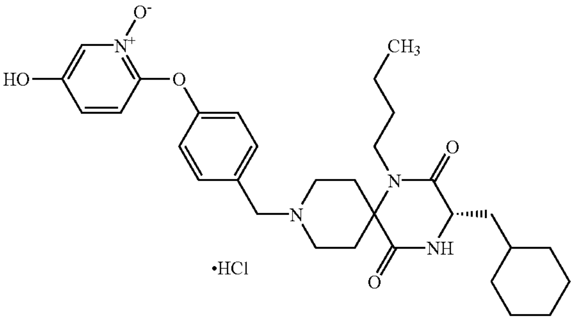

TLC: Rf 0.49 (chloroform:methanol=9:1);

NMR ($CD_3OD$): δ 7.77 (brs, 1H), 7.61 (d, J=7.5 Hz, 2H), 7.56 (dd, J 9.3, 2.4 Hz, 1H), 7.00 (d, J=7.5 Hz, 2H), 6.73 (d, J=9.3 Hz, 1H), 4.34 (s, 2H), 4.03 (dd, J=7.8, 4.8 Hz, 1H), 3.86–3.69 (m, 2H), 3.52–3.35 (m, 4H), 2.44 (m, 2H), 2.25–2.06 (m, 2H), 2.18 (s, 3H), 1.84–1.14 (m, 15H), 1.04–0.96 (m, 5H),

EXAMPLE 40(43)

(3S)-1-butyl-2,5-dioxo-3-cyclohexylmethyl-9-(4-(2-carboxy-1-ethynyl)phenylmethyl)-1,4,9-triazaspiro[5.5]undecane.hydrochloride

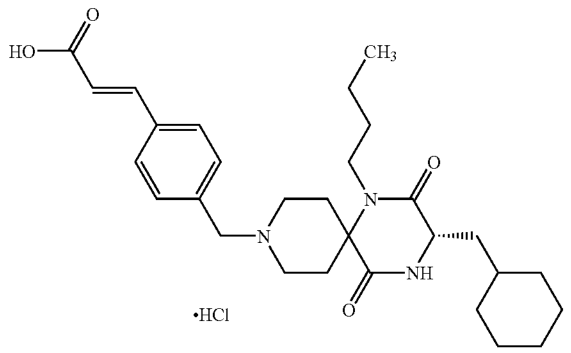

TLC: Rf 0.17 (chloroform:methanol=10:1);

NMR ($CD_3OD$): δ 7.75 (d, J=8.4 Hz, 2H), 7.70 (d, J=15.9 Hz, 1H), 7.61 (d, J=8.4 Hz, 2H), 6.57 (d, J=15.9 Hz, 1H), 4.39 (s, 2H),4.04 (dd, J=7.2, 4.8 Hz, 1H), 3.90–3.72 (m, 2H), 3.58–3.36 (m, 4H), 2.50–2.32 (m, 2H), 2.28–2.08 (m, 2H), 1.92–1.10 (m, 15H), 0.96 (t, J=7.2 Hz, 3H), 0.96 (m, 2H).

EXAMPLE 40(44)

(3S)-1-butyl-2,5-dioxo-3-cyclohexylmethyl-9-(4-(4-((1E)-2-carboxy-1-ethynyl) phenyloxy)phenylmethyl)-1,4,9-triazaspiro[5.5]undecane.hydrochloride

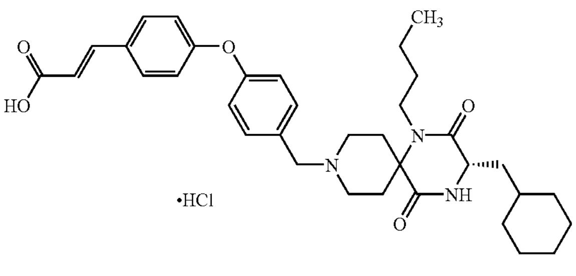

TLC: Rf 0.44 (chloroform:methanol=10:1);

NMR ($CD_3OD$): δ 7.69–7.63 (m, 3H), 7.57 (d, J=8.7 Hz, 2H), 7.14 (d, J=8.7 Hz, 2H), 7.05 (d, J=8.4 Hz, 2H), 6.42 (d, J=15.9 Hz, 1H), 4.36 (s, 2H), 4.03 (dd, J=7.5, 4.5 Hz, 1H), 3.90–3.74 (m, 2H), 3.55–3.36 (m, 4H), 2.50–2.30 (m, 2H), 2.30–2.08 (m, 2H), 1.82–1.10 (m, 15H), 1.02–0.88 (m, 5H).

EXAMPLE 40(45)

(3S)-1-butyl-2,5-dioxo-3-cyclohexylmethyl-9-(4-(4-aminocarbonylphenyloxy)phenylmethyl)-1,4,9-triazaspiro[5.5]undecane.hydrochloride

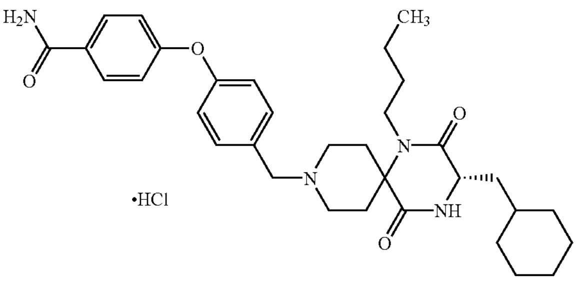

TLC: Rf 0.41 (chloroform:methanol=10:1);

NMR ($CD_3OD$): δ 7.90 (d, J=9.0 Hz, 2H), 7.60 (d, J=9.0 Hz, 2H), 7.15 (d, J=9.0 Hz, 2H), 7.07 (d, J=9.0 Hz, 2H), 4.36 (s, 2H), 4.04 (dd, J=7.5, 4.5, Hz, 1H), 3.90–3.72 (m, 2H), 3.56–3.35 (m, 4H), 2.53–2.35 (m, 2H), 2.28–2.08 (m, 2H), 1.84–1.13 (m, 15H), 1.06–0.86 (m, 5H).

EXAMPLE 40(46)

(3S)-1-butyl-2,5-dioxo-3-cyclohexylmethyl-9-(4-(4-aminosulfonylphenyloxy)phenylmethyl)-1,4,9-triazaspiro[5.5]undecane.hydrochloride

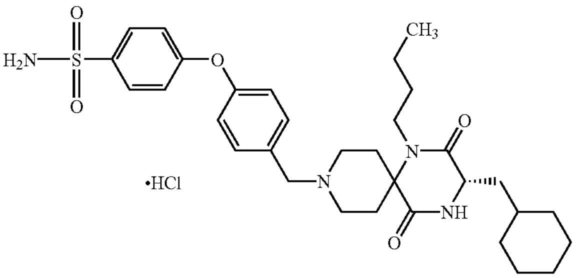

TLC: Rf 0.33 (chloroform:methanol=10:1); NMR ($d_6$-DMSO): δ 11.03 (brs, 1H), 8.42 (brs, 1H), 7.82 (d, J=8.7 Hz, 2H), 7.71 (d, J=8.7 Hz, 2H), 7.33 (brs, 2H), 7.16 (d, J=8.7 Hz, 4H), 4.38–4.23 (m, 2H), 3.91 (m, 1H), 3.61–3.23 (m, 6H), 2.58–2.30 (m, 2H), 2.18–1.91 (m, 2H), 1.76–1.00 (m, 15H), 0.98–0.71 (m, 5H).

EXAMPLE 40(47)

(3S)-1-butyl-2,5-dioxo-3-cyclohexylmethyl-9-(3,5-dimethyl-1-benzylpyrazol-4-ylmethyl)-1,4,9-triaza-spiro[5.5]undecane.2 hydrochloride

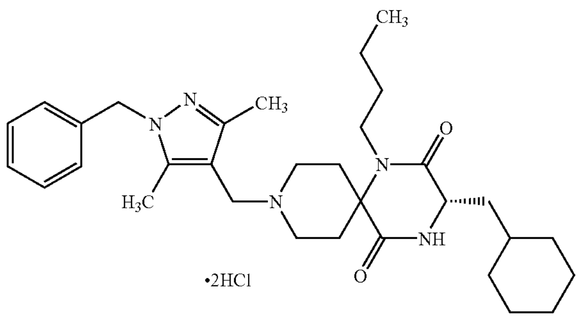

TLC: Rf 0.40 (chloroform:methanol=10:1);

NMR ($CD_3OD$): δ 7.41–7.33 (m, 3H), 7.22–7.20 (m, 2H), 5.46 (s, 2H), 4.31 (s, 2H), 4.04 (dd, J=7.5, 4.5 Hz, 1H), 3.88–3.74 (m, 2H), 3.58–3.48 (m, 4H), 2.61 (m, 2H), 2.47 (s, 6H), 2.24–2.09 (m, 2H), 1.80–1.16 (m, 15H), 0.95 (t, J=7.2

EXAMPLE 40(48)

(3S)-1-butyl-2,5-dioxo-3-cyclohexylmethyl-9-(3,5-dimethyl-1-(2,4-difluorophenyl)pyrazol-4-ylmethyl)-1,4,9-triazaspiro[5.5]undecane.2 hydrochloride

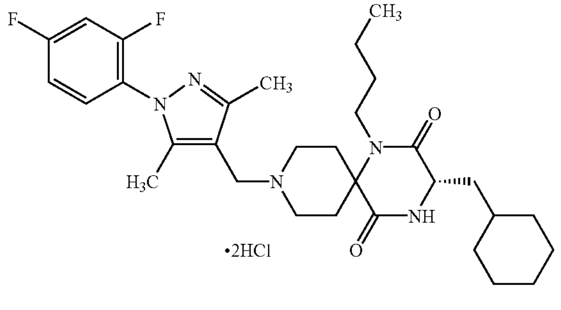

TLC: Rf 0.48 (chloroform:methanol=10:1);

NMR ($CD_3OD$): δ 7.58–7.51 (m, 1H), 7.33–7.25 (m, 1H), 7.22–7.16 (m, 1H),4.31 (s, 2H), 4.05 (dd, J=7.5, 4.5 Hz, 1H), 3.91–3.78 (m, 2H), 3.59 (m, 2H), 3.44 (m, 2H), 2.49 (m, 2H), 2.38 (s, 3H), 2.28 (s, 3H), 2.27–2.15 (m, 2H), 1.81–1.16 (m, 15H), 0.96 (t, J=7.0 Hz, 3H), 0.96 (m, 2H).

EXAMPLE 40(49)

(3S)-1-butyl-2,5-dioxo-3-cyclohexylmethyl-9-(4-(pyrrolidin-1-ylmethyl)phenylmethyl)-1,4,9-triaza-spiro[5.5]undecane.2 hydrochloride

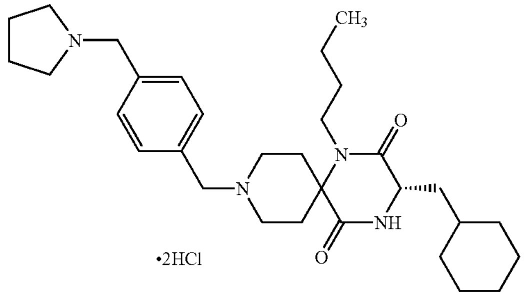

TLC: Rf 0.14 (chloroform:methanol=10:1);

NMR ($CD_3OD$): δ 7.74 (d, J=8.4 Hz, 2H), 7.65 (d, J=8.4 Hz, 2H), 4.43 (s, 2H), 4.40 (s, 2H), 4.03 (dd, J=7.5, 4.5 Hz, 1H), 3.90–3.70 (m, 2H), 3.56–3.38 (m, 6H), 3.28–3.10 (m, 2H), 2.66–2.48 (m, 2H), 2.26–1.92 (m, 6H), 1.83–1.10 (m, 15H), 1.06–0.83 (m, 2H), 0.94 (t, J=7.2 Hz, 3H).

EXAMPLE 40(50)

(3S)-1-butyl-2,5-dioxo-3-cyclohexylmethyl-9-(3,5-dimethyl-1-(4-(morpholin-4-ylsulfonyl)phenyl)pyrazol-4-ylmethyl)-1,4,9-triazaspiro[5.5]undecane.2 hydrochloride

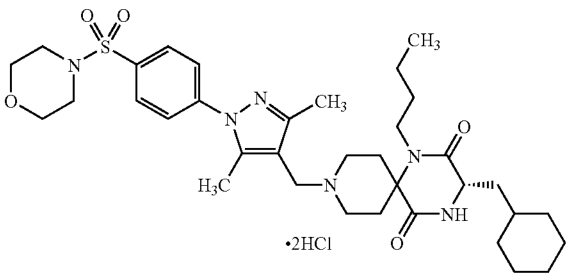

TLC: Rf 0.46 (chloroform:methanol=20:1);

NMR ($CD_3OD$): δ 7.95 (d, J=8.7 Hz, 2H), 7.80 (d, J=8.7 Hz, 2H), 4.32 (s, 2H), 4.05 (dd, J=7.8, 4.5 Hz, 1H), 3.94–3.74 (m, 2H), 3.76–3.67 (m, 4H), 3.66–3.56 (m, 2H), 3.56–3.42 (m, 2H), 3.10–2.92 (m, 4H), 2.68–2.50 (m, 2H), 2.50 (s, 3H), 2.42 (s, 3H), 2.30–2.08 (m, 2H), 1.84–1.08 (m, 15H), 1.08–0.83 (m, 2H), 0.95 (t, J=7.2 Hz, 3H).

EXAMPLE 40(51)

(3S)-1-butyl-2,5-dioxo-3-cyclohexylmethyl-9-(4-(4-cyanophenyloxy)phenylmethyl)-1,4,9-triazaspiro[5.5]undecane.hydrochloride

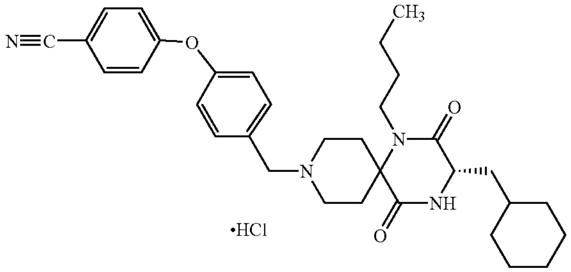

TLC: Rf 0.33 (chloroform:methanol=10:1);

NMR ($CD_3OD$): δ 7.75 (d, J=9.3 Hz, 2H), 7.64 (d, J=9.0 Hz, 2H), 7.22 (d, J=9.0 Hz, 2H), 7.14 (d, J=9.3 Hz, 2H), 4.40 (s, 2H), 4.05 (dd, J=7.5, 4.8 Hz, 1H), 3.92–3.74 (m, 2H), 3.58–3.36 (m, 4H), 2.52–2.36 (m, 2H), 2.32–2.08 (m, 2H), 1.84–1.12 (m, 15H), 0.96 (t, J=7.2 Hz, 3H), 0.96 (m, 2H).

EXAMPLE 40(52)

(3S)-1-butyl-2,5-dioxo-3-cyclohexylmethyl-9-(3,5-dimethyl-1-(4-(N-(2-hydroxyethyl)-N-methylamino-sulfonyl)phenyl)pyrazol-4-ylmethyl)-1,4,9-triaza-spiro[5.5]undecane.2 hydrochloride

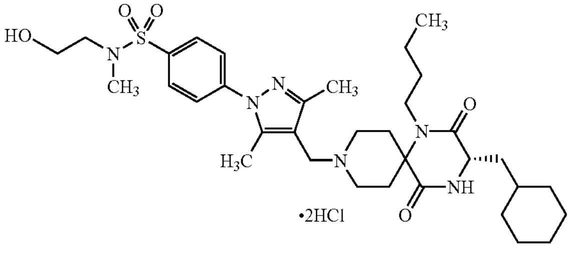

TLC: Rf 0.68 (chloroform:methanol=5:1);

NMR ($CD_3OD$): δ 8.00 (d, J=8.7 Hz, 2H), 7.78 (d, J=8.7 Hz, 2H), 4.33 (s, 2H), 4.06 (dd, J=7.5, 4.5 Hz, 1H), 3.86–3.76 (m, 2H), 3.70 (t, J=5.7 Hz, 2H), 3.68–3.60 (m, 2H), 3.58–3.42 (m, 2H), 3.20 (t, J=5.7 Hz, 2H), 2.88 (s, 3H), 2.72–2.58 (m, 2H), 2.50 (s, 3H), 2.44 (s, 3H), 2.28–2.06 (m, 2H), 1.82–1.10 (m, 15H), 0.96 (t, J=7.2 Hz, 3H), 0.96 (m, 2H).

EXAMPLE 40(53)

(3S)-1-butyl-2,5-dioxo-3-cyclohexylmethyl-9-(3,5-dimethyl-1-(2-phenylethyl)pyrazol-4-ylmethyl)-1,4,9-triazaspiro[5.5]undecane.2 hydrochloride

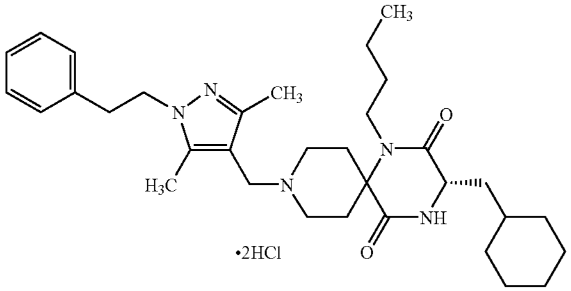

TLC: Rf 0.24 (chloroform:methanol=10:1);

NMR ($CD_3OD$): δ 7.28–7.23 (m, 3H), 7.10–7.07 (m, 2H), 4.40 (t, J=6.6 Hz, 2H), 4.19 (s, 2H), 4.06 (dd, J=7.2, 4.8 Hz, 1H), 3.80–3.60 (m, 2H), 3.58–3.36 (m, 4H), 3.12 (t, J=6.6 Hz, 2H), 2.64–2.45 (m, 2H), 2.45 (s, 3H), 2.26–2.04 (m, 2H), 1.95 (s, 3H), 1.84–1.14 (m, 15H), 0.97 (t, J=7.5 Hz, 3H), 0.97 (m, 2H),

EXAMPLE 40(54)

(3S)-1-butyl-2,5-dioxo-3-cyclohexylmethyl-9-(4-(dimethylaminomethyl)phenylmethyl)-1,4,9-triaza-spiro[5.5]undecane.2 hydrochloride

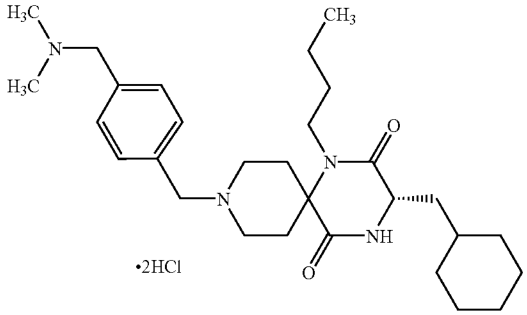

TLC: Rf 0.16 (chloroform:methanol=10:1);

NMR ($CD_3OD$): δ 7.76 (d, J=8.1 Hz, 2H), 7.63 (d, J=8.1 Hz, 2H), 4.41 (s, 2H), 4.37 (s, 2H), 4.03 (dd, J=7.8, 5.1 Hz, 1H), 3.90–3.75 (m, 2H), 3.52–3.38 (m, 4H), 2.87 (s, 6H), 2.64–2.48 (m, 2H), 2.22–2.04 (m, 2H), 1.80–1.15 (m, 15H), 1.00–0.86 (m, 5H).

EXAMPLE 40(55)

(3S)-1-butyl-2,5-dioxo-3-cyclohexylmethyl-9-(3-(4-hydroxyphenyl)phenylmethyl)-1,4,9-triazaspiro[5.5]undecane.hydrochloride

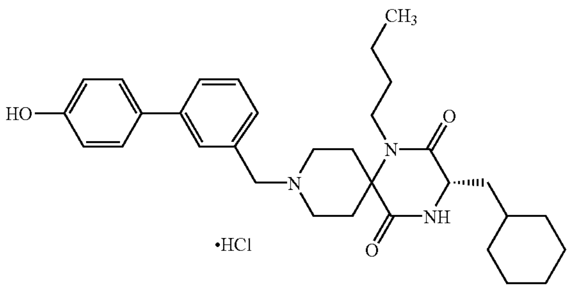

TLC: Rf 0.58 (chloroform:methanol=10:1);

NMR ($CD_3OD$): δ 7.81 (s, 1H), 7.69 (d, J=7.5 Hz, 1H), 7.54 (d, J=9.0 Hz, 2H), 7.55–7.48 (m, 1H), 7.45 (d, J=7.5 Hz, 1H), 6.87 (d, J=9.0 Hz, 2H), 4.40 (s, 2H), 4.03 (dd, J=7.5, 4.5 Hz, 1H), 3.92–3.73 (m, 2H), 3.58–3.43 (m, 2H), 3.43–3.32 (m, 2H), 2.55–2.35 (m, 2H), 2.28–2.06 (m, 2H), 1.82–1.10 (m, 15H), 1.08–0.83 (m, 2H), 0.94 (t, J=7.2 Hz, 3H).

EXAMPLE 40(56)

(3S)-1-butyl-2,5-dioxo-3-cyclohexylmethyl-9-(3,5-dimethyl-1-(quinoxalin-2-yl)pyrazol-4-ylmethyl)-1,4,9-triazaspiro[5.5]undecane.2 hydrochloride

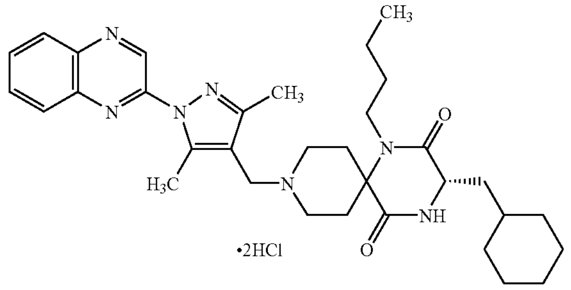

TLC: Rf 0.67 (chloroform:methanol=10:1);

NMR ($CD_3OD$): δ 9.51 (s, 1H), 8.13 (d, J=8.0 Hz, 1H),8.05 (d, J=8.0 Hz, 1H), 7.91–7.80 (m, 2H), 4.38 (s, 2H), 4.05 (dd, J=7.5, 4.5 Hz, 1H), 3.96–3.82 (m, 2H), 3.63 (m, 2H), 3.42 (m, 2H), 2.92 (s, 3H), 2.47 (s, 3H), 2.47 (m, 2H), 2.29–2.16 (m, 2H), 1.80–1.18 (m, 15H), 0.95 (t, J=7.2 Hz, 3H), 0.95 (m, 2H),

EXAMPLE 40(57)

(3S)-1-butyl-2,5-dioxo-3-cyclohexylmethyl-9-(4-(phenylcarbonyl) phenylmethyl)-1,4,9-triazaspiro[5.5]undecane.hydrochloride

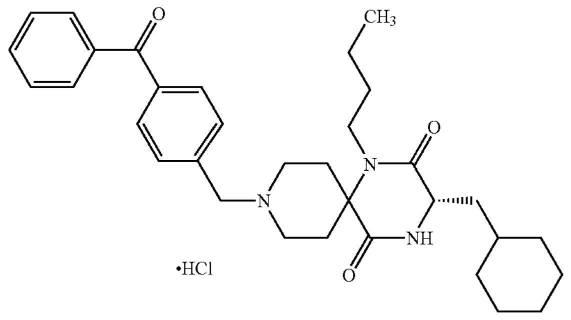

TLC: Rf 0.68 (chloroform:methanol=10:1);

NMR ($CD_3OD$): δ 7.87 (d, J=8.4 Hz, 2H), 7.82–7.74 (m, 4H), 7.67 (t, J=8.4 Hz, 1H), 7.57–7.51 (m, 2H), 4.48 (s, 2H), 4.04 (dd, J=7.8, 4.8 Hz, 1H), 3.84–3.78 (m, 2H), 3.58–3.38 (m, 4H), 2.58–2.40 (m, 2H), 2.30–2.10 (m, 2H), 1.82–1.14 (m, 15H), 1.02–0.86 (m, 5H).

EXAMPLE 40(58)

(3S)-1-butyl-2,5-dioxo-3-cyclohexylmethyl-9-(3,5-dimethyl-1-(4-methylaminosulfonylphenyl)pyrazol-4-ylmethyl)-1,4,9-triazaspiro[5.5]undecane.2 hydrochloride

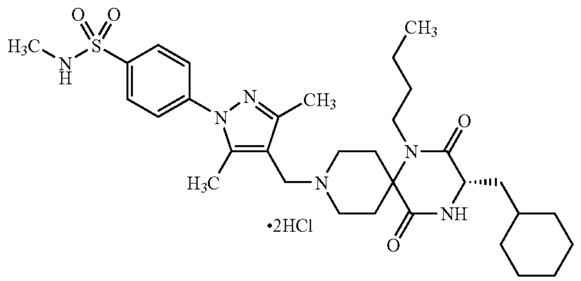

TLC: Rf 0.30 (chloroform:methanol=10:1);

NMR ($CD_3OD$): δ 8.01 (d, J=8.7 Hz, 2H), 7.74 (d, J=8.7 Hz, 2H), 4.33 (s, 2H), 4.06 (dd, J=7.8, 4.5 Hz, 1H), 3.86–3.78 (m, 2H), 3.68–3.58 (m, 2H), 3.52–3.36 (m, 2H), 2.59 (s, 3H), 2.59–2.38 (m, 2H), 2.48 (s, 3H), 2.41 (s, 3H), 2.34–2.10 (m, 2H), 1.84–1.16 (m, 15H), 0.97 (t, J=7.2 Hz, 3H), 0.97 (m, 2H),

EXAMPLE 40(59)

(3S)-1-butyl-2,5-dioxo-3-cyclohexylmethyl-9-(1,3,5-trimethylpyrazol-4-ylmethyl)-1,4,9-triazaspiro[5.5]undecane.2 hydrochloride

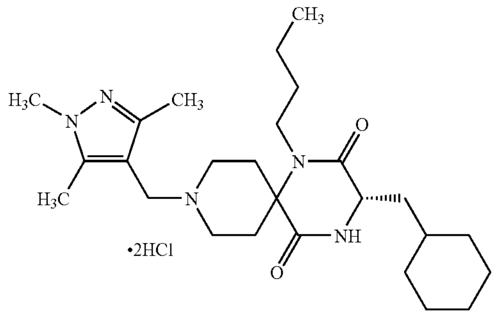

TLC: Rf 0.43 (chloroform:methanol=10:1);

NMR ($CD_3OD$): δ 4.28 (s, 2H), 4.03 (dd, J=7.8, 4.5 Hz, 1H), 3.87 (s, 3H), 3.87–3.69 (m, 2H), 3.61–3.43 (m, 4H), 2.69–2.50 (m, 2H), 2.46 (s, 3H), 2.44 (s, 3H), 2.25–2.06 (m, 2H), 1.83–1.12 (m, 15H), 1.05–0.86 (m, 5H).

EXAMPLE 40(60)

(3S)-1-butyl-2,5-dioxo-3-cyclohexylmethyl-9-(4-(morpholin-4-ylmethyl)phenylmethyl)-1,4,9-triazaspiro[5.5]undecane.2 hydrochloride

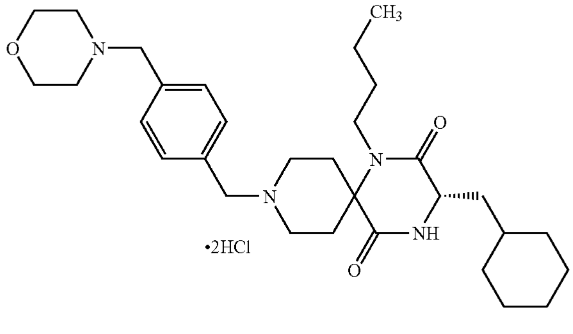

TLC: Rf 0.56 (chloroform:methanol=10:1);

NMR ($CD_3OD$): δ 7.74 (d, J=8.4 Hz, 2H), 7.66 (d, J=8.4 Hz, 2H), 4.40 (s, 4H), 4.03 (dd, J=7.5, 4.5 Hz, 1H), 4.00–3.70 (m, 6H), 3.54–3.40 (m, 4H), 3.35–3.18 (m, 4H), 2.63–2.47 (m, 2H), 2.24–2.02 (m, 2H), 1.83–1.12 (m, 15H), 1.06–0.85 (m, 5H).

EXAMPLE 40(61)

(3S)-1-butyl-2,5-dioxo-3-cyclohexylmethyl-9-(4-(3-methoxyphenyloxy)phenylmethyl)-1,4,9-triazaspiro[5.5]undecane.hydrochloride

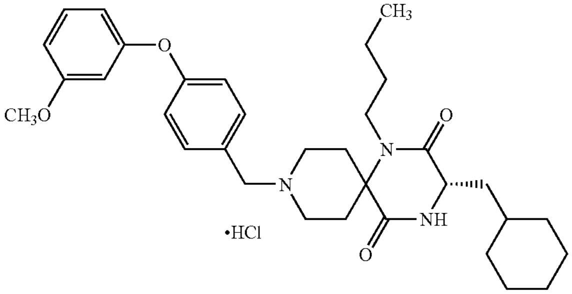

TLC: Rf 0.57 (chloroform:methanol=10:1);

NMR ($CD_3OD$): δ 7.53 (d, J=8.7 Hz, 2H), 7.28 (t, J=8.4 Hz, 1H), 7.07 (d, J=8.7 Hz, 2H), 6.75 (ddd, J=8.4, 2.4, 1.0 Hz, 1H), 6.61–6.57 (m, 2H), 4.34 (s, 2H), 4.04 (dd, J=7.5, 4.5 Hz, 1H), 3.85–3.55 (m, 2H), 3.77 (s, 3H), 3.53–3.47 (m, 2H), 3.40 (m, 2H), 2.50–2.35 (m, 2H), 2.25–2.11 (m, 2H), 1.80–1.23 (m, 15H), 0.95 (t, J=7.2 Hz, 3H), 0.95 (m, 2H).

EXAMPLE 40(62)

(3S)-1-butyl-2,5-dioxo-3-cyclohexylmethyl-9-(4-(4-methylpiperazin-1-ylmethyl)phenylmethyl)-1,4,9-triazaspiro[5.5]undecane.3 hydrochloride

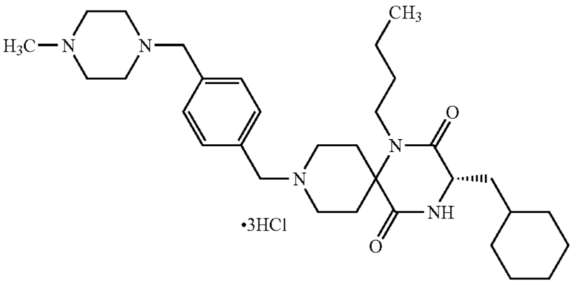

TLC: Rf 0.69 (chloroform:methanol=5:1);

NMR ($CD_3OD$): δ 7.74 (s, 4H), 4.54 (s, 2H), 4.41 (s, 2H), 4.03 (dd, J=7.5, 4.5 Hz, 1H), 3.87–3.42 (m, 14H), 3.00 (s, 3H), 2.61–2.46 (m, 2H), 2.21–2.07 (m, 2H), 1.79–1.15 (m, 15H), 1.02–0.92 (m, 2H), 0.94 (t, J=7.2 Hz, 3H).

EXAMPLE 40(63)

(3S)-1-butyl-2,5-dioxo-3-cyclohexylmethyl-9-(4-(pyridin-1-oxide-3-yloxy)phenylmethyl)-1,4,9-triazaspiro[5.5]undecane.hydrochloride

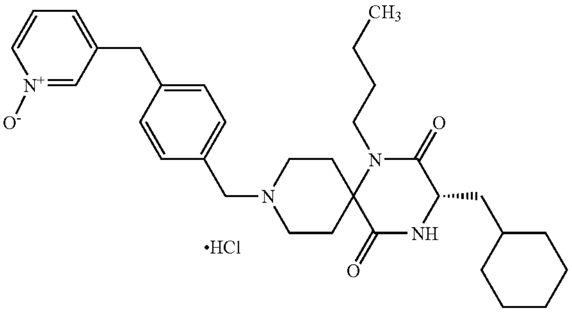

TLC: Rf 0.42 (chloroform:methanol=9:1);

NMR ($CD_3OD$): δ 8.45 (t, J=1.8 Hz, 1H), 8.37 (brd, J=6.3 Hz, 1H), 7.71 (dd, J=8.4, 6.3 Hz, 1H), 7.72 (d, J=8.7 Hz, 2H), 7.59 (brdd, J=8.4, 1.8 Hz, 1H), 7.31 (d, J=8.7 Hz, 2H), 4.40 (s, 2H), 4.04 (dd, J=7.8 Hz, 1H), 3.90–3.74 (m, 2H), 3.57–3.40 (m, 4H), 2.58–2.40 (m, 2H), 2.28–2.08 (m, 2H), 1.82–1.14 (m, 15H), 1.04–0.90 (m, 5H).

EXAMPLE 40(64)

(3S)-1-butyl-2,5-dioxo-3-cyclohexylmethyl-9-(4-phenylsulfonylphenylmethyl)-1,4,9-triazaspiro[5.5]undecane.hydrochloride

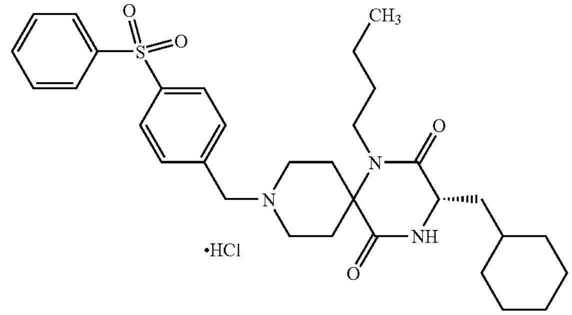

TLC: Rf 0.77 (ethyl acetate: methanol=9:1);

NMR ($CD_3OD$): δ 8.08 (d, J=8.4 Hz, 2H), 8.02–7.96 (m, 2H), 7.80 (d, J=8.4 Hz, 2H), 7.70–7.55 (m, 3H), 4.43 (s, 2H), 4.02 (dd, J=7.8, 4.8 Hz, 1H), 3.89–3.73 (m, 2H), 3.49–3.34 (m, 4H), 2.48–2.33 (m, 2H), 2.23–2.04 (m, 2H), 1.82–1.14 (m, 15H), 1.03–0.85 (m, 5H).

EXAMPLE 40(65)

(3S)-1-butyl-2,5-dioxo-3-cyclohexylmethyl-9-(3,5-dimethyl-1-cyclohexylpyrazol-4-ylmethyl)-1,4,9-triazaspiro[5.5]undecane.2 hydrochloride

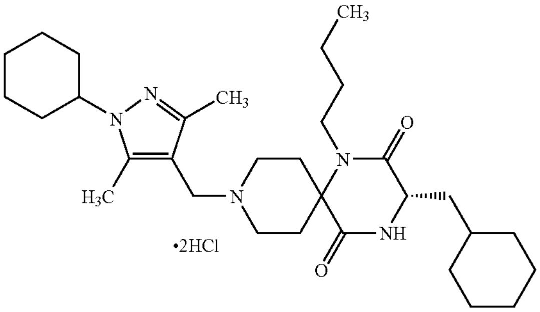

TLC: Rf 0.32 (ethyl acetate: methanol=9:1);

NMR ($CD_3OD$): δ 4.42–4.28 (m, 1H), 4.28 (s, 2H), 4.04 (dd, J=7.5, 4.5 Hz, 1H), 3.90–3.72 (m, 2H), 3.60–3.43 (m, 4H), 2.68–2.50 (m, 2H), 2.50 (s, 3H), 2.46 (s, 3H), 2.25–2.06 (m, 2H), 2.04–1.15 (m, 25H), 1.05–0.89 (m, 5H).

EXAMPLE 40(66)

(3S)-1-butyl-2,5-dioxo-3-cyclohexylmethyl-9-(4-(3-carboxyphenyloxy)phenylmethyl)-1,4,9-triazaspiro[5.5]undecane.hydrochloride

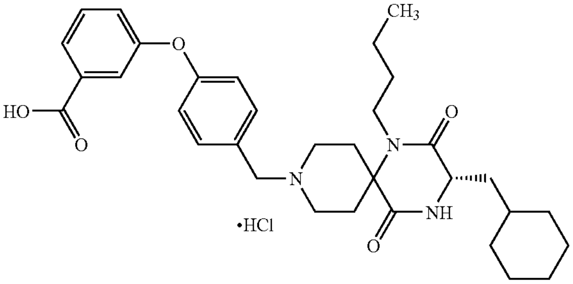

TLC: Rf 0.16 (ethyl acetate: methanol=9:1);

NMR ($CD_3OD$): δ 7.83 (ddd, J=7.8, 1.5, 1.2 Hz, 1H), 7.60 (dd, J=2.4, 1.5 Hz, 1H), 7.57 (d, J=8.7 Hz, 2H), 7.51 (t, J=7.8 Hz, 1H), 7.29 (ddd, J=7.8, 2.4, 1.2 Hz, 1H), 7.12 (d, J=8.7 Hz, 2H), 4.35 (s, 2H), 4.04 (dd, J 7.5, 4.5 Hz, 1H), 3.90–3.74 (m, 2H), 3.58–3.35 (m, 4H), 2.49–2.34 (m, 2H), 2.28–2.09 (m, 2H), 1.93–1.10 (m, 15H), 1.07–0.85 (m, 5H).

EXAMPLE 40(67)

(3S)-1-butyl-2,5-dioxo-3-cyclohexylmethyl-9-(4-(piperidin-1-ylmethyl)phenylmethyl)-1,4,9-triazaspiro[5.5]undecane.2 hydrochloride

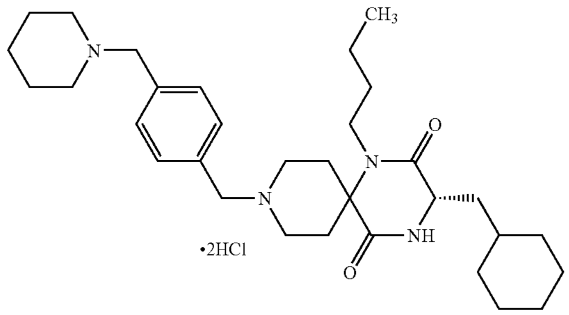

TLC: Rf 0.56 (chloroform:methanol=9:1);

NMR ($CD_3OD$): δ 7.75 (d, J=8.4 Hz, 2H), 7.64 (d, J=8.4 Hz, 2H), 4.40 (s, 2H), 4.34 (s, 2H), 4.03 (dd, J=7.8, 4.8 Hz, 1H), 3.90–3.72 (m, 2H), 3.53–3.38 (m, 6H), 3.05–2.91 (m, 2H), 2.66–2.49 (m, 2H), 2.24–2.04 (m, 2H), 2.00–1.13 (m, 21H), 1.04–0.86 (m, 5H).

EXAMPLE 40(68)

(3S)-1-butyl-2,5-dioxo-3-cyclohexylmethyl-9-(3,5-dimethyl-1-(4-(pyrrolidin-1-ylsulfonyl)phenyl)pyrazol-4-ylmethyl)-1,4,9-triazaspiro[5.5]undecane.2 hydrochloride

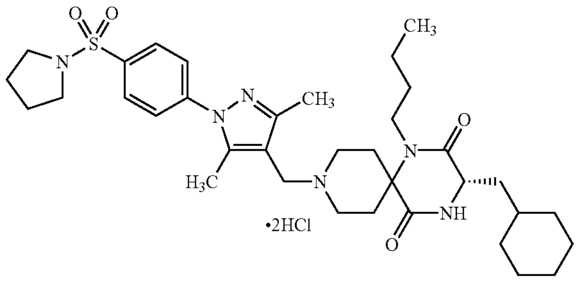

TLC: Rf 0.40 (ethyl acetate: methanol=9:1);

NMR ($CD_3OD$): δ 8.01 (d, J=8.7 Hz, 2H), 7.76 (d, J=8.7 Hz, 2H), 4.32 (s, 2H), 4.05 (dd, J=7.5, 4.5 Hz, 1H), 3.94–3.75 (m, 2H), 3.66–3.56 (m, 2H), 3.49–3.41 (m, 2H), 3.32–3.25 (m, 4H), 2.60–2.46 (m, 2H), 2.48 (s, 3H), 2.40 (s, 3H), 2.30–2.11 (m, 2H), 1.83–1.14 (m, 19H), 1.05–0.87 (m, 5H).

EXAMPLE 40(69)

(3S)-1-butyl-2,5-dioxo-3-cyclohexylmethyl-9-(2,3-dihydrobenzofuran-5-ylmethyl)-1,4,9-triazaspiro[5.5]undecane.hydrochloride

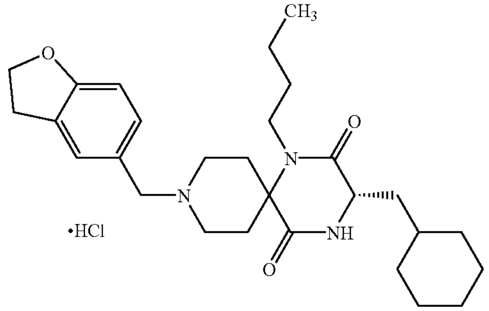

TLC: Rf 0.61 (ethyl acetate: methanol=9:1);

NMR ($CD_3OD$): δ 7.39 (d, J=1.8 Hz, 1H), 7.26 (dd, J=8.4, 1.8 Hz, 1H), 6.81 (d, J=8.4 Hz, 1H), 4.59 (t, J=8.7 Hz, 2H), 4.26 (s, 2H), 4.04 (dd, J=7.8, 4.8 Hz, 1H), 3.84–3.67 (m, 2H), 3.54–3.34 (m, 4H), 3.25 (t, J=8.7 Hz, 2H), 2.48–2.31 (m, 2H), 2.26–2.07 (m, 2H), 1.83–1.14 (m, 15H), 1.04–0.87 (m, 5H).

EXAMPLE 40(70)

(3S)-1-butyl-2,5-dioxo-3-cyclohexylmethyl-9-(4-(4-carboxyphenyloxy)phenylmethyl)-1,4,9-triazaspiro[5.5]undecane.hydrochloride

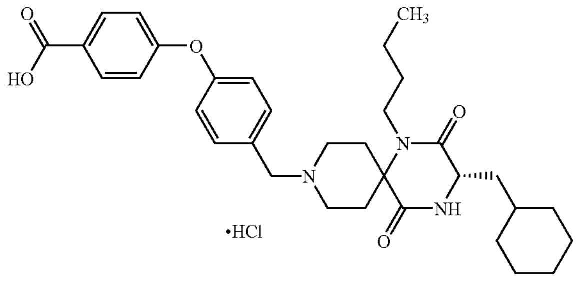

TLC: Rf 0.55 (ethyl acetate: methanol=9:1);

NMR ($CD_3OD$): δ 8.04 (d, J=8.7 Hz, 2H), 7.61 (d, J=8.7 Hz, 2H), 7.18 (d, J=8.7 Hz, 2H), 7.07 (d, J=8.7 Hz, 2H), 4.38 (s, 2H), 4.05 (dd, J=7.8, 4.8 Hz, 1H), 3.91–3.74 (m, 2H), 3.57–3.35 (m, 4H), 2.50–2.33 (m, 2H), 2.29–2.09 (m, 2H), 1.84–1.14 (m, 15H), 1.05–0.86 (m, 5H).

EXAMPLE 40(71)

(3S)-1-butyl-2,5-dioxo-3-cyclohexyl methyl-9-(3,5-dimethyl-1-(4-(2-hydroxyethylaminosulfonyl)phenyl)pyrazol-4-ylmethyl)-1,4,9-triazaspiro[5.5]undecane.2 hydrochloride

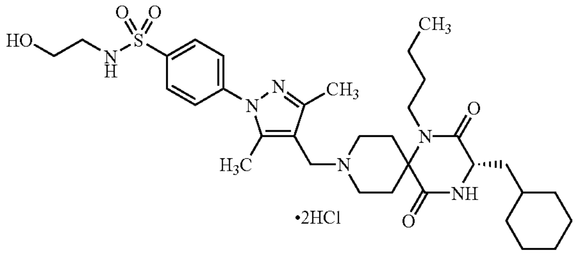

TLC: Rf 0.38 (chloroform:methanol=10:1);

NMR ($CD_3OD$): δ 8.03 (d, J=8.7 Hz, 2H), 7.72 (d, J=8.7 Hz, 2H), 4.31 (s, 2H), 4.05 (dd, J=7.5, 4.5 Hz, 1H), 3.94–3.74 (m, 2H), 3.66–3.56 (m, 2H), 3.56 (t, J=5.7 Hz, 2H), 3.51–3.41 (m, 2H), 3.01 (t, J=5.7 Hz, 2H), 2.63–2.43 (m, 2H), 2.47 (s, 3H), 2.40 (s, 3H), 2.32–2.10 (m, 2H), 1.93–1.10 (m, 15H), 1.06–0.93 (m, 2H), 0.96 (t, J=7.2 Hz, 3H).

EXAMPLE 40(72)

(3S)-1-butyl-2,5-dioxo-3-cyclohexylmethyl-9-(3,5-dimethyl-1-(4-(2-dimethylaminoethylaminosulfonyl)phenyl)pyrazol-4-ylmethyl)-1,4,9-triazaspiro[5.5]undecane.3 hydrochloride

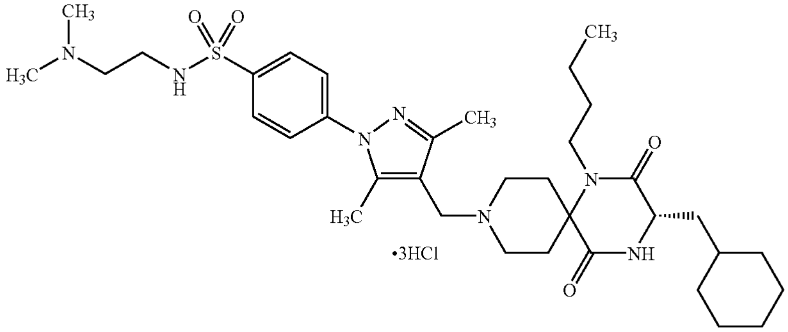

TLC: Rf 0.13 (chloroform:methanol=10:1);

NMR ($CD_3OD$): δ 8.07 (d, J=8.7 Hz, 2H), 7.79 (d, J=8.7 Hz, 2H), 4.31 (s, 2H), 4.04 (dd, J=7.5, 4.2 Hz, 1H), 3.82–3.76 (m, 2H), 3.68–3.48 (m, 4H), 3.34–3.24 (m, 4H), 2.95 (s, 6H), 2.76–2.52 (m, 2H), 2.50 (s, 3H), 2.43 (s, 3H), 2.25–2.08 (m, 2H), 1.82–1.14 (m, 15H), 1.02–0.88 (m, 5H).

EXAMPLE 40(73)

(3S)-1-butyl-2,5-dioxo-3-cyclohexylmethyl-9-(4-(1-hydroxy-1-phenylmethyl)phenylmethyl)-1,4,9-triazaspiro[5.5]undecane.hydrochloride

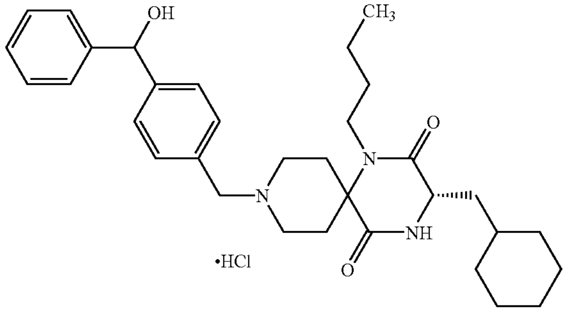

TLC: Rf 0.30 (chloroform:methanol=10:1);

NMR ($CD_3OD$): δ 7.62–7.18 (m, 9H), 5.82 (s, 1H), 4.34 (s, 2H), 4.03 (dd, J=7.5, 4.5 Hz, 1H), 3.88–3.72 (m, 2H), 3.58–3.30 (m, 4H), 2.42–2.04 (m, 4H), 1.82–1.24 (m, 15H), 0.94 (t, J=7.2 Hz, 3H), 0.94 (m, 2H).

EXAMPLE 40(74)

(3S)-1-butyl-2,5-dioxo-3-cyclohexylmethyl-9-(4-(carboxymethyloxy)phenylmethyl)-1,4,9-triazaspiro[5.5]undecane.hydrochloride

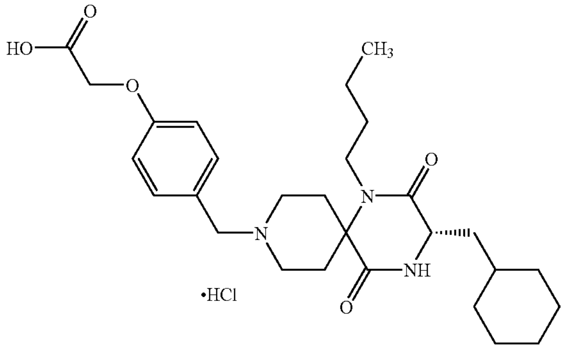

TLC: Rf 0.30 (chloroform:methanol=10:1);

NMR ($CD_3OD$): δ 7.47 (d, J=8.7 Hz, 2H), 7.04 (d, J=8.7 Hz, 2H), 4.70 (s, 2H), 4.29 (s, 2H), 4.03 (dd, J=7.5, 4.5 Hz, 1H), 3.86–3.69 (m, 2H), 3.54–3.33 (m, 4H), 2.44–2.28 (m, 2H), 2.26–2.06 (m, 2H), 1.83–1.12 (m, 15H), 1.04–0.85 (m, 5H).

EXAMPLE 40(75)

(3S)-1-butyl-2,5-dioxo-3-cyclohexylmethyl-9-(4-(4-hydroxypiperidin-1-ylmethyl)phenylmethyl)-1,4,9-triazaspiro[5.5]undecane.2 hydrochloride

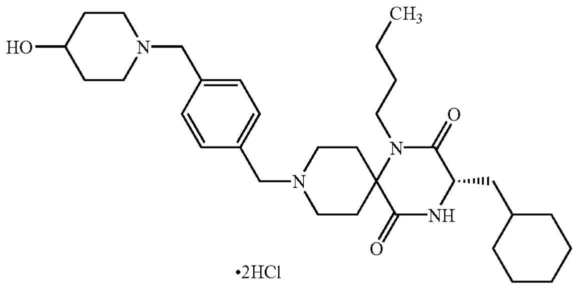

TLC: Rf 0.17 (chloroform:methanol=10:1);

NMR ($CD_3OD$): δ 7.76 (d, J=7.8 Hz, 2H), 7.70–7.61 (m, 2H), 4.40 (s, 2H), 4.38–4.32 (m, 2H), 4.10–4.05 (m, 1H), 4.03 (dd, J=7.5, 4.5 Hz, 1H), 3.90–3.68 (m, 2H), 3.56–3.40 (m, 4H), 3.18–3.00 (m, 1H), 2.70–2.48 (m, 2H), 2.23–1.82 (m, 5H), 1.82–1.10 (m, 19H), 1.06–0.83 (m, 2H), 0.94 (t, J=7.2 Hz, 3H).

EXAMPLE 40(76)

(3S)-1-butyl-2,5-dioxo-3-cyclohexyl methyl-9-(4-(3-carboxyphenylmethyloxy)phenylmethyl)-1,4,9-triazaspiro[5.5]undecane.hydrochloride

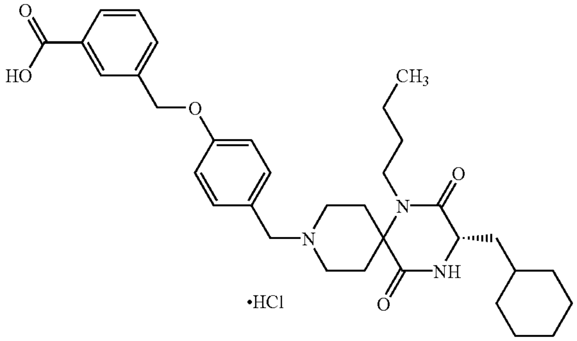

TLC: Rf 0.57 (chloroform:methanol=5:1);

NMR ($CD_3OD$): δ 8.10 (s, 1H), 7.98 (d, J=7.8 Hz, 1H), 7.68 (d, J=7.8 Hz, 1H), 7.50 (t, J=7.8 Hz, 1H), 7.46 (d, J=8.7 Hz, 2H), 7.13 (d, J=8.7 Hz, 2H), 5.22 (s, 2H), 4.28 (s, 2H), 4.04 (dd, J=7.8, 4.8 Hz, 1H), 3.84–3.68 (m, 2H), 3.52–3.32 (m, 4H), 2.42–2.08 (m, 4H), 1.82–1.16 (m, 15H), 0.95 (t, J=7.8 Hz, 3H), 0.95 (m, 2H).

EXAMPLE 40(77)

(3S)-1-butyl-2,5-dioxo-3-cyclohexylmethyl-9-(4-(1,4-benzodioxan-6-yloxy)phenylmethyl)-1,4,9-triazaspiro[5.5]undecane.hydrochloride

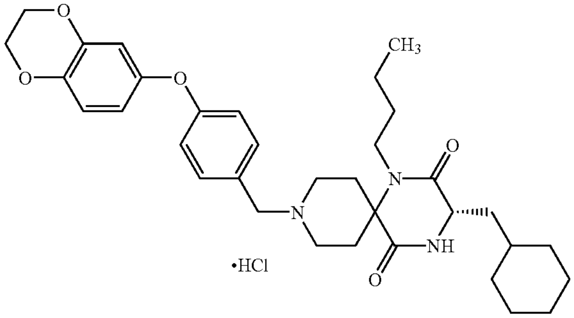

TLC: Rf 0.41 (chloroform:methanol=10:1);

NMR ($CD_3OD$): δ 7.48 (d, J=9.0 Hz, 2H), 7.02 (d, J=9.0 Hz, 2H), 6.86 (m, 1H), 6.55–6.51 (m, 2H), 4.31 (s, 2H), 4.24 (s, 4H), 4.05 (dd, J=7.5, 4.5 Hz, 1H), 3.86–3.70 (m, 2H), 3.58–3.36 (m, 4H), 2.42–2.08 (m, 4H), 1.82–1.12 (m, 15H), 0.96 (t, J=7.2 Hz, 3H), 0.96 (m, 2H).

EXAMPLE 40(78)

(3S)-1-butyl-2,5-dioxo-3-cyclohexyl methyl-9-(3-(3-hydroxyphenyl)phenylmethyl)-1,4,9-triazaspiro[5.5]undecane.hydrochloride

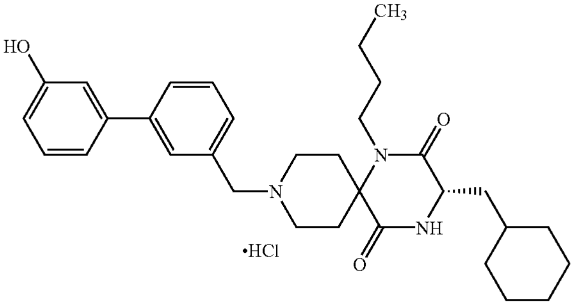

TLC: Rf 0.24 (chloroform:methanol=10:1);

NMR ($CD_3OD$): δ 7.81 (s, 1H), 7.74 (m, 1H), 7.60–7.50 (m, 2H), 7.28 (m, 1H), 7.15–7.08 (m, 2H), 6.82 (m, 1H), 4.43 (s, 2H), 4.04 (dd, J 7.5, 4.5 Hz, 1H), 3.86–3.78 (m, 2H), 3.58–3.34 (m, 4H), 2.48–2.08 (m, 4H), 1.84–1.12 (m, 15H), 0.95 (t, J=7.2 Hz, 3H), 0.95 (m, 2H).

EXAMPLE 40(79)

(3S)-1-butyl-2,5-dioxo-3-cyclohexylmethyl-9-(4-(methylsulfonylamino)phenylmethyl)-1,4,9-triazaspiro[5.5]undecane.hydrochloride

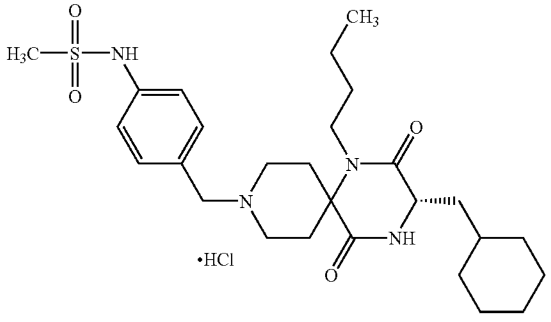

TLC: Rf 0.40 (chloroform:methanol=10:1);

NMR ($CD_3OD$): δ 7.53 (d, J=8.4 Hz, 2H), 7.34 (d, J=8.4 Hz, 2H), 4.32 (s, 2H), 4.03 (dd, J=7.8, 4.8 Hz, 1H), 3.86–3.72 (m, 2H), 3.52–3.34 (m, 4H), 3.01 (s, 3H), 2.50–2.32 (m, 2H), 2.24–2.06 (m, 2H), 1.82–1.10 (m, 15H), 1.02–0.86 (m, 5H).

EXAMPLE 40(80)

(3S)-1-butyl-2,5-dioxo-3-cyclohexylmethyl-9-(6-(4-methoxyphenyl) pyridin-3-ylmethyl)-1,4,9-triazaspiro[5.5]undecane.2 hydrochloride

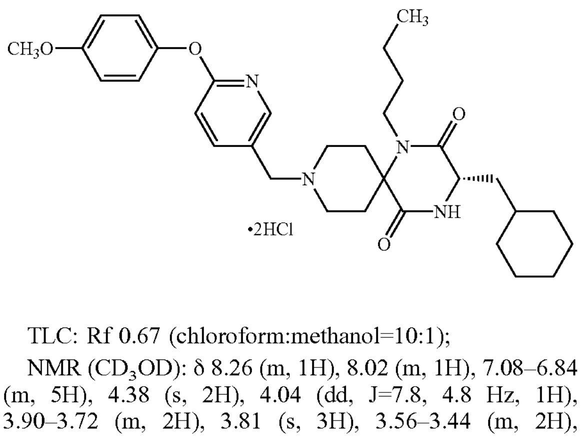

TLC: Rf 0.67 (chloroform:methanol=10:1);

NMR ($CD_3OD$): δ 8.26 (m, 1H), 8.02 (m, 1H), 7.08–6.84 (m, 5H), 4.38 (s, 2H), 4.04 (dd, J=7.8, 4.8 Hz, 1H), 3.90–3.72 (m, 2H), 3.81 (s, 3H), 3.56–3.44 (m, 2H), 3.42–3.32 (m, 2H), 2.50–2.30 (m, 2H), 2.30–2.08 (m, 2H), 1.82–1.14 (m, 15H), 1.02–0.88 (m, 5H).

EXAMPLE 40(81)

(3S)-1-butyl-2,5-dioxo-3-cyclohexylmethyl-9-(4-(4-methylaminocarbonylphenyloxy)phenylmethyl)-1,4,9-triazaspiro[5.5]undecane.hydrochloride

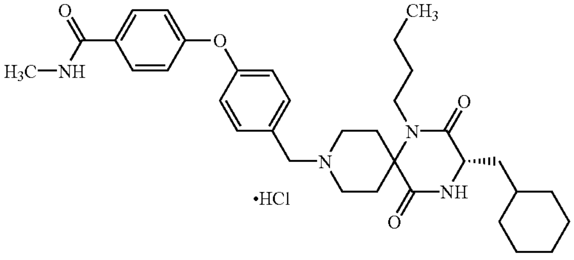

TLC: Rf 0.46 (chloroform:methanol=10:1);

NMR ($CD_3OD$): δ 8.39 (br d, J=4.5 Hz, 1H), 7.84 (d, J=9.0 Hz, 2H), 7.58 (d, J=8.4 Hz, 2H), 7.15 (d, J=8.4 Hz, 2H), 7.07 (d, J=9.0 Hz, 2H), 4.35 (s, 2H), 4.04 (m, 1H), 3.85–3.74 (m, 2H), 3.53–3.38 (m, 4H), 2.91 (d, J=4.5 Hz, 3H), 2.55–2.30 (m, 2H), 2.30–2.10 (m, 2H), 1.80–1.10 (m, 15H), 1.10–0.90 (m, 2H), 0.95 (t, J=7.2 Hz, 3H).

EXAMPLE 40(82)

(3S)-1-butyl-2,5-dioxo-3-cyclohexylmethyl-9-(4-(4-chlorophenyloxy)phenylmethyl)-1,4,9-triazaspiro[5.5]undecane.hydrochloride

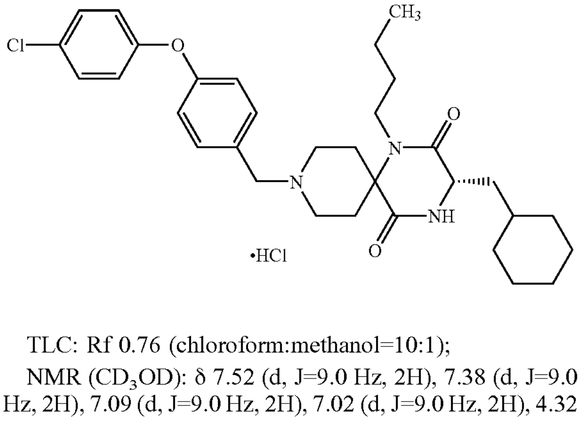

TLC: Rf 0.76 (chloroform:methanol=10:1);

NMR ($CD_3OD$): δ 7.52 (d, J=9.0 Hz, 2H), 7.38 (d, J=9.0 Hz, 2H), 7.09 (d, J=9.0 Hz, 2H), 7.02 (d, J=9.0 Hz, 2H), 4.32 (s, 2H), 4.04 (m, 1H), 3.90–3.70 (m, 2H), 3.60–3.30 (m, 4H), 2.50–2.10 (m, 4H), 1.90–1.10 (m, 15H), 1.10–0.90 (m, 2H), 0.95 (t, J=7.5 Hz, 3H).

EXAMPLE 40(83)

(3S)-1-butyl-2,5-dioxo-3-cyclohexyl methyl-9-(4-bis (methylsulfonyl)aminophenylmethyl)-1,4,9-triaza-spiro[5.5]undecane.hydrochloride

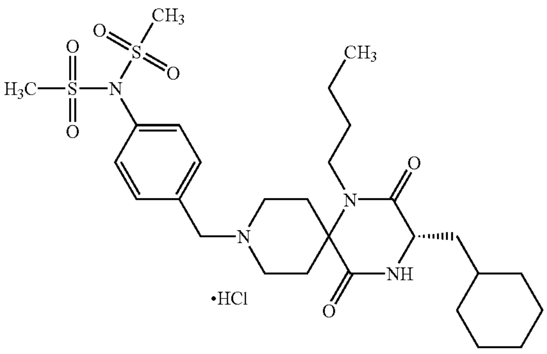

TLC: Rf 0.60 (chloroform:methanol=5:1);

NMR ($CD_3OD$): δ 7.69 (d, J=8.4 Hz, 2H), 7.60 (d, J=8.4 Hz, 2H), 4.41 (s, 2H), 4.05 (dd, J=7.8, 4.8 Hz, 1H), 3.92–3.70 (m, 2H), 3.56–3.36 (m, 4H), 3.47 (s, 6H), 2.46–2.08 (m, 4H), 1.84–1.16 (m, 15H), 0.96 (t, J=7.5 Hz, 3H), 0.96 (m, 2H).

EXAMPLE 40(84)

(3S)-1-butyl-2,5-dioxo-3-cyclohexylmethyl-9-(3-(4-carboxyphenyl)phenylmethyl)-1,4,9-triazaspiro[5.5] undecane.hydrochloride

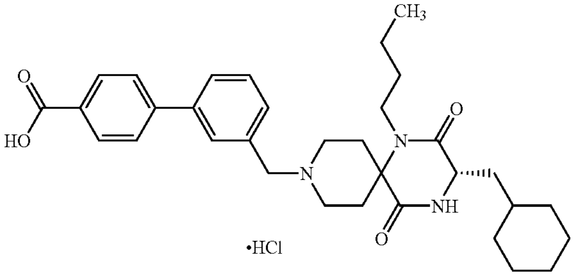

TLC: Rf 0.60 (chloroform:methanol=5:1);

NMR ($CD_3OD$): δ 8.13 (d, J=9.0 Hz, 2H), 7.95 (s, 1H), 7.84 (m, 1H), 7.82 (d, J=9.0 Hz, 2H), 7.66–7.61 (m, 2H), 4.46 (s, 2H), 4.04 (dd, J=7.5, 4.5 Hz, 1H), 3.96–3.78 (m, 2H), 3.62–3.36 (m, 4H), 2.54–2.32 (m, 2H), 2.28–2.08 (m, 2H), 1.82–1.08 (m, 15H), 0.95 (t, J=7.2 Hz, 3H), 0.95 (m, 2H).

EXAMPLE 40(85)

(3S)-1-butyl-2,5-dioxo-3-cyclohexylmethyl-9-(4-(phenylaminocarbonyl) phenylmethyl)-1,4,9-triaza-spiro[5.5]undecane.hydrochloride

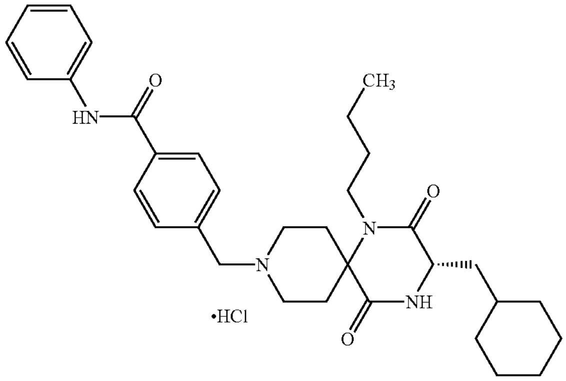

TLC: Rf 0.25 (chloroform:methanol=10:1);

NMR ($CD_3OD$): δ 8.07 (d, J=8.1 Hz, 2H), 7.73–7.67 (m, 2H), 7.71 (d, J=8.1 Hz, 2H), 7.38 (t, J=7.5 Hz, 2H), 7.17 (t, J=7.5 Hz, 1H), 4.45 (s, 2H), 4.05 (dd, J=7.8, 4.8 Hz, 1H), 3.92–3.72 (m, 2H), 3.58–3.36 (m, 4H), 2.50–2.08 (m, 4H), 1.84–1.08 (m, 15H), 0.96 (t, J=7.8 Hz, 3H), 0.96 (m, 2H).

EXAMPLE 40(86)

(3S)-1-butyl-2,5-dioxo-3-cyclohexylmethyl-9-(4-(4-methylthiophenyloxy)phenylmethyl)-1,4,9-triaza-spiro[5.5]undecane.hydrochloride

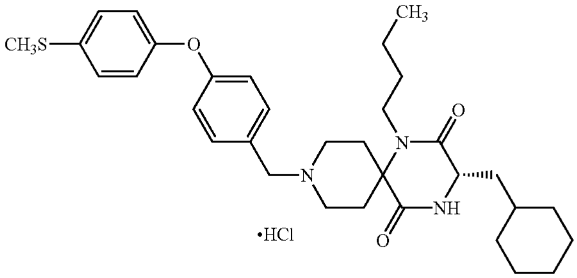

TLC: Rf 0.48 (chloroform:methanol=10:1);

NMR ($CD_3OD$): δ 7.54 (d, J=8.7 Hz, 2H), 7.33 (d, J=8.7 Hz, 2H), 7.06 (d, J=8.7 Hz, 2H), 7.00 (d, J=8.7 Hz, 2H), 4.34 (s, 2H), 4.05 (dd, J=7.5, 4.5 Hz, 1H), 3.86–3.70 (m, 2H), 3.56–3.36 (m, 4H), 2.48 (s, 3H), 2.48–2.32 (m, 2H), 2.28–2.08 (m, 2H), 1.82–1.14 (m, 15H), 0.96 (t, J=7.2 Hz, 3H), 0.96 (m, 2H),

EXAMPLE 40(87)

(3S)-1-butyl-2,5-dioxo-3-cyclohexylmethyl-9-(4-(4-(2-dimethylaminoethylaminocarbonyl)phenyloxy)phenylmethyl)-1,4,9-triazaspiro[5.5]undecane.hydrochloride

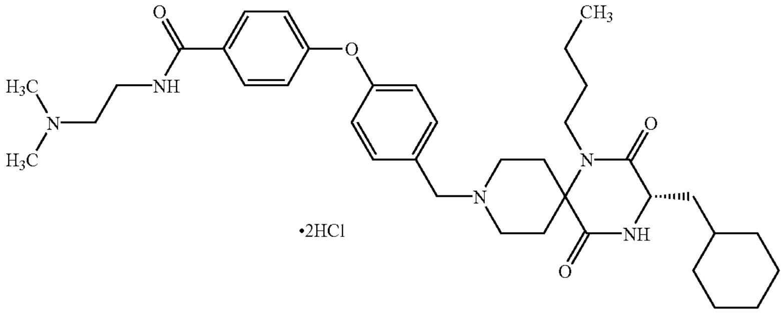

•2HCl

TLC: Rf 0.11 (chloroform:methanol=10:1);

NMR ($CD_3OD$): δ 7.94 (d, J=9.0 Hz, 2H), 7.64 (d, J=8.7 Hz, 2H), 7.15 (d, J=8.7 Hz, 2H), 7.10 (d, J=9.0 Hz, 2H), 4.36 (s, 2H), 4.04 (dd, J=7.8, 4.8 Hz, 1H), 3.88–3.72 (m, 4H), 3.52–3.36 (m, 6H), 2.98 (s, 6H), 2.62–2.44 (m, 2H), 2.24–2.08 (m, 2H), 1.80–1.10 (m, 15H), 1.00–0.88 (m, 5H).

EXAMPLE 40(88)

(3S)-1-butyl-2,5-dioxo-3-cyclohexylmethyl-9-(4-aminocarbonylphenylmethyl)-1,4,9-triazaspiro[5.5]undecane.hydrochloride

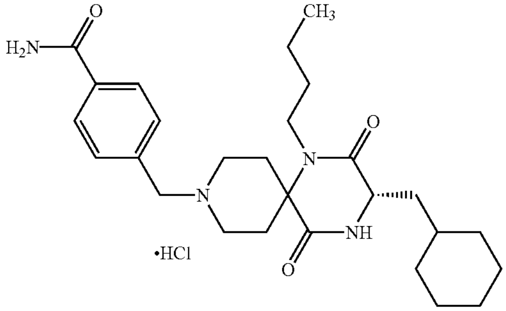

•HCl

TLC: Rf 0.19 (chloroform:methanol=10:1);

NMR ($CD_3OD$): δ 7.98 (d, J=8.4 Hz, 2H), 7.68 (d, J=8.4 Hz, 2H), 4.43 (s, 2H), 4.03 (dd, J=7.5, 4.8 Hz, 1H), 3.92–3.76 (m, 2H), 3.54–3.28 (m, 4H), 2.52–2.36 (m, 2H), 2.24–2.08 (m, 2H), 1.82–1.10 (m, 15H), 1.02–0.88 (m, 5H).

EXAMPLE 40(89)

(3S)-1-butyl-2,5-dioxo-3-cyclohexylmethyl-9-(4-(dimethylaminocarbonyl)phenylmethyl)-1,4,9-triazaspiro[5.5]undecane.hydrochloride

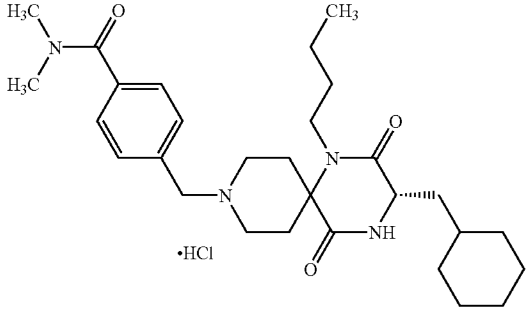

•HCl

TLC: Rf 0.33 (chloroform:methanol=10:1);

NMR ($CD_3OD$): δ 7.67 (d, J=8.1 Hz, 2H), 7.54 (d, J=8.1 Hz, 2H), 4.41 (s, 2H), 4.04 (dd, J=7.5, 4.2 Hz, 1H), 3.92–3.76 (m, 2H), 3.54–3.32 (m, 4H), 3.11 (s, 3H), 2.99 (s, 3H), 2.52–2.32 (m, 2H), 2.26–2.08 (m, 2H), 1.82–1.10 (m, 15H), 1.02–0.86 (m, 5H).

EXAMPLE 40(90)

(3S)-1-butyl-2,5-dioxo-3-cyclohexylmethyl-9-(4-phenyloxyphenylmethyl)-1,4,9-triazaspiro[5.5]undecane

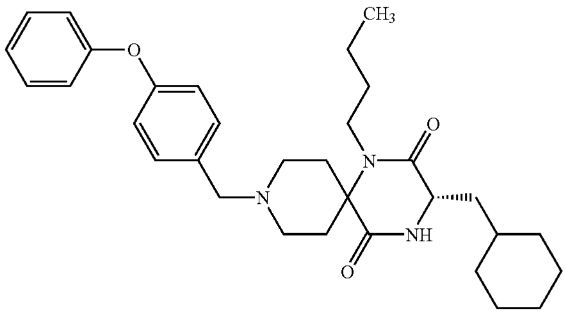

TLC: Rf 0.73 (chloroform:methanol=10:1);

NMR ($CDCl_3$): δ 7.37–7.25 (m, 4H), 7.10 (m, 1H), 7.04–6.98 (m, 2H), 6.96 (d, J=8.7 Hz, 2H), 5.81 (brs, 1H), 3.99 (m, 1H), 3.52 (s, 2H), 3.52–3.32 (m, 2H), 2.92–2.74 (m, 3H), 2.57 (dt, J=12.0, 3.0 Hz, 1H), 2.18–1.88 (m, 5H), 1.76–1.13 (m, 14H), 1.07–0.88 (m, 2H), 0.93 (t, J=7.5 Hz, 3H).

EXAMPLE 41

By the same procedure as described in Reference Example 3→Reference Example 4 using Resin (3) prepared in Reference Example 2, N-allyloxycarbonyl-4-piperidone, n-butylamine and (2R*, 3R*)-N-(t-butyloxycarbonyl)-2-amino-3-hydroxy-4-methylpentanoic acid, and furthermore by the same procedure as described in Reference Example 5→Reference Example 6→Example 1 using 1,4-benzodioxan-6-carboxyaldehyde, the following compounds (1) and (2) of the present invention were obtained respectively.

EXAMPLE 40(1)

1-butyl-2,5-dioxo-3-(1-hydroxy-2-methylpropyl)-9-(1,4-benzodioxan-6-ylmethyl)-1,4,9-triazaspiro[5.5]undecane.hydrochloride

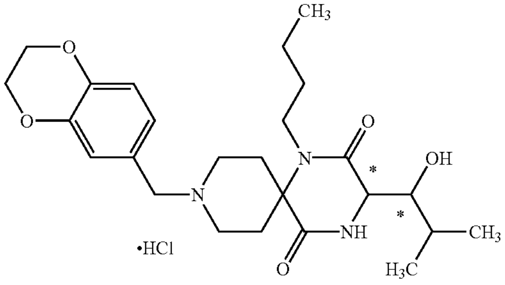

(Symbol * means the mixture of syn form and anti form (syn: anti=2:3.)

TLC: Rf 0.47 (chloroform:methanol=10:1);

NMR ($CD_3OD$): δ 7.04 (d, J=2.1 Hz, 1H), 6.97 (dd, J=8.4, 2.1 Hz, 1H), 6.93 (d, J=8.4 Hz, 1H), 4.26 (s, 4H), 4.23 (s, 2H), 4.13 (d, J=2.1 Hz, 0.6H), 4.08 (d, J=1.2 Hz, 0.4H), 4.05–3.90 (m, 1H), 3.76–3.63 (m, 1H), 3.62–3.35 (m, 3.4H), 3.19 (dd, J=9.6, 2.1 Hz, 0.6H), 3.20–3.10 (m, 1H), 2.55–2.33 (m, 2H), 2.30–1.95 (m, 3H), 1.80–1.60 (m, 1H), 1.55–1.25 (m, 3H), 1.05–0.89 (m, 9H),

EXAMPLE 41(2)

(Z)-1-butyl-2,5-dioxo-3-(2-methylpropylidene)-9-(1,4-benzodioxan-6-ylmethyl)-1,4,9-triazaspiro[5.5]undecane.hydrochloride

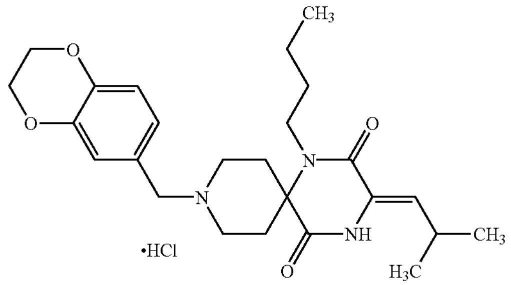

TLC: Rf 0.52 (chloroform:methanol=20:1);

NMR ($CD_3OD$): δ 7.04 (d, J=2.1 Hz, 1H), 6.97 (dd, J=8.4, 2.1 Hz, 1H), 6.93 (d, J=8.4 Hz, 1H), 5.84 (d, J=10.5 Hz, 1H), 4.26 (s, 4H), 4.23 (s, 2H), 3.72–3.55 (m, 2H), 3.53–3.35 (m, 4H), 2.80–2.60 (m, 1H), 2.43–2.26 (m, 2H), 2.25–2.15 (m, 2H), 1.62–1.48 (m, 2H), 1.45–1.30 (m, 2H), 1.04 (d, J=6.6 Hz, 6H), 0.95 (t, J=7.5 Hz, 3H).

EXAMPLE 41(3)~41(5)

By the same procedure as described in Example 41 using the corresponding compounds instead of (2R*, 3R*)-N-(t-butyloxycarbonyl)-2-amino-3-hydroxy-4-methylpentanoic acid, and the corresponding compounds instead of 1,4-benzodioxan-6-carboxyaldehyde, the following compounds of the present invention were obtained.

EXAMPLE 41(3)

(3S)-1-butyl-2,5-dioxo-3-((1R)-1-hydroxyethyl)-9-(4-phenyloxyphenylmethyl)-1,4,9-triazaspiro[5.5]undecane.hydrochloride

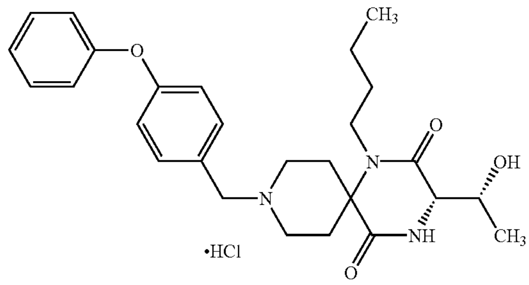

TLC: Rf 0.39 (chloroform:methanol=10:1);

NMR ($CD_3OD$): δ 7.54 (d, J=8.7 Hz, 2H), 7.43–7.35 (m, 2H), 7.21–7.14 (m, 1H), 7.08–7.00 (m, 4H), 4.32 (s, 2H), 4.19 (dq, J=1.5, 6.9 Hz, 1H), 4.10–3.97 (m, 1H), 3.78 (d,

J=1.5 Hz, 1H), 3.72–3.51 (m, 2H), 3.51–3.40 (m, 2H), 3.28–3.14 (m, 1H), 2.57–2.42 (m, 2H), 2.40–2.25 (m, 1H), 2.21–2.10 (m, 1H), 1.81–1.60 (m, 1H), 1.50–1.30 (m, 3H), 1.22 (d, J=6.9 Hz, 3H), 0.95 (t, J=7.2 Hz, 3H).

EXAMPLE 41(4)

(Z)-1-butyl-2,5-dioxo-3-ethylidene-9-(4-phenyloxyphenylmethyl)-1,4,9-triazaspiro[5.5]undecane.hydrochloride

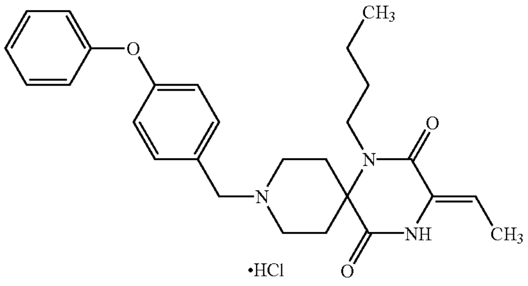

TLC: Rf 0.29 (chloroform:methanol=20:1);

NMR ($CD_3OD$): δ 7.53 (d, J=9.0 Hz, 2H), 7.43–7.35 (m, 2H), 7.18 (t, J=7.5 Hz, 1H), 7.09–7.00 (m, 4H), 6.08 (q, J=7.5 Hz, 1H), 4.33 (s, 2H), 3.76–3.61 (m, 2H), 3.57–3.40 (m, 4H), 2.45–2.30 (m, 2H), 2.28–2.15 (m, 2H), 1.77 (d, J=7.5 Hz, 3H), 1.62–1.46 (m, 2H), 1.44–1.28 (m, 2H), 0.96 (t, J=7.5 Hz, 3H).

EXAMPLE 41(5)

(Z)-1-butyl-2,5-dioxo-3-(2-methylpropylidene)-9-(4-phenyloxyphenylmethyl)-1,4,9-triazaspiro[5.5]undecane.hydrochloride

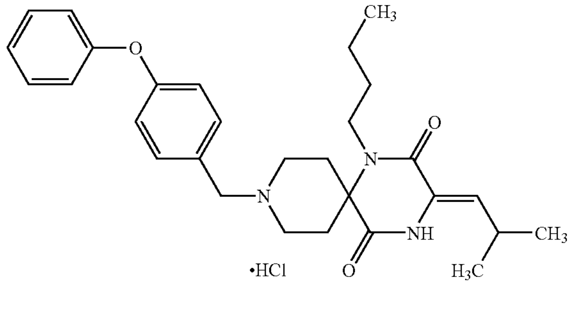

TLC: Rf 0.42 (chloroform:methanol=20:1);

NMR ($CD_3OD$): δ 7.51 (d, J=8.7 Hz, 2H), 7.43–7.35 (m, 2H), 7.18 (t, J=7.5 Hz, 1H), 7.06 (d, J=8.7 Hz, 2H), 7.08–7.01 (m, 2H), 5.85 (d, J=10.5 Hz, 1H), 4.34 (s, 2H), 3.78–3.64 (m, 2H), 3.57–3.40 (m, 4H), 2.78–2.62 (m, 1H), 2.43–2.18 (m, 4H), 1.62–1.48 (m, 2H), 1.46–1.30 (m, 2H), 1.04 (d, J=6.6 Hz, 6H), 0.96 (t, J=7.5 Hz, 3H).

EXAMPLE 42

(3R*)-1-butyl-2,5-dioxo-3-((1R*)-1-hydroxy-2-methylpropyl)-9-benzyloxycarbonyl-1,4,9-triazaspiro[5.5]undecane

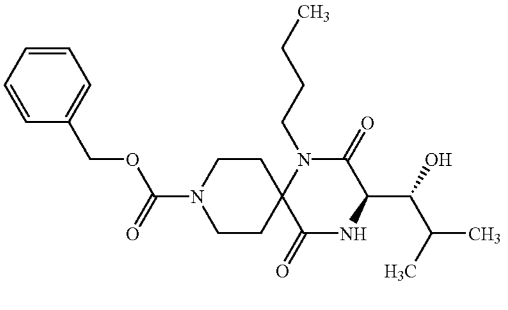

By the same procedure as described in Example 35 using (2R*,3R*)-N-(t-butyloxycarbonyl)-2-amino-3-hydroxy-4-methyl pentanoic acid instead of N-(t-butyloxycarbonyl)-L-leucine, the compound of the present invention having the following physical data was obtained.

TLC: Rf 0.43 (chloroform:methanol=10:1);

NMR ($CD_3OD$): δ 7.39–7.30 (m, 5H), 5.13 (br, 2H), 4.12 (d, J=2.5 Hz, 1H), 4.10–4.00 (m, 2H), 3.76–3.50 (m, 2H), 3.39–3.25 (m, 2H), 3.10–2.94 (m, 1H), 2.18 (m, 1H), 2.08–1.83 (m, 4H), 1.70–1.56 (m, 1H), 1.45–1.15 (m, 3H), 1.01–0.89 (m, 9H).

EXAMPLE 43

(3R*)-1-butyl-2,5-dioxo-3-((1R*)-1-hydroxy-2-methylpropyl)-1,4,9-triazaspiro[5.5]undecane.hydrochloride

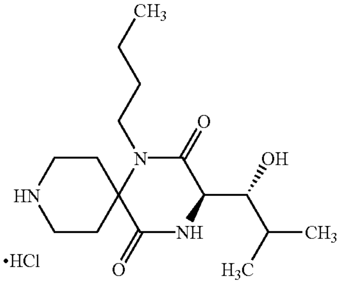

By the same procedure as described in Example 9 using the compound prepared in Example 42, the compound of the present invention having the following physical data was obtained.

TLC: Rf 0.08 (chloroform:methanol=10:1);

NMR ($CD_3OD$): δ 4.15 (d, J=2.0 Hz, 1H), 3.96 (dt, J=13.0, 4.0 Hz, 1H), 3.71 (dt, J=13.0, 4.0 Hz, 1H), 3.57–3.47 (m, 1H), 3.40–3.34 (m, 2H), 3.23–3.12 (m, 2H), 2.47–2.30 (m, 2H), 2.25–1.98 (m, 3H), 1.79–1.66 (m, 1H), 1.52–1.28 (m, 3H), 1.07–0.94 (m, 9H).

EXAMPLE 44(1)~44(13)

By the same procedure as described in Example 10 using the compound prepared in Example 43 and the corresponding aldehyde derivatives, the following compounds were obtained.

EXAMPLE 44(1)

(3R*)-1-butyl-2,5-dioxo-3-((1R*)-1-hydroxy-2-methylpropyl)-9-(4-phenyloxyphenylmethyl)-1,4,9-triazaspiro[5.5]undecane.hydrochloride

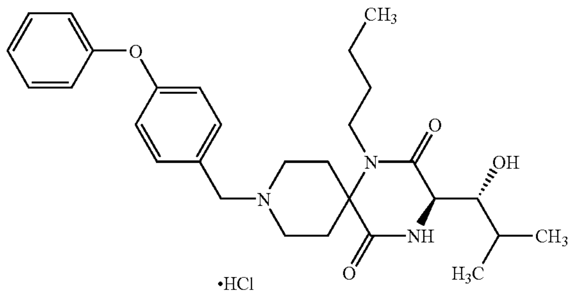

•HCl

TLC: Rf 0.51 (chloroform:methanol=10:1);

NMR ($CD_3OD$): δ 7.52 (d, J=8.7 Hz, 2H), 7.44–7.35 (m, 2H), 7.18 (t, J=7.5 Hz, 1H), 7.10–7.00 (m, 4H), 4.33 (s, 2H), 4.14 (d, J=2.1 Hz, 1H), 4.06–3.93 (m, 1H), 3.80–3.67 (m, 1H), 3.56–3.40 (m, 3H), 3.19 (dd, J=9.3, 2.1 Hz, 1H), 3.20–3.10 (m, 1H), 2.53–2.35 (m, 2H), 2.35–2.20 (m, 1H), 2.19–2.08 (m, 1H), 2.07–1.91 (m, 1H), 1.80–1.70 (m, 1H), 1.50–1.25 (m, 3H), 0.99 (d, J=6.6 Hz, 3H), 0.97 (d, J=6.6 Hz, 3H), 0.95 (t, J=7.2 Hz, 3H).

EXAMPLE 44(2)

(3R*)-1-butyl-2,5-dioxo-3-((1R*)-1-hydroxy-2-methylpropyl)-9-(3,5-dimethyl-1-phenylpyrazol-4-ylmethyl)-1,4,9-triazaspiro[5.5]undecane.2 hydrochloride

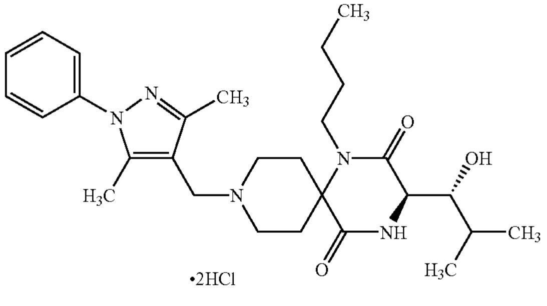

•2HCl

TLC: Rf 0.38 (chloroform:methanol=10:1);

NMR ($CD_3OD$): δ 7.60–7.45 (m, 5H), 4.30 (s, 2H), 4.15 (d, J=2.4 Hz, 1H), 4.05 (m, 1H), 3.79 (m, 1H), 3.62–3.48 (m, 3H), 3.29–3.16 (m, 2H), 2.60–2.45 (m, 2H), 2.44–2.30 (m, 7H), 2.17 (m, 1H), 2.01 (m, 1H), 1.70 (m, 1H), 1.51–1.31 (m, 3H), 1.03–0.91 (m, 9H).

EXAMPLE 44(3)

(3R*)-1-butyl-2,5-dioxo-3-((1R*)-1-hydroxy-2-methylpropyl)-9-(6-phenyloxypyridin-3-ylmethyl)-1,4,9-triazaspiro[5.5]undecane.2 hydrochloride

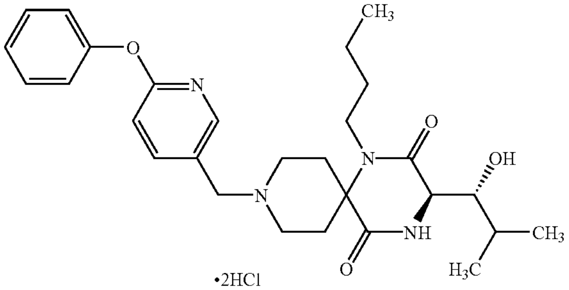

•2HCl

TLC: Rf 0.51 (chloroform:methanol=10:1);

NMR ($CD_3OD$): δ 8.39 (d, J=2.1 Hz, 1H), 8.16 (dd, J=8.4, 2.1 Hz, 1H), 7.46 (t, J=7.8 Hz, 2H), 7.29 (t, J=7.8 Hz, 1H), 7.17 (d, J=7.8 Hz, 2H), 7.08 (d, J=8.4 Hz, 1H), 4.40 (s, 2H), 4.13 (d, J=2.1 Hz, 1H), 4.07–3.94 (m, 1H), 3.83–3.69 (m, 1H), 3.60–3.42 (m, 3H), 3.29–3.22 (m, 1H), 3.19 (dd, J=9.6, 2.1 Hz, 1H), 2.62–2.32 (m, 3H), 2.18–2.07 (m, 1H), 2.06–1.94 (m, 1H), 1.78–1.60 (m, 1H), 1.50–1.31 (m, 3H), 1.07–0.87 (m, 9H).

EXAMPLE 44(4)

(3R*)-1-butyl-2,5-dioxo-3-((1R*)-1-hydroxy-2-methylpropyl)-9-(4-(4-methylphenyloxy)phenylmethyl)-1,4,9-triazaspiro[5.5]undecane.hydrochloride

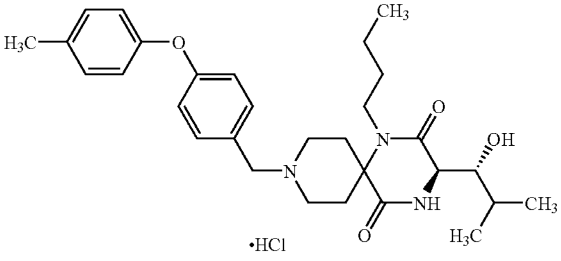

•HCl

TLC: Rf 0.46 (chloroform:methanol=10:1);

NMR ($CD_3OD$): δ 7.47 (d, J=8.7 Hz, 2H), 7.20 (d, J=8.7 Hz, 2H), 7.02 (d, J=8.7 Hz, 2H), 6.92 (d, J=8.7 Hz, 2H), 4.29 (s, 2H), 4.14 (d, J=2.1 Hz, 1H), 3.97 (m, 1H), 3.72 (m, 1H), 3.56–3.39 (m, 2H), 3.25–3.09 (m, 3H), 2.53–2.08 (m, 7H), 2.01 (m, 1H), 1.70 (m, 1H), 1.48–1.28 (m, 3H), 1.05–0.88 (m, 9H).

EXAMPLE 44(5)

(3R*)-1-butyl-2,5-dioxo-3-((1R*)-1-hydroxy-2-methylpropyl)-9-(4-cyclohexyloxyphenylmethyl)-1,4,9-triazaspiro[5.5]undecane.hydrochloride

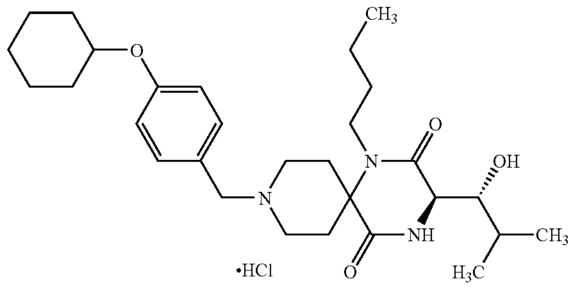

TLC: Rf 0.43 (chloroform:methanol=10:1);

NMR ($CD_3OD$): δ 7.40 (d, J=8.7 Hz, 2H), 7.00 (d, J=8.7 Hz, 2H), 4.37 (m, 1H), 4.24 (brs, 2H), 4.13 (d, J=2.1 Hz, 1H), 3.94 (m, 1H), 3.68 (m, 1H), 3.52–3.34 (m, 2H), 3.29–3.07 (m, 3H), 2.52–1.92 (m, 7H), 1.85–1.27 (m, 12H), 1.04–0.89 (m, 9H).

EXAMPLE 44(6)

(3R*)-1-butyl-2,5-dioxo-3-((1R*)-1-hydroxy-2-methylpropyl)-9-(4-(tetrahydropyran-4-yl oxy) phenylmethyl)-1,4,9-triazaspiro[5.5]undecane.hydrochloride

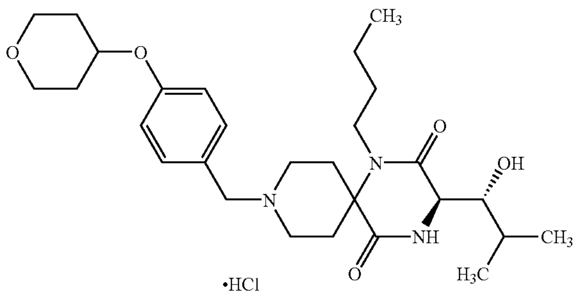

TLC: Rf 0.20 (ethyl acetate: methanol=10:1);

NMR ($CD_3OD$): δ 7.45 (d, J=8.7 Hz, 2H), 7.06 (d, J=8.7 Hz, 2H), 4.67–4.59 (m, 1H), 4.28 (s, 2H), 4.13 (d, J=2.5 Hz, 1H), 4.00–3.90 (m, 3H), 3.75–3.67 (m, 1H), 3.63–3.53 (m, 2H), 3.50–3.41 (m, 3H), 3.18 (dd, J=9.0, 2.0 Hz, 1H), 3.18 (m, 1H), 2.49–1.96 (m, 7H), 1.77–1.65 (m, 3H), 1.44–1.30 (m, 3H), 0.98 (d, J=6.5 Hz, 3H), 0.96 (d, J=6.5 Hz, 3H), 0.94 (t, J=7.2 Hz, 3H).

EXAMPLE 44(7)

(3R*)-1-butyl-2,5-dioxo-3-((1R*)-1-hydroxy-2-methylpropyl)-9-(4-(pyridin-3-yloxy)phenylmethyl)-1,4,9-triazaspiro[5.5]undecane.2 hydrochloride

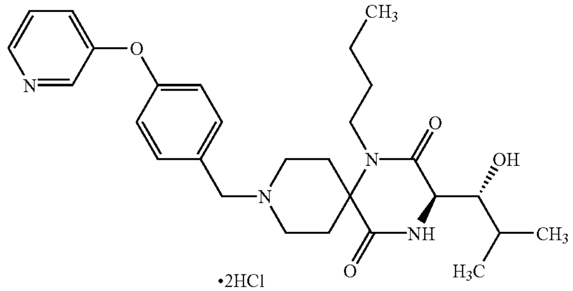

TLC: Rf 0.22 (ethyl acetate:methanol=10:1);

NMR ($CD_3OD$): δ 8.76 (d, J=2.5 Hz, 1H), 8.63 (d, J=6.0 Hz, 1H), 8.29 (dd, J=9.0, 2.5 Hz, 1H), 8.08 (dd, J=9.0, 6.0 Hz, 1H), 7.77 (d, J=9.0 Hz, 2H), 7.35 (d, J=9.0 Hz, 2H), 4.41 (s, 2H), 4.14 (d, J=2.0 Hz, 1H), 4.00 (m, 1H), 3.76 (m, 1H), 3.61–3.47 (m, 3H), 3.20 (dd, J=9.5, 2.0 Hz, 1H), 3.20 (m, 1H), 2.62 (m, 1H), 2.46 (m, 2H), 2.10 (m, 1H), 2.05–1.95 (m, 1H), 1.69 (m, 1H), 1.41–1.35 (m, 3H), 0.99 (d, J=6.5 Hz, 3H), 0.97 (d, J=6.5 Hz, 3H), 0.95 (t, J=7.5 Hz, 3H).

EXAMPLE 44(8)

(3R*)-1-butyl-2,5-dioxo-3-((1R*)-1-hydroxy-2-methylpropyl)-9-(4-isopropylphenylmethyl)-1,4,9-triazaspiro[5.5]undecane.hydrochloride

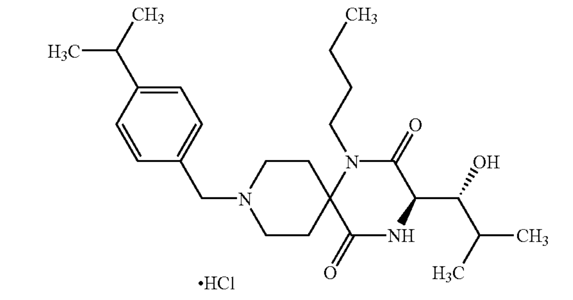

TLC: Rf 0.55 (chloroform:methanol=10:1);

NMR ($CD_3OD$) δ 7.47 (d, J=8.1 Hz, 2H), 7.37 (d, J=8.1 Hz, 2H), 4.31 (s, 2H), 4.13 (d, J=2.1 Hz, 1H), 4.05–3.91 (m, 1H), 3.80–3.65 (m, 1H), 3.57–3.38 (m, 3H), 3.26–3.13 (m, 1H), 3.19 (dd, J=9.3, 2.1 Hz, 1H), 3.03–2.86 (m, 1H), 2.53–2.38 (m, 2H), 2.38–2.23 (m, 1H), 2.16–2.05 (m, 1H), 2.06–1.92 (m, 1H), 1.77–1.56 (m, 1H), 1.49–1.26 (m, 3H), 1.25 (d, J=6.9 Hz, 6H), 0.98 (d, J=6.6 Hz, 3H), 0.97 (d, J=6.6 Hz, 3H), 0.94 (t, J=7.2 Hz, 3H).

EXAMPLE 44(9)

(3R*)-1-butyl-2,5-dioxo-3-((1R*)-1-hydroxy-2-methylpropyl)-9-(3,5-dimethyl-1-(4-methylphenyl) pyrazol-4-ylmethyl)-1,4,9-triazaspiro[5.5]undecane.2 hydrochloride

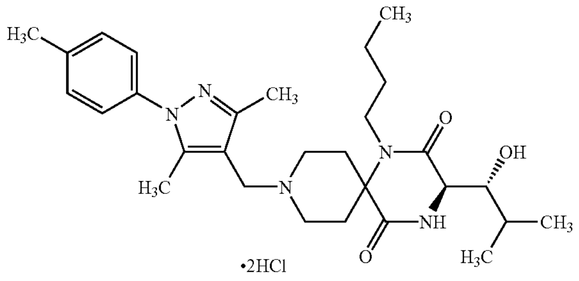

TLC: Rf 0.49 (chloroform:methanol=10:1);

NMR ($CD_3OD$): δ 7.40 (s, 4H), 4.33 (s, 2H), 4.15 (d, J=2.1 Hz, 1H), 4.11–3.97 (m, 1H), 3.86–3.72 (m, 1H), 3.64–3.50 (m, 3H), 3.39–3.30 (m, 1H), 3.21 (dd, J=9.3, 2.1 Hz, 1H), 2.72–2.55 (m, 1H), 2.53–2.40 (m, 2H), 2.46 (s, 3H), 2.44 (s, 3H), 2.40 (s, 3H), 2.18–2.07 (m, 1H), 2.07–1.96 (m, 1H), 1.78–1.60 (m, 1H), 1.50–1.30 (m, 3H), 1.00 (d, J=6.6 Hz, 3H), 0.98 (d, J=6.6 Hz, 3H), 0.95 (t, J=7.2 Hz, 3H).

EXAMPLE 44(10)

(3R*)-1-butyl-2,5-dioxo-3-((1R*)-1-hydroxy-2-methylpropyl)-9-(3-methyl-5-chloro-1-phenylpyrazol-4-ylmethyl)-1,4,9-triazaspiro[5.5]undecane.2 hydrochloride

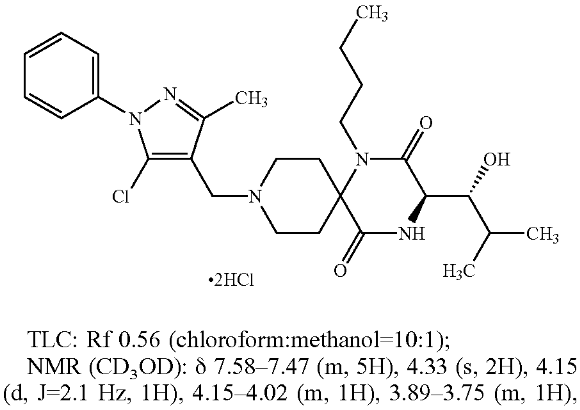

TLC: Rf 0.56 (chloroform:methanol=10:1);

NMR ($CD_3OD$): δ 7.58–7.47 (m, 5H), 4.33 (s, 2H), 4.15 (d, J=2.1 Hz, 1H), 4.15–4.02 (m, 1H), 3.89–3.75 (m, 1H), 3.65–3.48 (m, 3H), 3.30–3.20 (m, 1H), 3.20 (dd, J=9.6, 2.1 Hz, 1H), 2.64–2.46 (m, 2H), 2.44 (s, 3H), 2.44–2.32 (m, 1H), 2.21–2.10 (m, 1H), 2.08–1.93 (m, 1H), 1.80–1.60 (m, 1H), 1.52–1.30 (m, 3H), 0.99 (d, J=6.6 Hz, 3H), 0.98 (d, J=6.6 Hz, 3H), 0.96 (t, J=7.2 Hz, 3H).

EXAMPLE 44(11)

(3R*)-1-butyl-2,5-dioxo-3-((1R*)-1-hydroxy-2-methylpropyl)-9-(4-(4-carboxyphenyloxy)phenylmethyl)-1,4,9-triazaspiro[5.5]undecane.hydrochloride

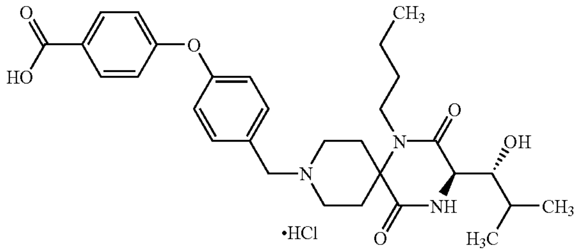

TLC: Rf 0.29 (chloroform:methanol=10:1);

NMR ($CD_3OD$): δ 8.04 (d, J=9.0 Hz, 2H), 7.60 (d, J=8.7 Hz, 2H), 7.18 (d, J=8.7 Hz, 2H), 7.07 (d, J=9.0 Hz, 2H), 4.37 (s, 2H), 4.14 (d, J=2.1 Hz, 1H), 4.10–3.94 (m, 1H), 3.83–3.69 (m, 1H), 3.59–3.40 (m, 3H), 3.25–3.12 (m, 1H), 3.19 (dd, J=9.3, 2.1 Hz, 1H), 2.55–2.37 (m, 2H), 2.37–2.22 (m, 1H), 2.19–2.08 (m, 1H), 2.08–1.94 (m, 1H), 1.79–1.60 (m, 1H), 1.52–1.26 (m, 3H), 0.99 (d, J=6.6 Hz, 3H), 0.97 (d, J=6.6 Hz, 3H), 0.95 (t, J=7.2 Hz, 3H).

EXAMPLE 44(12)

(3R*)-1-butyl-2,5-dioxo-3-((1R*)-1-hydroxy-2-methylpropyl)-9-(3,5-dimethyl-1-(pyridin-2-yl) pyrazol-4-ylmethyl)-1,4,9-triazaspiro[5.5]undecane.2 hydrochloride

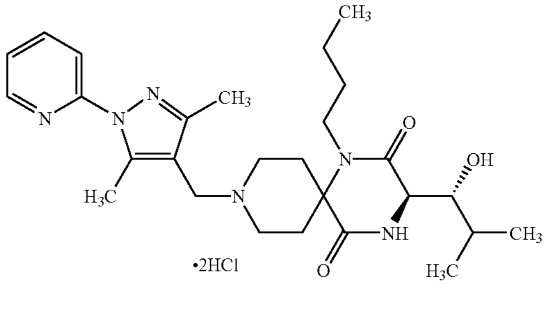

TLC: Rf 0.28 (chloroform:methanol=10:1);

NMR ($CD_3OD$): δ 8.53 (d, J=5.1 Hz, 1H), 8.05 (t, J=7.8 Hz, 1H), 7.81 (d, J=7.8 Hz, 1H), 7.44 (dd, J=7.8, 5.1 Hz, 1H), 4.33 (s, 2H), 4.16 (d, J=2.1 Hz, 1H), 4.06 (m, 1H), 3.78 (m, 1H), 3.62–3.44 (m, 3H), 3.26 (m, 1H), 3.21 (dd, J=9.6, 2.1 Hz, 1H), 2.68 (s, 3H), 2.60–2.30 (m, 3H), 2.42 (s, 3H), 2.16 (m, 1H), 2.02 (m, 1H), 1.72 (m, 1H), 1.50–1.26 (m, 3H), 1.00 (d, J=6.6 Hz, 3H), 0.99 (d, J=6.6 Hz, 3H), 0.96 (t, J=7.2 Hz, 3H).

EXAMPLE 44(13)

(3R*)-1-butyl-2,5-dioxo-3-((1R*)-1-hydroxy-2-methylpropyl)-9-(3,5-dimethyl-1-(4-carboxyphenyl)pyrazol-4-ylmethyl)-1,4,9-triazaspiro[5.5]undecane.2 hydrochloride

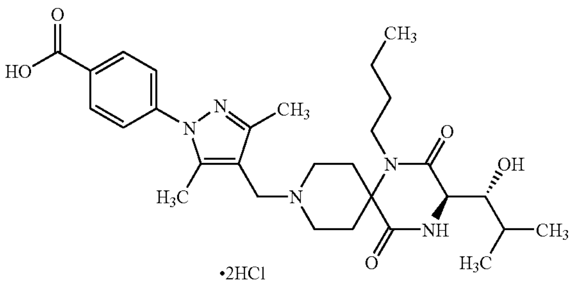

TLC: Rf 0.25 (chloroform:methanol: acetic acid=20:2:1);

NMR ($CD_3OD$): δ 8.19 (d, J=8.7 Hz, 2H), 7.62 (d, J=8.7 Hz, 2H), 4.32 (s, 2H), 4.16 (d, J=2.1 Hz, 1H), 4.12–3.98 (m, 1H), 3.87–3.74 (m, 1H), 3.63–3.45 (m, 3H), 3.30–3.10 (m, 1H), 3.20 (dd, J=9.3, 2.1 Hz, 1H), 2.59–2.48 (m, 2H), 2.44 (s, 3H), 2.40–2.23 (m, 1H), 2.39 (s, 3H), 2.23–2.10 (m, 1H), 2.10–1.96 (m, 1H), 1.80–1.62 (m, 1H), 1.52–1.24 (m, 3H), 1.00 (d, J=6.6 Hz, 3H), 0.98 (d, J =6.6 Hz, 3H), 0.96 (t, J=7.2 Hz, 3H).

EXAMPLE 45

(3R*)-1-butyl-2,5-dioxo-3-((1R*)-1-hydroxy-1-cyclohexylmethyl)-9-benzyloxycarbonyl-1,4,9-triazaspiro[5.5]undecane

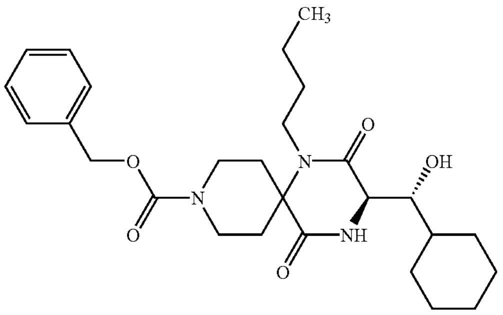

By the same procedure as described in Example 35 using (2R*,3R*)-N-(t-butyloxycarbonyl)-2-amino-3-hydroxy-3-cyclohexylpropanoic acid instead of N-(t-butyloxycarbonyl)-L-leucine, the compound of the present invention having the following physical data was obtained.

TLC: Rf 0.53 (chloroform:methanol=10:1);

NMR ($CD_3OD$): δ 7.39–7.27 (m, 5H), 5.13 (m, 2H), 4.13 (d, J=2.5 Hz, 1H), 4.06–4.02 (m, 2H), 3.78–3.48 (m, 2H), 3.36–3.29 (m, 2H), 3.02 (br, 1H), 2.17 (m, 1H), 2.03–1.58 (m, 10H), 1.47–1.13 (m, 6H), 1.02–0.89 (m, 5H).

EXAMPLE 46

(3R*)-1-butyl-2,5-dioxo-3-((1R*)-1-hydroxy-1-cyclohexylmethyl)-1,4,9-triazaspiro[5.5]undecane

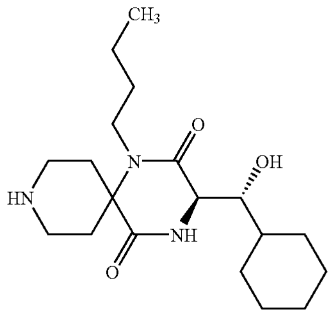

By the same procedure as described in Example 9 using the compound prepared in Example 45, the compound of the present invention having the following physical data was obtained.

TLC: Rf 0.33 (chloroform:methanol: acetic acid=20:6:1);

NMR ($CD_3OD$): δ 4.13 (d, J=2.5 Hz, 1H), 3.48–3.22 (m, 5H), 2.97–2.89 (m, 2H), 2.12–1.65 (m, 10H), 1.56–1.16 (m, 7H), 1.03–0.85 (m, 5H).

EXAMPLE 47(1)~47(8)

By the same procedure as described in Example 10 using the compound prepared in Example 46 and the corresponding aldehyde compounds, the following compounds of the present invention were obtained.

EXAMPLE 47(1)

(3R*)-1-butyl-2,5-dioxo-3-((1R*)-1-hydroxy-1-cyclohexylmethyl)-9-(4-phenyloxyphenylmethyl)-1,4,9-triazaspiro[5.5]undecane.hydrochloride

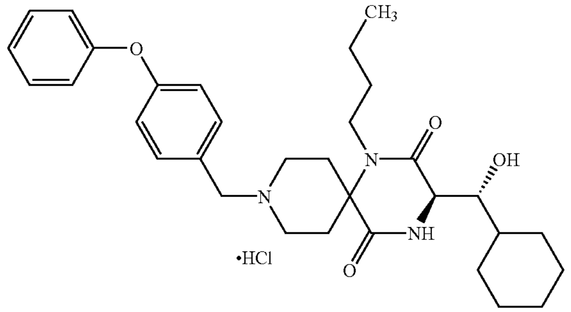

TLC: Rf 0.44 (chloroform:methanol=10:1);

NMR ($CD_3OD$): δ 7.55–7.51 (m, 2H), 7.42–7.36 (m, 2H), 7.18 (tt, J=7.5, 1.0 Hz, 1H), 7.08–7.01 (m, 4H), 4.32 (s, 2H), 4.15 (d, J=2.0 Hz, 1H), 3.98 (dt, J=3.5, 12.5 Hz, 1H), 3.73 (dt, J=3.5, 12.5 Hz, 1H), 3.57–3.39 (m, 3H), 3.26 (d, J=2.0 Hz, 1H), 3.20 (m, 1H), 2.52–2.39 (m, 2H), 2.30 (m, 1H), 2.12 (d, J=15.5 Hz, 1H), 2.04–1.92 (m, 2H), 1.80–1.62 (m, 5H), 1.48–1.11 (m, 6H), 1.01–0.82 (m, 5H).

EXAMPLE 47(2)

(3R*)-1-butyl-2,5-dioxo-3-((1R*)-1-hydroxy-1-cyclohexyl methyl)-9-(3,5-dimethyl-1-phenylpyrazol-4-ylmethyl)-1,4,9-triazaspiro[5.5]undecane.2 hydrochloride

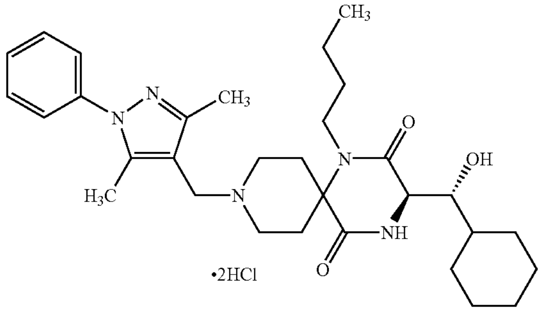

TLC: Rf 0.41 (chloroform:methanol=10:1);

NMR ($CD_3OD$): δ 7.60–7.50 (m, 5H), 4.33 (s, 2H), 4.17 (d, J=2.5 Hz, 1H), 4.04 (m, 1H), 3.85–3.75 (m, 1H), 3.61–3.51 (m, 3H), 3.35–3.27 (m, 2H), 2.62 (m, 1H), 2.49–2.44 (m, 5H), 2.41 (s, 3H), 2.15 (m, 1H), 2.05–1.92 (m, 2H), 1.77–1.65 (m, 5H), 1.44–1.15 (m, 6H), 1.01–0.85 (m, 5H).

EXAMPLE 47(3)

(3R*)-1-butyl-2,5-dioxo-3-((1R*)-1-hydroxy-1-cyclohexylmethyl)-9-(4-isopropyl phenylmethyl)-1,4,9-triazaspiro[5.5]undecane.hydrochloride

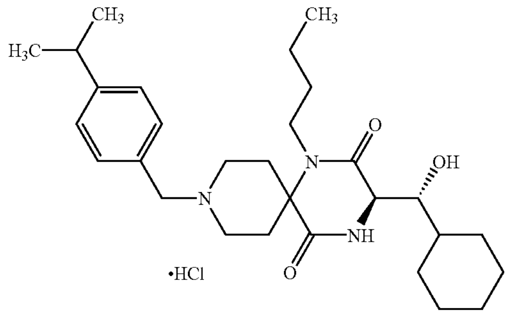

TLC: Rf 0.69 (chloroform:methanol=10:1);

NMR ($CD_3OD$): δ 7.48 (d, J=8.4 Hz, 2H), 7.36 (d, J=8.4 Hz, 2H), 4.31 (s, 2H), 4.14 (d, J=2.1 Hz, 1H), 3.98 (m, 1H), 3.72 (m, 1H), 3.55–3.40 (m, 3H), 3.29–3.16 (m, 2H), 2.95 (m, 1H), 2.52–2.24 (m, 3H), 2.15–1.86 (m, 3H), 1.80–1.60 (m, 5H), 1.48–1.10 (m, 6H), 1.25 (d, J=6.9 Hz, 6H), 1.02–0.82 (m, 5H).

EXAMPLE 47(4)

(3R*)-1-butyl-2,5-dioxo-3-((1R*)-1-hydroxy-1-cyclohexylmethyl)-9-(4-(6-methylpyridin-3-yloxy)phenylmethyl)-1,4,9-triazaspiro[5.5]undecane.2 hydrochloride

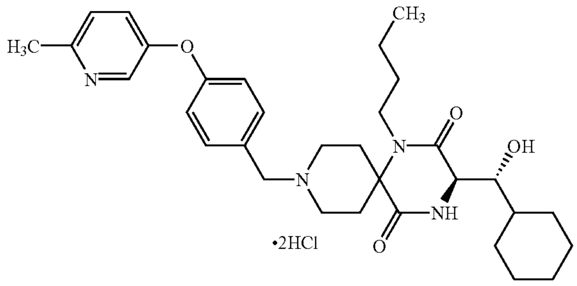

TLC: Rf 0.51 (ethyl acetate: methanol=10:1);

NMR ($CD_3OD$): δ 8.59 (d, J=2.7 Hz, 1H), 8.19 (dd, J=9.0, 2.7 Hz, 1H), 7.91 (d, J=9.0 Hz, 1H), 7.75 (d, J=8.4 Hz, 2H), 7.30 (d, J=8.4 Hz, 2H), 4.39 (s, 2H), 4.15 (d, J=2.0 Hz, 1H), 3.99 (m, 1H), 3.73 (m, 1H), 3.61–3.46 (m, 3H), 3.37–3.26 (m, 2H), 2.77 (s, 3H), 2.62 (m, 1H), 2.45 (m, 1H), 2.13–1.92 (m, 3H), 1.73 (m, 4H), 1.40–1.14 (m, 8H), 1.01–0.86 (m, 2H), 0.95 (t, J=7.0 Hz, 3H).

EXAMPLE 47(5)

(3R*)-1-butyl-2,5-dioxo-3-((1R*)-1-hydroxy-1-cyclohexylmethyl)-9-(3,5-dimethyl-1-(4-fluorophenyl)pyrazol-4-ylmethyl)-1,4,9-triazaspiro[5.5]undecane.2 hydrochloride

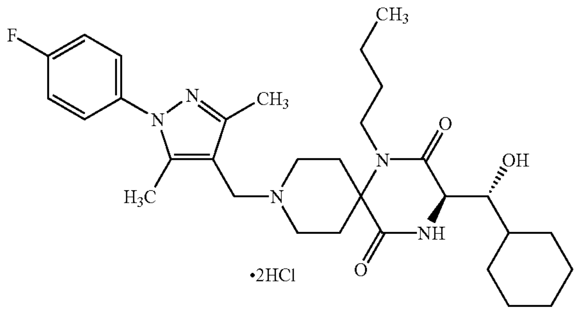

TLC: Rf 0.49 (ethyl acetate:methanol=10:1);

NMR ($CD_3OD$): δ 7.57 (m, 2H), 7.37–7.31 (m, 2H), 4.32 (s, 2H), 4.16 (d, J=2.0 Hz, 1H), 4.08–4.00 (m, 1H), 3.79 (m, 1H), 3.63–3.52 (m, 3H), 3.37–3.27 (m, 2H), 2.65 (m, 1H), 2.48 (m, 1H), 2.45 (s, 3H), 2.39 (s, 3H), 2.16–1.92 (m, 3H), 1.73 (m, 4H), 1.42–1.15 (m, 8H), 1.01–0.88 (m, 2H), 0.95 (t, J=7.0 Hz, 3H).

EXAMPLE 47(6)

(3R*)-1-butyl-2,5-dioxo-3-((1R*)-1-hydroxy-1-cyclohexylmethyl)-9-(4-(4-methoxyphenyloxy)phenylmethyl)-1,4,9-triazaspiro[5.5]undecane.hydrochloride

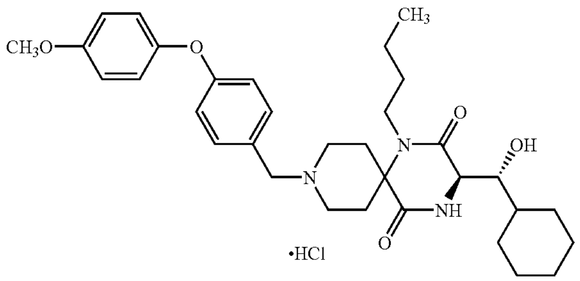

TLC: Rf 0.25 (chloroform:methanol=10:1);

NMR ($CD_3OD$): δ 7.47 (d, J=9.0 Hz, 2H), 7.00 (d, J=9.0 Hz, 2H), 6.99–6.92 (m, 4H), 4.30 (s, 2H), 4.16 (d, J=2.1 Hz, 1H), 3.98 (m, 1H), 3.80 (s, 3H), 3.72 (m, 1H), 3.58–3.38 (m, 3H), 3.30–3.08 (m, 2H), 2.54–1.88 (m, 6H), 1.82–1.60 (m, 5H), 1.50–1.10 (m, 6H), 0.96 (t, J=7.5 Hz, 3H), 0.96 (m, 2H).

EXAMPLE 47(7)

(3R*)-1-butyl-2,5-dioxo-3-((1R*)-1-hydroxy-1-cyclohexylmethyl)-9-(4-(4-fluorophenyloxy)phenylmethyl)-1,4,9-triazaspiro[5.5]undecane.hydrochloride

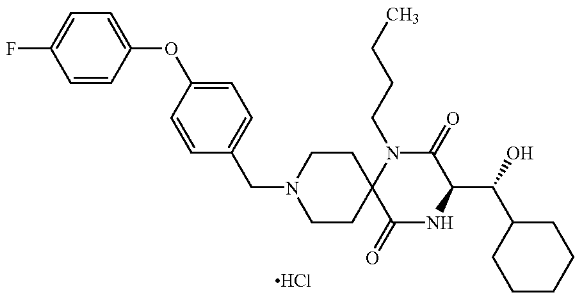

TLC: Rf 0.28 (chloroform:methanol=10:1);

NMR ($CD_3OD$): δ 7.51 (d, J=8.7 Hz, 2H), 7.13 (d, J=8.7 Hz, 2H), 7.10–7.04 (m, 4H), 4.33 (s, 2H), 4.16 (d, J=2.1 Hz, 1H), 4.00 (m, 1H), 3.72 (m, 1H), 3.58–3.40 (m, 3H), 3.30–3.08 (m, 2H), 2.56–1.88 (m, 6H), 1.82–1.60 (m, 5H), 1.54–1.10 (m, 6H), 0.96 (t, J=7.2 Hz, 3H), 0.96 (m, 2H).

EXAMPLE 47(8)

(3R*)-1-butyl-2,5-dioxo-3-((1R*)-1-hydroxy-1-cyclohexylmethyl)-9-(4-(4-methylsulfonylaminophenyloxy)phenylmethyl)-1,4,9-triazaspiro[5.5]undecane.hydrochloride

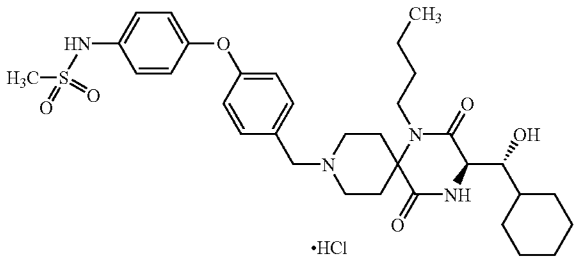

TLC: Rf 0.52 (ethyl acetate: methanol=10:1);

NMR ($CD_3OD$): δ 7.53 (d, J=8.1 Hz, 2H), 7.30 (d, J=9.0 Hz, 2H), 7.08 (d, J=8.1 Hz, 2H), 7.04 (d, J=9.0 Hz, 2H), 4.34 (s, 2H), 4.16 (d, J=2.1 Hz, 1H), 4.00 (m, 1H), 3.76 (m, 1H), 3.58–3.42 (m, 3H), 3.30–3.08 (m, 2H), 2.96 (s, 3H), 2.54–1.88 (m, 6H), 1.82–1.62 (m, 5H), 1.50–1.14 (m, 6H), 0.96 (t, J=7.2 Hz, 3H), 0.96 (m, 2H).

EXAMPLE 48

(3R*)-1-(2-butynyl)-2,5-dioxo-3-((1R*)-1-hydroxy-1-cyclohexylmethyl)-9-allyloxycarbonyl-1,4,9-triazaspiro[5.5]undecane

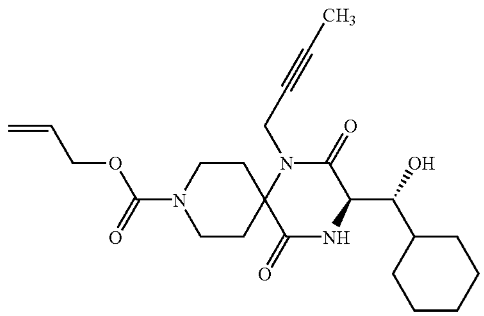

By the same procedure as described in Reference Example 3→Reference Example 6→Example 1 using Resin (3) prepared in Reference Example 2, N-allyloxycarbonyl-4-piperidone, 2-butynylamine, and (2R*,3R*)-N-(t-butyloxycarbonyl)-2-amino-3-hydroxy-3-cyclohexylpropanoic acid, the compound of the present invention having the following physical data was obtained.

TLC: Rf 0.32 (chloroform:methanol=15:1);

NMR ($CD_3OD$): δ 6.04–5.91 (m, 1H), 5.35–5.27 (m, 1H), 5.23–5.19 (m, 1H), 4.60–4.58 (m, 2H), 4.27 (dq, J=17.5, 2.5 Hz, 1H), 4.19 (d, J=2.5 Hz, 1H), 4.07–4.01 (m, 2H), 3.89 (dq, J=17.5, 2.5 Hz, 1H), 3.75–3.50 (m, 2H), 3.38 (dd, J=9.0, 2.5 Hz, 1H), 2.32–2.17 (m, 2H), 2.07–1.70 (m, 11H), 1.33–1.14 (m, 3H), 1.00–0.85 (m, 2H).

EXAMPLE 49

(3R*)-1-(2-butynyl)-2,5-dioxo-3-((1R*)-1-hydroxy-1-cyclohexylmethyl)-1,4,9-triazaspiro[5.5]undecane

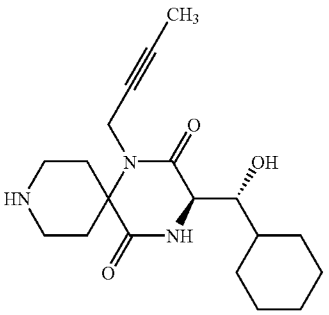

By the same procedure as described in Reference Example 4 using the compound prepared in Example 48, the compound of the present invention having the following physical data was obtained.

TLC: Rf 0.33 (chloroform:methanol: acetic acid=20:6:1);

NMR ($CD_3OD$): δ 4.28 (dq, J=17.5, 2.5 Hz, 1H), 4.18 (d, J=2.5 Hz, 1H), 4.03 (dq, J=17.5, 2.5 Hz, 1H), 3.48–3.29 (m, 3H), 2.99–2.90 (m, 2H), 2.26–1.73 (m, 14H), 1.32–1.18 (m, 3H), 1.01–0.91 (m, 2H).

EXAMPLE 50(1)~50(6)

By the same procedure as described in Example 10 using the compound prepared in Example 49 and the corresponding aldehyde compounds, the following compounds of the present invention were obtained.

EXAMPLE 50(1)

(3R*)-1-(2-butynyl)-2,5-dioxo-3-((1R*)-1-hydroxy-1-cyclohexylmethyl)-9-(3,5-dimethyl-1-phenylpyrazol-4-ylmethyl)-1,4,9-triazaspiro[5.5]undecane.2 hydrochloride

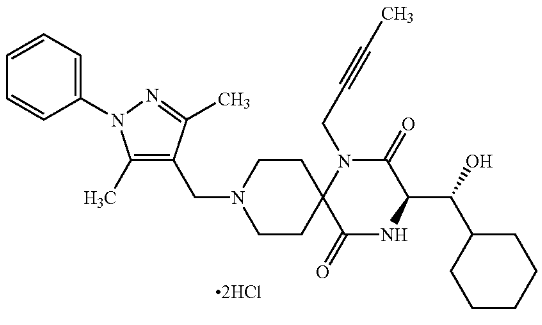

TLC: Rf 0.37 (chloroform:methanol=10:1);

NMR ($CD_3OD$): δ 7.60–7.50 (m, 5H), 4.42–4.33 (m, 3H), 4.21 (d, J=2.5 Hz, 1H), 4.08–3.99 (m, 2H), 3.85–3.75 (m, 1H), 3.65–3.57 (m, 2H), 3.32 (m, 1H), 2.79 (m, 1H), 2.48–2.43 (m, 5H), 2.40 (s, 3H), 2.22 (m, 1H), 2.05–1.93 (m, 2H), 1.80–1.64 (m, 7H), 1.39–1.11 (m, 3H), 1.03–0.84 (m, 2H).

EXAMPLE 50(2)

(3R*)-1-(2-butynyl)-2,5-dioxo-3-((1R*)-1-hydroxy-1-cyclohexylmethyl)-9-(3,5-dimethyl-1-(4-methylphenyl)pyrazol-4-ylmethyl)-1,4,9-triazaspiro[5.5]undecane.2 hydrochloride

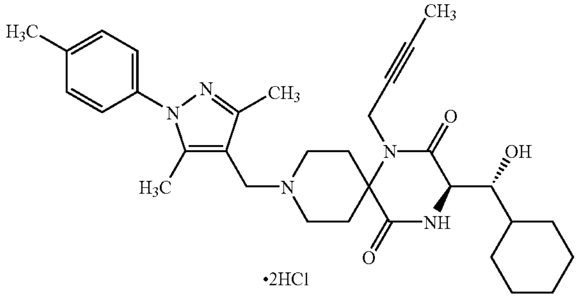

TLC: Rf 0.35 (chloroform:methanol=10:1);

NMR ($CD_3OD$): δ 7.40 (s, 4H),4.45–4.30 (m, 3H), 4.20 (m, 1H), 4.16–3.98 (m, 2H), 3.78 (m, 1H), 3.68–3.56 (m, 2H), 3.30 (m, 1H), 2.82 (m, 1H), 2.56–2.42 (m, 8H), 2.39 (s, 3H), 2.28–1.88 (m, 3H), 1.80–1.60 (m, 7H), 1.40–1.10 (m, 3H), 1.12–0.82 (m, 2H).

EXAMPLE 50(3)

(3R*)-1-(2-butynyl)-2,5-dioxo-3-((1R*)-1-hydroxy-1-cyclohexylmethyl)-9-(4-isopropylphenylmethyl)-1,4,9-triazaspiro[5.5]undecane.hydrochloride

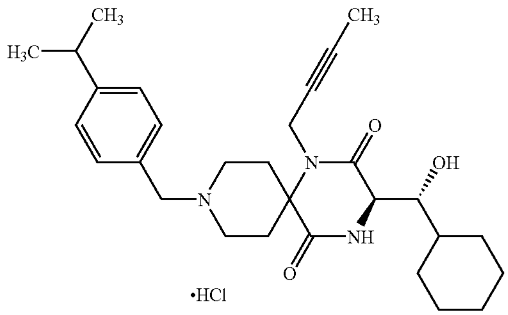

TLC: Rf 0.33 (chloroform:methanol=10:1);

NMR ($CD_3OD$): δ 7.47 (d, J=8.1 Hz, 2H), 7.36 (d, J=8.1 Hz, 2H), 4.38–4.28 (m, 3H), 4.17 (m, 1H), 4.04–3.88 (m, 2H), 3.74 (m, 1H), 3.50–3.40 (m, 2H), 3.28 (m, 1H), 2.92 (m, 1H), 2.64 (m, 1H), 2.50–1.86 (m, 5H),1.80–1.62 (m, 7H), 1.36–1.04 (m, 3H), 1.25 (d, J=7.2 Hz, 6H), 1.00–0.82 (m, 2H).

EXAMPLE 50(4)

(3R*)-1-(2-butynyl)-2,5-dioxo-3-((1R*)-1-hydroxy-1-cyclohexylmethyl)-9-(4-phenyloxyphenylmethyl)-1,4,9-triazaspiro[5.5]undecane.hydrochloride

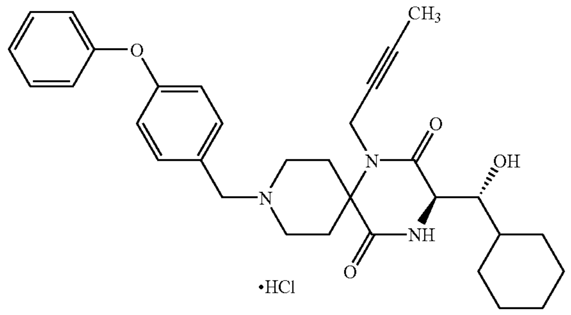

TLC: Rf 0.39 (chloroform:methanol=10:1);

NMR ($CD_3OD$): δ 7.53 (d, J=9.0 Hz, 2H), 7.42–7.37 (m, 2H), 7.17 (t, J=7.5 Hz, 1H), 7.06–7.02 (m, 4H), 4.40–4.30 (m, 3H), 4.18 (m, 1H), 4.04–3.90 (m, 2H), 3.72 (m, 1H), 3.30–3.20 (m, 2H), 3.28 (m, 1H), 2.68 (m, 1H), 2.52–1.86 (m, 5H), 1.80–1.60 (m, 7H), 1.38–1.10 (m, 3H), 1.02–0.82 (m, 2H).

EXAMPLE 50(5)

(3R*)-1-(2-butynyl)-2,5-dioxo-3-((1R*)-1-hydroxy-1-cyclohexylmethyl)-9-(4-(4-methylphenyloxy)phenylmethyl)-1,4,9-triazaspiro[5.5]undecane.hydrochloride

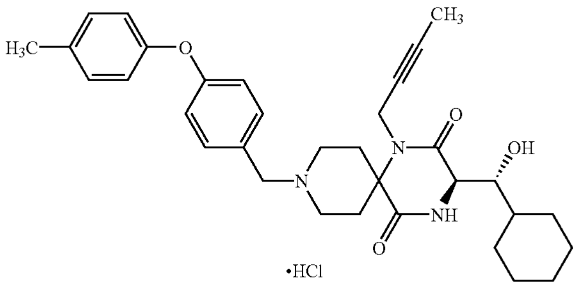

TLC: Rf 0.45 (chloroform:methanol=10:1);

NMR ($CD_3OD$): δ 7.50 (d, J=8.4 Hz, 2H), 7.20 (d, J=8.7 Hz, 2H), 7.01 (d, J=8.7 Hz, 2H), 6.92 (d, J=8.4 Hz, 2H), 4.40–4.28 (m, 3H), 4.18 (m, 1H), 4.04–3.88 (m, 2H), 3.74 (m, 1H), 3.52–3.40 (m, 2H), 3.26 (m, 1H), 2.64 (m, 1H), 2.54–1.86 (m, 5H), 2.33 (s, 3H), 1.80–1.62 (m, 7H), 1.38–1.10 (m, 3H), 1.02–0.82 (m, 2H).

EXAMPLE 50(6)

(3R*)-1-(2-butynyl)-2,5-dioxo-3-((1R*)-1-hydroxy-1-cyclohexylmethyl)-9-(1,4-benzodioxan-6-ylmethyl)-1,4,9-triazaspiro[5.5]undecane.hydrochloride

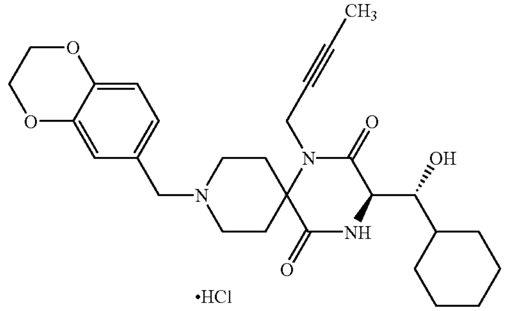

TLC: Rf 0.33 (chloroform:methanol=10:1);

NMR ($CD_3OD$): δ 7.04 (s, 1H), 6.99–6.91 (m, 2H), 4.35 (m, 1H), 4.27 (s, 4H), 4.24 (s, 2H), 4.18 (m, 1H), 4.04–3.84 (m, 2H), 3.70 (m, 1H), 3.56–3.38 (m, 2H), 3.28 (m, 1H), 2.68–1.88 (m, 6H), 1.80–1.60 (m, 7H), 1.40–1.10 (m, 3H), 1.02–0.80 (m, 2H).

EXAMPLE 51

(3R*)-1-(2-butynyl)-2,5-dioxo-3-((1R*)-1-hydroxy-2-methylpropyl)-1,4,9-triazaspiro[5.5]undecane.acetate

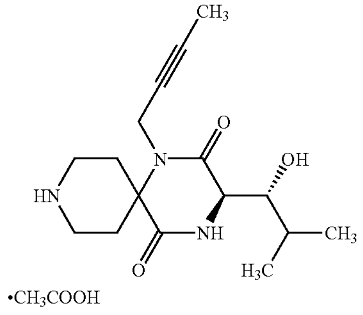

By the same procedure as described in Example 48→Example 49 using (2R*,3R*)-N-(t-butyloxycarbonyl)-2-amino-3-hydroxy-4-methylpentanoic acid instead of (2R*,3R*)-N-(t-butyloxycarbonyl)-2-amino-3-hydroxy-3-cyclohexylpropanoic acid, the compound of the present invention having the following physical data was obtained.

TLC: Rf 0.22 (chloroform:methanol: acetic acid=20:6:1);

NMR ($CD_3OD$): δ 4.36 (dq, J=17.0, 2.5 Hz, 1H), 4.19 (d, J=2.0 Hz, 1H), 3.95–3.79 (m, 2H), 3.62 (dt, J=3.5, 13.0 Hz, 1H), 3.34–3.26 (m, 2H), 3.22 (dd, J=9.5, 2.0 Hz, 1H), 2.54–2.43 (m, 1H), 2.37 (m, 1H), 2.20–1.98 (m, 3H), 1.91 (s, 3H), 1.75 (t, J=2.5 Hz, 3H), 1.01–0.97 (m, 6H).

EXAMPLE 52(1)~52(5)

By the same procedure as described in Example 10 using the compound prepared in Example 51 and the corresponding aldehyde compounds, the following compounds of the present invention were obtained.

EXAMPLE 52(1)

(3R*)-1-(2-butynyl)-2,5-dioxo-3-((1R*)-1-hydroxy-2-methylpropyl)-9-(3,5-dimethyl-1-(4-methylphenyl)pyrazol-4-ylmethyl)-1,4,9-triazaspiro[5.5]undecane.hydrochloride

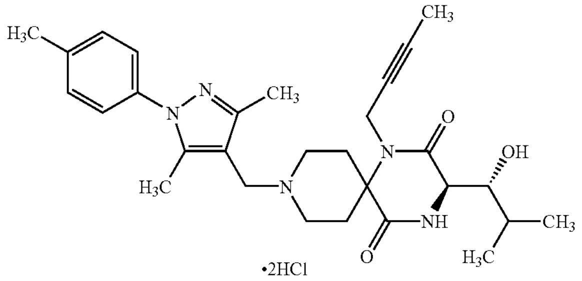

TLC: Rf 0.28 (chloroform:methanol=10:1);

NMR ($CD_3OD$): δ 7.38 (d, J=3.9 Hz, 2H), 7.35 (d, J=3.9 Hz, 2H), 4.33 (s, 2H), 4.20 (d, J=2.1 Hz, 1H), 4.10–3.90 (m, 2H), 3.78 (m, 1H), 3.68–3.52 (m, 2H), 3.22 (dd, J=9.3, 2.1 Hz, 1H), 2.74 (m, 1H), 2.54–2.20 (m, 3H), 2.44 (s, 3H), 2.40 (s, 3H), 2.36 (s, 3H), 1.98 (m, 1H), 1.75 (t, J=2.1 Hz, 3H), 1.01 (d, J=6.6 Hz, 3H), 0.99 (d, J=6.6 Hz, 3H).

EXAMPLE 52(2)

(3R*)-1-(2-butynyl)-2,5-dioxo-3-((1R*)-1-hydroxy-2-methylpropyl)-9-(4-(4-methylphenyloxy)phenylmethyl)-1,4,9-triazaspiro[5.5]undecane.hydrochloride

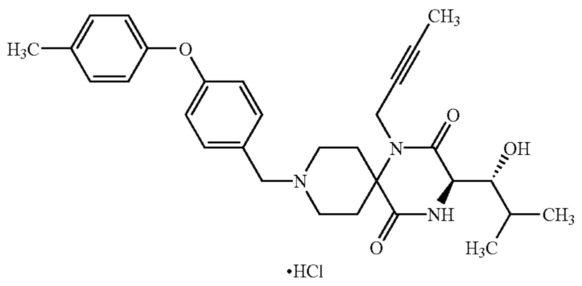

TLC: Rf 0.26 (chloroform:methanol=10:1);

NMR ($CD_3OD$): δ 7.49 (d, J=9.0 Hz, 2H), 7.21 (d, J=8.4 Hz, 2H), 7.04 (d, J=9.0 Hz, 2H), 6.93 (d, J=8.4 Hz, 2H), 4.40 (m, 1H), 4.34 (s, 2H), 4.19 (d, J=2.1 Hz, 1H), 4.08–3.82 (m, 2H), 3.76 (m, 1H), 3.58–3.40 (m, 2H), 3.20 (dd, J=9.6, 2.1 Hz, 1H), 2.72–2.42 (m, 2H), 2.35 (s, 3H), 2.35–2.18 (m, 2H), 2.00 (m, 1H), 1.74 (t, J=2.1 Hz, 3H), 1.00 (d, J=6.6 Hz, 3H), 0.98 (d, J=6.6 Hz, 3H).

EXAMPLE 52(3)

(3R*)-1-(2-butynyl)-2,5-dioxo-3-((1R*)-1-hydroxy-2-methylpropyl)-9-(1,4-benzodioxan-6-ylmethyl)-1,4,9-triazaspiro[5.5]undecane.hydrochloride

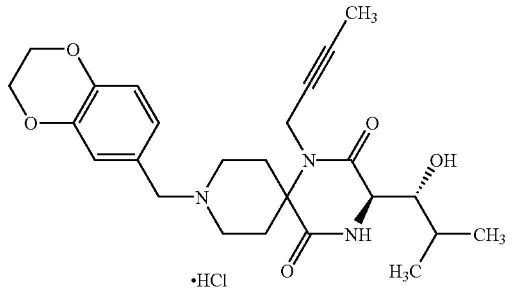

TLC: Rf 0.34 (chloroform:methanol=10:1);

NMR ($CD_3OD$): δ 7.06–6.92 (m, 3H), 4.38 (m, 1H), 4.28 (s, 4H), 4.25 (s, 2H), 4.19 (d, J=2.1 Hz, 1H), 4.02–3.84 (m, 2H), 3.70 (m, 1H), 3.52–3.36 (m, 2H), 3.20 (dd, J=9.6, 2.1 Hz, 1H), 2.60 (m, 1H), 2.48 (m, 1H), 2.32–2.16 (m, 2H), 2.00 (m, 1H), 1.74 (t, J=2.1 Hz, 3H), 1.00 (d, J=6.6 Hz, 3H), 0.98 (d, J=6.6 Hz, 3H).

EXAMPLE 52(4)

(3R*)-1-(2-butynyl)-2,5-dioxo-3-((1R*)-1-hydroxy-2-methylpropyl)-9-(4-isopropylphenylmethyl)-1,4,9-triazaspiro[5.5]undecane.hydrochloride

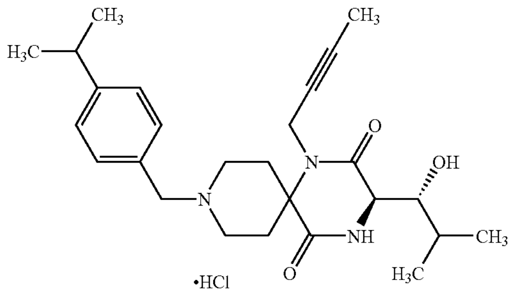

TLC: Rf 0.29 (chloroform:methanol=10:1);

NMR ($CD_3OD$): δ 7.47 (d, J=8.1 Hz, 2H), 7.38 (d, J=8.1 Hz, 2H), 4.40 (m, 1H), 4.33 (s, 2H), 4.19 (d, J=2.1 Hz, 1H), 4.08–3.84 (m, 2H), 3.76 (m, 1H), 3.52–3.40 (m, 2H), 3.20 (dd, J=9.6, 2.1 Hz, 1H), 2.96 (m, 1H), 2.62 (m, 1H), 2.48 (m, 1H), 2.36–2.12 (m, 2H), 2.00 (m, 1H), 1.74 (t, J=2.1 Hz, 3H), 1.24 (d, J=7.2 Hz, 6H), 1.00 (d, J=6.6 Hz, 3H), 0.98 (d, J=6.6 Hz, 3H).

EXAMPLE 52(5)

(3R*)-1-(2-butynyl)-2,5-dioxo-3-((1R*)-1-hydroxy-2-methylpropyl)-9-(4-phenyloxyphenylmethyl)-1,4,9-triazaspiro[5.5]undecane.hydrochloride

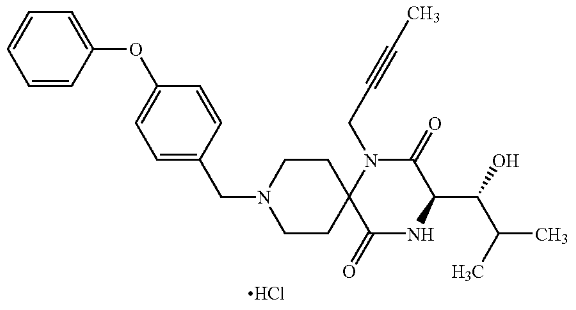

TLC: Rf 0.24 (chloroform:methanol=10:1);

NMR ($CD_3OD$): δ 7.52 (d, J=9.0 Hz, 2H), 7.41 (t, J=7.2 Hz, 2H), 7.19 (t, J=7.2 Hz, 1H), 7.09–7.03 (m, 4H), 4.40 (m, 1H), 4.35 (s, 2H), 4.19 (d, J=2.1 Hz, 1H), 4.08–3.84 (m, 2H), 3.78 (m, 1H), 3.58–3.42 (m, 2H), 3.21 (dd, J=9.6, 2.1 Hz, 1H), 2.72–2.42 (m, 2H), 2.38–2.18 (m, 2H), 2.00 (m, 1H), 1.74 (t, J=2.1 Hz, Hz, 3H), 1.00 (d, J=6.6 Hz, 3H), 0.98 (d, J=6.6 Hz, 3H).

EXAMPLE 53

(3R*)-1-butyl-2,5-dioxo-3-((1S*)-1-hydroxy-1-cyclohexylmethyl)-9-benzyl-1,4,9-triazaspiro[5.5]undecane

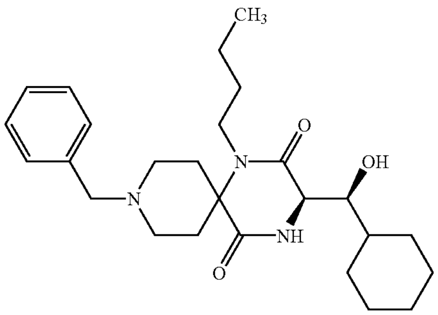

By the same procedure as described in Reference Example 3→Reference Example 6→Example 1 using Resin (3) prepared in Reference Example 2, N-benzyl-4-piperidone, n-butylamine, (2R*,3S*)—N-(t-butyloxycarbonyl)-2-amino-3-hydroxy-3-cyclohexylpropanoic acid, the compound of the present invention having the following physical data was obtained.

TLC: Rf 0.33 (chloroform:methanol=10:1);

NMR ($CD_3OD$): δ 7.40–7.20 (m, 5H), 4.04 (d, J=1.5 Hz, 1H), 3.65–3.45 (m, 2H), 3.57 (s, 2H), 3.30 (m, 1H), 3.05 (m 1H), 2.86–2.77 (m, 3H), 2.30–2.00 (m, 4H), 1.90–1.60 (m, 6H), 1.60–1.10 (m, 9H), 1.10–0.90 (m, 2H), 0.95 (t, J=7.2 Hz, 3H).

EXAMPLE 54

(3R*)-1-butyl-2,5-dioxo-3-((1 S*)-1-hydroxy-1-cyclohexylmethyl)-1,4,9-triazaspiro[5.5]undecane-.hydrochloride

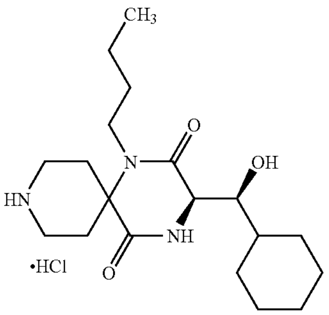

By the same procedure as described in Example 9 using the compound prepared in Example 53, the compound of the present invention having the following physical data was obtained.

TLC: Rf 0.59 (chloroform:methanol: acetic acid=10:2:1);

NMR ($CD_3OD$): δ 4.08 (d, J=1.5 Hz, 1H), 4.03 (m, 1H), 3.70–3.12 (m, 7H), 2.50–2.02 (m, 5H), 1.85–1.66 (m, 5H), 1.55–1.10 (m, 7H), 1.10–0.85 (m, 2H), 0.97 (t, J=6.9 Hz, 3H).

EXAMPLE 55(1)~55(3)

By the same procedure as described in Example 10 using the compound prepared in Example 54 and the corresponding aldehyde compounds, the following compounds of the present invention were obtained.

EXAMPLE 55(1)

(3R*)-1-butyl-2,5-dioxo-3-((1 S*)-1-hydroxy-1-cyclohexylmethyl)-9-(4-phenyloxyphenylmethyl)-1,4,9-triazaspiro[5.5]undecane.hydrochloride

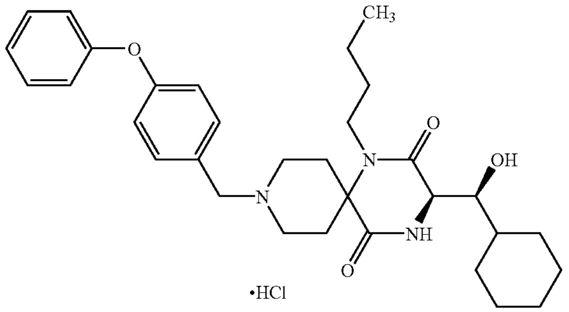

TLC: Rf 0.46 (chloroform:methanol=10:1);

NMR ($CD_3OD$): δ 7.50 (d, J=8.7 Hz, 2H), 7.39 (dd, J=8.7, 7.5 Hz, 2H), 7.17 (t, J=7.5 Hz, 1H), 7.09–7.00 (m, 4H), 4.30 (brs, 2H), 4.08 (d, J=1.2 Hz, 1H), 4.04 (m, 1H), 3.74–3.36 (m, 5H), 3.16 (m, 1H), 2.55–2.33 (m, 2H), 2.32–2.09 (m, 2H), 2.04 (m, 1H), 1.84–1.61 (m, 5H), 1.53–1.12 (m, 7H), 1.04–0.86 (m, 5H).

EXAMPLE 55(2)

(3R*)-1-butyl-2,5-dioxo-3-((1 S*)-1-hydroxy-1-cyclohexylmethyl)-9-(1,4-benzodioxan-6-ylmethyl)-1,4,9-triazaspiro[5.5]undecane.hydrochloride

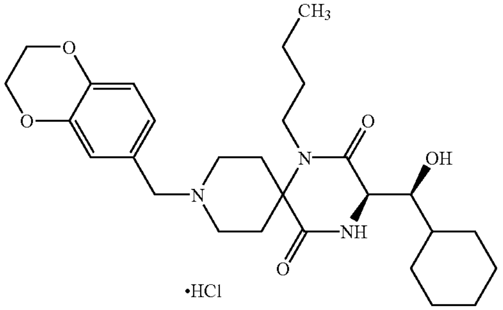

•HCl

TLC: Rf 0.41 (chloroform:methanol=10:1);

NMR ($CD_3OD$): δ 7.04 (d, J=2.1 Hz, 1H), 6.97 (dd, J=8.1, 2.1 Hz, 1H), 6.92 (d, J=8.1 Hz, 1H), 4.26 (s, 4H), 4.21 (s, 2H), 4.07 (d, J=1.2 Hz, 1H), 4.01 (m, 1H), 3.70–3.34 (m, 5H), 3.16 (m, 1H), 2.53–2.32 (m, 2H), 2.31–2.08 (m, 2H), 2.03 (m, 1H), 1.84–1.60 (m, 5H), 1.52–1.12 (m, 7H), 1.04–0.85 (m, 5H).

EXAMPLE 55(3)

(3R*)-1-butyl-2,5-dioxo-3-((1 S*)-1-hydroxy-1-cyclohexylmethyl)-9-(3,5-dimethyl-1-phenylpyrazol-4-ylmethyl)-1,4,9-triazaspiro[5.5]undecane.2 hydrochloride

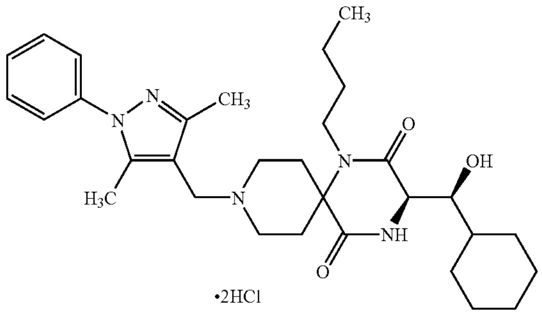

•2HCl

TLC: Rf 0.31 (chloroform:methanol=10:1);

NMR ($CD_3OD$): δ 7.61–7.44 (m, 5H), 4.31 (s, 2H), 4.19–4.06 (m, 2H), 3.73 (m 1H), 3.66–3.52 (m, 4H), 3.26 (m, 1H), 2.62–2.48 (m, 2H), 2.45–2.30 (m, 7H), 2.19 (m, 1H), 2.04 (m, 1H), 1.84–1.63 (m, 5H), 1.54–1.12 (m, 7H), 1.05–0.86 (m, 5H).

EXAMPLE 56

(3S)-1-butyl-2,5-dioxo-3-((1S)-1-hydroxy-2-methylpropyl)-1,4,9-triazaspiro[5.5]undecane.hydrochloride

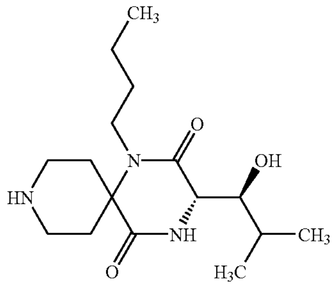

•HCl

By the same procedure as described in Example 42→Example 43 using (2S,3S)—N-(t-butyloxycarbonyl)-2-amino-3-hydroxy-4-methylpentanoic acid instead of (2R*, 3R*)-N-(t-butyloxycarbonyl)-2-amino-3-hydroxy-4-methylpentanoic acid, the compound of the present invention having the following physical data was obtained.

TLC: Rf 0.08 (chloroform:methanol=10:1);

NMR ($CD_3OD$): δ 4.15 (d, J=2.0 Hz, 1H), 3.96 (dt, J=13.0, 4.0 Hz, 1H), 3.71 (dt, J=13.0, 4.0 Hz, 1H), 3.57–3.47 (m, 1H), 3.40–3.34 (m, 2H), 3.23–3.12 (m, 2H), 2.47–2.30 (m, 2H), 2.25–1.98 (m, 3H), 1.79–1.66 (m, 1H), 1.52–1.28 (m, 3H), 1.07–0.94 (m, 9H);

Optical rotation: $[\alpha]_D$–13.8 (c 1.00, methanol).

EXAMPLE 57(1)~57(4)

By the same procedure as described in Example 10 using the compound prepared in Example 56 and the corresponding aldehyde compounds, the following compounds of the present invention were obtained.

EXAMPLE 57(1)

(3S)-1-butyl-2,5-dioxo-3-((1S)-1-hydroxy-2-methylpropyl)-9-(3,5-dimethyl-1-phenylpyrazol-4-ylmethyl)-1,4,9-triazaspiro[5.5]undecane.2 hydrochloride

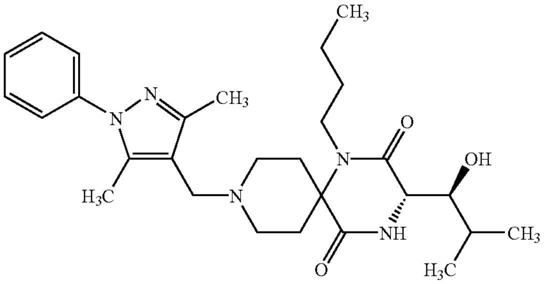

•2HCl

TLC: Rf 0.43 (chloroform:methanol=10:1);

NMR ($CD_3OD$): δ 7.61–7.43 (m, 5H), 4.32 (s, 2H), 4.16 (d, J=2.1 Hz, 1H), 4.12–3.99 (m, 1H), 3.90–3.72 (m, 1H), 3.64–3.44 (m, 3H), 3.30–3.12 (m, 1H), 3.20 (dd, J=9.3, 2.1 Hz, 1H), 2.60–2.30 (m, 9H), 2.24–2.10 (m, 1H), 2.10–1.95 (m, 1H), 1.78–1.60 (m, 1H), 1.54–1.30 (m, 3H), 1.00 (d, J=6.6 Hz, 3H), 0.98 (d, J=6.6 Hz, 3H), 0.96 (t, J=6.9 Hz, 3H).

EXAMPLE 57(2)

(3S)-1-butyl-2,5-dioxo-3-((1S)-1-hydroxy-2-methylpropyl)-9-(4-phenyloxyphenylmethyl)-1,4,9-triazaspiro[5.5]undecane.hydrochloride

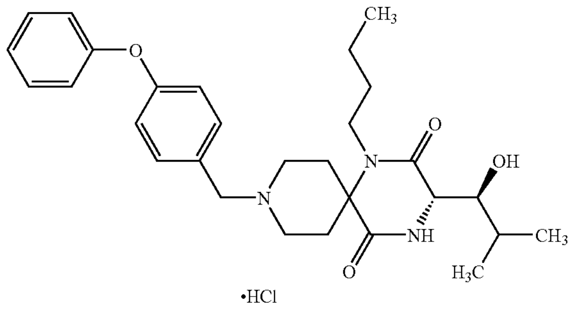

TLC: Rf 0.51 (chloroform:methanol=10:1);

NMR ($CD_3OD$): δ 7.52 (d, J=8.7 Hz, 2H), 7.43–7.36 (m, 2H), 7.21–7.14 (m, 1H), 7.10–7.00 (m, 4H), 4.33 (s, 2H), 4.14 (d, J=2.1 Hz, 1H), 4.06–3.92 (m, 1H), 3.81–3.66 (m, 1H), 3.58–3.40 (m, 3H), 3.30–3.10 (m, 1H), 3.19 (dd, J=9.6, 2.1 Hz, 1H), 2.53–2.37 (m, 2H), 2.37–2.18 (m, 1H), 2.18–2.08 (m, 1H), 2.06–1.95 (m, 1H), 1.78–1.60 (m, 1H), 1.50–1.26 (m, 3H), 0.99 (d, J=6.6 Hz, 3H), 0.97 (d, J=6.6 Hz, 3H), 0.95 (t, J=7.2 Hz, 3H).

EXAMPLE 57(3)

(3S)-1-butyl-2,5-dioxo-3-((1S)-1-hydroxy-2-methylpropyl)-9-(1,4-benzodioxan-6-ylmethyl)-1,4,9-triazaspiro[5.5]undecane.hydrochloride

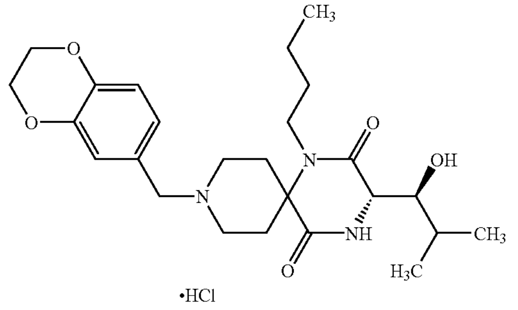

TLC: Rf 0.43 (chloroform:methanol=10:1);

NMR ($CD_3OD$): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.13 (d, J=2.4 Hz, 1H), 4.02–3.87 (m, 1H), 3.77–3.62 (m, 1H), 3.57–3.35 (m, 3H), 3.28–3.08 (m, 1H), 3.19 (dd, J=9.6, 2.4 Hz, 1H), 2.51–2.35 (m, 2H), 2.35–2.18 (m, 1H), 2.17–2.05 (m, 1H), 2.05–1.90 (m, 1H), 1.80–1.58 (m, 1H), 1.50–1.26 (m, 3H), 0.98 (d, J=6.6 Hz, 3H), 0.97 (d, J=6.6 Hz, 3H), 0.95 (t, J=7.2 Hz, 3H).

EXAMPLE 57(4)

(3S)-1-butyl-2,5-dioxo-3-((1S)-1-hydroxy-2-methylpropyl)-9-(4-(4-methylsulfonylaminophenyloxy)phenylmethyl)-1,4,9-triazaspiro[5.5]undecane.hydrochloride

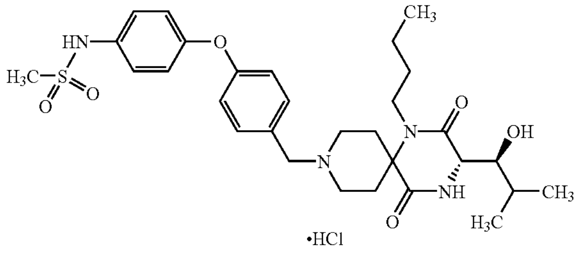

TLC: Rf 0.35 (chloroform:methanol=10:1);

NMR ($CD_3OD$): δ 7.53 (d, J=8.7 Hz, 2H), 7.29 (d, J=9.0 Hz, 2H), 7.10–7.00 (m, 4H), 4.33 (s, 2H), 4.14 (d, J=2.1 Hz, 1H), 4.06–3.92 (m, 1H), 3.81–3.66 (m, 1H), 3.58–3.40 (m, 3H), 3.25–3.10 (m, 1H), 3.19 (dd, J=9.6, 2.1 Hz, 1H), 2.95 (s, 3H),2.54–2.37 (m, 2H), 2.37–2.22 (m, 1H), 2.18–2.08 (m, 1H), 2.08–1.92 (m, 1H), 1.78–1.60 (m, 1H), 1.50–1.28 (m, 3H), 0.99 (d, J=6.6 Hz, 3H), 0.97 (d, J=6.6 Hz, 3H), 0.95 (t, J=7.5 Hz, 3H).

EXAMPLE 58

(3R)-1-butyl-2,5-dioxo-3-((1R)-1-hydroxy-2-methylpropyl)-1,4,9-triazaspiro[5.5]undecane.hydrochloride

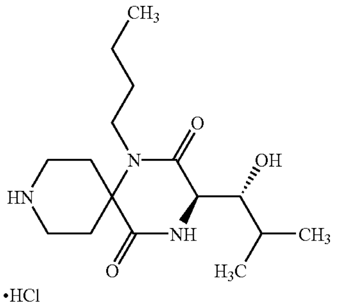

By the same procedure as described in Example 42→Example 43 using (2R,3R)-N-(t-butyloxycarbonyl)-2-amino-3-hydroxy-4-methylpentanoic acid instead of (2R*,3R*)-N-(t-butyloxycarbonyl)-2-amino-3-hydroxy-4-methylpentanoic acid, the compound of the present invention having the following physical data was obtained.

TLC: Rf 0.08 (chloroform:methanol=10:1);

NMR ($CD_3OD$): δ 4.15 (d, J=2.0 Hz, 1H), 3.96 (dt, J=13.0, 4.0 Hz, 1H), 3.71 (dt, J=13.0, 4.0 Hz, 1H), 3.57–3.47 (m, 1H), 3.40–3.34 (m, 2H), 3.23–3.12 (m, 2H), 2.47–2.30 (m, 2H), 2.25–1.98 (m, 3H), 1.79–1.66 (m, 1H), 1.52–1.28 (m, 3H), 1.07–0.94 (m, 9H);

Optical rotation: $[\alpha]_D$+13.9 (c 1.00, methanol).

EXAMPLE 59(1)~59(4)

By the same procedure as described in Example 10 using the compound prepared in Example 58 and the corresponding aldehyde compounds, the following compounds of the present invention were obtained.

EXAMPLE 59(1)

(3R)-1-butyl-2,5-dioxo-3-((1R)-1-hydroxy-2-methylpropyl)-9-(3,5-dimethyl-1-phenylpyrazol-4-ylmethyl)-1,4,9-triazaspiro[5.5]undecane.2 hydrochloride

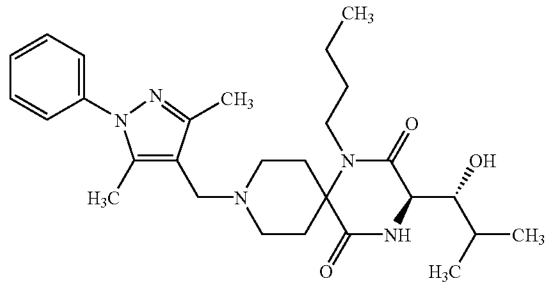

•2HCl

TLC: Rf 0.43 (chloroform:methanol=10:1);

NMR ($CD_3OD$): δ 7.61–7.43 (m, 5H), 4.32 (s, 2H), 4.16 (d, J=2.1 Hz, 1H), 4.12–3.99 (m, 1H), 3.90–3.72 (m, 1H), 3.64–3.44 (m, 3H), 3.30–3.12 (m, 1H), 3.20 (dd, J=9.3, 2.1 Hz, 1H), 2.60–2.30 (m, 9H), 2.24–2.10 (m, 1H), 2.10–1.95 (m, 1H), 1.78–1.60 (m, 1H), 1.54–1.30 (m, 3H), 1.00 (d, J=6.6 Hz, 3H), 0.98 (d, J=6.6 Hz, 3H), 0.96 (t, J=6.9 Hz, 3H).

EXAMPLE 59(2)

(3R)-1-butyl-2,5-dioxo-3-((1R)-1-hydroxy-2-methylpropyl)-9-(4-phenyloxyphenylmethyl)-1,4,9-triazaspiro[5.5]undecane.hydrochloride

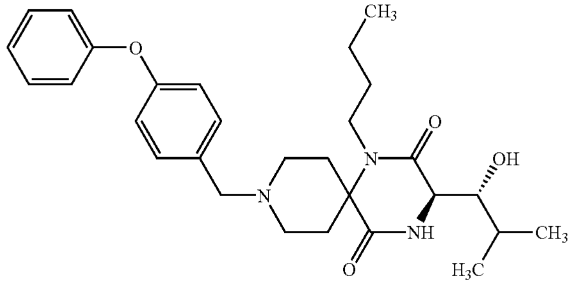

•HCl

TLC: Rf 0.51 (chloroform:methanol=10:1);

NMR ($CD_3OD$): δ 7.52 (d, J=8.7 Hz, 2H), 7.43–7.36 (m, 2H), 7.21–7.14 (m, 1H), 7.10–7.00 (m, 4H), 4.33 (s, 2H), 4.14 (d, J=2.1 Hz, 1H), 4.06–3.92 (m, 1H), 3.81–3.66 (m, 1H), 3.58–3.40 (m, 3H), 3.30–3.10 (m, 1H), 3.19 (dd, J=9.6, 2.1 Hz, 1H), 2.53–2.37 (m, 2H), 2.37–2.18 (m, 1H), 2.18–2.08 (m, 1H), 2.06–1.95 (m, 1H), 1.78–1.60 (m, 1H), 1.50–1.26 (m, 3H), 0.99 (d, J=6.6 Hz, 3H), 0.97 (d, J=6.6 Hz, 3H), 0.95 (t, J=7.2 Hz, 3H).

EXAMPLE 59(3)

(3R)-1-butyl-2,5-dioxo-3-((1R)-1-hydroxy-2-methylpropyl)-9-(1,4-benzodioxan-6-ylmethyl)-1,4,9-triazaspiro[5.5]undecane.hydrochloride

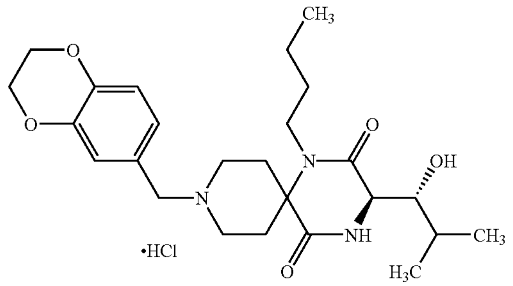

•HCl

TLC: Rf 0.43 (chloroform:methanol=10:1);

NMR ($CD_3OD$): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.13 (d, J=2.4 Hz, 1H), 4.02–3.87 (m, 1H), 3.77–3.62 (m, 1H), 3.57–3.35 (m, 3H), 3.28–3.08 (m, 1H), 3.19 (dd, J=9.6, 2.4 Hz, 1H), 2.51–2.35 (m, 2H), 2.35–2.18 (m, 1H), 2.17–2.05 (m, 1H), 2.05–1.90 (m, 1H), 1.80–1.58 (m, 1H), 1.50–1.26 (m, 3H), 0.98 (d, J=6.6 Hz, 3H), 0.97 (d, J=6.6 Hz, 3H), 0.95 (t, J=7.2 Hz, 3H).

EXAMPLE 594(4)

(3R)-1-butyl-2,5-dioxo-3-((1R)-11-hydroxy-2-methylpropyl)-9-(4-(4-methylsulfonylaminophenyloxy)phenylmethyl)-1,4,9-triazaspiro[5.5]undecane.hydrochloride

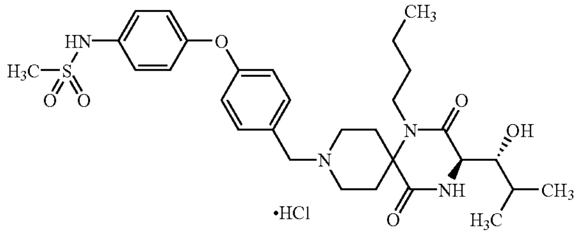

•HCl

TLC: Rf 0.35 (chloroform:methanol=10:1);

NMR ($CD_3OD$): δ 7.53 (d, J=8.7 Hz, 2H), 7.29 (d, J=9.0 Hz, 2H), 7.10–7.00 (m, 4H), 4.33 (s, 2H), 4.14 (d, J=2.1 Hz, 1H), 4.06–3.92 (m, 1H), 3.81–3.66 (m, 1H), 3.58–3.40 (m, 3H), 3.25–3.10 (m, 1H), 3.19 (dd, J=9.6, 2.1 Hz, 1H), 2.95 (s, 3H), 2.54–2.37 (m, 2H), 2.37–2.22 (m, 1H), 2.18–2.08 (m, 1H), 2.08–1.9 (m, 1H), 1.78–1.60 (m, 1H), 1.50–1.28 (m, 3H), 0.99 (d, J=6.6 Hz, 3H), 0.97 (d, J=6.6 Hz, 3H), 0.95 (t, J=7.5 Hz, 3H).

EXAMPLE 60

(3R)-11-butyl-2,5-dioxo-3-((1 S)-11-hydroxy-2-methylpropyl)-1,4,9-triazaspiro[5.5]undecane.hydrochloride

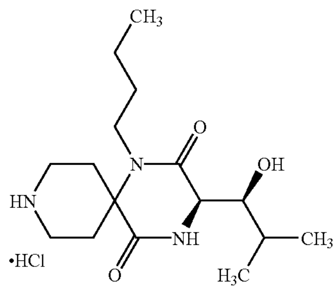

By the same procedure as described in Example 53→Example 54 using (2R,3S)—N-(t-butyloxycarbonyl)-2-amino-3-hydroxy-4-methyl pentanoic acid instead of (2 R*,3S*)-N-(t-butyloxycarbonyl)-2-amino-3-hydroxy-3-cyclohexylpropanoic acid, the compound of the present invention having the following physical data was obtained.

TLC: Rf 0.51 (chloroform:methanol: acetic acid=10:2:1);

NMR ($CD_3OD$): δ 4.08 (d, J=1.5 Hz, 1H), 4.02 (dt, J=12.6, 3.9 Hz, 1H), 3.70–3.00 (m, 6H), 2.50–2.10 (m, 4H), 1.80–1.60 (m, 2H), 1.55–1.35 (m, 3H), 1.02 (d, J=6.6 Hz, 3H), 0.99 (t, J=6.6 Hz, 3H), 0.93 (d, J=6.6 Hz, 3H);

Optical rotation: $[\alpha]_D$+21.2 (c 1.00, methanol).

EXAMPLE 61(1)~61(3)

By the same procedure as described in Example 10 using the compound prepared in Example 60 and the corresponding aldehyde compounds, the following compounds of the present invention were obtained.

EXAMPLE 61(1)

(3R)-1-butyl-2,5-dioxo-3-((1S)-1-hydroxy-2-methylpropyl)-9-(3,5-dimethyl-1-phenylpyrazol-4-ylmethyl)-1,4,9-triazaspiro[5.5]undecane.2 hydrochloride

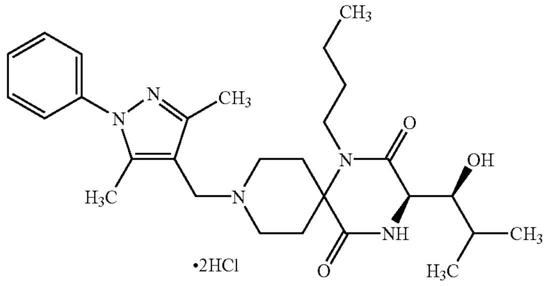

TLC: Rf 0.44 (chloroform:methanol=10:1);

NMR ($CD_3OD$): δ 7.64–7.46 (m, 5H), 4.32 (s, 2H), 4.19–4.06 (m, 1H), 4.10 (d, J=1.5 Hz, 1H), 3.80–3.53 (m, 4H), 3.51 (dd, J=10.2, 1.5 Hz, 1H), 3.40–3.20 (m, 1H), 2.70–2.30 (m, 9H), 2.23–2.10 (m, 1H), 1.83–1.60 (m, 2H), 1.53–1.30 (m, 3H), 1.02 (d, J=6.6 Hz, 3H), 0.96 (t, J=7.2 Hz, 3H), 0.93 (d, J=6.6 Hz, 3H).

EXAMPLE 61(2)

(3R)-1-butyl-2,5-dioxo-3-((1S)-1-hydroxy-2-methylpropyl)-9-(1,4-benzodioxan-6-ylmethyl)-1,4,9-triazaspiro[5.5]undecane.hydrochloride

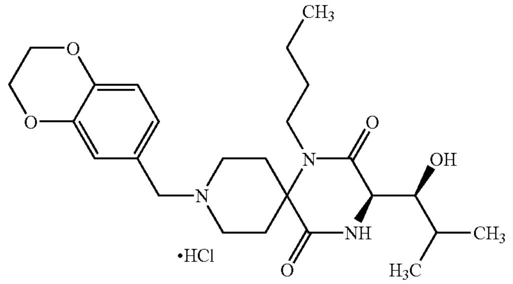

TLC: Rf 0.44 (chloroform:methanol=10:1);

NMR ($CD_3OD$): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.08 (d, J=1.5 Hz, 1H), 4.08–3.96 (m, 1H), 3.72–3.35 (m, 4H), 3.49 (dd, J=10.2, 1.5 Hz, 1H), 3.28–3.08 (m, 1H), 2.55–2.35 (m, 2H), 2.35–2.18 (m, 1H), 2.18–2.08 (m, 1H), 1.82–1.62 (m, 2H), 1.52–1.25 (m, 3H), 1.01 (d, J=6.6 Hz, 3H), 0.95 (t, J=7.2 Hz, 3H), 0.92 (d, J=6.6 Hz, 3H).

EXAMPLE 61(3)

(3R)-1-butyl-2,5-dioxo-3-((1S)-1-hydroxy-2-methylpropyl)-9-(4-(4-methylsulfonylaminophenyloxy)phenylmethyl)-1,4,9-triazaspiro[5.5]undecane.hydrochloride

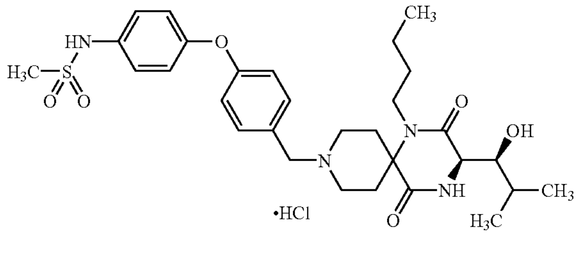

TLC: Rf 0.42 (chloroform:methanol=10:1);

NMR ($CD_3OD$): δ 7.53 (d, J=8.7 Hz, 2H), 7.29 (d, J=9.0 Hz, 2H), 7.07 (d, J=8.7 Hz, 2H), 7.03 (d, J=9.0 Hz, 2H), 4.33 (s, 2H), 4.13–4.00 (m, 1H), 4.09 (d, J=1.5 Hz, 1H), 3.75–3.62 (m, 1H), 3.62–3.39 (m, 3H), 3.49 (dd, J=10.5, 1.5 Hz, 1H), 3.26–3.12 (m, 1H), 2.95 (s, 3H), 2.56–2.37 (m, 2H), 2.37–2.20 (m, 1H), 2.20–2.10 (m, 1H), 1.82–1.63 (m, 2H), 1.50–1.30 (m, 3H), 1.01 (d, J=6.6 Hz, 3H), 0.95 (t, J=7.2 Hz, 3H), 0.92 (d, J=6.6 Hz, 3H).

EXAMPLE 62

(3S)-1-butyl-2,5-dioxo-3-((1R)-1-hydroxy-2-methylpropyl)-1,4,9-triazaspiro[5.5]undecane.hydrochloride

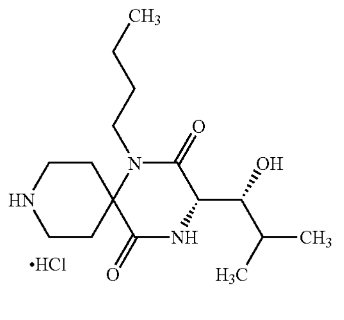

By the same procedure as described in Example 53→Example 54 using (2S,3R)-N-(t-butyloxycarbonyl)-2-amino-3-hydroxy-4-methylpentanoic acid instead of (2R*,3S*)-N-(t-butyloxycarbonyl)-2-amino-3-hydroxy-3-cyclohexylpropanoic acid, the compound of the present invention having the following physical data was obtained.

TLC: Rf 0.51 (chloroform:methanol: acetic acid=10:2:1);

NMR ($CD_3OD$): a 4.08 (d, J=1.5 Hz, 1H), 4.02 (dt, J=12.6, 3.9 Hz, 1H), 3.70–3.00 (m, 6H), 2.50–2.10 (m, 4H), 1.80–1.60 (m, 2H), 1.55–1.35 (m, 3H), 1.02 (d, J=6.6 Hz, 3H), 0.99 (t, J=6.6 Hz, 3H), 0.93 (d, J=6.6 Hz, 3H);

Optical rotation: $[\alpha]_D$–23.4 (c 1.00, methanol).

EXAMPLE 63(1)~63(3)

By the same procedure as described in Example 10 using the compound prepared in Example 62 and the corresponding aldehyde compounds, the following compounds of the present invention were obtained.

EXAMPLE 63(1)

(3S)-1-butyl-2,5-dioxo-3-((1R)-1-hydroxy-2-methylpropyl)-9-(3,5-dimethyl-1-phenylpyrazol-4-ylmethyl)-1,4,9-triazaspiro[5.5]undecane.2 hydrochloride

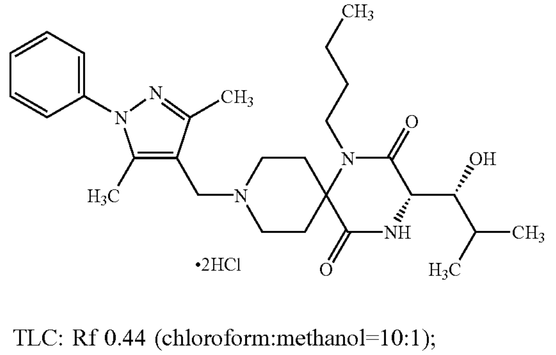

TLC: Rf 0.44 (chloroform:methanol=10:1);

NMR ($CD_3OD$): δ 7.64–7.46 (m, 5H), 4.32 (s, 2H), 4.19–4.06 (m, 1H), 4.10 (d, J=1.5 Hz, 1H), 3.80–3.53 (m, 4H), 3.51 (dd, J=10.2, 1.5 Hz, 1H), 3.40–3.20 (m, 1H), 2.70–2.30 (m, 9H), 2.23–2.10 (m, 1H), 1.83–1.60 (m, 2H), 1.53–1.3 (m, 3H), 1.02 (d, J=6.6 Hz, 3H), 0.96 (t, J=7.2 Hz, 3H), 0.93 (d, J=6.6 Hz, 3H).

EXAMPLE 63(2)

(3S)-1-butyl-2,5-dioxo-3-((1R)-1-hydroxy-2-methylpropyl)-9-(1,4-benzodioxan-6-ylmethyl)-1,4,9-triazaspiro[5.5]undecane.hydrochloride

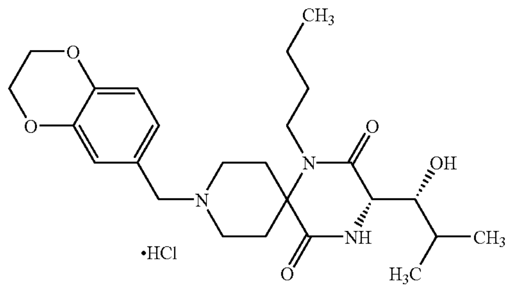

TLC: Rf 0.44 (chloroform:methanol=10:1);

NMR ($CD_3OD$): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.08 (d, J=1.5 Hz, 1H), 4.08–3.96 (m, 1H), 3.72–3.35 (m, 4H), 3.49 (dd, J=10.2, 1.5 Hz, 1H), 3.28–3.08 (m, 1H), 2.55–2.35 (m, 2H), 2.35–2.18 (m, 1H), 2.18–2.08 (m, 1H), 1.82–1.62 (m, 2H), 1.52–1.25 (m, 3H), 1.01 (d, J=6.6 Hz, 3H), 0.95 (t, J=7.2 Hz, 3H), 0.92 (d, J=6.6 Hz, 3H).

EXAMPLE 63(3)

(3S)-1-butyl-2,5-dioxo-3-((1R)-1-hydroxy-2-methylpropyl)-9-(4-(4-methylsulfonylaminophenyloxy)phenylmethyl)-1,4,9-triazaspiro[5.5]undecane.hydrochloride

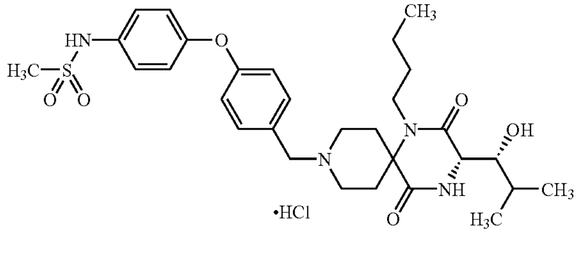

TLC: Rf 0.42 (chloroform:methanol=10:1);

NMR ($CD_3OD$): δ 7.53 (d, J=8.7 Hz, 2H), 7.29 (d, J=9.0 Hz, 2H), 7.07 (d, J=8.7 Hz, 2H), 7.03 (d, J=9.0 Hz, 2H), 4.33 (s, 2H), 4.13–4.00 (m, 1H), 4.09 (d, J=1.5 Hz, 1H), 3.75–3.62 (m, 1H), 3.62–3.39 (m, 3H), 3.49 (dd, J=10.5, 1.5 Hz, 1H), 3.26–3.12 (m, 1H), 2.95 (s, 3H), 2.56–2.37 (m, 2H), 2.37–2.20 (m, 1H), 2.20–2.10 (m, 1H), 1.82–1.63 (m, 2H), 1.50–1.30 (m, 3H), 1.01 (d, J=6.6 Hz, 3H), 0.95 (t, J=7.2 Hz, 3H), 0.92 (d, J=6.6 Hz, 3H).

EXAMPLE 64

(3S)-2,5-dioxo-3-(3-benzyloxycarbonylaminopropyl)-9-(2-phenylethyl)-1,4,9-triazaspiro[5.5]undecane.hydrochloride

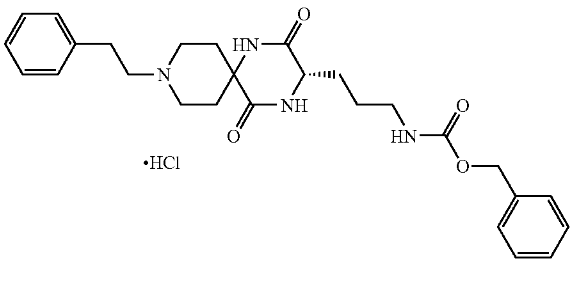

By the same procedure as described in Reference Example 9→Reference Example 10→Example 1 using Resin (3) prepared in Reference Example 2, N-(2-phenylethyl)-4-piperidone, 2,4,6-trimethoxybenzylamine and $N^{\alpha}$-(t-butyloxycarbonyl)-Nδ-(benzyloxycarbonyl)-L-ornithine, the compound of the present invention having the following physical data was obtained.

TLC: Rf 0.33 (chloroform:methanol=10:1);

NMR (DMSO-$d_6$): δ 10.80–10.00 (m, 1H), 8.65–8.45 (m, 1H), 8.33 (s, 1H), 7.50–7.20 (m, 10H), 5.01 (s, 2H), 4.01 (m, 1H), 3.70–3.45 (m, 3H), 3.45–3.20 (m, 3H), 3.15–2.90 (m, 4H), 2.50–2.30 (m, 2H), 2.10–1.90 (m, 1H), 1.87–1.60 (m, 3H), 1.60–1.35 (m, 2H).

EXAMPLE 65

(3S)-1-methyl-2,5-dioxo-3-(3-benzyloxycarbonylaminopropyl)-9-(2-phenylethyl)-1,4,9-triazaspiro[5.5]undecane.acetate

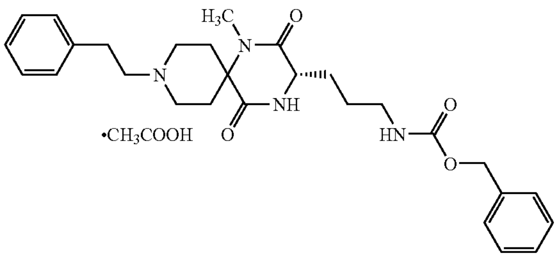

By the same procedure as described in Example 19 using Resin (3) prepared in Reference Example 2, N-(2-phenylethyl)-4-piperidone, methylamine and $N^{\alpha}$-(t-butyloxycarbonyl)-$N^{\delta}$-(benzyloxycarbonyl)-L-ornithine, the compound of the present invention having the following physical data was obtained.

TLC: Rf 0.36 (chloroform:methanol=10:1);

MS (ESI, Pos., 40 V): 493 $(M+H)^+$;

HPLC condition: F;

HPLC retention time: 3.36 min.

EXAMPLE 66

(3S)-1-butyl-2,5-dioxo-3-cyclohexylmethyl-9-(4-phenyloxyphenylmethyl)-9-oxide-1,4,9-triazaspiro[5.5]undecane

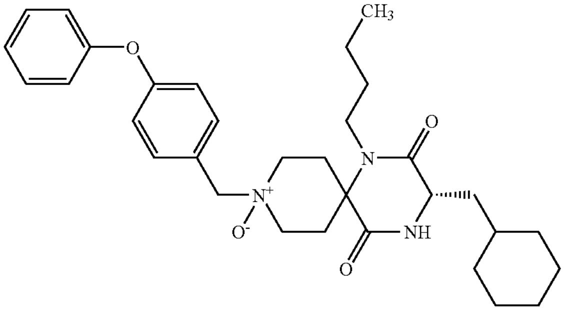

To a solution of the compound prepared in Example 40(90) (104 mg) in acetone (4 ml) were added water (1 ml), sodium hydrogen carbonate (210 mg) and OXONE (615 mg) (brand name). The reaction mixture was stirred for 1 hour at room temperature. The reaction mixture was diluted with ethyl acetate, washed with saturated aqueous solution of sodium hydrogen carbonate, and saturated aqueous solution of sodium chloride, dried over anhydrous magnesium sulfate, and concentrated. The residue was purified by preparative thin layer chromatography (chloroform:methanol=30:1, 20:1) to give the compound of the present invention (73 mg) having the following physical data.

TLC: Rf 0.50 (chloroform:methanol=9:1);

NMR ($CDCl_3$): δ 7.49 (dt, J=8.7, 2.1 Hz, 2H), 7.36 (ddt, J=8.7, 7.2, 2.1 Hz, 2H), 7.14 (tt, J=7.2, 1.2 Hz, 1H), 7.04 (dq, J=8.7, 1.2 Hz, 2H), 7.01 (dt, J=8.7, 2.1 Hz, 2H), 5.82 (brs, 1H), 4.32 (s, 2H), 4.07–3.85 (m, 3H), 3.55–3.46 (m, 2H), 3.19–2.97 (m, 4H), 2.02–1.49 (m, 11H), 1.48–1.12 (m, 6H), 1.08–0.90 (m, 2H), 0.90 (t, J=7.2 Hz, 3H).

EXAMPLE 67(H32-1)~67(H34-15)

By the same procedure as described in Example 23 using Resin (3) prepared in Reference Example 2, the corresponding 4-piperidone derivatives, the corresponding amine derivatives, the corresponding amino acid derivatives, and the corresponding aldehyde derivatives, the compounds of the present invention, whose names were shown in the following Table 32A-1~34A-2, and whose structures were shown in the following Table 32B-1~34B-3, were obtained. Also, physical data of the above compounds were shown in the following Table 32C-1~34C-1.

TABLE 32A-1

| Example No | Compound Name |
|---|---|
| 67(H32-1) | 1-butyl-2,5-dioxo-3-benzyl-9-(4-methoxyphenylmethyl)-1,4,9-triazaspiro[5.5]undecane |
| 67(H32-2) | 1-butyl-2,5-dioxo-3-benzyl-9-(1,4-benzodioxan-6-ylmethyl)-1,4,9-triazaspiro[5.5]undecane |
| 67(H32-3) | 1-butyl-2,5-dioxo-3-benzyl-9-(4-phenyloxyphenylmethyl)-1,4,9-triazaspiro[5.5]undecane |
| 67(H32-4) | 1-butyl-2,5-dioxo-3-benzyl-9-(4-benzyloxyphenylmethyl)-1,4,9-triazaspiro[5.5]undecane |
| 67(H32-5) | 1-butyl-2,5-dioxo-3-benzyl-9-(3,5-dimethyl-1-phenylpyrazol-4-ylmethyl)-1,4,9-triazaspiro[5.5]undecane |

TABLE 32A-1-continued

| Example No | Compound Name |
|---|---|
| 67(H32-6) | 1-butyl-2,5-dioxo-3-benzyl-9-(2-phenylimidazol-4-ylmethyl)-1,4,9-triazaspiro[5.5]undecane |
| 67(H32-7) | 1-(2-methoxyethyl)-2,5-dioxo-3-benzyl-9-(4-methoxyphenylmethyl)-1,4,9-triazaspiro[5.5]undecane |
| 67(H32-8) | 1-(2-methoxyethyl)-2,5-dioxo-3-benzyl-9-(1,4-benzodioxan-6-ylmethyl)-1,4,9-triazaspiro[5.5]undecane |
| 67(H32-9) | 1-(2-methoxyethyl)-2,5-dioxo-3-benzyl-9-(4-phenyloxyphenylmethyl)-1,4,9-triazaspiro[5.5]undecane |

TABLE 32A-2

| Example No | Compound Name |
|---|---|
| 67(H32-10) | 1-(2-methoxyethyl)-2,5-dioxo-3-benzyl-9-(4-benzyloxyphenylmethyl)-1,4,9-triazaspiro[5.5]undecane |
| 67(H32-11) | 1-(2-methoxyethyl)-2,5-dioxo-3-benzyl-9-(3,5-dimethyl-1-phenylpyrazol-4-ylmethyl)-1,4,9-triazaspiro[5.5]undecane |
| 67(H32-12) | 1-(2-methoxyethyl)-2,5-dioxo-3-benzyl-9-(2-phenylimidazol-4-ylmethyl)-1,4,9-triazaspiro[5.5]undecane |
| 67(H32-13) | 1-benzyl-2,5-dioxo-3-benzyl-9-(4-methoxyphenylmethyl)-1,4,9-triazaspiro[5.5]undecane |
| 67(H32-14) | 1-benzyl-2,5-dioxo-3-benzyl-9-(1,4-benzodioxan-6-ylmethyl)-1,4,9-triazaspiro[5.5]undecane |
| 67(H32-15) | 1-benzyl-2,5-dioxo-3-benzyl-9-(4-phenyloxyphenylmethyl)-1,4,9-triazaspiro[5.5]undecane |
| 67(H32-16) | 1-benzyl-2,5-dioxo-3-benzyl-9-(4-benzyloxyphenylmethyl)-1,4,9-triazaspiro[5.5]undecane |
| 67(H32-17) | 1-benzyl-2,5-dioxo-3-benzyl-9-(3,5-dimethyl-1-phenylpyrazol-4-ylmethyl)-1,4,9-triazaspiro[5.5]undecane |
| 67(H32-18) | 1-benzyl-2,5-dioxo-3-benzyl-9-(2-phenylimidazol-4-ylmethyl)-1,4,9-triazaspiro[5.5]undecane |

TABLE 32A-3

| Example No | Compound Name |
|---|---|
| 67(H32-19) | (3S)-1-butyl-2,5-dioxo-3-(4-methoxybenzyl)-9-cyclohexylmethyl-1,4,9-triazaspiro[5.5]undecane |
| 67(H32-20) | (3S)-1-butyl-2,5-dioxo-3-(4-methoxybenzyl)-9-(2-methylpropyl)-1,4,9-triazaspiro[5.5]undecane |
| 67(H32-21) | (3R)-1-butyl-2,5-dioxo-3-(4-methoxybenzyl)-9-cyclohexylmethyl-1,4,9-triazaspiro[5.5]undecane |
| 67(H32-22) | (3R)-1-butyl-2,5-dioxo-3-(4-methoxybenzyl)-9-(2-methylpropyl)-1,4,9-triazaspiro[5.5]undecane |
| 67(H32-23) | 1-butyl-2,5-dioxo-3-(2-methylpropyl)-9-(5-(4-chlorophenyl)thiophen-2-ylmethyl)-1,4,9-triazaspiro[5.5]undecane |
| 67(H32-24) | 1-butyl-2,5-dioxo-3-(2-methylpropyl)-9-(5-(4-methoxyphenyl)thiophen-2-ylmethyl)-1,4,9-triazaspiro[5.5]undecane |

TABLE 33A-1

| Example No | Compound Name |
|---|---|
| 67(H33-1) | 1-(2-chlorophenylmethyl)-2,5-dioxo-3-(2-methylpropyl)-9-(4-phenyloxyphenylmethyl)-1,4,9-triazaspiro[5.5]undecane |
| 67(H33-2) | 1-(2-fluorophenylmethyl)-2,5-dioxo-3-(2-methylpropyl)-9-(4-phenyloxyphenylmethyl)-1,4,9-triazaspiro[5.5]undecane |
| 67(H33-3) | 1-(2-trifluoromethylphenylmethyl)-2,5-dioxo-3-(2-methylpropyl)-9-(4-phenyloxyphenylmethyl)-1,4,9-triazaspiro[5.5]undecane |
| 67(H33-4) | 1-cyclopropylmethyl-2,5-dioxo-3-(2-methylpropyl)-9-(4-phenyloxyphenylmethyl)-1,4,9-triazaspiro[5.5]undecane |

TABLE 33A-1-continued

| Example No | Compound Name |
|---|---|
| 67(H33-5) | 1-(2,2-dimethylpropyl)-2,5-dioxo-3-(2-methylpropyl)-9-(4-phenyloxyphenylmethyl)-1,4,9-triazaspiro[5.5]undecane |
| 67(H33-6) | 1-(thiophen-2-ylmethyl)-2,5-dioxo-3-(2-methylpropyl)-9-(4-phenyloxyphenylmethyl)-1,4,9-triazaspiro[5.5]undecane |
| 67(H33-7) | 1-(furan-2-ylmethyl)-2,5-dioxo-3-(2-methylpropyl)-9-(4-phenyloxyphenylmethyl)-1,4,9-triazaspiro[5.5]undecane |
| 67(H33-8) | 1-((2E)-2-butenyl)-2,5-dioxo-3-(2-methylpropyl)-9-(4-phenyloxyphenylmethyl)-1,4,9-triazaspiro[5.5]undecane |

TABLE 33A-2

| Example No | Compound Name |
|---|---|
| 67(H33-9) | 1-(2-methoxyethyl)-2,5-dioxo-3-(2-methylpropyl)-9-(5-ethylthiophen-2-ylmethyl)-1,4,9-triazaspiro[5.5]undecane |
| 67(H33-10) | 1-(2-phenyloxyethyl)-2,5-dioxo-3-(2-methylpropyl)-9-(4-phenyloxyphenylmethyl)-1,4,9-triazaspiro[5.5]undecane |
| 67(H33-11) | 1-(thiophen-2-ylmethyl)-2,5-dioxo-3-cyclohexylmethyl-9-(2-chloro-4-hydroxyphenylmethyl)-1,4,9-triazaspiro[5.5]undecane |
| 67(H33-12) | 1-butyl-2,5-dioxo-3-cyclohexylmethyl-9-(2-chloro-4-hydroxyphenylmethyl)-1,4,9-triazaspiro[5.5]undecane |
| 67(H33-13) | 1-(thiophen-2-ylmethyl)-2,5-dioxo-3-cyclohexylmethyl-9-(4-hydroxyphenylmethyl)-1,4,9-triazaspiro[5.5]undecane |
| 67(H33-14) | 1-butyl-2,5-dioxo-3-cyclohexylmethyl-9-(4-hydroxyphenylmethyl)-1,4,9-triazaspiro[5.5]undecane |
| 67(H33-15) | 1-(thiophen-2-ylmethyl)-2,5-dioxo-3-(2-methylpropyl)-9-(2-chloro-4-hydroxyphenylmethyl)-1,4,9-triazaspiro[5.5]undecane |
| 67(H33-16) | 1-butyl-2,5-dioxo-3-(2-methylpropyl)-9-(2-chloro-4-hydroxyphenylmethyl)-1,4,9-triazaspiro[5.5]undecane |

TABLE 33A-3

| Example No | Compound Name |
|---|---|
| 67(H33-17) | 1-(thiophen-2-ylmethyl)-2,5-dioxo-3-(2-methylpropyl)-9-(4-hydroxyphenylmethyl)-1,4,9-triazaspiro[5.5]undecane |
| 67(H33-18) | 1-butyl-2,5-dioxo-3-(2-methylpropyl)-9-(4-hydroxyphenylmethyl)-1,4,9-triazaspiro[5.5]undecane |

TABLE 34A-1

| Example No | Compound Name |
|---|---|
| 67(H34-1) | (3S)-1-butyl-2,5-dioxo-3-((1S)-1-methylpropyl)-9-(4-phenyloxyphenylmethyl)-1,4,9-triazaspiro[5.5]undecane |
| 67(H34-2) | (3S)-1-butyl-2,5-dioxo-3-((1S)-1-methylpropyl)-9-(1,4-benzodioxan-6-ylmethyl)-1,4,9-triazaspiro[5.5]undecane |
| 67(H34-3) | (3S)-1-(2-methoxyethyl)-2,5-dioxo-3-((1S)-1-methylpropyl)-9-(4-phenyloxyphenylmethyl)-1,4,9-triazaspiro[5.5] |
| 67(H34-4) | (3S)-1-(2-methoxyethyl)-2,5-dioxo-3-((1S)-1-methylpropyl-9-(1,4-benzodioxan-6-ylmethyl)-1,4,9-triazaspiro[5.5]undecane |
| 67(H34-5) | (3S)-1-butyl-2,5-dioxo-3-(cyclohexylmethyloxymethyl)-9-(4-phenyloxypheflylmethyl)-1,4,9-triazaspiro[5.5]undecane |
| 67(H34-6) | (3S)-1-butyl-2,5-dioxo-3-(cyclohexylmethyloxymethyl)-9-(1,4-benzodioxan-6-ylmethyl)-1,4,9-triazaspiro[5.5]undecane |
| 67(H34-7) | (3S)-1-(2-methoxyethyl)-2,5-dioxo-3-(cyclohexylmethyloxymethyl)-9-(4-phenyloxyphenylmethyl)-1,4,9-triazaspiro[5.5]undecane |

TABLE 34A-2

| Example No | Compound Name |
|---|---|
| 67(H34-8) | (3S)-1-(2-methoxyethyl)-2,5-dioxo-3-(cyclohexylmethyloxymethyl)-9-(1,4-benzodioxan-6-ylmethyl)-1,4,9-triazaspiro[5.5]undecane |
| 67(H34-9) | 1-butyl-2,5-dioxo-3-(2-methylpropyl)-9-(4-chloro-1,3-benzodioxolan-5-ylmethyl)-1,4,9-triazaspiro[5.5]undecane |
| 67(H34-10) | 1-(2-methoxyethyl)-2,5-dioxo-3-(2-methylpropyl)-9-(4-chloro-1,3-benzodioxolan-5-ylmethyl)-1,4,9-triazaspiro[5.5] undecane |
| 67(H34-11) | 1-(3-methyl-2-butenyl)-2,5-dioxo-3-(2-methylpropyl)-9-(4-phenyloxyphenylmethyl)-1,4,9-triazaspiro[5.5]undecane |

TABLE 34A-2-continued

| Example No | Compound Name |
|---|---|
| 67(H34-12) | 1-butyl-2,5-dioxo-3-(2-methylpropyl)-9-((2E)-3-phenyl-2-propenyl)-1,4,9-triazaspiro[5.5]undecane |
| 67(H34-13) | 1-butyl-2,5-dioxo-3-cyclohexylmethyl-9-((2E)-3-phenyl-2-propenyl)-1,4,9-triazaspiro[5.5]undecane |
| 67(H34-14) | 1-butyl-2,5-dioxo-3-cyclohexylmethyl-9-(quinolin-3-ylmethyl)-1,4,9-triazaspiro[5.5]undecane |
| 67(H34-15) | 1-(3-methyl-2-butenyl)-2,5-dioxo-3-cyclohexylmethyl-9-(1,4-benzodioxan-6-ylmethyl)-1,4,9-triazaspiro[5.5]undecane |

TABLE 32B-1

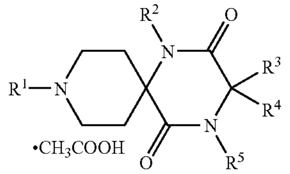

| Example No | $R^1$ | $R^2$ | $R^3$ | $R^4$ | $R^5$ |
|---|---|---|---|---|---|
| 67(H32-1) | 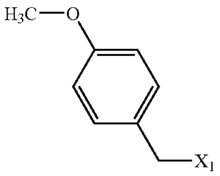 | 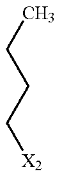 | H | 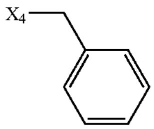 | H |
| 67(H32-2) | 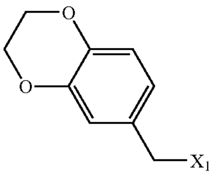 | 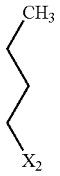 | H | 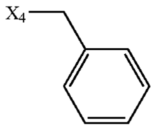 | H |
| 67(H32-3) | 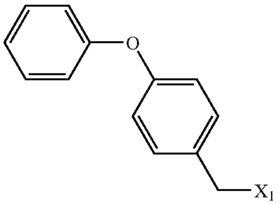 | 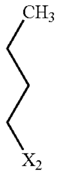 | H | 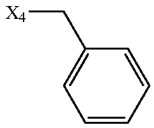 | H |
| 67(H32-4) | 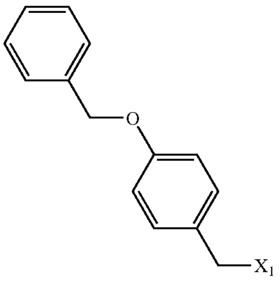 | 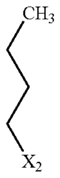 | H | 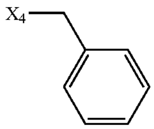 | H |

TABLE 32B-1-continued
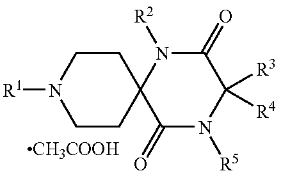
| Example No | $R^1$ | $R^2$ | $R^3$ | $R^4$ | $R^5$ |
|---|---|---|---|---|---|
| 67(H32-5) | 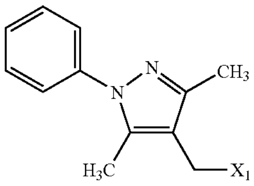 | 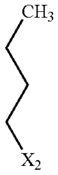 | H | 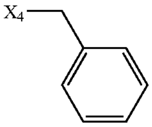 | H |
| 67(H32-6) | 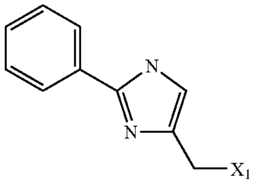 | 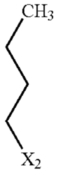 | H | 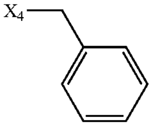 | H |
TABLE 32B-2
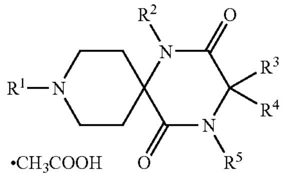
| Example No | $R^1$ | $R^2$ | $R^3$ | $R^4$ | $R^5$ |
|---|---|---|---|---|---|
| 67(H32-7) | 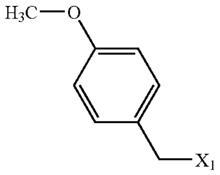 | 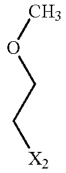 | H | 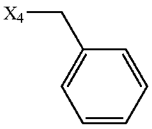 | H |
| 67(H32-8) | 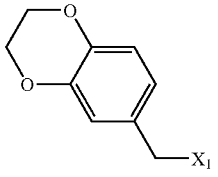 | 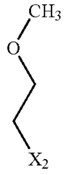 | H | 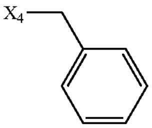 | H |
| 67(H32-9) | 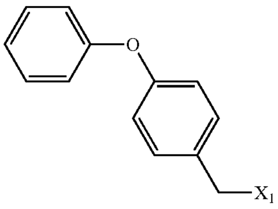 | 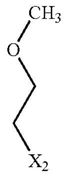 | H | 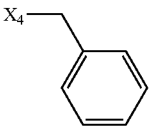 | H |

TABLE 32B-2-continued
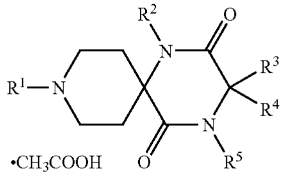
•$CH_3COOH$
| Example No | $R^1$ | $R^2$ | $R^3$ | $R^4$ | $R^5$ |
|---|---|---|---|---|---|
| 67(H32-10) | 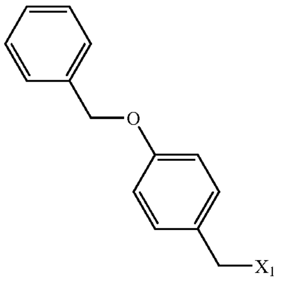 | 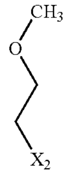 | H | 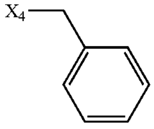 | H |
| 67(H32-11) | 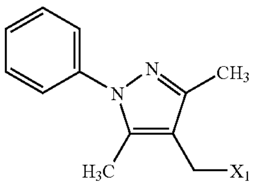 | 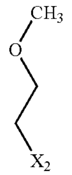 | H | 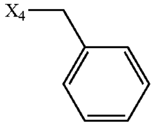 | H |
| 67(H32-12) | 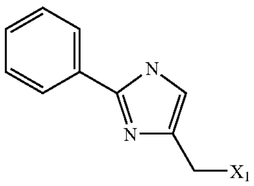 | 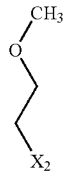 | H | 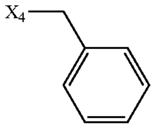 | H |
TABLE 32B-3
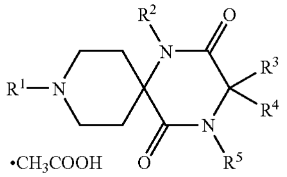
•$CH_3COOH$
| Example No | $R^1$ | $R^2$ | $R^3$ | $R^4$ | $R^5$ |
|---|---|---|---|---|---|
| 67(H32-13) | 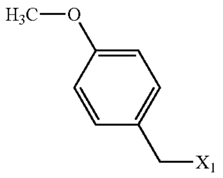 | 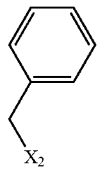 | H | 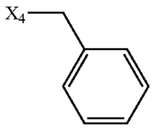 | H |

TABLE 32B-3-continued
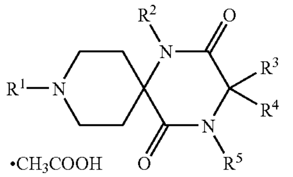
•$CH_3COOH$
| Example No | $R^1$ | $R^2$ | $R^3$ | $R^4$ | $R^5$ |
| --- | --- | --- | --- | --- | --- |
| 67(H32-14) | 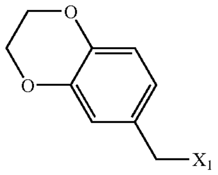 | 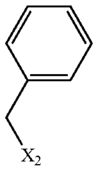 | H | 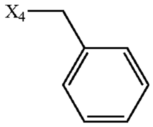 | H |
| 67(H32-15) | 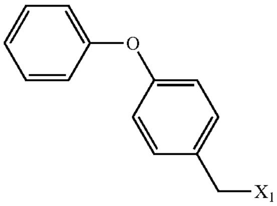 | 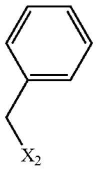 | H | 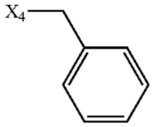 | H |
| 67(H32-16) | 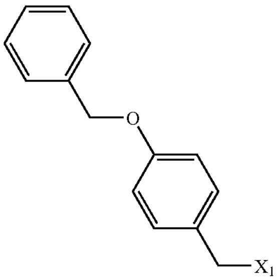 | 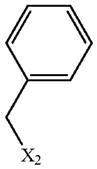 | H | 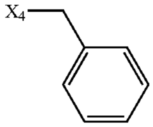 | H |
| 67(H32-17) | 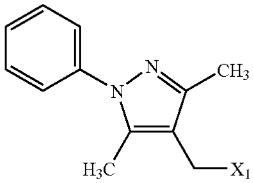 | 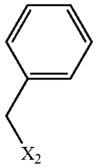 | H | 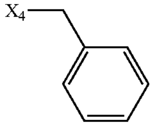 | H |
| 67(H32-18) | 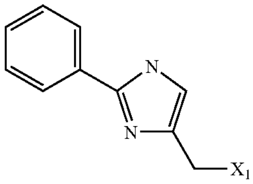 | 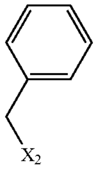 | H | 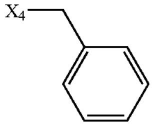 | H |
| 67(H32-19) | 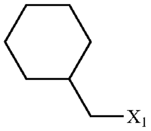 | 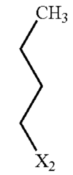 | H | 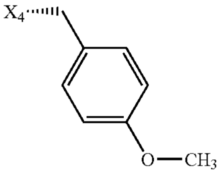 | H |

TABLE 32B-4
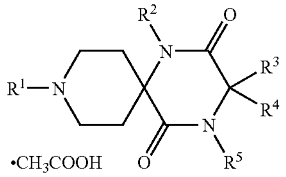
•$CH_3COOH$
| Example No | $R^1$ | $R^2$ | $R^3$ | $R^4$ | $R^5$ |
| --- | --- | --- | --- | --- | --- |
| 67(H32-20) | 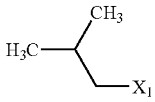 | 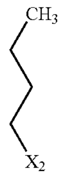 | H | 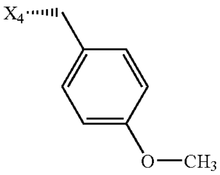 | H |
| 67(H32-21) | 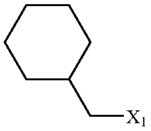 | 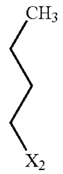 | H | 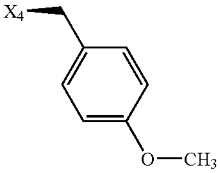 | H |
| 67(H32-22) | 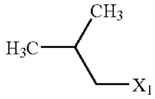 | 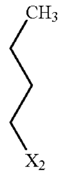 | H | 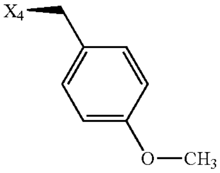 | H |
| 67(H32-23) | 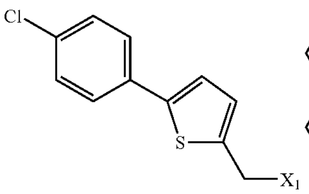 | 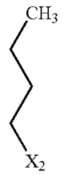 | H | 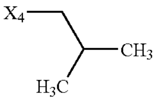 | H |
| 67(H32-24) | 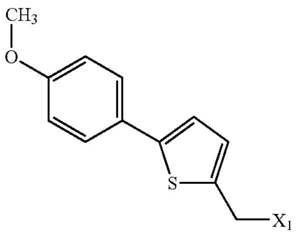 | 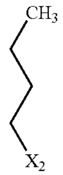 | H | 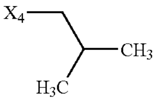 | H |

TABLE 33B-1
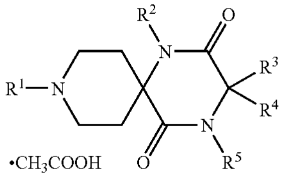
•$CH_3COOH$
| Example No | $R^1$ | $R^2$ | $R^3$ | $R^4$ | $R^5$ |
|---|---|---|---|---|---|
| 67(H33-1) | 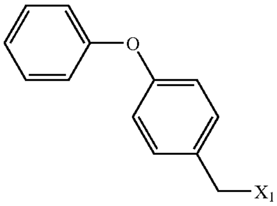 | 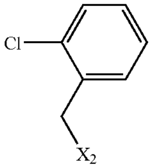 | H | 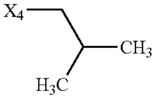 | H |
| 67(H33-2) | 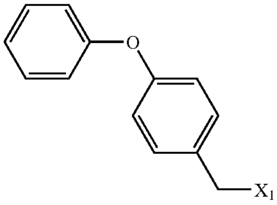 | 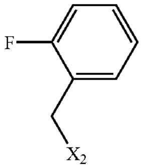 | H | 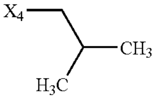 | H |
| 67(H33-3) | 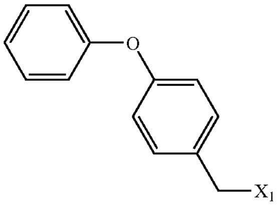 | 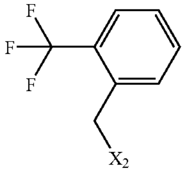 | H | 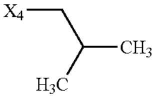 | H |
| 67(H33-4) | 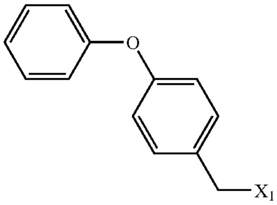 | 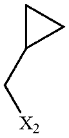 | H | 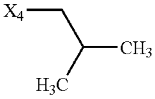 | H |
| 67(H33-5) | 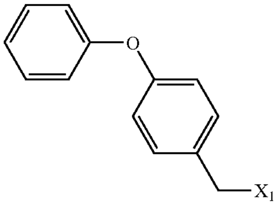 | 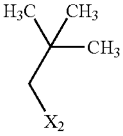 | H | 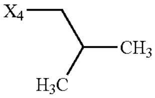 | H |
| 67(H33-6) | 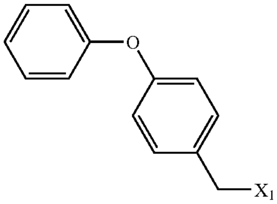 | 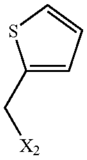 | H | 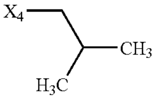 | H |

TABLE 33B-2
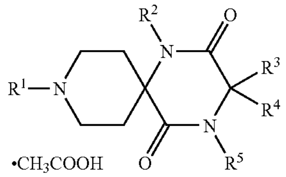
•$CH_3COOH$
| Example No | $R^1$ | $R^2$ | $R^3$ | $R^4$ | $R^5$ |
| --- | --- | --- | --- | --- | --- |
| 67(H33-7) | 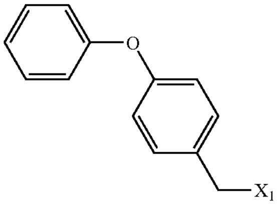 | 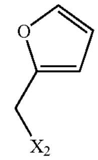 | H | 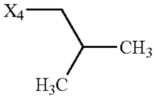 | H |
| 67(H33-8) | 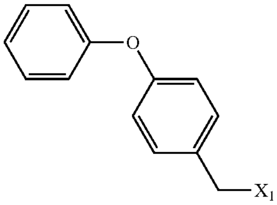 | 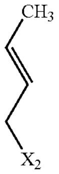 | H | 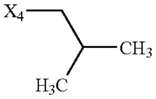 | H |
| 67(H33-9) | 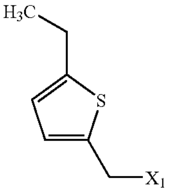 | 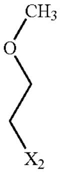 | H | 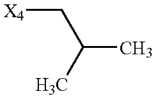 | H |
| 67(H33-10) | 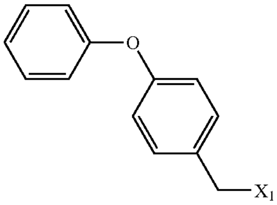 | 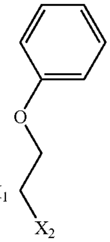 | H | 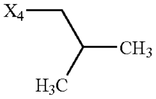 | H |
| 67(H33-11) | 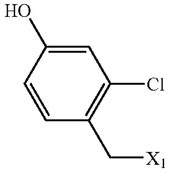 | 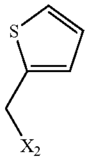 | H | 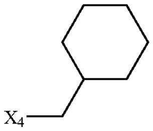 | H |
| 67(H33-12) | 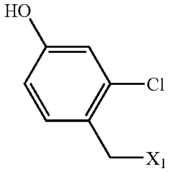 | 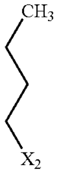 | H | 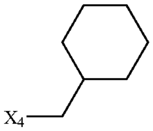 | H |

TABLE 33B-2-continued
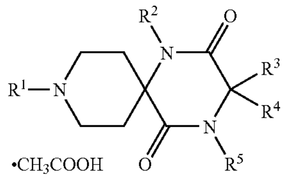
$\cdot CH_3COOH$
| Example No | $R^1$ | $R^2$ | $R^3$ | $R^4$ | $R^5$ |
|---|---|---|---|---|---|
| 67(H33-13) | 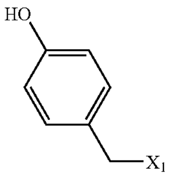 | 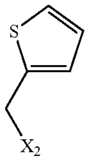 | H | 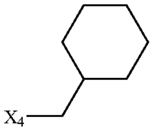 | H |
TABLE 33B-3
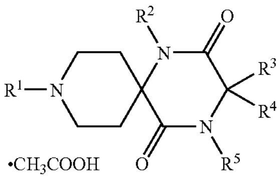
$\cdot CH_3COOH$
| Example No | $R^1$ | $R^2$ | $R^3$ | $R^4$ | $R^5$ |
|---|---|---|---|---|---|
| 67(H33-14) | 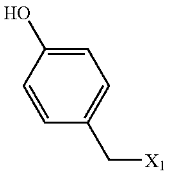 | 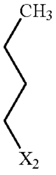 | H | 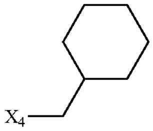 | H |
| 67(H33-15) | 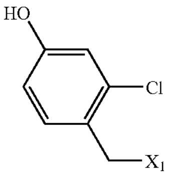 | 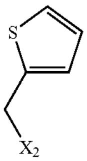 | H | 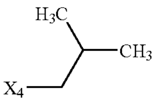 | H |
| 67(H33-16) | 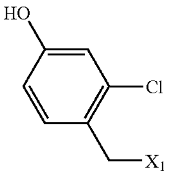 | 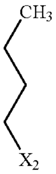 | H | 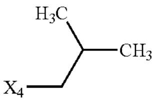 | H |
| 67(H33-17) | 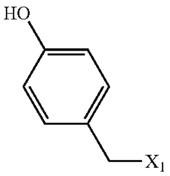 | 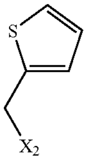 | H | 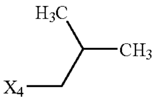 | H |
TABLE 33B-3-continued
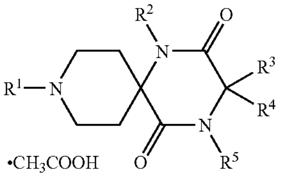
$\cdot CH_3COOH$
| Example No | $R^1$ | $R^2$ | $R^3$ | $R^4$ | $R^5$ |
|---|---|---|---|---|---|
| 67(H33-18) | 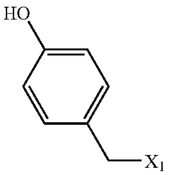 | 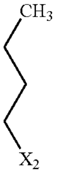 | H | 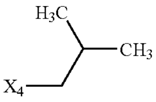 | H |
TABLE 34B-1
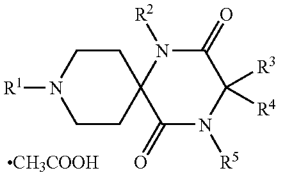
$\cdot CH_3COOH$
| Example No | $R^1$ | $R^2$ | $R^3$ | $R^4$ | $R^5$ |
|---|---|---|---|---|---|
| 67(H34-1) | 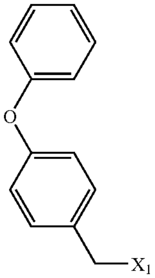 | 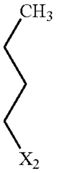 | H | 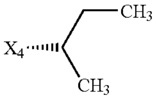 | H |

TABLE 34B-1-continued
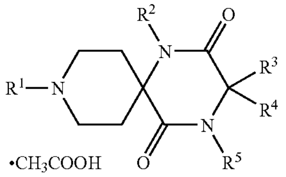
•$CH_3COOH$
| Example No | $R^1$ | $R^2$ | $R^3$ | $R^4$ | $R^5$ |
|---|---|---|---|---|---|
| 67(H34-2) | 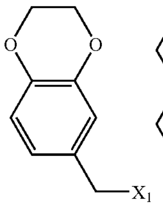 | 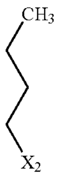 | H | 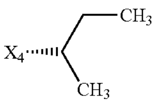 | H |
| 67(H34-3) | 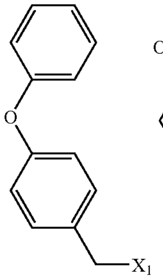 | 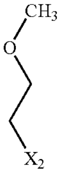 | H | 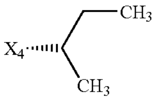 | H |
TABLE 34B-1-continued
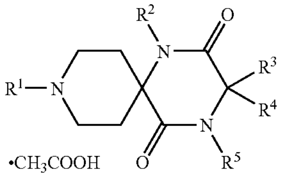
•$CH_3COOH$
| Example No | $R^1$ | $R^2$ | $R^3$ | $R^4$ | $R^5$ |
|---|---|---|---|---|---|
| 67(H34-4) | 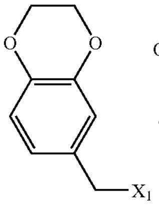 | 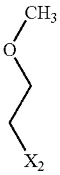 | H | 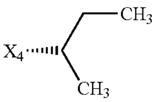 | H |
| 67(H34-5) | 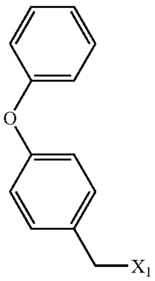 | 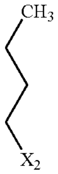 | H | 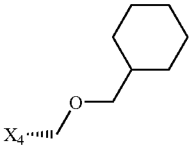 | H |
TABLE 34B-2
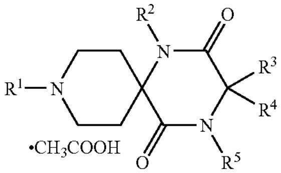
•$CH_3COOH$
| Example No | $R^1$ | $R^2$ | $R^3$ | $R^4$ | $R^5$ |
|---|---|---|---|---|---|
| 67(H34-6) | 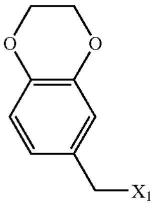 | 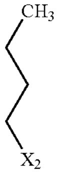 | H | 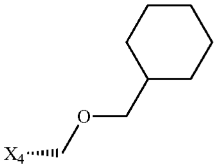 | H |

TABLE 34B-2-continued
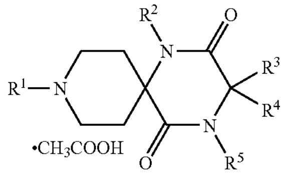
| Example No | $R^1$ | $R^2$ | $R^3$ | $R^4$ | $R^5$ |
|---|---|---|---|---|---|
| 67(H34-7) | 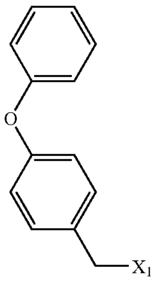 | 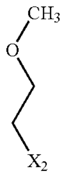 | H | 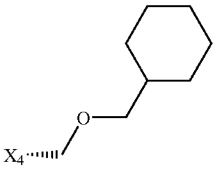 | H |
| 67(H34-8) | 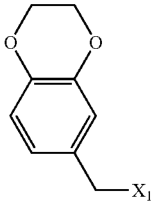 | 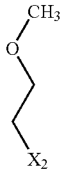 | H | 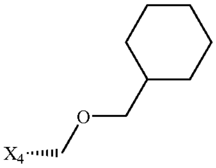 | H |
| 67(H34-9) | 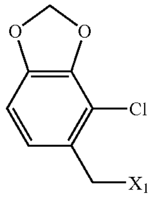 | 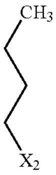 | H | 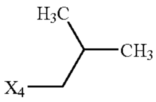 | H |
| 67(H34-10) | 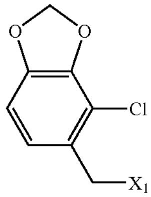 | 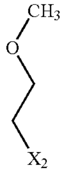 | H | 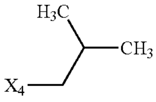 | H |
| 67(H34-11) | 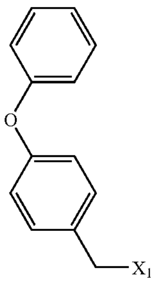 | 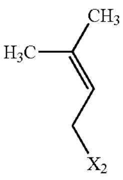 | H | 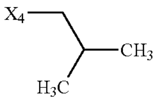 | H |

TABLE 34B-3

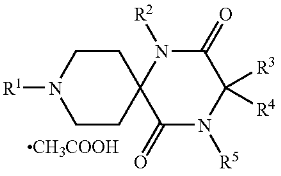

| Example No | $R^1$ | $R^2$ | $R^3$ | $R^4$ | $R^5$ |
|---|---|---|---|---|---|
| 67(H34-12) | 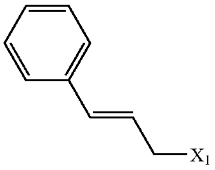 | 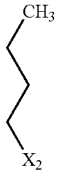 | H | 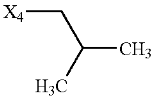 | H |
| 67(H34-13) | 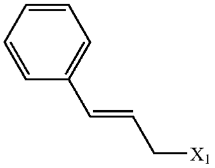 | 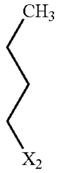 | H | 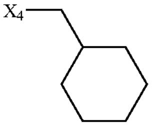 | H |
| 67(H34-14) | 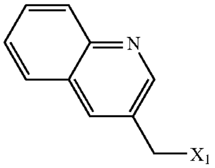 | 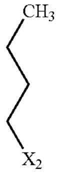 | H | 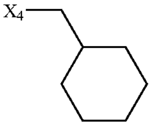 | H |
| 67(H34-15) | 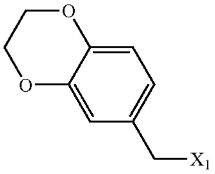 | 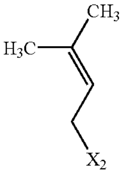 | H | 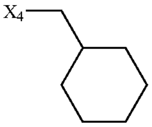 | H |

TABLE 32C-1

| Example No | HPLC condition | Retention time (min) | Mass data | Mass condition |
|---|---|---|---|---|
| 67(H32-1) | F | 3.42 | 450 $(M + H)^+$, 121. | ESI (Pos., 40 V) |
| 67(H32-2) | F | 3.40 | 478 $(M + H)^+$, 149. | ESI (Pos., 40 V) |
| 67(H32-3) | F | 3.72 | 512 $(M + H)^+$, 183. | ESI (Pos., 40 V) |
| 67(H32-4) | F | 3.71 | 526 $(M + H)^+$, 197. | ESI (Pos., 40 V) |
| 67(H32-5) | F | 3.42 | 514 $(M + H)^+$, 303, 185. | ESI (Pos., 40 V) |
| 67(H32-6) | F | 3.31 | 486 $(M + H)^+$. | ESI (Pos., 40 V) |
| 67(H32-7) | F | 3.27 | 452 $(M + H)^+$, 121. | ESI (Pos., 40 V) |
| 67(H32-8) | F | 3.27 | 480 $(M + H)^+$, 149. | ESI (Pos., 40 V) |
| 67(H32-9) | F | 3.55 | 514 $(M + H)^+$, 339, 183. | ESI (Pos., 40 V) |
| 67(H32-10) | F | 3.58 | 528 $(M + H)^+$, 339, 197. | ESI (Pos., 40 V) |
| 67(H32-11) | F | 3.29 | 516 $(M + H)^+$, 185. | ESI (Pos., 40 V) |
| 67(H32-12) | F | 3.12 | 488 $(M + H)^+$. | ESI (Pos., 40 V) |
| 67(H32-13) | F | 3.47 | 484 $(M + H)^+$, 303, 121. | ESI (Pos., 40 V) |
| 67(H32-14) | F | 3.47 | 512 $(M + H)^+$, 303, 148. | ESI (Pos., 40 V) |

TABLE 32C-1-continued

| Example No | HPLC condition | Retention time (min) | Mass data | Mass condition |
|---|---|---|---|---|
| 67(H32-15) | F | 3.73 | 546 $(M + H)^+$, 183. | ESI (Pos., 40 V) |
| 67(H32-16) | F | 3.75 | 560 $(M + H)^+$, 197. | ESI (Pos., 40 V) |
| 67(H32-17) | F | 3.49 | 548 $(M + H)^+$, 303, 185. | ESI (Pos., 40 V) |
| 67(H32-18) | F | 3.33 | 520 $(M + H)^+$, 404. | ESI (Pos., 40 V) |
| 67(H32-19) | F | 3.52 | 456 $(M + H)^+$. | ESI (Pos., 40 V) |
| 67(H32-20) | F | 3.29 | 416 $(M + H)^+$. | ESI (Pos., 40 V) |
| 67(H32-21) | F | 3.49 | 456 $(M + H)^+$. | ESI (Pos., 40 V) |
| 67(H32-22) | F | 3.31 | 416 $(M + H)^+$. | ESI (Pos., 40 V) |
| 67(H32-23) | F | 3.78 | 502 $(M + H)^+$, 206. | ESI (Pos., 40 V) |
| 67(H32-24) | F | 3.69 | 498 $(M + H)^+$, 279, 203. | ESI (Pos., 40 V) |

TABLE 33C-1

| Example No | HPLC condition | Retention time (min) | Mass data | Mass condition |
|---|---|---|---|---|
| 67(H33-1) | F | 3.78 | 546 (M + H)+, 183. | ESI (Pos., 40 V) |
| 67(H33-2) | F | 3.75 | 530 (M + H)+, 183. | ESI (Pos., 40 V) |
| 67(H33-3) | F | 3.84 | 580 (M + H)+. | ESI (Pos., 40 V) |
| 67(H33-4) | F | 3.66 | 476 (M + H)+, 339, 183. | ESI (Pos., 40 V) |
| 67(H33-5) | F | 3.80 | 492 (M + H)+, 183. | ESI (Pos., 40 V) |
| 67(H33-6) | F | 3.73 | 518 (M + H)+, 183. | ESI (Pos., 40 V) |
| 67(H33-7) | F | 3.67 | 502 (M + H)+, 182. | ESI (Pos., 40 V) |
| 67(H33-8) | F | 3.67 | 476 (M + H)+, 183. | ESI (Pos., 40 V) |
| 67(H33-9) | F | 3.36 | 422 (M + H)+, 298, 125. | ESI (Pos., 40 V) |
| 67(H33-10) | F | 3.80 | 542 (M + H)+, 183. | ESI (Pos., 40 V) |
| 67(H33-11) | F | 3.44 | 515 (M + H)+. | ESI (Pos., 20 V) |
| 67(H33-12) | F | 3.44 | 476 (M + H)+. | ESI (Pos., 20 V) |
| 67(H33-13) | F | 3.38 | 482 (M + H)+. | ESI (Pos., 20 V) |
| 67(H33-14) | F | 3.36 | 442 (M + H)+. | ESI (Pos., 20 V) |
| 67(H33-15) | F | 3.26 | 476 (M + H)+. | ESI (Pos., 20 V) |
| 67(H33-16) | F | 3.22 | 436 (M + H)+. | ESI (Pos., 20 V) |
| 67(H33-17) | F | 3.20 | 442 (M + H)+. | ESI (Pos., 20 V) |
| 67(H33-18) | F | 3.15 | 402 (M + H)+. | ESI (Pos., 20 V) |

TABLE 34C-1

| Example No | HPLC condition | Retention time (min) | Mass data | Mass condition |
|---|---|---|---|---|
| 67(H34-1) | F | 3.71 | 478 (M + H)+, 279, 183. | ESI (Pos., 40 V) |
| 67(H34-2) | F | 3.42 | 444 (M + H)+, 149. | ESI (Pos., 40 V) |
| 67(H34-3) | F | 3.55 | 480 (M + H)+, 183. | ESI (Pos., 40 V) |
| 67(H34-4) | F | 3.23 | 446 (M + H)+, 149. | ESI (Pos., 40 V) |
| 67(H34-5) | F | 3.9 | 548 (M + H)+. | ESI (Pos., 40 V) |
| 67(H34-6) | F | 3.65 | 514 (M + H)+, 279, 149. | ESI (Pos., 40 V) |
| 67(H34-7) | F | 3.76 | 550 (M + H)+, 183. | ESI (Pos., 40 V) |
| 67(H34-8) | F | 3.49 | 516 (M + H)+, 149. | ESI (Pos., 40 V) |
| 67(H34-9) | F | 3.47 | 464 (M + H)+. | ESI (Pos., 40 V) |
| 67(H34-10) | F | 3.31 | 466 (M + H)+. | ESI (Pos., 40 V) |
| 67(H34-11) | F | 3.73 | 490 (M + H)+, 279, 183. | ESI (Pos., 40 V) |
| 67(H34-12) | F | 3.55 | 412 (M + H)+, 117. | ESI (Pos., 40 V) |
| 67(H34-13) | F | 3.72 | 452 (M + H)+, 379, 279, 117. | ESI (Pos., 40 V) |
| 67(H34-14) | F | 3.44 | 477 (M + H)+, 404, 345. | ESI (Pos., 40 V) |
| 67(H34-15) | F | 3.64 | 496 (M + H)+, 279, 149. | ESI (Pos., 40 V) |

EXAMPLE 68(H35-1)~H35-61)

By the same procedure as described in Reference Example 11 using Resin (3) prepared in Reference Example 2, the corresponding 4-piperidone derivatives, the corresponding amine derivatives, and the corresponding amino acid derivatives, and by the same procedure as described in Reference Example 12→Example 33 using the corresponding alcohol derivatives, and by cleavage from resin, the compounds of the present invention, whose names were shown in the following Table 35A-1~35A-8, and whose structures were shown in the following Table 35B-1~35B-13, were obtained. Also, physical data of the above compounds were shown in the following Table 35C-1~35C-3.

TABLE 35A-1

| Example No | Compound Name |
|---|---|
| 68(H35-1) | 1-butyl-2,5-dioxo-3-cyclohexylmethyl-9-(2-chloro-4-(2-(N,N-diethylamino)ethyloxy)phenylmethyl)-1,4,9-triazaspiro[5.5]undecane |
| 68(H35-2) | 1-(thiophen-2-ylmethyl)-2,5-dioxo-3-cyclohexylmethyl-9-(4-(2-(N,N-diethylamino)ethyloxy)phenylmethyl)-1,4,9-triazaspiro[5.5]undecane |
| 68(H35-3) | 1-butyl-2,5-dioxo-3-cyclohexylmethyl-9-(4-(2-(N,N-diethylamino)ethyloxy)phenylmethyl)-1,4,9-triazaspiro[5.5]undecane |
| 68(H35-4) | 1-(thiophen-2-ylmethyl)-2,5-dioxo-3-(2-methylpropyl)-9-(2-chloro-4-(2-(N,N-diethylamino)ethyloxy)phenylmethyl)-1,4,9-triazaspiro[5.5]undecane |
| 68(H35-5) | 1-butyl-2,5-dioxo-3-(2-methylpropyl)-9-(2-chloro-4-(2-(N,N-diethylamino)ethyloxy)phenylmethyl)-1,4,9-triazaspiro[5.5]undecane |
| 68(H35-6) | 1-(thiophen-2-ylmethyl)-2,5-dioxo-3-(2-methylpropyl)-9-(4-(2-(N,N-diethylamino)ethyloxy)phenylmethyl)-1,4,9-triazaspiro[5.5]undecane |
| 68(H35-7) | 1-butyl-2,5-dioxo-3-(2-methylpropyl)-9-(4-(2-(N,N-diethylamino)ethyloxy)phenylmethyl)-1,4,9-triazaspiro[5.5]undecane |

TABLE 35A-2

| Example No | Compound Name |
|---|---|
| 68(H35-8) | 1-(thiophen-2-ylmethyl)-2,5-dioxo-3-cyclohexylmethyl-9-(2-chloro-4-methoxyphenylmethyl)-1,4,9-triazaspiro[5.5]undecane |
| 68(H35-9) | 1-butyl-2,5-dioxo-3-cyclohexylmethyl-9-(2-chloro-4-methoxyphenylmethyl)-1,4,9-triazaspiro[5.5]undecane |
| 68(H35-10) | 1-(thiophen-2-ylmethyl)-2,5-dioxo-3-cyclohexylmethyl-9-(4-methoxyphenylmethyl)-1,4,9-triazaspiro[5.5]undecane |
| 68(H35-11) | 1-butyl-2,5-dioxo-3-cyclohexylmethyl-9-(4-methoxyphenylmethyl)-1,4,9-triazaspiro[5.5]undecane |
| 68(H35-12) | 1-(thiophen-2-ylmethyl)-2,5-dioxo-3-(2-methylpropyl)-9-(2-chloro-4-methoxyphenylmethyl)-1,4,9-triazaspiro[5.5]undecane |
| 68(H35-13) | 1-butyl-2,5-dioxo-3-(2-methylpropyl)-9-(2-chloro-4-methoxyphenylmethyl)-1,4,9-triazaspiro[5.5]undecane |
| 68(H35-14) | 1-butyl-2,5-dioxo-3-(2-methylpropyl)-9-(4-methoxyphenylmethyl)-1,4,9-triazaspiro[5.5]undecane |
| 68(H35-15) | 1-(thiophen-2-ylmethyl)-2,5-dioxo-3-cyclohexylmethyl-9-(2-chloro-4-ethoxyphenylmethyl)-1,4,9-triazaspiro[5.5]undecane |

TABLE 35A-3

| Example No | Compound Name |
|---|---|
| 68(H35-16) | 1-butyl-2,5-dioxo-3-cyclohexylmethyl-9-(2-chloro-4-ethoxyphenylmethyl)-1,4,9-triazaspiro[5.5]undecane |
| 68(H35-17) | 1-(thiophen-2-ylmethyl)-2,5-dioxo-3-cyclohexylmethyl-9-(4-ethoxyphenylmethyl)-1,4,9-triazaspiro[5.5]undecane |
| 68(H35-18) | 1-butyl-2,5-dioxo-3-cyclohexylmethyl-9-(4-ethoxyphenylmethyl)-1,4,9-triazaspiro[5.5]undecane |
| 68(H35-19) | 1-(thiophen-2-ylmethyl)-2,5-dioxo-3-(2-methylpropyl)-9-(2-chloro-4-ethoxyphenylmethyl)-1,4,9-triazaspiro[5.5]undecane |

TABLE 35A-3-continued

| Example No | Compound Name |
|---|---|
| 68(H35-20) | 1-butyl-2,5-dioxo-3-(2-methylpropyl)-9-(2-chloro-4-ethoxyphenylmethyl)-1,4,9-triazaspiro[5.5]undecane |
| 68(H35-21) | 1-(thiophen-2-ylmethyl)-2,5-dioxo-3-(2-methylpropyl)-9-(4-ethoxyphenylmethyl)-1,4,9-triazaspiro[5.5]undecane |
| 68(H35-22) | 1-butyl-2,5-dioxo-3-(2-methylpropyl)-9-(4-ethoxyphenylmethyl)-1,4,9-triazaspiro[5.5]undecane |
| 68(H35-23) | 1-(thiophen-2-ylmethyl)-2,5-dioxo-3-cyclohexylmethyl-9-(2-chloro-4-propyloxyphenylmethyl)-1,4,9-triazaspiro[5.5]undecane |

TABLE 35A-4

| Example No | Compound Name |
|---|---|
| 68(H35-24) | 1-butyl-2,5-dioxo-3-cyclohexylmethyl-9-(2-chloro-4-propyloxyphenylmethyl)-1,4,9-triazaspiro[5.5]undecane |
| 68(H35-25) | 1-(thiophen-2-ylmethyl)-2,5-dioxo-3-cyclohexylmethyl-9-(4-propyloxyphenylmethyl)-1,4,9-triazaspiro[5.5]undecane |
| 68(H35-26) | 1-butyl-2,5-dioxo-3-cyclohexylmethyl-9-(4-propyloxyphenylmethyl)-1,4,9-triazaspiro[5.5]undecane |
| 68(H35-27) | 1-(thiophen-2-ylmethyl)-2,5-dioxo-3-(2-methylpropyl)-9-(2-chloro-4-propyloxyphenylmethyl)-1,4,9-triazaspiro[5.5]undecane |
| 68(H35-28) | 1-butyl-2,5-dioxo-3-(2-methylpropyl)-9-(2-chloro-4-propyloxyphenylmethyl)-1,4,9-triazaspiro[5.5]undecane |
| 68(H35-29) | 1-(thiophen-2-ylmethyl)-2,5-dioxo-3-(2-methylpropyl)-9-(4-propyloxyphenylmethyl)-1,4,9-triazaspiro[5.5]undecane |
| 68(H35-30) | 1-(thiophen-2-ylmethyl)-2,5-dioxo-3-cyclohexylmethyl-9-(2-chloro-4-isopropyloxyphenylmethyl)-1,4,9-triazaspiro[5.5]undecane |
| 68(H35-31) | 1-butyl-2,5-dioxo-3-cyclohexylmethyl-9-(2-chloro-4-isopropyloxyphenylmethyl)-1,4,9-triazaspiro[5.5]undecane |

TABLE 35A-5

| Example No | Compound Name |
|---|---|
| 68(H35-32) | 1-(thiophen-2-ylmethyl)-2,5-dioxo-3-cyclohexylmethyl-9-(4-isopropyloxyphenylmethyl)-1,4,9-triazaspiro[5.5]undecane |
| 68(H35-33) | 1-butyl-2,5-dioxo-3-cyclohexylmethyl-9-(4-isopropyloxyphenylmethyl)-1,4,9-triazaspiro[5.5]undecane |
| 68(H35-34) | 1-(thiophen-2-ylmethyl)-2,5-dioxo-3-(2-methylpropyl)-9-(2-chloro-4-isopropyloxyphenylmethyl)-1,4,9-triazaspiro[5.5]undecane |
| 68(H35-35) | 1-butyl-2,5-dioxo-3-(2-methylpropyl)-9-(2-chloro-4-isopropyloxyphenylmethyl)-1,4,9-triazaspiro[5.5]undecane |
| 68(H35-36) | 1-(thiophen-2-ylmethyl)-2,5-dioxo-3-(2-methylpropyl)-9-(4-isopropyloxyphenylmethyl)-1,4,9-triazaspiro[5.5]undecane |
| 68(H35-37) | 1-butyl-2,5-dioxo-3-(2-methylpropyl)-9-(4-isopropyloxyphenylmethyl)-1,4,9-triazaspiro[5.5]undecane |
| 68(H35-38) | 1-(thiophen-2-ylmethyl)-2,5-dioxo-3-cyclohexylmethyl-9-(2-chloro-4-(cyclopropylmethyloxy)phenylmethyl)-1,4,9-triazaspiro[5.5]undecane |

TABLE 35A-6

| Example No | Compound Name |
|---|---|
| 68(H35-39) | 1-butyl-2,5-dioxo-3-cyclohexylmethyl-9-(2-chloro-4-(cyclopropylmethyloxy)phenylmethyl)-1,4,9-triazaspiro[5.5]undecane |
| 68(H35-40) | 1-(thiophen-2-ylmethyl)-2,5-dioxo-3-cyclohexylmethyl-9-(4-(cyclopropylmethyloxy)phenylmethyl)-1,4,9-triazaspiro[5.5]undecane |
| 68(H35-41) | 1-butyl-2,5-dioxo-3-cyclohexylmethyl-9-(4-(cyclopropylmethyloxy)phenylmethyl)-1,4,9-triazaspiro[5.5]undecane |
| 68(H35-42) | 1-(thiophen-2-ylmethyl)-2,5-dioxo-3-(2-methylpropyl)-9-(2-chloro-4-(cyclopropylmethyloxy)phenylmethyl)-1,4,9-triazaspiro[5.5]undecane |

TABLE 35A-6-continued

| Example No | Compound Name |
|---|---|
| 68(H35-43) | 1-butyl-2,5-dioxo-3-(2-methylpropyl)-9-(2-chloro-4-(cyclopropylmethyloxy)phenylmethyl)-1,4,9-triazaspiro[5.5]undecane |
| 68(H35-44) | 1-(thiophen-2-ylmethyl)-2,5-dioxo-3-(2-methylpropyl)-9-(4-(cyclopropylmethyloxy)phenylmethyl)-1,4,9-triazaspiro[5.5]undecane |
| 68(H35-45) | 1-butyl-2,5-dioxo-3-(2-methylpropyl)-9-(4-(cyclopropylmethyloxy)phenylmethyl)-1,4,9-triazaspiro[5.5]undecane |

TABLE 35A-7

| Example No | Compound Name |
|---|---|
| 68(H35-46) | 1-(thiophen-2-ylmethyl)-2,5-dioxo-3-cyclohexylmethyl-9-(2-chloro-4-cyclobutyloxyphenylmethyl)-1,4,9-triazaspiro[5.5]undecane |
| 68(H35-47) | 1-butyl-2,5-dioxo-3-cyclohexylmethyl-9-(2-chloro-4-cyclobutyloxyphenylmethyl)-1,4,9-triazaspiro[5.5]undecane |
| 68(H35-48) | 1-(thiophen-2-ylmethyl)-2,5-dioxo-3-cyclohexylmethyl-9-(4-cyclobutyloxyphenylmethyl)-1,4,9-triaza-spiro[5.5]undecane |
| 68(H35-49) | 1-(thiophen-2-ylmethyl)-2,5-dioxo-3-cyclohexylmethyl-9-(2-chloro-4-cyclopentyloxylmethyl)-1,4,9-triazaspiro[5.5]undecane |
| 68(H35-50) | 1-butyl-2,5-dioxo-3-cyclohexylmethyl-9-(2-chloro-4-cyclopentyloxyphenylmethyl)-1,4,9-triaza-spiro[5.5]undecane |
| 68(H35-51) | 1-(thiophen-2-ylmethyl)-2,5-dioxo-3-cyclohexylmethyl-9-(4-cyclopentyloxyphenylmethyl)-1,4,9-triaza-spiro[5.5]undecane |
| 68(H35-52) | 1-butyl-2,5-dioxo-3-cyclohexylmethyl-9-(4-cyclopentyloxyphenylmethyl)-1,4,9-triaza-spiro[5.5]undecane |
| 68(H35-53) | 1-(thiophen-2-ylmethyl)-2,5-dioxo-3-(2-methylpropyl)-9-(2-chloro-4-cyclopentyloxyphenylmethyl)-1,4,9-triazaspiro[5.5]undecane |

TABLE 35A-8

| Example No | Compound Name |
|---|---|
| 68(H35-54) | 1-butyl-2,5-dioxo-3-(2-methylpropyl)-9-(2-chloro-4-cyclopentyloxyphenylmethyl)-1,4,9-triaza-spiro[5.5]undecane |
| 68(H35-55) | 1-(thiophen-2-ylmethyl)-2,5-dioxo-3-(2-methylpropyl)-9-(4-cyclopentyloxyphenylmethyl)-1,4,9-triaza-spiro[5.5]undecane |
| 68(H35-56) | 1-butyl-2,5-dioxo-3-(2-methylpropyl)-9-(4-cyclopentyloxyphenylmethyl)-1,4,9-triaza-spiro[5.5]undecane |
| 68(H35-57) | 1-(thiophen-2-ylmethyl)-2,5-dioxo-3-cyclohexylmethyl-9-(2-chloro-4-(tetrahydropyran-4-yloxy)phenylmethyl)-1,4,9-triazaspiro[5.5]undecane |
| 68(H35-58) | 1-butyl-2,5-dioxo-3-cyclohexylmethyl-9-(2-chloro-4-(tetrahydropyran-4-yloxy)phenylmethyl)-1,4,9-triazaspiro[5.5]undecane |
| 68(H35-59) | 1-(thiophen-2-ylmethyl)-2,5-dioxo-3-(2-methylpropyl)-9-(2-chloro-4-(tetrahydropyran-4-yloxy)phenylmethyl)-1,4,9-triazaspiro[5.5]undecane |
| 68(H35-60) | 1-butyl-2,5-dioxo-3-(2-methylpropyl)-9-(4-cyclobutyloxyphenylmethyl)-1,4,9-triazaspiro[5.5]undecane |
| 68(H35-61) | 1-butyl-2,5-dioxo-3-(2-methylpropyl)-9-(4-(tetrahydro-pyran-4-yloxy)phenylmethyl)-1,4,9-triaza-spiro[5.5]undecane |

TABLE 35B-1
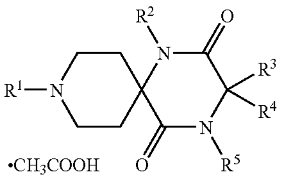
•$CH_3COOH$
| Example No | $R^1$ | $R^2$ | $R^3$ | $R^4$ | $R^5$ |
|---|---|---|---|---|---|
| 68(H35-1) | 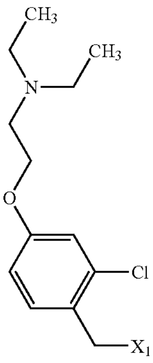 | 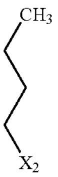 | H | 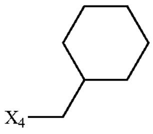 | H |
| 68(H35-2) | 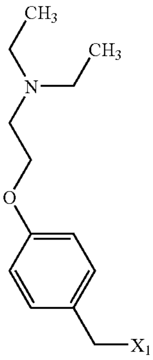 | 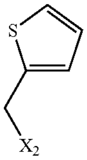 | H | 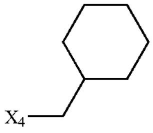 | H |
| 68(H35-3) | 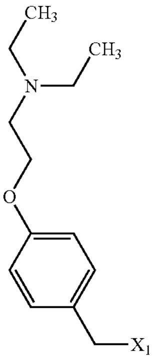 | 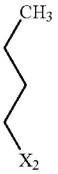 | H | 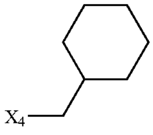 | H |
TABLE 35B-1-continued
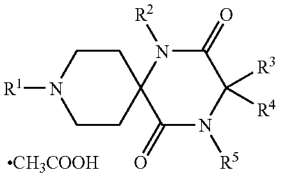
•$CH_3COOH$
| Example No | $R^1$ | $R^2$ | $R^3$ | $R^4$ | $R^5$ |
|---|---|---|---|---|---|
| 68(H35-4) | 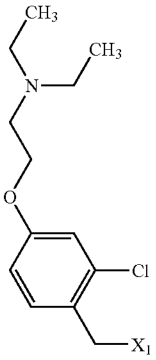 | 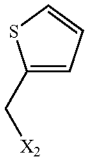 | H | 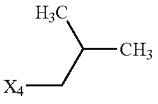 | H |
TABLE 35B-2
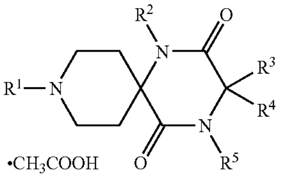
•$CH_3COOH$
| Example No | $R^1$ | $R^2$ | $R^3$ | $R^4$ | $R^5$ |
|---|---|---|---|---|---|
| 68(H35-5) | 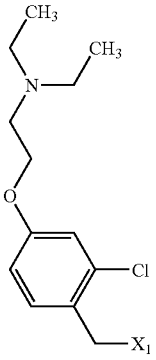 | 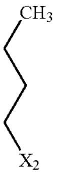 | H | 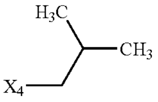 | H |

TABLE 35B-2-continued
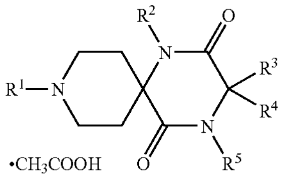
•$CH_3COOH$
| Example No | $R^1$ | $R^2$ | $R^3$ | $R^4$ | $R^5$ |
|---|---|---|---|---|---|
| 68(H35-6) | 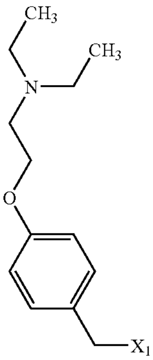 | 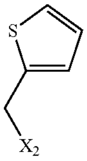 | H | 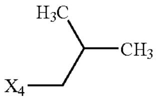 | H |
| 68(H35-7) | 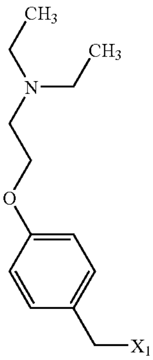 | 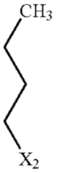 | H | 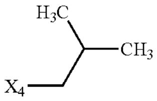 | H |
TABLE 35B-2-continued
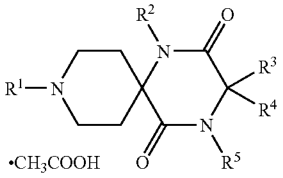
•$CH_3COOH$
| Example No | $R^1$ | $R^2$ | $R^3$ | $R^4$ | $R^5$ |
|---|---|---|---|---|---|
| 68(H35-8) | 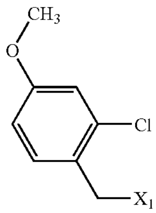 | 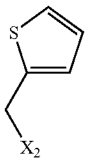 | H | 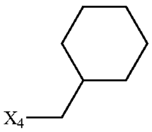 | H |
| 68(H35-9) | 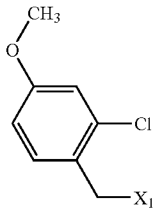 | 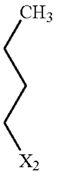 | H | 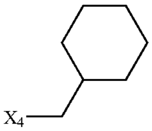 | H |
TABLE 35B-3
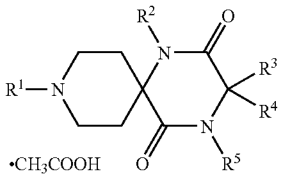
•$CH_3COOH$
| Example No | $R^1$ | $R^2$ | $R^3$ | $R^4$ | $R^5$ |
|---|---|---|---|---|---|
| 68(H35-10) | 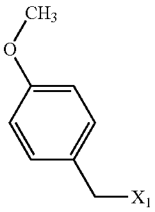 | 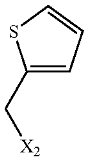 | H | 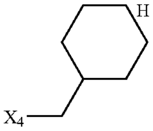 | H |

TABLE 35B-3-continued
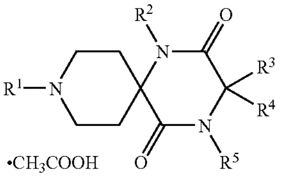
•$CH_3COOH$
| Example No | $R^1$ | $R^2$ | $R^3$ | $R^4$ | $R^5$ |
|---|---|---|---|---|---|
| 68(H35-11) | 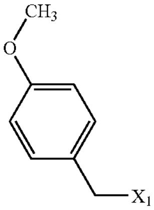 | 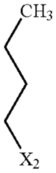 | H | 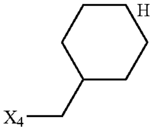 | H |
| 68(H35-12) | 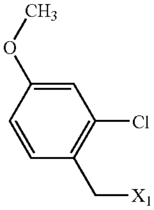 | 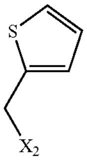 | H | 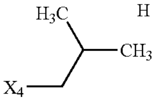 | H |
| 68(H35-13) | 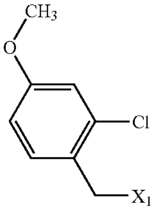 | 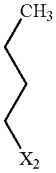 | H | 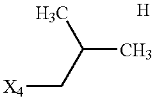 | H |
| 68(H35-14) | 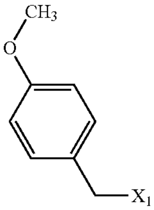 | 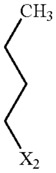 | H | 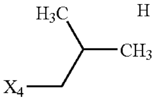 | H |
| 68(H35-15) | 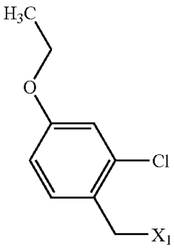 | 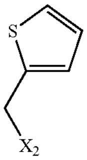 | H | 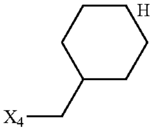 | H |

TABLE 35B-4
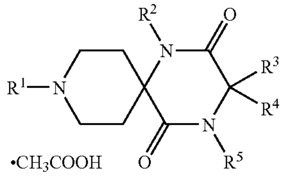
•$CH_3COOH$
| Example No | $R^1$ | $R^2$ | $R^3$ | $R^4$ | $R^5$ |
|---|---|---|---|---|---|
| 68(H35-16) | 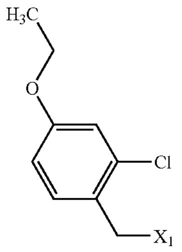 | 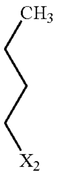 | H | 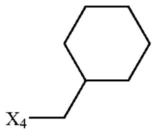 | H |
| 68(H35-17) | 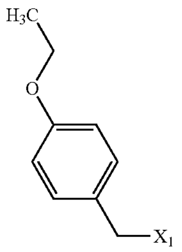 | 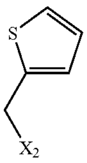 | H | 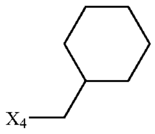 | H |
| 68(H35-18) | 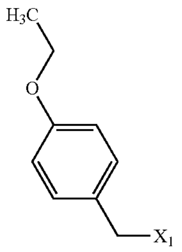 | 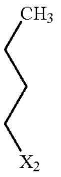 | H | 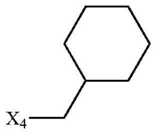 | H |
| 68(H35-19) | 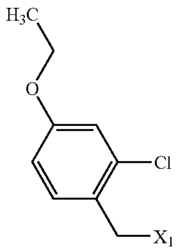 | 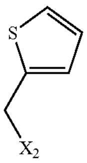 | H | 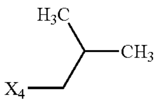 | H |
| 68(H35-20) | 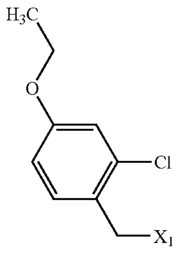 | 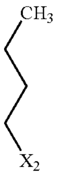 | H | 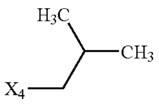 | H |

TABLE 35B-5
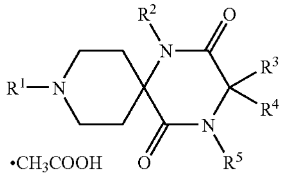
•$CH_3COOH$
| Example No | $R^1$ | $R^2$ | $R^3$ | $R^4$ | $R^5$ |
|---|---|---|---|---|---|
| 68(H35-21) | 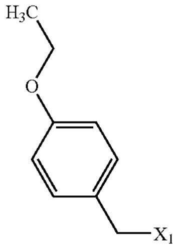 | 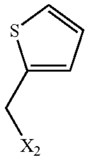 | H | 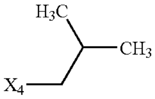 | H |
| 68(H35-22) | 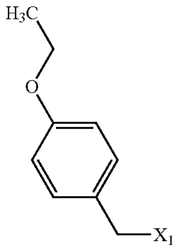 | 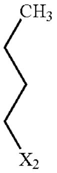 | H | 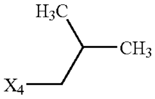 | H |
| 68(H35-23) | 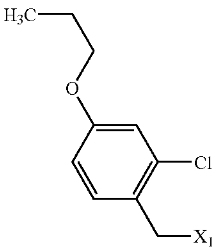 | 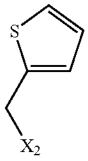 | H | 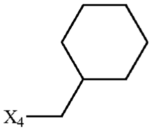 | H |
| 68(H35-24) | 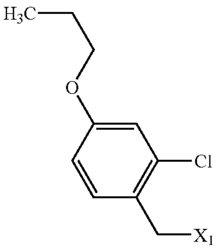 | 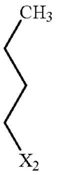 | H | 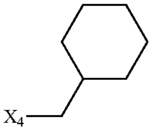 | H |
| 68(H35-25) | 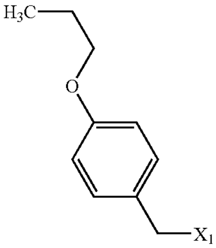 | 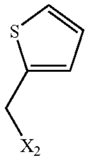 | H | 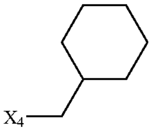 | H |

TABLE 35B-6
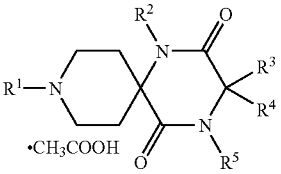
•$CH_3COOH$
| Example No | $R^1$ | $R^2$ | $R^3$ | $R^4$ | $R^5$ |
|---|---|---|---|---|---|
| 68(H35-26) | 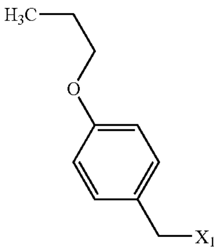 | 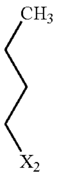 | H | 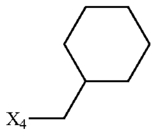 | H |
| 68(H35-27) | 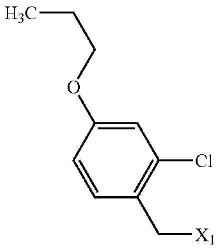 | 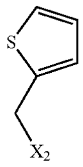 | H | 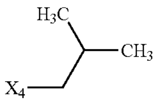 | H |
| 68(H35-28) | 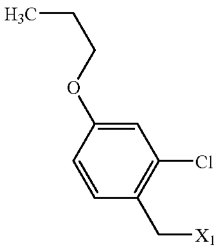 | 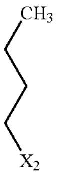 | H | 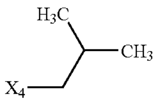 | H |
| 68(H35-29) | 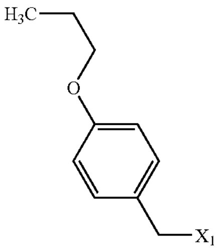 | 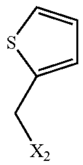 | H | 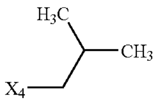 | H |
| 68(H35-30) | 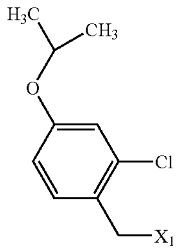 | 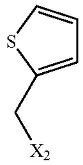 | H | 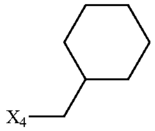 | H |

TABLE 35B-7
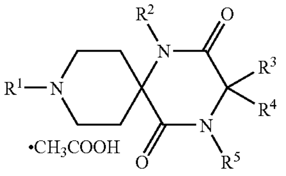
$\cdot CH_3COOH$
| Example No | $R^1$ | $R^2$ | $R^3$ | $R^4$ | $R^5$ |
|---|---|---|---|---|---|
| 68 (H35-31) | 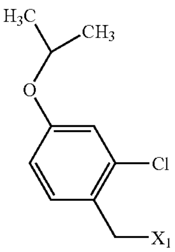 | 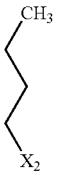 | H | 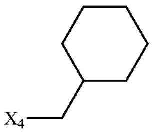 | H |
| 68 (H35-32) | 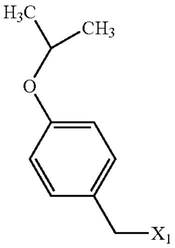 | 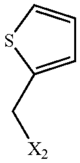 | H | 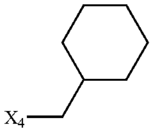 | H |
| 68 (H35-33) | 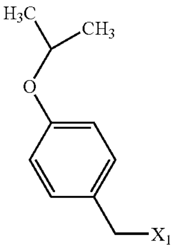 | 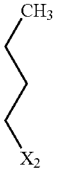 | H | 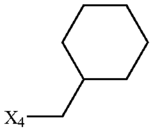 | H |
TABLE 35B-7-continued
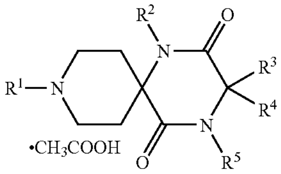
$\cdot CH_3COOH$
| Example No | $R^1$ | $R^2$ | $R^3$ | $R^4$ | $R^5$ |
|---|---|---|---|---|---|
| 68 (H35-34) | 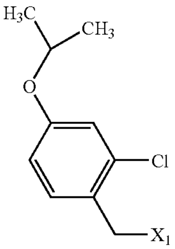 | 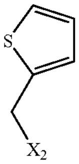 | H | 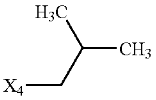 | H |
| 68 (H35-35) | 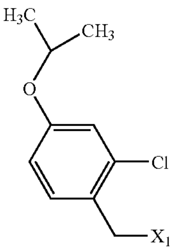 | 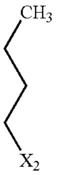 | H | 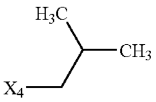 | H |
TABLE 35B-8
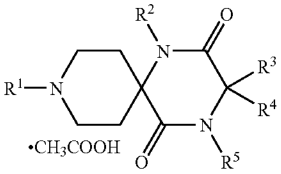
$\cdot CH_3COOH$
| Example No | $R^1$ | $R^2$ | $R^3$ | $R^4$ | $R^5$ |
|---|---|---|---|---|---|
| 68(H35-36) | 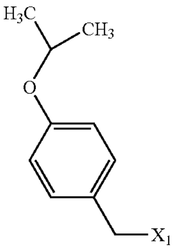 | 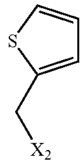 | H | 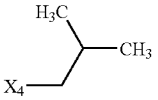 | H |

TABLE 35B-8-continued
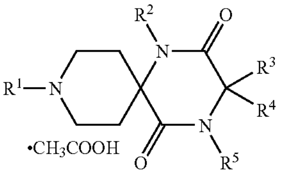
$\bullet CH_3COOH$
| Example No | $R^1$ | $R^2$ | $R^3$ | $R^4$ | $R^5$ |
|---|---|---|---|---|---|
| 68(H35-37) | 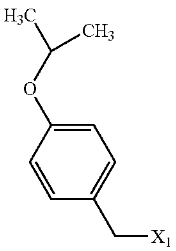 | 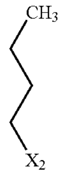 | H | 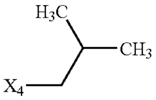 | H |
| 68(H35-38) | 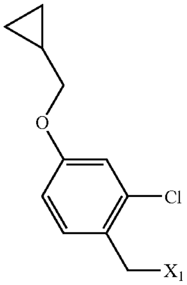 | 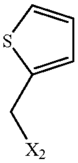 | H | 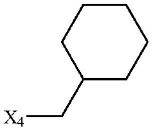 | H |
| 68(H35-39) | 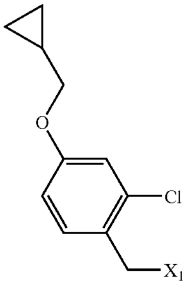 | 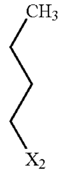 | H | 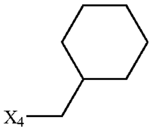 | H |
| 68(H35-40) | 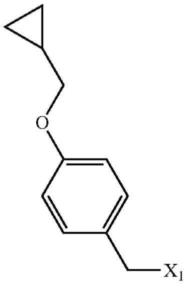 | 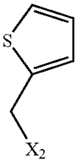 | H | 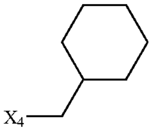 | H |

TABLE 35B-9
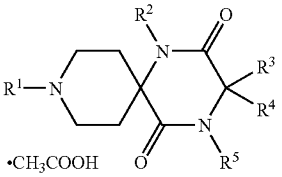
$\cdot CH_3COOH$
| Example No | $R^1$ | $R^2$ | $R^3$ | $R^4$ | $R^5$ |
| --- | --- | --- | --- | --- | --- |
| 68(H35-41) | 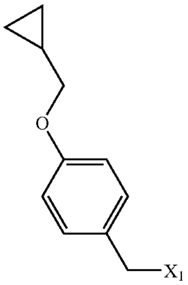 | 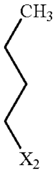 | H | 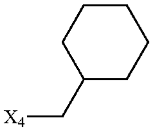 | H |
| 68(H35-42) | 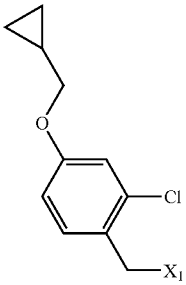 | 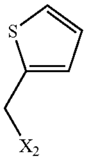 | H | 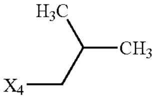 | H |
| 68(H35-43) | 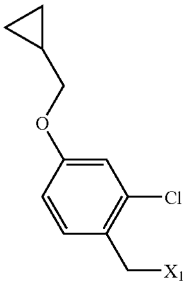 | 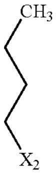 | H | 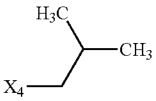 | H |
| 68(H35-44) | 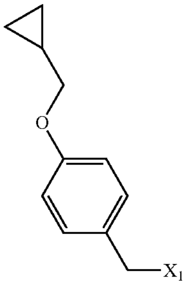 | 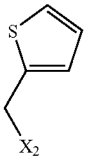 | H | 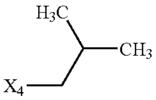 | H |

TABLE 35B-9-continued
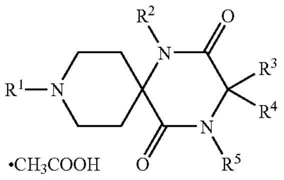
•$CH_3COOH$
| Example No | $R^1$ | $R^2$ | $R^3$ | $R^4$ | $R^5$ |
|---|---|---|---|---|---|
| 68(H35-45) | 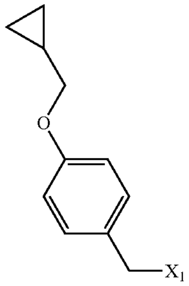 | 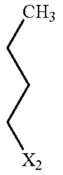 | H | 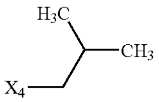 | H |
TABLE 35B-10
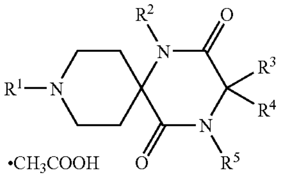
•$CH_3COOH$
| Example No | $R^1$ | $R^2$ | $R^3$ | $R^4$ | $R^5$ |
|---|---|---|---|---|---|
| 68(H35-46) | 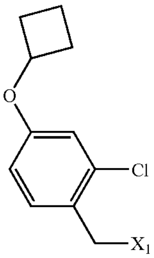 | 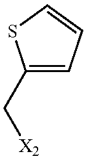 | H | 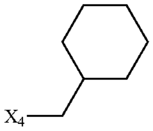 | H |
| 68(H35-47) | 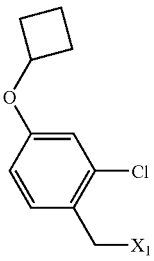 | 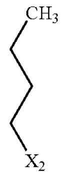 | H | 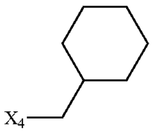 | H |
TABLE 35B-10-continued
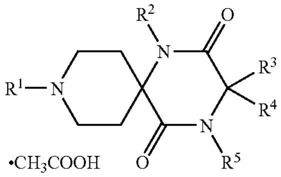
•$CH_3COOH$
| Example No | $R^1$ | $R^2$ | $R^3$ | $R^4$ | $R^5$ |
|---|---|---|---|---|---|
| 68(H35-48) | 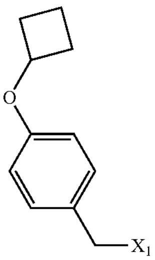 | 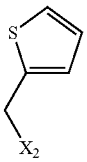 | H | 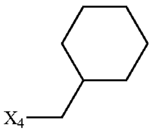 | H |
| 68(H35-49) | 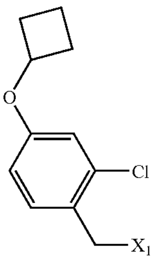 | 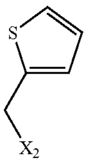 | H | 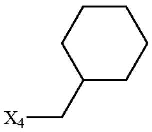 | H |

TABLE 35B-10-continued
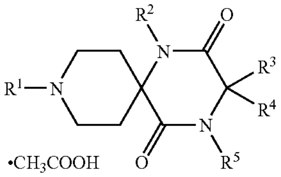
•$CH_3COOH$
| Example No | $R^1$ | $R^2$ | $R^3$ | $R^4$ | $R^5$ |
|---|---|---|---|---|---|
| 68(H35-50) | 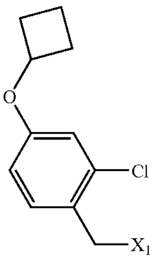 | 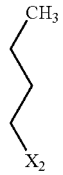 | H | 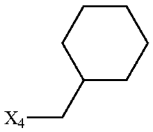 | H |
TABLE 35B-11
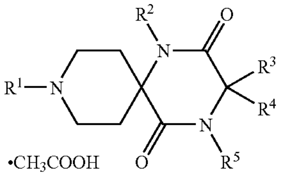
•$CH_3COOH$
| Example No | $R^1$ | $R^2$ | $R^3$ | $R^4$ | $R^5$ |
|---|---|---|---|---|---|
| 68(H35-51) | 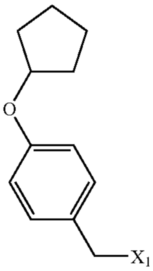 | 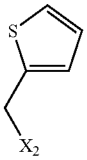 | H | 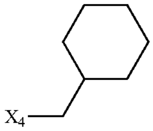 | H |
| 68(H35-52) | 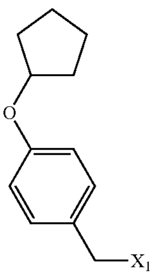 | 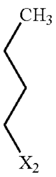 | H | 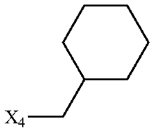 | H |
TABLE 35B-11-continued
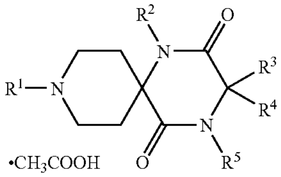
•$CH_3COOH$
| Example No | $R^1$ | $R^2$ | $R^3$ | $R^4$ | $R^5$ |
|---|---|---|---|---|---|
| 68(H35-53) | 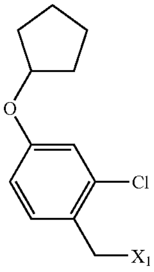 | 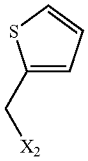 | H | 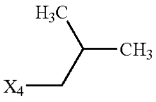 | H |
| 68(H35-54) | 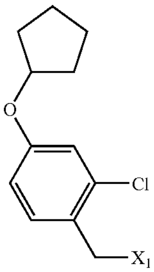 | 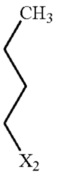 | H | 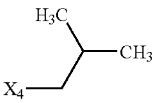 | H |
| 68(H35-55) | 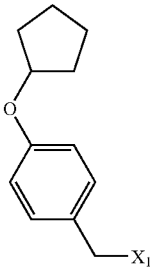 | 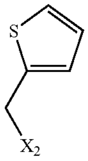 | H | 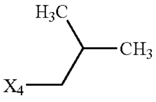 | H |

TABLE 35B-12

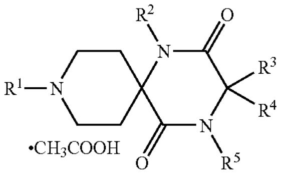

| Example No. | $R^1$ | $R^2$ | $R^3$ | $R^4$ | $R^5$ |
|---|---|---|---|---|---|
| 68 (H35-56) | 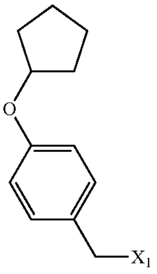 | 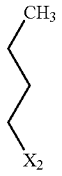 | H | 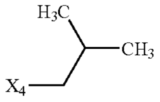 | H |
| 68 (H35-57) | 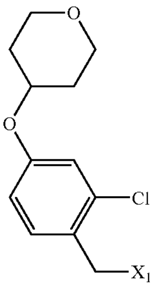 | 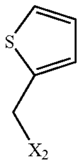 | H | 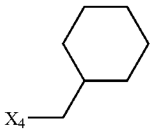 | H |
| 68 (H35-58) | 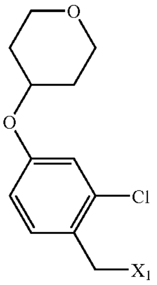 | 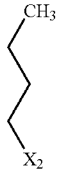 | H | 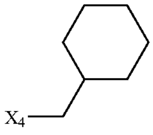 | H |
| 68 (H35-59) | 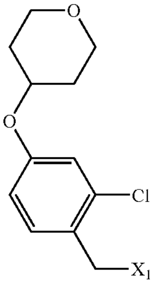 | 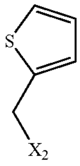 | H | 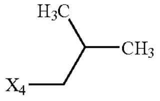 | H |

TABLE 35B-12-continued

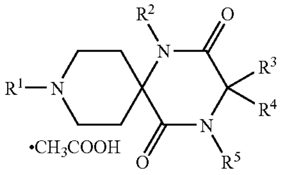

| Example No. | $R^1$ | $R^2$ | $R^3$ | $R^4$ | $R^5$ |
|---|---|---|---|---|---|
| 68 (H35-60) | 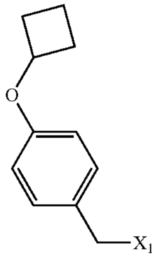 | 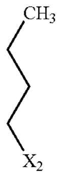 | H | 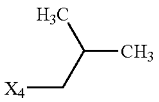 | H |

TABLE 35B-13

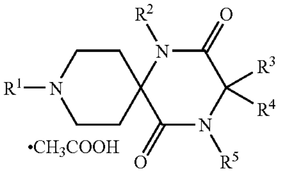

| Example No | $R^1$ | $R^2$ | $R^3$ | $R^4$ | $R^5$ |
|---|---|---|---|---|---|
| 68(H35-61) | 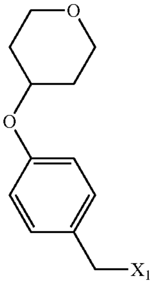 | 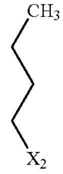 | H | 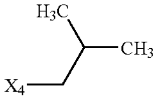 | H |

TABLE 35C-1

| Example No | HPLC condition | Retention time (min) | Mass data | Mass condition |
|---|---|---|---|---|
| 68(H35-1) | F | 3.31 | 575 $(M + H)^+$. | ESI (Pos., 20 V) |
| 68(H35-2) | F | 3.24 | 581 $(M + H)^+$. | ESI (Pos., 20 V) |
| 68(H35-3) | F | 3.22 | 541 $(M + H)^+$. | ESI (Pos., 20 V) |
| 68(H35-4) | F | 3.11 | 575 $(M + H)^+$. | ESI (Pos., 20 V) |
| 68(H35-5) | F | 3.11 | 534 $(M + H)^+$. | ESI (Pos., 20 V) |
| 68(H35-6) | F | 3.09 | 540 $(M + H)^+$. | ESI (Pos., 20 V) |
| 68(H35-7) | F | 3.05 | 501 $(M + H)^+$. | ESI (Pos., 20 V) |
| 68(H35-8) | F | 3.57 | 530 $(M + H)^+$. | ESI (Pos., 20 V) |
| 68(H35-9) | F | 3.57 | 548 $(M + H)^+$. | ESI (Pos., 20 V) |
| 68(H35-10) | F | 3.51 | 496 $(M + H)^+$. | ESI (Pos., 20 V) |
| 68(H35-11) | F | 3.49 | 456 $(M + H)^+$. | ESI (Pos., 20 V) |

TABLE 35C-1-continued

| Example No | HPLC condition | Retention time (min) | Mass data | Mass condition |
|---|---|---|---|---|
| 68(H35-12) | F | 3.40 | 490 $(M + H)^+$. | ESI (Pos., 20 V) |
| 68(H35-13) | F | 3.36 | 450 $(M + H)^+$. | ESI (Pos., 20 V) |
| 68(H35-14) | F | 3.29 | 415 $(M + H)^+$. | ESI (Pos., 20 V) |
| 68(H35-15) | F | 3.66 | 544 $(M + H)^+$. | ESI (Pos., 20 V) |
| 68(H35-16) | F | 3.64 | 504 $(M + H)^+$. | ESI (Pos., 20 V) |
| 68(H35-17) | F | 3.58 | 510 $(M + H)^+$. | ESI (Pos., 20 V) |
| 68(H35-18) | F | 3.59 | 469 $(M + H)^+$. | ESI (Pos., 20 V) |
| 68(H35-19) | F | 3.47 | 504 $(M + H)^+$. | ESI (Pos., 20 V) |
| 68(H35-20) | F | 3.45 | 463 $(M + H)^+$. | ESI (Pos., 20 V) |
| 68(H35-21) | F | 3.40 | 470 $(M + H)^+$. | ESI (Pos., 20 V) |
| 68(H35-22) | F | 3.38 | 430 $(M + H)^+$. | ESI (Pos., 20 V) |
| 68(H35-23) | F | 3.76 | 558 $(M + H)^+$. | ESI (Pos., 20 V) |
| 68(H35-24) | F | 3.74 | 518 $(M + H)^+$. | ESI (Pos., 20 V) |
| 68(H35-25) | F | 3.68 | 524 $(M + H)^+$. | ESI (Pos., 20 V) |
| 68(H35-26) | F | 3.66 | 484 $(M + H)^+$. | ESI (Pos., 20 V) |
| 68(H35-27) | F | 3.58 | 518 $(M + H)^+$. | ESI (Pos., 20 V) |
| 68(H35-28) | F | 3.57 | 478 $(M + H)^+$. | ESI (Pos., 20 V) |

TABLE 35C-2

| Example No | HPLC condition | Retention time (min) | Mass data | Mass condition |
|---|---|---|---|---|
| 68(H35-29) | F | 3.51 | 484 $(M + H)^+$. | ESI (Pos., 20 V) |
| 68(H35-30) | F | 3.71 | 558 $(M + H)^+$. | ESI (Pos., 20 V) |
| 68(H35-31) | F | 3.70 | 518 $(M + H)^+$. | ESI (Pos., 20 V) |
| 68(H35-32) | F | 3.66 | 524 $(M + H)^+$. | ESI (Pos., 20 V) |
| 68(H35-33) | F | 3.64 | 484 $(M + H)^+$. | ESI (Pos., 20 V) |
| 68(H35-34) | F | 3.55 | 518 $(M + H)^+$. | ESI (Pos., 20 V) |
| 68(H35-35) | F | 3.52 | 478 $(M + H)^+$. | ESI (Pos., 20 V) |
| 68(H35-36) | F | 3.48 | 484 $(M + H)^+$. | ESI (Pos., 20 V) |
| 68(H35-37) | F | 3.45 | 444 $(M + H)^+$. | ESI (Pos., 20 V) |
| 68(H35-38) | F | 3.71 | 570 $(M + H)^+$. | ESI (Pos., 20 V) |
| 68(H35-39) | F | 3.72 | 530 $(M + H)^+$. | ESI (Pos., 20 V) |
| 68(H35-40) | F | 3.66 | 536 $(M + H)^+$. | ESI (Pos., 20 V) |
| 68(H35-41) | F | 3.64 | 496 $(M + H)^+$. | ESI (Pos., 20 V) |
| 68(H35-42) | F | 3.55 | 530 $(M + H)^+$. | ESI (Pos., 20 V) |
| 68(H35-43) | F | 3.53 | 490 $(M + H)^+$. | ESI (Pos., 20 V) |
| 68(H35-44) | F | 3.48 | 496 $(M + H)^+$. | ESI (Pos., 20 V) |
| 68(H35-45) | F | 3.47 | 456 $(M + H)^+$. | ESI (Pos., 20 V) |
| 68(H35-46) | F | 3.78 | 570 $(M + H)^+$. | ESI (Pos., 20 V) |
| 68(H35-47) | F | 3.77 | 530 $(M + H)^+$. | ESI (Pos., 20 V) |
| 68(H35-48) | F | 3.54 | 557 $(M + H)^+$. | ESI (Pos., 20 V) |
| 68(H35-49) | F | 3.81 | 584 $(M + H)^+$. | ESI (Pos., 20 V) |
| 68(H35-50) | F | 3.83 | 545 $(M + H)^+$. | ESI (Pos., 20 V) |
| 68(H35-51) | F | 3.74 | 550 $(M + H)^+$. | ESI (Pos., 20 V) |
| 68(H35-52) | F | 3.74 | 510 $(M + H)^+$. | ESI (Pos., 20 V) |
| 68(H35-53) | F | 3.64 | 544 $(M + H)^+$. | ESI (Pos., 20 V) |
| 68(H35-54) | F | 3.65 | 504 $(M + H)^+$. | ESI (Pos., 20 V) |
| 68(H35-55) | F | 3.57 | 510 $(M + H)^+$. | ESI (Pos., 20 V) |
| 68(H35-56) | F | 3.57 | 470 $(M + H)^+$. | ESI (Pos., 20 V) |

TABLE 35C-3

| Example No | HPLC condition | Retention time (min) | Mass data | Mass condition |
|---|---|---|---|---|
| 68(H35-57) | F | 3.53 | 600 $(M + H)^+$. | ESI (Pos., 20 V) |
| 68(H35-58) | F | 3.59 | 560 $(M + H)^+$. | ESI (Pos., 20 V) |
| 68(H35-59) | F | 3.42 | 560 $(M + H)^+$. | ESI (Pos., 20 V) |
| 68(H35-60) | F | 3.66 | 456 $(M + H)^+$, 279, 161. | ESI (Pos., 40 V) |
| 68(H35-61) | F | 3.45 | 586 $(M + H)^+$, 369, 191. | ESI (Pos., 40 V) |

EXAMPLE 69(H36-1)~69(H36-24)

By the same procedure as described in Example 22 using the corresponding amine derivatives and acid chloride derivatives instead of the compound prepared in Example 14, the compounds of the present invention, whose names were shown in the following Table 36A-1~36A-4, and whose structures were shown in the following Table 36B-1~36B-5, were obtained. Also, physical data of the above compounds were shown in the following Table 36C-1.

TABLE 36A-1

| Example No | Compound Name |
|---|---|
| 69(H36-1) | (3S)-1-propyl-2,5-dioxo-3-((2-phenylphenyl)carbonylaminomethyl)-9-(2-phenylethyl)-1,4,9-triazaspiro[5.5]undecane |
| 69(H36-2) | (3S)-1-propyl-2,5-dioxo-3-((3-phenylphenyl)carbonylaminomethyl)-9-(2-phenylethyl)-1,4,9-triazaspiro[5.5]undecane |
| 69(H36-3) | (3S)-1-propyl-2,5-dioxo-3-((4-phenylphenyl)carbonylaminomethyl)-9-(2-phenylethyl)-1,4,9-triazaspiro[5.5]undecane |
| 69(H36-4) | (3S)-1-propyl-2,5-dioxo-3-((2-phenylphenyl)acetylaminomethyl)-9-(2-phenylethyl)-1,4,9-triazaspiro[5.5]undecane |
| 69(H36-5) | (3S)-1-propyl-2,5-dioxo-3-((3-phenylphenyl)acetylaminomethyl)-9-(2-phenylethyl)-1,4,9-triazaspiro[5.5]undecane |
| 69(H36-6) | (3S)-1-propyl-2,5-dioxo-3-((4-phenylphenyl)acetylaminomethyl)-9-(2-phenylethyl)-1,4,9-triazaspiro[5.5]undecane |
| 69(H36-7) | (3S)-1-propyl-2,5-dioxo-3-(2-(2-phenylphenyl)carbonylaminoethyl)-9-(2-phenylethyl)-1,4,9-triazaspiro[5.5]undecane |

TABLE 36A-2

| Example No | Compound Name |
|---|---|
| 69(H36-8) | (3S)-1-propyl-2,5-dioxo-3-(2-(3-phenylphenyl)carbonylaminoethyl)-9-(2-phenylethyl)-1,4,9-triazaspiro[5.5]undecane |
| 69(H36-9) | (3S)-1-propyl-2,5-dioxo-3-(2-(4-phenylphenyl)carbonylaminoethyl)-9-(2-phenylethyl)-1,4,9-triazaspiro[5.5]undecane |
| 69(H36-10) | (3S)-1-propyl-2,5-dioxo-3-(2-(2-phenylphenyl)acetylaminoethyl)-9-(2-phenylethyl)-1,4,9-triazaspiro[5.5]undecane |
| 69(H36-11) | (3S)-1-propyl-2,5-dioxo-3-(2-(3-phenylphenyl)acetylaminoethyl)-9-(2-phenylethyl)-1,4,9-triazaspiro[5.5]undecane |
| 69(H36-12) | (3S)-1-propyl-2,5-dioxo-3-(2-(4-phenylphenyl)acetylaminoethyl)-9-(2-phenylethyl)-1,4,9-triazaspiro[5.5]undecane |
| 69(H36-13) | (3S)-1-propyl-2,5-dioxo-3-(3-(2-phenylphenyl)carbonylaminopropyl)-9-(2-phenylethyl)-1,4,9-triazaspiro[5.5]undecane |
| 69(H36-14) | (3S)-1-propyl-2,5-dioxo-3-(3-(3-phenylphenyl)carbonylaminopropyl)-9-(2-phenylethyl)-1,4,9-triazaspiro[5.5]undecane |

TABLE 36A-3

| Example No | Compound Name |
|---|---|
| 69(H36-15) | (3S)-1-propyl-2,5-dioxo-3-(3-(4-phenylphenyl)carbonylaminopropyl)-9-(2-phenylethyl)-1,4,9-triazaspiro[5.5]undecane |
| 69(H36-16) | (3S)-1-propyl-2,5-dioxo-3-(3-(2-phenylphenyl)acetylaminopropyl)-9-(2-phenylethyl)-1,4,9-triazaspiro[5.5]undecane |
| 69(H36-17) | (3S)-1-propyl-2,5-dioxo-3-(3-(3-phenylphenyl)acetylaminopropyl)-9-(2-phenylethyl)-1,4,9-triazaspiro[5.5]undecane |
| 69(H36-18) | (3S)-1-propyl-2,5-dioxo-3-(3-(4-phenylphenyl)acetylaminopropyl)-9-(2-phenylethyl)-1,4,9-triazaspiro[5.5]undecane |
| 69(H36-19) | (3S)-1-propyl-2,5-dioxo-3-(4-(2-phenylphenyl)carbonylaminobutyl)-9-(2-phenylethyl)-1,4,9-triazaspiro[5.5]undecane |
| 69(H36-20) | (3S)-1-propyl-2,5-dioxo-3-(4-(3-phenylphenyl)carbonylaminobutyl)-9-(2-phenylethyl)-1,4,9-triazaspiro[5.5]undecane |
| 69(H36-21) | (3S)-1-propyl-2,5-dioxo-3-(4-(4-phenylphenyl)carbonylaminobutyl)-9-(2-phenylethyl)-1,4,9-triazaspiro[5.5]undecane |

TABLE 36A-4

| Example No | Compound Name |
|---|---|
| 69(H36-22) | (3S)-1-propyl-2,5-dioxo-3-(4-(2-phenylphenyl)acetylaminobutyl)-9-(2-phenylethyl)-1,4,9-triazaspiro[5.5]undecane |
| 69(H36-23) | (3S)-1-propyl-2,5-dioxo-3-(4-(3-phenylphenyl)acetylaminobutyl)-9-(2-phenlyethyl)-1,4,9-triazaspiro[5.5]undecane |
| 69(H36-24) | (3S)-1-propyl-2,5-dioxo-3-(4-(4-phenylphenyl)acetylaminobutyl)-9-(2-phenylethyl)-1,4,9-triazaspiro[5.5]undecane |

TABLE 36B-1

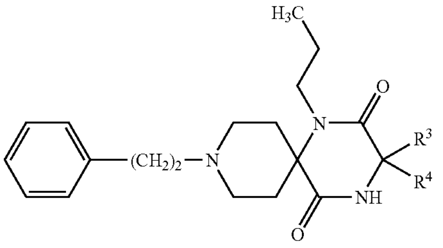

| Example No | $R^3$ | $R^4$ | $R^5$ |
|---|---|---|---|
| 69 (H36-1) | H | 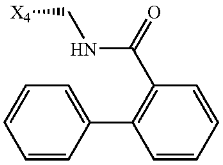 | H |

TABLE 36B-1-continued

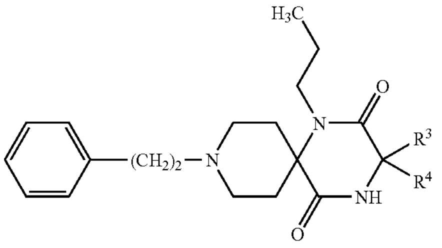

| Example No | $R^3$ | $R^4$ | $R^5$ |
|---|---|---|---|
| 69 (H36-2) | H | 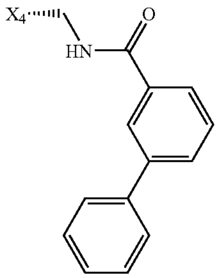 | H |
| 69 (H36-3) | H | 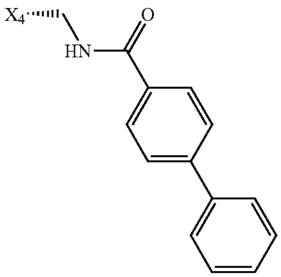 | H |
| 69 (H36-4) | H | 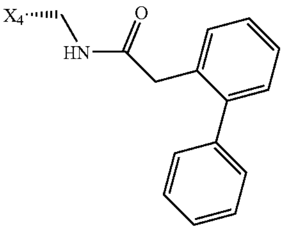 | H |
| 69 (H36-5) | H | 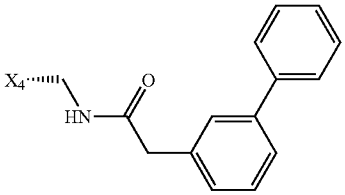 | H |
| 69 (H36-6) | H | 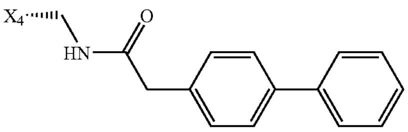 | H |

TABLE 36B-2
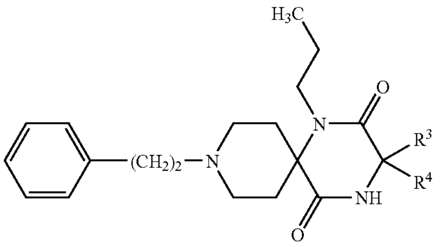
| Example No | $R^3$ | $R^4$ | $R^5$ |
|---|---|---|---|
| 69 (H36-7) | H | 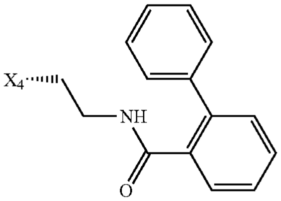 | H |
| 69 (H36-8) | H | 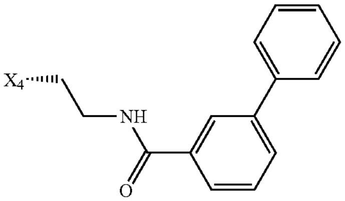 | H |
| 69 (H36-9) | H | 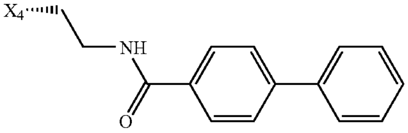 | H |
| 69 (H36-10) | H | 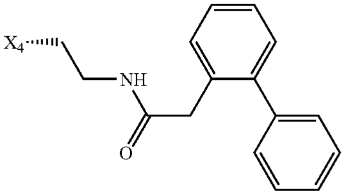 | H |
| 69 (H36-11) | H | 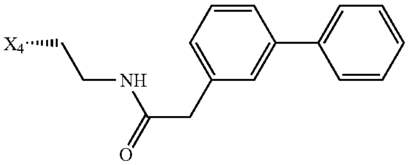 | H |
| 69 (H36-12) | H | 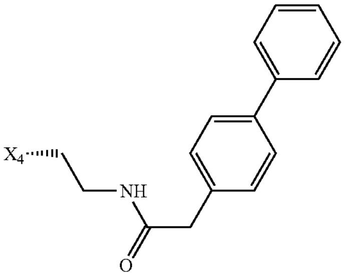 | H |
TABLE 36B-2-continued
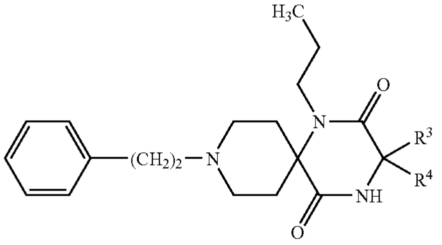
| Example No | $R^3$ | $R^4$ | $R^5$ |
|---|---|---|---|
| 69 (H36-13) | H | 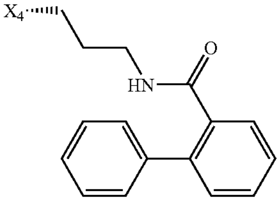 | H |
TABLE 36B-3
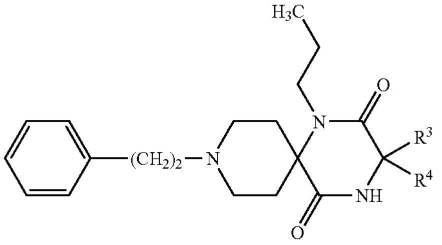
| Example No | $R^3$ | $R^4$ | $R^5$ |
|---|---|---|---|
| 69(H36-14) | H | 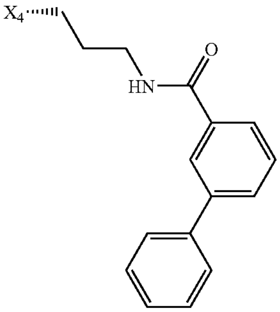 | H |
| 69(H36-15) | H | 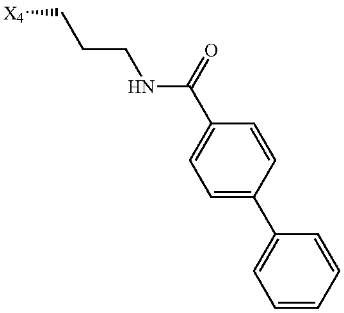 | H |

TABLE 36B-3-continued
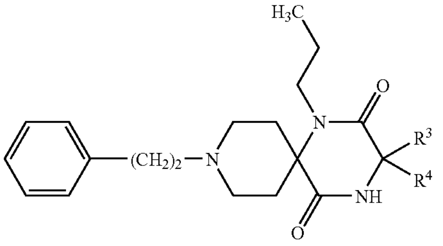
| Example No | $R^3$ | $R^4$ | $R^5$ |
|---|---|---|---|
| 69(H36-16) | H | 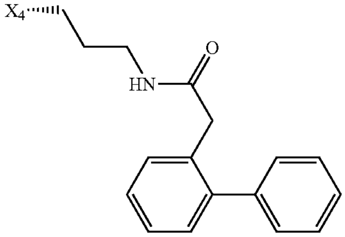 | H |
| 69(H36-17) | H | 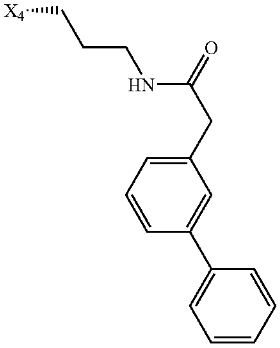 | H |
TABLE 36B-4
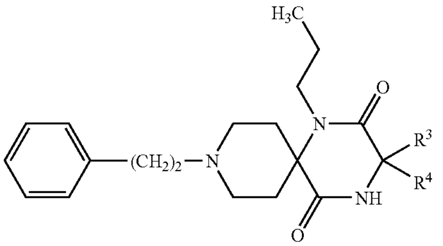
| Example No | $R^3$ | $R^4$ | $R^5$ |
|---|---|---|---|
| 69(H36-18) | H | 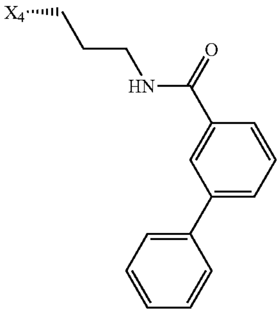 | H |
TABLE 36B-4-continued
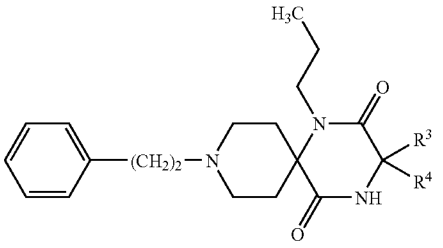
| Example No | $R^3$ | $R^4$ | $R^5$ |
|---|---|---|---|
| 69(H36-19) | H | 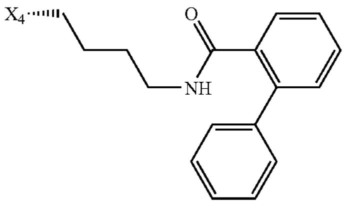 | H |
| 69(H36-20) | H | 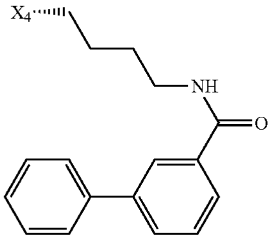 | H |
| 69(H36-21) | H | 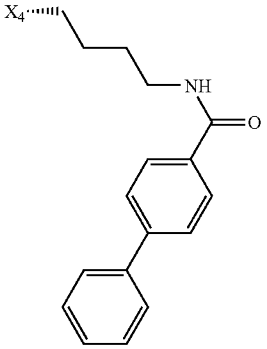 | H |
| 69(H36-22) | H | 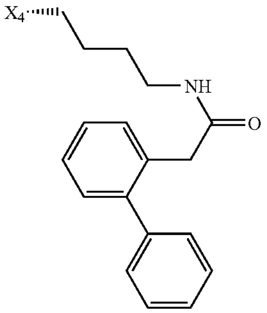 | H |

TABLE 36B-5

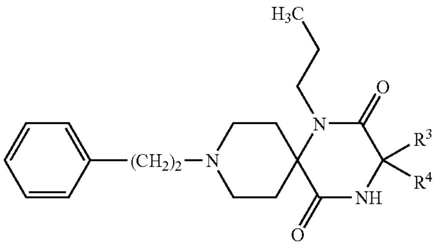

| Example No | $R^3$ | $R^4$ | $R^5$ |
|---|---|---|---|
| 69(H36-23) | H | 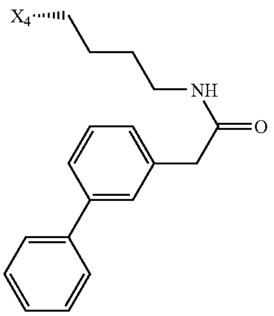 | H |
| 69(H36-24) | H | 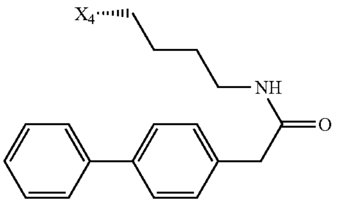 | H |

TABLE 36C-1

| Example No | HPLC condition | Retention time (min) | Mass data | Mass condition |
|---|---|---|---|---|
| 69(H36-1) | F | 3.38 | 539 $(M + H)^+$. | ESI (Pos., 20 V) |
| 69(H36-2) | F | 3.47 | 539 $(M + H)^+$. | ESI (Pos., 20 V) |
| 69(H36-3) | F | 3.47 | 539 $(M + H)^+$. | ESI (Pos., 20 V) |
| 69(H36-4) | F | 3.45 | 553 $(M + H)^+$. | ESI (Pos., 20 V) |
| 69(H36-5) | F | 3.44 | 553 $(M + H)^+$. | ESI (Pos., 20 V) |
| 69(H36-6) | F | 3.44 | 553 $(M + H)^+$. | ESI (Pos., 20 V) |
| 69(H36-7) | F | 3.40 | 553 $(M + H)^+$. | ESI (Pos., 20 V) |
| 69(H36-8) | F | 3.49 | 553 $(M + H)^+$. | ESI (Pos., 20 V) |
| 69(H36-9) | F | 3.49 | 553 $(M + H)^+$. | ESI (Pos., 20 V) |
| 69(H36-10) | F | 3.47 | 567 $(M + H)^+$. | ESI (Pos., 20 V) |
| 69(H36-11) | F | 3.49 | 567 $(M + H)^+$. | ESI (Pos., 20 V) |

TABLE 36C-1-continued

| Example No | HPLC condition | Retention time (min) | Mass data | Mass condition |
|---|---|---|---|---|
| 69(H36-12) | F | 3.49 | 567 $(M + H)^+$. | ESI (Pos., 20 V) |
| 69(H36-13) | F | 3.36 | 567 $(M + H)^+$. | ESI (Pos., 20 V) |
| 69(H36-14) | F | 3.47 | 567 $(M + H)^+$. | ESI (Pos., 20 V) |
| 69(H36-15) | F | 3.47 | 567 $(M + H)^+$. | ESI (Pos., 20 V) |
| 69(H36-16) | F | 3.45 | 581 $(M + H)^+$. | ESI (Pos., 20 V) |
| 69(H36-17) | F | 3.47 | 581 $(M + H)^+$. | ESI (Pos., 20 V) |
| 69(H36-18) | F | 3.47 | 581 $(M + H)^+$. | ESI (Pos., 20 V) |
| 69(H36-19) | F | 3.40 | 581 $(M + H)^+$. | ESI (Pos., 20 V) |
| 69(H36-20) | F | 3.49 | 581 $(M + H)^+$. | ESI (Pos., 20 V) |
| 69(H36-21) | F | 3.43 | 581 $(M + H)^+$. | ESI (Pos., 20 V) |
| 69(H36-22) | F | 3.47 | 595 $(M + H)^+$. | ESI (Pos., 20 V) |
| 69(H36-23) | F | 3.49 | 595 $(M + H)^+$. | ESI (Pos., 20 V) |
| 69(H36-24) | F | 3.49 | 595 $(M + H)^+$. | ESI (Pos., 20 V) |

FORMULATION EXAMPLE

FORMULATION EXAMPLE 1

The following components were admixed in a conventional technique, punched out to give 100 tablets each containing 50 mg of active ingredient.

| | |
|---|---|
| 9-((3,5-dimethyl-1-phenyl)-4-pyrazolyl)methyl)-2,5-dioxo-3-(2-methyl-propyl)-1-propyl-1,4,9-triazaspiro[5.5]undecane.2 hydrochloride | 5.0 g |
| calcium carboxymethylcellulose (disintegrant) | 0.2 g |
| magnesium stearate (lubricant) | 0.1 g |
| microcrystalline cellulose | 4.7 g |

FORMULATION EXAMPLE 2

The following components were admixed in a conventional technique. The solution was sterilized in a conventional technique, filled in ampoules 5 ml each and freeze-dried in a conventional technique to give 100 ampoules each containing 20 mg of active ingredient.

| | |
|---|---|
| 9-((3,5-dimethyl-1-phenyl)-4-pyrazolyl)methyl)-2,5-dioxo-3-(2-methyl-1-propyl)-1-propyl-1,4,9-triazaspiro[5.5]undecane.2 hydrochloride | 2.0 g |
| mannitol | 20 g |
| distilled water | 500 ml |

The invention claimed is:

1. A triazaspiro[5.5]undecane compound of the formula (I):

(I)

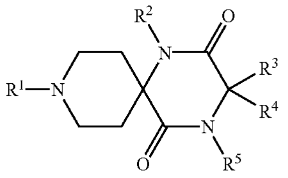

wherein $R^1$ is
(1) hydrogen,
(2) C1–18alkyl,
(3) C2–18 alkenyl,
(4) C2–18 alkynyl,
(5) $—COR^6$,
(6) $—CONR^7R^8$,
(7) $—COOR^9$,
(8) $—SO_2R^{10}$,
(9) $—COCOOR^{11}$,
(10) $—CONR^{12}COR^{13}$,
(11) Cyc 1, or
(12) C1–18 alkyl, C2–18 alkenyl or C2–18 alkynyl substituted by 1–5 substituent(s) selected from (a) halogen, (b) $—CONR^7R^8$, (c) —COOR , (d) $—OR^{14}$, (e) $—SR^{15}$, (f) $—NR^{16}R^{17}$, (g) $—NR^{18}COR^{19}$, (h) $—SO_2NR^{20}R^{21}$, (i) $—OCOR^{22}$, (j) $—NR^{23}SO_2R^{24}$, (k) $—NR^{25}COOR^{26}$, (l) $—NR^{27}CONR^{28}R^{29}$, (m) Cyc 1, (n) keto or (o) $—N(SO_2R^{24})_2$,
wherein $R^6$–$R^9$, $R^{11}$–$R^{21}$, $R^{23}$, $R^{25}$ and $R^{27}$–$R^{29}$ are each independently,
(1) hydrogen,
(2) C1–8 alkyl,
(3) C2–8 alkenyl,
(4) C2–8 alkynyl,
(5) Cyc 1, or
(6) C1–8 alkyl, C2–8 alkenyl or C2–8 alkynyl substituted by 1–5 substituents(s) selected from (a) Cyc 1, (b) halogen, (c) $—OR^{30}$, (d) $—SR^{31}$, (e) $—NR^{32}R^{33}$, (f) $—COOR^{34}$, (g) $—CONR^{35}R^{36}$, (h) $—NR^{37}COR^{38}$, (i) $—NR^{39}SO_2R^{40}$ or (j) $—N(SO_2R^{40})_2$, or
$R^7$ and $R^8$, $R^{20}$ and $R^{21}$, $R^{28}$ and $R^{29}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{195}$—(C2–6 alkylene)-,
wherein $R^{195}$ is hydrogen, C1–8 alkyl, phenyl or C1–8alkyl substituted by phenyl,
$R^{10}$, $R^{22}$, $R^{24}$ and $R^{26}$ are each independently,
(1) C1–8 alkyl,
(2) C2–8 alkenyl,
(3) C2–8 alkynyl,
(4) Cyc 1, or
(5) C1–8 alkyl, C2–8 alkenyl or C2–8 alkynyl substituted by 1–5 substituents(s) selected from (a) Cyc 1, (b) halogen, (c) $—OR^{30}$, (d) $—SR^{31}$, (e) $—NR^{32}R^{33}$, (f) $—COOR^{34}$, (g) $—CONR^{35}R^{36}$, (h) $—NR^{37}COR^{38}$, (i) $—NR^{39}SO_2R^{40}$ or (j) $—N(SO_2R^{40})_2$,
wherein $R^{30}$–$R^{37}$ and $R^{39}$ are each independently, hydrogen, C1–8 alkyl, Cyc 1 or C1–8 alkyl substituted by Cyc 1, or
$R^{35}$ and $R^{36}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{196}$—(C2–6 alkylene)-,
wherein $R^{196}$ is hydrogen, C1–8 alkyl, phenyl or C1–8 alkyl substituted by phenyl,
$R^{38}$ and $R^{40}$ are each independently C1–8 alkyl, Cyc 1 or C1–8 alkyl substituted by Cyc 1,
Cyc 1 is C3–15 mono-, bi- or tri-(fused or spiro) carbocyclic ring or 3–15 membered mono-, bi- or tri-(fused or spiro)cyclic hetero ring containing 1–4 nitrogen atom(s), 1–3 oxygen atom(s) and/or 1–3 sulfur atom(s),
wherein Cyc 1 maybe substituted by 1–5 of $R^{51}$,
$R^{51}$ is
(1) C1–8 alkyl,
(2) C2–8 alkenyl,
(3) C2–8 alkynyl,
(4) halogen,
(5) nitro,
(6) trifluoromethyl,
(7) trifluoromethoxy,
(8) nitrile,
(9) keto,
(10) Cyc 2
(11) $—OR^{52}$,
(12) $—SR^{53}$,
(13) $—NR^{54}R^{55}$,
(14) $—COOR^{56}$,
(15) $—CONR^{57}R^{58}$,
(16) $—NR^{59}COR^{60}$,
(17) $—SO_2NR^{61}R^{62}$,
(18) $—OCOR^{63}$,
(19) $—NR^{64}SO_2R^{65}$,

(20) —$NR^{66}COOR^{67}$,
(21) —$NR^{68}CONR^{69}R^{70}$,
(22) —$B(OR^{71})_2$,
(23) —$SO_2R^{72}$,
(24) —$N(SO_2R^{72})_2$, or
(25) C1–8 alkyl, C2–8 alkenyl or C2–8 alkynyl substituted by 1–5 substituents(s) selected from (a) halogen, (b) Cyc 2, (c) —$OR^{52}$, (d) —$SR^{53}$, (e) —$NR^{54}R^{55}$, (f) —$COOR^{56}$, (g) —$CONR^{57}R^{58}$, (h) —$NR^{59}COR^{60}$, (i) —$SO_2NR^{61}R^{62}$, (j) —$OCOR^{63}$, (k) —$NR^{64}SO_2R^{65}$, (l) —$NR^{66}COOR^{67}$, (m) —$NR^{68}CONR^{69}R^{70}$, (n) —$B(OR^{71})_2$, (o) —$SO_2R^{72}$ or (p) —$N(SO_2R^{72})_2$, wherein $R^{52}$–$R^{62}$, $R^{64}$, $R^{66}$ and $R^{68}$–$R^{71}$ are each independently 1) hydrogen, 2) C1–8 alkyl, 3) C2–8 alkenyl, 4) C2–8 alkynyl, 5) Cyc 2 or 6) C1–8 alkyl, C2–8 alkenyl or C2–8 alkynyl substituted by Cyc 2, —$OR^{73}$, —$COOR^{74}$, —$NR^{75}R^{76}$, or $R^{57}$ and $R^{58}$, $R^{61}$ and $R^{62}$, $R^{69}$ and $R^{70}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{197}$—(C2–6 alkylene)-, wherein $R^{197}$ is hydrogen, C1–8 alkyl, phenyl or C1–8alkyl substituted by phenyl, $R^{63}$, $R^{65}$, $R^{67}$ and $R^{72}$ are each independently 1) C1–8 alkyl, 2) C2–8 alkenyl, 3) C2–8 alkynyl, 4) Cyc 2 or 5) C1–8 alkyl, C2–8 alkenyl or C2–8 alkynyl substituted by Cyc 2, —$OR^{73}$, —$COOR^{74}$ or —$NR^{75}R^{76}$, wherein $R^{73}$–$R^{76}$ are independently hydrogen, C1–8 alkyl, Cyc 2 or C1–8 alkyl substituted by Cyc 2, Cyc 2 has the same meaning as Cyc 1, wherein Cyc 2 may be substituted by 1–5 of $R^{77}$, $R^{77}$ is 1) C1–8alkyl,
2) halogen,
3) nitro,
4) trifluoromethyl,
5) trifluoromethoxy,
6) nitrile,
7) —$OR^{78}$,
8) —$NR^{79}R^{80}$,
9) —$COOR^{81}$,
10) —$SR^{82}$,
11) —$CONR^{83}R^{84}$,
12) C2–8 alkenyl,
13) C2–8 alkynyl,
14) keto,
15) Cyc 6,
16) —$NR^{161}COR^{162}$,
17) —$SO_2NR^{163}R^{164}$,
18) —$OCOR^{165}$,
19) —$NR^{166}SO_2R^{167}$,
20) —$NR^{168}COOR^{169}$,
21) —$NR^{170}CONR^{171}R^{172}$,
22) —$SO_2R^{173}$,
23) —$N(SO_2R^{167})_2$, or
24) C1–8 alkyl, C2–8 alkenyl or C2–8 alkynyl substituted by 1–5 substituents(s) selected from (a) halogen, (b) —$OR^{78}$, (c) —$NR^{79}R^{80}$, (d) —$COOR^{81}$, (e) —$SR^{82}$, (f) —$CONR^{83}R^{84}$, (g) keto, (h) Cyc 6, (i) —$NR^{161}COR^{162}$, (j) —$SO_2NR^{163}R^{164}$, (k) —$OCOR^{165}$, (l) —$NR^{166}SO_2R^{167}$, (m) —$NR^{168}COOR^{169}$, (n) —$NR^{170}CONR^{171}R^{172}$, (o) —$SO^2R^{173}$ or (p) —$N(SO_2R^{167})_2$, wherein $R^{78}$–$R^{84}$, $R^{161}$–$R^{164}$, $R^{166}$, $R^{168}$ and $R^{170}$–$R^{172}$ are each independently (a) hydrogen, (b) C1–8 alkyl, (c) C2–8 alkenyl, (d) C2–8 alkynyl, (e) Cyc 6 or (f) C1–8 alkyl, C2–8 alkenyl or C2–8 alkynyl substituted by Cyc 6, —$OR^{174}$, —$COOR^{175}$, —$NR^{176}R^{177}$ or —$CONR^{178}R^{179}$, or $R^{83}$ and $R^{84}$, $R^{163}$ and $R^{164}$, $R^{171}$ and $R^{172}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{198}$—(C2–6 alkylene)-, wherein $R^{198}$ is hydrogen, C1–8 alkyl, phenyl or C1–8 alkyl substituted by phenyl, $R^{165}$, $R^{167}$, $R^{169}$ and $R^{173}$ are each independently (a) C1–8 alkyl, (b) C2–8 alkenyl, (c) C2–8 alkynyl, (d) Cyc 6 or (e) C1–8 alkyl, C2–8 alkenyl or C2–8 alkynyl substituted by Cyc 6, —$OR^{174}$, —$COOR^{175}$, —$NR^{176}R^{177}$ or —$CONR^{178}R^{179}$, wherein $R^{174}$–$R^{177}$ are each independently 1) hydrogen, 2) C1–8 alkyl, 3) Cyc 6 or 4) C1–8 alkyl substituted by Cyc 6, or $R^{178}$ and $R^{179}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{199}$—(C2–6 alkylene)-, wherein $R^{199}$ is hydrogen, C1–8 alkyl, phenyl or C1–8 alkyl substituted by phenyl, Cyc 6 is C3–8 mono-carbocyclic ring or 3–8 membered mono-cyclic hetero ring containing 1–4 nitrogen atom(s), 1–2 oxygen atom(s) and/or 1–2 sulfur atom (s), wherein Cyc 6 may be substituted by 1–5 of $R^{180}$, $R^{180}$ is, (1) C1–8 alkyl,
(2) halogen,
(3) nitro,
(4) trifluoromethyl,
(5) trifluoromethoxy,
(6) nitrile,
(7) —$OR^{181}$,
(8) —$NR^{182}R^{183}$,
(9) —$COOR^{184}$,
(10) —$SR^{185}$, or
(11) —$CONR^{186}R^{187}$, wherein $R^{181}$–$R^{187}$ are each independently 1) hydrogen, 2) C1–8 alkyl, 3) phenyl or 4) C1–8 alkyl substituted by phenyl, $R^{182}$ and $R^{183}$, $R^{186}$ and $R^{187}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{200}$—(C2–6 alkylene)-, wherein $R^{200}$ is hydrogen, C1–8 alkyl, phenyl or C1–8 alkyl substituted by phenyl, $R^2$ is (1) hydrogen,
(2) C1–8 alkyl,
(3) C2–8 alkenyl,
(4) C2–8 alkynyl,
(5) —$OR^{90}$,
(6) Cyc 3, or
(7) C1–8 alkyl, C2–8 alkenyl or C2–8 alkynyl substituted by 1–5 substituents(s) selected from (a) halogen, (b) —$OR^{90}$, (c) —$SR^{91}$, (d) —$NR^{92}R^{93}$, (e) —$COOR^{94}$, (f) —$CONR^{95}R^{96}$, (g) —$NR^{97}COR^{98}$, (h) —$SO_2NR^{99}R^{100}$, (i) —$OCOR^{101}$, (j) —$NR^{102}SO_2R^{103}$, (k) —$NR^{104}COOR^{105}$, (l) —$NR^{106}CONR^{107}R^{108}$, (m) Cyc 3, (n) keto or (o) —$N(SO_2R^{103})_2$, wherein $R^{90}$–$R^{100}$, $R^{102}$, $R^{104}$ and $R^{106}$–$R^{108}$ are each independently 1) hydrogen, 2) C1–8 alkyl, 3) C2–8 alkenyl, 4) C2–8 alkynyl, 5) Cyc 3 or 6) C1–8 alkyl, C2–8 alkenyl or C2–8 alkynyl substituted by Cyc 3, or $R^{95}$ and $R^{96}$, $R^{99}$ and $R^{100}$, $R^{107}$ and $R^{108}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{201}$—(C2–6 alkylene)-, wherein $R^{201}$ is hydrogen, C1–8 alkyl, phenyl or C1–8 alkyl substituted by phenyl, $R^{101}$, $R^{103}$ and $R^{105}$ are each independently 1) C1–8 alkyl, 2) C2–8 alkenyl, 3) C2–8 alkynyl, 4) Cyc 3, or 5) C1–8 alkyl, C2–8alkenyl or C2–8alkynyl substituted by Cyc 3, Cyc 3 has the same meaning as Cyc 1, wherein Cyc 3 may be substituted by 1–5 of $R^{109}$, $R^{109}$ has the same meaning as $R^{51}$, $R^3$ and $R^4$ are each independently (1) hydrogen,
(2) C1–8 alkyl,
(3) C2–8 alkenyl,
(4) C2–8 alkynyl,
(5) —$COOR^{120}$,
(6) —$CONR^{121}R^{122}$,
(7) Cyc 4, or
(8) C1–8 alkyl, C2–8 alkenyl or C2–8 alkynyl substituted by 1–5 substituents(s) selected from (a) halogen, (b) nitrile, (c) Cyc 4, (d) —$COOR^{120}$, (e) —$CONR^{121}R^{122}$, (f) —$OR^{123}$, (g) —$SR^{124}$, (h) —$NR^{125}R^{126}$, (i) —$NR^{127}COR^{128}$, (j) —$SO_2NR^{129}R^{130}$, (k) —$OCOR^{131}$, (l) —$NR^{132}SO_2R^{133}$, (m) —$NR^{134}COOR^{135}$, (n) —$NR^{136}CONR^{137}R^{138}$, (o) —S—$SR^{139}$, (p) —NHC(=NH)$NHR^{140}$, (q) keto, (r) —$NR^{145}CONR^{146}COR^{147}$ or (s) —$N(SO_2R^{133})_2$, wherein $R^{120}$–$R^{130}$, $R^{132}$, $R^{134}$, $R^{136}$–$R^{138}$, $R^{145}$ and $R^{146}$ are each independently 1) hydrogen, 2) C1–8 alkyl, 3) C2–8 alkenyl, 4) C2–8 alkynyl, 5) Cyc 4 or 6) C1–8 alkyl, C2–8 alkenyl or C2–8 alkynyl substituted by Cyc 4, halogen, $OR^{148}$, —$SR^{149}$, —$COOR^{150}$ or —$NHCOR^{141}$, or $R^{121}$ and $R^{122}$, $R^{129}$ and $R^{130}$, $R^{137}$ and $R^{138}$, taken together, are 1) C2–6 alkylene, 2) —(C2–6 alkylene)-O—(C2–6 alkylene)-, 3) —(C2–6 alkylene)-S—(C2–6 alkylene)- or 4) —(C2–6 alkylene)-$NR^{202}$—(C2–6 alkylene)-, wherein $R^{202}$ is hydrogen, C1–8 alkyl, phenyl or C1–8 alkyl substituted by phenyl, $R^{131}$, $R^{133}$, $R^{135}$, $R^{139}$ and $R^{147}$ are each independently 1) C1–8 alkyl, 2) C2–8 alkenyl, 3) C2–8 alkynyl, 4) Cyc 4 or 5) C1–8 alkyl, C2–8 alkenyl or C2–8 alkynyl substituted by Cyc 4, halogen, —$OR^{148}$, —$SR^{149}$, —$COOR^{150}$ or —$NHCOR^{141}$, $R^{140}$ is hydrogen, —$COOR^{142}$ or —$SO_2R^{143}$, wherein $R^{141}$–$R^{143}$ are each independently 1) C1–8 alkyl, 2) C2–8 alkenyl, 3) C2–8 alkynyl, 4) Cyc 4 or 5) C1–8 alkyl, C2–8 alkenyl or C2–8 alkynyl substituted by Cyc 4, $R^{148}$–$R^{150}$ are each independently 1) hydrogen, 2) C1–8 alkyl, 3) C2–8 alkenyl, 4) C2–8 alkynyl, 5) Cyc 4 or 6) C1–8 alkyl, C2–8 alkenyl or C2–8 alkynyl substituted by Cyc 4, Cyc 4 has the same meaning as Cyc 1, wherein Cyc 4 maybe substituted by 1–5 of $R^{144}$, $R^{144}$ has the same meaning as $R^{51}$ or $R^3$ and $R^4$, taken together, are

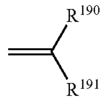

wherein $R^{190}$ and $R^{191}$ each has independently the same meaning as $R^3$ or $R^4$, $R^5$ is (1) hydrogen,
(2) C1–8 alkyl,
(3) Cyc5, or
(4) C1–8alkyl substituted by Cyc 5, wherein Cyc 5 have the same meaning as Cyc 1, wherein Cyc 5 may be substituted by 1–5 of $R^{160}$, $R^{160}$ has the same meaning as $R^{51}$, a quaternary ammonium salt thereof, an N-oxide thereof or a non-toxic salt thereof.

2. A compound according to claim 1, in which $R^3$ and $R^4$ are hydrogen in the formula (I) described in claim 1, or a quarternary ammonium salt thereof, an N-oxide thereof or a non-toxic salt thereof.

3. A compound according to claim 1, in which $R^3$ is hydrogen, and $R^4$ is (1) C1–8alkyl,
(2) C2–8 alkenyl,
(3) C2–8 alkynyl,
(4) —$COOR^{120}$,
(5) —$CONR^{121}R^{122}$,
(6) Cyc 4, or
(7) C1–8 alkyl, C2–8 alkenyl or C2–8 alkynyl substituted by 1–5 substituents(s) selected from (a) halogen, (b) nitrile, (c) Cyc 4, (d) —$COOR^{120}$, (e) —$CONR^{121}R^{122}$, (f) —$OR^{123}$, (g) —$SR^{124}$ (h) —$NR^{125}R^{126}$, (i) —$NR^{127}COR^{128}$, (j) —$SO_2NR^{129}R^{130}$, (k) —$OCOR^{131}$, (l) —$NR^{132}SO_2R^{133}$, m) —$NR^{134}COOR^{135}$, (n) —$NR^{136}CONR^{137}R^{138}$, (o) —S—$SR^{139}$, (p) —NHC(=NH)$NHR^{140}$, (q) keto, (r) —$NR^{145}CONR^{146}COR^{147}$, or (s) —$N(SO_2R^{133})_2$, wherein all of the symbols have the same meanings as defined in claim 1, in the formula (I) described in claim 1, or a quaternary ammonium salt thereof, an N-oxide thereof or a non-toxic salt thereof.

4. A compound according to claim 1, in which $R^3$ and $R^4$ are each independently, (1) C1–8alkyl,
(2) C2–8 alkenyl,
(3) C2–8 alkynyl,
(4) —$COOR^{120}$,
(5) —$CONR^{121}R^{122}$,
(6) Cyc 4, or
(7) C1–8 alkyl, C2–8 alkenyl or C2–8 alkynyl substituted by 1–5 substituents(s) selected from (a) halogen, (b) nitrile, (c) Cyc 4, (d) —$COOR^{120}$, (e) —$CONR^{121}R^{122}$, (f) —$OR^{123}$, (g) —$SR^{124}$, (h) —$NR^{125}R^{126}$, (i) —$NR^{127}COR^{128}$, (j) —$SO_2NR^{129}R^{130}$, (k) —$OCOR^{131}$, (l) —$NR^{132}SO_2R^{133}$, m) —$NR^{134}COOR^{135}$, (n) —$NR^{136}CONR^{137}R$ , (o) —S—$SR^{139}$, (p) —NHC(=NH)$NHR^{140}$, (4) keto, (r) —$NR^{145}CONR^{146}COR^{147}$, or (s) —$N(SO_2R^{133})_2$, wherein all of the symbols have the same meanings as defined in claim 1, in the formula (I) described in claim 1, or a quarternary ammonium salt thereof, an N-oxide thereof or a non-toxic salt thereof.

5. A compound according to claim 1, in which $R^3$ and $R^4$, taken together, are

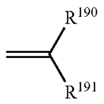

wherein all of the symbols have the same meaning as defined in claim 1, in the formula (I) described in claim 1, or a quaternary ammonium salt thereof, an N-oxide thereof or a non-toxic salt thereof.

6. A compound according to claim 1, which is (1) 9-(3,5-dimethyl-1-phenylpyrazol-4-ylmethyl)-2,5-dioxo-3-(2-methyl-1-propyl)-1-propyl-1,4,9-triazaspiro[5.5]undecane, (2) 9-(1,4-benzodioxan-6-ylmethyl)-1-butyl-3-cyclohexylmethyl-2,5-dioxo-1,4,9-triazaspiro[5.5]undecane, (3) 1-butyl-3-cyclohexylmethyl-2,5-dioxo-9-(2-phenylimidazol-4-ylmethyl)-1,4,9-triazaspiro[5.5]undecane, (4) 1-butyl-3-(2-methyl-1-propyl)-2,5-dioxo-9-(4-phenyloxyphenylmethyl)-1,4,9-triazaspiro[5.5]undecane, (5) (3S)-2,5-dioxo-3-(2-methylpropyl)-9-(6-phenylhexyl)-1-propyl-1,4,9-triazaspiro[5.5]undecane, (6) (3R)-2,5-dioxo-3-(2-methylpropyl)-9-(6-phenylhexyl)-1-propyl-1,4,9-triazaspiro[5.5]undecane, (7) 1-butyl-9-((3,5-dimethyl-1-phenyl)-4-pyrazolyl)methyl)-2,5-dioxo-3-(2-methyl-1-propyl)-1,4,9-triazaspiro[5.5]undecane, (8) 1-butyl-3-cyclohexylmethyl-2,5-dioxo-9-(4-phenyloxyphenylmethyl)-1,4,9-triazaspiro[5.5]undecane, (9) 9-(1,4-benzodioxan-6-ylmethyl)-1-butyl-3-(2-methyl-1-propyl)-2,5-dioxo-1,4,9-triazaspiro[5.5]undecane,

(10) 9-(4-benzyloxyphenylmethyl)-1-butyl-2,5-dioxo-3-(2-methyl-1-propyl)-1,4,9-triazaspiro[5.5]undecane,

(11) 1-butyl-2,5-dioxo-3-(2-methylpropyl)-9-(6-phenylhexyl)-1,4,9-triazaspiro[5.5]undecane,

(12) (3S)-1-(2-methylpropyl)-2,5-dioxo-3-(4-(N-benzyloxycarbonyl)aminobutyl)-9-(2-phenylethyl)-1,4,9-triazaspiro[5.5]undecane,

(13) (3S)-1-propyl-2,5-dioxo-3-(4-(N-benzyloxycarbonyl)aminobutyl)-9-(2-phenylethyl)-1,4,9-triazaspiro[5.5]undecane,

(14) (3R)-1-propyl-2,5-dioxo-3-(4-(N-benzyloxycarbonyl)aminobutyl)-9-(2-phenylethyl)-1,4,9-triazaspiro[5.5]undecane,

(15) (3S)-1-propyl-2,5-dioxo-3-(4-(N-benzyloxycarbonyl)aminobutyl)-9-(3-phenylpropyl)-1,4,9-triazaspiro[5.5]undecane,

(16) (3R)-1-propyl-2,5-dioxo-3-(4-(N-benzyloxycarbonyl)aminobutyl)-9-(3-phenylpropyl)-1,4,9-triazaspiro[5.5]undecane,

(17) (3S)-1-propyl-2,5-dioxo-3-(4-(N-benzyloxycarbonyl)aminobutyl)-9-(4-phenylbutyl)-1,4,9-triazaspiro[5.5]undecane,

(18) (3R)-1-propyl-2,5-dioxo-3-(4-(N-benzyloxycarbonyl)aminobutyl)-9-(4-phenylbutyl)-1,4,9-triazaspiro[5.5]undecane,

(19) (3S)-1-benzyl-2,5-dioxo-3-(2-methylpropyl)-9-benzyl-1,4,9-triazaspiro[5.5]undecane,

(20) (3R)-1-benzyl-2,5-dioxo-3-(2-methylpropyl)-9-benzyl-1,4,9-triazaspiro[5.5]undecane,

(21) (3S)-1-propyl-2,5-dioxo-3-(4-(N-benzyloxycarbonyl)aminobutyl)-9-(2-(2-phenyl-5-methyloxazol-4-yl)ethyl)-1,4,9-triazaspiro[5.5]undecane,

(22) (3S)-1-propyl-2,5-dioxo-3-(4-(N-(2-chlorophenylmethyl)oxycarbonyl)aminobutyl)-9-(2-phenylethyl)-1,4,9-triazaspiro[5.5]undecane,

(23) (3S)-1-propyl-2,5-dioxo-3-[3-(3-(2,4,6-trimethylphenylsulfonyl)guanidino)propyl]-9-(2-phenylethyl)-1,4,9-triazaspiro[5.5]undecane,

(24) 1-propyl-2,5-dioxo-3-(2-methylpropyl)-9-(4-phenyloxyphenylmethyl)-1,4,9-triazaspiro[5.5]undecane,

(25) 1-butyl-2,5-dioxo-3-cyclohexylmethyl-9-(4-methoxyphenylmethyl)-1,4,9-triazaspiro[5.5]undecane,

(26) 1-butyl-2,5-dioxo-3-cyclohexylmethyl-9-(4-allyloxyphenylmethyl)-1,4,9-triazaspirol[5.5]undecane,

(27) (3S)-1-propyl-9-(3,5-dimethyl-1-phenylpyrazol-4-ylmethyl)-2,5-dioxo-3-(2-methyl-1-propyl)-1,4,9-triazaspiro[5.5]undecane,

(28) (3R)-1-propyl-9-(3,5-dimethyl-1-phenylpyrazol-4-ylmethyl)-2,5-dioxo-3-(2-methyl-1-propyl)-1,4,9-triazaspiro[5.5]undecane,

(29) 1-butyl-2,5-dioxo-3-(2-methylpropyl)-9-phenylmethyl-1,4,9-triazaspiro[5.5]undecane,

(30) 1-butyl-2,5-dioxo-3-(2-methylpropyl)-9-benzyloxycarbonyl-1,4,9-triazaspiro[5.5]undecane,

(31) 1-butyl-2,5-dioxo-3-cyclohexylmethyl-9-benzyloxycarbonyl-1,4,9-triazaspiro[5.5]undecane,

(32) 1-benzyl-2,5-dioxo-3-(2-methylpropyl)-9-(4-phenyloxyphenylmethyl)-1,4,9-triazaspiro[5.5]undecane,

(33) 1-butyl-2,5-dioxo-3-propyl-9-(4-phenyloxyphenylmethyl)-1,4,9-triazaspiro[5.5]undecane,

(34) 1-butyl-2,5-dioxo-3-methoxymethyl-9-(4-phenyloxyphenylmethyl)-1,4,9-triazaspiro[5.5]undecane,

(35) 1-(1-methylpropyl)-2,5-dioxo-3-(2-methylpropyl)-9-(4-phenyloxyphenylmethyl)-1,4,9-triazaspiro[5.5]undecane,

(36) 1-(2-methylbutyl)-2,5-dioxo-3-(2-methylpropyl)-9-(4-phenyloxyphenylmethyl)-1,4,9-triazaspiro[5.5]undecane,

(37) 1-(2-methylpropyl)-2,5-dioxo-3-(2-methylpropyl)-9-(4-phenyloxyphenylmethyl)-1,4,9-triazaspiro[5.5]undecane,

(38) 1-(2-dimethylaminoethyl)-2,5-dioxo-3-(2-methylpropyl)-9-(4-phenyloxyphenylmethyl)-1,4,9-triazaspiro[5.5]undecane,

(39) 1-(2-methoxyethyl)-2,5-dioxo-3-(2-methylpropyl)-9-(4-phenyloxyphenylmethyl)-1,4,9-triazaspiro[5.5]undecane,

(40) 1-(2-methylthioethyl)-2,5-dioxo-3-(2-methylpropyl)-9-(4-phenyloxyphenylmethyl)-1,4,9-triazaspiro[5.5]undecane,

(41) 1-benzyl-2,5-dioxo-3-(2-methylpropyl)-9-(1,4-benzodioxan-6-ylmethyl)-1,4,9-triazaspiro[5.5]undecane,

(42) 1-benzyl-2,5-dioxo-3-(2-methylpropyl)-9-(4-benzyloxyphenylmethyl)-1,4,9-triazaspiro[5.5]undecane,

(43) 1-benzyl-2,5-dioxo-3-(2-methylpropyl)-9-(3,5-dimethyl-1-phenylpyrazol-4-ylmethyl)-1,4,9-triazaspiro[5.5]undecane,

(44) 1-(3-methylphenylmethyl)-2,5-dioxo-3-(2-methylpropyl)-9-(1,4-benzodioxan-6-ylmethyl)-1,4,9-triazaspiro[5.5]undecane,
(45) 1-(3-methylphenylmethyl)-2,5-dioxo-3-(2-methylpropyl)-9-(3,5-dimethyl-1-phenylpyrazol-4-ylmethyl)-1,4,9-triazaspiro[5.5]undecane,
(46) 1-(1-methylbutyl)-2,5-dioxo-3-(2-methylpropyl)-9-(4-phenyloxyphenylmethyl)-1,4,9-triazaspiro[5.5]undecane,
(47) 1-(3-methylbutyl)-2,5-dioxo-3-(2-methylpropyl)-9-(4-phenyloxyphenylmethyl)-1,4,9-triazaspiro[5.5]undecane,
(48) 1-(2-methoxyphenylmethyl)-2,5-dioxo-3-(2-methylpropyl)-9-((3,5-dimethyl-1-phenyl)-4-pyrazolyl)methyl)-1,4,9-triazaspiro[5.5]undecane,
(49) 1-(3-methoxyphenylmethyl)-2,5-dioxo-3-(2-methylpropyl)-9-((3,5-dimethyl-1-phenyl)-4-pyrazolyl)methyl)-1,4,9-triazaspiro[5.5]undecane,
(50) 1-(2-methylphenylmethyl)-2,5-dioxo-3-(2-methylpropyl)-9-(3,5-dimethyl-1-phenylpyrazol-4-ylmethyl)-1,4,9-triazaspiro[5.5]undecane,
(51) 1-(3-methylphenylmethyl)-2,5-dioxo-3-(2-methylpropyl)-9-(4-phenyloxyphenylmethyl)-1,4,9-triazaspiro[5.5]undecane,
(52) 1-butyl-2,5-dioxo-3-cyclohexylmethyl-9-(5-ethylthiophen-2-ylmethyl)-1,4,9-triazaspiro[5.5]undecane,
(53) 1-butyl-2,5-dioxo-3-cyclohexylmethyl-9-(5-ethylfuran-2-ylmethyl)-1,4,9-triazaspiro[5.5]undecane,
(54) (3S)-1-butyl-2,5-dioxo-3-((1R)-1-hydroxy-2-methylpropyl)-9-(4-phenyloxyphenylmethyl)-1,4,9-triazaspiro[5.5]undecane,
(55) (3R)-1-butyl-2,5-dioxo-3-((1S)-1-hydroxy-2-methylpropyl)-9-(4-phenyloxyphenylmethyl)-1,4,9-triazaspiro[5.5]undecane,
(56) (3S)-1-propyl-2,5-dioxo-3-(4-(N-benzyloxycarbonyl)aminobutyl)-9-allyloxycarbonyl-1,4,9-triazaspiro[5.5]undecane,
(57) (3S)-1-propyl-2,5-dioxo-3-(4-(N-benzyloxycarbonyl)aminobutyl)-1,4,9-triazaspiro[5.5]undecane,
(58) 1-propyl-2,5-dioxo-3-(2-methylpropyl)-1,4,9-triazaspiro[5.5]undecane,
(59) 1-butyl-2,5-dioxo-3-(2-methylpropyl)-1,4,9-triazaspiro[5.5]undecane,
(60) 1-butyl-2,5-dioxo-3-cyclohexylmethyl-1,4,9-triazaspiro[5.5]undecane,
(61) (3S)-1-propyl-2,5-dioxo-3-(4-(N-benzyloxycarbonyl)aminobutyl)-9-(4-dihydroxyboranephenylmethyl)-1,4,9-triazaspiro[5.5]undecane,
(62) (3S)-1-propyl-2,5-dioxo-3-(4-(N-benzyloxycarbonyl)aminobutyl)-9-(1,3-benzodioxalan-4-ylmethyl)-1,4,9-triazaspiro[5.5]undecane,
(63) 1-butyl-2,5-dioxo-3-(2-methylpropyl)-9-(1-(1,4-benzodioxan-6-yl)ethyl)-1,4,9-triazaspiro[5.5]undecane,
(64) 1-butyl-2,5-dioxo-3-(2-methylpropyl)-9-(1-(4-phenyloxyphenyl)ethyl)-1,4,9-triazaspiro[5.5]undecane,
(65) 1-butyl-2,5-dioxo-3-cyclohexylmethyl-9-(1-(1,4-benzodioxan-6-yl)ethyl)-1,4,9-triazaspiro[5.5]undecane,
(66) (3S)-1-propyl-2,5-dioxo-3-(4-(N-benzyloxycarbonyl)aminobutyl)-9-allyl-1,4,9-triazaspiro[5.5]undecane,
(67) (3S)-1-propyl-2,5-dioxo-3-(4-aminobutyl)-9-phenylethyl-1,4,9-triazaspiro[5.5]undecane,
(68) (3S)-1-propyl-2,5-dioxo-3-(4-(N-(4-phenyl)phenylcarbonyl)aminobutyl)-9-phenylethyl-1,4,9-triazaspiro[5.5]undecane,
(69) 1-butyl-2,5-dioxo-3-cyclohexylmethyl-9-methyl-9-(1-(1,4-benzodioxan-6-yl)ethyl)-1,4,-diaza-9-azoniaspiro[5.5]undecane iodide,
(70) (3S)-3-(4-(N-benzyloxycarbonyl)aminobutyl)-2,5-dioxo-9-(2-hydroxy-2-phenylethyl)-1-propyl-1,4,9-triazaspiro[5.5]undecane,
(71) (3S)-3-(4-(N-benzyloxycarbonyl)aminobutyl)-2,5-dioxo-9-(2-oxo-2-phenylethyl)-1-propyl-1,4,9-triazaspiro[5.5]undecane,
(72) (3S)-1-(2-methylpropyl)-2,5-dioxo-3-methyl-9-allyloxycarbonyl-1,4,9-triazaspiro[5.5]undecane,
(73) (3S)-1-(2-methylpropyl)-2,5-dioxo-3-methyl-9-(2-phenylethyl)-1,4,9-triazaspiro[5.5]undecane,
(74) (3S)-1-(2-methylpropyl)-2,5-dioxo-3-(4-(N-benzyloxycarbonyl)aminobutyl)-9-(2-phenylethyl)-1,4,9-triazaspiro[5.5]undecane,
(75) (3S)-1-(1-benzylpiperidin-4-yl)-2,5-dioxo-3-methyl-9-(2-phenylethyl)-1,4,9-triazaspiro[5.5]undecane,
(76) (3S)-1-(1-benzylpiperidin-4-yl)-2,5-dioxo-3-(4-(N-benzyloxycarbonyl)aminobutyl)-9-(2-phenylethyl)-1,4,9-triazaspiro[5.5]undecane,
(77) (3S)-1-(2,2-diphenylpropyl)-2,5-dioxo-3-methyl-9-(2-phenylethyl)-1,4,9-triazaspiro[5.5]undecane,
(78) (3S)-1-(2,2-diphenylpropyl)-2,5-dioxo-3-(4-(N-benzyloxycarbonyl)aminobutyl)-9-(2-phenylethyl)-1,4,9-triazaspiro[5.5]undecane,
(79) (3S)-1-propyl-2,5-dioxo-3-(4-benzyloxyphenylmethyl)-9-(2-phenylethyl)-1,4,9-triazaspiro[5.5]undecane,
(80) (3S)-1-propyl-2,5-dioxo-3-(4-(benzylcarbonylamino)butyl)-9-(2,4,6-trimethoxybenzyl)-1,4,9-triazaspiro[5.5]undecane,
(81) (3S)-1-propyl-2,5-dioxo-3-(4-(benzyloxycarbonylamino)butyl)-9-(2,2-dimethylpropyl)-1,4,9-triazaspiro[5.5]undecane,
(82) (3S)-1-propyl-2,5-dioxo-3-(4-(benzyloxycarbonylamino)butyl)-9-(3-phenylpropanoyl)-1,4,9-triazaspiro[5.5]undecane,
(83) (3S)-1-propyl-2,5-dioxo-3-(4-(benzyloxycarbonylamino)butyl)-9-benzenesulfonyl-1,4,9-triazaspiro[5.5]undecane,
(84) (3S)-1-propyl-2,5-dioxo-3-(4-(benzyloxycarbonylamino)butyl)-9-benzylaminocarbonyl-1,4,9-triazaspiro[5.5]undecane,
(85) (3S)-1-propyl-2,5-dioxo-3-(4-(3-phenylpropanoyl)aminobutyl)-9-(2-phenylethyl)-1,4,9-triazaspiro[5.5]undecane,
(86) (3S)-1-propyl-2,5-dioxo-3-(4-benzenesulfonylaminobutyl)-9-(2-phenylethyl)-1,4,9-triazaspiro[5.5]undecane,
(87) (3S)-1-propyl-2,5-dioxo-3-(4-(N-benzylcarbamoyl)aminobutyl)-9-(2-phenylethyl)-1,4,9-triazaspiro[5.5]undecane,
(88) (3S)-1-butyl-2,5-dioxo-3-(4-methoxyphenylmethyl)-9-cyclohexylmethyl-1,4,9-triazaspiro[5.5]undecane,
(89) 1-butyl-2,5-dioxo-3-(2-methylpropyl)-9-(2-(4-chlorophenyl)thiophen-5-ylmethyl)-1,4,9-triazaspiro[5.5]undecane,
(90) 1-butyl-2,5-dioxo-3-(2-methylpropyl)-9-(2-(4-methoxyphenyl)thiophen-5-ylmethyl)-1,4,9-triazaspiro[5.5]undecane,
(91) 1-((2E)-butenyl)-2,5-dioxo-3-(2-methylpropyl)-9-(4-phenyloxyphenylmethyl)-1,4,9-triazaspiro[5.5]undecane,
(92) 1-(furan-2-ylmethyl)-2,5-dioxo-3-(2-methylpropyl)-9-(4-phenyloxyphenylmethyl)-1,4,9-triazaspiro[5.5]undecane,

(93) 1-(thiophen-2-ylmethyl)-2,5-dioxo-3-(2-methylpropyl)-9-(4-phenyloxyphenylmethyl)-1,4,9-triazaspiro[5.5]undecane,

(94) 1-cyclopropylmethyl-2,5-dioxo-3-(2-methylpropyl)-9-(4-phenyloxyphenylmethyl)-1,4,9-triazaspiro[5.5]undecane,

(95) 1-(2-fluorophenylmethyl)-2,5-dioxo-3-(2-methylpropyl)-9-(4-phenyloxyphenylmethyl)-1,4,9-triazaspiro[5.5]undecane,

(96) 1-(3-methyl-2-butenyl)-2,5-dioxo-3-(2-methylpropyl)-9-(4-phenyloxyphenylmethyl-1,4,9-triazaspiro[5.5]undecane,

(97) 1-butyl-2,5-dioxo-3-(2-methylpropyl)-9-(quinolin-3-ylmethyl)-1,4,9-triazaspiro[5.5]undecane,

(98) 1-butyl-2,5-dioxo-3-(benzyloxycarbonylmethyl)-9-(4-phenyloxyphenylmethyl)-1,4,9-triazaspiro[5.5]undecane,

(99) 1-(3-methyl-2-butenyl)-2,5-dioxo-3-cyclohexylmethyl-9-(1,4-benzodioxan-6-ylmethyl)-1,4,9-triazaspiro[5.5]undecane, (100) 1-butyl-2,5-dioxo-3-cyclohexylmethyl-9-((2E)-3-phenyl-2-propenyl)-1,4,9-triazaspiro[5.5]undecane, (101) (3S)-1-butyl-2,5-dioxo-3-(1,1-dimethylethyl)-9-(4-phenyloxyphenylmethyl)-1,4,9-triazaspiro[5.5]undecane, (102) (3S)-1-butyl-2,5-dioxo-3-(1,1-dimethylethyl)-9-(1,4-benzodioxan-6-ylmethyl)-1,4,9-triazaspiro[5.5]undecane, (103) 1-butyl-2,5-dioxo-3-(2-methylpropyl)-9-(4-methylthiazol-2-ylmethyl)-1,4,9-triazaspiro[5.5]undecane, (104) 1-butyl-2,5-dioxo-3-cyclohexylmethyl-9-(5-methylthiazol-2-ylmethyl)-1,4,9-triazaspiro[5.5]undecane, (105) 1-butyl-2,5-dioxo-3-cyclohexylmethyl-9-(4-methylthiazol-2-ylmethyl)-1,4,9-triazaspiro[5.5]undecane, (106) 1-butyl-2,5-dioxo-3-(2-methylpropyl)-9-(5-methylthiazol-2-ylmethyl)-1,4,9-triazaspiro[5.5]undecane, (107) (3R)-1-butyl-2,5-dioxo-3-cyclohexylmethyl-9-(1,4-benzodioxan-6-ylmethyl)-1,4,9-triazaspiro[5.5]undecane, (108) (3S)-1-butyl-2,5-dioxo-3-cyclohexylmethyl-9-(1,4-benzodioxan-6-ylmethyl)-1,4,9-triazaspiro[5.5]undecane, (109) (3R)-1-butyl-2,5-dioxo-3-((1R)-1-methylpropyl)-9-(4-phenyloxyphenylmethyl)-1,4,9-triazaspiro[5.5]undecane, (110) (3S)-1-butyl-2,5-dioxo-3-((1S)-1-methylpropyl)-9-(4-phenyloxyphenylmethyl)-1,4,9-triazaspiro[5.5]undecane, (111) 1-(2-butynyl)-2,5-dioxo-3-(2-methylpropyl)-9-(4-phenyloxyphenylmethyl)-1,4,9-triazaspiro[5.5]undecane, (112) 1-(2-butynyl)-2,5-dioxo-3-cyclohexylmethyl-9-(1,4-benzodioxan-6-ylmethyl)-1,4,9-triazaspiro[5.5]undecane, (113) 1-pentyl-2,5-dioxo-3-cyclohexylmethyl-9-(1,4-benzodioxan-6-ylmethyl)-1,4,9-triazaspiro[5.5]undecane, (114) 1-(3-methoxyphenylmethyl)-2,5-dioxo-3-(benzyloxymethyl)-9-(3,5-dimethyl-1-phenylpyrazol-4-ylmethyl)-1,4,9-triazaspiro[5.5]undecane, (115) (3R)-1-butyl-2,5-dioxo-3-(2-methylpropyl)-9-(4-phenyloxyphenylmethyl)-1,4,9-triazaspiro[5.5]undecane, (116) (3S)-1-butyl-2,5-dioxo-3-(2-methylpropyl)-9-(4-phenyloxyphenylmethyl)-1,4,9-triazaspiro[5.5]undecane, (117) 1-butyl-2,5-dioxo-3-cyclopentylmethyl-9-(1,4-benzodioxan-6-ylmethyl)-1,4,9-triazaspiro[5.5]undecane, (118) 1-propyl-2,5-dioxo-3-(cyclohexylmethyloxymethyl)-9-(3,5-dimethyl-1-phenylpyrazol-4-ylmethyl)-1,4,9-triazaspiro[5.5]undecane, (119) (3S)-1-butyl-2,5-dioxo-3-(1-methylpropyl)-9-(1,4-benzodioxan-6-ylmethyl)-1,4,9-triazaspiro[5.5]undecane, (120) (3R)-1-butyl-2,5-dioxo-3-(1-methylpropyl)-9-(1,4-benzodioxan-6-ylmethyl)-1,4,9-triazaspiro[5.5]undecane, (121) 1-butyl-2,5-dioxo-3-(2-methylpropyl)-9-(5-phenylmethylthiophen-2-ylmethyl)-1,4,9-triazaspiro[5.5]undecane, (122) 1-butyl-2,5-dioxo-3-cyclohexylmethyl-9-(2-phenylmethylthiophen-5-ylmethyl)-1,4,9-triazaspiro[5.5]undecane, (123) (3R)-1-butyl-2,5-dioxo-3-(2,2-dimethylpropyl)-9-(1,4 -benzodioxan-6-ylmethyl)-1,4,9-triazaspiro[5.5]undecane, (124) (3S)-1-butyl-2,5-dioxo-3-(2,2-dimethylpropyl)-9-(1,4-benzodioxan-6-ylmethyl)-1,4,9-triazaspiro[5.5]undecane, (125) (3R)-1-(2-butynyl)-2,5-dioxo-3-(2,2-dimethylpropyl)-9-(4-phenyloxyphenylmethyl)-1,4,9-triazaspiro[5.5]undecane, (126) (3S)-1-(2-butynyl)-2,5-dioxo-3-(2,2-dimethylpropyl)-9-(4-phenyloxyphenylmethyl)-1,4,9-triazaspiro[5.5]undecane, (127) 1-butyl-2,5-dioxo-3-cycloheptylmethyl-9-(1,4-benzodioxan-6-ylmethyl)-1,4,9-triazaspiro[5.5]undecane, (128) 1-butyl-2,5-dioxo-3-cyclohexylmethyl-9-(2,4,6-trimethoxyphenylmethyl)-1,4,9-triazaspiro[5.5]undecane, (129) 1-butyl-2,5-dioxo-3-(3-cyclohexylpropyl)-9-(1,4-benzodioxan-6-ylmethyl)-1,4,9-triazaspiro[5.5]undecane, (130) 1-butyl-2,5-dioxo-3-(3-cyclohexylpropyl)-9-(4-phenyloxyphenylmethyl)-1,4,9-triazaspiro[5.5]undecane, (131) 1-butyl-2,5-dioxo-3-(3-cyclohexylpropyl)-9-(3,5-dimethyl-1-phenylpyrazol-4-ylmethyl)-1,4,9-triazaspiro[5.5]undecane, (132) 1-butyl-2,5-dioxo-3-(2-hydroxy-2-methylpropyl)-9-(4-phenyloxyphenylmethyl)-1,4,9-triazaspiro[5.5]undecane, (133) 1-(2-butynyl)-2,5-dioxo-3-(2-methylpropyl)-9-(3,5-dimethyl-1-phenylpyrazol-4-ylmethyl)-1,4,9-triazaspiro[5.5]undecane, (134) 1-(2-butynyl)-2,5-dioxo-3-cyclohexylmethyl-9-(3,5-dimethyl-1-phenylpyrazol-4-ylmethyl)-1,4,9-triazaspiro[5.5]undecane, (135) 1-butyl-2,5-dioxo-3-cyclohexylmethyl-9-(3,5-dimethyl-1-phenylpyrazol-4-ylmethyl)-1,4,9-triazaspiro[5.5]undecane, (136) 1-butyl-2,5-dioxo-3-(2-methylpropyl)-9-(2-phenyloxypyridin-3-ylmethyl)-1,4,9-triazaspiro[5.5]undecane, (137) 1-butyl-2,5-dioxo-3-cyclohexylmethyl-9-(2-phenyloxypyridin-3-ylmethyl)-1,4,9-triazaspiro[5.5]undecane, (138) 1-butyl-2,5-dioxo-3-cyclohexylmethyl-9-(4-methylbenzomorpholin-7-ylmethyl)-1,4,9-triazaspiro[5.5]undecane, (139) 1-butyl-2,5-dioxo-3-(2-methylpropyl)-9-(4-methylbenzomorpholin-7-ylmethyl)-1,4,9-triazaspiro[5.5]undecane, (140) 1-butyl-2,5-dioxo-3-(2-methylpropyl)-9-(4-(N-methyl-N-phenylamino)phenylmethyl)-1,4,9-triazaspiro[5.5]undecane, (141) 1-butyl-2,5-dioxo-3-cyclohexylmethyl-9-(4-(N-methyl-N-phenylamino)phenylmethyl)-1,4,9-triazaspiro[5.5]undecane, (142) 1-butyl-2,5-dioxo-3-(2-methylpropyl)-9-(2-(3,5-dimethylpyrazol-1-yl)-5-methoxyphenylmethyl)-1,4,9-triazaspiro[5.5]undecane, (143) 1-butyl-2,5-dioxo-3-cyclohexylmethyl-9-(2-(3,5-dimethylpyrazol-1-yl)-5-methoxyphenylmethyl)-1,4,9-triazaspiro[5.5]undecane, (144) 1-butyl-2,5-dioxo-3-(2-methylpropyl)-9-(3,5-diethyl-1-(4-chlorophenyl)pyrazol-4-ylmethyl)-1,4,9-triazaspiro[5.5]undecane, (145) 1-butyl-2,5-dioxo-3-cyclohexylmethyl-9-(3,5-diethyl-1-(4-chlorophenyl)pyrazol-4-ylmethyl)-1,4,9-triazaspiro[5.5]undecane, (146) 1-butyl-2,5-dioxo-3-(2-methylpropyl)-9-(6-phenyloxypyridin-3-ylmethyl)-1,4,9-triazaspiro[5.5]undecane, (147) 1-butyl-2,5-dioxo-3-cyclohexylmethyl-9-(6-phenyloxypyridin-3-ylmethyl)-1,4,9-triazaspiro[5.5]undecane, (148) 1-butyl-2,5-dioxo-3-(2-methylpropyl)-9-(1,3-benzodioxolan-5-ylmethyl)-1,4,9-triazaspiro[5.5]undecane, (149) 1-butyl-2,5-dioxo-3-cyclohexylmethyl-9-(1,3-benzodioxolan-5-ylmethyl)-1,4,9-triazaspiro[5.5]undecane, (150) 1-butyl-2,5-dioxo-3-cyclohexylmethyl-9-(2-hydroxy-4-methoxyphenylmethyl)-1,4,9-triazaspiro[5.5]undecane, (151) 1-butyl-2,5-dioxo-3-cyclohexylmethyl-9-(4-methylthiophenylmethyl)-1,4,9-triazaspiro[5.5]undecane, (152) 1-butyl-2,5-dioxo-3-(2-methylpropyl)-9-(4-(N,N-diphenylamino)phenylmethyl)-1,4,9-triazaspiro[5.5]undecane, (153) 1-butyl-2,5-dioxo-3-cyclohexylmethyl-9-(4-(N,N-diphenylamino)phenylmethyl)-1,4,9-triazaspiro[5.5]undecane, (154) (3S)-1-(2-butynyl)-2,5-dioxo-3-cyclohexylmethyl-9-(3,5-dimethyl-1-phenylpyrazol-4-ylmethyl)-1,4,9-triazaspiro[5.5]undecane, (155) (3S)-1-(2-butynyl)-2,5-dioxo-3-(2-methylpropyl)-9-(3,5-dimethyl-1-phenylpyrazol-4-ylmethyl)-1,4,9-triazaspiro[5.5]undecane, (156) (3S)-1-butyl-2,5-dioxo-3-cyclohexylmethyl-9-(3,5-dimethyl-1-phenylpyrazol-4-ylmethyl)-1,4,9-triazaspiro[5.5]undecane, (157) 1-butyl-2,5-dioxo-3-(2-methylpropyl)-9-(3,5-dimethyl-1-(4-methylphenyl)pyrazol-4-ylmethyl)-1,4,9-triazaspiro[5.5]undecane, (158) 1-butyl-2,5-dioxo-3-cyclohexylmethyl-9-(3,5-dimethyl-1-(4-methylphenyl)pyrazol-4-ylmethyl)-1,4,9-triazaspiro[5.5]undecane, (159) 1-butyl-2,5-dioxo-3-(2-methylpropyl)-9-(3,5-dimethyl-1-(4-chlorophenyl)pyrazol-4-ylmethyl)-1,4,9-triazaspiro[5.5]undecane, (160) 1-butyl-2,5-dioxo-3-cyclohexylmethyl-9-(3,5-dimethyl-1-(4-chlorophenyl)pyrazol-4-ylmethyl)-1,4,9-triazaspiro[5.5]undecane, (161) 1-butyl-2,5-dioxo-3-(2-methylpropyl)-9-(3,5-dimethyl-1-(4-trifluoromethylphenyl)pyrazol-4-ylmethyl)-1,4,9-triazaspiro[5.5]undecane, (162) 1-butyl-2,5-dioxo-3-cyclohexylmethyl-9-(3,5-dimethyl-1-(4-trifluoromethylphenyl)pyrazol-4-ylmethyl)-1,4,9-triazaspiro[5.5]undecane, (163) 1-butyl-2,5-dioxo-3-(2-methylpropyl)-9-(3,5-diethyl-1-phenylpyrazol-4-ylmethyl)-1,4,9-triazaspiro[5.5]undecane, (164) 1-butyl-2,5-dioxo-3-cyclohexylmethyl-9-(3,5-diethyl-1-phenylpyrazol-4-ylmethyl)-1,4,9-triazaspiro[5.5]undecane, (165) 1-butyl-2,5-dioxo-3-cyclohexylmethyl-9-(2-phenylthiazol-4-ylmethyl)-1,4,9-triazaspiro[5.5]undecane, (166) 1-butyl-2,5-dioxo-3-(2-methylpropyl)-9-(2-phenylthiazol-4-ylmethyl)-1,4,9-triazaspiro[5.5]undecane, (167) 1-butyl-2,5-dioxo-3-(2-methylpropyl)-9-(2-(1,4-benzodioxan-2-yl)thiazol-4-ylmethyl)-1,4,9-triazaspiro[5.5]undecane, (168) 1-butyl-2,5-dioxo-3-(2-methylpropyl)-9-(4-trifluoromethyl-2-(morpholin-1-yl)thiazol-5-ylmethyl)-1,4,9-triazaspiro[5.5]undecane, (169) 1-butyl-2,5-dioxo-3-(tetrahydropyran-4-ylmethyl)-9-(3,5-dimethyl-1-phenylpyrazol-4-ylmethyl)-1,4,9-triazaspiro[5.5]undecane, (170) 1-butyl-2,5-dioxo-3-(tetrahydropyran-4-ylmethyl)-9-(1,4-benzodioxan-6-ylmethyl)-1,4,9-triazaspiro[5.5]undecane, (171) 1-butyl-2,5-dioxo-3-cyclohexylmethyl-9-(4-carboxyphenylmethyl)-1,4,9-triazaspiro[5.5]undecane, (172) 1-butyl-2,5-dioxo-3-(2-cyclohexylethyl)-9-(3,5-dimethyl-1-phenylpyrazol-4-ylmethyl)-1,4,9-triazaspiro[5.5]undecane, (173) 1-butyl-2,5-dioxo-3-(2-cyclohexylethyl)-9-(1,4-benzodioxan-6-ylmethyl)-1,4,9-triazaspiro[5.5]undecane, (174) (3R)-1-butyl-2,5-dioxo-3-cyclohexylmethyl-9-(3,5-dimethyl-1-phenylpyrazol-4-ylmethyl)-1,4,9-triazaspiro[5.5]undecane, (175) 1-butyl-2,5-dioxo-3-(2-methylpropyl)-9-(4-methyl-2-phenylthiazol-5-ylmethyl)-1,4,9-triazaspiro[5.5]undecane, (176) 1-butyl-2, S -dioxo-3-(2-methylpropyl)-9-(2-(thiophen-1-yl)thiazol-4-ylmethyl)-1,4,9-triazaspiro[5.5]undecane, (177) 1-butyl-2,5-dioxo-3-(2-methylpropyl)-9-(2-(pyridin-4-yl)thiazol-4-ylmethyl)-1,4,9-triazaspiro[5.5]undecane, (178) 1-butyl-2,5-dioxo-3-cyclohexylmethyl-9-(3,4-dimethoxyphenylmethyl)-1,4,9-triazaspiro[5.5]undecane, (179) 1-butyl-2,5-dioxo-3-cyclohexylmethyl-9-(3,5-dimethoxyphenylmethyl)-1,4,9-triazaspiro[5.5]undecane, (180) 1-butyl-2,5-dioxo-3-(2-methylpropyl)-9-(5-(pyridin-2-yl)furan-2-ylmethyl)-1,4,9-triazaspiro[5.5]undecane, (181) 1-butyl-2,5-dioxo-3-(2-methylpropyl)-9-(5-(pyridin-3-yl)furan-2-ylmethyl)-1,4,9-triazaspiro[5.5]undecane, (182) 1-butyl-2,5-dioxo-3-(2-methylpropyl)-9-(4-(3,5-dimethylpyrazol-1-yl)phenylmethyl)-1,4,9-triazaspiro[5.5]undecane, (183) 1-butyl-2,5-dioxo-3-(2-methylpropyl)-9-(4-(5-chloropyridin-3-yloxy)phenylmethyl)-1,4,9-triazaspiro[5.5]undecane, (184) 1-butyl-2,5-dioxo-3-(2-methylpropyl)-9-(4-(pyrimidin-2-yloxy)phenylmethyl)-1,4,9-triazaspiro[5.5]undecane, (185) 1-butyl-2,5-dioxo-3-(2-methylpropyl)-9-(4-(pyridin-3-yloxy)phenylmethyl)-1,4,9-triazaspiro[5.5]undecane, (186) 1-(2-butynyl)-2,5-dioxo-3-(2-methylpropyl)-9-(3,5-dimethyl-1-(4-methylphenyl)pyrazol-4-ylmethyl)-1,4,9-triazaspiro[5.5]undecane, (187) (3R)-1-(2-butynyl)-2,5-dioxo-3-cyclohexylmethyl-9-(3,5-dimethyl-1-phenylpyrazol-4-ylmethyl)-1,4,9-triazaspiro[5.5]undecane, (188) 1-butyl-2,5-dioxo-3-(2-methylpropyl)-9-(4-(4-hydroxyphenyloxy)phenylmethyl)-1,4,9-triazaspiro[5.5]undecane, (189) 1-butyl-2,5-dioxo-3-(2-methylpropyl)-9-(4-(pyridin-2-yl)phenylmethyl)-1,4,9-triazaspiro[5.5]undecane, (190) 1-butyl-2,5-dioxo-3-(2-methylpropyl)-9-(4-(pyridin-3-yl)phenylmethyl)-1,4,9-triazaspiro[5.5]undecane, (191) 1-butyl-2,5-dioxo-3-(2-methylpropyl)-9-(3,5-dimethyl-1-(4-carboxyphenyl)pyrazol-4-ylmethyl)-1,4,9-triazaspiro[5.5]undecane, (192) 1-butyl-2,5-dioxo-3-(2-methylpropyl)-9-(4-(pyrazin-2-yloxy)phenylmethyl)-1,4,9-triazaspiro[5.5]undecane, (193) 1-butyl-2,5-dioxo-3-(2-methylpropyl)-9-(4-(4-carboxyphenyl)phenylmethyl)-1,4,9-triazaspiro[5.5]undecane, (194) 1-butyl-2,5-dioxo-3-(2-methylpropyl)-9-(4-(pyridin-4-yl)phenylmethyl)-1,4,9-triazaspiro[5.5]undecane, (195) 1-butyl-2,5-dioxo-3-(2-methylpropyl)-9-(4-(pyridin-2-yloxy)phenylmethyl)-1,4,9-triazaspiro[5.5]undecane, (196) 1-butyl-2,5-dioxo-3-cyclohexylmethyl-9-(naphthalen-2-ylmethyl)-1,4,9-triazaspiro[5.5]undecane, (197) 1-butyl-2,5-dioxo-3-cyclohexylmethyl-9-(6-methoxynaphthalen-2-ylmethyl)-1,4,9-triazaspiro[5.5]undecane, (198) 1-butyl-2,5-dioxo-3-(2-methylpropyl)-9-(4-(4-carboxyphenyloxy)phenylmethyl)-1,4,9-triazaspiro[5.5]undecane, (199) 1-butyl-2,5-dioxo-3-(2-methylpropyl)-9-(5-(pyridin-4-yl)furan-2-ylmethyl)-1,4,9-triazaspiro[5.5]undecane, (200) 1-butyl-2,5-dioxo-3-cyclopentylmethyl-9-(4-phenyloxyphenylmethyl)-1,4,9-triazaspiro[5.5]undecane, (201) (3R)-1-butyl-2,5-dioxo-3-(2,2-dimethylpropyl)-9-(4-phenyloxyphenylmethyl)-1,4,9-triazaspiro[5.5]undecane, (202) (3S)-1-butyl-2,5-dioxo-3-(2,2-dimethylpropyl)-9-(4-phenyloxyphenylmethyl)-1,4,9-triazaspiro[5.5]undecane, (203) 1-butyl-2,5-dioxo-3-cyclohexylmethyl-9-(4-nitrophenylmethyl)-1,4,9-triazaspiro[5.5]undecane, (204) (3R)-1-(tetrahydrofuran-2-ylmethyl)-2,5-dioxo-3-phenylmethyl-9-(4-phenylbutyl)-1,4,9-triazaspiro[5.5]undecane, (205) (3S)-1-(tetrahydrofuran-2-ylmethyl)-2,5-dioxo-3-phenylmethyl-9-(4-phenylbutyl)-1,4,9-triazaspiro[5.5]undecane, (206) (3S)-1-propyl-2,5-dioxo-3-(3-(benzyloxycarbonylamino)propyl)-9-(2-phenylethyl)-1,4,9-triazaspiro[5.5]undecane, (207) 1-butyl-2,5-dioxo-3-(carboxymethyl)-9-(4-phenyloxyphenylmethyl)-1,4,9-triazaspiro[5.5]undecane, (208) 1-(3-hydroxybutyl)-2,5-dioxo-3-(2-methylpropyl)-9-(4-phenyloxyphenylmethyl)-1,4,9-triazaspiro[5.5]undecane, (209) 1-(3-hydroxypropyl)-2,5-dioxo-3-(2-methylpropyl)-9-(4-phenyloxyphenylmethyl)-1,4,9-triazaspiro[5.5]undecane, (210) 1-(2-hydroxybutyl)-2,5-dioxo-3-(2-methylpropyl)-9-(4-phenyloxyphenylmethyl)-1,4,9-triazaspiro[5.5]undecane, (211) 1-butyl-2,5-dioxo-3-cyclohexylmethyl-9-(4-aminophenylmethyl)-1,4,9-triazaspiro[5.5]undecane, (212) 1-butyl-2,5-dioxo-3-cyclohexylmethyl-9-(4-(phenylcarbonylamino)phenylmethyl)-1,4,9-triazaspiro[5.5]undecane, (213) 1-butyl-2,5-dioxo-3-cyclohexylmethyl-9-(4-((4-methylphenyl)sulfonylamino)phenylmethyl)-1,4,9-triazaspiro[5.5]undecane, (214) (3S)-1-butyl-2,5-dioxo-3-benzyloxymethyl-9-benzyloxycarbonyl-1,4,9-triazaspiro[5.5]undecane, (215) (3S)-1-butyl-2,5-dioxo-3-hydroxymethyl-9-benzyloxycarbonyl-1,4,9-triazaspiro[5.5]undecane, (216) (3S)-1-butyl-2,5-dioxo-3-hydroxymethyl-1,4,9-triazaspiro[5.5]undecane, (217) (3S)-1-butyl-2,5-dioxo-3-hydroxymethyl-9-(4-phenyloxyphenylmethyl)-1,4,9-triazaspiro[5.5]undecane, (218) (3S)-1-butyl-2,5-dioxo-3-hydroxymethyl-9-(3,5-dimethyl-1-phenylpyrazol-4-ylmethyl)-1,4,9-triazaspiro[5.5]undecane, (219) 1-butyl-2,5-dioxo-3-(2-methylpropyl)-9-(4-cyclopentyloxyphenylmethyl)-1,4,9-triazaspiro[5.5]undecane, (220) 1-butyl-2,5-dioxo-3-cyclohexylmethyl-9-(4-(2-diethylaminoethyloxy)phenylmethyl)-1,4,9-triazaspiro[5.5]undecane, (221) 1-butyl-2,5-dioxo-3-cyclohexylmethyl-9-(4-(2-dimethylaminoethyloxy)phenylmethyl)-1,4,9-triazaspiro[5.5]undecane, (222) 1-butyl-2,5-dioxo-3-cyclohexylmethyl-9-(4-propyloxyphenylmethyl)-1,4,9-triazaspiro[5.5]undecane, (223) 1-(thiophen-2-ylmethyl)-2,5-dioxo-3-cyclohexylmethyl-9-(4-cyclopropylmethyloxyphenylmethyl)-1,4,9-triazaspiro[5.5]undecane, (224) 1-butyl-2,5-dioxo-3-cyclohexylmethyl-9-(4-cyclopropylmethyloxyphenylmethyl)-1,4,9-triazaspiro[5.5]undecane, (225) 1-butyl-2,5-dioxo-3-(2-methylpropyl)-9-(4-cyclopropylmethyloxyphenylmethyl)-1,4,9-triazaspiro[5.5]undecane, (226) 1-butyl-2,5-dioxo-3-cyclohexylmethyl-9-(4-(dimethylamino)phenylmethyl)-1,4,9-triazaspiro[5.5]undecane, (227) 1-butyl-2,5-dioxo-3-cyclohexylmethyl-9-(4-(diethylamino)phenylmethyl)-1,4,9-triazaspiro[5.5]undecane, (228) (3S)-1-butyl-2,5-dioxo-3-(2-methylpropyl)-9-benzyloxycarbonyl-1,4,9-triazaspiro[5.5]undecane, (229) (3S)-1-butyl-2,5-dioxo-3-(2-methylpropyl)-1,4,9-triazaspiro[5.5]undecane, (230) (3S)-1-butyl-2,5-dioxo-3-(2-methylpropyl)-9-(5-(3-methyl-4-chlorophenyl)-1-(4-methylphenylmethyl)pyrazol-3-ylmethyl)-1,4,9-triazaspiro[5.5]undecane, (231) (3S)-1-butyl-2,5-dioxo-3-(2-methylpropyl)-9-(4-dimethylaminophenylmethyl)-1,4,9-triazaspiro[5.5]undecane, (232) (3S)-1-butyl-2,5-dioxo-3-(2-methylpropyl)-9-(4-diethylaminophenylmethyl)-1,4,9-triazaspiro[5.5]undecane, (233) (3S)-1-butyl-2,5-dioxo-3-(2-methylpropyl)-9-(4-cyclohexyloxyphenylmethyl)-1,4,9-triazaspiro[5.5]undecane, (234) (3S)-1-butyl-2,5-dioxo-3-(2-methylpropyl)-9-(4-(4-methylphenyloxy)phenylmethyl)-1,4,9-triazaspiro [5.5]*undecane*, (235) (3S)-1-butyl-2,5-dioxo-3-(2-methylpropyl)-9-(4-(4-methoxyphenyloxy)phenylmethyl)-1,4,9-triazaspiro [5.5]undecane, (236) (3S)-1-butyl-2,5-dioxo-3-(2-methylpropyl)-9-(4-butylphenylmethyl)-1,4,9-triazaspiro[5.5]undecane, (237) (3S)-1-butyl-2,5-dioxo-3-(2-methylpropyl)-9-(4-(2-methylpropyl)phenylmethyl)-1,4,9-triazaspiro[5.5] undecane, (238) (3S)-1-butyl-2,5-dioxo-3-(2-methylpropyl)-9-(4-(4-fluorophenyloxy)phenylmethyl)-1,4,9-triazaspiro [5.5]undecane, (239) (3S)-1-butyl-2,5-dioxo-3-(2-methylpropyl)-9-(3-hydroxy-4-methoxyphenylmethyl)-1,4,9-triazaspiro [5.5]undecane, (240) (3S)-1-butyl-2,5-dioxo-3-(2-methylpropyl)-9-(2-fluorophenylmethyl)-1,4,9-triazaspiro[5.5]undecane, (241) (3S)-1-butyl-2,5-dioxo-3-(2-methylpropyl)-9-(3-fluorophenylmethyl)-1,4,9-triazaspiro[5.5]undecane, (242) (3S)-1-butyl-2,5-dioxo-3-(2-methylpropyl)-9-(4-fluorophenylmethyl)-1,4,9-triazaspiro[5.5]undecane, (243) (3S)-1-butyl-2,5-dioxo-3-(2-methylpropyl)-9-(2-chlorophenylmethyl)-1,4,9-triazaspiro[5.5]undecane, (244) (3S)-1-butyl-2,5-dioxo-3-(2-methylpropyl)-9-(4-chlorophenylmethyl)-1,4,9-triazaspiro[5.5]undecane, (245) (3S)-1-butyl-2,5-dioxo-3-(2-methylpropyl)-9-(3-chlorophenylmethyl)-1,4,9-triazaspiro[5.5]undecane, (246) (3S)-1-butyl-2,5-dioxo-3-(2-methylpropyl)-9-(3-methyl-4-methoxyphenylmethyl)-1,4,9-triazaspiro [5.5]undecane, (247) (3S)-1-butyl-2,5-dioxo-3-(2-methylpropyl)-9-(7-methoxy-1,3-benzodioxolan-5-ylmethyl)-1,4,9-triazaspiro[5.5]undecane, (248) (3S)-1-butyl-2,5-dioxo-3-(2-methylpropyl)-9-(4-phenylthiophenylmethyl)-1,4,9-triazaspiro[5.5]undecane, (249) (3S)-1-butyl-2,5-dioxo-3-(2-methylpropyl)-9-(2-methylphenylmethyl)-1,4,9-triazaspiro[5.5]undecane, (250) (3S)-1-butyl-2,5-dioxo-3-(2-methylpropyl)-9-(3-methylphenylmethyl)-1,4,9-triazaspiro[5.5]undecane, (251) (3S)-1-butyl-2,5-dioxo-3-(2-methylpropyl)-9-(4-methylphenylmethyl)-1,4,9-triazaspiro[5.5]undecane, (252) (3S)-1-butyl-2,5-dioxo-3-(2-methylpropyl)-9-(4-(1-methylethyl)phenylmethyl)-1,4,9-triazaspiro[5.5] undecane, (253) (3S)-1-butyl-2,5-dioxo-3-(2-methylpropyl)-9-(3-fluoro-4-methoxyphenylmethyl)-1,4,9-triazaspiro[5.5] undecane, (254) (3S)-1-butyl-2,5-dioxo-3-(2-methylpropyl)-9-(4-(2-hydroxyethyloxy)phenylmethyl)-1,4,9-triazaspiro [5.5]undecane, (255) (3S)-1-butyl-2,5-dioxo-3-(2-methylpropyl)-9-(2-hydroxy-3-methylphenylmethyl)-1,4,9-triazaspiro[5.5] undecane, (256) (3S)-1-butyl-2,5-dioxo-3-(2-methylpropyl)-9-(4-trifluoromethyloxyphenylmethyl)-1,4,9-triazaspiro [5.5]undecane, (257) (3S)-1-butyl-2,5-dioxo-3-(2-methylpropyl)-9-(3-methyl-5-chloro-1-phenylpyrazol-4-ylmethyl)-1,4,9-triazaspiro[5.5]undecane, (258) (3S)-1-butyl-2,5-dioxo-3-(2-methylpropyl)-9-(6-phenylpyridin-3-ylmethyl)-1,4,9-triazaspiro[5.5]undecane, (259) (3S)-1-butyl-2,5-dioxo-3-(2-methylpropyl)-9-(4-(4-methylsulfonylaminophenyloxy)phenylmethyl)-1,4,9-triazaspiro[5.5]undecane, (260) (3S)-1-butyl-2,5-dioxo-3-(2-methylpropyl)-9-(3,5-dimethyl-1-(4-methylsulfonylaminophenyl)pyrazol-4-ylmethyl)-1,4,9-triazaspiro[5.5]undecane, (261) (3S)-1-butyl-2,5-dioxo-3-(2-methylpropyl)-9-(4-(5-methylpyridin-2-yloxy)phenylmethyl)-1,4,9-triazaspiro[5.5]undecane, (262) (3S)-1-butyl-2,5-dioxo-3-(2-methylpropyl)-9-(4-(6-methylpyridin-1-oxide-3-yloxy)phenylmethyl)-1,4,9-triazaspiro[5.5]undecane, (263) (3S)-1-butyl-2,5-dioxo-3-(2-methylpropyl)-9-(1-(2-methylpropyloxycarbonyl)indol-5-ylmethyl)-1,4,9-triazaspiro[5.5]undecane, (264) (3S)-1-butyl-2,5-dioxo-3-(2-methylpropyl)-9-(2-phenyl-5-methyloxazol-4-ylmethyl)-1,4,9-triazaspiro [5.5]undecane, (265) (3S)-1-butyl-2,5-dioxo-3-(2-methylpropyl)-9-(4-(tetrahydropyran-4-yloxy)phenylmethyl)-1,4,9-triazaspiro[5.5]undecane, (266) (3S)-1-butyl-2,5-dioxo-3-(2-methylpropyl)-9-(4-(6-methylpyridin-3-yloxy)phenylmethyl)-1,4,9-triazaspiro[5.5]undecane, (267) (3S)-1-butyl-2,5-dioxo-3-(2-methylpropyl)-9-(3,5-dimethyl-1-(4-fluorophenyl)pyrazol-4-ylmethyl)-1,4,9-triazaspiro[5.5]undecane, (268) (3S)-1-butyl-2,5-dioxo-3-(2-methylpropyl)-9-(3,5-dimethyl-1-(pyridin-2-yl)pyrazol-4-ylmethyl)-1,4,9-triazaspiro[5.5]undecane, (269) (3S)-1-butyl-2,5-dioxo-3-(2-methylpropyl)-9-(3,5-dimethyl-1-(4-hydroxyphenyl)pyrazol-4-ylmethyl)-1,4,9-triazaspiro[5.5]undecane, (270) (3S)-1-butyl-2,5-dioxo-3-(2-methylpropyl)-9-(4-(2-carboxyethyl)phenylmethyl)-1,4,9-triazaspiro[5.5] undecane, (271) (3S)-1-butyl-2,5-dioxo-3-(2-methylpropyl)-9-(3,5-dimethyl-1-(4-(dimethylaminosulfonyl)phenyl)pyrazol-4-ylmethyl)-1,4,9-triazaspiro[5.5]undecane, (272) (3S)-1-butyl-2,5-dioxo-3-(2-methylpropyl)-9-(4-(5-methylpyridin-1-oxide-2-yloxy)phenylmethyl)-1,4,9-triazaspiro[5.5]undecane, (273) (3S)-1-butyl-2,5-dioxo-3-(2-methylpropyl)-9-(4-(2-carboxy-1-ethenyl)phenylmethyl)-1,4,9-triazaspiro [5.5]undecane, (274) (3S)-1-butyl-2,5-dioxo-3-(2-methylpropyl)-9-(4-(4-(2-carboxy-1-ethenyl)phenyloxy)phenylmethyl)-1,4,9-triazaspiro[5.5]undecane, (275) (3S)-1-butyl-2,5-dioxo-3-(2-methylpropyl)-9-(4-(4-aminocarbonylphenyloxy)phenylmethyl)-1,4,9-triazaspiro[5.5]undecane, (276) (3S)-1-butyl-2,5-dioxo-3-(2-methylpropyl)-9-(4-(4-aminosulfonylphenyloxy)phenylmethyl)-1,4,9-triazaspiro[5.5]undecane, (277) (3S)-1-butyl-2,5-dioxo-3-(2-methylpropyl)-9-(3,5-dimethyl-1-benzylpyrazol-4-ylmethyl)-1,4,9-triazaspiro[5.5]undecane, (278) (3S)-1-butyl-2,5-dioxo-3-(2-methylpropyl)-9-(3,5-dimethyl-1-(2,4-difluorophenyl)pyrazol-4-ylmethyl)-1,4,9-triazaspiro[5.5]undecane, (279) (3S)-1-butyl-2,5-dioxo-3-(2-methylpropyl)-9-(4-(pyrrolidin-1-ylmethyl)phenylmethyl)-1,4,9-triazaspiro[5.5]undecane, (280) (3S)-1-butyl-2,5-dioxo-3-(2-methylpropyl)-9-(3,5-dimethyl-1-(4-(morpholin-4-ylsulfonyl)phenyl)pyrazol-4-ylmethyl)-1,4,9-triazaspiro[5.5]undecane, (281) (3S)-1-butyl-2,5-dioxo-3-(2-methylpropyl)-9-(3,5-dimethyl-1-(4-(methylaminosulfonyl)phenyl)pyrazol-4-ylmethyl)-1,4,9-triazaspiro[5.5]undecane, (282) (3S)-1-butyl-2,5-dioxo-3-(2-methylpropyl)-9-(4-(4-cyanophenyloxy)phenylmethyl)-1,4,9-triazaspiro[5.5]undecane, (283) (3S)-1-butyl-2,5-dioxo-3-(2-methylpropyl)-9-(4-(dimethylaminomethyl)phenylmethyl)-1,4,9-triazaspiro[5.5]undecane, (284) (3S)-1-butyl-2,5-dioxo-3-(2-methylpropyl)-9-(3,5-dimethyl-1-(4-(2-dimethylaminoethylaminosulfonyl)phenyl)pyrazol-4-ylmethyl)-1,4,9-triazaspiro[5.5]undecane,3

(285) (3S)-1-butyl-2,5-dioxo-3-(2-methylpropyl)-9-(3-(4-hydroxyphenyl)phenylmethyl)-1,4,9-triazaspiro[5.5]undecane, (286) (3S)-1-butyl-2,5-dioxo-3-(2-methylpropyl)-9-(4-(3-methoxyphenyloxy)phenylmethyl)-1,4,9-triazaspiro[5.5]undecane, (287) (3S)-1-butyl-2,5-dioxo-3-(2-methylpropyl)-9-(3,5-dimethyl-1-(quinoxalin-2-yl)pyrazol-4-ylmethyl)-1,4,9-triazaspiro[5.5]undecane, (288) (3S)-1-butyl-2,5-dioxo-3-(2-methylpropyl)-9-(4-phenylcarbonylphenylmethyl)-1,4,9-triazaspiro[5.5]undecane, (289) (3S)-1-butyl-2,5-dioxo-3-(2-methylpropyl)-9-(3,5-dimethyl-1-(4-(N-(2-hydroxyethyl)-N-methylaminosulfonyl)phenyl)pyrazol-4-ylmethyl)-1,4,9-triazaspiro[5.5]undecane, (290) (3S)-1-butyl-2,5-dioxo-3-(2-methylpropyl)-9-(3,5-dimethyl-1-(2-phenylethyl)pyrazol-4-ylmethyl)-1,4,9-triazaspiro[5.5]undecane, (291) (3S)-1-butyl-2,5-dioxo-3-(2-methylpropyl)-9-(1,3,5-trimethylpyrazol-4-ylmethyl)-1,4,9-triazaspiro[5.5]undecane, (292) (3S)-1-butyl-2,5-dioxo-3-(2-methylpropyl)-9-(4-(morpholin-4-ylmethyl)phenylmethyl)-1,4,9-triazaspiro[5.5]undecane, (293) (3S)-1-butyl-2,5-dioxo-3-(2-methylpropyl)-9-(4-(4-methylpiperazin-1-ylmethyl)phenylmethyl)-1,4,9-triazaspiro[5.5]undecane,3

(294) (3S)-1-butyl-2,5-dioxo-3-(2-methylpropyl)-9-(4-phenylsulfonylphenylmethyl)-1,4,9-triazaspiro[5.5]undecane, (295) (3S)-1-butyl-2,5-dioxo-3-(2-methylpropyl)-9-(3,5-dimethyl-1-cyclohexylpyrazol-4-ylmethyl)-1,4,9-triazaspiro[5.5]undecane, (296) (3S)-1-butyl-2,5-dioxo-3-(2-methylpropyl)-9-(4-(3-carboxyphenyloxy)phenylmethyl)-1,4,9-triazaspiro[5.5]undecane, (297) (3S)-1-butyl-2,5-dioxo-3-(2-methylpropyl)-9-(4-(piperidin-1-ylmethyl)phenylmethyl)-1,4,9-triazaspiro[5.5]undecane, (298) (3S)-1-butyl-2,5-dioxo-3-(2-methylpropyl)-9-(3,5-dimethyl-1-(4-(pyrrolidin-1-ylsulfonyl)phenyl)pyrazol-4-ylmethyl)-1,4,9-triazaspiro[5.5]undecane, (299) (3S)-1-butyl-2,5-dioxo-3-(2-methylpropyl)-9-(2,3-dihydrobenzofuran-5-ylmethyl)-1,4,9-triazaspiro[5.5]undecane, (300) (3S)-1-butyl-2,5-dioxo-3-(2-methylpropyl)-9-(3,5-dimethyl-1-(4-(2-hydroxyethylaminosulfonyl)phenyl)pyrazol-4-ylmethyl)-1,4,9-triazaspiro[5.5]undecane, (301) (3S)-1-butyl-2,5-dioxo-3-(2-methylpropyl)-9-(4-(carboxymethyloxy)phenylmethyl)-1,4,9-triazaspiro[5.5]undecane, (302) (3S)-1-butyl-2,5-dioxo-3-(2-methylpropyl)-9-(4-(1-phenyl-1-hydroxymethyl)phenylmethyl)-1,4,9-triazaspiro[5.5]undecane, (303) (3S)-1-butyl-2,5-dioxo-3-(2-methylpropyl)-9-(4-(4-hydroxypiperidin-1-ylmethyl)phenylmethyl)-1,4,9-triazaspiro[5.5]undecane, (304) (3S)-1-butyl-2,5-dioxo-3-(2-methylpropyl)-9-(4-(3-carboxyphenylmethyloxy)phenylmethyl)-1,4,9-triazaspiro[5.5]undecane, (305) (3S)-1-butyl-2,5-dioxo-3-(2-methylpropyl)-9-(4-(bis(methylsulfonyl)amino)phenylmethyl)-1,4,9-triazaspiro[5.5]undecane, (306) (3S)-1-butyl-2,5-dioxo-3-(2-methylpropyl)-9-(4-(1,4-benzodioxan-6-yloxy)phenylmethyl)-1,4,9-triazaspiro[5.5]undecane, (307) (3S)-1-butyl-2,5-dioxo-3-(2-methylpropyl)-9-(3-(3-hydroxyphenyl)phenylmethyl)-1,4,9-triazaspiro[5.5]undecane, (308) (3S)-1-butyl-2,5-dioxo-3-(2-methylpropyl)-9-(4-(methylsulfonylamino)phenylmethyl)-1,4,9-triazaspiro[5.5]undecane, (309) (3S)-1-butyl-2,5-dioxo-3-(2-methylpropyl)-9-(6-(4-methoxyphenyloxy)pyridin-3-ylmethyl)-1,4,9-triazaspiro[5.5]undecane, (310) (3S)-1-butyl-2,5-dioxo-3-(2-methylpropyl)-9-(4-(4-methylaminocarbonylphenyloxy)phenylmethyl)-1,4,9-triazaspiro[5.5]undecane, (311) (3S)-1-butyl-2,5-dioxo-3-(2-methylpropyl)-9-(4-(4-chlorophenyloxy)phenylmethyl)-1,4,9-triazaspiro[5.5]undecane, (312) (3S)-1-butyl-2,5-dioxo-3-(2-methylpropyl)-9-(3-(4-carboxyphenyl)phenylmethyl)-1,4,9-triazaspiro[5.5]undecane, (313) (3S)-1-butyl-2,5-dioxo-3-(2-methylpropyl)-9-(4-(phenylaminocarbonyl)phenylmethyl)-1,4,9-triazaspiro[5.5]undecane, (314) (3S)-1-butyl-2,5-dioxo-3-(2-methylpropyl)-9-(4-(4-methylthiophenyloxy)phenylmethyl)-1,4,9-triazaspiro[5.5]undecane, (315) (3S)-1-butyl-2,5-dioxo-3-(2-methylpropyl)-9-(4-(4-(2-dimethylaminoethylaminocarbonyl)phenyloxy)phenylmethyl)-1,4,9-triazaspiro[5.5]undecane, (316) (3S)-1-butyl-2,5-dioxo-3-(2-methylpropyl)-9-(4-aminocarbonylphenylmethyl)-1,4,9-triazaspiro[5.5]undecane, (317) (3S)-1-butyl-2,5-dioxo-3-(2-methylpropyl)-9-(4-dimethylaminocarbonylphenylmethyl)-1,4,9-triazaspiro[5.5]undecane, (318) (3S)-1-butyl-2,5-dioxo-3-cyclohexylmethyl-9-benzyloxycarbonyl-1,4,9-triazaspiro[5.5]undecane, (319) (3S)-1-butyl-2,5-dioxo-3-cyclohexylmethyl-1,4,9-triazaspiro[5.5]undecane, (320) (3S)-1-butyl-2,5-dioxo-3-cyclohexylmethyl-9-(4-(4-methylphenyloxy)phenylmethyl)-1,4,9-triazaspiro[5.5]undecane, (321) (3S)-1-butyl-2,5-dioxo-3-cyclohexylmethyl-9-(4-(4-methoxyphenyloxy)phenylmethyl)-1,4,9-triazaspiro[5.5]undecane, (322) (3S)-1-butyl-2,5-dioxo-3-cyclohexylmethyl-9-(2-fluorophenylmethyl)-1,4,9-triazaspiro[5.5]undecane, (323) (3S)-1-butyl-2,5-dioxo-3-cyclohexylmethyl-9-(3-fluorophenylmethyl)-1,4,9-triazaspiro[5.5]undecane, (324) (3S)-1-butyl-2,5-dioxo-3-cyclohexylmethyl-9-(4-fluorophenylmethyl)-1,4,9-triazaspiro[5.5]undecane, (325) (3S)-1-butyl-2,5-dioxo-3-cyclohexylmethyl-9-(3-chlorophenylmethyl)-1,4,9-triazaspiro[5.5]undecane, (326) (3S)-1-butyl-2,5-dioxo-3-cyclohexylmethyl-9-(4-cyclohexyloxyphenylmethyl)-1,4,9-triazaspiro[5.5]undecane, (327) (3S)-1-butyl-2,5-dioxo-3-cyclohexylmethyl-9-(4-methoxy-3-hydroxyphenylmethyl)-1,4,9-triazaspiro[5.5]undecane, (328) (3S)-1-butyl-2,5-dioxo-3-cyclohexylmethyl-9-(2-chlorophenylmethyl)-1,4,9-triazaspiro[5.5]undecane, (329) (3S)-1-butyl-2,5-dioxo-3-cyclohexylmethyl-9-(2-methylphenylmethyl)-1,4,9-triazaspiro[5.5]undecane, (330) (3S)-1-butyl-2,5-dioxo-3-cyclohexylmethyl-9-(3-methylphenylmethyl)-1,4,9-triazaspiro[5.5]undecane, (331) (3S)-1-butyl-2,5-dioxo-3-cyclohexylmethyl-9-(4-methylphenylmethyl)-1,4,9-triazaspiro[5.5]undecane, (332) (3S)-1-butyl-2,5-dioxo-3-cyclohexylmethyl-9-(4-phenylthiophenylmethyl)-1,4,9-triazaspiro[5.5]undecane, (333) (3S)-1-butyl-2,5-dioxo-3-cyclohexylmethyl-9-(3-(2-methylpropyl)phenylmethyl)-1,4,9-triazaspiro[5.5]undecane, (334) (3S)-1-butyl-2,5-dioxo-3-cyclohexylmethyl-9-(3-butylphenylmethyl)-1,4,9-triazaspiro[5.5]undecane, (335) (3S)-1-butyl-2,5-dioxo-3-cyclohexylmethyl-9-(4-isopropylphenylmethyl)-1,4,9-triazaspiro[5.5]undecane, (336) (3S)-1-butyl-2,5-dioxo-3-cyclohexylmethyl-9-(4-methoxy-3-fluorophenylmethyl)-1,4,9-triazaspiro[5.5]undecane, (337) (3S)-1-butyl-2,5-dioxo-3-cyclohexylmethyl-9-(4-(2-hydroxyethoxy)phenylmethyl)-1,4,9-triazaspiro[5.5]undecane, (338) (3S)-1-butyl-2,5-dioxo-3-cyclohexylmethyl-9-(2-hydroxy-3-methylphenylmethyl)-1,4,9-triazaspiro[5.5]undecane, (339) (3S)-1-butyl-2,5-dioxo-3-cyclohexylmethyl-9-(4-chlorophenylmethyl)-1,4,9-triazaspiro[5.5]undecane, (340) (3S)-1-butyl-2,5-dioxo-3-cyclohexylmethyl-9-(7-methoxy-1,3-benzodioxolan-5-ylmethyl)-1,4,9-triazaspiro[5.5]undecane, (341) (3S)-1-butyl-2,5-dioxo-3-cyclohexylmethyl-9-(3-methyl-4-methoxyphenylmethyl)-1,4,9-triazaspiro[5.5]undecane, (342) (3S)-1-butyl-2,5-dioxo-3-cyclohexylmethyl-9-(4-(4-fluorophenyloxy)phenylmethyl)-1,4,9-triazaspiro[5.5]undecane, (343) (3S)-1-butyl-2,5-dioxo-3-cyclohexylmethyl-9-(4-trifluoromethoxyphenylmethyl)-1,4,9-triazaspiro[5.5]undecane, (344) (3S)-1-butyl-2,5-dioxo-3-cyclohexylmethyl-9-(3-methyl-5-chloro-1-phenylpyrazol-4-ylmethyl)-1,4,9-triazaspiro[5.5]undecane, (345) (3S)-1-butyl-2,5-dioxo-3-cyclohexylmethyl-9-(2,3-dimethyl-5-oxo-1-phenylpyrazolin-4-ylmethyl)-1,4,9-triazaspiro[5.5]undecane, (346) (3S)-1-butyl-2,5-dioxo-3-cyclohexylmethyl-9-(1-(2-methylpropyloxycarbonyl)indol-5-ylmethyl)-1,4,9-triazaspiro[5.5]undecane, (347) (3S)-1-butyl-2,5-dioxo-3-cyclohexylmethyl-9-(5-methyl-2-phenyloxazol-4-ylmethyl)-1,4,9-triazaspiro[5.5]undecane, (348) (3S)-1-butyl-2,5-dioxo-3-cyclohexylmethyl-9-(3,5-dimethyl-1-(4-methylsulfonylaminophenyl)pyrazol-4-ylmethyl)-1,4,9-triazaspiro[5.5]undecane, (349) (3S)-1-butyl-2,5-dioxo-3-cyclohexylmethyl-9-(4-(4-methylsulfonylaminophenyloxy)phenylmethyl)-1,4,9-triazaspiro[5.5]undecane, (350) (3S)-1-butyl-2,5-dioxo-3-cyclohexylmethyl-9-(4-(6-methylpyridin-3-yloxy)phenylmethyl)-1,4,9-triazaspiro[5.5]undecane, (351) (3S)-1-butyl-2,5-dioxo-3-cyclohexylmethyl-9-(4-(6-methylpyridin-1-oxide-3-yloxy)phenylmethyl)-1,4,9-triazaspiro[5.5]undecane, (352) (3S)-1-butyl-2,5-dioxo-3-cyclohexylmethyl-9-(4-(tetrahydropyran-4-yloxy)phenylmethyl)-1,4,9-triazaspiro[5.5]undecane, (353) (3S)-1-butyl-2,5-dioxo-3-cyclohexylmethyl-9-(6-phenylpyridin-3-ylmethyl)-1,4,9-triazaspiro[5.5]undecane, (354) (3S)-1-butyl-2,5-dioxo-3-cyclohexylmethyl-9-(3,5-dimethyl-1-(4-fluorophenyl)pyrazol-4-ylmethyl)-1,4,9-triazaspiro[5.5]undecane, (355) (3S)-1-butyl-2,5-dioxo-3-cyclohexylmethyl-9-(3,5-dimethyl-1-(pyridin-2-yl)pyrazol-4-ylmethyl)-1,4,9-triazaspiro[5.5]undecane, (356) (3S)-1-butyl-2,5-dioxo-3-cyclohexylmethyl-9-(3,5-dimethyl-1-(4-hydroxyphenyl)pyrazol-4-ylmethyl)-1,4,9-triazaspiro[5.5]undecane, (357) (3S)-1-butyl-2,5-dioxo-3-cyclohexylmethyl-9-(4-(2-carboxyethyl)phenylmethyl)-1,4,9-triazaspiro[5.5]undecane, (358) (3S)-1-butyl-2,5-dioxo-3-cyclohexylmethyl-9-(4-(4-hydroxyphenyloxy)phenylmethyl)-1,4,9-triazaspiro[5.5]undecane, (359) (3S)-1-butyl-2,5-dioxo-3-cyclohexylmethyl-9-(3,5-dimethyl-1-(4-carboxyphenyl)pyrazol-4-ylmethyl)-1,4,9-triazaspiro[5.5]undecane, (360) (3S)-1-butyl-2,5-dioxo-3-cyclohexylmethyl-9-(3,5-dimethyl-1-(4-(dimethylaminosulfonyl)phenyl)pyrazol-4-ylmethyl)-1,4,9-triazaspiro[5.5]undecane, (361) (3S)-1-butyl-2,5-dioxo-3-cyclohexylmethyl-9-(4-(5-methylpyridin-1-oxide-2-yloxy)phenylmethyl)-1,4,9-triazaspiro[5.5]undecane, (362) (3S)-1-butyl-2,5-dioxo-3-cyclohexylmethyl-9-(4-(2-carboxy-1-ethynyl)phenylmethyl)-1,4,9-triazaspiro[5.5]undecane, (363) (3S)-1-butyl-2,5-dioxo-3-cyclohexylmethyl-9-(4-(4-((1E)-2-carboxy-1-ethynyl)phenyloxy)phenylmethyl)-1,4,9-triazaspiro[5.5]undecane, (364) (3S)-1-butyl-2,5-dioxo-3-cyclohexylmethyl-9-(4-(4-aminocarbonylphenyloxy)phenylmethyl)-1,4,9-triazaspiro[5.5]undecane, (365) (3S)-1-butyl-2,5-dioxo-3-cyclohexylmethyl-9-(4-(4-aminosulfonylphenyloxy)phenylmethyl)-1,4,9-triazaspiro[5.5]undecane, (366) (3S)-1-butyl-2,5-dioxo-3-cyclohexylmethyl-9-(3,5-dimethyl-1-benzylpyrazol-4-ylmethyl)-1,4,9-triazaspiro[5.5]undecane, (367) (3S)-1-butyl-2,5-dioxo-3-cyclohexylmethyl-9-(3,5-dimethyl-1-(2,4-difluorophenyl)pyrazol-4-ylmethyl)-1,4,9-triazaspiro[5.5]undecane, (368) (3S)-1-butyl-2,5-dioxo-3-cyclohexylmethyl-9-(4-(pyrrolidin-1-ylmethyl)phenylmethyl)-1,4,9-triazaspiro[5.5]undecane, (369) (3S)- I -butyl-2,5-dioxo-3-cyclohexylmethyl-9-(3,5-dimethyl-1-(4-(morpholin-4-ylsulfonyl)phenyl)pyrazol-4-ylmethyl)-1,4,9-triazaspiro[5.5]undecane, (370) (3S)-1-butyl-2,5-dioxo-3-cyclohexylmethyl-9-(4-(4-cyanophenyloxy)phenylmethyl)-1,4,9-triazaspiro[5.5]undecane, (371) (3S)-1-butyl-2,5-dioxo-3-cyclohexylmethyl-9-(3,5-dimethyl-1-(4-(N-(2-hydroxyethyl)-N-methylamino-sulfonyl)phenyl)pyrazol-4-ylmethyl)-1,4,9-triazaspiro[5.5]undecane, (372) (3S)-1-butyl-2,5-dioxo-3-cyclohexylmethyl-9-(3,5-dimethyl-1-(2-phenylethyl)pyrazol-4-ylmethyl)-1,4,9-triazaspiro[5.5]undecane, (373) (3S)-1-butyl-2,5-dioxo-3-cyclohexylmethyl-9-(4-(dimethylaminomethyl)phenylmethyl)-1,4,9-triaza-spiro[5.5]undecane, (374) (3S)-1-butyl-2,5-dioxo-3-cyclohexylmethyl-9-(3-(4-hydroxyphenyl)phenylmethyl)-1,4,9-triazaspiro[5.5]undecane, (375) (3S)-1-butyl-2,5-dioxo-3-cyclohexylmethyl-9-(3,5-dimethyl-1-(quinoxalin-2-yl)pyrazol-4-ylmethyl)-1,4,9-triazaspiro[5.5]undecane, (376) (3S)-1-butyl-2,5-dioxo-3-cyclohexylmethyl-9-(4-(phenylcarbonyl)phenylmethyl)-1,4,9-triazaspiro[5.5]undecane, (377) (3S)-1-butyl-2,5-dioxo-3-cyclohexylmethyl-9-(3,5-dimethyl-1-(4-methylaminosulfonylphenyl)pyrazol-4-ylmethyl)-1,4,9-triazaspiro[5.5]undecane, (378) (3S)-1-butyl-2,5-dioxo-3-cyclohexylmethyl-9-(1,3,5-trimethylpyrazol-4-ylmethyl)-1,4,9-triazaspiro[5.5]undecane, (379) (3S)-1-butyl-2,5-dioxo-3-cyclohexylmethyl-9-(4-(morpholin-4-ylmethyl)phenylmethyl)-1,4,9-triaza-spiro[5.5]undecane, (380) (3S)-1-butyl-2,5-dioxo-3-cyclohexylmethyl-9-(4-(3-methoxyphenyloxy)phenylmethyl)-1,4,9-triazaspiro[5.5]undecane, (381) (3S)-1-butyl-2,5-dioxo-3-cyclohexylmethyl-9-(4-(4-methylpiperazin-1-ylmethyl)phenylmethyl)-1,4,9-triazaspiro[5.5]undecane,3

(382) (3S)-1-butyl-2,5-dioxo-3-cyclohexylmethyl-9-(4-(pyridin-1-oxide-3-yloxy)phenylmethyl)-1,4,9-triaza-spiro[5.5]undecane, (383) (3S)-1-butyl-2,5-dioxo-3-cyclohexylmethyl-9-(4-phenylsulfonylphenylmethyl)-1,4,9-triazaspiro[5.5]undecane, (384) (3S)-1-butyl-2,5-dioxo-3-cyclohexylmethyl-9-(3,5-dimethyl-1-cyclohexylpyrazol-4-ylmethyl)-1,4,9-triazaspiro[5.5]undecane, (385) (3S)-1-butyl-2,5-dioxo-3-cyclohexylmethyl-9-(4-(3-carboxyphenyloxy)phenylmethyl)-1,4,9-triazaspiro[5.5]undecane, (386) (3S)-1-butyl-2,5-dioxo-3-cyclohexylmethyl-9-(4-(piperidin-1-ylmethyl)phenylmethyl)-1,4,9-triazaspiro[5.5]undecane, (387) (3S)-1-butyl-2,5-dioxo-3-cyclohexylmethyl-9-(3,5-dimethyl-1-(4-pyrrolidin-1-ylsulfonyl)phenyl)pyrazol-4-ylmethyl)-1,4,9-triazaspiro[5.5]undecane, (388) (3S)-1-butyl-2,5-dioxo-3-cyclohexylmethyl-9-(2,3-dihydrobenzofuran-5-ylmethyl)-1,4,9-triazaspiro[5.5]undecane, (389) (3S)-1-butyl-2,5-dioxo-3-cyclohexylmethyl-9-(4-(4-carboxyphenyloxy)phenylmethyl)-1,4,9-triazaspiro[5.5]undecane, (390) (3S)-1-butyl-2,5-dioxo-3-cyclohexylmethyl-9-(3,5-dimethyl-1-(4-(2-hydroxyethylaminosulfonyl)phenyl)pyrazol-4-ylmethyl)-1,4,9-triazaspiro[5.5]undecane, (391) (3S)-1-butyl-2,5-dioxo-3-cyclohexylmethyl-9-(3,5-dimethyl-1-(4-(2-dimethylaminoethylaminosulfonyl)phenyl)pyrazol-4-ylmethyl)-1,4,9-triazaspiro[5.5]undecane,3

(392) (3S)-1-butyl-2,5-dioxo-3-cyclohexylmethyl-9-(4-(1-hydroxy-1-phenylmethyl)phenylmethyl)-1,4,9-triazaspiro[5.5]undecane, (393) (3S)-1-butyl-2,5-dioxo-3-cyclohexylmethyl-9-(4-(carboxymethyloxy)phenylmethyl)-1,4,9-triazaspiro[5.5]undecane, (394) (3S)-1-butyl-2,5-dioxo-3-cyclohexylmethyl-9-(4-(4-hydroxypiperidin-1-ylmethyl)phenylmethyl)-1,4,9-triazaspiro[5.5]undecane, (395) (3S)-1-butyl-2,5-dioxo-3-cyclohexylmethyl-9-(4-(3-carboxyphenylmethyloxy)phenylmethyl)-1,4,9-triazaspiro[5.5]undecane, (396) (3S)-1-butyl-2,5-dioxo-3-cyclohexylmethyl-9-(4-(1,4-benzodioxan-6-yloxy)phenylmethyl)-1,4,9-triaza-spiro[5.5]undecane, (397) (3S)-1-butyl-2,5-dioxo-3-cyclohexylmethyl-9-(3-(3-hydroxyphenyl)phenylmethyl)-1,4,9-triazaspiro[5.5]undecane, (398) (3S)-1-butyl-2,5-dioxo-3-cyclohexylmethyl-9-(4-(methylsulfonylamino)phenylmethyl)-1,4,9-triazaspiro[5.5]undecane, (399) (3S)-1-butyl-2,5-dioxo-3-cyclohexylmethyl-9-(6-(4-methoxyphenyl)pyridin-3-ylmethyl)-1,4,9-triaza-spiro[5.5]undecane, (400) (3S)-1-butyl-2,5-dioxo-3-cyclohexylmethyl-9-(4-(4-methylaminocarbonylphenyloxy)phenylmethyl)-1,4,9-triazaspiro[5.5]undecane, (401) (3S)-1-butyl-2,5-dioxo-3-cyclohexylmethyl-9-(4-(4-chlorophenyloxy)phenylmethyl)-1,4,9-triazaspiro[5.5]undecane, (402) (3S)-1-butyl-2,5-dioxo-3-cyclohexylmethyl-9-(4-bis(methylsulfonyl)aminophenylmethyl)-1,4,9-triaza-spiro[5.5]undecane, (403) (3S)-1-butyl-2,5-dioxo-3-cyclohexylmethyl-9-(3-(4-carboxyphenyl)phenylmethyl)-1,4,9-triazaspiro[5.5]undecane, (404) (3S)-1-butyl-2,5-dioxo-3-cyclohexylmethyl-9-(4-(phenylaminocarbonyl)phenylmethyl)-1,4,9-triaza-spiro[5.5]undecane, (405) (3S)-1-butyl-2,5-dioxo-3-cyclohexylmethyl-9-(4-(4-methylthiophenyloxy)phenylmethyl)-1,4,9-triaza-spiro[5.5]undecane, (406) (3S)-1-butyl-2,5-dioxo-3-cyclohexylmethyl-9-(4-(4-(2-dimethylaminoethylaminocarbonyl)phenyloxy)phenylmethyl)-1,4,9-triazaspiro[5.5]undecane, (407) (3S)-1-butyl-2,5-dioxo-3-cyclohexylmethyl-9-(4-aminocarbonylphenylmethyl)-1,4,9-triazaspiro[5.5]undecane, (408) (3S)-1-butyl-2,5-dioxo-3-cyclohexylmethyl-9-(4-(dimethylaminocarbonyl)phenylmethyl)-1,4,9-triaza-spiro[5.5]undecane, (409) (3S)-1-butyl-2,5-dioxo-3-cyclohexylmethyl-9-(4-phenyloxyphenylmethyl)-1,4,9-triazaspiro[5.5]undecane, (410) 1-butyl-2,5-dioxo-3-(1-hydroxy-2-methylpropyl)-9-(1,4-benzodioxan-6-ylmethyl)-1,4,9-triazaspiro[5.5]undecane, (411) (Z)-1-butyl-2,5-dioxo-3-(2-methylpropylidene)-9-(1,4-benzodioxan-6-ylmethyl)-1,4,9-triazaspiro[5.5]undecane, (412) (3S)-1-butyl-2,5-dioxo-3-((1R)-1-hydroxyethyl)-9-(4-phenyloxyphenylmethyl)-1,4,9-triazaspiro[5.5]undecane, (413) (Z)-1-butyl-2,5-dioxo-3-ethylidene9-(4-phenyloxyphenylmethyl)-1,4,9-triazaspiro[5.5]undecane, (414) (Z)-1-butyl-2,5-dioxo-3-(2-methylpropylidene)-9-(4-phenyloxyphenylmethyl)-1,4,9-triazaspiro[5.5]undecane, (415) (3R*)-1-butyl-2,5-dioxo-3-((1R*)-1-hydroxy-2-methylpropyl)-9-benzyloxycarbonyl-1,4,9-triazaspiro[5.5]undecane, (416) (3R*)-1-butyl-2,5-dioxo-3-((1R*)-1-hydroxy-2-methylpropyl)-1,4,9-triazaspiro[5.5]undecane, (417) (3R*)-1-butyl-2,5-dioxo-3-((1R*)-1-hydroxy-2-methylpropyl)-9-(4-phenyloxyphenylmethyl)-1,4,9-triazaspiro[5.5]undecane, (418) (3R*)-1-butyl-2,5-dioxo-3-((1R*)-1-hydroxy-2-methylpropyl)-9-(3,5-dimethyl-1-phenylpyrazol-4-ylmethyl)-1,4,9-triazaspiro[5.5]undecane, (419) (3R*)-1-butyl-2,5-dioxo-3-((1R*)-1-hydroxy-2-methylpropyl)-9-(6-phenyloxypyridin-3-ylmethyl)-1,4,9-triazaspiro[5.5]undecane, (420) (3R*)-1-butyl-2,5-dioxo-3-((1R*)-1-hydroxy-2-methylpropyl)-9-(4-(4-methylphenyloxy)phenylmethyl)-1,4,9-triazaspiro[5.5]undecane, (421) (3R*)-1-butyl-2,5-dioxo-3-((1R*)-1-hydroxy-2-methylpropyl)-9-(4-cyclohexyloxyphenylmethyl)-1,4,9-triazaspiro[5.5]undecane, (422) (3R*)-1-butyl-2,5-dioxo-3-((1R*)-1-hydroxy-2-methylpropyl)-9-(4-(tetrahydropyran-4-yloxy)phenylmethyl)-1,4,9-triazaspiro[5.5]undecane, (423) (3R*)-1-butyl-2,5-dioxo-3-((1R*)-1-hydroxy-2-methylpropyl)-9-(4-(pyridin-3-yloxy)phenylmethyl)-1,4,9-triazaspiro[5.5]undecane, (424) (3R*)-1-butyl-2,5-dioxo-3-((1R*)-1-hydroxy-2-methylpropyl)-9-(4-isopropylphenylmethyl)-1,4,9-triazaspiro[5.5]undecane, (425) (3R*)-1-butyl-2,5-dioxo-3-((1R*)-1-hydroxy-2-methylpropyl)-9-(3,5-dimethyl-1-(4-methylphenyl)pyrazol-4-ylmethyl)-1,4,9-triazaspiro[5.5]undecane, (426) (3R*)-1-butyl-2,5-dioxo-3-((1R*)-1-hydroxy-2-methylpropyl)-9-(3-methyl-5-chloro-1-phenylpyrazol-4-ylmethyl)-1,4,9-triazaspiro[5.5]undecane, (427) (3R*)-1-butyl-2,5-dioxo-3-((1R*)-1-hydroxy-2-methylpropyl)-9-(4-(4-carboxyphenyloxy)phenylmethyl)-1,4,9-triazaspiro[5.5]undecane, (428) (3R*)-1-butyl-2,5-dioxo-3-((1R*)-1-hydroxy-2-methylpropyl)-9-(3,5-dimethyl-1-(pyridin-2-yl)pyrazol-4-ylmethyl)-1,4,9-triazaspiro[5.5]undecane, (429) (3R*)-1-butyl-2,5-dioxo-3-((1R*)-1-hydroxy-2-methylpropyl)-9-(3,5-dimethyl-1-(4-carboxyphenyl)pyrazol-4-ylmethyl)-1,4,9-triazaspiro[5.5]undecane, (430) (3R*)-1-butyl-2,5-dioxo-3-((1R*)-1-hydroxy-1-cyclohexylmethyl)-9-benzyloxycarbonyl-1,4,9-triazaspiro[5.5]undecane, (431) (3R*)-1-butyl-2,5-dioxo-3-((1R*)-1-hydroxy-1-cyclohexylmethyl)-1,4,9-triazaspiro[5.5]undecane, (432) (3R*)-1-butyl-2,5-dioxo-3-((1R*)-1-hydroxy-1-cyclohexylmethyl)-9-(4-phenyloxyphenylmethyl)-1,4,9-triazaspiro[5.5]undecane, (433) (3R*)-1-butyl-2,5-dioxo-3-((1R*)-1-hydroxy-1-cyclohexylmethyl)-9-(3,5-dimethyl-1-phenylpyrazol-4-ylmethyl)-1,4,9-triazaspiro[5.5]undecane, (434) (3R*)-1-butyl-2,5-dioxo-3-((1R*)-1-hydroxy-1-cyclohexylmethyl)-9-(4-isopropylphenylmethyl)-1,4,9-triazaspiro[5.5]undecane, (435) (3R*)-1-butyl-2,5-dioxo-3-((1R*)-1-hydroxy-1-cyclohexylmethyl)-9-(4-(6-methylpyridin-3-yloxy)phenylmethyl)-1,4,9-triazaspiro[5.5]undecane, (436) (3R*)-1-butyl-2,5-dioxo-3-((1R*)-1-hydroxy-1-cyclohexylmethyl)-9-(3,5-dimethyl-1-(4-fluorophenyl)pyrazol-4-ylmethyl)-1,4,9-triazaspiro[5.5]undecane, (437) (3R*)-1-butyl-2,5-dioxo-3-((1R*)-1-hydroxy-1-cyclohexylmethyl)-9-(4-(4-methoxyphenyloxy)phenylmethyl)-1,4,9-triazaspiro[5.5]undecane, (438) (3R*)-1-butyl-2,5-dioxo-3-((1R*)-1-hydroxy-1-cyclohexylmethyl)-9-(4-(4-fluorophenyloxy)phenylmethyl)-1,4,9-triazaspiro[5.5]undecane, (439) (3R*)-1-butyl-2,5-dioxo-3-((1R*)-1-hydroxy-1-cyclohexylmethyl)-9-(4-(4-methylsulfonylaminophenyloxy)phenylmethyl)-1,4,9-triazaspiro[5.5]undecane, (440) (3R*)-1-(2-butynyl)-2,5-dioxo-3-((1R*)-1-hydroxy-1-cyclohexylmethyl)-9-allyloxycarbonyl-1,4,9-triazaspiro[5.5]undecane, (441) (3R*)-1-(2-butynyl)-2,5-dioxo-3-((1R*)-1-hydroxy-1-cyclohexylmethyl)-1,4,9-triazaspiro[5.5]undecane, (442) (3R*)-1-(2-butynyl)-2,5-dioxo-3-((1R*)-1-hydroxy-1-cyclohexylmethyl)-9-(3,5-dimethyl-1-phenylpyrazol-4-ylmethyl)-1,4,9-triazaspiro[5.5]undecane, (443) (3R*)-1-(2-butynyl)-2,5-dioxo-3-((1R*)-1-hydroxy-1-cyclohexylmethyl)-9-(3,5-dimethyl-1-(4-methylphenyl)pyrazol-4-ylmethyl)-1,4,9-triazaspiro[5.5]undecane, (444) (3R*)-1-(2-butynyl)-2,5-dioxo-3-((1R*)-1-hydroxy-1-cyclohexylmethyl)-9-(4-isopropylphenylmethyl)-1,4,9-triazaspiro[5.5]undecane, (445) (3R*)-1-(2-butynyl)-2,5-dioxo-3-((1R*)-1-hydroxy-1-cyclohexylmethyl)-9-(4-phenyloxyphenylmethyl)-1,4,9-triazaspiro[5.5]undecane, (446) (3R*)-1-(2-butynyl)-2,5-dioxo-3-((1R*)-1-hydroxy-1-cyclohexylmethyl)-9-(4-(4-methylphenyloxy)phenylmethyl)-1,4,9-triazaspiro[5.5]undecane, (447) (3R*)-1-(2-butynyl)-2,5-dioxo-3-((1R*)-1-hydroxy-1-cyclohexylmethyl)-9-(1,4-benzodioxan-6-ylmethyl)-1,4,9-triazaspiro[5.5]undecane, (448) (3R*)-1-(2-butynyl)-2,5-dioxo-3-((1R*)-1-hydroxy-2-methylpropyl)-1,4,9-triazaspiro[5.5]undecane, (449) (3R*)-1-(2-butynyl)-2,5-dioxo-3-((1R*)-1-hydroxy-2-methylpropyl)-9-(3,5-dimethyl-1-(4-methylphenyl)pyrazol-4-ylmethyl)-1,4,9-triazaspiro[5.5]undecane, (450) (3R*)-1-(2-butynyl)-2,5-dioxo-3-((1R*)-1-hydroxy-2-methylpropyl)-9-(4-(4-methylphenyloxy)phenylmethyl)-1,4,9-triazaspiro[5.5]undecane, (451) (3R*)-1-(2-butynyl)-2,5-dioxo-3-((1R*)-1-hydroxy-2-methylpropyl)-9-(1,4-benzodioxan-6-ylmethyl)-1,4,9-triazaspiro[5.5]undecane, (452) (3R*)-1-(2-butynyl)-2,5-dioxo-3-((1R*)-1-hydroxy-2-methylpropyl)-9-(4-isopropylphenylmethyl)-1,4,9-triazaspiro[5.5]undecane, (453) (3R*)-1-(2-butynyl)-2,5-dioxo-3-((1R*)-1-hydroxy-2-methylpropyl)-9-(4-phenyloxyphenylmethyl)-1,4,9-triazaspiro[5.5]undecane, (454) (3R*)-1-butyl-2,5-dioxo-3-((1S*)-1-hydroxy-1-cyclohexylmethyl)-9-benzyl-1,4,9-triazaspiro[5.5]undecane, (455) (3R*)-1-butyl-2,5-dioxo-3-((1S*)-1-hydroxy-1-cyclohexylmethyl)-1,4,9-triazaspiro[5.5]undecane, (456) (3R*)-1-butyl-2,5-dioxo-3-((1S*)-1-hydroxy-1-cyclohexylmethyl)-9-(4-phenyloxyphenylmethyl)-1,4,9-triazaspiro[5.5]undecane, (457) (3R*)-1-butyl-2,5-dioxo-3-((1S*)-1-hydroxy-1-cyclohexylmethyl)-9-(1,4-benzodioxan-6-ylmethyl)-1,4,9-triazaspiro[5.5]undecane, (458) (3R*)-1-butyl-2,5-dioxo-3-((1S*)-1-hydroxy-1-cyclohexylmethyl)-9-(3,5-dimethyl-1-phenylpyrazol-4-ylmethyl)-1,4,9-triazaspiro[5.5]undecane, (459) (3S)-1-butyl-2,5-dioxo-3-((1S)-1-hydroxy-2-methylpropyl)-1,4,9-triazaspiro[5.5]undecane, (460) (3S)-1-butyl-2,5-dioxo-3-((1S)-1-hydroxy-2-methylpropyl)-9-(3,5-dimethyl-1-phenylpyrazol-4-ylmethyl)-1,4,9-triazaspiro[5.5]undecane, (461) (3S)-1-butyl-2,5-dioxo-3-((1S)-1-hydroxy-2-methylpropyl)-9-(4-phenyloxyphenylmethyl)-1,4,9-triazaspiro[5.5]undecane, (462) (3S)-1-butyl-2,5-dioxo-3-((1S)-1-hydroxy-2-methylpropyl)-9-(1,4-benzodioxan-6-ylmethyl)-1,4,9-triazaspiro[5.5]undecane, (463) (35)-1-butyl-2,5-dioxo-3-((15)-1-hydroxy-2-methylpropyl)-9-(4-(4-methylsulfonylaminophenyloxy)phenylmethyl)-1,4,9-triazaspiro[5.5]undecane, (464) (3R)-1-butyl-2,5-dioxo-3-((1R)-1-hydroxy-2-methylpropyl)-1,4,9-triazaspiro[5.5]undecane, (465) (3R)-1-butyl-2,5-dioxo-3-((1R)-1-hydroxy-2-methylpropyl)-9-(3,5-dimethyl-1-phenylpyrazol-4-ylmethyl)-1,4,9-triazaspiro[5.5]undecane, (466) (3R)-1-butyl-2,5-dioxo-3-((1R)-1-hydroxy-2-methylpropyl)-9-(4-phenyloxyphenylmethyl)-1,4,9-triazaspiro[5.5]undecane, (467) (3R)-1-butyl-2,5-dioxo-3-((1R)-1-hydroxy-2-methylpropyl)-9-(1,4-benzodioxan-6-ylmethyl)-1,4,9-triazaspiro[5.5]undecane, (468) (3R)-1-butyl-2,5-dioxo-3-((1R)-1-hydroxy-2-methylpropyl)-9-(4-(4-methylsulfonylaminophenyloxy)phenylmethyl)-1,4,9-triazaspiro[5.5]undecane, (469) (3R)-1-butyl-2,5-dioxo-3-((1S)-1-hydroxy-2-methylpropyl)-1,4,9-triazaspiro[5.5]undecane, (470) (3R)-1-butyl-2,5-dioxo-3-((1S)-1-hydroxy-2-methylpropyl)-9-(3,5-dimethyl-1-phenylpyrazol-4-ylmethyl)-1,4,9-triazaspiro[5.5]undecane, (471) (3R)-1-butyl-2,5-dioxo-3-((1S)-1-hydroxy-2-methylpropyl)-9-(1,4-benzodioxan-6-ylmethyl)-1,4,9-triazaspiro[5.5]undecane, (472) (3R)-1-butyl-2,5-dioxo-3-((1S)-1-hydroxy-2-methylpropyl)-9-(4-(4-methylsulfonylaminophenyloxy)phenylmethyl)-1,4,9-triazaspiro[5.5]undecane, (473) (3S)-1-butyl-2,5-dioxo-3-((1R)-1-hydroxy-2-methylpropyl)-1,4,9-triazaspiro[5.5]undecane, (474) (3S)-1-butyl-2,5-dioxo-3-((1R)-1-hydroxy-2-methylpropyl)-9-(3,5-dimethyl-1-phenylpyrazol-4-ylmethyl)-1,4,9-triazaspiro[5.5]undecane, (475) (3S)-1-butyl-2,5-dioxo-3-((1R)-1-hydroxy-2-methylpropyl)-9-(1,4-benzodioxan-6-ylmethyl)-1,4,9-triazaspiro[5.5]undecane, (476) (3S)-1-butyl-2,5-dioxo-3-((1R)-1-hydroxy-2-methylpropyl)-9-(4-(4-methylsulfonylaminophenyloxy)phenylmethyl)-1,4,9-triazaspiro[5.5]undecane, (477) (3S)-2,5-dioxo-3-(3-benzyloxycarbonylaminopropyl)-9-(2-phenylethyl)-1,4,9-triazaspiro[5.5]undecane, (478) (3S)-1-methyl-2,5-dioxo-3-(3-benzyloxycarbonylaminopropyl)-9-(2-phenylethyl)-1,4,9-triazaspiro[5.5]undecane, or (479) (3S)-1-butyl-2,5-dioxo-3-cyclohexylmethyl-9-(4-phenyloxyphenylmethyl)-9-oxide-1,4,9-triazaspiro[5.5]undecane, a quaternary ammonium salt thereof, an N-oxide thereof or a non-toxic salt thereof.

7. A pharmaceutical composition comprising a triazaspiro[5.5]undecane compound of the formula (I) described in claim 1, a quaternary ammonium salt thereof, an N-oxide thereof or a non-toxic salt thereof, as an active ingredient, and a carrier.

* * * * *

SEQUENCE LISTING

<160> NUMBER OF SEQ ID NOS: 2
<210> SEQ ID NO 1
<211> LENGTH: 37
<212> TYPE: DNA
<213> ORGANISM: Artificial Sequence
<220> FEATURE:
<223> OTHER INFORMATION: Forward primer hCCR5Xba1

-continued

<400> SEQUENCE: 1
agctagtcta gatccgttcc cctacaagaa actctcc 37

<210> SEQ ID NO 2
<211> LENGTH: 37
<212> TYPE: DNA
<213> ORGANISM: Artificial Sequence
<220> FEATURE:
<223> OTHER INFORMATION: Reverse primer hCCR5Xba1

<400> SEQUENCE: 2
agctagtcta gagtgcacaa ctctgactgg gtcacca 37